United States Patent
Vasbinder et al.

(10) Patent No.: US 10,870,641 B2
(45) Date of Patent: *Dec. 22, 2020

(54) PYRIDAZINONES AS PARP7 INHIBITORS

(71) Applicant: Ribon Therapeutics Inc., Lexington, MA (US)

(72) Inventors: Melissa Marie Vasbinder, Newton, MA (US); Laurie B. Schenkel, Somerville, MA (US); Kerren Kalai Swinger, Lexington, MA (US); Kevin Wayne Kuntz, Woburn, MA (US)

(73) Assignee: Ribon Therapeutics, Inc., Cambridge, MA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/662,409

(22) Filed: Oct. 24, 2019

(65) Prior Publication Data

US 2020/0123134 A1 Apr. 23, 2020

Related U.S. Application Data

(63) Continuation of application No. 16/397,103, filed on Apr. 29, 2019, now Pat. No. 10,550,105.

(60) Provisional application No. 62/664,544, filed on Apr. 30, 2018.

(51) Int. Cl.
| | | |
|---|---|---|
| *C07D 403/14* | (2006.01) | |
| *A61P 35/00* | (2006.01) | |
| *C07D 401/14* | (2006.01) | |
| *C07D 413/14* | (2006.01) | |
| *C07D 417/14* | (2006.01) | |
| *C07D 487/04* | (2006.01) | |
| *C07D 495/04* | (2006.01) | |

(52) U.S. Cl.
CPC .......... *C07D 403/14* (2013.01); *A61P 35/00* (2018.01); *C07D 401/14* (2013.01); *C07D 413/14* (2013.01); *C07D 417/14* (2013.01); *C07D 487/04* (2013.01); *C07D 495/04* (2013.01)

(58) Field of Classification Search
CPC ... C07D 403/12; C07D 403/14; A61K 31/501
USPC ...................... 544/238; 514/252.02
See application file for complete search history.

(56) References Cited

U.S. PATENT DOCUMENTS

| | | | |
|---|---|---|---|
| 6,432,632 B2 | 8/2002 | Nakayama | |
| 10,550,105 B2* | 2/2020 | Vasbinder | C07D 401/12 |
| 2003/0082665 A1 | 5/2003 | Ingraham et al. | |
| 2019/0331688 A1 | 10/2019 | Wigle et al. | |

FOREIGN PATENT DOCUMENTS

| | | |
|---|---|---|
| WO | WO 2016/116602 | 7/2016 |
| WO | WO 2019/055966 | 7/2016 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*
Barbarulo et al, "Poly(ADP-ribose) polymerase family member 14 (PARP14) is a novel effector of the JNK2-dependent pro-survival signal in multiple myeloma," Oncogene, 2013, 4231-4242.
Belosouva et al, "DNA is a New Target of Parp3," Scientific Reports, Mar. 2018, 8:4176, 12 pages.
Bindesboll et al., "TCDD-inducible poly-ADP-ribose polymerase (TIPARP/PARP7) mono-ADP-ribosylates and co-activates liver X receptors," Biochem. J., 2016, 473:899-910.
Bock "Aryl hydrocarbon receptor (AHR) functions in NAD+ metabolism, myelopoiesis and obesity", Biochemical Pharmacology 163 (2019) 128-132.
Bock, "Toward elucidation of dioxin-mediated chloracne and Ah receptor functions," Biochem. Pharmacol., 2016, 112:1-5.
Bolton et al., "Cell- and gene-specific regulation of primary target genes by the androgen receptor," Genes Dev., 2007, 21:2005-2017.
Caprara et al, "PARP14 Controls the Nuclear Accumulation of a Subset of Type I IFN-Inducible Proteins," The Journal of Immunology, Mar. 2018, 16 pages.
Cerami et al, "The cBio Cancer Genomics Portal: An Open Platform for Exploring Multidimensional Cancer Genomics Data," Cancer Discov. 2, 2012, 401-404.
Chen et al, "A macrodomain-linked immunosorbent assay (MLISA) for mono-ADPribosyltransferases," Analytical Biochemistry, 2018, 543:132-139.
Cohen & Chang, "Insights into the biogenesis, function, and regulation of ADP-ribosylation," Nat. Chem. Biol., 2018, 14:236-243.
Czarnik, "Encoding strategies in combinatorial chemistry," Curr. Opin. Chem. Bio., 1997, 94(24):12378-12739.
Davis & Erlanson, "Learning from our mistakes: The 'unknown knowns' in fragment screening," Bioorganic & Medicinal Chemistry Letters, 2013, 23:2844-2852.
Diani-Moore et al, "Aryl Hydrocarbon Receptor Activation by Dioxin Targets Phosphoenolpyruvate Carboxykinase (PEPCK) for ADP-ribosylation via 2,3,7,8-Tetrachlorodibenzo-p-dioxin (TCDD)-inducible Poly(ADP-ribose) Polymerase (TiPARP)," The Journal of Biological Chemistry, 2013, 288:30:21514-21525.

(Continued)

*Primary Examiner* — Deepak R Rao
(74) *Attorney, Agent, or Firm* — Fish & Richardson P.C.

(57) ABSTRACT

The present invention relates to pyridazinones and related compounds which are inhibitors of PARP7 and are useful in the treatment of cancer.

30 Claims, 11 Drawing Sheets

(56) References Cited

OTHER PUBLICATIONS

Diani-Moore et al, "Identification of the Aryl Hydrocarbon Receptor Target Gene TiPARP as a Mediator of Suppression of Hepatic Gluconeogenesis by 2,3,7,8-Tetrachlorodibenzo-p-dioxin and of Nicotinamide as a Corrective Agent for This Effect," The Journal of Biological Chemistry, 2010, 285:50:38801-38810.
Dillon et al, "A FlashPlate Assay for the Identification of PARP-1 Inhibitors,"Journal of Biomolecular Screening, 2003, 3(3):347-352.
Feng et al, "Role of aryl hydrocarbon receptor in cancer," Biochim. Biophys. Acta., 2013, 1836:197-210.
Gao et al., "Integrative analysis of complex cancer genomics and clinical profiles using the cBioPortal," Sci. Signal, 2013, 6:269, 19 pages.
Goode et al., "A genome-wide association study identifies susceptibility loci for ovarian cancer at 2q31 and 8q24," Nat. Genet., 2010, 42:874-879.
Hao et al, "Xenobiotics and loss of cell adhesion drive distinct transcriptional outcomes by aryl hydrocarbon receptor signaling," Mol. Pharmacol., 2012, 82:1082-1093.
Ji et al, "The Development of a Biotinylated NAD+-Applied Human Poly(ADP-Ribose) Polymerase 3 (PARP3) Enzymatic Assay," SLAS Discovery, Feb. 2018, 9 pages.
Jwa & Chang, "PARP16 is a tail-anchored endoplasmic reticulum protein required for the PERK- and IRE1-mediated unfolded protein response," Nature Cell Biology, 14(11):1223-1230.
Kim et al, "A Quantitative Assay Reveals Ligand Specificity of the DNA Scaffold Repair Protein XRCC1 and Efficient Disassembly of Complexes of XRCC1 and the Poly(ADP-ribose) Polymerase 1 by Poly(ADP-ribose) Glycohydrolase," Journal of Biological Chemistry, Dec. 2014, 290(6):3775-3783.
Kozaki et al, "Mitochondrial damage elicits a TCDD-inducible poly(ADP-ribose) polymerase-mediated antiviral response," Proc. Natl. Acad. Sci. USA, 2017, 114:2681-2686.
Lea et al, "Fluorescence polarization assays in small molecule screening," Expert Opinion on Drug Discovery, 6(1):17-32.
Leidecker et al, "Serine is a new target residue for endogenous ADP-ribosylation on histones," Nature Checmical Biology, Oct. 2016, 6 pages.
Ma "Induction and superinduction of 2, 3, 7, 8-tetrachlorodibenzopdioxin-inducible poly(ADP-ribose) polymerase:Role of the aryl hydrocarbon receptor/aryl hydrocarbon receptor nuclear translocator transcription activation domains and a labile transcription repressor," Archives of Biochemistry and Biophysics, 2002, 404:309-316.
Ma et al, "TCDD-Inducible Poly(ADP-ribose) Polymerase: A Novel Response to 2,3,7,8-Tetrachlorodibenzo-p-dioxin," Biochemical and Biophysical Research Communications, 2001, 289:499-506.
Machleidt et al, "NanoBRET—A Novel Bret Platform for the Analysis of Protein-Protein Interactions," ACS Chemical Biology, Aug. 2015, 10(8): 1554-8929.
MacPherson et al, "2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation," Nucleic Acids Res., 2013, 41:1604-1621.
MacPherson et al., "Aryl hydrocarbon receptor repressor and TIPARP (ARTD14) use similar, but also distinct mechanisms to repress aryl hydrocarbon receptor signaling," Int. J. Mol. Sci., 2014, 15:7939-7957.
Matthews, "AHR toxicity and signaling: Role of TIPARP and ADP-ribosylation," Current Opinion in Toxicology, 2017, 2:50-57.

Ohmoto & Yachida, "Current status of poly(ADP-ribose) polymerase inhibitors and future directions," Onco. Targets Ther., 2017, 10:5195-5208.
Opitz et al, "An endogenous tumour-promoting ligand of the human aryl hydrocarbon receptor," Nature, 2011, 478:197-203.
Pan et al, "A major chromatin regulator determines resistance of tumor cells to T cell-mediated killing," Science, 2018, 359:770-775.
Papeo et al, "Insights into PARP Inhibitors' Selectivity Using Fluorescence Polarization and Surface Plasmon Resonance Binding Assays," Journal of Biomolecular Screening, 2014, 19(8):1212-1219.
PCT International Search Report and Written Opinion in International Appln. No. PCT/US2019/029599, dated Jul. 19, 2019, 35 pages.
PCT International Serach Report and Written Opinion in International Appln. No. PCT/US2019/029582, dated Jun. 19, 2019.
Peng et al, "Small Molecule Microarray Based Discovery of PARP14 Inhibitors," Angew. Chem. Int. Ed., 2016, 55:1-7.
Roper et al, "ADP-ribosyltransferases Parp1 and Parp7 safeguard pluripotency of ES cells," Nucleic Acids Research, 2014, 42:14:8914-8927.
Schmahl et al, "PDGF signaling specificity is mediated through multiple immediate early genes," Nat. Genet., 2007, 39:52-60.
STN Search, conducted Mar. 23, 2018, 44 pages.
STN Search, conducted Mar. 5, 2018, 14 pages.
STN Search, conducted Mar. 5, 2018, 31 pages.
Stockinger et al, "The aryl hydrocarbon receptor: multitasking in the immune system," Annu. Rev. Immunol., 2014, 32:403-432.
Thorsell et al, "Structural Basis for Potency and Promiscuity in Poly(ADP-ribose) Polymerase (PARP) and Tankyrase Inhibitors," J. Med. Chem., Dec. 2016, A-J.
Tokunaga et al, "CXCL9, CXCL10, CXCL11/CXCR3 axis for immune activation—A target for novel cancer therapy," Cancer Treatment Rev 63, 2018, 40-47.
Venkannagari et al, "Activity-based assay for human mono-ADP-ribosyltransferases ARTD7/PARP15 and ARTD10/PARP10 aimed at screening and profiling inhibitors," European Journal of Pharmaceutical Sciences, 2013, 49:148-156.
Vyas et al, "A systematic analysis of the PARP protein family identifies new functions critical for cell physiology," Nat. Commun., 2013, 4:2240, 13 pages.
Vyas et al, "New PARP targets for cancer therapy Nat Rev Cancer," Jun. 5, 2014, 14:502-509.
Vyas et al., "Family-wide analysis of poly(ADP-ribose) polymerase activity," 2014, Nat. Commun., 5:4426, 13 pages.
Wahlberg et al, "Family-wide chemical profiling and structural analysis of PARP and tankyrase inhibitors," Nature Biotechnology, Mar. 2012, 30(3):283-288.
Yamada et al, "Constitutive aryl hydrocarbon receptor signaling constrains Type I interferon-mediated antiviral innate defense," Nat. Immunol., 2016, 17:687-694.
Yoneyama-Hirozane et al, "Identification of PARP14 inhibitors using novel methods for detecting auto-ribosylation," Biochemical and Biophysical Research Communications, 2017, 1-6.
Yuen et al ,"A Focused DNA-encoded Chemical Library for the Discovery of Inhibitors of NAD+-dependent Enzymes," J. Am. Chem. Soc., Mar. 2019, 15 pages.
Zaffini et al, "Asthma and poly(ADP-ribose) polymerase inhibition: a new therapeutic approach," Drug Design, Development and Therapy, 2018, 12:281-2913.
Zitvogel et al., Type I interferons in anticancer immunity. Nat Rev Immun 15, 2015, 405.

\* cited by examiner

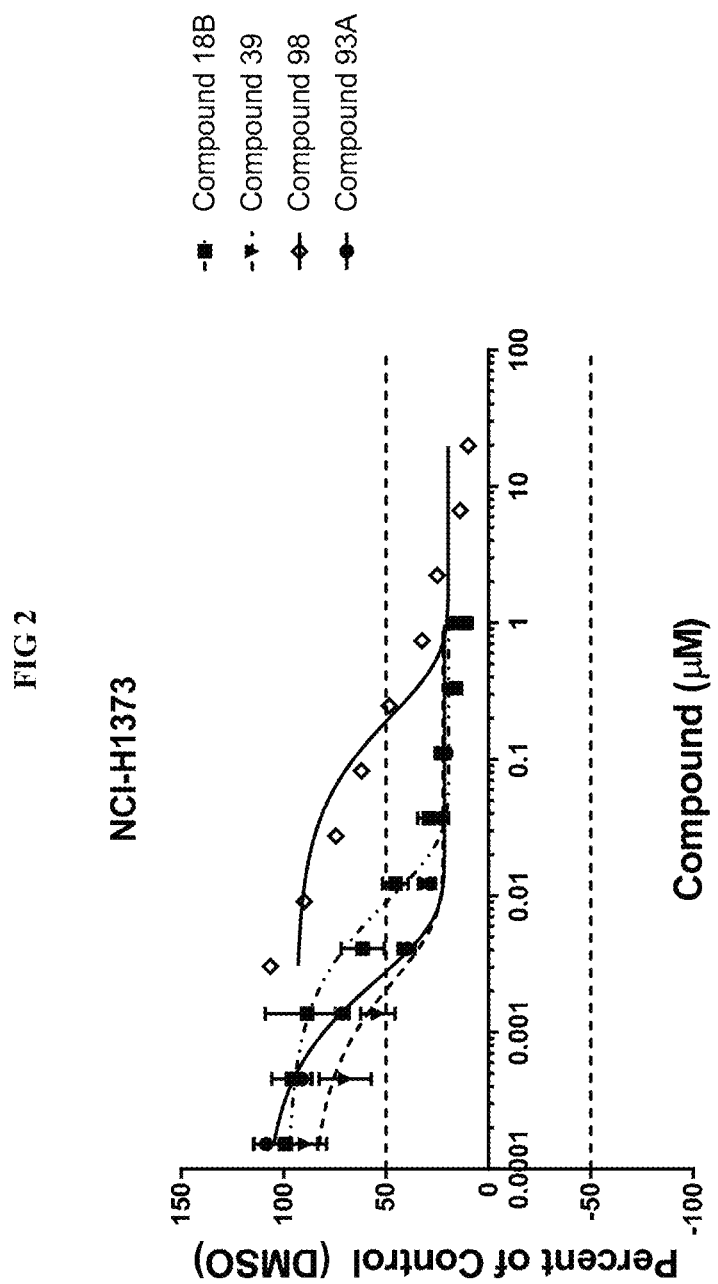

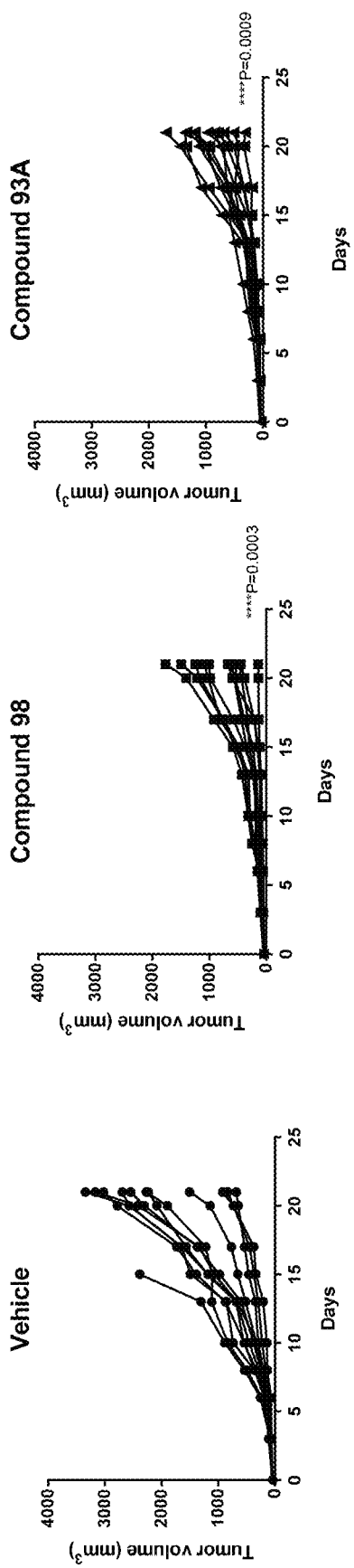
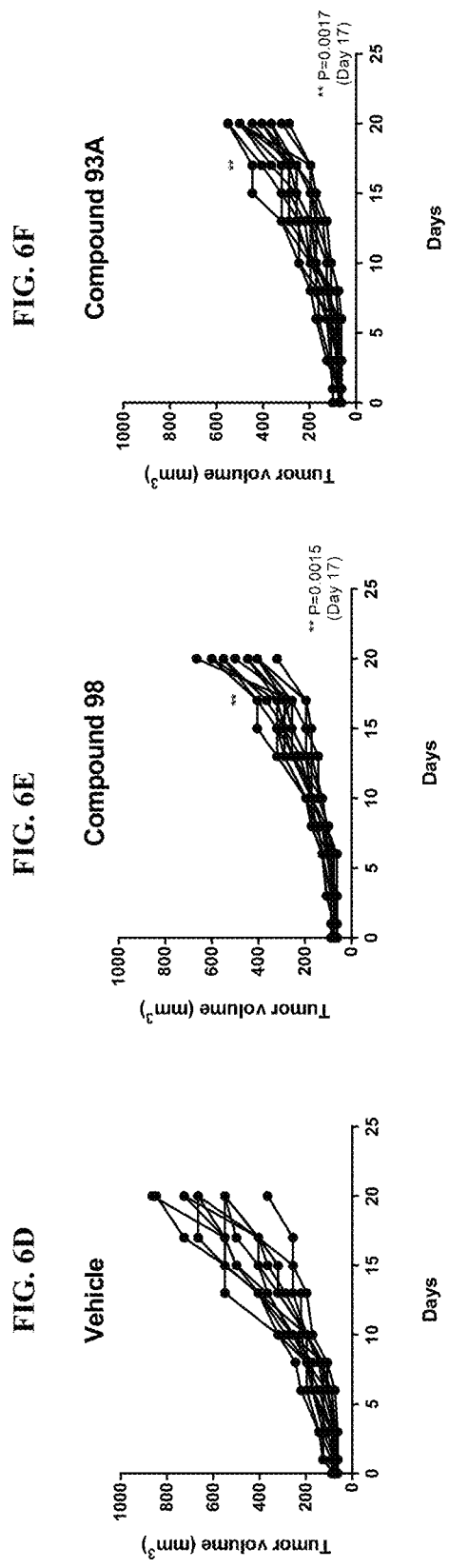

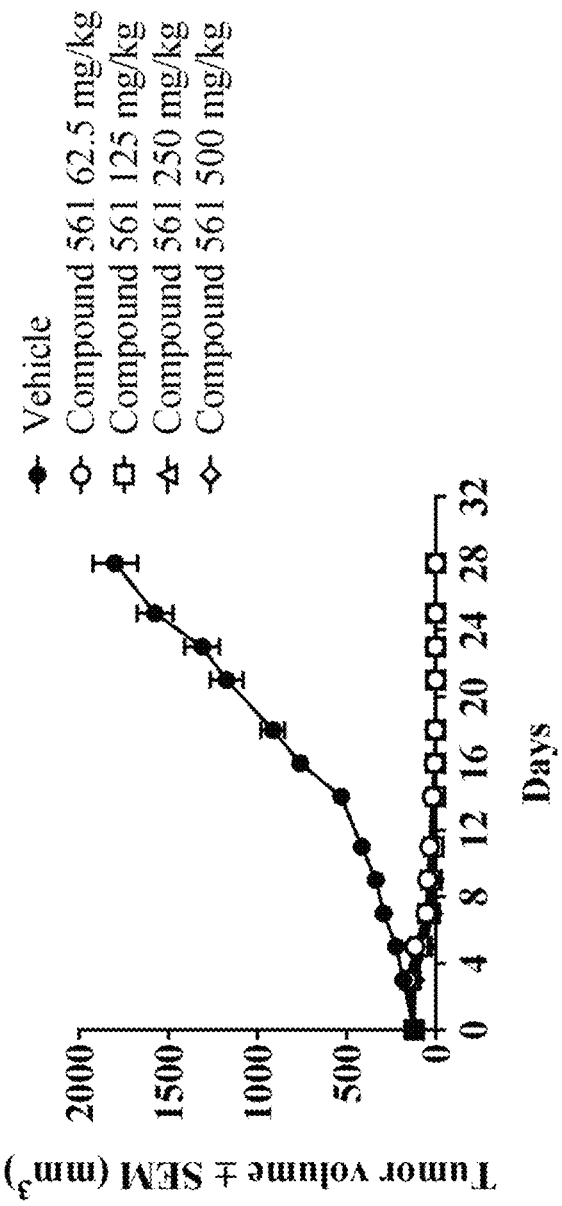
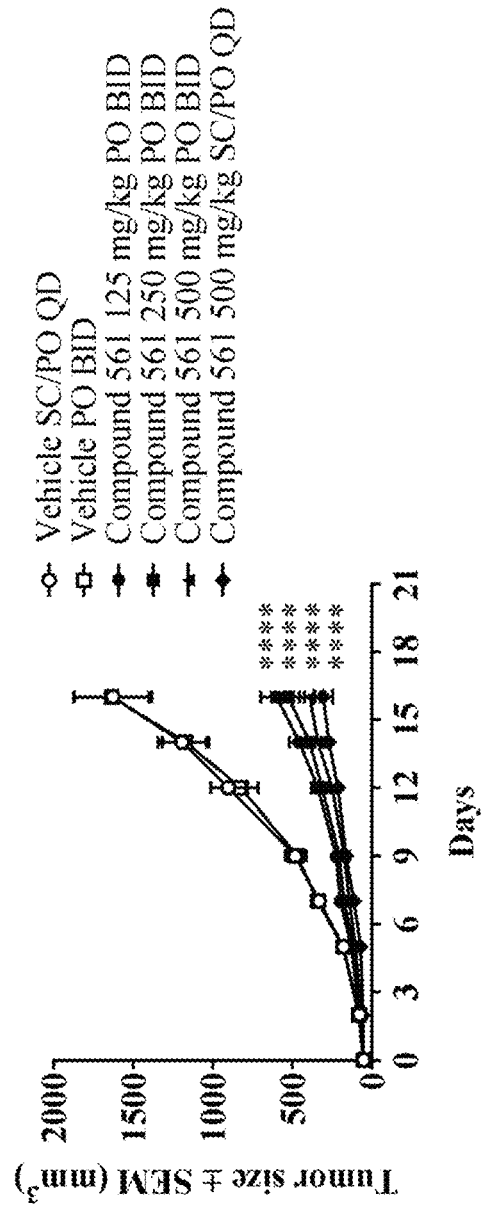
FIG 7A
FIG 7B

PYRIDAZINONES AS PARP7 INHIBITORS

CLAIM OF PRIORITY

This application claims priority to U.S. Provisional Patent Application Ser. No. 62/664,544, filed on Apr. 30, 2018, the entire contents of which are hereby incorporated by reference.

FIELD OF THE INVENTION

The present invention relates to pyridazinones and related compounds which are inhibitors of PARP7 and are useful in the treatment of cancer.

BACKGROUND OF THE INVENTION

Poly(ADP-ribose) polymerases (PARPs) are members of a family of seventeen enzymes that regulate fundamental cellular processes including gene expression, protein degradation, and multiple cellular stress responses (M. S. Cohen, P. Chang, Insights into the biogenesis, function, and regulation of ADP-ribosylation. *Nat Chem Biol* 14, 236-243 (2018)). The ability of cancer cells to survive under stress is a fundamental cancer mechanism and an emerging approach for novel therapeutics. One member of the PARP family, PARP1, has already been shown to be an effective cancer target in connection to cellular stress induced by DNA damage, either induced by genetic mutation or with cytotoxic chemotherapy, with three approved drugs in the clinic and several others in late stage development (A. Ohmoto, S. Yachida, Current status of poly(ADP-ribose) polymerase inhibitors and future directions. *Onco Targets Ther* 10, 5195-5208 (2017)).

The seventeen members of the PARP family were identified in the human genome based on the homology within their catalytic domains (S. Vyas, M. Chesarone-Cataldo, T. Todorova, Y. H. Huang, P. Chang, A systematic analysis of the PARP protein family identifies new functions critical for cell physiology. *Nat Commun* 4, 2240 (2013)). However, their catalytic activities fall into 3 different categories (S. Vyas et al., Family-wide analysis of poly(ADP-ribose) polymerase activity. *Nat Commun* 5, 4426 (2014)). The majority of PARP family members catalyze the transfer of mono-ADP-ribose units onto their substrates (monoPARPs), while others (PARP1, PARP2, TNKS, TNKS2) catalyze the transfer of poly-ADP-ribose units onto substrates (polyPARPs). Finally, PARP13 is thus far the only PARP for which catalytic activity could not be demonstrated either in vitro or in vivo.

The aryl hydrocarbon receptor (AHR) is a ligand-activated transcription factor involved in regulating multiple cellular functions including proinflammatory responses and xenobiotic metabolism (S. Feng, Z. Cao, X. Wang, Role of aryl hydrocarbon receptor in cancer. *Biochim Biophys Acta* 1836, 197-210 (2013); and B. Stockinger, P. Di Meglio, M. Gialitakis, J. H. Duarte, The aryl hydrocarbon receptor: multitasking in the immune system. *Annu Rev Immunol* 32, 403-432 (2014)). The AHR can be activated by a broad number of ligands including endogenous tryptophan metabolites such as kynurenine (C. A. Opitz et al., An endogenous tumour-promoting ligand of the human aryl hydrocarbon receptor. *Nature* 478, 197-203 (2011)) and certain polycyclic aromatic hydrocarbons such as 2,3,7,8-tetrachlorodibenzo-p-dioxin (TCDD) (K. W. Bock, Toward elucidation of dioxin-mediated chloracne and Ah receptor functions. *Biochem Pharmacol* 112, 1-5 (2016)). Activation of the AHR induces target gene expression including genes involved in metabolism such as cytochrome P4501A1 and P4501B1. Activation of AHR also leads to an increase in the AHR target gene, TCDD-inducible poly(ADP-ribose)polymerase (TIPARP, also referred to as PARP7), which functions as a negative regulator of certain AHR transcriptional targets (L. MacPherson et al., Aryl hydrocarbon receptor repressor and TIPARP (ARTD14) use similar, but also distinct mechanisms to repress aryl hydrocarbon receptor signaling. *Int J Mot Sci* 15, 7939-7957 (2014); and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)).

PARP7 can also be regulated by other transcription factors and signaling pathways including androgen receptor (E. C. Bolton et al., Cell- and gene-specific regulation of primary target genes by the androgen receptor. *Genes Dev* 21, 2005-2017 (2007)), platelet derived growth factor (J. Schmahl, C. S. Raymond, P. Soriano, PDGF signaling specificity is mediated through multiple immediate early genes. *Nat Genet* 39, 52-60 (2007)) and hypoxia inducible factor 1 (N. Hao et al., Xenobiotics and loss of cell adhesion drive distinct transcriptional outcomes by aryl hydrocarbon receptor signaling. *Mot Pharmacol* 82, 1082-1093 (2012)). The PARP7 gene is located on chromosome 3 (3q25) in a region that is frequently amplified in cancers of squamous histology (http://www.cbioportal.org/index.do?session_id=5ae1bcde498eb8b3d565d8b2). A genome-wide association study identified 3q25 as susceptibility loci for ovarian cancer suggesting a role for PARP7 in this cancer type (E. L. Goode et al., A genome-wide association study identifies susceptibility loci for ovarian cancer at 2q31 and 8q24. *Nat Genet* 42, 874-879 (2010)). PARP7 has multiple cellular functions. In the context of AHR signaling PARP7 acts as a negative feedback mechanism to regulate the expression of P4501A1 and P4501B1 (L. MacPherson et al., Aryl hydrocarbon receptor repressor and TIPARP (ARTD14) use similar, but also distinct mechanisms to repress aryl hydrocarbon receptor signaling. *Int J Mot Sci* 15, 7939-7957 (2014), and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)). PARP7 has also been described to ADP-ribosylate liver X receptors which leads to the modulation of their transcriptional activity (C. Bindesboll et al., TCDD-inducible poly-ADP-ribose polymerase (TIPARP/PARP7) mono-ADP-ribosylates and co-activates liver X receptors. *Biochem J* 473, 899-910 (2016). During viral infection PARP7 can bind to Sindbis virus (SINV) to promote viral RNA degradation (T. Kozaki et al., Mitochondrial damage elicits a TCDD-inducible poly(ADP-ribose) polymerase-mediated antiviral response. *Proc Natl Acad Sci USA* 114, 2681-2686 (2017)). Also in the context of viral infection, AHR-induced PARP7 can interact with TBK1, a major kinase that is activated during the onset of pathogen-associated molecular pattern pathways leading to an activation of the Type I interferon response and antiviral immunity (T. Yamada et al., Constitutive aryl hydrocarbon receptor signaling constrains Type I interferon-mediated antiviral innate defense. *Nat Immunol* 17, 687-694 (2016)). PARP7 was shown to ADP-ribosylate TBK1 which prevents its activation, thereby repressing the Type I interferon response.

Based on these results from viral infection one could hypothesize that cancer cells can use aberrantly expressed and/or activated PARP7 as a mechanism to evade the host immune system through suppression of the Type I interferons and thereby T cell mediated antitumor immunity. Indeed, in a recent genetic screen to identify tumor factors that suppress T cell activation PARP7 was identified as a hit (D. Pan et al., A major chromatin regulator determines resistance of tumor cells to T cell-mediated killing. *Science* 359, 770-775 (2018)). PARP7 knockout in a mouse melanoma cell line was shown to increase the proliferation and activation of co-cultured T cells suggesting that PARP7 inhibition may be a viable strategy to activate T cell mediated tumor killing.

SUMMARY OF THE INVENTION

The present invention is directed to a compound of Formula I:

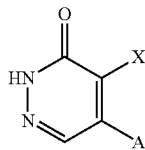

or a pharmaceutically acceptable salt thereof, wherein constituent members are defined below.

The present invention is further directed to a pharmaceutical composition comprising a compound of Formula I, or a pharmaceutically acceptable salt thereof, and at least one pharmaceutically acceptable carrier.

The present invention is further directed to a method of inhibiting the activity of PARP7 comprising contacting a compound of Formula I, or a pharmaceutically acceptable salt thereof, with PARP7.

The present invention is further directed to a method of treating a disease or disorder in a patient in need of treatment, where the disease or disorder is characterized by overexpression or increased activity of PARP7, comprising administering to the patient a therapeutically effective amount of a compound of Formula I, or a pharmaceutically acceptable salt thereof.

The present invention is further directed to a method of treating cancer in a subject in need thereof, the method comprising administering to the subject a therapeutically effective amount of an agent that inhibits PARP7 activity, such as a compound of Formula I, or a pharmaceutically acceptable salt thereof. The present disclosure also provides uses of the compounds described herein in the manufacture of a medicament for use in therapy. The present disclosure also provides the compounds described herein for use in therapy.

BRIEF DESCRIPTION OF THE DRAWINGS

FIG. 2 illustrates the inhibition of cancer cell growth by PARP7 inhibitors (compounds of Examples 18B, 39, 98, and 93A), showing a dose-dependent decrease in growth of NCI-H1373 lung cancer cells.

FIG. 6A illustrates tumor growth in the murine syngeneic model CT26 (control).

FIG. 6B illustrates tumor growth in the murine syngeneic model CT26 in the presence of the compound of Example 98.

FIG. 6C illustrates tumor growth in the murine syngeneic model CT26 in the presence of the compound of Example 93A.

FIG. 6D illustrates tumor growth in the murine syngeneic model 4T1 (control).

FIG. 6E illustrates tumor growth in the murine syngeneic model 4T1 in the presence of the compound of Example 98.

FIG. 6F illustrates tumor growth in the murine syngeneic model 4T1 in the presence of the compound of Example 93A.

FIG. 7A illustrates that once daily administration of the PARP7 inhibitor of Example 561 significantly reduces tumor growth in a human NCI-H1373 lung cancer xenograft.

FIG. 7B illustrates that once or twice daily administration of the PARP7 inhibitor of Example 561 significantly reduces tumor growth in a murine CT26 colon cancer syngeneic model.

DETAILED DESCRIPTION

Figure 1A:
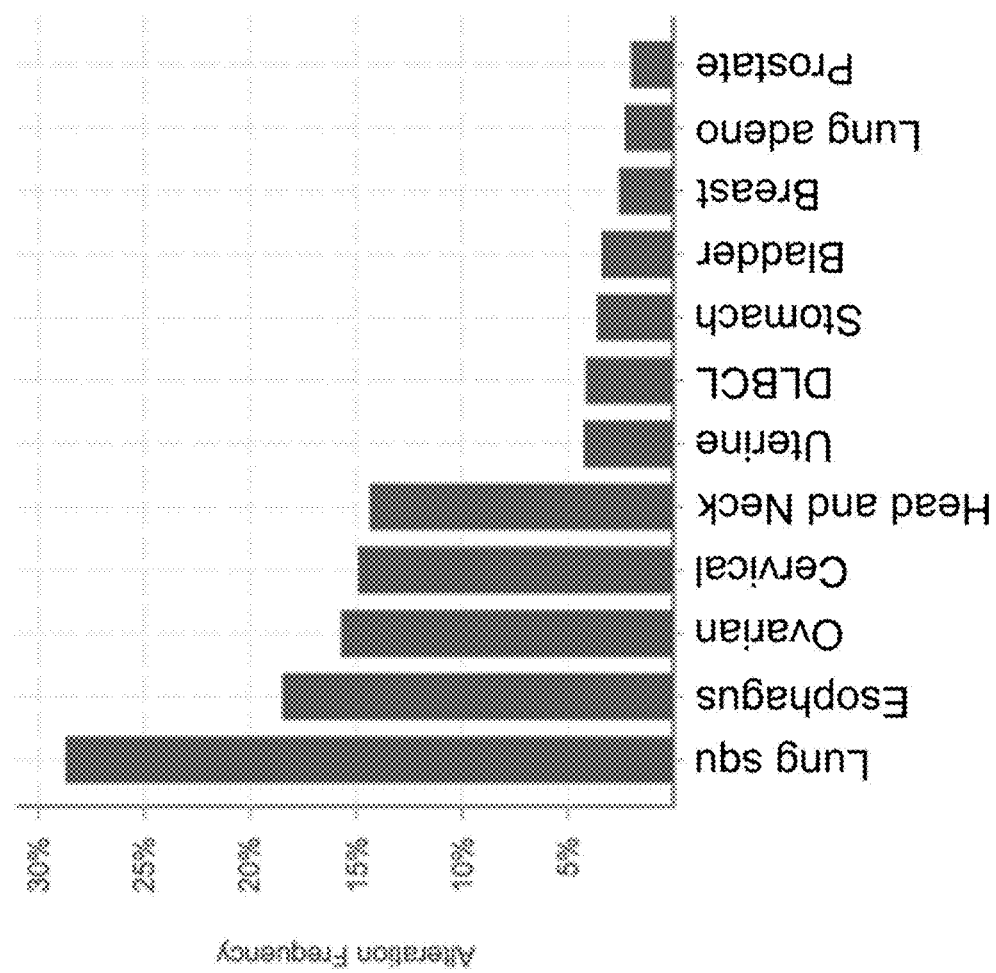
FIG. 1A illustrates PARP7 amplification across TCGA (The Cancer Genome Atlas) primary tumor samples.

The present invention is directed to a compound of Formula I:

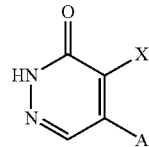

or a pharmaceutically acceptable salt thereof, wherein:

X is Cl, Br, CH$_3$, CF$_3$, CN, OCH$_3$, ethyl, cyclopropyl, SCH$_3$, or isopropyl;

A is a group having a formula selected from (A-1), (A-2), and (A-3):

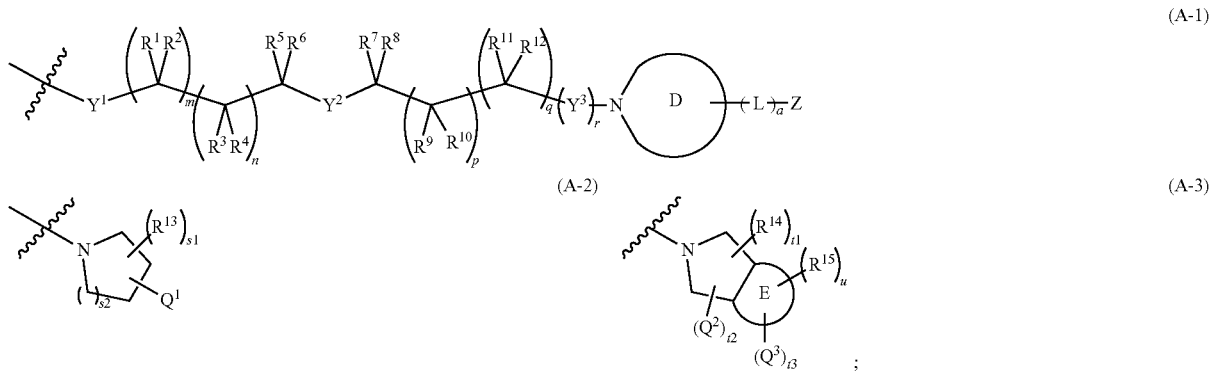

$Y^1$, $Y^2$, and $Y^3$ are each independently selected from O, S, NR, C(=O), C(=O)O, C(=O)$NR^Y$, S(=O), S(=O)$_2$, S(=O)$_2NR^Y$, S(=O)$_2NR^Y$ or $NR^YC$(=O)$NR^Y$, wherein each $R^Y$ is independently H or $C_{1-4}$ alkyl;

L is $C_{1-3}$ alkylene, O, S, $NR^Y$, C(=O), C(=O)O, C(=O)$NR^Y$, S(=O), S(=O)$NR^Y$, or $NR^YC$(=O)$NR^Y$;

Z is H, $Cy^Z$, halo, $C_{1-6}$ alkyl, $C_{2-6}$ alkenyl, $C_{2-6}$ alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$S(O)R$^b$, S(O)NR$^c$R$^d$, S(O)$_2$R$^b$, and S(O)$_2$NR$^c$R$^d$;

$Cy^Z$ is selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^c$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein the alkyl, $C_{2-6}$ alkenyl, and $C_{2-6}$ alkynyl are optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^c$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

Ring D is a monocyclic or polycyclic 4-10 membered heterocycloalkyl group optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$ S(O)NR$^{c2}$R$^{d2}$, S(O)$_2$R$^{b2}$, and S(O)$_2$NR$^{c2}$R$^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

$R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^3$, $R^4$, $R^5$, $R^6$, $R^7$, $R^8$, $R^9$, $R^{10}$, $R^{11}$, and $R^{12}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a3}$, SR$^{a3}$C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

or $R^1$ and $R^3$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

or $R^3$ and $R^5$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^7$ and $R^9$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^9$ and $R^{11}$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^5$ and $R^7$ together with the carbon atoms to which they are attached and together with $Y^2$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^3C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and $R^3$ together form a double bond between the carbon atoms to which they are attached;

or $R^3$ and $R^5$ together form a double bond between the carbon atoms to which they are attached;

or $R^7$ and $R^9$ together form a double bond between the carbon atoms to which they are attached;

or $R^9$ and $R^{11}$ together form a double bond between the carbon atoms to which they are attached;

or $R^9$, $R^{10}$, $R^{11}$, and $R^{12}$ together form a triple bond between the carbon atoms to which they are attached;

$R^{13}$, $R^{14}$, and $R^{15}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^{13}$, $R^{14}$, and $R^{15}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

Ring E is a mono- or polycyclic ring selected from $C_{6-10}$ aryl, $C_{3-7}$ cycloalkyl, 5-10 membered heteroaryl, and 4-10 membered heterocycloalkyl;

$Q^1$, $Q^2$, and $Q^3$ are each a group of formula (B-1):

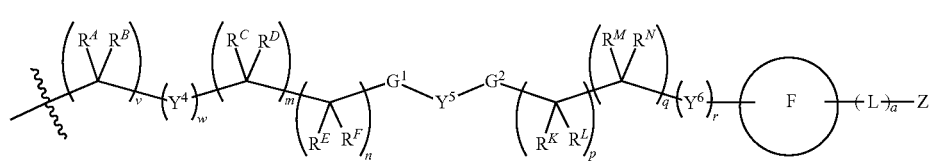

(B-1)

$Y^4$, $Y^5$, and $Y^6$ are each independently selected from O, S, $NR^Y$, $C(=O)$, $C(=O)O$, $C(=O)NR^Y$, $S(=O)$, $S(=O)_2$, $S(=O)NR^Y$, $S(=O)_2NR^Y$ or $NR^YC(=O)NR^Y$;

$G^1$ is $-C(R^G)(R^H)-$ or a group of formula (C-1), (C-2), or (C-3):

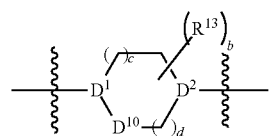

(C-1)

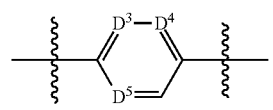

(C-2)

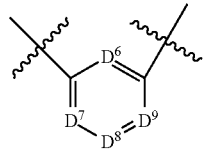

(C-3)

$G^2$ is $-C(R^I)(R^J)-$ or a group of formula (C-1), (C-2), or (C-3);

$R^A$, $R^B$, $R^C$, $R^D$, $R^E$, $R^F$, $R^G$, $R^H$, $R^I$, $R^J$, $R^K$, $R^L$, $R^M$, and $R^N$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $-NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b}$, and $S(O)_2NR^{c5}R^{d5}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^A$, $R^B$, $R^C$, $R^D$, $R^E$, $R^F$, $R^G$, $R^H$, $R^I$, $R^J$, $R^K$, $R^L$, $R^M$, and $R^N$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or $R^G$ and $R^I$ together with the carbon atoms to which they are attached and together with $Y^5$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^3C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^C$ and $R^E$ together form a double bond between the carbon atoms to which they are attached;

or $R^E$ and $R^G$ together form a double bond between the carbon atoms to which they are attached;

or $R^I$ and $R^K$ together form a double bond between the carbon atoms to which they are attached;

or $R^K$ and $R^M$ together form a double bond between the carbon atoms to which they are attached;

or $R^K$, $R^L$, $R^M$, and $R^N$ together form a triple bond between the carbon atoms to which they are attached;

$D^1$ and $D^2$ are each independently selected from N and CH;

$D^3$, $D^4$, $D^5$, $D^6$, $D^7$, $D^8$, and $D^9$ are each independently selected from N and $CR^X$, wherein each $R^X$ is independently selected from H, halo, and $C_{1-4}$ alkyl;

$D^{10}$ is O, S, NH or $CH_2$;

Ring F is a mono- or polycyclic ring selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein the alkyl, $C_{2-6}$ alkenyl, and $C_{2-6}$ alkynyl are optionally substituted with 1, 2, or 3 substituents independently selected from halo, CN, $NO_2$, $OR^{a6}$, $SR^{a6}C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^d$, $R^{d1}R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^a$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c2}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c4}$ and $R^{d4}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c5}$ and $R^{d5}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^a$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c6}$ and $R^{d6}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$ and $S(O)_2NR^{c7}R^{d7}$;

$R^{a7}$, $R^{b7}$, $R^7$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, $R^{e3}$, $R^{e4}$, $R^{e5}$, $R^{e6}$ and $R^{e7}$ is independently selected from H, $C_{1-4}$ alkyl, and CN;

a is 0 or 1;
b is 0, 1, 2, or 3;
c is 0, 1, or 2;
d is 0, 1, or 2;
m is 0 or 1;
n is 0 or 1;
p is 0 or 1;
q is 0 or 1;
r is 0 or 1;
s1 is 0, 1, or 2;
s2 is 0, 1, 2, or 3;
t1 is 0 or 1;
t2 is 0 or 1;
t3 is 0 or 1;
u is 0, 1, 2, or 3;
v is 0 or 1; and
w is 0 or 1;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by an oxo (=O) group.

In some embodiments, A is the group having the formula A-1.

In some embodiments, provided herein is a compound of Formula (I), or a pharmaceutically acceptable salt thereof, wherein:

X is Cl, Br, $CH_3$, $CF_3$, CN, $OCH_3$, ethyl, cyclopropyl, $SCH_3$, or isopropyl;

A is a group having the formula (A-1):

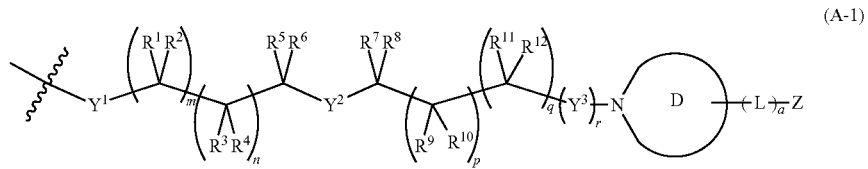

(A-1)

$Y^1$, $Y^2$, and $Y^3$ are each independently selected from O, S, $NR^Y$, $C(=O)$, $C(=O)O$, $C(=O)NR^Y$, $S(=O)$, $S(=O)_2$, $S(=O)NR^Y$, $S(=O)_2NR^Y$ or $NR^YC(=O)NR^Y$, wherein each $R^Y$ is independently H or $C_{1-4}$ alkyl;

L is $C_{1-3}$ alkylene, O, S, $NR^Y$, $C(=O)$, $C(=O)O$, $C(=O)NR^Y$, $S(=O)$, $S(=O)NR^Y$, or $NR^YC(=O)NR^Y$;

Z is H, $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^eR^d$, $S(O)R^b$, $S(O)NR^eR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$Cy^Z$ is selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^cC(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^d$;

Ring D is a monocyclic or polycyclic 4-10 membered heterocycloalkyl group optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^3C(O)OR^{a3}$, $NR^3C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^3$, $R^4$, $R^5$, $R^6$, $R^7$, $R^8$, $R^9$, $R^{10}$, $R^{11}$, and $R^{12}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and $R^3$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^3$ and $R^5$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^7$ and $R^9$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^9$ and $R^{11}$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^5$ and $R^7$ together with the carbon atoms to which they are attached and together with $Y^2$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and $R^3$ together form a double bond between the carbon atoms to which they are attached;

or $R^3$ and $R^5$ together form a double bond between the carbon atoms to which they are attached;

or $R^7$ and $R^9$ together form a double bond between the carbon atoms to which they are attached;

or $R^9$ and $R^{11}$ together form a double bond between the carbon atoms to which they are attached;

or $R^9$, $R^{10}$, $R^{11}$, and $R^{12}$ together form a triple bond between the carbon atoms to which they are attached;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c2}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

$R^{a7}$, $R^{b7}$, $R^7$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, $R^{e3}$, and $R^{e7}$ is independently selected from H, $C_{1-4}$ alkyl, and CN;

a is 0 or 1;
m is 0 or 1;
n is 0 or 1;
p is 0 or 1;
q is 0 or 1;
r is 0 or 1;
wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by an oxo (=O) group.

In some embodiments, A is group having the formula (A-1a):

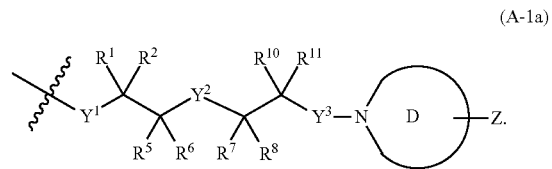

(A-1a)

In some embodiments, A is group having the formula (A-1b):

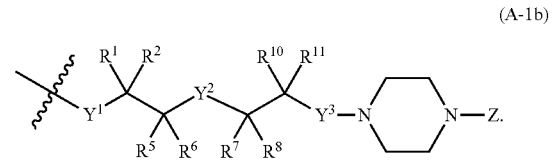

(A-1b)

In some embodiments, A is group having the formula (A-1c):

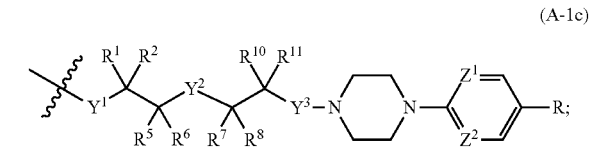

(A-1c)

wherein $Z^1$ and $Z^2$ are each independently selected from N and CH, and wherein R is CN, Cl, or $CF_3$.

In some embodiments, A is group having the formula (A-1d):

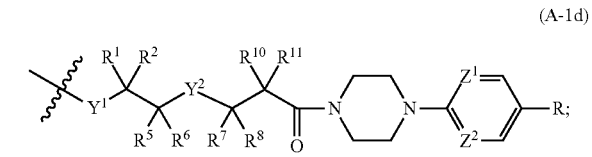

(A-1d)

wherein $Z^1$ and $Z^2$ are each independently selected from N and CH, and wherein R is CN, Cl, or $CF_3$.

In some embodiments, L is $NR^Y$ or O. In some embodiments, L is $NH_2$ or O. In some embodiments, L is $NR^Y$. In some embodiments, L is O. In some embodiments, L is $NH_2$.

In some embodiments, X is $CF_3$, $CH_3$, CN, Cl or Br.

In some embodiments, $Y^1$ is $NR^Y$ or O. In some embodiments, $Y^1$ is $NR^Y$. In some embodiments, $Y^1$ is O. In some embodiments, $Y^1$ is $NR^Y$, O, or S. In some embodiments, $Y^1$ is S.

In some embodiments, $Y^2$ is $NR^Y$ or O. In some embodiments, $Y^2$ is O. In some embodiments, $Y^2$ is $NR^Y$, O, or S. In some embodiments, $Y^2$ is $NR^Y$. In some embodiments, $Y^2$ is S.

In some embodiments, $Y^3$ is C(=O). In some embodiments, $Y^3$ is C(=O) or S(=O)$_2$. In some embodiments, $Y^3$ is S(=O)$_2$.

In some embodiments, $R^Y$ is H or $C_{1-4}$ alkyl. In some embodiments, $R^Y$ is methyl. In some embodiments, $R^Y$ is H.

In some embodiments, Z is H, $Cy^Z$, halo, $C_{1-6}$ alkyl, $C_{1-6}$ haloalkyl, CN, $NO_2$, $OR^a$, $C(O)R^b$, $C(O)NR^cR^d$, $C(O)OR^a$, $NR^cR^d$, and $NR^cC(O)R^b$; wherein said $C_{1-6}$ alkyl and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, and $NR^cC(O)R^b$. In some embodiments, Z is $Cy^Z$.

In some embodiments, $Cy^Z$ is selected from 5-10 membered heteroaryl and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $Cy^Z$ is 5-10 membered heteroaryl, optionally substituted by CN, $CF_3$, or Cl. In some embodiments, $Cy^Z$ is pyridinyl or pyrimidinyl, each optionally substituted by CN, $CF_3$, or Cl. In some embodiments, $Cy^Z$ is 5-10 membered heteroaryl, optionally substituted by CN, $C_{1-6}$ alkyl, $C_{1-6}$ haloalkyl, halo, or $NR^{c1}R^{d1}$, wherein $C_{1-6}$alkyl is optionally substituted with CN or $NR^{c1}R^{d1}$. In some embodiments, $Cy^Z$ is pyridinyl, pyrimidinyl, or pyrazinyl, each optionally substituted by CN, $C_{1-6}$ alkyl, $C_{1-6}$ haloalkyl, halo, or $NR^{c1}R^{d1}$ wherein $C_{1-6}$alkyl is optionally substituted with CN or $NR^{c1}R^{d1}$. In some embodiments, $Cy^Z$ is pyridinyl, pyrimidinyl, pyrazinyl, or thiazolyl, each optionally substituted by CN, $C_{1-6}$ alkyl, $C_{1-6}$ haloalkyl, halo, or $NR^{c1}R^{d1}$, wherein $C_{1-6}$alkyl is optionally substituted with CN or $NR^{c1}R^{d1}$.

In some embodiments, Ring D is a monocyclic or polycyclic 4-10 membered heterocycloalkyl group optionally substituted with 1, 2, or 3 groups independently selected from halo, $C_{1-6}$ alkyl, $C_{1-6}$ haloalkyl, CN, $NO_2$, $OR^a$, $C(O)R^{b2}$, $C(O)NR^{c2}R^{d2}$, $C(O)OR^{a2}$, $NR^{c2}R^{d2}$, $NR^{c2}C(O)R^{b2}$, wherein the $C_{1-6}$ alkyl is optionally substituted with 1, 2, or 3 groups independently selected from halo, CN, $NO_2$, $OR^{a2}$, $C(O)R^{b2}$, $NR^{c2}R^{d2}$, and $NR^{c2}C(O)R^{b2}$ In some embodiments, Ring D is a monocyclic 4-10 membered heterocycloalkyl group.

In some embodiments, Ring D is piperazinyl. In some embodiments, Ring D is piperazinyl, dihydropyridazinyl, diazepanyl, pyrrolidinyl, or hexahydropyrrolo[3,2-b]pyrrol-1(2H)-yl. In some embodiments, Ring D is piperazinyl, dihydropyridazinyl, diazepanyl, pyrrolidinyl, or hexahydropyrrolo[3,2-b]pyrrol-1(2H)-yl, each optionally substituted with 1, 2, or 3 groups independently selected from halo, $C_{1-6}$ alkyl, $C_{1-6}$ haloalkyl, CN, $NO_2$, $OR^a$, $C(O)R^{b2}$, $C(O)NR^{c2}R^{d2}$, $C(O)OR^{a2}$, $NR^{c2}R^{d2}$, $NR^{c2}C(O)R^{b2}$, wherein the $C_{1-6}$ alkyl is optionally substituted with 1, 2, or 3 groups independently selected from halo, CN, $NO_2$, $OR^{a2}$, $C(O)R^{b2}$, $NR^{c2}R^{d2}$, and $NR^{c2}C(O)R^{b2}$. In some embodiments, Ring D is piperazinyl optionally substituted by $C_{1-6}$ alkyl. In some embodiments, Ring D is piperazinyl optionally substituted by one to eight deuterium atoms. In some embodiments, Ring D is piperazin-1-yl-2,2,3,3,5,5,6,6-d8.

In some embodiments, $R^1$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$. In some embodiments, $R^1$ is H, halo, $OR^{a3}$, $C_{1-6}$ alkyl, $C_{6-10}$ aryl, 5-10 membered heteroaryl, 4-10 membered heterocycloalkyl, $C_{6-10}$ aryl-$C_{1-4}$ alkyl, 5-10 membered heteroaryl-$C_{1-4}$ alkyl, or 4-10 membered heterocycloalkyl-$C_{1-4}$ alkyl, wherein said $C_{1-6}$ alkyl, $C_{6-10}$ aryl, 5-10 membered heteroaryl, $C_{6-10}$ aryl-$C_{1-4}$ alkyl, 5-10 membered heteroaryl-$C_{1-4}$ alkyl or 4-10 membered heterocycloalkyl-$C_{1-4}$ alkyl is optionally substituted with $OR^{a3}$ or $NR^{c3}R^{d3}$.

In some embodiments, $R^1$ is $C_{1-6}$ alkyl. In some embodiments, $R^1$ is $C_{1-6}$ alkyl, optionally substituted with $OR^{a3}$. In some embodiments, $R^1$ is H. In some embodiments, $R^1$ is methyl, ethyl, or isopropyl. In some embodiments, $R^1$ is methoxymethyl or hydroxymethyl. In some embodiments, $R^1$ is phenyl, phenylmethyl, or pyridinyl. In some embodiments, $R^1$ is 5-10 membered heteroaryl-$C_{1-4}$ alkyl or 4-10 membered heterocycloalkyl-$C_{1-4}$ alkyl. In some embodiments, $R^1$ is pyridinylmethyl, piperidinylmethyl, or morpholinylmethyl. In some embodiments, $R^1$ is tetrahydrofuranyl or piperidinyl. In some embodiments, $R^1$ is phenyl, pyridinyl, tetrahydrofuranyl or piperidinyl.

In some embodiments, $R^2$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$. In some embodiments, $R^2$ is H, halo, $OR^{a3}$, $C_{1-6}$ alkyl, $C_{6-10}$ aryl, 5-10 membered heteroaryl, 4-10 membered heterocycloalkyl, $C_{6-10}$ aryl-$C_{1-4}$ alkyl, 5-10 membered heteroaryl-$C_{1-4}$ alkyl, or 4-10 membered heterocycloalkyl-$C_{1-4}$ alkyl, wherein said $C_{1-6}$ alkyl, $C_{6-10}$ aryl, 5-10 membered heteroaryl, $C_{6-10}$ aryl-$C_{1-4}$ alkyl, 5-10 membered heteroaryl-$C_{1-4}$ alkyl or 4-10 membered heterocycloalkyl-$C_{1-4}$ alkyl is optionally substituted with $OR^{a3}$ or $NR^{c3}R^{d3}$.

In some embodiments, $R^2$ is $OR^{a3}$. In some embodiments, $R^2$ is H.

In some embodiments, $R^3$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^3$ is H. In some embodiments, $R^3$ is methyl, ethyl, or isopropyl. In some embodiments, $R^3$ is methoxymethyl or hydroxymethyl. In some embodiments, $R^3$ is phenyl, phenylmethyl, or pyridinyl.

In some embodiments, $R^4$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^4$ is H.

In some embodiments, $R^5$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^5$ is H. In some embodiments, $R^5$ is methyl, ethyl, or isopropyl. In some embodiments, $R^5$ is methoxymethyl or hydroxymethyl. In some embodiments, $R^5$ is phenyl, phenylmethyl, or pyridinyl.

In some embodiments, $R^6$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^6$ is H.

In some embodiments, $R^7$ is H, halo, $OR^{a3}$, $C_{1-6}$ alkyl, $C_{6-10}$ aryl, 5-10 membered heteroaryl, $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^7$ is $C_{1-6}$ alkyl. In some embodiments, $R^7$ is methyl.

In some embodiments, $R^8$ is H, halo, $OR^{a3}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^8$ is H.

In some embodiments, $R^9$ is H, halo, $OR^{a3}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^9$ is H.

In some embodiments, $R^{10}$ is H, halo, $OR^{a3}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^{10}$ is H.

In some embodiments, $R^{11}$ is H, halo, $OR^{a3}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^{11}$ is H.

In some embodiments, $R^{12}$ is H, halo, $OR^{a3}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a3}$ or $NR^{c3}R^{d3}$.

In some embodiments, $R^{12}$ is H.

In some embodiments, $R^1$, $R^2$, $R^3$, $R^4$, $R^5$, $R^6$, $R^7$, and $R^8$ are each H.

In some embodiments, $R^7$, $R^8$, $R^9$, $R^{10}$, $R^{11}$, and $R^{12}$ are each H.

In some embodiments, $R^1$, $R^2$, $R^5$, $R^6$, $R^7$, $R^8$, $R^9$, and $R^{10}$ are each H.

In some embodiments, $R^2$, $R^5$, $R^6$, $R^7$, $R^8$, $R^9$, and $R^{10}$ are each H.

In some embodiments, $R^5$, $R^6$, $R^7$, $R^8$, $R^9$, and $R^{10}$ are each H

In some embodiments, $R^3$ and $R^5$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$.

In some embodiments, $R^3$ and $R^5$ together with the carbon atoms to which they are attached form a $C_{5-10}$ cycloalkyl ring or a 5-10 membered heterocycloalkyl ring.

In some embodiments, $R^3$ and $R^5$ together with the carbon atoms to which they are attached form a tetrahydrofuranyl ring.

In some embodiments, $R^3$ and $R^5$ together with the carbon atoms to which they are attached form a cyclobutyl or cyclopentyl ring.

In some embodiments, $R^5$ and $R^7$ together with the carbon atoms to which they are attached and together with $Y^2$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^5$ and $R^7$ together with the carbon atoms to which they are attached and together with $Y^2$ form a 5-10 membered heterocycloalkyl ring.

In some embodiments, $R^5$ and $R^7$ together with the carbon atoms to which they are attached and together with $Y^2$ form a tetrahydrofuranyl ring or tetrahydropyranyl ring. In some embodiments, $R^5$ and $R^7$ together with the carbon atoms to which they are attached and together with $Y^2$ form a tetrahydrofuranyl ring, tetrahydropyranyl ring, or pyrrolidinyl ring. In some embodiments, $R^5$ and $R^7$ together with the carbon atoms to which they are attached and together with $Y^2$ form a pyrrolidinyl ring.

In some embodiments, $R^{a3}$ is $C_{1-6}$ alkyl or H. In some embodiments, $R^{a3}$ is methyl. In some embodiments, $R^{a3}$ is H.

In some embodiments, $R^{c3}$ and $R^{d3}$ are each independently selected from $C_{1-6}$ alkyl and H. In some embodiments, $R^{c3}$ is $C_{1-6}$ alkyl or H. In some embodiments, $R^{d3}$ is $C_{1-6}$ alkyl or H. In some embodiments, $R^{c3}$ and $R^{d3}$ are each methyl. In some embodiments, $R^{c3}$ and $R^{d3}$ are each H.

In some embodiments, m is 1.

In some embodiments, n is 0. In some embodiments, n is 1.

In some embodiments, p is 0. In some embodiments, p is 1.

In some embodiments, q is 0. In some embodiments, q is 1.

In some embodiments, r is 0.

In some embodiments, a is 0.

In some embodiments, provided herein is a compound of Formula (I), or a pharmaceutically acceptable salt thereof, having Formula IIa:

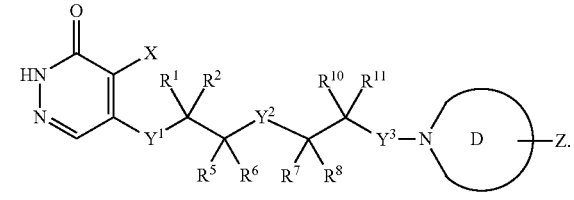

IIa

In some embodiments, provided herein is a compound of Formula (I), or a pharmaceutically acceptable salt thereof, having Formula IIb:

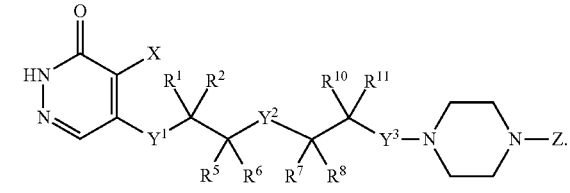

IIb

In some embodiments, provided herein is a compound of Formula (I), or a pharmaceutically acceptable salt thereof, having Formula IIc:

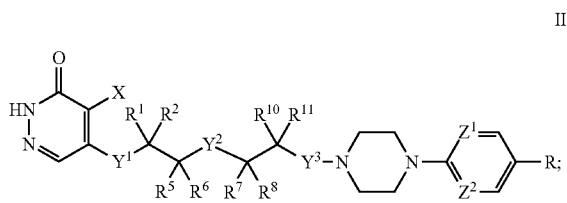

IIc wherein $Z^1$ and $Z^2$ are each independently selected from N and CH, and wherein R is CN, Cl, or $CF_3$.

In some embodiments, provided herein is a compound of Formula (I), or a pharmaceutically acceptable salt thereof, having Formula IId:

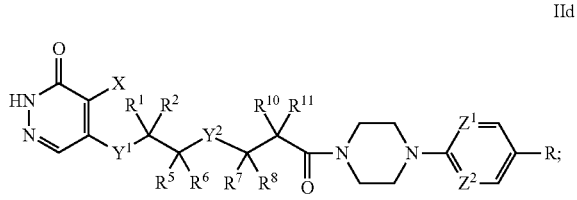

IId wherein $Z^1$ and $Z^2$ are each independently selected from N and CH, and wherein R is CN, Cl, or $CF_3$.

In some embodiments, A is the group having the formula A-2.

In some embodiments, provided herein is a compound of Formula (I), or a pharmaceutically acceptable salt thereof, wherein:

X is Cl, Br, $CH_3$, $CF_3$, CN, $OCH_3$, cyclopropyl, $SCH_3$, or isopropyl;

A is a group having the formula (A-2):

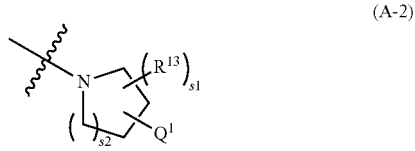

(A-2)

L is $C_{1-3}$ alkylene, O, S, $NR^Y$, $C(=O)$, $C(=O)O$, $C(=O)NR^Y$, $S(=O)$, $S(=O)NR^Y$, or $NR^YC(=O)NR^Y$;

Z is H, $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$Cy^Z$ is selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$ $NR^{c1}S(O)R^{b1}$, $NR^{c11}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^{13}$, $R^{14}$, and $R^{15}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a4}$, $SR^{a4}C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^4S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^{13}$, $R^{14}$, and $R^{15}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

$Q^1$, $Q^2$, and $Q^3$ are each a group of formula (B-1):

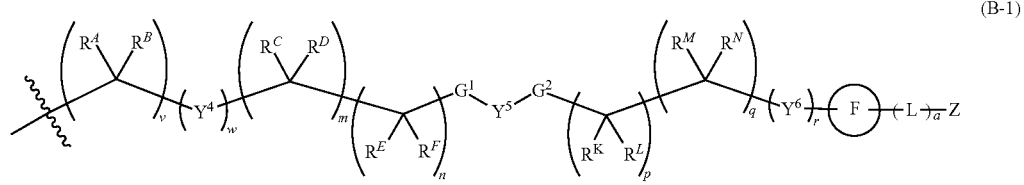

(B-1)

$Y^4$, $Y^5$, and $Y^6$ are each independently selected from O, S, $NR^Y$, $C(=O)$, $C(=O)O$, $C(=O)NR^Y$, $S(=O)$, $S(=O)_2$, $S(=O)NR^Y$, $S(=O)_2NR^Y$ or $NR^YC(=O)NR^Y$;

$G^1$ is —$C(R^G)(R^H)$— or a group of formula (C-1), (C-2), or (C-3):

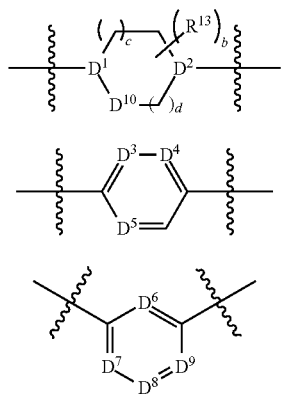

(C-1)

(C-2)

(C-3)

$G^2$ is —$C(R^I)(R^J)$— or a group of formula (C-1), (C-2), or (C-3);

$R^A$, $R^B$, R, $R^D$, $R^E$, $R^F$, $R^G$, $R^H$, $R^I$, $R^J$, $R^K$, $R^L$, $R^M$, and $R^N$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^e)NR^{c5}R^{d5}$, $NR^{c5}C(=NR^e)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^A$, $R^B$, $R^C$, $R^D$, $R^E$, $R^F$, $R^G$, $R^H$, $R^I$, $R^J$, $R^K$, $R^L$, $R^M$, and $R^N$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or $R^G$ and $R^I$ together with the carbon atoms to which they are attached and together with $Y^5$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^3C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^C$ and $R^E$ together form a double bond between the carbon atoms to which they are attached;

or $R^E$ and $R^G$ together form a double bond between the carbon atoms to which they are attached;

or $R^I$ and $R^K$ together form a double bond between the carbon atoms to which they are attached;

or $R^K$ and $R^M$ together form a double bond between the carbon atoms to which they are attached;

or $R^K$, $R^L$, $R^M$, and $R^N$ together form a triple bond between the carbon atoms to which they are attached;

$D^1$ and $D^2$ are each independently selected from N and CH;

$D^3$, $D^4$, $D^5$, $D^6$, $D^7$, $D^8$, and $D^9$ are each independently selected from N and $CR^X$, wherein each $R^X$ is independently selected from H, halo, and $C_{1-4}$ alkyl;

$D^{10}$ is O, S, NH or $CH_2$;

Ring F is a mono- or polycyclic ring selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein the alkyl, $C_{2-6}$ alkenyl, and $C_{2-6}$ alkynyl are optionally substituted with 1, 2, or 3 substituents independently selected from halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^a$, $R^b$, $R^c$, $R^d$, $R^{a1}$, $R^{b1}$, $R^{c1}$, $R^{d1}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c4}$ and $R^{d4}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c5}$ and $R^{d5}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^a$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c6}$ and $R^{d6}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

$R^{a7}$, $R^{b7}$, $R^{c7}$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e3}$, $R^{e4}$, $R^{e5}$, $R^{e6}$ and $R^{e7}$ is independently selected from H, $C_{1-4}$ alkyl, and CN;

a is 0 or 1;
b is 0, 1, 2, or 3;
c is 0, 1, or 2;
d is 0, 1, or 2;
m is 0 or 1;
n is 0 or 1;
p is 0 or 1;
q is 0 or 1;
r is 0 or 1;
s1 is 0, 1, or 2;
s2 is 0, 1, 2, or 3;
v is 0 or 1; and
w is 0 or 1;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by an oxo (=O) group.

In some embodiments, $Q^1$ is a group of formula (B-1a):

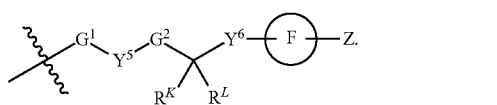

(B-1a)

In some embodiments, $Q^1$ is a group of formula (B-1b):

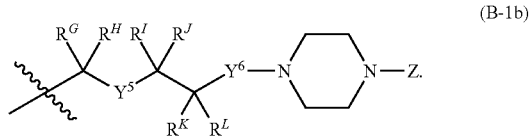

(B-1b)

In some embodiments, $Q^1$ is a group of formula (B-1c):

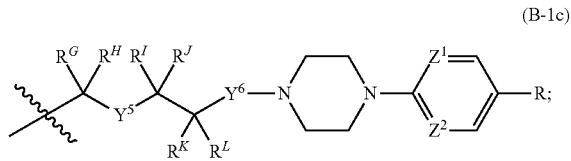

(B-1c)

wherein $Z^1$ and $Z^2$ are each independently selected from N and CH, and wherein R is CN, Cl, or $CF_3$.

In some embodiments, X is $CF_3$, $CH_3$, CN, Cl, or Br.

In some embodiments, Ring F is 4-10 membered heterocycloalkyl or $C_{3-7}$ cycloalkyl optionally substituted with $C_{1-6}$ alkyl, wherein said $C_{1-6}$ alkyl is optionally substituted with $OR^{a6}$ In some embodiments, Ring F is 4-10 membered heterocycloalkyl or $C_{3-7}$ cycloalkyl, each optionally substituted with methyl.

In some embodiments, Ring F is piperazinyl, piperidinyl, pyrrolidinyl, 5,6,7,8-tetrahydro-[1,2,4]triazolo[4,3-a]pyrazinyl, 2,8-diazaspiro[4.5]decanyl, 2,5-diazabicyclo[2.2.2]octanyl, 1,4-diazepanyl, azetidinyl, 2,6-diazaspiro[3.3]heptanyl, 2,6-diazaspiro[3.4]octanyl, octahydropyrrolo[3,2-b]pyrrolyl, 2,7-diazaspiro[4.4]nonanyl, 2,5-diazabicyclo[2.2.1]heptanyl, octahydropyrrolo[3,4-c]pyrrolyl, or 2,7-diazaspiro[3.5]nonanyl.

In some embodiments, Ring F is piperazinyl.
In some embodiments, Ring F is cyclohexyl.
In some embodiments, Ring F is 4-10 membered heterocycloalkyl, optionally substituted by an oxo (=O) group.

In some embodiments, Z is $Cy^Z$, $C_{1-6}$ alkyl, or $C(O)R^b$, wherein said $C_{1-6}$ alkyl is optionally substituted by halo. In some embodiments, Z is $CF_3$.

In some embodiments, $Cy^Z$ is selected from 5-10 membered heteroaryl and $C_{6-10}$ aryl, optionally substituted by $C_{1-6}$ alkyl, CN or $CF_3$, wherein said $C_{1-6}$ alkyl is optionally substituted with CN.

In some embodiments, $Cy^Z$ is pyridinyl, pyrimidinyl, or pyrazinyl, optionally substituted by $C_{1-6}$ alkyl, CN, Cl, $S(O)_2R^{b1}$, or $CF_3$.

In some embodiments, $Cy^Z$ is pyridinyl, pyrimidinyl, or pyrazinyl, optionally substituted by methyl, CN, Cl, $CF_3$, or $S(O)_2CH_3$.

In some embodiments, $Cy^Z$ is phenyl, optionally substituted with cyanomethyl or CN.

In some embodiments, $R^b$ is $C_{1-6}$ alkyl. In some embodiments, $R^b$ is methyl.

In some embodiments, $Y^4$ is O or $NR^Y$. In some embodiments, $Y^4$ is O. In some embodiments, $Y^4$ is $NR^Y$.

In some embodiments, $Y^5$ is O, $NR^Y$, or $C(=O)NR^Y$.

In some embodiments, $Y^6$ is $C(=O)$ or $C(=O)NR^Y$.

In some embodiments, $R^Y$ is H or $C_{1-4}$ alkyl. In some embodiments, $R^Y$ is H. In some embodiments, $R^Y$ is methyl.

In some embodiments, L is O or $NR^Y$.

In some embodiments, $G^1$ is $-C(R^G)(R^H)-$.

In some embodiments, $G^2$ is C-1. In some embodiments, $D^1$ and $D^2$ are each CH and $D^{10}$ is $CH_2$. In some embodiments, $D^1$ is CH, $D^2$ is N, and $D^{10}$ is $CH_2$. In some embodiments, $D^3$ is CH, $D^4$ is N, $D^5$ is CH. In some embodiments, $D^{10}$ is $CH_2$.

In some embodiments, b is 0, c is 1, and d is 1. In some embodiments, b is 0, c is 2, and d is 0. In some embodiments, b is 0, c is 0, and d is 0. In some embodiments, b is 0, c is 1, and d is 0.

In some embodiments, $G^2$ is C-2. In some embodiments, $D^3$, $D^4$, and $D^5$ are each $CR^X$, wherein each $R^X$ is independently selected from H, halo, and $C_{1-4}$ alkyl.

In some embodiments, $G^2$ is C-3. In some embodiments, $D^6$, $D^7$, and $D^9$ are $CR^X$, and $D^8$ is N. In some embodiments, $D^6$ and $D^7$ are each N, and $D^8$ and $D^9$ are each $CR^X$. In some embodiments, $D^6$, $D^7$, $D^8$, and $D^9$ are each $CR^X$. In some embodiments, $D^6$, $D^8$, and $D^9$ are each $CR^X$, and $D^7$ is N. In some embodiments, $D^6$, $D^7$, and $D^8$ are each $CR^X$ and $D^9$ is N. In some embodiments, $D^6$ and $D^8$ are each N, and $D^7$ and $D^9$ are each $CR^X$.

In some embodiments, each $R^X$ is H or halo. In some embodiments, $R^X$ is H or F. In some embodiments, $R^X$ is H.

In some embodiments, $G^2$ is $-C(R^I)(R^J)-$

In some embodiments, $R^{13}$ is $C_{1-6}$ alkyl, $OR^{a4}$, CN, or $NR^{c4}R^{d4}$, wherein said $C_{1-6}$ alkyl is optionally substituted with 1, 2, or 3 substituents independently selected from halo and $OR^{a4}$ and $NR^{c4}R^{d4}$.

In some embodiments, $R^{13}$ is methyl. In some embodiments, $R^{13}$ is CN. In some embodiments, $R^{13}$ is $CF_3$. In some embodiments, $R^{13}$ is amino. In some embodiments, $R^{13}$ is aminomethyl.

In some embodiments, $R^A$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^A$ is $C_{1-6}$ alkyl or H. In some embodiments, $R^A$ is methyl. In some embodiments, $R^A$ is H.

In some embodiments, $R^B$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^B$ is $C_{1-6}$ alkyl or H. In some embodiments, $R^B$ is methyl. In some embodiments, $R^B$ is H.

In some embodiments, $R^c$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^c$ is $C_{1-6}$ alkyl or H. In some embodiments, $R^c$ is methyl. In some embodiments, $R^c$ is H.

In some embodiments, $R^D$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^D$ is $C_{1-6}$ alkyl or H. In some embodiments, $R^D$ is methyl. In some embodiments, $R^D$ is H.

In some embodiments, $R^E$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^E$ is $C_{1-6}$ alkyl or H. In some embodiments, $R^E$ is methyl. In some embodiments, $R^E$ is H.

In some embodiments, $R^F$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^F$ is $C_{1-6}$ alkyl or H. In some embodiments, R is methyl. In some embodiments, $R^E$ is H.

In some embodiments, $R^G$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^G$ is $C_{1-6}$ alkyl or H. In some embodiments, $R^G$ is methyl. In some embodiments, $R^G$ is H.

In some embodiments, $R^H$ is H, halo, $OR^5$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^H$ is $C_{1-6}$ alkyl or H. In some embodiments, $R^H$ is methyl. In some embodiments, $R^H$ is H.

In some embodiments, $R^I$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^I$ is $C_{1-6}$ alkyl or H. In some embodiments, $R^I$ is methyl. In some embodiments, $R^I$ is H.

In some embodiments, $R^J$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^J$ is $C_{1-6}$ alkyl or H. In some embodiments, $R^I$ is methyl. In some embodiments, $R^J$ is H.

In some embodiments, $R^K$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^K$ is $C_{1-6}$ alkyl or H. In some embodiments, $R^K$ is methyl. In some embodiments, $R^K$ is H.

In some embodiments, $R^L$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^L$ is $C_{1-6}$ alkyl or H. In some embodiments, $R^L$ is methyl. In some embodiments, $R^L$ is H.

In some embodiments, $R^M$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^M$ is $C_{1-6}$ alkyl or H. In some embodiments, $R^M$ is methyl. In some embodiments, $R^M$ is H.

In some embodiments, $R^N$ is H, halo, $OR^5$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^N$ is $C_{1-6}$ alkyl or H. In some embodiments, $R^N$ is methyl. In some embodiments, $R^N$ is H.

In some embodiments, $R^I$ and $R^K$ together form a double bond between the carbon atoms to which they are attached.

In some embodiments, $R^K$ and $R^M$ together form a double bond between the carbon atoms to which they are attached.

In some embodiments, $R^K$, $R^L$, $R^M$, and $R^N$ together form a triple bond between the carbon atoms to which they are attached.

In some embodiments, $R^G$ and $R^I$ together with the carbon atoms to which they are attached and together with $Y^5$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^G$ and $R^I$ together with the carbon atoms to which they are attached and together with $Y^5$ form a tetrahydrofuranyl ring.

In some embodiments, $R^{a6}$ is H.

In some embodiments, $R^{b1}$ is $C_{1-6}$ alkyl. In some embodiments, $R^{b1}$ is methyl.

In some embodiments, $R^{a4}$ is H or $C_{1-6}$ alkyl. In some embodiments, $R^{a4}$ is methyl.

In some embodiments, $R^{c4}$ and $R^{d4}$ are each H.

In some embodiments, $R^{c5}$ and $R^{d5}$ are each H.

In some embodiments, $R^v$ is H.

In some embodiments, a is 0. In some embodiments, a is 1.

In some embodiments, s1 is 0. In some embodiments, s1 is 1. In some embodiments, s1 is 2.

In some embodiments, s2 is 0. In some embodiments, s2 is 1. In some embodiments, s2 is 2.

In some embodiments, v is 0. In some embodiments, v is 1.

In some embodiments, w is 0. In some embodiments, w is 1.

In some embodiments, m is 0. In some embodiments, m is 1.

In some embodiments, n is 0. In some embodiments, n is 1.

In some embodiments, p is 0. In some embodiments, p is 1.

In some embodiments, in q is 0. In some embodiments, q is 1.

In some embodiments, r is 0. In some embodiments, r is 1.

In some embodiments, provided herein is a compound of Formula (I), or a pharmaceutically acceptable salt thereof, having Formula IIIa:

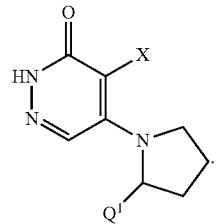

IIIa

In some embodiments, provided herein is a compound of Formula (I), or a pharmaceutically acceptable salt thereof, having Formula IIIb:

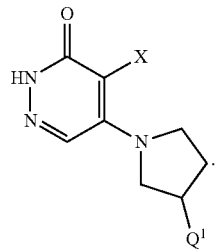

IIIb

In some embodiments, A is the group having the formula A-3.

In some embodiments, provided herein is a compound of Formula (I), or a pharmaceutically acceptable salt thereof, wherein:

X is Cl, Br, $CH_3$, $CF_3$, CN, $OCH_3$, ethyl, cyclopropyl, $SCH_3$, or isopropyl;

A is a group having the formula (A-3):

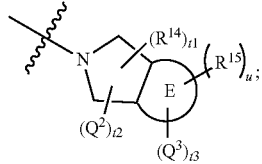

(A-3)

$Y^1$, $Y^2$, and $Y^3$ are each independently selected from O, S, $NR^Y$, $C(=O)$, $C(=O)O$, $C(=O)NR^Y$, $S(=O)$, $S(=O)_2$, $S(=O)NR^Y$, $S(=O)_2NR^Y$ or $NR^YC(=O)NR^Y$, wherein each $R^Y$ is independently H or $C_{1-4}$ alkyl;

L is $C_{1-3}$ alkylene, O, S, $NR^Y$, $C(=O)$, $C(=O)O$, $C(=O)NR^Y$, $S(=O)$, $S(=O)NR^Y$, or $NR^YC(=O)NR^Y$;

Z is H, $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

Cy$^Z$ is selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein the alkyl, C$_{2-6}$ alkenyl, and C$_{2-6}$ alkynyl are optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c}$C(O)OR$^{a1}$, NR$^{c1}$C(O)NR$^{c1}$R$^{d1}$, NR$^{c}$S(O)R$^{b1}$, NR$^{c}$1S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^{13}$, R$^{14}$, and R$^{15}$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of said R$^{13}$, R$^{14}$, and R$^{15}$ are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

Ring E is a mono- or polycyclic ring selected from C$_{6-10}$ aryl, C$_{3-7}$ cycloalkyl, 5-10 membered heteroaryl, and 4-10 membered heterocycloalkyl;

Q$^2$ and Q$^3$ are each a group of formula (B-1):

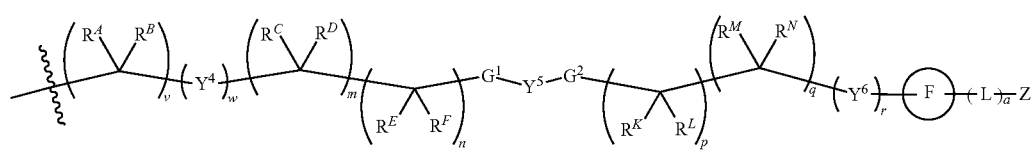

(B-1)

Y$^4$, Y$^5$, and Y$^6$ are each independently selected from O, S, NR$^Y$, C(=O), C(=O)O, C(=O)NR$^Y$, S(=O), S(=O)$_2$, S(=O)NR$^Y$, S(=O)$_2$NR$^Y$ or NR$^Y$C(=O)NR$^Y$;

G$^1$ is —C(R$^G$)(R$^H$)— or a group of formula (C-1), (C-2), or (C-3):

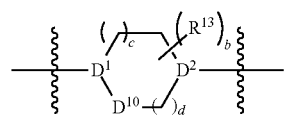

(C-1)

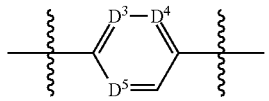

(C-2)

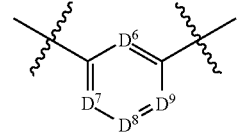

(C-3)

G$^2$ is —C(R$^I$)(R$^J$)— or a group of formula (C-1), (C-2), or (C-3);

R$^A$, R$^B$, R, R$^D$, R$^E$, R$^F$, R$^G$, R$^H$, R$^I$, R$^J$, R$^K$, R$^L$, R$^M$, and R$^N$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^e$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of said R$^A$, R$^B$, R$^C$, R$^D$, R$^E$, R$^F$, R$^G$, R$^H$, R$^I$, R$^J$, R$^K$, R$^L$, R$^M$, and R$^N$ are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

or R$^G$ and R$^I$ together with the carbon atoms to which they are attached and together with Y$^5$ form a 5-10 membered heterocycloalkyl ring optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$ S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

or R$^C$ and R$^E$ together form a double bond between the carbon atoms to which they are attached;

or R$^E$ and R$^G$ together form a double bond between the carbon atoms to which they are attached;

or $R^I$ and $R^K$ together form a double bond between the carbon atoms to which they are attached;

or $R^K$ and $R^M$ together form a double bond between the carbon atoms to which they are attached;

or $R^K$, $R^L$, $R^M$, and $R^N$ together form a triple bond between the carbon atoms to which they are attached;

$D^1$ and $D^2$ are each independently selected from N and CH;

$D^3$, $D^4$, $D^5$, $D^6$, $D^7$, $D^8$, and $D^9$ are each independently selected from N and $CR^X$, wherein each $R^X$ is independently selected from H, halo, and $C_{1-4}$ alkyl;

$D^{10}$ is O, S, NH or $CH_2$;

Ring F is a mono- or polycyclic ring selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(=NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, wherein the alkyl, $C_{2-6}$ alkenyl, and $C_{2-6}$ alkynyl are optionally substituted with 1, 2, or 3 substituents independently selected from halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $C(=NR^{e6})NR^{c6}R^{d6}$, $NR^{c6}C(NR^{e6})NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$;

each $R^a$, $R^b$, $R^c$, $R^d$, $R^{a1}$, $R^{b1}$, $R^{c1}$, $R^{d1}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^a$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c3}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

or $R^{c1}$ and $R^{d1}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c3}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c3}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

or $R^{c4}$ and $R^{d4}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c3}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

or $R^{c5}$ and $R^{d5}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c7}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

or $R^{c6}$ and $R^{d6}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)$ $NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})$ $NR^{c3}R^{d7}$, $S(O)R^{b7}$, $S(O)NR^{c7}R^{d7}$, $S(O)_2R^{b7}$, $NR^{c7}$ $S(O)_2R^{b7}$, $NR^{c7}S(O)_2NR^{c7}R^{d7}$, and $S(O)_2NR^{c7}R^{d7}$;

$R^{a7}$, $R^{b7}$, $R^7$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e3}$, $R^{e4}$, $R^{e5}$, $R^{e6}$ and $R^{e7}$ is independently selected from H, $C_{1-4}$ alkyl, and CN;

a is 0 or 1;

b is 0, 1, 2, or 3;

c is 0, 1, or 2;

d is 0, 1, or 2;

m is 0 or 1;

n is 0 or 1;
p is 0 or 1;
q is 0 or 1;
r is 0 or 1;
t1 is 0 or 1;
t2 is 0 or 1;
t3 is 0 or 1;
u is 0, 1, 2, or 3;
v is 0 or 1; and
w is 0 or 1;
wherein any aforementioned heteroaryl or heterocycloalkyl group comprises 1, 2, 3, or 4 ring-forming heteroatoms independently selected from O, N, and S; and
wherein one or more ring-forming C or N atoms of any aforementioned heterocycloalkyl group is optionally substituted by an oxo (=O) group.

In some embodiments, $Q^2$ is a compound having the formula B-2a:

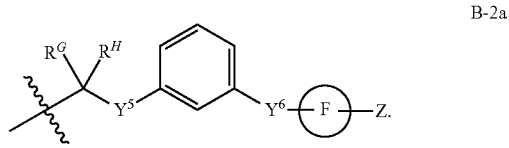

B-2a

In some embodiments, $Q^2$ is a compound having the formula B-2a:

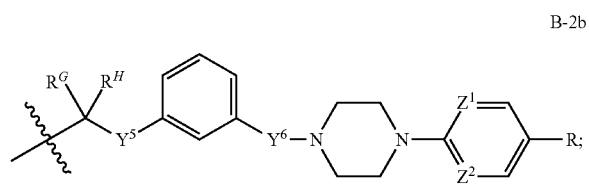

B-2b wherein $Z^1$ and $Z^2$ are each independently selected from N and CH, and wherein R is CN, Cl, or $CF_3$.

In some embodiments, $Q^3$ is a compound having the formula B-3a:

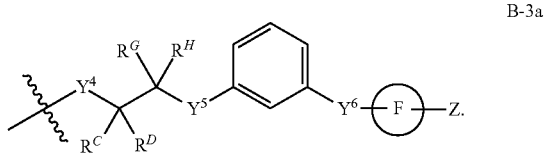

B-3a

In some embodiments, $Q^3$ is a compound having the formula B-3b:

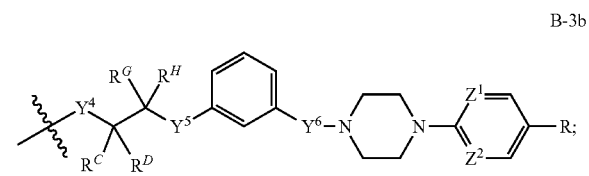

B-3b wherein $Z^1$ and $Z^2$ are each independently selected from N and CH, and wherein R is CN, Cl, or $CF_3$.

In some embodiments, X is Cl, Br, $CH_3$, $CF_3$, CN, $OCH_3$, ethyl, cyclopropyl, $SCH_3$, or isopropyl.

In some embodiments, Ring E is a mono- or polycyclic ring selected from $C_{6-10}$ aryl, $C_{3-7}$ cycloalkyl, 5-10 membered heteroaryl, and 4-10 membered heterocycloalkyl. In some embodiments, Ring E is a mono- or polycyclic ring selected from $C_{6-10}$ aryl. In some embodiments, Ring E is a mono- or polycyclic ring selected from 5-10 membered heteroaryl. In some embodiments, Ring E is a mono- or polycyclic ring selected from $C_{3-7}$ cycloalkyl. In some embodiments, Ring E is a mono- or polycyclic ring selected from 4-10 membered heterocycloalkyl.

In some embodiments, Ring E is phenyl. In some embodiments, Ring E is pyridinyl. In some embodiments, Ring E is cyclohexyl. In some embodiments, Ring E is pyridine-4(1H)-onyl, 4-pyridonyl, or piperidinyl In some embodiments, each $R^{14}$ is independently selected from H, halo, $OR^{a4}$, and $C_{1-6}$ alkyl, wherein said $C_{1-6}$ alkyl is optionally substituted with CN, $OR^{a7}$, $NR^{c4}R^{d4}$, or $NR^{c4}C(O)R^{b4}$.

In some embodiments, each $R^{14}$ is independently selected from halo, methyl, ethyl, and cyanomethyl, each optionally substituted with CN, $OR^{a}$, $NR^{c4}R^{d4}$, or $NR^{c4}C(O)R^{b4}$ In some embodiments, each $R^{15}$ is independently selected from H, halo, CN, $NR^{c4}R^{d4}$, $OR^{a4}$, $C(O)R^{b4}$, $NRc4C(O)R^{b4}$, $C(O)NR^{c4}R^{d4}$ and $C_{1-6}$ alkyl, wherein said $C_{1-6}$ alkyl is optionally substituted with CN, $OR^{a7}$, $NR^{c4}R^{d4}$, or $NR^{c4}C(O)R^{b4}$.

In some embodiments, $R^{15}$ is F or Cl. In some embodiments, each $R^{15}$ is independently selected from halo and $OR^{a4}$. In some embodiments, each $R^{15}$ is independently selected from halo and $NR^{c4}R^{d4}$. In some embodiments, each $R^{15}$ is independently selected from halo, $NR^{c4}C(O)R^{b4}$, $C(O)R^{b4}$, and $C(O)NR^{c4}R^{d4}$. In some embodiments, $R^{15}$ is CN. In some embodiments, $R^{15}$ is halo. In some embodiments, $R^{15}$ is 4-10 membered heterocycloalkyl, optionally substituted with $C_{1-6}$ alkyl, $NR^{c4}R^{d4}$ or $C(O)R^{b4}$. In some embodiments, $R^{15}$ is morpholinyl, piperidinyl, pyrrolidinyl, optionally substituted with $OR^{a4}$, $NR^{c4}R^{d4}$ or $C(O)R^{b4}$.

In some embodiments, $R^{a4}$ is selected from $C_{1-6}$ alkyl, $C_{6-10}$ aryl, 5-10 membered heteroaryl, 4-10 membered heterocycloalkyl, $C_{6-10}$ aryl-$C_{1-4}$ alkyl, cycloalkyl-$C_{1-4}$ alkyl, 5-10 membered heteroaryl-$C_{1-4}$ alkyl, and 4-10 membered heterocycloalkyl-$C_{1-4}$ alkyl, each optionally substituted with $C_{1-4}$ alkyl, $OR^{a7}$, $NR^{c7}R^{d7}$, $C(O)NR^{c7}R^{d7}$, $C(O)R^{b7}$, $C(O)OR^{a7}$ or $NR^{c7}C(O)R^{b7}$.

In some embodiments, $R^{a4}$ is H or $C_{1-6}$ alkyl. In some embodiments, $R^{a4}$ is pyridinyl. In some embodiments, $R^{a4}$ is phenyl. In some embodiments, $R^{a4}$ is pyridinylmethyl, pyridinylethyl, tetrahydropyranylmethyl, tetrahydrofuranylmethyl, piperidinylmethyl, piperidinylethyl, morpholinylethyl, piperazinylethyl, pyrrolidinylmethyl. In some embodiments, $R^{a4}$ is methyl, ethyl, or isopropyl. In some embodiments, $R^{a4}$ is piperidinyl, tetrahydropyranyl, tetrahydrofuranyl, morpholinyl, pyrrolidinyl, each optionally substituted by an oxo (=O) group, $C_{1-4}$ alkyl, $OR^{a7}$, $NR^{c7}R^{d7}$, $C(O)NR^{c7}R^{d7}$, $C(O)R^{b7}$, or $NR^{c7}C(O)R^{b7}$. In some embodiments, $R^{a4}$ is pyrimidinyl.

In some embodiments, $R^{b4}$ is $C_{1-6}$ alkyl. In some embodiments, $R^{b4}$ is methyl.

In some embodiments, $R^4$ is H or $C_{1-6}$ alkyl. In some embodiments, $R^4$ is methyl.

In some embodiments, $R^{d4}$ is H, $C_{1-6}$ alkyl, $C_{6-10}$ aryl, 4-10 membered heterocycloalkyl, 5-10 membered heteroaryl, 5-10 membered heteroaryl-$C_{1-4}$ alkyl, 4-10 membered heterocycloalkyl-$C_{1-4}$ alkyl, optionally substituted with 1, 2, 3, or 4 substituents independently selected from $C_{1-6}$ alkyl, $C(O)R^{b7}$, and $C(O)OR^{a7}$. In some embodiments, $R^{d4}$ is methyl. In some embodiments, $R^{d4}$ is tetrehydrofuranylmethyl, pyridinylmethyl, pyridinylethyl, morpholinyl, piperidinyl, tetrahydropyranyl, or pyridinyl.

In some embodiments, $R^{a7}$ is H or $C_{1-6}$ alkyl. In some embodiments, $R^{a7}$ is methyl.

In some embodiments, $R^{b7}$ is H or $C_{1-6}$ alkyl.

In some embodiments, $R^{c7}$ is H or $C_{1-6}$ alkyl.

In some embodiments, $R^{d7}$ is H or $C_{1-6}$ alkyl.

In some embodiments, $R^{b7}$ is H or methyl.

In some embodiments, $R^{c7}$ is H or methyl.

In some embodiments, $R^{d7}$ is H or methyl.

In some embodiments, $Y^4$ is O.

In some embodiments, $Y^5$ is O, $NR^Y$, $C(=O)$, or $C(=O)NR^Y$.

In some embodiments, $G^1$ is $-C(R^G)(R^H)-$. In some embodiments, $G^1$ is C-2.

In some embodiments, $D^3$, $D^4$, and $D^5$ are each $CR^X$, wherein each $R^X$ is independently selected from H, halo, and $C_{1-4}$ alkyl.

In some embodiments, $R^X$ is H.

In some embodiments, $G^2$ is $-C(R^I)(R^J)-$. In some embodiments, $G^2$ is C-3.

In some embodiments, $D^6$, $D^7$, and $D^9$ are each $CR^X$, and $D^8$ is N. In some embodiments, $D^6$ and $D^7$ are each N, and $D^8$ and $D^9$ are each $CR^X$. In some embodiments, $D^6$, $D^7$, $D^8$, and $D^9$ are each $CR^X$. In some embodiments, $D^6$, $D^8$, and $D^9$ are each $CR^X$, and $D^7$ is N. In some embodiments, $D^6$, $D^7$, and $D^8$ are each $CR^X$ and $D^9$ is N. In some embodiments, $D^6$ and $D^8$ are each N, and $D^7$ and $D^9$ are each $CR^X$. In some embodiments, $D^6$ and $D^9$ are each N, and $D^7$ and $D^8$ are each $CR^X$.

In some embodiments, $G^2$ is C-1.

In some embodiments, $D^1$ and $D^2$ are each N and $D^{10}$ is $CH_2$.

In some embodiments, b is 0, c is 1, and d is 1.

In some embodiments, Ring F is 4-10 membered heterocycloalkyl, 5-10 membered heteroaryl, or $C_{3-7}$ cycloalkyl, each optionally substituted with $C_{1-6}$ alkyl, wherein said $C_{1-6}$ alkyl is optionally substituted with $OR^{a6}$. In some embodiments, Ring F is 4-10 membered heterocycloalkyl or $C_{3-7}$ cycloalkyl, each optionally substituted with methyl.

In some embodiments, Ring F is piperazinyl, piperidinyl, pyrrolidinyl, pyridinyl, 5,6,7,8-tetrahydro-[1,2,4]triazolo[4,3-a]pyrazinyl, 2,8-diazaspiro[4.5]decanyl, 2,5-diazabicyclo[2.2.2]octanyl, 1,4-diazepanyl, azetidinyl, 2,6-diazaspiro[3.3]heptanyl, 2,6-diazaspiro[3.4]octanyl, octahydropyrrolo[3,2-b]pyrrolyl, 2,7-diazaspiro[4.4]nonanyl, 2,5-diazabicyclo[2.2.1]heptanyl, octahydropyrrolo[3,4-c]pyrrolyl, 2,7-diazaspiro[3.5]nonanyl, or 4,5,6,7-tetrahydropyrazolo[1,5-a]pyrazine.

In some embodiments, Ring F is piperzinyl. In some embodiments, Ring F is cyclohexyl. In some embodiments, Ring F is 4-10 membered heterocycloalkyl, optionally substituted by an oxo (=O) group.

In some embodiments, Z is $Cy^Z$, CN, $C_{1-6}$ alkyl, or $C(O)R^b$, wherein said $C_{1-6}$ alkyl is optionally substituted by halo. In some embodiments, Z is $CF_3$, $CH_3$, or CN. In some embodiments, Z is H.

In some embodiments, $R^b$ is $C_{1-6}$ alkyl, optionally substituted with CN. In some embodiments, $R^b$ is methyl.

In some embodiments, $Cy^Z$ is selected from 5-10 membered heteroaryl and $C_{6-10}$ aryl, each optionally substituted by $C_{1-6}$ alkyl, halo, CN or $CF_3$, wherein said $C_{1-6}$ alkyl is optionally substituted with CN. In some embodiments, $Cy^Z$ is pyridinyl, pyrimidinyl, or pyrazinyl, each optionally substituted by $C_{1-6}$ alkyl, CN, Cl, F, $S(O)_2R^{b1}$, or $CF_3$. In some embodiments, $Cy^Z$ is pyridinyl, pyrimidinyl, pyrazinyl, each optionally substituted by methyl, CN, Cl, F, $CF_3$, or $S(O)_2CH_3$. In some embodiments, $Cy^Z$ is phenyl, optionally substituted with cyanomethyl or CN.

In some embodiments, $R^{b1}$ is $C_{1-6}$ alkyl. In some embodiments, $R^{b1}$ is methyl.

In some embodiments, $R^A$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^A$ is $C_{1-6}$ alkyl or H. In some embodiments, $R^A$ is methyl. In some embodiments, $R^A$ is H.

In some embodiments, $R^B$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^B$ is $C_{1-6}$ alkyl or H. In some embodiments, $R^B$ is methyl. In some embodiments, $R^B$ is H.

In some embodiments, $R^C$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^C$ is $C_{1-6}$ alkyl or H. In some embodiments, $R^C$ is methyl. In some embodiments, $R^C$ is H.

In some embodiments, $R^D$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^D$ is $C_{1-6}$ alkyl or H. In some embodiments, $R^D$ is methyl. In some embodiments, $R^D$ is H.

In some embodiments, $R^E$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^E$ is $C_{1-6}$ alkyl or H. In some embodiments, $R^E$ is methyl. In some embodiments, $R^E$ is H.

In some embodiments, $R^F$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^F$ is $C_{1-6}$ alkyl or H. In some embodiments, $R^F$ is methyl. In some embodiments, $R^E$ is H.

In some embodiments, $R^G$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^G$ is $C_{1-6}$ alkyl or H. In some embodiments, $R^G$ is methyl. In some embodiments, $R^G$ is H.

In some embodiments, $R^H$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^H$ is $C_{1-6}$ alkyl or H. In some embodiments, $R^H$ is methyl. In some embodiments, $R^H$ is H.

In some embodiments, $R^I$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^I$ is $C_{1-6}$ alkyl or H. In some embodiments, $R^I$ is methyl. In some embodiments, $R^I$ is H.

In some embodiments, $R^J$ is H, halo, $OR^5$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^J$ is $C_{1-6}$ alkyl or H. In some embodiments, $R^J$ is methyl. In some embodiments, $R^J$ is H.

In some embodiments, $R^K$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^K$ is $C_{1-6}$ alkyl or H. In some embodiments, $R^K$ is methyl. In some embodiments, $R^K$ is H.

In some embodiments, $R^L$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^L$ is $C_{1-6}$ alkyl or H. In some embodiments, $R^L$ is methyl. In some embodiments, $R^L$ is H.

In some embodiments, $R^M$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^M$ is $C_{1-6}$ alkyl or H. In some embodiments, $R^M$ is methyl. In some embodiments, $R^M$ is H.

In some embodiments, $R^N$ is H, halo, $OR^{a5}$, $C_{1-6}$ alkyl, $C_{6-10}$ aryl, 5-10 membered heteroaryl, or $C_{6-10}$ aryl-$C_{1-4}$ alkyl, wherein said $C_{1-6}$ alkyl, $C_{6-10}$ aryl, 5-10 membered heteroaryl, or $C_{6-10}$ aryl-$C_{1-4}$ alkyl is optionally substituted with $OR^{a5}$ or $NR^{c5}R^{d5}$.

In some embodiments, $R^N$ is $C_{1-6}$ alkyl or H. In some embodiments, $R^N$ is methyl. In some embodiments, $R^N$ is H.

In some embodiments, $R^K$ and $R^M$ together form a double bond between the carbon atoms to which they are attached.

In some embodiments, $R^I$ and $R^K$ together form a double bond between the carbon atoms to which they are attached.

In some embodiments, each $R^X$ is H or halo. In some embodiments, $R^X$ is H. In some embodiments, $R^X$ is F In some embodiments, $Y^6$ is C(=O), $NR^Y$, or C(=O) $NR^Y$.

In some embodiments, $R^Y$ is H or $C_{1-4}$ alkyl. In some embodiments, $R^Y$ is H. In some embodiments, $R^Y$ is methyl.

In some embodiments, t1 is 0. In some embodiments, t1 is 1.

In some embodiments, t2 is 0. In some embodiments, t2 is 1.

In some embodiments, t3 is 0. In some embodiments, t3 is 1.

In some embodiments, u is 0. In some embodiments, u is 1. In some embodiments, u is 2.

In some embodiments, a is 0.

In some embodiments, v is 0. In some embodiments, v is 1.

In some embodiments, w is 0.
In some embodiments, w is 1.

In some embodiments, m is 0. In some embodiments, m is 1.

In some embodiments, n is 0. In some embodiments, n is 1.

In some embodiments, p is 0. In some embodiments, p is 1.

In some embodiments, q is 0. In some embodiments, q is 1.

In some embodiments, r is 1.

In other embodiments, provided herein is a compound of Formula I, or a pharmaceutically acceptable salt thereof, having Formula IVa:

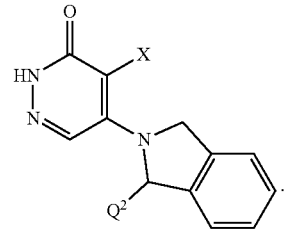

IVa

In other embodiments, provided herein is a compound of Formula I, or a pharmaceutically acceptable salt thereof, having Formula IVb:

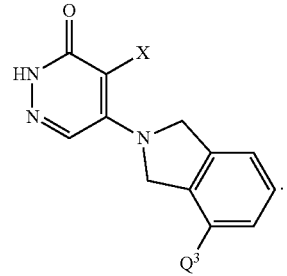

IVb

In other embodiments, provided herein is a compound of Formula I, or a pharmaceutically acceptable salt thereof, having Formula IVc:

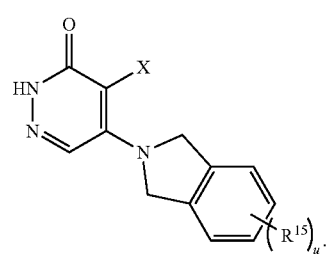

IVc

In other embodiments, provided herein is a compound of Formula I, or a pharmaceutically acceptable salt thereof, having Formula IVd:

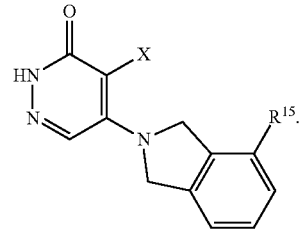

IVd

In other embodiments, provided herein is a compound of Formula I, or a pharmaceutically acceptable salt thereof, having Formula IVe:

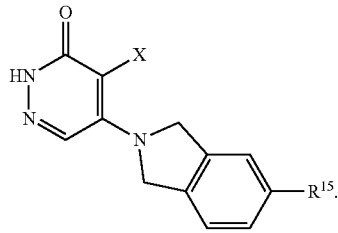

IVe

Crystalline 5-[[(2S)-1-(3-Oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one In some embodiments, the compound of Formula I is 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one (see Example 561). The compound of Example 561, 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one, can also be referred to as:

(S)-5-((1-(3-Oxo-3-(4-(5-(trifluoromethyl)pyrimidin-2-yl)piperazin-1-yl)propoxy)propan-2-yl)amino)-4-(trifluoromethyl)pyridazin-3 (2H)-one; or (S)-5-(1-(3-Oxo-3-(4-(5-(trifluoromethyl)pyrimidin-2-yl)piperazin-1-yl)propoxy)propan-2-ylamino)-4-(trifluoromethyl)pyridazin-3 (2H)-one.

In some embodiments, 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one is crystalline and has the characteristics of Form A described below. The synthesis and characterization of 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one, including Form A, is described for example in Example 561.

In some embodiments, Form A has characteristic XRPD peaks selected from about 5.8, about 10.8, about 11.9, and about 17.2 degrees 2-theta. In some embodiments, Form A has at least one characteristic XRPD peak selected from about 5.8, about 10.8, about 11.9, and about 17.2 degrees 2-theta. In some embodiments, Form A has at least two characteristic XRPD peaks selected from about 5.8, about 10.8, about 11.9, and about 17.2 degrees 2-theta. In some embodiments, Form A has a characteristic XRPD peak at about 5.8 degrees 2-theta. In some embodiments, Form A has a characteristic XRPD peak at about 10.8 degrees 2-theta. In some embodiments, Form A has a characteristic XRPD peak at about 11.9 degrees 2-theta. In some embodiments, Form A has a characteristic XRPD peak at about 17.2 degrees 2-theta.

In some embodiments, Form A has at least one characteristic XRPD peak selected from about 5.8, about 10.8, about 11.9, about 13.3, about 13.5, and about 17.2 degrees 2-theta. In some embodiments, Form A has at least one characteristic XRPD peak selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least two characteristic XRPD peaks selected from about 5.8, about 10.8, about 11.9, about 13.3, about 13.5, about 15.5, and about 17.2 degrees 2-theta. In some embodiments, Form A has at least two characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least three characteristic XRPD peaks selected from about 5.8, about 10.8, about 11.9, about 13.3, about 13.5, about 15.5, and about 17.2 degrees 2-theta. In some embodiments, Form A has at least three characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

In some embodiments, Form A has at least four characteristic XRPD peaks selected from about 5.8, about 10.8, about 11.9, about 13.3, about 13.5, about 15.5, and about 17.2 degrees 2-theta. In some embodiments, Form A has at least four characteristic XRPD peaks selected from about 5.8, about 10.8, about 11.2, about 11.9, about 12.3, about 13.3, about 13.5, about 15.5, about 17.2, about 17.7, about 18.0, about 18.4, about 19.5, about 21.0, and about 21.6 degrees 2-theta.

Figure 8:
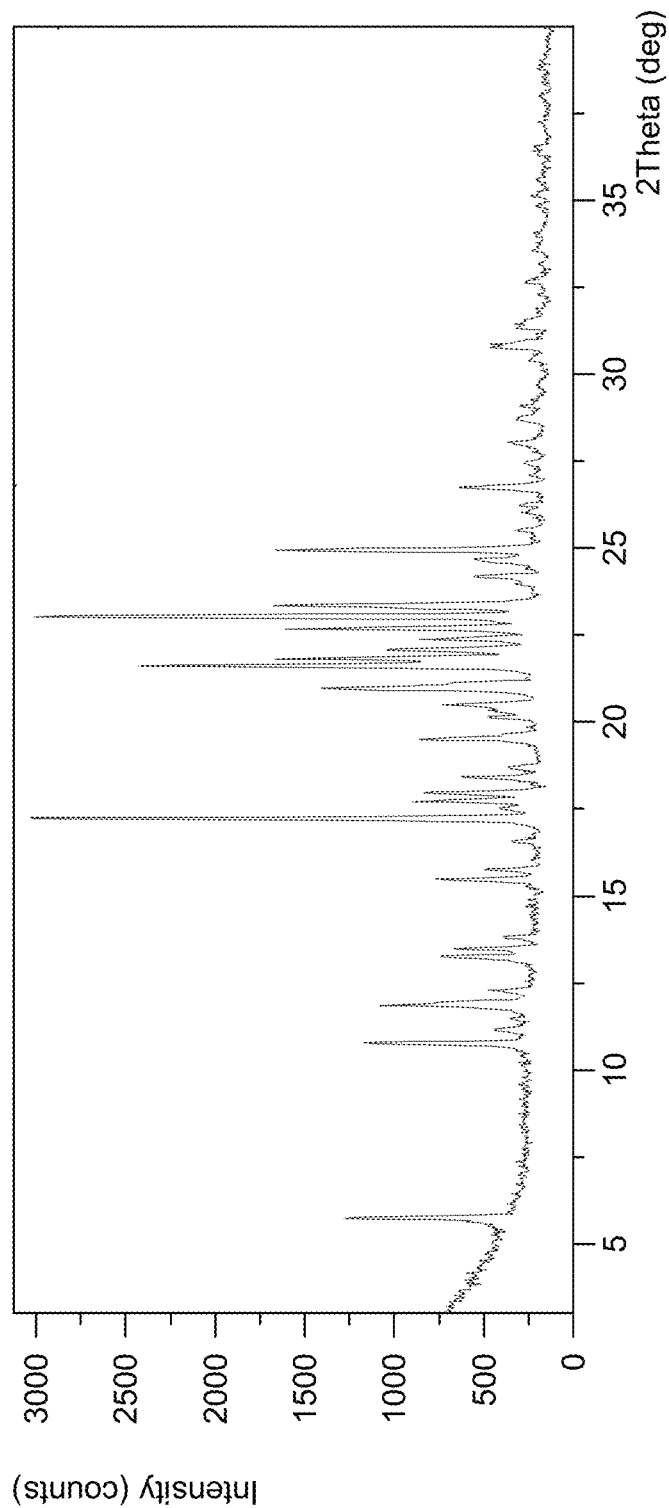
FIG. 8 shows an X-ray powder diffraction (XRPD) pattern of the compound of Example 561 Form A.

In some embodiments, Form A has an XRPD pattern with characteristic peaks as substantially shown in FIG. 8.

Figure 9:
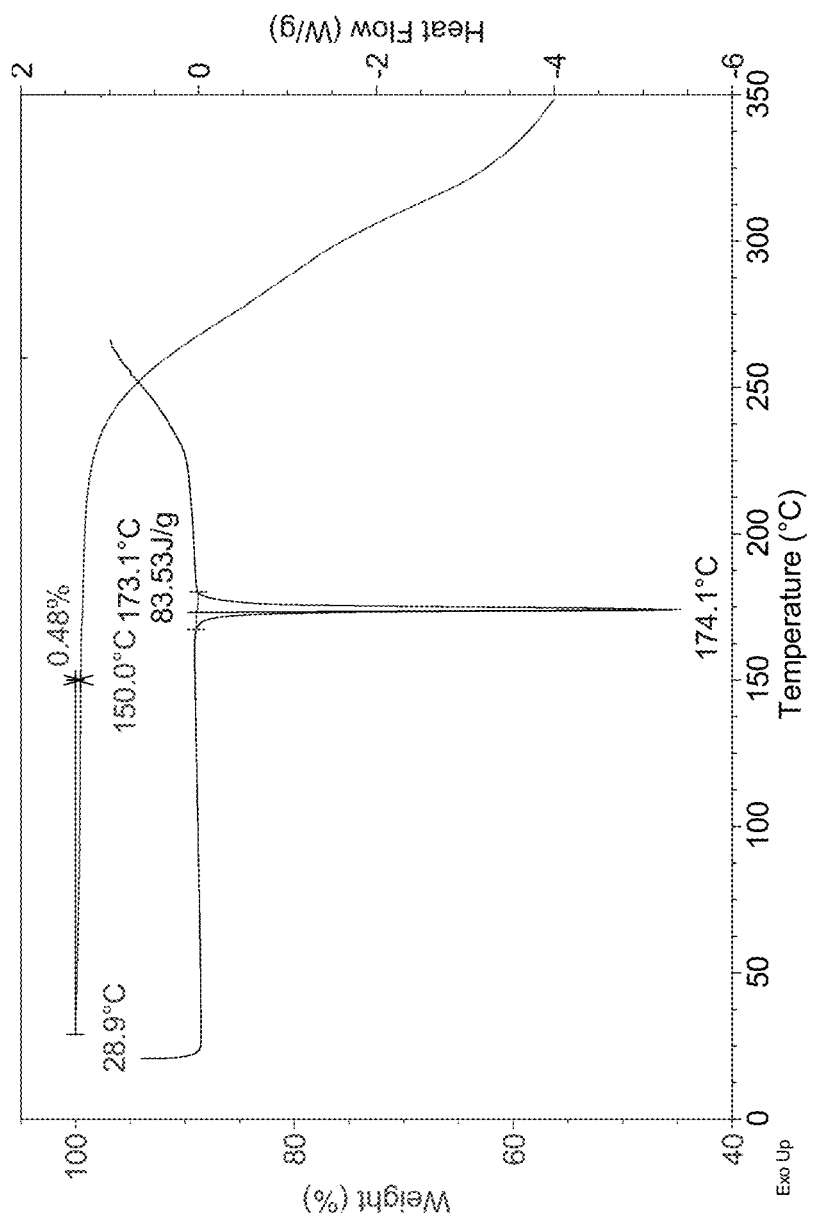
FIG. 9 shows a differential scanning calorimetry (DSC) and thermogravimetric analysis (TGA) thermogram of the compound of Example 561 Form A.
Figure 10:
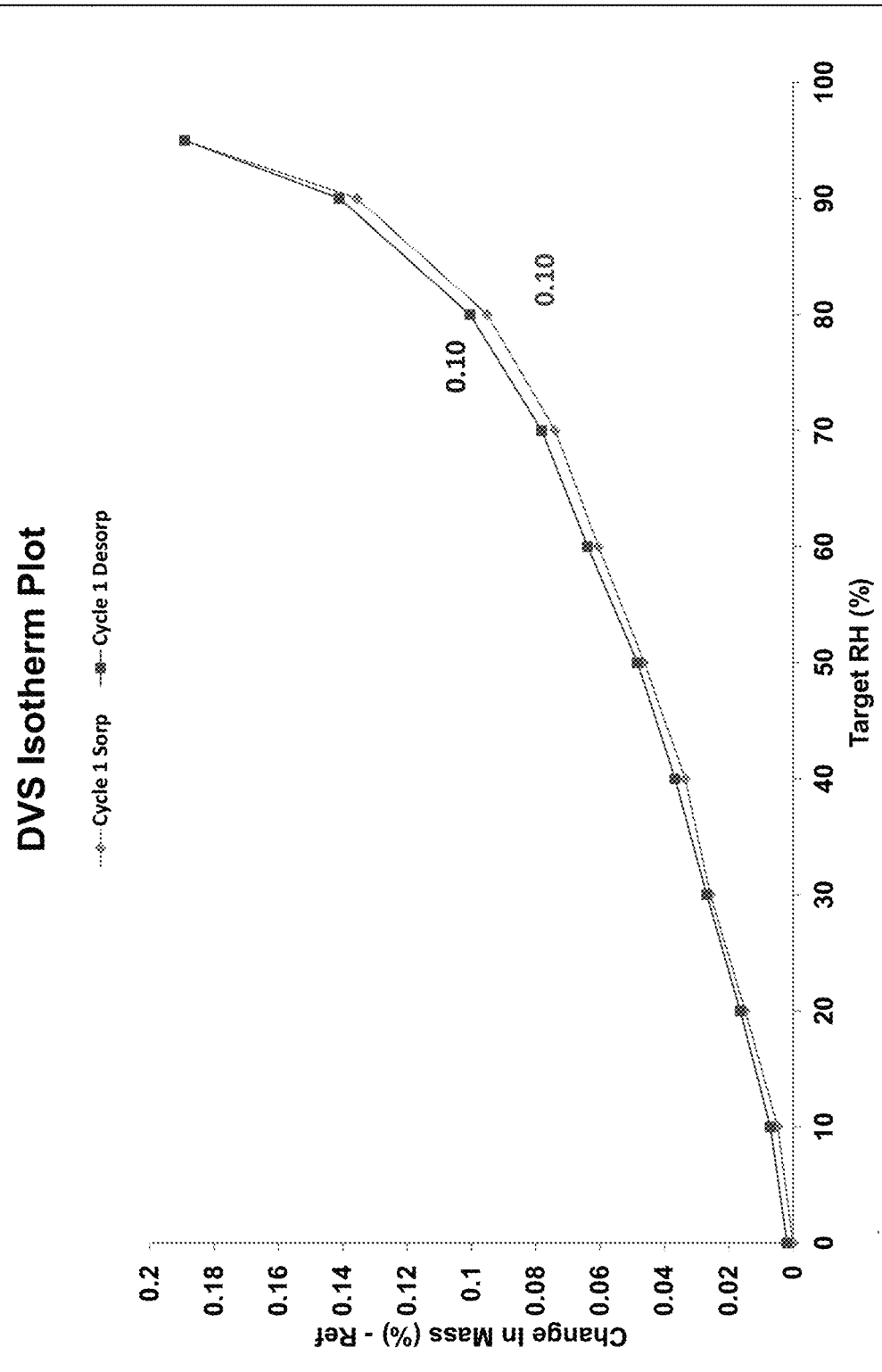
FIG. 10 shows a dynamic vapor sorption (DVS) isotherm of the compound of Example 561 Form A.

In some embodiments, Form A has an endotherm peak at a temperature of about 174° C. In some embodiments, Form A shows a weight loss of about 0.5% when heated to about 150° C. In some embodiments, Form A has a DSC thermogram substantially as depicted in FIG. 9. In some embodiments, Form A has a TGA thermogram substantially as depicted in FIG. 9. In some embodiments, Form A has a DVS isotherm substantially as depicted in FIG. 10.

In some embodiments, Form A has at least one characteristic XRPD peak selected from about 5.8, about 10.8, about 11.9, and about 17.2 degrees 2-theta; and has an endotherm peak at a temperature of about 174° C. In some embodiments, Form A has at least one characteristic XRPD peak selected from about 5.8, about 10.8, about 11.9, and about 17.2 degrees 2-theta; and a DSC thermogram substantially as depicted in FIG. 9. In some embodiments, Form A has at least one characteristic XRPD peak selected from about 5.8, about 10.8, about 11.9, and about 17.2 degrees 2-theta; and a DVS isotherm substantially as depicted in FIG. 10.

In some embodiments, Form A can be isolated with a crystalline purity of at least about 80%, about 85%, about 90%, about 95%, about 96%, about 97%, about 98%, or about 99%. In some embodiments, Form A can be isolated with a crystalline purity greater than about 99%. In some embodiments, Form A can be isolated with a crystalline purity greater than about 99.9%. In some embodiments, Form A is substantially free of other crystalline form. In some embodiments, Form A is substantially free of amorphous form.

In some embodiments, provided is Form A prepared by precipitating 5-[[(2S)-1-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one from a solution comprising the compound and S1, wherein S1 is a solvent. In some embodiments, S1 is an organic solvent. In some embodiments, S1 is selected from one of the following solvents: ethyl alcohol, methyl isobutyl ketone, isopropyl acetate, methy t-butyl ether, 2-methyltetrahydrofuran, 1,4-dioxane, toluene, acetone, dichloromethane, and water. In some embodiments, S1 is a mixture of organic solvents. In some embodiments, S1 is a mixture of acetonitrile and heptane. In some embodiments, S1 is a mixture of isopropyl alcohol and ethyl acetate. In some embodiments, S1 is a mixture of chloroform and ethyl acetate. In some embodiments, S1 is a mixture of 1,4-dioxane and methanol. In some embodiments, S1 is a mixture of NMP and toluene. In some embodiments, S1 is a mixture of petroleum ether and hexanes. In some embodiments, the precipitating is carried out by concentration of the solution, evaporation of solvent, reduction of temperature of the solution, addition of anti-solvent, or combination thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups.

Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl," employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-azaspiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl," employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl," employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl," employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. An example of tautomeric forms, pyridazin-3(2H)-one and pyridazin-3-ol, is depicted below:

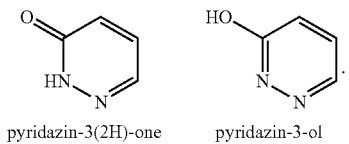 [SMILES: O=c1cccn[nH]1 ; Oc1cccnn1]

pyridazin-3(2H)-one     pyridazin-3-ol

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric iosomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

As used herein, the term "crystalline" or "crystalline form" refers to a crystalline solid form of a chemical compound, including, but not limited to, a single-component or multiple-component crystal form, e.g., including solvates, hydrates, clathrates, and co-crystals. As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

As used herein, the term "substantially crystalline," means a majority of the weight of a sample or preparation of a salt (or hydrate or solvate thereof) of the invention is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values.

Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±3° C. Accordingly, a crystalline form reported herein having a DSC thermogram "substantially" as shown in any of the Figures is understood to accommodate such variation.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}$C NMR, DSC, TGA and XRPD), indicate that the value or range of values may deviate to an extent deemed reasonable to one of ordinary skill in the art while still describing the particular solid form.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "RT", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared according to numerous preparatory routes known in the literature. Example synthetic methods for preparing compounds of the invention are provided in the Schemes below. Unless noted otherwise, all substituents are as defined herein.

In the process depicted in Scheme 1, an appropriately substituted, halogen containing compound (i.e., $X^a$=Cl or Br) of Formula (1-1) is protected as the 2-(trimethylsilyl)ethoxymethyl ether ("SEM") compound of Formula (1-2) by treatment with 2-(trimethylsilyl)ethoxymethyl chloride ("SEM-Cl") in the presence of sodium hydride (NaH).

Scheme 1

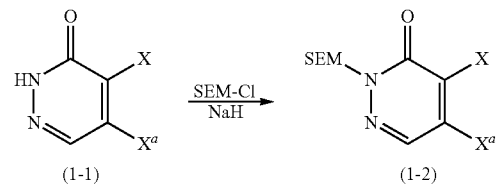

Compound of Formula (1-2) can be reacted with a variety of nucleophiles to provide compounds of Formula (I) following deprotection of the SEM protecting group, as shown in Schemes 2-4.

In the process depicted in Scheme 2, the compound of Formula (1-2) (wherein $Y^a$ is O, $NR^Y$, or S) is reacted with a compound having Formula (1-3) in the presence of a base (e.g., triethylamine or $Cs_2CO_3$) to provide a compound of formula (1-4). Deprotection with an acid (e.g., trifluoroacetic acid or hydrochloric acid) provides a compound of Formula (IA).

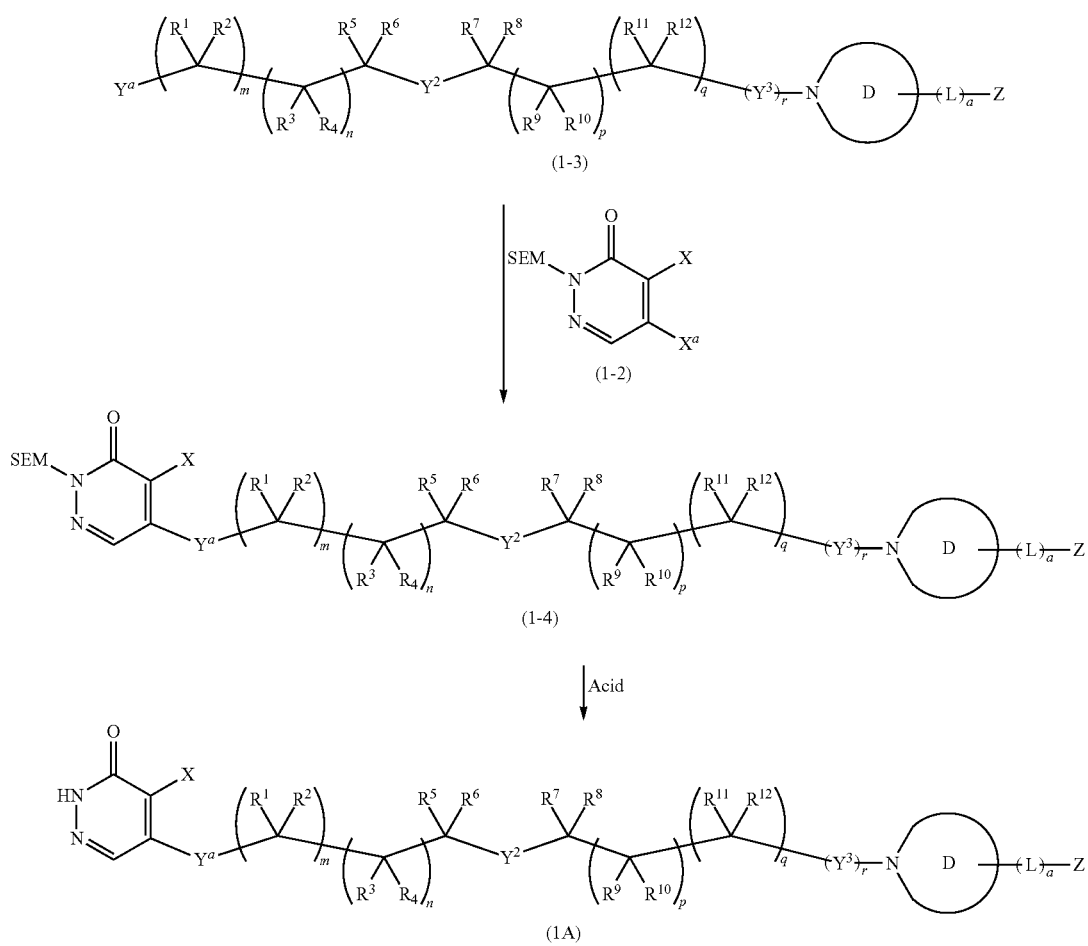

In the process depicted in Scheme 3, the compound of Formula (1-2) is reacted with a compound having Formula (1-5) in the presence of a base (e.g., triethylamine or $Cs_2CO_3$) to provide a compound of Formula (1-6). Deprotection with an acid (e.g., trifluoroacetic acid or hydrochloric acid) provides a compound of Formula (IB).

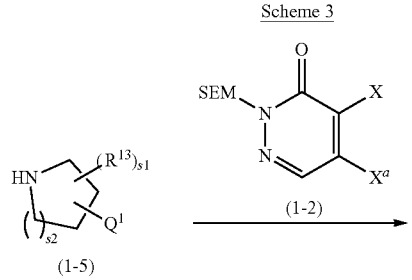

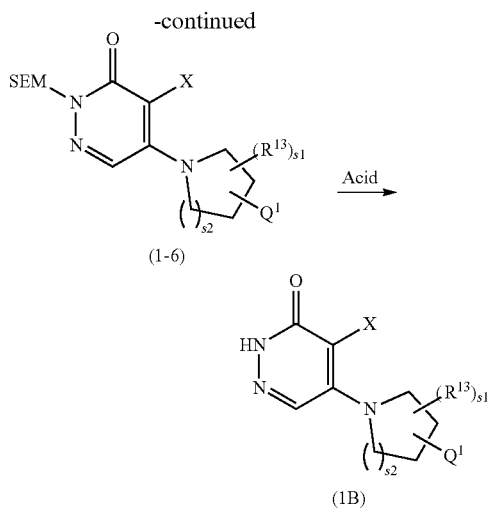

In the process depicted in Scheme 4, the compound of Formula (1-2) is reacted with a compound having Formula (1-7) in the presence of a base (e.g., triethylamine or $Cs_2CO_3$) to provide a compound of Formula (1-8). Deprotection with an acid (e.g., trifluoroacetic acid or hydrochloric acid) provides a compound of Formula (IC).

Scheme 4

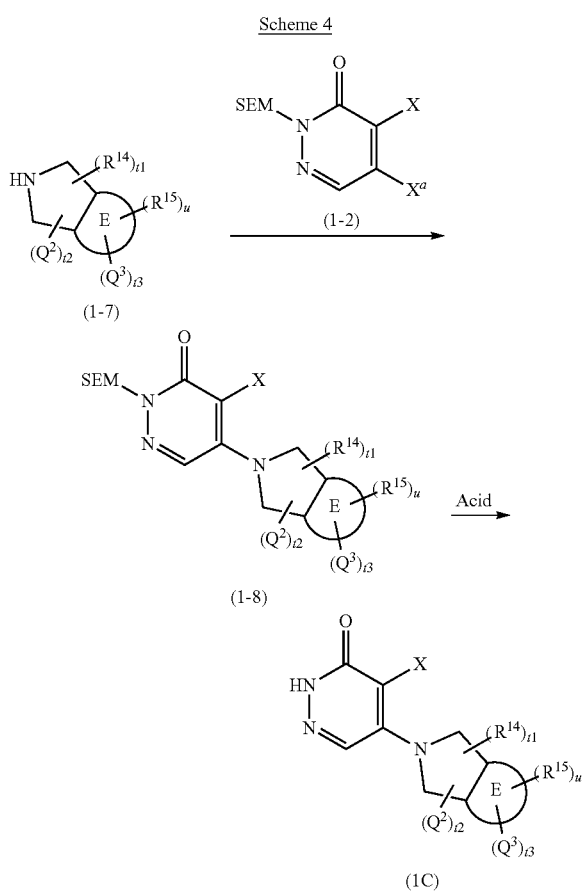

Methods of Use

Compounds of the invention can inhibit the activity of PARP7. For example, the compounds of the invention can be used to inhibit activity of PARP7 in a cell or in an individual or patient in need of inhibition of the enzyme by administering an inhibiting amount of a compound of the invention to the cell, individual, or patient.

As PARP7 inhibitors, the compounds of the invention are useful in the treatment of various diseases associated with abnormal expression or activity of PARP7. For example, the compounds of the invention are useful in the treatment of cancer. In some embodiments, the cancers treatable according to the present invention include breast, central nervous system, endometrium, kidney, large intestine, lung, oesophagus, ovary, pancreas, prostate, stomach, head and neck (upper aerodigestive), urinary tract, colon, and others.

In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

Other cancers treatable by the administration of the compounds of the invention include liver cancer (e.g., hepatocellular carcinoma), bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, head and neck cancer (upper aerodigestive cancer), intestinal cancers, Kaposi's sarcoma, kidney cancer, laryngeal cancer, liver cancer (e.g., hepatocellular carcinoma), lung cancer, prostate cancer, rectal cancer, skin cancer, stomach cancer, testicular cancer, thyroid cancer, and uterine cancer.

In some embodiments, the cancer treatable by administration of the compounds of the invention is multiple myeloma, DLBCL, hepatocellular carcinoma, bladder cancer, esophageal cancer, head and neck cancer (upper aerodigestive cancer), kidney cancer, prostate cancer, rectal cancer, stomach cancer, thyroid cancer, uterine cancer, and breast cancer.

The PARP7 inhibitors of the invention may also have therapeutic utility in PARP7-related disorders in disease areas such as cardiology, virology, neurodegeneration, inflammation, and pain, particularly where the diseases are characterized by overexpression or increased activity of PARP7.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PARP7 or "contacting" a cell with a compound of the invention includes the administration of a compound of the present invention to an individual or patient, such as a human, having PARP7, as well as, for example, introducing a compound of the invention into a sample containing a cellular or purified preparation containing PARP7.

As used herein, the term "individual" or "patient," used interchangeably, refers to mammals, and particularly humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease.

Combination Therapy

One or more additional pharmaceutical agents or treatment methods such as, for example, chemotherapeutics or other anti-cancer agents, immune enhancers, immunosuppressants, immunotherapies, radiation, anti-tumor and anti-viral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to checkpoint or costimulatory molecules such as CTLA-4, PD-1, PD-L1 or 4-1BB, respectively, or antibodies to cytokines (IL-10, TGF-β, etc.). Exemplary cancer immunotherapy antibodies include pembrolizumab, ipilimumab, nivolumab, atezolizumab and durvalumab. Additional anti-cancer agent(s) include antibody therapeutics directed to surface molecules of hematological cancers such as ofatumumab, rituximab and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, anti-cancer agents, vaccines, antibodies, immune enhancers, immune suppressants, anti-inflammatory agents and the like.

EXAMPLES

Equipment:

$^1$H NMR Spectra were recorded at 300 or 400 MHz using a Bruker AVANCE 300 MHz/400 MHz spectrometer. NMR interpretation was performed using Bruker Topspin software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

1. LC (basic condition): Shimadzu LC-20AD, Binary Pump, Diode Array Detector. Column: Kinetex 2.6 m EVO C18 100 A, 50*3.0 mm, 2.6 um. Mobile phase: A: Water/5 mM NH$_4$HCO$_3$, B: Acetonitrile. Flow Rate: 1.2 mL/min at 40° C. Detector: 254 nm, 220 nm. Gradient stop time, 2.9 min. Timetable:

| T (min) | A (%) | B (%) |
| --- | --- | --- |
| 0.01 | 90 | 10 |
| 2.10 | 5 | 95 |
| 2.70 | 5 | 95 |
| 2.90 | 90 | 10 |

2. LC (acidic condition): Shimadzu LC-20AD, Binary Pump, Diode Array Detector. Column: Ascentis Express C18, 50*3.0 mm, 2.7 um. Mobile phase: A: Water/0.05% TFA, B: Acetonitrile/0.05% TFA. Flow Rate: 1.5 mL/min at 40° C. Detector: 254 nm, 220 nm. Gradient stop time, 2.9 min. Timetable:

| T (min) | A (%) | B (%) |
| --- | --- | --- |
| 0.01 | 90 | 5 |
| 2.10 | 5 | 95 |
| 2.70 | 5 | 95 |
| 2.90 | 90 | 5 |

1. S:LCMS-2020, Quadrupole LC/MS, Ion Source: ES-API, TIC: 90~900 m/z, Fragmentor: 60, Drying gas flow: 15 L/min, Nebulizing Gas Flow: 1.5 L/min, Drying gas temperature: 250° C., Vcap: 1100V
2. Sample preparation: samples were dissolved in ACN or methanol at 1-10 mg/mL, then filtered through a 0.22 µm filter membrane. Injection volume: 1~10 µL.

XRPD Analysis:

For XRPD analysis, PANalytical Empyrean/X' Pert3 X-ray powder diffractometers were used. The XRPD parameters used are listed below:

| XRPD Parameters | | | |
|---|---|---|---|
| Parameters | CPE-026 (Reflection Mode) | CPE-135 (Reflection Mode) | CPE-221 (Reflection Mode) |
| Model | Empyrean | X' Pert3 | X' Pert3 |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA | 45 kV, 40 mA |
| Divergence slit | Automatic | ⅛° | ⅛° |
| Scan mode | Continuous | Continuous | Continuous |
| Scan range (2θ/°) | 3°~40° | 3°~40° | 3°~40° |
| Step size (2θ/°) | 0.0167 | 0.0263 | 0.0263 |
| Scan step time (s) | 17.780 | 46.665 | 39.525 |
| Test time (s) | 5 min 30 s | 5 min 04 s | 4 min 27 s |

The term "2Th" refers to 2-theta. The term "FWIM" refers to full width at half maximum. The term "rel. int." refers to relative intensity.

DSC/TGA Analysis:

TGA data were collected using a TA Q5000/Q5500 TGA from TA Instruments. DSC was performed using a TA Q2000/Q2500 DSC from TA Instruments. Detailed parameters used are listed below:

| Parameters for TGA and DSC | | |
|---|---|---|
| Parameters | TGA | DSC |
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

DVS Analysis:

DVS was measured via a SMS (Surface Measurement Systems) DVS Intrinsic. The relative humidity at 25° C. were calibrated against deliquescence point of LiCl, $Mg(NO_3)_2$ and KCl. Parameters for DVS test are listed below:

| Parameters for DVS test | |
|---|---|
| Parameters | DVS |
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 95% RH-0% RH-95% RH |
| RH step size | 10% (90% RH-0% RH-90% RH) 5% (95% RH-90% RH and 90% RH-95% RH) |

RH = relative humidity.
dm/dt = rate of change in moisture content over time.

Definitions

ACN (acetonitrile); $Ac_2O$ (acetic anhydride); AIBN (2,2'-azobis(2-methylpropionitrile); BHMPO (N1,N2-bis(4-hydroxy-2,6-dimethylphenyl)oxalamide); Boc (tert-butoxycarbonyl); $Boc_2O$ (di-tert-butyl dicarbonate); CAN (cerium (IV) ammonium nitrate); CsF (cesium fluoride); CuI (copper iodide); $CCl_4$ (carbon tetrachloride); $CH_3CN$ (acetonitrile); $CDCl_3$ (deuterated chloroform); $CD_3OD$ (deuterated methanol); $Cu(acac)_2$ (copper(II) acetylacetonate); Dess Martin (1,1,1-Tris(acetyloxy)-1,1-dihydro-1,2-benziodoxol-3-(1H)-one); DBU (1,8-diazabicyclo[5.4.0]undec-7-ene); DCM (dichloromethane); DEA (diethylamine); DEAD (diethyl azodicarboxylate); DIAD (diisopropyl azodicarboxylate); DIPEA (N,N-diisopropylethylamine); DMF (N,N-dimethylformamide); DMAP (4-dimethyl aminopyridine); DMSO (dimethylsulfoxide); DMSO-$d_6$ (deuterated dimethylsulfoxide); DPPA (diphenylphosphoryl azide); eq (equivalent); EDCI (1-ethyl-3-(3-dimethylaminopropyl)carbodiimide); EtOAc (ethyl acetate); EtOH (ethanol); g (gram); h (hour); Grubbs 2nd generation catalyst (1,3-Bis(2,4,6-trimethylphenyl)-2-imidazolidinylidene)dichloro(phenylmethylene)(tricyclohexylphosphine)ruthenium; (HATU (1-[bis (dimethylamino)methylene]-1H-1,2,3-triazolo[4,5-b] pyridinium 3-oxide hexafluorophosphate); HOBT (hydroxybenzotriazole); $^1$H NMR (proton nuclear magnetic resonance); HCl (hydrochloric acid); Hz (hertz); IPA (isopropyl alcohol); $K_2CO_3$ (potassium carbonate); L (litre); LiCl (lithium chloride); LCMS (liquid chromatography-mass spectrometry); M (molar); MeOH (methanol); mg (milligrams); MHz (megahertz); min (minutes); MtBE (methyl tert-butyl ether); mL (milliliters), mmol (millimoles); $Ms_2O$ (methanesulfonic anhydride); NaCl (sodium chloride); NaH (sodium hydride); NaHMDS (sodium bis (trimethylsilyl)amide); $NH_4Cl$ (ammonium chloride); $NaN_3$ (sodium azide); NBS (N-bromo succinimide); NMP (N-methyl-2-pyrrolidone); $Pd(allyl)Cl_2$ (Bis(η3-allyl)di(μ-chloro)dipalladium(II)); $Pd(dppf)Cl_2$ ([1,1'-Bis(diphenylphosphino)ferrocene]dichloropalladium(II)); prep-HPLC (preparative high-performance liquid chromatography); ppm (parts per million); PMB (4-methoxy benzyl); Rockphos (2-Di(tert-butyl)phosphino-2,4,6'-triisopropyl-3-methoxy-6-methylbiphenyl)); RT (room temperature); SEM (2-(trimethylsilyl)ethoxymethyl); SEMCl (2-(trimethylsilyl)ethoxymethyl chloride); TBAF (tetrabutyl ammonium fluoride); TEA (triethyl amine); THF (tetrahydrofuran); TsCl (tosyl chloride); tR (retention time); T3P (1-propanephosphonic anhydride); TfOH (trifluoromethanesulfonic acid); TFA (trifluoroacetic acid); TLC (thin layer chromatography); TMSI (iodotrimethyl silane); v/v (volume/volume).

Synthesis of Intermediates

Int-A1: 2-(Piperazin-1-yl)pyrimidine-5-carbonitrile Dihydrochloride

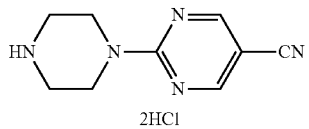 [SMILES: N#Cc1cnc(N2CCNCC2)nc1]

Step 1: Tert-butyl 4-(5-cyanopyrimidin-2-yl)piperazine-1-carboxylate

A solution of 2-chloropyrimidine-5-carbonitrile (5 g, 35.83 mmol, 1 equiv), tert-butyl piperazine-1-carboxylate (6.7 g, 35.97 mmol, 1.00 equiv) and $K_2CO_3$ (9.9 g, 71.63 mmol, 2.00 equiv) in NMP (80 mL) was stirred for 1 h at 80° C. The resulting mixture was diluted with 1 L of water, and the solids were collected by filtration and dried by oven to afford 8.4 g of the title compound as a white solid. LCMS: $[M+H]^+$ 290.15.

Step 2: 2-(Piperazin-1-yl)pyrimidine-5-carbonitrile Dihydrochloride

A solution of tert-butyl 4-(5-cyanopyrimidin-2-yl)piperazine-1-carboxylate (8.4 g, 29.03 mmol, 1 equiv) in HCl/dioxane (40 mL, 4M) was stirred for 1 h at RT, and then the resulting solution was concentrated under vacuum to afford 6.4 g (76%) of the title compound as a white solid. LCMS: $[M+H]^+$ 190.10.

Int-A2: 2-(Piperazin-1-yl)-5-(trifluoromethyl)pyrimidine Dihydrochloride

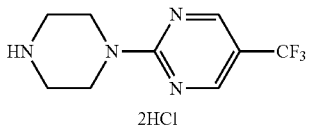 [SMILES: FC(F)(F)c1cnc(N2CCNCC2)nc1]

Step 1: Tert-butyl 4-[5-(trifluoromethyl)pyrimidin-2-yl]piperazine-1-carboxylate A solution of 2-chloro-5-(trifluoromethyl)pyrimidine (100 g, 550 mmol, 1.05 equiv), tert-butyl piperazine-1-carboxylate (96.7 g, 520 mmol, 1 equiv), and $K_2CO_3$ (151.8 g, 1100 mmol, 2 equiv) in NMP (800 mL) was stirred for 1 h at 80° C. followed by the addition of 2.5 L of $H_2O$. The solids were collected by filtration to afford 190 g (94%) of the title compound as a white solid. LCMS: $[M+H]^+$ 333.16.

Step 2: 2-(Piperazin-1-yl)-5-(trifluoromethyl)pyrimidine

A solution of tert-butyl 4-[5-(trifluoromethyl)pyrimidin-2-yl]piperazine-1-carboxylate (190 g, 571.73 mmol, 1 equiv) in HCl/dioxane (800 mL/4M) was stirred for 1 h at RT. The solids were collected by filtration to afford 154 g (99%) of the title compound as a white solid. LCMS: $[M+H]^+$ 199.08.

Int-A3: 5-Chloro-2-(piperazin-1-yl)pyrimidine Dihydrochloride

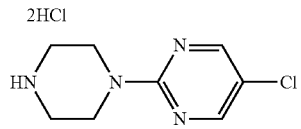 [SMILES: Clc1cnc(N2CCNCC2)nc1]

Step 1: Tert-butyl 4-(5-cyanopyridin-2-yl)piperazine-1-carboxylate

A solution of 2,5-dichloropyrimidine (19.4 g, 13.00 mmol, 1.05 equiv), tert-butyl piperazine-1-carboxylate (23 g, 12.40 mmol, 1 equiv), and $K_2CO_3$ (34 g, 25.00 mmol, 2 equiv) in NMP (500 mL) was stirred for 1 h at 80° C. followed by the addition of 600 mL of $H_2O$ which was added to the resulting solution. The solids were collected by filtration to afford 41 g crude of the title compound as a white solid. LCMS: $[M+H]^+$ 299.13.

Step 2: 5-Chloro-2-(piperazin-1-yl)pyrimidine Dihydrochloride

A solution of tert-butyl 4-(5-chloropyrimidin-2-yl)piperazine-1-carboxylate (41 g, 14.00 mmol, 1 equiv) in HCl/dioxane (500 mL/4M) was stirred for 1 h at RT. The solids were collected by filtration to afford 26.7 g of the title compound as a white solid. LCMS: $[M+H]^+$ 199.08.

Int-A4: 6-(Piperazin-1-yl)pyridine-3-carbonitrile Dihydrochloride

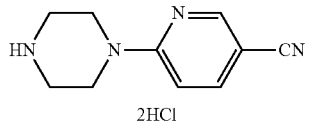 [SMILES: N#Cc1ccc(N2CCNCC2)nc1]

Step 1: Tert-butyl 4-(5-cyanopyridin-2-yl)piperazine-1-carboxylate

A solution of 6-chloropyridine-3-carbonitrile (90 g, 650 mmol, 1.05 equiv), tert-butyl piperazine-1-carboxylate (114.3 g, 620 mmol, 1 equiv), and $K_2CO_3$ (171.1 g, 124 mmol, 2 equiv) in NMP (500 mL) was stirred for 1 h at 80° C. followed by the addition of 1.5 L of $H_2O$ which was added to the resulting solution. The solids were collected by filtration to afford 195 g of title compound as a white solid. LCMS: $[M+H]^+$ 289.17.

Step 2: 6-(Piperazin-1-yl)pyridine-3-carbonitrile Dihydrochloride

Tert-butyl 4-(5-cyanopyridin-2-yl)piperazine-1-carboxylate (195 g, 680 mmol, 1 equiv) and HCl/dioxane (800 mL/4M) was stirred for 1 h at RT. The solids were collected

Int-A5: 1-(5-Chloropyridin-2-yl)piperazine Dihydrochloride

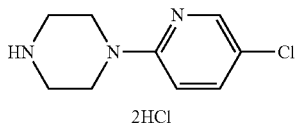 [SMILES: Clc1ccc(N2CCNCC2)nc1]

Step 1: Tert-butyl 4-(5-chloropyridin-2-yl)piperazine-1-carboxylate

A solution of tert-butyl piperazine-1-carboxylate (10 g, 53.69 mmol, 1.00 equiv), NMP (30 mL), potassium carbonate (13.4 g, 96.95 mmol, 1.80 equiv), and 2,5-dichloropyridine (8.7 g, 58.79 mmol, 1.10 equiv) was stirred for 20 h at 110° C. To the reaction mixture was then added 500 mL of H$_2$O. The solids were collected by filtration to afford 10.2 g (64%) of the title compound as a light yellow solid. LCMS: [M+H]$^+$ 298.12.

Step 2: 1-(5-Chloropyridin-2-yl)piperazine Dihydrochloride

A solution of tert-butyl 4-(5-chloropyridin-2-yl)piperazine-1-carboxylate (10.2 g, 34.25 mmol, 1.00 equiv) and HCl/dioxane (50 mL/4M) was stirred for 1 h at RT. The solids were collected by filtration to afford 7.4 g (800%) of the title compound as a light yellow solid. LCMS: [M+H]$^+$ 198.07.

Int-A6: 5-Chloro-4-(trifluoromethyl)-2-((2-(trimethylsilyl)ethoxy)methyl)pyridazin-3(2H)-one

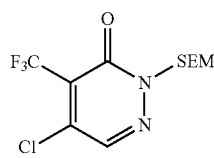

Step 1: 4,5-Dibromo-2-[[2-(trimethylsilyl)ethoxy]methyl]-2,3-dihydropyridazin-3-one To a solution of 4,5-dibromo-2,3-dihydropyridazin-3-one (3500 g, 13.78 mol, 1.00 equiv) in DMF (30 L) was added sodium hydride (400 g, 16.56 mol, 1.20 equiv) in batches at 0° C. under nitrogen. The resulting solution was stirred for 1 h at RT followed by addition of [2-(chloromethoxy)ethyl]trimethylsilane (2500 g, 15.2 mol, 1.10 equiv) dropwise at 0° C. The reaction mixture was stirred for 2 h at RT. The reaction was then quenched by the addition of 30 L of water. The resulting solution was extracted with 3×50 L of EtOAc and the organic layers combined. The organic layers were washed with 3×30 L of brine, dried over anhydrous sodium sulfate and concentrated under reduced pressure to afford 4.2 kg of title compound. LCMS: [M+H]$^+$ 384.70.

Step 2: 4-Bromo-5-chloro-2-[[2-(trimethylsilyl)ethoxy]methyl]-2,3-dihydropyridazin-3-one To a solution of 4,5-dibromo-2-[[2-(trimethylsilyl)ethoxy]methyl]-2,3-dihydropyridazin-3-one (2200 g, 5.73 mol, 1.00 equiv) in NMP (6 L) was added chlorolithium (231 g, 5.73 mol, 1.00 equiv) and the resulting solution was stirred for 4 h at 95° C. This reaction was repeated again with a 2000 g scale batch. After completion, the two batch reactions were combined and then diluted by the addition of 10 L of water, extracted with 3×20 L of EtOAc and the organic layers combined. The organic layers were washed with 3×20 L of brine, dried over anhydrous sodium sulfate and concentrated under reduced pressure. The residue was purified by column chromatography (EtOAc:petroleum ether, 1:50, v/v). In total, from 4.2 kg of 4,5-dibromo-2-[[2-(trimethylsilyl)ethoxy]methyl]-2,3-dihydropyridazin-3-one material starting material, 2.2 kg (59% yield) of title compound was obtained. LCMS: [M+H]$^+$ 340.90.

Step 3: 5-Chloro-4-(trifluoromethyl)-2-[[2-(trimethylsilyl)ethoxy]methyl]-2,3-dihydropyridazin-3-one To a solution of 4-bromo-5-chloro-2-[[2-(trimethylsilyl)ethoxy]methyl]-2,3-dihydropyridazin-3-one (1100 g, 3.23 mol, 1.00 equiv) in NMP (6 L) at RT was added CuI (56 g, 0.64 mol, 0.20 equiv) followed by dropwise addition of methyl 2,2-difluoro-2-(fluorosulfonyl)acetate (1865 g, 9.7 mol, 3.00 equiv). The resulting solution was stirred for 2 h at 80° C. The reaction was then quenched by the addition of 10 L of water and extracted with 3×10 L of EtOAc. The organic layers were combined and washed with 3×10 L of brine, dried over anhydrous sodium sulfate, and concentrated under reduced pressure. The residue was purified by column chromatography (EtOAc/petroleum ether, 1/100, v/v) to afford 1030 g (76%) of the title compound. LCMS: [M+H]$^+$ 329.00. $^1$H NMR (300 MHz, CDCl$_3$) δ 7.82 (s, 1H), 5.50 (d, J=27.3 Hz, 2H), 3.74 (dt, J=12.9, 8.2 Hz, 2H), 0.97 (td, J=8.3, 5.0 Hz, 2H), 0.01 (d, J=2.1 Hz, 9H).

Int-A7: 4,5-Dichloro-2-[[2-(trimethylsilyl)ethoxy]methyl]-2,3-dihydropyridazin-3-one

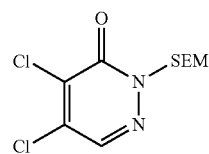

A solution of 4,5-dichloro-2,3-dihydropyridazin-3-one (10 g, 60.62 mmol, 1 equiv) in DMF (40 mL) was stirred at 0° C. and NaH (2.9 g, 121.23 mmol, 2 equiv) was added at 0° C. in several batches. The mixture was stirred for 30 min at 0° C. followed by the addition of [2-(chloromethoxy)ethyl]trimethylsilane (13 g, 78.80 mmol, 1.3 equiv) slowly at 0° C. The resulting solution was stirred for an additional 10 min at 0° C. The reaction was then quenched by the addition of 100 mL of water. The resulting solution was extracted with 2×80 mL of EtOAc and the organic layers combined. The resulting solution was extracted with 3×60 mL of NaCl (aq) and the organic layers combined and concentrated under vacuum. The residue was applied onto a silica gel column eluting with EtOAc/petroleum ether (4/96) to afford 9 g (50%) of the title compound as a yellow oil. LCMS: [M−Cl]+295.04.

Int-A8: 4,5-Dibromo-2-[[2-(trimethylsilyl)ethoxy] methyl]-2,3-dihydropyridazin-3-one

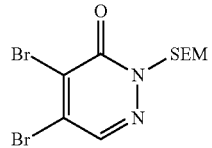 [SMILES: C[Si](C)(C)CCOCn1ncc(Br)c(Br)c1=O]

To a solution of 4,5-dibromo-2,3-dihydropyridazin-3-one (3500 g, 13.78 mol, 1.00 equiv) in DMF (30 L) was added NaH (400 g, 16.56 mol, 1.20 equiv) in batches at 0° C. under nitrogen. The resulting solution was stirred for 1 h at RT, then dropwise 2-(chloromethoxy)ethyl]trimethylsilane (2500 g, 15.2 mol, 1.10 equiv) was added at 0° C. and stirred for 2 h at RT. The reaction was then quenched by the addition of 30 L of water. The resulting solution was extracted with 3×50 L of EtOAc and the organic layers combined. The organic layers were washed with 3×30 L of brine, dried over anhydrous sodium sulfate and concentrated under vacuum to afford 4.2 kg of title compound. LCMS: [M+H]+ 384.70.

Int-A9: 3-[2-[(5-Chloro-6-oxo-1,6-dihydro-pyridazin-4-yl)oxy]ethoxy]propanoic Acid

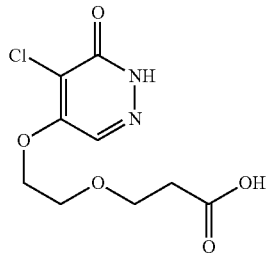 [SMILES: O=C(O)CCOCCOc1cn[nH]c(=O)c1Cl]

Step 1: Tert-butyl 3-[2-[(5-chloro-6-oxo-1-[[2-(trimethylsilyl)ethoxy]methyl]-1,6-dihydropyridazin-4-yl) oxy]ethoxy]propanoate A solution of tert-butyl 3-(2-hydroxyethoxy)propanoate (778.8 mg, 4.09 mmol, 1.00 equiv), Cs₂CO₃ (2.66 g, 8.16 mmol, 2.00 equiv), and 4,5-dichloro-2-[2-(trimethylsilyl) ethoxy]methyl-2,3-dihydropyridazin-3-one (1.2 g, 4.06 mmol, 1.00 equiv) in ACN (15 mL) was stirred for 3 h at 80° C. The solids were filtered and the resulting mixture was concentrated under reduced pressure. The residue was purified by silica gel column chromatography with EtOAc/petroleum ether (1:1) to afford 200 mg (11%) of title compound as a white solid. LCMS: [M+H]+ 449.01.

Step 2: 3-[2-[(5-Chloro-6-oxo-1,6-dihydropyridazin-4-yl)oxy]ethoxy]propanoic Acid A solution of tert-butyl 3-[2-[(5-chloro-6-oxo-1-[[2-(trimethylsilyl)ethoxy]methyl]-1,6-dihydropyridazin-4-yl)oxy] ethoxy]propanoate (10 mg, 0.02 mmol, 1.00 equiv) in TFA (2 mL) and DCM (10 mL) was stirred for 0.5 h at RT. After completion, the crude product was directly concentrated under reduced pressure to afford 776 mg of title compound as a white solid. LCMS: [M+H]+ 263.01.

Int-A10: 3-[2-[(5-Chloro-6-oxo-1,6-dihydro-pyridazin-4-yl)amino]ethoxy]propanoic Acid

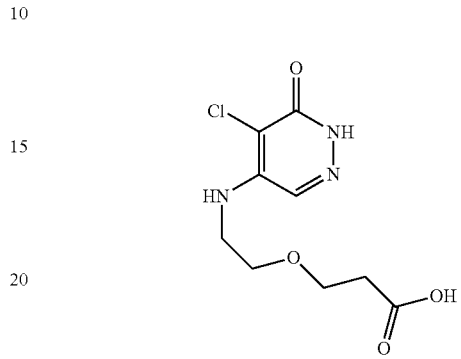

Step 1: Methyl 3-(2-(tert-butoxycarbonylamino)ethoxy)propanoate

A solution of tert-butyl N-(2-hydroxyethyl)carbamate (6 g, 37.2 mmol, 1.00 equiv), sodium hydride (2 g, 83.3 mmol, 1.50 equiv), methyl 3-bromopropanoate (6.18 g, 37.0 mmol, 1.00 equiv) in THF (40 mL) was stirred overnight at 25° C. The resulting mixture was concentrated under reduced pressure and the residue was purified by silica gel column chromatography eluting with EtOAc/petroleum ether (1:3, v:v) to afford 1.6 g (17%) of title compound as a colorless oil. LCMS: [M+H]+ 248.14.

Step 2: Methyl 3-(2-aminoethoxy)propanoate Hydrochloride

A solution of 3 methyl 3-(2-[[(tert-butoxy)carbonyl] amino]ethoxy)propanoate (1.6 g, 6.47 mmol, 1.00 equiv) in HCl/dioxane (20 mL/4M) was stirred for 1 h at 25° C. The resulting mixture was concentrated under vacuum to afford 900 mg (95%) of title compound as a colorless oil. LCMS: [M+H]+ 148.09.

Step 3: Methyl 3-[2-[(5-chloro-6-oxo-1,6-dihydro-pyridazin-4-yl)amino]ethoxy]propanoate A solution of methyl 3-(2-aminoethoxy)propanoate (955 mg, 6.5 mmol, 1.00 equiv), 4,5-dichloro-2,3-dihydro-pyridazin-3-one (1.06 g, 6.43 mmol, 1.00 equiv), and TEA (1.95 g, 19.3 mmol, 3.00 equiv) in EtOH (20 mL) was stirred overnight at 80° C. The resulting mixture was concentrated under reduced pressure and purified by silica gel column chromatography eluting with EtOAc/petroleum ether (3:1) to afford 1.2 g (67%) of title compound as a yellow oil. LCMS: [M+H]+ 276.07.

Step 4: 3-[2-[(5-Chloro-6-oxo-1,6-dihydropyridazin-4-yl)amino]ethoxy]propanoic Acid A solution of methyl 3-[2-[(5-chloro-6-oxo-1,6-dihydro-pyridazin-4-yl)amino]ethoxy]propanoate (1.2 g, 4.35 mmol, 1.00 equiv) and LiOH.H₂O (488 mg, 11.6 mmol, 2.00 equiv)

in water (50 mL) and MeOH (50 mL) was stirred overnight at 50° C. The resulting mixture was concentrated under reduced pressure to afford 800 mg (70%) of title compound as a yellow oil. LCMS: [M+H]+ 262.05.

Int-A11: 3-(2-[[6-Oxo-5-(trifluoromethyl)-1,6-dihydropyridazin-4-yl]oxy]ethoxy)propanoic Acid

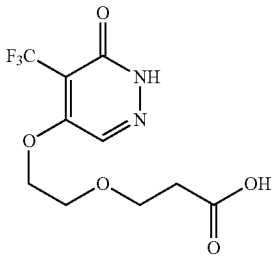 [SMILES: O=C(O)CCOCCOc1cn[nH]c(=O)c1C(F)(F)F]

Step 1: Tert-butyl 3-(2-[[6-oxo-5-(trifluoromethyl)-1-[[2-(trimethylsilyl)ethoxy]methyl]-1,6-dihydropyridazin-4-yl]oxy]ethoxy)propanoate A solution of Int-A6 (1.1 g, 3.4 mmol, 1 equiv), Cs$_2$CO$_3$ (2.2 g, 6.8 mmol, 2 equiv), tert-butyl 3-(2-hydroxyethoxy)propanoate (649.2 mg, 3.41 mmol, 1 equiv) in MeCN (20 mL) was stirred for 18 h at RT. The resulting mixture was concentrated under reduced pressure. The residue was applied onto a silica gel column eluting with EtOAc/petroleum ether (16/84) to afford 1 g (61%) of title compound as a yellow oil. LCMS: [M+H]+ 483.21.

Step 2: 3-(2-[[6-Oxo-5-(trifluoromethyl)-1,6-dihydropyridazin-4-yl]oxy]ethoxy)propanoic Acid A solution of tert-butyl 3-(2-[[6-oxo-5-(trifluoromethyl)-1-[[2-(trimethylsilyl)ethoxy]methyl]-1,6-dihydropyridazin-4-yl]oxy]ethoxy)propanoate (450 mg, 0.93 mmol, 1 equiv) and TFA (1 mL) in DCM (10 mL) was stirred for 3 h at RT. The resulting mixture was concentrated under reduced pressure and the residue was purified by C18 reverse phase chromatography eluting with H$_2$O/CH$_3$CN to afford 110 mg (40%) of title compound as a white oil. LCMS: [M+H]+ 297.06.

Int-A12: 3-(2-[[6-Oxo-5-(trifluoromethyl)-1,6-dihydropyridazin-4-yl]amino]ethoxy)propanoic Acid Step 1: Methyl 3-(2-aminoethoxy)propanoate A solution of methyl 3-(2-[[(tert-butoxy)carbonyl]amino]ethoxy)propanoate (800 mg, 3.24 mmol, 1 equiv) in HCl/dioxane (10 mL) was stirred for 30 min at RT. The resulting mixture was concentrated under reduced pressure to afford 476 mg of title compound as a yellow crude oil. LCMS: [M+H]+ 148.09.

Step 2: Methyl 3-(2-[[6-oxo-5-(trifluoromethyl)-1-[[2-(trimethylsilyl)ethoxy]methyl]-1,6-dihydropyridazin-4-yl]amino]ethoxy)propanoate A solution of methyl 3-(2-aminoethoxy)propanoate (476 mg, 3.23 mmol, 1 equiv), TEA (981.8 mg, 9.70 mmol, 3 equiv), and Int-A6 (1.06 g, 3.23 mmol, 1 equiv) in EtOH (10 mL) was stirred for 60 min at RT. The resulting mixture was concentrated under vacuum. The residue was purified by silica gel column chromatography eluting with EtOAc/petroleum ether (28/72, v/v) to afford 259 mg (18%) of title compound as a yellow oil. LCMS: [M+H]+ 440.18.

Step 3: Methyl 3-(2-[[6-oxo-5-(trifluoromethyl)-1,6-dihydropyridazin-4-yl]amino]ethoxy)propanoate A solution of methyl 3-(2-[[6-oxo-5-(trifluoromethyl)-1-[[2-(trimethylsilyl)ethoxy]methyl]-1,6-dihydropyridazin-4-yl]amino]ethoxy)propanoate (259 mg, 0.59 mmol, 1 equiv) in HCl/dioxane (10 mL/4M) was stirred for 16 h at RT. The resulting mixture was concentrated under reduced pressure to afford 182 mg of title compound as a yellow oil. LCMS: [M+H]+ 310.09.

Step 4: 3-(2-[[6-Oxo-5-(trifluoromethyl)-1,6-dihydropyridazin-4-yl]amino]ethoxy)propanoic Acid A solution of methyl 3-(2-[[6-oxo-5-(trifluoromethyl)-1,6-dihydropyridazin-4-yl]amino]ethoxy)propanoate (182 mg, 0.59 mmol, 1 equiv) and LiOH.H$_2$O (123.5 mg, 2.94 mmol, 5 equiv) in MeOH (5 mL) and H$_2$O (1 mL) was stirred for 3 h at RT. The pH value of the solution was adjusted to 7 with aqueous HCl. The resulting solution was extracted with 3×3 mL of DCM and the aqueous layers combined and concentrated under vacuum. After concentration, the residue was purified by C18 reverse phase chromatography eluting with H$_2$O/ACN to afford 100 mg (58%) of title compound as a white solid. LCMS: [M+H]+ 296.08.

Int-A13: 3-[(2S)-2-[[6-Oxo-5-(trifluoromethyl)-1,6-dihydropyridazin-4-yl]amino]propoxy]propanoic Acid

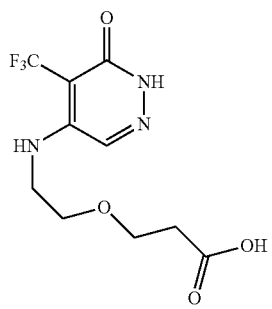 [SMILES: O=C(O)CCOCCNc1cn[nH]c(=O)c1C(F)(F)F]

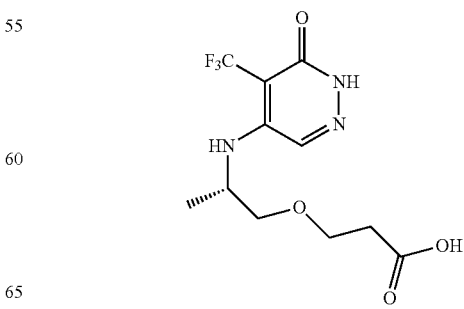

Step 1: 5-[[(2S)-1-Hydroxypropan-2-yl]amino]-4-(trifluoromethyl)-2-[[2-(trimethylsilyl)ethoxy]methyl]-2,3-dihydropyridazin-3-one A solution of Int-A6 (8 g, 24 mmol, 1 equiv), TEA (2.463 g, 24 mmol, 1 equiv), and (2S)-2-aminopropan-1-ol (1.829 g, 24 mmol, 1 equiv) in EtOH (60 mL) was stirred for 1 h at 60° C. The solvent was concentrated under vacuum and the residue was applied onto a silica gel column eluting with EtOAc/petroleum ether (1/1) to afford 5.39 g (58%) of title compound as a yellow oil. LCMS [M+H]+ 367.44.

Step 2: 3-[(2S)-2-[[6-Oxo-5-(trifluoromethyl)-1-[[2-(trimethylsilyl)ethoxy]methyl]-1,6-dihydro-pyridazin-4-yl]amino]propoxy]propanoate A solution of 5-[[(2S)-1-hydroxypropan-2-yl]amino]-4-(trifluoromethyl)-2-[[2-(trimethylsilyl)ethoxy]methyl]-2,3-dihydropyridazin-3-one (5.39 g, 15 mmol, 1 equiv), methyl prop-2-enoate (13.24 g, 147 mmol, 10 equiv), and Cs$_2$CO$_3$ (4.773 g, 15 mmol, 1 equiv) in MeCN (50 mL) was stirred for 4 h at 25° C. The solvent was concentrated under vacuum, the residue was applied onto a silica gel column eluting with EtOAc/petroleum ether (1/1) to afford 3.12 g (42%) of title compound as a white solid. LCMS [M+H]+ 454.53.

Step 3: 3-[(2S)-2-[[6-Oxo-5-(trifluoromethyl)-1,6-dihydropyridazin-4-yl]amino]propoxy]propanoate A solution of methyl 3-[(2S)-2-[[6-oxo-5-(trifluoromethyl)-1-[[2-(trimethyl silyl)ethoxy]methyl]-1,6-dihydropyridazin-4-yl]amino]propoxy]propanoate (3.12 g, 1 equiv) and TFA (10 mL) in DCM (40 mL) was stirred 0.5 h at 25° C. The resulting mixture was concentrated under vacuum to afford 2.1 g (93%) of title compound as a white solid.

Step 4: 3-[(2S)-2-[[6-Oxo-5-(trifluoromethyl)-1,6-dihydropyridazin-4-yl]amino]propoxy]propanoic Acid A solution of methyl 3-[(2S)-2-[[6-oxo-5-(trifluoromethyl)-1,6-dihydropyridazin-4-yl]amino]propoxy]propanoate (2.12 g, 7 mmol, 1 equiv), LiOH.H$_2$O (1.378 g, 33 mmol, 5 equiv) in MeOH (15 mL) and H$_2$O (15 mL) was stirred for 0.5 h at 25° C. The pH value of the solution was adjusted to 6 with TFA. The resulting mixture was concentrated under vacuum and the residue was purified by C18 reverse phase chromatography eluting with H$_2$O/CH$_3$CN (6:1) to afford 2.1 g (90%) of title compound as a yellow oil. LCMS [M+H]+ 310.25.

Int-A14: 3-[2-[(5-Bromo-6-oxo-1,6-dihydro-pyridazin-4-yl)oxy]ethoxy]propanoic Acid

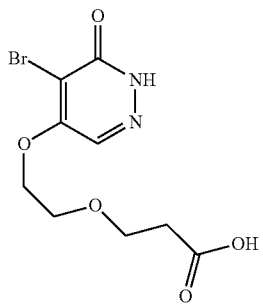 [SMILES: O=C(O)CCOCCOc1cn[nH]c(=O)c1Br]

Step 1: Tert-butyl 3-[2-[(5-bromo-6-oxo-1-[[2-(trimethylsilyl)ethoxy]methyl]-1,6-dihydropyridazin-4-yl)oxy]ethoxy]propanoate A solution of Int-A8 (4 g, 10.4 mmol, 1.0 equiv), tert-butyl 3-(2-hydroxyethoxy)propanoate (1.99 g, 10.4 mmol, 1.0 equiv) and Cs$_2$CO$_3$ (6.82 g, 20.9 mmol, 2 equiv) in MeCN (30 mL) was stirred for 2 h at 60° C., and then the solid was filtered and the resulting solution was concentrated under reduced pressure. The residue was purified by silica gel column chromatography eluting with EtOAc/petroleum ether to afford 2.2 g (43%) of title compound as a light yellow oil. LCMS [M+H]+ 493.13, 495.13

Step 2: 3-[2-[(5-Bromo-6-oxo-1,6-dihydropyridazin-4-yl)oxy]ethoxy]propanoic Acid A solution of tert-butyl 3-[2-[(5-bromo-6-oxo-1-[[2-(trimethylsilyl)ethoxy]methyl]-1,6-dihydropyridazin-4-yl)oxy]ethoxy]propanoate (1.66 g, 1 equiv) and TFA (2 mL) in DCM (10 mL) was stirred for 2 h at RT, and then the resulting solution was concentrated under reduced pressure to afford 380 mg (37%) of title compound as a yellow oil. LCMS [M+H]+ 307.10.

Int-A15: 3-[2-[(5-Methyl-6-oxo-1,6-dihydro-pyridazin-4-yl)oxy]ethoxy]propanoic Acid

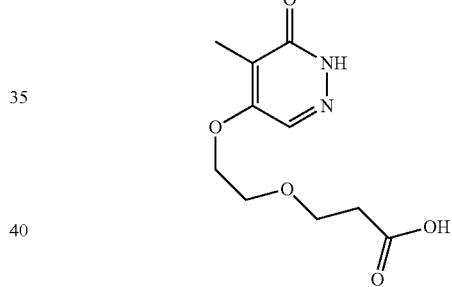

Step 1: Tert-butyl 3-(2-((5-methyl-6-oxo-1-((2-(trimethylsilyl)ethoxy)methyl)-1,6-dihydropyridazin-4-yl)oxy)ethoxy)propanoate A solution of tert-butyl 3-[2-[(5-bromo-6-oxo-1-[[2-(trimethylsilyl)ethoxy]methyl]-1,6-dihydropyridazin-4-yl)oxy]ethoxy]propanoate (2 g, 4.05 mmol, 1 equiv), methylboronic acid (485.2 mg, 8.11 mmol, 2 equiv), Pd(dppf)Cl$_2$ (296.6 mg, 0.41 mmol, 0.1 equiv), and CsF (1847.0 mg, 12.16 mmol, 3 equiv) in dioxane (15 mL) and H$_2$O (3 mL) was stirred for 2 h at 80° C. The solvent was concentrated under vacuum and the residue was applied onto a silica gel column eluting with EtOAc/petroleum ether to afford 1.5 g (86%) of title compound as a yellow oil. LCMS [M+H]+ 429.23.

Step 2: 3-[2-[(5-Methyl-6-oxo-1,6-dihydropyridazin-4-yl)oxy]ethoxy]propanoic Acid A solution of tert-butyl 3-[2-[(5-methyl-6-oxo-1-[[2-(trimethylsilyl)ethoxy]methyl]-1,6-dihydropyridazin-4-yl)oxy]ethoxy]propanoate (1.5 g, 1 equiv) in HCl/dioxane (30 mL/4M) was stirred overnight at 25° C. The resulting mixture was concentrated under reduced pressure to afford 800 mg (94%) of title compound as a yellow crude oil. LCMS [M+H]+ 243.09.

Int-A16: 3-[2-[(5-Cyano-6-oxo-1,6-dihydro-pyridazin-4-yl)oxy]ethoxy]propanoic Acid

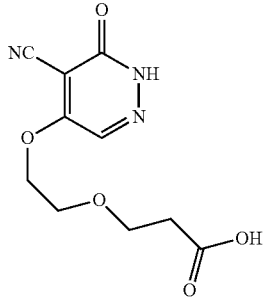 [SMILES: N#Cc1c(OCCOCCC(=O)O)cn[nH]c1=O]

Step 1: 3-[2-[(5-Bromo-6-oxo-1-[[2-(trimethylsilyl)ethoxy]methyl]-1,6-dihydropyridazin-4-yl)oxy]ethoxy]propanoate A solution of Int-A8 (4 g, 10.41 mmol, 1 equiv), Cs₂CO₃ (10.14 g, 31.12 mmol, 2.99 equiv), and tert-butyl 3-(2-hydroxyethoxy)propanoate (3.97 g, 20.87 mmol, 2.00 equiv) in DMF (40 mL) was stirred for 18 h at RT. The reaction was then quenched by the addition of 40 mL of water. The resulting solution was extracted with 3×50 mL of EtOAc and the organic layers combined and dried over anhydrous sodium sulfate. The organic layers were concentrated under vacuum and the residue was applied onto a silica gel column eluting with EtOAc/petroleum ether (1/9) to afford 2.2 g (43%) of title compound as a yellow oil. LCMS [M+H]+ 493.13, 495.13. 2 g of 4-bromo-5-(2-hydroxyethoxy)-2-((2-(trimethylsilyl)ethoxy)methyl)pyridazin-3 (2H)-one was isolated as a by-product of the reaction during purification and was used as a starting material for the synthesis of Int-A19, Step 1. LCMS [M+H]+: 365.05, 367.05.

Step 2: Tert-butyl 3-[2-[(5-cyano-6-oxo-1-[[2-(trimethylsilyl)ethoxy]methyl]-1,6-dihydropyridazin-4-yl)oxy]ethoxy]propanoate A solution of tert-butyl 3-[2-[(5-bromo-6-oxo-1-[[2-(trimethylsilyl)ethoxy]methyl]-1,6-dihydropyridazin-4-yl)oxy]ethoxy]propanoate (2.2 g, 4.46 mmol, 1 equiv), and CuCN (800 mg, 8.93 mmol, 2.00 equiv) in NMP (20 mL) was stirred for 23 h at 120° C. The reaction was then quenched by the addition of 20 mL of water and the resulting solution was extracted with 3×30 mL of EtOAc and the organic layers were combined and dried over anhydrous calcium chloride. The organic layers were concentrated under reduced pressure and the residue was purified by silica gel column chromatography with EtOAc/petroleum ether (3/7) to afford 800 mg (41%) of title compound as a yellow oil. LCMS [M+H]+ 254.07.

Step 3: 3-[2-[(5-Cyano-6-oxo-1,6-dihydropyridazin-4-yl)oxy]ethoxy]propanoic Acid A solution of tert-butyl 3-[2-[(5-cyano-6-oxo-1-[[2-(trimethylsilyl)ethoxy]methyl]-1,6-dihydropyridazin-4-yl)oxy]

ethoxy]propanoate (800 mg, 1.82 mmol, 1 equiv) in HCl/dioxane (10 mL/4M) was stirred 18 h at RT. The resulting mixture was concentrated under reduced pressure to afford 350 mg (76%) of title compound as a yellow crude oil. LCMS [M+H]+ 254.07.

Int-A17: 2-[5-(Hydroxymethyl)oxolan-2-yl]-1-[4-[5-(trifluoromethyl)pyridin-2-yl]piperazin-1-yl]ethan-1-one

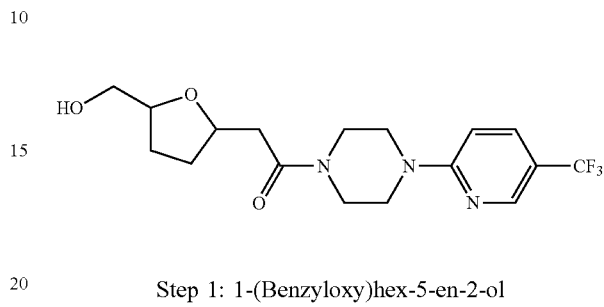

Step 1: 1-(Benzyloxy)hex-5-en-2-ol

To a solution of bromo(prop-2-en-1-yl)magnesium (27.4 mL, 1.50 equiv) in THF (20 mL) was added dropwise 2-[(benzyloxy)methyl]oxirane (3 g, 18.27 mmol, 1.00 equiv) under nitrogen at −40° C. The resulting solution was stirred for 1 h at −40° C. and the resulting solution was quenched by 100 mL with aqueous NH₄Cl, and extracted with 3×100 mL of EtOAc. The organic layers were combined, washed with 1×100 mL of brine, dried over anhydrous sodium sulfate and concentrated under vacuum. The residue was applied onto a silica gel column eluting with EtOAc/petroleum ether (1:5) to afford 2.16 g (57%) of title compound as a yellow oil. LCMS [M+H]+ 207.13.

Step 2: Methyl (2Z)-7-(benzyloxy)-6-hydroxyhept-2-enoate

Under nitrogen, a solution of 1-(benzyloxy)hex-5-en-2-ol (2 g, 9.70 mmol, 1.00 equiv), methyl prop-2-enoate (4.17 g, 48.44 mmol, 5.00 equiv) and Grubbs 2nd generation catalyst (82 mg, 0.01 equiv) in DCM (25 mL) was stirred for 4 h at 40° C. The resulting solution was concentrated under vacuum and the residue was purified by C18 reverse phase chromatography eluting with H₂O/ACN to afford 1.4 g (55%) of title compound as yellow oil. LCMS [M+H]+ 265.14.

Step 3: Methyl 2-[5-[(benzyloxy)methyl]oxolan-2-yl]acetate

A solution of methyl (2Z)-7-(benzyloxy)-6-hydroxyhept-2-enoate (46 g, 1 equiv) and NaH (0.7 g, 0.1 equiv) in THF (200 mL) was stirred for 12 h at 25° C. The resulting solution was then quenched with 200 mL of water, extracted with 3×200 mL of DCM, and the organic layers combined and washed with 1×100 mL of brine, dried over anhydrous sodium sulfate and concentrated under vacuum to afford 46 g of title compound as brown oil. LCMS [M+H]+ 265.14.

Step 4: 2-[5-[(Benzyloxy)methyl]oxolan-2-yl]acetic Acid

A solution of methyl 2-[5-[(benzyloxy)methyl]oxolan-2-yl]acetate (46 g, 174.03 mmol, 1 equiv) and LiOH.H₂O (14.6 g, 350 mmol, 2 equiv) in THF (200 mL) and H₂O (200 mL) was stirred for 2 h at 25° C. The resulting solution was washed with 1×200 ml of DCM, the aqueous layers was combined and the pH value of the aqueous layer was adjusted to 4 with HCl (1M). After concentration, the residue were dissolved in 100 mL of EtOH and the solids were filtered out. The resulting solution was concentrated under vacuum to afford 40 g (92%) of title compound as a light yellow oil. LCMS [M+H]+ 251.12.

Step 5: 2-[5-[(Benzyloxy)methyl]oxolan-2-yl]-1-[4-[5-(trifluoromethyl)pyridin-2-yl]piperazin-1-yl]ethan-1-one A solution of 2-[5-[(benzyloxy)methyl]oxolan-2-yl]acetic acid (3 g, 11.99 mmol, 1 equiv), 1-[5-(trifluoromethyl)pyridin-2-yl]piperazine (1.7 g, 7.35 mmol, 0.61 equiv), HATU (4.6 g, 11.99 mmol, 1 equiv), and DIPEA (4.6 g, 35.96 mmol, 3 equiv) in DMF (50 mL) was stirred for 4 h at RT. The reaction was then quenched by the addition of 100 mL of water. The resulting solution was extracted with 3×60 mL of EtOAc and concentrated under reduced pressure. The residue was purified by silica gel column chromatography eluting with EtOAc/petroleum ether (3/2) to afford 3.2 g (58%) of title compound as a yellow oil. LCMS [M+H]+ 464.15.

Step 6: 2-[5-(Hydroxymethyl)oxolan-2-yl]-1-[4-[5-(trifluoromethyl)pyridin-2-yl]piperazin-1-yl]ethan-1-one Under H₂ (g) atmosphere, a solution 2-[5-[(benzyloxy)methyl]oxolan-2-yl]-1-[4-[5-(trifluoromethyl)pyridin-2-yl]piperazin-1-yl]ethan-1-one (3.2 g, 6.90 mmol, 1 equiv), palladium 10% on carbon (1 g, 9.40 mmol, 1.36 equiv) in MeOH (50 mL) was stirred overnight at 50° C. The solids were filtered and the resulting mixture was concentrated under reduced pressure to afford 1.7 g (66%) of title compound as a colorless oil. LCMS [M+H]+ 374.10.

Int-A18: 1-[5-(Trifluoromethyl)pyridin-2-yl]piperazine

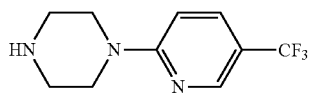 [SMILES: FC(F)(F)c1ccc(N2CCNCC2)nc1]

This compound was purchased from commercial sources: CAS [132834-58-3].

Int-A19: 6-[4-(3-[2-[(5-Bromo-6-oxo-1-[[2-(trimethylsilyl)ethoxy]methyl]-1,6-dihydropyridazin-4-yl)oxy]ethoxy]propanoyl)piperazin-1-yl]pyridine-3-carbonitrile

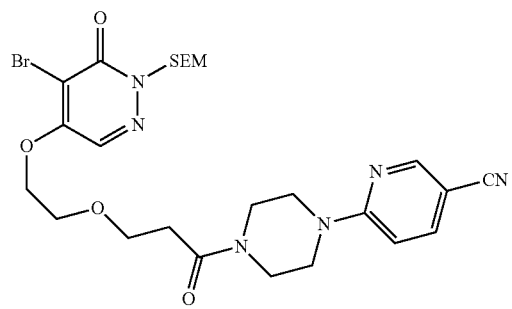 [SMILES: C[Si](C)(C)CCOCn1ncc(OCCOCCC(=O)N2CCN(c3ccc(C#N)cn3)CC2)c(Br)c1=O]

Step 1: 6-[4-(3-[2-[(5-Bromo-6-oxo-1-[[2-(trimethylsilyl)ethoxy]methyl]-1,6-dihydropyridazin-4-yl)oxy]ethoxy]propanoyl)piperazin-1-yl]pyridine-3-carbonitrile A solution of 4-bromo-5-(2-hydroxyethoxy)-2-[[2-(trimethylsilyl)ethoxy]methyl]-2,3-dihydropyridazin-3-one (1.0 g, 2.74 mmol, 1 equiv), Cs₂CO₃ (2.652 g, 8.14 mmol, 2.97 equiv), and Int-A25 (0.99 g, 4.09 mmol, 1.49 equiv) in DMF (20 mL) was stirred for 24 h at RT. The reaction was then quenched by the addition of 20 mL of water and the resulting solution was extracted with 3×30 mL of EtOAc and the organic layers were combined and dried over anhydrous sodium sulfate. The organic layers were concentrated under reduced pressure and the residue was applied onto a silica gel column eluting with EtOAc/petroleum ether (9/1) to afford 350 mg (21%) of title compound as a yellow oil. LCMS [M+H]+ 609.16.

Int-A20: 5-Chloro-2-(4-methoxybenzyl)-4-(trifluoromethyl)pyridazin-3(2H)-one

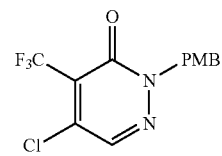

Step 1: 4,5-Dibromo-2-[(4-methoxyphenyl)methyl]-2,3-dihydropyridazin-3-one

To a solution of 4,5-dibromo-2,3-dihydropyridazin-3-one (250 g, 984.71 mmol, 1 equiv) in DMF (2.5 L) was added NaH (59.1 g, 1477.07 mmol, 1.50 equiv, 60%) in several batches at 0-10° C. followed by the addition of 1-(chloromethyl)-4-methoxybenzene (230.3 g, 1470.53 mmol, 1.49 equiv) at 0° C. The resulting solution was stirred for 3 h at RT. The reaction was then quenched by the addition of 5 L of water/ice and extracted with 2×2.5 L of DCM. The organic layers were combined and concentrated. The solids were washed by MeOH (500 mL×2) to afford 290 g (79%) of title compound as a solid. LCMS [M+H]+ 378.00.

Step 2: 5-Methoxy-2-[(4-methoxyphenyl)methyl]-4-(trifluoromethyl)-2,3-dihydropyridazin-3-one A solution of 4,5-dibromo-2-[(4-methoxyphenyl)methyl]-2,3-dihydropyridazin-3-one (290 g, 775.33 mmol, 1 equiv), potassium hydroxide (130.5 g, 2326.00 mmol, 3.00 equiv) in MeOH (2.5 L) was stirred for 2 h at RT. The resulting mixture was concentrated to 500 mL and the solids were collected by filtration. The resulting cake was slurried for 1 h in water (1 L) to afford 232 g (92%) of title compound as a solid. LCMS [M+H]+ 326.90.

Step 3: 5-Methoxy-2-[(4-methoxyphenyl)methyl]-4-(trifluoromethyl)-2,3-dihydropyridazin-3-one A solution of 4-bromo-5-methoxy-2-[(4-methoxyphenyl)methyl]-2,3-dihydropyridazin-3-one (232 g, 713.49 mmol, 1 equiv), methyl 2,2-difluoro-2-sulfoacetate (411.2 g, 2140.44 mmol, 3.00 equiv), and CuI (67.9 g, 356.52 mmol, 0.50 equiv) in NMP (1.2 L) was stirred for 3 h at 100° C. The reaction was then quenched by the addition of 1.5 L of water. The resulting solution was extracted with 3×1 L of DCM. The organic layers were combined and concentrated. The residue was applied onto a silica gel column with EtOAc/petroleum ether (1/1). The collected fractions were combined and concentrated to afford the crude oil to which was added 1 L of water. The solids were collected by filtration and washed with 100 mL of MeOH to afford 170 g (76%) of title compound as a solid. LCMS [M+H]+ 315.10.

Step 4: 5-Hydroxy-2-[(4-methoxyphenyl)methyl]-4-(trifluoromethyl)-2,3-dihydropyridazin-3-one To a solution of 5-methoxy-2-[(4-methoxyphenyl) methyl]-4-(trifluoromethyl)-2,3-dihydropyridazin-3-one (170 g, 540.95 mmol, 1 equiv) in DMF (850 mL) was added TMSI (140 g, 699.67 mmol, 1.29 equiv) dropwise at 20° C. The resulting solution was stirred for 20 h at 85° C. The reaction mixture was then quenched by the addition of 850 mL of water and the resulting solution was extracted with 3×850 mL of DCM and the organic layers combined and dried over anhydrous sodium sulfate. The organic layers were concentrated under vacuum and the crude product was purified by silica gel column chromatography and then recrystallized with MtBE to afford 120 g (74%) of title compound as a white solid. LCMS [M+H]+ 301.07.

Step 5: 5-Chloro-2-[(4-methoxyphenyl)methyl]-4-(trifluoromethyl)-2,3-dihydropyridazin-3-one To a solution of 5-hydroxy-2-[(4-methoxyphenyl) methyl]-4-(trifluoromethyl)-2,3-dihydropyridazin-3-one (110 g, 366.38 mmol, 1 equiv) in DMF (550 mL) was added oxalic dichloride (93 g, 732.75 mmol, 2.00 equiv) dropwise at 0-5° C. The resulting solution was stirred for 8 h at RT. The reaction was then quenched by the addition of 550 mL of water. The solids were collected by filtration to afford 108 g (93%) of title compound as a white solid. LCMS [M+H]+ 319.04 [M+H]+, 1H NMR (30 MHz, DMSO-d6) δ 8.22 (d, J=0.8 Hz, 1H), 7.33-7.22 (m, 2H), 6.94-6.84 (m, 2H), 5.18 (s, 2H), 3.71 (s, 3H).

Int-A21: 1-[4-[5-(Trifluoromethyl)pyrimidin-2-yl] piperazin-1-yl]prop-2-en-1-one

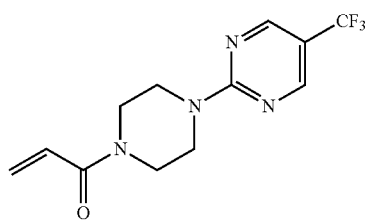 [SMILES: C=CC(=O)N1CCN(c2ncc(C(F)(F)F)cn2)CC1]

A solution of Int-A2 (2.2 g, 7 mmol, 1 equiv), TEA (2.924 g, 29 mmol, 4 equiv), and prop-2-enoyl chloride (1.954 g, 11 mmol, 10.00 equiv) in MeOH (20 mL) was stirred for 4.5 h at 0° C. The solids were filtered out and washed by 30 mL x 2 of EtOAc. The organic layers were then combined, concentrated, and then applied onto a silica gel column with chloroform/methanol (11/1) to afford 1.83 g (58%) of the title compound as a yellow solid. LCMS [M+H]+ 287.25.

Int-A22: 1-[4-(5-Chloropyridin-2-yl)piperazin-1-yl] prop-2-en-1-one

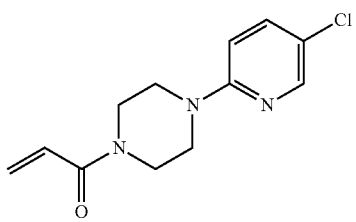 [SMILES: C=CC(=O)N1CCN(c2ccc(Cl)cn2)CC1]

A solution of Int-A5 (2.4 g, 8.92 mmol, 1.00 equiv), TEA (4 g, 39.5 mmol, 4.00 equiv), and prop-2-enoyl prop-2-enoate (3.64 g, 28.9 mmol, 3.00 equiv) in DCM (20 mL) was stirred for 1.5 h at RT. The solvent was concentrated under vacuum and the residue was applied onto a silica gel column eluting with EtOAc/petroleum ether (1:1) to afford 1280 mg (57%) of title compound as a yellow oil. LCMS [M+H]+ 252.09.

Int-A23: 1-[4-(5-Chloropyrimidin-2-yl)piperazin-1-yl]prop-2-en-1-one

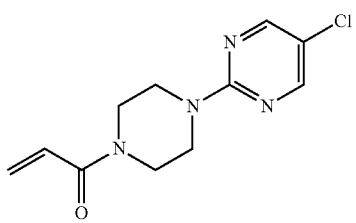 [SMILES: C=CC(=O)N1CCN(c2ncc(Cl)cn2)CC1]

A solution of Int-A3 (1 g, 3.70 mmol, 1.00 equiv), TEA (1.5 g, 14.82 mmol, 4.00 equiv), and prop-2-enoyl prop-2-enoate (700 mg, 5.55 mmol, 1.50 equiv) in DCM (20 mL) was stirred for 1 h at RT. The solvent was concentrated under vacuum and the residue was applied onto a silica gel column eluting with EtOAc/petroleum ether (2:3) to afford 720 mg (77%) of title compound as a white solid. LCMS [M+H]+ 253.07.

Int-A24: 2-[4-(Prop-2-enoyl)piperazin-1-yl]pyrimidine-5-carbonitrile

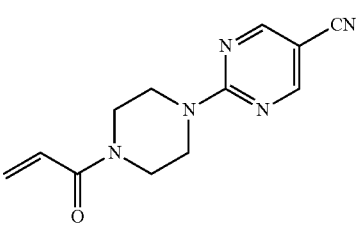 [SMILES: C=CC(=O)N1CCN(c2ncc(C#N)cn2)CC1]

A solution of Int-A1 (6.4 g, 33.82 mmol, 1 equiv), prop-2-enoyl prop-2-enoate (5.1 g, 40.44 mmol, 1.20 equiv) and TEA (6.8 g, 67.20 mmol, 1.99 equiv) in DCM (40 mL)

was stirred for 1 h at room temperature, then the resulting solution was concentrated under vacuum, and the residue was applied onto a silica gel column eluting with EtOAc/petroleum ether (7:3) to afford 3.6 g (43.75%) of the title compound as a white solid. LCMS [M+H]+: 244.12.

Int-A25: 6-[4-(Prop-2-enoyl)piperazin-1-yl]pyridine-3-carbonitrile

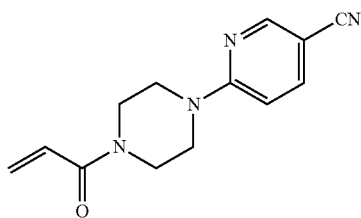 [SMILES: C=CC(=O)N1CCN(c2ccc(C#N)cn2)CC1]

Prop-2-enoyl prop-2-enoate (17.42 g, 138.132 mmol, 1.30 equiv) was added to a solution of Int-A4 (20 g, 106.251 mmol, 1 equiv), and TEA (32.25 g, 318.752 mmol, 3 equiv) in DCM (500 mL) at −40° C. The resulting solution was stirred for another 1 h at −40° C. The reaction was quenched by 500 mL of water and extracted with 2×500 mL of DCM. After concentration, the residue was applied onto a silica gel column eluting with EtOAc/petroleum ether (70:30) to afford 16.4 g (64%) of title compound as a yellow solid. LCMS [M+H]+ 243.13.

Int-A26: 5-(Trifluoromethyl)-2-(4-(vinylsulfonyl)piperazin-1-yl)pyrimidine

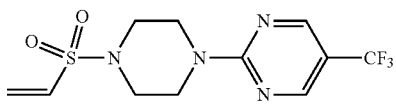 [SMILES: C=CS(=O)(=O)N1CCN(c2ncc(C(F)(F)F)cn2)CC1]

A solution of Int-A2, 2-chloroethane-1-sulfonyl chloride, and TEA (305.0 mg, 3.02 mmol, 3.50 equiv) in DCM (6 mL) was stirred for 2 h at RT. The resulting mixture was concentrated under reduced pressure and the residue was eluted onto a silica gel column with EtOAc/petroleum ether (1:5) to afford 210 mg (75.7%) of title compound as a white solid. LCMS [M+H]+ 323.07.

Int-A27: 1-[5-(Trifluoromethyl)-1,3-thiazol-2-yl]piperazine Hydrochloride

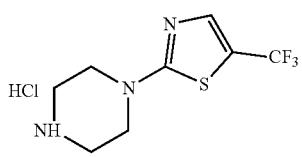 [SMILES: Cl ; FC(F)(F)c1cnc(N2CCNCC2)s1]

Step 1: Tert-butyl 4-(5-(trifluoromethyl) thiazol-2-yl)piperazine-1-carboxylate

A solution of 2-bromo-5-(trifluoromethyl)thiazole (3.00 g, 12.9 mmol, 1.00 equiv), tert-butyl piperazine-1-carboxylate (2.41 g, 12.9 mmol, 1.00 equiv), and Cs₂CO₃ (8.43 g, 25.9 mmol, 2.00 equiv) in NMP (20.0 mL) was stirred for 1 h at 110° C. The reaction was then quenched by the addition of 50 mL of water and extracted with 3×50 mL of EtOAc. After concentration under reduced pressure, the residue was purified by silica gel column chromatography with EtOAc/petroleum ether (15/85) to afford 2.56 g (95%) of title compound as a yellow solid. LCMS [M+H]+ 338.11.

Step 2: 1-[5-(Trifluoromethyl)-1,3-thiazol-2-yl]piperazine Hydrochloride

A solution of tert-butyl 4-(5-(trifluoromethyl)thiazol-2-yl)piperazine-1-carboxylate (2.50 g, 7.41 mmol, 1.00 equiv) and HCl (gas) in 1,4-dioxane (20.0 mL) was stirred for 30 min at RT. The resulting mixture was concentrated under vacuum to afford 2.26 g (95%) of the title compound as a white solid. LCMS [M+H]+ 274.03.

Int-A28: 5-(Trifluoromethyl)-2-(4-(vinylsulfonyl)piperazin-1-yl)thiazole

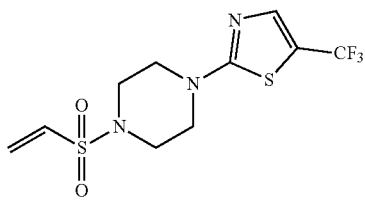 [SMILES: C=CS(=O)(=O)N1CCN(c2ncc(C(F)(F)F)s2)CC1]

A solution of Int-A27 (2.25 g, 9.48 mmol, 1.00 equiv), TEA (4.80 g, 0.047 mmol, 5 equiv), and 2-chloroethane-1-sulfonyl chloride (1.86 g, 0.011 mmol, 1.20 equiv) in DCM (30.0 mL) was stirred for 1 h at 0° C. in a water/ice bath. The reaction mixture was quenched by the addition of MeOH followed by concentration under reduced pressure. The residue was purified by a silica gel column with EtOAc/petroleum ether (18/82) to afford 1.74 g (54.9%) of title compound as a white solid. LCMS [M+H]+ 328.03.

Int-A29: 5-Mercapto-2-(4-methoxybenzyl)-4-(trifluoromethyl)pyridazin-3(2H)-one

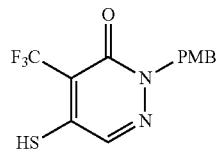

A solution of Int-A20 (2 g, 6.3 mmol, 1 equiv), NaHS (1.4 g, 25.1 mmol, 4 equiv), and TEA (1.9 g, 18.9 mmol, 3 equiv) in EtOH (10 mL) was stirred for 40 min at 70° C. After concentration under reduced pressure, the residue was purified by C18 reverse phase chromatography eluting with H₂O/CH₃CN to afford 1.8 g (90.7%) of title compound as a yellow solid. LCMS [M+H]+ 317.06.

SYNTHESIS OF EXAMPLE COMPOUNDS

Example 1: 5-[5-[(1-acetylpiperidin-4-yl)oxy]-6-fluoro-2,3-dihydro-1H-isoindol-2-yl]-4-(trifluoromethyl)-2,3-dihydropyridazin-3-one

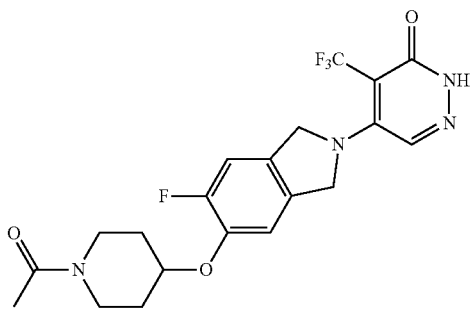 [SMILES: CC(=O)N1CCC(Oc2cc3c(cc2F)CN(c2cn[nH]c(=O)c2C(F)(F)F)C3)CC1]

Step 1: Synthesis of 1-bromo-4,5-bis(bromomethyl)-2-fluorobenzene

A solution of 1-bromo-2-fluoro-4,5-dimethylbenzene (5 g, 24.62 mmol, 1 equiv), NBS (10.85 g, 60.96 mmol, 2.476 equiv), AIBN (1.98 g, 12.06 mmol, 0.490 equiv) in $CCl_4$ (50 mL) was stirred for 12 h at 80° C. After concentration, the residue was purified by C18 reverse phase chromatography eluting with $H_2O/CH_3CN$ to afford 5.4 g (61%) of the title compound as a yellow solid. LCMS (ESI, m/z): 360.80 [M+H]+.

Step 2: Synthesis of 5-bromo-6-fluoro-2,3-dihydro-1H-isoindole

A solution of 1-bromo-4,5-bis(bromomethyl)-2-fluorobenzene (3 g, 8.31 mmol, 1 equiv) in $NH_3$/MeOH (300 mL, 1M) was stirred for 2 h at 5° C. The resulting mixture was concentrated under vacuum to afford 2.8 g (crude) of the title compound as a yellow solid. LCMS (ESI, m/z): 215.97 [M+H]+.

Step 3: Synthesis of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one A solution of 5-bromo-6-fluoro-2,3-dihydro-1H-isoindole (1.2 g, 5.55 mmol, 1 equiv), Int-A6 (2.17 g, 6.60 mmol, 1.188 equiv), TEA (1.7 g, 16.80 mmol, 3.025 equiv) in EtOH (40 mL) was stirred for 2 h at 80° C. The resulting mixture was concentrated under vacuum. The residue was applied onto a silica gel column eluting with EtOAc/petroleum ether (15/85) to afford 870 mg (30.81%) of the title compound as a brown solid. LCMS (ESI, m/z): 510.06 [M+H]+.

Step 4: Synthesis of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (850 mg, 1.67 mmol, 1 equiv), $LiOH \cdot H_2O$ (154.6 mg, 3.68 mmol, 2.203 equiv), BHMPO (287 mg, 0.84 mmol, 0.5 equiv), $Cu(acac)_2$ (220 mg, 0.84 mmol, 0.5 equiv) in DMSO (16 mL) and $H_2O$ (4 mL) was stirred for 2 h at 80° C. The reaction was then quenched by the addition of 20 mL of water. The resulting solution was extracted with 3×30 ml of EtOAc and the organic layers combined and dried over anhydrous sodium sulfate. After concentration, the residue was applied onto a silica gel column eluting with EtOAc/petroleum ether (25/75) to afford 260 mg (35%) of the title compound as a yellow solid. LCMS (ESI, m/z): 446.14 [M+H]+.

Step 5: Synthesis of Tert-Butyl 4-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (260 mg, 0.58 mmol, 1 equiv), tert-butyl 4-iodopiperidine-1-carboxylate (362.6 mg, 1.17 mmol, 1.997 equiv), $K_2CO_3$ (126 mg, 0.91 mmol, 1.562 equiv) in DMF (20 mL) was stirred for 12 h at 80° C. The reaction was then quenched by the addition of 20 mL of water. The resulting solution was extracted with 3×30 ml of EtOAc and the organic layers combined and dried over anhydrous sodium sulfate. After concentration, the residue was applied onto a silica gel column eluting with EtOAc/petroleum ether (20/80) to afford 500 mg (crude) of the title compound as brown oil. LCMS (ESI, m/z): 629.25 [M+H]+.

Step 6: Synthesis of 5-[5-fluoro-6-(piperidin-4-yloxy)-2,3-dihydro-1H-isoindol-2-yl]-4-(trifluoromethyl)-2,3-dihydropyridazin-3-one A solution of tert-butyl 4-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (500 mg, 0.80 mmol, 1 equiv) in HCl/dioxane (5 mL) was stirred for 12 h at room temperature. After concentration, the residue was purified by C18 reverse phase chromatography eluting with $H_2O/CH_3CN$ to afford 330 mg (crude) of the title compound as a yellow oil. LCMS (ESI, m/z): 399.25 [M+H]+.

Step 7: Synthesis of 5-[5-[(1-acetylpiperidin-4-yl)oxy]-6-fluoro-2,3-dihydro-1H-isoindol-2-yl]-4-(trifluoromethyl)-2,3-dihydropyridazin-3-one A solution of 5-[5-fluoro-6-(piperidin-4-yloxy)-2,3-dihydro-1H-isoindol-2-yl]-4-(trifluoromethyl)-2,3-dihydropyridazin-3-one (330 mg, 0.83 mmol, 1 equiv), $Ac_2O$ (85.2 mg, 0.83 mmol, 1.007 equiv), TEA (372 mg, 3.68 mmol, 4.438 equiv) in DCM (5 mL) was stirred for 1 h at room temperature. After concentration, the residue was purified by C18 reverse phase chromatography eluting with $H_2O/CH_3CN$. Then the residue was further purified by Prep-HPLC yielding the title compound (44 mg, 12%) as a white solid. LCMS (ESI, m/z): 441.39 [M+H]+, 1HNMR (DMSO-$d_6$, 300 MHz) δ: 12.52 (s, 1H), 7.96 (s, 1H), 7.29 (dd, J=11.8, 9.4 Hz, 2H), 4.90 (br, 4H), 4.59 (dt, J=8.0, 4.2 Hz, 1H), 3.83 (dd, J=13.3, 6.4 Hz, 1H), 3.73-3.61 (m, 1H), 3.59-3.47 (m, 1H), 3.39-3.13 (m, 1H), 2.01-1.81 (m, 5H), 1.88-1.42 (m, 2H).

Example 2: 5-[4-[(1-acetylpiperidin-4-yl)oxy]-7-fluoro-2,3-dihydro-1H-isoindol-2-yl]-4-(trifluoromethyl)-2,3-dihydropyridazin-3-one

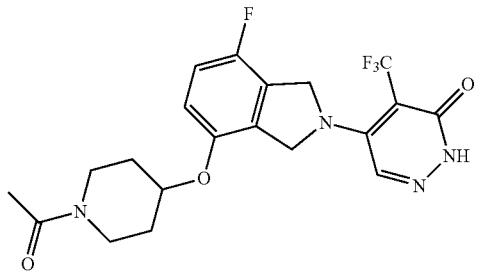 [SMILES: CC(=O)N1CCC(Oc2ccc(F)c3c2CN(c2cn[nH]c(=O)c2C(F)(F)F)C3)CC1]

Step 1: Synthesis of 2-benzyl-4-bromo-7-fluoro-2,3-dihydro-1H-isoindole

A solution of 1-bromo-2,3-bis(bromomethyl)-4-fluorobenzene (2.2 g, 6.10 mmol, 1 equiv), phenylmethanamine (0.66 g, 6.16 mmol, 1.010 equiv), KHCO$_3$ (1.5 g, 14.98 mmol, 2.457 equiv) in ACN (200 mL) was stirred for 3 h at 75° C. in an oil bath. The resulting mixture was concentrated under vacuum. The residue was applied onto a silica gel column eluting with EtOAc/petroleum ether (5/95) to afford 660 mg (35%) of the title compound as a yellow solid. LCMS (ESI, m/z): 306.02 [M+H]$^+$.

Step 2: Synthesis of 2-benzyl-4-fluoro-7-methoxy-2,3-dihydro-1H-isoindole

A solution of MeOH (5 mL), 2-benzyl-4-bromo-7-fluoro-2,3-dihydro-1H-isoindole (700 mg, 2.29 mmol, 1 equiv), Pd$_2$(allyl)$_2$Cl$_2$ (56.0 mg, 0.15 mmol, 0.067 equiv), RockPhos (107.2 mg, 0.23 mmol, 0.100 equiv), Cs$_2$CO$_3$ (1492.1 mg, 4.58 mmol, 2.003 equiv) in Toluene (12 mL) was stirred for 3 h at 80° C. in an oil bath with the atmosphere of nitrogen. The resulting mixture was concentrated under vacuum. The residue was applied onto a silica gel column eluting with EtOAc/petroleum ether (5/95) to afford 500 mg (85%) of the title compound as yellow oil. LCMS (ESI, m/z): 258.12 [M+H]$^+$.

Step 3: Synthesis of 2-benzyl-7-fluoro-2,3-dihydro-1H-isoindol-4-ol

A solution of 2-benzyl-4-fluoro-7-methoxy-2,3-dihydro-1H-isoindole (500 mg, 1.94 mmol, 1 equiv) in DCM (5 mL) was stirred at 0° C. To this was added BBr$_3$ (5 mL, 52.89 mmol, 27.217 equiv) dropwise with stirring at 0° C. The resulting solution was stirred for 12 h at room temperature. The reaction was then quenched by the addition of 10 mL of methanol. The resulting mixture was concentrated under vacuum. The residue was applied onto a silica gel column eluting with EtOAc/petroleum ether (15/85) to afford 456 mg (96.5%) of the title compound as a white solid. LCMS (ESI, m/z): 244.11 [M+H]$^+$.

Step 4: Synthesis of 7-fluoro-2,3-dihydro-1H-isoindol-4-ol Hydrochloride

A solution of 2-benzyl-7-fluoro-2,3-dihydro-1H-isoindol-4-ol (400 mg, 1.64 mmol, 1 equiv), Pd/C (40.1 mg), HCl (1M, 3 mL). The resulting solution was stirred for 1 h at room temperature. The solids were filtered out. The filtrate was concentrated under vacuum. This resulted in 210 mg (67%) of the title compound as a yellow solid. LCMS (ESI, m/z): 154.06 [M+H]$^+$.

Step 5: Synthesis of 5-(4-fluoro-7-hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 7-fluoro-2,3-dihydro-1H-isoindol-4-ol hydrochloride (100 mg, 0.53 mmol, 1 equiv), Int-A6 (214 mg, 0.65 mmol, 1.234 equiv), TEA (194.7 mg, 1.92 mmol, 3.648 equiv) in EtOH (3 mL) was stirred for 2 h at 80° C. in an oil bath. The resulting mixture was concentrated under vacuum. The residue was applied onto a silica gel column eluting with EtOAc/petroleum ether to afford 140 mg (60%) of the title compound as yellow oil. LCMS (ESI, m/z): 446.14 [M+H]$^+$.

Step 6: Synthesis of Tert-Butyl 4-([7-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]oxy)piperidine-1-carboxylate A solution of 5-(4-fluoro-7-hydroxy-2,3-dihydro-1H-isoindol-2-yl)-4-(trifluoromethyl)-2-[[2-(trimethylsilyl)ethoxy]methyl]-2,3-dihydropyridazin-3-one (400 mg, 0.90 mmol, 1 equiv), tert-butyl 4-iodopiperidine-1-carboxylate (558 mg, 1.79 mmol, 1.997 equiv), K$_2$CO$_3$ (193.8 mg, 1.40 mmol, 1.562 equiv) in DMF (5 mL) was stirred for 4 days at 80° C. The reaction was then quenched by the addition of 5 mL of water. The resulting solution was extracted with 3×30 ml of EtOAc and the organic layers combined and dried over anhydrous sodium sulfate. The organic layer was concentrated under vacuum. The residue was applied onto a silica gel column eluting with EtOAc/petroleum ether (50/50) to afford 130 mg (23%) of the title compound as a yellow solid. LCMS (ESI, m/z): 629.27 [M+H]$^+$.

Step 7: Synthesis of 5-[4-fluoro-7-(piperidin-4-yloxy)-2,3-dihydro-1H-isoindol-2-yl]-4-(trifluoromethyl)-2,3-dihydropyridazin-3-one A solution of tert-butyl 4-([7-fluoro-2-[6-oxo-5-(trifluoromethyl)-1-[[2-(trimethyl silyl)ethoxy]methyl]-1,6-dihydropyridazin-4-yl]-2,3-dihydro-1H-isoindol-4-yl]oxy)piperidine-1-carboxylate (130 mg, 0.21 mmol, 1.00 equiv) in hydrogen chloride/dioxane (10 mL) was stirred for 16 h at room temperature. After concentration, the residue was purified by C18 reverse phase chromatography eluting with H$_2$O/CH$_3$CN to afford 80 mg (96%) of the title compound as a white solid. LCMS (ESI, m/z): 399.14 [M+H]$^+$.

Step 8: Synthesis of 5-[4-[(1-acetylpiperidin-4-yl)oxy]-7-fluoro-2,3-dihydro-1H-isoindol-2-yl]-4-(trifluoromethyl)-2,3-dihydropyridazin-3-one A solution of TEA (90 mg, 0.89 mmol, 3.00 equiv), 5-[4-fluoro-7-(piperidin-4-yloxy)-2,3-dihydro-1H-isoindol-2-yl]-4-(trifluoromethyl)-2,3-dihydropyridazin-3-one (80 mg, 0.20 mmol, 1.00 equiv), Ac$_2$O (20.65 mg, 0.20 mmol, 1.00 equiv) in DCM (5 mL) was stirred for 2 h at room temperature. After concentration, the residue was purified by C18 reverse phase chromatography eluting with H$_2$O/CH$_3$CN. Then the residue was further purified by Prep- HPLC yielding the title compound (18.5 mg, 21%) as a white solid. LCMS (ESI, m/z): 441.39 [M+H]+, 1HNMR (DMSO-d6, 300 MHz) δ 12.56 (s, 1H), 8.11 (s, 1H), 7.15-7.07 (m, 2H), 5.02 (s, 2H), 4.92 (s, 2H), 4.68 (dt, J=6.6, 3.4 Hz, 1H), 3.74-3.57 (m, 2H), 3.45-3.32 (m, 2H), 2.02 (s, 3H), 2.00-1.84 (m, 2H), 1.72-1.51 (m, 2H).

Example 3: 5-[4-fluoro-6-(piperidin-4-yloxy)-2,3-dihydro-1H-isoindol-2-yl]-4-(trifluoromethyl)-2,3-dihydropyridazin-3-one; Formic Acid

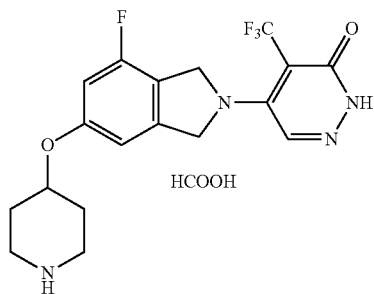 [SMILES: O=c1[nH]ncc(N2Cc3cc(OC4CCNCC4)cc(F)c3C2)c1C(F)(F)F ; "HCOOH"]

Step 1: Synthesis of Methyl 4-bromo-2-(bromomethyl)-6-fluorobenzoate

A solution of methyl 4-bromo-6-fluoro-2-methylbenzoate (10 g, 40.48 mmol, 1.00 equiv), NBS (7.23 g, 40.62 mmol, 1.10 equiv) and AIBN (3.33 g, 20.28 mmol, 0.50 equiv) in CCl4 (150 mL) was stirred for 12 h at 80° C., and then the resulting solution was concentrated under vacuum and the crude product was purified by C18 reverse phase chromatography eluting with H2O/CH3CN to afford 10 g (76%) of the title compound as yellow oil. LCMS (ESI, m/z): 324.88 [M+H]+.

Step 2: Synthesis of 5-bromo-7-fluoro-2,3-dihydro-1H-isoindol-1-one

A solution of 4-bromo-2-(bromomethyl)-6-fluorobenzoate (10 g, 30.68 mmol, 1.00 equiv) in NH3(gas)/MeOH (40 mL, 7M) was stirred for 40 min at 40° C., and then the resulting solution was concentrated under vacuum to afford 9.1 g (crude) of the title compound as an off-white solid. LCMS (ESI, m/z): 230.04 [M+H]+.

Step 3: Synthesis of Tert-Butyl 5-bromo-7-fluoro-1-oxo-2,3-dihydro-1H-isoindole-2-carboxylate To a solution of 5-bromo-7-fluoro-2,3-dihydro-1H-isoindol-1-one (9.1 g, 39.56 mmol, 1.00 equiv) and DMAP (977 mg, 8.00 mmol, 0.20 equiv) in THF (70 mL), was added (Boc)2O (12.99 g, 59.52 mmol, 1.50 equiv), and the resulting solution was stirred for 2 h at room temperature, and then the resulting solution was concentrated under vacuum, The crude product was purified by C18 reverse phase chromatography eluting with H2O/CH3CN to afford 5.7 g (44%) of the title compound as a white solid. LCMS (ESI, m/z): 330.15 [M+H]+.

Step 4: Synthesis of 6-bromo-4-fluoro-2,3-dihydro-1H-isoindole

Under nitrogen, to a solution of tert-butyl 5-bromo-7-fluoro-1-oxo-2,3-dihydro-1H-isoindole-2-carboxylate (5.7 g, 17.26 mmol, 1.00 equiv) and NaBH4 (7.9 g, 208.83 mmol, 12.00 equiv) in THF (60 mL), BF3/Et2O (36.9 g, 15.00 equiv, 1M) added dropwise, and then the resulting solution was stirred for 3 h at 70° C. The resulting solution was quenched by the addition of 200 mL of water, extracted with 3×200 mL of EtOAc and the organic layers combined, washed with 1×200 mL of brine, dried over anhydrous sodium sulfate and concentrated under vacuum, and then the residue was applied onto a silica gel column eluting with DCM/methanol (2:3) to give 2.05 g (55%) of the title compound ndole as an off-white solid. LCMS (ESI, m/z): 216.05 [M+H]+.

Step 5: Synthesis of 5-(6-bromo-4-fluoro-2,3-dihydro-1H-isoindol-2-yl)-4-(trifluoromethyl)-2-[[2-(trimethylsilyl)ethoxy]methyl]-2,3-dihydropyridazin-3-one A solution of 6-bromo-4-fluoro-2,3-dihydro-1H-isoindole (2.05 g, 9.49 mmol, 1.00 equiv), 5-chloro-4-(trifluoromethyl)-2-[[2-(trimethylsilyl)ethoxy]methyl]-2,3-dihydropyridazin-3-one (3.12 g, 9.49 mmol, 1.00 equiv) and TEA (2.88 g, 28.46 mmol, 3.00 equiv) in ethanol (20 mL) was stirred for 2 h at 60° C., and then the resulting solution was concentrated under vacuum, and then the residue was applied onto a silica gel column eluting with EtOAc/petroleum ether (1:5) to afford 2.1 g (44%) of the title compound as a light brown solid. LCMS (ESI, m/z): 508.39 [M+H]+.

Step 6: Synthesis of 5-(4-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 5-(6-bromo-4-fluoro-2,3-dihydro-1H-isoindol-2-yl)-4-(trifluoromethyl)-2-[[2-(trimethylsilyl)ethoxy]methyl]-2,3-dihydropyridazin-3-one (2 g, 3.93 mmol, 1.00 equiv), BHMPO (135 mg, 0.41 mmol, 0.10 equiv), Cu(acac)2 (103 mg, 0.39 mmol, 0.10 equiv) and LiOH.H2O (363 mg, 8.64 mmol, 2.20 equiv), DMSO (20 mL) and water (5 mL) was stirred for 12 h at 80° C., and then the solids were filtered out, and the resulting solution was diluted with 100 mL of H2O, extracted with 3×100 mL of EtOAc and the organic layers combined, washed with 1×100 mL of brine and concentrated under vacuum, and then the residue was applied onto a silica gel column eluting with EtOAc/petroleum ether (3:1) to afford 680 mg (39%) of the title compound as a green solid. LCMS (ESI, m/z): 446.14 [M+H]+.

Step 7: Synthesis of Tert-Butyl 4-([7-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(4-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (300 mg, 0.67 mmol, 1.00 equiv), tert-butyl 4-iodopiperidine-1-carboxylate (629 mg, 2.02 mmol, 3.00 equiv) and potassium carbonate (279 mg, 2.02 mmol, 3.00 equiv) in DMF (5 mL) was stirred for 12 h at 80° C., and then the resulting solution was diluted with 50 mL of H2O, extracted with 3×50 mL of EtOAc and the organic layers combined, washed with 1×50 mL of brine, dried over anhydrous sodium sulfate and concentrated under vacuum, and then the residue was applied onto a silica gel column eluting with EtOAc/petroleum ether (3:1) to give 153 mg (36%) of the title compound as yellow oil. LCMS (ESI, m/z): 629.27 [M+H]+.

Step 8: Synthesis of 5-[4-fluoro-6-(piperidin-4-yloxy)-2,3-dihydro-1H-isoindol-2-yl]-4-(trifluoromethyl)-2,3-dihydropyridazin-3-one; Formic Acid A solution of tert-butyl 4-([7-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (135 mg, 0.21 mmol, 1.00 equiv) in HCl(gas)/dioxane (6 mL, 4M) was stirred for 2 h at room temperature, and then the resulting solution was concentrated under vacuum, and then the crude product was further purified by Pre-HPLC yielding the title compound (34.2 mg, 36%) as a white solid. LCMS (ESI, m/z): 399.05 [M+H]+. $^1$HNMR (DMSO-$d_6$, 300 MHz): δ 12.54 (s, 1H), 8.32 (s, 1H), 8.02 (s, 1H), 6.91 (s, 1H), 6.87 (d, J=11.4 Hz, 1H), 4.96 (d, J=12.2 Hz, 4H), 4.53 (dr, 1H), 3.05 (dr, 2H), 2.79 (dr, 2H), 2.01-1.97 (m, 2H), 1.62-1.60 (m, 2H).

Example 4: 5-[6-[(1-acetylpiperidin-4-yl)oxy]-4-fluoro-2,3-dihydro-1H-isoindol-2-yl]-4-(trifluoromethyl)-2,3-dihydropyridazin-3-one

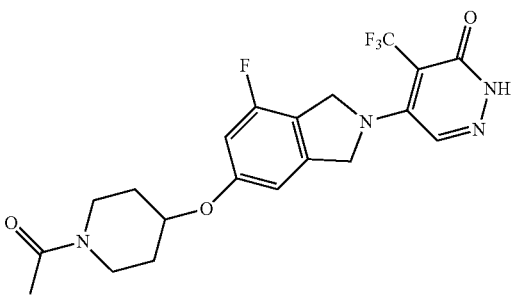 [SMILES: CC(=O)N1CCC(Oc2cc(F)c3c(c2)CN(c2cn[nH]c(=O)c2C(F)(F)F)C3)CC1]

A solution of 5-[4-fluoro-6-(piperidin-4-yloxy)-2,3-dihydro-1H-isoindol-2-yl]-4-(trifluoromethyl)-2,3-dihydropyridazin-3-one; formic acid (110 mg, 0.28 mmol, 1.00 equiv), TEA (90 mg, 0.89 mmol, 3.00 equiv) and Ac$_2$O (150 mg, 1.47 mmol, 5.00 equiv) in DCM (20 mL) was stirred for 4 h at room temperature, and then the resulting solution was concentrated under vacuum, and then the residue was purified by Prep-HPLC yielding the title compound (18.3 mg, 15%) as a white solid. LCMS (ESI, m/z): 441.05 [M+H]+. $^1$HNMR (DMSO-$d_6$, 300 MHz): δ 12.56 (s, 1H), 8.03 (s, 1H), 6.92 (d, J=2.0 Hz, 1H), 6.86 (dd, J=11.2, 2.0 Hz, 1H), 4.96 (d, J=12.2 Hz, 4H), 4.63 (dt, J=8.1, 4.3 Hz, 1H), 3.88-3.84 (m, 1H), 3.69-3.64 (m, 1H), 3.32-3.30 (m, 1H), 3.22-3.14 (m, 1H), 2.01 (s, 3H), 1.94-1.88 (m, 2H), 1.67-1.56 (m, 1H), 1.53-1.39 (m, 1H).

Example 5: 5-[6-[(1-acetylpiperidin-4-yl)oxy]-5-fluoro-1-methyl-2,3-dihydro-1H-isoindol-2-yl]-4-(trifluoromethyl)-2,3-dihydropyridazin-3-one

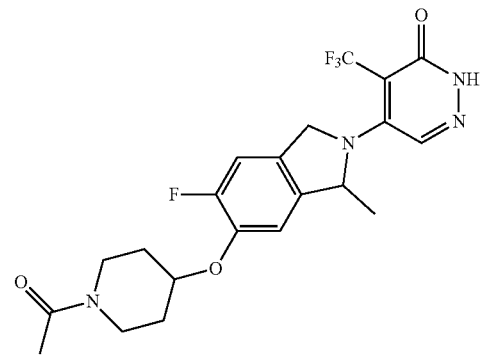 [SMILES: CC(=O)N1CCC(Oc2cc3c(cc2F)CN(c2cn[nH]c(=O)c2C(F)(F)F)C3C)CC1]

Step 1: Synthesis of 4-bromo-2-(bromomethyl)-5-fluorobenzoate

A solution of methyl 4-bromo-5-fluoro-2-methylbenzoate (9.5 g, 38.45 mmol, 1.00 equiv), AIBN (3.15 g, 19.18 mmol, 0.50 equiv), NBS (10.31 g, 57.93 mmol, 1.50 equiv) in CCl$_4$ (100 mL) was stirred for 1 overnight at 80° C. The resulting mixture was concentrated under vacuum. The residue was applied onto a silica gel column eluting with EtOAc/petroleum ether (1/50) to afford 12.5 g of the title compound as yellow crude oil. LCMS (ESI, m/z): 324.88 [M+H]+.

Step 2: Synthesis of 5-bromo-6-fluoro-2,3-dihydro-1H-isoindol-1-one

A solution of methyl 4-bromo-2-(bromomethyl)-5-fluorobenzoate (12.5 g, 38.35 mmol, 1.00 equiv) in NH$_3$/MeOH (150 mL, 7M) was stirred for 3 h at 40° C. The solids were collected by filtration after the resulting solution was cooled to room temperature. This resulted in 7.1 g (80%) of the title compound as a white solid. LCMS (ESI, m/z): 229.95 [M+H]+.

Step 3: Synthesis of Tert-Butyl 5-bromo-6-fluoro-1-oxo-2,3-dihydro-1H-isoindole-2-carboxylate A solution 5-bromo-6-fluoro-2,3-dihydro-1H-isoindol-1-one (7.1 g, 30.87 mmol, 1.00 equiv), 4-dimethylaminopyridine (759 mg, 6.21 mmol, 0.20 equiv), (Boc)$_2$O (8 g, 36.66 mmol, 1.20 equiv) in THF (100 mL) was stirred for 2 h at room temperature. The reaction was then quenched by the addition of 100 mL of water. The resulting solution was extracted with 2×100 mL of EtOAc and the organic layers combined and concentrated under vacuum. This resulted in 9.8 g (96%) of the title compound as a white solid. LCMS (ESI, m/z): 330.01 [M+H]+.

Step 4: Synthesis of Tert-Butyl 5-bromo-6-fluoro-3-methyl-1-oxo-2,3-dihydro-1H-isoindole-2-carboxylate A solution of tert-butyl 5-bromo-6-fluoro-1-oxo-2,3-dihydro-1H-isoindole-2-carboxylate (500 mg, 1.51 mmol, 1.00 equiv) in THF (5 mL) was stirred at −70° C. This was followed by the addition of NaHMDS in THF (1.8 mL, 1.20 equiv, 1M) with stirring at −70° C. The resulting solution was stirred for 30 min at −70° C. To this was added iodomethane (213.7 mg, 1.51 mmol, 1.00 equiv). The resulting solution was stirred for 2 h at room temperature. The reaction was then quenched by the addition of 10 mL of water. The resulting solution was extracted with 3×10 mL of EtOAc and the organic layers combined and concentrated under vacuum. The residue was applied onto a silica gel column eluting with EtOAc/petroleum ether (1/15) to afford 210 mg (40%) of the title compound as a brown solid. LCMS (ESI, m/z): 344.02 [M+H]$^+$.

Step 5: Synthesis of Tert-Butyl 6-bromo-5-fluoro-1-methyl-2,3-dihydro-1H-isoindole-2-carboxylate A solution of tert-butyl 5-bromo-6-fluoro-3-methyl-1-oxo-2,3-dihydro-1H-isoindole-2-carboxylate (210 mg, 0.61 mmol, 1.00 equiv), NaBH$_4$ (220 mg, 5.97 mmol, 10.00 equiv), BH$_3$.Et$_2$O (0.86 mL, 12.00 equiv) in THF (5 mL) was stirred for 3 h at 70° C. The reaction was then quenched by the addition of 10 mL of water. The resulting solution was extracted with 3×10 mL of EtOAc and the organic layers combined. The resulting mixture was washed with 2×10 mL of brine. The resulting mixture was concentrated under vacuum. This resulted in 180 mg (89%) of the title compound as yellow oil. LCMS (ESI, m/z): 330.04 [M+H]$^+$.

Step 6: Synthesis of 6-bromo-5-fluoro-1-methyl-2,3-dihydro-1H-isoindole Hydrochloride A solution of tert-butyl 6-bromo-5-fluoro-1-methyl-2,3-dihydro-1H-isoindole-2-carboxylate (180 mg, 0.55 mmol, 1.00 equiv) in HCl/dioxane (5 mL, 4M) was stirred for 2 h at room temperature. The solids were collected by filtration to afford 130 mg (89%) of the title compound as yellow crude oil. LCMS (ESI, m/z): 229.99 [M+H]$^+$.

Step 7: Synthesis of 5-(6-bromo-5-fluoro-1-methyl-2,3-dihydro-1H-isoindol-2-yl)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (161 mg, 0.49 mmol, 1.00 equiv), TEA (100 mg, 0.99 mmol, 2.00 equiv), 6-bromo-5-fluoro-1-methyl-2,3-dihydro-1H-isoindole hydrochloride (130 mg, 0.49 mmol, 1.00 equiv) in ethanol (5 mL) was stirred for 3 h at 40° C. The resulting mixture was concentrated under vacuum. The residue was applied onto a silica gel column eluting with EtOAc/petroleum ether (1/6) to afford 114 mg (45%) of the title compound as yellow oil. LCMS (ESI, m/z): 522.08 [M+H]$^+$.

Step 8: Synthesis of 5-(5-fluoro-6-hydroxy-1-methyl-2,3-dihydro-1H-isoindol-2-yl)-4-(trifluoromethyl)-2-[[2-(trimethylsilyl)ethoxy]methyl]-2,3-dihydropyridazin-3-one A solution of 5-(6-bromo-5-fluoro-1-methyl-2,3-dihydro-1H-isoindol-2-yl)-4-(trifluoromethyl)-2-[[2-(trimethylsilyl) ethoxy]methyl]-2,3-dihydropyridazin-3-one (1.5 g, 2.87 mmol, 1.00 equiv), BHMPO (472 mg, 1.43 mmol, 0.50 equiv), Cu(acac)$_2$ (376 mg, 1.44 mmol, 0.50 equiv), LiOH.H$_2$O (241 mg, 5.74 mmol, 2.00 equiv) in DMSO (20 mL) and water (5 mL) was stirred for 2 hr at 80° C. The reaction was then quenched by the addition of 50 mL of water. The resulting solution was extracted with 3×20 mL of EtOAc and the organic layers combined and concentrated under vacuum. The residue was applied onto a silica gel column eluting with EtOAc/petroleum ether (1/3) to afford 136 mg (10%) of the title compound as a brown solid. LCMS (ESI, m/z): 460.19 [M+H]$^+$.

Step 9: Synthesis of Tert-Butyl 4-([6-fluoro-3-methyl-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-fluoro-6-hydroxy-1-methyl-2,3-dihydro-1H-isoindol-2-yl)-4-(trifluoromethyl)-2-[[2-(trimethylsilyl)ethoxy]methyl]-2,3-dihydropyridazin-3-one (136 mg, 0.30 mmol, 1.00 equiv), potassium carbonate (81.6 mg, 0.59 mmol, 2.00 equiv), tert-butyl 4-iodopiperidine-1-carboxylate (276 mg, 0.89 mmol, 3.00 equiv) in DMF (10 mL) was stirred for 3 days at 80° C. The reaction was then quenched by the addition of 10 mL of water. The resulting solution was extracted with 3×10 mL of EtOAc and the organic layers combined and concentrated under vacuum. The residue was applied onto a silica gel column eluting with EtOAc/petroleum ether (1/4) to afford 190 mg of the title compound as yellow crude oil. LCMS (ESI, m/z): 643.29 [M+H]$^+$.

Step 10: Synthesis of 5-[5-fluoro-1-methyl-6-(piperidin-4-yloxy)-2,3-dihydro-1H-isoindol-2-yl]-4-(trifluoromethyl)-2,3-dihydropyridazin-3-one A solution of tert-butyl 4-([6-fluoro-3-methyl-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl] oxy)piperidine-1-carboxylate (180 mg, 0.28 mmol, 1 equiv) in HCl/dioxane (5 mL) was stirred for 12 hr at room temperature. The resulting mixture was concentrated under vacuum to afford 200 mg (crude) of the title compound as yellow oil.

Step 11: Synthesis of 5-[6-[(1-acetylpiperidin-4-yl)oxy]-5-fluoro-1-methyl-2,3-dihydro-1H-isoindol-2-yl]-4-(trifluoromethyl)-2,3-dihydropyridazin-3-one A solution of 5-[5-fluoro-1-methyl-6-(piperidin-4-yloxy)-2,3-dihydro-1H-isoindol-2-yl]-4-(trifluoromethyl)-2,3-dihydropyridazin-3-one (120 mg, 0.29 mmol, 1 equiv), acetic anhydride (30 mg, 0.29 mmol, 1.010 equiv), TEA (131 mg, 1.29 mmol, 4.449 equiv) in DCM (5 mL) was stirred for 2 h at room temperature. After concentration, the residue was purified by C18 reverse phase chromatography eluting with H$_2$O/CH$_3$CN. Then the residue was further purified by Prep-HPLC yielding the title compound (9.9 mg, 7.5%) as a white solid. LCMS (ESI, m/z): 455.42 [M+H]$^+$, $^1$HNMR (DMSO-d$_6$, 300 MHz) δ: 12.60 (s, 1H), 8.12 (s, 1H), 7.30 (s, 1H), 7.27 (s, 1H), 5.64 (d, J=6.9 Hz, 1H), 5.05 (d, J=14.8 Hz, 1H), 4.80-4.65 (br, 1H), 4.50 (d, J=14.8 Hz, 1H), 3.90-4.75 (m, 1H), 3.73-3.56 (m, 1H), 3.40-3.20 (m, 2H), 2.03 (s, 3H), 1.95-1.80 (m, 2H), 1.72-1.80 (m, 2H), 1.49-1.43 (m, 3H).

Example 6: 5-[2-[(1-methylpiperidin-4-yl)oxy]-5H, 6H,7H-pyrrolo[3,4-b]pyridin-6-yl]-4-(trifluoromethyl)-2,3-dihydropyridazin-3-one

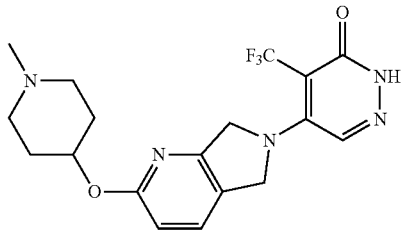 [SMILES: CN1CCC(Oc2ccc3c(n2)CN(c2cn[nH]c(=O)c2C(F)(F)F)C3)CC1]

Step 1: Synthesis of 5-[2-chloro-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 2-chloro-5H,6H,7H-pyrrolo[3,4-b]pyridin-6-yl hydrochloride (5 g, 26.31 mmol, 1.00 equiv), TEA (8 g, 79.06 mmol, 3.00 equiv), 5-chloro-4-(trifluoromethyl)-2-{[2-(trimethylsilyl)ethoxy]methyl}-2,3-dihydropyridazin-3-one (14.3 g, 43.49 mmol, 1.00 equiv) in EtOH (30 mL) was stirred for 2 h at 80° C. The solvent was concentrated under vacuum and the residue was applied onto a silica gel column eluting with EtOAc/petroleum ether (1/4) to afford 9.3 g (79%) of the title compound as yellow oil. LCMS (ESI, m/z): 447.12 [M+H]$^+$.

Step 2: Synthesis of 5-[2-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-[2-chloro-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (1.2 g, 2.69 mmol, 1.00 equiv), t-BuBrettphos (196 mg, 0.15 equiv), K$_3$PO$_4$ (1.711 g, 8.06 mmol, 3.00 equiv), Pd(OAc)$_2$ (61 mg, 0.27 mmol, 0.10 equiv) in dioxane (15 mL) and water (5 mL) under nitrogen atmosphere was stirred for 2 h at 100° C. The solvent was concentrated under vacuum and the residue was applied onto a silica gel column eluting with DCM/methanol (9/1) to afford 700 mg (61%) of the title compound as a yellow solid. LCMS (ESI, m/z): 429.15 [M+H]$^+$.

Step 3: Synthesis of Tert-Butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-2-yl]oxy)piperidine-1-carboxylate A solution of 5-[2-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (500 mg, 1.17 mmol, 1.00 equiv), Ag$_2$CO$_3$ (640 mg, 2.00 equiv), tert-butyl 4-iodopiperidine-1-carboxylate (1 g, 3.21 mmol, 3.00 equiv) in DMF (15 mL) was stirred for 4 h at 80° C. The resulting solution was diluted with 15 mL of water and extracted with 3×15 mL of EtOAc, the organic layers combined. The resulting solution was dried over anhydrous sodium sulfate and concentrated under vacuum. The residue was applied onto a silica gel column eluting with EtOAc/petroleum ether (1/4) to afford 500 mg (73%) of the title compound as yellow oil. LCMS (ESI, m/z): 612.28 [M+H]$^+$.

Step 4: Synthesis of 5-[2-(piperidin-4-yloxy)-5H,6H,7H-pyrrolo[3,4-b]pyridin-6-yl]-4-(trifluoromethyl)-2,3-dihydropyridazin-3-one A solution of tert-butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-2-yl]oxy)piperidine-1-carboxylate (500 mg, 0.82 mmol, 1.00 equiv) in HCl/dioxane (20 mL, 4M) was stirred overnight at 25° C. The resulting solution was concentrated under vacuum to afford 200 mg (64%) of the title compound as yellow crude oil. LCMS (ESI, m/z): 382.14 [M+H]$^+$.

Step 5: Synthesis of 5-[2-[(1-methylpiperidin-4-yl)oxy]-5H,6H,7H-pyrrolo[3,4-b]pyridin-6-yl]-4-(trifluoromethyl)-2,3-dihydropyridazin-3-one A solution of 5-(2-(piperidin-4-yloxy)-5,7-dihydro-6H-pyrrolo[3,4-b]pyridin-6-yl)-4-(trifluoromethyl)pyridazin-3(2H)-one (200 mg, 0.52 mmol, 1.00 equiv), (HCHO)$_n$ (45 mg, 3.00 equiv), acetic acid (60 mg, 1.00 mmol, 2.00 equiv), NaBH$_3$CN (95 mg, 1.51 mmol, 3.00 equiv) in MeOH (5 mL) was stirred for overnight at 25° C. After concentration, the residue was purified by Prep-HPLC yielding the title compound (27.8 mg, 13%) as a white solid. LCMS (ESI, m/z): 396.16 [M+H]$^+$, $^1$H NMR (300 MHz, Methanol-d$_4$) δ: 8.08 (s, 1H), 7.68 (d, J=8.4 Hz, 1H), 6.74 (d, J=8.4 Hz, 1H), 5.12 (dq, J=8.1, 4.1 Hz, 1H), 5.02 (s, 2H), 4.92 (s, 2H), 2.78 (m, 2H), 2.35 (m, 5H), 2.09 (dd, J=11.9, 7.5 Hz, 2H), 1.86 (qd, J=11.8, 10.1, 3.5 Hz, 2H).

Example 7: 5-[3-(piperidin-4-yloxy)-5H,6H,7H-pyrrolo[3,4-b]pyridin-6-yl]-4-(trifluoromethyl)-2,3-dihydropyridazin-3-one

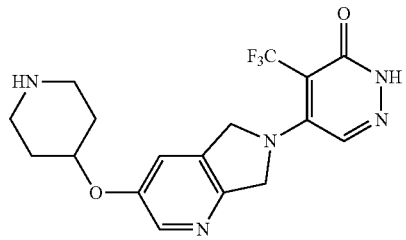 [SMILES: O=c1[nH]ncc(N2Cc3cc(OC4CCNCC4)cnc3C2)c1C(F)(F)F]

Step 1: Synthesis of 5-[3-bromo-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 3-bromo-5H,6H,7H-pyrrolo[3,4-b]pyridine hydrochloride (1 g, 4.25 mmol, 1.00 equiv) in ethanol (5 mL), 5-chloro-4-(trifluoromethyl)-2-[2-(trimethylsilyl)ethoxy]methyl-2,3-dihydropyridazin-3-one (1.6 g, 4.87 mmol, 1.15 equiv) and TEA (1.2 mL) was stirred for 1 h at 80° C. The resulting mixture was concentrated under vacuum. The residue was applied onto a silica gel column with EtOAc/petroleum ether (1:2). This resulted in 1.5 g (72%) of the title compound as a solid. LCMS (ESI, m/z): 491.07 [M+H]$^+$.

Step 2: Synthesis of 5-[3-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-[3-bromo-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (1 g, 2.04 mmol, 1.00 equiv), Pd(OAc)$_2$ (92 mg, 0.41 mmol, 0.20 equiv), t-Bu-Brettphos (200 mg), K$_3$PO$_4$ (1.3 g, 6.12 mmol, 3.01 equiv) in dioxane/H$_2$O (12.5 mL) was stirred for 4 h at 80° C. under an inert atmosphere of nitrogen. The resulting solution was extracted with 250 mL of EtOAc. The resulting mixture was washed with 2×50 mL of water and 1×50 mL of Brine. The organic layer was dried over anhydrous sodium sulfate and concentrated under vacuum. The residue was applied onto a silica gel column with DCM/methanol (9:1). This resulted in 680 mg (78%) of the title compound as a solid. LCMS (ESI, m/z): 429.16 [M+H]$^+$.

Step 3: Synthesis of Tert-Butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-3-yl]oxy)piperidine-1-carboxylate as Oil A solution of 5-[3-hydroxy-5H,6H,7H-pyrrolo[3,4-b]pyridin-6-yl]-4-(trifluoromethyl)-2-[[2-(trimethyl-silyl)ethoxy]methyl]-2,3-dihydropyridazin-3-one (190 mg, 0.44 mmol, 1.00 equiv), Ag$_2$CO$_3$ (370 mg) and tert-butyl 4-iodopiperidine-1-carboxylate (450 mg, 1.45 mmol, 3.26 equiv) in DMF (5 mL) was stirred for 2 h at 80° C. The solids were filtered out. The resulting mixture was concentrated under vacuum. The residue was applied onto a silica gel column with DCM/methanol (95:5). This resulted in 60 mg (22%) of the title compound as oil. LCMS (ESI, m/z): 612.28 [M+H]$^+$.

Step 4: Synthesis of 5-[3-(piperidin-4-yloxy)-5H,6H,7H-pyrrolo[3,4-b]pyridin-6-yl]-4-(trifluoromethyl)-2,3-dihydropyridazin-3-one To a stirred solution of tert-butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-3-yl]oxy)piperidine-1-carboxylate (60 mg, 0.10 mmol, 1.00 equiv) in DCM (5 mL), trifluoroacetic acid (2 mL) was added. The resulting solution was stirred for 1 h at room temperature. After concentration, the residue was purified by C18 reverse phase chromatography eluting with H$_2$O/CH$_3$CN. Then the residue was further purified by Prep-HPLC yielding the title compound (13.1 mg, 35%) as an off-white solid. LCMS (ESI, m/z): 382.15 [M+H]$^+$. $^1$H NMR (400 MHz, DMSO-d$_6$) δ 8.17 (d, J=2.7 Hz, 1H), 8.02 (s, 1H), 7.50 (d, J=2.6 Hz, 1H), 4.93 (s, 2H), 4.86 (s, 2H), 4.49 (tt, J=8.6, 3.9 Hz, 1H), 3.05-2.95 (m, 2H), 2.71-2.60 (m, 2H), 2.00-1.90 (m, 2H), 1.58-1.44 (m, 2H).

Example 8: 5-[3-[(1-acetylpiperidin-4-yl)oxy]-5H,6H,7H-pyrrolo[3,4-b]pyridin-6-yl]-4-(trifluoromethyl)-2,3-dihydropyridazin-3-one

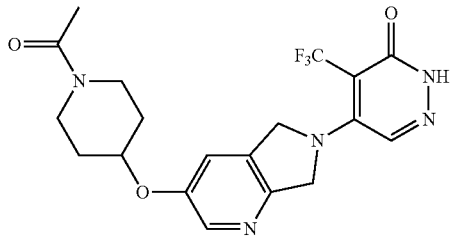 [SMILES: CC(=O)N1CCC(Oc2cnc3c(c2)CN(c2cn[nH]c(=O)c2C(F)(F)F)C3)CC1]

To a stirred solution of 5-[3-(piperidin-4-yloxy)-5H,6H,7H-pyrrolo[3,4-b]pyridin-6-yl]-4-(trifluoromethyl)-2,3-dihydropyridazin-3-one (150 mg, 0.39 mmol, 1.00 equiv) in pyridine (5 mL), Ac$_2$O (0.5 mL) was added. The resulting solution was stirred for 2 h at room temperature. After concentration, the residue was purified by C18 reverse phase chromatography eluting with H$_2$O/CH$_3$CN. Then the residue was further purified by Prep-HPLC yielding the title compound (50.4 mg, 30%) as a white solid. LCMS (ESI, m/z): 424.05 [M+H]$^+$. $^1$H NMR (300 MHz, Methanol-d$_4$) δ 8.22 (d, J=2.6 Hz, 1H), 8.08 (s, 1H), 7.53 (d, J=2.6 Hz, 1H), 5.09 (s, 2H), 4.97 (s, 2H), 4.78-4.67 (m, 1H), 3.94-3.73 (m, 2H), 3.61-3.44 (m, 2H), 2.14 (s, 3H), 2.11-1.93 (m, 2H), 1.88-1.67 (m, 2H).

Example 9: 5-[4-(piperidin-4-yloxy)-5H,6H,7H-pyrrolo[3,4-b]pyridin-6-yl]-4-(trifluoromethyl)-2,3-dihydropyridazin-3-one

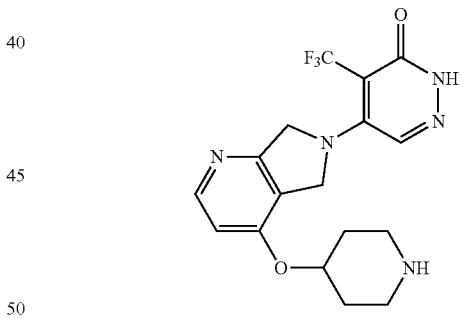

Step 1: Synthesis of 5-[4-bromo-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (2.3 g, 7.00 mmol, 1.00 equiv), 4-bromo-5H,6H,7H-pyrrolo[3,4-b]pyridine hydrobromide (1.95 g, 6.97 mmol, 1.00 equiv), TEA (3.6 g, 35.58 mmol, 5.00 equiv) in EtOH (30 mL) was stirred for 2 h at 80° C. The solvent was concentrated under vacuum and the residue was applied onto a silica gel column eluting with EtOAc/petroleum ether (1/4) to afford 1.1 g (32%) of the title compound as a yellow solid. LCMS (ESI, m/z): 491.06 [M+H]$^+$.

Step 2: Synthesis of 5-[4-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-[4-bromo-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (400 mg, 0.81 mmol, 1.00 equiv), Pd(OAc)$_2$ (19 mg, 0.08 mmol, 0.10 equiv), K$_3$PO$_4$ (520 mg, 2.45 mmol, 3.00 equiv), t-BuBrettphos (60 mg, 0.15 equiv) in dioxane (10 mL) and water (3 mL) under nitrogen atmosphere was stirred for 2 h at 100° C. The solvent was concentrated under vacuum and the residue was applied onto a silica gel column eluting with DCM/methanol (19/1) to afford 215 mg (62%) of the title compound as a yellow solid. LCMS (ESI, m/z): 429.15 [M+H]$^+$.

Step 3: Synthesis of Tert-Butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-4-yl]oxy)piperidine-1-carboxylate A solution of 5-[4-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (250 mg, 0.58 mmol, 1.00 equiv), Ag$_2$CO$_3$ (322 mg, 2.00 equiv), tert-butyl 4-iodopiperidine-1-carboxylate (545 mg, 1.75 mmol, 3.00 equiv) in DMF (15 mL) was stirred for 4 h at 80° C. The resulting solution was diluted with 15 mL of water and extracted with 3×15 mL of EtOAc, the organic layers combined. The resulting solution was dried over anhydrous sodium sulfate and concentrated under vacuum. The residue was applied onto a silica gel column eluting with DCM/methanol (19/1) to afford 240 mg (67%) of the title compound as a yellow solid. LCMS (ESI, m/z): 612.28 [M+H]$^+$.

Step 4: Synthesis of 5-[4-(piperidin-4-yloxy)-5H,6H,7H-pyrrolo[3,4-b]pyridin-6-yl]-4-(trifluoromethyl)-2,3-dihydropyridazin-3-one A solution of tert-butyl 4-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-4-yl]oxy)piperidine-1-carboxylate (240 mg, 0.39 mmol, 1.00 equiv) in dioxane/HCl (15 mL, 4 M) was stirred for 1 overnight at 25° C. After concentration, the residue was purified by Prep-HPLC yielding the title compound (31.5 mg, 21%) as a white solid. LCMS (ESI, m/z): 382.14 [M+H]$^+$, $^1$H NMR (400 MHz, Methanol-d$_4$) δ: 8.36 (d, J=6.0 Hz, 1H), 8.11 (s, 1H), 7.07 (d, J=6.1 Hz, 1H), 5.03 (d, J=11.7 Hz, 4H), 4.78 (dq, J=8.3, 4.1 Hz, 1H), 3.11 (dt, J=12.9, 4.6 Hz, 2H), 2.79 (ddd, J=12.7, 9.2, 3.2 Hz, 2H), 2.39-1.85 (m, 2H), 1.75 (dtd, J=13.0, 8.9, 3.8 Hz, 2H).

Example 10: 5-[4-[2-(morpholin-4-yl)ethoxy]-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one

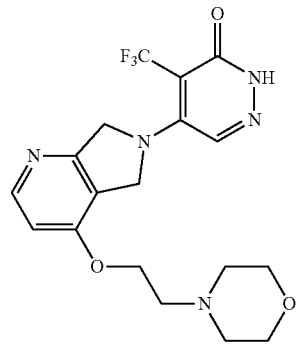 [SMILES: O=c1[nH]ncc(N2Cc3nccc(OCCN4CCOCC4)c3C2)c1C(F)(F)F]

Step 1: Synthesis of 5-[4-[2-(morpholin-4-yl)ethoxy]-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of 5-[4-hydroxy-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (200 mg, 0.47 mmol, 1.00 equiv), Ag$_2$CO$_3$ (387 mg, 3.00 equiv), NaI (140 mg, 2.00 equiv), 4-(2-chloroethyl)morpholine (280 mg, 1.87 mmol, 4.00 equiv) in DMF (15 mL) was stirred for 2 h at 80° C. The resulting solution was diluted with 15 mL of water and extracted with 3×15 mL of EtOAc, the organic layers combined. The resulting solution was dried over anhydrous sodium sulfate and concentrated under vacuum. The residue was applied onto a silica gel column eluting with DCM/methanol (9/1) to afford 200 mg (79%) of the title compound as yellow oil. LCMS (ESI, m/z): 542.23 [M+H]$^+$.

Step 2: Synthesis of 5-[4-[2-(morpholin-4-yl)ethoxy]-5H,6H,7H-pyrrolo[3,4-b]pyridin-6-yl]-4-(trifluoromethyl)-2,3-dihydropyridazin-3-one A solution of 5-[4-[2-(morpholin-4-yl)ethoxy]-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one (80 mg, 0.15 mmol, 1.00 equiv) in dioxane/HCl (15 mL, 4 M) was stirred for overnight at 25° C. After concentration, the residue was purified by Prep-HPLC yielding the title compound (22.6 mg, 37%) as a white solid. LCMS (ESI, m/z): 412.15 [M+H]+, 1H NMR (300 MHz, Methanol-d4) δ: 8.40 (d, J=5.9 Hz, 1H), 8.11 (s, 1H), 7.06 (d, J=6.0 Hz, 1H), 5.04 (d, J=11.1 Hz, 4H), 4.38 (t, J=5.5 Hz, 2H), 3.91-3.56 (m, 4H), 2.89 (t, J=5.4 Hz, 2H), 2.77-2.51 (m, 4H).

Example 11: 5-[6-methoxy-1H,2H,3H-pyrrolo[3,4-c]pyridin-2-yl]-4-(trifluoromethyl)-2,3-dihydropyridazin-3-one

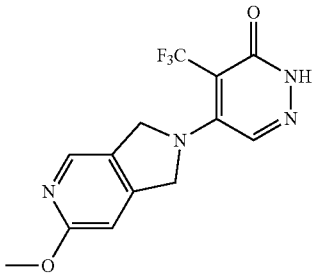 [SMILES: COc1cc2c(cn1)CN(c1cn[nH]c(=O)c1C(F)(F)F)C2]

Step 1: Synthesis of 5-[6-chloro-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (6 g, 18.25 mmol, 1.00 equiv), TEA (5.5 g, 54.35 mmol, 3.00 equiv), 6-chloro-1H,2H,3H-pyrrolo[3,4-c]pyridine hydrochloride (3.5 g, 18.32 mmol, 1.00 equiv) in ethanol (70 mL) was stirred for 3 h at 80° C. The reaction mixture was concentrated under vacuum and the residue was applied onto a silica gel column eluting with EtOAc/petroleum ether (4/6) to afford 4.9 g (60%) of the title compound as a yellow solid. LCMS (ESI, m/z): 447.12 [M+H]+.

Step 2: Synthesis of 5-[6-methoxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 5-[6-chloro-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (500 mg, 1.12 mmol, 1.00 equiv), [Pd(ally)Cl]$_2$ (41 mg, 0.11 mmol, 0.10 equiv), Rockphos (53 mg, 0.11 mmol, 0.10 equiv), Cs$_2$CO$_3$ (730 mg, 2.24 mmol, 2.00 equiv), methanol (76 mg, 2.37 mmol, 2.12 equiv) in toluene (10 mL) was stirred for 3 h under an atmosphere of nitrogen at 80° C. The resulting mixture was concentrated under vacuum. The residue was applied onto a silica gel column eluting with EtOAc/petroleum ether (3/7) to afford 336 mg (68%) of the title compound as yellow oil. LCMS (ESI, m/z): 443.16 [M+H]+.

Step 3: Synthesis of 5-[6-methoxy-1H,2H,3H-pyrrolo[3,4-c]pyridin-2-yl]-4-(trifluoromethyl)-2,3-dihydropyridazin-3-one A solution of 5-[6-methoxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (336 mg, 0.76 mmol, 1.00 equiv) in hydrogen chloride/dioxane (10 mL) was stirred for 12 h at room temperature. After concentration, the residue was purified by C18 reverse phase chromatography eluting with H$_2$O/CH$_3$CN. Then the residue was further purified by Prep-HPLC yielding the title compound (44.3 mg, 19%) as a white solid. LCMS (ESI, m/z): 313.25 [M+H]+, $^1$H NMR (400 MHz, DMSO-d$_6$) δ: 12.56 (s, 1H), 8.19 (d, J=1.1 Hz, 1H), 8.00 (s, 1H), 6.88-6.83 (m, 1H), 4.98-4.93 (m, 4H), 3.86 (s, 3H).

Example 12: 5-[6-(piperidin-4-yloxy)-1H,2H,3H-pyrrolo[3,4-c]pyridin-2-yl]-4-(trifluoromethyl)-2,3-dihydropyridazin-3-one

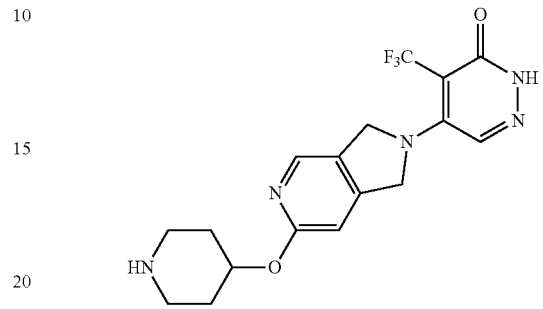

Step 1: Synthesis of 5-[6-hydroxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 5-[6-chloro-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (2.5 g, 5.59 mmol, 1.00 equiv), Pd(OAc)$_2$ (125 mg, 0.56 mmol, 0.10 equiv), t-Bubrettphos (407 mg, 0.84 mmol, 0.15 equiv), K$_3$PO$_4$ (2.4 g, 11.31 mmol, 2.00 equiv) in dioxane (40 mL) and water (4 mL) was stirred for 3 h at 100° C. The reaction mixture was concentrated under vacuum. The residue was applied onto a silica gel column eluting with DCM/methanol (9/1) to afford 890 mg (37%) of the title compound as a brown solid. LCMS (ESI, m/z): 429.15 [M+H].

Step 2: Synthesis of Tert-Butyl 4-([2-[6-oxo-5-(trifluoromethyl)-1-[[2-(trimethylsilyl)ethoxy]methyl]-1,6-dihydropyridazin-4-yl]-1H,2H,3H-pyrrolo[3,4-c]pyridin-6-yl]oxy)piperidine-1-carboxylate A solution of 5-[6-hydroxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (870 mg, 2.03 mmol, 1.00 equiv), Ag$_2$CO$_3$ (1.13 g, 2.00 equiv), tert-butyl 4-iodopiperidine-1-carboxylate (1.27 g, 4.08 mmol, 2.00 equiv) in DMF (25 mL) was stirred for 10 h at 80° C. The resulting solution was diluted with 20 mL of water and extracted with 3×100 ml of EtOAc. The organic layers combined, washed with 3×100 mL of brine, dried over Na$_2$SO$_4$. The resulting mixture was concentrated under vacuum. The residue was applied onto a silica gel column eluting with EtOAc/petroleum ether (3/7) to afford 1.21 g (97%) of the title compound as yellow oil. LCMS (ESI, m/z): 612.28 [M+H].

Step 3: Synthesis of of 5-[6-(piperidin-4-yloxy)-1H,2H,3H-pyrrolo[3,4-c]pyridin-2-yl]-4-(trifluoromethyl)-2,3-dihydropyridazin-3-one A solution of 5 tert-butyl 4-([2-[6-oxo-5-(trifluoromethyl)-1-[[2-(trimethylsilyl)ethoxy]methyl]-1,6-dihydropyridazin-4-yl]-1H,2H,3H-pyrrolo[3,4-c]pyridin-6-yl]oxy)

piperidine-1-carboxylate (1.21 g, 1.98 mmol, 1.00 equiv) in hydrogen chloride/dioxane (20 mL) was stirred for 2.5 h at room temperature. After concentration, the residue was purified by C18 reverse phase chromatography eluting with H$_2$O/CH$_3$CN. Then the residue was further purified by Prep-HPLC yielding the title compound (17.3 mg, 2%) as a white solid. LCMS (ESI, m/z): 382.35 [M+H]$^+$, $^1$H NMR (400 MHz, Methanol-d4) δ: 8.17-8.11 (m, 1H), 8.07 (s, 1H), 6.81 (d, J=1.1 Hz, 1H), 5.14 (dt, J=8.6, 4.5 Hz, 1H), 5.02 (m, 4H), 3.16-3.07 (m, 2H), 2.79 (ddd, J=12.7, 9.4, 3.2 Hz, 2H), 2.13-2.01 (m, 2H), 1.72 (dtd, J=13.0, 9.0, 3.8 Hz, 2H).

Example 13: 5-[6-(piperidin-4-yloxy)-1H,2H,3H-pyrrolo[3,4-c]pyridin-2-yl]-4-(trifluoromethyl)-2,3-dihydropyridazin-3-one

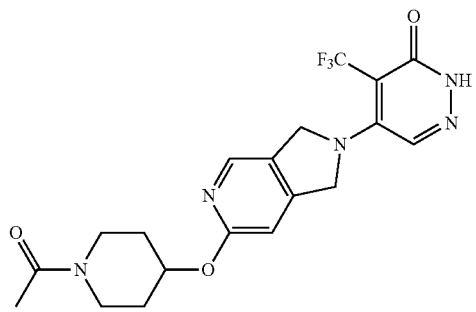 [SMILES: CC(=O)N1CCC(Oc2cc3c(cn2)CN(c2cn[nH]c(=O)c2C(F)(F)F)C3)CC1]

A solution of 5-[6-(piperidin-4-yloxy)-1H,2H,3H-pyrrolo[3,4-c]pyridin-2-yl]-4-(trifluoromethyl)-2,3-dihydropyridazin-3-one (290 mg, 0.76 mmol, 1.00 equiv), TEA (154 mg, 1.52 mmol, 2.00 equiv), Ac$_2$O (93 mg, 0.91 mmol, 1.20 equiv) in DCM (10 mL) was stirred for 2 h at room temperature. After concentration, the residue was purified by C18 reverse phase chromatography eluting with H$_2$O/CH$_3$CN. Then the residue was further purified by Prep-HPLC yielding the title compound (100.1 mg, 31%) as white solid. LCMS (ESI, m/z): 424.39[M+H]$^+$, $^1$H NMR (300 MHz, Methanol-d$_4$) δ: 8.18-8.11 (m, 1H), 8.06 (s, 1H), 6.82 (d, J=1.0 Hz, 1H), 5.28 (dq, J=7.5, 3.7 Hz, 1H), 4.89 (m, 4H), 3.98-3.83 (m, 1H), 3.79 (ddd, J=11.5, 7.3, 3.8 Hz, 1H), 3.48 (dd, J=15.3, 6.4 Hz, 2H), 2.13 (s, 3H), 2.11-1.94 (m, 2H), 1.89-1.65 (m, 2H).

Example 14: 5-[5-[2-(dimethylamino)ethoxy]-6-fluoro-2,3-dihydro-1H-isoindol-2-yl]-4-(trifluoromethyl)-2,3-dihydropyridazin-3-one; Formic Acid

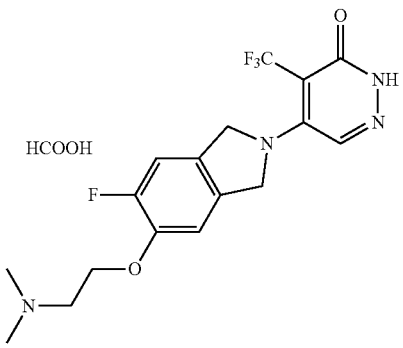 [SMILES: "HCOOH" ; CN(C)CCOc1cc2c(cc1F)CN(c1cn[nH]c(=O)c1C(F)(F)F)C2]

Step 1: Synthesis of 5-(5-fluoro-6-hydroxyisoindolin-2-yl)-4-(trifluoromethyl)-2-((2-(trimethylsilyl)ethoxy)methyl)pyridazin-3(2H)-one A solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (508 mg, 1.00 mmol, 1.00 equiv), Cu(acac)$_2$ (27 mg, 0.10 equiv), BHMPO (35 mg, 0.10 equiv), LiOH.H$_2$O (89 mg, 3.72 mmol, 2.10 equiv), water (1 mL) in DMSO (4 mL) was stirred for 3 h at 80° C. The solution was quenched with 20 ml water, then extracted with EtOAc (3×30 mL) and the organic layers combined. After concentrated under vacuum the residue was applied onto a silica gel column eluting with EtOAc/petroleum ether (7:3) to afford 180 mg (40%) of the title compound as brown oil. LCMS (ESI, m/z): 446.15 [M+H]$^+$.

Step 2: Synthesis of 5-[5-[2-(dimethylamino)ethoxy]-6-fluoro-2,3-dihydro-1H-isoindol-2-yl]-4-(trifluoromethyl)-2-[[2-(trimethylsilyl)ethoxy]methyl]-2,3-dihydropyridazin-3-one A solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (254 mg, 0.50 mmol, 1.00 equiv), 2-(dimethylamino)ethan-1-ol (222.5 mg, 2.50 mmol, 5.00 equiv), [Pd(allyl)Cl]$_2$ (18.3 mg, 0.05 mmol, 0.10 equiv), Rockphos (23.4 mg, 0.05 mmol, 0.10 equiv), Cs$_2$CO$_3$ (326 mg, 1.00 mmol, 2.00 equiv) in Toluene (20 mL) was stirred for 3 h at 80° C. The resulting mixture was concentrated, the residue was applied onto a silica gel column eluting with EtOAc/petroleum ether (5/95) to afford 97 mg (38%) of the title compound as a brown oil. LCMS (ESI, m/z): 517.00 [M+H]$^+$.

Step 3: Synthesis of 5-[5-[2-(dimethylamino)ethoxy]-6-fluoro-2,3-dihydro-NH-isoindol-2-yl]-4-(trifluoromethyl)-2,3-dihydropyridazin-3-one; Formic Acid A solution of 5-[5-[2-(dimethylamino)ethoxy]-6-fluoro-2,3-dihydro-1H-isoindol-2-yl]-4-(trifluoromethyl)-2-[[2-(trimethylsilyl)ethoxy]methyl]-2,3-dihydropyridazin-3-one (88 mg, 0.17 mmol, 1.00 equiv) in HCl/dioxane (15 mL) was stirred for 2 h at room temperature. After concentration, the residue was purified by C18 reverse phase chromatography eluting with H$_2$O/CH$_3$CN. Then the residue was further purified by Prep-HPLC yielding the title compound (19.5 mg, 26%) as a white solid. LCMS (ESI, m/z): 387.10 [M+H]$^+$, $^1$HNMR (300 MHz, Methanol-d4) δ 8.46 (s, 1H), 8.05 (s, 1H), 7.24-7.21 (m, 2H), 5.04-5.01 (m, 4H), 4.39 (t, J=5.1 Hz, 2H), 3.52-3.40 (m, 2H), 2.87 (s, 6H).

Example 15: 5-[4-(pyridin-3-ylmethoxy)-1H,2H,3H-pyrrolo[3,4-c]pyridin-2-yl]-4-(trifluoromethyl)-2,3-dihydropyridazin-3-one

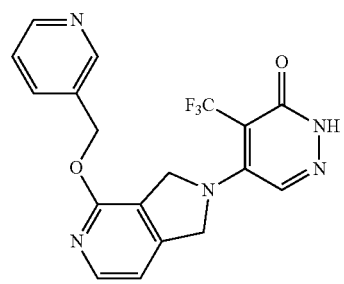 [SMILES: O=c1[nH]ncc(N2Cc3ccnc(OCc4cccnc4)c3C2)c1C(F)(F)F]

Step 1: Synthesis of 2-bromo-3,4-bis(bromomethyl)pyridine

A solution of 2-bromo-3,4-dimethylpyridine (5 g, 26.87 mmol, 1.00 equiv), NBS (10 g, 56.19 mmol, 2.00 equiv) and AIBN (2.22 g, 13.52 mmol, 0.50 equiv) in CCl$_4$ (40 mL) was stirred for 2 h at 80° C., and then the resulting solution was concentrated under vacuum, and then the residue was applied onto a silica gel column eluting with EtOAc/petroleum ether (2:98) to afford 5.7 g (62%) of the title compound as red oil. LCMS (ESI, m/z): 341.81 [M+H]+.

Step 2: Synthesis of 4-bromo-2-[(4-methylbenzene) sulfonyl]-1H,2H,3H-pyrrolo[3,4-c]pyridine A solution of 2-bromo-3,4-bis(bromomethyl)pyridine (2.7 g, 7.85 mmol, 1.00 equiv) and sodium hydride (380 mg, 15.83 mmol, 1.20 equiv) in DMF (20 mL), TosNH2 (1.485 g, 1.10 equiv) was added in, and then the resulting solution was stirred for 0.5 h at 0° C., and stirred for another 1 h at 25° C., and then the resulting solution was quenched by the addition of 50 mL of water, extracted with 3×15 mL of EtOAc and the organic layers combined and concentrated under vacuum. The residue was applied onto a silica gel column eluting with EtOAc/petroleum ether (3:7) to afford 2 g (72%) of the title compound as a light yellow solid. LCMS (ESI, m/z): 353.23 [M+H]$^+$.

Step 3: Synthesis of 4-bromo-1H,2H,3H-pyrrolo[3,4-c]pyridine hydrobromide

A solution of 4-bromo-2-[(4-methylbenzene)sulfonyl]-1H,2H,3H-pyrrolo[3,4-c]pyridine (2 g, 5.66 mmol, 1.00 equiv) and Phenol (3.2 g, 6.00 equiv) in 48% HBr/HOAc (5 mL) and acetic acid (10 mL) was stirred for 1 overnight at 90° C., and then the resulting solution was concentrated under vacuum, and the crude product purified by re-crystallization from EtOAc to afford 1.4 g (88%) of the title compound as a yellow solid. LCMS (ESI, m/z): 199.05 [M+H]$^+$.

Step 4: Synthesis of (5-[4-bromo-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 4-bromo-1H,2H,3H-pyrrolo[3,4-c]pyridine hydrobromide (1.4 g, 5.00 mmol, 1.00 equiv), 5-chloro-4-(trifluoromethyl)-2-{[2-(trimethylsilyl)ethoxy]methyl}-2,3-dihydropyridazin-3-one (2.55 g, 7.76 mmol, 1.10 equiv) and TEA (2.15 g, 21.25 mmol, 3.00 equiv) in ethanol (15 mL) was stirred for 2 h at 60° C., and then the resulting solution was concentrated under vacuum, and then the residue was applied onto a silica gel column eluting with EtOAc/petroleum ether (4:6) to afford 400 mg (16%) of the title compound as a dark green solid. LCMS (ESI, m/z): 491.38 [M+H]$^+$.

Step 5: Synthesis of 5-[4-(pyridin-3-ylmethoxy)-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 5-[4-bromo-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (150 mg, 0.31 mmol, 1.00 equiv), (Pd(allyl)C$_1$)$_2$ (14 mg, 0.10 equiv), Rockphos (11 mg, 0.10 equiv), pyridin-3-ylmethanol (134 mg, 1.23 mmol, 4.00 equiv) and Cs$_2$CO$_3$ (200 mg, 0.61 mmol, 2.00 equiv) in toluene (5 mL) was stirred for 2 h at 80° C. under an atmosphere of nitrogen, and then the resulting solution was concentrated under vacuum, and then the residue was applied onto a silica gel column eluting with EtOAc/petroleum ether (6:4) to afford 80 mg (50%) of the title compound as yellow oil. LCMS (ESI, m/z): 520.19 [M+H]$^+$.

Step 6: Synthesis of 5-[4-(pyridin-3-ylmethoxy)-1H,2H,3H-pyrrolo[3,4-c]pyridin-2-yl]-4-(trifluoromethyl)-2,3-dihydropyridazin-3-one A solution of 5-[4-(pyridin-3-ylmethoxy)-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (200 mg, 0.38 mmol, 1.00 equiv), in HCl/dioxane (5 mL, 4M) was stirred overnight at room temperature, and then the resulting solution was concentrated under vacuum, and then the residue was purified by Prep-HPLC yielding the title compound (2.7 mg, 2.0%) as a white solid. LCMS (ESI, m/z): 390.15 [M+H]+, $^1$HNMR (DMSO-d$_6$, 400 MHz) δ 8.71 (d, J=1.6 Hz, 1H), 8.54 (dd, J=4.8, 1.6 Hz, 1H), 8.16 (d, J=5.6 Hz, 1H), 8.07 (s, 1H), 7.90 (d, J=8.0 Hz, 1H), 7.43 (dd, J=8.4, 4.8 Hz, 1H), 7.13 (d, J=5.2 Hz, 1H), 5.51 (s, 2H), 4.97 (d, J=11.6 Hz, 4H).

Example 16: 5-[4-(piperidin-4-yloxy)-1H,2H,3H-pyrrolo[3,4-c]pyridin-2-yl]-4-(trifluoromethyl)-2,3-dihydropyridazin-3-one

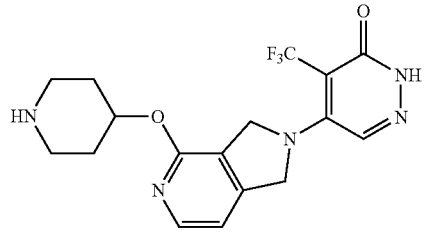 [SMILES: O=c1[nH]ncc(N2Cc3ccnc(OC4CCNCC4)c3C2)c1C(F)(F)F]

Step 1: Synthesis of 5-[4-bromo-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of (4-bromo-1H,2H,3H-pyrrolo[3,4-c]pyridine hydrobromide (700 mg, 2.50 mmol, 1.00 equiv), TEA (1.07 g, 10.57 mmol, 3.00 equiv), 5-chloro-4-(trifluoromethyl)-2-{[2-(trimethylsilyl)ethoxy]methyl}-2,3-dihydropyridazin-3-one (1.25 g, 3.80 mmol, 1.10 equiv) in ethanol (20 mL, 1.00 equiv) was stirred for 2 h at 60° C. The resulting mixture was concentrated under vacuum. The residue was applied onto a silica gel column eluting with EtOAc/petroleum ether (4/6) to afford 300 mg (24%) of the title compound as a dark green solid. LCMS (ESI, m/z): 493.06[M+H]$^+$.

Step 2: Synthesis of 5-[4-hydroxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one A solution of 5-[4-bromo-1H,2H,3H-pyrrolo[3,4-c]pyridin-2-yl]-4-(trifluoromethyl)-2-[[2-(trimethylsilyl)ethoxy]

methyl]-2,3-dihydropyridazin-3-one (440 mg, 0.90 mmol, 1.00 equiv), t-BuBrettphos (65 mg, 0.15 equiv), $K_3PO_4$ (571 mg, 2.69 mmol, 3.00 equiv), Pd(OAc)$_2$ (20 mg, 0.09 mmol, 0.10 equiv) in dioxane (5 mL) and water (1 mL) was stirred for 1 h at 100° C. The reaction mixture was concentrated under vacuum. The residue was applied onto a silica gel column eluting with ethyl DCM/methanol (95/5) to afford 125 mg (33%) of the title compound as a yellow solid. LCMS (ESI, m/z): 429.15 [M+H].

Step 3: Synthesis of Tert-Butyl 4-([2-[6-oxo-5-(trifluoromethyl)-1-[[2-(trimethylsilyl)ethoxy]methyl]-1,6-dihydropyridazin-4-yl]-1H,2H,3H-pyrrolo[3,4-c]pyridin-4-yl]oxy)piperidine-1-carboxylate A solution of 5-[4-hydroxy-1H,2H,3H-pyrrolo[3,4-c]pyridin-2-yl]-4-(trifluoromethyl)-2-[[2-(trimethylsilyl)ethoxy]methyl]-2,3-dihydropyridazin-3-one (115 mg, 0.27 mmol, 1.00 equiv), $Ag_2CO_3$ (149 mg, 0.54 mmol, 20.00 equiv), tert-butyl 4-iodopiperidine-1-carboxylate (168 mg, 0.54 mmol, 2.00 equiv) in DMF (10 mL) was stirred for 48 h at 80° C. The resulting solution was diluted with 20 mL of water and extracted with 3×20 ml of EtOAc. The organic layers combined, washed with 3×40 mL of brine, dried over $Na_2SO_4$. The resulting mixture was concentrated under vacuum. The residue was applied onto a silica gel column eluting with EtOAc/petroleum ether (1/1) to afford 146 mg (89%) of the title compound as yellow oil. LCMS (ESI, m/z): 612.28 [M+H].

Step 4: Synthesis of 5-[4-(piperidin-4-yloxy)-1H,2H,3H-pyrrolo[3,4-c]pyridin-2-yl]-4-(trifluoromethyl)-2,3-dihydropyridazin-3-one A solution of 5 tert-butyl 4-([2-[6-oxo-5-(trifluoromethyl)-1-[[2-(trimethylsilyl)ethoxy]methyl]-1,6-dihydropyridazin-4-yl]-1H,2H,3H-pyrrolo[3,4-c]pyridin-4-yl]oxy)piperidine-1-carboxylate (146 mg, 0.24 mmol, 1.00 equiv) in methanol (2 mL) and hydrogen chloride/Et2O (10 mL) was stirred for 4 h at room temperature. After concentration, the residue was purified by C18 reverse phase chromatography eluting with $H_2O/CH_3CN$. Then the residue was further purified by Prep-HPLC yielding the title compound (6 mg, 7%) as a brown solid. LCMS (ESI, m/z): 382.35 [M+H]$^+$, $^1$H NMR (400 MHz, DMSO-d$_6$) δ: 12.56 (s, 1H), 8.14-8.03 (m, 2H), 7.04 (d, J=5.3 Hz, 1H), 5.18 (dt, J=9.0, 4.8 Hz, 1H), 4.97-4.94 (m, 2H), 4.88-4.83 (m, 2H), 2.97 (dd, J=11.0, 6.4 Hz, 2H), 2.62 (t, J=10.0 Hz, 2H), 1.94 (dd, J=12.5, 8.1 Hz, 2H), 1.60-1.47 (m, 2H).

Example 17: 5-(5-[[(pyridin-4-yl)amino]methyl]-2,3-dihydro-1H-isoindol-2-yl)-4-(trifluoromethyl)-2,3-dihydropyridazin-3-one

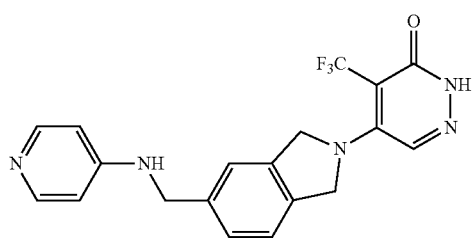 [SMILES: O=c1[nH]ncc(N2Cc3ccc(CNc4ccncc4)cc3C2)c1C(F)(F)F]

Step 1: Synthesis of 5-(5-bromo-2,3-dihydro-1H-isoindol-2-yl)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (3.29 g, 10.01 mmol, 1.00 equiv), 5-bromo-2,3-dihydro-1H-isoindole hydrochloride (2.35 g, 10.02 mmol, 1.00 equiv), TEA (2.02 g, 19.96 mmol, 2.00 equiv) in ethanol (50 mL) was stirred for 3 hours at 40° C. The solvent was concentrated under vacuum and the residue was applied onto a silica gel column eluting with EtOAc/petroleum ether (1/5) to afford 3.65 g (74%) of the title compound as a yellow solid. LCMS (ESI, m/z): 490.07 [M+H]$^+$.

Step 2: Synthesis of 2-[6-oxo-5-(trifluoromethyl)-1-[[2-(trimethylsilyl)ethoxy]methyl]-1,6-dihydropyridazin-4-yl]-2,3-dihydro-1H-isoindole-5-carbonitrile A solution of 5-(5-bromo-2,3-dihydro-1H-isoindol-2-yl)-4-(trifluoromethyl)-2-[[2-(trimethylsilyl)ethoxy]methyl]-2,3-dihydropyridazin-3-one (1.3 g, 2.65 mmol, 1 equiv), Pd(PPh$_3$)$_4$ (0.6 g, 0.52 mmol, 0.196 equiv), Zn(CN)$_2$ (0.62 g, 5.28 mmol, 1.991 equiv) in NMP (15 mL) was stirred for 2 hours at 120 degrees C. in an oil bath. The reaction was then quenched by the addition of 20 mL of water. The resulting solution was extracted with 3×30 ml of EtOAc dried over anhydrous sodium sulfate and concentrated under vacuum. The residue was applied onto a silica gel column eluting with EtOAc/petroleum ether (25/75) to afford 1.8 g crude of the title compound as yellow oil. LCMS (ESI, m/z): 437.15 [M+H]$^+$.

Step 3: Synthesis of 5-[5-(aminomethyl)-2,3-dihydro-1H-isoindol-2-yl]-4-(trifluoromethyl)-2-[[2-(trimethylsilyl)ethoxy]methyl]-2,3-dihydropyridazin-3-one A solution of 2-[6-oxo-5-(trifluoromethyl)-1-[[2-(trimethylsilyl)ethoxy]methyl]-1,6-dihydropyridazin-4-yl]-2,3-dihydro-1H-isoindole-5-carbonitrile (1 g, 2.29 mmol, 1.00 equiv), Palladium carbon (500 mg), hydrogen chloride (0.2 mL) in ethanol (20 mL) was stirred for 2 days at 30° C. under the atmosphere of hydrogen with the pressure of 30 atm. The solids were filtered out and the filtration was concentrated under vacuum. The residue was applied onto a silica gel column eluting with DCM/methanol (96:4) to afford 700 mg (69%) of the title compound as yellow oil. LCMS (ESI, m/z): 441.19 [M+H]$^+$.

Step 4: Synthesis of 5-(5-[[(pyridin-4-yl)amino]methyl]-2,3-dihydro-1H-isoindol-2-yl)-4-(trifluoromethyl)-2-[[2-(trimethylsilyl)ethoxy]methyl]-2,3-dihydropyridazin-3-one A solution of 5-[5-(aminomethyl)-2,3-dihydro-1H-isoindol-2-yl]-4-(trifluoromethyl)-2-[[2-(trimethylsilyl)ethoxy]methyl]-2,3-dihydropyridazin-3-one (200 mg, 0.45 mmol, 1.00 equiv), Pd$_2$(dba)$_3$.CHCl$_3$ (50 mg, 0.05 mmol, 0.10 equiv), Xantphos (28 mg, 0.05 mmol, 0.10 equiv), 4-bromopyridine (152 mg, 0.96 mmol, 2.00 equiv), Cs$_2$CO$_3$ (315 mg, 2.00 equiv) in dioxane (15 mL) was stirred for 2 h at 100° C. in an oil bath under the atmosphere of nitrogen. After concentration the residue was applied onto a silica gel column eluting with DCM/methanol (9:1) to afford 130 mg (55%) of the title compound as a yellow solid. LCMS (ESI, m/z): 518.21 [M+H]+.

Step 5: Synthesis of 5-(5-[[(pyridin-4-yl)amino]methyl]-2,3-dihydro-1H-isoindol-2-yl)-4-(trifluoromethyl)-2,3-dihydropyridazin-3-one A solution of 5-(5-[[(pyridin-4-yl)amino]methyl]-2,3-dihydro-1H-isoindol-2-yl)-4-(trifluoromethyl)-2-[[2-(trimethylsilyl)ethoxy]methyl]-2,3-dihydropyridazin-3-one (130 mg, 0.25 mmol, 1.00 equiv) in hydrogen chloride/dioxane (20 mL) was stirred for 14 h at room temperature. The resulting mixture was concentrated under vacuum. The pH value of the solution was adjusted to 9 with saturated sodium bicarbonate aqueous. The resulting solution was extracted with DCM and the organic layers combined and dried over anhydrous sodium sulfate. After concentration the residue was applied onto a silica gel column eluting with DCM/methanol (9:1). Then the residue was further purified by Prep-HPLC yielding the title compound (35.7 mg 37%) as a white solid. LCMS (ESI, m/z): 388.13 [M+H]+, 1HNMR (DMSO-$d_6$, 400 MHz) δ: 12.52 (s, 1H), 8.00 (d, J=5.2 Hz, 3H), 7.38-7.27 (m, 3H), 7.25 (t, J=6.1 Hz, 1H), 6.54-6.48 (m, 2H), 4.95 (d, J=9.1 Hz, 4H), 4.36 (d, J=6.1 Hz, 2H).

Example 18 Isomer A: 6-[4-[(3-[[(1R)-2-[6-Oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile and Example 18 Isomer B: 6-[4-[(3-[[(1S)-2-[6-Oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile Example 18

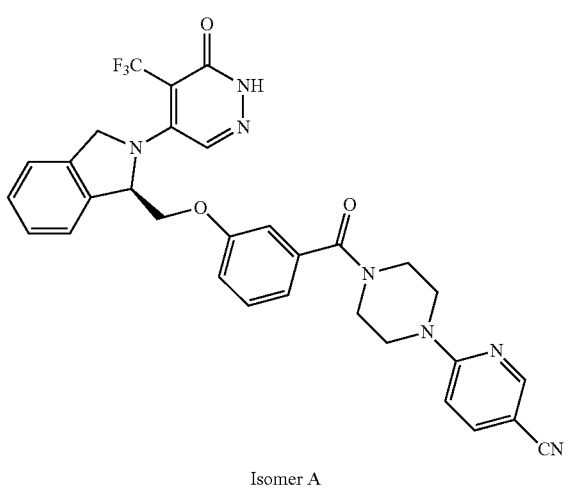

Isomer A

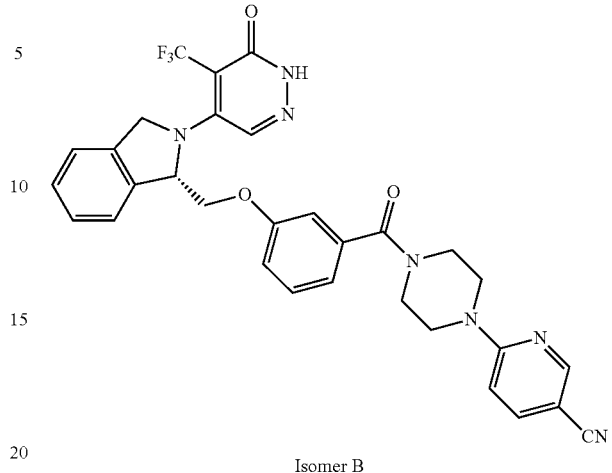

Isomer B

Step 1: 5-[1-(Hydroxymethyl)-2,3-dihydro-1H-isoindol-2-yl]-4-(trifluoromethyl)-2-[[2-(trimethylsilyl)ethoxy]methyl]-2,3-dihydropyridazin-3-one A solution of 5-chloro-4-(trifluoromethyl)-2-[2-(trimethylsilyl)ethoxy]methyl-2,3-dihydropyridazin-3-one (Int-A6, 4.8 g, 14.60 mmol, 1.00 equiv), 2,3-dihydro-1H-isoindol-1-ylmethanol hydrochloride (2.7 g, 14.54 mmol, 1.00 equiv) and TEA (4.4 g, 43.48 mmol, 2.99 equiv) in ethanol (100 mL) was stirred for 1 h at 60° C., and then the resulting solution was concentrated under vacuum and the residue was applied onto a silica gel column eluting with EtOAc/petroleum ether (45:55) to afford 2.9 g (45%) of the title compound as a brown solid. LCMS: [M+H]+ 442.17.

Step 2: Methyl 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoate Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (2.93 g, 6.64 mmol, 1.00 equiv), methyl 3-bromobenzoate (2.84 g, 13.21 mmol, 1.99 equiv), Pd(allyl)Cl$_2$ (243 mg), Rockphos (311 mg) and Cs$_2$CO$_3$ (4.3 g, 13.20 mmol, 1.99 equiv) in Toluene (100 mL) was stirred for 18 h at 80° C. The resulting solution was concentrated under vacuum and then the residue was applied onto a silica gel column eluting with EtOAc/petroleum ether (1:3) to afford 3 g (79%) of the title compound as a brown solid. LCMS: [M+H]+ 576.21.

Step 3: 3-([2-[6-Oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic Acid A solution of methyl 3-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)benzoate (1.15 g, 2.00 mmol, 1.00 equiv) and LiOH (240 mg, 10.02 mmol, 5.02 equiv) in THF (12 mL) and water (3 mL) was stirred for 3 h at 60° C. The resulting solution was concentrated under vacuum and the residue was diluted with 10 mL of H$_2$O, and then the pH value of the solution was adjusted to 5 with HCl (36.5%). The solid was collected by filtration to afford 1.1 g (98%) of the title compound as a light yellow solid. LCMS: [M+H]+ 562.19.

Step 4: 3-([2-[6-Oxo-5-(trifluoromethyl)-1,6-dihydropyridazin-4-yl]-2,3-dihydro-1H-isoindol-1-yl]methoxy)benzoic Acid A solution of 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic acid (1.1 g, 1.96 mmol, 1.00 equiv) in HCl/dioxane (20 mL, 4M) was stirred for 3 h at RT, and then the resulting solution was concentrated under vacuum to afford 1 g of the title compound as a crude brown solid. LCMS: [M+H]+ 432.11.

Step 5: 6-[4-[(3-[[(1R)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile and 6-[4-[(3-[[(1S)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile A solution of 3-([2-[6-oxo-5-(trifluoromethyl)-1,6-dihydropyridazin-4-yl]-2,3-dihydro-1H-isoindol-1-yl]methoxy)benzoic acid (500 mg, 1.16 mmol, 1.00 equiv), HATU (528 mg, 1.39 mmol, 1.20 equiv), DIPEA (449 mg, 3.47 mmol, 3.00 equiv) and Int-A4 (240 mg, 1.27 mmol, 1.1 equiv) in DMF (5 mL) was stirred for 2 h at RT. After concentration by reduced pressure, the resulting solution was purified by C18 reverse phase chromatography eluting with H2O/ACN. The residue was further purified by Prep-HPLC and Chiral-Prep-HPLC (CHIRAL Repaired IA, 5 μm, 0.46×10 cm column, eluting with a gradient of (Hexanes:DCM=3:1) (0.1% DEA):EtOH=50:50, at a flow rate of 1 mL/min) yielding the title compounds as white solids. The absolute stereochemistry was assigned based on a protein X-ray crystal structure obtained of Example 18 Isomer B which confirmed (S)-absolute stereochemistry and was observed to be the more potent enantiomer.

Example 18 Isomer A 153.2 mg, 22%, LCMS: [M+H]+ 602.05, 1H NMR (300 MHz, Methanol-d4) δ 8.43 (d, J=1.8 Hz, 1H), 8.42 (s, 1H), 7.79 (dd, J=9.0, 2.4 Hz, 1H), 7.53-7.50 (m, 1H), 7.41-7.35 (m, 4H), 7.05-6.99 (m, 2H), 6.94-6.87 (m, 2H), 6.20 (s, 1H), 5.33 (d, J=14.8 Hz, 1H), 4.68 (d, J=14.7 Hz, 1H), 4.53 (dd, J=10.2, 3.3 Hz, 1H), 4.29 (dd, J=10.2, 6.6 Hz, 1H), 3.91-3.44 (m, 8H). tR=4.369 min.

Example 18 Isomer B 153.3 mg, 22%, 1H NMR (300 MHz, Methanol-d4) δ 8.43 (d, J=1.8 Hz, 1H), 8.38 (s, 1H), 7.79 (dd, J=9.0, 2.4 Hz, 1H), 7.52-7.50 (m, 1H), 7.41-7.35 (m, 4H), 7.04-6.99 (m, 2H), 6.94-6.87 (m, 2H), 6.19 (s, 1H), 5.32 (d, J=14.7 Hz, 1H), 4.67 (d, J=14.7 Hz, 1H), 4.53 (dd, J=10.2, 3.6 Hz, 1H), 4.26 (dd, J=10.2, 6.6 Hz, 1H), 3.92-3.41 (m, 8H). LCMS: [M+H]+ 602.05. tR=5.955 min.

Example 19: 5-[5-fluoro-6-[2-(morpholin-4-yl)ethoxy]-2,3-dihydro-1H-isoindol-2-yl]-4-(trifluoromethyl)-2,3-dihydropyridazin-3-one

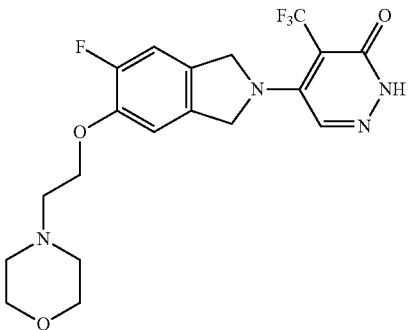 [SMILES: O=c1[nH]ncc(N2Cc3cc(F)c(OCCN4CCOCC4)cc3C2)c1C(F)(F)F]

Step 1: Synthesis of 5-[5-fluoro-6-[2-(morpholin-4-yl)ethoxy]-2,3-dihydro-1H-isoindol-2-yl]-4-(trifluoromethyl)-2-[[2-(trimethylsilyl)ethoxy]methyl]-2,3-dihydropyridazin-3-one A solution of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (200 mg, 0.45 mmol, 1 equiv), 4-(2-chloroethyl)morpholine hydrochloride (99.6 mg, 0.54 mmol, 1.192 equiv), K2CO3 (123.6 mg, 0.89 mmol, 1.992 equiv) in DMF (10 mL) was stirred for 12 h at 80° C. The reaction was then quenched by the addition of 5 mL of water. The resulting solution was extracted with 3×15 ml of EtOAc and the organic layers combined and dried over anhydrous sodium sulfate. The organic layers concentrated under vacuum. The residue was applied onto a silica gel column eluting with EtOAc/petroleum ether (90/10) to afford 180 mg (72%) of the title compound as yellow oil. LCMS (ESI, m/z): 559.23 [M+H]+.

Step 2: Synthesis of 5-[5-fluoro-6-[2-(morpholin-4-yl)ethoxy]-2,3-dihydro-1H-isoindol-2-yl]-4-(trifluoromethyl)-2,3-dihydropyridazin-3-one A solution of 5-[5-fluoro-6-[2-(morpholin-4-yl)ethoxy]-2,3-dihydro-1H-isoindol-2-yl]-4-(trifluoromethyl)-2-[[2-(trimethyl silyl)ethoxy]methyl]-2,3-dihydropyridazin-3-one (180 mg, 0.32 mmol, 1 equiv) in HCl/dioxane (10 mL) was stirred for 12 h at room temperature. After concentration, the residue was purified by C18 reverse phase chromatography eluting with H2O/CH3CN. Then the residue was further purified by Prep-HPLC yielding the title compound (52.1 mg, 37.8%) as a white solid. LCMS (ESI, m/z): 429.38 [M+H]+, 1HNMR (DMSO-d6, 300 MHz) δ: 12.55 (s, 1H), 7.98 (s, 1H), 7.27 (m, 2H), 4.91 (m, 4H), 4.18 (t, J=5.7 Hz, 2H), 3.64-3.54 (m, 4H), 3.31 (m, 2H), 2.73 (t, J=5.7 Hz, 2H), 2.48 (m, 2H).

Example 20: 5-[5-fluoro-6-(piperidin-4-ylmethoxy)-2,3-dihydro-1H-isoindol-2-yl]-4-(trifluoromethyl)-2,3-dihydropyridazin-3-one Example 21: 5-[5-[(1-acetylpiperidin-4-yl)methoxy]-6-fluoro-2,3-dihydro-1H-isoindol-2-yl]-4-(trifluoromethyl)-2,3-dihydropyridazin-3-one

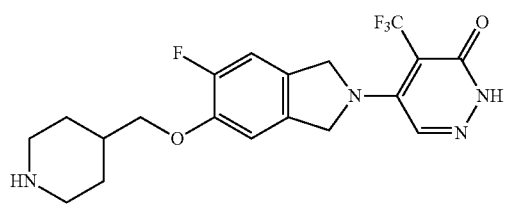 [SMILES: O=c1[nH]ncc(N2Cc3cc(F)c(OCC4CCNCC4)cc3C2)c1C(F)(F)F]

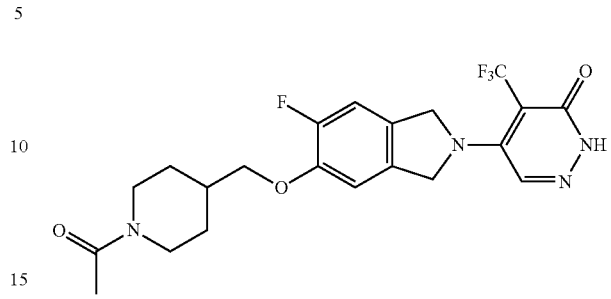

Step 1: Synthesis of Tert-Butyl 4-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]piperidine-1-carboxylate A solution of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (1 g, 2.24 mmol, 1.00 equiv), potassium carbonate (3.1 g, 22.43 mmol, 10.00 equiv), tert-butyl 4-(iodomethyl)piperidine-1-carboxylate (4.4 g, 13.53 mmol, 6.00 equiv) in DMF (15 mL) was stirred for 1.5 h at 80° C. The solution was quenched with 50 ml water, then the resulting solution was extracted with EtOAc (3×60 mL) and the organic layers combined. The solution was dried over anhydrous sodium sulfate and concentrated under vacuum. The residue was applied onto a silica gel column eluting with EtOAc/petroleum ether (5/95) to afford 1 g (69%) of the title compound as a white solid. LCMS (ESI, m/z): 643.30 [M+H]+.

Step 2: Synthesis of 5-[5-fluoro-6-(piperidin-4-ylmethoxy)-2,3-dihydro-1H-isoindol-2-yl]-4-(trifluoromethyl)-2,3-dihydropyridazin-3-one A solution of tert-butyl 4-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]piperidine-1-carboxylate (200 mg, 0.31 mmol, 1.00 equiv), trifluoroacetic acid (2 mL) in DCM (10 mL) was stirred for 3 h at room temperature. After concentration, the residue was purified by C18 reverse phase chromatography eluting with H$_2$O/CH$_3$CN. Then the residue was further purified by Prep-HPLC yielding the title compound (24.2 mg, 19%) as a white solid. LCMS (ESI, m/z): 413.10 [M+H]+, $^1$HNMR (DMSO-d$_6$, 300 MHz) δ 7.98 (d, J=13.8 Hz, 1H), 7.28-7.18 (m, 2H), 4.90-4.88 (m, 4H), 3.87 (dd, J=6.4, 3.9 Hz, 2H), 3.01-2.95 (m, 2H), 2.45-2.44 (m, 2H), 1.84 (d, J=4.2 Hz, 1H), 1.75-1.58 (m, 2H), 1.22-1.13 (m, 2H).

A solution of 5-[5-fluoro-6-(piperidin-4-ylmethoxy)-2,3-dihydro-1H-isoindol-2-yl]-4-(trifluoromethyl)-2,3-dihydropyridazin-3-one (325.35 mg, 0.79 mmol, 1.00 equiv), TEA (227.25 mg, 2.25 mmol, 4.00 equiv), Ac$_2$O (45.9 mg, 0.45 mmol, 1.00 equiv) in DCM (15 mL) was stirred for 2 h at room temperature. After concentration, the residue was purified by C18 reverse phase chromatography eluting with H$_2$O/CH$_3$CN. Then the residue was further purified by Prep-HPLC yielding the title compound (68.2 mg, 19%) as a white solid. LCMS (ESI, m/z): 455.05 [M+H]+, $^1$HNMR (Methanol-d$_4$, 300 MHz) δ 8.04 (s, 1H), 7.14 (dd, J=9.2, 4.7 Hz, 2H), 5.00-4.99 (s, 4H), 4.59 (d, J=12.9 Hz, 1H), 4.06-3.84 (m, 3H), 3.25-3.13 (m, 1H), 2.80-2.56 (m, 1H), 2.13 (s, 3H), 2.12-2.11 (m, 1H), 2.04-1.84 (m, 2H), 1.50-1.22 (m, 2H).

Example 22: 5-[5-fluoro-6-[(1-methylpiperidin-4-yl)methoxy]-2,3-dihydro-1H-isoindol-2-yl]-4-(trifluoromethyl)-2,3-dihydropyridazin-3-one

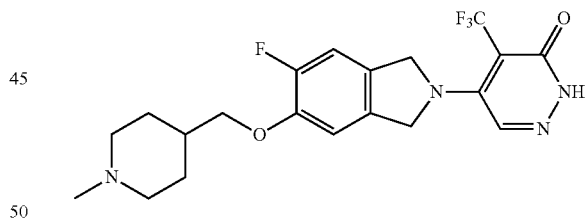

A solution of 5-[5-fluoro-6-(piperidin-4-ylmethoxy)-2,3-dihydro-1H-isoindol-2-yl]-4-(trifluoromethyl)-2,3-dihydropyridazin-3-one (150 mg, 0.36 mmol, 1.00 equiv), (HCHO)$_n$ (62.1 mg, 3.00 equiv), acetic acid (0.5 mL), NaBH$_3$CN (43.47 mg, 0.69 mmol, 3.00 equiv) in methanol (15 mL) was stirred for 15 h at room temperature. After concentration, the residue was purified by C18 reverse phase chromatography eluting with H$_2$O/CH$_3$CN. Then the residue was further purified by Prep-HPLC yielding the title compound (57.9 mg, 37%) as a white solid. LCMS (ESI, m/z): 427.10 [M+H]+, $^1$HNMR (Methanol-d4, 300 MHz) δ 8.04 (s, 1H), 7.12 (dd, J=9.2, 4.5 Hz, 2H), 4.96 (s, 4H) 3.93 (d, J=5.7 Hz, 2H), 2.95 (d, J=11.5 Hz, 2H), 2.31 (s, 3H), 2.11 (t, J=6.3 Hz, 2H), 1.98-1.81 (m, 3H), 1.65-1.26 (m, 2H).

Example 23: 5-(5-fluoro-6-[[(piperidin-4-yl)amino]methyl]-2,3-dihydro-1H-isoindol-2-yl)-4-(trifluoromethyl)-2,3-dihydropyridazin-3-one

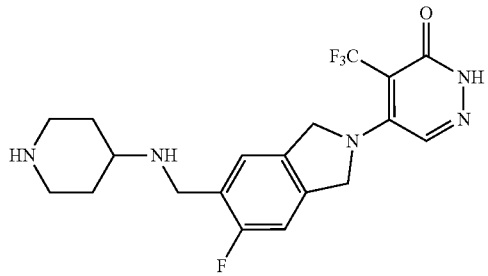 [SMILES: O=c1[nH]ncc(N2Cc3cc(F)c(CNC4CCNCC4)cc3C2)c1C(F)(F)F]

Step 1: Synthesis of 6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindole-5-carbonitrile A solution of 6-fluoro-2,3-dihydro-1H-isoindole-5-carbonitrile (600 mg, 3.70 mmol, 1 equiv), 5-chloro-4-(trifluoromethyl)-2-[[2-(trimethylsilyl)ethoxy]methyl]-2,3-dihydropyridazin-3-one (1.45 g, 4.41 mmol, 1.192 equiv), TEA (1.12 g, 11.07 mmol, 2.991 equiv) in EtOH (15 mL) was stirred for 2 h at 80° C. The resulting mixture was concentrated under vacuum. The residue was applied onto a silica gel column eluting with EtOAc/petroleum ether (15/85) to afford 1.2 g (71%) of the title compound as a yellow solid. LCMS (ESI, m/z): 455.14 [M+H]+.

Step 2: Synthesis of 5-[5-(aminomethyl)-6-fluoro-2,3-dihydro-1H-isoindol-2-yl]-4-(trifluoromethyl)-2-[[2-(trimethylsilyl)ethoxy]methyl]-2,3-dihydropyridazin-3-one A solution of 6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindole-5-carbonitrile (3 g, 6.60 mmol, 1 equiv), Pd/C (300 mg, 2.82 mmol, 0.427 equiv) in EtOH (30 mL) was stirred 7 days at room temperature with an atmosphere of hydrogen. The solids were filtered out. The resulting mixture was concentrated under vacuum. The residue was applied onto a silica gel column eluting with DCM/methanol (93/7) to afford 1.58 g (52.2%) of the title compound as a yellow solid. LCMS (ESI, m/z): 459.18 [M+H]+.

Step 3: Synthesis of Tert-Butyl 4-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]methyl)amino]piperidine-1-carboxylate A solution of 5-[5-(aminomethyl)-6-fluoro-2,3-dihydro-1H-isoindol-2-yl]-4-(trifluoromethyl)-2-[[2-(trimethylsilyl)ethoxy]methyl]-2,3-dihydropyridazin-3-one (200 mg, 0.44 mmol, 1 equiv), tert-butyl 4-oxopiperidine-1-carboxylate (104.6 mg, 0.52 mmol, 1.204 equiv), NaBH3CN (137.34 mg, 2.19 mmol, 5.010 equiv) in MeOH (10 mL) was stirred for 2 h at room temperature. After concentration, the residue was purified by C18 reverse phase chromatography eluting with H2O/CH3CN to afford 100 mg (35.7%) of the title compound as yellow oil. LCMS (ESI, m/z): 642.30 [M+H]+.

Step 4: Synthesis of 5-(5-fluoro-6-[[(piperidin-4-yl)amino]methyl]-2,3-dihydro-1H-isoindol-2-yl)-4-(trifluoromethyl)-2,3-dihydropyridazin-3-one A solution of tert-butyl 4-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]methyl)amino]piperidine-1-carboxylate (100 mg, 0.16 mmol, 1 equiv) in HCl/dioxane (12 mL) was stirred for 12 h at room temperature. After concentration, the residue was purified by C18 reverse phase chromatography eluting with H2O/CH3CN. Then the residue was further purified by Prep-HPLC yielding the title compound (20.4 mg, 31.8%) as a white solid. LCMS (ESI, m/z): 412.40 [M+H]+, 1HNMR (300 MHz, DMSO-d6) δ: 8.01 (s, 1H), 7.48 (d, J=6.7 Hz, 1H), 7.21 (d, J=10.0 Hz, 1H), 4.95 (s, 4H), 3.77 (s, 2H), 2.91 (d, J=12.0 Hz, 2H), 2.47-2.33 (m, 3H), 1.77 (d, J=11.9 Hz, 2H), 1.13 (m, 2H).

Example 24: 5-(5-[[(1-acetylpiperidin-4-yl)amino]methyl]-6-fluoro-2,3-dihydro-1H-isoindol-2-yl)-4-(trifluoromethyl)-2-[[2-(trimethylsilyl)ethoxy]methyl]-2,3-dihydropyridazin-3-one

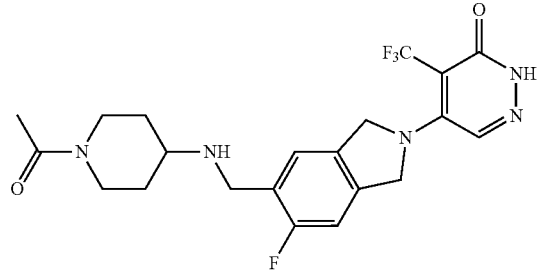 [SMILES: CC(=O)N1CCC(NCc2cc3c(cc2F)CN(c2cn[nH]c(=O)c2C(F)(F)F)C3)CC1]

Step 1: Synthesis of 5-(5-[[(1-acetylpiperidin-4-yl)amino]methyl]-6-fluoro-2,3-dihydro-1H-isoindol-2-yl)-4-(trifluoromethyl)-2-[[2-(trimethylsilyl)ethoxy]methyl]-2,3-dihydropyridazin-3-one A solution of 5-[5-(aminomethyl)-6-fluoro-2,3-dihydro-1H-isoindol-2-yl]-4-(trifluoromethyl)-2-[[2-(trimethylsilyl)ethoxy]methyl]-2,3-dihydropyridazin-3-one (300 mg, 0.65 mmol, 1 equiv), 1-acetylpiperidin-4-one (110.6 mg, 0.78 mmol, 1.197 equiv), NaBH3CN (206 mg, 3.28 mmol, 5.01 equiv) in MeOH (10 mL) was stirred 2 h at room temperature. After concentration, the residue was purified by C18 reverse phase chromatography eluting with H2O/CH3CN to afford 250 mg (65.5%) of the title compound as yellow oil. LCMS (ESI, m/z): 584.26 [M+H]+.

Step 2: Synthesis of 5-(5-[[(1-acetylpiperidin-4-yl)amino]methyl]-6-fluoro-2,3-dihydro-1H-isoindol-2-yl)-4-(trifluoromethyl)-2,3-dihydropyridazin-3-one A solution of 5-(5-[[(1-acetylpiperidin-4-yl)amino]methyl]-6-fluoro-2,3-dihydro-1H-isoindol-2-yl)-4-(trifluoromethyl)-2-[[2-(trimethylsilyl)ethoxy]methyl]-2,3-dihydropyridazin-3-one (250 mg, 0.43 mmol, 1 equiv) in HCl/dioxane (12 mL) was stirred for 12 h at room temperature. After concentration, the residue was purified by C18 reverse phase chromatography eluting with H2O/CH3CN. Then the residue was further purified by Prep-HPLC yielding the title compound (70.3 mg, 36.2%) as a white solid. LCMS (ESI, m/z): 454.43 [M+H]+, 1HNMR (300 MHz, DMSO-d6) δ: 12.56 (s, 1H), 8.01 (s, 1H), 7.49 (d, J=6.8 Hz, 1H), 7.21 (d, J=10.0 Hz, 1H), 4.95 (s, 4H), 4.14 (d, J=13.1 Hz, 1H), 3.78 (s, 2H), 3.78-3.72 (m, 1H), 3.05 (t, J=11.3 Hz, 1H), 2.79-2.56 (m, 2H), 2.38-2.22 (m, 1H), 1.99 (s, 3H), 1.88-1.72 (m, 2H), 1.33-1.12 (m, 2H).

Example 25: 5-(5-fluoro-6-[[(1-methylpiperidin-4-yl)amino]methyl]-2,3-dihydro-1H-isoindol-2-yl)-4-(trifluoromethyl)-2-[[2-(trimethylsilyl)ethoxy]methyl]-2,3-dihydropyridazin-3-one

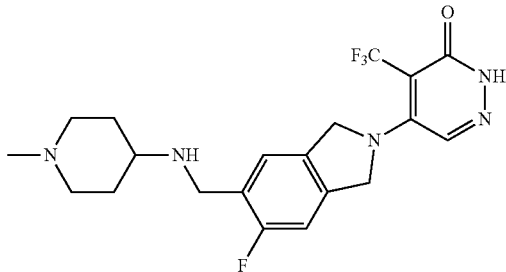 [SMILES: CN1CCC(NCc2cc3c(cc2F)CN(c2cn[nH]c(=O)c2C(F)(F)F)C3)CC1]

Step 1: Synthesis of 5-(5-fluoro-6-[[(1-methylpiperidin-4-yl)amino]methyl]-2,3-dihydro-1H-isoindol-2-yl)-4-(trifluoromethyl)-2-[[2-(trimethylsilyl)ethoxy]methyl]-2,3-dihydropyridazin-3-one A solution of 5-[5-(aminomethyl)-6-fluoro-2,3-dihydro-1H-isoindol-2-yl]-4-(trifluoromethyl)-2-[[2-(trimethylsilyl)ethoxy]methyl]-2,3-dihydropyridazin-3-one (300 mg, 0.65 mmol, 1 equiv), 1-methylpiperidin-4-one (89.4 mg, 0.79 mmol, 1.208 equiv), NaBH3CN (206.01 mg, 3.28 mmol, 5.010 equiv) in MeOH (10 mL) was stirred 2 h at room temperature. After concentration, the residue was purified by C18 reverse phase chromatography eluting with H2O/CH3CN to afford 200 mg (55%) of the title compound as yellow oil. LCMS (ESI, m/z): 556.27 [M+H]+.

Step 2: Synthesis of 5-(5-fluoro-6-[[(1-methylpiperidin-4-yl)amino]methyl]-2,3-dihydro-1H-isoindol-2-yl)-4-(trifluoromethyl)-2,3-dihydropyridazin-3-one A solution of 5-(5-fluoro-6-[[(1-methylpiperidin-4-yl)amino]methyl]-2,3-dihydro-1H-isoindol-2-yl)-4-(trifluoromethyl)-2-[[2-(trimethylsilyl)ethoxy]methyl]-2,3-dihydropyridazin-3-one (200 mg, 0.36 mmol, 1 equiv) in HCl/dioxane (12 mL) was stirred for 12 h at room temperature. After concentration, the residue was purified by C18 reverse phase chromatography eluting with H2O/CH3CN. Then the residue was further purified by Prep-HPLC yielding the title compound (41.0 mg, 26.8%) as a white solid. LCMS (ESI, m/z): 426.42 [M+H]+, 1HNMR (300 MHz, DMSO-d6) δ: 12.52 (s, 1H), 7.97 (s, 1H), 7.44 (d, J=6.8 Hz, 1H), 7.17 (d, J=10.0 Hz, 1H), 4.92 (s, 4H), 3.72 (s, 2H), 2.66 (d, J=11.2 Hz, 2H), 2.34-2.24 (m, 1H), 2.10 (s, 3H), 1.89-1.70 (m, 5H), 1.34-1.16 (m, 2H).

Example 26: 5-[5-fluoro-6-(morpholin-4-yl)-2,3-dihydro-1H-isoindol-2-yl]-4-(trifluoromethyl)-2,3-dihydropyridazin-3-one

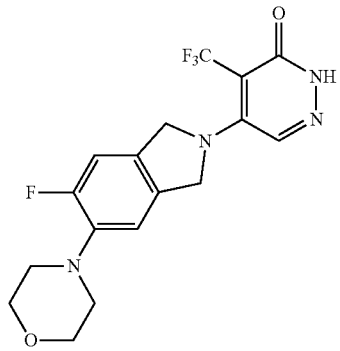 [SMILES: O=c1[nH]ncc(N2Cc3cc(F)c(N4CCOCC4)cc3C2)c1C(F)(F)F]

Step 1: Synthesis of 5-[5-fluoro-6-(morpholin-4-yl)-2,3-dihydro-1H-isoindol-2-yl]-4-(trifluoromethyl)-2-[[2-(trimethylsilyl)ethoxy]methyl]-2,3-dihydropyridazin-3-one A solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (300 mg, 0.59 mmol, 1 equiv), morpholine (62 mg, 0.71 mmol, 1.206 equiv), Pd2(dba)3 (108 mg, 0.12 mmol, 0.200 equiv), Xantphos (68.2 mg, 0.12 mmol, 0.200 equiv), t-BuOK (131.7 mg, 1.17 mmol, 1.989 equiv) in Toluene (10 mL) was stirred for 12 h at 80° C. with an inert atmosphere of nitrogen. The resulting mixture was concentrated under vacuum. The residue was applied onto a silica gel column eluting with EtOAc/petroleum ether (25/75) to afford 170 mg (56%) of the title compound as a yellow solid. LCMS (ESI, m/z): 515.20 [M+H]+.

Step 2: Synthesis of 5-[5-fluoro-6-(morpholin-4-yl)-2,3-dihydro-1H-isoindol-2-yl]-4-(trifluoromethyl)-2,3-dihydropyridazin-3-one A solution of 5-[5-fluoro-6-(morpholin-4-yl)-2,3-dihydro-1H-isoindol-2-yl]-4-(trifluoromethyl)-2-[[2-(trimethylsilyl)ethoxy]methyl]-2,3-dihydropyridazin-3-one (170 mg, 0.33 mmol, 1 equiv) in HCl/dioxane (10 mL) was stirred for 12 h at room temperature. After concentration, the residue was purified by C18 reverse phase chromatography eluting with H2O/CH3CN. Then the residue was further purified by Prep-HPLC yielding the title compound (20.7 mg, 16.3%) as a white solid. LCMS (ESI, m/z): 385.33 [M+H]+, 1HNMR (DMSO-d6, 300 MHz) δ 12.54 (s, 1H), 7.98 (s, 1H), 7.22 (d, J=12.4 Hz, 1H), 7.08 (d, J=8.0 Hz, 1H), 4.91 (br, 4H), 3.79-3.68 m, 4H), 3.04-2.94 (m, 4H).

Example 27: 5-(4-[[1-(diphenylmethyl)piperidin-4-yl]oxy]-2,3-dihydro-1H-isoindol-2-yl)-4-(trifluoromethyl)-2,3-dihydropyridazin-3-one

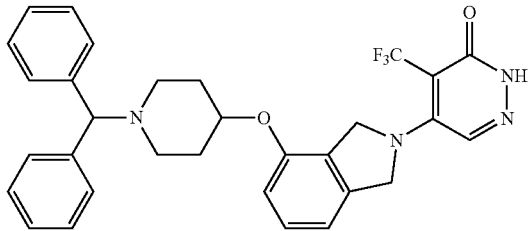 [SMILES: O=c1[nH]ncc(N2Cc3cccc(OC4CCN(C(c5ccccc5)c5ccccc5)CC4)c3C2)c1C(F)(F)F]

Step 1: Synthesis of Tert-Butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]oxy)piperidine-1-carboxylate A solution of 5-(4-hydroxy-2,3-dihydro-1H-isoindol-2-yl)-4-(trifluoromethyl)-2-[[2-(trimethylsilyl)ethoxy]methyl]-2,3-dihydropyridazin-3-one (1.1 g, 2.57 mmol, 1.00 equiv), potassium carbonate (1.8 g, 13.02 mmol, 5.00 equiv), tert-butyl 4-iodopiperidine-1-carboxylate (4.0 g, 12.86 mmol, 5.00 equiv) in DMF (30 mL) was stirred for 3 days at 80° C. in an oil bath. After concentration, the residue was applied onto a silica gel column eluting with EtOAc/petroleum ether (1:3) to afford 1.3 g (83%) of the title compound as a yellow solid. LCMS (ESI, m/z): 611.28 [M+H]$^+$.

Step 2: Synthesis of 5-[4-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one A solution of tert-butyl 4-([2-[6-oxo-5-(trifluoromethyl)-1-[[2-(trimethyl silyl)ethoxy]methyl]-1,6-dihydropyridazin-4-yl]-2,3-dihydro-1H-isoindol-4-yl]oxy)piperidine-1-carboxylate (600 mg, 0.98 mmol, 1.00 equiv) in hydrogen chloride/dioxane (120 ml, 1M) was stirred for 12 h at room temperature. After concentration, the residue was applied onto a silica gel column eluting with DCM/methanol (2:1) to afford 270 mg (54%) of the title compound as a yellow solid. LCMS (ESI, m/z): 511.23 [M+H]$^+$.

Step 3: Synthesis of 5-(4-[[1-(diphenylmethyl)piperidin-4-yl]oxy]-2,3-dihydro-1H-isoindol-2-yl)-4-(trifluoromethyl)-2-[[2-(trimethylsilyl)ethoxy]methyl]-2,3-dihydropyridazin-3-one A solution of 5-[4-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one (250 mg, 0.49 mmol, 1.00 equiv), TEA (99 mg, 0.98 mmol, 2.00 equiv), [bromo(phenyl)methyl]benzene (241 mg, 0.98 mmol, 2.00 equiv) in dioxane (8 mL) was stirred for 2 days at 100° C. in an oil bath. After concentration, the residue was applied onto a silica gel column eluting with EtOAc/petroleum ether (1:3) to afford 154 mg (46%) of the title compound as a solid. LCMS (ESI, m/z): 677.31 [M+H]$^+$.

Step 4: Synthesis of 5-(4-[[1-(diphenylmethyl)piperidin-4-yl]oxy]-2,3-dihydro-1H-isoindol-2-yl)-4-(trifluoromethyl)-2,3-dihydropyridazin-3-one A solution of 5-(4-[[1-(diphenylmethyl)piperidin-4-yl]oxy]-2,3-dihydro-1H-isoindol-2-yl)-4-(trifluoromethyl)-2-[[2-(trimethylsilyl)ethoxy]methyl]-2,3-dihydropyridazin-3-one (154 mg, 0.23 mmol, 1.00 equiv) in hydrogen chloride/dioxane (15 mL) was stirred for 12 h at room temperature. After concentration, the residue was applied onto a silica gel column with DCM/methanol (2:1) and the crude product was purified by Prep-HPLC yielding the title compound (15.7 mg 13%) as a white solid. LCMS (ESI, m/z): 547.22 [M+H]$^+$, $^1$H NMR (DMSO-d$_6$, 300 MHz) δ: 12.51 (s, 1H), 8.01 (s, 1H), 7.41 (d, J=7.4 Hz, 4H), 7.31-7.15 (m, 7H), 6.97-6.90 (dd, J=14.1, 7.9 Hz, 2H), 4.95 (s, 2H), 4.84 (s, 2H), 4.53-4.49 (dr, 1H), 4.35 (s, 1H), 2.58-2.51 (m, 2H), 2.27-2.22 (m, 2H), 1.93-1.91 (dr, 2H), 1.74-1.68 (dr, 2H).

Example 28: 5-(5-[[1-(diphenylmethyl)piperidin-4-yl]oxy]-2,3-dihydro-1H-isoindol-2-yl)-4-(trifluoromethyl)-2,3-dihydropyridazin-3-one

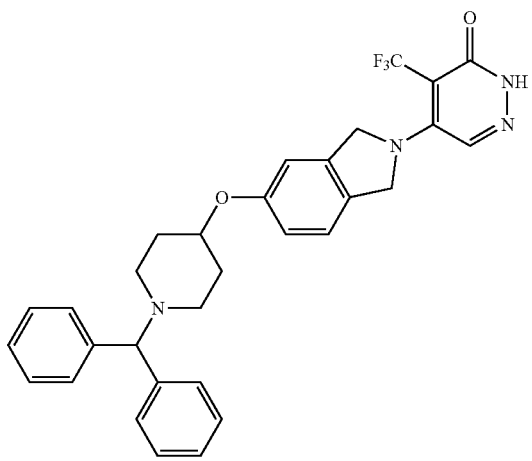 [SMILES: O=c1[nH]ncc(N2Cc3ccc(OC4CCN(C(c5ccccc5)c5ccccc5)CC4)cc3C2)c1C(F)(F)F]

Step 1: Synthesis of 1-(diphenylmethyl)piperidin-4-ol

A solution of piperidin-4-ol (5 g, 49.43 mmol, 1.00 equiv), TEA (5 g, 49.41 mmol, 1.00 equiv), [bromo(phenyl)methyl]benzene (9 g, 36.42 mmol, 0.80 equiv) in THF (30 mL) was stirred for 2 days at room temperature. After concentration, the residue was applied onto a silica gel column eluting with EtOAc/petroleum ether (1:2) to afford 3.8 g (29%) of the title compound as a solid. LCMS (ESI, m/z): 268.16 [M+H]$^+$.

Step 2: Synthesis of 1-(diphenylmethyl)piperidin-4-yl methanesulfonate

A solution of 1-(diphenylmethyl)piperidin-4-ol (3.8 g, 14.21 mmol, 1.00 equiv), MsCl (1.44 g, 1.10 equiv), TEA (1.52 g, 15.02 mmol, 2.00 equiv) in DCM (20 mL) was stirred for 30 min at room temperature. The resulting solution was extracted with of DCM and the organic layers combined and concentrated under vacuum to afford 3.2 g (65%) of the title compound as a yellow solid. LCMS (ESI, m/z): 346.14 [M+H]$^+$.

Step 3: Synthesis of 5-(5-[[1-(diphenylmethyl)piperidin-4-yl]oxy]-2,3-dihydro-1H-isoindol-2-yl)-4-(trifluoromethyl)-2-[[2-(trimethylsilyl)ethoxy]methyl]-2,3-dihydropyridazin-3-one A solution of 5-(5-hydroxy-2,3-dihydro-1H-isoindol-2-yl)-4-(trifluoromethyl)-2-[[2-(trimethylsilyl)ethoxy]

methyl]-2,3-dihydropyridazin-3-one (400 mg, 0.94 mmol, 1.00 equiv), potassium carbonate (1.3 g, 9.41 mmol, 10.00 equiv), 1-(diphenylmethyl)piperidin-4-yl methanesulfonate (649 mg, 1.88 mmol, 2.00 equiv) in DMF (40 mL) was stirred for 2 days at 80° C. in an oil bath. After concentration, the residue was applied onto a silica gel column eluting with EtOAc/petroleum ether (1:3) to afford 200 mg (32%) of the title compound as a yellow solid. LCMS (ESI, m/z): 677.31 [M+H]+.

Step 4: Synthesis of 5-(5-[[1-(diphenylmethyl)piperidin-4-yl]oxy]-2,3-dihydro-1H-isoindol-2-yl)-4-(trifluoromethyl)-2,3-dihydropyridazin-3-one A solution of 5-(5-[[1-(diphenylmethyl)piperidin-4-yl]oxy]-2,3-dihydro-1H-isoindol-2-yl)-4-(trifluoromethyl)-2-[[2-(trimethylsilyl)ethoxy]methyl]-2,3-dihydropyridazin-3-one (200 mg, 0.30 mmol, 1.00 equiv) in hydrogen chloride/dioxane (20 mL) was stirred for 12 h at room temperature. The residue was applied onto a silica gel column eluting with EtOAc/petroleum ether (1:2). The crude product was purified by Prep-HPLC yielding the title compound (14.3 mg 9%) as a white solid. LCMS (ESI, m/z): 547.22 [M+H]+, $^1$H NMR (Methanol-d$_4$, 300 MHz) δ: 8.02 (s, 1H), 7.45-7.42 (d, J=7.8 Hz, 4H), 7.31-7.14 (m, 7H), 6.92-6.87 (m, 2H), 4.97-4.94 (d, J=8.4 Hz, 4H), 4.41 (dr, 1H), 4.29 (s, 1H), 2.72 (dr, 2H), 2.27-2.21 (m, 2H), 2.03-1.97 (m, 2H), 1.78-1.71 (m, 2H).

Example 29: 6-(4-[[3-(2-[methyl[6-oxo-5-(trifluoromethyl)-1,6-dihydropyridazin-4-yl]amino]ethoxy)phenyl]carbonyl]piperazin-1-yl)pyridine-3-carbonitrile

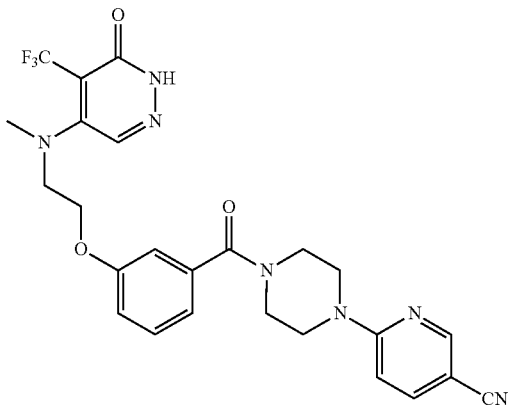 [SMILES: CN(CCOc1cccc(C(=O)N2CCN(c3ccc(C#N)cn3)CC2)c1)c1cn[nH]c(=O)c1C(F)(F)F]

Step 1: Synthesis of 5-[(2-hydroxyethyl) (methyl) amino]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (1 g, 3.04 mmol, 1.00 equiv), TEA (600 mg, 5.93 mmol, 2.00 equiv), 2-(methylamino)ethan-1-ol (1.1 g, 14.65 mmol, 5.00 equiv) in ethanol (14 mL) was stirred for 2 h at 60° C. in an oil bath. The resulting mixture was concentrated under vacuum. The residue was applied onto a silica gel column eluting with EtOAc/petroleum ether (8:1) to afford 1.1 g (98%) of the title compound as yellow oil. LCMS (ESI, m/z): 368.15 [M+H]+.

Step 2: Synthesis of Methyl 3-(2-[methyl[6-oxo-5-(trifluoromethyl)-1-[[2-(trimethylsilyl)ethoxy]methyl]-1,6-dihydropyridazin-4-yl]amino]ethoxy)benzoate A solution of 5-[(2-hydroxyethyl)(methyl)amino]-4-(trifluoromethyl)-2-[[2-(trimethylsilyl)ethoxy]methyl]-2,3-dihydropyridazin-3-one (800 mg, 2.18 mmol, 1.00 equiv), [Pd(allyl)Cl]$_2$ (80 mg, 0.22 mmol, 0.10 equiv), rockphos (102 mg, 0.22 mmol, 0.10 equiv), Cs$_2$CO$_3$ (1.4 g, 4.30 mmol, 2.00 equiv), methyl 3-bromobenzoate (466 mg, 2.17 mmol, 1.00 equiv) in toulene (12 mL) was stirred for 2 h at 85 degrees C. in an oil bath. The resulting mixture was concentrated under vacuum. The residue was applied onto a silica gel column eluting with EtOAc/petroleum ether (3:2) to afford 700 mg (64%) of the title compound as a yellow solid. LCMS (ESI, m/z): 502.19 [M+H]+.

Step 3: Synthesis of Methyl 3-(2-[methyl[6-oxo-5-(trifluoromethyl)-1,6-dihydropyridazin-4-yl]amino] ethoxy)benzoate A solution of methyl 3-(2-[methyl[6-oxo-5-(trifluoromethyl)-1-[[2-(trimethylsilyl)ethoxy]methyl]-1,6-dihydropyridazin-4-yl]amino]ethoxy)benzoate (700 mg, 1.40 mmol, 1.00 equiv) in hydrogen chloride/dioxane (30 mL) was stirred for 14 h at room temperature. The resulting mixture was concentrated under vacuum to afford 600 mg crude of the title compound as yellow oil. LCMS (ESI, m/z): 372.11 [M+H]+.

Step 4: Synthesis of 3-(2-[methyl[6-oxo-5-(trifluoromethyl)-1,6-dihydropyridazin-4-yl]amino]ethoxy) benzoic Acid A solution of methyl 3-(2-[methyl[6-oxo-5-(trifluoromethyl)-1,6-dihydropyridazin-4-yl]amino]ethoxy)benzoate (700 mg, 1.89 mmol, 1 equiv), LiOH.H$_2$O (553 mg, 13.18 mmol, 6.990 equiv) in methanol (10 mL) was stirred for 4 h at room temperature. The resulting solution was extracted with 2×20 ml of EtOAc and the aqueous combined. The pH value of the solution was adjusted to 2 with HCl (10%). The solids were collected by filtration to afford 380 mg (56. %) of the title compound as a yellow solid. LCMS (ESI, m/z): 358.09 [M+H]+.

Step 5: Synthesis of 6-(4-[[3-(2-[methyl[6-oxo-5-(trifluoromethyl)-1,6-dihydropyridazin-4-yl]amino] ethoxy)phenyl]carbonyl]piperazin-1-yl)pyridine-3-carbonitrile A solution of 3-(2-[methyl[6-oxo-5-(trifluoromethyl)-1,6-dihydropyridazin-4-yl]amino]ethoxy)benzoic acid (100 mg, 0.28 mmol, 1 equiv), HATU (111 mg, 0.29 mmol, 1.043 equiv), DIPEA (108 mg, 0.84 mmol, 2.986 equiv), Int-A4 (58.1 mg, 0.31 mmol, 1.103 equiv) in DMF (2 mL) was stirred for 1 h at room temperature. After concentration, the residue was purified by C18 reverse phase chromatography eluting with H$_2$O/CH$_3$CN. Then the residue was further purified by Prep-HPLC yielding the title compound (98.0 mg, 66.4%) as a white solid. LCMS (ESI, m/z): 528.50 [M+H]+, $^1$H NMR (300 MHz, DMSO-d$_6$) δ: 12.51 (s, 1H), 8.52 (d, J=2.3 Hz, 1H), 8.06 (s, 1H), 7.90 (d, J=9.1, 2.4 Hz, 1H), 7.37 (t, J=7.9 Hz, 1H), 7.05-6.89 (m, 4H), 4.26 (t, J=5.0 Hz, 2H), 3.86 (t, J=5.1 Hz, 2H), 3.62-3.52 (m, 6H), 3.33 (m, 2H), 3.10 (d, J=2.3 Hz, 3H).

Example 30 Isomer A: (R)-4-(Trifluoromethyl)-5-(1-((3-(4-(5-(trifluoromethyl)pyridin-2-yl)piperazine-1-carbonyl)phenoxy)methyl)isoindolin-2-yl)pyridazin-3(2H)-one and Example 30 Isomer B: (S)-4-(Trifluoromethyl)-5-(1-((3-(4-(5-(trifluoromethyl)pyridin-2-yl)piperazine-1-carbonyl)phenoxy)methyl)isoindolin-2-yl)pyridazin-3(2H)-one

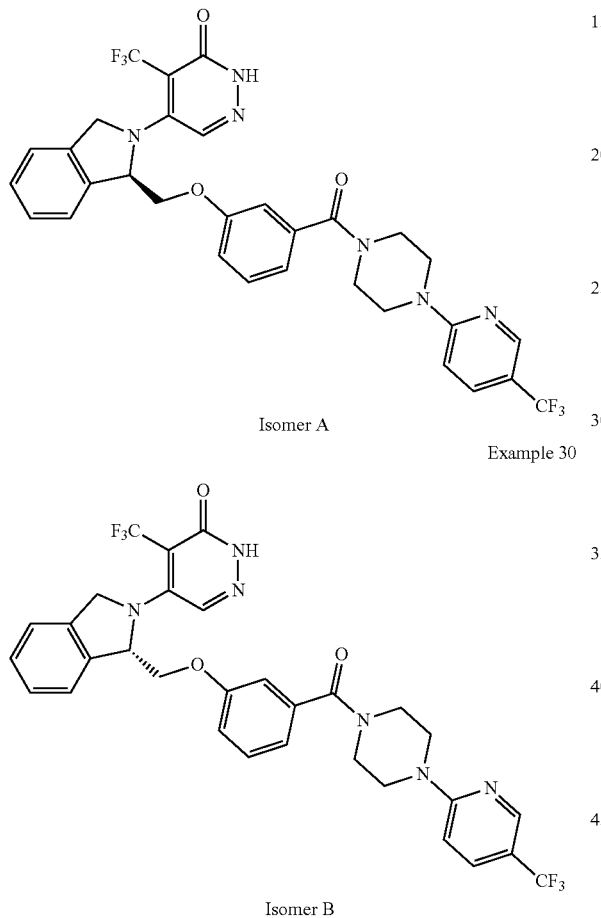

A solution of 3-([2-[6-oxo-5-(trifluoromethyl)-1,6-dihydropyridazin-4-yl]-2,3-dihydro-1H-isoindol-1-yl]methoxy)benzoic acid (300 mg, 0.70 mmol, 1.00 equiv), HATU (278 mg, 0.73 mmol, 1.05 equiv), DIPEA (269 mg, 2.08 mmol, 3.00 equiv), and Int-A18 (161 mg, 0.70 mmol, 1.00 equiv) in DCM (2 mL) was stirred overnight at 25° C. After concentration, the residue was purified by C18 reverse phase chromatography eluting with H₂O/ACN. The residue was further purified by Prep-HPLC and Chiral-Prep-HPLC (CHIRALPAK IA-3, 3 µm, 0.46×5 cm column, eluting with a gradient of MtBE (10 mM NH₃):EtOH=80:20, at a flow rate of 1 mL/min) yielding the title compounds as yellow solids. The absolute stereochemistry was assigned based on a protein X-ray crystal structure obtained of Example 18 Isomer B which confirmed (S)-absolute stereochemistry and was observed to be the more potent enantiomer (see Table A-1).

Example 30 Isomer A 76.1 mg, 42%, LCMS: [M+H]⁺ 645.20, ¹H NMR (400 MHz, Methanol-d₄) δ 8.40-8.39 (d, J=3.5 Hz, 2H), 7.78-7.76 (dd, J=9.1, 2.6 Hz, 1H), 7.53-7.51 (m, 1H), 7.42-7.37 (m, 4H), 7.05-7.00 (m, 2H), 6.94-6.92 (m, 2H), 6.20 (dr, 1H), 5.33-5.29 (d, J=14.7 Hz, 1H), 4.68-4.64 (d, J=14.8 Hz, 1H), 4.54-4.50 (dd, J=10.3, 3.5 Hz, 1H), 4.29-4.25 (dd, J=10.2, 6.8 Hz, 1H), 3.83-3.53 (m, 8H). tR=1.562 min.

Example 30 Isomer B 76.1 mg, 42%, LCMS: [M+H]⁺ 645.20, tR=1.562 min.

Example 31: 6-[4-[(3-[[(2R)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile

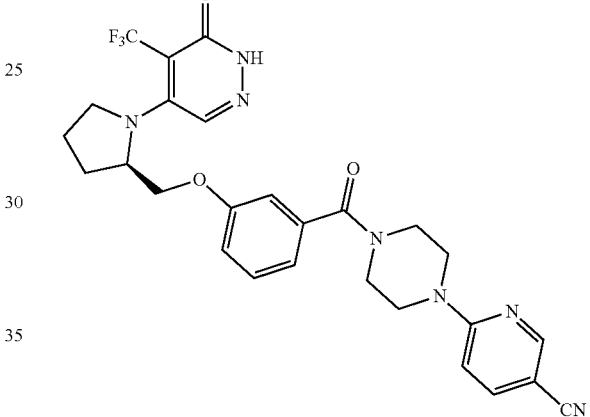

Step 1: Synthesis of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (15 g, 45.62 mmol, 1 equiv), (2R)-pyrrolidin-2-ylmethanol (4.6 g, 45.48 mmol, 0.997 equiv), TEA (14 g, 138.35 mmol, 3.033 equiv) in EtOH (200 mL) was stirred for 4 h at 60° C. The resulting mixture was concentrated under vacuum. The residue was crystallized with Et₂O to afford 8.6 g (47.9%) of the title compound as a white solid. LCMS (ESI, m/z): 394.17 [M+H]⁺.

Step 2: Synthesis of Methyl 3-[[(2R)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (8.6 g, 21.86 mmol, 1 equiv), methyl 3-bromobenzoate (5.2 g, 24.18 mmol, 1.106 equiv), Rockphos (1.02 g, 2.18 mmol, 0.100 equiv), Cs₂CO₃ (14.2 g, 43.58 mmol, 1.994 equiv), Pd₂(allyl)₂Cl₂ (0.798 g, 2.18 mmol, 0.100 equiv) in Toluene (100 mL) was stirred for 12 h at 80° C. with an inert atmosphere of nitrogen. The resulting mixture was concentrated under vacuum. The residue was applied onto a silica gel column eluting with EtOAc/petroleum ether (20/80) to afford 7.1 g (61.6%) of the title compound as yellow oil. LCMS (ESI, m/z): 528.21 [M+H]⁺.

Step 3: Synthesis of Methyl 3-[[(2R)-1-[6-oxo-5-(trifluoromethyl)-1,6-dihydropyridazin-4-yl]pyrrolidin-2-yl]methoxy]benzoate A solution of 3-[[(2R)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (9.1 g, 17.25 mmol, 1 equiv) in HCl/dioxane (100 mL) was stirred for 12 h at room temperature. The resulting mixture was concentrated under vacuum to afford 9.5 g (crude) of the title compound as yellow oil. LCMS (ESI, m/z): 398.12 [M+H]⁺.

Step 4: Synthesis of 3-[[(2R)-1-[6-oxo-5-(trifluoromethyl)-1,6-dihydropyridazin-4-yl]pyrrolidin-2-yl]methoxy]benzoic Acid A solution of 3-[[(2R)-1-[6-oxo-5-(trifluoromethyl)-1,6-dihydropyridazin-4-yl]pyrrolidin-2-yl]methoxy]benzoate (1.5 g, 3.78 mmol, 1 equiv), LiOH.H₂O (0.795 g, 18.94 mmol, 5.0 equiv) in MeOH (30 mL) was stirred for 4 h at room temperature. The resulting solution was extracted with 3×30 ml of EtOAc. The pH value of the solution was adjusted to 2 with HCl (12 M). The solids were collected by filtration to afford 600 mg (41%) of the title compound as a white solid. LCMS (ESI, m/z): 384.11 [M+H]⁺.

Step 5: Synthesis of 6-[4-[(3-[[(2R)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 3-[[(2R)-1-[6-oxo-5-(trifluoromethyl)-1,6-dihydropyridazin-4-yl]pyrrolidin-2-yl]methoxy]benzoic acid (100 mg, 0.26 mmol, 1 equiv), HATU (103.7 mg, 0.27 mmol, 1.045 equiv), DIPEA (100.6 mg, 0.78 mmol, 2.984 equiv), Int-A4 (54 mg, 0.29 mmol, 1.100 equiv) in DMF (2 mL) was stirred for 2 h at room temperature. After concentration, the residue was purified by C18 reverse phase chromatography eluting with H₂O/CH₃CN. Then the residue was further purified by Prep-HPLC yielding the title compound (76.9 mg, 53%) as a white solid. LCMS (ESI, m/z): 554.54 [M+H]⁺, ¹HNMR (DMSO-d₆, 300 MHz) δ: 12.44 (s, 1H), 8.53 (d, J=2.3 Hz, 1H), 8.15 (s, 1H), 7.91 (dd, J=9.1, 2.4 Hz, 1H), 7.37 (t, J=7.9 Hz, 1H), 6.98 (dd, J=18.8, 8.6 Hz, 4H), 4.83 (s, 1H), 4.15 (dd, J=10.4, 4.0 Hz, 1H), 4.04 (dd, J=10.3, 6.0 Hz, 1H), 3.67-3.48 (m, 9H), 3.30 (d, J=8.9 Hz, 1H), 2.23 (s, 1H), 1.99 (d, J=6.7 Hz, 1H), 1.93-1.81 (m, 2H).

Example 32: 6-[4-[(3-[[(2S)-1-[6-Oxo-5-(trifluoromethyl)-1,6-dihydropyridazin-4-yl]pyrrolidin-2-yl]methoxy]phenyl)carbonyl]piperazin-1-yl]pyridine-3-carbonitrile

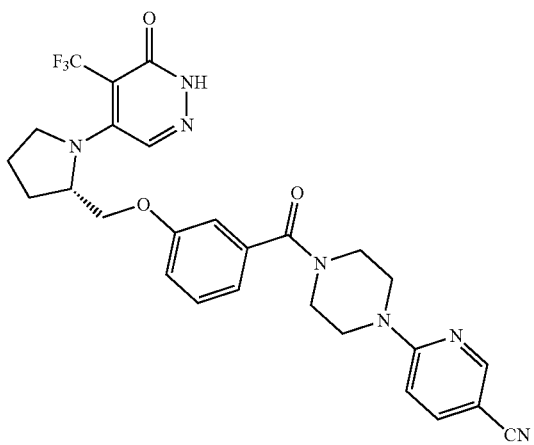 [SMILES: N#Cc1ccc(N2CCN(C(=O)c3cccc(OC[C@@H]4CCCN4c4cn[nH]c(=O)c4C(F)(F)F)c3)CC2)nc1]

Step 1: 5-[(2S)-2-(Hydroxymethyl)pyrrolidin-1-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (10 g, 30.41 mmol, 1.00 equiv), TEA (13.4 g, 132.42 mmol, 3.00 equiv), (S)-pyrrolidin-2-ylmethanol (3.4 g, 33.61 mmol, 1.10 equiv) in ethanol (60 mL) was stirred for 2 h at 60° C. The resulting mixture was concentrated under vacuum and the residue was applied onto a silica gel column eluting with EtOAc/petroleum ether (26:74) to afford 5 g (42%) of the title compound. LCMS (ESI, m/z): 394.18 [M+H]+.

Step 2: Synthesis of Methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1 g, 2.54 mmol, 1.00 equiv), [Pd(allyl)Cl]₂ (93 mg, 0.10 equiv), Rockphos (119 mg, 0.10 equiv), Cs₂CO₃ (2.5 g, 7.67 mmol, 3.00 equiv), methyl 3-bromobenzoate (1.09 g, 5.07 mmol, 2.00 equiv) in toluene (80 mL) was stirred for 20 h at 80° C. The solvent was concentrated under vacuum and the residue was applied onto a silica gel column eluting with EtOAc/hexane (1:1) to afford 969 mg (72%) of the title compound as a brown oil. LCMS (ESI, m/z): 528.22 [M+H]⁺.

Step 3: Synthesis of 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic Acid A solution of methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (969 mg, 1.84 mmol, 1.00 equiv), LiOH (220 mg, 9.19 mmol, 5.00 equiv), water (4 mL) in methanol (20 mL) was stirred for 3 h at room temperature. The pH value of the solution was adjusted to 5 with hydrogen chloride. The solvent was concentrated under vacuum and the residue was applied onto a silica gel column eluting with EtOAc/hexane (1:1) to afford 900 mg (95%) of the title compound as a brown solid. LCMS (ESI, m/z): 514.20 [M+H]+.

Step 4: Synthesis of 3-[[(2S)-1-[6-oxo-5-(trifluoromethyl)-1,6-dihydropyridazin-4-yl]pyrrolidin-2-yl]methoxy]benzoic Acid A solution 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic acid (900 mg, 1.75 mmol, 1.00 equiv) in hydrogen chloride/dioxane (30 mL) was stirred for 3 h at room temperature. After concentration, the residue was purified by C18 reverse phase chromatography eluting with H2O/CH3CN to afford 600 mg (89%) of the title compound as a yellow solid. LCMS (ESI, m/z): 384.12 [M+H]+.

Step 5: Synthesis of 6-[4-[(3-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 3-[[(2S)-1-[6-oxo-5-(trifluoromethyl)-1,6-dihydropyridazin-4-yl]pyrrolidin-2-yl]methoxy]benzoic acid (200 mg, 0.52 mmol, 1.00 equiv), HATU (239.4 mg, 0.63 mmol, 1.20 equiv), DIPEA (205.11 mg, 1.59 mmol, 3.00 equiv), Int-A4 nitrile (118.44 mg, 0.63 mmol, 1.20 equiv) in DMF (3 mL) was stirred for 3 h at room temperature. After concentration, The residue was purified by C18 reverse phase chromatography eluting with H2O/CH3CN yielding the title compound (132.9 mg, 46%) as a white solid. LCMS (ESI, m/z): 554.05 [M+H]+, 1HNMR (300 MHz, Methanol-d4) δ 8.44 (s, 1H), 8.24 (s, 1H), 7.78 (dd, J=9.1, 2.4 Hz, 1H), 7.40 (d, J=7.9 Hz, 1H), 7.17-7.00 (m, 2H), 7.00-6.84 (m, 2H), 4.86 (d, J=4.1 Hz, 1H), 4.25 (dd, J=10.3, 3.7 Hz, 1H), 4.07 (dd, J=10.3, 6.9 Hz, 1H), 3.98-3.62 (m, 7H), 3.61-3.37 (m, 3H), 2.47-2.25 (m, 1H), 2.07 (dd, J=11.4, 5.7 Hz, 1H), 1.88-1.84 (m, 2H).

Example 33: 6-[3-(hydroxymethyl)-4-[(3-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile

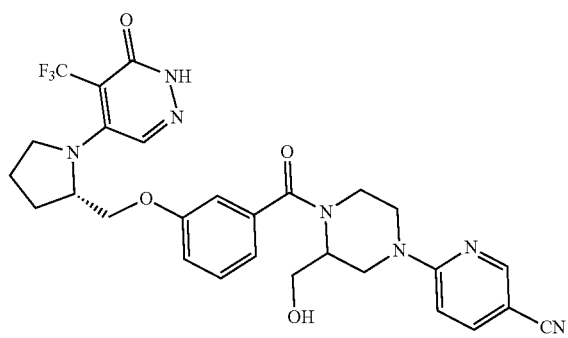 [SMILES: N#Cc1ccc(N2CCN(C(=O)c3cccc(OC[C@@H]4CCCN4c4cn[nH]c(=O)c4C(F)(F)F)c3)C(CO)C2)nc1]

Step 1: Synthesis of Tert-Butyl 4-(5-cyanopyridin-2-yl)-2-(hydroxymethyl)piperazine-1-carboxylate A solution of tert-butyl 2-(hydroxymethyl)piperazine-1-carboxylate (780 mg, 3.61 mmol, 1.20 equiv), 6-chloropyridine-3-carbonitrile (520 mg, 3.75 mmol, 1.00 equiv), DIPEA (780 mg, 6.04 mmol, 2.00 equiv) in NMP (15 mL) was stirred for 8 h at 100° C. The resulting solution was quenched with water. The resulting solution was extracted with of EtOAc and the organic layers combined. After concentrated under vacuum. The residue was applied onto a silica gel column with EtOAc/petroleum ether (1:1) to afford of 900 mg (75%) of the title compound as a solid. LCMS (ESI, m/z): 319.18 [M+H]+.

Step 2: Synthesis of 6-[3-(hydroxymethyl)piperazin-1-yl]pyridine-3-carbonitrile

A solution of tert-butyl 4-(5-cyanopyridin-2-yl)-2-(hydroxymethyl)piperazine-1-carboxylate (900 mg, 2.83 mmol, 1.00 equiv) in hydrogen chloride/dioxane (15 mL) was stirred for 0.5 h at room temperature. The resulting mixture was concentrated under vacuum to afford 600 mg of the title compound as a solid. LCMS (ESI, m/z): 219.15 [M+H]+.

Step 3: Synthesis of 6-[3-(hydroxymethyl)-4-[(3-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 3-[[(2S)-1-[6-oxo-5-(trifluoromethyl)-1,6-dihydropyridazin-4-yl]pyrrolidin-2-yl]methoxy]benzoic acid (114.9 mg, 0.30 mmol, 1.00 equiv), HATU (136.8 mg, 0.36 mmol, 1.20 equiv), DIPEA (116.1 mg, 0.90 mmol, 3.00 equiv), 6-[3-(hydroxymethyl)piperazin-1-yl]pyridine-3-carbonitrile (78.48 mg, 0.36 mmol, 1.20 equiv) in DMF (3 mL) was stirred for 3 h at room temperature. After concentration, the residue was purified by C18 reverse phase chromatography eluting with H2O/CH3CN. Then the residue was further purified by Prep-HPLC yielding the title compound (35.2 mg, 20%) as a white solid. LCMS (ESI, m/z): 584.10 [M+H]+, 1HNMR (300 MHz, Methanol-d4) δ 8.50 (s, 1H), 8.24 (d, J=5.0 Hz, 1H), 7.77 (dd, J=9.1, 2.4 Hz, 1H), 7.39 (d, J=8.0 Hz, 1H), 7.07-6.86 (m, 4H), 4.87-4.83 (m, 2H), 4.54 (s, 2H), 4.37-3.89 (m, 3H), 3.72-3.41 (m, 3H), 3.44 (t, J=8.9 Hz, 2H), 3.28-3.01 (m, 2H), 2.49-2.22 (m, 1H), 2.07 (dd, J=11.2, 5.6 Hz, 1H), 2.00-1.69 (m, 2H).

Example 34: 6-[2-oxo-4-[(3-[[(2S)-1-[6-oxo-5-(trifluoromethyl)-1,6-dihydropyridazin-4-yl]pyrrolidin-2-yl]m ethoxy]phenyl)carbonyl]piperazin-1-yl]pyridine-3-carbonitrile

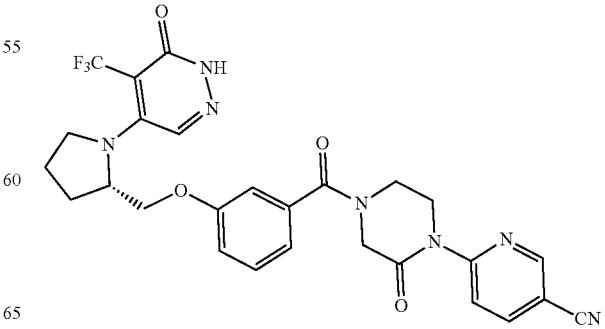

Step 1: Synthesis of Tert-Butyl 4-(5-cyanopyridin-2-yl)-3-oxopiperazine-1-carboxylate A solution of tert-butyl 3-oxopiperazine-1-carboxylate (2.0 g, 10.00 mmol, 1.00 equiv), tripotassium phosphate (4.24 g, 20.00 mmol, 2.00 equiv), CuI (95.0 mg, 0.50 mmol, 0.05 equiv), 6-bromopyridine-3-carbonitrile (1.82 g, 10.00 mmol, 1.00 equiv), (1R,2R)-1-N,2-N-dimethylcyclohexane-1,2-diamine (142.0 mg, 1.00 mmol, 0.10 equiv) in dioxane (80 mL) was stirred for 3 h at 110° C. The resulting mixture was concentrated under vacuum and the residue was applied onto a silica gel column eluting with EtOAc/petroleum ether (6:1) to afford 1.2 g (40%) of the title compound as a white solid. LCMS (ESI, m/z): 303.15 [M+H]$^+$.

Step 2: Synthesis of 6-(2-oxopiperazin-1-yl)pyridine-3-carbonitrile

A solution of tert-butyl 4-(5-cyanopyridin-2-yl)-3-oxopiperazine-1-carboxylate (200 mg, 0.66 mmol, 1.00 equiv) in hydrogen chloride/dioxane (20 mL) was stirred for 0.5 h at room temperature. The resulting mixture was concentrated under vacuum to afford 170 mg crude of the title compound as a white solid. LCMS (ESI, m/z): 203.10 [M+H]$^+$.

Step 3: Synthesis of 6-[2-oxo-4-[(3-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 3-[[(2S)-1-[6-oxo-5-(trifluoromethyl)-1,6-dihydropyridazin-4-yl]pyrrolidin-2-yl]methoxy]benzoic acid (300 mg, 0.78 mmol, 1.00 equiv), HATU (296.4 mg, 0.78 mmol, 1.20 equiv), DIPEA (251.55 mg, 1.95 mmol, 3.00 equiv), 6-(2-oxopiperazin-1-yl)pyridine-3-carbonitrile (131.3 mg, 0.65 mmol, 1.20 equiv) in DMF (3 mL, 3.00 equiv) was stirred for 2 h at room temperature. After concentration, the residue was purified by C18 reverse phase chromatography eluting with H$_2$O/CH$_3$CN. Then the residue was further purified by Prep-HPLC yielding the title compound (7.9 mg, 2%) as a white solid. LCMS (ESI, m/z): 568.20 [M+H]$^+$, $^1$HNMR (300 MHz, Chloroform-d) δ 10.69 (s, 1H), 8.68 (d, J=2.3 Hz, 1H), 8.36 (d, J=8.9 Hz, 1H), 8.08-7.79 (m, 2H), 7.49-7.29 (m, 1H), 7.05 (d, J=7.6, 1.2 Hz, 1H), 6.99 (d, J=2.1 Hz, 2H), 4.64 (dd, J=6.0, 4.8 Hz, 1H), 4.48 (s, 2H), 4.23 (s, 2H), 4.11 (dd, J=9.8, 4.2 Hz, 1H), 4.06-3.56 (m, 4H), 3.45 (dd, J=10.9, 6.0 Hz, 1H), 2.40 (t, J=6.3 Hz, 1H), 2.19-2.00 (m, 1H), 1.95-1.72 (m, 2H).

Example 35: 6-[4-[(4-[[(1 S)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile and 6-[4-[(4-[[(1R)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile

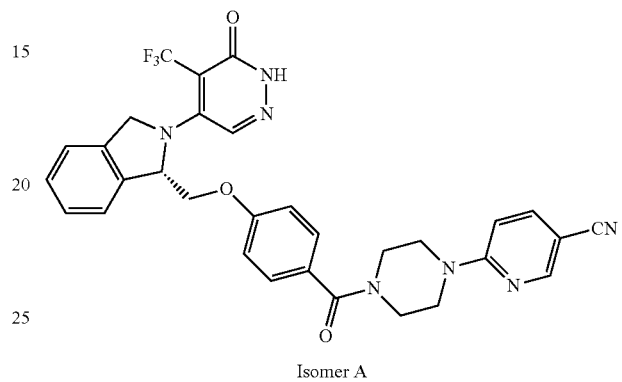

Example 35

Isomer A

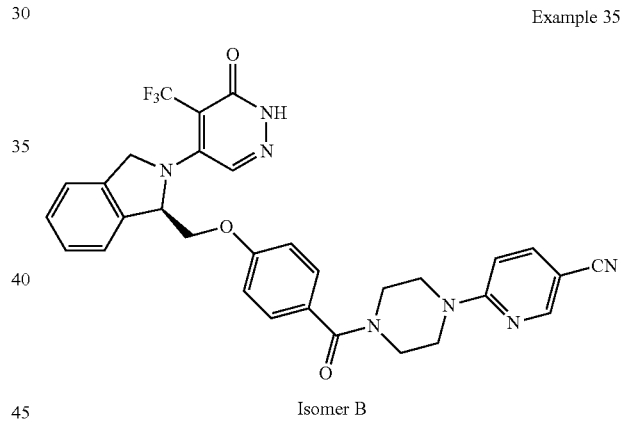

Example 35

Isomer B

Step 1: Synthesis of Methyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoate A solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (440 mg, 1.00 mmol, 1.00 equiv), [Pd(allyl)Cl]$_2$ (37 mg, 0.10 mmol, 0.10 equiv), Rockphos (47 mg, 0.10 mmol, 0.10 equiv), Cs2CO3 (970 mg, 2.98 mmol, 2.00 equiv), and methyl 4-bromobenzoate (430 mg, 2.00 mmol, 2.00 equiv) in Toluene (10 mL) was stirred for 5 h at 80° C. The reaction was then quenched by the addition of 150 mL of water. The resulting mixture was concentrated under vacuum. The residue was applied onto a silica gel column with EtOAc/petroleum ether (1/4) to afford 470 mg (82%) of the title compound as yellow oil. LCMS (ESI, m/z): 576.21 [M+H]$^+$.

Step 2: Synthesis of 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic A solution of methyl 4-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)benzoate (470 mg, 0.82 mmol, 1.00 equiv), water (2 mL), and LiOH (100 mg, 4.18 mmol, 5.00 equiv) in THF (8 mL) was stirred for 1 overnight at 60° C. under N2 (g) atmosphere. The pH value of the solution was adjusted to 5-6 with hydrogen chloride (6 M). The resulting solution was extracted with 2×200 mL of EtOAc and the organic layers combined and concentrated under vacuum, to afford 400 mg (87%) of the title compound as a yellow solid. LCMS (ESI, m/z): 562.19 [M+H]$^+$.

Step 3: Synthesis of 4-([2-[6-oxo-5-(trifluoromethyl)-1,6-dihydropyridazin-4-yl]-2,3-dihydro-1H-isoindol-1-yl]methoxy)benzoic A solution of 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)benzoic acid (400 mg, 0.71 mmol, 1.00 equiv) in hydrogen chloride/dioxane (20 mL) was stirred for 1 overnight at 25° C. The resulting mixture was concentrated under vacuum to afford 300 mg (98%) of the title compound as a black solid. LCMS (ESI, m/z): 432.11 [M+H]$^+$.

Step 4: Synthesis of 6-[4-[(4-[[(1S)-2-[6-oxo-5-(trifluoromethyl)-1,6-dihydropyridazin-4-yl]-2,3-dihydro-1H-isoindol-1-yl]methoxy]phenyl)carbonyl]piperazin-1-yl]pyridine-3-carbonitrile, and 6-[4-[(4-[[(1R)-2-[6-oxo-5-(trifluoromethyl)-1,6-dihydropyridazin-4-yl]-2,3-dihydro-1H-isoindol-1-yl]methoxy]phenyl) carbonyl]piperazin-1-yl]pyridine-3-carbonitrile A solution of 4-([2-[6-oxo-5-(trifluoromethyl)-1,6-dihydropyridazin-4-yl]-2,3-dihydro-1H-isoindol-1-yl]methoxy)benzoic acid (350 mg, 0.81 mmol, 1.00 equiv), Int-A4 (153 mg, 0.81 mmol, 1.00 equiv), DIPEA (300 mg, 2.32 mmol, 3.00 equiv), and HATU (313 mg, 0.82 mmol, 1.01 equiv) in DMF (3 mL) was stirred for 1 h at 25° C. After concentration, the residue was purified by C18 reverse phase chromatography eluting with H$_2$O/CH$_3$CN. Then Chiral-Prep-HPLC yielding (after arbitrary assignment of the stereochemistry) the title compounds, respectively, isomer A 54.1 mg (54%) as a yellow solid. LCMS (ESI, m/z): 602.20 [M+H]$^+$, $^1$H NMR (400 MHz, Methanol-d$_4$) δ 8.44-8.39 (m, 2H), 7.79-7.76 (dd, J=9.1, 2.4 Hz, 1H), 7.54-7.51 (d, J=5.8 Hz, 1H), 7.43-7.37 (td, J=5.5, 5.0, 2.0 Hz, 5H), 6.98-6.96 (m, 2H), 6.91-6.88 (m, 1H), 6.21 (s, 1H), 5.33-5.29 (d, J=14.7 Hz, 1H), 4.67-4.62 (m, 1H), 4.55-4.52 (dd, J=10.4, 3.5 Hz, 1H), 4.31-4.27 (dd, J=10.3, 6.8 Hz, 1H), 3.79-3.50 (m, 8H). tR=3.517 min (CHIRALPAK IG-3, 0.46*10 cm; 3 um, MtBE (0.1% DEA):EtOH=70:30, 1.0 mL/min) and isomer B 48.6 mg (49%) as a yellow solid. LCMS (ESI, m/z): 602.20 [M+H]$^+$, tR=3.515 min (CHIRALPAK IG-3, 0.46*10 cm; 3 um, MtBE (0.1% DEA):EtOH=70:30, 1.0 mL/min).

Example 36: 6-[4-[(2-[[(1R)-2-[6-oxo-5-(trifluoromethyl)-1,6-dihydropyridazin-4-yl]-2,3-dihydro-1H-isoindol-1-yl]methoxy]pyridin-4-yl)carbonyl]piperazin-1-yl]pyridine-3-carbonitrile and 6-[4-[(2-[[(1S)-2-[6-oxo-5-(trifluoromethyl)-1,6-dihydropyridazin-4-yl]-2,3-dihydro-1H-isoindol-1-yl]methoxy]pyridin-4-yl)carbonyl]piperazin-1-yl]pyridine-3-carbonitrile

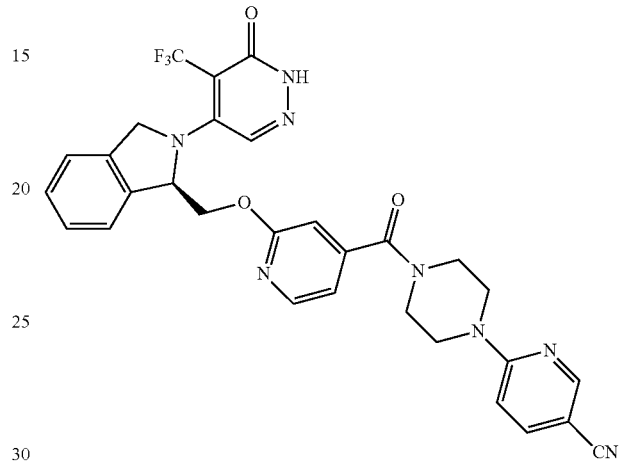

Example 36

Isomer A

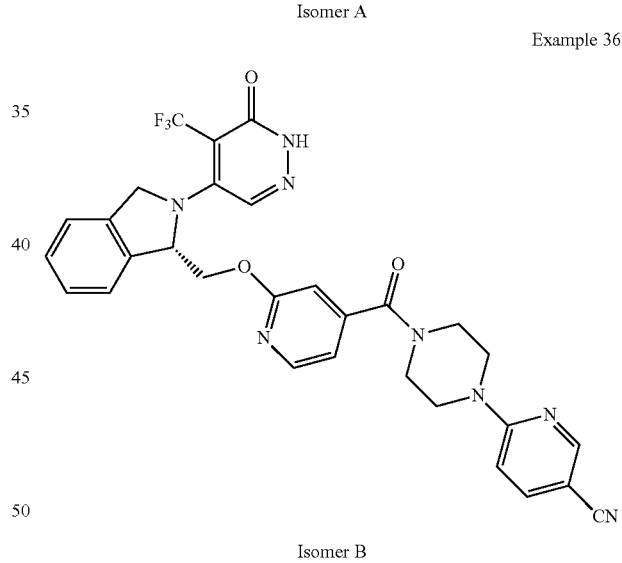

Example 36

Isomer B

Step 1: Synthesis of Methyl 2-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-4-carboxylate A solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (441 mg, 1.00 mmol, 1.00 equiv), [Pd(allyl)Cl]$_2$ (36.6 mg, 0.10 mmol, 0.10 equiv), Rockphos (46.8 mg, 0.10 mmol, 0.10 equiv), Cs$_2$CO$_3$ (65.2 mg, 0.20 mmol, 2.00 equiv), methyl 2-bromopyridine-4-carboxylate (430 mg, 1.99 mmol, 2.00 equiv) in toluene (10 mL) was stirred for 3 h at 80° C. The solvent was concentrated under vacuum and the residue was applied onto a silica gel column eluting with EtOAc/petroleum ether (3:7) to afford 420 mg (73%) of the title compound as a yellow solid. LCMS (ESI, m/z): 577.21 [M+H]⁺.

Step 2: Synthesis of 2-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-4-carboxylic Acid A solution of methyl 2-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyridine-4-carboxylate (420 mg, 0.73 mmol, 1.00 equiv), LiOH (87.6 mg, 3.66 mmol, 5.00 equiv), water (2 ml) in methanol (10 ml) was stirred for 3 h at room temperature. The pH value of the solution was adjusted to 5 with hydrogen chloride. The solvent was concentrated under vacuum and the residue was applied onto a silica gel column eluting with acetate/petroleum ether (2:1) to afford 300 mg (73%) of the title compound as a solid. LCMS (ESI, m/z): 563.20 [M+H]⁺.

Step 3: Synthesis of 2-([2-[6-oxo-5-(trifluoromethyl)-1,6-dihydropyridazin-4-yl]-2,3-dihydro-1H-isoindol-1-yl]methoxy)pyridine-4-carboxylic Acid A solution of 2-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-4-carboxylic acid (300 mg, 0.52 mmol, 1.00 equiv) in hydrogen chloride/dioxane (20 mL) was stirred for 2 h at room temperature. After concentration, the residue was purified by C18 reverse phase chromatography eluting with H₂O/CH₃CN to afford 261 mg crude of the title compound as a solid. LCMS (ESI, m/z): 433.11 [M+H]⁺.

Step 4: Synthesis of 6-[4-[(2-[[(1R)-2-[6-oxo-5-(trifluoromethyl)-1,6-dihydropyridazin-4-yl]-2,3-dihydro-1H-isoindol-1-yl]methoxy]pyridin-4-yl)carbonyl]piperazin-1-yl]pyridine-3-carbonitrile and 6-[4-[(2-[[(1S)-2-[6-oxo-5-(trifluoromethyl)-1,6-dihydropyridazin-4-yl]-2,3-dihydro-1H-isoindol-1-yl]methoxy]pyridin-4-yl)carbonyl]piperazin-1-yl]pyridine-3-carbonitrile A solution of 2-([2-[6-oxo-5-(trifluoromethyl)-1,6-dihydropyridazin-4-yl]-2,3-dihydro-1H-isoindol-1-yl]methoxy)pyridine-4-carboxylic acid (261 mg, 0.60 mmol, 1.00 equiv), HATU (277.4 mg, 0.73 mmol, 1.20 equiv), DIPEA (309.6 mg, 2.40 mmol, 4.00 equiv), Int-A4 (136.3 mg, 0.72 mmol, 1.20 equiv) in DMF (3 mL) was stirred for 2 h at room temperature. After concentration, the residue was purified by C18 reverse phase chromatography eluting with H₂O/CH₃CN. Then the residue was further purified by Prep-HPLC and Chiral-Prep-HPLC yielding the title compounds. The absolute stereochemistry was assigned based on a protein X-ray crystal structure obtained of Example 18 Isomer B which confirmed (S)-absolute stereochemistry and was observed to be the more potent enantiomer.

Example 36 Isomer A (11 mg, 20%) as a white solid. LCMS (ESI, m/z): 603.10 [M+H]+, ¹HNMR (Methanol-d4, 300 MHz) δ: 8.45 (d, J=2.1 Hz, 1H), 8.35 (s, 1H), 8.25 (d, J=5.2 Hz, 1H), 7.79 (dd, J=9.1, 2.4 Hz, 1H), 7.50 (d, J=4.2 Hz 1H), 7.40 (d, J=2.0 Hz, 3H), 7.02 (dd, J=5.2, 1.3 Hz, 1H), 6.92 (d, J=8.9 Hz, 1H), 6.74 (s, 1H), 6.18 (t, J=2.1 Hz, 1H), 5.24 (d, J=14.7 Hz, 1H), 4.84 (d, J=4.2 Hz, 1H), 4.75-4.71 (m, 1H), 4.70-4.64 (m, 1H), 3.86 (s, 4H), 3.74-3.68 (m, 2H), 3.61-3.49 (m, 2H). tR=2.208 min (CHIRALPAK IG-3, 0.46*5 cm; 3 um, Hex:DCM=1:1 (0.1% DEA):EtOH=30:70, 1.0 mL/min)

Example 36 Isomer B (10.7 mg, 10%) as a white solid. LCMS (ESI, m/z): 603.10 [M+H]⁺. tR=2.947 min(CHIRALPAK IG-3, 0.46*5 cm; 3 um, Hex:DCM=1:1 (0.1% DEA):EtOH=30:70, 1.0 mL/min).

Example 37: 5-[[(2S)-1-(3-Oxo-3-[4-[5-(trifluoromethyl)pyrimidin-2-yl]piperazin-1-yl]propoxy)butan-2-yl]oxy]-4-(trifluoromethyl)-2,3-dihydropyridazin-3-one

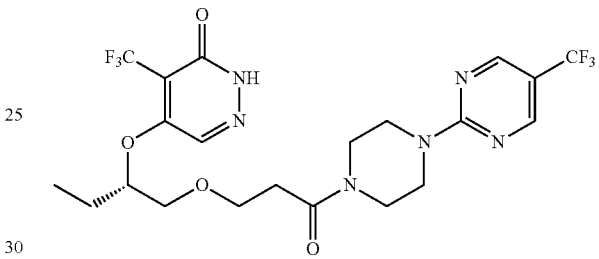

Step 1: 3-[(2S)-2-Hydroxybutoxy]-1-[4-[5-(trifluoromethyl)pyrimidin-2-yl]piperazin-1-yl]propan-1-one A solution of Int-20 (1 g, 3.49 mmol, 1 equiv), (2S)-butane-1,2-diol (1574.1 mg, 17.47 mmol, 5 equiv), and Cs₂CO₃ (2276.4 mg, 6.99 mmol, 2.00 equiv) in MeCN (10 mL) was stirred for 4 h at 75° C. The resulting solution was diluted with 300 mL of DCM. The resulting mixture was washed with 45 mL×2 of H₂O and 45 mL×2 of saturated sodium chloride aqueous solution. The residue was applied onto a silica gel column with DCM/EtOAc (1/1) to afford 1.16 g (81.2%) of the title compound as yellow solids. LCMS (ESI, m/z): 377.37 [M+H]⁺

Step 2: 2-[(4-Methoxyphenyl)methyl]-5-[[(2S)-1-(3-oxo-3-[4-[5-(trifluoromethyl)pyrimidin-2-yl]piperazin-1-yl]propoxy)butan-2-yl]oxy]-4-(trifluoromethyl)-2,3-dihydropyridazin-3-one A solution of 3-[(2S)-2-hydroxybutoxy]-1-[4-[5-(trifluoromethyl)pyrimidin-2-yl]piperazin-1-yl]propan-1-one (0.37 g, 0.98 mmol, 1 equiv), Cs₂CO₃ (0.64 g, 1.96 mmol, 2 equiv), and 5-chloro-2-[(4-methoxyphenyl)methyl]-4-(trifluoromethyl)-2,3-dihydropyridazin-3-one (0.939 g, 1.96 mmol, 3.00 equiv) in MeCN (6 mL) was stirred for 18 h at 80° C. The resulting solution was diluted with 300 mL of EtOAc. The resulting mixture was washed with 45 mL×2 of water and 45 mL×2 of saturated sodium chloride, then dried over anhydrous sodium sulfate and concentrated. The residue was applied onto a silica gel column with EtOAc/petroleum ether (2/3) to afford 0.28 g (32.0%) of the title compound as white solids. LCMS (ESI, m/z): 721.85 [M+H]⁺

Step 3: 5-[[(2S)-1-(3-Oxo-3-[4-[5-(trifluoromethyl)pyrimidin-2-yl]piperazin-1-yl]propoxy)butan-2-yl]oxy]-4-(trifluoromethyl)-2,3-dihydropyridazin-3-one A solution of 2-[(4-methoxyphenyl)methyl]-5-[[(2S)-1-(3-oxo-3-[4-[5-(trifluoromethyl)pyrimidin-1-yl]piperazin-1-yl]propoxy)butan-2-yl]oxy]-4-(trifluoromethyl)-2,3-dihydropyridazin-3-one (0.27 g, 0.410 mmol, 1 equiv), and $H_2SO_4$ (0.402 g, 4.1 mmol, 10 equiv) in TFA (7 mL) was stirred for 3 days at 25° C. The reaction mixture was cooled with a water/ice bath. The resulting solution was diluted with 300 mL of DCM. The resulting mixture was washed with 45 mL x 2 of water and 45 mL×2 of saturated sodium chloride aqueous solution, then dried over anhydrous sodium sulfate and concentrated. The residue was purified by C18 reverse phase chromatography eluting with $H_2O$/$CH_3CN$ yielding the title compound (16.1 mg, 33.7%) as white solids. LCMS (ESI, m/z): 539.25 [M+H]$^+$, $^1$H-NMR (400 MHz, DMSO-$d_6$) δ: 13.22 (s, 1H), 8.74 (s, 2H), 8.28 (s, 1H), 5.01 (d, J=6.7 Hz, 1H), 3.86-3.75 (m, 4H), 3.76-3.58 (m, 3H), 3.54-3.50 (m, 5H), 2.55 (d, J=6.3 Hz, 2H), 1.71-1.58 (m, 2H), 0.91 (t, J=7.4 Hz, 3H).

Example 38 Isomer A: 6-[4-[(2-[[(1S)-2-[6-Oxo-5-(trifluoromethyl)-1,6-dihydropyridazin-4-yl]-2,3-dihydro-1H-isoindol-1-yl]methoxy]pyrimidin-4-yl)carbonyl]piperazin-1-yl]pyridine-3-carbonitrile and Example 38 Isomer B: 6-[4-[(2-[[(1R)-2-[6-Oxo-5-(trifluoromethyl)-1,6-dihydropyridazin-4-yl]-2,3-dihydro-1H-isoindol-1-yl]methoxy]pyrimidin-4-yl)carbonyl]piperazin-1-yl]pyridine-3-carbonitrile Example 38

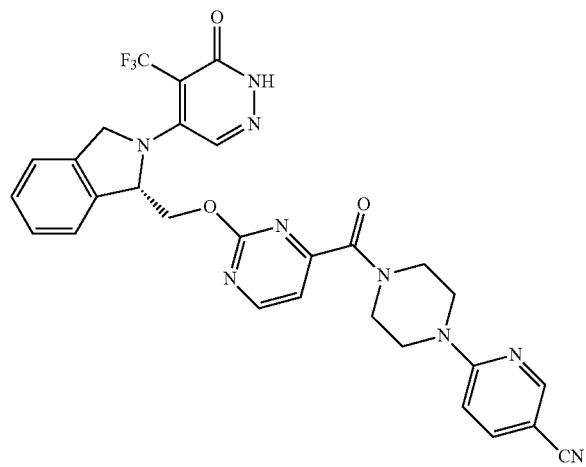

Isomer A

Example 38

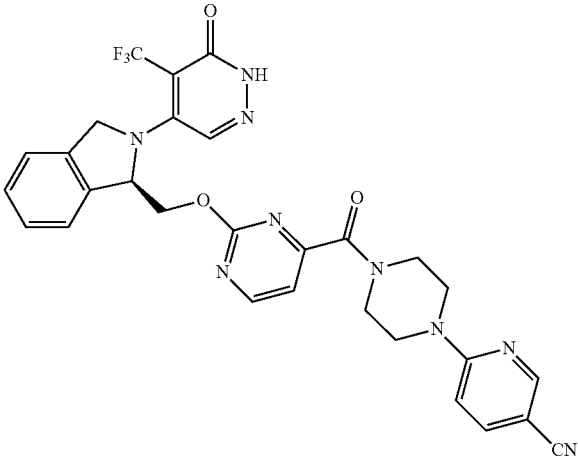

Isomer B

Step 1: Methyl 2-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrimidine-4-carboxylate A solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1.00 equiv), (Pd(allyl)$C_1$)$_2$ (53 mg, 0.10 equiv), Rockphos (41 mg, 0.10 equiv), $Cs_2CO_3$ (1.1 mg, 3.00 equiv), methyl 2-chloropyrimidine-4-carboxylate (292 mg, 1.69 mmol, 1.50 equiv) in toluene (10 mL) under nitrogen condition was stirred for overnight at 85° C. The solvent was concentrated under vacuum and the residue was applied onto a silica gel column eluting with EtOAc/petroleum ether (1/1) to afford 420 mg (64%) of the title compound as a yellow solid. LCMS (ESI, m/z): 578.20 [M+H]$^+$ Step 2: Synthesis of Methyl 2-([2-[6-oxo-5-(trifluoromethyl)-1,6-dihydropyridazin-4-yl]-2,3-dihydro-1H-isoindol-1-yl]methoxy)pyrimidine-4-carboxylate A solution of methyl 2-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyrimidine-4-carboxylate (420 mg, 0.73 mmol, 1.00 equiv) in dioxane/HCl (20 mL, 4 M) was stirred for overnight at 25° C. The solvent was concentrated under vacuum to afford 300 mg (92%) of the title compound as yellow oil. LCMS (ESI, m/z): 448.12 [M+H]$^+$ Step 3: Synthesis of 2-([2-[6-oxo-5-(trifluoromethyl)-1,6-dihydropyridazin-4-yl]-2,3-dihydro-1H-isoindol-1-yl]methoxy)pyrimidine-4-carboxylic Acid A solution of methyl 2-([2-[6-oxo-5-(trifluoromethyl)-1,6-dihydropyridazin-4-yl]-2,3-dihydro-1H-isoindol-1-yl]methoxy)pyrimidine-4-carboxylate (400 mg, 0.89 mmol, 1.00 equiv), LiOH.$H_2O$ (200 mg, 4.77 mmol, 5.00 equiv) in MeOH (10 mL) and water (2 mL) was stirred for 2 h at 25° C. The resulting solution was concentrated under vacuum. The residue was diluted with 3 mL of water, then the pH value of the solution was adjusted to 2 with hydrochloric acid and the solid was filtered to afford 215 mg (55%) of the title compound as a pink solid. LCMS (ESI, m/z): 434.10 [M+H]$^+$ Step 4: Synthesis of 6-[4-[(2-[[(1R)-2-[6-oxo-5-(trifluoromethyl)-1,6-dihydropyridazin-4-yl]-2,3-dihydro-1H-isoindol-1-yl]methoxy]pyrimidin-4-yl)carbonyl]piperazin-1-yl]pyridine-3-carbonitrile and 6-[4-[(2-[[(1S)-2-[6-oxo-5-(trifluoromethyl)-1,6-dihydropyridazin-4-yl]-2,3-dihydro-1H-isoindol-1-yl]methoxy]pyrimidin-4-yl)carbonyl]piperazin-1-yl]pyridine-3-carbonitrile A solution of 2-([2-[6-oxo-5-(trifluoromethyl)-1,6-dihydropyridazin-4-yl]-2,3-dihydro-1H-isoindol-1-yl]methoxy)pyrimidine-4-carboxylic acid (100 mg, 0.23 mmol, 1.00 equiv), HOBT (47 mg, 0.35 mmol, 1.50 equiv), EDCI (67 mg, 0.35 mmol, 1.50 equiv), DIPEA (90 mg, 0.70 mmol, 3.00 equiv), Int-A4 (87 mg, 0.46 mmol, 2.00 equiv) in DMF (3 mL) was stirred for overnight at 25° C. After concentration, the residue was purified by C18 reverse phase chromatography eluting with H$_2$O/CH$_3$CN. Then the residue was further purified by Prep-HPLC and Chiral-Prep-HPLC yielding the title compounds. The absolute stereochemistry was assigned based on a protein X-ray crystal structure obtained of Example 18 Isomer B which confirmed (S)-absolute stereochemistry and was observed to be the more potent enantiomer.

Isomer A (6.1 mg, 23%) as a white solid. LCMS (ESI, m/z): 604.20 [M+H]+, 1H NMR (300 MHz, DMSO-d6) δ: 12.57 (s, 1H), 8.69 (d, J=4.9 Hz, 1H), 8.51 (d, J=2.3 Hz, 1H), 8.31 (s, 1H), 7.89 (d, J=8.5 Hz, 1H), 7.48 (s, 1H), 7.38 (d, J=9.9 Hz, 3H), 7.28 (d, J=4.9 Hz, 1H), 6.92 (d, J=9.0 Hz, 1H), 6.14 (s, 1H), 5.04 (d, J=14.4 Hz, 1H), 4.90 (d, J=11.8 Hz, 1H), 4.71-4.41 (m, 2H), 3.97-3.55 (m, 6H), 3.40 (m, 2H). tR=4.448 min (CHIRALPAK IC-3, 0.46*10 cm; 3 um, MtBE (0.1% DEA):EtOH=80:20, 1.0 mL/min) and isomer B (6.4 mg, 25%) as a white solid. LCMS (ESI, m/z): 604.20 [M+H]$^+$, tR=5.550 min (CHIRALPAK IC-3, 0.46*10 cm; 3 um, MtBE (0.1% DEA):EtOH=80:20, 1.0 mL/min).

Example 39: 6-[4-([3-[2-([2-[6-Oxo-5-(trifluoromethyl)-1,6-dihydropyridazin-4-yl]-2,3-dihydro-1H-isoindol-4-yl]oxy]ethoxy]phenyl]carbonyl)piperazin-1-yl]pyridine-3-carbonitrile

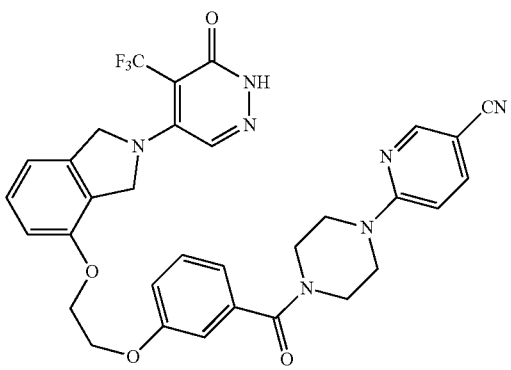 [SMILES: N#Cc1ccc(N2CCN(C(=O)c3cccc(OCCOc4cccc5c4CN(c4cn[nH]c(=O)c4C(F)(F)F)C5)c3)CC2)nc1]

Step 1: Synthesis of 5-[4-(2-hydroxyethoxy)-2,3-dihydro-1H-isoindol-2-yl]-4-(trifluoromethyl)-2-[[2-(trimethylsilyl)ethoxy]methyl]-2,3-dihydropyridazin-3-one A solution of 5-(4-hydroxy-2,3-dihydro-1H-isoindol-2-yl)-4-(trifluoromethyl)-2-[[2-(trimethylsilyl)ethoxy]methyl]-2,3-dihydropyridazin-3-one (2 g, 4.68 mmol, 1.00 equiv), potassium carbonate (3.2 g, 23.15 mmol, 5.00 equiv), 2-bromoethan-1-ol (2.9 g, 23.21 mmol, 5.00 equiv) in DMF (30 mL, 5.00 equiv) was stirred for 12 h at 80° C. in an oil bath. The reaction mixture was diluted with H$_2$O (200 mL). The resulting solution was extracted with EtOAc (4×100 mL) and the organic layers were combined. After concentration, the residue was applied onto a silica gel column eluting with EtOAc/petroleum ether (1:4) to afford 1.35 g (61%) of the title compound as a yellow solid. LCMS (ESI, m/z): 472.18 [M+H]$^+$ Step 2: Synthesis of Methyl 3-[2-([2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]oxy)ethoxy]benzoate Under nitrogen, a solution of 5-[4-(2-hydroxyethoxy)-2,3-dihydro-1H-isoindol-2-yl]-4-(trifluoromethyl)-2-[[2-(trimethylsilyl)ethoxy]methyl]-2,3-dihydropyridazin-3-one (675 mg, 1.43 mmol, 1.00 equiv), [Pd(allyl)Cl]$_2$ (67 mg, 0.10 equiv), Rockphos (52 mg, 0.10 equiv), CS$_2$CO$_3$ (932 mg, 2.86 mmol, 2.00 equiv), methyl 3-bromobenzoate (612 mg, 2.85 mmol, 2.00 equiv) in Toluene (10 mL) was stirred for 12 h at 80° C. in an oil bath. After filtration, the filtrate was concentrated under reduced pressure. The residue was applied onto a silica gel column eluting with EtOAc/petroleum ether (1:1) to afford 624 mg (72%) of the title compound as a yellow solid. LCMS (ESI, m/z): 606.22 [M+H]$^+$ Step 3: Synthesis of Methyl 4-[2-([2-[6-oxo-5-(trifluoromethyl)-1,6-dihydropyridazin-4-yl]-2,3-dihydro-1H-isoindol-4-yl]oxy)ethoxy]benzoate A solution of methyl 4-[2-([2-[6-oxo-5-(trifluoromethyl)-1-[[2-(trimethyl silyl)ethoxy]methyl]-1,6-dihydropyridazin-4-yl]-2,3-dihydro-1H-isoindol-4-yl]oxy)ethoxy]benzoate (624 mg, 1.03 mmol, 1.00 equiv) in hydrogen chloride/dioxane (20 mL) was stirred for 12 h at room temperature. After concentration, the residue was applied onto a silica gel column eluting with EtOAc/petroleum ether (1:2) to afford 400 mg (82%) of the title compound as a yellow solid. LCMS (ESI, m/z): 476.22 [M+H]$^+$ Step 4: Synthesis of 4-[2-([2-[6-oxo-5-(trifluoromethyl)-1,6-dihydropyridazin-4-yl]-2,3-dihydro-1H-isoindol-4-yl]oxy)ethoxy]benzoic Acid A solution of methyl 4-[2-([2-[6-oxo-5-(trifluoromethyl)-1,6-dihydropyridazin-4-yl]-2,3-dihydro-1H-isoindol-4-yl]oxy)ethoxy]benzoate (400 mg, 0.84 mmol, 1.00 equiv), LiOH (120 mg, 5.01 mmol, 5.00 equiv) in MeOH (5 mL) and water (1 mL) was stirred for 2 h at room temperature. The pH value of the solution was adjusted to 3 with hydrogen chloride. The solids were collected by filtration to afford 260 mg (67%) of the title compound as a gray solid. LCMS (ESI, m/z): 462.12 [M+H]+

Step 5: Synthesis of 6-[4-([3-[2-([2-[6-oxo-5-(trifluoromethyl)-1,6-dihydropyridazin-4-yl]-2,3-dihydro-1H-isoindol-4-yl]oxy)ethoxy]phenyl]carbonyl)piperazin-1-yl]pyridine-3-carbonitrile A solution of 3-[2-([2-[6-oxo-5-(trifluoromethyl)-1,6-dihydropyridazin-4-yl]-2,3-dihydro-1H-isoindol-4-yl]oxy)ethoxy]benzoic acid (260 mg, 0.56 mmol, 1.00 equiv), HATU (232 mg, 0.61 mmol, 1.00 equiv), DIPEA (315 mg, 2.44 mmol, 4.00 equiv), Int-A4 (115 mg, 0.61 mmol, 1.00 equiv) in DMF (2 mL) was stirred for 30 min at room temperature. After concentration, the residue was purified by C18 reverse phase chromatography eluting with $H_2O$/$CH_3CN$ yielding the title compound (89.8 mg, 25%) as a white solid. LCMS (ESI, m/z): 632.22 [M+H]+, $^1$H NMR (Methanol-$d_4$, 400 MHz) δ: 8.43-8.41 (d, J=2.3 Hz, 1H), 8.03 (s, 1H), 7.77-7.74 (dd, J=9.1, 2.3 Hz, 1H), 7.44-7.30 (dt, J=25.9, 7.9 Hz, 2H), 7.14-6.95 (m, 5H), 6.89-6.86 (d, J=9.0 Hz, 1H), 5.02-4.98 (m, 2H), 4.92-4.88 (m, 2H), 4.47-4.43 (m, 4H), 3.91-3.53 (m, 8H).

Example 40: 6-(4-[[3-([1-[6-oxo-5-(trifluoromethyl)-1,6-dihydropyridazin-4-yl]piperidin-2-yl]methoxy)phenyl]carbonyl]piperazin-1-yl)pyridine-3-carbonitrile

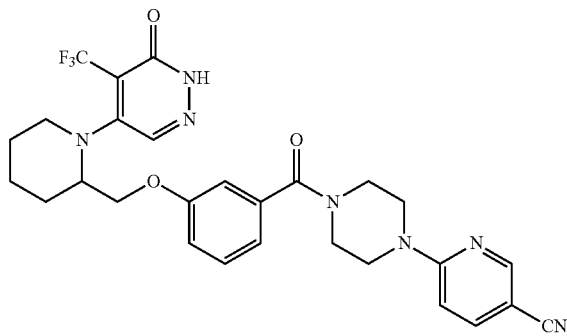 [SMILES: N#Cc1ccc(N2CCN(C(=O)c3cccc(OCC4CCCCN4c4cn[nH]c(=O)c4C(F)(F)F)c3)CC2)nc1]

Step 1: Synthesis of 5-[2-(hydroxymethyl)piperidin-1-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (2 g, 6.08 mmol, 1.00 equiv), piperidin-2-ylmethanol (772.3 mg, 6.71 mmol, 1.10 equiv) and TEA (1.35796 g, 13.42 mmol, 2.00 equiv) in ethanol (40 mL) was stirred for 2 h at 60° C., and then the resulting solution was concentrated under vacuum, and then the residue was applied onto a silica gel column eluting with EtOAc/petroleum ether (3:1) to afford 639 mg (26%) of the title compound as yellow oil. LCMS (ESI, m/z): 408.19 [M+H]+.

Step 2: Synthesis of Methyl 3-([1-[6-oxo-5-(trifluoromethyl)-1-[[2-(trimethylsilyl)ethoxy]methyl]-1,6-dihydropyridazin-4-yl]piperidin-2-yl]methoxy)benzoate A solution of 5-[2-(hydroxymethyl)piperidin-1-yl]-4-(trifluoromethyl)-2-[[2-(trimethylsilyl)ethoxy]methyl]-2,3-dihydropyridazin-3-one (560 mg, 1.37 mmol, 1.00 equiv), Pd(allyl)Cl$_2$ (50.3616 mg, 0.10 equiv), Rockphos (64.5344 mg, 0.10 equiv), Cs$_2$CO$_3$ (1.3457 g, 4.13 mmol, 3.00 equiv) and methyl 3-bromobenzoate (586.176 mg, 2.73 mmol, 2.00 equiv) in toluene (5 mL) was stirred for 12 h at 80° C. under in atmosphere of nitrogen, and then the resulting solution was concentrated under vacuum, and then the residue was applied onto a silica gel column eluting with EtOAc/petroleum ether (1:2) to afford 153 mg (21%) of the title compound as a light brown solid. LCMS (ESI, m/z): 542.23 [M+H]+.

Step 3: Synthesis of 3-([1-[6-oxo-5-(trifluoromethyl)-1-[[2-(trimethylsilyl)ethoxy]methyl]-1,6-dihydropyridazin-4-yl]piperidin-2-yl]methoxy)benzoic Acid A solution of methyl 3-([1-[6-oxo-5-(trifluoromethyl)-1-[[2-(trimethylsilyl)ethoxy]methyl]-1,6-dihydropyridazin-4-yl]piperidin-2-yl]methoxy)benzoate (153 mg, 0.28 mmol, 1.00 equiv) and LiOH (33.9 mg, 1.42 mmol, 5.00 equiv) in methanol (6 mL) and water (2 mL) was stirred for 24 h at room temperature, and then the residue was concentrated under vacuum, and then diluted with 3 mL of water, and then the pH value of the resulting solution was adjusted to 4 by HCl (1M), and then the residue solution was concentrated under vacuum to afford 107 mg of the title compound as a crude light yellow solid. LCMS(ESI, m/z): 528.21 [M+H]+

Step 4: Synthesis of 3-([1-[6-oxo-5-(trifluoromethyl)-1,6-dihydropyridazin-4-yl]piperidin-2-yl]methoxy)benzoic Acid A solution of 3-([1-[6-oxo-5-(trifluoromethyl)-1-[[2-(trimethylsilyl)ethoxy]methyl]-1,6-dihydropyridazin-4-yl]piperidin-2-yl]methoxy)benzoic acid (125 mg, 0.24 mmol, 1.00 equiv) in hydrogen chloride/dioxane (5 mL, 4M) was stirred for 2 h at room temperature, and then the resulting solution was concentrated under vacuum to afford 116 mg of the title compound as a crude yellow oil. LCMS (ESI, m/z): 398.12 [M+H]+

Step 5: Synthesis of 6-(4-[[3-([1-[6-oxo-5-(trifluoromethyl)-1,6-dihydropyridazin-4-yl]piperidin-2-yl]methoxy)phenyl]carbonyl]piperazin-1-yl)pyridine-3-carbonitrile A solution of 3-([1-[6-oxo-5-(trifluoromethyl)-1,6-dihydropyridazin-4-yl]piperidin-2-yl]methoxy)benzoic acid (69 mg, 0.17 mmol, 1.00 equiv), HATU (66.0 mg, 0.17 mmol, 1.00 equiv), DIPEA (67.4 mg, 0.52 mmol, 3.00 equiv) and Int-A4 (39.2 mg, 0.22 mmol, 1.20 equiv) in DMF (2 mL) was stirred for 4 h at room temperature, and then the resulting solution was purified by C18 reverse phase chromatography eluting with $H_2O$/$CH_3CN$, then the crude product was further purified by Prep-HPLC yielding the title compound (26.7 mg, 27.0%) as a white solid. LCMS (ESI, m/z): 568.25[M+H]+, $^1$HNMR (CD$_3$OD-$d_4$, 300 MHz) δ 8.43 (d, J=2.1 Hz, 1H), 7.99 (s, 1H), 7.79 (dd, J=9.0, 2.1 Hz, 1H), 7.35 (t, J=8.4 Hz, 1H), 7.02 (d, J=7.2 Hz, 1H), 6.92-6.83 (m, 3H), 4.54 (t, J=9.9 Hz, 1H), 4.37 (d, J=3.9 Hz, 1H), 4.15 (dd, J=10.2, 3.6 Hz, 1H), 3.92-3.50 (m, 9H), 3.43-3.37 (m, 1H), 2.03-1.59 (m, 6H).

Example 41: 6-(4-[[3-(2-[[6-oxo-5-(trifluoromethyl)-1,6-dihydropyridazin-4-yl]amino]ethoxy)phenyl]carbonyl]piperazin-1-yl)pyridine-3-carbonitrile

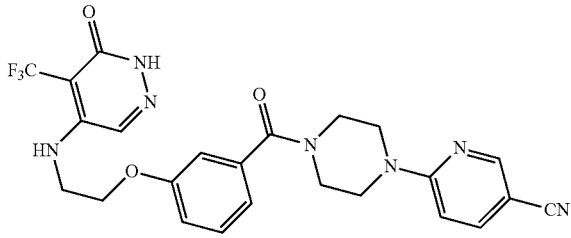 [SMILES: N#Cc1ccc(N2CCN(C(=O)c3cccc(OCCNc4cn[nH]c(=O)c4C(F)(F)F)c3)CC2)nc1]

Step 1: Synthesis of Methyl 3-(2-[[(tert-butoxy)carbonyl]amino]ethoxy)benzoate A solution of methyl 3-hydroxybenzoate (760 mg, 5.00 mmol, 1 equiv), tert-butyl N-(2-bromoethyl)carbamate (1679.1 mg, 7.49 mmol, 1.500 equiv), $K_2CO_3$ (1380.7 mg, 9.99 mmol, 2 equiv) in DMF (5 mL) was stirred for 2 h at 80° C. The resulting solution was extracted with 3×30 ml of EtOAc and the organic layers combined. The resulting solution was extracted with 3×30 mL of NaCl(aq) and the organic layers combined and concentrated under vacuum. The residue was applied onto a silica gel column eluting with EtOAc/petroleum ether (21/79) to afford 1.323 g (89.68%) of the title compound as white oil. LCMS (ESI, m/z): 296.14 [M+H]$^+$

Step 2: Synthesis of 3-(2-[[(tert-butoxy)carbonyl]amino]ethoxy)benzoic Acid A solution of methyl 3-(2-[[(tert-butoxy)carbonyl]amino]ethoxy)benzoate (1.223 g, 4.14 mmol, 1.00 equiv), sodium hydroxide (830 mg, 20.75 mmol, 5.00 equiv) in methanol (5 mL) was stirred for 2 h at room temperature. The resulting mixture was concentrated under vacuum. The pH value of the solution was adjusted to 6 with hydrogen chloride (40%). The solids were collected by filtration. This resulted in 531 mg (46%) of the title compound as a white solid. LCMS (ESI, m/z): 282.13 [M+H]$^+$

Step 3: Synthesis of Tert-Butyl N-[2-(3-[[4-(5-cyanopyridin-2-yl)piperazin-1-yl]carbonyl]phenoxy)ethyl]carbamate A solution of 3-(2-[[(tert-butoxy)carbonyl]amino]ethoxy)benzoic acid (531 mg, 1.89 mmol, 1.00 equiv), DIPEA (731 mg, 5.66 mmol, 3.00 equiv), HATU (790 mg, 2.08 mmol, 1.10 equiv), Int-A4 (466 mg, 2.07 mmol, 1.10 equiv) in DMF (5 mL) was stirred for 8 h at room temperature. The resulting solution was extracted with 3×30 mL of EtOAc and the organic layers combined. The resulting solution was extracted with 3×30 mL of saturated sodium chloride aqueous and the organic layers combined and dried over anhydrous sodium sulfate and concentrated under vacuum. This resulted in 1.142 g (crude) of the title compound as yellow oil. LCMS (ESI, m/z): 452.22 [M+H]$^+$

Step 4: Synthesis of 6-(4-[[3-(2-aminoethoxy)phenyl]carbonyl]piperazin-1-yl)pyridine-3-carbonitrile Hydrochloride A solution of tert-butyl N-[2-(3-[[4-(5-cyanopyridin-2-yl)piperazin-1-yl]carbonyl]phenoxy)ethyl]carbamate (1.142 g) in HCl/dioxane (5 mL) was stirred for 30 min at room temperature. The resulting mixture was concentrated under vacuum to afford 0.980 g of the title compound as a yellow solid. LCMS (ESI, m/z): 352.17 [M+H]$^+$

Step 5: Synthesis of 6-(4-[[3-(2-[[6-oxo-5-(trifluoromethyl)-1-[[2-(trimethylsilyl)ethoxy]methyl]-1,6-dihydropyridazin-4-yl]amino]ethoxy)phenyl]carbonyl]piperazin-1-yl)pyridine-3-carbonitrile A solution of 5-chloro-4-(trifluoromethyl)-2-[[2-(trimethylsilyl)ethoxy]methyl]-2,3-dihydropyridazin-3-one (758 mg, 2.31 mmol, 1 equiv), 6-(4-[[3-(2-aminoethoxy)phenyl]carbonyl]piperazin-1-yl)pyridine-3-carbonitrile dihydrochloride (980 mg, 2.31 mmol, 1 equiv), TEA (700 mg, 6.93 mmol, 3 equiv) in EtOH (5 mL) was stirred for 3 h at 60° C. The resulting mixture was concentrated under vacuum. The residue was applied onto a silica gel column eluting with EtOAc/petroleum ether (93/7) to afford 615 mg (41.4%) of the title compound as yellow oil. LCMS (ESI, m/z): 644.26 [M+H]$^+$

Step 6: Synthesis of 6-(4-[[3-(2-[[6-oxo-5-(trifluoromethyl)-1,6-dihydropyridazin-4-yl]amino]ethoxy)phenyl]carbonyl]piperazin-1-yl)pyridine-3-carbonitrile A solution of 6-(4-[[3-(2-[[6-oxo-5-(trifluoromethyl)-1-[[2-(trimethylsilyl)ethoxy]methyl]-1,6-dihydropyridazin-4-yl]amino]ethoxy)phenyl]carbonyl]piperazin-1-yl)pyridine-3-carbonitrile (300 mg) in DCM (5 mL) and TFA (1 mL) was stirred for 2 h at room temperature. The reaction was then quenched by the addition of 5 mL of NaHCO$_3$(aq). The resulting solution was extracted with 3×30 ml of DCM and the organic layers combined. After concentration, the residue was purified by C18 reverse phase chromatography eluting with H$_2$O/CH$_3$CN. Then the residue was further purified by Prep-HPLC yielding the title compound (61.9 mg, 25.9%) as a white solid. LCMS (ESI, m/z): 514.17 [M+H]$^+$, $^1$H NMR (300 MHz, DMSO-d6) δ: 12.50 (s, 1H), 8.53 (dd, J=2.4, 0.6 Hz, 1H), 8.01 (s, 1H), 7.91 (dd, J=9.1, 2.4 Hz, 1H), 7.39 (dd, J=8.4, 7.4 Hz, 1H), 7.16 (d, J=3.5 Hz, 1H), 7.07-6.90 (m, 4H), 4.18 (t, J=5.4 Hz, 2H), 3.81-3.57 (m, 8H), 3.51 (m, 2H).

Example 42: 6-(4-[[3-(2-[[6-oxo-5-(trifluoromethyl)-1,6-dihydropyridazin-4-yl]oxy]ethoxy)phenyl]carbonyl]piperazin-1-yl)pyridine-3-carbonitrile

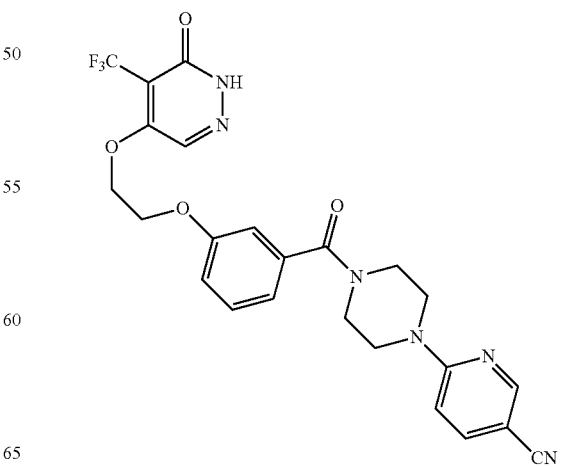

Step 1: Synthesis of 5-(2-bromoethoxy)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (4 g, 12.17 mmol, 1.00 equiv), 2-bromoethan-1-ol (1.66 g, 13.28 mmol, 1.10 equiv) and $Cs_2CO_3$ (7.95 g, 24.32 mmol, 2.00 equiv) in DMF (15 mL) was stirred for 2 h at room temperature, and then the residue was dissolved in 50 mL of $H_2O$, extracted with 3×50 mL of EtOAc and the organic layers combined, washed with 1×50 mL of brine, dried over anhydrous sodium sulfate and concentrated under vacuum, and then the residue was applied onto a silica gel column eluting with EtOAc/petroleum ether (35/65) to afford 2.0 g (39%) of the title compound as yellow oil. LCMS (ESI, m/z): 417.04 $[M+H]^+$.

Step 2: Synthesis of Methyl 3-(2-[[6-oxo-5-(trifluoromethyl)-1-[[2-(trimethylsilyl)ethoxy]methyl]-1,6-dihydropyridazin-4-yl]oxy]ethoxy)benzoate A solution of 5-(2-bromoethoxy)-4-(trifluoromethyl)-2-[[2-(trimethylsilyl)ethoxy]methyl]-2,3-dihydropyridazin-3-one (1 g, 2.40 mmol, 1.00 equiv), methyl 3-hydroxybenzoate (730 mg, 4.80 mmol, 2.00 equiv) and $Cs_2CO_3$ (1.567 g, 4.79 mmol, 2.00 equiv) in DMF (25 mL) was stirred for 3 h at 60° C., and then the residue was dissolved in 60 mL of H2O, extracted with 3×60 mL of EtOAc and the organic layers combined, washed with 1×60 mL of brine, dried over anhydrous sodium sulfate and concentrated under vacuum, and then the residue was applied onto a silicagel column eluting with EtOAc/petroleum ether (27/73) to afford 302 mg (26%) of the title compound as yellow oil. LCMS (ESI, m/z): 489.16 $[M+H]^+$.

Step 3: Synthesis of Methyl 3-(2-[[6-oxo-5-(trifluoromethyl)-1,6-dihydropyridazin-4-yl]oxy]ethoxy)benzoate A solution of methyl 3-(2-[[6-oxo-5-(trifluoromethyl)-1-[[2-(trimethylsilyl)ethoxy]methyl]-1,6-dihydropyridazin-4-yl]oxy]ethoxy)benzoate (330 mg, 0.68 mmol, 1.00 equiv) in HCl/dioxane (13 mL, 4M) was stirred for 1 h at room temperature, and then the resulting solution was concentrated under vacuum to afford 280 mg of crude the title compound as yellow oil. LCMS (ESI, m/z): 359.08$[M+H]^+$.

Step 4: Synthesis of 3-(2-[[6-oxo-5-(trifluoromethyl)-1,6-dihydropyridazin-4-yl]oxy]ethoxy)benzoic Acid A solution of methyl 3-(2-[[6-oxo-5-(trifluoromethyl)-1,6-dihydropyridazin-4-yl]oxy]ethoxy)benzoate (300 mg, 0.84 mmol, 1.00 equiv) and LiOH (60.3 mg, 2.52 mmol, 3.00 equiv) in water (2 mL) and THF (10 mL) was stirred for 2 h at room temperature, and then the resulting solution was concentrated under vacuum, and then the residue was diluted with 10 mL of H2O, and then the pH value of the solution was adjusted to 4 with hydrogen chloride (36%), and then the resulting solution was concentrated under vacuum to afford 255 mg of the title compound as a crude yellow solid. LCMS (ESI, m/z): 345.06 $[M+H]^+$.

Step 5: Synthesis of 6-(4-[[3-(2-[[6-oxo-5-(trifluoromethyl)-1,6-dihydropyridazin-4-yl]oxy]ethoxy)phenyl]carbonyl]piperazin-1-yl)pyridine-3-carbonitrile A solution of 3-(2-[[6-oxo-5-(trifluoromethyl)-1,6-dihydropyridazin-4-yl]oxy]ethoxy)benzoic acid (230 mg, 0.67 mmol, 1.00 equiv), HATU (254 mg, 0.67 mmol, 1.00 equiv), DIPEA (258 mg, 2.00 mmol, 3.00 equiv) and Int-A4 (125 mg, 0.66 mmol, 1.00 equiv) in DMF (8 mL) was stirred for 40 min at room temperature, and then the resulting solution was purified by C18 reverse phase chromatography eluting with $H_2O/CH_3CN$. After concentration, the residue was further purified by Prep-HPLC yielding the title compound (11.8 mg 3%) as a white solid. LCMS (ESI, m/z): 515.15 $[M+H]^+$, $^1$HNMR (DMSO-$d_6$, 400 MHz,) δ 13.56 (s, 1H), 8.51 (d, J=2.0 Hz, 1H), 8.32 (s, 1H), 7.91 (dd, J=9.2, 2.4 Hz, 1H), 7.40 (t, J=8.0 Hz, 1H), 7.06-7.00 (m, 3H), 6.94 (d, J=9.2 Hz, 1H), 4.78-4.76 (m, 2H), 4.36-4.34 (m, 2H), 3.77-3.69 (m, 8H).

Example 43: 6-[4-([4-[2-([2-[6-oxo-5-(trifluoromethyl)-1,6-dihydropyridazin-4-yl]-2,3-dihydro-1H-isoindol-4-yl]oxy)ethoxy]phenyl]carbonyl)piperazin-1-yl]pyridine-3-carbonitrile

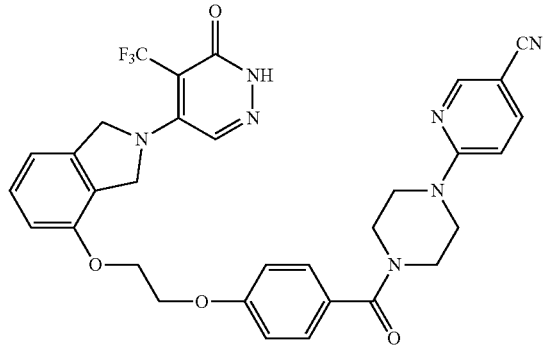 [SMILES: N#Cc1ccc(N2CCN(C(=O)c3ccc(OCCOc4cccc5c4CN(c4cn[nH]c(=O)c4C(F)(F)F)C5)cc3)CC2)nc1]

Step 1: Synthesis of Methyl 4-[2-([2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]oxy)ethoxy]benzoate Under nitrogen, a solution of 5-[4-(2-hydroxyethoxy)-2,3-dihydro-1H-isoindol-2-yl]-4-(trifluoromethyl)-2-[[2-(trimethylsilyl)ethoxy]methyl]-2,3-dihydropyridazin-3-one (675 mg, 1.43 mmol, 1.00 equiv), [Pd(allyl)Cl]$_2$ (67 mg, 0.10 equiv), Rockphos (52 mg, 0.10 equiv), $CS_2CO_3$ (932 mg, 2.86 mmol, 2.00 equiv), methyl 4-bromobenzoate (612 mg, 2.85 mmol, 2.00 equiv) in Toluene (10 mL) was stirred for 12 h at 80° C. in an oil bath. After filtration, the filtrate was concentrated under reduced pressure. the residue was applied onto a silica gel column with EtOAc/petroleum ether (1:1) to afford 430 mg (50%) of the title compound as a yellow solid. LCMS (ESI, m/z): 606.22 $[M+H]^+$ Step 2: Synthesis of Methyl 4-[2-([2-[6-oxo-5-(trifluoromethyl)-1,6-dihydropyridazin-4-yl]-2,3-dihydro-1H-isoindol-4-yl]oxy)ethoxy]benzoate A solution of methyl 4-[2-([2-[6-oxo-5-(trifluoromethyl)-1-[[2-(trimethyl silyl)ethoxy]methyl]-1,6-dihydropyridazin-4-yl]-2,3-dihydro-1H-isoindol-4-yl]oxy)ethoxy]benzoate (430 mg, 0.71 mmol, 1.00 equiv) in hydrogen chloride/dioxane (20 mL) was stirred for 12 h at room temperature. The resulting mixture was concentrated under vacuum to afford 300 mg (89%) of the title compound as a yellow solid. LCMS (ESI, m/z): 476.14 $[M+H]^+$ Step 3: Synthesis of 4-[2-([2-[6-oxo-5-(trifluoromethyl)-1,6-dihydropyridazin-4-yl]-2,3-dihydro-1H-isoindol-4-yl]oxy)ethoxy]benzoic Acid A solution of methyl 4-[2-([2-[6-oxo-5-(trifluoromethyl)-1,6-dihydropyridazin-4-yl]-2,3-dihydro-1H-isoindol-4-yl]oxy)ethoxy]benzoate (300 mg, 0.63 mmol, 1.00 equiv), LiOH (76 mg, 3.17 mmol, 5.00 equiv) in MeOH (5 mL) and water (1 mL) was stirred for 2 h at room temperature. The pH value of the solution was adjusted to 3 with hydrogen chloride. The solids were collected by filtration to afford 250 mg (86%) of the title compound as a gray solid. LCMS (ESI, m/z): 462.12 [M+H]+

Step 4: Synthesis of 6-[4-([4-[2-([2-[6-oxo-5-(trifluoromethyl)-1,6-dihydropyridazin-4-yl]-2,3-dihydro-1H-isoindol-4-yl]oxy)ethoxy]phenyl]carbonyl)piperazin-1-yl]pyridine-3-carbonitrile A solution of 4-[2-([2-[6-oxo-5-(trifluoromethyl)-1,6-dihydropyridazin-4-yl]-2,3-dihydro-1H-isoindol-4-yl]oxy)ethoxy]benzoic acid (270 mg, 0.59 mmol, 1.00 equiv), HATU (239 mg, 0.63 mmol, 1.00 equiv), DIPEA (325 mg, 2.51 mmol, 4.00 equiv), Int-A4 (118 mg, 0.63 mmol, 1.00 equiv) in DMF (2 mL) was stirred for 30 min at room temperature. After concentration, the residue was purified by C18 reverse phase chromatography eluting with H$_2$O/CH$_3$CN yielding the title compound (163.6 mg 44%) as a white solid. LCMS (ESI, m/z): 632.22 [M+H]+, $^1$H NMR (DMSO-d$_6$, 300 MHz) δ:12.52 (s, 1H), 8.49 (d, J=2.3 Hz, 1H), 7.99 (s, 1H), 7.87 (dd, J=9.1, 2.3 Hz, 1H), 7.41 (d, J=8.4 Hz, 2H), 7.31 (t, J=7.8 Hz, 1H), 7.09-6.87 (m, 5H), 4.96 (s, 2H), 4.86 (s, 2H), 4.43-4.40 (d, J=9.3 Hz, 4H), 3.73 (dr, 4H), 3.59 (dr, 4H).

Example 44: 5-[5-fluoro-6-(piperidin-3-ylmethoxy)-2,3-dihydro-1H-isoindol-2-yl]-4-(trifluoromethyl)-2,3-dihydropyridazin-3-one

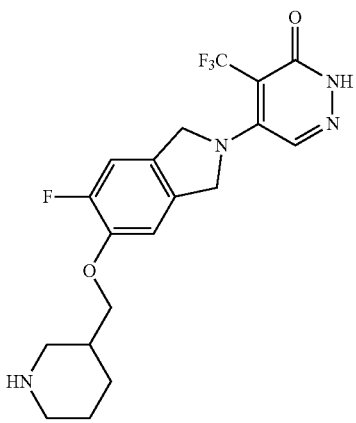 [SMILES: O=c1[nH]ncc(N2Cc3cc(F)c(OCC4CCCNC4)cc3C2)c1C(F)(F)F]

Step 1: Synthesis of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one A solution of 5-bromo-6-fluoro-2,3-dihydro-1H-isoindole (6 g, 27.77 mmol, 1 equiv), 5-chloro-4-(trifluoromethyl)-2-[[2-(trimethylsilyl)ethoxy]methyl]-2,3-dihydropyridazin-3-one (10.8 g, 32.85 mmol, 1.183 equiv), TEA (8 g, 79.06 mmol, 2.847 equiv) in ethanol (60 mL) was stirred for 2 h at 80° C. The resulting mixture was concentrated under vacuum. The residue was applied onto a silica gel column eluting with EtOAc/petroleum ether (2/8) to afford 2.8 g (19.8%) of the title compound as a white solid. LCMS (ESI, m/z): 510.06[M+H]+

Step 2: Synthesis of Tert-Butyl 3-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]piperidine-1-carboxylate A solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (1 g, 1.97 mmol, 1.00 equiv), Rockphos (92 mg, 0.20 mmol, 0.10 equiv), [Pd(ally)Cl]$_2$, Cs$_2$CO$_3$ (72 mg, 0.20 mmol, 0.10 equiv), tert-butyl 3-(hydroxymethyl)piperidine-1-carboxylate (844 mg, 3.92 mmol, 2.00 equiv), Cs$_2$CO$_3$ (1.28 g, 3.93 mmol, 2.00 equiv) in toluene (8 mL) was stirred for 2 h under the atmosphere of nitrogen at 80° C. The reaction mixture was concentrated under vacuum and the residue was applied onto a silica gel column eluting with EtOAc/petroleum ether (3/7) to afford 920 mg (92%) of the title compound as yellow oil. LCMS (ESI, m/z): 643.29 [M+H]+

Step 3: Synthesis of 5-[5-fluoro-6-(piperidin-3-ylmethoxy)-2,3-dihydro-1H-isoindol-2-yl]-4-(trifluoromethyl)-2,3-dihydropyridazin-3-one A solution of tert-butyl 3-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]piperidine-1-carboxylate (910 mg, 1.42 mmol, 1 equiv) in hydrogen chloride/dioxane (10 mL) was stirred for 3 h at room temperature. After concentration, the residue was purified by C18 reverse phase chromatography eluting with H$_2$O/CH$_3$CN. Then the residue was further purified by Prep-HPLC yielding the title compound (29.4 mg, 5.04%) as a white solid. $^1$H NMR (300 MHz, DMSO-d$_6$) δ: 7.98 (s, 1H), 7.28-7.23 (m, 2H), 4.90 (m, 4H), 3.90 (d, J=6.6 Hz, 2H), 3.04 (d, J=11.9 Hz, 1H), 2.86 (d, J=12.2 Hz, 1H), 2.50-2.28 (m, 1H), 1.92-1.6 (m, 2H), 1.59 (d, J=12.9 Hz, 1H), 1.41 (t, J=11.8 Hz, 1H), 1.28-1.15 (m, 1H).

Example 45: 5-[5-[(1-acetylpiperidin-3-yl)methoxy]-6-fluoro-2,3-dihydro-1H-isoindol-2-yl]-4-(trifluoromethyl)-2,3-dihydropyridazin-3-one

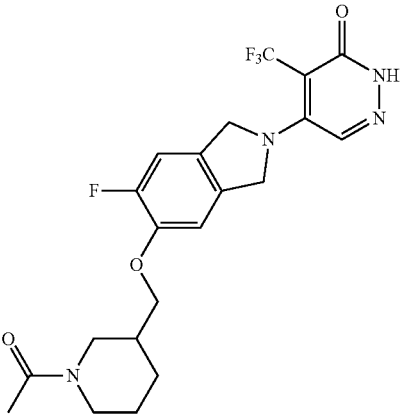 [SMILES: CC(=O)N1CCCC(COc2cc3c(cc2F)CN(c2cn[nH]c(=O)c2C(F)(F)F)C3)C1]

A solution of 5-[5-fluoro-6-(piperidin-3-ylmethoxy)-2,3-dihydro-1H-isoindol-2-yl]-4-(trifluoromethyl)-2,3-dihydropyridazin-3-one (120 mg, 0.29 mmol, 1 equiv), TEA (88.3 mg, 0.87 mmol, 3.0 equiv), Ac₂O (44.6 mg, 0.44 mmol, 1.5 equiv) in DCM (10 mL) was stirred for 2 h at room temperature. After concentration, the residue was purified by C18 reverse phase chromatography eluting with H₂O/CH₃CN. Then the residue was further purified by Prep-HPLC yielding the title compound (31.2 mg, 23.6%) as white solid. LCMS (ESI, m/z): 455.42 [M+H]⁺, ¹H NMR (Methanol-d₄, 300 MHz) δ: 8.04 (s, 1H), 7.15 (d, J=10.4 Hz, 2H), 5.11-4.90 (m, 4H), 4.51 (d, J=12.9 Hz, 1H), 4.11-3.87 (m, 3H), 3.26-3.21 (m, 1H), 3.04-2.78 (m, 1H), 2.12-1.82 (m, 5H), 1.79-1.54 (s, 3H)

Example 46: 6-(4-[[4-([2-[6-oxo-5-(trifluoromethyl)-1,6-dihydropyridazin-4-yl]-2,3-dihydro-1H-isoindol-1-yl]methoxy)pyrimidin-2-yl]carbonyl]piperazin-1-yl)pyridine-3-carbonitrile

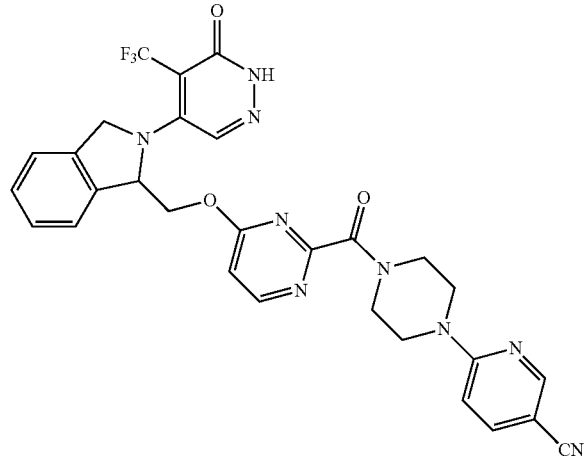

Step 1: Synthesis of Methyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrimidine-2-carboxylate A solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1 equiv), methyl 4-bromopyrimidine-2-carboxylate (491 mg, 2.26 mmol, 2 equiv), Pd₂(dba)₃·CHCl₃ (117 mg, 0.11 mmol, 0.1 equiv), xantphos (65.5 mg, 0.11 mmol, 0.1 equiv), Cs₂CO₃ (738 mg, 2.26 mmol, 2 equiv) in toluene (5 mL) with an inert atmosphere of nitrogen was stirred for 5 h at 85° C. The resulting solution was concentrated under vacuum. The residue was applied onto a silica gel column eluting with EtOAc/petroleum ether (69/31) to afford 478 mg (73.1%) of the title compound as a white solid. LCMS (ESI, m/z): 578.20 [M+H]⁺

Step 2: Synthesis of 4-((2-(6-oxo-5-(trifluoromethyl)-1-((2-(trimethylsilyl)ethoxy)methyl)-1,6-dihydropyridazin-4-yl)isoindolin-1-yl)methoxy)pyrimidine-2-carboxylate A solution of methyl 4-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyrimidine-2-carboxylate (458 mg, 0.79 mmol, 1 equiv), LiOH·H₂O (166 mg, 3.97 mmol, 5 equiv) in MeOH (5 mL) and H₂O (1 mL) was stirred for 6 h at room temperature. The resulting solution was diluted with 6 mL of water. The resulting solution was extracted with 3×30 mL of DCM and the organic layers combined and concentrated under vacuum. This resulted in 167 mg (37.3%) of the title compound as a yellow oil. LCMS (ESI, m/z): 564.18[M+H]⁺

Step 3: Synthesis of 4-([2-[6-oxo-5-(trifluoromethyl)-1,6-dihydropyridazin-4-yl]-2,3-dihydro-1H-isoindol-1-yl]methoxy)pyrimidine-2-carboxylic Acid A solution of 4-((2-(6-oxo-5-(trifluoromethyl)-1-((2-(trimethylsilyl)ethoxy)methyl)-1,6-dihydropyridazin-4-yl)isoindolin-1-yl)methoxy)pyrimidine-2-carboxylate (157 mg) in HCl/dioxane (4 mL) was stirred for 7 h at room temperature. The resulting mixture was concentrated under vacuum. This resulted in 141 mg of the title compound as yellow oil. LCMS (ESI, m/z): 434.10 [M+H]⁺

Step 4: Synthesis of 6-(4-[[4-([2-[6-oxo-5-(trifluoromethyl)-1,6-dihydropyridazin-4-yl]-2,3-dihydro-1H-isoindol-1-yl]methoxy)pyrimidin-2-yl]carbonyl]piperazin-1-yl)pyridine-3-carbonitrile A solution of 4-([2-[6-oxo-5-(trifluoromethyl)-1,6-dihydropyridazin-4-yl]-2,3-dihydro-1H-isoindol-1-yl]methoxy)pyrimidine-2-carboxylic acid (131 mg, 0.30 mmol, 1 equiv), DIPEA (117.2 mg, 0.91 mmol, 3 equiv), EDC·HCl (86.9 mg, 0.45 mmol, 1.5 equiv), HOBT (61.3 mg, 0.45 mmol, 1.5 equiv), Int-A4 (74.7 mg, 0.33 mmol, 1.1 equiv) in DMF (2 mL) was stirred for 5 h at room temperature. After concentration, the residue was purified by C18 reverse phase chromatography eluting with H₂O/CH₃CN. Then the residue was further purified by Prep-HPLC yielding the title compound (8.5 mg, 4.66%) as a white solid. LCMS (ESI, m/z): 604.20 [M+H]+, ¹H NMR (400 MHz, DMSO-d6) δ: 12.61 (s, 1H), 8.61 (d, J=7 Hz, 1H), 8.58 (s, 1H), 8.33 (s, 1H), 7.91 (dd, J=9.1, 2.4 Hz, 1H), 7.53-7.29 (m, 4H), 6.98-6.88 (m, 2H), 6.15 (s, 1H), 5.10 (d, J=14.5 Hz, 1H), 4.86 (dd, J=11.5, 4.4 Hz, 1H), 4.66 (dd, J=11.5, 4.6 Hz, 1H), 4.55 (d, J=14.9 Hz, 1H), 3.80 (d, J=5.5 Hz, 2H), 3.72 (t, J=4.2 Hz, 2H), 3.63 (t, J=5.2 Hz, 2H), 3.29 (m, 2H).

Example 47: N-[4-[(5-cyanopyridin-2-yl)oxy]cyclohexyl]-2-[[(2S)-1-[6-oxo-5-(trifluoromethyl)-1,6-dihydropyridazin-4-yl]pyrrolidin-2-yl]methoxy]acetamide

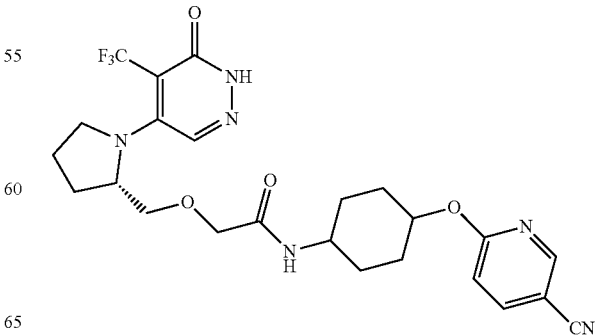

Step 1: Synthesis of Tert-Butyl N-[4-[(5-cyanopyridin-2-yl)oxy]cyclohexyl]carbamate To a solution of tert-butyl N-(4-hydroxycyclohexyl)carbamate (2 g, 9.29 mmol, 1.00 equiv) in DMF (10 mL), sodium hydride (223 mg, 9.29 mmol, 2.00 equiv) was added in at 0° C., then the resulting solution was stirred for 10 min at room temperature, then 6-chloropyridine-3-carbonitrile (1.3 g, 9.38 mmol, 1.00 equiv) was added in, the resulting solution was stirred for another 8 h at room temperature, and then the resulting solution was diluted with 50 mL of water, extracted with 2×50 mL of EtOAc, and the organic layers combined and washed with 1×50 mL of brine, dried over anhydrous sodium sulfate and then concentrated under vacuum and then the residue was applied onto a silica gel column eluting with EtOAc/petroleum ether (2:3) to afford 1.7 g (58%) of the title compound as a white solid. LCMS (ESI, m/z): 318.18 [M+H]+.

Step 2: Synthesis of 6-[(4-aminocyclohexyl)oxy]pyridine-3-carbonitrile

A solution of tert-butyl N-[4-[(5-cyanopyridin-2-yl)oxy]cyclohexyl]carbamate (700 mg, 2.21 mmol, 1.00 equiv) in hydrogen chloride/dioxane (5 mL, 4M) was stirred for 30 min at room temperature, and then the resulting solution was concentrated under vacuum to afford 100 mg of the title compound as a crude white solid. LCMS (ESI, m/z): 218.12 [M+H]+.

Step 3: Synthesis of N-[4-[(5-cyanopyridin-2-yl)oxy]cyclohexyl]-2-[[(2S)-1-[6-oxo-5-(trifluoromethyl)-1,6-dihydropyridazin-4-yl]pyrrolidin-2-yl]methoxy]acetamide A solution of 2-[(2S)-1-[6-oxo-5-(trifluoromethyl)-1,6-dihydropyridazin-4-yl]pyrrolidin-2-yl]methoxyacetic acid (72 mg, 0.22 mmol, 1.00 equiv), EDC.HCl (86 mg, 0.55 mmol, 2.00 equiv), DMAP (55 mg, 0.45 mmol, 2.00 equiv) and 6-[(4-aminocyclohexyl)oxy]pyridine-3-carbonitrile (58 mg, 0.27 mmol, 1.20 equiv) in DMF (4 mL) was stirred for 16 h at room temperature, and then the resulting solution was diluted with 20 ml of H2O, extracted with 3×20 ml of EtOAc and the organic layer was combined, washed with 1×20 mL of brine and concentrated under vacuum, and then the residue was purified by C18 reverse phase chromatography eluting with H$_2$O/CH$_3$CN. After concentration, the residue was further purified by Pre-HPLC yielding the title compound (23 mg, 20%) as a yellow solid. LCMS (ESI, m/z): 521.20[M+H]+, $^1$H NMR (CD3OD, 400 MHz) δ 8.55 (dd, J=2.4, 0.8 Hz, 1H), 8.27 (s, 1H), 7.97 (dd, J=8.4, 2.4 Hz, 1H), 6.88 (dd, J=8.8, 0.8 Hz, 1H), 5.13-5.06 (m, 1H), 4.79-4.71 (m, 1H), 3.97 (d, J=8.8 Hz, 2H), 3.82-3.71 (m, 3H), 3.42-3.37 (m, 2H), 2.32-2.17 (m, 3H), 2.06-1.92 (m, 3H), 1.83-1.69 (m, 2H), 1.68-1.58 (m, 2H), 1.45-1.38 (m, 2H)

Example 48: 5-[5-fluoro-6-(pyrrolidin-2-ylmethoxy)-2,3-dihydro-1H-isoindol-2-yl]-4-(trifluoromethyl)-2,3-dihydropyridazin-3-one

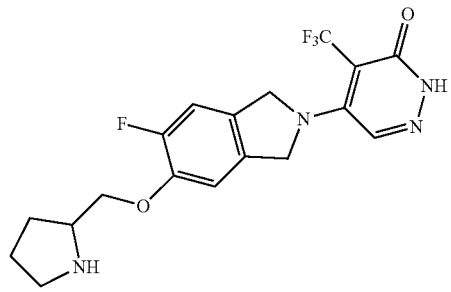 [SMILES: O=c1[nH]ncc(N2Cc3cc(F)c(OCC4CCCN4)cc3C2)c1C(F)(F)F]

Step 1: Synthesis of Tert-Butyl 2-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]pyrrolidine-1-carboxylate Under nitrogen, a solution of 5-(5-bromo-6-fluoro-2,3-dihydro-1H-isoindol-2-yl)-4-(trifluoromethyl)-2-[[2-(trimethylsilyl)ethoxy]methyl]-2,3-dihydropyridazin-3-one (800 mg, 1.57 mmol, 1.00 equiv), tert-butyl 2-(hydroxymethyl)pyrrolidine-1-carboxylate (952 mg, 4.73 mmol, 3.00 equiv), [Pd(allyl)Cl]$_2$ (17 mg, 0.05 mmol, 0.03 equiv), Rockphos (37 mg, 0.08 mmol, 0.05 equiv), Cs$_2$CO$_3$ (1.03 mg, 2.00 equiv) in toluene (4 mL) was stirred for 5 h at 90° C. in an oil bath. After concentration, the residue was applied onto a silica gel column eluting with EtOAc/petroleum ether (23:77) to afford 800 mg (81%) of the title compound as yellow oil. LCMS (ESI, m/z): 629.27 [M+H]+

Step 2: Synthesis of 5-[5-fluoro-6-(pyrrolidin-2-ylmethoxy)-2,3-dihydro-1H-isoindol-2-yl]-4-(trifluoromethyl)-2,3-dihydropyridazin-3-one A solution of tert-butyl 2-[([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)methyl]pyrrolidine-1-carboxylate (800 mg, 1.27 mmol, 1.00 equiv) in hydrogen chloride/dioxane (30 mL) was stirred for 1 overnight at 25° C. After concentration, the crude product was purified by Prep-HPLC yielding the title compound (18.6 mg 4%) as a white solid. LCMS (ESI, m/z): 399.14 [M+H]+, $^1$H NMR (DMSO-d$_6$, 400 MHz) δ: 12.50 (s, 1H), 7.93 (s, 1H), 7.28-7.20 (m, 2H), 4.90 (s, 4H), 3.88-3.85 (m, 2H), 3.37-3.33 (m, 1H), 2.83-2.78 (m, 2H), 1.87-1.80 (m, 1H), 1.73-1.66 (m, 2H), 1.49-1.41 (m, 1H).

Example 49: 5-[5-fluoro-6-[(1-methylpyrrolidin-2-yl)methoxy]-2,3-dihydro-1H-isoindol-2-yl]-4-(trifluoromethyl)-2,3-dihydropyridazin-3-one; Formic Acid

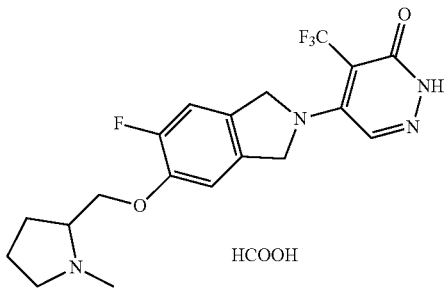 [SMILES: CN1CCCC1COc1cc2c(cc1F)CN(c1cn[nH]c(=O)c1C(F)(F)F)C2 ; "HCOOH"]

HCOOH

A solution of 5-[5-fluoro-6-(pyrrolidin-2-ylmethoxy)-2,3-dihydro-1H-isoindol-2-yl]-4-(trifluoromethyl)-2,3-dihydropyridazin-3-one (150 mg, 0.38 mmol, 1.00 equiv), CH$_2$O (20 mg, 0.67 mmol, 1.80 equiv), potassium hydroxide (42 mg, 0.75 mmol, 2.00 equiv), NaBH$_4$ (29 mg, 0.77 mmol, 2.00 equiv) in methanol (20 mL) was stirred for 3 h at 25° C. After concentration, the residue was purified by Prep-HPLC yielding the title compound (41.6 mg 24%) as a colorless solid. LCMS (ESI, m/z): 413.15 [M+H]$^+$, $^1$H NMR (DMSO-d$_6$, 400 MHz, ppm) δ: 12.50 (s, 1H), 7.97 (s, 1H), 7.22-7.28 (m, 2H), 4.89 (s, 4H), 4.04-3.91 (m, 2H), 2.99-2.95 (m, 1H), 2.67-2.62 (m, 1H), 2.38 (s, 3H), 2.23-2.19 (m, 1H), 2.00-1.92 (s, 1H), 1.73-1.66 (m, 2H), 1.59-1.56 (m, 1H).

Example 50: 5-[5-[(1-acetylpyrrolidin-2-yl)methoxy]-6-fluoro-2,3-dihydro-1H-isoindol-2-yl]-4-(trifluoromethyl)-2,3-dihydropyridazin-3-one

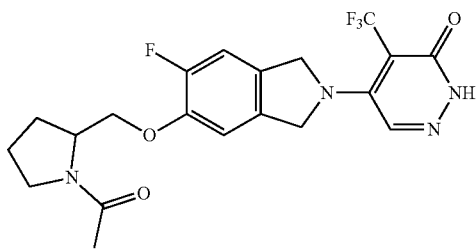 [SMILES: CC(=O)N1CCCC1COc1cc2c(cc1F)CN(c1cn[nH]c(=O)c1C(F)(F)F)C2]

A solution of 5-[5-fluoro-6-(pyrrolidin-2-ylmethoxy)-2,3-dihydro-1H-isoindol-2-yl]-4-(trifluoromethyl)-2,3-dihydropyridazin-3-one (100 mg, 0.25 mmol, 1.00 equiv), TEA (51 mg, 0.50 mmol, 2.00 equiv) and Ac$_2$O (26 mg, 0.25 mmol, 1.00 equiv) in DCM (3 mL) was stirred for 1 h at room temperature, and then the resulting solution concentrated under vacuum and then the residue was purified by C18 reverse phase chromatography eluting with H$_2$O/CH$_3$CN, after concentration, the residue was further purified by Pre-HPLC yielding the title compound (20 mg, 18.0%) as a light yellow solid. LCMS (ESI, m/z): 441.05 [M+H]$^+$. $^1$HNMR (Methanol-d$_4$, 300 MHz) δ 8.02 (s, 1H), 7.17 (dd, J=8.1, 3.0 Hz, 1H), 7.10 (s, 1H), 4.87-4.97 (d, J=4.5 Hz, 4H), 4.37 (d, J=3.3 Hz, 1H), 4.17 (t, J=3.0 Hz, 1H), 4.06 (d, J=1.2 Hz, 1H), 3.68-3.53 (m, 2H), 2.27-1.92 (m, 7H).

Example 51: 6-[4-(3-[[(2S,4S)-4-Hydroxy-1-[6-oxo-5-(trifluoromethyl)-1,6-dihydropyridazin-4-yl]pyrrolidin-2-yl]methoxy]benzoyl)piperazin-1-yl]pyridine-3-carbonitrile

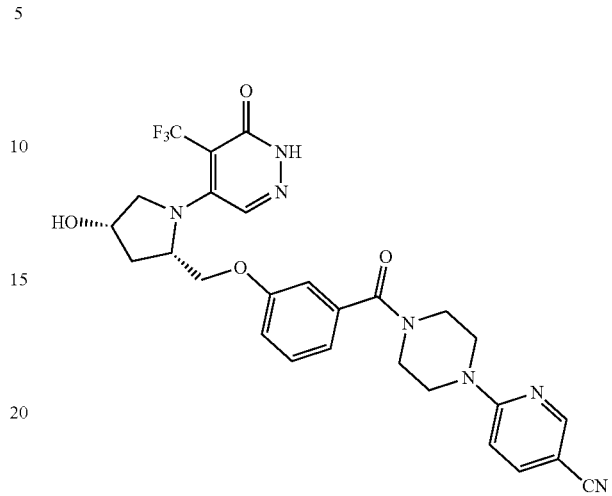

Step 1: 5-[(2S,4S)-4-Hydroxy-2-(hydroxymethyl)pyrrolidin-1-yl]-4-(trifluoromethyl)-2-[[2-(trimethylsilyl)ethoxy]methyl]-2,3-dihydropyridazin-3-one A solution of (3S,5S)-5-(hydroxymethyl)pyrrolidin-3-ol hydrochloride (653 mg, 4.25 mmol, 1.00 equiv), Int-A6 (2.1 g, 6.39 mmol, 1.50 equiv) and TEA (1.3 g, 12.85 mmol, 3.00 equiv) in ethanol (50 mL) was stirred for 1 h at 60° C. The resulting solution was concentrated under vacuum and the residue was applied onto a silica gel column eluting with EtOAc/petroleum ether (100:0) to afford 1.2 g (69%) of the title compound as a white solid. LCMS (ESI, m/z): 410.16 [M+H]$^+$.

Step 2: Synthesis of Methyl 3-[[(2S,4S)-4-hydroxy-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate Under nitrogen, a solution of 5-[(2S,4S)-4-hydroxy-2-(hydroxymethyl)pyrrolidin-1-yl]-4-(trifluoromethyl)-2-[[2-(trimethylsilyl)ethoxy]methyl]-2,3-dihydropyridazin-3-one (700 mg, 1.71 mmol, 1.00 equiv), [Pd(allyl)Cl]$_2$ (63 mg, 0.10 equiv), Rockphos (80 mg, 0.10 equiv), Cs$_2$CO$_3$ (1.1 g) and methyl 3-bromobenzoate (731 mg, 3.40 mmol, 2.00 equiv) in toluene (25 mL) was stirred for 20 h at 80° C. The resulting mixture was concentrated under vacuum, and the residue was diluted with 80 mL of EtOAc, washed with 3×60 mL of H$_2$O, dried over anhydrous sodium sulfate, and concentrated under vacuum. The residue was applied onto a silica gel column eluting with EtOAc/petroleum ether (1:1) to afford 390 mg (42%) of the title compound as a brown solid. LCMS (ESI, m/z): 544.20 [M+H]$^+$.

Step 3: Synthesis of 3-[[(2S,4S)-4-hydroxy-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic Acid A solution of methyl 3-[[(2S,4S)-4-hydroxy-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (140 mg, 0.26 mmol, 1.00 equiv) and LiOH (31 mg, 1.29 mmol, 5.00 equiv) in methanol (3 mL) and water (1 mL) was stirred for 2 h at room temperature. The resulting solution was concentrated under vacuum and the residue was diluted with 10 mL of H$_2$O, and then the pH value of the solution was adjusted to 3 with hydrogen chloride (36.5%). The solid was collected by filtration to afford 127 mg (93%) of the title compound as a white solid. LCMS (ESI, m/z): 530.19 [M+H]$^+$.

Step 4: Synthesis of 6-[4-[(3-[[(2S,4S)-4-hydroxy-1-[6-oxo-5-(trifluoromethyl)-1-[[2-(trimethylsilyl) ethoxy]methyl]-1,6-dihydropyridazin-4-yl]pyrrolidin-2-yl]methoxy]phenyl)carbonyl]piperazin-1-yl] pyridine-3-carbonitrile A solution of 3-[[(2S,4S)-4-hydroxy-1-[6-oxo-5-(trifluoromethyl)-1,6-dihydropyridazin-4-yl]pyrrolidin-2-yl] methoxy]benzoic acid (120 mg, 0.30 mmol, 1.00 equiv), HATU (87 mg, 0.23 mmol, 1.00 equiv), DIPEA (59 mg, 0.46 mmol, 2.00 equiv) and Int-A4 (51 mg, 0.27 mmol, 1.20 equiv) in DMF (1 mL) was stirred for 1 h at room temperature. The residue was purified by C18 reverse phase chromatography eluting with H$_2$O/CH$_3$CN to afford 131 mg (62%) of the title compound as a white solid. LCMS (ESI, m/z): 700.28[M+H]$^+$.

Step 5: Synthesis of 6-[4-(3-[[(2S,4S)-4-hydroxy-1-[6-oxo-5-(trifluoromethyl)-1,6-dihydropyridazin-4-yl]pyrrolidin-2-yl]methoxy]benzoyl)piperazin-1-yl] pyridine-3-carbonitrile A solution of 6-[4-(3-[[(2S,4S)-4-hydroxy-1-[6-oxo-5-(trifluoromethyl)-1-[[2-(trimethylsilyl)ethoxy]methyl]-1,6-dihydropyridazin-4-yl]pyrrolidin-2-yl]methoxy]benzoyl) piperazin-1-yl]pyridine-3-carbonitrile (130 g, 185.77 mmol, 1.00 equiv) in hydrogen chloride/dioxane (5 mL, 4M) was stirred for 2 h at room temperature. The resulting solution was concentrated under vacuum and the residue was purified by C18 reverse phase chromatography eluting with 1H$_2$O/ CH$_3$CN. After concentration, the residue was further purified by Prep-HPLC yielding the title compound (18.9 mg, 18%) as a white solid. LCMS (ESI, m/z): 570.10[M+H]$^+$. $^1$HNMR (Methanol-d$_4$, 300 MHz) δ 8.45 (d, J=2.1 Hz, 1), 8.22 (s, 1H), 7.81 (dd, J=9.0, 2.4 Hz, 1H), 7.42 (t, J=7.8 Hz, 1H), 7.06 (dt, J=8.4, 2.2 Hz, 2H), 6.97 (d, J=1.5 Hz, 1H), 6.92-6.87 (m, 1H), 4.96-4.91 (m, 1H), 4.37-4.21 (m, 2H), 4.18 (dd, J=10.2, 6.9 Hz, 2H), 3.92-3.51 (m, 10H), 2.54 (dt, J=14.4, 7.4 Hz, 1H), 1.86 (dt, J=12.6, 8.0 Hz, 1H).

Example 52: 6-[4-[(4-[[(2S,4R)-4-hydroxy-1-[6-oxo-5-(trifluoromethyl)-1,6-dihydropyridazin-4-yl] pyrrolidin-2-yl]methoxy]cyclohexyl)carbonyl]piperazin-1-yl]pyridine-3-carbonitrile

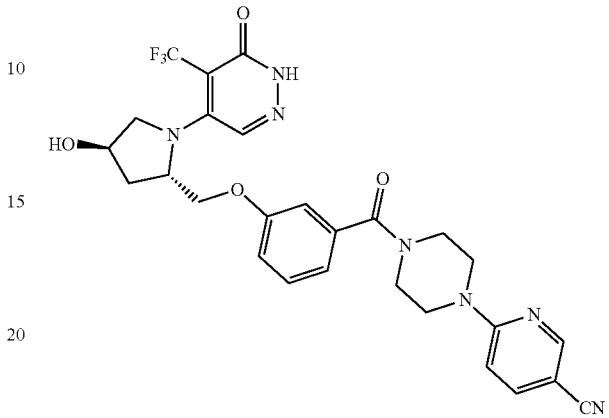

Step 1: Synthesis of 1-tert-butyl 2-methyl (2S,4R)-4-[(tert-butyldimethylsilyl)oxy]pyrrolidine-1,2-dicarboxylate To a stirred solution of 1-tert-butyl 2-methyl (2S,4R)-4-hydroxypyrrolidine-1,2-dicarboxylate (2.5 g, 10.19 mmol, 1.00 equiv) in DCM (50 mL), imidazole (1.5 g) and TBSCl (3 g) were added. The resulting solution was stirred for 2 h at room temperature. The resulting solution was diluted with 300 mL of DCM. The resulting mixture was washed with 50 mL of 1M hydrogen chloride and 50 mL of brine. The organic layer was dried over anhydrous sodium sulfate and concentrated under vacuum. This resulted in 3.5 g (crude) of the title compound as a solid. LCMS (ESI, m/z): 360.22 [M+H]$^+$.

Step 2: Synthesis of Tert-Butyl (2S,4R)-4-[(tert-butyldimethylsilyl)oxy]-2-(hydroxymethyl)pyrrolidine-1-carboxylate To a stirred solution of 1-tert-butyl 2-methyl (2S,4R)-4-[(tert-butyldimethylsilyl)oxy]pyrrolidine-1,2-dicarboxylate (3.5 g, 9.73 mmol, 1.00 equiv) in THF (30 mL), LiBH$_4$ (20 mL) was added dropwise at 0° C. The resulting solution was stirred overnight at room temperature. The reaction was then quenched by the addition of 10 mL of methanol. The resulting mixture was concentrated under vacuum. The resulting solution was diluted with 250 mL of EtOAc. The resulting mixture was washed with 2×50 mL of water and 1×50 mL of brine. The organic layer was dried over anhydrous sodium sulfate and concentrated under vacuum. The residue was applied onto a silica gel column with EtOAc/ petroleum ether (1:3). This resulted in 3 g (93%) of the title compound as an oil. LCMS (ESI, m/z): 332.23 [M+H]$^+$.

Step 3: Synthesis of Tert-Butyl (2S,4R)-4-[(tert-butyldimethylsilyl)oxy]-2-[3-(methoxycarbonyl) phenoxy-ethyl]pyrrolidine-1-carboxylate A solution of tert-butyl (2S,4R)-4-[(tert-butyldimethylsilyl)oxy]-2-(hydroxymethyl)pyrrolidine-1-carboxylate (2 g, 6.03 mmol, 1.00 equiv), methyl 3-bromobenzoate (2.8 g, 13.02 mmol, 2.16 equiv), Rockphos (300 mg), Pd(allyl)Cl$_2$ (240 mg) and Cs$_2$CO$_3$ (5 g, 15.35 mmol, 2.54 equiv) in toluene (30 mL) was stirred overnight at 90° C. under an inert atmosphere of nitrogen. The solids were filtered out. The resulting solution was diluted with 250 mL of EtOAc. The resulting mixture was washed with 2×50 mL of water and 50 mL of brine. The organic layer was dried over anhydrous sodium sulfate and concentrated under vacuum. The residue was applied onto a silica gel column with EtOAc/petroleum ether (1:9). This resulted in 1.7 g (crude) of the title compound as oil. LCMS (ESI, m/z): 466.26 [M+H]$^+$.

Step 4: Synthesis of Methyl 3-[[(2S,4R)-4-hydroxy-pyrrolidin-2-yl]methoxy]benzoate Hydrochloride A solution of tert-butyl (2S,4R)-4-[(tert-butyldimethylsilyl)oxy]-2-[3-(methoxycarbonyl)phenoxymethyl]-pyrrolidine-1-carboxylate (1.6 g, 3.44 mmol, 1.00 equiv) in hydrogen chloride/dioxane (15 mL) was stirred for 2 h at room temperature. The solids were collected by filtration. This resulted in 660 mg (67%) of the title compound as a solid. LCMS (ESI, m/z): 252.12 [M+H]$^+$.

Step 5: Synthesis of Methyl 3-[[(2S,4R)-4-hydroxy-1-[6-oxo-5-(trifluoromethyl)-1-[[2-(trimethylsilyl)-ethoxy]methyl]-1,6-dihydropyridazin-4-yl]pyrrolidin-2-yl]methoxy]benzoate A solution of methyl 3-[[(2S,4R)-4-hydroxypyrrolidin-2-yl]methoxy]benzoate hydrochloride (660 mg, 2.29 mmol, 1.00 equiv), Int-A6 (750 mg, 2.28 mmol, 0.99 equiv) and TEA (3 mL) in ethanol (20 mL) was stirred for 1 h at 60° C. The resulting mixture was concentrated under vacuum. The residue was applied onto a silica gel column with EtOAc/petroleum ether (1:1). This resulted in 550 mg (44%) of the title compound as an oil. LCMS (ESI, m/z): 544.21 [M+H]$^+$.

Step 6: Synthesis of 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic Acid To a stirred solution of methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (550 mg, 1.04 mmol, 1.00 equiv) in THF (15 mL) and water (5 mL), LiOH (150 mg, 6.26 mmol, 6.01 equiv) was added. The resulting solution was stirred overnight at room temperature. The pH value of the solution was adjusted to 1 with hydrogen chloride (1 M). The resulting solution was extracted with 250 mL of EtOAc and washed with 50 mL of brine. The organic layer was dried over anhydrous sodium sulfate and concentrated under vacuum. This resulted in 550 mg (crude) of the title compound as a solid. LCMS (ESI, m/z): 530.19 [M+H]$^+$.

Step 7: Synthesis of 3-[[(2S)-1-[6-oxo-5-(trifluoromethyl)-1,6-dihydropyridazin-4-yl]pyrrolidin-2-yl]methoxy]benzoic Acid A solution of 3-[[(2S)-1-[6-oxo-5-(trifluoromethyl)-1-[[2-(trimethylsilyl)ethoxy]methyl]-1,6-dihydrop-yridazin-4-yl]pyrrolidin-2-yl]methoxy]benzoic acid (550 mg, 1.07 mmol, 1.00 equiv) in hydrogen chloride/dioxane (10 mL) was stirred overnight at room temperature. The resulting mixture was concentrated under vacuum. This resulted in 400 mg (crude) of the title compound as oil. LCMS (ESI, m/z): 400.11 [M+H]$^+$.

Step 8: Synthesis of 6-[4-[(4-[[(2S,4R)-4-hydroxy-1-[6-oxo-5-(trifluoromethyl)-1,6-dihydropyridazin-4-yl]pyrrolidin-2-yl]methoxy]cyclohexyl)carbonyl] piperazin-1-yl]pyridine-3-carbonitrile To a stirred solution of 4-[[(2S,4R)-4-hydroxy-1-[6-oxo-5-(trifluoromethyl)-1,6-dihydropyridazin-4-yl]pyrrolidin-2-yl]methoxy]cyclohexane-1-carboxylic acid (400 mg, 0.99 mmol, 1.00 equiv) in DMF (10 mL), Int-A4 (188 mg, 1.00 mmol, 1.01 equiv), DIPEA (1 mL) and HATU (500 mg, 1.31 mmol, 1.33 equiv) were added. The resulting solution was stirred for 2 h at room temperature. After concentration, the residue was purified by C18 reverse phase chromatography eluting with H$_2$O/CH$_3$CN. Then the residue was further purified by Prep-HPLC yielding the title compound (88.8 mg, 16%) as a white solid. LCMS (ESI, m/z): 570.15 [M+H]$^+$. $^1$H NMR (300 MHz, DMSO-d$_6$) δ 12.46 (s, 1H), 8.49 (d, J=2.3 Hz, 1H), 8.20 (s, 1H), 7.87 (dd, J=9.1, 2.4 Hz, 1H), 7.33 (t, J=7.9 Hz, 1H), 7.03-6.84 (m, 4H), 5.02 (d, J=3.0 Hz, 1H), 4.98-4.87 (m, 1H), 4.36-4.24 (m, 1H), 4.16 (dd, J=10.4, 3.8 Hz, 1H), 4.02 (dd, J=10.4, 5.9 Hz, 1H), 3.89-3.51 (m, 8H), 3.41-3.38 (m, 1H), 3.10 (d, J=11.6 Hz, 1H), 2.16-2.02 (m, 1H), 2.02-1.88 (m, 1H).

Example 53: 5-(5-fluoro-6-(pyrrolidin-3-yloxy)isoindolin-2-yl)-4-(trifluoromethyl)pyridazin-3(2H)-one

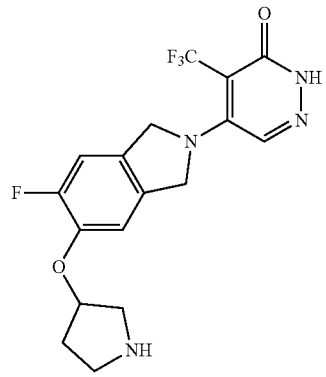 [SMILES: O=c1[nH]ncc(N2Cc3cc(F)c(OC4CCNC4)cc3C2)c1C(F)(F)F]

Step 1: Synthesis of Tert-Butyl 3-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)pyrrolidine-1-carboxylate A solution of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (400 mg, 0.90 mmol, 1.00 equiv), potassium carbonate (248 mg, 1.79 mmol, 2.00 equiv), and tert-butyl 3-bromopyrrolidine-1-carboxylate (447.6 mg, 1.79 mmol, 1.99 equiv) in DMF (10 mL, 2.00 equiv) was stirred overnight at 80° C. The reaction was quenched by the addition of 20 mL of water. The resulting solution was extracted with 3×10 mL of EtOAc and the organic layers combined and concentrated under vacuum. The residue was applied onto a silica gel column with EtOAc/petroleum ether (1/5). This resulted in 382 mg (69%) of the title compound as a yellow oil. LCMS (ESI, m/z): 615.25 [M+H]+.

Step 2: Synthesis of 5-[5-fluoro-6-(pyrrolidin-3-yloxy)-2,3-dihydro-1H-isoindol-2-yl]-4-(trifluoromethyl)-2,3-dihydropyridazin-3-one Hydrochloride A solution of tert-butyl 3-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)pyrrolidine-1-carboxylate (382 mg, 0.62 mmol, 1.00 equiv) in HCl in dioxane (4 M) (10 mL) was stirred overnight at room temperature. The resulting mixture was concentrated under vacuum. After concentration, the residue was purified by C18 reverse phase chromatography eluting with $H_2O$/$CH_3CN$ yielding the title compound (32 mg, 19%) as a white solid. LCMS (ESI, m/z): 385.15 [M+H]+, 1H NMR (Methanol-$d_4$, 300 MHz) δ: 8.04 (s, 1H), 7.15 (dd, J=9.2, 6.3 Hz, 2H), 5.05-4.99 (m, 5H), 3.22-3.07 (m, 3H), 2.99-2.97 (m, 1H), 2.23-2.09 (m, 2H).

Example 54: 5-(5-(1-acetylpyrrolidin-3-yloxy)-6-fluoroisoindolin-2-yl)-4-(trifluoromethyl)pyridazin-3(2H)-one

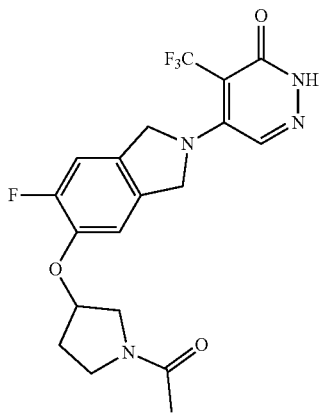 [SMILES: CC(=O)N1CCC(Oc2cc3c(cc2F)CN(c2cn[nH]c(=O)c2C(F)(F)F)C3)C1]

A solution of 5-[5-fluoro-6-(pyrrolidin-3-yloxy)-2,3-dihydro-1H-isoindol-2-yl]-4-(trifluoromethyl)-2,3-dihydropyridazin-3-one (135 mg, 0.35 mmol, 1.00 equiv), $Ac_2O$ (43.04 mg, 0.42 mmol, 1.20 equiv), and TEA (106.66 mg, 1.05 mmol, 3.00 equiv) in DCM (10 mL) was stirred for 8.5 h at room temperature. After concentration, the residue was purified by C18 reverse phase chromatography eluting with $H_2O$/$CH_3CN$ yielding the title compound (63.2 mg, 42%) as a white solid. LCMS (ESI, m/z): 427.20 [M+H]+, 1HNMR (Methanol-$d_4$, 300 MHz) δ: 8.05 (s, 1H), 7.24-7.13 (m, 2H), 5.10 (d, J=14.4 Hz, 1H), 4.91 (d, J=23.4 Hz, 4H), 3.92-3.65 (m, 3H), 3.68-3.45 (m, 1H), 2.37-2.23 (m, 2H), 2.10 (d, J=12.4 Hz, 3H).

Example 55: 5-[5-fluoro-6-[(1-methylpyrrolidin-3-yl)oxy]-2,3-dihydro-1H-isoindol-2-yl]-4-(trifluoromethyl)-2,3-dihydropyridazin-3-one

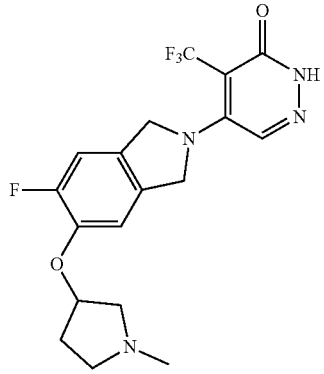 [SMILES: CN1CCC(Oc2cc3c(cc2F)CN(c2cn[nH]c(=O)c2C(F)(F)F)C3)C1]

A solution of 5-[5-fluoro-6-(pyrrolidin-3-yloxy)-2,3-dihydro-1H-isoindol-2-yl]-4-(trifluoromethyl)-2,3-dihydropyridazin-3-one hydrochloride (260 mg, 0.62 mmol, 1.00 equiv), paraformaldehyde (33.3 mg, 1.11 mmol, 1.80 equiv), and potassium hydroxide (69.2 mg, 1.23 mmol, 2.00 equiv) in methanol (10 mL) was stirred for 3 h at room temperature. $NaBH_4$ (46.9 mg, 1.24 mmol, 2.00 equiv) was added to the resulting solution. The resulting solution was stirred for an additional 0.5 h at room temperature. The resulting mixture was concentrated under vacuum. The crude product was purified by Prep-HPLC yielding the title compound (20.2 mg, 8%) as a white solid. LCMS (ESI, m/z): 399.10 [M+H]+. 1H NMR (300 MHz, DMSO-d6) δ 12.54 (s, 1H), 7.96 (s, 1H), 7.27 (d, J=11.0 Hz, 1H), 7.14 (d, J=7.9 Hz, 1H), 4.90 (s, 5H), 2.77 (dd, J=10.5, 5.9 Hz, 1H), 2.65 (ddd, J=18.8, 9.4, 3.2 Hz, 2H), 2.40-2.25 (m, 2H), 2.26 (s, 3H), 1.86-1.72 (m, 1H).

Example 56 Isomer A: 6-(4-[[(3S,5S)-5-[[(2S)-1-[6-oxo-5-(trifluoromethyl)-1,6-dihydropyridazin-4-yl]pyrrolidin-2-yl]methoxy]piperidin-3-yl]carbonyl]piperazin-1-yl)pyridine-3-carbonitrile and Example 56 Isomer B: 6-(4-[[(3R,5R)-5-[[(2S)-1-[6-oxo-5-(trifluoromethyl)-1,6-dihydropyridazin-4-yl]pyrrolidin-2-yl]methoxy]piperidin-3-yl]carbonyl]piperazin-1-yl)pyridine-3-carbonitrile

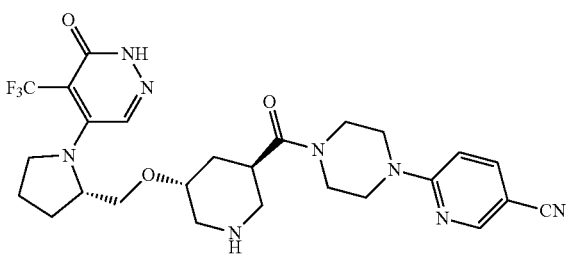

Isomer A

-continued

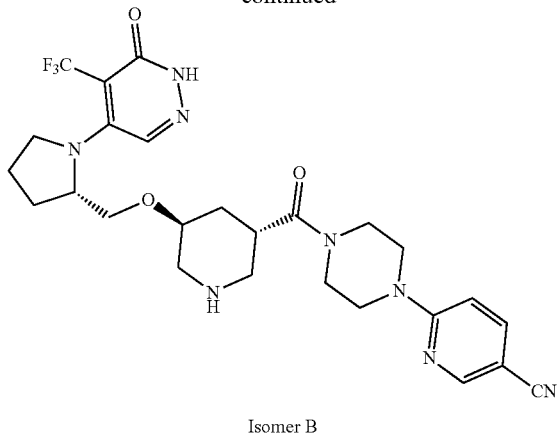

Isomer B

Step 1: Synthesis of Methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-3-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1 g, 2.54 mmol, 1.00 equiv), [Pd(allyl)Cl]$_2$ (93 mg, 0.10 equiv), Rockphos (119.2 mg, 0.10 equiv), Cs$_2$CO$_3$ (2.48 g, 7.61 mmol, 3.00 equiv), and methyl 5-bromopyridine-3-carboxylate (656 mg, 3.04 mmol, 1.20 equiv) in toluene (20 mL) was stirred for 15 h at 80° C. The resulting mixture was concentrated under vacuum and the residue was applied onto a silica gel column eluting with EtOAc/petroleum ether (1:1) to afford 350 mg (26%) of the title compound as brown oil. LCMS (ESI, m/z): 529.21 [M+H]$^+$.

Step 2: Synthesis of Methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-3-carboxylate A solution of methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-3-carboxylate (1 g, 1.89 mmol, 1.00 equiv), PtO$_2$ (1 g), acetic acid (4 mL) in methanol (25 mL) under hydrogen atmosphere was stirred for 8 h at room temperature. The solids were filtered out. The resulting solution was concentrated under vacuum to afford 1 g crude of the title compound as white oil. LCMS (ESI, m/z): 535.26 [M+H]$^+$.

Step 3: Synthesis of 1-tert-butyl 3-methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-1,3-dicarboxylate A solution of methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-3-carboxylate (614 mg, 1.15 mmol, 1.00 equiv), (Boc)$_2$O (250.6 mg, 1.15 mmol, 1.00 equiv), and 4-dimethylaminopyridine (28.06 mg, 0.23 mmol, 0.20 equiv) in THF (20 mL) was stirred for 1 h at room temperature. After concentration, the residue was applied onto a silica gel column eluting with EtOAc/petroleum ether (30:70) to afford 370 mg (51%) of the title compound as a white solid. LCMS (ESI, m/z): 635.31[M+H]$^+$.

Step 4: Synthesis of 1-[(tert-butoxy)carbonyl]-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-3-carboxylic Acid A solution of 1-tert-butyl 3-methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-1,3-dicarboxylate (370 mg, 0.58 mmol, 1.00 equiv), LiOH (70 mg, 2.92 mmol, 5.00 equiv), water (2 mL) in methanol (10 mL) was stirred for 2 h at room temperature. The resulting mixture was concentrated under vacuum to afford 344 mg crude of the title compound as a yellow solid. LCMS (ESI, m/z): 621.30 [M+H]$^+$.

Step 5: Synthesis of Tert-Butyl 3-[[4-(5-cyanopyridin-2-yl)piperazin-1-yl]carbonyl]-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-1-carboxylate A solution of 1-[(tert-butoxy)carbonyl]-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-3-carboxylic acid (286 mg, 0.46 mmol, 1.00 equiv), HATU (262.2 mg, 0.69 mmol, 1.50 equiv), DIPEA (178 mg, 1.38 mmol, 3.00 equiv), Int-A4 (86.7 mg, 0.46 mmol, 1.00 equiv) in DMF (5 mL) was stirred for 3 h at room temperature. The resulting solution was quenched with H2O. The solution was extracted with EtOAc (3×50 mL) and the organic layers combined. The solution was dried over anhydrous sodium sulfate and concentrated under vacuum. The residue was applied onto a silica gel column eluting with EtOAc/petroleum ether (40:60) to afford 450 mg (crude) of the title compound as brown oil. LCMS (ESI, m/z): 791.39 [M+H]$^+$.

Step 6: Synthesis of 6-(4-[[(3S,5S)-5-[[(2S)-1-[6-oxo-5-(trifluoromethyl)-1,6-dihydropyridazin-4-yl]pyrrolidin-2-yl]methoxy]piperidin-3-yl]carbonyl]piperazin-1-yl)pyridine-3-carbonitrile and 6-(4-[[(3R,5R)-5-[[(2S)-1-[6-oxo-5-(trifluoromethyl)-1,6-dihydropyridazin-4-yl]pyrrolidin-2-yl]methoxy]piperidin-3-yl]carbonyl]piperazin-1-yl)pyridine-3-carbonitrile A solution of tert-butyl 3-[[4-(5-cyanopyridin-2-yl)piperazin-1-yl]carbonyl]-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]piperidine-1-carboxylate (450 mg, 0.57 mmol, 1.00 equiv) in hydrogen chloride-dioxane (15 mL) was stirred for 2 h at room temperature. After concentration, the residue was purified by C18 reverse phase chromatography eluting with H$_2$O/CH$_3$CN. The residue was further purified by Prep-HPLC and Chiral-Prep-HPLC min (CHIRALPAK IE-3, 0.46*10 cm; 3 um, MtBE (0.1% DEA): EtOH=50:50, 1.0 mL/min) yielding the title compounds as white solids. The assignment of Example 56 Isomer A and Isomer B was arbitrarily assigned with assumed structures as drawn and two isomers were isolated during chiral prep-HPLC.

Example 56 Isomer A 7.8 mg, 2%, LCMS (ESI, m/z): 561.10 [M+H]+, $^1$H NMR (400 MHz, Methanol-d$_4$) δ 8.45 (dd, J=2.4, 0.8 Hz, 1H), 8.14 (s, 1H), 7.79 (dd, J=9.1, 2.4 Hz, 1H), 6.91 (d, J=8.4 Hz, 1H), 4.58 (s, 1H), 3.90-3.80 (m, 2H), 3.79-3.49 (m, 8H), 3.47 (dd, J=10.0, 7.1 Hz, 1H), 3.43-3.34 (m, 2H), 3.09 (dd, J=12.3, 4.1 Hz, 1H), 2.93-2.88 (m, 2H), 2.65-2.62 (m, 1H), 2.30-2.13 (m, 3H), 2.01 (q, J=11.3, 6.0 Hz, 1H), 1.87-1.73 (m, 2H), 1.73-1.68 (m, 1H). tR=3.570.

Example 56 Isomer B

2%, LCMS (ESI, m/z): 561.10 [M+H]+, (400 MHz, Methanol-d4) δ 8.45 (dd, J=2.4, 0.7 Hz, 1H), 8.14 (s, 1H), 7.79 (dd, J=9.0, 2.3 Hz, 1H), 6.90 (dd, J=9.1, 0.9 Hz, 1H), 4.60 (s, 1H), 3.78 (d, J=5.7 Hz, 3H), 3.79-3.71 (m, 2H), 3.69 (d, J=4.7 Hz, 5H), 3.46 (dd, J=10.1, 7.4 Hz, 1H), 3.43-3.34 (m, 2H), 3.18 (d, J=11.8 Hz, 1H), 3.04-2.74 (m, 2H), 2.63 (dd, J=12.5, 10.1 Hz, 1H), 2.40-2.15 (m, 2H), 2.01 (t, J=9.5 Hz, 2H), 1.74 (tt, J=12.0, 7.0 Hz, 1H), 1.45 (q, J=11.2 Hz, 1H).

Example 57 Isomer A: 6-[4-[(1S,3S)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile and Example 57 Isomer B: 6-[4-[(1R,3R)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile and Example 57 Isomer C: 6-[4-[(1S,3R)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile and Example 57 Isomer D: 6-[4-[(1R,3S)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile

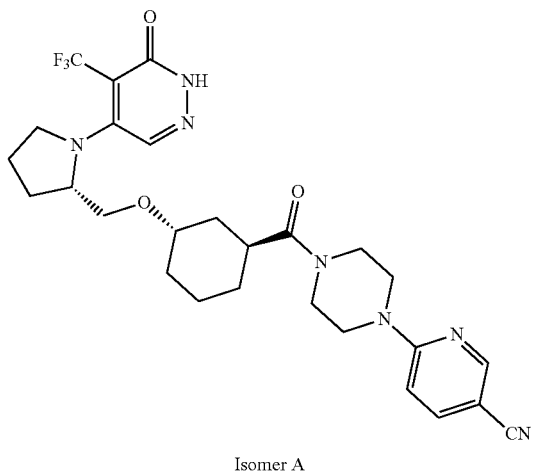 [SMILES: N#Cc1ccc(N2CCN(C(=O)[C@@H]3CCC[C@H](OC[C@@H]4CCCN4c4cn[nH]c(=O)c4C(F)(F)F)C3)CC2)nc1]

Isomer A

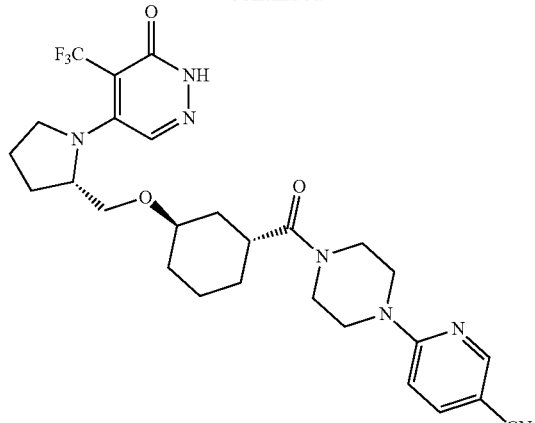

Isomer B

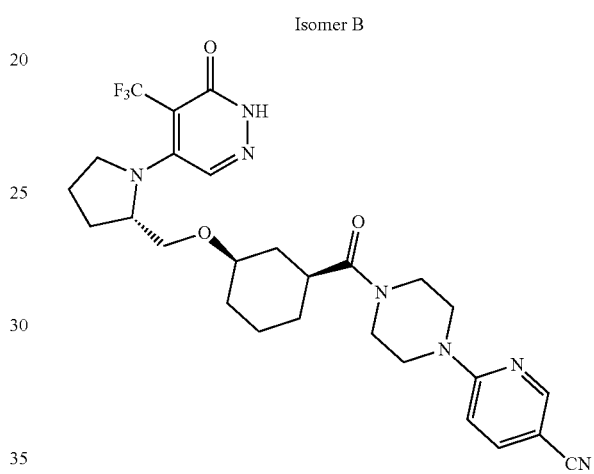

Isomer C

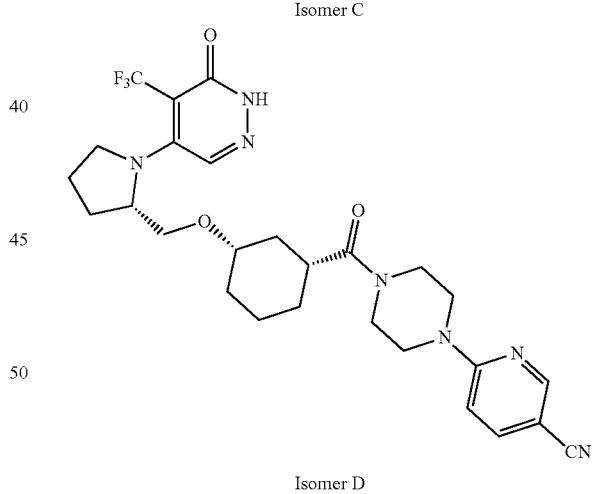

Isomer D

Step 1: Synthesis of Tert-Butyl (2S)-2-[3-(methoxycarbonyl)phenoxymethyl]pyrrolidine-1-carboxylate A solution of tert-butyl (2S)-2-(hydroxymethyl)pyrrolidine-1-carboxylate (1 g, 4.97 mmol, 1.00 equiv), methyl 3-hydroxybenzoate (1.14 g, 7.49 mmol, 1.50 equiv), PPh$_3$ (1.97 g, 7.51 mmol, 1.50 equiv), and DEAD (1.3 g, 7.46 mmol, 1.50 equiv) in THF (20 mL) was stirred for 16 h at room temperature. The resulting mixture was concentrated under vacuum. The residue was applied onto a silica gel column eluting with EtOAc/petroleum ether (5:95) to afford 960 mg (58%) of the title compound as white oil. LCMS (ESI, m/z): 336.18 [M+H]⁺.

Step 2: Synthesis of Tert-Butyl (2S)-2-([[3-(methoxycarbonyl)cyclohexyl]oxy]methyl)pyrrolidine-1-carboxylate A solution of tert-butyl (2S)-2-[3-(methoxycarbonyl)phenoxymethyl]pyrrolidine-1-carboxylate (1 g, 2.98 mmol, 1.00 equiv), Rh/Al$_2$O$_3$ (2 g), acetic acid (3 mL) in methanol (20 mL) was stirred for 16 h at room temperature under an atmosphere of hydrogen. The solids were filtered out. The resulting solution was concentrated under vacuum to afford 1.02 g crude of the title compound as a yellow oil. LCMS (ESI, m/z): 342.23 [M+H]⁺.

Step 3: Synthesis of Methyl 3-[(2S)-pyrrolidin-2-ylmethoxy]cyclohexane-1-carboxylate A solution of tert-butyl (2S)-2-([[3-(methoxycarbonyl)cyclohexyl]oxy]methyl)pyrrolidine-1-carboxylate (1.02 g, 2.99 mmol, 1.00 equiv) in hydrogen chloride/dioxane (15 mL) was stirred for 1 h at room temperature. The resulting mixture was concentrated under vacuum to afford 723 mg crude of the title compound as a white solid. LCMS (ESI, m/z): 242.18[M+H]⁺.

Step 4: Synthesis of Methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylate A solution of Int-A6 (1 g, 3.04 mmol, 1.00 equiv), methyl 3-[(2S)-pyrrolidin-2-ylmethoxy]cyclohexane-1-carboxylate (723 mg, 3.00 mmol, 1.00 equiv), TEA (900 mg, 8.89 mmol, 3.00 equiv) in ethanol (15 mL) was stirred for 1 h at 80° C. The resulting mixture was concentrated under vacuum. The residue was applied onto a silica gel column with EtOAc/petroleum ether (1:4) to afford 1.2 g (74%) of the title compound as a colorless oil. LCMS (ESI, m/z): 534.26[M+H]⁺.

Step 5: Synthesis of 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylic Acid A solution of methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylate (1.3 g, 2.44 mmol, 1.00 equiv), LiOH (180 mg, 7.52 mmol, 3.09 equiv), water (5 mL) in methanol (25 mL) was stirred for 2 h at room temperature. The resulting mixture was concentrated under vacuum to afford 1.2 g crude of the title compound as a white solid. LCMS (ESI, m/z): 520.24[M+H]⁺.

Step 6: Synthesis of 6-[4-[(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexyl)carbonyl]piperazin-1-yl]pyridine-3-carbonitrile A solution of 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylic acid (400 mg, 0.77 mmol, 1.10 equiv), HATU (346 mg, 0.91 mmol, 1.30 equiv), DIPEA (180 mg, 1.39 mmol, 2.00 equiv), Int-A4 (132 mg, 0.70 mmol, 1.00 equiv) in DMF (3 mL) was stirred for 2 h at room temperature. The resulting solution was quenched with 40 ml water. The solution was extracted with EtOAc (3×50 mL) and the organic layers were combined. The solution was dried over anhydrous sodium sulfate and concentrated under vacuum. The residue was applied onto a silica gel column eluting with EtOAc/petroleum ether (1:1) to afford 500 mg (94%) of the title compound as a white solid. LCMS (ESI, m/z): 690.34[M+H]⁺.

Step 7: Synthesis of 6-[4-[(1S,3S)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile, 6-[4-[(1R,3R)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile, 6-[4-[(1S,3R)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile and 6-[4-[(1R,3S)-3-[[(2S)-1-[6-oxo-5-(trifluoromethyl)-1,6-dihydropyridazin-4-yl]pyrrolidin-2-yl]methoxy]cyclohexanecarbonyl]piperazin-1-yl]pyridine-3-carbonitrile A solution of 6-[4-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexanecarbonyl)piperazin-1-yl]pyridine-3-carbonitrile (500 mg, 0.72 mmol, 1 equiv) in HCl/dioxane (15 mL) was stirred for 2 h at room temperature. After concentration, the residue was purified by C18 reverse phase chromatography eluting with H$_2$O/CH$_3$CN. The residue was further purified by Prep-HPLC and Chiral-Prep-HPLC (Repaired IC, 0.46*10 cm; 5 um, (Hex: DCM=1:1)(0.1% DEA):EtOH=70:30, 1.0 mL/min) yielding (after arbitrary assignment of the stereochemistry) the title compounds as white solids.

Example 57 Isomer A 28.4 mg, 7.12%, LCMS (ESI, m/z): 560.15 [M+H]⁺, ¹H NMR (300 MHz, Methanol-d4) δ 8.44 (dd, J=2.4, 0.7 Hz, 1H), 8.16 (s, 1H), 7.78 (dd, J=9.1, 2.4 Hz, 1H), 6.90 (dd, J=9.1, 0.8 Hz, 1H), 4.59 (q, J=7.6, 3.6 Hz, 1H), 3.81-3.68 (m, 10H), 3.47-3.35 (m, 2H), 2.72 (t, J=11.7 Hz, 1H), 2.23 (s, 1H), 2.13-1.96 (m, 2H), 1.92-1.60 (m, 5H), 1.56-0.85 (m, 5H). tR=3.718 min.

Example 57 Isomer B 31.2 mg, 7.69%, LCMS (ESI, m/z): 560.15 [M+H]⁺, ¹H NMR (300 MHz, Methanol-d4) δ 8.45 (dd, J=2.4, 0.8 Hz, 1H), 8.15 (s, 1H), 7.78 (dd, J=9.1, 2.4 Hz, 1H), 6.89 (dd, J=9.1, 0.8 Hz, 1H), 4.58 (q, J=7.4, 3.5 Hz, 1H), 3.84-3.66 (m, 10H), 3.47 (dd, J=10.0, 7.2 Hz, 1H), 3.36 (s, 1H), 2.75 (t, J=11.6 Hz, 1H), 2.27-2.18 (m, 1H), 2.09-1.92 (m, 3H), 1.88-1.66 (m, 4H), 1.48-1.24 (m, 4H), 1.08 (t, J=11.5 Hz, 1H). tR=4.396 min.

Example 57 Isomer C 6.2 mg, 1.53%, LCMS (ESI, m/z): 560.15 [M+H]⁺, ¹H NMR (300 MHz, Methanol-d4) δ 8.46 (d, J=2.3 Hz, 1H), 8.35 (s, 1H), 7.80 (dd, J=9.0, 2.4 Hz, 1H), 6.93 (d, J=9.1 Hz, 1H), 4.75 (s, 1H), 3.91-3.78 (m, 7H), 3.77-3.58 (m, 3H), 3.57-3.43 (m, 3H), 2.79 (t, J=11.2 Hz, 1H), 2.28 (d, J=10.7 Hz, 1H), 2.06-1.59 (m, 7H), 1.58-1.21 (m, 4H). tR=3.555 min.

Example 57 Isomer D 4.7 mg, 1.16%, LCMS (ESI, m/z): 560.15 [M+H]+, 1H NMR (300 MHz, Methanol-d4) δ 8.46 (d, J=2.4 Hz, 1H), 8.34 (s, 1H), 7.80 (dd, J=9.0, 2.4 Hz, 1H), 6.92 (d, J=9.0 Hz, 1H), 4.92 (s, 1H), 3.93-3.65 (m, 9H), 3.64-3.55 (m, 2H), 3.54-3.43 (m, 2H), 2.86 (t, J=11.7 Hz, 1H), 2.27 (dd, J=11.9, 6.9 Hz, 1H), 2.09-1.91 (m, 2H), 1.84-1.62 (m, 7H), 1.61-1.43 (m, 2H). tR=4.035 min.

Example 58: 5-[5-fluoro-6-(piperidin-3-yloxy)-2,3-dihydro-1H-isoindol-2-yl]-4-(trifluoromethyl)-2,3-dihydropyridazin-3-one

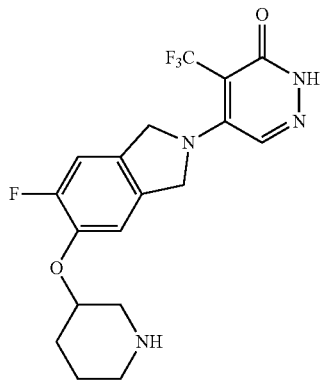 [SMILES: O=c1[nH]ncc(N2Cc3cc(F)c(OC4CCCNC4)cc3C2)c1C(F)(F)F]

Step 1: Synthesis of Tert-Butyl 3-(methanesulfonyloxy)piperidine-1-carboxylate

A solution of tert-butyl 3-hydroxypiperidine-1-carboxylate (950 mg, 4.72 mmol, 1.00 equiv), TEA (955 mg, 9.44 mmol, 2.00 equiv), methanesulfonyl methanesulfonate (1.64 g, 9.41 mmol, 2.00 equiv) in DCM (10 mL) was stirred overnight at room temperature. The resulting solution was diluted with 50 mL of DCM. The resulting mixture was washed with 3×30 mL of sodium bicarbonate/H2O. The resulting mixture was concentrated under vacuum. This resulted in 826 mg (63%) of the title compound as a solid. LCMS (ESI, m/z): 280.10 [M+H]+.

Step 2: Synthesis of Tert-Butyl 3-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-fluoro-6-hydroxy-2,3-dihydro-1H-isoindol-2-yl)-4-(trifluoromethyl)-2-[[2-(trimethylsilyl)ethoxy]methyl]-2,3-dihydropyridazin-3-one (445 mg, 1.00 mmol, 1.00 equiv), Cs2CO3 (652 mg, 2.00 mmol, 2.00 equiv), tert-butyl 3-(methanesulfonyloxy)piperidine-1-carboxylate (840 mg, 3.01 mmol, 3.00 equiv) in DMF (10 mL) was stirred for 2 days at 80° C. The reaction was quenched by the addition of 20 mL of water. The resulting solution was extracted with 3×10 mL of EtOAc and the organic layers combined and concentrated under vacuum. The residue was applied onto a silica gel column with EtOAc/petroleum ether (1/4). The collected fractions were combined and concentrated under vacuum. This resulted in 208 mg (33%) of the title compound as yellow crude oil. LCMS (ESI, m/z): 629.27 [M+H]+.

Step 3: 5-[5-fluoro-6-(piperidin-3-yloxy)-2,3-dihydro-1H-isoindol-2-yl]-4-(trifluoromethyl)-2,3-dihydropyridazin-3-one A solution of tert-butyl 3-([6-fluoro-2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (208 mg, 0.33 mmol, 1.00 equiv) in HCl/dioxane (4 M) (10 mL) was stirred overnight at room temperature. The resulting mixture was concentrated under vacuum. The crude product was purified by Prep-HPLC yielding the title compound (23.1 mg, 18%) as a white solid. LCMS (ESI, m/z): 399.20 [M+H]+. 1H NMR (300 MHz, DMSO-d6) δ 8.05 (s, 1H), 7.2-7.15 (m, 2H), 5.01 (s, 4H), 4.42 (s, 1H), 3.21 (d, J=12.7 Hz, 1H), 2.99-2.89 (m, 3H), 2.05~1.90 (m, 2H), 1.89-1.80 (m, 1H), 1.64-1.58 (m, 1H).

Example 59: 4-Chloro-5-(5-fluoro-2,3-dihydro-1H-isoindol-2-yl)-2,3-dihydropyridazin-3-one

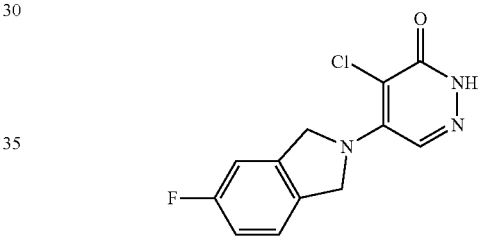

A solution of 4,5-dichloro-2,3-dihydropyridazin-3-one (211 mg, 1.28 mmol, 1.00 equiv), 5-fluoro-2,3-dihydro-1H-isoindole hydrochloride (200 mg, 1.15 mmol, 1.00 equiv), and TEA (251 mg, 2.48 mmol, 2.00 equiv) was stirred for 6 h at 80° C. The solids were collected by filtration, washed with 2×5 mL of MeOH and 2×5 mL of H2O to afford 139.9 mg (41%) of title compound as a white solid. LCMS: [M+H]+ 266.05, 1H NMR (400 MHz, DMSO-d6) δ 12.70 (s, 1H), 7.80 (s, 1H), 7.41 (dd, J=8.4, 5.1 Hz, 1H), 7.24 (dd, J=9.0, 2.4 Hz, 1H), 7.21-7.11 (m, 1H), 5.19 (s, 2H), 5.13 (s, 2H).

Example 60: 4-Chloro-5-(4-fluoro-2,3-dihydro-1H-isoindol-2-yl)-2,3-dihydropyridazin-3-one

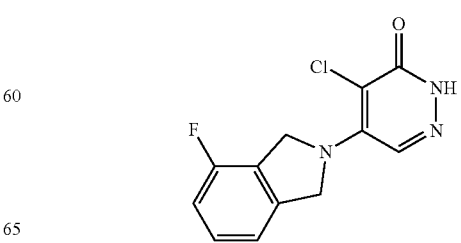

A solution of 4,5-dichloro-2,3-dihydropyridazin-3-one (212 mg, 1.29 mmol, 1.00 equiv), 4-fluoro-2,3-dihydro-1H-isoindole hydrochloride (200 mg, 1.15 mmol, 1.00 equiv), and TEA (249 mg, 2.46 mmol, 2.00 equiv) in EtOH (4 mL) was stirred for 6 h at 80° C. The solids were collected by filtration, and washed with 2×10 mL of MeOH and 2×10 mL of H$_2$O to afford 121.3 mg (36%) of title compound as a white solid. LCMS: [M+H]$^+$ 266.05, $^1$H NMR (400 MHz, DMSO-d$_6$) δ12.72 (s, 1H), 7.87 (s, 1H), 7.40 (td, J=7.9, 5.2 Hz, 1H), 7.24 (d, J=7.5 Hz, 1H), 7.16 (dd, J=9.5, 8.2 Hz, 1H), 5.23 (s, 4H).

Example 61: 6-(4-[[2-fluoro-5-([2-[6-oxo-5-(trifluoromethyl)-1,6-dihydropyridazin-4-yl]-2,3-dihydro-1H-isoindol-1-yl]methoxy)pyridin-3-yl]carbonyl]piperazin-1-yl)pyridine-3-carbonitrile

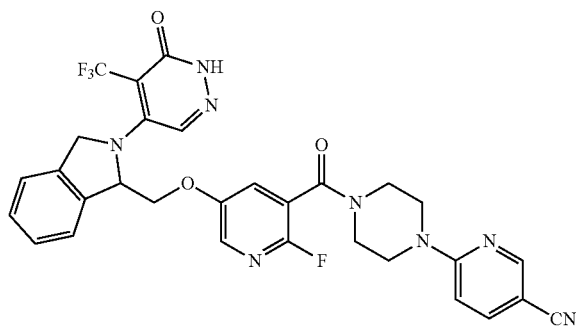 [SMILES: N#Cc1ccc(N2CCN(C(=O)c3cc(OCC4c5ccccc5CN4c4cn[nH]c(=O)c4C(F)(F)F)cnc3F)CC2)nc1]

Step 1: Synthesis of Methyl 2-fluoro-5-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-3-carboxylate Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (1 g, 2.26 mmol, 1.00 equiv), methyl 5-bromo-2-fluoropyridine-3-carboxylate (2 g, 8.55 mmol, 4.00 equiv), [Pd(allyl)Cl]$_2$ (125 mg, 0.34 mmol, 0.15 equiv), Rockphos (160 mg, 0.34 mmol, 0.15 equiv), Cs$_2$CO$_3$ (1.85 g, 5.68 mmol, 2.51 equiv) in toluene (20 mL) was stirred overnight at 80° C. in an oil bath. After concentration, the residue was purified by C18 reverse phase chromatography eluting with H$_2$O/CH$_3$CN to afford 300 mg (22%) of the title compound as a yellow solid. LCMS (ESI, m/z): 595.19 [M+H]$^+$.

Step 2: Synthesis of 2-fluoro-5-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-3-carboxylic Acid A solution of methyl 2-fluoro-5-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyridine-3-carboxylate (300 mg, 0.50 mmol, 1.00 equiv), LiOH (40 mg, 1.67 mmol, 1.70 equiv) in water (1 mL) and methanol (40 mL) was stirred overnight at 25° C. The pH value of the solution was adjusted to 5-6 with hydrogen chloride (6 M). After concentration, the residue was purified by C18 reverse phase chromatography eluting with H$_2$O/CH$_3$CN to afford 290 mg (99%) of the title compound as red oil. LCMS (ESI, m/z): 581.18 [M+H]$^+$ Step 3: Synthesis of 2-fluoro-5-([2-[6-oxo-5-(trifluoromethyl)-1,6-dihydropyridazin-4-yl]-2,3-dihydro-1H-isoindol-1-yl]methoxy)pyridine-3-carboxylic Acid A solution of 2-fluoro-5-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyridine-3-carboxylic acid (290 mg, 0.50 mmol, 1.00 equiv) and hydrogen chloride/dioxane (10 mL) in dioxane (2 mL) was stirred overnight at 25° C. The resulting mixture was concentrated under vacuum to afford 200 mg (89%) of the title compound as a crude red oil. LCMS (ESI, m/z): 451.10 [M+H]$^+$.

Step 4: Synthesis of 6-(4-[[2-fluoro-5-([2-[6-oxo-5-(trifluoromethyl)-1,6-dihydropyridazin-4-yl]-2,3-dihydro-1H-isoindol-1-yl]methoxy)pyridin-3-yl]carbonyl]piperazin-1-yl)pyridine-3-carbonitrile A solution of 2-fluoro-5-([2-[6-oxo-5-(trifluoromethyl)-1,6-dihydropyridazin-4-yl]-2,3-dihydro-1H-isoindol-1-yl]methoxy)pyridine-3-carboxylic acid (130 mg, 0.29 mmol, 1.00 equiv), HATU (112 mg, 0.29 mmol, 1.02 equiv), DIPEA (112 mg, 0.87 mmol, 3.00 equiv), and Int-A4 (55 mg, 0.29 mmol, 1.00 equiv) in DMF (2 mL) was stirred for 1 h at 25° C. After concentration, the residue was purified by C18 reverse phase chromatography eluting with H$_2$O/CH$_3$CN yielding the title compound (20.4 mg 11%) as an off-white solid. LCMS (ESI, m/z): 621.19 [M+H]$^+$, 1H NMR (Methanol-d$_4$, 400 MHz) δ: 8.45-8.44 (d, J=2.3 Hz, 1H), 8.39 (s, 1H), 7.93-7.91 (dd, J=3.1, 1.7 Hz, 1H), 7.79-7.77 (dd, J=9.1, 2.4 Hz, 1H), 7.57-7.51 (m, 2H), 7.42-7.37 (m, 3H), 6.92-6.89 (d, J=9.0 Hz, 1H), 6.21 (s, 1H), 5.34-5.30 (d, J=14.8 Hz, 1H), 4.69-4.67 (d, J=14.6 Hz, 1H), 4.59-4.56 (dd, J=10.2, 3.6 Hz, 1H), 4.40-4.32 (dd, J=10.1, 6.3 Hz, 1H), 3.87 (dr, 4H), 3.76-3.73 (m, 2H), 3.47-3.44 (d, J=5.6 Hz, 2H).

Example 62: 2-(4-[[2-fluoro-5-([2-[6-oxo-5-(trifluoromethyl)-1,6-dihydropyridazin-4-yl]-2,3-dihydro-1H-isoindol-1-yl]methoxy)pyridin-3-yl]carbonyl]piperazin-1-yl)pyrimidine-5-carbonitrile

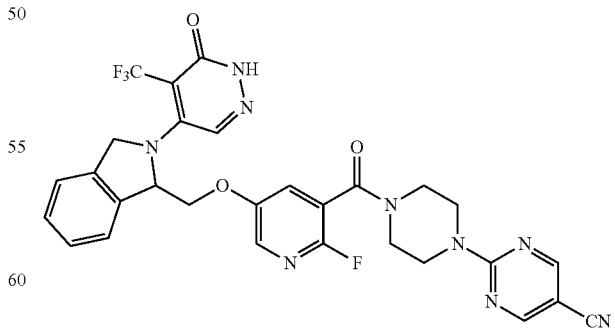

A solution of 2-fluoro-5-([2-[6-oxo-5-(trifluoromethyl)-1,6-dihydropyridazin-4-yl]-2,3-dihydro-1H-isoindol-1-yl]methoxy)pyridine-3-carboxylic acid (130 mg, 0.29 mmol, 1.00 equiv), DIPEA (200 mg, 1.55 mmol, 6.00 equiv), HATU (180 mg, 0.47 mmol, 2.00 equiv), and Int-A1 (100 mg, 0.44 mmol, 1.00 equiv) in DMF (2 mL) was stirred for 1 h at 25° C. After concentration, the residue was purified by C18 reverse phase chromatography eluting with $H_2O$/$CH_3CN$ and further purified by Prep-HPLC to yield the title compound (25.1 mg 14%) as a white solid. LCMS (ESI, m/z): 622.19 [M+H]$^+$, $^1$H NMR (Methanol-d$_4$, 400 MHz) δ: 8.65 (m, 2H), 8.37 (s, 1H), 7.90-7.89 (dd, J=3.1, 1.7 Hz, 1H), 7.55-7.49 (m, 2H), 7.40-7.34 (m, 3H), 6.19 (s, 1H), 5.32-5.28 (d, J=14.4 Hz, 1H), 4.69-4.53 (m, 2H), 4.37-4.30 (m, 1H), 4.06-4.03 (t, J=5.5 Hz, 2H), 3.95-3.92 (t, J=5.3 Hz, 2H), 3.83-3.81 (t, J=5.4 Hz, 2H), 3.48-3.41 (t, J=5.2 Hz, 2H).

Example 63: 3-[(5-cyanopyridin-2-yl)amino]-N-[5-([2-[6-oxo-5-(trifluoromethyl)-1,6-dihydropyridazin-4-yl]-2,3-dihydro-1H-isoindol-1-yl]methoxy)pyridin-3-yl]propanamide

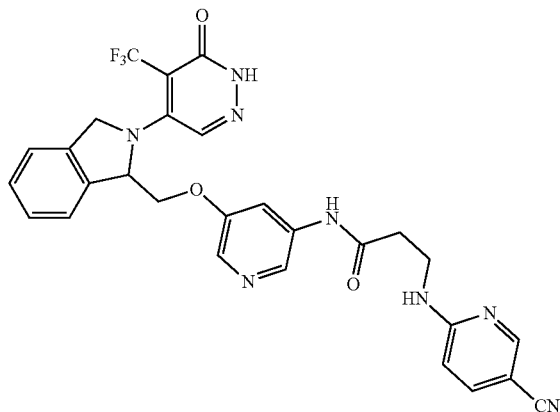 [SMILES: N#Cc1ccc(NCCC(=O)Nc2cncc(OCC3c4ccccc4CN3c3cn[nH]c(=O)c3C(F)(F)F)c2)nc1]

Step 1: Synthesis of 5-(1-[[(5-nitropyridin-3-yl)oxy]methyl]-2,3-dihydro-1H-isoindol-2-yl)-4-(trifluoromethyl)-2-[[2-(trimethylsilyl)ethoxy]methyl]-2,3-dihydropyridazin-3-one Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1.00 equiv), (Pd(allyl)C$_1$)$_2$ (41 mg), Rockphos (53 mg), Cs$_2$CO$_3$ (1.1 g, 3.38 mmol, 2.98 equiv) and 3-bromo-5-nitropyridine (465 mg, 2.29 mmol, 2.02 equiv) in toluene (10 mL) was stirred for 16 h at 80° C. The resulting solution was concentrated under vacuum and the residue was applied onto a silica gel column eluting with EtOAc/petroleum ether (2:3) to afford 500 mg (78%) of the title compound as a brown solid. LCMS (ESI, m/z): 564.18 [M+H]$^+$.

Step 2: Synthesis of 5-(1-[[(5-aminopyridin-3-yl)oxy]methyl]-2,3-dihydro-1H-isoindol-2-yl)-4-(trifluoromethyl)-2-[[2-(trimethylsilyl)ethoxy]methyl]-2,3-dihydropyridazin-3-one A solution of 5-(1-[[(5-nitropyridin-3-yl)oxy]methyl]-2,3-dihydro-1H-isoindol-2-yl)-4-(trifluoromethyl)-2-[[2-(trimethylsilyl)ethoxy]methyl]-2,3-dihydropyridazin-3-one (500 mg, 0.89 mmol, 1.00 equiv) and Fe (149 mg, 3.00 equiv) in acetic acid (4 mL) was stirred for 4 h at 60° C. The solid was filtered out and the resulting solution was concentrated under vacuum, and the residue was applied onto a silica gel column eluting with EtOAc/petroleum ether (3:1) to afford 415 mg (88%) of the title compound as a light yellow solid. LCMS (ESI, m/z): 534.21[M+H]$^+$.

Step 3: Synthesis of 3-[(5-cyanopyridin-2-yl)amino]-N-[5-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridin-3-yl]propanamide A solution of 5-(1-[[(5-aminopyridin-3-yl)oxy]methyl]-2,3-dihydro-1H-isoindol-2-yl)-4-(trifluoromethyl)-2-[[2-(trimethylsilyl)ethoxy]methyl]-2,3-dihydropyridazin-3-one (300 mg, 0.56 mmol, 1.00 equiv), EDC.HCl (325 mg, 1.70 mmol, 3.00 equiv), 4-dimethylaminopyridine (122 mg, 3.00 equiv) and 3-[(5-cyanopyridin-2-yl)amino]propanoic acid (215 mg, 1.12 mmol, 2.00 equiv) in DMF (2.5 mL) was stirred for 5 h at 60° C. The resulting solution was diluted with 10 mL of H$_2$O, extracted with 3×15 mL of EtOAc, dried over anhydrous sodium sulfate and concentrated under vacuum. The residue was applied onto a silica gel column eluting with EtOAc/petroleum ether (2:3) to afford 100 mg (25%) of the title compound as a light yellow solid. LCMS (ESI, m/z): 707.27[M+H]$^+$ Step 4: Synthesis of 3-[(5-cyanopyridin-2-yl)amino]-N-[5-([2-[6-oxo-5-((trifluoromethyl))-1,6-dihydropyridazin-4-yl]-2,3-dihydro-1H-isoindol-1-yl]methoxy)pyridin-3-yl]propanamide A solution of 3-[(5-cyanopyridin-2-yl)amino]-N-[5-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridin-3-yl]propanamide (90 mg, 0.13 mmol, 1.00 equiv) and TFA (0.5 mL) in DCM (2 mL) was stirred for 3 h at room temperature. The resulting solution was concentrated under vacuum and then the residue was purified by Prep-HPLC yielding the title compound (40 mg, 54%) as a white solid. LCMS (ESI, m/z): 577.15[M+H]$^+$. $^1$HNMR (Methanol-d$_4$, 300 MHz) δ 8.40 (s, 1H), 8.32 (dd, J=2.1, 0.8 Hz, 1H), 8.21 (d, J=2.1 Hz, 1H), 7.88 (d, J=2.7 Hz, 1H), 7.84 (dd, J=4.5, 2.4 Hz, 1H), 7.59-7.50 (m, 2H), 7.41-7.37 (m, 3H), 6.59 (d, J=8.7 Hz, 1H), 6.22 (s, 1H), 5.30 (d, J=14.4 Hz, 1H), 4.67 (dd, J=14.4, 3.0 Hz, 1H), 4.58 (dd, J=10.2, 3.3 Hz, 1H) 4.30 (dd, J=10.2, 6.6 Hz, 1H), 3.75 (t, J=6.3 Hz, 2H), 2.70 (t, J=6.3 Hz, 2H).

Example 64 Isomer A: (R)-2-(4-(4-((2-(6-Oxo-5-(trifluoromethyl)-1,6-dihydropyridazin-4-yl)isoindolin-1-yl)methoxy)picolinoyl)piperazin-1-yl)pyrimidine-5-carbonitrile and

Example 64 Isomer B: (S)-2-(4-(4-((2-(6-Oxo-5-(trifluoromethyl)-1,6-dihydropyridazin-4-yl)isoindolin-1-yl)methoxy)picolinoyl)piperazin-1-yl)pyrimidine-5-carbonitrile

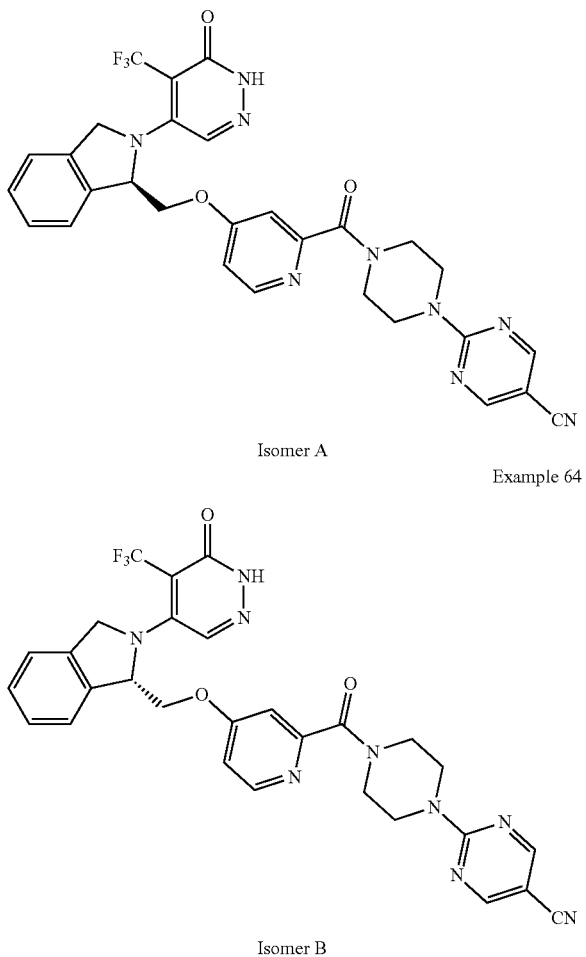

Example 64

Isomer A

Example 64

Isomer B

Step 1: Synthesis of Methyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-2-carboxylate Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1.00 equiv), [Pd(allyl)Cl]$_2$ (42 mg, 0.10 equiv), Rockphos (53 mg, 0.10 equiv), Cs$_2$CO$_3$ (1.1 g, 3.38 mmol, 3.00 equiv) and methyl 4-bromopyridine-2-carboxylate (488 mg, 2.26 mmol, 2.00 equiv) in toluene (40 mL) was stirred for 12 h at 80° C. The resulting solution was concentrated under vacuum and the residue was applied onto a silica gel column eluting with EtOAc/petroleum ether (3:1) to afford 233 mg (36%) of the title compound as a solid. LCMS (ESI, m/z): 577.20 [M+H]$^+$.

Step 2: Synthesis of 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-2-carboxylic Acid A solution of methyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-2-carboxylate (233 mg, 0.40 mmol, 1.00 equiv) and LiOH (48 mg, 2.00 mmol, 5.00 equiv) in water (0.5 mL) and methanol (1.5 mL) was stirred for 1 h at room temperature. The pH value of the solution was adjusted to 2 with hydrogen chloride (12 M) and the solids were collected by filtration to afford 271 mg (crude) of the title compound as a brown solid. LCMS (ESI, m/z): 563.19[M+H]$^+$.

Step 3: Synthesis of 4-([2-[6-oxo-5-(trifluoromethyl)-1,6-dihydropyridazin-4-yl]-2,3-dihydro-1H-isoindol-1-yl]methoxy)pyridine-2-carboxylic Acid Hydrochloride A solution of 4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyridine-2-carboxylic acid (271 mg, 0.48 mmol, 1.00 equiv) in hydrogen chloride/dioxane (5 mL, 4M) was stirred for 1 h at room temperature, and the resulting mixture was concentrated under vacuum to afford 198 mg of the title compound as a solid. LCMS (ESI, m/z): 433.10[M+H]$^+$.

Step 4: Synthesis of (R)-2-(4-(4-((2-(6-oxo-5-(trifluoromethyl)-1,6-dihydropyridazin-4-yl)isoindolin-1-yl)methoxy)picolinoyl)piperazin-1-yl)pyrimidine-5-carbonitrile and (S)-2-(4-(4-((2-(6-oxo-5-(trifluoromethyl)-1,6-dihydropyridazin-4-yl)isoindolin-1-yl)methoxy)picolinoyl)piperazin-1-yl)pyrimidine-5-carbonitrile A solution of 4-([2-[6-oxo-5-(trifluoromethyl)-1,6-dihydropyridazin-4-yl]-2,3-dihydro-1H-isoindol-1-yl]methoxy)pyridine-2-carboxylic acid hydrochloride (198 mg, 0.46 mmol, 1.00 equiv), HATU (174.116 mg, 0.46 mmol, 1.00 equiv), DIPEA (177.653 mg, 1.37 mmol, 3.00 equiv) and Int-A1 (104.05 mg, 0.55 mmol, 1.20 equiv) in DMF (2 mL) was stirred for 1 h at room temperature. The resulting solution was purified by C18 reverse phase chromatography eluting with H$_2$O/CH$_3$CN, and the residue was further purified by Prep-HPLC and Chiral-Prep-HPLC (CHIRAL-PAK IG-3, 0.46*10 cm; 3 um, MtBE (0.1% DEA): EtOH=70:30, 1.0 mL/min) yielding the title compounds. The absolute stereochemistry was assigned based on a protein X-ray crystal structure obtained of Example 18 Isomer B which confirmed (S)-absolute stereochemistry and was observed to be the more potent enantiomer.

Example 64 Isomer A 12.8 mg, 34.0%, LCMS (ESI, m/z): 604.45 [M+H]$^+$, $^1$HNMR (Methanol-d$_4$, 300 MHz) δ 8.48 (s, 2H), 2.28-8.21 (m, 2H), 7.39-7.30 (m, 1H), 7.28-7.19 (m, 3H), 6.99 (d, J=2.4 Hz, 1H), 6.90-6.86 (b, 1H), 6.08 (s, 1H), 2.18-5.13 (m, 2H), 5.56-4.41 (m, 2H), 4.30-4.21 (m, 1H), 3.95-6.34 (m, 6H), 3.41-3.31 (m, 2H), tR=3.145 min.

Example 64 Isomer B 14.5 mg, 38%, LCMS (ESI, m/z): 604.45 [M+H]+, tR=3.844 min Example 65: 2-[4-[(5-[[(2S)-1-[6-oxo-5-(trifluoromethyl)-1,6-dihydropyridazin-4-yl]pyrrolidin-2-yl]methoxy]pyridin-3-yl)carbonyl]piperazin-1-yl]pyrimidine-5-carbonitrile

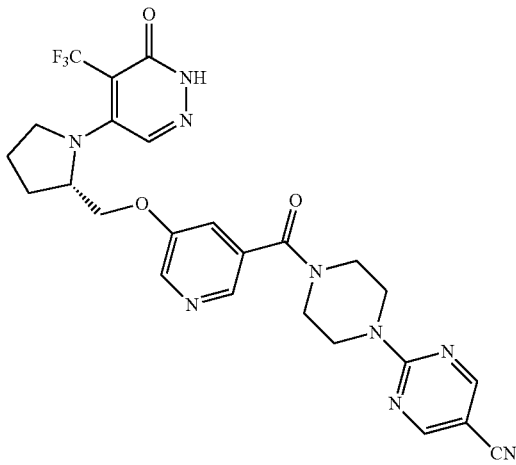 [SMILES: N#Cc1cnc(N2CCN(C(=O)c3cncc(OC[C@@H]4CCCN4c4cn[nH]c(=O)c4C(F)(F)F)c3)CC2)nc1]

Step 1: Synthesis of Methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-3-carboxylate Under nitrogen, a solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1.97 g, 5.01 mmol, 1.00 equiv), Cs2CO3 (3.25 g, 9.97 mmol, 2.00 equiv), [Pd(ally)Cl]2 (183 mg, 0.10 equiv), RockPhos (704 mg, 0.30 equiv) and methyl 5-bromopyridine-3-carboxylate (2.16 g, 10.00 mmol, 2.00 equiv) in toluene (40 mL) was stirred for 24 h at 80° C. The solids were filtered out, the resulting solution was concentrated under vacuum, and the residue was purified by C18 reverse phase chromatography eluting with H2O/CH3CN to afford 1.28 g (48%) of the title compound as light yellow oil. LCMS (ESI, m/z): 529.20 [M+H]+.

Step 2: Synthesis of Methyl 5-[[(2S)-1-[6-oxo-5-(trifluoromethyl)-1,6-dihydropyridazin-4-yl]pyrrolidin-2-yl]methoxy]pyridine-3-carboxylate A solution of methyl 5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-3-carboxylate (1.28 g, 2.42 mmol, 1.00 equiv) in hydrogen chloride/dioxane (40 mL, 4 M) was stirred for 5 h at room temperature, and the resulting solution was concentrated under vacuum to afford 1 g of the title compound as crude yellow oil. LCMS (ESI, m/z): 399.12 [M+H]+.

Step 3: Synthesis of 5-[[(2S)-1-[6-oxo-5-(trifluoromethyl)-1,6-dihydropyridazin-4-yl]pyrrolidin-2-yl]methoxy]pyridine-3-carboxylic Acid A solution of methyl 5-[[(2S)-1-[6-oxo-5-(trifluoromethyl)-1,6-dihydropyridazin-4-yl]pyrrolidin-2-yl]methoxy]pyridine-3-carboxylate (1 g, 2.26 mmol, 1.00 equiv, 90%) and LiOH (480 mg, 20.04 mmol, 8.00 equiv) in methanol (30 mL) and water (3 mL) was stirred for 2 h at 25° C. The pH value of the solution was adjusted to 4 with hydrogen chloride (2 M). The resulting solution was concentrated under vacuum and the residue was purified by C18 reverse phase chromatography eluting with H2O/CH3CN to afford 600 mg (69%) of the title compound as a gray solid. LCMS (ESI, m/z): 384.10 [M+H]+.

Step 4: Synthesis of 2-[4-[(5-[[(2S)-1-[6-oxo-5-(trifluoromethyl)-1,6-dihydropyridazin-4-yl]pyrrolidin-2-yl]methoxy]pyridin-3-yl)carbonyl]piperazin-1-yl]pyrimidine-5-carbonitrile A solution of 5-[[(2S)-1-[6-oxo-5-(trifluoromethyl)-1,6-dihydropyridazin-4-yl]pyrrolidin-2-yl]methoxy]pyridine-3-carboxylic acid (100 mg, 0.26 mmol, 1.00 equiv), HATU (99 mg, 0.26 mmol, 1.00 equiv), DIPEA (101 mg, 0.78 mmol, 3.00 equiv) and Int-A1 (49.2 mg, 0.26 mmol, 1.00 equiv) in DMF (3 mL) was stirred for 1 h at room temperature. The residue was dissolved in 10 mL of H2O, extracted with 3×20 mL of EtOAc, and the organic layers were combined and washed with 20 mL of brine, dried over anhydrous sodium sulfate, and concentrated under vacuum. The residue was purified by purified by C18 reverse phase chromatography eluting with H2O/CH3CN. After concentration, the residue was further purified by Prep-HPLC yielding the title compound (25.7 mg 18%) as a white solid. LCMS (ESI, m/z): 556.05 [M+H]+, 1HNMR (DMSO-d6, 400 MHz,) δ 12.44 (s, 1H), 8.80 (s, 2H), 8.28 (d, J=2.8 Hz, 1H), 8.24 (d, J=1.6 Hz, 1H), 8.13 (s, 1H), 7.42 (t, J=2.4 Hz, 1H), 4.82 (br, 1H), 4.23-4.14 (m, 2H), 3.95-3.80 (m, 4H), 3.78-3.61 (m, 3H), 3.54-3.39 (m, 2H), 3.30-3.24 (m, 1H), 2.25-2.19 (m, 1H), 1.99-1.90 (m, 1H), 1.89-1.69 (m, 2H).

Example 66: 6-[4-[(4-[[(2S)-1-[6-oxo-5-(trifluoromethyl)-1,6-dihydropyridazin-4-yl]pyrrolidin-2-yl]methoxy]pyrimidin-2-yl)carbonyl]piperazin-1-yl]pyridine-3-carbonitrile

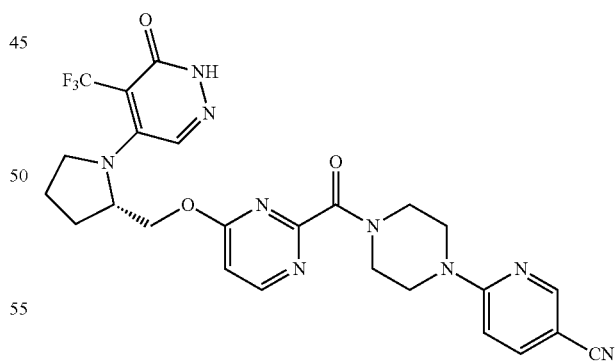

Step 1: Synthesis of Methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-2-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (786 mg, 2.00 mmol, 1.00 equiv), methyl 4-bromopyrimidine-2-carboxylate (561 mg, 2.59 mmol, 1.30 equiv), and potassium carbonate (1.1 g, 7.96 mmol, 4.00 equiv) in DMF (10 mL) was stirred for 16 h at 80° C. After concentration, the residue was purified by C18 reverse phase chromatography eluting with H₂O/CH₃CN to afford 600 mg (57%) of the title compound as a solid. LCMS (ESI, m/z): 530.21 [M+H]⁺.

Step 2: Synthesis of 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-2-carboxylic Acid A solution of methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-2-carboxylate (529 mg, 1.00 mmol, 1.00 equiv), LiOH (96 mg, 4.01 mmol, 4.00 equiv), water (5 mL) in methanol (10 mL) was stirred for 2 h at room temperature. The pH value of the solution was adjusted to 6 with hydrogen chloride. The solvent was concentrated under vacuum and the residue was applied onto a silica gel column eluting with ethyl DCM/methanol (5:1) to afford 300 mg (58%) of the title compound as a solid. LCMS (ESI, m/z): 516.19 [M+H]⁺.

Step 3: Synthesis of 6-[4-[(4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidin-2-yl)carbonyl]piperazin-1-yl]pyridine-3-carbonitrile A solution of 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-2-carboxylic acid (260 mg, 0.50 mmol, 1.00 equiv), Int-A4 (95 mg, 0.50 mmol, 1.00 equiv), EDC.HCl (288 mg, 3.00 equiv), 4-dimethylaminopyridine (244 mg, 2.00 mmol, 4.00 equiv) in DMF (3 mL) was stirred for 2 h at 60° C. After concentration, the residue was purified by C18 reverse phase chromatography eluting with H₂O/CH₃CN to afford 100 mg (29%) of the title compound as a white solid. LCMS (ESI, m/z): 686.29 [M+H]+.

Step 4: Synthesis of 6-[4-[(4-[[(2S)-1-[6-oxo-5-(trifluoromethyl)-1,6-dihydropyridazin-4-yl]pyrrolidin-2-yl]methoxy]pyrimidin-2-yl)carbonyl]piperazin-1-yl]pyridine-3-carbonitrile A solution of 6-[4-[(4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidin-2-yl)carbonyl]piperazin-1-yl]pyridine-3-carbonitrile (100 mg, 0.15 mmol, 1.00 equiv) in hydrogen chloride/dioxane (15 mL) was stirred for 2 h at room temperature. After concentration, the residue was purified by C18 reverse phase chromatography eluting with H₂O/CH₃CN yielding the title compound (14.2 mg, 18%) as a white solid. LCMS (ESI, m/z): 556.25 [M+H]+, ¹HNMR (CD3OD-d4, 300 MHz) δ 8.57 (d, J=5.9 Hz, 1H), 8.42 (d, J=2.3 Hz, 1H), 8.31 (s, 1H), 7.77 (dd, J=9.1, 2.4 Hz, 1H), 6.92 ((d, J=7.5 Hz, 1H), 6.89 (d, J=15.8 Hz, 1H), 4.76 (d, J=6.5 Hz, 1H), 4.70-4.52 (m, 2H), 3.95-3.72 (m, 7H), 3.54-3.32 (m, 3H), 2.39-2.27 (m, 1H), 2.07-1.93 (m, 2H), 1.92-1.77 (m, 1H).

Example 67: 6-[4-[(2-fluoro-5-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile

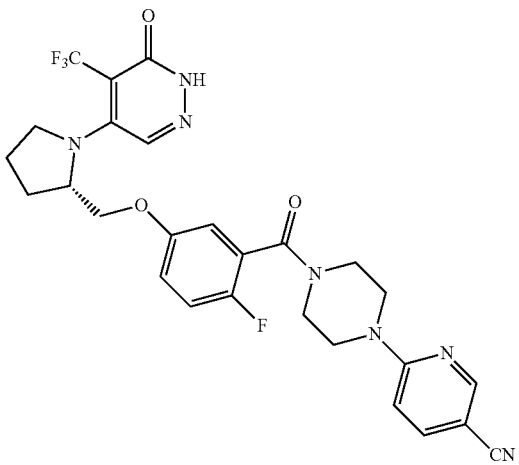 [SMILES: N#Cc1ccc(N2CCN(C(=O)c3cc(OC[C@@H]4CCCN4c4cn[nH]c(=O)c4C(F)(F)F)ccc3F)CC2)nc1]

Step 1: Synthesis of Methyl 2-fluoro-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (500 mg, 1.27 mmol, 1.00 equiv), [Pd(allyl)Cl]₂ (443 mg, 1.21 mmol, 1.50 equiv), Rockphos (60 mg, 0.13 mmol, 0.10 equiv), Cs₂CO₃ (830 mg, 2.55 mmol, 2.00 equiv), methyl 5-bromo-2-fluorobenzoate (443 mg, 1.90 mmol, 1.50 equiv) in toluene (14 mL) was stirred for 2 h at 80° C. in an oil bath under an atmosphere of nitrogen. The resulting mixture was concentrated under vacuum. The residue was applied onto a silica gel column eluting with EtOAc/petroleum ether (3:7) to afford 400 mg (58%) of the title compound as a yellow solid. LCMS (ESI, m/z): 546.20 [M+H]⁺

Step 2: Synthesis of Methyl 2-fluoro-5-[[(2S)-1-[6-oxo-5-(trifluoromethyl)-1,6-dihydropyridazin-4-yl]pyrrolidin-2-yl]methoxy]benzoate A solution of methyl 2-fluoro-5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (400 mg, 0.73 mmol, 1.00 equiv) in hydrogen chloride/dioxane (20 mL) was stirred for 14 h at room temperature. The resulting solution was concentrated under vacuum to afford 320 mg crude of the title compound as yellow crude oil. LCMS (ESI, m/z): 416.12 [M+H]⁺.

Step 3: Synthesis of 2-fluoro-5-[[(2S)-1-[6-oxo-5-(trifluoromethyl)-1,6-dihydropyridazin-4-yl]pyrrolidin-2-yl]methoxy]benzoic Acid A solution of methyl 2-fluoro-5-[[(2S)-1-[6-oxo-5-(trifluoromethyl)-1,6-dihydropyridazin-4-yl]pyrrolidin-2-yl]methoxy]benzoate (320 mg, 0.77 mmol, 1.00 equiv), LiOH.H₂O (162 mg, 3.86 mmol, 5.00 equiv) in methanol (20 mL) and water (5 mL) was stirred for 2 h at room temperature. The resulting mixture was concentrated under vacuum. The pH value of the solution was adjusted to 6 with hydrogen chloride (2 M). The solids were collected by filtration and dried in an oven under reduced pressure. This resulted in 240 mg (78%) of the title compound as a yellow solid. LCMS (ESI, m/z): 402.10 [M+H]$^+$.

Step 4: Synthesis of 6-[4-[(2-fluoro-5-[[(2S)-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 2-fluoro-5-[[(2S)-1-[6-oxo-5-(trifluoromethyl)-1,6-dihydropyridazin-4-yl]pyrrolidin-2-yl]methoxy]benzoic acid (240 mg, 0.60 mmol, 1.00 equiv), Int-A4 (161 mg, 0.86 mmol, 1.20 equiv), DIPEA (232 mg, 1.80 mmol, 3.00 equiv), HATU (250 mg, 0.66 mmol, 1.10 equiv) in DMF (4 mL) was stirred for 2 h at room temperature. The crude product was purified by C18 reverse phase column eluting with water ACN/water. The residue was further purified by Prep-HPLC yielding the title compound (64.2 mg, 19%) as a white solid. LCMS (ESI, m/z): 572.20 [M+H]$^{+1}$, $^1$H NMR (Methanol-d$_4$, 300 MHz) δ: 8.42 (dd, J=2.4, 0.7 Hz, 1H), 8.20 (s, 1H), 7.76 (dd, J=9.1, 2.4 Hz, 1H), 7.13 (t, J=9.0 Hz, 1H), 7.01 (dt, J=9.1, 3.8 Hz, 1H), 6.95-6.84 (m, 2H), 4.19 (dd, J=10.2, 3.7 Hz, 1H), 4.02 (dd, J=10.2, 6.8 Hz, 1H), 3.91-3.90-3.85 (m, 4H), 3.76-3.69 (m, 3H), 3.50-3.35 (m, 3H), 2.39-2.29 (m, 1H), 2.10-2.00 (m, 1H), 1.97-1.75 (m, 1H), 1.90-1.70 (m, 2H).

Example 68: 6-[4-[(2-[[(2S)-1-[6-oxo-5-(trifluoromethyl)-1,6-dihydropyridazin-4-yl]pyrrolidin-2-yl]methoxy]pyrimidin-4-yl)carbonyl]piperazin-1-yl]pyridine-3-carbonitrile

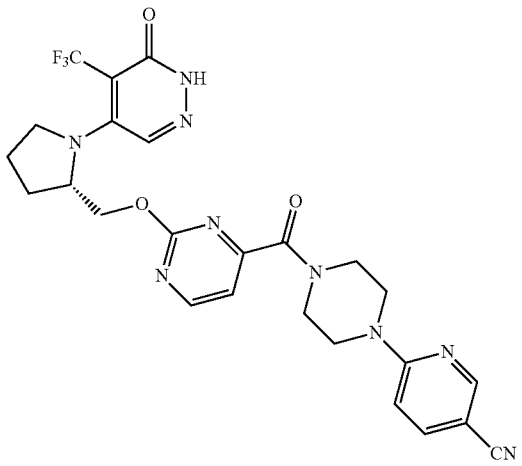 [SMILES: N#Cc1ccc(N2CCN(C(=O)c3ccnc(OC[C@@H]4CCCN4c4cn[nH]c(=O)c4C(F)(F)F)n3)CC2)nc1]

Step 1: Synthesis of Methyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-4-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (500 mg, 1.27 mmol, 1.00 equiv), (Pd(allyl)C)$_2$ (47 mg, 0.10 equiv), Rockphos (60 mg, 0.10 equiv), Cs$_2$CO$_3$ (829 mg, 2.54 mmol, 2.00 equiv), methyl 2-chloropyrimidine-4-carboxylate (547 mg, 3.17 mmol, 2.50 equiv) in toluene (10 mL) under nitrogen atmosphere was stirred overnight at 85° C. The solvent was concentrated under vacuum and the residue was applied onto a silica gel column eluting with EtOAc/petroleum ether (3/7) to afford 425 mg (63%) of the title compound as a yellow solid. LCMS (ESI, m/z): 530.20 [M+H]$^+$.

Step 2: Synthesis of Methyl 2-[[(2S)-1-[6-oxo-5-(trifluoromethyl)-1,6-dihydropyridazin-4-yl]pyrrolidin-2-yl]methoxy]pyrimidine-4-carboxylate A solution of methyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrimidine-4-carboxylate (425 mg, 0.80 mmol, 1.00 equiv) in dioxane/HCl (20 mL, 4 M) was stirred for overnight at 25° C. The solvent was concentrated under vacuum to afford 290 mg (91%) of the title compound as yellow oil. LCMS (ESI, m/z): 400.12 [M+H]$^+$ Step 3: Synthesis of 2-[[(2S)-1-[6-oxo-5-(trifluoromethyl)-1,6-dihydropyridazin-4-yl]pyrrolidin-2-yl]methoxy]pyrimidine-4-carboxylic Acid A solution of methyl 2-[[(2S)-1-[6-oxo-5-(trifluoromethyl)-1,6-dihydropyridazin-4-yl]pyrrolidin-2-yl]methoxy]pyrimidine-4-carboxylate (360 mg, 0.90 mmol, 1.00 equiv), LiOH.H$_2$O (285 mg, 6.79 mmol, 10.00 equiv) in MeOH (10 mL) and water (2 mL) was stirred for 2 h at 25° C. The resulting solution was concentrated under vacuum. The residue was diluted with 3 mL of water, and the pH value of the solution was adjusted to 3 with hydrogen chloride (2M). The residue was purified by C18 reverse phase chromatography eluting with H$_2$O/CH$_3$CN to afford 70 mg (20%) of the title compound as a off-white solid. LCMS (ESI, m/z): 386.10 [M+H]$^+$.

Step 4: Synthesis of 6-[4-[(2-[[(2S)-1-[6-oxo-5-(trifluoromethyl)-1,6-dihydropyridazin-4-yl]pyrrolidin-2-yl]methoxy]pyrimidin-4-yl)carbonyl]piperazin-1-yl]pyridine-3-carbonitrile A solution of 2-[[(2S)-1-[6-oxo-5-(trifluoromethyl)-1,6-dihydropyridazin-4-yl]pyrrolidin-2-yl]methoxy]pyrimidine-4-carboxylic acid (60 mg, 0.16 mmol, 1.00 equiv), HOBt (45 mg, 0.33 mmol, 1.50 equiv), EDCI (32 mg, 0.17 mmol, 1.50 equiv), DIPEA (60 mg, 0.46 mmol, 3.00 equiv), Int-A4 (70 mg, 0.37 mmol, 2.00 equiv) in DMF (3 mL) was stirred for overnight at 25° C. After concentration, the residue was purified by C18 reverse phase chromatography eluting with H$_2$O/CH$_3$CN. The residue was further purified by Prep-HPLC yielding the title compound (16.5 mg, 19%) as a white solid. LCMS (ESI, m/z): 556.20 [M+H]$^+$, $^1$H NMR (DMSO-d$_6$, 300 MHz) δ: 12.43 (s, 1H), 8.71 (d, J=4.9 Hz, 1H), 8.50 (d, J=2.2 Hz, 1H), 8.17 (s, 1H), 7.89 (dd, J=9.1, 2.3 Hz, 1H), 7.28 (d, J=4.9 Hz, 1H), 6.92 (d, J=9.3 Hz, 1H), 4.74 (s, 1H), 4.62-4.49 (m, 1H), 4.45-4.33 (m, 1H), 3.88-3.57 (m, 7H), 3.47-3.39 (m, 2H), 3.27-3.18 (m, 1H), 2.26-2.11 (m, 1H), 1.98-1.88 (m, 2H), 1.75-1.63 (m, 1H).

Example 69: 6-[4-[(2-[[(2S)-1-[6-oxo-5-(trifluoromethyl)-1,6-dihydropyridazin-4-yl]pyrrolidin-2-yl]methoxy]pyridin-4-yl)carbonyl]piperazin-1-yl]pyridine-3-carbonitrile

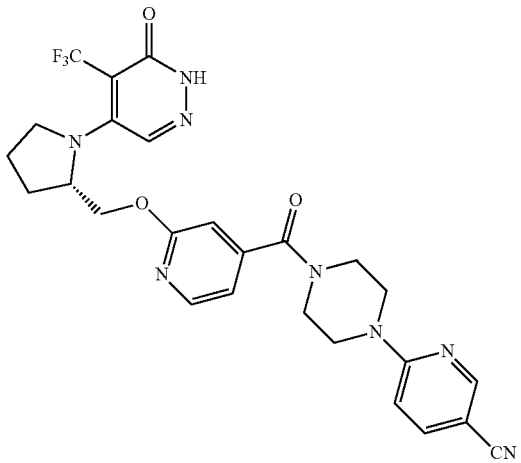 [SMILES: N#Cc1ccc(N2CCN(C(=O)c3ccnc(OC[C@@H]4CCCN4c4cn[nH]c(=O)c4C(F)(F)F)c3)CC2)nc1]

Step 1: Synthesis of Methyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-4-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (400 mg, 1.02 mmol, 1.00 equiv), methyl 2-bromopyridine-4-carboxylate (328 mg, 1.52 mmol, 1.50 equiv), Pd[(allyl)Cl]$_2$ (37.3 mg, 0.10 mmol, 0.10 equiv), Rockphos (95.5 mg, 0.20 equiv) and Cs$_2$CO$_3$ (664 mg, 2.04 mmol, 2.00 equiv) in toluene (15 mL) was stirred for 15 h at 80° C. in an oil bath. The solid was filtered out and the resulting solution was concentrated under vacuum. The residue was applied onto a silica gel column with eluting EtOAc/petroleum ether (31/69) to afford 237 mg (44%) of the title compound as a solid. LCMS (ESI, m/z): 529.20 [M+H]$^+$.

Step 2: Synthesis of Methyl 2-[[(2S)-1-[6-oxo-5-(trifluoromethyl)-1,6-dihydropyridazin-4-yl]pyrrolidin-2-yl]methoxy]pyridine-4-carboxylate Hydrochloride A solution of methyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-4-carboxylate (237 mg, 0.45 mmol, 1.00 equiv) in hydrogen chloride/dioxane (10 mL, 4M) was stirred for 2 h at room temperature, and the resulting solution was concentrated under vacuum to afford 195 mg of the title compound as a crude yellow solid. LCMS (ESI, m/z): 399.12 [M+H]$^+$.

Step 3: Synthesis of 2-[[(2S)-1-[6-oxo-5-(trifluoromethyl)-1,6-dihydropyridazin-4-yl]pyrrolidin-2-yl]methoxy]pyridine-4-carboxylic Acid A solution of methyl 2-[[(2S)-1-[6-oxo-5-(trifluoromethyl)-1,6-dihydropyridazin-4-yl]pyrrolidin-2-yl]methoxy]pyridine-4-carboxylate (175 mg, 0.44 mmol, 1.00 equiv) and LiOH (42.2 mg, 1.76 mmol, 4.00 equiv) in water (2.5 mL) and THF (10 mL) was stirred for 2 h at room temperature. The resulting solution was concentrated under vacuum, and the residue was diluted with 10 mL of H$_2$O, and the pH value of the solution was adjusted to 4 with hydrogen chloride (36%). The solids were collected by filtration to afford 138 mg (82%) of the title compound as a yellow solid. LCMS (ESI, m/z): 385.10[M+H]$^+$.

Step 4: Synthesis of 6-[4-[(2-[[(2S)-1-[6-oxo-5-(trifluoromethyl)-1,6-dihydropyridazin-4-yl]pyrrolidin-2-yl]methoxy]pyridin-4-yl)carbonyl]piperazin-1-yl]pyridine-3-carbonitrile A solution of 2-[[(2S)-1-[6-oxo-5-(trifluoromethyl)-1,6-dihydropyridazin-4-yl]pyrrolidin-2-yl]methoxy]pyridine-4-carboxylic acid (118 mg, 0.31 mmol, 1.00 equiv), HATU (116.7 mg, 0.31 mmol, 1.00 equiv), DIPEA (118.9 mg, 0.92 mmol, 3.00 equiv) and Int-A4 (58 mg, 0.31 mmol, 1.00 equiv) in DMF (4 mL) was stirred for 40 min at room temperature. The resulting solution was dissolved in 20 mL of H$_2$O and extracted with 3×20 mL of EtOAc. The organic layers were combined and dried over anhydrous sodium sulfate and then concentrated under vacuum, and the residue was purified by Prep-HPLC yielding the title compound (18.0 mg, 11%) as a white solid. LCMS (ESI, m/z): 555.20 [M+H]+, 1H NMR (DMSO-d$_6$, 400 MHz,) δ 12.44 (s, 1H), 8.52 (d, J=2.0 Hz, 1H), 8.20-8.16 (m, 2H), 7.92 (dd, J=9.2, 2.4 Hz, 1H), 7.02 (dd, J=5.2, 1.2 Hz, 1H), 6.96 (d, J=8.8 Hz, 1H), 6.74 (s, 1H), 4.79-4.73 (m, 1H), 4.51-4.47 (m, 1H), 4.41-4.36 (m, 1H), 3.80-3.57 (m, 7H), 3.33-3.21 (m, 3H), 2.21-2.19 (m, 1H), 1.97-1.69 (m, 3H).

Example 70: 6-[4-[(3-[[(2S,4S)-4-methyl-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile

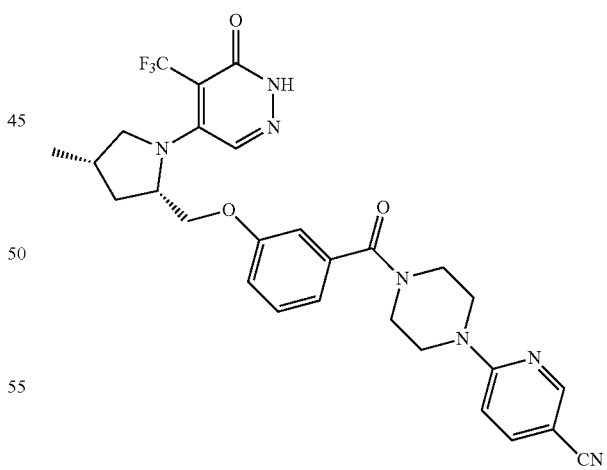

Step 1: Synthesis of [(2S,4S)-4-methylpyrrolidin-2-yl]methanol Hydrochloride

A solution of tert-butyl (2S,4S)-2-(hydroxymethyl)-4-methylpyrrolidine-1-carboxylate (1 g, 4.64 mmol, 1.00 equiv) in dioxane/HCl (8 mL) at 25° C. The resulting mixture was concentrated under vacuum to afford 520 mg (crude) of the title compound as crude colorless oil. LCMS (ESI, m/z): 116.10 [M–Cl]⁺.

Step 2: Synthesis of 5-[(2S,4S)-2-(hydroxymethyl)-4-methylpyrrolidin-1-yl]-4-(trifluoromethyl)-2-[[2-(trimethylsilyl)ethoxy]methyl]-2,3-dihydropyridazin-3-one A solution of Int-A6 (1 g, 3.04 mmol, 1.00 equiv), [(2S,4S)-4-methylpyrrolidin-2-yl]methanol hydrochloride (520 mg, 3.43 mmol, 1.00 equiv) in ethanol (10 mL) and TEA (5 mL) was stirred for 60 min at 60° C. After concentration, the residue was applied onto a silica gel column eluting with EtOAc/petroleum ether (1/2) to afford 900 mg (73%) of the title compound as a white solid. LCMS (ESI, m/z): 408.19 [M+H]⁺.

Step 3: Synthesis of Methyl 3-[[(2S,4S)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate Under nitrogen, a solution of 5-[(2S,4S)-2-(hydroxymethyl)-4-methylpyrrolidin-1-yl]-4-(trifluoromethyl)-2-[[2-(trimethylsilyl)ethoxy]methyl]-2,3-dihydropyridazin-3-one (900 mg, 2.21 mmol, 1.00 equiv), methyl 3-bromobenzoate (946 mg, 4.40 mmol, 2.00 equiv), Pd(dba)CHCl₃ (228 mg, 0.10 equiv), Rockphos (104 mg, 0.10 equiv), Cs₂CO₃ (2.16 g, 6.63 mmol, 3.00 equiv) in toluene (50 mL) was stirred overnight at 80° C. After concentration, the residue was applied onto a silica gel column eluting with EtOAc/petroleum ether (2/3) to afford 700 mg (59%) of the title compound as yellow oil. LCMS (ESI, m/z): 542.22 [M+H]⁺.

Step 4: Synthesis of Methyl 3-[[(2S,4S)-4-methyl-1-[6-oxo-5-(trifluoromethyl)-1,6-dihydropyridazin-4-yl]pyrrolidin-2-yl]methoxy]benzoate A solution of methyl 3-[[(2S,4S)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate (700 mg, 1.29 mmol, 1.00 equiv) in dioxane/HCl (10 mL) was stirred for 6 h at 25° C. After concentration, the residue was purified by C18 reverse phase chromatography eluting with H₂O/CH₃CN (1/1) to afford 300 mg (56%) of the title compound as a yellow solid. LCMS (ESI, m/z): 412.14 [M+H]⁺.

Step 5: Synthesis of 3-[[(2S,4S)-4-methyl-1-[6-oxo-5-(trifluoromethyl)-1,6-dihydropyridazin-4-yl]pyrrolidin-2-yl]methoxy]benzoic Acid A solution of methyl 3-[[(2S,4S)-4-methyl-1-[6-oxo-5-(trifluoromethyl)-1,6-dihydropyridazin-4-yl]pyrrolidin-2-yl]methoxy]benzoate (300 mg, 0.73 mmol, 1.00 equiv), LiOH (96 mg, 4.01 mmol, 5.00 equiv) in THF (10 mL) and water (2 mL) was stirred overnight at 25° C. The pH value was adjusted to 3 with hydrogen chloride (1 M). The resulting solution was extracted with 2×50 mL of DCM and the organic layers were combined and concentrated under vacuum to afford 100 mg (35%) of the title compound as a yellow solid. LCMS (ESI, m/z): 398.12 [M+H]⁺.

Step 6: Synthesis of 6-[4-[(3-[[(2S,4S)-4-methyl-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile A solution of 3-[[[(2S,4S)-4-methyl-1-[6-oxo-5-(trifluoromethyl)-1,6-dihydropyridazin-4-yl]pyrrolidin-2-yl] methoxy]benzoic acid (100 mg, 0.25 mmol, 1.00 equiv), HATU (96 mg, 0.25 mmol, 1.00 equiv), DIPEA (65 mg, 0.50 mmol, 2.00 equiv), Int-A4 (47 mg, 0.25 mmol, 1.00 equiv) in DMF (2 mL) was stirred overnight at 25° C. After concentration, the residue was purified by C18 reverse phase chromatography eluting with H₂O/CH₃CN yielding the title compound (56.1 mg 39%) as a white solid. LCMS (ESI, m/z): 568.22 [M+H]⁺, ¹H NMR (Methanol-d₄, 400 MHz) δ: 8.42 (dd, J=2.3, 0.8 Hz, 1H), 8.21 (s, 1H), 7.77-7.74 (dd, J=9.1, 2.4 Hz, 1H), 7.40-7.36 (t, J=7.9 Hz, 1H), 7.04-7.00 (m, 2H), 6.94-6.87 (m, 2H), 4.24-4.21 (dd, J=10.3, 3.5 Hz, 1H), 4.07-4.03 (dd, J=10.3, 6.8 Hz, 1H), 3.83 (dr, 4H), 3.77-3.35 (m, 2H), 3.41-3.35 (m, 2H), 2.43-2.40 (m, 3H), 2.21-2.19 (m, 1H), 1.55-1.47 (m, 1H), 1.14-1.22 (d, J=6.3 Hz, 3H).

Example 71: 6-(4-[[3-([4-[6-oxo-5-(trifluoromethyl)-1,6-dihydropyridazin-4-yl]morpholin-3-yl]methoxy)phenyl]carbonyl]piperazin-1-yl)pyridine-3-carbonitrile

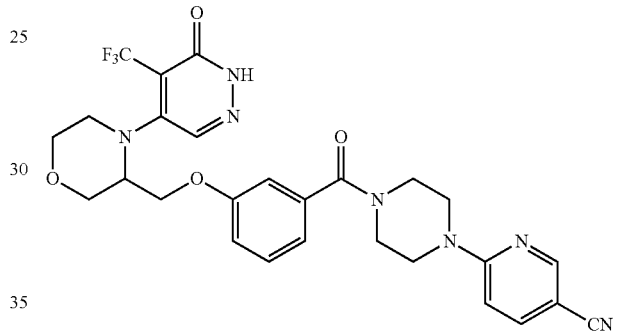

Step 1: Synthesis of 5-[3-(hydroxymethyl)morpholin-4-yl]-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (1000 mg, 3.04 mmol, 1 equiv), piperidin-2-ylmethanol hydrochloride (922.4 mg, 6.08 mmol, 2 equiv), TEA (923.3 mg, 9.12 mmol, 3 equiv) in EtOH (10 mL) was stirred for 4 h at 60° C. The resulting mixture was concentrated under vacuum. The residue was applied onto a silica gel column eluting with EtOAc/petroleum ether (80/20) to afford 442 mg (35.49%) of the title compound as a yellow solid. LCMS (ESI, m/z): 410.16 [M+H]⁺.

Step 2: Synthesis of Methyl 3-([4-[6-oxo-5-(trifluoromethyl)-1-[[2-(trimethylsilyl)ethoxy]methyl]-1,6-dihydropyridazin-4-yl]morpholin-3-yl]methoxy)benzoate A solution of 5-[3-(hydroxymethyl)morpholin-4-yl]-4-(trifluoromethyl)-2-[[2-(trimethylsilyl)ethoxy]methyl]-2,3-dihydropyridazin-3-one (420 mg, 1.03 mmol, 1 equiv), [Pd(allyl)Cl]₂ (37 mg, 0.10 mmol, 0.099 equiv), Rockphos (48.1 mg, 0.10 mmol, 0.1 equiv), Cs₂CO₃ (668.4 mg, 2.05 mmol, 2 equiv), methyl 3-bromobenzoate (286.7 mg, 1.33 mmol, 1.3 equiv) in toluene (5 mL) under an inert atmosphere of nitrogen was stirred for 6 h at 80° C. After concentration, the residue was applied onto a silica gel column eluting with EtOAc/petroleum ether (43/57) to afford 427 mg (76.58%) of the title compound as red oil. LCMS (ESI, m/z): 544.20 [M+H]+.

Step 3: Synthesis of Methyl 3-([4-[6-oxo-5-(trifluoromethyl)-1,6-dihydropyridazin-4-yl]morpholin-3-yl]methoxy)benzoate Hydrochloride A solution of methyl 3-([4-[6-oxo-5-(trifluoromethyl)-1-[[2-(trimethylsilyl)ethoxy]methyl]-1,6-dihydropyridazin-4-yl]morpholin-3-yl]methoxy)benzoate (427 mg) in HCl/dioxane (5 mL) was stirred for 24 h at room temperature. The resulting mixture was concentrated under vacuum. This resulted in 353 mg of the title compound as yellow oil. LCMS (ESI, m/z): 414.12 [M+H]+.

Step 4: Synthesis of 3-([4-[6-oxo-5-(trifluoromethyl)-1,6-dihydropyridazin-4-yl]morpholin-3-yl]methoxy)benzoic Acid A solution of methyl 3-([4-[6-oxo-5-(trifluoromethyl)-1,6-dihydropyridazin-4-yl]morpholin-3-yl]methoxy)benzoate (353 mg, 0.85 mmol, 1 equiv), LiOH.H2O (165.0 mg, 3.93 mmol, 4.604 equiv) in MeOH (4 mL) and H2O (1 mL) was stirred for 5 h at room temperature. The resulting solution was diluted with 5 mL of H2O, and the pH value of the solution was adjusted to 6 with HCl (40%). The solids were collected by filtration. This resulted in 254 mg (74.48%) of the title compound as a white solid. LCMS (ESI, m/z): 400.10 [M+H]+.

Step 5: Synthesis of 6-(4-[[3-([4-[6-oxo-5-(trifluoromethyl)-1,6-dihydropyridazin-4-yl]morpholin-3-yl]methoxy)phenyl]carbonyl]piperazin-1-yl)pyridine-3-carbonitrile A solution of 3-([4-[6-oxo-5-(trifluoromethyl)-1,6-dihydropyridazin-4-yl]morpholin-3-yl]methoxy)benzoic acid (244 mg, 0.61 mmol, 1 equiv), DIPEA (236.9 mg, 1.83 mmol, 3 equiv), HATU (255.6 mg, 0.67 mmol, 1.1 equiv), Int-A4 (151.0 mg, 0.67 mmol, 1.1 equiv) in DMF (5 mL) was stirred for 5 h at room temperature. After concentration, the residue was purified by C18 reverse phase chromatography eluting with H2O/CH3CN. The residue was further purified by Prep-HPLC yielding the title compound (137.2 mg, 39.42%) as a white solid. LCMS (ESI, m/z): 570.20 [M+H]+, 1H NMR (300 MHz, DMSO-d6) δ: 12.72 (s, 1H), 8.53 (d, J=2.3 Hz, 1H), 8.01 (s, 1H), 7.91 (dd, J=9.1, 2.4 Hz, 1H), 7.34 (t, J=7.8 Hz, 1H), 7.04-6.91 (m, 2H), 6.86 (d, J=9.6 Hz, 2H), 4.44-4.33 (t, J=9.9 Hz, 2H), 4.11 (s, 1H), 3.93 (t, J=13.4 Hz, 2H), 3.69 (d, J=11.2 Hz, 7H), 3.55 (d, J=11.2 Hz, 4H), 3.19 (d, J=12.4 Hz, 1H).

Example 72 Isomer A: 6-[4-[(6-[[(1S)-2-[6-oxo-5-(trifluoromethyl)-1,6-dihydropyridazin-4-yl]-2,3-dihydro-1H-isoindol-1-yl]methoxy]pyrazin-2-yl)carbonyl]piperazin-1-yl]pyridine-3-carbonitrile and Example 72 Isomer B: 6-[4-[(6-[[(1R)-2-[6-oxo-5-(trifluoromethyl)-1,6-dihydropyridazin-4-yl]-2,3-dihydro-1H-isoindol-1-yl]methoxy]pyrazin-2-yl)carbonyl]piperazin-1-yl]pyridine-3-carbonitrile

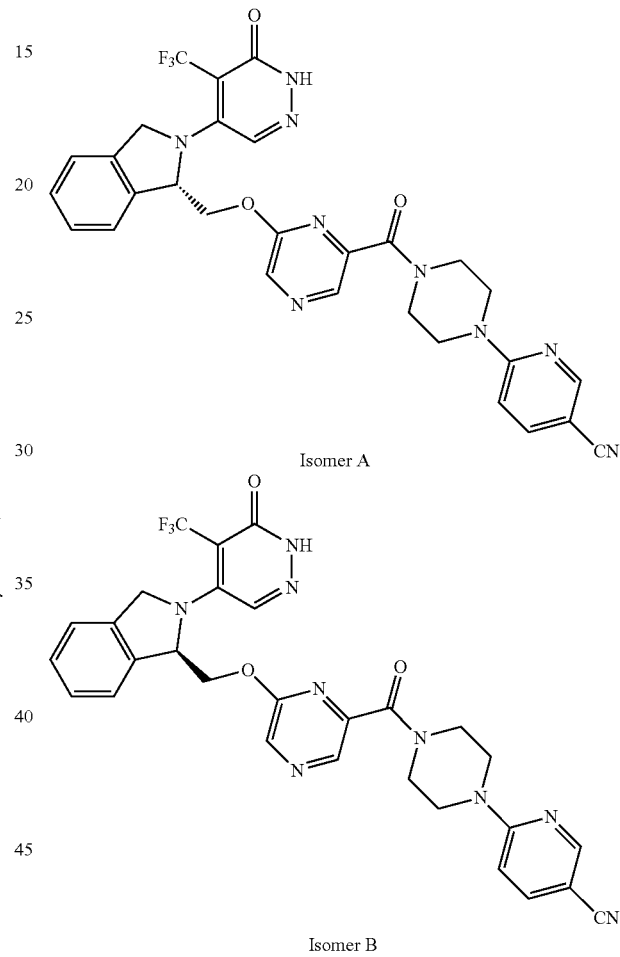

Isomer A

Isomer B

Step 1: Synthesis of Methyl 6-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrazine-2-carboxylate A solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1.00 equiv), [Pd(allyl)Cl]2 (42 mg, 0.11 mmol, 0.10 equiv), Rockphos (53 mg, 0.11 mmol, 0.10 equiv), methyl 6-bromopyrazine-2-carboxylate (490 mg, 2.26 mmol, 2.00 equiv), Cs2CO3 (740 mg, 2.27 mmol, 2.00 equiv) in toluene (7 mL) was stirred for 5 h under an atmosphere of nitrogen at 80° C. The reaction mixture was concentrated under vacuum and the residue was applied onto a silica gel column eluting with EtOAc/petroleum ether (4/6) to afford 555 mg (85%) of the title compound as a yellow solid. LCMS (ESI, m/z): 578.20 [M+H]+.

Step 2: Synthesis of 6-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrazine-2-carboxylic Acid A solution of 6-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrazine-2-carboxylate (555 mg, 0.96 mmol, 1.00 equiv), LiOH hydrate (202 mg, 4.81 mmol, 5.00 equiv) in THF (15 mL) and water (3 mL) was stirred for 2 h at room temperature. The resulting mixture was concentrated under vacuum. The pH value of the solution was adjusted to 6 with hydrochloric acid (1 M). The solids were collected by filtration to afford 468 mg (86%) of the title compound as an off-white solid. LCMS (ESI, m/z): 564.18 [M+H]+.

Step 3: Synthesis of 6-(4-[[6-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrazin-2-yl]carbonyl]piperazin-1-yl)pyridine-3-carbonitrile A solution of 6-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)pyrazine-2-carboxylic acid (220 mg, 0.39 mmol, 1.00 equiv), Int-A4 (88 mg, 0.39 mmol, 1.00 equiv), DIPEA (151 mg, 1.17 mmol, 3.00 equiv), HATU (223 mg, 0.59 mmol, 1.50 equiv) in DMF (3 mL) was stirred for 1.5 h at room temperature. The resulting solution was purified by C18 reverse phase chromatography eluting with H2O/CH3CN to afford 133 mg (46%) of the title compound as a white solid. LCMS (ESI, m/z): 734.28 [M+H]+

Step 4: Synthesis of 6-[4-[(6-[[(1S)-2-[6-oxo-5-(trifluoromethyl)-1,6-dihydropyridazin-4-yl]-2,3-dihydro-1H-isoindol-1-yl]methoxy]pyrazin-2-yl)carbonyl]piperazin-1-yl]pyridine-3-carbonitrile and 6-[4-[(6-[[(1R)-2-[6-oxo-5-(trifluoromethyl)-1,6-dihydropyridazin-4-yl]-2,3-dihydro-1H-isoindol-1-yl]methoxy]pyrazin-2-yl)carbonyl]piperazin-1-yl]pyridine-3-carbonitrile A solution of 6-(4-[[6-([2-[6-oxo-5-(trifluoromethyl)-1-[[2-(trimethyl silyl)ethoxy]methyl]-1,6-dihydropyridazin-4-yl]-2,3-dihydro-1H-isoindol-1-yl]methoxy)pyrazin-2-yl]carbonyl]piperazin-1-yl)pyridine-3-carbonitrile in hydrogen chloride/dioxane (7 mL) was stirred for 4 h at room temperature. After concentration, the residue was purified by C18 reverse phase chromatography eluting with H2O/CH3CN. The residue was further purified by Prep-HPLC and Chiral-Prep-HPLC (CHIRALPAK IC-3, 0.46*5 cm; 3 um, (Hex:DCM=1:1) (0.1% DEA):(MeOH:EtOH=1:1)=30:70, 1.0 mL/min) yielding the title compounds as white solids. The absolute stereochemistry was assigned based on a protein X-ray crystal structure obtained of Example 18 Isomer B which confirmed (S)-absolute stereochemistry and was observed to be the more potent enantiomer.

Example 72 Isomer A 12 mg, 34%, LCMS (ESI, m/z): 604.55 [M+H]+, 1H NMR (400 MHz, Methanol-d4) δ: 8.48-8.38 (m, 3H), 8.27 (s, 1H), 7.79 (dd, J=9.1, 2.4 Hz, 1H), 7.50 (d, J=6.2 Hz, 1H), 7.44-7.34 (m, 3H), 6.89 (dd, J=9.1, 0.8 Hz, 1H), 6.14 (s, 1H), 5.23 (d, J=14.7 Hz, 1H), 4.99 (dd, J=11.6, 4.6 Hz, 1H), 4.75-4.61 (m, 2H), 3.89 (m, 4H), 3.76 (d, J=5.8 Hz, 2H), 3.69 (d, J=5.3 Hz, 2H). tR=3.172 min.

Example 72 Isomer B 11.5 mg, 33%, LCMS (ESI, m/z): 604.55 [M+H]+, tR=4.791 min.

Example 73: 6-[4-[(4-[[(2S)-1-[6-oxo-5-(trifluoromethyl)-1,6-dihydropyridazin-4-yl]pyrrolidin-2-yl]methoxy]pyridin-2-yl)carbonyl]piperazin-1-yl]pyridine-3-carbonitrile

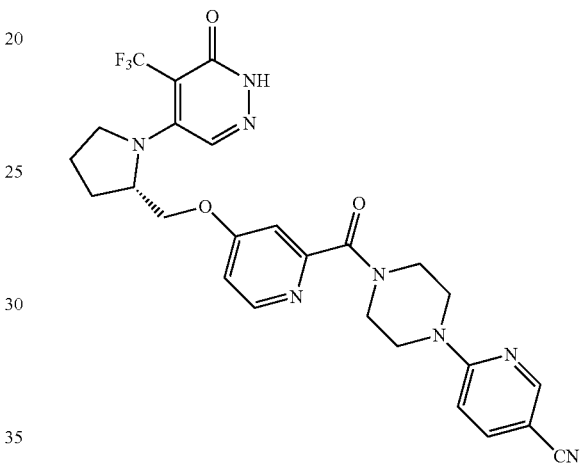

Step 1: Synthesis of Methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-2-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (360 mg, 0.91 mmol, 1.00 equiv), [Pd(allyl)Cl]2 (35.519 mg, 0.10 equiv), Rockphos (42.94164 mg, 0.09 mmol, 0.10 equiv), methyl 4-bromopyridine-2-carboxylate (393.649 mg, 1.82 mmol, 2.00 equiv) and Cs2CO3 (895.45 mg, 3.00 equiv) in toluene (15 mL) was stirred for 5 h at 80° C. under an atmosphere of nitrogen. The resulting solution was concentrated under vacuum and the residue was applied onto a silica gel column eluting with EtOAc/petroleum ether (1:3) to afford 210 mg (43%) of the title compound as a yellow oil. LCMS (ESI, m/z): 529.20 [M+H]+.

Step 2: Synthesis of 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-2-carboxylic Acid A solution of methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-2-carboxylate (189 mg, 0.36 mmol, 1.00 equiv) and LiOH (25.7726 mg, 1.08 mmol, 3.00 equiv) in water (4 mL) and THF (16 mL) was stirred for 2 h at room temperature. The pH value of the solution was adjusted to 2 with hydrogen chloride (12 M) and the solids were collected by filtration to afford 160 mg (87%) of the title compound as a solid. LCMS (ESI, m/z): 515.19[M+H]$^+$.

Step 3: Synthesis of 4-[[(2S)-1-[6-oxo-5-(trifluoromethyl)-1,6-dihydropyridazin-4-yl]pyrrolidin-2-yl]methoxy]pyridine-2-carboxylic Acid A solution of 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridine-2-carboxylic acid (160 mg, 0.31 mmol, 1.00 equiv) in hydrogen chloride/dioxane (5 mL, 4 M) was stirred for 3 h at room temperature, and the resulting solution was concentrated under vacuum to afford 85 mg (71%) of the title compound as a solid. LCMS (ESI, m/z): 385.10[M+H]$^+$.

Step 4: Synthesis of 6-[4-[(4-[[(2S)-1-[6-oxo-5-(trifluoromethyl)-1,6-dihydropyridazin-4-yl]pyrrolidin-2-yl]methoxy]pyridin-2-yl)carbonyl]piperazin-1-yl]pyridine-3-carbonitrile A solution of 4-[[(2S)-1-[6-oxo-5-(trifluoromethyl)-1,6-dihydropyridazin-4-yl]pyrrolidin-2-yl]methoxy]pyridine-2-carboxylic acid (15 mg, 0.04 mmol, 1.00 equiv), HATU (14.82 mg, 1.00 equiv), DIPEA (15.12108 mg, 3.00 equiv) and Int-A4 (8.8125 mg, 0.05 mmol, 1.20 equiv) in DMF (2 mL) was stirred for 2 h at room temperature. The resulting solution was purified by C18 reverse phase chromatography eluting with H$_2$O/CH$_3$CN. After concentrating the residue was further purified by Prep-HPLC yielding the title compound (12 mg, 3.0%) as a white solid. LCMS (ESI, m/z): 555.10 [M+H]$^+$. $^1$HNMR (Methanol-d$_4$, 400 MHz) δ 8.44 (dd, J=8.8, 3.2 Hz, 2H), 8.22 (s, 1H), 7.79 (dd, J=9.2, 2.4 Hz, 1H), 7.156 (s, 1H), 7.07 (dd, J=5.6, 2.4 Hz, 1H), 6.91 (d, J=8.8 Hz, 1H), 4.95-4.91 (m, 1H), 4.37 (dd, J=10.4, 3.6 Hz, 1H), 4.24 (dd, J=10.4, 6.4 Hz, 1H), 3.92-3.84 (m, 4H), 3.76-3.74 (m, 3H), 3.55 (t, J=5.2 Hz, 2H), 3.47-3.38 (m, 1H), 2.39 (m, 1H), 2.08 (t, J=5.6 Hz, 1H), 1.99-1.78 (m, 2H).

Example 74: 6-[4-[(6-[[(2S)-1-[6-oxo-5-(trifluoromethyl)-1,6-dihydropyridazin-4-yl]pyrrolidin-2-yl]methoxy]pyrazin-2-yl)carbonyl]piperazin-1-yl]pyridine-3-carbonitrile

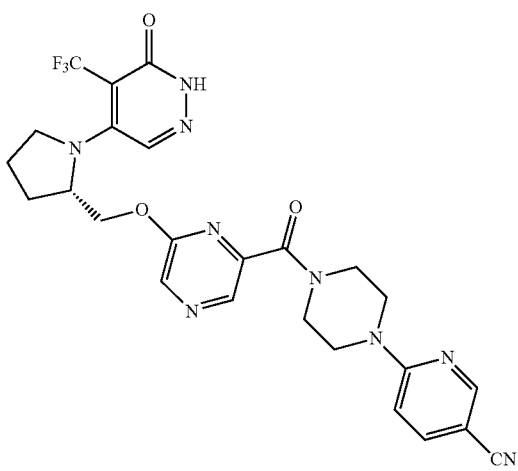 [SMILES: N#Cc1ccc(N2CCN(C(=O)c3cncc(OC[C@@H]4CCCN4c4cn[nH]c(=O)c4C(F)(F)F)n3)CC2)nc1]

Step 1: Synthesis of 6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazine-2-carboxylate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (700 mg, 1.78 mmol, 1 equiv), K$_2$CO$_3$ (740 mg, 5.35 mmol, 3.010 equiv), methyl 6-bromopyrazine-2-carboxylate (464 mg, 2.14 mmol, 1.202 equiv) in DMF (15 mL) was stirred for 12 h at 90° C. The reaction was quenched by the addition of 5 mL of water. The resulting solution was extracted with 3×20 ml of EtOAc and the organic layers were combined and concentrated under vacuum. The residue was applied onto a silica gel column eluting with EtOAc/petroleum ether (25/75) to afford 500 mg (53.07%) of the title compound as yellow oil. LCMS (ESI, m/z): 530.20 [M+H]$^+$.

Step 2: Synthesis of 6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazine-2-carboxylic Acid A solution of methyl 6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazine-2-carboxylate (500 mg, 0.94 mmol, 1 equiv), LiOH.H$_2$O (198 mg, 4.72 mmol, 4.998 equiv) in MeOH (20 mL) was stirred for 2 h at room temperature. The resulting solution was extracted with 2×15 ml of EtOAc. The pH value of the solution was adjusted to 5 with HCl (35%). The resulting solution was extracted with 3×30 mL of DCM and the organic layers combined and dried over anhydrous sodium sulfate. The organic layers was concentrated under vacuum to afford 400 mg (crude) of the title compound as yellow oil. LCMS (ESI, m/z): 516.18 [M+H]$^+$.

Step 3: Synthesis of 6-[4-[(6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazin-2-yl)carbonyl]piperazin-1-yl]pyridine-3-carbonitrile A solution of 6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazine-2-carboxylic acid (270 mg, 0.52 mmol, 1 equiv), Int-A4 (118.7 mg, 0.63 mmol, 1.204 equiv), DIPEA (202 mg, 1.56 mmol, 2.984 equiv), HATU (298 mg, 0.78 mmol, 1.497 equiv) in DMF (2 mL) was stirred for 2 h at room temperature. After concentration, the residue was purified by C18 reverse phase chromatography eluting with H$_2$O/CH$_3$CN to afford 300 mg (83.53%) of the title compound as yellow oil. LCMS (ESI, m/z): 686.28 [M+H]$^+$.

Step 4: Synthesis of 6-[4-[(6-[[(2S)-1-[6-oxo-5-(trifluoromethyl)-1,6-dihydropyridazin-4-yl]pyrrolidin-2-yl]methoxy]pyrazin-2-yl)carbonyl]piperazin-1-yl]pyridine-3-carbonitrile A solution of 6-[4-[(6-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrazin-2-yl)carbonyl]piperazin-1-yl]pyridine-3-carbonitrile (300 mg, 0.44 mmol, 1 equiv) in HCl/dioxane (10 ml) was stirred for 12 h at room temperature. After concentration, the residue was purified by C18 reverse phase chromatography eluting with H₂O/CH₃CN. Then the residue was further purified by Prep-HPLC yielding the title compound (48.0 mg, 19.75%) as a white solid. LCMS (ESI, m/z): 556.51 [M+H]⁺, ¹HNMR (DMSO-d₆, 300 MHz) δ: 12.48 (s, 1H), 8.53 (d, J=2.3 Hz, 1H), 8.45 (s, 1H), 8.37 (s, 1H), 8.21 (s, 1H), 7.92 (dd, J=9.1, 2.4 Hz, 1H), 6.94 (d, J=9.1 Hz, 1H), 4.60 (dd, J=11.4, 5.0 Hz, 1H), 4.39 (dd, J=11.4, 4.2 Hz, 1H), 3.88-3.79 (m, 1H), 3.87-3.81 (m, 6H), 3.41-3.30 (m, 3H), 3.24 (t, J=8.7 Hz, 1H), 2.28-2.16 (m, 1H), 1.95 (m, 2H), 1.79-1.68 (m, 1H).

Example 75: 6-[4-[(3-[[(2S,4R)-4-methyl-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile

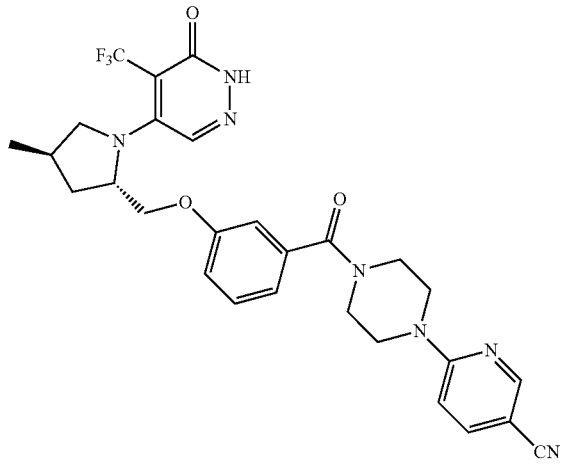 [SMILES: C[C@@H]1C[C@@H](COc2cccc(C(=O)N3CCN(c4ccc(C#N)cn4)CC3)c2)N(c2cn[nH]c(=O)c2C(F)(F)F)C1]

Step 1: Synthesis of Tert-Butyl (2S,4R)-2-(hydroxymethyl)-4-methylpyrrolidine-1-carboxylate To a stirred solution of (2S,4R)-1-[(tert-butoxy)carbonyl]-4-methylpyrrolidine-2-carboxylic acid (1.8 g, 7.85 mmol, 1.00 equiv) in THF (20 mL) BH₃-THF (10 mL) was added dropwise at 0° C. The resulting solution was stirred for 2 h at room temperature. The reaction was then quenched by the addition of 10 mL of methanol. The resulting mixture was concentrated under vacuum. The residue was applied onto a silica gel column with EtOAc/petroleum ether (2:3). This resulted in 1.4 g (83%) of the title compound as a solid. LCMS (ESI, m/z): 216.16 [M+H]⁺.

Step 2: Synthesis of [(2S,4R)-4-methylpyrrolidin-2-yl]methanol

A solution of tert-butyl (2S,4R)-2-(hydroxymethyl)-4-methylpyrrolidine-1-carboxylate (1.4 g, 6.50 mmol, 1.00 equiv) in hydrogen chloride/dioxane (10 mL) was stirred for 1 h at room temperature. The resulting mixture was concentrated under vacuum. This resulted in 1 g (crude) of the title compound as oil. LCMS (ESI, m/z): 116.11 [M+H]⁺.

Step 3: Synthesis of 5-[(2S,4R)-2-(hydroxymethyl)-4-methylpyrrolidin-1-yl]-4-(trifluoromethyl)-2-[[2-(trimethylsilyl)ethoxy]methyl]-2,3-dihydropyridazin-3-one A solution of [(2S,4R)-4-methylpyrrolidin-2-yl]methanol hydrochloride (1 g, 6.59 mmol, 1.00 equiv), Int-A6 (2.1 g, 6.39 mmol, 0.97 equiv) and TEA (3 mL) in ethanol (15 mL) was stirred for 1 h at 60° C. The resulting mixture was concentrated under vacuum. The residue was applied onto a silica gel column with EtOAc/petroleum ether (1:1). This resulted in 1.5 g (56%) of the title compound as a solid. LCMS (ESI, m/z): 408.19 [M+H]⁺.

Step 4: Synthesis of Methyl 3-[[(2S,4R)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]benzoate A solution of 5-[(2S,4R)-2-(hydroxymethyl)-4-methylpyrrolidin-1-yl]-4-(trifluoromethyl)-2-[[2-(trimethylsilyl)ethoxy]methyl]-2,3-dihydropyridazin-3-one (850 mg, 2.09 mmol, 1.00 equiv), methyl 3-bromobenzoate (900 mg, 4.19 mmol, 2.01 equiv), Pd₂(dba)₃·CHCl₃ (217 mg), Rockphos (200 mg) and Cs₂CO₃ (2 g, 6.14 mmol, 2.94 equiv) in toluene (10 mL) was stirred overnight at 80° C. under an inert atmosphere of nitrogen. The resulting solution was diluted with 200 mL of EtOAc. The resulting mixture was washed with 50 mL of water and 50 mL of brine. The organic layer was dried over anhydrous sodium sulfate and concentrated under vacuum. The residue was applied onto a silica gel column with EtOAc/petroleum ether (1:1). This resulted in 1 g (89%) of the title compound as oil. LCMS (ESI, m/z): 542.23 [M+H]⁺.

Step 5: Synthesis of 3-[[(2S,4R)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic Acid To a stirred solution of methyl 3-[[(2S,4R)-4-methyl-1-[6-oxo-5-(trifluoromethyl)-1-[[2-(trimethyl-silyl)ethoxy]methyl]-1,6-dihydropyridazin-4-yl]pyrrolidin-2-yl]methoxy]benzoate (1 g, 1.85 mmol, 1.00 equiv) in THF (15 mL) and water (5 mL), LiOH (250 mg, 10.44 mmol, 5.65 equiv) was added. The resulting solution was stirred overnight at room temperature. The pH of the solution was adjusted to 1 with hydrogen chloride (1 M). The resulting solution was diluted with 250 mL of EtOAc. The resulting mixture was washed with 50 mL of brine. The organic layer was dried over anhydrous sodium sulfate and concentrated under vacuum. This resulted in 900 mg (92%) of the title compound as a solid. LCMS (ESI, m/z): 528.21 [M+H]⁺.

Step 6: Synthesis of 3-[[(2S,4R)-4-methyl-1-[6-oxo-5-(trifluoromethyl)-1,6-dihydropyridazin-4-yl]pyrrolidin-2-yl]methoxy]benzoic Acid A solution of 3-[[(2S,4R)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]benzoic acid (350 mg, 0.66 mmol, 1.00 equiv) in hydrogen chloride/dioxane (10 mL) was stirred for 6 h at room temperature. The resulting mixture was concentrated under vacuum. This resulted in 250 mg (crude) of the title compound as a solid. LCMS (ESI, m/z): 398.13 [M+H]⁺.

Step 7: Synthesis of 6-[4-[(3-[[(2S,4R)-4-methyl-1-[6-oxo-5-(trifluoromethyl)-1,6-dihydropyridazin-4-yl]pyrrolidin-2-yl]methoxy]phenyl)carbonyl]piperazin-1-yl]pyridine-3-carbonitrile To a stirred solution of 3-[[(2S,4R)-4-methyl-1-[6-oxo-5-(trifluoromethyl)-1,6-dihydropyridazin-4-yl]pyrrolidin-2- yl]methoxy]benzoic acid (250 mg, 0.63 mmol, 1.00 equiv) in DMF (10 mL), DIPEA (0.5 mL), Int-A4 (154 mg, 0.82 mmol, 1.30 equiv) and HATU (310 mg, 0.82 mmol, 1.30 equiv) were added. The resulting solution was stirred overnight at room temperature. After concentration, the residue was purified by C18 reverse phase chromatography eluting with $H_2O/CH_3CN$. The residue was further purified by Prep-HPLC yielding the title compound (48.2 mg, 13%) as a white solid. LCMS (ESI, m/z): 568.30 [M+H]$^+$. $^1$H NMR (300 MHz, DMSO-$d_6$) δ 12.45 (s, 1H), 8.49 (d, J=2.2 Hz, 1H), 8.17 (s, 1H), 7.88 (dd, J=9.1, 2.4 Hz, 1H), 7.33 (t, J=7.9 Hz, 1H), 6.99-6.86 (m, 4H), 4.96-4.86 (m, 1H), 4.12 (dd, J=10.2, 4.0 Hz, 1H), 3.99 (dd, J=10.3, 6.2 Hz, 1H), 3.89-3.52 (m, 8H), 3.41-3.37 (m, 1H), 2.88 (d, J=10.8 Hz, 1H), 2.45-2.36 (m, 1H), 1.98-1.89 (m, 1H), 1.88-1.78 (m, 1H), 0.85 (d, J=6.9 Hz, 3H).

Example 76: 6-[4-(2-[[(2S)-1-[6-oxo-5-(trifluoromethyl)-1,6-dihydropyridazin-4-yl]pyrrolidin-2-yl]methoxy]acetyl)piperazin-1-yl]pyridine-3-carbonitrile

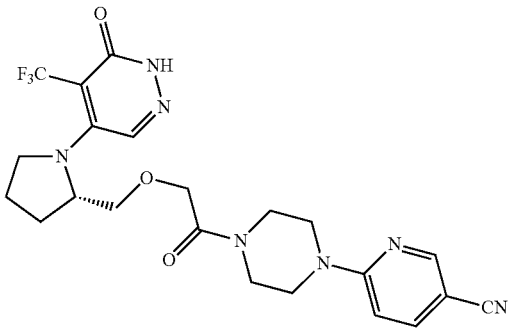 [SMILES: N#Cc1ccc(N2CCN(C(=O)COC[C@@H]3CCCN3c3cn[nH]c(=O)c3C(F)(F)F)CC2)nc1]

Step 1: Synthesis of Tert-Butyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]acetate To a solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (10 g, 25.41 mmol, 1.00 equiv) and $Cs_2CO_3$ (41 g, 125.84 mmol, 5.00 equiv) in DMF (150 mL) was added tert-butyl 2-chloroacetate (38 g, 252.32 mmol, 10.00 equiv), and the resulting solution was stirred for 20 h at 60° C. The solids were filtered out, and the resulting solution was diluted with 200 mL of EtOAc, washed with 3×200 mL of water and 2×200 mL of sodium chloride. The organic layer was dried over anhydrous sodium sulfate and concentrated under vacuum, and the residue was applied onto a silica gel column eluting with EtOAc/petroleum ether (18:82) to afford 4.5 g (35%) of the title compound as brown oil. LCMS (ESI, m/z): 508.24[M+H]$^+$.

Step 2: Synthesis of 2-[[(2S)-1-[6-oxo-5-(trifluoromethyl)-1,6-dihydropyridazin-4-yl]pyrrolidin-2-yl]methoxy]acetic Acid A solution of tert-butyl 2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]acetate (1.5 g, 2.95 mmol, 1.00 equiv) and TFA (3 mL) in DCM (15 mL) was stirred for 2 h at room temperature. The resulting solution was concentrated under vacuum, and the residue was further purified by C18 reverse phase chromatography eluting with $H_2O/CH_3CN$ to afford 504 mg (53%) of the title compound as brown oil. LCMS (ESI, m/z): 322.09[M+H]$^+$.

Step 4: Synthesis of 6-[4-(2-[[(2S)-1-[6-oxo-5-(trifluoromethyl)-1,6-dihydropyridazin-4-yl]pyrrolidin-2-yl]methoxy]acetyl)piperazin-1-yl]pyridine-3-carbonitrile A solution of 2-[[(2S)-1-[6-oxo-5-(trifluoromethyl)-1,6-dihydropyridazin-4-yl]pyrrolidin-2-yl]methoxy]acetic acid (115 mg, 0.36 mmol, 1.00 equiv), HATU (136 mg, 0.36 mmol, 1.00 equiv), DIPEA (92 mg, 0.71 mmol, 2.00 equiv) and Int-A4 (80 mg, 0.43 mmol, 1.20 equiv) in DMF (1 mL) was stirred for 2 h at room temperature. The resulting solution was purified by C18 reverse phase chromatography eluting with $H_2O/CH_3CN$ and Prep-HPLC yielding the title compound (11 mg, 6.0%) as a white solid. LCMS (ESI, m/z): 492.15[M+H]$^+$. $^1$H NMR (Methanol-$d_4$, 300 MHz) δ 8.41 (d, J=2.4, 1H), 8.20 (s, 1H), 7.78 (dd, J=9.0, 2.4 Hz, 1H), 6.85 (d, J=9.3 Hz, 1H), 4.69 (s, 1H), 4.27 (s, 2H), 3.77-3.64 (m, 8H), 3.62-3.50 (m, 3H), 3.40-3.36 (m, 1H), 2.28 (t, J=6.0 Hz, 1H), 1.99 (d, J=4.8 Hz, 1H), 1.80-1.68 (m, 2H).

Example 77: 6-[4-(4-[[(2S)-1-[6-oxo-5-(trifluoromethyl)-1,6-dihydropyridazin-4-yl]pyrrolidin-2-yl]methoxy]butanoyl)piperazin-1-yl]pyridine-3-carbonitrile

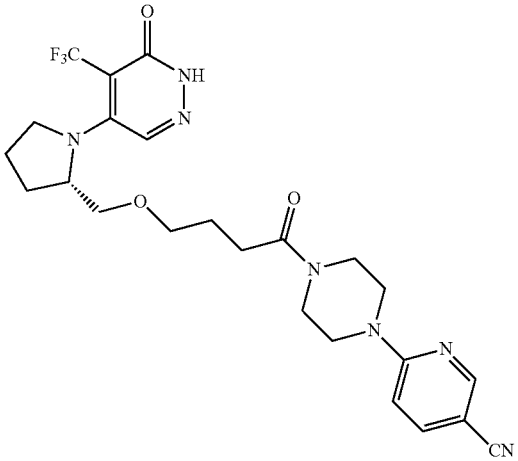 [SMILES: N#Cc1ccc(N2CCN(C(=O)CCCOC[C@@H]3CCCN3c3cn[nH]c(=O)c3C(F)(F)F)CC2)nc1]

Step 1: Synthesis of Methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (600 mg, 1.52 mmol, 1.00 equiv), methyl (2E)-4-bromobut-2-enoate (1.358 g, 7.59 mmol, 5.00 equiv), [Pd(allyl)Cl]$_2$ (28 mg, 0.08 mmol, 0.05 equiv), Rockphos (71 mg, 0.15 mmol, 0.10 equiv) and $Cs_2CO_3$ (995 mg, 3.05 mmol, 2.00 equiv) in toluene (16 mL) was stirred for 12 h at 80° C. The resulting solution was concentrated under vacuum, and the residue was applied onto a silica gel column eluting with EtOAc/petroleum ether (2:3) to afford 400 mg (53%) of the title compound as a light yellow solid. LCMS (ESI, m/z): 492.21 [M+H]⁺.

Step 2: Synthesis of Methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate A solution of methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate (400 mg, 0.81 mmol, 1.00 equiv) and Pd/C (40 mg, 0.10 equiv) in methanol (10 mL) was stirred for 1 h at room temperature under an atmosphere of hydrogen. The solids were filtered out and the resulting solution was concentrated under vacuum to afford 380 mg (95%) of the title compound as a light brown solid. LCMS (ESI, m/z): 494.23 [M+H]⁺.

Step 3: Synthesis of Methyl (S)-4-((1-(6-oxo-5-(trifluoromethyl)-1,6-dihydropyridazin-4-yl)pyrrolidin-2-yl)methoxy)butanoate A solution of methyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate (370 mg, 0.75 mmol, 1.00 equiv) and TFA (1 mL) in DCM (5 mL) was stirred for 45 min at room temperature, and the resulting solution was concentrated under vacuum to afford 357 mg of the title compound as a a crude light brown solid. LCMS (ESI, m/z): 364.14 [M+H]⁺.

Step 4: Synthesis of (S)-4-((1-(6-oxo-5-(trifluoromethyl)-1,6-dihydropyridazin-4-yl)pyrrolidin-2-yl)methoxy)butanoic Acid A solution of methyl 4-[[(2S)-1-[6-oxo-5-(trifluoromethyl)-1,6-dihydropyridazin-4-yl]pyrrolidin-2-yl]methoxy]butanoate (350 mg, 0.96 mmol, 1.00 equiv) and LiOH (115.70 mg, 4.83 mmol, 5.00 equiv) in water (2 mL) and THF (8 mL) was stirred for 40 min at room temperature, and then the resulting solution was concentrated under vacuum. The pH value of the solution was adjusted to 4 with HCl (1 M). The resulting solution was extracted with 3×10 ml of EtOAc and the organic layer were combined and concentrated under vacuum to afford 350 mg of the title compound crude as a a light brown solid. LCMS(ESI, m/z): 350.13 [M+H]+.

Step 3: Synthesis of 6-[4-(4-[[(2S)-1-[6-oxo-5-(trifluoromethyl)-1,6-dihydropyridazin-4-yl]pyrrolidin-2-yl]methoxy]butanoyl)piperazin-1-yl]pyridine-3-carbonitrile A solution of 4-[[(2S)-1-[6-oxo-5-(trifluoromethyl)-1,6-dihydropyridazin-4-yl]pyrrolidin-2-yl]methoxy]butanoic acid (300 mg, 0.86 mmol, 1.00 equiv), Int-A4 (177.24 mg, 0.94 mmol, 1.10 equiv), HATU (325.698 mg, 0.86 mmol, 1.00 equiv) and DIPEA (332.31 mg, 2.57 mmol, 3.00 equiv) in DMF (2 mL) was stirred for 4 h at 80° C. The resulting solution was diluted with 20 ml of water, extracted with 3×20 ml of EtOAc and the organic layers were combined, washed with 20 ml of brine and concentrated under vacuum, and the residue was purified by Prep-HPLC yielding the title compound (135 mg, 30%) as a white solid. LCMS (ESI, m/z): 520.10 [M+H]+, ¹HNMR (CD₃OD-d₄, 300 MHz) δ 8.45 (d, J=2.4 Hz, 1H), 8.21 (s, 1H), 7.80 (dd, J=9.0, 2.4 Hz, 1H), 6.91 (dd, J=9.0, 0.6 Hz, 1H), 4.67 (dt, J=7.9, 4.0 Hz, 1H), 3.82-3.33 (m, 14H), 2.41 (td, J=7.3, 2.4 Hz, 2H), 2.25 (dt, J=13.3, 6.6 Hz, 1H), 2.09-1.94 (m, 1H), 1.90-1.57 (m, 4H).

Example 78: 6-[4-(3-[[(2S,4S)-4-methyl-1-[6-oxo-5-(trifluoromethyl)-1,6-dihydropyridazin-4-yl]pyrrolidin-2-yl]methoxy]propanoyl)piperazin-1-yl]pyridine-3-carbonitrile

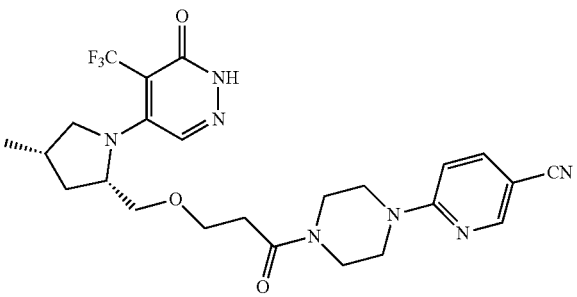 [SMILES: C[C@H]1C[C@@H](COCCC(=O)N2CCN(c3ccc(C#N)cn3)CC2)N(c2cn[nH]c(=O)c2C(F)(F)F)C1]

Step 1: Synthesis of Ethyl 3-[[(2S,4S)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate A solution of 5-[(2S,4S)-2-(hydroxymethyl)-4-methylpyrrolidin-1-yl]-4-(trifluoromethyl)-2-[[2-(trimethylsilyl)ethoxy]methyl]-2,3-dihydropyridazin-3-one (1.1 g, 2.70 mmol, 1.00 equiv), sodium hydride (108 mg, 4.50 mmol, 1.00 equiv), ethyl prop-2-enoate (2.7 g, 26.97 mmol, 10.00 equiv) in THF (25 mL) was stirred for 1 h at 0° C. in an ice/salt bath. After concentration, the residue was applied onto a silica gel column eluting with EtOAc/petroleum ether (3:7) to afford 1 g (73%) of the title compound as a yellow oil. LCMS (ESI, m/z): 508.24 [M+H]⁺.

Step 2: Synthesis of Ethyl 3-[[(2S,4S)-4-methyl-1-[6-oxo-5-(trifluoromethyl)-1,6-dihydropyridazin-4-yl]pyrrolidin-2-yl]methoxy]propanoate A solution of ethyl 3-[[(2S,4S)-4-methyl-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate (1 g, 1.97 mmol, 1.00 equiv) and hydrogen chloride/dioxane (20 mL) in dioxane (2 mL) was stirred overnight at 25° C. After concentration, the residue was purified by C18 reverse phase chromatography eluting with water/CH₃CN (65:35) to afford 530 mg (71%) of the title compound as yellow oil. LCMS (ESI, m/z): 378.16 [M+H]⁺.

Step 3: Synthesis of 3-[[(2S,4S)-4-methyl-1-[6-oxo-5-(trifluoromethyl)-1,6-dihydropyridazin-4-yl]pyrrolidin-2-yl]methoxy]propanoic Acid A solution of ethyl 3-[[(2S,4S)-4-methyl-1-[6-oxo-5-(trifluoromethyl)-1,6-dihydropyridazin-4-yl]pyrrolidin-2-yl]methoxy]propanoate (489 mg, 1.30 mmol, 1.00 equiv), LiOH (93 mg, 3.88 mmol, 3.00 equiv), water (25 mL) in methanol (25 mL) was stirred overnight at 25° C. After concentration, the residue was purified by C18 reverse phase chromatography eluting with water/CH₃CN (77:23) to afford 234 mg (52%) of the title compound as a white solid. LCMS (ESI, m/z): 350.12 [M+H]⁺.

Step 4: Synthesis of 6-[4-(3-[[(2S,4S)-4-methyl-1-[6-oxo-5-(trifluoromethyl)-1,6-dihydropyridazin-4-yl]pyrrolidin-2-yl]methoxy]propanoyl)piperazin-1-yl]pyridine-3-carbonitrile A solution of 3-[[(2S,4S)-4-methyl-1-[6-oxo-5-(trifluoromethyl)-1,6-dihydropyridazin-4-yl]pyrrolidin-2-yl]methoxy]propanoic acid (234 mg, 0.67 mmol, 1.00 equiv), DIPEA (173 mg, 1.34 mmol, 2.00 equiv), HATU (254 mg, 0.67 mmol, 1.00 equiv), Int-A4 (126 mg, 0.67 mmol, 1.00 equiv) in DMF (2 mL) was stirred overnight at 25° C. After concentration, the residue was purified by C18 reverse phase chromatography eluting with water/CH₃CN yielding the title compound (188.8 mg 54%) as a white solid. LCMS (ESI, m/z): 520.22 [M+H]⁺, ¹H NMR (Methanol-d₄, 400 MHz) δ: 8.44 (dd, J=2.3, 0.8 Hz, 1H), 8.13 (s, 1H), 7.79-7.76 (dd, J=9.0, 2.3 Hz, 1H), 6.89-6.88 (dd, J=9.1, 0.9 Hz, 1H), 4.67-4.60 (m, 1H), 3.83-3.65 (m, 11H), 3.48-3.44 (m, 1H), 3.37-3.35 (m, 1H), 3.28 (m, 1H), 2.66-2.62 (m, 2H), 2.32-2.29 (m, 1H), 2.20-2.03 (m, 1H), 1.33-1.30 (td, J=12.1, 9.0 Hz, 1H), 1.10-1.09 (d, J=6.3 Hz, 3H).

Example 79 Isomer A: 6-[4-[(2Z)-4-[[(1S)-2-[6-oxo-5-(trifluoromethyl)-1,6-dihydropyridazin-4-yl]-2,3-dihydro-1H-isoindol-1-yl]methoxy]but-3-enoyl]piperazin-1-yl]pyridine-3-carbonitrile and Example 79 Isomer B: 6-[4-[(2Z)-4-[[(1R)-2-[6-oxo-5-(trifluoromethyl)-1,6-dihydropyridazin-4-yl]-2,3-dihydro-1H-isoindol-1-yl]methoxy]but-3-enoyl]piperazin-1-yl]pyridine-3-carbonitrile and Example 79 Isomer C: 6-[4-[(2E)-4-[[(1S)-2-[6-oxo-5-(trifluoromethyl)-1,6-dihydropyridazin-4-yl]-2,3-dihydro-1H-isoindol-1-yl]methoxy]but-2-enoyl]piperazin-1-yl]pyridine-3-carbonitrile and Example 79 Isomer D: 6-[4-[(2E)-4-[[(1R)-2-[6-oxo-5-(trifluoromethyl)-1,6-dihydropyridazin-4-yl]-2,3-dihydro-1H-isoindol-1-yl]methoxy]but-2-enoyl]piperazin-1-yl]pyridine-3-carbonitrile

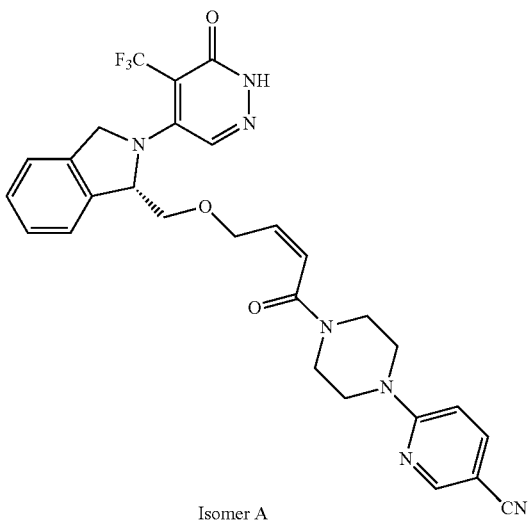

Isomer A

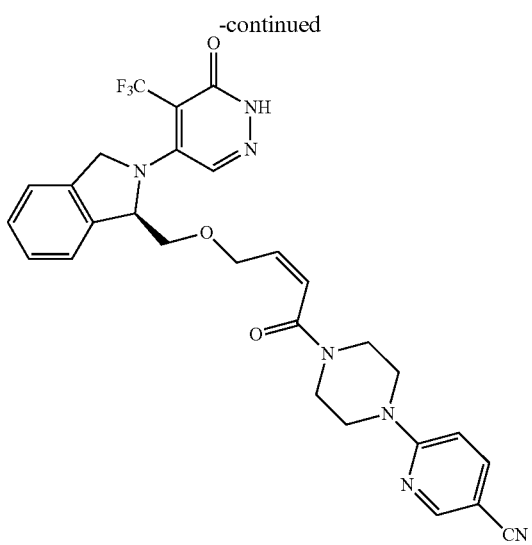

Isomer B

Isomer C

Isomer D

Step 1: Synthesis of 2,3-dihydro-H-isoindol-1-ylmethanol Hydrochloride

A solution of tert-butyl 1-(hydroxymethyl)-2,3-dihydro-1H-isoindole-2-carboxylate (1.05 g, 4.21 mmol, 1.00 equiv) in hydrogen chloride/dioxane (10 mL, 4 M) was stirred for 2 h at room temperature. The resulting solution was concentrated under vacuum to afford 997 mg of the title compound as a pink crude solid. LCMS (ESI, m/z): 150.08 [M+H]+.

Step 2: Synthesis of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one A solution of 2,3-dihydro-1H-isoindol-1-ylmethanol hydrochloride (997 mg, 5.37 mmol, 1.00 equiv), TEA (1.08 g, 10.67 mmol, 2.00 equiv) and Int-A6 (1.77 g, 5.38 mmol, 1.00 equiv) in ethanol (10 mL) was stirred for 2 h at 60° C. and concentrated under vacuum to afford 1.3 g (55%) of the title compound as a pink solid. LCMS (ESI, m/z): 442.17 [M+H]+.

Step 3: Synthesis of Methyl (2E)-4-([2-[6-oxo-5-(trifluoromethyl)-1-[[2-(trimethylsilyl)ethoxy] methyl]-1,6-dihydropyridazin-4-yl]-2,3-dihydro-1H-isoindol-1-yl]methoxy)but-2-enoate Under nitrogen, a solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (1.3 g, 2.94 mmol, 1.00 equiv), methyl (2E)-4-bromobut-2-enoate (2.61 g, 14.58 mmol, 5.00 equiv), Pd$_2$(dba)$_3$ (60 mg, 0.07 mmol, 0.05 equiv), RuPhos (55 mg, 0.12 mmol, 0.10 equiv) and Cs$_2$CO$_3$ (1.91 g, 5.86 mmol, 2.00 equiv) in toluene (30 mL) was stirred for 12 h at 80° C. The resulting solution was concentrated under vacuum, and the residue was applied onto a silica gel column eluting with EtOAc/petroleum ether (1:4) to afford 1.02 g (64%) of the title compound as a yellow solid. LCMS (ESI, m/z): 540.21 [M+H]+.

Step 4: Synthesis of (2E)-4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)but-2-enoic Acid A solution of methyl (2E)-4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)but-2-enoate (1.02 g, 1.89 mmol, 1.00 equiv) and LiOH (397 mg, 16.58 mmol, 5.00 equiv) in THF (10 mL) and water (2 mL) was stirred for 1 h at room temperature. The resulting solution was diluted with 3 mL of water, and the pH value of the solution was adjusted to 4 with hydrogen chloride (1 M). The resulting solution was filtered and the solid was collected to afford 832 mg (84%) of the title compound as a yellow solid. LCMS (ESI, m/z): 525.19 [M+H]+.

Step 5: Synthesis of (2E)-1-([2-[6-oxo-5-(trifluoromethyl)-1,6-dihydropyridazin-4-yl]-2,3-dihydro-1H-isoindol-1-yl]methoxy)but-2-enoic Acid A solution of (2E)-4-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)but-2-enoic acid (110 mg, 0.21 mmol, 1.00 equiv) and TFA (1 mL) in DCM (5 mL) was stirred for 1 h at room temperature, and the resulting solution was concentrated under vacuum to afford 100 mg of the title compound as crude brown oil. LCMS (ESI, m/z): 396.11 [M+H]+.

Step 6: Synthesis of 6-[4-[(2Z)-4-[[(1S)-2-[6-oxo-5-(trifluoromethyl)-1,6-dihydropyridazin-4-yl]-2,3-dihydro-1H-isoindol-1-yl]methoxy]but-2-enoyl]piperazin-1-yl]pyridine-3-carbonitrile, 6-[4-[(2Z)-4-[[(1R)-2-[6-oxo-5-(trifluoromethyl)-1,6-dihydropyridazin-4-yl]-2,3-dihydro-1H-isoindol-1 yl]methoxy]but-2-enoyl]piperazin-1-yl]pyridine-3-carbonitrile, 6-[4-[(2E)-4-[[(1S)-2-[6-oxo-5-(trifluoromethyl)-1,6-dihydropyridazin-4-yl]-2,3-dihydro-1H-isoindol-1-yl]methoxy]but-2-enoyl]piperazin-1-yl]pyridine-3-carbonitrile and 6-[4-[(2E)-4-[[(1R)-2-[6-oxo-5-(trifluoromethyl)-1,6-dihydropyridazin-4-yl]-2,3-dihydro-1H-isoindol-1-yl]methoxy]but-2-enoyl]piperazin-1-yl]pyridine-3-carbonitrile A solution of (2E)-4-([2-[6-oxo-5-(trifluoromethyl)-1,6-dihydropyridazin-4-yl]-2,3-dihydro-1H-isoindol-1-yl]methoxy)but-2-enoic acid (500 mg, 1.27 mmol, 1.00 equiv), Int-A4 (239 mg, 1.27 mmol, 1.00 equiv), HATU (386 mg, 1.01 mmol, 0.8 equiv) and DIPEA (492 mg, 3.81 mmol, 3.0 equiv) in DMF (5 mL) was stirred for 2h at room temperature, The resulting solution was purified by reverse phase chromatography eluting with water/CH$_3$CN. After concentration, the residue was further purified by Prep-HPLC and Chiral-Prep-HPLC (Chiralpak Cellulose-SB, 0.46*15 cm; 3 um, MtBE (0.1% DEA):EtOH=80:20, 1.0 mL/min) yielding the title compounds as white solids. The absolute stereochemistry was assigned based on a protein X-ray crystal structure obtained of Example 18b which confirmed (S)-absolute stereochemistry and was observed to be the more potent enantiomer (see Table A-1).

Example 79 Isomer A 4.3 mg, 0.60%, LCMS (ESI, m/z): 566.10 [M+H]+, $^1$H NMR (DMSO-d$_6$, 300 MHz): δ12.59 (s, 1H), 8.53 (dd, J=2.4, 0.7 Hz, 1H), 8.26 (s, 1H), 7.93 (dd, J=9.1, 2.4 Hz, 1H), 7.51-7.29 (m, 4H), 6.94 (d, J=9.1 Hz, 1H), 6.17 (d, J=6.0 Hz, 1H), 6.07 (d, J=3.6 Hz, 1H), 5.13 (d, J=14.7 Hz, 1H), 4.56-4.46 (m, 2H), 4.27 (dd, J=10.8, 3.0 Hz, 1H), 3.96 (dd, J=11.0, 6.7 Hz, 1H), 3.80-3.35 (m, 8H), 2.84 (dd, J=6.8, 1.7 Hz, 2H). tR=4.876 min.

Example 79 Isomer B 3.4 mg, 0.37%, LCMS (ESI, m/z): 566.10[M+H]+, 1H NMR (DMSO-d$_6$, 300 MHz): δ12.58 (s, 1H), 8.53 (d, J=2.3 Hz, 1H), 8.26 (s, 1H), 7.92 (dd, J=9.1, 2.4 Hz, 1H), 7.56-7.27 (m, 4H), 6.94 (d, J=9.1 Hz, 1H), 6.16 (d, J=6.0 Hz, 1H), 6.06 (s, 1H), 5.13 (d, J=14.8 Hz, 1H), 4.61-4.42 (m, 2H), 4.26 (dd, J=11.0, 3.1 Hz, 1H), 3.97 (dd, J=11.0, 6.6 Hz, 1H), 3.74-3.33 (m, 8H), 2.83 (dd, J=6.8, 1.7 Hz, 2H). tR=9.413 min.

Example 79 Isomer C 10.3 mg, 1.44%, LCMS (ESI, m/z): 566.10[M+H]+, $^1$H NMR (DMSO-d$_6$, 300 MHz) δ12.58 (s, 1H), 8.53 (dd, J=2.3, 0.7 Hz, 1H), 8.32 (s, 1H), 7.94 (dd, J=9.1, 2.4 Hz, 1H), 7.50-7.25 (m, 4H), 6.98 (d, J=9.1 Hz, 1H), 6.69 (dt, J=15.1, 3.9 Hz, 1H), 6.39 (d, J=15.1 Hz, 1H), 6.06 (s, 1H), 5.12 (d, J=14.7 Hz, 1H), 4.58 (d, J=14.8 Hz, 1H), 4.19 (m, 2H), 3.92 (dd, J=10.0, 3.4 Hz, 1H), 3.78-3.45 (m, 9H). tR=6.804 min.

Example 79 Isomer D 6.3 mg, 0.88%, $^1$H NMR (CD$_3$OD, 400 MHz) δ8.50-8.42 (m, 2H), 7.79 (dd, J=9.1, 2.4 Hz, 1H), 7.50-7.29 (m, 4H), 6.92 (dd, J=9.1, 0.9 Hz, 1H), 6.83 (dt, J=15.2, 3.7 Hz, 1H), 6.45 (dt, J=15.1, 2.2 Hz, 1H), 6.07 (d, J=6.4 Hz, 1H), 5.27 (d, J=14.8 Hz, 1H), 4.65 (d, J=15.2 Hz, 1H), 4.27 (m, 1H), 4.18 (m, 1H), 4.04 (dd, J=9.9, 3.4 Hz, 1H), 3.82-3.56 (m, 9H). tR=8.206 min.

Example 80 Isomer A: 2-[[(2S)-1-[6-oxo-5-(trifluoromethyl)-1,6-dihydropyridazin-4-yl]pyrrolidin-2-yl]methoxy]-N-[(1r,4r)-4-[(pyridin-2-yl)amino]cyclohexyl]acetamide and Example 80 Isomer B: 2-[[(2S)-1-[6-oxo-5-(trifluoromethyl)-1,6-dihydropyridazin-4-yl]pyrrolidin-2-yl]methoxy]-N-[(1s,4s)-4-[(pyridin-2-yl)amino]cyclohexyl]acetamide

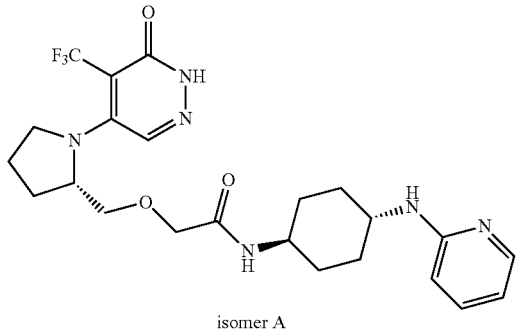

isomer A

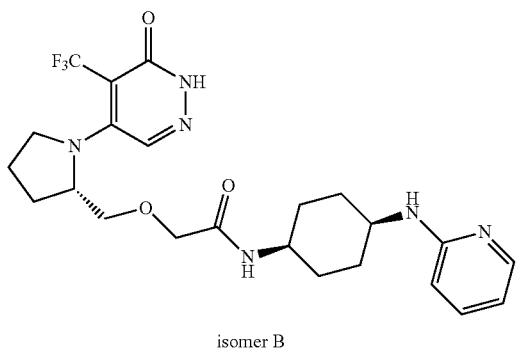

isomer B

Step 1: Synthesis of Tert-Butyl N-[4-[(pyridin-2-yl)amino]cyclohexyl]carbamate

Under nitrogen, a solution of tert-butyl N-(4-aminocyclohexyl)carbamate (1 g, 4.67 mmol, 2.50 equiv), Pd$_2$(dba)$_3$CHCl$_3$ (196 mg, 0.10 equiv), Xantphos, Cs$_2$CO$_3$ (2.19 g, 2.0 equiv), 2-chloropyridine (212 mg, 1.87 mmol, 1.00 equiv) in dioxane (10 mL) was stirred for 12 h at 80° C. in an oil bath. The residue was applied onto a silica gel column with EtOAc/petroleum ether (1:4) to afford 330 mg (61%) of the title compound as a solid. LCMS (ESI, m/z): 292.19 [M+H]$^+$ Step 2: Synthesis of 1-N-(pyridin-2-yl)cyclohexane-1,4-diamine Hydrochloride A solution of tert-butyl N-[4-[(pyridin-2-yl)amino]cyclohexyl]carbamate (330 mg, 1.13 mmol, 1.00 equiv), hydrogen chloride/dioxane (15 mL) was stirred for 2 h at room temperature. The resulting mixture was concentrated under vacuum. This resulted in 220 mg (crude) of the title compound as a solid. LCMS (ESI, m/z): 192.14 [M−Cl]$^+$.

Step 3: Synthesis of 2-[[(2S)-1-[6-oxo-5-(trifluoromethyl)-1,6-dihydropyridazin-4-yl]pyrrolidin-2-yl]methoxy]-N-[(1r,4r)-4-[(pyridin-2-yl)amino]cyclohexyl]acetamide and 2-[[(2S)-1-[6-oxo-5-(trifluoromethyl)-1,6-dihydropyridazin-4-yl]pyrrolidin-2-yl]methoxy]-N-[(1s,4s)-4-[(pyridin-2-yl)amino]cyclohexyl]acetamide A solution of 1-N-(pyridin-2-yl)cyclohexane-1,4-diamine hydrochloride (124 mg, 0.54 mmol, 1.00 equiv), HATU (178 mg, 0.47 mmol, 1.00 equiv), DIPEA (243 mg, 1.88 mmol, 4.00 equiv), DMF (2 mL), 2-[[(2S)-1-[6-oxo-5-(trifluoromethyl)-1,6-dihydropyridazin-4-yl]pyrrolidin-2-yl]methoxyacetic acid (150 mg, 0.47 mmol, 1.00 equiv) was stirred for 2 h at room temperature. The crude product was purified by C18 reverse phase chromatography eluting with water/CH$_3$CN yielding (after arbitrary assignment of the stereochemistry) the title compounds as white solids.

Example 80 Isomer A 2.5 mg, 1%, LCMS (ESI, m/z): 495.23 [M+H]$^+$, $^1$HNMR (DMSO-d$_6$, 300 MHz) δ: 12.41 (s, 1H), 8.11 (s, 1H), 7.92 (dd, J=5.1, 1.9 Hz, 1H), 7.31 (ddd, J=8.7, 7.0, 2.0 Hz, 1H), 7.21 (d, J=7.4 Hz, 1H), 6.50 (d, J=8.4 Hz, 1H), 6.41 (ddd, J=7.1, 5.0, 1.0 Hz, 1H), 6.16 (d, J=6.6 Hz, 1H), 4.60 (dr, 1H), 3.86 (s, 2H), 3.79 (dr, 1H), 3.69 (dr, 1H), 3.60-3.50 (m, 2H), 3.28-3.10 (m, 2H), 2.10 (dr, 1H), 1.89 (dr, 1H), 1.63-1.55 (m, 10H).

Example 80 Isomer B 4.3 mg, 2%, LCMS (ESI, m/z): 495.23 [M+H]$^+$, $^1$HNMR (DMSO-d$_6$, 300 MHz) δ: 12.42 (s, 1H), 8.12 (d, J=1.5 Hz, 1H), 7.91 (dd, J=5.5, 2.0 Hz, 1H), 7.30 (ddd, J=8.7, 7.1, 2.0 Hz, 1H), 7.16 (d, J=8.2 Hz, 1H), 6.45-6.35 (m, 2H), 6.31 (d, J=7.6 Hz, 1H), 4.61 (dr, 1H), 3.83 (d, J=2.7 Hz, 2H), 3.58-3.47 (m, 5H), 3.26-3.20 (m, 1H), 2.10 (drs, 1H), 1.97-1.91 (m, 3H), 1.89-1.73 (m, 4H), 1.30-1.22 (m, 4H).

Example 81 Isomer A: 3-[[(2S)-1-[6-oxo-5-(trifluoromethyl)-1,6-dihydropyridazin-4-yl]pyrrolidin-2-yl]methoxy]-N-[(1r,4r)-4-[(pyridin-2-yl)amino]cyclohexyl]propanamide and Example 81 Isomer B: 3-[[(2S)-1-[6-oxo-5-(trifluoromethyl)-1,6-dihydropyridazin-4-yl]pyrrolidin-2-yl]methoxy]-N-[(1s,4s)-4-[(pyridin-2-yl)amino]cyclohexyl]propanamide

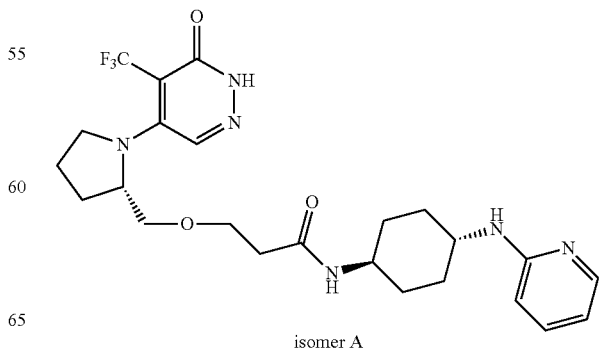

isomer A

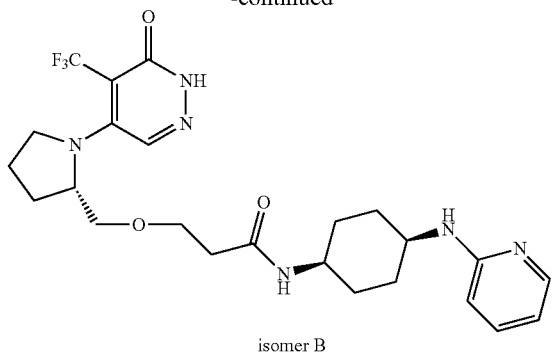

isomer B

Step 1: Synthesis of 3-[[(2S)-1-[6-oxo-5-(trifluoromethyl)-1,6-dihydropyridazin-4-yl]pyrrolidin-2-yl]methoxy]-N-[(1r,4r)-4-[(pyridin-2-yl)amino]cyclohexyl]propanamide and 3-[[(2S)-1-[6-oxo-5-(trifluoromethyl)-1,6-dihydropyridazin-4-yl]pyrrolidin-2-yl]methoxy]-N-[(1s,4s)-4-[(pyridin-2-yl)amino]cyclohexyl]propanamide A solution of 3-[[(2S)-1-[6-oxo-5-(trifluoromethyl)-1,6-dihydropyridazin-4-yl]pyrrolidin-2-yl]methoxy]propanoic acid (75 mg, 0.22 mmol, 1 equiv), DIPEA (115.6 mg, 0.89 mmol, 4.00 equiv), HATU (85.1 mg, 0.22 mmol, 1 equiv), N1-(pyridin-2-yl)cyclohexane-1,4-diamine dihydrochloride (118.2 mg, 0.45 mmol, 2.00 equiv) in DMF (2 mL) was stirred for 2 h at room temperature. The crude product was purified by Prep-HPLC yielding (after arbitrary assignment of the stereochemistry) the title compounds as white solids.

Example 81 Isomer A 3.0 mg 2.42%, LCMS (ESI, m/z): 632.22 [M+H]+, 1H NMR (DMSO-$d_6$, 300 MHz) δ: 12.35 (s, 1H), 8.15 (s, 1H), 8.00 (s, 1H), 7.95 (d, J=3.6 Hz, 1H), 7.70 (d, J=7.7 Hz, 1H), 7.35-7.29 (m, 1H), 6.51-6.39 (m, 2H), 6.25 (d, J=7.8 Hz, 1H), 4.50 (dr, 1H), 3.74-3.52 (m, 7H), 3.20 (dr, 1H), 2.30-2.26 (m, 2H), 2.07-1.91 (m, 1H), 1.87 (d, J=18.5 Hz, 1H), 1.71-1.56 (m, 10H).

Example 81 Isomer B 4.9 mg 3.95%, LCMS (ESI, m/z): 632.22 [M+H]+, 1H NMR (DMSO-$d_6$, 300 MHz) δ: 12.37 (s, 1H), 8.31 (s, 1H), 8.00 (s, 1H), 7.95 (d, J=3.6 Hz, 1H), 7.72 (d, J=7.2 Hz, 1H), 7.34-7.28 (m, 1H), 6.42-6.38 (m, 2H), 6.27 (d, J=6.5 Hz, 1H), 4.50 (dr, 1H), 3.61-3.50 (m, 7H), 3.23 (dr, 1H), 2.27-2.25 (m, 2H), 2.07-1.95 (m, 1H), 1.87-1.62 (m, 7H), 1.23-1.16 (m, 4H).

Example 82 Isomer A: 6-[4-(1S,4r)-[(4-[[(2S)-1-[6-oxo-5-(trifluoromethyl)-1,6-dihydro-pyridazin-4-yl]pyrrolidin-2-yl]methoxy]cyclohexyl)carbonyl]piperazin-1-yl]pyridine-3-carbonitrile and Example 82 Isomer B: 6-[4-(1R,4s)-[(4-[[(2S)-1-[6-oxo-5-(trifluoromethyl)-1,6-dihydropyridazin-4-yl]pyrrolidin-2-yl]methoxy]cyclohexyl)-carbonyl]piperazin-1-yl]pyridine-3-carbonitrile

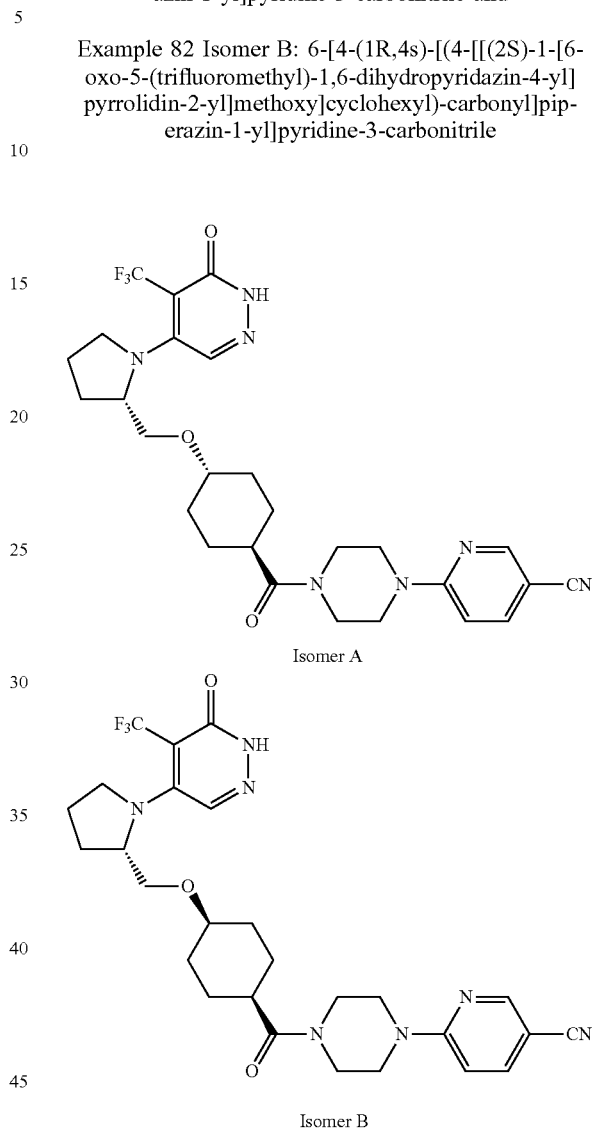

Isomer A

Isomer B

Step 1: Synthesis of Tert-Butyl (2S)-2-[4-(ethoxycarbonyl)phenoxymethyl]pyrrolidine-1-carboxylate To a stirred solution of tert-butyl (2S)-2-(hydroxymethyl)pyrrolidine-1-carboxylate (1 g, 4.97 mmol, 1.00 equiv) in THF (20 mL), ethyl 4-hydroxybenzoate (1.2 g, 7.22 mmol, 1.45 equiv), and PPh$_3$ (2 g, 7.63 mmol, 1.53 equiv) were added at 0° C. This was followed by the addition of DEAD (1.2 mL) dropwise. The resulting solution was stirred for 5 h at room temperature. The reaction was then quenched by the addition of 20 mL of water. The resulting solution was diluted with 250 mL of EtOAc and washed with 50 mL of NH$_4$Cl and 50 mL of brine. The organic layer was dried over anhydrous sodium sulfate and concentrated under vacuum. The residue was applied onto a silica gel column with EtOAc/petroleum ether (1:4). This resulted in 1.5 g (86%) of the title compound as a solid. LCMS (ESI, m/z): 350.20 [M+H]+.

Step 2: Synthesis of Tert-Butyl (2S)-2-([[4-(ethoxycarbonyl)cyclohexyl]oxy]methyl)pyrrolidine-1-carboxylate A solution of tert-butyl (2S)-2-[4-(ethoxycarbonyl)phenoxymethyl]pyrrolidine-1-carboxylate (1.4 g, 4.01 mmol, 1.00 equiv) and Rh/Al$_2$O$_3$ (2 g) in ethanol (80 mL) and AcOH (4 mL) was stirred for 5 h at room temperature under hydrogen. The solids were filtered out. The resulting mixture was concentrated under vacuum. The resulting solution was diluted with 250 mL of EtOAc. The resulting mixture was washed with 2×50 mL of sodium bicarbonate, 50 mL of NH$_4$Cl and 50 mL of brine. The organic layer was dried over anhydrous sodium sulfate and concentrated under vacuum. This resulted in 1.25 g (crude) of the title compound as oil. LCMS (ESI, m/z): 356.24 [M+H]$^+$.

Step 3: Synthesis of Ethyl 4-[(2S)-pyrrolidin-2-ylmethoxy]cyclohexane-1-carboxylate Hydrochloride A solution of tert-butyl (2S)-2-([[4-(ethoxycarbonyl)cyclohexyl]oxy]methyl)pyrrolidine-1-carboxylate (1.25 g, 3.52 mmol, 1.00 equiv) in hydrogen chloride/dioxane (15 mL) was stirred for 1 h at room temperature. The resulting mixture was concentrated under vacuum. This resulted in 900 mg (crude) of the title compound as oil. LCMS (ESI, m/z): 256.19 [M+H]$^+$.

Step 4: Synthesis of Ethyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylate A solution of ethyl 4-[(2S)-pyrrolidin-2-ylmethoxy]cyclohexane-1-carboxylate hydrochloride (900 mg, 3.08 mmol, 1.00 equiv), Int-A6 (1.15 g, 3.50 mmol, 1.13 equiv) and TEA (2 mL) in ethanol (15 mL) was stirred for 1 h at 60° C. The resulting mixture was concentrated under vacuum. The residue was applied onto a silica gel column with EtOAc/petroleum ether (1:3). This resulted in 1.2 g (71%) of the title compound as colorless oil. LCMS (ESI, m/z): 548.28 [M+H]$^+$.

Step 5: Synthesis of 4-[[(2S)-1-[6-oxo-5-(trifluoromethyl)-1-[[2-(trimethylsilyl)-ethoxy]methyl]-1,6-dihydropyridazin-4-yl]pyrrolidin-2-yl]methoxy]cyclohexane-1-carboxylic Acid To a stirred solution of ethyl 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclohexane-1-carboxylate (550 mg, 1.00 mmol, 1.00 equiv) in THF (12 mL) and water (4 mL), LiOH-water (200 mg, 8.35 mmol, 8.32 equiv) was added at 0° C. The resulting solution was stirred overnight at room temperature. The pH value of the solution was adjusted to 1 with hydrogen chloride (1 M). The resulting solution was diluted with 250 mL of EtOAc. The resulting mixture was washed with 50 mL of brine. The organic layer was dried over anhydrous sodium sulfate and concentrated under vacuum. This resulted in 550 mg (crude) of the title compound as a solid. LCMS (ESI, m/z): 520.24 [M+H]$^+$.

Step 6: Synthesis of 4-[[(2S)-1-[6-oxo-5-(trifluoromethyl)-1,6-dihydropyridazin-4-yl]pyrrolidin-2-yl]methoxy]cyclohexane-1-carboxylic Acid as a Solid A solution of 4-[[(2S)-1-[6-oxo-5-(trifluoromethyl)-1-[[2-(trimethylsilyl)ethoxy]methyl]-1,6-dihydro-pyridazin-4-yl]pyrrolidin-2-yl]methoxy]cyclohexane-1-carboxylic acid (550 mg, 1.06 mmol, 1.00 equiv) in hydrogen chloride/dioxane (10 mL) was stirred overnight at room temperature. The resulting mixture was concentrated under vacuum. The crude product was purified by C18 reverse phase chromatography eluting with water/CH$_3$CN. This resulted in 170 mg (41%) of the title compound as a solid. LCMS (ESI, m/z): 390.16 [M+H]$^+$.

Step 7: Synthesis of 6-[4-(1S,4r)-[(4-[[(2S)-1-[6-oxo-5-(trifluoromethyl)-1,6-dihydropyridazin-4-yl]pyrrolidin-2-yl]methoxy]cyclohexyl)carbonyl]piperazin-1-yl]pyridine-3-carbonitrile and 6-[4-(1R,4s)-[(4-[[(2S)-1-[6-oxo-5-(trifluoromethyl)-1,6-dihydropyridazin-4-yl]pyrrolidin-2-yl]methoxy]cyclohexyl)carbonyl]piperazin-1-yl]pyridine-3-carbonitrile To a stirred solution of 4-[[(2S)-1-[6-oxo-5-(trifluoromethyl)-1,6-dihydropyridazin-4-yl]pyrrolidin-2-yl]methoxy]cyclohexane-1-carboxylic acid (175 mg, 0.45 mmol, 1.00 equiv) in DMF (5 mL), were added Int-A4 (90 mg, 0.48 mmol, 1.06 equiv), DIPEA (0.5 mL) and HATU (200 mg, 0.53 mmol, 1.17 equiv). The resulting solution was stirred overnight at room temperature. After concentration, the residue was purified by C18 reverse phase chromatography eluting with water/CH$_3$CN. The residue was further purified by Prep-HPLC yielding (after arbitrary assignment of stereoisomers) the title compounds as white solids.

Example 82 Isomer A 70.2 mg, 28%, LCMS (ESI, m/z): 560.15 [M+H]$^+$. $^1$H NMR (400 MHz, DMSO-d$_6$) δ 12.30 (s, 1H), 8.51 (dd, J=2.3, 0.6 Hz, 1H), 8.07 (s, 1H), 7.88 (dd, J=9.1, 2.4 Hz, 1H), 6.98-6.88 (m, 1H), 4.64-4.53 (m, 1H), 3.77-3.42 (m, 11H), 3.31-3.17 (m, 2H), 2.67-2.54 (m, 1H), 2.16-2.09 (m, 1H), 1.96-1.87 (m, 1H), 1.83-1.73 (m, 1H), 1.72-1.49 (m, 5H), 1.48-1.31 (m, 4H).

Example 82 Isomer B 1.8 mg, 0.7%, LCMS (ESI, m/z): 560.30 [M+H]$^+$. $^1$H NMR (400 MHz, DMSO-d$_6$) δ 12.32 (s, 1H), 8.51 (d, J=2.3 Hz, 1H), 8.05 (s, 1H), 7.88 (dd, J=9.1, 2.4 Hz, 1H), 6.93 (d, J=9.1 Hz, 1H), 4.61-4.49 (m, 1H), 3.78-3.45 (m, 10H), 3.28-3.09 (m, 3H), 2.62-2.53 (m, 1H), 2.17-2.02 (m, 1H), 1.99-1.79 (m, 3H), 1.73-1.54 (m, 4H), 1.42-1.25 (m, 2H), 1.21-1.03 (m, 2H).

Example 83: 2-[[(2S)-1-[6-oxo-5-(trifluoromethyl)-1,6-dihydropyridazin-4-yl]pyrrolidin-2-yl]methoxy]-N-[4-(pyridin-2-yloxy)cyclohexyl]acetamide

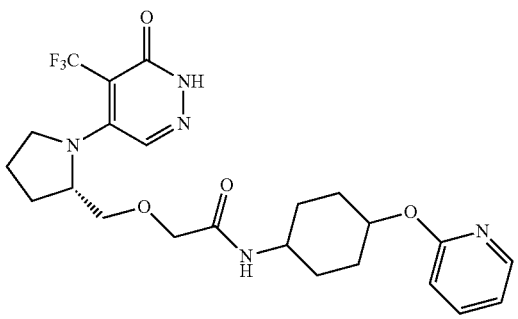 [SMILES: O=C(COC[C@@H]1CCCN1c1cn[nH]c(=O)c1C(F)(F)F)NC1CCC(Oc2ccccn2)CC1]

Step 1: Synthesis of Tert-Butyl N-[4-(pyridin-2-yloxy)cyclohexyl]carbamate

Under nitrogen, a solution of tert-butyl N-(4-hydroxycyclohexyl)carbamate (1.2 g, 5.57 mmol, 1.00 equiv), pyridin-2-ol (795 mg, 8.36 mmol, 1.50 equiv), PPh$_3$ (2.19 g, 8.35 mmol, 1.50 equiv), and DIAD (1.69 g, 8.36 mmol, 1.50 equiv) in THF (10 mL) was stirred for 3 h at 25° C. After concentration, the residue was applied onto a silica gel column eluting with EtOAc/petroleum ether (15:85) to afford 650 mg (40%) of the title compound as a colorless solid. LCMS (ESI, m/z): 293.18 [M+H]$^+$.

Step 2: Synthesis of 4-(pyridin-2-yloxy)cyclohexan-1-amine

A solution of tert-butyl N-[4-(pyridin-2-yloxy)cyclohexyl]carbamate (650 mg, 2.22 mmol, 1.00 equiv) in hydrogen chloride/dioxane (20 mL) was stirred for 0.5 h at 25° C. After concentration, the reaction mixture was adjusted to pH 7-8 with aqueous NaHCO$_3$. The resulting solution was extracted with DCM (5×40 mL), and the organic layers were combined and dried over anhydrous sodium sulfate and concentrated under vacuum to afford 300 mg (59%) of the title compound as a white solid. LCMS (ESI, m/z): 193.13 [M+H]$^+$.

Step 3: Synthesis of 2-[[(2S)-1-[6-oxo-5-(trifluoromethyl)-1,6-dihydropyridazin-4-yl]pyrrolidin-2-yl]methoxy]-N-[4-(pyridin-2-yloxy)cyclohexyl]acetamide A solution of 2-[[(2S)-1-[6-oxo-5-(trifluoromethyl)-1,6-dihydropyridazin-4-yl]pyrrolidin-2-yl]methoxy]acetic acid (200 mg, 0.62 mmol, 1.00 equiv), DIPEA (161 mg, 1.25 mmol, 2.00 equiv), HATU (237 mg, 0.62 mmol, 1.00 equiv), 4-(pyridin-2-yloxy)cyclohexan-1-amine (142 mg, 0.62 mmol, 1.00 equiv) in DMF (2 mL) was stirred for 1 h at 25° C. After concentration, the residue was purified by C18 reverse phase chromatography eluting with water/CH$_3$CN yielding the title compound (88.5 mg 29%) as a white solid. LCMS (ESI, m/z): 496.21 [M+H]$^+$, $^1$H NMR (Methanol-d$_4$, 400 MHz) δ: 8.26 (s, 1H), 8.12 (d, J=1.6 Hz, 1H), 7.71-7.67 (m, 1H), 6.95-6.92 (m, 1H), 6.87-6.85 (m, 1H), 5.14 (s, 1H), 4.72 (s, 1H), 4.01-3.92 (m, 2H), 3.85-3.74 (dr, 1H), 3.70-3.72 (m, 2H), 3.54-3.50 (m, 1H), 3.41 (m, 1H), 2.28 (s, 1H), 2.05-2.01 (m 3H), 1.76-1.67 (m, 8H).

Example 84: 3-[[(2S)-1-[6-oxo-5-(trifluoromethyl)-1,6-dihydropyridazin-4-yl]pyrrolidin-2-yl]methoxy]-N-[4-(pyridin-2-yloxy)cyclohexyl]propanamide

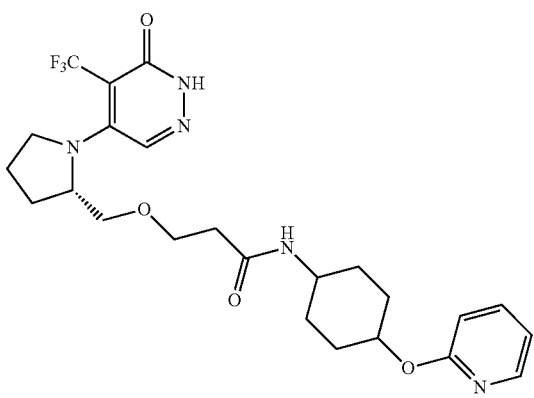 [SMILES: O=C(CCOC[C@@H]1CCCN1c1cn[nH]c(=O)c1C(F)(F)F)NC1CCC(Oc2ccccn2)CC1]

Step 1: Synthesis of 3-[[(2S)-1-[6-oxo-5-(trifluoromethyl)-1,6-dihydropyridazin-4-yl]pyrrolidin-2-yl]methoxy]-N-[4-(pyridin-2-yloxy)cyclohexyl]propanamide A solution of 3-[[(2S)-1-[6-oxo-5-(trifluoromethyl)-1,6-dihydropyridazin-4-yl]pyrrolidin-2-yl]methoxy]propanoic acid (140 mg, 0.42 mmol, 1.00 equiv), DIPEA (108 mg, 0.84 mmol, 2.00 equiv), HATU (159 mg, 0.42 mmol, 1.00 equiv), and 4-(pyridin-2-yloxy)cyclohexan-1-amine hydrochloride (95 mg, 0.42 mmol, 1.00 equiv) in DMF (2 mL) was stirred for 40 min at 25° C. After concentration, the residue was purified by C18 reverse phase chromatography eluting with water/CH$_3$CN and was purified by Prep-HPLC yielding the title compound (46.3 mg 22%) as a white solid. LCMS (ESI, m/z): 510.22 [M+H]$^+$, $^1$H NMR (Methanol-d$_4$, 400 MHz) δ: 8.12-8.10 (m, 2H), 7.70-7.66 (m, 1H), 6.95-6.88 (m, 1H), 6.80 (dt, J=8.5, 0.9 Hz, 1H), 5.13 (s, 1H), 4.50 (m, 1H), 3.77-3.60 (m, 5H), 3.48-3.44 (m, 1H), 3.35-3.40 (m, 1H), 2.39 (t, J=6.1 Hz, 2H), 2.23 (d, J=6.9 Hz, 1H), 2.02 (dr, 3H), 1.72 (m, 8H).

Example 85: 3-[(5-cyanopyridin-2-yl)amino]-N-(3-[[(2S)-1-[6-oxo-5-(trifluoromethyl)-1,6-dihydropyridazin-4-yl]pyrrolidin-2-yl]methoxy]phenyl)propanamide

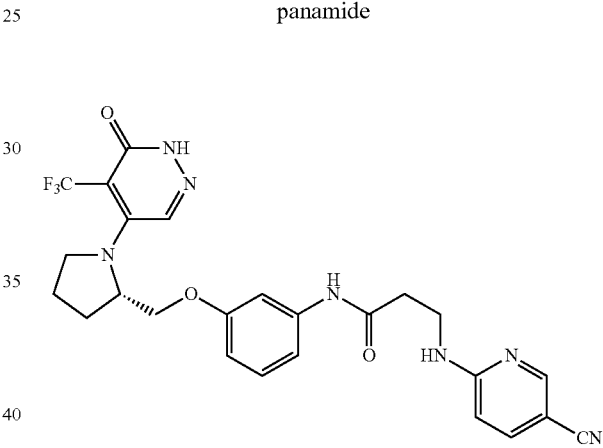

Step 1: Synthesis of 5-[(2S)-2-(3-nitrophenoxymethyl)pyrrolidin-1-yl]-4-(trifluoromethyl)-2-[[2-(trimethylsilyl)ethoxy]methyl]-2,3-dihydropyridazin-3-one A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (500 mg, 1.27 mmol, 1.00 equiv), [Pd(allyl)Cl]$_2$ (50 mg, 0.14 mmol, 0.10 equiv), Rockphos (120 mg, 0.26 mmol, 0.20 equiv), 1-bromo-3-nitrobenzene (310 mg, 1.53 mmol, 1.20 equiv) and Cs$_2$CO$_3$ (830 mg, 2.55 mmol, 2.00 equiv) in toluene (10 mL) was stirred for 16 h at 80° C. The solid was filtered out and the resulting solution was concentrated under vacuum. The residue was applied onto a silica gel column eluting with EtOAc/petroleum ether (1:1) to afford 364 mg (56%) of the title compound as light brown oil. LCMS (ESI, m/z): 515.19[M+H]$^+$.

Step 2: Synthesis of 5-[(2S)-2-(3-aminophenoxymethyl)pyrrolidin-1-yl]-4-(trifluoromethyl)-2,3-dihydropyridazin-3-one Under an atmosphere of hydrogen, a solution of 5-[(2S)-2-(3-aminophenoxymethyl)pyrrolidin-1-yl]-4-(trifluoromethyl)-2-[[2-(trimethylsilyl)ethoxy]methyl]-2,3-dihydropyridazin-3-one (255 mg, 0.53 mmol, 1.00 equiv) and Pd/C (25 mg) in MeOH (10 mL) was stirred for 3 h at room temperature. The solids were filtered out and the resulting solution was concentrated under vacuum to afford 45 mg (24%) of the title compound as a brown solid. LCMS(ESI, m/z): 485.22 [M+H]+.

Step 3: Synthesis of 3-[(5-cyanopyridin-2-yl)amino]-N-[3-([1-[6-oxo-5-(trifluoromethyl)-1-[[2-(trimethylsilyl)ethoxy]methyl]-1,6-dihydropyridazin-4-yl]pyrrolidin-2-yl]methoxy)phenyl]propanamide A solution of 3-[(5-cyanopyridin-2-yl)amino]propanoic acid (62 mg, 0.32 mmol, 1.20 equiv), EDC.HCl (104 mg, 0.67 mmol, 2.00 equiv), DMAP (66 mg, 0.54 mmol, 2.00 equiv) and 5-[(2S)-2-(3-aminophenoxymethyl)pyrrolidin-1-yl]-4-(trifluoromethyl)-2-[[2-(trimethylsilyl)ethoxy]methyl]-2,3-dihydropyridazin-3-one (131 mg, 0.27 mmol, 1.00 equiv) in DMF (5 mL) was stirred for 8 h at room temperature. The resulting solution was diluted with 20 ml of water, extracted with 3×50 ml of EtOAc, and the organic layers were combined, washed with 50 ml of brine and concentrated under vacuum. The residue was purified by C18 reverse phase chromatography eluting with water/CH$_3$CN to afford 60 mg (34%) of the title compound as a brown solid. LCMS (ESI, m/z): 658.27[M+H]+.

Step 4: Synthesis of 3-[(5-cyanopyridin-2-yl)amino]-N-(3-[[(2S)-1-[6-oxo-5-(trifluoromethyl)-1,6-dihydropyridazin-4-yl]pyrrolidin-2-yl]methoxy]phenyl)propanamide A solution of 3-[(5-cyanopyridin-2-yl)amino]-N-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]phenyl)propanamide (300 mg, 0.46 mmol, 1.00 equiv) and TFA (2 mL) in DCM (10 mL) was stirred for 2 h at room temperature. The resulting solution was concentrated under vacuum and the residue was purified by C18 reverse phase chromatography eluting with water/CH$_3$CN. After concentration the residue was further purified by Prep-HPLC yielding the title compound (28.5 mg, 12.00%) as a white solid. LCMS (ESI, m/z): 528.15[M+H]+, $^1$H NMR (CD3OD, 300 MHz) δ 8.33 (d, J=2.2 Hz, 1H), 8.22 (s, 1H), 7.60 (dd, J=9.0, 2.1 Hz, 1H), 7.28 (t, J=2.1 Hz, 1H), 7.21 (d, J=8.1 Hz, 1H), 7.04 (d, J=8.1 Hz, 1H), 6.64-6.56 (m, 2H), 4.89-4.82 (m, 1H), 4.19 (dd, J=10.2, 3.9 Hz, 1H), 4.01 (dd, J=10.2, 6.9 Hz, 1H), 3.76 (t, J=6.3 Hz, 3H), 3.45-3.39 (m, 1H), 2.67 (t, J=6.6 Hz, 2H), 2.36 (d, J=10.8 Hz, 1H), 2.06 (dd, J=10.2, 5.9 Hz, 1H), 1.92-1.79 (m, 2H).

Example 86: N-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]phenyl)prop-2-enamide

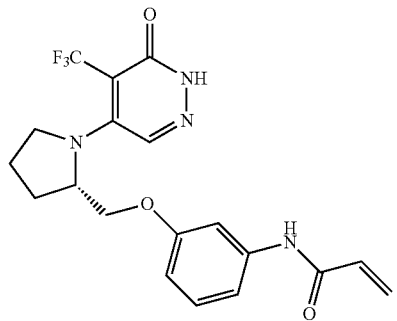 [SMILES: C=CC(=O)Nc1cccc(OC[C@@H]2CCCN2c2cn[nH]c(=O)c2C(F)(F)F)c1]

Step 1: Synthesis of N-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]phenyl)prop-2-enamide To a solution of 5-[(2S)-2-(3-aminophenoxymethyl)pyrrolidin-1-yl]-4-(trifluoromethyl)-2-[[2-(trimethylsilyl)ethoxy]methyl]-2,3-dihydropyridazin-3-one (150 mg, 0.31 mmol, 1.00 equiv) and TEA (93 mg, 0.92 mmol, 2.00 equiv) in DCM (2.5 mL) was added prop-2-enoyl chloride (31 mg, 0.34 mmol, 1.10 equiv). The resulting solution was stirred for 1 h at room temperature, quenched with 10 ml of water and extracted with 3×15 ml of EtOAc. The organic layers were combined, washed with 10 ml of brine and concentrated under vacuum. The residue was purified by C18 reverse phase chromatography eluting with water/CH$_3$CN to afford 21 mg (13%) of the title compound as a brown solid. LCMS (ESI, m/z): 539.23 [M+H]+.

Step 2: Synthesis of N-(3-[[(2S)-1-[6-oxo-5-(trifluoromethyl)-1,6-dihydropyridazin-4-yl]pyrrolidin-2-yl]methoxy]phenyl)prop-2-enamide A solution of N-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]phenyl)prop-2-enamide (279 mg, 0.52 mmol, 1.00 equiv) and TFA (1 mL) in DCM (5 mL) was stirred for 3 h at room temperature. The resulting solution was concentrated under vacuum and the residue was purified by C18 reverse phase chromatography eluting with water/CH$_3$CN. After concentration, the residue was further purified by Prep-HPLC yielding the title compound 11.1 mg (5.01%) as a white solid. LCMS (ESI, m/z): 409.15 [M+H]+, $^1$HNMR (DMSO-d$_6$, 300 MHz) δ 12.35 (s, 1H), 10.14 (s, 1H), 8.16 (s, 1H), 7.30 (s, 1H), 7.21 (d, J=5.1 Hz, 2H), 6.63 (td, J=4.5, 2.5 Hz, 1H), 6.45 (dd, J=17.0, 10.0 Hz, 1H), 6.27 (dd, J=17.0, 2.1 Hz, 1H), 5.77 (dd, J=9.9, 2.1 Hz, 1H), 4.83 (s, 1H), 4.07 (dd, J=10.2, 4.2 Hz, 1H), 3.94 (dd, J=10.2, 6.3 Hz, 1H), 3.62 (s, 1H), 3.28-3.20 (m, 1H), 2.23 (dd, J=13.0, 6.9 Hz, 1H), 1.98-1.90 (m, 1H), 1.86-1.67 (m, 2H).

Example 87: 3-[(5-cyanopyridin-2-yl)amino]-N-(5-[[(2S)-1-[6-oxo-5-(trifluoromethyl)-1,6-dihydro-pyridazin-4-yl]pyrrolidin-2-yl]methoxy]pyridin-3-yl)propanamide

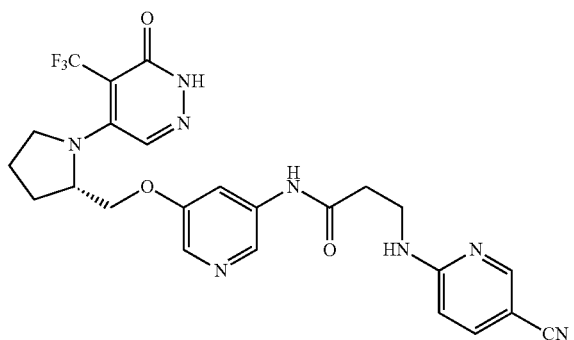 [SMILES: N#Cc1ccc(NCCC(=O)Nc2cncc(OC[C@@H]3CCCN3c3cn[nH]c(=O)c3C(F)(F)F)c2)nc1]

Step 1: Synthesis of 5-[(2S)-2-[[(5-nitropyridin-3-yl)oxy]methyl]pyrrolidin-1-yl]-4-(trifluoromethyl)-2-[[2-(trimethylsilyl)ethoxy]methyl]-2,3-dihydropyridazin-3-one A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1 g, 2.54 mmol, 1.00 equiv), [Pd(allyl)Cl]$_2$ (92.96 mg, 0.10 equiv), Rockphos (119.03 mg, 0.10 equiv), Cs$_2$CO$_3$ (2.48 g, 7.61 mmol, 3.00 equiv), 3-bromo-5-nitropyridine (1.026 g, 5.05 mmol, 2.00 equiv) in toluene (20 mL) was stirred for 5 h at 80° C. The resulting mixture was concentrated under vacuum. The residue was applied onto a silica gel column eluting with EtOAc/petroleum ether (1:1) to afford 600 mg (46%) of the title compound as brown oil. LCMS (ESI, m/z): 516.19 [M+H]$^+$.

Step 2: Synthesis of 5-[(2S)-2-[[(5-aminopyridin-3-yl)oxy]methyl]pyrrolidin-1-yl]-4-(trifluoromethyl)-2-[[2-(trimethylsilyl)ethoxy]methyl]-2,3-dihydropyridazin-3-one A solution of 5-[(2S)-2-[[(5-nitropyridin-3-yl)oxy]methyl]pyrrolidin-1-yl]-4-(trifluoromethyl)-2-[[2-(trimethylsilyl)ethoxy]methyl]-2,3-dihydropyridazin-3-one (467 mg, 0.91 mmol, 1.00 equiv), Fe (253.9 mg, 5.00 equiv) in acetic acid (5 mL) was stirred for 15 h at 70° C. After concentration, the residue was purified by C18 reverse phase chromatography eluting with water/CH$_3$CN to afford 400 mg (91%) of the title compound as a brown solid. LCMS (ESI, m/z): 486.22[M+H]$^+$.

Step 3: Synthesis of 3-[(5-cyanopyridin-2-yl)amino]-N-(5-[[(2S)-1-[6-oxo-5-(trifluoromethyl)-1-[[2-(trimethylsilyl)ethoxy]methyl]-1,6-dihydro-pyridazin-4-yl]pyrrolidin-2-yl]methoxy]pyridin-3-yl)propanamide A solution of 5-[(2S)-2-[[(5-aminopyridin-3-yl)oxy]methyl]pyrrolidin-1-yl]-4-(trifluoromethyl)-2-[[2-(trimethylsilyl)ethoxy]methyl]-2,3-dihydropyridazin-3-one (364 mg, 0.75 mmol, 1.00 equiv), EDC.HCl (360.5 mg, 1.88 mmol, 2.50 equiv), 4-dimethylaminopyridine (274.87 mg, 2.25 mmol, 3.00 equiv), 3-[(5-cyanopyridin-2-yl)amino]propanoic acid (172 mg, 0.90 mmol, 1.20 equiv) in DMF (4 mL) was stirred for 3 h at 60° C. The resulting solution was quenched with 40 ml water and extracted with 4×50 mL of EtOAc. The organic layers were combined. After the resulting mixture was concentrated under vacuum, the residue was applied onto a silica gel column with MeOH/CH$_2$Cl$_2$ (1:10) to afford 350 mg (71%) of the title compound as a brown solid. LCMS (ESI, m/z): 659.28[M+H]$^+$.

Step 4: Synthesis of 3-[(5-cyanopyridin-2-yl)amino]-N-(5-[[(2S)-1-[6-oxo-5-(trifluoromethyl)-1,6-dihydropyridazin-4-yl]pyrrolidin-2-yl]methoxy]pyridin-3-yl)propanamide A solution of 3-[(5-cyanopyridin-2-yl)amino]-N-(5-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyridin-3-yl)propanamide (134 mg, 0.20 mmol, 1.00 equiv), trifluoroacetic acid (1 mL) in DCM (5 mL) was stirred for 1 h at room temperature. After concentration, the residue was purified by Prep-HPLC yielding the title compound (39.1 mg, 36%) as a white solid. LCMS (ESI, m/z): 529.25 [M+H]$^+$, $^1$HNMR (300 MHz, Methanol-d4) δ 8.33 (d, J=2.3 Hz, 1H), 8.29 (dd, J=2.3, 1.8 Hz, 2H), 7.93 (d, J=2.6 Hz, 1H), 7.85 (d, J=2.3 Hz, 1H), 7.59 (dd, J=8.9, 2.3 Hz, 1H), 6.59 (d, J=9.0 Hz, 1H), 4.87 (s, 1H) 4.30 (d, J=10.3 Hz, 1H), 4.11 (d, J=10.3 Hz, 1H), 3.77 (dd, J=6.6, 7.5 Hz, 3H), 3.55-3.36 (m, 1H), 2.87-2.58 (m, 2H), 2.39-2.31 (m, 1H), 2.11-2.04 (m, 1H), 2.04-1.67 (m, 2H).

Example 88: (S)-6-(4-(2-(2-(1-(6-oxo-5-(trifluoromethyl)-1,6-dihydropyridazin-4-yl)pyrrolidin-2-yl)ethoxy)acetyl)piperazin-1-yl)nicotinonitrile

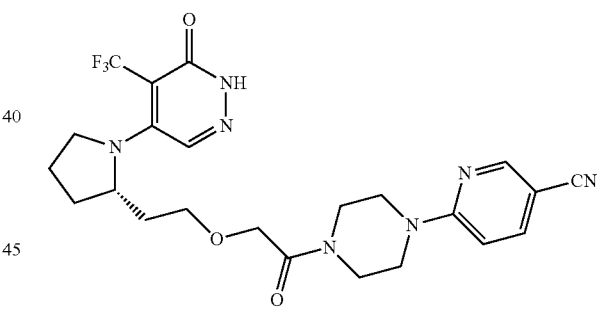

Step 1: Synthesis of (S)-tert-butyl 2-(2-hydroxyethyl)pyrrolidine-1-carboxylate A solution of 2-[(2S)-1-[(tert-butoxy)carbonyl]pyrrolidin-2-yl]acetic acid (460 mg, 2.01 mmol, 1.00 equiv), BH$_3$/Me$_2$S (2 mL) in THF (8 mL) was stirred for 2 h at 80° C. The resulting solution was quenched with MeOH. After concentrating under vacuum, the residue was applied onto a silica gel column eluting with EtOAc/petroleum ether (1:1) to afford 210 mg (49%) of the title compound as white oil. LCMS (ESI, m/z): 216.15 [M+H]$^+$.

Step 2: Synthesis of (S)-2-(pyrrolidin-2-yl)ethanol Hydrochloride

A solution of (S)-tert-butyl 2-(2-hydroxyethyl)pyrrolidine-1-carboxylate (210 mg, 1.00 mmol, 1.00 equiv) in hydrogen chloride/dioxane (5 mL) was stirred for 1 h at room temperature. The resulting mixture was concentrated under vacuum to afford 150 mg crude of the title compound. LCMS (ESI, m/z): 116.10 [M+H]+.

Step 3: Synthesis of (S)-5-(2-(2-hydroxyethyl)pyrrolidin-1-yl)-4-(trifluoromethyl)-2-((2-(trimethylsilyl)ethoxy)methyl)pyridazin-3(2H)-one A solution of Int-A6 (360 mg, 1.09 mmol, 1.10 equiv), (S)-2-(pyrrolidin-2-yl)ethanol hydrochloride (150 mg, 0.99 mmol, 1.00 equiv), TEA (1 mL) in ethanol (10 mL) was stirred for 1 h at 60° C. After concentration, the residue was applied onto a silica gel column eluting with EtOAc/petroleum ether (1:1) to afford 250 mg (62%) of the title compound as a white solid. LCMS (ESI, m/z): 408.20 [M+H]+.

Step 4: Synthesis of (S)-6-(4-(2-(2-(1-(6-oxo-5-(trifluoromethyl)-1-((2-(trimethylsilyl)ethoxy)methyl)-1,6-dihydropyridazin-4-yl)pyrrolidin-2-yl)ethoxy)acetyl)piperazin-1-yl)nicotinonitrile A solution of (S)-5-(2-(2-hydroxyethyl)pyrrolidin-1-yl)-4-(trifluoromethyl)-2-((2-(trimethylsilyl)ethoxy)methyl)pyridazin-3(2H)-one (200 mg, 0.49 mmol, 1.00 equiv), 6-[4-(2-chloroacetyl)piperazin-1-yl]pyridine-3-carbonitrile (132 mg, 0.50 mmol, 1.00 equiv), sodium hydride (30 mg, 1.25 mmol, 1.50 equiv) in DMF (5 mL) was stirred for 2 h at room temperature. The resulting solution was quenched with water and extracted with EtOAc (3×50 mL), and the organic layers were combined. The solution was dried over anhydrous sodium sulfate and concentrated under vacuum. The residue was applied onto a silica gel column eluting with EtOAc/petroleum ether (1:10) to afford 80 mg (26%) of the title compound as a white solid. LCMS (ESI, m/z): 636.29 [M+H]+.

Step 5: Synthesis of (S)-6-(4-(2-(2-(1-(6-oxo-5-(trifluoromethyl)-1,6-dihydropyridazin-4-yl)pyrrolidin-2-yl)ethoxy)acetyl)piperazin-1-yl)nicotinonitrile A solution of (S)-6-(4-(2-(2-(1-(6-oxo-5-(trifluoromethyl)-1-((2-(trimethyl silyl)ethoxy)methyl)-1,6-dihydropyridazin-4-yl)pyrrolidin-2-yl)ethoxy)acetyl)piperazin-1-yl)nicotinonitrile (80 mg, 0.13 mmol, 1.00 equiv) in hydrogen chloride/dioxane (10 mL) was stirred for 2 h at room temperature. After concentration, the residue was purified by C18 reverse phase chromatography eluting with water/CH3CN yielding the title compound (12.6 mg, 20%) as a white solid. LCMS (ESI, m/z): 506.15 [M+H]+, 1HNMR (Methanol-d4, 300 MHz) δ: 8.45 (d, J=2.4 Hz, 1H), 8.08 (s, 1H), 7.78 (dd, J=9.1, 2.4 Hz, 1H), 6.90 (dd, J=9.1, 0.8 Hz, 1H), 4.55-4.48 (m, 1H), 4.30 (s, 2H), 3.85-3.63 (m, 11H), 3.41-3.32 (m, 1H), 2.39 (t, J=5.4 Hz, 1H), 2.24-2.07 (m, 1H), 2.03-1.95 (m, 1H), 1.87-1.73 (m, 3H).

Example 89: 6-[4-[2-([2-[(2S)-1-[6-oxo-5-(trifluoromethyl)-1,6-dihydropyridazin-4-yl]pyrrolidin-2-yl]ethyl]amino)acetyl]piperazin-1-yl]pyridine-3-carbonitrile

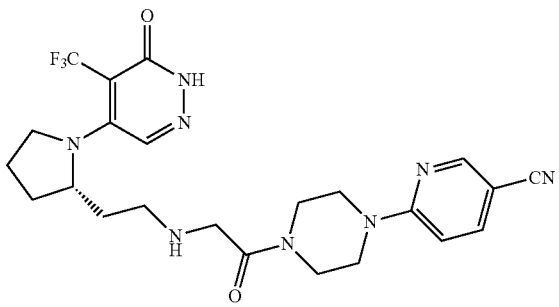 [SMILES: N#Cc1ccc(N2CCN(C(=O)CNCC[C@@H]3CCCN3c3cn[nH]c(=O)c3C(F)(F)F)CC2)nc1]

Step 1: Synthesis of 5-[(2S)-2-(2-azidoethyl)pyrrolidin-1-yl]-4-(trifluoromethyl)-2-[[2-(trimethylsilyl)ethoxy]methyl]-2,3-dihydropyridazin-3-one A solution of 5-[(2S)-2-(2-hydroxyethyl)pyrrolidin-1-yl]-4-(trifluoromethyl)-2-[[2-(trimethylsilyl)ethoxy]methyl]-2,3-dihydropyridazin-3-one (1.2 g, 2.94 mmol, 1.00 equiv), DPPA (1.32 g, 4.80 mmol, 1.60 equiv), DBU (730 mg, 4.80 mmol, 1.60 equiv) in toluene (10 mL) was stirred for 3 h at 60° C. The solvent was concentrated under vacuum and the residue was applied onto a silica gel column eluting with EtOAc/petroleum ether (1:1) to afford 1 g (79%) of the title compound as a white solid. LCMS (ESI, m/z): 433.20 [M+H]+.

Step 2: Synthesis of 5-[(2S)-2-(2-aminoethyl)pyrrolidin-1-yl]-4-(trifluoromethyl)-2-[[2-(trimethylsilyl)ethoxy]methyl]-2,3-dihydropyridazin-3-one A solution of 5-[(2S)-2-(2-azidoethyl)pyrrolidin-1-yl]-4-(trifluoromethyl)-2-[[2-(trimethylsilyl)ethoxy]methyl]-2,3-dihydropyridazin-3-one (864 mg, 2.00 mmol, 1.00 equiv), and Pd/C (100 mg) in methanol (10 mL) was stirred for 2 h at room temperature under H2 atmosphere. After the solids were filtered out, the resulting mixture was concentrated under vacuum to afford 700 mg crude of the title compound as white oil. LCMS (ESI, m/z): 407.21 [M+H]+.

Step 3: Synthesis of Tert-Butyl N-[2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]carbamate A solution of 5-[(2S)-2-(2-aminoethyl)pyrrolidin-1-yl]-4-(trifluoromethyl)-2-[[2-(trimethylsilyl)ethoxy]methyl]-2,3-dihydropyridazin-3-one (406 mg, 1.00 mmol, 1.00 equiv), (Boc)2O (218 mg, 1.00 mmol, 1.00 equiv) in ethanol (5 mL) was stirred for 2 h at 100° C. After concentration, the residue was applied onto a silica gel column eluting with EtOAc/petroleum ether (1:1) to afford 380 mg (75%) of the title compound as a white solid. LCMS (ESI, m/z): 507.26 [M+H]+.

Step 4: Synthesis of Tert-Butyl N-[2-[4-(5-cyanopyridin-2-yl)piperazin-1-yl]-2-oxoethyl]-N-[2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]carbamate A solution of 6-[4-(2-chloroacetyl)piperazin-1-yl]pyridine-3-carbonitrile (158 mg, 0.6 mmol, 1.00 equiv), tert-butyl N-[2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]carbamate (300 mg, 0.6 mmol, 1.00 equiv), and sodium hydride (72 mg, 1.8 mmol, 3.00 equiv) in THF (10 mL) was stirred for 5 h at room temperature. After concentration, the residue was applied onto a silica gel column eluting with EtOAc/petroleum ether (1:1) to afford 100 mg crude of the title compound as a white solid.

Step 5: Synthesis of 6-[4-[(4-[[(2S)-1-[6-oxo-5-(trifluoromethyl)-1,6-dihydropyridazin-4-yl]pyrrolidin-2-yl]methoxy]pyrimidin-2-yl)carbonyl]piperazin-1-yl]pyridine-3-carbonitrile A solution of tert-butyl N-[2-[4-(5-cyanopyridin-2-yl)piperazin-1-yl]-2-oxoethyl]-N-[2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]carbamate (80 mg, 0.11 mmol, 1.00 equiv) in hydrogen chloride/dioxane (10 mL) was stirred for 2 h at room temperature. After concentration, the residue was purified by C18 reverse phase chromatography eluting with water/CH$_3$CN yielding the title compound (20.9 mg, 38%) as a white solid. LCMS (ESI, m/z): 505.23 [M+H]+, 1HNMR (300 MHz, Methanol-d4) δ 8.45 (d, J=2.4 Hz, 1H), 8.08 (s, 1H), 7.78 (dd, J=9.0, 2.3 Hz, 1H), 6.88 (d, J=6.0 Hz, 1H), 4.48-4.30 (m, 1H), 3.87-3.63 (m, 9H), 3.56 (s, 2H), 3.48-3.41 (m, 1H), 2.78-2.63 (m, 2H), 2.39-2.28 (m, 1H), 2.10-1.98 (m, 2H), 1.89-1.76 (m, 3H).

Example 90: (S)-(6-[4-(3-[[1-[6-oxo-5-(trifluoromethyl)-1,6-dihydropyridazin-4-yl]pyrrolidin-2-yl]methoxy]propyl)piperazin-1-yl]pyridine-3-carbonitrile; Formic Acid

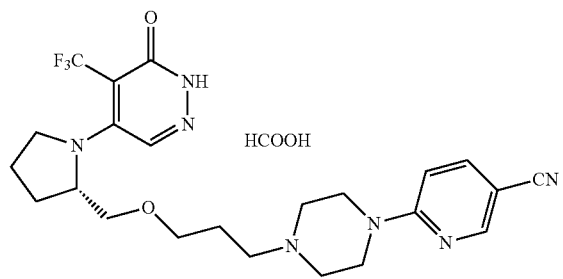 [SMILES: N#Cc1ccc(N2CCN(CCCOC[C@@H]3CCCN3c3cn[nH]c(=O)c3C(F)(F)F)CC2)nc1 ; "HCOOH"]

Step 1: Synthesis of 6-[4-(3-hydroxypropyl)piperazin-1-yl]pyridine-3-carbonitrile A solution of 3-(piperazin-1-yl)propan-1-ol (1.44 g, 9.98 mmol, 1.00 equiv), 6-chloropyridine-3-carbonitrile (1.38 g, 9.96 mmol, 1.00 equiv), and potassium carbonate (2 g, 14.47 mmol, 1.50 equiv) in DMF (20 mL) was stirred for 1 h at 80° C. The solids were filtered out. The filtrate was concentrated under vacuum to afford 2.2 g (89%) of the title compound as a yellow solid. LCMS (ESI, m/z): 247.16 [M+H]+.

Step 2: Synthesis of Tert-Butyl (S)-2-([3-[4-(5-cyanopyridin-2-yl)piperazin-1-yl]propoxy]methyl)pyrrolidine-1-carboxylate To a solution of (2S)-2-[(methanesulfonyloxy)methyl]pyrrolidine-1-carboxylate (3 g, 10.74 mmol, 1.00 equiv), and 6-[4-(3-hydroxypropyl)piperazin-1-yl]pyridine-3-carbonitrile (5.1 g, 20.71 mmol, 1.50 equiv) in DMF (150 mL) was added sodium hydride (1 g, 41.67 mmol, 2.00 equiv) in several batches, and the resulting solution was stirred for 6 h at 70° C. The mixture was extracted with 2×100 mL of EtOAc and the organic layers were combined. The residue was applied onto a silica gel column with EtOAc/petroleum ether to afford 1 g (22%) of the title compound as yellow oil. LCMS (ESI, m/z): 430.27 [M+H]+.

Step 3: Synthesis of (S)-6-[4-(3-[[pyrrolidin-2-yl]methoxy]propyl)piperazin-1-yl]pyridine-3-carbonitrile A solution of tert-butyl (S)-2-([3-[4-(5-cyanopyridin-2-yl)piperazin-1-yl]propoxy]methyl)pyrrolidine-1-carboxylate (1 g, 2.33 mmol, 1.00 equiv) in dioxane/HCl (20 mL) was stirred for 1 h at 25° C. The residue was purified by C18 reverse phase chromatography eluting with water/CH$_3$CN. The collected fractions were combined and concentrated under vacuum to afford 600 mg (78%) of the title compound as a yellow solid. LCMS (ESI, m/z): 330.22 [M+H]+.

Step 4: Synthesis of (S)-6-[4-(3-[[1-[6-oxo-5-(trifluoromethyl)-1-[[2-(trimethylsilyl)ethoxy]methyl]-1,6-dihydropyridazin-4-yl]pyrrolidin-2-yl]methoxy]propyl)piperazin-1-yl]pyridine-3-carbonitrile A solution of Int-A6 (600 mg, 1.82 mmol, 1.00 equiv), (S)-6-[4-(3-[[pyrrolidin-2-yl]methoxy]propyl)piperazin-1-yl]pyridine-3-carbonitrile (600 mg, 1.82 mmol, 1.00 equiv), and TEA (5 mL) in ethanol (20 mL) was stirred for 1 h at 50° C. The resulting mixture was concentrated under vacuum. The residue was purified by C18 reverse phase chromatography eluting with water/CH$_3$CN to afford 600 mg (53%) of the title compound as yellow oil. LCMS (ESI, m/z): 622.31 [M+H]+.

Step 5: Synthesis of (S)-(6-[4-(3-[[1-[6-oxo-5-(trifluoromethyl)-1,6-dihydropyridazin-4-yl]pyrrolidin-2-yl]methoxy]propyl)piperazin-1-yl]pyridine-3-carbonitrile Formic Acid Salt A solution of 6-[4-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propyl)piperazin-1-yl]pyridine-3-carbonitrile (600 mg, 0.96 mmol, 1.00 equiv), and TBAF (2.2 g, 8.41 mmol, 10.00 equiv) in dioxane (20 mL) was stirred for 3 days at 70° C. After concentrating, the residue was purified by Prep-HPLC yielding the title compound as a formate salt (21.8 mg, 4%) as a white solid. LCMS (ESI, m/z): 492.20 [M+H]+, 1HNMR (DMSO-d$_6$, 400 MHz) δ: δ: 12.35 (s, 1H), 8.47 (d, J=4.0 Hz, 1H), 8.14 (s, 1H), 8.05 (s, 1H), 7.85 (d, J=4.0 Hz, 1H), 6.90 (d, J=12.0 Hz, 1H), 4.60-4.57 (s, 1H), 3.62-3.19 (m, 10H), 2.34 (t, 4H), 2.24 (t, 2H), 2.10-2.07 (m, 1H), 1.87-1.91 (m, 1H), 1.55-1.67 (m, 4H).

Example 91: 6-(4-[2-[methyl([2-[(2S)-1-[6-oxo-5-(trifluoromethyl)-1,6-dihydropyridazin-4-yl]pyrrolidin-2-yl]ethyl])amino]acetyl]piperazin-1-yl)pyridine-3-carbonitrile

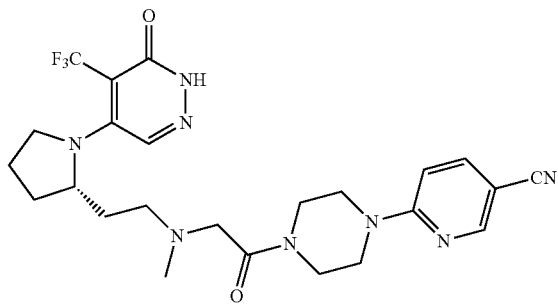 [SMILES: CN(CC[C@@H]1CCCN1c1cn[nH]c(=O)c1C(F)(F)F)CC(=O)N1CCN(c2ccc(C#N)cn2)CC1]

Step 1: Synthesis of 6-[4-[2-([2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]amino)acetyl]piperazin-1-yl]pyridine-3-carbonitrile A solution of 5-[(2S)-2-(2-aminoethyl)pyrrolidin-1-yl]-4-(trifluoromethyl)-2-[[2-(trimethylsilyl)ethoxy]methyl]-2,3-dihydropyridazin-3-one (260 mg, 0.64 mmol, 1.00 equiv), Cs$_2$CO$_3$ (416 mg, 1.28 mmol, 2.00 equiv) and 6-[4-(2-bromoacetyl)piperazin-1-yl]pyridine-3-carbonitrile (196 mg, 0.63 mmol, 1.00 equiv) in MeCN (13 mL) was stirred for 4 h at room temperature. The solids was filtered out, the resulting solution was concentrated under vacuum, and the residue was purified by C18 reverse phase chromatography eluting with water/CH$_3$CN to afford 90 mg (22%) of the title compound as a yellow solid. LCMS (ESI, m/z): 635.31 [M+H]$^+$.

Step 2: Synthesis of 6-(4-[2-[methyl([2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl])amino]acetyl]piperazin-1-yl)pyridine-3-carbonitrile A solution of 6-[4-[2-([2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl]amino)acetyl]piperazin-1-yl]pyridine-3-carbonitrile (90 mg, 0.14 mmol, 1.00 equiv), paraformaldehyde (19 mg, 0.21 mmol, 1.50 equiv), potassium hydroxide (16 mg, 0.29 mmol, 2.00 equiv) and AcOH (0.1 mL) in methanol (5 mL) was stirred for 1.5 h at room temperature. The solution was stirred for another 3 h at 60° C., NaBH$_4$ (10.7 mg, 0.28 mmol, 2.00 equiv) was added, and the resulting solution was stirred for another 30 min at room temperature. The resulting solution was quenched with 10 mL of water and extracted with 3×10 mL of EtOAc. The organic layers were combined, washed with 1×10 mL of brine, dried over anhydrous sodium sulfate and concentrated under vacuum to afford 90 mg (98%) of the title compound as a yellow oil. LCMS (ESI, m/z): 649.32 [M+H]$^+$.

Step 3: Synthesis of 6-(4-[2-[methyl([2-[(2S)-1-[6-oxo-5-(trifluoromethyl)-1,6-dihydropyridazin-4-yl]pyrrolidin-2-yl]ethyl])amino]acetyl]piperazin-1-yl)pyridine-3-carbonitrile A solution of 6-(4-[2-[methyl([2-[(2S)-1-[6-oxo-5-(trifluoromethyl)-1-[[2-(trimethylsilyl)ethoxy]methyl]-1,6-dihydropyridazin-4-yl]pyrrolidin-2-yl]ethyl])amino]acetyl]piperazin-1-yl)pyridine-3-carbonitrile (80 mg, 0.12 mmol, 1 equiv) and TFA (1 mL) in DCM (5 mL) was stirred for 1 h at room temperature. The resulting solution was concentrated under vacuum, and the residue was purified by Prep-HPLC yielding the title compound (11.4 mg, 17.83%) as a white solid. LCMS (ESI, m/z): 519.10 [M+H]+, $^1$HNMR (CD3OD-d$_4$, 300 MHz,) δ 8.44 (d, J=1.8 Hz, 1H), 8.04 (s, 1H), 7.79 (dd, J=9.0, 2.4 Hz, 1H), 6.89 (d, J=9.3 Hz, 1H), 4.36 (s, 1H), 3.77-3.61 (m, 10H), 3.43-3.35 (m, 2H), 2.65-2.43 (m, 2H), 2.41-2.29 (m, 4H), 2.12-1.95 (m, 2H), 1.84-1.71 (m, 3H).

Example 92: 6-[4-[(2E)-4-(2-[[6-oxo-5-(trifluoromethyl)-1,6-dihydropyridazin-4-yl]amino]ethoxy)but-2-enoyl]piperazin-1-yl]pyridine-3-carbonitrile

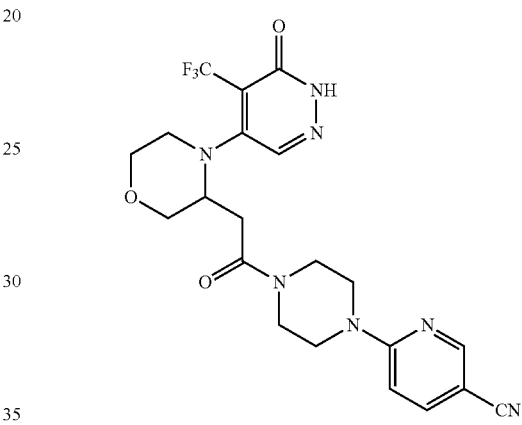

Step 1: Synthesis of 5-[(2-hydroxyethyl)amino]-4-(trifluoromethyl)-2-[[2-(trimethylsilyl)ethoxy]methyl]-2,3-dihydropyridazin-3-one A solution of Int-A6 (5 g, 15.21 mmol, 1 equiv), TEA (4.6 g, 45.46 mmol, 2.989 equiv), and 2-aminoethan-1-ol (1.04 g, 17.03 mmol, 1.120 equiv) in EtOH (50 mL) was stirred for 5 h at 50° C. The resulting mixture was concentrated under vacuum. The residue was applied onto a silica gel column eluting with EtOAc/petroleum ether (70/30) to afford 3.7 g (68.84%) of the title compound as yellow oil. LCMS (ESI, m/z): 354.14 [M+H]$^+$.

Step 2: Synthesis of Methyl (2E)-4-(2-[[6-oxo-5-(trifluoromethyl)-1-[[2-(trimethylsilyl)ethoxy]methyl]-1,6-dihydropyridazin-4-yl]amino]ethoxy)but-2-enoate A solution of 5-[(2-hydroxyethyl)amino]-4-(trifluoromethyl)-2-[[2-(trimethylsilyl)ethoxy]methyl]-2,3-dihydropyridazin-3-one (2 g, 5.66 mmol, 1 equiv), methyl (2E)-4-bromobut-2-enoate (1.106 g, 6.18 mmol, 1.092 equiv), Pd$_2$(dba)$_3$ (0.52 g, 0.57 mmol, 0.100 equiv), Ruphos (0.53 g, 1.14 mmol, 0.201 equiv), and Cs$_2$CO$_3$ (3.7 g, 11.36 mmol, 2.007 equiv) in toluene (20 mL) was stirred for 4 h at 80° C. under an atmosphere of nitrogen. The resulting mixture was concentrated under vacuum. The residue was applied onto a silica gel column eluting with EtOAc/petroleum ether (40/60) to afford 130 mg (5.09%) of the title compound as a yellow oil. LCMS (ESI, m/z): 452.18 [M+H]$^+$.

Step 3: Synthesis of (2E)-4-(2-[[6-oxo-5-(trifluoromethyl)-1-[[2-(trimethylsilyl)ethoxy]methyl]-1,6-dihydropyridazin-4-yl]amino]ethoxy)but-2-enoic Acid A solution of methyl (2E)-4-(2-[[6-oxo-5-(trifluoromethyl)-1-[[2-(trimethyl silyl)ethoxy]methyl]-1,6-dihydropyridazin-4-yl]amino]ethoxy)but-2-enoate (1.6 g, 3.54 mmol, 1 equiv), and LiOH-water (0.743 g, 17.71 mmol, 5.00 equiv) in MeOH (30 mL) was stirred for 2 h at room temperature. The resulting solution was extracted with 3×30 ml of EtOAc. The pH value of the solution was adjusted to 6 with HCl (35%). The solids were collected by filtration to afford 300 mg (19.35%) of the title compound as yellow oil. LCMS (ESI, m/z): 438.16 [M+H]$^+$.

Step 4: Synthesis of 6-[4-[(2E)-4-(2-[[6-oxo-5-(trifluoromethyl)-1-[[2-(trimethylsilyl)ethoxy]methyl]-1,6-dihydropyridazin-4-yl]amino]ethoxy)but-2-enoyl]piperazin-1-yl]pyridine-3-carbonitrile A solution of (2E)-4-(2-[[6-oxo-5-(trifluoromethyl)-1-[[2-(trimethylsilyl)ethoxy]methyl]-1,6-dihydropyridazin-4-yl]amino]ethoxy)but-2-enoic acid (300 mg, 0.69 mmol, 1 equiv), Int-A4 (168.3 mg, 0.89 mmol, 1.30 equiv), HATU (138.7 mg, 1.03 mmol, 1.50 equiv), and DIPEA (178 mg, 1.38 mmol, 2.01 equiv) in DMF (4 mL) was stirred for 2 h at room temperature. After concentration, the residue was purified by C18 reverse phase chromatography eluting with water/CH$_3$CN to afford 140 mg (33.60%) of the title compound as a yellow oil. LCMS (ESI, m/z): 608.26 [M+H]$^+$.

Step 5: Synthesis of 6-(4-(2-(4-(6-oxo-5-(trifluoromethyl)-1,6-dihydropyridazin-4-yl)morpholin-3-yl)acetyl)piperazin-1-yl)nicotinonitrile A solution of 6-[4-[(2E)-4-(2-[[6-oxo-5-(trifluoromethyl)-1-[[2-(trimethylsilyl)ethoxy]methyl]-1,6-dihydropyridazin-4-yl]amino]ethoxy)but-2-enoyl]piperazin-1-yl]pyridine-3-carbonitrile (150 mg, 0.25 mmol, 1 equiv) in DCM (8 mL) was stirred for 1 h at room temperature. After concentration, the residue was purified by C18 reverse phase chromatography eluting with water/CH$_3$CN. The residue was further purified by Prep-HPLC yielding the title compound (9.5 mg, 8.06%) as a white solid. LCMS (ESI, m/z): 478.44 [M+H]$^+$, $^1$HNMR (300 MHz, DMSO-d$_6$) δ: 8.53 (d, J=2.2 Hz, 1H), 8.02 (s, 1H), 7.90 (dd, J=8.9, 2.5 Hz, 1H), 6.96 (d, J=9.0 Hz, 1H), 4.36 (s, 1H), 3.84-3.62 (m, 13H), 3.13-2.94 (m, 2H), 2.84 (d, J=6.0 Hz, 1H).

Example 93 Isomer A: 6-[4-(3-[[(1S)-2-[6-oxo-5-(trifluoromethyl)-1,6-dihydropyridazin-4-yl]-2,3-dihydro-1H-isoindol-1-yl]methoxy]propanoyl)piperazin-1-yl]pyridine-3-carbonitrile and Example 93 Isomer B: 6-[4-(3-[[(1R)-2-[6-oxo-5-(trifluoromethyl)-1,6-dihydropyridazin-4-yl]-2,3-dihydro-1H-isoindol-1-yl]methoxy]propanoyl)piperazin-1-yl]pyridine-3-carbonitrile

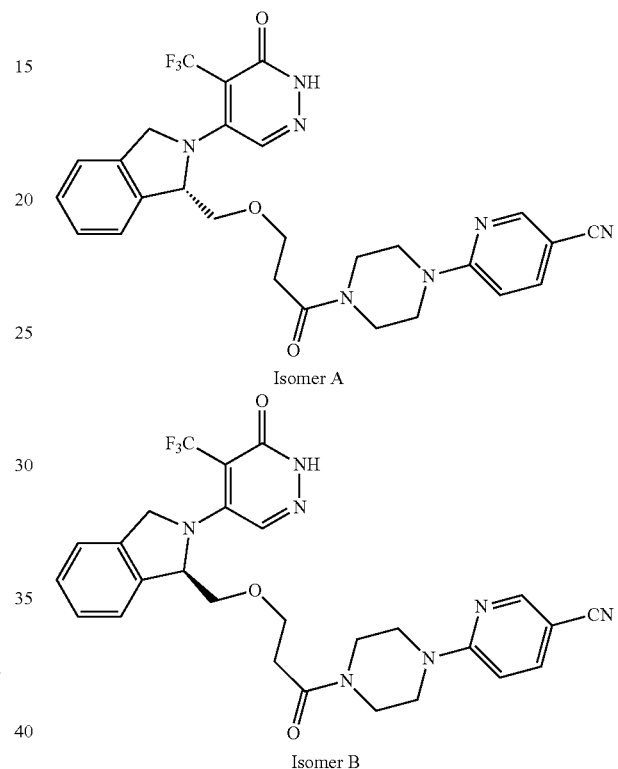

Isomer A

Isomer B

Step 1: Synthesis of Tert-Butyl 1-(hydroxymethyl)-2,3-dihydro-1H-isoindole-2-carboxylate To a stirred solution of 2-[(tert-butoxy)carbonyl]-2,3-dihydro-1H-isoindole-1-carboxylic acid (100 g, 379.81 mmol, 1.00 equiv) in THF (500 mL) at 0° C., BH$_3$.THF (1M, 800 mL) was added dropwise. The resulting solution was stirred overnight at room temperature. The reaction was quenched with saturated aq. NaHCO$_3$ at 0° C. The resulting mixture was concentrated under vacuum and extracted with 2 L EtOAc. The resulting mixture was washed with 5×500 mL of water and 2×500 mL of brine. The organic layer was dried over anhydrous sodium sulfate and concentrated under vacuum. This resulted in 95 g (crude) of the title compound as oil. LCMS (ESI, m/z): 250.14 [M+H]$^+$.

Step 2: Synthesis of (2,3-dihydro-1H-isoindol-1-yl)methanol Hydrochloride

A solution of tert-butyl 1-(hydroxymethyl)-2,3-dihydro-1H-isoindole-2-carboxylate (95 g, 381.05 mmol, 1.00 equiv) in hydrogen chloride/dioxane (800 mL) was stirred for 2 h at room temperature. The solids were collected by filtration. This resulted in 63 g (89%) of the title compound as a white solid. LCMS (ESI, m/z): 150.09 [M+H]+

Step 3: Synthesis of 5-[1-(hydroxymethyl)-2,3-dihydro-1H-isoindol-2-yl]-4-(trifluoromethyl)-2-[[2-(trimethylsilyl)ethoxy]-methyl]-2,3-dihydropyridazin-3-one A solution of (2,3-dihydro-1H-isoindol-1-yl)methanol hydrochloride (63 g, 339.35 mmol, 1.00 equiv), Int-A6 (147 g, 80%) and TEA (104 mL) in ethanol (500 mL) was stirred for 2 h at 60° C. The resulting mixture was concentrated under vacuum. The resulting solution was diluted with 2 L of EtOAc. The resulting mixture was washed with 2×500 mL of $NH_4Cl$ and 2×500 mL of brine. The organic layer was dried over anhydrous sodium sulfate and concentrated under vacuum. The residue was dissolved in 500 mL of EtOAc and added into 2.5 L hexane dropwise at 0° C. The solids were collected by filtration. This resulted in 115 g (crude) of the title compound as a solid. LCMS (ESI, m/z): 442.18 [M+H]+.

Step 4: Synthesis of Tert-Butyl 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)propanoate To a stirred solution of 5-[1-(hydroxymethyl)-2,3-dihydro-1H-isoindol-2-yl]-4-(trifluoromethyl)-2-[[2-(trimethylsilyl)ethoxy]methyl]-2,3-dihydropyridazin-3-one (115 g, 260.46 mmol, 1.00 equiv) in MeCN (1.2 L), $Cs_2CO_3$ (127 g, 389.79 mmol, 1.50 equiv) and tert-butyl prop-2-enoate (67 g, 522.74 mmol, 2.01 equiv) were added. The resulting solution was stirred for 24 h at 35° C. and concentrated under vacuum. The residue was diluted with 2 L of EtOAc and washed with 2×500 mL of water and 500 mL of brine. The organic layer was dried over anhydrous sodium sulfate and concentrated under vacuum. The residue was applied onto a silica gel column with EtOAc/petroleum ether (1:3). This resulted in 77 g (52%) of the title compound as a white solid. LCMS (ESI, m/z): 570.26 [M+H]+.

Step 5: Synthesis of 3-([2-[6-oxo-5-(trifluoromethyl)-1,6-dihydropyridazin-4-yl]-2,3-dihydro-1H-isoindol-1-yl]methoxy) Propanoic Acid A solution of tert-butyl 3-([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methoxy)propanoate (76 g, 133.40 mmol, 1.00 equiv) in hydrogen chloride/dioxane (1 L) was stirred overnight at room temperature. The resulting mixture was concentrated under vacuum. The residue was dissolved in 400 mL of $NH_3$/MeOH and stirred at room temperature for 30 min. The resulting mixture was concentrated under vacuum. This resulted in 50 g (crude) of the title compound as a white solid. LCMS (ESI, m/z): 384.12 [M+H]+.

Step 6: Synthesis of 6-[4-(3-[[(1S)-2-[6-oxo-5-(trifluoromethyl)-1,6-dihydropyridazin-4-yl]-2,3-dihydro-1H-isoindol-1-yl]methoxy]propanoyl)piperazin-1-yl]pyridine-3-carbonitrile and 6-[4-(3-[[(1R)-2-[6-oxo-5-(trifluoromethyl)-1,6-dihydropyridazin-4-yl]-2,3-dihydro-1H-isoindol-1-yl]methoxy]propanoyl)-piperazin-1yl]-pyridine-3-carbonitrile To a stirred solution of 3-([2-[6-oxo-5-(trifluoromethyl)-1,6-dihydropyridazin-4-yl]-2,3-dihydro-1H-isoindol-1-yl] methoxy)propanoic acid (50 g, 130.44 mmol, 1.00 equiv) in DMF (1 L), Int-A4 (45 g, 172.31 mmol, 1.32 equiv), DIPEA (116 mL) and T3P (125 mL, 50% in EtOAc) were added. The resulting solution was stirred overnight at 30° C. After concentration, the residue was purified by C18 reverse phase chromatography eluting with water/$CH_3CN$. The residue was further purified by Chiral-Prep-HPLC (CHIRALPAK IF-3, 0.46*5 cm; 3 um, (Hex:DCM=5:1)(0.1% DEA): EtOH=50:50, 1.0 ml/min) yielding the title compounds as off-white solids. The absolute stereochemistry was assigned based on a protein X-ray crystal structure obtained of Example 18 Isomer B which confirmed (S)-absolute stereochemistry and was observed to be the more potent enantiomer.

Example 93 Isomer A 20.5913 g, 85%, LCMS (ESI, m/z): 554.30 [M+H]+. 1H NMR (400 MHz, Methanol-$d_4$) δ 8.44 (dd, J=2.4, 0.8 Hz, 1H), 8.27 (s, 1H), 7.78 (dd, J=9.1, 2.3 Hz, 1H), 7.43-7.37 (m, 1H), 7.33 (dd, J=4.8, 3.2 Hz, 3H), 6.86 (d, J=9.2 Hz, 1H), 5.94-5.87 (m, 1H), 5.21 (d, J=14.7 Hz, 1H), 4.59 (d, J=14.8 Hz, 1H), 3.93 (dd, J=10.2, 3.5 Hz, 1H), 3.82 (dt, J=9.3, 5.9 Hz, 1H), 3.77-3.60 (m, 8H), 3.61-3.51 (m, 2H), 2.67-2.58 (m, 2H). Rt=2.690 min.

Example 93 Isomer B 20.7982 g, 86%, LCMS (ESI, m/z): 554.30 [M+H]+. Rt=3.263 min.

Example 94 Isomer A: 6-[4-[(2R)-2-methyl-3-[[(2S)-1-[6-oxo-5-(trifluoromethyl)-1,6-dihydropyridazin-4-yl]pyrrolidin-2-yl]methoxy]propanoyl]piperazin-1-yl]pyridine-3-carbonitrile and Example 94 Isomer B: 6-[4-[(2S)-2-methyl-3-[[(2S)-1-[6-oxo-5-(trifluoromethyl)-1,6-dihydropyridazin-4-yl]pyrrolidin-2-yl]methoxy]propanoyl]piperazin-1-yl]pyridine-3-carbonitrile

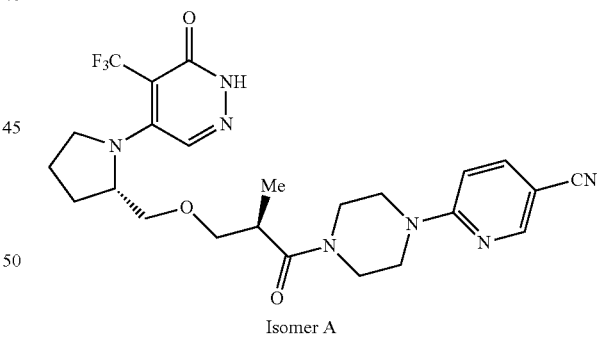

Isomer A

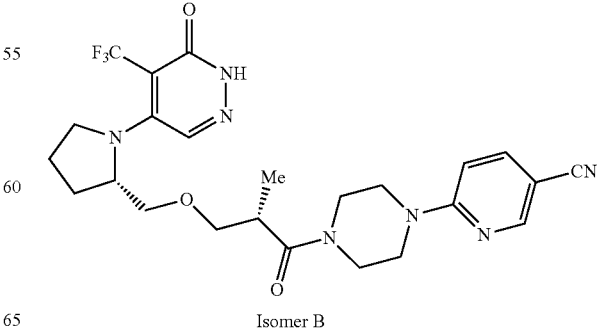

Isomer B

Step 1: Synthesis of Methyl 2-([[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]methyl)prop-2-enoate To a solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (500 mg, 1.27 mmol, 1.00 equiv) and NBu$_4$I (93 mg, 0.25 mmol, 0.20 equiv) in toluene (16 mL) was added sodium hydride (91 mg, 3.79 mmol, 3.00 equiv). After 30 min at room temperature, methyl 2-(bromomethyl)prop-2-enoate (2.24 g, 12.51 mmol, 10.00 equiv) was added dropwise. The resulting solution was stirred for 1.5 h at 80° C. The reaction was quenched with 50 mL of water, extracted with 2×50 mL of EtOAc, the organic layers were combined, washed with 50 mL of brine, dried over anhydrous sodium sulfate and concentrated under vacuum. The residue was applied onto a silica gel column eluting with EtOAc/petroleum ether (28/72) to afford 549 mg (88%) of the title compound as yellow oil. LCMS(ESI, m/z): 492.21 [M+H]$^+$.

Step 2: Synthesis of Methyl 2-methyl-3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate Under an atmosphere of hydrogen, a solution of methyl 2-([[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]methyl)prop-2-enoate (549 mg, 1.12 mmol, 1.00 equiv) and Pd/C (50 mg) in methanol (20 mL) was stirred for 2 h at room temperature. The solids were filtered out, and the resulting solution was concentrated under vacuum to afford 300 mg (54%) of the title compound as a yellow solid. LCMS (ESI, m/z): 494.22[M+H]$^+$.

Step 3: Synthesis of 2-methyl-3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoic Acid A solution of methyl 2-methyl-3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate (200 mg, 0.41 mmol, 1.00 equiv) and LiOH (58 mg, 2.42 mmol, 4.00 equiv) in THF (4 mL) and water (1 mL) was stirred for 2 h at room temperature. The resulting solution was diluted with 5 mL of water, extracted with 3×10 mL of EtOAc, and the organic layers combined. The pH value of the resulting solution was adjusted to 4 with hydrogen chloride and then concentrated under vacuum. The residue was purified by C18 reverse phase chromatography eluting with water/CH$_3$CN to afford 236 mg of the title compound as a crude yellow solid. LCMS (ESI, m/z): 480.21 [M+H]$^+$.

Step 4: Synthesis of 2-methyl-3-[[(2S)-1-[6-oxo-5-(trifluoromethyl)-1,6-dihydropyridazin-4-yl]pyrrolidin-2-yl]methoxy]propanoic Acid A solution of 2-methyl-3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoic acid (236 mg, 0.49 mmol, 1.00 equiv) and TFA (2 mL) in DCM (10 mL) was stirred for 2 h at room temperature. The resulting mixture was diluted with 30 mL of EtOAc, extracted with 5 mL of water, and the aqueous layer was concentrated under vacuum to afford 200 mg of the title compound as a solid. LCMS (ESI, m/z): 350.12[M+H]$^+$.

Step 5: 6-[4-[(2R)-2-methyl-3-[[(2S)-1-[6-oxo-5-(trifluoromethyl)-1,6-dihydropyridazin-4-yl]pyrrolidin-2-yl]methoxy]propanoyl]piperazin-1-yl]pyridine-3-carbonitrile and 6-[4-[(2S)-2-methyl-3-[[(2S)-1-[6-oxo-5-(trifluoromethyl)-1,6-dihydropyridazin-4-yl]pyrrolidin-2-yl]methoxy]propanoyl]piperazin-1-yl]pyridine-3-carbonitrile A solution of 2-methyl-3-[[(2S)-1-[6-oxo-5-(trifluoromethyl)-1,6-dihydropyridazin-4-yl]pyrrolidin-2-yl]methoxy]propanoic acid (280 mg, 0.8 mmol, 1.00 equiv), HATU (305 mg, 0.8 mmol, 1.00 equiv), DIPEA (310 mg, 2.4 mmol, 3.00 equiv) and Int-A4 (151 mg, 0.8 mmol, 1.00 equiv) in DMF (10 mL) was stirred for 2 h at room temperature. The resulting solution was diluted with 10 mL of water, extracted with 3×10 mL of EtOAc and the organic layers were combined, washed with 10 mL of brine, dried over anhydrous sodium sulfate and concentrated under vacuum. The residue was purified by C18 reverse phase chromatography eluting with water/CH$_3$CN. After concentration the residue was further purified by Prep-HPLC and Chiral-HPLC yielding (after arbitrary assignment of stereochemistry) the title compounds, as white solids.

Example 94 Isomer A 11.6 mg, 18.4%, LCMS (ESI, m/z): 520.30 [M+H]+, $^1$HNMR (DMSO-d$_6$, 400 MHz,) δ 12.35 (s, 1H), 8.51 (d, J=2.0 Hz, 1H), 8.00 (s, 1H), 7.90 (dd, J=9.2, 2.4 Hz, 1H), 6.93 (d, J=9.2 Hz, 1H), 4.52 (d, J=7.4 Hz, 1H), 3.70-3.46 (m, 11H) 3.40-3.34 (m, 2H), 3.32 (d, J=5.5 Hz, 1H), 3.00 (dt, J=13.6, 6.8 Hz, 1H), 2.11-2.02 (m, 1H), 1.86 (d, J=6.4 Hz, 1H), 1.68-1.52 (m, 2H), 0.93 (d, J=6.8 Hz, 3H).

Example 94 Isomer B 18 mg, 28.5%, LCMS (ESI, m/z): 520.25[M+H]+, $^1$HNMR (DMSO-d$_6$, 400 MHz,) δ 12.34 (s, 1H), 8.51 (d, J=2.4 Hz, 1H), 8.00 (s, 1H), 7.89 (dd, J=9.2, 2.4 Hz, 1H), 6.92 (d, J=9.2 Hz, 1H), 4.53 (d, J=7.6 Hz, 1H), 3.69-3.48 (m, 11H), 3.34-3.15 (m, 2H), 2.99 (d, J=6.8 Hz, 1H), 2.10-2.02 (m, 1H), 1.87 (d, J=6.5 Hz, 1H), 1.71-1.54 (m, 2H), 0.91 (d, J=6.8 Hz, 3H).

Example 95: 6-(4-((1R,3S)-3-(((S)-1-(6-Oxo-5-(trifluoromethyl)-1,6-dihydropyridazin-4-yl)pyrrolidin-2-yl)methoxy)cyclobutane-1-carbonyl)piperazin-1-yl)nicotinonitrile and 6-(4-((1 S,3R)-3-(((S)-1-(6-Oxo-5-(trifluoromethyl)-1,6-dihydropyridazin-4-yl)pyrrolidin-2-yl)methoxy)cyclobutane-1-carbonyl)piperazin-1-yl)nicotinonitrile Example 95

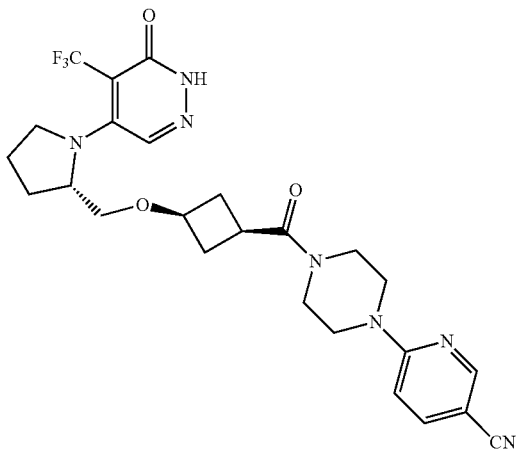

isomer A

Example 95

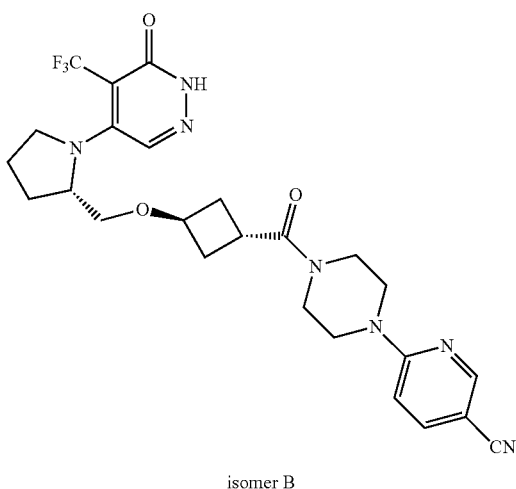

isomer B

Step 1: Tert-butyl (2S)-2-([[(4-methylbenzene)sulfonyl]oxy]methyl)pyrrolidine-1-carboxylate A solution of tert-butyl (2S)-2-(hydroxymethyl)pyrrolidine-1-carboxylate (2 g, 9.94 mmol, 1.00 equiv), TEA (2 g, 19.76 mmol, 2.00 equiv), DMAP (121 mg, 0.99 mmol, 0.10 equiv), TsCl (2.83 g, 14.8 mmol, 1.50 equiv) in DCM (20 mL) was stirred for overnight at 25° C. To the resulting solution was added 20 mL of saturated sodium bicarbonate and the resulting solution was extracted with 3×20 mL of DCM and the organic layers combined. The resulting solution was washed with 3×20 mL of saturated NH$_4$Cl, the organic layers combined and dried over anhydrous sodium sulfate and concentrated under vacuum to afford 2.9 g (82%) of the title compound as a yellow oil. LCMS: [M+H]$^+$ 356.15.

Step 2: Tert-butyl (2S)-2-[[3-(methoxycarbonyl)cyclobutoxy]methyl]pyrrolidine-1-carboxylate A solution of methyl 3-hydroxycyclobutane-1-carboxylate (800 mg, 6.15 mmol, 1.00 equiv), NaH (492 mg, 20.50 mmol, 2.00 equiv), tert-butyl (2S)-2-([[(4-methylbenzene)sulfonyl]oxy]methyl)pyrrolidine-1-carboxylate (2.2 g, 6.19 mmol, 1.00 equiv) in THF (20 mL) was stirred overnight at 70° C. The residue was quenched with 20 mL of water, extracted with 3×20 mL of EtOAc and the organic layers combined. The resulting solution was washed with 3×20 mL of saturated NH$_4$Cl, the organic layers combined and dried over anhydrous sodium sulfate and concentrated under vacuum. The residue was purified by C18 reverse phase chromatography eluting with H$_2$O/CH$_3$CN to afford 250 mg (13%) of the title compound as a yellow oil. LCMS: [M+H]$^+$ 314.19.

Step 3: Methyl 3-[(2S)-pyrrolidin-2-ylmethoxy]cyclobutane-1-carboxylate Hydrochloride A solution of tert-butyl (2 S)-2-[[3-(methoxycarbonyl)cyclobutoxy]methyl]pyrrolidine-1-carboxylate (250 mg, 0.80 mmol, 1.00 equiv) in dioxane/HCl (15 mL, 4M) was stirred for 1 h at 25° C. The resulting solution was concentrated under vacuum to afford 250 mg of the title compound as a yellow crude oil. LCMS: [M+H]$^+$ 250.11.

Step 4: Methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclobutane-1-carboxylate A solution of Int-A6 (262 mg, 0.80 mmol, 1.00 equiv), TEA (242 mg, 2.39 mmol, 3.00 equiv), methyl 3-[(2S)-pyrrolidin-2-ylmethoxy]cyclobutane-1-carboxylate hydrochloride (250 mg, 1.00 mmol, 1.00 equiv) in EtOH (15 mL) was stirred for 2 h at 60° C. The resulting solution was concentrated and the residue was applied onto a silica gel column with EtOAc/petroleum ether (1/4) to afford 320 mg (79%) of the title compound as a yellow oil. LCMS: [M+H]$^+$ 506.22.

Step 5: Methyl 3-[[(2S)-1-[6-oxo-5-(trifluoromethyl)-1,6-dihydropyridazin-4-yl]pyrrolidin-2-yl]methoxy]cyclobutane-1-carboxylate A solution of methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]cyclobutane-1-carboxylate (320 mg, 0.63 mmol, 1.00 equiv), TFA (2 mL) in DCM (20 mL) was stirred for 2 h at 25° C. The pH value of the solution was adjusted to 8 with ethanolamine. The resulting solution was extracted with 3×20 mL of DCM and the organic layers combined, dried over anhydrous sodium sulfate and concentrated under vacuum to afford 260 mg of the title compound as yellow oil. LCMS: [M+H]$^+$ 376.16.

Step 6: 3-[[(2S)-1-[6-Oxo-5-(trifluoromethyl)-1,6-dihydropyridazin-4-yl]pyrrolidin-2-yl]methoxy]cyclobutane-1-carboxylic Acid A solution of methyl 3-[[(2S)-1-[6-oxo-5-(trifluoromethyl)-1,6-dihydropyridazin-4-yl]pyrrolidin-2-yl]methoxy]cyclobutane-1-carboxylate (260 mg, 0.69 mmol, 1.00 equiv), LiOH.H$_2$O (200 mg, 4.77 mmol, 5.00 equiv) in MeOH (20 mL) and water (4 mL) was stirred for 2 h at 25° C. The pH value of the solution was adjusted to 4 with HCl (2M). The resulting solution was filtered and the solid was collected to afford 115 mg (46%) of the title compound as a yellow solid. LCMS: [M+H]$^+$ 362.12.

Step 7: 6-(4-((1R,3S)-3-(((S)-1-(6-Oxo-5-(trifluoromethyl)-1,6-dihydropyridazin-4-yl)pyrrolidin-2-yl)methoxy)cyclobutane-1-carbonyl)piperazin-yl)piperazin-1-yl)nicotinonitrile and 6-(4-((1S,3R)-3-(((S)-1-(6-oxo-5-(trifluoromethyl)-1,6-dihydropyridazin-4-yl)pyrrolidin-2-yl)methoxy)cyclobutane-1-carbonyl)piperazin-1-yl)nicotinonitrile A solution of 3-[[(2S)-1-[6-oxo-5-(trifluoromethyl)-1,6-dihydropyridazin-4-yl]pyrrolidin-2-yl]methoxy]cyclobutane-1-carboxylic acid (100 mg, 0.28 mmol, 1.00 equiv), DIPEA (107 mg, 0.83 mmol, 3.00 equiv), Int-A4 (68 mg, 0.36 mmol, 1.10 equiv), HATU (116 mg, 0.31 mmol, 1.10 equiv) in DMF (8 mL) was stirred for 1 h at 25° C. After concentration, the residue was purified by C18 reverse phase chromatography eluting with H$_2$O/CH$_3$CN. The residue was further purified by Prep-HPLC and Chiral-Prep-HPLC (CHIRALPAK IG-3, 3 μm, 0.46×10 cm column, eluting with a gradient of MtBE (0.1% DEA):EtOH (50:50), at a flow rate of 1 mL/min) yielding (after arbitrary assignment of the stereochemistry) the title compounds, respectively, as white solids, isomer A LCMS: [M+H]$^+$ 532.22; $^1$H NMR (400 MHz, Methanol-d$_4$) δ: 8.43 (dd, J=2.3, 0.7 Hz, 1H), 8.19 (s, 1H), 7.77 (dd, J=9.1, 2.4 Hz, 1H), 6.88 (dd, J=9.1, 0.8 Hz, 1H), 4.89-4.33 (m, 1H), 4.04 (p, J=6.0 Hz, 1H), 3.79-3.63 (m, 7H), 3.57 (dd, J=10.0, 3.5 Hz, 1H), 3.49 (dd, J=6.6, 4.1 Hz, 2H), 3.44-3.37 (m, 1H), 3.35 (s, 1H), 3.33-3.18 (m, 1H), 2.62-2.39 (m, 2H), 2.24 (d, J=6.9 Hz, 1H), 2.19-1.89 (m, 3H), 1.74 (tt, J=17.3, 6.0 Hz, 2H). tR=3.607 min and isomer B LCMS: [M+H]$^+$ 532.22; $^1$H NMR (400 MHz, Methanol-d$_4$) δ: 8.43 (dd, J=2.3, 0.8 Hz, 1H), 8.13 (s, 1H), 7.77 (dd, J=9.1, 2.3 Hz, 1H), 6.87 (dd, J=9.1, 0.9 Hz, 1H), 4.84-4.31 (m, 1H), 4.05-3.88 (m, 1H), 3.88-3.61 (m, 7H), 3.56 (dt, J=10.7, 4.0 Hz, 3H), 3.46-3.34 (m, 2H), 3.06-2.85 (m, 1H), 2.70-2.43 (m, 2H), 2.25 (d, J=6.9 Hz, 1H), 2.18-1.80 (m, 3H), 1.74 (td, J=11.3, 7.1 Hz, 2H). tR=5.473 min.

Example 96: 6-[4-[(3Z)-4-[[(2S)-1-[6-Oxo-5-(trifluoromethyl)-1,6-dihydropyridazin-4-yl]pyrrolidin-2-yl]methoxy]but-3-enoyl]piperazin-1-yl]pyridine-3-carbonitrile and 6-[4-[(2E)-4-[[(2S)-1-[6-oxo-5-(trifluoromethyl)-1,6-dihydropyridazin-4-yl]pyrrolidin-2-yl]methoxy]but-2-enoyl]piperazin-1-yl]pyridine-3-carbonitrile

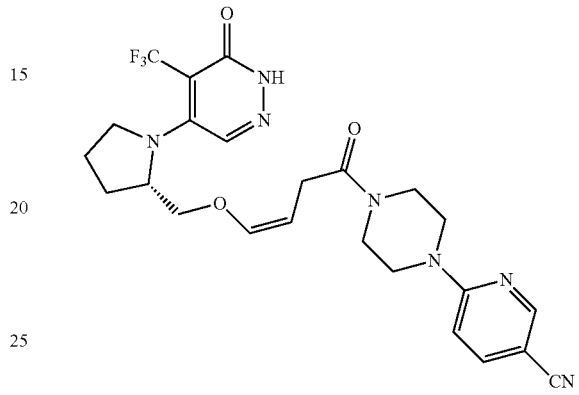

Example 96 isomer A

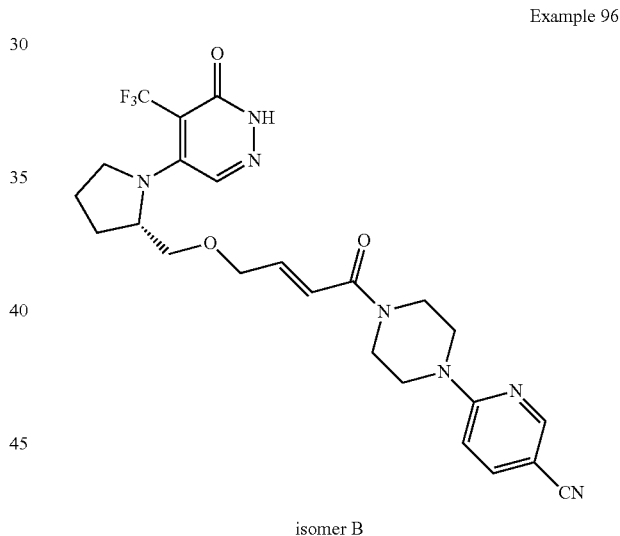

Example 96 isomer B

Step 1: Methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (600 mg, 1.52 mmol, 1.00 equiv), Cs$_2$CO$_3$ (995 mg, 3.05 mmol, 2.00 equiv), [Pd(ally)Cl]$_2$ (28 mg, 0.05 equiv), Rockphos (71 mg, 0.10 equiv), methyl (2E)-4-bromobut-2-enoate (1.36 g, 7.60 mmol, 5.00 equiv) in toluene (16 mL) was stirred for 2 h at 80° C. After concentration under reduced pressure, the residue was purified by silica gel column chromatography eluting with EtOAc/petroleum ether to afford 370 mg (49%) of the title compound as a yellow solid. LCMS: [M+H]$^+$ 492.21.

Step 2: (2E)-4-[[(2S)-1-[6-Oxo-5-(trifluoromethyl)-1-[[2-(trimethylsilyl)ethoxy]methyl]-1,6-dihydropyridazin-4-yl]pyrrolidin-2-yl]methoxy]but-2-enoic Acid A solution of methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate (350 mg, 0.71 mmol, 1.00 equiv), LiOH (30 mg, 1.25 mmol, 1.00 equiv) in MeOH (1.5 mL) and water (1.5 mL) was stirred for 12 h at RT. The resulting mixture was concentrated under reduced pressure to afford 200 mg of the title compound. LCMS: [M+H]+ 478.19.

Step 3: (2E)-4-[[(2S)-1-[6-Oxo-5-(trifluoromethyl)-1,6-dihydropyridazin-4-yl]pyrrolidin-2-yl]methoxy]but-2-enoic Acid A solution of (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoic acid (200 mg, 0.42 mmol, 1.00 equiv) in TFA (2 mL) and DCM (10 mL) was stirred for 2 h at RT. After concentration, the residue was purified by C18 reverse phase chromatography eluting with H$_2$O/CH$_3$CN to afford 90 mg (62%) of the title compound as a white solid. LCMS: [M+H]+ 348.11.

Step 4: 6-[4-[(3Z)-4-[[(2S)-1-[6-Oxo-5-(trifluoromethyl)-1,6-dihydropyridazin-4-yl]pyrrolidin-2-yl]methoxy]but-3-enoyl]piperazin-1-yl]pyridine-3-carbonitrile and 6-[4-[(3E)-4-[[(2S)-1-[6-Oxo-5-(trifluoromethyl)-1,6-dihydropyridazin-4-yl]pyrrolidin-2-yl]methoxy]but-2-enoyl]piperazin-1-yl]pyridine-3-carbonitrile A solution of (2E)-4-[[(2S)-1-[6-oxo-5-(trifluoromethyl)-1,6-dihydropyridazin-4-yl]pyrrolidin-2-yl]methoxy]but-2-enoic acid (80 mg, 0.23 mmol, 1 equiv), DIPEA (119.1 mg, 0.92 mmol, 4 equiv), HATU (87.6 mg, 0.23 mmol, 1.00 equiv), Int-A4 (43.4 mg, 0.23 mmol, 1.00 equiv) in DMF (2 mL) was stirred for 2 h at RT. The crude product was purified by C18 reverse phase chromatography eluting with H$_2$O/CH$_3$CN yielding the title compounds, respectively, as white solids, isomer A (4.2 mg, 3.5%). LCMS: [M+H]+ 518.20; $^1$H NMR (CD$_3$OD, 300 MHz) δ: 8.45 (dd, J=2.4, 0.8 Hz, 1H), 8.22 (s, 1H), 7.79 (dd, J=9.1, 2.4 Hz, 1H), 6.89 (dd, J=9.2, 0.8 Hz, 1H), 6.18 (d, J=6.1, 1.6 Hz, 1H), 4.81-4.72 (m, 1H), 4.57 (q, J=6.9 Hz, 1H), 4.04 (dd, J=10.8, 3.4 Hz, 1H), 3.84-3.62 (m, 8H), 3.57 (d, J=5.3 Hz, 2H), 3.41 (d, J=11.1 Hz, 1H), 3.10 (dd, J=7.2, 0.6 Hz, 2H), 2.33-2.22 (m, 1H), 2.10-1.98 (m, 1H), 1.87-1.60 (m, 2H), 1.40-1.28 (m, 1H) and isomer B (604 mg, 5.4%), LCMS: [M+H]+ 518.20; $^1$H NMR (CD$_3$OD, 300 MHz) δ: 8.46 (dd, J=2.4, 0.8 Hz, 1H), 8.31 (s, 1H), 7.80 (dd, J=9.1, 2.4 Hz, 1H), 6.93 (dd, J=9.1, 0.8 Hz, 1H), 6.83 (dt, J=15.2, 3.6 Hz, 1H), 6.47 (dt, J=15.2, 2.1 Hz, 1H), 4.82-4.68 (m, 1H), 4.33-4.10 (m, 2H), 3.90-3.60 (m, 10H), 3.50-3.38 (m, 2H), 2.45-2.20 (m, 1H), 2.10-1.95 (m, 1H), 1.86-1.59 (m, 2H), 1.40-1.30 (m, 1H).

Example 97: 6-[4-[4-([1-[6-oxo-5-(trifluoromethyl)-1,6-dihydropyridazin-4-yl]pyrrolidin-3-yl]methoxy)cyclohexanecarbonyl]piperazin-1-yl]pyridine-3-carbonitrile

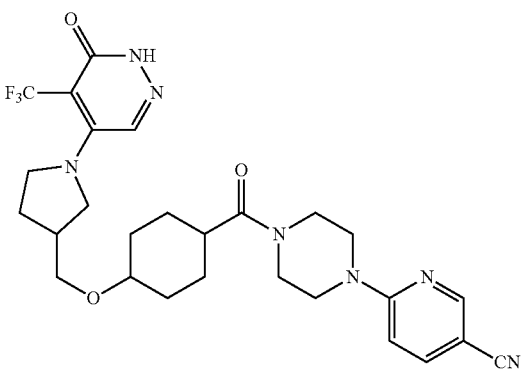 [SMILES: N#Cc1ccc(N2CCN(C(=O)C3CCC(OCC4CCN(c5cn[nH]c(=O)c5C(F)(F)F)C4)CC3)CC2)nc1]

Step 1: Methyl 4-([1-[6-oxo-5-(trifluoromethyl)-1-[[2-(trimethylsilyl)ethoxy]methyl]-1,6-dihydropyridazin-4-yl]pyrrolidin-3-yl]methoxy)benzoate Under nitrogen, a solution of 5-[3-(hydroxymethyl)pyrrolidin-1-yl]-4-(trifluoromethyl)-2-[[2-(trimethylsilyl)ethoxy]methyl]-2,3-dihydropyridazin-3-one (300 mg, 0.76 mmol, 1.00 equiv), methyl 4-bromobenzoate (242 mg, 1.13 mmol, 1.50 equiv), Pd[(allyl)Cl$_2$]$_2$ (30 mg, 0.10 equiv), Rockphos (60 mg, 0.20 equiv) and Cs$_2$CO$_3$ (480 mg, 2.00 equiv) in toluene (3 mL) was stirred for 1 h at 80° C., and then the resulting solution was diluted with 50 mL of EtOAc and washed with 3×40 mL of H$_2$O, and then the organic layers were concentrated under reduced pressure and the residue was purified by silica gel column chromatography eluting with EtOAc/petroleum ether (46/54, v/v) to afford 330 mg (82%) of the title compound as a yellow oil. LCMS: [M+H]+ 528.21.

Step 2: Methyl 4-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclohexane-1-carboxylate Under a hydrogen atmosphere, a solution of methyl 4-([1-[6-oxo-5-(trifluoromethyl)-1-[[2-(trimethylsilyl)ethoxy]methyl]-1,6-dihydropyridazin-4-yl]pyrrolidin-3-yl]methoxy)benzoate (295 mg, 0.56 mmol, 1.00 equiv) and Rh/Al$_2$O$_3$ (600 mg, 2.00 equiv) in MeOH (10 mL) was stirred for 16 h at RT, and then the solids were filtered out, and the resulting solution was concentrated under vacuum to afford 310 mg of crude title compound as a yellow green oil. LCMS: [M+H]+ 534.25.

Step 3: 4-([1-[6-Oxo-5-(trifluoromethyl)-1-[[2-(trimethylsilyl)ethoxy]methyl]-1,6-dihydropyridazin-4-yl]pyrrolidin-3-yl]methoxy)cyclohexane-1-carboxylic Acid A solution of methyl 4-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclohexane-1-carboxylate (290 mg, 0.54 mmol, 1.00 equiv) and LiOH (136 mg) in water (0.5 mL) and THF (2.5 mL) was stirred for 16 h at 40°

C., and then the resulting solution was concentrated under vacuum and the residue was purified by C18 reverse phase chromatography eluting with $H_2O/CH_3CN$ to afford 145 mg (51%) of the title compound as a yellow oil. LCMS: [M+H]$^+$ 520.24.

Step 4: 4-([1-[6-Oxo-5-(trifluoromethyl)-1,6-dihydropyridazin-4-yl]pyrrolidin-3-yl]methoxy)cyclohexane-1-carboxylic Acid A solution of 4-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclohexane-1-carboxylic acid (145 mg, 0.28 mmol, 1.00 equiv) and TFA (0.5 mL) in DCM (2.5 mL) was stirred for 2 h at RT, and then the resulting solution was concentrated under vacuum to afford 120 mg of the title compound as a yellow oil. LCMS: [M+H]$^+$ 390.16.

Step 5: 6-[4-[4-([1-[6-Oxo-5-(trifluoromethyl)-1,6-dihydropyridazin-4-yl]pyrrolidin-3-yl]methoxy)cyclohexanecarbonyl]piperazin-1-yl]pyridine-3-carbonitrile A solution of 4-([1-[6-oxo-5-(trifluoromethyl)-1,6-dihydropyridazin-4-yl]pyrrolidin-3-yl]methoxy)cyclohexane-1-carboxylic acid (120 mg, 0.31 mmol, 1.00 equiv), Int-A4 (62 mg, 0.33 mmol, 1.10 equiv), HATU (114 mg, 0.30 mmol, 1.00 equiv) and DIPEA (77 mg, 0.60 mmol, 2.00 equiv) in DMF (5 mL) was stirred for 1 h at RT and then the resulting solution was purified by C18 reverse phase chromatography eluting with $H_2O/CH_3CN$. After concentration by reduced pressure, the residue was further purified by Prep-HPLC yielding the title compound as a white solid (13.8 mg, 8%). LCMS: [M+H]$^+$ 560.30. $^1$H NMR (Methanol-d$_4$, 300 MHz) δ 8.44 (d, J=1.8 Hz, 1H), 7.94 (s, 1H), 7.79 (dd, J=9.0, 2.4 Hz, 1H), 6.90 (d, J=8.7 Hz, 1H), 3.86-3.69 (m, 11H), 3.59-3.43 (m, 4H), 2.79-2.71 (m, 1H), 2.63-2.54 (m, 1H), 2.20-2.10 (m, 1H), 2.03-1.78 (m, 5H), 1.55 (t, J=12.9 Hz, 4H).

Example 98: 6-[4-(3-[[(2S)-1-[6-Oxo-5-(trifluoromethyl)-1,6-dihydropyridazin-4-yl]pyrrolidin-2-yl]methoxy]propanoyl)piperazin-1-yl]pyridine-3-carbonitrile

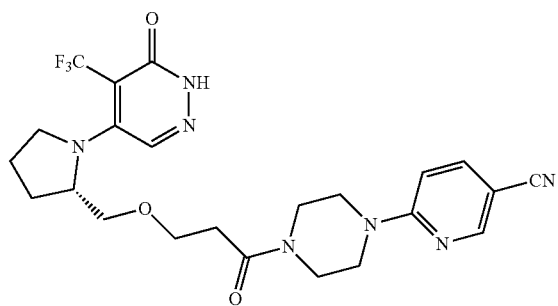 [SMILES: N#Cc1ccc(N2CCN(C(=O)CCOC[C@@H]3CCCN3c3cn[nH]c(=O)c3C(F)(F)F)CC2)nc1]

Step 1: Methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (Example 31, Step 1; 1.97 g, 5.01 mmol, 1.00 equiv), NaH (2 g, 83.3 mmol, 10.0 equiv), methyl prop-2-enoate (1.72 g, 20.0 mmol, 4.00 equiv) in THF (100 mL) was stirred overnight at RT. The reaction was then quenched by the addition of 200 mL of water. The resulting solution was extracted with 3×150 mL of EtOAc and the organic layers combined and concentrated under vacuum. The residue was purified by silica gel chromatography using EtOAc/petroleum ether (3/1, v/v) to afford 700 mg (29%) of the title compound as a light yellow solid. LCMS: [M+H]$^+$ 480.21.

Step 2: Methyl 3-[[(2S)-1-[6-oxo-5-(trifluoromethyl)-1,6-dihydropyridazin-4-yl]pyrrolidin-2-yl]methoxy]propanoate A solution of methyl 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate (700 mg, 1.46 mmol, 1.00 equiv) in HCl/dioxane (30 mL) was stirred overnight at RT. The resulting mixture was concentrated under vacuum to afford 500 mg of the title compound. LCMS: [M+H]$^+$ 350.12.

Step 3: 3-[[(2S)-1-[6-Oxo-5-(trifluoromethyl)-1,6-dihydropyridazin-4-yl]pyrrolidin-2-yl]methoxy]propanoic A solution of methyl 3-[[(2S)-1-[6-oxo-5-(trifluoromethyl)-1,6-dihydropyridazin-4-yl]pyrrolidin-2-yl]methoxy] propanoate (500 mg, 1.43 mmol, 1.00 equiv), LiOH (171 mg, 7.41 mmol, 5.00 equiv) in MeOH (20 mL) and water (5 mL) was stirred for 2 h at RT. After concentration, the residue was purified by C18 reverse phase chromatography eluting with $H_2O/CH_3CN$ to afford 120 mg of the title compound. LCMS: [M+H]$^+$ 336.11.

Step 4: 6-[4-(3-[[(2S)-1-[6-oxo-5-(trifluoromethyl)-1,6-dihydropyridazin-4-yl]pyrrolidin-2-yl]methoxy]propanoyl)piperazin-1-yl]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (110 mg, 0.33 mmol, 1.00 equiv), HATU (125 mg, 0.33 mmol, 1.00 equiv), DIPEA (170 mg, 1.32 mmol, 4.00 equiv), Int-A (62 mg, 0.33 mmol, 1.00 equiv) in DMF (2 mL) was stirred for 30 min at RT. After concentration, the residue was purified by C18 reverse phase chromatography eluting with $H_2O/CH_3CN$ to afford the title compound (77.7 mg 47%) as a white solid. LCMS: [M+H]$^+$ 506.20, $^1$H NMR (Methanol-d$_4$, 300 MHz) δ: 8.42-8.41 (d, J=2.3 Hz, 1H), 8.12 (s, 1H), 7.77-7.73 (dd, J=9.1, 2.3 Hz, 1H), 6.86-6.84 (d, J=9.0 Hz, 1H), 4.59-4.55 (dd, J=7.8, 3.8 Hz, 1H), 3.82-3.61 (m, 12H), 3.45-3.30 (m, 2H), 2.64-2.59 (td, J=5.9, 2.0 Hz, 2H), 2.22-2.18 (dr, 1H), 1.98-1.93 (p, J=5.4, 4.7 Hz, 1H), 1.69-1.63 (br s, 2H).

Example 99: N-[4-[(5-cyanopyridin-2-yl)oxy]cyclohexyl]-3-[[(2S)-1-[6-oxo-5-(trifluoromethyl)-1,6-dihydropyridazin-4-yl]pyrrolidin-2-yl]methoxy]propanamide

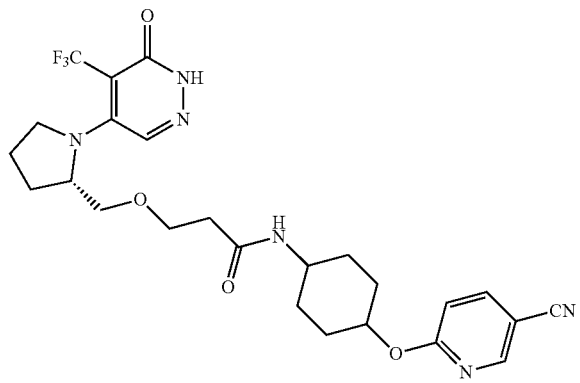 [SMILES: N#Cc1ccc(OC2CCC(NC(=O)CCOC[C@@H]3CCCN3c3cn[nH]c(=O)c3C(F)(F)F)CC2)nc1]

Step 1: Synthesis of Tert-Butyl N-[4-[(5-cyanopyridin-2-yl)oxy]cyclohexyl]carbamate A solution of tert-butyl N-(4-hydroxycyclohexyl)carbamate (2.26 g, 10.50 mmol, 1.05 equiv), sodium hydride (440 mg, 18.3 mmol, 1.10 equiv), 6-chloropyridine-3-carbonitrile (1.38 g, 9.96 mmol, 1.00 equiv) in DMF (45 mL) was stirred for 2 h at room temperature. The resulting solution was quenched with 30 ml water, extracted with EtOAc (3×30 mL) and the organic layers combined. The resulting mixture was concentrated under vacuum. The residue was applied onto a silica gel column with EtOAc/petroleum ether (1:4) to afford 2 g (63%) of the title compound as a white solid. LCMS (ESI, m/z): 318.18 [M+H]$^+$

Step 2: Synthesis of 6-(4-aminocyclohexyloxy)nicotinonitrile Hydrogen Chloride A solution of tert-butyl N-[4-[(5-cyanopyridin-2-yl)oxy]cyclohexyl]carbamate (146 mg, 0.46 mmol, 1.00 equiv) in hydrogen chloride/dioxane (3 mL) was stirred for 6 min at room temperature. The resulting mixture was concentrated under vacuum to afford 1.2 g crude of the title compound as a white solid. LCMS (ESI, m/z): 218.13 [M+H]$^+$

Step 3: Synthesis of N-[4-[(5-cyanopyridin-2-yl)oxy]cyclohexyl]-3-[[(2S)-1-[6-oxo-5-(trifluoromethyl)-1,6-dihydropyridazin-4-yl]pyrrolidin-2-yl]methoxy]propanamide A solution of 6-(4-aminocyclohexyloxy)nicotinonitrile hydrogen chloride (52 mg, 0.24 mmol, 1.20 equiv), 3-[[(2S)-1-[6-oxo-5-(trifluoromethyl)-1,6-dihydropyridazin-4-yl]pyrrolidin-2-yl]methoxy]propanoic acid (70 mg, 0.21 mmol, 1.00 equiv), HATU (100 mg, 0.26 mmol, 1.50 equiv), DIPEA (62 mg, 0.48 mmol, 2.00 equiv) in DMF (40 mL) was stirred 2 h at room temperature. After concentration, the residue was purified by C18 reverse phase chromatography eluting with H$_2$O/CH$_3$CN. Then the residue was further purified by Prep-HPLC yielding the title compound (46.3 mg 41%) as a white solid. LCMS (ESI, m/z): 535.30 [M+H]$^+$, $^1$H NMR (300 MHz, Chloroform-d) δ 8.53 (s, 1H), 8.15 (s, 1H), 7.95 (dd, J=8.7, 2.4 Hz, 1H), 6.87 (dd, J=8.7, 0.8 Hz, 1H), 5.09-4.91 (m, 1H), 4.69-4.68 (m, 1H), 3.75-3.60 (m, 5H), 3.49-3.34 (m, 2H), 2.40-2.36 (m, 2H), 2.21-2.15 (m, 3H), 2.06-1.97 (m, 3H), 1.74-1.57 (m, 4H), 1.44-1.39 (m, 2H).

Example 100: 6-[(3R)-3-methyl-4-(3-[[(2S)-1-[6-oxo-5-(trifluoromethyl)-1,6-dihydropyridazin-4-yl]pyrrolidin-2-yl]methoxy]propanoyl)piperazin-1-yl]pyridine-3-carbonitrile and 6-[(3S)-3-methyl-4-(3-[[[(2S)-1-[6-oxo-5-(trifluoromethyl)-1,6-dihydropyridazin-4-yl]pyrrolidin-2-yl]methoxy]propanoyl)piperazin-1-yl]pyridine-3-carbonitrile Example 100

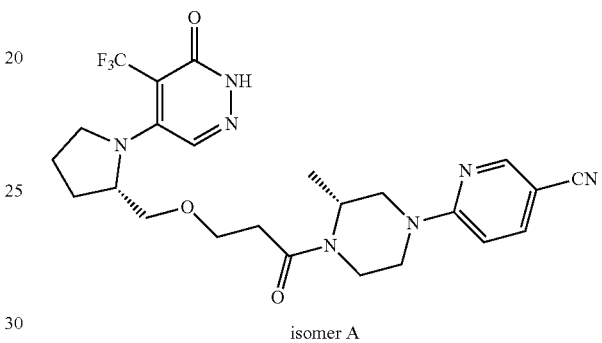

isomer A

Example 100

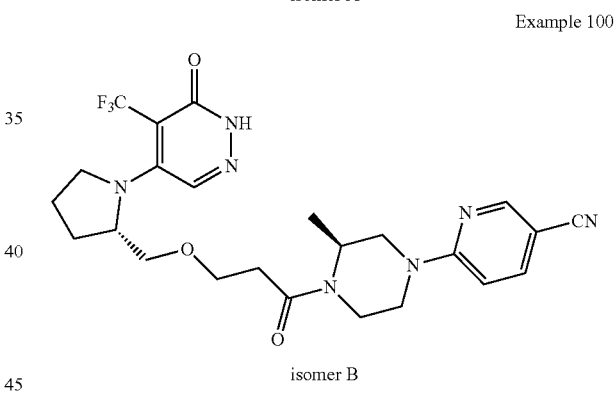

isomer B

Step 1: Synthesis of Tert-Butyl 4-(5-cyanopyridin-2-yl)piperazine-1-carboxylate A solution of tert-butyl piperazine-1-carboxylate (1 g, 5.37 mmol, 1.00 equiv), 6-chloropyridine-3-carbonitrile (690 mg, 4.98 mmol, 1.00 equiv), potassium carbonate (1.4 g, 10.13 mmol, 2.00 equiv), NMP (20 mL) was stirred for 1 h at 80° C. The resulting solution was quenched by 100 ml of water and extracted with 2×100 mL of EtOAc and the organic layers combined and concentrated under vacuum to afforded 1.2 g (78%) of the title compound as yellow oil. LCMS (ESI, m/z): 303.15 [M+H]$^+$

Step 2. Synthesis of 6-(piperazin-1-yl)pyridine-3-carbonitrile Hydrochloride A solution of tert-butyl 4-(5-cyanopyridin-2-yl)piperazine-1-carboxylate (1.2 g, 4.16 mmol, 1.00 equiv), dioxane/HCl (10 mL). The resulting solution was stirred for 30 min at 25° C. The solids were collected by filtration to afforded 800 mg (86%) of the title compound as a white solid. LCMS (ESI, m/z): 203.22 [M+H]+

Step 3. Synthesis of 6-[(3R)-3-methyl-4-(3-[[(2S)-1-[6-oxo-5-(trifluoromethyl)-1,6-dihydropyridazin-4-yl]pyrrolidin-2-yl]methoxy]propanoyl)piperazin-1-yl]pyridine-3-carbonitrile and 6-[(3S)-3-methyl-4-(3-[[(2S)-1-[6-oxo-5-(trifluoromethyl)-1,6-dihydropyridazin-4-yl]pyrrolidin-2-yl]methoxy] propanoyl)piperazin-1-yl]pyridine-3-carbonitrile A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.00 equiv), 6-(3-methylpiperazin-1-yl)pyridine-3-carbonitrile hydrochloride (60 mg, 0.25 mmol, 1.00 equiv), HATU (110 mg, 0.29 mmol, 1.00 equiv), DIPEA (1 mL), DMF (2 mL). The resulting solution was stirred for 2 h at 25° C. After concentration, the residue was purified by C18 reverse phase chromatography eluting with H2O/CH3CN. Then the residue was further purified by Prep-HPLC and Chiral-Prep-HPLC yielding (after arbitrary assignment of the stereochemistry) the title compounds, respectively, as white solids, isomer A (6.0 mg, 15%). LCMS (ESI, m/z): 520.30 [M+H]+, 1HNMR (DMSO-d6, 400 MHz) δ: 12.07 (s, 1H), 8.42 (d, J=2.4 Hz, 1H), 7.93 (s, 1H), 7.81 (d, J=4.0 Hz, 1H), 6.86 (d, J=11.6 Hz, 1H), 4.60-4.30 (m, 2H), 4.25-4.18 (m, 2H), 4.01-3.80 (br, 1H), 3.72-3.58 (m, 2H), 3.50-3.10 (m, 7H), 2.62-3.32 (m, 2H), 2.15-2.01 (br, 1H), 1.98-1.82 (br, 1H), 1.68-1.73 (m, 2H), 1.12-1.23 (d, J=8.8 Hz, 3H). tR=1.238 min (CHIRALPAK IG, 20*250 mm, 5 um, Hex (0.1% DEA):EtOH=80:20, 1.0 mL/min) and isomer B (4.7 mg, 12%) as a white solid. LCMS (ESI, m/z): 520.30 [M+H]+, tR=1.233 min (CHIRAL Cellulose-SB, 0.46*15 cm; 5 um, Hex(0.1% DEA):EtOH=80:20, 1.0 mL/min). 1HTME-NMR (DMSO-d6, 353 k, 400 MHz) δ: 12.07 (s, 1H), 8.42 (d, J=2.4 Hz, 1H), 7.93 (s, 1H), 7.81 (d, J=4.0 Hz, 1H), 6.86 (d, J=11.6 Hz, 1H), 4.60-4.30 (m, 2H), 4.25-4.18 (m, 2H), 4.01-3.80 (br, 1H), 3.72-3.58 (m, 2H), 3.50-3.10 (m, 7H), 2.62-3.32 (m, 2H), 2.15-2.01 (br, 1H), 1.98-1.82 (br, 1H), 1.68-1.73 (m, 2H), 1.12-1.23 (d, J=8.8 Hz, 3H).

Example 101: 6-[5-(3-[[(2S)-1-[6-oxo-5-(trifluoromethyl)-1,6-dihydropyridazin-4-yl]pyrrolidin-2-yl] methoxy]propanoyl)-2,5-diazabicyclo[2.2.2]octan-2-yl]pyridine-3-carbonitrile bonate (1.3 g, 9.41 mmol, 2.00 equiv), 6-chloropyridine-3-carbonitrile (651 mg, 4.70 mmol, 1.00 equiv) in DMF (10 mL) was stirred for 2 h at 80° C. in an oil bath. After concentration, the residue was applied onto a silica gel column eluting with EtOAc/petroleum ether (1:3) to afford 940 mg (63%) of the title compound as a solid. LCMS (ESI, m/z): 315.17 [M+H]+

Step 2: Synthesis of 6-[2,5-diazabicyclo[2.2.2]octan-2-yl]pyridine-3-carbonitrile Hydrochloride A solution of tert-butyl 5-(5-cyanopyridin-2-yl)-2,5-diazabicyclo[2.2.2]octane-2-carboxylate (300 mg, 0.95 mmol, 1.00 equiv) in hydrogen chloride/dioxane (5 mL) was stirred for 1 h at room temperature. After filtration, the filtrate was concentrated under reduced pressure to afford 180 mg (75%) of the title compound as a solid. LCMS (ESI, m/z): 215.12 [M−Cl]+

Step 3: Synthesis of 6-[5-(3-[[(2S)-1-[6-oxo-5-(trifluoromethyl)-1,6-dihydropyridazin-4-yl]pyrrolidin-2-yl]methoxy]propanoyl)-2,5-diazabicyclo[2.2.2] octan-2-yl]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (114 mg, 0.30 mmol, 1.00 equiv), DIPEA (155 mg, 1.20 mmol, 4.00 equiv), 6-2,5-diazabicyclo[2.2.2]octan-2-ylpyridine-3-carbonitrile hydrochloride (86 mg, 0.30 mmol, 1.00 equiv) in DMF (2 mL) was stirred for 1 h at room temperature. After concentration, the residue was purified by C18 reverse phase chromatography eluting with H2O/CH3CN and purified by Prep-HPLC yielding the title compound (42.7 mg 27%) as a white solid. LCMS (ESI, m/z): 532.22 [M+H]+, 1H NMR (Methanol-d4, 400 MHz) δ: 8.39-8.38 (d, J=2.3 Hz, 1H), 8.11-8.07 (m, 1H), 7.75-7.71 (dt, J=9.0, 2.1 Hz, 1H), 6.55-6.65 (dr, 1H), 5.05 (dr, 1H), 4.56-4.49 (dr, 2H), 3.79-3.36 (m, 10H), 2.64-2.56 (m, 1H), 2.51-2.47 (m, 1H), 2.17 (dr, 1H), 2.03-1.88 (m, 5H), 1.69-1.67 (d, J=5.9 Hz, 2H).

Example 102: 6-[3-(3-[[(2S)-1-[6-oxo-5-(trifluoromethyl)-1,6-dihydropyridazin-4-yl]pyrrolidin-2-yl] methoxy]propanoyl)-3,8-diazabicyclo[3.2.1]octan-8-yl]pyridine-3-carbonitrile

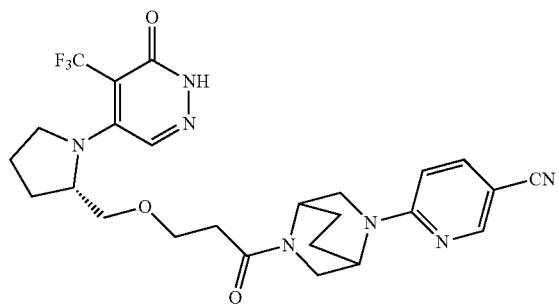 [SMILES: N#Cc1ccc(N2CC3CCC2CN3C(=O)CCOC[C@@H]2CCCN2c2cn[nH]c(=O)c2C(F)(F)F)nc1]

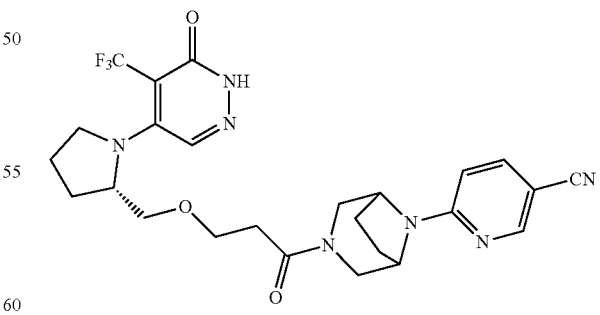

Step 1: Synthesis of Tert-Butyl 5-(5-cyanopyridin-2-yl)-2,5-diazabicyclo[2.2.2]octane-2-carboxylate A solution of tert-butyl 2,5-diazabicyclo[2.2.2]octane-2-carboxylate (1 g, 4.71 mmol, 1.00 equiv), potassium car- Step 1: Synthesis of Tert-Butyl 8-(5-cyanopyridin-2-yl)-3,8-diazabicyclo[3.2.1]octane-3-carboxylate A solution of tert-butyl 3,8-diazabicyclo[3.2.1]octane-3-carboxylate (1 g, 4.71 mmol, 1.00 equiv), potassium carbonate (1.3 g, 9.41 mmol, 2.00 equiv), 5-chloropyridin-2-carbonitrile (651 mg, 4.67 mmol, 1.00 equiv) in DMF (10 mL) was stirred for 2 h at 80° C. in an oil bath. The solids were filtered out. The resulting solution was extracted with 3×20 mL of ether and the organic layers combined. After concentration, the residue was applied onto a silica gel column eluting with EtOAc/petroleum ether (1:2) to afford 1 g (68%) of the title compound as a solid. LCMS (ESI, m/z): 315.17 [M+H]$^+$ Step 2: Synthesis of 6-3,8-diazabicyclo[3.2.1]octan-8-ylpyridine-3-carbonitrile Hydrochloride A solution of tert-butyl 8-(5-cyanopyridin-2-yl)-3,8-diazabicyclo[3.2.1]octane-3-carboxylate (300 mg, 0.95 mmol, 1.00 equiv) in dioxane/HCl (10 mL) was stirred for 1 h at room temperature. The solids were collected by filtration to afford 170 mg (83%) of the title compound as a yellow solid. LCMS (ESI, m/z): 215.12 [M−Cl]$^+$ Step 3: Synthesis of 6-[3-(3-[[(2S)-1-[6-oxo-5-(trifluoromethyl)-1,6-dihydropyridazin-4-yl]pyrrolidin-2-yl]methoxy]propanoyl)-3,8-diazabicyclo[3.2.1]octan-8-yl]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (114 mg, 0.30 mmol, 1.00 equiv), DIPEA (155 mg, 1.20 mmol, 4.00 equiv), 6-3,8-diazabicyclo[3.2.1]octan-8-ylpyridine-3-carbonitrile hydrochloride (86 mg, 0.30 mmol, 1.00 equiv) in DMF (2 mL) was stirred for 1 h at room temperature. After concentration, the residue was purified by C18 reverse phase chromatography eluting with H$_2$O/CH$_3$CN and purified by Prep-HPLC yielding the title compound (85.4 mg 54%) as a white solid. LCMS (ESI, m/z): 532.22 [M+H]$^+$, $^1$H NMR (Methanol-d$_4$, 400 MHz) δ: 8.42 (dd, J=2.4, 0.8 Hz, 1H), 8.09 (d, J=4.2 Hz, 1H), 7.75 (dd, J=9.0, 2.3 Hz, 1H), 6.84 (dd, J=9.0, 0.8 Hz, 1H), 4.85 (m, 1H) 4.71 (dr, 2H), 4.55 (dr, 1H), 4.27-4.23 (d, J=13.1 Hz, 1H), 3.75-3.69 (m, 5H), 3.44-3.41 (m, 2H), 2.91-2.86 (d, J=13.3 Hz, 1H), 2.60-2.55 (m, 2H), 2.03-2.01 (dr, 1H), 1.96-1.82 (m, 3H), 1.75-1.68 (m, 4H).

Example 103: 6-[2-(3-[[(2S)-1-[6-oxo-5-(trifluoromethyl)-1,6-dihydropyridazin-4-yl]pyrrolidin-2-yl]methoxy]propanoyl)-2,8-diazaspiro[4.5]decan-8-yl]pyridine-3-carbonitrile dine-3-carbonitrile (345 mg, 2.49 mmol, 2.00 equiv) and potassium carbonate (345 mg, 2.50 mmol, 2.00 equiv) in NMP (10 mL) was stirred for 1 h at 80° C., and then the resulting solution was diluted with 45 mL of water, extracted with 2×20 mL of EtOAc, and then the organic layers combined and concentrated under vacuum to afford 650 mg (crude) of the title compound as a brown solid. LCMS (ESI, m/z): 343.21 [M+H]$^+$ Step 2: Synthesis of 6-[2,8-diazaspiro[4.5]decan-8-yl]pyridine-3-carbonitrile A solution of tert-butyl 8-(5-cyanopyridin-2-yl)-2,8-diazaspiro[4.5]decane-2-carboxylate (640 mg, 1.87 mmol, 1.00 equiv) and TFA (1 mL) in DCM (5 mL) was stirred for 1 h at room temperature, and then the resulting solution was concentrated under vacuum to afford 1 g (crude) of the title compound as brown oil. LCMS (ESI, m/z): 243.16 [M+H]$^+$.

Step 3: Synthesis of 6-[2-(3-[[(2S)-1-[6-oxo-5-(trifluoromethyl)-1,6-dihydropyridazin-4-yl]pyrrolidin-2-yl]methoxy]propanoyl)-2,8-diazaspiro[4.5]decan-8-yl]pyridine-3-carbonitrile A solution of 6-[2,8-diazaspiro[4.5]decan-8-yl]pyridine-3-carbonitrile (109 mg, 0.45 mmol, 1.50 equiv), 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (114 mg, 0.30 mmol, 1.00 equiv) and DIPEA (77 mg, 0.60 mmol, 2.00 equiv) in DMF (2 mL) was stirred for 1 h at room temperature, and then the resulting solution was purified by C18 reverse phase chromatography eluting with H$_2$O/CH$_3$CN. After concentration, and then the residue was further purified by Prep-HPLC yielding the title compound (97 mg, 58%) as a white solid. LCMS (ESI, m/z): 560.30 [M+H]$^+$, $^1$HNMR (Methanol-d$_4$, 300 MHz) δ 8.44 (d, J=1.8 Hz, 1H), 7.94 (s, 1H), 7.79 (dd, J=9.0, 2.4 Hz, 1H), 6.90 (d, J=8.7 Hz, 1H), 3.86-3.69 (m, 11H), 3.59-3.43 (m, 4H), 2.79-2.71 (m, 1H), 2.63-2.54 (m, 1H), 2.20-2.10 (m, 1H), 2.03-1.78 (m, 5H), 1.55 (t, J=12.9 Hz, 4H).

Example 104: 6-[8-(3-[[(2S)-1-[6-oxo-5-(trifluoromethyl)-1,6-dihydropyridazin-4-yl]pyrrolidin-2-yl]methoxy]propanoyl)-2,8-diazaspiro[4.5]decan-2-yl]pyridine-3-carbonitrile

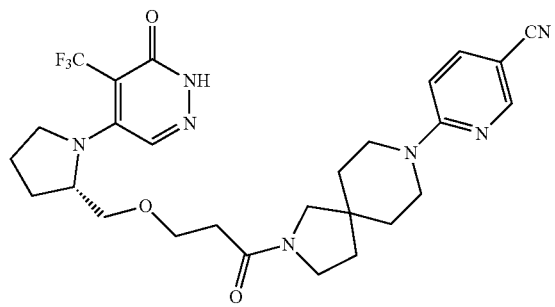 [SMILES: N#Cc1ccc(N2CCC3(CCN(C(=O)CCOC[C@@H]4CCCN4c4cn[nH]c(=O)c4C(F)(F)F)C3)CC2)nc1]

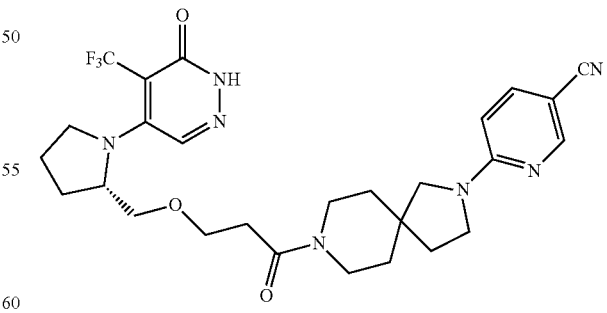

Step 1: Synthesis of Tert-Butyl 8-(5-cyanopyridin-2-yl)-2,8-diazaspiro[4.5]decane-2-carboxylate A solution of tert-butyl 2,8-diazaspiro[4.5]decane-2-carboxylate (300 mg, 1.25 mmol, 1.00 equiv), 6-chloropyri- Step 1: Synthesis of Tert-Butyl 2-(5-cyanopyridin-2-yl)-2,8-diazaspiro[4.5]decane-8-carboxylate A solution of tert-butyl 2,8-diazaspiro[4.5]decane-8-carboxylate (300 mg, 1.25 mmol, 1.00 equiv), K$_2$CO$_3$ (345 mg, 2.50 mmol, 2.00 equiv) and 6-bromopyridine-3-carbonitrile (465 mg, 2.54 mmol, 2.00 equiv) in NMP (20 mL) was stirred for 2 h at 80° C. in an oil bath, and then the resulting solution was diluted with 200 mL of H2O, extracted with 3×50 mL of EtOAc and the organic layers combined, washed with 1×50 mL of brine, dried over anhydrous sodium sulfate and concentrated under vacuum to afford 220 mg (51%) of the title compound as a brown solid. LCMS (ESI, m/z): 343.21[M+H]$^+$.

Step 2: Synthesis of 6-[2,8-diazaspiro[4.5]decan-2-yl]pyridine-3-carbonitrile

A solution of tert-butyl 2-(5-cyanopyridin-2-yl)-2,8-diazaspiro[4.5]decane-8-carboxylate (200 mg, 0.58 mmol, 1.00 equiv) and TFA (1.5 mL) in DCM (7 mL) was stirred for 1 h at room temperature, and then the resulting solution was concentrated under vacuum to afford 155 mg (57.5%) of the title compound as a brown solid. LCMS (ESI, m/z): 243.16 [M+H]$^+$.

Step 3: Synthesis of 6-[8-(3-[[(2S)-1-[6-oxo-5-(trifluoromethyl)-1,6-dihydropyridazin-4-yl]pyrrolidin-2-yl]methoxy]propanoyl)-2,8-diazaspiro[4.5]decan-2-yl]pyridine-3-carbonitrile A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.20 equiv), HATU (100 mg, 0.26 mmol, 1.00 equiv), DIPEA (67 mg, 0.52 mmol, 2.00 equiv) and 6-[2,8-diazaspiro[4.5]decan-2-yl]pyridine-3-carbonitrile (51 mg, 0.21 mmol, 1.00 equiv) in DMF (15 mL) was stirred for 40 min at room temperature, and then the resulting solution was diluted with 50 mL of H2O, extracted with 3×50 mL of EtOAc and the organic layers combined, washed with 1×50 mL of brine and concentrated under vacuum, and then the residue was purified by Prep-HPLC yielding the title compound (45.6 mg, 45.6%) as a white solid. LCMS (ESI, m/z): 560.15 [M+H]+, $^1$HNMR (CD3OD, 300 MHz) δ 8.38 (d, J=2.3 Hz, 1H), 8.15 (s, 1H), 7.74 (dd, J=9.0, 2.4 Hz, 1H), 6.61 (d, J=9.0 Hz, 1H), 4.61 (s, 1H), 3.82-3.36 (m, 14H), 2.61 (d, J=4.8 Hz, 2H), 2.25-2.21 (m, 1H), 2.05-1.97 (m, 3H), 1.76-1.57 (m, 6H).

Example 105: 6-[2-(3-[[(2S)-1-[6-oxo-5-(trifluoromethyl)-1,6-dihydropyridazin-4-yl]pyrrolidin-2-yl]methoxy]propanoyl)-2,7-diazaspiro[3.5]nonan-7-yl]pyridine-3-carbonitrile

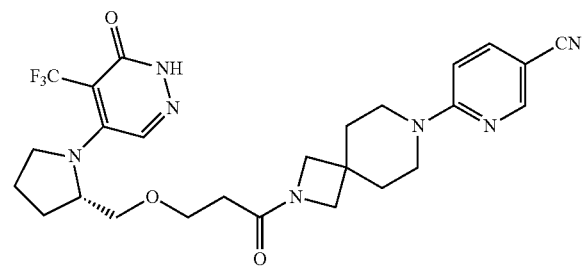 [SMILES: N#Cc1ccc(N2CCC3(CC2)CN(C(=O)CCOC[C@@H]2CCCN2c2cn[nH]c(=O)c2C(F)(F)F)C3)nc1]

Step 1: Synthesis of Tert-Butyl 7-(5-cyanopyridin-2-yl)-2,7-diazaspiro[3.5]nonane-2-carboxylate A solution of tert-butyl 2,7-diazaspiro[3.5]nonane-2-carboxylate (300 mg, 1.33 mmol, 1.00 equiv), 6-chloropyridine-3-carbonitrile (495 mg, 3.57 mmol, 2.00 equiv) and K$_2$CO$_3$ (375 mg, 2.71 mmol, 2.00 equiv) in NMP (20 mL) was stirred for 2 h at 80° C., and then the resulting solution was diluted with 200 mL of H2O, extracted with 3×50 mL of EtOAc and the organic layers combined, washed with 1×50 mL of brine, dried over anhydrous sodium sulfate and concentrated under vacuum to afford 336 mg (77%) of the title compound as a brown solid. LCMS (ESI, m/z): 329.19 [M+H]$^+$.

Step 2: Synthesis of 6-[2,7-diazaspiro[3.5]nonan-7-yl]pyridine-3-carbonitrile

A solution of tert-butyl 7-(5-cyanopyridin-2-yl)-2,7-diazaspiro[3.5]nonane-2-carboxylate (316 mg, 0.96 mmol, 1 equiv) and TFA (1.5 mL) in DCM (7 mL) was stirred for 1 h at room temperature, and then the resulting solution was concentrated to afford 198 mg (90.14%) of the title compound as a light brown solid. LCMS (ESI, m/z): 229.14 [M+H]$^+$.

Step 3: Synthesis of 6-[2-(3-[[(2S)-1-[6-oxo-5-(trifluoromethyl)-1,6-dihydropyridazin-4-yl]pyrrolidin-2-yl]methoxy]propanoyl)-2,7-diazaspiro[3.5]nonan-7-yl]pyridine-3-carbonitrile A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.20 equiv), HATU (100 mg, 0.26 mmol, 1.00 equiv), DIPEA (66 mg, 0.51 mmol, 2.00 equiv) and 6-[2,7-diazaspiro[3.5]nonan-7-yl]pyridine-3-carbonitrile (58 mg, 0.25 mmol, 1.00 equiv) in DMF (15 mL) was stirred for 40 min at room temperature, and then the resulting solution was diluted with 20 ml of H2O, extracted with 3×20 ml of EtOAc and the organic layer was combined, washed with 1×20 ml of brine and concentrated under vacuum, and then the residue was purified by Prep-HPLC yielding the title compound (73.5 mg, 53.0%) as a white solid. LCMS (ESI, m/z): 546.15 [M+H]$^+$, $^1$HNMR (CD3OD, 300 MHz) δ 8.40 (d, J=2.4, 1H), 8.16 (s, 1H), 7.74 (dd, J=9.0, 2.4 Hz, 1H), 6.90 (d, J=8.7 Hz, 1H), 4.61 (s, 1H), 3.92 (s, 2H), 3.80-3.61 (m, 10H), 3.43 (dd, J=10.1, 7.7 Hz, 2H), 2.34 (t, J=6.0 Hz, 2H), 2.23 (t, J=5.4 Hz, 1H), 2.05-1.97 (m, 1H), 1.87-1.65 (m, 6H).

Example 106: (S)-6-(4-(3-((1-(6-oxo-5-(trifluoromethyl)-1,6-dihydropyridazin-4-yl)pyrrolidin-2-yl)methoxy)propanoyl)-1,4-diazepan-1-yl)nicotinonitrile

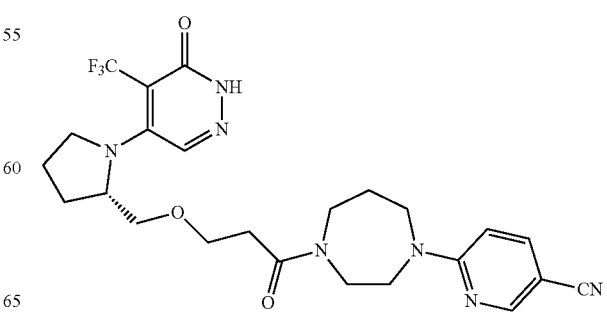

Step 1: Synthesis of Tert-Butyl 4-(5-cyanopyridin-2-yl)-1,4-diazepane-1-carboxylate A solution of tert-butyl 1,4-diazepane-1-carboxylate (1.5 g, 7.49 mmol, 1.00 equiv), 6-chloropyridine-3-carbonitrile (1.174 g, 8.47 mmol, 1.05 equiv), potassium carbonate (3.353 g, 24.26 mmol, 3.00 equiv) in NMP (20 mL) was stirred for 1.5 h at 80° C. The resulting solution was quenched with 30 ml H$_2$O, extracted with EtOAc (3×30 mL) and the organic layers combined. The solution was dried over anhydrous sodium sulfate and concentrated under vacuum. The residue was applied onto a silica gel column eluting with EtOAc/petroleum ether (1:1) to afford 2 g (88%) of the title compound as a yellow oil. LCMS (ESI, m/z): 303.17 [M+H]$^+$

Step 2: Synthesis of 6-(1,4-diazepan-1-yl)pyridine-3-carbonitrile

A solution of tert-butyl 4-(5-cyanopyridin-2-yl)-1,4-diazepane-1-carboxylate (1 g, 3.31 mmol, 1.00 equiv) in hydrogen chloride/dioxane (20 mL) was stirred for 1 h at room temperature. After concentration, the residue was purified by C18 reverse phase chromatography eluting with H$_2$O/CH$_3$CN to afford 225 mg (34%) of the title compound as a white solid. LCMS (ESI, m/z): 203.12 [M+H]$^+$

Step 3: Synthesis of (S)-6-(4-(3-((1-(6-oxo-5-(trifluoromethyl)-1,6-dihydropyridazin-4-yl)pyrrolidin-2-yl)methoxy)propanoyl)-1,4-diazepan-1-yl)nicotinonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), 6-(1,4-diazepan-1-yl)pyridine-3-carbonitrile (72.72 mg, 0.36 mmol, 1.20 equiv), HATU (171 mg, 0.45 mmol, 1.50 equiv), DIPEA (116.1 mg, 0.90 mmol, 3.00 equiv) in DMF (3 mL) was stirred for 2 h at room temperature. After concentration, the residue was purified by Prep-HPLC eluting with H$_2$O/CH$_3$CN yielding the title compound (139 mg, 90%) as a white solid. LCMS (ESI, m/z): 520.15 [M+H]$^+$, $^1$HNMR (Methanol-d$_4$, 300 MHz) δ:8.41 (t, J=3.2 Hz, 1H), 8.11 (dd, J=7.1 Hz, 5.9 Hz, 1H), 7.74-7.71 (m, 1H), 6.79 (dd, J=2.4 Hz, 2.7 Hz, 1H), 4.87 (s, 1H), 3.95 (t, J=5.8 Hz, 1H), 3.89-3.63 (m, 9H), 3.62-3.50 (m, 2H), 3.49-3.37 (m, 2H), 2.55-2.54 (m, 2H), 2.05 (s, 1H), 1.94-1.91 (m, 3H), 1.89-1.68 (m, 2H).

Example 107: 6-[[1-(3-[[(2S)-1-[6-oxo-5-(trifluoromethyl)-1,6-dihydropyridazin-4-yl]pyrrolidin-2-yl]methoxy]propanoyl)azetidin-3-yl]amino]pyridine-3-carbonitrile

Step 1: Synthesis of Tert-Butyl 3-[(5-cyanopyridin-2-yl)amino]azetidine-1-carboxylate A solution of tert-butyl 3-aminoazetidine-1-carboxylate (1 g, 5.81 mmol, 1.00 equiv), potassium carbonate (1.6 g, 11.58 mmol, 2.00 equiv), and 5-chloropyridin-2-carbonitrile (801 mg, 5.74 mmol, 1.00 equiv) in DMF (10 mL) was stirred for 2 h at 80° C. The resulting mixture was concentrated under vacuum. The residue was applied onto a silica gel column eluting with EtOAc/petroleum ether (1/1)) to afford 300 mg (19%) of the title compound as colorless oil. LCMS (ESI, m/z): 275.32 [M+H]$^+$

Step 2: Synthesis of 6-[(azetidin-3-yl)amino]pyridine-3-carbonitrile Hydrochloride A solution of tert-butyl 3-[(5-cyanopyridin-2-yl)amino]azetidine-1-carboxylate (264 mg, 0.96 mmol, 1.00 equiv) in hydrogen chloride/dioxane (10 mL) was stirred for 2 h at 25° C. The solids were collected by filtration to afford 170 mg (crude) of the title compound as yellow solids. LCMS (ESI, m/z): 175.20 [M+H]$^+$

Step 3: Synthesis of 6-[[1-(3-[[(2S)-1-[6-oxo-5-(trifluoromethyl)-1,6-dihydropyridazin-4-yl]pyrrolidin-2-yl]methoxy]propanoyl)azetidin-3-yl]amino]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (114 mg, 0.30 mmol, 1.00 equiv), DIPEA (155 mg, 1.20 mmol, 4.00 equiv), and 6-[(azetidin-3-yl)amino]pyridine-3-carbonitrile hydrochloride (74 mg, 0.30 mmol, 1.00 equiv) in DMF (2 mL) was stirred for 1 h at 25° C. The crude product was purified by Flash-Prep yielding the title compound (94.7 mg, 65%) as white solids. LCMS (ESI, m/z): 492.20 [M+H]$^+$, $^1$H-NMR (CD$_3$OD, 400 MHz) δ: 8.36 (d, J=2.3 Hz, 1H), 8.14 (d, J=5.1 Hz, 1H), 7.65 (dd, J=8.8, 2.3 Hz, 1H), 6.60 (d, J=8.8 Hz, 1H), 4.66 (d, J=7.6 Hz, 1H), 4.58 (s, 1H), 4.47 (dt, J=16.5, 8.5 Hz, 1H), 4.29 (dt, J=17.8, 8.5 Hz, 1H), 4.00 (d, J=5.0 Hz, 1H), 3.83 (dd, J=10.2, 5.1 Hz, 1H), 3.76-3.55 (m, 2H), 3.48-3.33 (m, 1H), 2.33 (dd, J=14.9, 8.1 Hz, 1H), 2.45-2.20 (m, 3H), 2.00-1.91 (m, 1H), 1.81-1.68 (m, 2H).

Example 108: 6-[6-(3-[[(2S)-1-[6-oxo-5-(trifluoromethyl)-1,6-dihydropyridazin-4-yl]pyrrolidin-2-yl]methoxy]propanoyl)-2,6-diazaspiro[3.3]heptan-2-yl]pyridine-3-carbonitrile

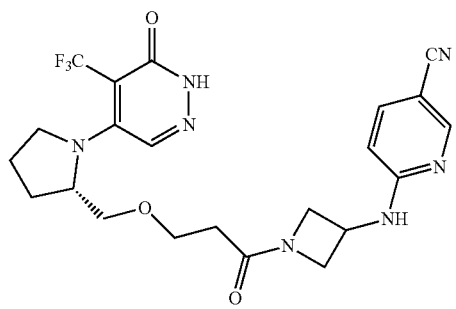 [SMILES: N#Cc1ccc(NC2CN(C(=O)CCOC[C@@H]3CCCN3c3cn[nH]c(=O)c3C(F)(F)F)C2)nc1]

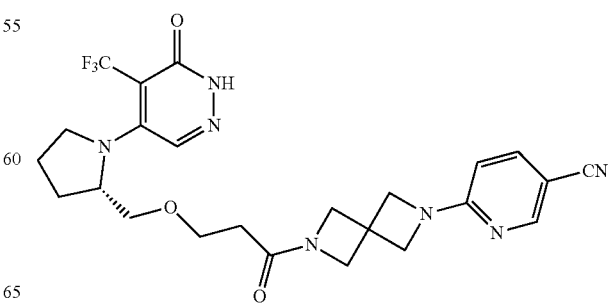

Step 1: Synthesis of Tert-Butyl 6-(5-cyanopyridin-2-yl)-2,6-diazaspiro[3.3]heptane-2-carboxylate A solution of tert-butyl 2,6-diazaspiro[3.3]heptane-2-carboxylate (500 mg, 2.52 mmol, 1.00 equiv), potassium carbonate (1.05 mg, 0.01 mmol, 3.00 equiv), 6-chloropyridine-3-carbonitrile (383.3 mg, 2.77 mmol, 1.10 equiv) in DMF (10 mL) was stirred for 2 h at 100° C. The resulting solution was quenched with 50 ml water. Then the solution was extracted with (3×50 mL) EtOAc and the organic layers combined. The residue was applied onto a silica gel column eluting with EtOAc/hexane (50:50) to afford 360 mg (48%) of the title compound as a yellow solid. LCMS (ESI, m/z): 301.17 [M+H]+

Step 2: Synthesis of 6-[2,6-diazaspiro[3.3]heptan-2-yl]pyridine-3-carbonitrile A solution of tert-butyl 6-(5-cyanopyridin-2-yl)-2,6-diazaspiro[3.3]heptane-2-carboxylate (300 mg, 1.00 mmol, 1.00 equiv), TFA (2 mL) in DCM (10 mL) was stirred for 1 h at room temperature. The resulting mixture was concentrated under vacuum to afford 180 mg crude of the title compound as a white solid. LCMS (ESI, m/z): 201.12 [M+H]+

Step 3: Synthesis of 6-[6-(3-[[(2S)-1-[6-oxo-5-(trifluoromethyl)-1,6-dihydropyridazin-4-yl]pyrrolidin-2-yl]methoxy]propanoyl)-2,6-diazaspiro[3.3]heptan-2-yl]pyridine-3-carbonitrile A solution of 6-[2,6-diazaspiro[3.3]heptan-2-yl]pyridine-3-carbonitrile (100 mg, 0.50 mmol, 1.00 equiv), HATU (136 mg, 0.36 mmol, 1.20 equiv), DIPEA (115 mg, 0.89 mmol, 3.00 equiv), 3-[(2S)-1-[6-oxo-5-(trifluoromethyl)-1,6-dihydropyridazin-4-yl]pyrrolidin-2-yl]methoxypropanoic acid (72 mg, 0.21 mmol, 1.20 equiv) in DMF (3 mL) was stirred for 2 h at room temperature. After concentration, the residue was purified by C18 reverse phase chromatography eluting with H$_2$O/CH$_3$CN. Then the residue was further purified by Prep-HPLC yielding the title compound (42.7 mg, 17%) as a white solid. LCMS (ESI, m/z): 518.10 [M+H]+, $^1$H NMR (300 MHz, Methanol-d4) δ 8.37 (s, 1H), 8.17 (s, 1H), 7.74 (dd, J=8.8, 2.2 Hz, 1H), 6.48 (dd, J=8.9, 0.8 Hz, 1H), 4.61 (q, J=7.8, 3.3 Hz, 1H), 4.41-4.21 (m, 6H), 4.17 (s, 2H), 3.86-3.54 (m, 4H), 3.49-3.33 (m, 1H), 3.33-3.31 (m, 1H), 2.33-2.22 (m, 3H), 2.02-1.98 (m, 1H), 1.77-1.65 (m, 2H).

Example 109: 6-[2-(3-[[(2S)-1-[6-oxo-5-(trifluoromethyl)-1,6-dihydropyridazin-4-yl]pyrrolidin-2-yl]methoxy]propanoyl)-2,6-diazaspiro[3.4]octan-6-yl]pyridine-3-carbonitrile

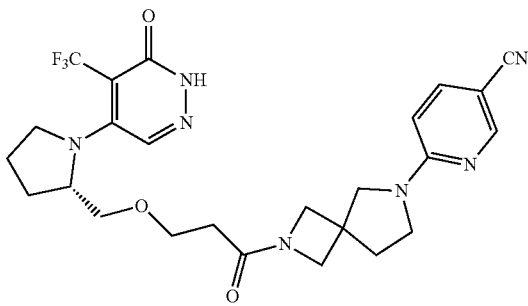 [SMILES: N#Cc1ccc(N2CCC3(CN(C(=O)CCOC[C@@H]4CCCN4c4cn[nH]c(=O)c4C(F)(F)F)C3)C2)nc1]

Step 1: Synthesis of Tert-Butyl 6-(5-cyanopyridin-2-yl)-2,6-diazaspiro[3.4]octane-2-carboxylate A solution of tert-butyl 2,6-diazaspiro[3.4]octane-2-carboxylate (300 mg, 1.41 mmol, 1.00 equiv), 6-chloropyridine-3-carbonitrile (390 mg, 2.81 mmol, 2.00 equiv) and K$_2$CO$_3$ (390 mg, 2.82 mmol, 2.00 equiv) in NMP (10 mL) was stirred for 4 h at 80° C., and then the resulting solution was diluted with 200 mL of H$_2$O, extracted with 3×50 mL of EtOAc and the organic layers combined, washed with 1×50 mL of brine, dried over anhydrous sodium sulfate and concentrated under vacuum, and then the residue was applied onto a silica gel column eluting with EtOAc/petroleum ether (40/60) to afford 380 mg (86%) of the title compound as a yellow solid. LCMS (ESI, m/z): 315.17 [M+H]$^+$.

Step 2: Synthesis of 6-[2,6-diazaspiro[3.4]octan-6-yl]pyridine-3-carbonitrile A solution of tert-butyl 6-(5-cyanopyridin-2-yl)-2,6-diazaspiro[3.4]octane-2-carboxylate (360 mg, 1.15 mmol, 1.00 equiv) and TFA (4 mL) in DCM (20 mL) was stirred for 2 h at room temperature, and then the resulting solution was concentrated under vacuum to afford 730 mg of the title compound as a yellow solid. LCMS (ESI, m/z): 215.12 [M+H]$^+$.

Step 3: Synthesis of 6-[2-(3-[[(2S)-1-[6-oxo-5-(trifluoromethyl)-1,6-dihydropyridazin-4-yl]pyrrolidin-2-yl]methoxy]propanoyl)-2,6-diazaspiro[3.4]octan-6-yl]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (113 mg, 0.30 mmol, 1.00 equiv), DIPEA (116 mg, 0.90 mmol, 3.00 equiv) and 6-2,6-diazaspiro[3.4]octan-6-ylpyridine-3-carbonitrile (96 mg, 0.45 mmol, 1.50 equiv) in DMF (8 mL) was stirred for 2 h at room temperature, and then the resulting solution was diluted with 30 mL of H$_2$O, extracted with 3×30 mL of EtOAc and the organic layers combined, washed with 2×30 mL of brine, dried over anhydrous sodium sulfate and concentrated under vacuum, and then the residue was purified by Prep-HPLC yielding the title compound (22.6 mg, 14%) as a white solid. LCMS (ESI, m/z): 532.10 [M+H]+, $^1$H NMR (DMSO-d$_6$, 400 MHz) δ 12.36 (s, 1H), 8.47 (d, J=2.0 Hz, 1H), 8.02 (s, 1H), 7.84 (dd, J=9.0, 2.3 Hz, 1H), 6.56 (dd, J=8.8, 2.4 Hz, 1H), 4.53 (s, 1H), 4.06 (dd, J=8.4, 3.8 Hz, 1H), 3.99 (d, J=9.3 Hz, 1H), 3.82-3.77 (m, 2H), 3.68-3.49 (m, 8H), 3.38-3.36 (m, 1H), 3.24-3.19 (m, 1H), 2.27-2.07 (m, 5H), 1.89 (d, J=5.2 Hz, 1H), 1.65 (dd, J=17.2, 5.9 Hz, 2H).

Example 110: 6-[4-(3-[[(2S)-1-[6-oxo-5-(trifluoromethyl)-1,6-dihydropyridazin-4-yl]pyrrolidin-2-yl]methoxy]propanoyl)-octahydropyrrolo[3,2-b]pyrrol-1-yl]pyridine-3-carbonitrile

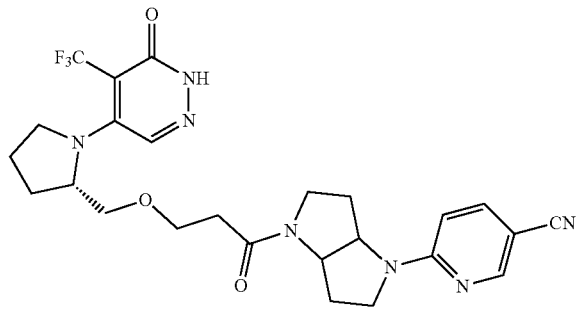 [SMILES: N#Cc1ccc(N2CCC3C2CCN3C(=O)CCOC[C@@H]2CCCN2c2cn[nH]c(=O)c2C(F)(F)F)nc1]

Step 1: Synthesis of Tert-Butyl 4-(5-cyanopyridin-2-yl)-octahydropyrrolo[3,2-b]pyrrole-1-carboxylate A solution of tert-butyl octahydropyrrolo[3,2-b]pyrrole-1-carboxylate (200 mg, 0.94 mmol, 1.00 equiv), 6-chloropyridine-3-carbonitrile (260 mg, 1.88 mmol, 2.00 equiv) and $K_2CO_3$ (260 mg, 1.88 mmol, 2.00 equiv) in NMP (10 mL) was stirred for 2 h at 80° C., and then the resulting solution was diluted with 200 mL of H2O, extracted with 3×50 mL of EtOAc and the organic layers combined, washed with 1×50 mL of brine, dried over anhydrous sodium sulfate and concentrated under vacuum, and then the residue was applied onto a silica gel column eluting with EtOAc/petroleum ether (2:3) to afford 284 mg (96%) of the title compound as light yellow oil. LCMS (ESI, m/z): 315.18[M+H]$^+$.

Step 2: Synthesis of 6-[octahydropyrrolo[3,2-b]pyrrol-1-yl]pyridine-3-carbonitrile A solution of tert-butyl 4-(5-cyanopyridin-2-yl)-octahydropyrrolo[3,2-b]pyrrole-1-carboxylate (238 mg, 0.76 mmol, 1.00 equiv) and TFA (1 mL) in DCM (5 mL) was stirred for 1 h at room temperature, and then the resulting solution was concentrated under vacuum to afford 150 mg of the title compound as a crude yellow oil. LCMS (ESI, m/z): 215.13 [M+H]$^+$.

Step 3: Synthesis of 6-[4-(3-[[(2S)-1-[6-oxo-5-(trifluoromethyl)-1,6-dihydropyridazin-4-yl]pyrrolidin-2-yl]methoxy]propanoyl)-octahydropyrrolo[3,2-b]pyrrol-1-yl]pyridine-3-carbonitrile A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.50 equiv), HATU (113 mg, 0.30 mmol, 1.00 equiv), DIPEA (77 mg, 0.60 mmol, 2.00 equiv) and 6-[octahydropyrrolo[3,2-b]pyrrol-1-yl]pyridine-3-carbonitrile (100 mg, 0.47 mmol, 1.00 equiv) in DMF (10 mL) was stirred for 40 min at room temperature, and then the resulting solution was diluted with 20 ml of $H_2O$, extracted with 3×20 ml of EtOAc and the organic layer was combined, washed with 1×20 ml of brine and concentrated under vacuum, and then the residue was purified by Prep-HPLC yielding the title compound (46.7 mg, 19.0%) as a white solid. LCMS (ESI, m/z): 532.10 [M+H]+, $^1$HNMR (CD3OD, 300 MHz) δ 8.43 (d, J=1.5 Hz, 1H), 8.15 (d, J=1.8 Hz, 1H), 7.78 (dt, J=8.9, 2.5 Hz, 1H), 6.67 (d, J=9.6 Hz, 1H), 4.70-4.62 (m, 3H), 3.78-3.36 (m, 10H), 2.59 (t, J=2.1 Hz, 2H), 2.40-1.97 (m, 6H), 1.82-1.69 (m, 2H).

Example 111: 6-[7-(3-[[(2S)-1-[6-oxo-5-(trifluoromethyl)-1,6-dihydropyridazin-4-yl]pyrrolidin-2-yl]methoxy]propanoyl)-2,7-diazaspiro[4.4]nonan-2-yl]pyridine-3-carbonitrile

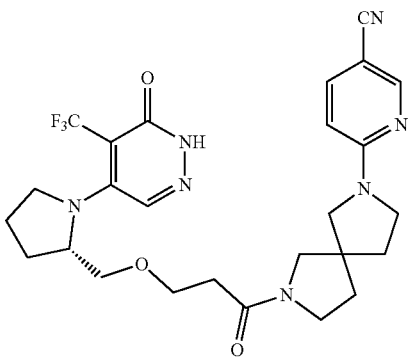 [SMILES: N#Cc1ccc(N2CCC3(CCN(C(=O)CCOC[C@@H]4CCCN4c4cn[nH]c(=O)c4C(F)(F)F)C3)C2)nc1]

Step 1: Synthesis of Tert-Butyl 7-(5-cyanopyridin-2-yl)-2,7-diazaspiro[4.4]nonane-2-carboxylate A solution of 6-chloropyridine-3-carbonitrile (610 mg, 4.40 mmol, 1.00 equiv), potassium carbonate (1.2 g, 8.68 mmol, 3.00 equiv), tert-butyl 2,7-diazaspiro[4.4]nonane-2-carboxylate (1 g, 4.42 mmol, 1.00 equiv) in DMF (30 mL) was stirred for 2 h at 80° C. The resulting solution was quenched with 30 ml water. Then the solution was extracted with EtOAc (3×30 mL) and the organic layers combined. The residue was applied onto a silica gel column with EtOAc/petroleum ether (1:4) to afford 1.2 g (83.1%) of the title compound as a white solid. LCMS (ESI, m/z): 329.20 [M+H]$^+$

Step 2: Synthesis of 6-[2,7-diazaspiro[4.4]nonan-2-yl]pyridine-3-carbonitrile A solution of tert-butyl 7-(5-cyanopyridin-2-yl)-2,7-diazaspiro[4.4]nonane-2-carboxylate (118 mg, 0.36 mmol, 1.00 equiv) in hydrogen chloride/dioxane (5 mL) was stirred for 20 min at room temperature. The resulting mixture was concentrated under vacuum to afford 100 mg crude of the title compound as yellow oil. LCMS (ESI, m/z): 229.14 [M+H]$^+$

Step 3: Synthesis of 6-[7-(3-[[(2S)-1-[6-oxo-5-(trifluoromethyl)-1,6-dihydropyridazin-4-yl]pyrrolidin-2-yl]methoxy]propanoyl)-2,7-diazaspiro[4.4]nonan-2-yl]pyridine-3-carbonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), HATU (148 mg, 0.39 mmol, 1.30 equiv), DIEA (77.4 mg, 0.60 mmol, 2.00 equiv), 6-[2,7-diazaspiro[4.4]nonan-2-yl]pyridine-3-carbonitrile (82 mg, 0.36 mmol, 1.20 equiv) in DMF (5 mL) was stirred for 2 h at room temperature. After concentration, the residue was purified by C18 reverse phase chromatography eluting with $H_2O/CH_3CN$ yielding the title compound (75.1 mg, 46%) as a white solid. LCMS (ESI, m/z): 546.20 [M+H]+, 1H NMR (300 MHz, Chloroform-d) δ 8.39 (s, 1H), 8.13 (dd, J=2.4, 0.8 Hz, 1H), 7.73 (dd, J=8.7, 2.4 Hz, 1H), 6.59 (dd, J=8.7, 0.8 Hz, 1H), 4.71-4.45 (m, 1H), 3.93-3.74 (m, 1H), 3.74-3.61 (m, 6H), 3.57-3.49 (m, 4H), 3.48-3.39 (m, 3H), 2.53-2.50 (m, 2H), 2.26-2.14 (m, 1H), 2.11-1.92 (m, 5H), 1.83-1.53 (m, 2H).

Example 112: 6-((1S,4S)-5-(3-(((S)-1-(6-oxo-5-(trifluoromethyl)-1,6-dihydropyridazin-4-yl)pyrrolidin-2-yl)methoxy)propanoyl)-2,5-diaza-bicyclo[2.2.1]heptan-2-yl)nicotinonitrile and 6-((1R,4R)-5-(3-(((S)-1-(6-oxo-5-(trifluoromethyl)-1,6-dihydropyridazin-4-yl)pyrrolidin-2-yl)methoxy)propanoyl)-2,5-diaza-bicyclo[2.2.1]heptan-2-yl)nicotinonitrile

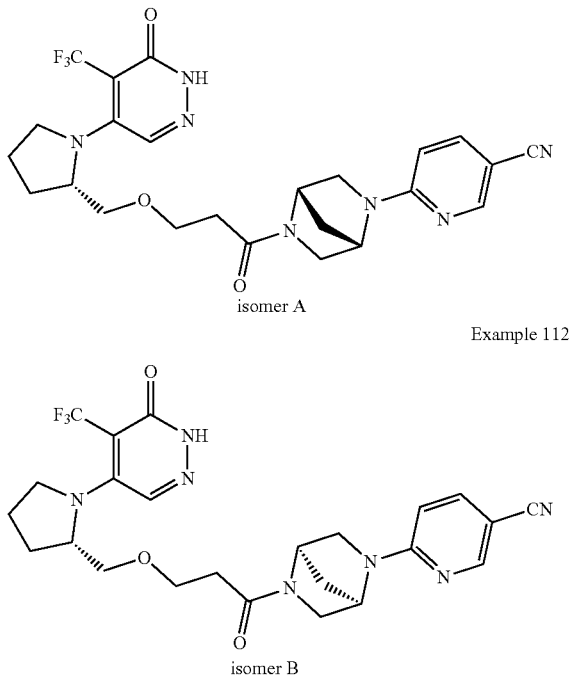

Example 112
isomer A

Example 112
isomer B

Step 1: Synthesis of Tert-Butyl 5-(5-cyanopyridin-2-yl)-2,5-diazabicyclo[2.2.1]heptane-2-carboxylate A solution of tert-butyl 2,5-diazabicyclo[2.2.1]heptane-2-carboxylate (600 mg, 3.03 mmol, 1.00 equiv), 6-chloropyridine-3-carbonitrile (460 mg, 3.32 mmol, 1.10 equiv), potassium carbonate (1.254 g, 17.16 mmol, 3.00 equiv) in DMF (10 mL) was stirred for 1.5 h at 80° C. The resulting solution was quenched with 40 ml water. The solution was extracted with EtOAc (3×40 mL) and the organic layers combined. The solution was dried over anhydrous sodium sulfate and concentrated under vacuum. The residue was applied onto a silica gel column eluting with EtOAc/hexane (1:1) to afford 770 mg (85%) of the title compound as a yellow solid. LCMS (ESI, m/z): 301.16 [M+H]+

Step 2: Synthesis of 6-[2,5-diazabicyclo[2.2.2.]heptan-2-yl]pyridine-3-carbonitrile A solution of tert-butyl 5-(5-cyanopyridin-2-yl)-2,5-diazabicyclo[2.2.1]heptane-2-carboxylate (740 mg, 2.46 mmol, 1.00 equiv) in hydrogen chloride/dioxane (15 mL) was stirred for 0.5 h at room temperature. The resulting mixture was concentrated under vacuum to afford 480 mg crude of the title compound as a light yellow solid. LCMS (ESI, m/z): 201.11 [M+H]+

Step 3: Synthesis of 6-((1S,4S)-5-(3-(((S)-1-(6-oxo-5-(trifluoromethyl)-1,6-dihydropyridazin-4-yl)pyrrolidin-2-yl)methoxy)propanoyl)-2,5-diaza-bicyclo[2.2.1]heptan-2-yl)nicotinonitrile and 6-((1R,4R)-5-(3-(((S)-1-(6-oxo-5-(trifluoromethyl)-1,6-dihydropyridazin-4-yl)pyrrolidin-2-yl)methoxy)propanoyl)-2,5-diaza-bicyclo[2.2.1]heptan-2-yl)nicotinonitrile A solution of 3-[[(2S)-1-[6-oxo-5-(trifluoromethyl)-1,6-dihydropyridazin-4-yl]pyrrolidin-2-yl]methoxy]propanoic acid (100 mg, 0.30 mmol, 1.00 equiv), 6-[2,5-diazabicyclo[2.2.1]heptan-2-yl]pyridine-3-carbonitrile (72 mg, 0.36 mmol, 1.20 equiv), HATU (171 mg, 0.45 mmol, 1.50 equiv), DIEA (116.1 mg, 0.90 mmol, 3.00 equiv) in DMF (3 mL) was stirred for 1.5 h at room temperature. After concentration, the residue was purified by C18 reverse phase chromatography eluting with H2O/CH3CN. Then the residue was further purified by Prep-HPLC and Chiral-Prep-HPLC yielding (after arbitrary assignment of the stereochemistry) the title compounds, respectively, as white solids, isomer A (11.4 mg, 20%) LCMS (ESI, m/z): 518.15 [M+H]+, 1HNMR (Methanol-d4, 300 MHz) δ: 8.39 (s, 1H), 8.07 (d, J=14.4 Hz, 1H), 7.74 (d, J=8.9 Hz, 1H), 6.61 (s, 1H), 5.07-4.95 (m, 2H), 4.80 (s, 1H), 4.69-4.42 (m, 1H), 3.95-3.30 (m, 9H), 2.69 (d, J=15 Hz, 1H), 2.41 (s, 1H), 2.33-2.06 (m, 4H), 1.97 (d, J=10.0 Hz, 2H). tR=5.199 min (CHIRAL Cellulose-SB, 0.46*10 cm; 3 um, Hex(20mMNH3):EtOH=60:40, 1.0 mL/min) and isomer B (19 mg, 20%) LCMS (ESI, m/z): 518.15 [M+H]+, tR=6.858 min ((CHIRAL Cellulose-SB, 0.46*10 cm; 3 um, Hex(20mMNH3):EtOH=60:40, 1.0 mL/min)

Example 113: (S)-6-[5-(3-[[1-[6-oxo-5-(trifluoromethyl)-1,6-dihydropyridazin-4-yl]pyrrolidin-2-yl]methoxy]propanoyl)-octahydropyrrolo[3,4-c]pyrrol-2-yl]pyridine-3-carbonitrile

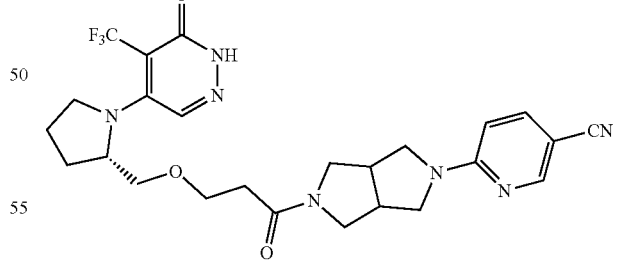

Step 1: Synthesis of Tert-Butyl 5-(5-cyanopyridin-2-yl)-octahydropyrrolo[3,4-c]pyrrole-2-carboxylate A solution of tert-butyl octahydropyrrolo[3,4-c]pyrrole-2-carboxylate (1 g, 4.71 mmol, 1.00 equiv), 6-chloropyridine-3-carbonitrile (650 mg, 4.69 mmol, 1.00 equiv), potassium carbonate (1.3 g, 9.41 mmol, 2.00 equiv), NMP (20 mL). The resulting solution was stirred for 1 h at 80° C. The resulting solution was extracted with 100 mL of EtOAc and the organic layers combined and concentrated under vacuum to afforded 1.1 g (74%) of the title compound as yellow oil. LCMS (ESI, m/z): 315.25 [M+H]+

Step 2: Synthesis of 6-[octahydropyrrolo[3,4-c] pyrrol-2-yl]pyridine-3-carbonitrile Hydrogen Chloride A solution of tert-butyl 5-(5-cyanopyridin-2-yl)-octahydropyrrolo[3,4-c]pyrrole-2-carboxylate (860 mg, 2.74 mmol, 1.00 equiv), dioxane/HCl (10 mL). The resulting solution was stirred for 1 h at 25° C. The solids were filtered out. The resulting mixture was concentrated under vacuum to afforded 500 mg (85%) of the title compound as yellow oil. LCMS (ESI, m/z): 215.22 [M+H]+

Step 3: Synthesis of (S)-6-[5-(3-[[1-[6-oxo-5-(trifluoromethyl)-1,6-dihydropyridazin-4-yl]pyrrolidin-2-yl]methoxy]propanoyl)-octahydropyrrolo[3,4-c] pyrrol-2-yl]pyridine-3-carbonitrile A solution of (S)-3-[[1-[6-oxo-5-(trifluoromethyl)-1,6-dihydropyridazin-4-yl]pyrrolidin-2-yl]methoxy]propanoic acid (170 mg, 0.51 mmol, 1.00 equiv), 6-[octahydropyrrolo[3,4-c]pyrrol-2-yl]pyridine-3-carbonitrile hydrogen chloride (200 mg, 0.93 mmol, 1.00 equiv), HATU (190 mg, 0.50 mmol, 1.00 equiv), DIEA (1 mL), DMF (4 mL). The resulting solution was stirred for 1 h at 25° C. The crude product was purified by Flash-Prep-HPLC yielding the title compound (49.3 mg, 18%) as a white solid. LCMS (ESI, m/z): 510.15 [M+H]+, ¹HNMR (DMSO-d₆, 400 MHz) δ: 12.35 (s, 1H), 8.47 (s, 1H), 8.00 (d, J=4.0 Hz, 1H), 7.82 (d, J=8.8 Hz, 1H), 6.54 (d, J=5.2 Hz, 1H), 4.49-4.51 (m, 1H), 4.01-3.46 (m, 12H), 3.26-3.20 (m, 2H), 3.11-2.90 (m, 2H), 2.46-2.38 (m, 2H), 2.10-2.03 (m, 1H), 1.92-1.88 (m, 1H), 1.65-1.78 (m, 2H). tR=2.648 min (XBridge Prep OBD C18 Column 30*150 mm 5 um Water (NH₄HCO₃):CH₃CN=70:30, 1.0 mL/min)

Example 114: N-[1-(5-cyanopyridin-2-yl)piperidin-3-yl]-3-[[(2S)-1-[6-oxo-5-(trifluoromethyl)-1,6-dihydropyridazin-4-yl]pyrrolidin-2-yl]methoxy]propanamide

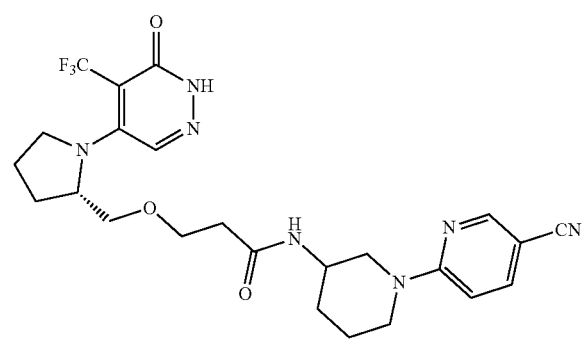 [SMILES: N#Cc1ccc(N2CCCC(NC(=O)CCOC[C@@H]3CCCN3c3cn[nH]c(=O)c3C(F)(F)F)C2)nc1]

Step 1: Synthesis of Tert-Butyl N-[1-(5-cyanopyridin-2-yl)piperidin-4-yl]carbamate A solution of 6-chloropyridine-3-carbonitrile (690 mg, 4.98 mmol, 1.00 equiv), potassium carbonate (1.38 g, 9.98 mmol, 2.00 equiv), tert-butyl N-(piperidin-4-yl)carbamate (1 g, 4.99 mmol, 1.00 equiv) in DMF (20 mL) was stirred for 1 h at 80° C. The resulting solution was quenched with 30 ml water. Then the solution was extracted with EtOAc (3×30 mL) and the organic layers combined. The residue was applied onto a silica gel column with EtOAc/petroleum ether (2:3) to afford 1.5 g (99%) of the title compound as a white solid. LCMS (ESI, m/z): 303.18 [M+H]+

Step 2: Synthesis of 6-(3-aminopiperidin-1-yl)pyridine-3-carbonitrile

A solution of tert-butyl N-[1-(5-cyanopyridin-2-yl)piperidin-3-yl]carbamate (118 mg, 0.39 mmol, 1.00 equiv) in hydrogen chloride/dioxane (10 mL) was stirred for 30 min at room temperature. The resulting mixture was concentrated under vacuum to afford 79 mg crude of the title compound as a white solid. LCMS (ESI, m/z): 203.13 [M+H]+

Step 3: Synthesis of N-[1-(5-cyanopyridin-2-yl) piperidin-3-yl]-3-[[(2S)-1-[6-oxo-5-(trifluoromethyl)-1,6-dihydropyridazin-4-yl]pyrrolidin-2-yl] methoxy]propanamide A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.00 equiv), HATU (147 mg, 0.39 mmol, 1.30 equiv), DIEA (155 mg, 1.20 mmol, 4.00 equiv), 6-(3-aminopiperidin-1-yl)pyridine-3-carbonitrile (79 mg, 0.39 mmol, 1.30 equiv) in DMF (10 mL) was stirred for 1 h at room temperature. After concentration, the residue was purified by C18 reverse phase chromatography eluting with H₂O/CH₃CN. Then the residue was further purified by Prep-HPLC yielding the title compound (72.2 mg, 47%) as a white solid. LCMS (ESI, m/z): 520.15 [M+H]+, ¹H NMR (300 MHz, Methanol-d₄) δ 8.36 (s, 1H), 8.11 (s, 1H), 7.69 (dd, J=9.1, 2.4 Hz, 1H), 6.86-6.83 (m, 1H), 4.61-4.48 (m, 1H), 4.23-4.05 (m, 2H), 3.85-3.57 (m, 5H), 3.46-3.39 (m, 2H), 3.29-3.12 (m, 1H), 3.11-3.02 (m, 1H), 2.37 (t, J=6.0 Hz, 2H), 2.29-2.10 (m, 1H), 2.05-1.92 (m, 2H), 1.90-1.85 (m, 1H), 1.78-1.68 (m, 2H), 1.62-1.56 (m, 2H).

Example 115: N-[1-(5-cyanopyridin-2-yl)piperidin-4-yl]-3-[[(2S)-1-[6-oxo-5-(trifluoromethyl)-1,6-dihydropyridazin-4-yl]pyrrolidin-2-yl]methoxy]propanamide

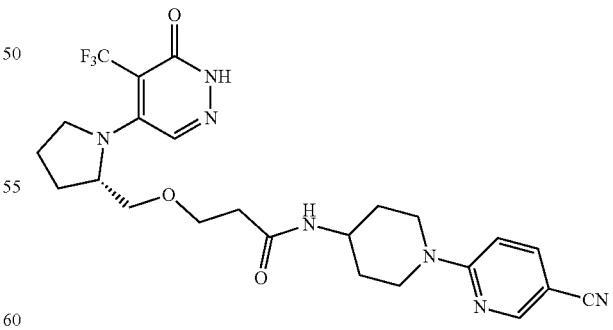

Step 1: Synthesis of Tert-Butyl N-[1-(5-cyanopyridin-2-yl)piperidin-4-yl]carbamate A solution of 6-chloropyridine-3-carbonitrile (1 g, 7.22 mmol, 1.00 equiv), potassium carbonate (2 g, 14.47 mmol, 2.00 equiv), tert-butyl N-(piperidin-4-yl)carbamate (1.45 g, 7.24 mmol, 1.00 equiv) in DMF (20 mL) was stirred for 1.5 h at 80° C. The resulting solution was quenched with 30 ml water. The solution was extracted with EtOAc (3×30 mL) and the organic layers combined. The solution was dried over anhydrous sodium sulfate and concentrated under vacuum. The residue was applied onto a silica gel column with EtOAc/petroleum ether (2:3) to afford 1.7 g (78%) of the title compound as a white solid. LCMS (ESI, m/z): 303.18[M+H]+

Step 2: Synthesis of 6-(4-aminopiperidin-1-yl)pyridine-3-carbonitrile

A solution of tert-butyl N-[1-(5-cyanopyridin-2-yl)piperidin-4-yl]carbamate (118 mg, 0.39 mmol, 1.00 equiv) in hydrogen chloride/dioxane (10 mL) was stirred for 30 min at room temperature. The resulting mixture was concentrated under vacuum to afford 79 mg crude of the title compound as a white solid. LCMS (ESI, m/z): 203.13 [M+H]+

Step 3: Synthesis of N-[1-(5-cyanopyridin-2-yl)piperidin-4-yl]-3-[[(2S)-1-[6-oxo-5-(trifluoromethyl)-1,6-dihydropyridazin-4-yl]pyrrolidin-2-yl]methoxy]propanamide A solution of 6-(4-aminopiperidin-1-yl)pyridine-3-carbonitrile (79 mg, 0.39 mmol, 1.00 equiv), HATU (148 mg, 0.39 mmol, 1.30 equiv), DIEA (155 mg, 1.20 mmol, 2.00 equiv), 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.30 equiv) in DMF (10 mL) was stirred for 1 h at room temperature. After concentration, the residue was purified by C18 reverse phase chromatography eluting with $H_2O/CH_3CN$. Then the residue was further purified by Prep-HPLC yielding the title compound (74.2 mg, 37%) as a white solid. LCMS (ESI, m/z): 520.30 [M+H]+, 1H NMR (300 MHz, Methanol-$d_4$) δ 8.39 (s, 1H), 8.14 (s, 1H), 7.72 (dd, J=9.1, 2.4 Hz, 1H), 6.88 (dd, J=9.2, 0.8 Hz, 1H), 4.58-4.50 (m, 1H), 4.45-4.35 (m, 2H), 4.01-3.88 (m, 1H), 3.75-3.60 (m, 4H), 3.47-3.34 (m, 2H), 3.12 (t, J=11.7 Hz, 2H), 2.38 (t, J=5.8 Hz, 2H), 2.26-2.15 (m, 1H), 2.05-1.92 (m, 3H), 1.80-1.60 (m, 2H), 1.46-1.30 (m, 2H).

Example 116: 6-[[1-(3-[[(2S)-1-[6-oxo-5-(trifluoromethyl)-1,6-dihydropyridazin-4-yl]pyrrolidin-2-yl]methoxy]propanoyl)piperidin-4-yl]amino]pyridine-3-carbonitrile

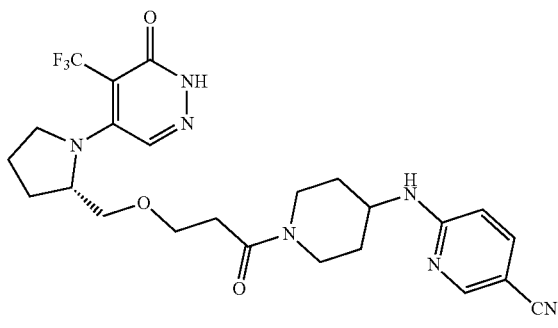 [SMILES: N#Cc1ccc(NC2CCN(C(=O)CCOC[C@@H]3CCCN3c3cn[nH]c(=O)c3C(F)(F)F)CC2)nc1]

Step 1: Synthesis of Tert-Butyl 4-[(5-cyanopyridin-2-yl)amino]piperidine-1-carboxylate A solution of 6-chloropyridine-3-carbonitrile (760 mg, 5.49 mmol, 1.00 equiv), potassium carbonate (1.52 g, 11.0 mmol, 2.00 equiv), tert-butyl 4-aminopiperidine-1-carboxylate (1.1 g, 5.49 mmol, 1.00 equiv) in DMF (20 mL) was stirred for 1.5 h at 80° C. The resulting solution was quenched with 50 ml water. The solution was extracted with EtOAc (3×50 mL) and the organic layers combined. The solution was dried over anhydrous sodium sulfate and concentrated under vacuum. The residue was applied onto a silica gel column with EtOAc/petroleum ether (2:3) to afford 460 mg (28%) of the title compound as a yellow solid. LCMS (ESI, m/z): 303.18 [M+H]+

Step 2: Synthesis of 6-[(piperidin-4-yl)amino]pyridine-3-carbonitrile

A solution of tert-butyl 4-[(5-cyanopyridin-2-yl)amino]piperidine-1-carboxylate (118 mg, 0.39 mmol, 1.00 equiv) in hydrogen chloride/dioxane (10 mL) was stirred for 30 min at room temperature. The resulting mixture was concentrated under vacuum to afford 79 mg crude of the title compound as a white solid. LCMS (ESI, m/z): 203.13 [M+H]+

Step 3: Synthesis of 6-[[1-(3-[[(2S)-1-[6-oxo-5-(trifluoromethyl)-1,6-dihydropyridazin-4-yl]pyrrolidin-2-yl]methoxy]propanoyl)piperidin-4-yl]amino]pyridine-3-carbonitrile A solution of 6-[(piperidin-4-yl)amino]pyridine-3-carbonitrile (79 mg, 0.39 mmol, 1.30 equiv), HATU (148 mg, 0.39 mmol, 1.30 equiv), DIEA (155 mg, 1.20 mmol, 2.00 equiv), 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.00 equiv) in DMF (2 mL) was stirred for 1 h at room temperature. After concentration, the residue was purified by C18 reverse phase chromatography eluting with $H_2O/CH_3CN$. Then the residue was further purified by Prep-HPLC yielding the title compound (43.9 mg, 28%) as a white solid. LCMS (ESI, m/z): 520.15 [M+H]+, 1H NMR (300 MHz, Methanol-$d_4$) δ 8.33 (s, 1H), 8.14 (s, 1H), 7.60 (dd, J=8.9, 2.3 Hz, 1H), 6.56 (dd, J=8.9, 0.8 Hz, 1H), 4.63-4.52 (m, 1H), 4.42 (d, J=13.5 Hz, 1H), 4.18-4.02 (m, 1H), 3.98-3.86 (m, 1H), 3.81-3.60 (m, 4H), 3.49-3.38 (m, 2H), 3.22 (t, J=12.3 Hz, 1H), 2.88 (q, J=12.1, 11.6 Hz, 1H), 2.72-2.48 (m, 2H), 2.24-2.12 (m, 1H), 2.10-2.03 (m, 1H), 2.02-1.98 (m, 2H), 1.82-1.64 (m, 2H), 1.50-1.42 (m, 2H).

Example 117: N-[1-(5-cyanopyridin-2-yl)pyrrolidin-3-yl]-3-[[(2S)-1-[6-oxo-5-(trifluoromethyl)-1,6-dihydropyridazin-4-yl]pyrrolidin-2-yl]methoxy]propanamide

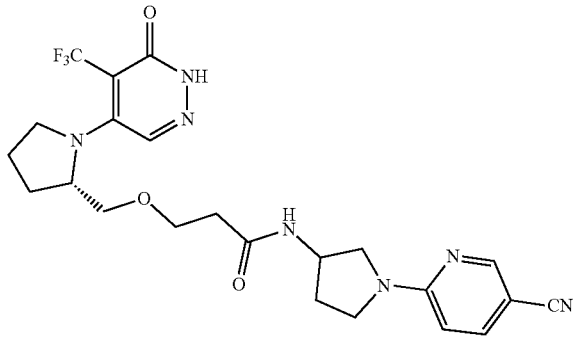 [SMILES: N#Cc1ccc(N2CCC(NC(=O)CCOC[C@@H]3CCCN3c3cn[nH]c(=O)c3C(F)(F)F)C2)nc1]

Step 1: Synthesis of Tert-Butyl N-[1-(5-cyanopyridin-2-yl)pyrrolidin-3-yl]carbamate A solution of tert-butyl N-(pyrrolidin-3-yl)carbamate (1 g, 5.37 mmol, 1.00 equiv), potassium carbonate (1.5 g, 10.85 mmol, 2.00 equiv), 6-chloropyridine-3-carbonitrile (742 mg, 5.36 mmol, 1.00 equiv) in DMF (10 mL) was stirred for 1 h at 80° C. The resulting solution was quenched with 40 ml water. The solution was extracted with EtOAc (3×40 mL) and the organic layers combined. The solution was dried over anhydrous sodium sulfate and concentrated under vacuum. The residue was applied onto a silica gel column eluting with EtOAc/hexane (4:1) to afford 1.37 g (88%) of the title compound as a white solid. LCMS (ESI, m/z): 289.17 [M+H]$^+$

Step 2: Synthesis of 6-(3-aminopyrrolidin-1-yl)pyridine-3-carbonitrile

A solution of tert-butyl N-[[1-(5-cyanopyridin-2-yl)pyrrolidin-3-yl]methyl]carbamate (112 mg, 0.37 mmol, 1 equiv) in HCl/dioxane (10 mL) was stirred for 40 min at room temperature. The solvent was concentrated under vacuum to afford 73 mg crude of the title compound as a white solid. LCMS (ESI, m/z): 189.11 [M+H]$^+$

Step 3: Synthesis of N-[1-(5-cyanopyridin-2-yl)pyrrolidin-3-yl]-3-[[(2S)-1-[6-oxo-5-(trifluoromethyl)-1,6-dihydropyridazin-4-yl]pyrrolidin-2-yl]methoxy]propanamide A solution of 3-[(2S)-1-[6-oxo-5-(trifluoromethyl)-1,6-dihydropyridazin-4-yl]pyrrolidin-2-yl]methoxypropanoic acid (100 mg, 0.30 mmol, 1.00 equiv), HATU (148 mg, 0.39 mmol, 1.30 equiv), DIEA (155 mg, 1.20 mmol, 4.00 equiv), 6-(3-aminopyrrolidin-1-yl)pyridine-3-carbonitrile (73 mg, 0.39 mmol, 1.30 equiv) in DMF (3 mL) was stirred for 1 h at room temperature. After concentration, the residue was purified by C18 reverse phase chromatography eluting with H$_2$O/CH$_3$CN yielding the title compound (59.6 mg, 40%) as a white solid. LCMS (ESI, m/z): 506.15 [M+H]$^+$, $^1$H NMR (300 MHz, Methanol-d$_4$) δ 8.39 (s, 1H), 8.12 (s, 1H), 7.73 (dd, J=8.9, 2.3 Hz, 1H), 6.58 (dd, J=8.9, 0.8 Hz, 1H), 4.59-4.42 (m, 2H), 3.92-3.59 (m, 7H), 3.6-3.32 (m, 3H), 2.39 (t, J=6.3 Hz, 2H), 2.27-2.12 (m, 2H), 2.10-1.92 (m, 2H), 1.72-1.58 (m, 2H).

Example 118: 6-[4-(3,3-dimethyl-4-[[(2S)-1-[6-oxo-5-(trifluoromethyl)-1,6-dihydropyridazin-4-yl]pyrrolidin-2-yl]methoxy]butanoyl)piperazin-1-yl]pyridine-3-carbonitrile

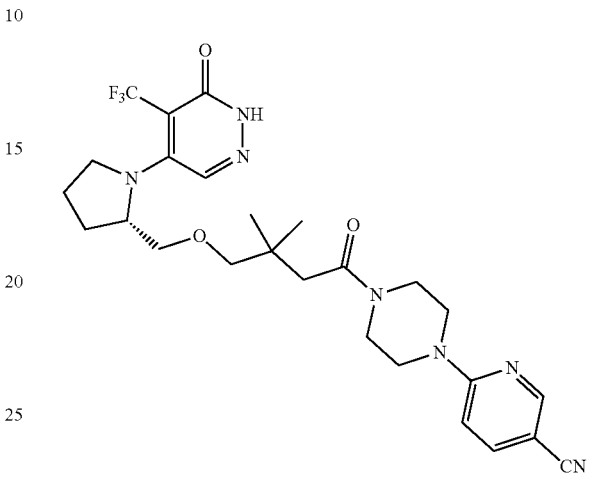

Step 1: Synthesis of 6-[4-(4-hydroxy-3,3-dimethylbutanoyl)piperazin-1-yl]pyridine-3-carbonitrile A solution of Int-A4 (1.56 g, 5.97 mmol, 1.00 equiv), 4,4-dimethyloxolan-2-one (2.05 g, 18.0 mmol, 3.00 equiv), and Al(CH$_3$)$_3$ (12 mL, 2.00 equiv) in toluene (5 mL) was stirred overnight at 70° C. The reaction mixture was diluted with DCM (50 mL). The resulting mixture was washed with 2×15 mL of saturated sodium chloride aqueous solution. The resulting mixture was concentrated under vacuum. The residue was applied onto a silica gel column with DCM/methanol (1/1) to afford 1.17 g (65%) of the title compound as a white solid. LCMS (ESI, m/z): 303.37 [M+H]$^+$

Step 2: Synthesis of Tert-Butyl (2S)-2-([4-[4-(5-cyanopyridin-2-yl)piperazin-1-yl]-2,2-dimethyl-4-oxobutoxy]methyl)pyrrolidine-1-carboxylate A solution of 6-[4-(4-hydroxy-3,3-dimethylbutanoyl)piperazin-1-yl]pyridine-3-carbonitrile (970 mg, 3.21 mmol, 1.00 equiv), sodium hydride (140 mg, 5.83 mmol, 1.10 equiv), and tert-butyl (2S)-2-[(methanesulfonyloxy)methyl]pyrrolidine-1-carboxylate (896 mg, 3.21 mmol, 1.00 equiv) in DMF (15 mL) was stirred for 3 days 50° C. The reaction mixture was diluted with H$_2$O (200 mL). The resulting solution was extracted with 3×150 mL of EtOAc, and the organic layers combined and concentrated under vacuum. The residue was applied onto a silica gel column with EtOAc/petroleum ether (4/6) to afford 125 mg (8%) of the title compound as brown oil. LCMS (ESI, m/z): 486.62 [M+H]$^+$

Step 3: Synthesis of 6-[4-(3,3-dimethyl-4-[[(2S)-pyrrolidin-2-yl]methoxy]butanoyl)piperazin-1-yl]pyridine-3-carbonitrile A solution of tert-butyl (2S)-2-([4-[4-(5-cyanopyridin-2-yl)piperazin-1-yl]-2,2-dimethyl-4-oxobutoxy]methyl)pyrrolidine-1-carboxylate (125 mg, 0.26 mmol, 1.00 equiv), and a solution of hydrogen chloride/dioxane (5 mL) in dioxane (5 mL) was stirred for 0.5 h at 25° C. The resulting mixture was concentrated under vacuum to afford 99 mg (100%) of the title compound as yellow oil. LCMS (ESI, m/z): 386.50 [M+H]$^+$ Step 4: Synthesis of 6-[4-(3,3-dimethyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoyl)piperazin-1-yl]pyridine-3-carbonitrile A solution of 6-[4-(3,3-dimethyl-4-[[(2S)-pyrrolidin-2-yl]methoxy]butanoyl)piperazin-1-yl]pyridine-3-carbonitrile (99 mg, 0.26 mmol, 1.00 equiv), Int-A6 (85 mg, 0.26 mmol, 1.00 equiv), and TEA (78 mg, 0.77 mmol, 3.00 equiv) in EtOH (2 mL) was stirred for 1 h at 60° C. The resulting mixture was concentrated under vacuum. The residue was applied onto a silica gel column with petroleum ether/EtOAc (1/19) to afford 118 mg (68%) of the title compound as yellow oil. LCMS (ESI, m/z): 678.83 [M+H]$^+$ Step 5: Synthesis of 6-[4-(3,3-dimethyl-4-[[(2S)-1-[6-oxo-5-(trifluoromethyl)-1,6-dihydropyridazin-4-yl]pyrrolidin-2-yl]methoxy]butanoyl)piperazin-1-yl]pyridine-3-carbonitrile A solution of 6-[4-(3,3-dimethyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoyl)piperazin-1-yl]pyridine-3-carbonitrile (118 mg, 0.17 mmol, 1.00 equiv) in TFA/DCM (12 mL) was stirred for 1 h at 25° C. The pH value of the solution was adjusted to 8-9 with $NH_2CH_2CH_2OH$. The resulting mixture was washed with 2×100 mL of $H_2O$. The mixture was dried over anhydrous sodium sulfate. After concentration, the residue was purified by C18 reverse phase chromatography eluting with $H_2O$/$CH_3CN$ yielding the title compound 60.3 mg (63%) as white solids. LCMS (ESI, m/z): 548.57 [M+H]$^+$, $^1$H-NMR (400 MHz, Methanol-$d_4$) δ: 8.45 (d, J=2.0 Hz, 1H), 8.23 (s, 1H), 7.79-7.77 (m, 1H), 6.90-6.88 (d, J=8.8 Hz, 1H), 4.71-4.69 (d, J=5.2 Hz, 1H), 3.75-3.62 (m, 10H), 3.43-3.33 (m, 3H), 3.23-3.21 (m, 1H), 2.34 (s, 2H), 2.29-2.20 (m, 1H), 2.15-2.03 (m, 1H), 1.81-1.73 (m, 2H), 0.97 (d, J=17.2 Hz, 6H).

Example 119: 6-[4-(4-[[(2S)-1-[6-oxo-5-(trifluoromethyl)-1,6-dihydropyridazin-4-yl]pyrrolidin-2-yl]methoxy]but-2-ynoyl)piperazin-1-yl]pyridine-3-carbonitrile

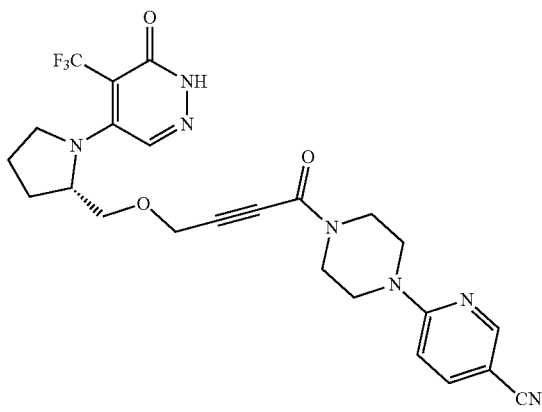 [SMILES: N#Cc1ccc(N2CCN(C(=O)C#CCOC[C@@H]3CCCN3c3cn[nH]c(=O)c3C(F)(F)F)CC2)nc1]

Step 1: Synthesis of Tert-Butyl (2S)-2-[(prop-2-yn-1-yloxy)methyl]pyrrolidine-1-carboxylate To a solution of tert-butyl (2S)-2-(hydroxymethyl)pyrrolidine-1-carboxylate (5 g, 24.84 mmol, 1.00 equiv) in THF (100 mL) was added sodium hydride (2 g, 83.33 mmol, 2.00 equiv) in several batches at 0° C. over 15 min. To this was added 3-bromoprop-1-yne (8.8 g, 73.97 mmol, 3.00 equiv) dropwise with stirring at 0° C. The resulting solution was stirred for 1 h at room temperature. The reaction was then quenched by the addition 50 mL of water. The resulting solution was extracted with 3×100 mL of EtOAc and the organic layers combined and dried over anhydrous sodium sulfate. After concentration, the residue was applied onto a silica gel column eluting with EtOAc/petroleum ether (1:15) to afford 5.3 g (89%) of the title compound as light yellow oil. LCMS (ESI, m/z): 240.15 [M+H]$^+$ Step 2: Synthesis of 2-[(prop-2-yn-1-yloxy)methyl]pyrrolidine A solution of tert-butyl 2-[(prop-2-yn-1-yloxy)methyl]pyrrolidine-1-carboxylate (2.5 g, 10.45 mmol, 1.00 equiv) in hydrogen chloride/dioxane (30 mL) was stirred for 30 min at room temperature. The resulting mixture was concentrated under vacuum to afford 2 g crude of the title compound as yellow oil. LCMS (ESI, m/z): 140.10 [M+H]$^+$ Step 3: Synthesis of 5-[(2S)-2-[(prop-2-yn-1-yloxy)methyl]pyrrolidin-1-yl]-4-(trifluoromethyl)-2-[[2-(trimethylsilyl)ethoxy]methyl]-2,3-dihydropyridazin-3-one A solution of (2S)-2-[(prop-2-yn-1-yloxy)methyl]pyrrolidine hydrochloride (2 g, 11.39 mmol, 1.00 equiv), TEA (3.4 g, 33.60 mmol, 3.00 equiv), Int-A6 (4.48 g, 13.63 mmol, 1.20 equiv) in ethanol (40 mL) was stirred for 1 h at 60° C. in an oil bath. The resulting mixture was concentrated under vacuum. The residue was applied onto a silica gel column eluting with EtOAc/petroleum ether (5:95) to afford 3 g (61%) of the title compound as a red oil. LCMS (ESI, m/z): 432.19 [M+H]$^+$ Step 4: Synthesis of 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-ynoic Acid To a solution of 5-[(2S)-2-[(prop-2-yn-1-yloxy)methyl]pyrrolidin-1-yl]-4-(trifluoromethyl)-2-[[2-(trimethylsilyl)ethoxy]methyl]-2,3-dihydropyridazin-3-one (2 g, 4.63 mmol, 1.00 equiv) in THF (100 mL) was added n-BuLi (2.24 mL, 1.20 equiv) dropwise with stirring at −70° C. The mixture was stirred for 20 min at −70 degrees C. To this was added $CO_2$ (2 g, 10.00 equiv) in several batches at −70° C. The resulting solution was stirred for 20 min at room temperature. The pH value of the solution was adjusted to 6 with hydrogen chloride (2 M). The resulting solution was extracted with 3×100 mL of DCM and the organic layers combined and dried over anhydrous sodium sulfate and concentrated under vacuum. The crude product was purified by C18 reverse phase column eluting with ACN/water to afford 1.4 g (64%) of the title compound as an off-white solid. LCMS (ESI, m/z): 476.18 [M+H]+

Step 5: Synthesis of 6-[4-(4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-ynoyl)piperazin-1-yl]pyridine-3-carbonitrile A solution of Int-A4 (600 mg, 2.67 mmol, 1.00 equiv), 4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-ynoic acid (340 mg, 0.71 mmol, 1.20 equiv), DIEA (488 mg, 3.78 mmol, 3.00 equiv), HATU (720 mg, 1.89 mmol, 1.50 equiv) in DMF (5 mL) was stirred for 2 h at room temperature. The crude product was purified by C18 reverse phase column eluting with ACN/H2O to afford 750 mg (43%) of the title compound as an off-white solid. LCMS (ESI, m/z): 646.27 [M+H]+

Step 6: Synthesis of 6-[4-(4-[[(2S)-1-[6-oxo-5-(trifluoromethyl)-1,6-dihydropyridazin-4-yl]pyrrolidin-2-yl]methoxy]but-2-ynoyl)piperazin-1-yl]pyridine-3-carbonitrile A solution of 6-[4-(4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-ynoyl)piperazin-1-yl]pyridine-3-carbonitrile (200 mg, 0.31 mmol, 1.00 equiv), TFA (2 mL) in DCM (20 mL) was stirred for 1 h at room temperature. The pH value of the solution was adjusted to 8 with ethanolamine. The resulting solution was extracted with 3×100 mL of DCM and the organic layers combined and dried over anhydrous sodium sulfate. After concentration, the residue was purified by C18 reverse phase column eluting with ACN/water yielding the title compound (73.1 mg, 46%) as a white solid. LCMS (ESI, m/z): 516.19 [M+H]+, 1HNMR (DMSO-d6, 400 MHz) δ: 12.41 (s, 1H), 8.56-8.51 (m, 1H), 8.07 (s, 1H), 7.92 (dd, J=9.1, 2.4 Hz, 1H), 6.96 (d, J=9.1 Hz, 1H), 4.62 (s, 1H), 4.43 (s, 2H), 3.80-3.65 (m, 6H), 3.70-3.48 (m, 5H), 3.31-3.23 (m, 1H), 2.18-2.11 (m, 1H), 1.98-1.91 (m, 1H), 1.82-1.64 (m, 2H).

Example 120: 6-[4-[3-(3-hydroxy-2-[[6-oxo-5-(trifluoromethyl)-1,6-dihydropyridazin-4-yl]amino]propoxy)propanoyl]piperazin-1-yl]pyridine-3-carbonitrile

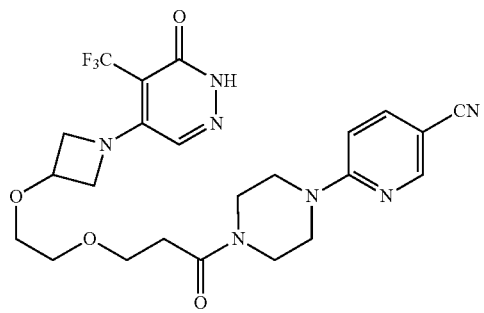 [SMILES: N#Cc1ccc(N2CCN(C(=O)CCOCCOC3CN(c4cn[nH]c(=O)c4C(F)(F)F)C3)CC2)nc1]

Step 1: Synthesis of 5-[3-[2-(benzyloxy)ethoxy]azetidin-1-yl]-4-(trifluoromethyl)-2-[[2-(trimethylsilyl)ethoxy]methyl]-2,3-dihydropyridazin-3-one To a solution of 5-(3-hydroxyazetidin-1-yl)-4-(trifluoromethyl)-2-[[2-(trimethylsilyl)ethoxy]methyl]-2,3-dihydropyridazin-3-one (300 mg, 0.82 mmol, 1.00 equiv) in DMF (20 mL), sodium hydride (20 mg, 0.83 mmol, 2.00 equiv) was added in at 0° C., and then the resulting solution was stirred for 5 min, and then [(bromoethoxy)methyl] benzene (331 mg, 1.65 mmol, 2.00 equiv) was dropped in, and then the resulting solution was stirred for another 3 h at 0° C., and then the resulting solution was quenched with 50 mL of H2O, extracted with 3×50 mL of EtOAc and the organic layers combined, washed with 1×50 mL of brine and concentrated under vacuum, and then the residue was applied onto a silica gel column eluting with EtOAc/petroleum ether (3:7) to afford 295 mg (72%) of the title compound as light yellow oil. LCMS (ESI, m/z): 500.21[M+H]+.

Step 2: Synthesis of 5-[3-(2-hydroxyethoxy)azetidin-1-yl]-4-(trifluoromethyl)-2-[[2-(trimethylsilyl)ethoxy]methyl]-2,3-dihydropyridazin-3-one Under an atmosphere of hydrogen, a solution of 5-[3-[2-(benzyloxy)ethyl]azetidin-1-yl]-4-(trifluoromethyl)-2-[[2-(trimethylsilyl)ethoxy]methyl]-2,3-dihydropyridin-3-one (265 mg, 0.55 mmol, 1.00 equiv) and Palladium carbon (13.5 mg, 0.05 equiv) in methanol (20 mL) was stirred for 2 h at room temperature, and then the solids were filtered out and the resulting solution was concentrated under vacuum to afford 221 mg (98%) of the title compound as white oil. LCMS (ESI, m/z): 410.17M+H]+.

Step 3: Synthesis of Tert-Butyl 3-[2-([1-[6-oxo-5-(trifluoromethyl)-1-[[2-(trimethylsilyl)ethoxy]methyl]-1,6-dihydropyridazin-4-yl]azetidin-3-yl]oxy)ethoxy]propanoate To a solution of 5-[3-(2-hydroxyethoxy)cyclobutyl]-4-(trifluoromethyl)-2,3-dihydropyridazin-3-one (180 mg, 0.65 mmol, 1.00 equiv) in THF (6 mL), sodium hydride (21 mg, 0.88 mmol, 2.00 equiv) was added in, the resulting solution was stirred for 20 min at room temperature and then tert-butyl prop-2-enoate (112 mg, 0.87 mmol, 2.00 equiv) was dropped in, and then the resulting solution was stirred for 1 h at room temperature, and then the resulting solution was quenched with of 15 mL of water, extracted with 15 mL of EtOAc and the organic layers combined, washed with 1×15 mL of brine, dried over anhydrous sodium sulfate and concentrated under vacuum, and then the residue was applied onto a silica gel column eluting with EtOAc/petroleum ether (1:3) to afford 80 mg (23%) of the title compound as light brown oil. LCMS (ESI, m/z): 538.25[M+H]+.

Step 4: Synthesis of 3-(2-(1-(6-oxo-5-(trifluoromethyl)-1,6-dihydropyridazin-4-yl)azetidin-3-yloxy)ethoxy)propanoic Acid A solution of tert-butyl 3-[2-([1-[6-oxo-5-(trifluoromethyl)-1-[[2-(trimethylsilyl)ethoxy]methyl]-1,6-dihydropyridazin-4-yl]azetidin-3-yl]oxy)ethoxy]propanoate (180 mg, 0.34 mmol, 1.00 equiv) and TFA (2 mL) in DCM (10 mL) was stirred for 40 min at room temperature, and then the resulting solution was concentrated under vacuum to afford 50 mg (28%) of the title compound as light yellow oil. LCMS (ESI, m/z): 352.11 [M+H]+.

Step 5: Synthesis of 6-(4-[3-[2-([1-[6-oxo-5-(trifluoromethyl)-1,6-dihydropyridazin-4-yl]pyrrolidin-3-yl]oxy)ethoxy]propanoyl]piperazin-1-yl)pyridine-3-carbonitrile A solution of 3-[2-([1-[6-oxo-5-(trifluoromethyl)-1,6-dihydropyridazin-4-yl]pyrrolidin-3-yl]oxy)ethoxy]propanoic acid (50 mg, 0.14 mmol, 1 equiv), DIEA (35.4 mg, 0.27 mmol, 2.00 equiv), HATU (52.0 mg, 0.14 mmol, 1.00 equiv) and Int-A4 (30.9 mg, 0.16 mmol, 1.20 equiv) in DMF (20 mL) was stirred for 40 min at room temperature, and then the resulting solution was diluted with 20 ml of H2O, extracted with 3×20 ml of EtOAc and the organic layer was combined, washed with 1×20 ml of brine and concentrated under vacuum, and the residue was purified by Prep-HPLC yielding the title compound (37.0 mg, 50.48%) as a white solid. LCMS (ESI, m/z): 522.05 [M+H]+, $^1$HNMR (CD3OD, 300 MHz) δ 8.41 (d, J=1.8 Hz, 1H), 7.76 (dd, J 9.0, 2.4 Hz, 1H), 7.44 (s, 1H), 6.87 (dd, J=9.0, 0.9 Hz, 1H), 4.57-4.40 (m, 3H), 4.21-4.17 (m, 2H), 3.90-3.73 (m, 10H), 3.64 (s, 4H), 2.75 (t, J=6.1 Hz, 2H)

Example 121: 6-(4-((1R,3R)-3-((1-(6-oxo-5-(trifluoromethyl)-1,6-dihydropyridazin-4-yl)pyrrolidin-3-yl)methoxy)cyclobutanecarbonyl)piperazin-1-yl)nicotinonitrile and 6-(4-((1S,3S)-3-((1-(6-oxo-5-(trifluoromethyl)-1,6-dihydropyridazin-4-yl)pyrrolidin-3-yl)methoxy)cyclobutanecarbonyl)piperazin-1-yl)nicotinonitrile

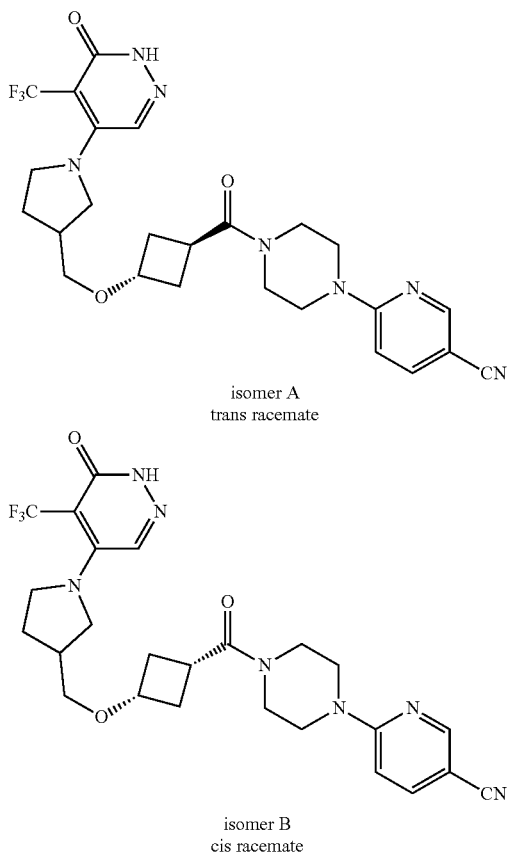

isomer A
trans racemate isomer B
cis racemate

Step 1: Synthesis of (pyrrolidin-3-yl)methanol Hydrochloride

A solution of tert-butyl 3-(hydroxymethyl)pyrrolidine-1-carboxylate (2.10 g, 10.44 mmol, 1.00 equiv) in hydrogen chloride/dioxane (10 mL) was stirred for 1 h at room temperature. The solvent was concentrated under vacuum to afford 1.3 g crude of the title compound as a crude white solid. LCMS (ESI, m/z): 102.09 [M+H]+

Step 2: Synthesis of 5-[3-(hydroxymethyl)pyrrolidin-1-yl]-4-(trifluoromethyl)-2-[[2-(trimethylsilyl)ethoxy]methyl]-2,3-dihydropyridazin-3-one A solution of (pyrrolidin-3-yl)methanol hydrochloride (900 mg, 6.54 mmol, 1.00 equiv), Int-A6 (1.64 g, 4.99 mmol, 1.00 equiv), TEA (2 g, 19.76 mmol, 5.00 equiv) in ethanol (20 mL) was stirred for 4 h at 80° C. The solvent was concentrated under vacuum and the residue was applied onto a silica gel column eluting with EtOAc/petroleum ether (1:1) to afford 1.1 g (43%) of the title compound as a white solid. LCMS (ESI, m/z): 394.18 [M+H]+

Step 3: Synthesis of [1-[6-oxo-5-(trifluoromethyl)-1-[[2-(trimethylsilyl)ethoxy]methyl]-1,6-dihydropyridazin-4-yl]pyrrolidin-3-yl]methyl 4-methylbenzene-1-sulfonate A solution of 5-[3-(hydroxymethyl)pyrrolidin-1-yl]-4-(trifluoromethyl)-2-[[2-(trimethylsilyl)ethoxy]methyl]-2,3-dihydropyridazin-3-one (780 mg, 1.98 mmol, 1.00 equiv), 4-methylbenzene-1-sulfonyl chloride (570 mg, 2.99 mmol, 1.50 equiv), TEA (606 mg, 5.99 mmol, 3.00 equiv), 4-dimethylaminopyridine (50 mg, 0.41 mmol, 0.20 equiv) in DCM (15 mL) was stirred for 8 h at room temperature. The solvent was concentrated under vacuum and the residue was applied onto a silica gel column eluting with EtOAc/petroleum ether (1:1) to afford 500 mg (46%) of the title compound as a white solid. LCMS (ESI, m/z): 548.19 [M+H]+.

Step 4: Synthesis of Methyl 3-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclobutane-1-carboxylate A solution of [1-[6-oxo-5-(trifluoromethyl)-1-[[2-(trimethylsilyl)ethoxy]methyl]-1,6-dihydropyridazin-4-yl]pyrrolidin-3-yl]methyl 4-methylbenzene-1-sulfonate (1.09 g, 1.99 mmol, 1.00 equiv), methyl 3-hydroxycyclobutane-1-carboxylate (390 mg, 3.00 mmol, 1.50 equiv), sodium hydride (160 mg, 6.67 mmol, 2.00 equiv) in DMF (10 mL) was stirred for 6 h at 80° C. The resulting solution was quenched with 60 ml H2O, then the solution was extracted with EtOAc (3×60 mL) and the organic layers combined. The solution was dried over anhydrous sodium sulfate and concentrated under vacuum. The residue was applied onto a silica gel column eluting with EtOAc/petroleum ether (1:2) to afford 200 mg (20%) of the title compound as a white solid. LCMS (ESI, m/z): 506.23 [M+H]+

Step 5: Synthesis of 3-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclobutane-1-carboxylic Acid A solution of methyl 3-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclobutane-1-carboxylate (200 mg, 0.40 mmol, 1.00 equiv), LiOH (48 mg, 2.00 mmol, 5.00 equiv), water (1 mL) in MeOH (5 ml) was stirred for 1 h at room temperature. The pH value of the solution was adjusted to 5 with hydrogen chloride. After concentration, the residue was applied onto a silica gel column eluting with EtOAc/petroleum ether (2:1) to afford 130 mg (67%) of the title compound as a white solid. LCMS (ESI, m/z): 492.22 [M+H]+.

Step 6: Synthesis of 6-(4-[3-[(2R)-2-[[6-oxo-5-(trifluoromethyl)-1,6-dihydropyridazin-4-yl]amino]-2-phenylethoxy]propanoyl]piperazin-1-yl)pyridine-3-carbonitrile and 6-(4-[3-[(2S)-2-[[6-oxo-5-(trifluoromethyl)-1,6-dihydropyridazin-4-yl]amino]-2-phenylethoxy]propanoyl]piperazin-1-yl)pyridine-3-carbonitrile A solution of 3-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclobutane-1-carboxylic acid (117 mg, 0.24 mmol, 1.00 equiv), HATU (117 mg, 0.31 mmol, 1.30 equiv), DIEA (61.5 mg, 0.48 mmol, 2.00 equiv), Int-A4 (5 mL, 1.00 equiv) in DMF (2 mL) was stirred for 1 h at room temperature. The residue was purified by C18 reverse phase chromatography eluting with H₂O/CH₃CN to afford 100 mg (63%) of the title compound as a white solid. LCMS (ESI, m/z): 662.31 [M+H]+.

Step 7: Synthesis of 6-(4-((1r,3r)-3-((1-(6-oxo-5-(trifluoromethyl)-1,6-dihydropyridazin-4-yl)pyrrolidin-3-yl)methoxy)cyclobutanecarbonyl)piperazin-1-yl)nicotinonitrile and 6-(4-((is, 3s)-3-((1-(6-oxo-5-(trifluoromethyl)-1,6-dihydropyridazin-4-yl)pyrrolidin-3-yl)methoxy)cyclobutanecarbonyl)piperazin-1-yl)nicotinonitrile A solution of 6-[4-[3-([1-[6-oxo-5-(trifluoromethyl)-1-[[2-(trimethylsilyl)ethoxy]methyl]-1,6-dihydropyridazin-4-yl]pyrrolidin-3-yl]methoxy)cyclobutanecarbonyl]piperazin-1-yl]pyridine-3-carbonitrile (100 mg, 0.15 mmol, 1.00 equiv), TFA (1 mL) in DCM (5 mL) was stirred for 1 h at room temperature. After concentration, the residue was purified by C18 reverse phase chromatography eluting with H₂O/CH₃CN. Then the residue was further purified by Prep-HPLC yielding (after arbitrary assignment of the stereochemistry) the title compounds, respectively, isomer A (12.9 mg, 16%) as a white solid. LCMS (ESI, m/z): 532.30 [M+H]+, $^1$H NMR (300 MHz, Methanol-d4) δ 8.44 (s, 1H), 7.92 (s, 1H), 7.78 (dd, J=9.1, 2.4 Hz, 1H), 6.89 (dd, J=9.1, 0.8 Hz, 1H), 4.01-3.97 (m, 1H), 3.80-3.69 (m, 9H), 3.68-3.60 (m, 2H), 3.59-3.40 (m, 3H), 3.09-2.92 (m, 1H), 2.54 (q, J=8.4, 7.6 Hz, 3H), 2.23-2.02 (m, 3H), 1.84-1.79 (m, 1H) and isomer B (4.1 mg, 5%) as a white solid. LCMS (ESI, m/z): 532.30 [M+H]+, $^1$H NMR (300 MHz, Methanol-d4) δ 8.44 (s, 1H), 7.92 (s, 1H), 7.78 (dd, J=9.1, 2.3 Hz, 1H), 6.89 (dd, J=9.1, 0.9 Hz, 1H), 4.15-3.93 (m, 1H), 3.82-3.67 (m, 9H), 3.66-3.60 (m, 2H), 3.59-3.40 (m, 2H), 3.39-3.31 (m, 2H), 2.55-2.50 (m, 3H), 2.26-2.11 (m, 3H), 1.92-1.75 (m, 1H).

Example 122: 6-[4-(3-[[(2S,4S)-4-methoxy-1-[6-oxo-5-(trifluoromethyl)-1,6-dihydropyridazin-4-yl]pyrrolidin-2-yl]methoxy]propanoyl)piperazin-1-yl]pyridine-3-carbonitrile

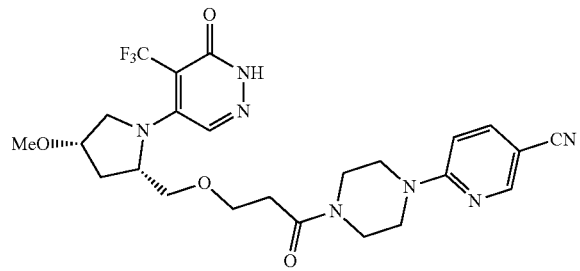 [SMILES: CO[C@H]1C[C@@H](COCCC(=O)N2CCN(c3ccc(C#N)cn3)CC2)N(c2cn[nH]c(=O)c2C(F)(F)F)C1]

Step 1: Synthesis of 1-tert-butyl 2-methyl (2S,4S)-4-methoxypyrrolidine-1,2-dicarboxylate A solution of 1-tert-butyl 2-methyl (2S,4S)-4-hydroxypyrrolidine-1,2-dicarboxylate (5 g, 20.39 mmol, 1.00 equiv), sodium hydride (1.63 g, 40.75 mmol, 2.00 equiv), iodomethane (5.7 g, 40.16 mmol, 2.00 equiv) in THF (50 mL) was stirred for 12 h at room temperature. The reaction was quenched by the addition of 50 mL ammonium chloride saturated aqueous solution. The resulting solution was extracted with 3×70 mL of EtOAc and the organic layers combined and concentrated under vacuum. Then the residue was applied onto a silica gel column eluting with EtOAc/petroleum ether (3/7) to afford 2.48 mg (47%) of the title compound as a yellow oil. LCMS (ESI, m/z): 246.13[M+H]

Step 2: Synthesis of Tert-Butyl (2S,4S)-2-(hydroxymethyl)-4-methoxypyrrolidine-1-carboxylate A solution of (2S,4S)-1-[(tert-butoxy)carbonyl]-4-methoxypyrrolidine-2-carboxylic acid (1.1 g, 4.48 mmol, 1.00 equiv), B₂H₆/THF (10 mL) in THF (20 mL) was stirred for 48h at room temperature. The resulting solution was diluted with 20 mL of water and extracted with 3×30 ml of EtOAc. The organic layers combined and dried over Na₂SO₄. The resulting mixture was concentrated under vacuum to afford 1.1 g (crude) of the title compound as a yellow oil. LCMS (ESI, m/z): 232.15[M+H]

Step 3: Synthesis of [(2S,4S)-4-methoxypyrrolidin-2-yl]methanol Hydrochloride

A solution of tert-butyl (2S,4S)-2-(hydroxymethyl)-4-methoxypyrrolidine-1-carboxylate (1.1 g, 4.76 mmol, 1.00 equiv) in hydrogen chloride/dioxane (10 mL) was stirred for 30 min at room temperature. The resulting mixture was concentrated under vacuum to afford 818 mg of the title compound as yellow oil. LCMS (ESI, m/z): 132.09[M+H]

Step 4: Synthesis of 5-[(2S,4S)-2-(hydroxymethyl)-4-methoxypyrrolidin-1-yl]-4-(trifluoromethyl)-2-[[2-(trimethylsilyl)ethoxy]methyl]-2,3-dihydropyridazin-3-one A solution of [(2S,4S)-4-methoxypyrrolidin-2-yl]methanol hydrochloride (818 mg, 4.88 mmol, 1.00 equiv), Int-A6 (805 mg, 2.45 mmol, 0.50 equiv), TEA (959 mg, 9.48 mmol, 2.00 equiv) in EtOH (10 mL) was stirred for 1 h at 80° C.

The reaction mixture was concentrated under vacuum and the residue was applied onto a silica gel column eluting with EtOAc/petroleum ether (1/1) to afford 460 mg (18%) of the title compound as a white solid. LCMS (ESI, m/z): 424.18 [M+H]+

Step 5: Synthesis of Methyl 3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate A solution of 5-[(2S,4S)-2-(hydroxymethyl)-4-methoxypyrrolidin-1-yl]-4-(trifluoromethyl)-2-[[2-(trimethylsilyl)ethoxy]methyl]-2,3-dihydropyridazin-3-one (440 mg, 1.04 mmol, 1.00 equiv), sodium hydride (42 mg, 1.05 mmol, 1.00 equiv), methyl prop-2-enoate (895 mg, 10.40 mmol, 10.00 equiv) in THF (10 mL) was stirred for 12 h at room temperature. Then the reaction was quenched by the addition of water. The resulting solution was extracted with 3×30 mL of EtOAc and the organic layers combined and concentrated under vacuum. The residue was applied onto a silica gel column eluting with EtOAc/petroleum ether (4/6) to afford 80 mg (15%) of the title compound as a yellow oil. LCMS (ESI, m/z): 510.22 [M+H]+

Step 6: Synthesis of 3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoic Acid A solution of methyl 3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate (80 mg, 0.16 mmol, 1.00 equiv), LiOH.H2O (33 mg, 0.79 mmol, 5.00 equiv) in methanol (3 mL) and water (1 mL) was stirred for 2 h at room temperature. The pH value of the solution was adjusted to 6 with hydrogen chloride (1 M) and the solids were collected by filtration to afford 70 mg (90%) of the title compound as a white solid. LCMS (ESI, m/z): 496.20 [M+H]+

Step 7: Synthesis of 6-[4-(3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoyl)piperazin-1-yl]pyridine-3-carbonitrile A solution of 3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoic acid (70 mg, 0.14 mmol, 1.00 equiv), HATU (80.6 mg, 0.21 mmol, 1.50 equiv), DIEA (54.7 mg, 0.42 mmol, 3.00 equiv), Int-A4 (31.7 mg, 0.14 mmol, 1.00 equiv) in DMF (3 mL) was stirred for 1 h at room temperature. The residue was purified by C18 reverse phase chromatography eluting with H2O/CH3CN to afford 45 mg (48%) of the title compound as a yellow solid. LCMS (ESI, m/z): 666.30 [M+H]+

Step 8: Synthesis of 6-[4-(3-[[(2S,4S)-4-methoxy-1-[6-oxo-5-(trifluoromethyl)-1,6-dihydropyridazin-4-yl]pyrrolidin-2-yl]methoxy]propanoyl)piperazin-1-yl]pyridine-3-carbonitrile A solution of 6-[4-(3-[[(2S,4S)-4-methoxy-1-[6-oxo-5-(trifluoromethyl)-1-[[2-(trimethylsilyl)ethoxy]methyl]-1,6-dihydropyridazin-4-yl]pyrrolidin-2-yl]methoxy]propanoyl)piperazin-1-yl]pyridine-3-carbonitrile (40 mg, 0.06 mmol, 1.00 equiv) in DCM (3 mL) and TFA (0.3 mL) was stirred for 1 h at room temperature. After concentration, the residue was purified by C18 reverse phase chromatography eluting with H2O/CH3CN. Then the residue was further purified by Prep-HPLC yielding the title compound (15.6 mg, 48%) as a white solid. LCMS (ESI, m/z): 536.52 [M+H]+, 1H NMR (400 MHz, DMSO-d6) δ: 12.40 (s, 1H), 8.51 (d, J=2.3 Hz, 1H), 8.01 (s, 1H), 7.89 (dd, J=9.1, 2.4 Hz, 1H), 6.93 (d, J=9.1 Hz, 1H), 4.60 (s, 1H), 3.90 (p, J=7.3 Hz, 1H), 3.90-3.63 (m, 6H), 3.61-3.51 (m, 5H), 3.51-3.43 (m, 3H), 3.47-3.34 (m, 3H), 2.55 (d, J=6.2 Hz, 2H), 2.31 (dt, J=12.4, 7.4 Hz, 1H), 1.62 (dt, J=12.5, 7.5 Hz, 1H).

Example 123: 6-[4-[(3R)-3-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile and 6-[4-[(3S)-3-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile

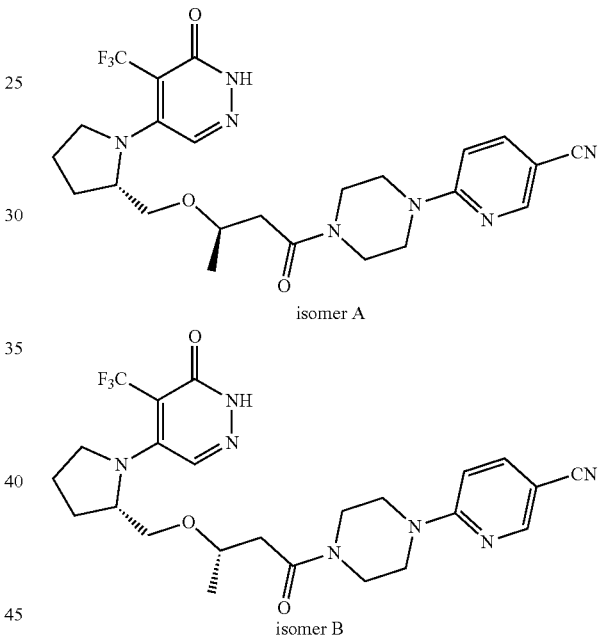

isomer A isomer B

Step 1: Synthesis of Methyl 3-(methanesulfonyloxy)butanoate

A solution of methyl 3-hydroxybutanoate (980 mg, 8.30 mmol, 1.00 equiv), TEA (1.68 g, 16.60 mmol, 2.00 equiv), methanesulfonyl methanesulfonate (2.17 g, 12.46 mmol, 1.50 equiv) in DCM (10 mL) was stirred for 2 h at room temperature. The resulting solution was extracted with 3×30 mL of DCM and the organic layers combined, then the resulting mixture was washed with 3×20 mL of ammonium chloride saturated aqueous solution and dried over Na2SO4. The reaction mixture was concentrated under vacuum to afford 1.51 g (93%) of the title compound as yellow oil. LCMS (ESI, m/z): 197.04 [M+H]+

Step 2: Synthesis of 3-[[(2S)-1-[(tert-butoxy)carbonyl]pyrrolidin-2-yl]methoxy]butanoic Acid A solution of methyl 3-(methanesulfonyloxy)butanoate (1.51 g, 7.70 mmol, 1.00 equiv), sodium hydride (616 mg, 15.40 mmol, 2.00 equiv), tert-butyl (2S)-2-(hydroxymethyl)pyrrolidine-1-carboxylate (1.54 g, 7.65 mmol, 1.00 equiv) in THF (15 mL) was stirred for 12 h at room temperature. The reaction was quenched by the addition of 20 mL of water. The resulting solution was extracted with 4×30 mL of EtOAc and the water layers combined. The pH value of the water layers was adjusted to 6 with hydrogen chloride (1 M). The resulting solution was extracted with 5×20 mL of DCM and the organic layers combined and concentrated under vacuum to afford 220 mg (9%) of the title compound as yellow oil. LCMS (ESI, m/z): 288.17 [M+H]$^+$ Step 3: Synthesis of Methyl 3-[[(2S)-pyrrolidin-2-yl]methoxy]butanoate Hydrochloride A solution of 3-[[(2S)-1-[(tert-butoxy)carbonyl]pyrrolidin-2-yl]methoxy]butanoic acid (220 mg, 0.73 mmol, 1.00 equiv) in hydrogen chloride/dioxane (10 mL) was stirred for 30 min at room temperature. The resulting mixture was concentrated under vacuum to afford 200 mg (crude) of the title compound as yellow oil. LCMS (ESI, m/z): 188.17 [M+H]$^+$ Step 4: Synthesis of 3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoic Acid A solution of 3-[[(2S)-pyrrolidin-2-yl]methoxy]butanoic acid hydrochloride (200 mg, 0.89 mmol, 1.00 equiv), Int-A6 (147 mg, 0.45 mmol, 0.50 equiv), TEA (181 mg, 1.79 mmol, 2.00 equiv) in EtOH (10 mL) was stirred for 2 h at 80° C. The reaction mixture was concentrated under vacuum and the residue was applied onto a silica gel column eluting with DCM/methanol (9/1) to afford 190 mg (44%) of the title compound as yellow oil. LCMS (ESI, m/z): 480.21 [M+H]$^+$ Step 5: Synthesis of 3-[[(2S)-1-[6-oxo-5-(trifluoromethyl)-1,6-dihydropyridazin-4-yl]pyrrolidin-2-yl]methoxy]butanoic Acid A solution of 3-[[(2S)-1-[6-oxo-5-(trifluoromethyl)-1,6-dihydropyridazin-4-yl]pyrrolidin-2-yl]methoxy]butanoic acid in DCM (3 mL) and TFA (0.3 mL) was stirred for 1 h at room temperature. After concentration, the residue was purified by C18 reverse phase chromatography eluting with H$_2$O/CH$_3$CN to afford 45 mg (88%) of the title compound as a white solid. LCMS (ESI, m/z): 350.12 [M+H]$^+$ Step 6: Synthesis of 6-[4-[(3R)-3-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile and 6-[4-[(3S)-3-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile A solution of 3-[[(2S)-1-[6-oxo-5-(trifluoromethyl)-1,6-dihydropyridazin-4-yl]pyrrolidin-2-yl]methoxy]butanoic acid (45 mg, 0.13 mmol, 1.00 equiv), HATU (73.5 mg, 0.19 mmol, 1.50 equiv), DIEA (50 mg, 0.39 mmol, 3.00 equiv), Int-A4 (28.8 mg, 0.13 mmol, 1.00 equiv) in DMF (3 mL) was stirred for 1 h at room temperature. The resulting solution was purified by C18 reverse phase chromatography eluting with H$_2$O/CH$_3$CN. Then the residue was further purified by Prep-HPLC yielding (after arbitrary assignment of the stereochemistry) the title compounds, respectively, isomer A (14.4 mg, 22%) as a white solid. LCMS (ESI, m/z): 520.52 [M+H]$^+$, $^1$H NMR (400 MHz, DMSO-d$_6$) δ: 12.34 (s, 1H), 8.51 (d, J=2.4 Hz, 1H), 8.01 (s, 1H), 7.93-7.82 (m, 1H), 6.93 (d, J=9.1 Hz, 1H), 4.47 (m, 1H), 3.82 (q, J=6.1 Hz, 1H), 3.69-3.51 (m, 10H), 3.59-3.48 (m, 1H), 3.21-3.16 (m, 1H), 2.59 (dd, J=15.5, 6.7 Hz, 1H), 2.29 (dd, J=15.5, 5.7 Hz, 1H), 2.07 (m, 1H), 1.87 (s, 1H), 1.64 (m, 2H), 1.09 (d, J=6.1 Hz, 3H) and isomer B (9 mg, 13%) as a white solid. LCMS (ESI, m/z): 520.55[M+H]$^+$, $^1$H NMR (400 MHz, DMSO-d$_6$) δ: 12.34 (s, 1H), 8.51 (d, J=2.4 Hz, 1H), 8.01 (s, 1H), 7.93-7.82 (m, 1H), 6.93 (d, J=9.1 Hz, 1H), 4.47 (m, 1H), 3.82 (q, J=6.1 Hz, 1H), 3.69-3.51 (m, 10H), 3.59-3.48 (m, 1H), 3.21-3.16 (m, 1H), 2.59 (dd, J=15.5, 6.7 Hz, 1H), 2.29 (dd, J=15.5, 5.7 Hz, 1H), 2.07 (m, 1H), 1.87 (s, 1H), 1.64 (m, 2H), 1.09 (d, J=6.1 Hz, 3H).

Example 124: 6-(4-[2-[2-([2-[6-oxo-5-(trifluoromethyl)-1,6-dihydropyridazin-4-yl]-2,3-dihydro-1H-isoindol-4-yl]methoxy)ethoxy]acetyl]piperazin-1-yl)pyridine-3-carbonitrile

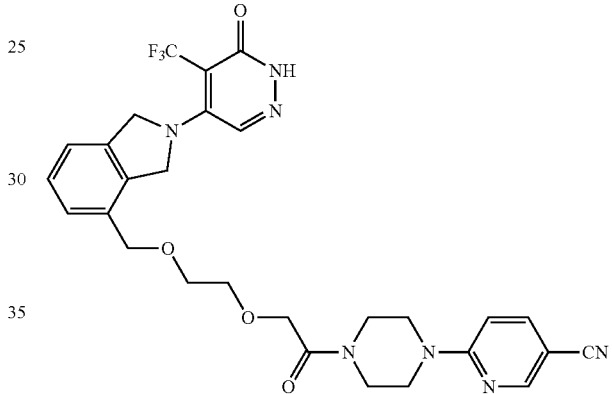

Step 1: Synthesis of 6-[4-(2-[2-[(tert-butyldimethylsilyl)oxy]ethoxy]acetyl)piperazin-1-yl]pyridine-3-carbonitrile A solution of 2-[(tert-butyldimethylsilyl)oxy]ethan-1-ol (1111 mg, 6.30 mmol, 1 equiv) in DMF (10 mL) was added NaH (302.4 mg, 12.60 mmol, 2 equiv) in several batches at 0 degrees. The resulting solution was stirred for 15 min at 0° C. Then 6-[4-(2-chloroacetyl)piperazin-1-yl]pyridine-3-carbonitrile (2001 mg, 7.56 mmol, 1.2 equiv) was added. The resulting solution was stirred for an additional 4 h at room temperature. The reaction was then quenched by the addition of 10 mL of water. The resulting solution was extracted with 3×30 mL of EtOAc and the organic layers combined. The resulting solution was washed with 3×30 mL of NaCl (aq) and the organic layers combined and concentrated under vacuum. The residue was applied onto a silica gel column eluting with EtOAc/petroleum ether (95/5) to afford 751 mg (29.5%) of the title compound as colorless oil. LCMS (ESI, m/z): 405.22 [M+H]$^+$ Step 2: Synthesis of 6-[4-[2-(2-hydroxyethoxy)acetyl]piperazin-1-yl]pyridine-3-carbonitrile A solution of 6-[4-(2-[2-[(tert-butyldimethylsilyl)oxy]ethoxy]acetyl)piperazin-1-yl]pyridine-3-carbonitrile (650 mg, 1.61 mmol, 1 equiv), TBAF (504.1 mg, 1.93 mmol, 1.2 equiv) in THF (10 mL) was stirred for 2 h at room temperature. The reaction was then quenched by the addition of 10 mL of water. The resulting solution was extracted with 3×30 ml of DCM and the organic layers combined and concentrated under vacuum. The residue was applied onto a silica gel column eluting with DCM/methanol (95/5) to afford 222 mg (47.6%) of the title compound as a white solid. LCMS (ESI, m/z): 291.14 [M+H]$^+$ Step 3: Synthesis of 6-(4-[2-[2-([2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]methoxy)ethoxy]acetyl]piperazin-1-yl)pyridine-3-carbonitrile A solution of 6-[4-[2-(2-hydroxyethoxy)acetyl]piperazin-1-yl]pyridine-3-carbonitrile (100.6 mg, 0.35 mmol, 1.2 equiv) in THF (5 mL) was added NaH (13.9 mg, 0.58 mmol, 2 equiv) at 0° C. The resulting solution was stirred for 15 min at 0° C. Then [2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]methyl methanesulfonate (150 mg, 0.29 mmol, 1 equiv) was added. The resulting solution was stirred for an additional 2 h at room temperature. The reaction was then quenched by the addition of 10 mL of water. The resulting solution was extracted with 3×30 mL of EtOAc and the organic layers combined and dried over anhydrous sodium sulfate. The resulting mixture was concentrated under vacuum. The residue was applied onto a silica gel column eluting with DCM/methanol (99/1) to afford 33 mg (16%) of the title compound as yellow oil. LCMS (ESI, m/z): 714.30 [M+H]$^+$ Step 4: Synthesis of 6-(4-[2-[2-([2-[6-oxo-5-(trifluoromethyl)-1,6-dihydropyridazin-4-yl]-2,3-dihydro-1H-isoindol-4-yl]methoxy)ethoxy]acetyl]piperazin-1-yl)pyridine-3-carbonitrile A solution of 6-(4-[2-[2-([2-[6-oxo-5-(trifluoromethyl)-1-[[2-(trimethylsilyl)ethoxy]methyl]-1,6-dihydropyridazin-4-yl]-2,3-dihydro-1H-isoindol-4-yl]methoxy)ethoxy]acetyl]piperazin-1-yl)pyridine-3-carbonitrile (33 mg, 0.05 mmol, 1 equiv) in DCM (5 mL) and TFA (0.5 mL) was stirred for 2 h at room temperature. After concentration, the residue was purified by C18 reverse phase chromatography eluting with H$_2$O/CH$_3$CN. Then the residue was further purified by Prep-HPLC yielding the title compound (5.1 mg, 18.9%) as a white solid. LCMS (ESI, m/z): 584.22 [M+H]$^+$, $^1$H NMR (300 MHz, DMSO-d6) δ: 12.49 (s, 1H), 8.47 (d, J=2.3 Hz, 1H), 8.01 (s, 1H), 7.85 (dd, J=9.1, 2.4 Hz, 1H), 7.27 (q, J=4.7 Hz, 3H), 6.85 (d, J=9.1 Hz, 1H), 4.99 (s, 2H), 4.93 (s, 2H), 4.53 (s, 2H), 4.19 (s, 2H), 3.61 (d, J=4.2 Hz, 8H), 3.49 (m, 4H).

Example 125: 6-[4-(3-[[(2S)-1-[6-oxo-5-(trifluoromethyl)-1,6-dihydropyridazin-4-yl]pyrrolidin-2-yl]methoxy]azetidine-1-carbonyl)piperazin-1-yl]pyridine-3-carbonitrile

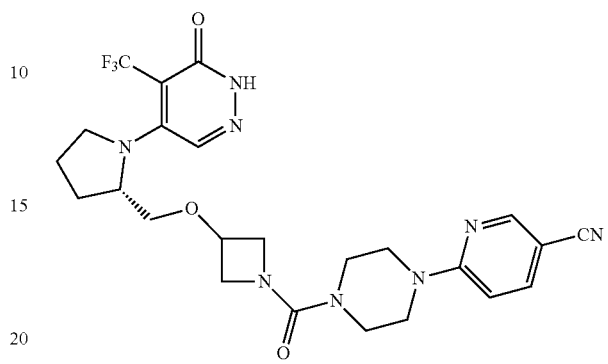

Step 1: Synthesis of 4-nitrophenyl 4-(5-cyanopyridin-2-yl)piperazine-1-carboxylate A solution of Int-A4 (1 g, 5.31 mmol, 1 equiv), DIEA (1.38 g, 10.68 mmol, 2.01 equiv), 4-nitrophenyl carbonochloridate (1.07 g, 5.31 mmol, 1.00 equiv) in DCM (20 mL) was stirred for 2 h at room temperature. The resulting mixture was concentrated under vacuum. The residue was applied onto a silica gel column eluting with EtOAc/petroleum ether (70/30) to afford 1.7 g (90%) of the title compound as a yellow solid. LCMS (ESI, m/z): 354.33 [M+H]$^+$ Step 2: Synthesis of 6-[4-(3-hydroxyazetidine-1-carbonyl)piperazin-1-yl]pyridine-3-carbonitrile A solution of 4-nitrophenyl 4-(5-cyanopyridin-2-yl)piperazine-1-carboxylate (1.7 g, 4.81 mmol, 1 equiv), DIEA (1.25 g, 9.67 mmol, 2.01 equiv), azetidin-3-ol hydrochloride (1.05 g, 9.58 mmol, 1.99 equiv) in butan-1-ol (20 mL) was stirred for 16 h at 120° C. The resulting mixture was concentrated under vacuum. The residue was dissolved in 30 mL of DCM. The organic layer was washed with 20 ml of saturated sodium carbonate aqueous. The organic layers combined and dried over anhydrous sodium sulfate and concentrated under vacuum. The residue was applied onto a silica gel column eluting with DCM/methanol (5/95) to afford 600 mg (43%) of the title compound as a white solid. LCMS (ESI, m/z): 288.32 [M+H]$^+$ Step 3: Synthesis of Tert-Butyl (2S)-2-[([1-[4-(5-cyanopyridin-2-yl)piperazine-1-carbonyl]azetidin-3-yl]oxy)methyl]pyrrolidine-1-carboxylate A solution of 6-[4-(3-hydroxyazetidine-1-carbonyl)piperazin-1-yl]pyridine-3-carbonitrile (600 mg, 2.09 mmol, 1.00 equiv), NaH (250 mg, 10.42 mmol, 4.99 equiv), tert-butyl (2S)-2-[(methanesulfonyloxy)methyl]pyrrolidine-1-carboxylate (583 mg, 2.09 mmol, 1 equiv) in THF (30 mL) was stirred for 3 days at 80° C. The reaction was then quenched by the addition of 30 mL of water. The resulting solution was extracted with 3×30 mL of EtOAc and the organic layers combined and dried over anhydrous sodium sulfate. The organic layer was concentrated under vacuum. The residue was applied onto a silica gel column eluting with EtOAc/ petroleum ether (90/10) to afford 250 mg (25%) of the title compound as yellow oil. LCMS (ESI, m/z): 471.56 [M+H]+

Step 4: Synthesis of 6-[4-(3-[[(2S)-pyrrolidin-2-yl]methoxy]azetidine-1-carbonyl)piperazin-1-yl]pyridine-3-carbonitrile A solution of tert-butyl (2S)-2-[([1-[4-(5-cyanopyridin-2-yl)piperazine-1-carbonyl]azetidin-3-yl]oxy)methyl]pyrrolidine-1-carboxylate (150 mg, 0.32 mmol, 1 equiv), TFA (0.3 mL) in DCM (5 mL) was stirred for 2 h at room temperature. The resulting mixture was concentrated under vacuum to afford 130 mg (crude) of the title compound as yellow oil. LCMS (ESI, m/z): 371.45 [M+H]+

Step 5: Synthesis of 6-[4-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]azetidine-1-carbonyl)piperazin-1-yl]pyridine-3-carbonitrile A solution of 6-[4-(3-[[(2S)-pyrrolidin-2-yl]methoxy]azetidine-1-carbonyl)piperazin-1-yl]pyridine-3-carbonitrile (120 mg, 0.32 mmol, 1 equiv), TEA (98 mg, 0.97 mmol, 2.99 equiv), Int-A6 (127.3 mg, 0.39 mmol, 1.20 equiv) in EtOH (20 mL) was stirred for 16 h at 70° C. The resulting mixture was concentrated under vacuum. The residue was applied onto a silica gel column eluting with EtOAc to afford 120 mg (56%) of the title compound as yellow oil. LCMS (ESI, m/z): 663.78 [M+H]+

Step 6: Synthesis of 6-[4-(3-[[(2S)-1-[6-oxo-5-(trifluoromethyl)-1,6-dihydropyridazin-4-yl]pyrrolidin-2-yl]methoxy]azetidine-1-carbonyl)piperazin-1-yl]pyridine-3-carbonitrile A solution of 6-[4-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]azetidine-1-carbonyl)piperazin-1-yl]pyridine-3-carbonitrile (120 mg, 0.18 mmol, 1 equiv), TFA (0.8 mL) in DCM (8 mL) was stirred for 1 h at room temperature. After concentration, the residue was purified by C18 reverse phase chromatography eluting with H₂O/CH₃CN. Then the residue was further purified by Prep-HPLC yielding the title compound (35.0 mg, 36.3%) as a white solid. LCMS (ESI, m/z): 532.52 [M+H]+, 1HNMR (300 MHz, DMSO-d₆) δ: 12.36 (s, 1H), 8.50 (d, J=2.2 Hz, 1H), 8.06 (s, 1H), 7.92-7.82 (m, 1H), 6.91 (d, J=9.2 Hz, 1H), 4.58 (s, 1H), 4.25 (s, 1H), 4.05 (d, J=8.2 Hz, 2H), 3.64-3.44 (m, 10H), 3.32-3.15 (m, 4H), 2.36-2.11 (m, 1H), 1.91 (s, 1H), 1.67 (m, 2H).

Example 126: 4-(5-cyanopyridin-2-yl)-N-(2-[[(2S)-1-[6-oxo-5-(trifluoromethyl)-1,6-dihydropyridazin-4-yl]pyrrolidin-2-yl]methoxy]ethyl)piperazine-1-carboxamide

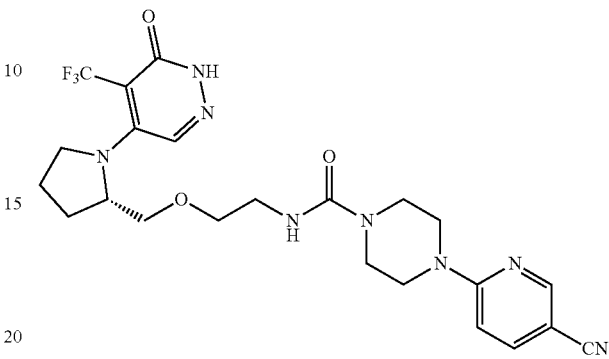

Step 1: Synthesis of 5-[(2S)-2-[(2-hydroxyethoxy)methyl]pyrrolidin-1-yl]-4-(trifluoromethyl)-2-[[2-(trimethylsilyl)ethoxy]methyl]-2,3-dihydropyridazin-3-one A solution of [(2S)-1-[6-oxo-5-(trifluoromethyl)-1-[[2-(trimethylsilyl)ethoxy]methyl]-1,6-dihydropyridazin-4-yl]pyrrolidin-2-yl]methyl methanesulfonate (900 mg, 1.91 mmol, 1.00 equiv), and Cs₂CO₃ (1.868 g, 5.73 mmol, 3.00 equiv) in ethane-1,2-diol (20 mL) was stirred for 6 h at 80° C. The reaction was quenched by the addition 150 ml of water and extracted with 300 mL of EtOAc, the organic layers combined and concentrated under vacuum. The residue was applied onto a silica gel column with EtOAc/petroleum ether (1/1) to afford 400 mg (48%) of the title compound as yellow oil. LCMS (ESI, m/z): 438.53 [M+H]+

Step 2: Synthesis of 5-[(2S)-2-[(2-azidoethoxy)methyl]pyrrolidin-1-yl]-4-(trifluoromethyl)-2-[[2-(trimethylsilyl)ethoxy]methyl]-2,3-dihydropyridazin-3-one A solution of 5-[(2S)-2-[(2-hydroxyethoxy)methyl]pyrrolidin-1-yl]-4-(trifluoromethyl)-2-[[2-(trimethylsilyl)ethoxy]methyl]-2,3-dihydropyridazin-3-one (400 mg, 0.91 mmol, 1.00 equiv), DBU (278 mg, 1.83 mmol, 3.00 equiv), and DPPA (502 mg, 1.82 mmol, 2.00 equiv) in toluene (5 mL) was stirred for 5 h at 80° C. After added EtOAc 300 mL to the resulting solution, the resulting mixture was washed with 2×100 mL of sodium carbonate and concentrated under vacuum. The residue was applied onto a silica gel column with EtOAc/petroleum ether (3/7) to afford 320 mg (76%) of the title compound as yellow oil. LCMS (ESI, m/z): 463.54 [M+H]+

Step 3: Synthesis of 5-[(2S)-2-[(2-aminoethoxy)methyl]pyrrolidin-1-yl]-4-(trifluoromethyl)-2-[[2-(trimethylsilyl)ethoxy]methyl]-2,3-dihydropyridazin-3-one A solution of 5-[(2S)-2-[(2-azidoethoxy)methyl]pyrrolidin-1-yl]-4-(trifluoromethyl)-2-[[2-(trimethylsilyl)ethoxy]methyl]-2,3-dihydropyridazin-3-one (320 mg, 0.69 mmol, 1.00 equiv), and Palladium carbon (80 mg) in methanol (20 mL) was stirred 5 h at 60° C. under the atmosphere of Hydrogen. The solids were filtered out. The resulting mixture was concentrated under vacuum to afford 260 mg (86%) of the title compound as green solids. LCMS (ESI, m/z): 437.54 [M+H]⁺

Step 4: Synthesis of 4-nitrophenyl 4-(5-cyanopyridin-2-yl)piperazine-1-carboxylate A solution of Int-A4 (1 g, 3.83 mmol, 1.00 equiv), TEA (1.36 g, 13.44 mmol, 3.50 equiv), and 4-nitrophenyl carbonochloridate (773 mg, 3.84 mmol, 1.00 equiv) in DCM (50 mL) was stirred 1 h at 25° C. Then added 5 mL EA. The solids were collected by filtration to afford 1 g (74%) of the title compound as light yellow solids. LCMS (ESI, m/z): 354.33 [M+H]⁺.

Step 5: Synthesis of 4-(5-cyanopyridin-2-yl)-N-(2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]ethyl)piperazine-1-carboxamide A solution of 5-[(2S)-2-[(2-aminoethoxy)methyl]pyrrolidin-1-yl]-4-(trifluoromethyl)-2-[[2-(trimethylsilyl)ethoxy]methyl]-2,3-dihydropyridazin-3-one (250 mg, 0.57 mmol, 1.00 equiv), potassium carbonate (237 mg, 1.71 mmol, 3.00 equiv), and 4-nitrophenyl 4-(5-cyanopyridin-2-yl)piperazine-1-carboxylate (364 mg, 1.03 mmol, 1.80 equiv) in DMF (4 mL) was stirred 5 h at 80° C. The reaction mixture was diluted with H₂O (200 mL). The resulting solution was extracted with EtOAc 3×150 mL, then the organic layers was combined and concentrated under vacuum. The residue was applied onto a silica gel column with EtOAc to afford 322 mg (86%) of the title compound as colorless oil. LCMS (ESI, m/z): 651.77 [M+H]⁺

Step 6: Synthesis of 4-(5-cyanopyridin-2-yl)-N-(2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]ethyl)piperazine-1-carboxamide A solution of 4-(5-cyanopyridin-2-yl)-N-(2-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]ethyl)piperazine-1-carboxamide (300 mg, 0.46 mmol, 1.00 equiv), and TFA/DCM (12 mL) in DCM (10 mL) was stirred 1 h at 25° C. The pH value of the solution was adjusted to 8 with NH3/CH3OH. After concentration, the residue was purified by C18 reverse phase chromatography eluting with H₂O/CH₃CN yielding the title compound 88.2 mg (37%) as a white solid. LCMS (ESI, m/z): 521.2 [M+H]⁺, ¹H NMR (400 MHz, Methanol-d₄) δ 8.43-8.42 (d, J=1.6, 1H), 8.18 (s, 1H), 7.79-7.75 (m, 1H), 7.21-6.86 (m, 1H), 4.62-4.59 (d, 1H), 3.79-3.71 (m, 4H), 3.66-3.64 (m, 2H), 3.60-3.42 (m, 8H), 3.43-3.26 (m, 2H), 2.26-2.23 (t, J=6.4 Hz, 1H), 2.01-1.99 (t, J=5.4 Hz, 1H), 1.74-1.70 (m, 2H).

Example 127: 4-(5-cyanopyridin-2-yl)-N-(2-[[(2S)-1-[6-oxo-5-(trifluoromethyl)-1,6-dihydropyridazin-4-yl]pyrrolidin-2-yl]methoxy]ethyl)piperazine-1-carboxamide

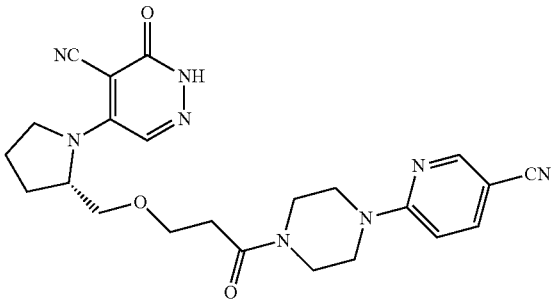 [SMILES: N#Cc1ccc(N2CCN(C(=O)CCOC[C@@H]3CCCN3c3cn[nH]c(=O)c3C#N)CC2)nc1]

Step 1: Synthesis of 4-bromo-5-[(2S)-2-(hydroxymethyl)pyrrolidin-1-yl]-2-[[2-(trimethylsilyl)ethoxy]methyl]-2,3-dihydropyridazin-3-one A solution of Int-A8 (5.6 g, 14.58 mmol, 1.00 equiv), TEA (2.95 g, 29.15 mmol, 2.00 equiv), and [(2S)-pyrrolidin-2-yl]methanol (1.47 g, 14.53 mmol, 1.00 equiv) in ethanol (200 mL) was stirred for 1 h at 80° C. The resulting solution was extracted with EtOAc 3×50 mL. Then the organic layers was combined and concentrated under vacuum to afford 5 g (85%) of the title compound as yellow solids. LCMS (ESI, m/z): 405.37 [M+H]⁺

Step 2: Synthesis of 5-[(2S)-2-(hydroxymethyl)pyrrolidin-1-yl]-3-oxo-2-[[2-(trimethylsilyl)ethoxy]methyl]-2,3-dihydropyridazine-4-carbonitrile A solution of 4-bromo-5-[(2S)-2-(hydroxymethyl)pyrrolidin-1-yl]-2-[[2-(trimethylsilyl)ethoxy]methyl]-2,3-dihydropyridazin-3-one (2 g, 4.95 mmol, 1.00 equiv), and CuCN (1.3 g, 3.00 equiv) in NMP (10 mL) was stirred for 2 h at 120° C. The resulting solution was extracted with 3×30 mL of ether and the organic layers combined. The residue was applied onto a silica gel column with EtOAc/petroleum ether (1/O) to afford 680 mg (39%) of the title compound as white solids. LCMS (ESI, m/z): 351.49 [M+H]⁺

Step 3: Synthesis of 3-[[2-(5-cyano-6-oxo-1-[[2-(trimethylsilyl)ethoxy]methyl]-1,6-dihydropyridazin-4-yl)-2,3-dihydro-1H-isoindol-1-yl]methoxy]propanoate A solution of 5-[1-(hydroxymethyl)-2,3-dihydro-1H-isoindol-2-yl]-3-oxo-2-[[2-(trimethylsilyl)ethoxy]methyl]-2,3-dihydropyridazine-4-carbonitrile (360 mg, 0.90 mmol, 1.00 equiv), Cs₂CO₃ (368 mg, 1.13 mmol, 1.10 equiv), and tert-butyl prop-2-enoate (659 mg, 5.14 mmol, 5.00 equiv) in CH₃CN (20 mL) was stirred 2 days at 40° C. The residue was applied onto a silica gel column with EtOAc/petroleum ether (1/2) to afford 130 mg (27%) of the title compound as white solids. LCMS (ESI, m/z): 479.66 [M+H]⁺

Step 4: Synthesis of 3-[[(2S)-1-(5-cyano-6-oxo-1,6-dihydropyridazin-4-yl)pyrrolidin-2-yl]methoxy]propanoic Acid A solution of tert-butyl 3-[[(2S)-1-(5-cyano-6-oxo-1-[[2-(trimethylsilyl)ethoxy]methyl]-1,6-dihydropyridazin-4-yl)

pyrrolidin-2-yl]methoxy]propanoate (130 mg, 0.27 mmol, 1.00 equiv), in hydrogen chloride/dioxane (20 mL) was stirred for 1 h at 25° C. The crude product was purified by C18 reverse phase chromatography eluting with H$_2$O/CH$_3$CN (1/1) to afford 70 mg (88%) of the title compound as white solids. LCMS (ESI, m/z): 293.29 [M+H]$^+$.

Step 5: Synthesis of 5-[(2S)-2-([3-[4-(5-cyanopyridin-2-yl)piperazin-1-yl]-3-oxopropoxy]methyl)pyrrolidin-1-yl]-3-oxo-2,3-dihydropyridazine-4-carbonitrile A solution of 3-[[(2S)-1-(5-cyano-6-oxo-1,6-dihydropyridazin-4-yl)pyrrolidin-2-yl]methoxy]propanoic acid (60 mg, 0.21 mmol, 1.00 equiv), HATU (80 mg, 0.21 mmol, 1.00 equiv), DIEA (108 mg, 0.84 mmol, 4.00 equiv), and Int-A4 (55 mg, 0.21 mmol, 1.00 equiv) in DMF (2 mL) was stirred for 1 h at 25° C. The crude product was purified by C18 reverse phase chromatography eluting with H$_2$O/CH3CN yielding the title compound 18.7 mg (20%) as white solids. LCMS (ESI, m/z): 463.19 [M+H]$^+$, $^1$H NMR (Methanol-d$_4$, 400 MHz) δ: 8.42 (dd, J=2.4, 0.8 Hz, 1H), 7.89 (s, 1H), 7.76 (dd, J=9.1, 2.4 Hz, 1H), 6.86 (dd, J=9.1, 0.8 Hz, 1H), 4.70 (dr, 1H), 4.03 (dr, 1H), 3.78-3.58 (dd, J=6.3, 4.9 Hz, 13H), 2.67-2.63 (t, J=5.8 Hz, 2H), 2.17-1.95 (m, 4H).

Example 128: 6-[4-[(3R)-methyl-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile and 6-[4-[(3S)-methyl-4-[[(2S)-1-[6-oxo-5-(trifluoromethyl)-1,6-dihydropyridazin-4-yl]pyrrolidin-2-yl]methoxy]butanoyl]-piperazin-1-yl]pyridine-3-carbonitrile

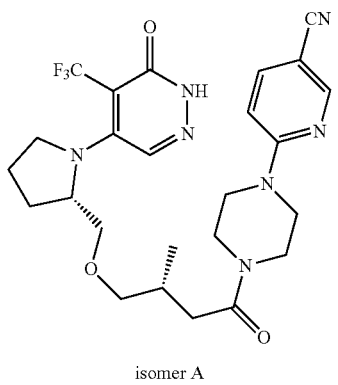

isomer A

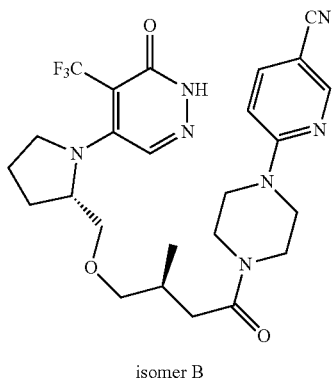

isomer B

Step 1: Synthesis of Methyl (2E)-4-bromo-3-methylbut-2-enoate

A solution of methyl 3-methylbut-2-enoate (5 g, 43.80 mmol, 1.00 equiv), NBS (8.5 g, 47.76 mmol, 1.09 equiv) and BPO (1.1 g, 4.29 mmol, 0.10 equiv) in CCl$_4$ (200 mL) was stirred overnight at 80° C. The resulting mixture was concentrated under vacuum. The residue was applied onto a silica gel column with EtOAc/petroleum ether (1:10). This resulted in 6 g (71%) of the title compound as an oil. GCMS (m/z): 190.

Step 2: Synthesis of (2E)-3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1.6 g, 4.07 mmol, 1.00 equiv), methyl (2E)-4-bromo-3-methylbut-2-enoate (870 mg, 4.51 mmol, 1.11 equiv), Rockphos (574 mg), Cs$_2$CO$_3$ (2.7 g, 8.29 mmol, 2.04 equiv) and Pd$_2$(dba)$_3$-CHCl$_3$ (870 mg) in dioxane (30 mL) was stirred for 20 h at 100° C. under an inert atmosphere of nitrogen. The resulting solution was diluted with 200 mL of EtOAc. The resulting mixture was washed with 2×50 mL of water and 1×50 mL of Brine. The organic layer was dried over anhydrous sodium sulfate and concentrated under vacuum. The residue was applied onto a silica gel column with EtOAc/petroleum ether (1:2). This resulted in 1.3 g (crude) of the title compound as oil. LCMS (ESI, m/z): 506.23 [M+H]$^+$ Step 3: Synthesis of 3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate A solution of methyl (2E)-3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate (1.3 g, 2.57 mmol, 1.00 equiv) and palladium carbon (200 mg) in DCM (30 mL) and methanol (30 mL) was stirred for 2 h at room temperature under an inert atmosphere of hydrogen. The solids were filtered out. The resulting mixture was concentrated under vacuum. The residue was applied onto a silica gel column with EtOAc/petroleum ether (1:2). This resulted in 1 g (crude) of the title compound as a solid. LCMS (ESI, m/z): 508.24 [M+H]$^+$.

Step 4: Synthesis of 3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoic Acid To a stirred solution of methyl 3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate (330 mg, 0.65 mmol, 1.00 equiv) in THF (6 mL) and water (2 mL), LiOH.H$_2$O (100 mg, 2.38 mmol, 3.67 equiv) was added. The resulting solution was stirred for 5 h at room temperature. The pH value of the solution was adjusted to 1 with hydrogen chloride (1 M M). The resulting solution was diluted with 200 mL of EtOAc. The resulting mixture was washed with 2×50 mL of Brine. The organic layer was dried over anhydrous sodium sulfate and concentrated under vacuum. This resulted in 300 mg (crude) of the title compound as an oil. LCMS (ESI, m/z): 494.23 [M+H]$^+$.

Step 5: Synthesis of 3-methyl-4-[[(2S)-1-[6-oxo-5-(trifluoromethyl)-1,6-dihydropyridazin-4-yl]pyrrolidin-2-yl]methoxy]butanoic Acid A solution of 3-methyl-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoic acid (300 mg, 0.61 mmol, 1.00 equiv) in hydrogen chloride/dioxane (10 mL) was stirred overnight at room temperature. The resulting mixture was concentrated under vacuum. This resulted in 200 mg (crude) of the title compound as a solid. LCMS (ESI, m/z): 364.15 [M+H]$^+$.

Step 6: Synthesis of 6-[4-[(3R)-methyl-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile and 6-[4-[(3S)-methyl-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile To a stirred solution of 3-methyl-4-[[(2S)-1-[6-oxo-5-(trifluoromethyl)-1,6-dihydropyridazin-4-yl]pyrrolidin-2-yl]methoxy]butanoic acid (200 mg, 0.55 mmol, 1.00 equiv) in DMF (10 mL), Int-A4 (125 mg, 0.66 mmol, 1.21 equiv), DIPEA (0.5 mL) and HATU (280 mg, 0.74 mmol, 1.34 equiv) was added. The resulting solution was stirred for 2 h at room temperature. After concentration, the residue was purified by C18 reverse phase chromatography eluting with H$_2$O/CH$_3$CN. Then the residue was further purified by Prep-HPLC and Chiral-Prep-HPLC yielding (after arbitrary assignment of the stereochemistry) the title compounds, respectively, isomer A (47.7 mg, 73%) as a white solid. LCMS (ESI, m/z): 534.35 [M+H]$^+$. $^1$H NMR (400 MHz, Methanol-d$_4$) δ 8.45 (dd, J=2.3, 0.8 Hz, 1H), 8.22 (s, 1H), 7.78 (dd, J=9.1, 2.4 Hz, 1H), 6.90 (dd, J=9.1, 0.8 Hz, 1H), 4.73-4.63 (m, 1H), 3.78-3.62 (m, 8H), 3.59-3.53 (m, 2H), 3.43-3.35 (m, 4H), 2.45 (q, J=8.8 Hz, 1H), 2.29-2.13 (m, 3H), 2.07-1.97 (m, 1H), 1.83-1.61 (m, 2H), 0.95 (d, J=6.4 Hz, 3H). Rt=4.919 min (CHIRALPAK IG-3, 0.46*10 cm; 3 um, MtBE (0.1% DEA):MeOH=90:10, 1.0 ml/min) and isomer B (41.3 mg, 64%) as a white solid. LCMS (ESI, m/z): 534.15 [M+H]$^+$. $^1$H NMR (400 MHz, Methanol-d$_4$) δ 8.45 (dd, J=2.3, 0.8 Hz, 1H), 8.20 (s, 1H), 7.78 (dd, J=9.1, 2.3 Hz, 1H), 6.89 (dd, J=9.1, 0.8 Hz, 1H), 4.68 (qd, J=7.9, 2.7 Hz, 1H), 3.79-3.65 (m, 8H), 3.64-3.57 (m, 2H), 3.46 (dd, J=9.1, 4.2 Hz, 1H), 3.43-3.34 (m, 2H), 3.25 (dd, J=9.2, 6.0 Hz, 1H), 2.47 (q, J=9.0 Hz, 1H), 2.29-2.14 (m, 3H), 2.06-1.98 (m, 1H), 1.83-1.62 (m, 2H), 0.90 (d, J=6.3 Hz, 3H). Rt=6.472 min (CHIRALPAK IG-3, 0.46*10 cm; 3 um, MtBE (0.1% DEA):MeOH=90:10, 1.0 ml/min).

Example 129: 6-[4-[(3R)-3-[[(2S)-1-[6-oxo-5-(trifluoromethyl)-1,6-dihydropyridazin-4-yl]pyrrolidin-2-yl]methoxy]pyrrolidine-1-carbonyl]piperazin-1-yl]pyridine-3-carbonitrile and 6-[4-[(3S)-3-[[(2S)-1-[6-oxo-5-(trifluoromethyl)-1,6-dihydropyridazin-4-yl]pyrrolidin-2-yl]methoxy]pyrrolidine-1-carbonyl]piperazin-1-yl]pyridine-3-carbonitrile

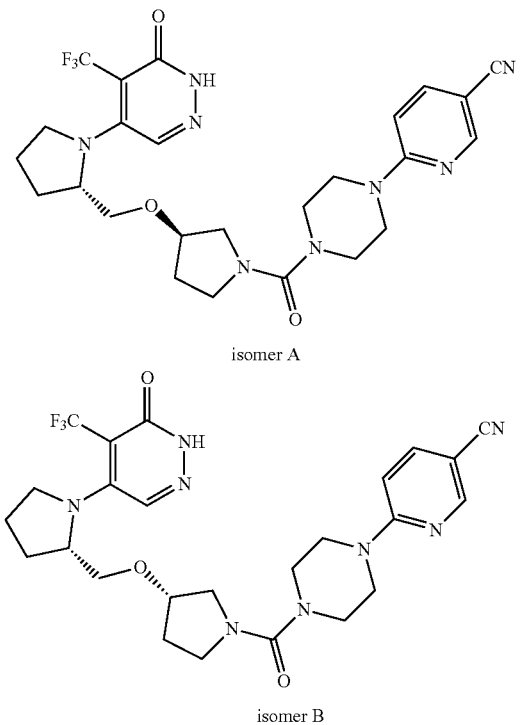

isomer A isomer B

Step 1: Synthesis of 4-nitrophenyl 4-(5-cyanopyridin-2-yl)piperazine-1-carboxylate A solution of Int-A4 (500 mg, 2.23 mmol, 1.00 equiv) and TEA (676 mg, 6.68 mmol, 3.00 equiv) in DCM (10 mL), then 4-nitrophenyl carbonochloridate (450 mg, 2.23 mmol, 1.00 equiv) was added in, then the resulting solution was stirred for 1 h at room temperature, and then the resulting solution was diluted with 10 mL of Water, extracted with 2×10 mL of DCM and the organic layers were combined, washed with 1×10 mL of brine, dried over anhydrous sodium sulfate and concentrated under vacuum, and then the residue was applied onto a silica gel column eluting with EtOAc/petroleum ether to afford 520 mg (66%) of the title compound as a yellow solid. LCMS (ESI, m/z): 354.11 [M+H]$^+$.

Step 2: Synthesis of 6-[4-(3-hydroxypyrrolidine-1-carbonyl)piperazin-1-yl]pyridine-3-carbonitrile A solution of pyrrolidin-3-ol hydrochloride (175 mg, 1.42 mmol, 1.00 equiv), 4-nitrophenyl 4-(5-cyanopyridin-2-yl)piperazine-1-carboxylate (500 mg, 1.42 mmol, 1.00 equiv) and potassium carbonate (390 mg, 2.82 mmol, 2.00 equiv) in DMF (5 mL) was stirred for 2 h at 80° C., and then the resulting solution was diluted with 15 mL of water, extracted with 3×15 mL of EtOAc and the organic layers were combined, washed with 1×15 mL of brine, dried over anhydrous sodium sulfate and concentrated under vacuum, and then the residue was applied onto a silica gel column eluting with EtOAc/petroleum ether to afford 280 mg (66%) of the title compound as a yellow solid. LCMS (ESI, m/z): 302.15 [M+H]$^+$.

Step 3: Synthesis of Tert-Butyl (2S)-2-[([1-[4-(5-cyanopyridin-2-yl)piperazine-1-carbonyl]pyrrolidin-3-yl]oxy)methyl]pyrrolidine-1-carboxylate A solution of 6-[4-(3-hydroxypyrrolidine-1-carbonyl)piperazin-1-yl]pyridine-3-carbonitrile (400 mg, 1.33 mmol, 1.00 equiv) in DMF (8 mL), and then sodium hydride (159 mg, 6.62 mmol, 3.00 equiv) was added in, then the resulting solution was stirred for 15 min at room temperature, and then tert-butyl (2S)-2-[(methanesulfonyloxy)methyl]pyrrolidine-1-carboxylate (556 mg, 1.99 mmol, 1.50 equiv) was added in, the resulting solution was stirred for 12 h at 80° C. in an oil bath, then the resulting solution was quenched by the addition of 15 mL of water, extracted with 3×15 mL of EtOAc and the organic layers were combined, washed with 1×15 mL of brine and dried over anhydrous sodium sulfate and concentrated under vacuum, and then the residue was applied onto a silica gel column eluting with EtOAc to afford 85 mg (13%) of the title compound as a light yellow solid. LCMS (ESI, m/z): 485.28 [M+H]$^+$ Step 4: Synthesis of 6-[4-(3-[[(2S)-pyrrolidin-2-yl]methoxy]pyrrolidine-1-carbonyl)piperazin-1-yl]pyridine-3-carbonitrile A solution of tert-butyl (2S)-2-[([1-[4-(5-cyanopyridin-2-yl)piperazine-1-carbonyl]pyrrolidin-3-yl]oxy)methyl]pyrrolidine-1-carboxylate (85 mg, 0.18 mmol, 1.00 equiv) and TFA (0.2 mL) in DCM (1.0 mL) was stirred for 1 h at room temperature, and then the resulting solution was concentrated under vacuum to afford 56 mg of the title compound as crude yellow oil. LCMS (ESI, m/z): 385.23 [M+H]$^+$.

Step 5: Synthesis of 6-[4-(3-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]pyrrolidine-1-carbonyl)piperazin-1-yl]pyridine-3-carbonitrile A solution of Int-A6 (47.7 mg, 0.15 mmol, 1.00 equiv), 6-[4-(3-[[(2S)-pyrrolidin-2-yl]methoxy]pyrrolidine-1-carbonyl)piperazin-1-yl]pyridine-3-carbonitrile (50 mg, 0.13 mmol, 1.00 equiv) and TEA (51.7 mg, 0.51 mmol, 3.00 equiv) in ethanol (5 mL) was stirred for 1 h at 60° C., and then the resulting solution was concentrated under vacuum, and then the residue was applied onto a silica gel column eluting with DCM/methanol (15:1) to afford 89 mg (91%) of the title compound as a light yellow solid. LCMS (ESI, m/z): 677.31 [M+H]+.

Step 6: Synthesis of 6-[4-[(3R)-3-[[(2S)-1-[6-oxo-5-(trifluoromethyl)-1,6-dihydropyridazin-4-yl]pyrrolidin-2-yl]methoxy]pyrrolidine-1-carbonyl]piperazin-1-yl]pyridine-3-carbonitrile and 6-[4-[(3S)-3-[[(2S)-1-[6-oxo-5-(trifluoromethyl)-1,6-dihydropyridazin-4-yl]pyrrolidin-2-yl]methoxy]pyrrolidine-1-carbonyl]piperazin-1-yl]pyridine-3-carbonitrile A solution of 6-[4-(3-[[(2S)-1-[6-oxo-5-(trifluoromethyl)-1-[[2-(trimethyl silyl)ethoxy]methyl]-1,6-dihydropyridazin-4-yl]pyrrolidin-2-yl]methoxy]pyrrolidine-1-carbonyl)piperazin-1-yl]pyridine-3-carbonitrile (85 mg, 0.13 mmol, 1 equiv) and TFA (1 mL) in DCM (5 mL) was stirred for 2 h at room temperature, and then the resulting solution was concentrated under vacuum and then the residue was purified by Prep-HPLC yielding (after arbitrary assignment of the stereochemistry), the title compounds, respectively, isomer A (14.1 mg, 20.5%) as a white solid. LCMS (ESI, m/z): 547.15 [M+H]$^+$, $^1$HNMR (Methanol-d4, 300 MHz): δ 8.43 (d, J=2.3 Hz, 1H), 8.16 (s, 1H), 7.78 (dd, J=9.1, 2.4 Hz, 1H), 6.89 (d, J=9.6 Hz, 1H), 4.67-4.61 (m, 1H), 4.07 (s, 1H), 3.80-3.65 (m, 6H), 3.57-3.35 (m, 7H), 3.33-3.26 (m, 3H), 2.27 (d, J=7.7 Hz, 1H), 2.03-1.82 (m, 3H), 1.81-1.56 (m, 2H); tR=3.580 min (CHIRALPAK AS-3, 0.46*100 mm; 3 um, EtOH (0.1% DEA), 4.0 mL/min) and isomer B (9.7 mg, 14.1%) as a white solid. LCMS (ESI, m/z): 547.15 [M+H]$^+$, $^1$HNMR (Methanol-d4, 300 MHz): δ 8.43 (d, J=2.4, 1H), 8.15 (s, 1H), 7.78 (dd, J=9.1, 2.4 Hz, 1H), 6.90 (d, J=9.0 Hz, 1H), 4.65-4.61 (m, 1H), 4.09 (s, 1H), 3.81-3.66 (m, 6H), 3.57 (dd, J=12.0, 4.2 Hz, 1H), 3.47-3.34 (m, 6H), 3.31-3.24 (m, 3H), 2.26 (dt, J=13.8, 6.7 Hz, 1H), 2.06-1.97 (m, 2H), 1.93-1.55 (m, 3H). tR=2.821 min (CHIRALPAK IA, 0.46*55 cm; 5 um, EtOH (0.1% DEA), 4.0 mL/min).

Example 130: 6-[4-[3-([1-[6-oxo-5-(trifluoromethyl)-1,6-dihydropyridazin-4-yl]piperidin-2-yl]methoxy)propanoyl]piperazin-1-yl]pyridine-3-carbonitrile

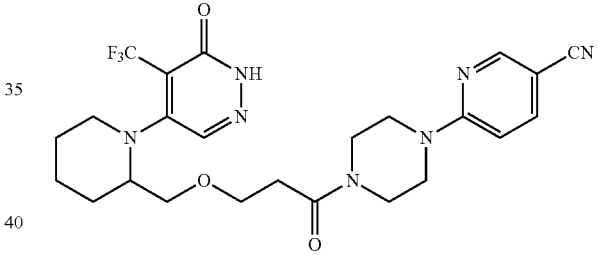

Step 1: Synthesis of 4-bromo-5-[2-(hydroxymethyl)piperidin-1-yl]-2-[[2-(trimethylsilyl)ethoxy]methyl]-2,3-dihydropyridazin-3-one A solution of (piperidin-2-yl)methanol (2 g, 17.3 mmol, 1.00 equiv), DIEA (9 g, 69.6 mmol, 4.00 equiv), Int-A8 (6.6 g, 17.2 mmol, 1.00 equiv) in IPA (30 mL) was stirred for 12 h at 100° C. The solvent was concentrated under vacuum and the residue was applied onto a silica gel column eluting with EtOAc/petroleum ether (1:2) to afford 4.17 g (58%) of the title compound as a solid. LCMS (ESI, m/z): 418.12 [M+H]+

Step 2: Synthesis of Methyl 3-[[1-(5-bromo-6-oxo-1-[[2-(trimethylsilyl)ethoxy]methyl]-1,6-dihydropyridazin-4-yl)piperidin-2-yl]methoxy]propanoate A solution of 4-bromo-5-[2-(hydroxymethyl)piperidin-1-yl]-2-[[2-(trimethylsilyl)ethoxy]methyl]-2,3-dihydropyridazin-3-one (830 mg, 2.00 mmol, 1.00 equiv), Cs$_2$CO$_3$ (1300 mg, 4 mmol, 2.00 equiv), methyl prop-2-enoate (720 mg, 8.00 mmol, 4.00 equiv) in DMF (15 mL) was stirred for 16 h at room temperature. The resulting solution was quenched with 60 ml H$_2$O, then the solution was extracted with EtOAc (3×60 mL) and the organic layers combined. The solution was dried over anhydrous sodium sulfate and concentrated under vacuum. The residue was applied onto a silica gel column eluting with EtOAc/petroleum ether (20:80) to afford 800 mg (95%) of the title compound as a solid. LCMS (ESI, m/z): 504.16 [M+H]+

Step 3: Synthesis of Methyl 3-([1-[6-oxo-5-(trifluoromethyl)-1-[[2-(trimethylsilyl)ethoxy]methyl]-1,6-dihydropyridazin-4-yl]piperidin-2-yl]methoxy)propanoate A solution of methyl 3-[[1-(5-bromo-6-oxo-1-[[2-(trimethylsilyl)ethoxy]methyl]-1,6-dihydropyridazin-4-yl)piperidin-2-yl]methoxy]propanoate (750 mg, 1.49 mmol, 1.00 equiv), CuI (30 mg, 0.16 mmol, 0.10 equiv), ethyl 2,2-difluoro-2-sulfoacetate (1.5 g, 7.28 mmol, 5.00 equiv) in DMF (10 mL) was stirred for 5 h at 80° C. The resulting solution was quenched with 30 ml H₂O, then the solution was extracted with EtOAc (3×30 mL) and the organic layers combined. The solution was dried over anhydrous sodium sulfate and concentrated under vacuum. The residue was applied onto a silica gel column eluting with EtOAc/petroleum ether (30:70) to afford 750 mg (80%) of the title compound as a solid. LCMS (ESI, m/z): 494.23 [M+H]+.

Step 4: Synthesis of 3-([1-[6-oxo-5-(trifluoromethyl)-1-[[2-(trimethylsilyl)ethoxy]methyl]-1,6-dihydropyridazin-4-yl]piperidin-2-yl]methoxy)propanoic Acid A solution of methyl 3-([1-[6-oxo-5-(trifluoromethyl)-1-[[2-(trimethylsilyl)ethoxy]methyl]-1,6-dihydropyridazin-4-yl]piperidin-2-yl]methoxy)propanoate (750 mg, 1.52 mmol, 1.00 equiv), water (2 mL), LiOH (180 mg, 7.52 mmol, 5.00 equiv) in THF (10 mL) was stirred for 2h at room temperature. After concentration, the residue was purified by C18 reverse phase chromatography eluting with H₂O/CH₃CN to afford 500 mg (66%) of the title compound as a solid. LCMS (ESI, m/z): 480.23 [M+H]+

Step 5: Synthesis of 6-[4-[3-([1-[6-oxo-5-(trifluoromethyl)-1-[[2-(trimethylsilyl)ethoxy]methyl]-1,6-dihydropyridazin-4-yl]piperidin-2-yl]methoxy)propanoyl]piperazin-1-yl]pyridine-3-carbonitrile A solution of 3-([1-[6-oxo-5-(trifluoromethyl)-1-[[2-(trimethylsilyl)ethoxy]methyl]-1,6-dihydropyridazin-4-yl]piperidin-2-yl]methoxy)propanoic acid (500 mg, 1.04 mmol, 1.00 equiv), HATU (520 mg, 1.37 mmol, 1.30 equiv), DIEA (270 mg, 2.09 mmol, 2.00 equiv), Int-A4 (200 mg, 1.06 mmol, 1.00 equiv) in DMF (3 mL) was stirred for 1 h at room temperature. The resulting solution was quenched with of 20 ml H₂O, then the solution was extracted with EtOAc (3×30 mL) and the organic layers combined. The solution was dried over anhydrous sodium sulfate and concentrated under vacuum. The residue was applied onto a silica gel column eluting with EtOAc/petroleum ether (1:1) to afford 550 mg (81%) of the title compound as a solid LCMS (ESI, m/z): 650.31 [M+H]+

Step 6: Synthesis of 6-[4-[3-([1-[6-oxo-5-(trifluoromethyl)-1,6-dihydropyridazin-4-yl]piperidin-2-yl]methoxy)propanoyl]piperazin-1-yl]pyridine-3-carbonitrile A solution of 6-[4-[3-([1-[6-oxo-5-(trifluoromethyl)-1-[[2-(trimethylsilyl)ethoxy]methyl]-1,6-dihydropyridazin-4-yl]piperidin-2-yl]methoxy)propanoyl]piperazin-1-yl]pyridine-3-carbonitrile (550 mg, 0.85 mmol, 1.00 equiv), TFA (2 mL) in DCM (10 mL) was stirred for 1 h at room temperature. After concentration, the residue was purified by C18 reverse phase chromatography eluting with H₂O/CH₃CN. Then the residue was further purified by Prep-HPLC yielding the title compound (57.0 mg, 13.1%) as a white solid. LCMS (ESI, m/z): 520.30 [M+H]+, ¹HNMR (DMSO-d6, 300 MHz) δ: 12.53 (s, 1H), 8.51 (d, J=1.8 Hz, 1H), 7.92-7.87 (m, 2H), 6.93 (d, J=9.0 Hz, 1H), 3.96 (s, 1H), 3.79 (t, J=2.1 Hz, 1H), 3.66-3.42 (m, 12H), 3.24-3.20 (m, 1H), 2.49-2.43 (m, 2H), 1.84-1.73 (m, 3H), 1.71-1.52 (m, 3H).

Example 131: 6-(4-(3-((1-(5-bromo-6-oxo-1,6-dihydropyridazin-4-yl)piperidin-2-yl)methoxy)propanoyl)piperazin-1-yl)nicotinonitrile

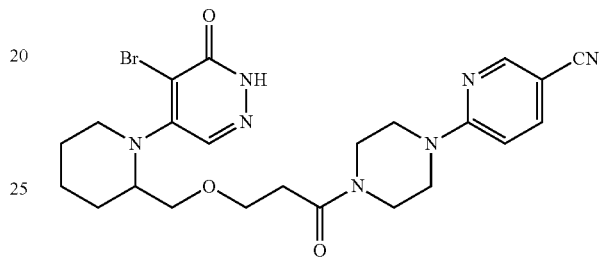

Step 1: 3-((1-(5-bromo-6-oxo-1-((2-(trimethylsilyl)ethoxy)methyl)-1,6-dihydropyridazin-4-yl)piperidin-2-yl)methoxy)propanoic Acid A solution of methyl 3-((1-(5-bromo-6-oxo-1-((2-(trimethylsilyl)ethoxy)methyl)-1,6-dihydropyridazin-4-yl)piperidin-2-yl)methoxy)propanoate (503 mg, 1.00 mmol, 1.00 equiv), water (2 mL), LiOH (120 mg, 5.00 mmol, 5.00 equiv) in THF (10 mL) was stirred for 2h at room temperature. After concentration, the residue was purified by C18 reverse phase chromatography eluting with H₂O/CH₃CN to afford 395 mg (81%) of the title compound as a solid. LCMS (ESI, m/z): 490.14 [M+H]+.

Step 2: 6-(4-(3-((1-(5-bromo-6-oxo-1-((2-(trimethylsilyl)ethoxy)methyl)-1,6-dihydropyridazin-4-yl)piperidin-2-yl)methoxy)propanoyl)piperazin-1-yl)nicotinonitrile A solution of 3-((1-(5-bromo-6-oxo-1-((2-(trimethylsilyl)ethoxy)methyl)-1,6-dihydropyridazin-4-yl)piperidin-2-yl)methoxy)propanoic acid (395 mg, 0.80 mmol, 1.00 equiv), HATU (365 mg, 0.96 mmol, 1.20 equiv), DIEA (230 mg, 1.60 mmol, 2.00 equiv), Int-A4 (150 mg, 0.80 mmol, 1.00 equiv) in DMF (3 mL) was stirred for 1 h at room temperature. The resulting solution was quenched with of 20 ml H₂O, then the solution was extracted with EtOAc (3×30 mL) and the organic layers combined. The solution was dried over anhydrous sodium sulfate and concentrated under vacuum. The residue was applied onto a silica gel column eluting with EtOAc/petroleum ether (1:1) to afford 417 mg (79%) of the title compound as a solid LCMS (ESI, m/z): 660.24 [M+H]+.

Step 3: 6-(4-(3-((1-(5-bromo-6-oxo-1,6-dihydropyridazin-4-yl)piperidin-2-yl)methoxy)propanoyl)piperazin-1-yl)nicotinonitrile A solution of 6-(4-(3-((1-(5-bromo-6-oxo-1-((2-(trimethylsilyl)ethoxy)methyl)-1,6-dihydropyridazin-4-yl)piperidin-2-yl)methoxy)propanoyl)piperazin-1-yl)nicotinonitrile (417 mg, 0.63 mmol, 1.00 equiv), TFA (2 mL) in DCM (10 mL) was stirred for 1 h at room temperature. After concentration, the residue was purified by C18 reverse phase chromatography eluting with $H_2O/CH_3CN$. Then the residue was further purified by Prep-HPLC yielding the title compound (32.5 mg, 30.1%) as a white solid. LCMS (ESI, m/z): 532.25 [M+H]+, $^1$HNMR (DMSO-$d_6$, 300 MHz) δ: 12.68 (s, 1H), 8.51 (d, J=1.8 Hz, 1H), 7.89 (dd, J=9.0, 2.4 Hz, 1H), 7.68 (s, 1H), 6.93 (d, J=9.0 Hz, 1H), 4.15 (s, 1H), 3.83 (t, J=2.1 Hz, 1H), 3.68-3.66 (m, 4H), 3.65-3.40 (m, 8H), 3.26-3.20 (m, 1H), 2.49-2.43 (m, 2H), 1.84-1.52 (m, 6H).

Example 132: N-[3-[4-(5-cyanopyridin-2-yl)piperazin-1-yl]-3-oxopropyl]-2-[(2S)-1-[6-oxo-5-(trifluoromethyl)-1,6-dihydropyridazin-4-yl]pyrrolidin-2-yl] acetamide

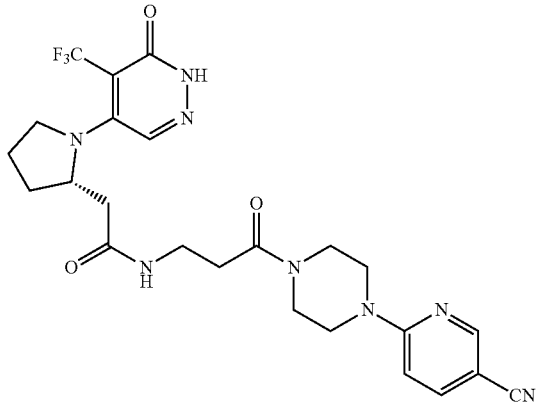 [SMILES: N#Cc1ccc(N2CCN(C(=O)CCNC(=O)C[C@@H]3CCCN3c3cn[nH]c(=O)c3C(F)(F)F)CC2)nc1]

Step 1: Synthesis of Tert-Butyl N-[3-[4-(5-cyanopyridin-2-yl)piperazin-1-yl]-3-oxopropyl]carbamate A solution of Int-A4 (500 mg, 2.23 mmol, 1.00 equiv), DIEA (863 mg, 6.68 mmol, 3.00 equiv), HATU (1.27 g, 3.34 mmol, 1.50 equiv), 3-{[(tert-butoxy)carbonyl]amino}propanoic acid (422 mg, 2.23 mmol, 1.00 equiv) in DMF (5 mL) was stirred for 1 h at room temperature. The resulting solution was purified by C18 reverse phase chromatography eluting with $H_2O/CH_3CN$ to afford 620 mg (78%) of the title compound as a white solid. LCMS (ESI, m/z): 360.20 [M+H]$^+$ Step 2: Synthesis of 6-[4-(3-aminopropanoyl)piperazin-1-yl]pyridine-3-carbonitrile Hydrochloride A solution of tert-butyl N-[3-[4-(5-cyanopyridin-2-yl)piperazin-1-yl]-3-oxopropyl]carbamate (610 mg, 1.70 mmol, 1.00 equiv) in hydrogen chloride/dioxane (5 mL, 1.00 equiv) was stirred for 30 min at room temperature. The resulting solution was concentrated under vacuum to afford 260 mg (52%) of the title compound as a white solid. LCMS (ESI, m/z): 260.14[M+H]$^+$ Step 3: Synthesis of 2-[(2S)-pyrrolidin-2-yl]acetic Acid Hydrochloride A solution of 2-[(2S)-1-[(tert-butoxy)carbonyl]pyrrolidin-2-yl]acetic acid (200 mg, 0.87 mmol, 1.00 equiv) in hydrogen chloride/dioxane (5 mL) was stirred for 30 min at room temperature. The resulting mixture was concentrated under vacuum to afford 160 mg (crude) of the title compound as a white solid. LCMS (ESI, m/z): 130.08 [M+H]$^+$ Step 4: Synthesis of 2-[(2S)-1-[6-oxo-5-(trifluoromethyl)-1-[[2-(trimethylsilyl)ethoxy]methyl]-1,6-dihydropyridazin-4-yl]pyrrolidin-2-yl]acetic Acid A solution of 2-(pyrrolidin-2-yl)acetic acid hydrochloride (160 mg, 0.97 mmol, 1.00 equiv), Int-A6 (319 mg, 0.97 mmol, 1.00 equiv), TEA (195 mg, 1.93 mmol, 2.00 equiv) in ethanol (5 mL) was stirred for 2 h at 80° C. The reaction mixture was concentrated under vacuum, the residue was applied onto a silica gel column eluting with DCM/methanol (9/1) to afford 320 mg (79%) of the title compound as yellow oil. LCMS (ESI, m/z): 422.16 [M+H]$^+$ Step 5: Synthesis of 2-[(2S)-1-[6-oxo-5-(trifluoromethyl)-1,6-dihydropyridazin-4-yl]pyrrolidin-2-yl] acetic Acid A solution of 2-[(2S)-1-[6-oxo-5-(trifluoromethyl)-1-[[2-(trimethylsilyl)ethoxy]methyl]-1,6-dihydropyridazin-4-yl]pyrrolidin-2-yl]acetic acid (310 mg, 0.74 mmol, 1.00 equiv) in hydrogen chloride/dioxane (5 mL) was stirred for 2 h at room temperature. After concentration, the residue was purified by C18 reverse phase chromatography eluting with $H_2O/CH_3CN$ to afford 80 mg (37%) of the title compound as a white solid. LCMS (ESI, m/z): 292.08 [M+H]$^+$ Step 6: Synthesis of N-[3-[4-(5-cyanopyridin-2-yl)piperazin-1-yl]-3-oxopropyl]-2-[(2S)-1-[6-oxo-5-(trifluoromethyl)-1,6-dihydropyridazin-4-yl]pyrrolidin-2-yl]acetamide A solution of 2-[(2S)-1-[6-oxo-5-(trifluoromethyl)-1,6-dihydropyridazin-4-yl]pyrrolidin-2-yl]acetic acid (60 mg, 0.21 mmol, 1.00 equiv), DIEA (80 mg, 0.62 mmol, 3.00 equiv), HOBT (42 mg, 0.31 mmol, 1.50 equiv), EDCI (59.4 mg, 0.31 mmol, 1.50 equiv), 6-[4-(3-aminopropanoyl)piperazin-1-yl]pyridine-3-carbonitrile hydrochloride (122 mg, 0.41 mmol, 2.00 equiv) in DMF (2 mL) was stirred for 12 h at room temperature. The resulting solution was purified by C18 reverse phase chromatography eluting with $H_2O/CH_3CN$. Then the residue was further purified by Prep-HPLC yielding the title compound amide (30.2 mg, 28%) as a white solid. LCMS (ESI, m/z): 533.52 [M+H]$^+$, $^1$H NMR (400 MHz, DMSO-$d_6$) δ: 12.45 (s, 1H), 8.51 (d, J=2.3 Hz, 1H), 8.07 (t, J=5.8 Hz, 1H), 7.96 (s, 1H), 7.89 (dd, J=9.1, 2.3 Hz, 1H), 6.94 (d, J=9.0 Hz, 1H), 4.52 (t, J=6.7 Hz, 1H), 3.72-3.66 (m, 4H), 3.58-3.49 (m, 5H), 3.27-3.20 (m, 3H), 2.51-2.41 (m, 3H), 2.26 (dd, J=13.9, 7.9 Hz, 1H), 2.17-2.09 (m, 1H), 1.89 (s, 1H), 1.79-1.65 (m, 2H).

Example 133: 6-[4-(3-[[(2S,4S)-1-[6-oxo-5-(trifluoromethyl)-1,6-dihydropyridazin-4-yl]-4-(trifluoromethyl)pyrrolidin-2-yl]methoxy]propanoyl)piperazin-1-yl]pyridine-3-carbonitrile

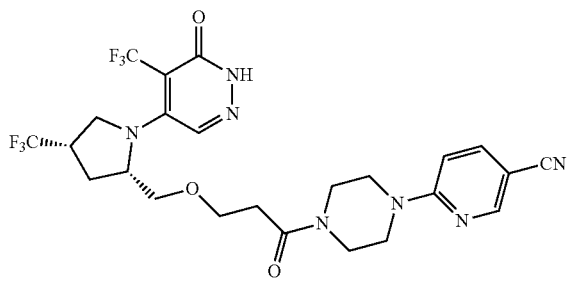 [SMILES: N#Cc1ccc(N2CCN(C(=O)CCOC[C@@H]3C[C@H](C(F)(F)F)CN3c3cn[nH]c(=O)c3C(F)(F)F)CC2)nc1]

Step 1: Synthesis of Tert-Butyl (2S,4S)-2-(hydroxymethyl)-4-(trifluoromethyl)pyrrolidine-1-carboxylate Under nitrogen, A solution of (2S,4S)-1-[(tert-butoxy)carbonyl]-4-(trifluoromethyl)pyrrolidine-2-carboxylic acid (1.5 g, 5.30 mmol, 1.00 equiv) and BH3THF (7 mL, 4.00 equiv, 1M) in THF (20 mL) was stirred for 2 h at room temperature, and then the reaction was then quenched by the addition of 20 mL of water, extracted with 4×20 mL of EtOAc and the organic layers combined, washed with 1×20 mL of brine, dried over anhydrous sodium sulfate and concentrated under vacuum to afford 1.35 g of the title compound as crude yellow oil. LCMS (ESI, m/z): 270.12 [M+H]$^+$.

Step 2: Synthesis of [(2S,4S)-4-(trifluoromethyl)pyrrolidin-2-yl]methanol Hydrochloride A solution of tert-butyl (2S,4S)-2-(hydroxymethyl)-4-(trifluoromethyl)pyrrolidine-1-carboxylate (1.35 g, 5.01 mmol, 1.00 equiv) in hydrogen chloride/dioxane (15 mL, 4M) was stirred for 1.5 h at room temperature, and then the resulting solution was concentrated under vacuum to afford 1.2 g of the title compound as yellow oil. LCMS (ESI, m/z): 170.07 [M+H]$^+$.

Step 3: Synthesis of 5-[(2S,4S)-2-(hydroxymethyl)-4-(trifluoromethyl)pyrrolidin-1-yl]-4-(trifluoromethyl)-2-[[2-(trimethylsilyl)ethoxy]methyl]-2,3-dihydropyridazin-3-one A solution of [(2S,4S)-4-(trifluoromethyl)pyrrolidin-2-yl]methanol hydrochloride (1.1 g, 5.35 mmol, 1.00 equiv), TEA (1.08 g, 10.67 mmol, 2.00 equiv) and Int-A6 (1.76 g, 5.35 mmol, 1.00 equiv) in ethanol (15 mL) was stirred for 1 h at 60° C., and then the resulting solution was concentrated under vacuum and then the residue was applied onto a silica gel column eluting with EtOAc/petroleum ether (1;3) to afford 1.3 g (53%) of the title compound as a light brown solid. LCMS (ESI, m/z): 462.16 [M+H]$^+$.

Step 4: Synthesis of Methyl 3-[[(2S,4S)-1-[6-oxo-5-(trifluoromethyl)-1-[[2-(trimethylsilyl)ethoxy]methyl]-1,6-dihydropyridazin-4-yl]-4-(trifluoromethyl)pyrrolidin-2-yl]methoxy]propanoate A solution of 5-[(2S,4S)-2-(hydroxymethyl)-4-(trifluoromethyl)pyrrolidin-1-yl]-4-(trifluoromethyl)-2-[[2-(trimethylsilyl)ethoxy]methyl]-2,3-dihydropyridazin-3-one (600 mg, 1.30 mmol, 1.00 equiv), Cs$_2$CO$_3$ (1.27 g, 3.90 mmol, 3.00 equiv) and methyl prop-2-enoate (559 mg, 6.49 mmol, 5.00 equiv) in MeCN (15 mL) was stirred for 3 h at room temperature, and then the resulting solution was concentrated under vacuum and then the residue was applied onto a silica gel column eluting with EtOAc/petroleum ether (1:3) to afford 374 mg (53%) the title compound as light yellow oil. LCMS (ESI, m/z): 548.19 [M+H]$^+$.

Step 5: Synthesis of Methyl 3-[[(2S,4S)-1-[6-oxo-5-(trifluoromethyl)-1,6-dihydropyridazin-4-yl]-4-(trifluoromethyl)pyrrolidin-2-yl]methoxy]propanoate A solution of methyl 3-[[(2S,4S)-1-[6-oxo-5-(trifluoromethyl)-1-[[2-(trimethylsilyl)ethoxy]methyl]-1,6-dihydropyridazin-4-yl]-4-(trifluoromethyl)pyrrolidin-2-yl]methoxy]propanoate (374 mg, 0.68 mmol, 1.00 equiv) and TFA (1 mL) in DCM (5 mL) was stirred for 1 h at room temperature, and then the resulting solution was concentrated under vacuum to afford 250 mg of the title compound as light crude yellow oil. LCMS (ESI, m/z): 418.11 [M+H]$^+$.

Step 6: Synthesis of 3-[[(2S,4S)-1-[6-oxo-5-(trifluoromethyl)-1,6-dihydropyridazin-4-yl]-4-(trifluoromethyl)pyrrolidin-2-yl]methoxy]propanoic Acid A solution of methyl 3-[[(2S,4S)-1-[6-oxo-5-(trifluoromethyl)-1,6-dihydropyridazin-4-yl]-4-(trifluoromethyl)pyrrolidin-2-yl]methoxy]propanoate (250 mg, 0.60 mmol, 1.00 equiv) and LiOH (76 mg, 3.17 mmol, 3.00 equiv) in THF (10 mL) and water (2 mL) was stirred for 1 h at room temperature, and then the resulting solution was diluted with 3 mL of water, extracted with 2×5 mL of EtOAc and the aqueous layers combined, and the pH value of the aqueous layers was adjusted to 4 with hydrogen chloride (1 M), and then the resulting aqueous was extracted with 2×5 mL of EtOAc and the organic layers combined, dried over anhydrous sodium sulfate and concentrated under vacuum to afford 180 mg of the title compound as light crude yellow oil. LCMS (ESI, m/z): 404.10 [M+H]$^+$.

Step 7: Synthesis of 6-[4-(3-[[(2S,4S)-1-[6-oxo-5-(trifluoromethyl)-1,6-dihydropyridazin-4-yl]-4-(trifluoromethyl)pyrrolidin-2-yl]methoxy]propanoyl)piperazin-1-yl]pyridine-3-carbonitrile A solution of 3-[[(2S,4S)-1-[6-oxo-5-(trifluoromethyl)-1,6-dihydropyridazin-4-yl]-4-(trifluoromethyl)pyrrolidin-2-yl]methoxy]propanoic acid (170 mg, 0.42 mmol, 1 equiv), DIEA (163.4 mg, 1.26 mmol, 3.00 equiv), HATU (160.3 mg, 0.42 mmol, 1.00 equiv) and Int-A4 (87.3 mg, 0.46 mmol, 1.10 equiv) in DMF (10 mL) was stirred for 40 min at room temperature, and then the resulting solution was extracted with 3×50 ml of EtOAc, washed with 3×50 ml of brine and the organic layers combined, dried over anhydrous sodium sulfate and concentrated under vacuum, and then the residue was purified by Prep-HPLC yielding the title compound (25.1 mg, 10.38%) as a white solid. LCMS (ESI, m/z): 574.05 [M+H]$^+$. $^1$HNMR: (CD3OD, 400 MHz): δ 8.42 (d, J=2.0 Hz, 1H), 8.10 (s, 1H), 7.77 (dd, J=9.2, 2.4 Hz, 1H), 6.86 (d, J=8.8 Hz, 1H), 4.74 (dt, J=11.0, 5.5 Hz, 1H), 3.79-3.61 (m, 12H), 3.53-3.47 (m, 2H), 3.08 (d, J=7.6 Hz, 1H), 2.64 (dd, J=11.6, 5.2 Hz, 2H), 2.43-2.40 (m, 1H), 1.92 (td, J=12.2, 8.3 Hz, 1H).

Example 134: (S)-3-(4-(5-cyanopyridin-2-yl)piperazin-1-yl)-N-((1-(6-oxo-5-(trifluoromethyl)-1,6-dihydropyridazin-4-yl)pyrrolidin-2-yl)methyl)propanamide

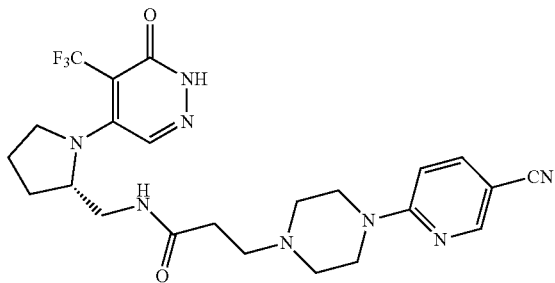 [SMILES: N#Cc1ccc(N2CCN(CCC(=O)NC[C@@H]3CCCN3c3cn[nH]c(=O)c3C(F)(F)F)CC2)nc1]

Step 1: Synthesis of Ethyl 3-(4-(5-cyanopyridin-2-yl)piperazin-1-yl)propanoate

A solution of ethyl prop-2-enoate (600 mg, 5.99 mmol, 1.20 equiv), Int-A4 (940 mg, 4.99 mmol, 1.00 equiv) in ethanol (10 mL) was stirred for 5.5 h at 80° C. The resulting solution was concentrated under vacuum to afford 1.29 g crude of the title compound as white oil. LCMS (ESI, m/z): 289.16 [M+H]$^+$ Step 2: Synthesis of 3-(4-(5-cyanopyridin-2-yl)piperazin-1-yl)propanoic Acid A solution of ethyl 3-[4-(5-cyanopyridin-2-yl)piperazin-1-yl]propanoate (1.56 g, 5.41 mmol, 1.00 equiv), LiOH (648 mg, 27.06 mmol, 5.00 equiv), water (3 mL) in methanol (15 mL) was stirred for 2 h at room temperature. The pH value of the solution was adjusted to 5 with hydrogen chloride. The residue was applied onto a silica gel column eluting with DCM/methanol (10:1) to afford 687 mg (49%) of the title compound as a white solid LCMS (ESI, m/z): 261.13 [M+H]$^+$ Step 3: Synthesis of 5-[(2S)-2-(azidomethyl)pyrrolidin-1-yl]-4-(trifluoromethyl)-2-[[2-(trimethylsilyl)ethoxy]methyl]-2,3-dihydropyridazin-3-one A solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (1 g, 2.54 mmol, 1.00 equiv), DPPA (1.4 g, 5.09 mmol, 2.00 equiv), DBU (772.6 mg, 5.07 mmol, 2.00 equiv) in toluene (15 mL) was stirred for 6 h at 100° C. After concentrated under vacuum, The residue was applied onto a silica gel column eluting with EtOAc/petroleum ether (1:1) to afford 1 g (94%) of the title compound as yellow oil. LCMS (ESI, m/z): 419.18 [M+H]$^+$ Step 4: Synthesis of 5-[(2S)-2-(aminomethyl)pyrrolidin-1-yl]-4-(trifluoromethyl)-2-[[2-(trimethylsilyl)ethoxy]methyl]-2,3-dihydropyridazin-3-one A solution of 5-[(2S)-2-(azidomethyl)pyrrolidin-1-yl]-4-(trifluoromethyl)-2-[[2-(trimethylsilyl)ethoxy]methyl]-2,3-dihydropyridazin-3-one (1 g, 2.39 mmol, 1.00 equiv), Palladium carbon (200 mg) in methanol (15 mL) was stirred for 0.5 h at room temperature under H$_2$ atmosphere. The solids were filtered out. The resulting solution was concentrated under vacuum to afford 864 mg crude of the title compound as black oil. LCMS (ESI, m/z): 393.19 [M+H]$^+$ Step 5: Synthesis of (S)-3-(4-(5-cyanopyridin-2-yl)piperazin-1-yl)-N-((1-(6-oxo-5-(trifluoromethyl)-1-((2-(trimethylsilyl)ethoxy)methyl)-1,6-dihydropyridazin-4-yl)pyrrolidin-2-yl)methyl)propanamide A solution of 3-[4-(5-cyanopyridin-2-yl)piperazin-1-yl]propanoic acid (220.22 mg, 0.85 mmol, 1.10 equiv), 5-[(2S)-2-(aminomethyl)pyrrolidin-1-yl]-4-(trifluoromethyl)-2-[[2-(trimethylsilyl)ethoxy]methyl]-2,3-dihydropyridazin-3-one (300 mg, 0.76 mmol, 1.00 equiv), HATU (441 mg, 1.16 mmol, 1.50 equiv), DIEA (298 mg, 2.31 mmol, 3.00 equiv) in DMF (3 mL) was stirred for 2 h at room temperature. After concentration, the residue was purified by C18 reverse phase chromatography eluting with H$_2$O/CH$_3$CN to afford 224 mg (46%) of the title compound as yellow oil. LCMS (ESI, m/z): 635.30 [M+H]$^+$ Step 6: Synthesis of (S)-3-(4-(5-cyanopyridin-2-yl)piperazin-1-yl)-N-((1-(6-oxo-5-(trifluoromethyl)-1,6-dihydropyridazin-4-yl)pyrrolidin-2-yl)methyl)propanamide A solution of 3-[4-(5-cyanopyridin-2-yl)piperazin-1-yl]-N-[[(2S)-1-[6-oxo-5-(trifluoromethyl)-1-[[2-(trimethylsilyl)ethoxy]methyl]-1,6-dihydropyridazin-4-yl]pyrrolidin-2-yl]methyl]propanamide (202 mg, 0.32 mmol, 1.00 equiv), TFA (2 mL) in DCM (10 mL) was stirred for 2 h at room temperature. After concentration, the residue was purified by Prep-HPLC eluting with eluting with H$_2$O/CH$_3$CN yielding the title compound (105 mg, 65%) as a white solid. LCMS (ESI, m/z): 505.10 [M+H]$^+$, 1HNMR (Methanol-d$_4$, 300 MHz) δ:8.41 (dd, J=2.4, 0.7 Hz, 1H), 8.25 (s, 1H), 7.74 (dd, J=9.1, 2.4 Hz, 1H), 6.87 (dd, J=9.2, 0.9 Hz, 1H), 4.46 (t, J=5.3 Hz, 1H), 3.73 (t, J=5.2 Hz, 5H), 3.48 (dd, J=13.8, 4.7 Hz, 1H), 3.38 (d, J=9.2 Hz, 2H), 2.69-2.67 (m, 2H), 2.58 (t, J=5.2 Hz, 4H), 2.44 (t, J=7.0 Hz, 2H), 2.35-2.26 (m, 1H), 2.02 (s, 1H), 1.89-1.69 (m, 2H).

Example 135: 6-[4-[3-([[(2S)-1-[6-oxo-5-(trifluoromethyl)-1,6-dihydropyridazin-4-yl]pyrrolidin-2-yl]methyl]amino)propanoyl]piperazin-1-yl]pyridine-3-carbonitrile

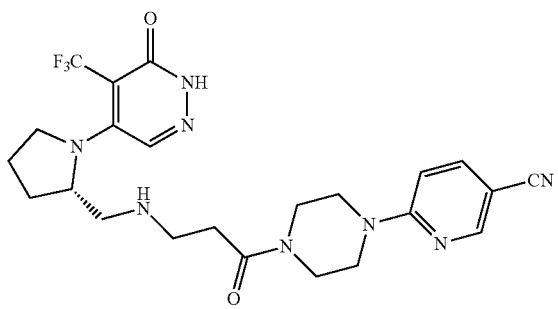 [SMILES: N#Cc1ccc(N2CCN(C(=O)CCNC[C@@H]3CCCN3c3cn[nH]c(=O)c3C(F)(F)F)CC2)nc1]

Step 1: Synthesis of 6-[4-[3-([[(2S)-1-[6-oxo-5-(trifluoromethyl)-1-[[2-(trimethylsilyl)ethoxy]methyl]-1,6-dihydropyridazin-4-yl]pyrrolidin-2-yl]methyl]amino)propanoyl]piperazin-1-yl]pyridine-3-carbonitrile A solution of 5-[(2S)-2-(aminomethyl)pyrrolidin-1-yl]-4-(trifluoromethyl)-2-[[2-(trimethylsilyl)ethoxy]methyl]-2,3- dihydropyridazin-3-one (470 mg, 1.20 mmol, 1.00 equiv), DIEA (14.45 mg, 0.11 mmol, 0.10 equiv), 6-[4-(prop-2-enoyl)piperazin-1-yl]pyridine-3-carbonitrile (257.5 mg, 1.06 mmol, 0.95 equiv) in i-propanol (10 mL) was stirred for 20 h at 100° C. After concentration, the residue was applied onto a silica gel column eluting with EtOAc/petroleum ether (1:1) to afford 410 mg (54%) of the title compound as brown oil. LCMS (ESI, m/z): 635.31[M+H]+

Step 2: Synthesis of 6-[4-[3-([[(2S)-1-[6-oxo-5-(trifluoromethyl)-1,6-dihydropyridazin-4-yl]pyrrolidin-2-yl]methyl]amino)propanoyl]piperazin-1-yl]pyridine-3-carbonitrile A solution of 6-[4-[3-([[(2S)-1-[6-oxo-5-(trifluoromethyl)-1-[[2-(trimethylsilyl)ethoxy]methyl]-1,6-dihydropyridazin-4-yl]pyrrolidin-2-yl]methyl]amino)propanoyl]piperazin-1-yl]pyridine-3-carbonitrile (400 mg, 0.63 mmol, 1.00 equiv), TFA (3 mL) in DCM (15 mL) was stirred for 1 h at room temperature. After concentration, the residue was purified by C18 reverse phase chromatography eluting with H$_2$O/CH$_3$CN yielding the title compound (46 mg, 14%) as a white solid. LCMS (ESI, m/z): 505.10 [M+H]+, $^1$HNMR (300 MHz, DMSO-d6) δ 12.36 (s, 1H), 8.52 (d, J=2.3 Hz, 1H), 8.04 (s, 1H), 7.89 (d, J=9.1 Hz, 1H), 6.94 (d, J=9.1 Hz, 1H), 4.34 (d, J=6.7 Hz, 1H), 3.86-3.60 (m, 4H), 3.56-3.50 (m, 5H), 3.20 (d, J=11.0 Hz, 1H), 2.88-2.53 (m, 4H), 2.49-2.43 (m, 2H), 2.13 (s, 1H), 1.90 (s, 1H), 1.67-1.60 (m, 2H).

Example 136: (S)-6-(4-(3-(methyl((1-(6-oxo-5-(trifluoromethyl)-1,6-dihydropyridazin-4-yl)pyrrolidin-2-yl)methyl)amino)propanoyl)piperazin-1-yl)nicotinonitrile

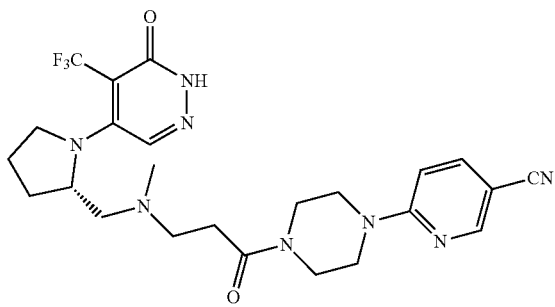 [SMILES: CN(CCC(=O)N1CCN(c2ccc(C#N)cn2)CC1)C[C@@H]1CCCN1c1cn[nH]c(=O)c1C(F)(F)F]

Step 1: Synthesis of (S)-tert-butyl 2-((3-(4-(5-cyanopyridin-2-yl)piperazin-1-yl)-3-oxopropylamino)methyl)pyrrolidine-1-carboxylate A solution of 6-(4-acryloylpiperazin-1-yl)nicotinonitrile (500 mg, 2.07 mmol, 1.00 equiv), DIEA (26.7 mg, 0.21 mmol, 0.10 equiv), (S)-tert-butyl 2-(aminomethyl)pyrrolidine-1-carboxylate (454.5 mg, 2.27 mmol, 1.10 equiv) in i-PrOH (10 ml) was stirred for 15 h at 100° C. After concentration, the residue was applied onto a silica gel column eluting with EtOAc/petroleum ether (1:1) to afford 700 mg (76.7%) of the title compound as white oil. LCMS (ESI, m/z): 443.28 [M+H]+

Step 2: Synthesis of (S)-tert-butyl 2-(((3-(4-(5-cyanopyridin-2-yl)piperazin-1-yl)-3-oxopropyl)(methyl)amino)methyl)pyrrolidine-1-carboxylate A solution of (S)-tert-butyl 2-((3-(4-(5-cyanopyridin-2-yl)piperazin-1-yl)-3-oxopropylamino)methyl)pyrrolidine-1-carboxylate (511 mg, 1.15 mmol, 1.00 equiv), (HCHO)n (312 mg, 3.00 equiv), acetic acid (0.5 mL), NaBH3CN (218.6 mg, 3.48 mmol, 3.00 equiv) in methanol (20 mL) was stirred for 20 h at room temperature. After concentration, the residue was applied onto a silica gel column eluting with EtOAc/petroleum ether (40:60) to afford 500 mg (95%) of the title compound as a white solid. LCMS (ESI, m/z): 457.29[M+H]+

Step 3: Synthesis of (S)-6-(4-(3-(methyl(pyrrolidin-2-ylmethyl)amino)propanoyl)piperazin-1-yl)nicotinonitrile A solution of (S)-tert-butyl 2-(((3-(4-(5-cyanopyridin-2-yl)piperazin-1-yl)-3-oxopropyl)(methyl)amino)methyl)pyrrolidine-1-carboxylate (500 mg, 1.10 mmol, 1.00 equiv) in hydrogen chloride-dioxane (20 mL) was stirred for 1 h at room temperature. The resulting mixture was concentrated under vacuum to afford 400 mg crude of the title compound as brown solid. LCMS (ESI, m/z): 357.24 [M+H]+

Step 4: Synthesis of (S)-6-(4-(3-(methyl((1-(6-oxo-5-(trifluoromethyl)-1-((2-(trimethylsilyl)ethoxy)methyl)-1,6-dihydropyridazin-4-yl)pyrrolidin-2-yl)methyl)amino)propanoyl)piperazin-1-yl)nicotinonitrile A solution of (S)-6-(4-(3-(methyl(pyrrolidin-2-ylmethyl)amino)propanoyl)piperazin-1-yl)nicotinonitrile (400 mg, 1.12 mmol, 1.00 equiv), TEA (339.4 mg, 3.35 mmol, 3.00 equiv), Int-A6 (479 mg, 1.46 mmol, 1.30 equiv) in ethanol (20 mL) was stirred for 3 h at 70° C. After concentration, the residue was applied onto a silica gel column eluting with EtOAc/petroleum ether (80:20) to afford 980 mg crude of the title compound as a yellow solid. LCMS (ESI, m/z): 649.33 [M+H]+

Step 5: Synthesis of (S)-6-(4-(3-(methyl((1-(6-oxo-5-(trifluoromethyl)-1,6-dihydropyridazin-4-yl)pyrrolidin-2-yl)methyl)amino)propanoyl)piperazin-1-yl)nicotinonitrile A solution of (S)-6-(4-(3-(methyl((1-(6-oxo-5-(trifluoromethyl)-1-((2-(trimethylsilyl)ethoxy)methyl)-1,6-dihydropyridazin-4-yl)pyrrolidin-2-yl)methyl)amino)propanoyl)piperazin-1-yl)nicotinonitrile (900 mg, 1.39 mmol, 1.00 equiv) in hydrogen chloride/dioxane (20 mL) was stirred for 1 h at room temperature. After concentration, the residue was purified by C18 reverse phase chromatography eluting with H$_2$O/CH3CN. Then the residue was further purified by Prep-HPLC yielding the title compound (38 mg, 5%) as a white solid. LCMS (ESI, m/z): 519.10 [M+H]+, $^1$H NMR (300 MHz, Chloroform-d) δ 10.81 (s, 1H), 8.44 (d, J=2.3 Hz, 1H), 7.91 (s, 1H), 7.67 (dd, J=9.0, 2.3 Hz, 1H), 6.64 (d, J=9.1 Hz, 1H), 4.33 (q, J=7.5 Hz, 1H), 3.75 (d, J=10.3 Hz, 4H), 3.69 (d, J=5.5 Hz, 3H), 3.58 (d, J=6.3 Hz, 2H), 3.47-3.26 (m, 1H), 2.88-2.83 (m, 1H), 2.77-2.70 (m, 1H), 2.62-2.38 (m, 4H), 2.31 (s, 4H), 2.15-1.87 (m, 1H), 1.76-1.67 (m, 1H), 1.66-1.61 (m, 1H).

Example 137: 6-[4-(3-[[(7S)-6-[6-oxo-5-(trifluoromethyl)-1,6-dihydropyridazin-4-yl]-5H,6H,7H-pyrrolo[3,4-b]pyridin-7-yl]methoxy]propanoyl)piperazin-1-yl]pyridine-3-carbonitrile and 6-[4-(3-[[(7R)-6-[6-oxo-5-(trifluoromethyl)-1,6-dihydropyridazin-4-yl]-5H,6H,7H-pyrrolo[3,4-b]pyridin-7-yl]methoxy]propanoyl)piperazin-1-yl]pyridine-3-carbonitrile

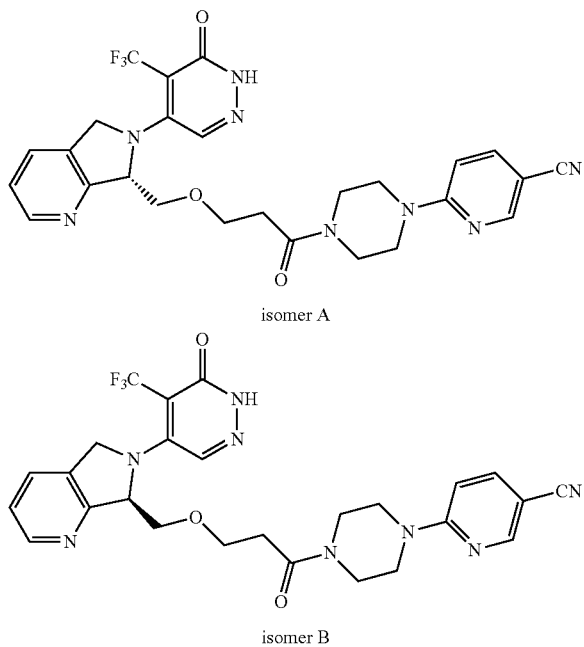

isomer A isomer B

Step 1: Synthesis of Methyl 2-[[(2-chloropyridin-3-yl)methyl]amino]acetate

A solution of methyl 2-aminoacetate hydrochloride (39.89 g, 317.71 mmol, 1.50 equiv), 2-chloropyridine-3-carbaldehyde (30 g, 211.93 mmol, 1.00 equiv) and TEA (42.9 g, 423.95 mmol, 2.00 equiv) in methanol (200 mL) was stirred for 12h at room temperature, and then NaBH4 (16.17 g, 427.44 mmol, 2.00 equiv) was added in, and then the resulting solution was stirred for another 40 min at room temperature, and then the resulting solution was quenched by the addition of 250 mL of water, extracted with 2×300 mL of EtOAc and the organic layers combined, washed with 1×300 mL of brine, dried over anhydrous sodium sulfate and concentrated under vacuum, and then the residue was applied onto a silica gel column eluting with EtOAc/petroleum ether (3:2) to afford 26.1 g (57%) of the title compound as yellow oil. LCMS (ESI, m/z): 215.05 [M+H]$^+$.

Step 2: Synthesis of Methyl 2-[[(tert-butoxy)carbonyl][(2-chloropyridin-3-yl)methyl]amino]acetate A solution of methyl 2-[[(2-chloropyridin-3-yl)methyl]amino]acetate (26.6 g, 123.9 mmol, 1.00 equiv) and TEA (37.6 g, 371.6 mmol, 3.00 equiv) in DCM (200 mL) was stirred for 10 min at room temperature, and then (Boc)$_2$O (40.6 g, 186 mmol, 1.50 equiv) was added in, and then the resulting solution was stirred for another 1.5 h at room temperature, the resulting solution was concentrated under vacuum and then the residue was applied onto a silica gel column eluting with EtOAc/petroleum ether (1:6) to afford 26.8 g (69%) of the title compound as yellow oil. LCMS (ESI, m/z): 315.05 [M+H]$^+$.

Step 3: Synthesis of 6-tert-butyl 7-methyl 5H,6H,7H-pyrrolo[3,4-b]pyridine-6,7-dicarboxylate Under nitrogen, a solution of methyl 2-[[(tert-butoxy)carbonyl][(2-chloropyridin-3-yl)methyl]amino]acetate (4 g, 12.71 mmol, 1.00 equiv), Pd(PPh3)4 (1.47 g, 1.27 mmol, 0.10 equiv), K3PO4 (8.1 g, 3.00 equiv) and PhOH (358 mg, 0.30 equiv) in DMF (75 mL) was stirred for 2.5h at 90° C., and then the resulting solution was diluted with 100 mL of EA, washed with 3×80 mL of H$_2$O, dried over anhydrous sodium sulfate, concentrated under vacuum and then the residue was applied onto a silica gel column eluting with EtOAc/petroleum ether (1:3) to afford 620 mg (18%) of the title compound as light yellow oil. LCMS (ESI, m/z): 279.13 [M+H]$^+$.

Step 4: Synthesis of Tert-Butyl 7-(hydroxymethyl)-5H,6H,7H-pyrrolo[3,4-b]pyridine-6-carboxylate A solution of 6-tert-butyl 7-methyl 5H,6H,7H-pyrrolo[3,4-b]pyridine-6,7-dicarboxylate (1.46 g, 5.25 mmol, 1.00 equiv) and LAH (597 mg, 17.6 mmol, 3.00 equiv) in THF (60 mL) was stirred for 0.5 h at room temperature, and then the resulting solution was quenched by the addition of 2 mL of water and 2 mL of 20% aqueous of NaOH, and then the mixture was dried over anhydrous sodium sulfate, and then the resulting solution was concentrated under vacuum and then the residue was applied onto a silica gel column eluting with EtOAc/petroleum ether (7:3) to afford 210 mg (16%) of the title compound as an orange solid. LCMS (ESI, m/z): 251.13 [M+H]$^+$.

Step 5: Synthesis of [5H,6H,7H-pyrrolo[3,4-b]pyridin-7-yl]methanol Hydrochloride A solution of tert-butyl 7-(hydroxymethyl)-5H,6H,7H-pyrrolo[3,4-b]pyridine-6-carboxylate (210 mg, 0.84 mmol, 1.00 equiv) in hydrogen chloride/dioxane (10 mL, 4M) was stirred for 1 h at room temperature, and then the resulting solution was concentrated under vacuum to afford 156 mg (crude) of the title compound as a brown solid. LCMS (ESI, m/z): 151.08 [M+H]$^+$.

Step 6: Synthesis of 5-[7-(hydroxymethyl)-5H,6H,7H-pyrrolo[3,4-b]pyridin-6-yl]-4-(trifluoromethyl)-2-[[2-(trimethylsilyl)ethoxy]methyl]-2,3-dihydropyridazin-3-one A solution of [5H,6H,7H-pyrrolo[3,4-b]pyridin-7-yl]methanol hydrochloride (500 mg, 3.33 mmol, 1.00 equiv), Int-A6 (1.08 g, 3.28 mmol, 1.00 equiv) and TEA (1 g, 9.88 mmol, 3.00 equiv) in ethanol (25 mL) was stirred for 1 h at 60° C., and then the resulting solution was concentrated under vacuum and then the residue was applied onto a silica gel column eluting with EtOAc/petroleum ether (8:2) to afford 464 mg (31%) of the title compound as a brown solid. LCMS (ESI, m/z): 443.16 [M+H]$^+$.

Step 7: Synthesis of Methyl 3-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-7-yl]methoxy)propanoate A solution of 5-[7-(hydroxymethyl)-5H,6H,7H-pyrrolo[3,4-b]pyridin-6-yl]-4-(trifluoromethyl)-2-[[2-(trimethylsilyl)

ethoxy]methyl]-2,3-dihydropyridazin-3-one (270 mg, 0.61 mmol, 1.00 equiv), Cs₂CO₃ (595 mg, 1.83 mmol, 3.00 equiv) and methyl prop-2-enoate (157 mg, 1.82 mmol, 3.00 equiv) in MeCN (12 mL) was stirred for 18 h at room temperature, and then the resulting solution was diluted with 20 mL of EtOAc, washed with 3×15 mL of H₂O, and the organic layers was dried over anhydrous sodium sulfate and concentrated under vacuum, and then the residue was applied onto a silica gel column with EtOAc/petroleum ether (67:33) to afford 114 mg (35%) of the title compound as a colorless solid. LCMS (ESI, m/z): 529.20 [M+H]⁺.

Step 8: Synthesis of 3-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-7-yl]methoxy)propanoic Acid A solution of methyl 3-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-7-yl]methoxy)propanoate (540 mg, 1.02 mmol, 1.00 equiv) and LiOH.H₂O (214 mg, 5.10 mmol, 5.00 equiv) in methanol (5 mL) and water (1 mL) was stirred for 2 h at room temperature, and then the pH value of the solution was adjusted to 5 with hydrogen chloride (12 M), and then the resulting solution was concentrated under vacuum to afford 420 mg of the title compound as acrude brown solid. LCMS (ESI, m/z): 515.19 [M+H]⁺.

Step 9: Synthesis of 3-([6-[6-oxo-5-(trifluoromethyl)-1,6-dihydropyridazin-4-yl]-5H,6H,7H-pyrrolo[3,4-b]pyridin-7-yl]methoxy)propanoic Acid A solution of 3-([6-[6-oxo-5-(trifluoromethyl)-1-[[2-(trimethylsilyl)ethoxy]methyl]-1,6-dihydropyridazin-4-yl]-5H,6H,7H-pyrrolo[3,4-b]pyridin-7-yl]methoxy)propanoic acid (460 mg, 0.89 mmol, 1.00 equiv) and TFA (5 mL) in DCM (20 mL) was stirred for 1 h at room temperature, and then the resulting solution was concentrated under vacuum to afford 344 mg of the title compound as crude brown oil. LCMS (ESI, m/z): 385.10 [M+H]⁺.

Step 10: Synthesis of 6-[4-(3-[[(7S)-6-[6-oxo-5-(trifluoromethyl-1,6-dihydropyridazin-4-yl]-5H,6H,7H-pyrrolo[3,4-b]pyridin-7-yl]methoxy]propanoyl)piperazin-1-yl]pyridine-3-carbonitrile and 6-[4-(3-[[(7R)-6-[6-oxo-5-(trifluoromethyl)-1,6-dihydropyridin-4-yl]-5H,6H,7H-pyrrolo[3,4-b]pyridin-7-yl]methoxy]propanol)piperazin-1-yl]pyridine-3-carbonitrile A solution of placed 3-([6-[6-oxo-5-(trifluoromethyl)-1,6-dihydropyridazin-4-yl]-5H,6H,7H-pyrrolo[3,4-b]pyridin-7-yl]methoxy)propanoic acid (344 mg, 0.90 mmol, 1.00 equiv), HATU (339 mg, 0.89 mmol, 1.00 equiv), DIEA (576 mg, 4.46 mmol, 5.00 equiv) and Int-A4 (232 mg, 0.89 mmol, 1.00 equiv) in DMF (4 mL) was stirred for 1 h at room temperature, and then the residue was purified by C18 reverse phase chromatography eluting with H₂O/CH₃CN, after concentration, and then the residue was further purified by Prep-HPLC and Chiral-Prep-HPLC yielding the title compounds. The absolute stereochemistry was assigned based on a protein X-ray crystal structure obtained of Example 18 Isomer B which confirmed (S)-absolute stereochemistry and was observed to be the more potent enantiomer.

Isomer A (39.8 mg, 30%) as a white solid. LCMS (ESI, m/z): 555.10 [M+H]⁺, ¹HNMR (Methanol-d4, 300 MHz) δ 8.50 (d, J=3.9 Hz, 1H), 8.45 (s, 1H), 8.29 (s, 1H), 7.82-7.76 (m, 2H), 7.38 (dd, J=8.4, 5.1 Hz, 1H), 6.89 (d, J=8.7 Hz, 1H), 5.78 (t, J=3.0 Hz, 1H), 5.28 (d, J=14.7 Hz, 1H), 4.70 (d, J==14.7 Hz, 1H), 4.10 (dd, J=10.2, 2.7 Hz, 1H), 3.87-3.54 (m, 11H), 2.61 (dd, J=10.5, 5.4 Hz, 2H), tR=4.838 min (CHIRALPAK IC-3, 0.46*10 cm; 3 um, MtBE (0.1% DEA): EtOH=70:30, 1.0 mL/min) and isomer B (38.1 mg, 29%) as a white solid. LCMS (ESI, m/z): 555.10 [M+H]⁺, tR=5.930 min (CHIRALPAK IC-3, 0.46*10 cm; 3 um, MtBE (0.1% DEA):EtOH=70:30, 1.0 mL/min).

Example 138: 3-[4-(5-cyanopyridin-2-yl)piperazin-1-yl]-N-methyl-N-[[(2S)-1-[6-oxo-5-(trifluoromethyl)-1,6-dihydropyridazin-4-yl]pyrrolidin-2-yl]methyl]propanamide

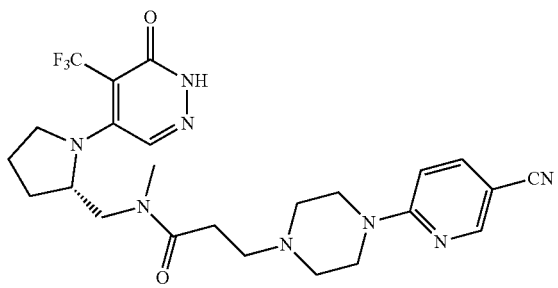 [SMILES: CN(C[C@@H]1CCCN1c1cn[nH]c(=O)c1C(F)(F)F)C(=O)CCN1CCN(c2ccc(C#N)cn2)CC1]

Step 1: Synthesis of 5-[(2S)-2-[(methylamino)ethyl]pyrrolidin-1-yl]-4-(trifluoromethyl)-2-[[2-(trimethylsilyl)ethoxy]methyl]-2,3-dihydropyridazin-3-one A solution of 5-[(2S)-2-(aminomethyl)pyrrolidin-1-yl]-4-(trifluoromethyl)-2-[[2-(trimethylsilyl)ethoxy]methyl]-2,3-dihydropyridazin-3-one (570 mg, 1.45 mmol, 1.00 equiv), potassium hydroxide (15 mg, 0.27 mmol, 0.20 equiv), CH₂O (47 mg, 1.57 mmol, 1.20 equiv), NaBH₄ (100 mg, 2.64 mmol, 2.00 equiv) in methanol (20 mL) was stirred for 4 h at 50° C. in an oil bath. The resulting solution was extracted with 2×200 mL of DCM and the organic layers combined and concentrated under vacuum. The residue was applied onto a silica gel column eluting with DCM/methanol (96:4) to afford 380 mg (64%) of the title compound as yellow oil. LCMS (ESI, m/z): 407.20 [M+H]⁺

Step 2: Synthesis of 3-[4-(5-cyanopyridin-2-yl)piperazin-1-yl]-N-methyl-N-[[(2S)-1-[6-oxo-5-(trifluoromethyl)-1-[[2-(trimethylsilyl)ethoxy]methyl]-1,6-dihydropyridazin-4-yl]pyrrolidin-2-yl]methyl]propanamide A solution of 3-[4-(5-cyanopyridin-2-yl)piperazin-1-yl]propanoic acid (248 mg, 0.95 mmol, 1.00 equiv), DIEA (368 mg, 2.85 mmol, 3.00 equiv), HATU (365 mg, 0.96 mmol, 1.02 equiv), 5-[(2S)-2-[(methylamino)methyl]pyrrolidin-1-yl]-4-(trifluoromethyl)-2-[[2-(trimethylsilyl)ethoxy]methyl]-2,3-dihydropyridazin-3-one (386 mg, 0.95 mmol, 1.00 equiv) in DMF (3 mL) was stirred for 1 h at 25° C. After concentration, the residue was purified by C18 reverse phase chromatography eluting with H₂O/CH₃CN (15:85) to afford 300 mg of the title compound as yellow oil. LCMS (ESI, m/z): 649.32 [M+H]⁺

Step 3: Synthesis of 3-[4-(5-cyanopyridin-2-yl)piperazin-1-yl]-N-methyl-N-[[(2S)-1-[6-oxo-5-(trifluoromethyl)-1,6-dihydropyridazin-4-yl]pyrrolidin-2-yl]methyl]propanamide A solution of 3-[4-(5-cyanopyridin-2-yl)piperazin-1-yl]-N-methyl-N-[[(2S)-1-[6-oxo-5-(trifluoromethyl)-1-[[2-(trimethylsilyl)ethoxy]methyl]-1,6-dihydropyridazin-4-yl]pyrrolidin-2-yl]methyl]propanamide (300 mg, 0.46 mmol, 1.00 equiv), a solution of TFA/DCM (12 mL) in DCM (10 mL) was stirred for 1 h at 25° C. The pH value of the solution was adjusted to 8 with NH₂CH₂CH₂OH. The crude product (150 mg) was purified by Flash-Prep-HPLC yielding the title compound (97.9 mg 41%) as a white solid. LCMS (ESI, m/z): 519.24 [M+H]⁺, ¹H NMR (Methanol-d₄, 400 MHz) δ: 8.41 (d, J=2.0 Hz, 1H), 8.24 (s, 1H), 7.75-7.73 (m, 1H), 6.87-6.85 (m, 1H), 4.63-4.60 (m, 1H), 3.74-3.72 (m, 6H), 3.40-3.37 (m, 1H), 3.31-3.29 (m, 1H), 3.14 (s, 3H), 2.74-2.70 (m, 2H), 2.68-2.53 (m, 6H), 2.32-2.27 (m, 1H), 2.06-2.05 (m, 1H), 1.85-1.76 (m, 2H)

Example 139: 6-[4-(3-[[(2S)-4-(methoxymethyl)-1-[6-oxo-5-(trifluoromethyl)-1,6-dihydropyridazin-4-yl]pyrrolidin-2-yl]methoxy]propanoyl)piperazin-1-yl]pyridine-3-carbonitrile

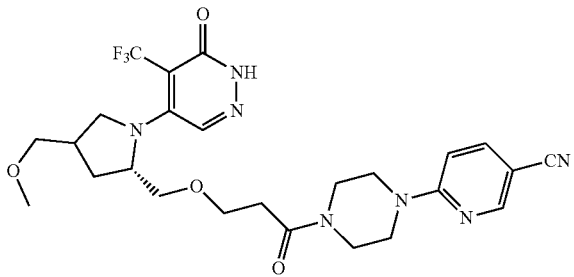 [SMILES: COCC1C[C@@H](COCCC(=O)N2CCN(c3ccc(C#N)cn3)CC2)N(c2cn[nH]c(=O)c2C(F)(F)F)C1]

Step 1: Synthesis of 1-tert-butyl 2-methyl (2S)-4-(hydroxymethyl)pyrrolidine-1,2-dicarboxylate A solution of 1-tert-butyl 2-methyl (2S)-4-methylidenepyrrolidine-1,2-dicarboxylate (5 g, 20.72 mmol, 1.00 equiv), BH₃SMe₂ (3.47 g, 2.20 equiv), sodium hydroxide (1.05 g, 26.25 mmol, 1.25 equiv), water (20 mL), H₂O₂ (2.14 g, 3.00 equiv) in THF (100 mL) was stirred for 5 h at room temperature. The resulting solution was quenched with H₂O. The resulting solution was extracted with 5×20 mL of EtOAc and the organic layers combined. The residue was applied onto a silica gel column eluting with EtOAc/petroleum ether (1:1) to afford 2.5 g (47%) of the title compound as a red solid. LCMS (ESI, m/z): 260.15 [M+H]+

Step 2: Synthesis of (2S)-1-[(tert-butoxy)carbonyl]-4-(methoxymethyl)pyrrolidine-2-carboxylic Acid A solution of 1-tert-butyl 2-methyl (2S)-4-(hydroxymethyl)pyrrolidine-1,2-dicarboxylate (1.5 g, 5.78 mmol, 1.00 equiv), sodium hydride (461.6 g, 19.23 mol, 2.00 equiv), MeI (4.1 g, 5.00 equiv) in THF (25 mL) was stirred for 3 h at room temperature. The resulting solution was quenched with H₂O and the resulting solution was extracted with 5×20 mL of EtOAc and the organic layers combined. The residue was applied onto a silica gel column eluting with DCM/methanol (15:85) to afford 1.1 g (73%) of the title compound as a white solid. LCMS (ESI, m/z): 260.15[M+H]+

Step 3: Synthesis of Tert-Butyl (2S)-2-(hydroxymethyl)-4-(methoxyethyl)pyrrolidine-1-carboxylate A solution of diborane (1.37 g, 15.94 mmol, 1.00 equiv), (2S)-1-[(tert-butoxy)carbonyl]-4-(methoxymethyl)pyrrolidine-2-carboxylic acid (15 mL) in was stirred for 3 h at room temperature. The resulting solution was quenched with H₂O. The resulting solution was extracted with 3×20 mL of EtOAc and the organic layers combined. The resulting mixture was concentrated under vacuum to afford 1.3 g (33%) of the title compound as brown oil. LCMS (ESI, m/z): 246.17[M+H]+

Step 4: Synthesis of [(2S)-4-(methoxymethyl)pyrrolidin-2-yl]methanol

A solution of tert-butyl (2S)-2-(hydroxymethyl)-4-(methoxymethyl)pyrrolidine-1-carboxylate (1.3 g, 5.30 mmol, 1.00 equiv) in hydrogen chloride-1,4dioxane (15 mL) was stirred for 1 h at room temperature. The resulting mixture was concentrated under vacuum to afford 1 g (crude) of the title compound as brown oil. LCMS (ESI, m/z): 146.12 [M+H]+

Step 5: Synthesis of 5-[(2S)-2-(hydroxymethyl)-4-(methoxymethyl)pyrrolidin-1-yl]-4-(trifluoromethyl)-2-[[2-(trimethylsilyl)ethoxy]methyl]-2,3-dihydropyridazin-3-one A solution of [(2S)-4-(methoxymethyl)pyrrolidin-2-yl]methanol (760 mg, 5.23 mmol, 1.00 equiv), TEA (1.69 g, 16.70 mmol, 3.00 equiv), Int-A6 (1.72 g, 5.23 mmol, 1.00 equiv) in ethanol (15 mL) was stirred for 2 h at 60° C. The resulting solution was quenched with H₂O. The solution was extracted with EtOAc (3×50 mL) and the organic layers combined. The solution was dried over anhydrous sodium sulfate and concentrated under vacuum. The residue was applied onto a silica gel column eluting with EtOAc/petroleum ether (1:1) to afford 375 mg (16%) of the title compound as a yellow solid. LCMS (ESI, m/z): 438.21 [M+H]⁺

Step 6: Synthesis of Tert-Butyl 3-[[(2S)-4-(methoxymethyl)-1-[6-oxo-5-(trifluoromethyl)-1-[[2-(trimethylsilyl)ethoxy]methyl]-1,6-dihydropyridazin-4-yl]pyrrolidin-2-yl]methoxy]propanoate A solution of Cs₂CO₃ (312.5 mg, 0.96 mmol, 1.50 equiv), 5-[(2S)-2-(hydroxymethyl)-4-(methoxymethyl)pyrrolidin-1-yl]-4-(trifluoromethyl)-2-[2-(trimethylsilyl)ethoxy]methyl-2,3-dihydropyridazin-3-one (280 mg, 0.64 mmol, 1.00 equiv), tert-butyl prop-2-enoate (410 mg, 3.20 mmol, 5.00 equiv) in MeCN (15 mL) in was stirred for 20 h at 40° C. The resulting mixture was concentrated under vacuum and the residue was applied onto a silica gel column eluting with EtOAc/petroleum ether (1:1) to afford 152 mg (42%) of the title compound as brown oil. LCMS (ESI, m/z): 566.29 [M+H]⁺

Step 7: Synthesis of 3-[[(2S)-4-(methoxymethyl)-1-[6-oxo-5-(trifluoromethyl)-1,6-dihydropyridazin-4-yl]pyrrolidin-2-yl]methoxy]propanoic A solution of tert-butyl 3-[[(2S)-4-(methoxymethyl)-1-[6-oxo-5-(trifluoromethyl)-1-[[2-(trimethylsilyl)ethoxy]

methyl]-1,6-dihydropyridazin-4-yl]pyrrolidin-2-yl]
methoxy]propanoate (140 mg, 0.25 mmol, 1.00 equiv), TFA (2 mL) in DCM (10 mL) was stirred for 1 h at room temperature. The resulting mixture was concentrated under vacuum and the residue was applied onto a silica gel column eluting with DCM/methanol (10:1) to afford 90 mg (96%) of the title compound as brown oil. LCMS (ESI, m/z): 380.15 [M+H]+

Step 8: Synthesis of 6-[4-(3-[[(2S)-4-(methoxymethyl)-1-[6-oxo-5-(trifluoromethyl)-1,6-dihydropyridazin-4-yl]pyrrolidin-2-yl]methoxy]propanoyl)piperazin-1-yl]pyridine-3-carbonitrile A solution of 3-[[(2S)-4-(methoxymethyl)-1-[6-oxo-5-(trifluoromethyl)-1,6-dihydropyridazin-4-yl]pyrrolidin-2-yl]methoxy]propanoic acid (78 mg, 0.21 mmol, 1.00 equiv), EDC/HCl (99 mg, 2.50 equiv), 4-dimethylaminopyridine (50.3 mg, 0.41 mmol, 2.00 equiv), Int-A4 (46.4 mg, 0.25 mmol, 1.20 equiv) in DMF (3 mL) was stirred for 2 h at 60° C. After concentration, the residue was purified by C18 reverse phase chromatography eluting with H$_2$O/CH$_3$CN. Then the residue was further purified by Prep-HPLC yielding the title compound (6.1 mg, 5%) as a white solid. LCMS (ESI, m/z): 550.20 [M+H]+, 1H NMR (300 MHz, Methanol-d4) δ 8.45 (d, J=2.3 Hz, 1H), 8.13 (d, J=2.9 Hz, 1H), 7.79 (dd, J=9.1, 2.4 Hz, 1H), 6.89 (d, J=9.1 Hz, 1H), 4.66 (d, J=7.6 Hz, 1H), 3.87-3.60 (m, 11H), 3.54-3.40 (m, 3H), 3.36 (s, 3H), 3.27 (s, 1H), 3.25-3.08 (m, 1H), 2.64-2.62 (m, 2H), 2.58-1.39 (m, 3H)

Example 140: 6-(4-[3-[(1R)-1-[(2S)-1-[6-oxo-5-(trifluoromethyl)-1,6-dihydropyridazin-4-yl]pyrrolidin-2-yl]ethoxy]propanoyl]piperazin-1-yl)pyridine-3-carbonitrile and 6-(4-[3-[(1S)-1-[(2S)-1-[6-oxo-5-(trifluoromethyl)-1,6-dihydropyridazin-4-yl]pyrrolidin-2-yl]ethoxy]propanoyl]piperazin-1-yl)pyridine-3-carbonitrile

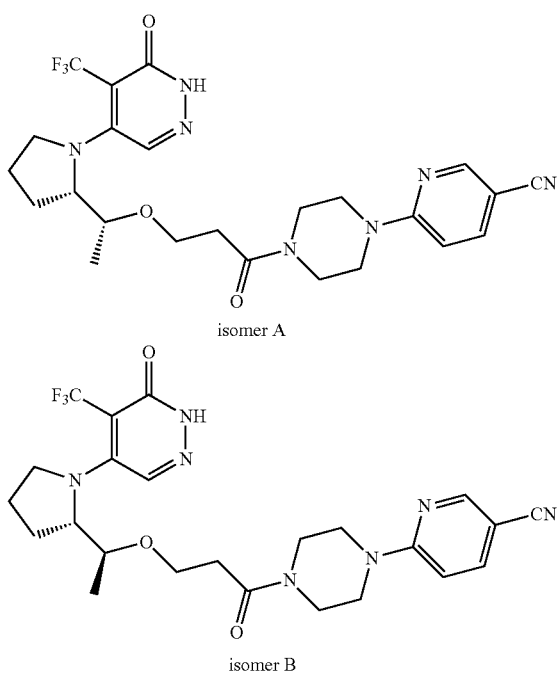

isomer A isomer B

Step 1: Synthesis of (2S)-1-[6-oxo-5-(trifluoromethyl)-1-[[2-(trimethylsilyl)ethoxy]methyl]-1,6-dihydropyridazin-4-yl]pyrrolidine-2-carboxylic Acid A solution of Int-A6 (3.28 g, 9.98 mmol, 1 equiv), (2S)-pyrrolidine-2-carboxylic acid (1.15 g, 9.99 mmol, 1.00 equiv), TEA (2.02 g, 19.96 mmol, 2.00 equiv) in MeCN (20 mL) was stirred for 3 hr at 60° C. The solids were filtered out after the resulting solution were cooled to room temperature. The resulting mixture was concentrated. This resulted in 3.91 g (96.19%) of the title compound as yellow oil. LCMS (ESI, m/z): 408.15 [M+H]+

Step 2: Synthesis of (2S)—N-methoxy-N-methyl-1-[6-oxo-5-(trifluoromethyl)-1-[[2-(trimethylsilyl)ethoxy]methyl]-1,6-dihydropyridazin-4-yl]pyrrolidine-2-carboxamide A solution of (2S)-1-[6-oxo-5-(trifluoromethyl)-1-[[2-(trimethylsilyl)ethoxy]methyl]-1,6-dihydropyridazin-4-yl]pyrrolidine-2-carboxylic acid (3.91 g, 9.60 mmol, 1 equiv), SOCl2 (1.4 mL, 11.70 mmol, 2 equiv) in DCM (20 mL) was stirred for 2 hr at room temperature. Then the resulting solution was concentrated and dissolved in DCM (30 mL), then methoxy(methyl)amine hydrochloride (1.9 g, 19.19 mmol, 2 equiv) and TEA (2.9 g, 28.79 mmol, 3 equiv) were added. The resulting solution was allowed to react, with stirring, for an additional 1 hr at room temperature. The resulting mixture was washed with 2×10 of H$_2$O. Then organic were combined and concentrated. The residue was applied onto a silica gel column with EtOAc/petroleum ether (1/2). This resulted in 2.02 g (46.7%) of the title compound as yellow oil. LCMS (ESI, m/z): 451.19 [M+H]+

Step 3: Synthesis of 5-[(2S)-2-acetylpyrrolidin-1-yl]-4-(trifluoromethyl)-2-[[2-(trimethylsilyl)ethoxy]methyl]-2,3-dihydropyridazin-3-one A solution of (2S)—N-methoxy-N-methyl-1-[6-oxo-5-(trifluoromethyl)-1-[[2-(trimethylsilyl)ethoxy]methyl]-1,6-dihydropyridazin-4-yl]pyrrolidine-2-carboxamide (2.02 g, 4.48 mmol, 1 equiv) in THF (30 mL) maintained with an inert atmosphere of nitrogen. This was followed by the addition of a solution of bromo(methyl)magnesium (4.5 mL, 37.60 mmol, 3.00 equiv) in THF (mL). The resulting solution was stirred for 4 hr at room temperature. The reaction was then quenched by the addition of 50 mL of water. The resulting solution was extracted with 3×50 ml of EtOAc and the organic layers was concentrated. The residue was applied onto a silica gel column with EtOAc/petroleum ether (1/2). This resulted in 1.434 g (78.88%) of the title compound as yellow oil. LCMS (ESI, m/z): 406.17 [M+H]+

Step 4: Synthesis of 5-[(2S)-2-(1-hydroxyethyl)pyrrolidin-1-yl]-4-(trifluoromethyl)-2-[[2-(trimethylsilyl)ethoxy]methyl]-2,3-dihydropyridazin-3-one A solution of 5-[(2S)-2-acetylpyrrolidin-1-yl]-4-(trifluoromethyl)-2-[[2-(trimethylsilyl)ethoxy]methyl]-2,3-dihydropyridazin-3-one (1.434 g, 3.54 mmol, 1 equiv), CaCl2 (784 mg, 7.06 mmol, 2.00 equiv), NaBH$_4$ (268 mg, 7.08 mmol, 2.00 equiv) in THF (20 mL) was stirred for 2 hr at room temperature. The solids were filtered out. The resulting mixture was concentrated. The residue was applied onto a silica gel column with EtOAc/petroleum ether (2/3). This resulted in 1.02 g (70.8%) of the title compound as yellow oil. LCMS (ESI, m/z): 408.19 [M+H]+

Step 5: Synthesis of Tert-Butyl 3-[1-[(2S)-1-[6-oxo-5-(trifluoromethyl)-1-[[2-(trimethylsilyl)ethoxy]methyl]-1,6-dihydropyridazin-4-yl]pyrrolidin-2-yl]ethoxy]propanoate A solution of 5-[(2S)-2-(1-hydroxyethyl)pyrrolidin-1-yl]-4-(trifluoromethyl)-2-[[2-(trimethylsilyl)ethoxy]methyl]-2,3-dihydropyridazin-3-one (600 mg, 1.47 mmol, 1 equiv), tert-butyl prop-2-enoate (941.7 mg, 7.35 mmol, 4.99 equiv), Cs$_2$CO$_3$ (479.7 mg, 1.47 mmol, 1.00 equiv) in MeCN (10 mL) was stirred for 5 hr at 80° C. The solids were filtered out. The resulting mixture was concentrated. The residue was applied onto a silica gel column with EtOAc/petroleum ether (1/4). This resulted in 190 mg (24.1%) of the title compound as yellow oil. LCMS (ESI, m/z): 536.27 [M+H]+

Step 6: Synthesis of 3-[1-[(2S)-1-[6-oxo-5-(trifluoromethyl)-1,6-dihydropyridazin-4-yl]pyrrolidin-2-yl]ethoxy]propanoic Acid A solution of tert-butyl 3-[1-[(2S)-1-[6-oxo-5-(trifluoromethyl)-1-[[2-(trimethylsilyl)ethoxy]methyl]-1,6-dihydropyridazin-4-yl]pyrrolidin-2-yl]ethoxy]propanoate (180 mg, 0.34 mmol, 1 equiv) in DCM (3 mL) and TFA (0.5 mL). The resulting solution was stirred for 3 hr at room temperature. The resulting mixture was concentrated. The resulting solution was dissolved in 5 mL NH3(g) in MeOH and allowed to react, with stirring, for an additional 1 hr at room temperature. The resulting mixture was concentrated again. This resulted in 117 mg (99.7%) of the title compound as a yellow solid. LCMS (ESI, m/z): 350.12 [M+H]+

Step 7: Synthesis of 6-(4-[3-[(1R)-1-[(2S)-1-[6-oxo-5-(trifluoromethyl)-1,6-dihydropyridazin-4-yl]pyrrolidin-2-yl]ethoxy]propanoyl]piperazin-1-yl)pyridine-3-carbonitrile and 6-(4-[3-[(1S)-1-[(2S)-1-[6-oxo-5-(trifluoromethyl)-1,6-dihydropyridazin-4-yl]pyrrolidin-2-yl]ethoxy]propanoyl]piperazin-1-yl)pyridine-3-carbonitrile A solution of 3-[1-[(2S)-1-[6-oxo-5-(trifluoromethyl)-1,6-dihydropyridazin-4-yl]pyrrolidin-2-yl]ethoxy]propanoic acid (117 mg, 0.33 mmol, 1 equiv), Int-A4 (66.2 mg, 0.35 mmol, 1.05 equiv), HATU (127.4 mg, 0.33 mmol, 1 equiv), DIEA (129.9 mg, 1.01 mmol, 3.00 equiv) in was placed DMF (10 mL) was stirred for 1 overnight at room temperature. The reaction was then quenched by the addition of 10 mL of water. The resulting solution was extracted with 3×10 ml of EtOAc concentrated. The residue was applied onto a silica gel column with EtOAc/petroleum ether (1/2). Then the residue was further purified by Prep-HPLC and Chiral-Prep-HPLC yielding (after arbitrary assignment of stereochemistry) the title compounds, respectively, isomer A (15.3 mg, 8.79%) as a white solid. LCMS (ESI, m/z): 520.10 [M+H]+, $^1$HNMR (Methanol-d4, 300 MHz) δ 8.44 (dd, J=2.3, 0.8 Hz, 1H), 8.13 (s, 1H), 7.78 (dd, J=9.1, 2.4 Hz, 1H), 6.88 (dd, J=9.1, 0.8 Hz, 1H), 4.36 (q, J=7.9 Hz, 1H), 3.90 (dt, J=9.1, 6.1 Hz, 1H), 3.78-3.63 (m, 7H), 3.67-3.48 (m, 3H), 3.37 (d, J=6.1 Hz, 2H), 2.49 (t, J=5.9 Hz, 2H), 2.21 (dt, J=13.3, 6.6 Hz, 1H), 1.98 (q, J=5.1, 4.7 Hz, 1H), 1.81-1.52 (m, 2H), 1.20 (d, J=6.1 Hz, 3H). tR=3.117 min (CHIRALPAK ID-3, 0.46*10 cm; 3 um, MtBE (0.1% DEA):EtOH=70:30, 1.0 mL/min) and isomer B (4.6 mg, 2.64%) as a white solid. LCMS (ESI, m/z): 520.10 [M+H]+, $^1$H NMR (300 MHz, Methanol-d$_4$) δ 8.44 (dd, J=2.4, 0.8 Hz, 1H), 8.12 (s, 1H), 7.78 (dd, J=9.1, 2.3 Hz, 1H), 6.88 (dd, J=9.1, 0.9 Hz, 1H), 4.52 (t, J=7.6 Hz, 1H), 3.91-3.60 (m, 12H), 3.42 (s, 2H), 2.65 (td, J=6.0, 2.4 Hz, 2H), 2.23-2.07 (m, 1H), 2.09-1.82 (m, 2H), 1.70 (dt, J=14.3, 7.4 Hz, 1H), 1.16 (d, J=6.3 Hz, 3H). tR=3.770 min (CHIRALPAK ID-3, 0.46*10 cm; 3 um, MtBE (0.1% DEA):EtOH=70:30, 1.0 mL/min).

Example 141: 6-(4-[2-[(2S,5S)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile, 6-(4-[2-[(2R,5S)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile, 6-(4-[2-[(2S,5R)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile and 6-(4-[2-[(2R,5R)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile

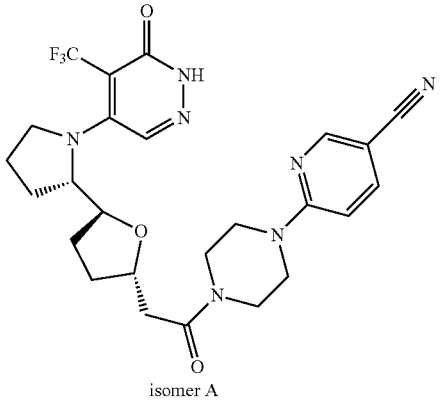

isomer A

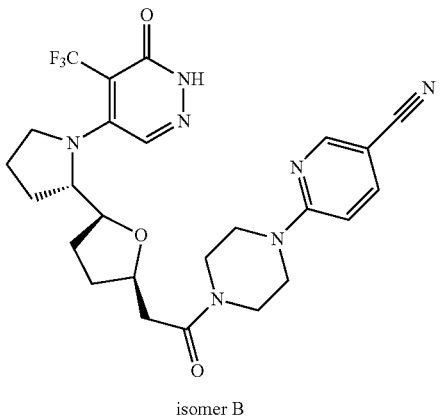

isomer B

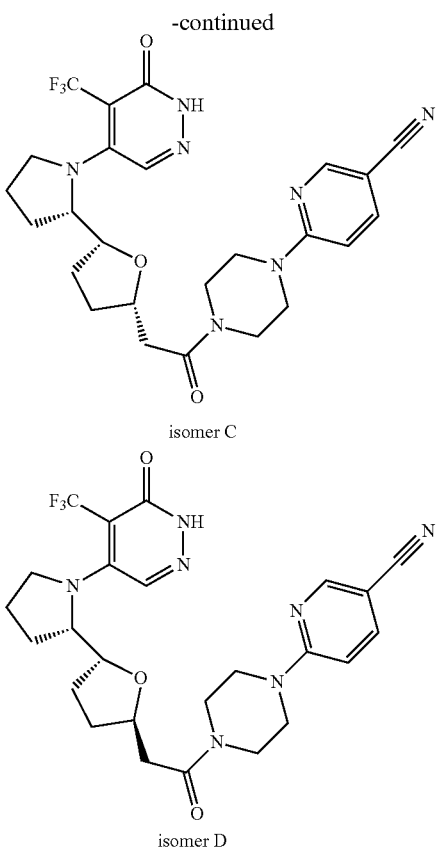

isomer C isomer D

Step 1: Synthesis of Tert-Butyl (2S)-2-(1-hydroxy-pent-4-en-1-yl)pyrrolidine-1-carboxylate Under maintained with an inert atmosphere of nitrogen, A solution of tert-butyl (2S)-2-formylpyrrolidine-1-carboxylate (10 g, 50.19 mmol, 1.00 equiv) in THF (50 mL), then the bromo(but-3-en-1-yl)magnesium in THF (120 mL) (1M, 1.20 equiv) was added to the resulting solution at −10° C., then the resulting solution was stirred overnight at room temperature. The resulting mixture was concentrated under vacuum. The residue was applied onto a silica gel column eluting with DCM to afford 7 g (55%) of the title compound as yellow oil. LCMS (ESI, m/z): 256.18[M+H]+

Step 2: Synthesis of Tert-Butyl (2S)-2-[(4E)-1-hydroxy-6-oxohex-4-en-1-yl]pyrrolidine-1-carboxylate A solution of tert-butyl (2S)-2-(1-hydroxypent-4-en-1-yl)pyrrolidine-1-carboxylate (5.1 g, 19.97 mmol, 1.00 equiv), Grubbs 2$^{nd}$ generation catalyst (0.85 g, 0.05 equiv), (2E)-but-2-enal (7 g, 99.87 mmol, 5.00 equiv) in DCM (30 mL) was stirred overnight at 50° C. in an oil bath. The resulting mixture was concentrated under vacuum and the residue was applied onto a silica gel column eluting with DCM. This resulted in 2.85 g (50%) of the title compound as light yellow oil. LCMS (ESI, m/z): 284.18 [M+H]+

Step 3: Synthesis of Tert-Butyl (2S)-2-[5-(2-oxo-ethyl)oxolan-2-yl]pyrrolidine-1-carboxylate A solution of tert-butyl (2S)-2-[(4E)-1-hydroxy-6-oxo-hex-4-en-1-yl]pyrrolidine-1-carboxylate (2.83 g, 9.99 mmol, 1.00 equiv), sodium hydride (40 mg, 1.67 mmol, 0.10 equiv) in THF (30 mL) was stirred overnight at room temperature. The resulting mixture was concentrated under vacuum to afford 2.83 g (crude) of the title compound as light yellow oil. LCMS (ESI, m/z): 284.18 [M+H]+

Step 4: Synthesis of 2-[5-[(2S)-1-[(tert-butoxy)carbonyl]pyrrolidin-2-yl]oxolan-2-yl]acetic Acid A solution of tert-butyl (2S)-2-[5-(2-oxoethyl)oxolan-2-yl]pyrrolidine-1-carboxylate (2.83 g, 9.99 mmol, 1.00 equiv), AgNO3 (7.2 g, 4.00 equiv), sodium hydroxide (1.6 g, 40.00 mmol, 4.00 equiv) in methanol (20 mL) and water (40 mL) was stirred for 2 days at room temperature. The solids were filtered out. The pH value of the solution was adjusted to 4 with hydrogen chloride acqueous (2M). The resulting mixture was concentrated under vacuum. The resulting mixture was extracted with 100 mL×3 of DCM and the organic layers combined. This resulted in 0.75 g (25%) of the title compound as a solid. LCMS (ESI, m/z): 300.17 [M+H]+

Step 5: Synthesis of Tert-Butyl (2S)-2-(5-[2-[4-(5-cyanopyridin-2-yl)piperazin-1-yl]-2-oxoethyl]oxo-lan-2-yl)pyrrolidine-1-carboxylate A solution of 2-[5-[(2S)-1-[(tert-butoxy)carbonyl]pyrrolidin-2-yl]oxolan-2-yl]acetic acid (300 mg, 1.00 mmol, 1.00 equiv), DIEA (645 mg, 4.99 mmol, 5.00 equiv), HATU (260 mg, 0.68 mmol, 2.00 equiv), Int-A4 (450 mg, 2.00 mmol, 2.00 equiv) in DMF (10 mL), was stirred overnight at room temperature. The reaction was then quenched by the addition of 100 mL of water. The resulting solution was extracted with 3×50 mL of EtOAc and the organic layers combined and concentrated under vacuum. The residue was applied onto a silica gel column eluting with DCM to afford 200 mg (43%) of the title compound as light yellow oil. LCMS (ESI, m/z): 470.27 [M+H]+

Step 6: Synthesis of 6-[4-(2-[5-[(2S)-pyrrolidin-2-yl]oxolan-2-yl]acetyl)piperazin-1-yl]pyridine-3-carbonitrile Hydrochloride A solution of tert-butyl (2S)-2-(5-[2-[4-(5-cyanopyridin-2-yl)piperazin-1-yl]-2-oxoethyl]oxolan-2-yl)pyrrolidine-1-carboxylate (1.1 g, 2.34 mmol, 1.00 equiv) in hydrogen chloride/dioxane (20 mL) was stirred overnight at 25° C. The resulting mixture was concentrated under vacuum to afford 0.9 g (95%) of the title compound as a yellow solid. LCMS (ESI, m/z): 370.22 [M−Cl]+

Step 7: Synthesis of 6-[4-(2-[5-[(2S)-1-[6-oxo-5-(trifluoromethyl)-1-[[2-(trimethylsilyl)ethoxy]methyl]-1,6-dihydropyridazin-4-yl]pyrrolidin-2-yl]oxolan-2-yl]acetyl)piperazin-1-yl]pyridine-3-carbonitrile A solution of 6-[4-(2-[5-[(2S)-pyrrolidin-2-yl]oxolan-2-yl]acetyl)piperazin-1-yl]pyridine-3-carbonitrile hydrochloride (900 mg, 2.22 mmol, 1.00 equiv), TEA (670 mg, 6.62 mmol, 3.00 equiv), Int-A6 (880 mg, 2.68 mmol, 1.20 equiv) in ethanol (20 mL) was stirred for 2 h at 80° C. in an oil bath. The resulting mixture was concentrated under vacuum. The residue was applied onto a silica gel column eluting with DCM to afford 650 mg (44%) of the title compound as yellow oil. LCMS (ESI, m/z): 662.30 [M+H]

Step 8: Synthesis of 6-(4-[2-[(2S,5S)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile, 6-(4-[2-[(2R,5S)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile, 6-(4-[2-[(2S,5R)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile and 6-(4-[2-[(2R,5R)-5-[(2S)-1-[6-oxo-5-(trifluoromethyl)-1,6-dihydropyridazin-4-yl]pyrrolidin-2-yl]oxolan-2-yl]acetyl]piperazin-1-yl)pyridine-3-carbonitrile A solution of 6-[4-(2-[5-[(2S)-1-[6-oxo-5-(trifluoromethyl)-1-[[2-(trimethylsilyl)ethoxy]methyl]-1,6-dihydropyridazin-4-yl]pyrrolidin-2-yl]oxolan-2-yl]acetyl)piperazin-1-yl]pyridine-3-carbonitrile (650 mg, 0.98 mmol, 1.00 equiv) in DCM (5 mL) and TFA (5 mL) was stirred for 2 h at room temperature. After concentration, the residue was purified by C18 reverse phase chromatography eluting with H₂O/ACN. The residue was further purified by Prep-HPLC and Chiral-Prep-HPLC yielding the title compounds. The absolute stereochemistry of Isomer B was assigned based on a protein X-ray crystal structure obtained of Example 141 Isomer B, which confirmed the absolute stereochemistry of the more potent enantiomer. The absolute stereochemistry of the remaining diastereoisomers A, C, and D was arbitrarily assigned.

Isomer A (29.2 mg, 19%) as a white solid. LCMS (ESI, m/z): 532.30 [M+H]⁺, HNMR (400 MHz, DMSO-d₆) δ 12.24 (s, 1H), 8.49 (d, J=2.3 Hz, 1H), 8.05 (s, 1H), 7.87 (dd, J=9.1, 2.4 Hz, 1H), 6.88 (d, J=9.1 Hz, 1H), 4.46 (q, J=7.8 Hz, 1H), 4.35-4.23 (m, 1H), 3.82 (q, J=7.4 Hz, 1H), 3.70-3.62 (m, 3H), 3.52 (d, J=10.2 Hz, 4H), 3.23-3.14 (m, 1H), 2.66 (dd, J=14.8, 6.5 Hz, 1H), 2.40 (dd, J=14.8, 6.2 Hz, 1H), 2.19-2.01 (m, 1H), 2.02 (m, 2H), 1.90-1.81 (m, 1H), 1.71-1.40 (m, 4H). tR=6.92 min CHIRALPAK ID-3, 0.46*10 cm; 3 um, MtBE (0.1% DEA):EtOH=80:20, 1.0 mL/min)

Isomer B (26.9 mg, 18%) as a white solid. LCMS (ESI, m/z): 532.30 [M+H]⁺, HNMR (400 MHz, DMSO-d₆) δ12.29 (s, 1H), 8.51 (d, J=2.3 Hz, 1H), 8.16 (s, 1H), 7.89 (dd, J=9.1, 2.3 Hz, 1H), 6.93 (d, J=9.0 Hz, 1H), 4.48 (q, J=7.6 Hz, 1H), 4.19 (p, J=6.3 Hz, 1H), 3.72 (dd, J=13.0, 6.0 Hz, 5H), 3.54 (d, J=6.3 Hz, 7H), 3.25-3.15 (m, 1H), 2.70 (dd, J=15.4, 6.1 Hz, 1H), 2.51-2.43 (m, 1H), 2.13-1.95 (m, 2H), 1.90 (tt, J=9.4, 4.6 Hz, 2H), 1.71-1.47 (m, 4H). tR=3.95 min CHIRALPAK ID-3, 0.46*10 cm; 3 um, MtBE (0.1% DEA):EtOH=80:20, 1.0 mL/min), isomer C (0.6 mg) as a white solid. LCMS (ESI, m/z): 532.30 [M+H]⁺, HNMR (400 MHz, DMSO-d₆) δ12.29 (s, 1H), 8.51 (d, J=2.4 Hz, 1H), 8.16 (s, 1H), 7.89 (dd, J=9.1, 2.4 Hz, 1H), 6.93 (d, J=9.2 Hz, 1H), 4.48 (q, J=7.5 Hz, 1H), 4.19 (t, J=6.3 Hz, 1H), 3.72 (d, J=9.6 Hz, 3H), 3.65 (s, 2H), 3.54 (s, 5H), 3.19 (d, J=9.7 Hz, 1H), 2.75-2.67 (m, 1H), 2.55 (m, 1H), 2.08 (d, J=6.9 Hz, 1H), 2.01 (d, J=6.1 Hz, 1H), 1.89 (dd, J=13.1, 5.4 Hz, 2H), 1.64 (s, 3H), 1.64-1.50 (m, 1H). tR=8.23 min CHIRALPAK ID-3, 0.46*10 cm; 3 um, MtBE (0.1% DEA):EtOH=80:20, 1.0 mL/min) and isomer D (1.6 mg) as a white solid. LCMS (ESI, m/z): 532.30 [M+H]⁺, HNMR (400 MHz, DMSO-d₆) δ12.37 (s, 1H), 8.52 (d, J=2.3 Hz, 1H), 8.08 (s, 1H), 7.89 (dd, J=9.1, 2.4 Hz, 1H), 6.93 (d, J=9.0 Hz, 1H), 4.71 (d, J=8.4 Hz, 1H), 4.20 (t, J=6.4 Hz, 1H), 4.01 (d, J=7.1 Hz, 1H), 3.64-3.46 (m, 9H), 3.24 (s, 1H), 2.42 (dd, J=15.5, 6.7 Hz, 1H), 2.26 (dd, J=15.5, 6.1 Hz, 1H), 2.06-1.86 (m, 4H), 1.63-1.44 (m, 4H). tR=4.27 min CHIRALPAK ID-3, 0.46*10 cm; 3 um, MtBE (0.1% DEA):EtOH=80:20, 1.0 mL/min)

Example 142: 5-[(4aR,7aR)-1-acetyl-octahydro-1H-pyrrolo[3,4-b]pyridin-6-yl]-4-(trifluoromethyl)-2,3-dihydropyridazin-3-one

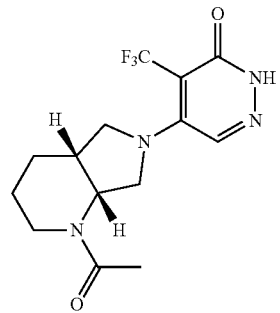 [SMILES: CC(=O)N1CCC[C@@H]2CN(c3cn[nH]c(=O)c3C(F)(F)F)C[C@@H]21]

Step 1: Synthesis of Tert-Butyl (4aR,7aR)-6-[6-oxo-5-(trifluoromethyl)-1-[[2-(trimethylsilyl)ethoxy]methyl]-1,6-dihydropyridazin-4-yl]-octahydro-1H-pyrrolo[3,4-b]pyridine-1-carboxylate A solution of tert-butyl (4aR,7aR)-octahydro-1H-pyrrolo[3,4-b]pyridine-1-carboxylate (500 mg, 2.21 mmol, 1 equiv), Cs₂CO₃ (1439.6 mg, 4.42 mmol, 2.0 equiv) and Int-A6 (1086.3 mg, 3.31 mmol, 1.50 equiv) in MeCN (30 mL) was stirred for 2 h at 60° C., and then the resulting solution was diluted with 50 ml of H₂O, extracted with 3×50 ml of EtOAc, the organic layer was washed with 1×50 ml of brine, dried over anhydrous sodium sulfate and concentrated. Under vacuum, and then the residue was applied onto a silica gel column eluting with EtOAc/petroleum ether (16/84) to afford (85.96%) of the title compound as yellow oil. LCMS (ESI, m/z): δ 18.25 [M+H]⁺.

Step 2: Synthesis of 5-[(4aR,7aR)-octahydro-1H-pyrrolo[3,4-b]pyridin-6-yl]-4-(trifluoromethyl)-2,3-dihydropyridazin-3-one A solution of tert-butyl (4aR,7aR)-6-[6-oxo-5-(trifluoromethyl)-1-[[2-(trimethyl silyl)ethoxy]methyl]-1,6-dihydropyridazin-4-yl]-octahydro-1H-pyrrolo[3,4-b]pyridine-1-carboxylate (500 mg, 0.96 mmol, 1.00 equiv) and TFA (2 mL) in DCM (10 mL) was stirred for 2h at room temperature, and then the resulting solution was concentrated under vacuum to afford 200 mg of the title compound as a crude white solid. LCMS (ESI, m/z): 289.12[M+H]⁺.

Step 3: Synthesis of 5-[(4aR,7aR)-1-acetyl-octahydro-1H-pyrrolo[3,4-b]pyridin-6-yl]-4-(trifluoromethyl)-2,3-dihydropyridazin-3-one A solution of 5-[(4aR,7aR)-octahydro-1H-pyrrolo[3,4-b]pyridin-6-yl]-4-(trifluoromethyl)-2,3-dihydropyridazin-3-one (190 mg, 0.66 mmol, 1 equiv), Ac₂O (134.6 mg, 1.32 mmol, 2.00 equiv) and TEA (200.1 mg, 1.98 mmol, 3.0 equiv) in DCM (30 mL) was stirred for 2 h at room temperature, and then the resulting solution was diluted with 30 mL of DCM, washed with 3×30 ml of H₂O, the organic layer was combined and washed with 1×30 ml of brine, dried over anhydrous sodium sulfate and concentrated under vacuum, and then the residue was purified by Prep-HPLC yielding the title compound (86.4 mg, 39.69%) as a white solid. LCMS (ESI, m/z): 331.20 [M+H]+, 1HNMR (DMSO-d6, 300 MHz,) δ 7.87 (s, 1H), 4.84-4.71 (m, 1H), 3.84 (d, J=5.4 Hz, 2H), 3.64 (d, J=9.9 Hz, 2H), 3.53-3.20 (m, 2H), 2.28-2.19 (m, 1H), 2.03 (s, 3H), 1.78-1.35 (m, 4H).

Example 143: 5-[(4aS,7aS)-1-acetyl-octahydro-1H-pyrrolo[3,4-b]pyridin-6-yl]-4-(trifluoromethyl)-2,3-dihydropyridazin-3-one

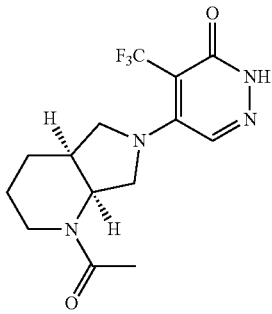 [SMILES: CC(=O)N1CCC[C@H]2CN(c3cn[nH]c(=O)c3C(F)(F)F)C[C@H]21]

Step 1: Synthesis of Tert-Butyl (4aS,7aS)-6-[6-oxo-5-(trifluoromethyl)-1-[[2-(trimethylsilyl)ethoxy]methyl]-1,6-dihydropyridazin-4-yl]-octahydro-1H-pyrrolo[3,4-b]pyridine-1-carboxylate A solution of tert-butyl (4aS,7aS)-octahydro-1H-pyrrolo[3,4-b]pyridine-1-carboxylate (500 mg, 2.21 mmol, 1 equiv), Int-A6 (726.4 mg, 2.21 mmol, 1.00 equiv) and TEA (670.7 mg, 6.63 mmol, 3.00 equiv) in EtOH (10 mL) was stirred for 2 h at 60° C., and then the resulting solution was concentrated under vacuum, and then the residue was applied onto a silica gel column eluting with EtOAc/petroleum ether (1:5) to afford 678 mg (59.17%) of the title compound as yellow oil. LCMS (ESI, m/z): 519.26[M+H]+.

Step 2: Synthesis of 5-[(4aS,7aS)-octahydro-1H-pyrrolo[3,4-b]pyridin-6-yl]-4-(trifluoromethyl)-2,3-dihydropyridazin-3-one A solution of tert-butyl (4aS,7aS)-6-[6-oxo-5-(trifluoromethyl)-1-[[2-(trimethyl silyl)ethoxy]methyl]-1,6-dihydropyridazin-4-yl]-octahydro-1H-pyrrolo[3,4-b]pyridine-1-carboxylate (300 mg, 0.58 mmol, 1 equiv) in HCl/dioxane (9 mL, 4M) was stirred for 2h at room temperature, and then the resulting solution was concentrated under vacuum to afford 190 mg (63.33%) of the title compound as yellow oil. LCMS (ESI, m/z): 289.12 [M+H]+.

Step 3: Synthesis of 5-[(4aS,7aS)-1-acetyl-octahydro-1H-pyrrolo[3,4-b]pyridin-6-yl]-4-(trifluoromethyl)-2,3-dihydropyridazin-3-one A solution of 5-[(4aS,7aS)-octahydro-1H-pyrrolo[3,4-b]pyridin-6-yl]-4-(trifluoromethyl)-2,3-dihydropyridazin-3-one (729 mg, 2.53 mmol, 1 equiv), Ac2O (516.3 mg, 5.06 mmol, 2.0 equiv) and TEA (767.7 mg, 7.59 mmol, 3.00 equiv) in DCM (10 mL, 0.12 mmol) was stirred for 1.5h at room temperature, and then the resulting solution was concentrated under vacuum, and then the residue was purified by C18 reverse phase chromatography eluting with H2O/CH3CN, after concentration, the residue was further purified by Prep-HPLC yielding the title compound (41.9 mg, 5.02%) as a white solid. LCMS (ESI, m/z): 331.15 [M+H]+, 1HNMR (DMSO-d6, 300 MHz) δ 7.80 (s, 1H), 4.84-4.71 (m, 1H), 3.82-3.20 (m, 6H), 2.32-2.19 (m, 1H), 2.03 (s, 3H), 1.76-1.27 (m, 4H).

Example 144: 6-[4-[2-([2-[(1R)-2-[6-oxo-5-(trifluoromethyl)-1,6-dihydropyridazin-4-yl]-2,3-dihydro-1H-isoindol-1-yl]ethyl]amino)acetyl]piperazin-1-yl]pyridine-3-carbonitrile and 6-[4-[2-([2-[(1 S)-2-[6-oxo-5-(trifluoromethyl)-1,6-dihydropyridazin-4-yl]-2,3-dihydro-1H-isoindol-1-yl]ethyl]amino)acetyl]piperazin-1-yl]pyridine-3-carbonitrile

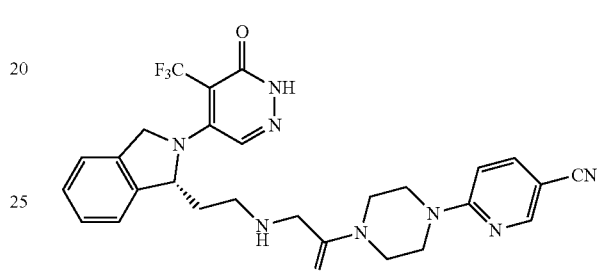

isomer A

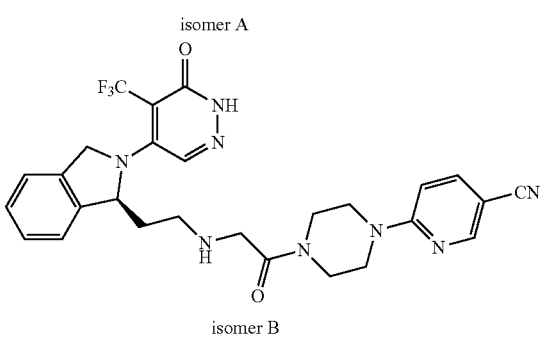

isomer B

Step 1: Synthesis of 5-[1-(2-aminoethyl)-2,3-dihydro-1H-isoindol-2-yl]-4-(trifluoromethyl)-2-[[2-(trimethylsilyl)ethoxy]methyl]-2,3-dihydropyridazin-3-one A solution of 5-[1-(2-azidoethyl)-2,3-dihydro-1H-isoindol-2-yl]-4-(trifluoromethyl)-2-[[2-(trimethylsilyl)ethoxy]methyl]-2,3-dihydropyridazin-3-one (370 mg, 0.77 mmol, 1 equiv), PPh3 (242.3 mg, 0.92 mmol, 1.2 equiv) in THF (15 mL) and H2O (5 mL) was stirred for 1 h at 60° C. The resulting mixture was concentrated under vacuum. The residue was applied onto a silica gel column eluting with DCM/methanol (94/6) to afford 217 mg (62.00%) of the title compound as yellow oil. LCMS (ESI, m/z): 455.20 [M+H]+

Step 2: Synthesis of 6-[4-(2-chloroacetyl)piperazin-1-yl]pyridine-3-carbonitrile To a solution of Int-A4 (1100 mg, 4.90 mmol, 1 equiv), TEA (1486.2 mg, 14.69 mmol, 3 equiv) in DCM (10 mL), 2-chloroacetyl chloride (663.5 mg, 5.87 mmol, 1.2 equiv) was added at 0° C. The resulting solution was stirred for 1 h at 0° C. The resulting mixture was concentrated under vacuum. The residue was applied onto a silica gel column eluting with EtOAc/petroleum ether (56/44) to afford 752 mg (58.03%) of the title compound as a yellow solid. LCMS (ESI, m/z): 265.08[M+H]+

Step 3: Synthesis of 6-(4-[2-[(2-[2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]ethyl)amino]acetyl]piperazin-1-yl)pyridine-3-carbonitrile A solution of 5-[1-(2-aminoethyl)-2,3-dihydro-1H-isoindol-2-yl]-4-(trifluoromethyl)-2-[[2-(trimethylsilyl)ethoxy]methyl]-2,3-dihydropyridazin-3-one (200 mg, 0.44 mmol, 1 equiv), TEA (89.0 mg, 0.88 mmol, 2 equiv), 6-[4-(2-chloroacetyl)piperazin-1-yl]pyridine-3-carbonitrile (116.5 mg, 0.44 mmol, 1 equiv) in EtOH (10 mL) was stirred for 25 h at 80° C. The resulting mixture was concentrated under vacuum. The residue was applied onto a silica gel column eluting with DCM/methanol (97/3). After concentration, the residue was purified by C18 reverse phase chromatography eluting with $H_2O$/$CH_3CN$ to afford 96 mg (31.95%) of the title compound as a yellow solid. LCMS (ESI, m/z): 683.30 [M+H]+

Step 4: Synthesis of 6-[4-[2-([2-[(1S)-2-[6-oxo-5-(trifluoromethyl)-1,6-dihydropyridazin-4-yl]-2,3-dihydro-1H-isoindol-1-yl]ethyl]amino)acetyl]piperazin-1-yl]pyridine-3-carbonitrile and 6-[4-[2-([2-[(1R)-2-[6-oxo-5-(trifluoromethyl)-1,6-dihydropyridazin-4-yl]-2,3-dihydro-1H-isoindol-1-yl]ethyl]amino)acetyl]piperazin-1-yl]pyridine-3-carbonitrile A solution of 6-(4-[2-[(2-[2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]ethyl)amino]acetyl]piperazin-1-yl)pyridine-3-carbonitrile (80 mg, 0.12 mmol, 1 equiv) in DCM (1 mL) and TFA (0.05 mL) was stirred for 2 h at room temperature. The reaction was then quenched by the addition of 5 mL of saturated sodium bicarbonate aqueous. The resulting solution was extracted with 3×30 ml of DCM and the organic layers combined. After concentration, the residue was purified by C18 reverse phase chromatography eluting with $H_2O$/$CH_3CN$. Then the residue was further purified by Prep-HPLC and Chiral-Prep-HPLC yielding (after arbitrary assignment of stereochemistry) the title compounds, respectively, isomer A: (10.2 mg, 15.76%) as a white solid. LCMS (ESI, m/z): 553.22 [M+H]+, $^1$H NMR (300 MHz, DMSO-d6) δ: 8.52 (d, J=2.4 Hz, 1H), 8.26 (d, J=8.0 Hz, 1H), 7.89 (dd, J=9.0, 2.4 Hz, 1H), 7.45-7.27 (m, 4H), 6.94 (d, J=9.1 Hz, 1H), 5.88 (d, J=5.7 Hz, 1H), 5.06 (d, J=14.9 Hz, 1H), 4.51 (d, J=15.0 Hz, 1H), 3.73-3.62 (m, 8H), 3.53 (d, J=15.1 Hz, 2H), 2.47 (d, J=7.0 Hz, 2H), 1.99 (d, J=14.4 Hz, 2H). tR=3.565 min (Chiralpak IG-3, 2*25 cm, 5 um, MtBE (0.1% TEA):MeOH=70:30, 1.0 mL/min) and isomer B: (10.0 mg, 15.45%) as a white solid. LCMS (ESI, m/z): 553.22 [M+H]+, tR=4.753 min (Chiralpak IG-3, 2*25 cm, 5 um, MtBE (0.1% TEA):MeOH=70:30, 1.0 mL/min)

Example 145: 6-[4-[(3R)-3-amino-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile; formic acid and 6-[4-[(3S)-3-amino-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile; Formic Acid

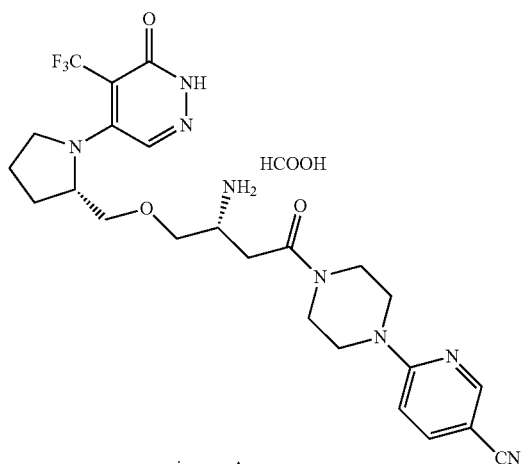

isomer A

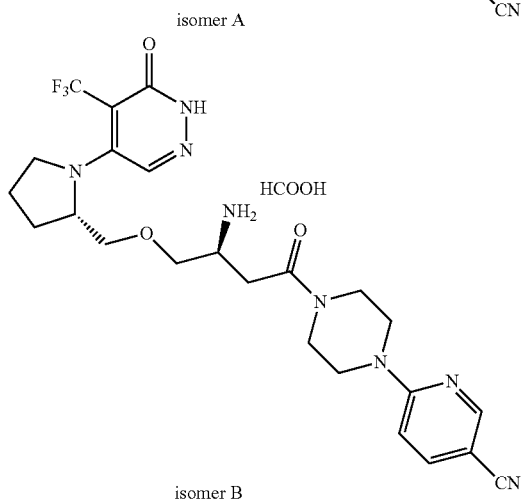

isomer B

Step 1: Synthesis of Methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate Under $N_2$ (g) atmosphere, a solution of 5-[(2S)-2-(hydroxymethyl)pyrrolidin-1-yl]-4-(trifluoromethyl)-2-[[2-(trimethylsilyl)ethoxy]methyl]-2,3-dihydropyridazin-3-one (2.0 g, 5.08 mmol, 1.00 equiv), Pd[(allyl)Cl]$_2$ (93.0 mg, 0.25 mmol, 0.05 equiv), Rockphos (239 mg, 0.51 mmol, 0.10 equiv), $Cs_2CO_3$ (2.0 g, 6.14 mmol, 1.30 equiv), methyl (2E)-4-bromobut-2-enoate (4.6 mg, 0.03 mmol, 5.00 equiv) in toluene (5 mL) was stirred overnight at 80° C. in an oil bath. After concentration, the residue was applied onto a silica gel column eluting with EtOAc/petroleum ether (27:73) to afford 800 mg (32%) of the title compound as yellow oil. LCMS (ESI, m/z): 492.21 [M+H]+

Step 2: Synthesis of Methyl 3-(benzylamino)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate A solution of methyl (2E)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]but-2-enoate (650 mg, 1.32 mmol, 1.00 equiv), 1-phenylmethanamine (700 mg, 6.53 mmol, 5.00 equiv) in n-BuOH (15 mL) was stirred for 3 h at 100° C. in an oil bath. After concentration, the residue was applied onto a silica gel column eluting with EtOAc/petroleum ether (61:39) to afford 630 mg (80%) of the title compound as a yellow oil. LCMS (ESI, m/z): 599.28 [M+H]$^+$ Step 3: Synthesis of Methyl 3-[[(tert-butoxy)carbonyl]amino]-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate Under $H_2$, a solution of methyl 3-(benzylamino)-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate (600 mg, 1.00 mmol, 1.00 equiv), Palladium carbon (200 mg), (Boc)$_2$O (700 mg, 3.21 mmol, 3.00 equiv) in methanol (30 mL) was stirred overnight at 25° C. The solids were filtered out. After concentration, the residue was applied onto a silica gel column eluting with EtOAc/petroleum ether (30:70) to afford 200 mg (33%) of the title compound as a light yellow oil. LCMS (ESI, m/z): 609.29 [M+H]$^+$ Step 4: Synthesis of 3-[[(tert-butoxy)carbonyl]amino]-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoic Acid A solution of methyl 3-[[(tert-butoxy)carbonyl]amino]-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoate (190 mg, 0.31 mmol, 1.00 equiv), LiOH.H$_2$O (26 mg, 0.62 mmol, 2.00 equiv) in methanol (1 mL) and water (1 mL) was stirred for 6 h at 25° C. The resulting mixture was concentrated under vacuum to afford 180 mg (97%) of the title compound d as a yellow oil. LCMS (ESI, m/z): 595.27 [M+H]$^+$ Step 5: Synthesis of Tert-Butyl N-[4-[4-(5-cyanopyridin-2-yl)piperazin-1-yl]-4-oxo-1-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butan-2-yl]carbamate A solution of 3-[[(tert-butoxy)carbonyl]amino]-4-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butanoic acid (180 mg, 0.30 mmol, 1.00 equiv), DIEA (40 mg, 0.31 mmol, 1.00 equiv), HATU (115 mg, 0.30 mmol, 1.00 equiv), Int-A4 (59 mg, 0.31 mmol, 1.00 equiv) in DMF (4 mL) was stirred for 1 overnight at 25° C. After concentration, the residue was applied onto a silica gel column eluting with EtOAc/petroleum ether (98:2) to afford 200 mg (86%) of the title compound as a white solid. LCMS (ESI, m/z): 766.37 [M+H]$^+$ Step 6: Synthesis of 6-[4-[(3R)-3-amino-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile; Formic Acid and 6-[4-[(3S)-3-amino-4-[[(2S)-1-[6-oxo-5-(trifluoromethyl)-1,6-dihydropyridazin-4-yl]pyrrolidin-2-yl]methoxy]butanoyl]piperazin-1-yl]pyridine-3-carbonitrile; Formic Acid A solution of tert-butyl N-[4-[4-(5-cyanopyridin-2-yl)piperazin-1-yl]-4-oxo-1-[[(2S)-1-[6-oxo-5-(trifluoromethyl)-1-[[2-(trimethylsilyl)ethoxy]methyl]-1,6-dihydropyridazin-4-yl]pyrrolidin-2-yl]methoxy]butan-2-yl]carbamate (200 mg, 0.26 mmol, 1.00 equiv), a solution of TFA/DCM (12 mL) in DCM (10 mL) was stirred for 1 h at 25° C. The resulting mixture was concentrated under vacuum. Then adjusted its pH to 8 with $NH_2CH_2CH_2OH$. After concentration, the residue was purified by C18 reverse phase chromatography eluting with $H_2O/CH_3CN$ and Chiral-Prep-HPLC yielding (after arbitrary assignment of stereochemistry) the title compounds, respectively, isomer A (10.5 mg 16%) as a white solid. LCMS (ESI, m/z): 535.35 [M+H]$^+$, $^1$HNMR (Methanol-d$_4$, 300 MHz) δ: 8.55 (s, 1H), 8.47 (d, J=2.2 Hz, 1H), 8.25 (s, 1H), 7.81 (dd, J=9.1, 2.4 Hz, 1H), 6.92 (d, J=9.1 Hz, 1H), 4.70 (dr, 1H), 3.81-3.74 (m, 10H), 3.69-3.61 (m, 1H), 3.59-3.40 (m, 4H), 2.68-2.67 (m, 1H), 2.58-2.55 (m, 1H), 2.30-2.28 (m, 1H), 2.04-2.02 (m, 1H), 1.84-1.72 (m, 2H). tR=4.088 min (CHIRALPAK ID-3, 0.46*10 cm; 3 um, MtBE (0.1% DEA):EtOH=70:30, 1.0 mL/min) and isomer B (20.9 mg 32%) as a white solid. LCMS (ESI, m/z): 535.30 [M+H]$^+$, $^1$HNMR (Methanol-d$_4$, 300 MHz) δ8.53 (s, 1H), 8.46 (d, J=1.8 Hz, 1H), 8.18 (s, 1H), 7.82-7.78 (dd, J=9.1, 2.4 Hz, 1H), 6.93-6.90 (d, J=9.0 Hz, 1H), 4.66 (dr, 1H), 3.84-3.60 (m, 11H), 3.58-3.40 (m, 3H), 3.45-3.38 (m, 1H), 2.85-2.79 (m, 1H), 2.69-2.61 (m, 1H), 2.30-2.28 (m, 1H), 2.04-2.02 (m, 1H), 1.84-1.72 (m, 2H). tR=6.124 min (CHIRALPAK ID-3, 0.46*10 cm; 3 um, MtBE (0.1% DEA):EtOH=70:30, 1.0 mL/min)

Example 146: 6-[4-[3-([[(1S)-2-[6-oxo-5-(trifluoromethyl)-1,6-dihydropyridazin-4-yl]-2,3-dihydro-1H-isoindol-1-yl]methyl]amino)propanoyl]piperazin-1-yl]pyridine-3-carbonitrile and 6-[4-[3-([[(1R)-2-[6-oxo-5-(trifluoromethyl)-1,6-dihydropyridazin-4-yl]-2,3-dihydro-1H-isoindol-1-yl]methyl]amino)propanoyl]piperazin-1-yl]pyridine-3-carbonitrile

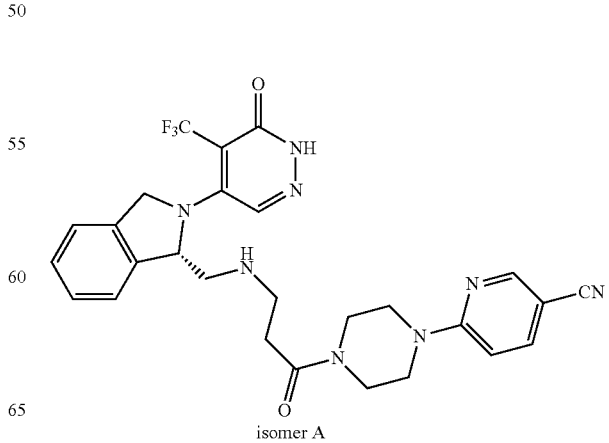

isomer A

301

-continued

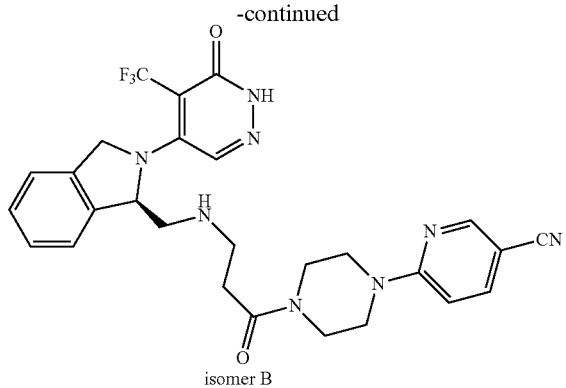

isomer B

Step 1: Synthesis of 5-[1-(azidomethyl)-2,3-dihydro-1H-isoindol-2-yl]-4-(trifluoromethyl)-2-[[2-(trimethylsilyl)ethoxy]methyl]-2,3-dihydropyridazin-3-one To a stirred solution of 5-[1-(hydroxymethyl)-2,3-dihydro-1H-isoindol-2-yl]-4-(trifluoromethyl)-2-[[2-(trimethyl silyl)ethoxy]methyl]-2,3-dihydropyridazin-3-one (900 mg, 2.04 mmol, 1.00 equiv) in toluene (15 mL), DBU (0.8 mL) and DPPA (1 mL) were added. The resulting solution was stirred for 10 h at 80° C. The resulting solution was diluted with 200 mL of EtOAc. The resulting mixture was washed with 1×50 mL of NH$_4$Cl and 1×50 mL of NaHCO$_3$. The resulting mixture was washed with 1×50 mL of Brine. The organic layer was dried over anhydrous sodium sulfate and concentrated under vacuum. The residue was applied onto a silica gel column with EtOAc/petroleum ether (1:4). This resulted in 700 mg (crude) of the title compound as a white solid. LCMS (ESI, m/z): 467.18 [M+H]$^+$.

Step 2: Synthesis of 5-[1-(aminomethyl)-2,3-dihydro-1H-isoindol-2-yl]-4-(trifluoromethyl)-2-[[2-(trimethylsilyl)ethoxy]methyl]-2,3-dihydropyridazin-3-one A solution of 5-[1-(azidomethyl)-2,3-dihydro-1H-isoindol-2-yl]-4-(trifluoromethyl)-2-[[2-(trimethylsilyl)ethoxy]methyl]-2,3-dihydropyridazin-3-one (700 mg, 1.50 mmol, 1.00 equiv) and Palladium carbon (100 mg) in EtOAc (50 mL) was stirred for 3 h at room temperature under hydrogen. The solids were filtered out. The resulting mixture was concentrated under vacuum. This resulted in 500 mg (crude) of the title compound as a white solid. LCMS (ESI, m/z): 441.19 [M+H]$^+$

Step 3: Synthesis of Tert-Butyl 3-[([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methyl)amino]propanoate A solution of 5-[1-(aminomethyl)-2,3-dihydro-1H-isoindol-2-yl]-4-(trifluoromethyl)-2-[[2-(trimethylsilyl)ethoxy]methyl]-2,3-dihydropyridazin-3-one (500 mg, 1.13 mmol, 1.00 equiv) and tert-butyl prop-2-enoate (0.5 mL) in ethanol (10 mL) was stirred overnight at 100° C. The resulting mixture was concentrated under vacuum. The residue was applied onto a silica gel column with EtOAc/petroleum ether (1:1). This resulted in 200 mg (31%) of the title compound as yellow oil. LCMS (ESI, m/z): 569.28 [M+H]$^+$.

Step 4: Synthesis of 3-[([2-[6-oxo-5-(trifluoromethyl)-1,6-dihydropyridazin-4-yl]-2,3-dihydro-1H-isoindol-1-yl]methyl)amino]propanoic Acid A solution of tert-butyl 3-[([2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]methyl)amino]propanoate (110 mg, 0.19 mmol, 1.00 equiv) in hydrogen chloride/dioxane (10 mL) was stirred overnight at room temperature. The resulting mixture was concentrated under vacuum. This resulted in 90 mg (crude) of the title compound as a solid. LCMS (ESI, m/z): 383.13 [M+H]$^+$.

Step 5: Synthesis of 3-[[(tert-butoxy)carbonyl]([2-[6-oxo-5-(trifluoromethyl)-1,6-dihydropyridazin-4-yl]-2,3-dihydro-1H-isoindol-1-yl]methyl)amino] propanoic Acid A stirred solution of 3-[([2-[6-oxo-5-(trifluoromethyl)-1,6-dihydropyridazin-4-yl]-2,3-dihydro-1H-isoindol-1-yl]methyl)amino]propanoic acid (90 mg, 0.24 mmol, 1.00 equiv) in THF (5 mL) and water (5 mL), sodium bicarbonate (50 mg, 0.60 mmol, 2.53 equiv) and Boc$_2$O (50 mg, 0.23 mmol, 0.97 equiv) were added. The resulting solution was stirred overnight at room temperature. The pH value of the solution was adjusted to 2 with hydrogen chloride (1 M). The resulting solution was diluted with 100 mL of EtOAc. The resulting mixture was washed with 1×20 mL of water and 1×20 mL of Brine. The organic layer was dried over anhydrous sodium sulfate and concentrated under vacuum. This resulted in 100 mg (crude) of the title compound as a solid. LCMS (ESI, m/z): 483.18 [M+H]$^+$.

Step 6: Synthesis of Tert-Butyl N-[3-[4-(5-cyanopyridin-2-yl)piperazin-1-yl]-3-oxopropyl]-N-([2-[6-oxo-5-(trifluoromethyl)-1,6-dihydropyridazin-4-yl]-2,3-dihydro-1H-isoindol-1-yl]methyl)carbamate To a stirred solution of 3-[[(tert-butoxy)carbonyl]([2-[6-oxo-5-(trifluoromethyl)-1,6-dihydropyridazin-4-yl]-2,3-dihydro-1H-isoindol-1-yl]methyl)amino]propanoic acid (100 mg, 0.21 mmol, 1.00 equiv) in DMF (5 mL), Int-A4 (39 mg, 0.21 mmol, 1.0 equiv), DIPEA (0.3 mL) and HATU (79 mg, 0.21 mmol, 1.0 equiv) were added. The resulting solution was stirred for 2 h at room temperature. After concentration, the residue was purified by C18 reverse phase chromatography eluting with H$_2$O/CH$_3$CN. This resulted in 70 mg (52%) of the title compound as a white solid. LCMS (ESI, m/z): 653.28 [M+H]$^+$.

Step 7: Synthesis of 6-[4-[3-([[(1S)-2-[6-oxo-5-(trifluoromethyl)-1,6-dihydropyridazin-4-yl]-2,3-dihydro-1H-isoindol-1-yl]ethyl]amino)propanoyl]piperazin-1-yl]pyridine-3-carbonitrile and 6-[4-[3-([[(1R)-2-[6-oxo-5-(trifluoromethyl)-1,6-dihydropyridazin-4-yl]-2,3-dihydro-1H-isoindol-1-yl]methyl]amino)propanoyl]piperazin-1-yl]pyridine-3-carbonitrile To a stirred solution of tert-butyl N-[3-[4-(5-cyanopyridin-2-yl)piperazin-1-yl]-3-oxopropyl]-N-([2-[6-oxo-5-(trifluoromethyl)-1,6-dihydropyridazin-4-yl]-2,3-dihydro-1H-isoindol-1-yl]methyl)carbamate (70 mg, 0.11 mmol, 1.00 equiv) in DCM (5 mL), TFA (1.5 mL) was added. The resulting solution was stirred for 1 h at room temperature. After concentration, the residue was purified by C18 reverse phase chromatography eluting with H$_2$O/CH$_3$CN. Then the residue was further purified by Prep-HPLC and Chiral-Prep-HPLC yielding (after arbitrary assignment of stereochemistry) the title compounds, respectively, isomer A (3.1 mg, 25%) as a white solid. LCMS (ESI, m/z): 553.30 [M+H]⁺. ¹HNMR (Methanol-d₄, 400 MHz) δ 8.44 (d, J=2.3 Hz, 1H), 8.27 (s, 1H), 7.77 (dd, J=9.1, 2.4 Hz, 1H), 7.43 (dd, J=6.3, 3.4 Hz, 1H), 7.35 (d, J=3.0 Hz, 3H), 6.87 (d, J=9.1 Hz, 1H), 5.79 (t, J=5.3 Hz, 1H), 5.23 (d, J=14.7 Hz, 1H), 4.60 (d, J=15.1 Hz, 1H), 3.80-3.57 (m, 8H), 3.15 (dd, J=13.0, 4.8 Hz, 1H), 2.99 (dd, J=13.0, 5.8 Hz, 1H), 2.94-2.83 (m, 2H), 2.55 (t, J=6.4 Hz, 2H). Rt=2.778 min (CHIRELPAK IF-3, 0.46*10 cm; 3 um, MtBE (0.1% DEA):EtOH=70:30, 1.0 mL/min) and isomer B (4.1 mg, 33%) as a white solid. LCMS (ESI, m/z): 553.30 [M+H]⁺. Rt=3.698 min (CHIRELPAK IF-3, 0.46*10 cm; 3 um, MtBE (0.1% DEA):EtOH=70:30, 1.0 mL/min).

Example 147: 5-[(2S)-2-[(2S,5S)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2 S,5R)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2R,5S)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2R,5R)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one

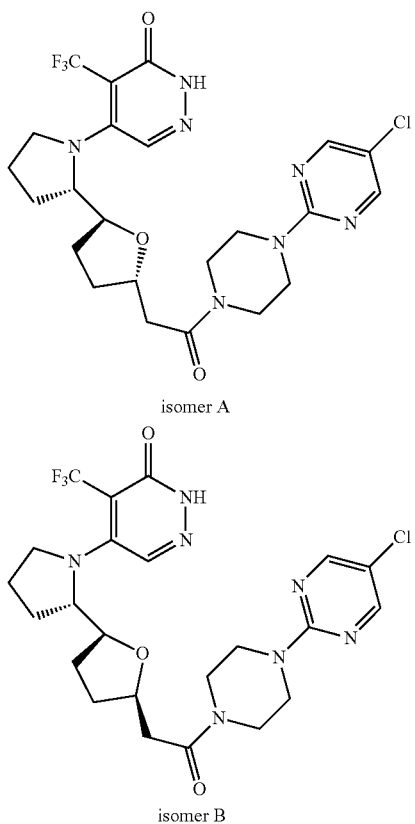

isomer A isomer B

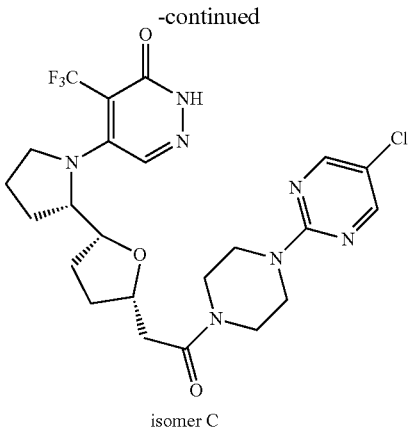

isomer C

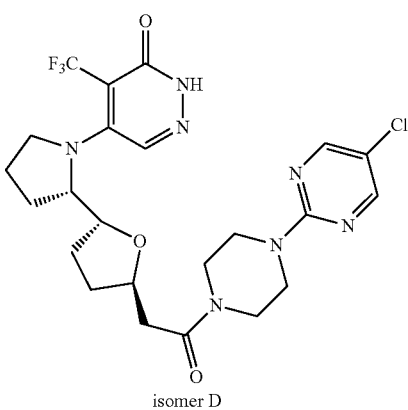

isomer D

Step 1: Synthesis of 5-[(2S)-2-(5-[2-[4-(5-chloropyrimidin-2-yl)piperazin-1-yl]-2-oxoethyl]oxolan-2-yl)pyrrolidin-1-yl]-4-(trifluoromethyl)-2-[[2-(trimethylsilyl)ethoxy]methyl]-2,3-dihydropyridazin-3-one A solution of 2-[5-[(2S)-1-[6-oxo-5-(trifluoromethyl)-1-[[2-(trimethylsilyl)ethoxy]methyl]-1,6-dihydropyridazin-4-yl]pyrrolidin-2-yl]oxolan-2-yl]acetic acid (400 mg, 0.81 mmol, 1 equiv), Int-A3 (161 mg, 0.81 mmol, 1.00 equiv), HATU (370.7 mg, 0.97 mmol, 1.20 equiv), DIEA (211.4 mg, 1.64 mmol, 2.01 equiv) in DMF (4 mL) was stirred for 1 h at room temperature. After concentration, the residue was purified by C18 reverse phase chromatography eluting with H₂O/CH₃CN to afford 450 mg (82.27%) of the title compound as yellow oil. LCMS (ESI, m/z): 672.26[M+H]⁺

Step 2: Synthesis of 5-[(2S)-2-[(2S,5S)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2S,5R)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2R,5S)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2R,5R)-5-[2-[4-(5-chloropyrimidin-2-yl)piperazin-1-yl]-2-oxoethyl]oxolan-2-yl]pyrrolidin-1-yl]-4-(trifluoromethyl)-2,3-dihydropyridazin-3-one Example 148: 5-[(2S)-2-[(2S,5S)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2R,5S)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one, 5-[(2S)-2-[(2R,5R)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2S,5R)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one A solution of 5-[(2S)-2-(5-[2-[4-(5-chloropyrimidin-2-yl)piperazin-1-yl]-2-oxoethyl]oxolan-2-yl)pyrrolidin-1-yl]-4-(trifluoromethyl)-2-[[2-(trimethylsilyl)ethoxy]methyl]-2,3-dihydropyridazin-3-one (450 mg, 0.67 mmol, 1 equiv), TFA (1 mL) in DCM (10 mL) was stirred for 4 h at room temperature. After concentration, the residue was purified by C18 reverse phase chromatography eluting with $H_2O$/$CH_3CN$. Then the residue was further purified by Prep-HPLC and Chiral-Prep-HPLC yielding (after arbitrary assignment of stereochemistry) the title compounds, respectively, isomer A (14.4 mg, 3.97%) as a white solid. LCMS (ESI, m/z): 542.95 [M+H]$^+$, $^1$HNMR (300 MHz, DMSO-d$_6$) δ: 12.23 (s, 1H), 8.46 (s, 2H), 8.13-8.03 (m, 1H), 4.66 (s, 1H), 4.32-3.91 (m, 2H), 3.78-3.35 (m, 9H), 3.28-3.18 (m, 1H), 2.72-2.60 (m, 1H), 2.41-2.38 (m, 1H), 2.16-1.85 (m, 4H), 1.72-1.37 (m, 4H). tR=3.467 min (CHIRALPAK IG-3, 0.46*10 cm; 3 um, MtBE (0.1% DEA):MeOH=80:20, 1.0 mL/min), isomer B (71.1 mg, 19.60%) as a white solid. LCMS (ESI, m/z): 542.95 [M+H]$^+$, $^1$HNMR (300 MHz, DMSO-d$_6$) δ: 12.23 (s, 1H), 8.44 (s, 2H), 8.05 (s, 1H), 4.50-4.39 (m, 1H), 4.35-4.25 (m, 1H), 3.83 (q, J=7.5 Hz, 1H), 3.78-3.66 (m, 2H), 3.63-3.40 (m, 7H), 3.20 (m, 1H), 2.67 (dd, J=14.7, 6.6 Hz, 1H), 2.40 (dd, J=14.7, 6.1 Hz, 1H), 2.22-1.97 (m, 3H), 1.93-1.80 (m, 1H), 1.72-1.44 (m, 4H). tR=4.847 min (CHIRALPAK IG-3, 0.46*10 cm; 3 um, MtBE (0.1% DEA):MeOH=80:20, 1.0 mL/min), isomer C (6.8 mg, 1.87%) as a white solid. LCMS (ESI, m/z): 542.95 [M+H]$^+$, $^1$HNMR (300 MHz, DMSO-d6) δ: 12.23 (s, 1H), 8.44 (s, 2H), 8.05 (s, 1H), 4.46 (d, J=8.3 Hz, 1H), 4.30 (s, 1H), 3.88-3.63 (m, 3H), 3.62-3.41 (m, 7H), 3.24-3.13 (m, 1H), 2.67 (dd, J=14.7, 6.6 Hz, 1H), 2.40 (dd, J=14.7, 6.3 Hz, 1H), 2.23-1.97 (m, 3H), 1.93-1.80 (m, 1H), 1.71-1.47 (m, 4H). tR=5.783 min (CHIRALPAK IG-3, 0.46*10 cm; 3 um, MtBE (0.1% DEA):MeOH=80:20, 1.0 mL/min) and isomer D (23.5 mg, 6.48%) as a white solid. LCMS (ESI, m/z): 542.95 [M+H]$^+$, $^1$HNMR (300 MHz, DMSO-d6) δ: 12.28 (s, 1H), 8.46 (s, 2H), 8.16 (s, 1H), 4.48 (d, J=7.5 Hz, 1H), 4.20 (t, J=6.2 Hz, 1H), 3.77-3.66 (m, 5H), 3.61-3.45 (m, 5H), 3.26-3.14 (m, 1H), 2.71 (dd, J=15.4, 6.1 Hz, 1H), 2.49-2.43 (m, 1H), 2.13-1.96 (m, 2H), 1.93-1.80 (m, 2H), 1.72-1.50 (m, 4H). tR=6.854 min (CHIRALPAK IG-3, 0.46*10 cm; 3 um, MtBE (0.1% DEA):MeOH=80:20, 1.0 mL/min)

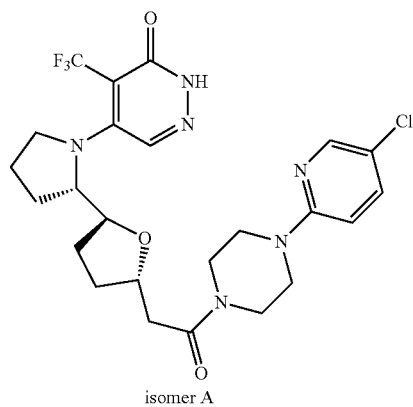

isomer A

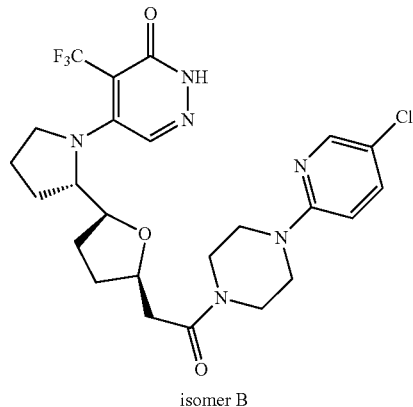

isomer B

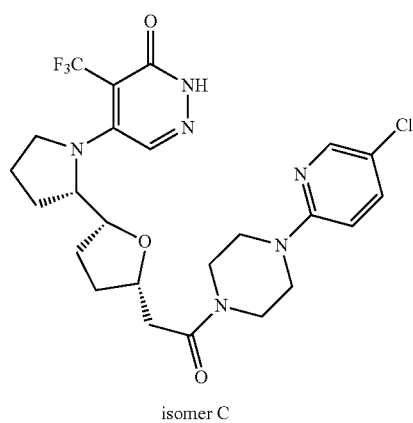

isomer C

-continued

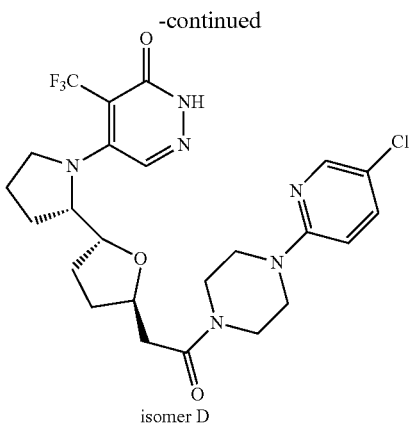

isomer D

Step 1: Synthesis of 2-[5-[(2S)-1-[6-oxo-5-(trifluoromethyl)-1-[[2-(trimethylsilyl)ethoxy]methyl]-1,6-dihydropyridazin-4-yl]pyrrolidin-2-yl]oxolan-2-yl]acetic Acid A solution of 2-[5-[(2S)-pyrrolidin-2-yl]oxolan-2-yl]acetic acid (980 mg, 4.92 mmol, 1.00 equiv), TEA (900 mg, 8.89 mmol, 3.00 equiv) and Int-A6 (600 mg, 1.82 mmol, 1.00 equiv) in methanol (20 mL) was stirred for 3 h at 60° C., and then the resulting solution was concentrated under vacuum, and then the residue was purified by C18 reverse phase chromatography eluting with H₂O/CH₃CN to afford 1.0 g (41%) of the title compound as yellow oil. LCMS (ESI, m/z): 492.21 [M+H]⁺

Step 2: Synthesis of 5-[(2S)-2-(5-[2-[4-(5-chloropyridin-2-yl)piperazin-1-yl]-2-oxoethyl]oxolan-2-yl)pyrrolidin-1-yl]-4-(trifluoromethyl)-2-[[2-(trimethylsilyl)ethoxy]methyl]-2,3-dihydropyridazin-3-one A solution of 2-[5-[(2S)-1-[6-oxo-5-(trifluoromethyl)-1-[[2-(trimethylsilyl)ethoxy]methyl]-1,6-dihydropyridazin-4-yl]pyrrolidin-2-yl]oxolan-2-yl]acetic acid (400 mg, 0.81 mmol, 1.00 equiv), HATU (310 mg, 0.82 mmol, 1.00 equiv), DIEA (421 mg, 3.26 mmol, 4.00 equiv) and Int-A5 (219 mg, 0.81 mmol, 1.00 equiv) in DMF (6 mL) was stirred for 1 h at room temperature, and then the resulting solution was diluted with 10 mL of EtOAc, washed with 3×8 mL of H₂O, the organic layer was combined, dried over anhydrous sodium sulfate and concentrated under vacuum, and then the residue was purified by C18 reverse phase chromatography eluting with H₂O/CH₃CN to afford 450 mg (82%) of the title compound as a light brown solid. LCMS (ESI, m/z): 671.27 [M+H]⁺

Step 3: Synthesis of 5-[(2S)-2-[(2S,5S)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2R,5S)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2R,5R)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one and 5-[(2S)-2-[(2S,5R)-5-[2-[4-(5-chloropyridin-2-yl)piperazin-1-yl]-2-oxoethyl]oxolan-2-yl]pyrrolidin-1-yl]-4-(trifluoromethyl)-2,3-dihydropyridazin-3-one A solution of 5-[(2S)-2-(5-[2-[4-(5-chloropyridin-2-yl)piperazin-1-yl]-2-oxoethyl]oxolan-2-yl)pyrrolidin-1-yl]-4-(trifluoromethyl)-2-[[2-(trimethylsilyl)ethoxy]methyl]-2,3-dihydropyridazin-3-one (450 mg, 0.67 mmol, 1.00 equiv) and TFA (1 mL) in DCM (5 mL) was stirred for 1.5 h at room temperature, and then the resulting solution was concentrated under vacuum and then the residue was purified by C18 reverse phase chromatography eluting with H₂O/CH₃CN, after concentration, the residue was further purified by Prep-HPLC and Chiral-Prep-HPLC yielding (after arbitrary assignment of stereochemistry) the title compounds, respectively, isomer A (7.7 mg 2.10%) as a white solid. LCMS (ESI, m/z): 541.10[M+H]⁺, 1HNMR (Methanol-d₄, 400 MHz) δ 8.21 (s, 1H), 8.08 (d, J=2.4 Hz, 1H), 7.56 (dd, J=10.4, 2.8 Hz, 1H), 6.83 (dd, J=8.8, 0.8 Hz, 1H), 4.73 (t, J=7.7 Hz, 1H), 4.34-4.31 (m, 1H), 4.12 (dd, J=8.6, 4.5 Hz, 1H), 3.81-3.52 (m, 9H), 3.39 (dd, J=11.0, 5.9 Hz, 1H), 2.73 (dd, J=14.2, 7.9 Hz, 1H), 2.57 (dd, J=14.2, 4.4 Hz, 1H), 2.26-2.13 (m, 3H), 2.05-1.94 (m, 1H), 1.82-1.64 (m, 4H). tR=4.786 min (CHIRALPAK IG-3, 0.46*10 cm; 3 um, MtBE (0.3% IPAmine):EtOH=80:20, 1.0 mL/min), isomer B (4.8 mg 1.32%) as a white solid. LCMS (ESI, m/z): 541.10 [M+H]⁺, ¹HNMR (Methanol-d4, 400 MHz) δ 8.20 (s, 1H), 8.06 (d, J=2.7 Hz, 1H), 7.55 (dd, J=9.2, 2.8 Hz, 1H), 6.82 (dd, J=9.2, 0.7 Hz, 1H), 4.78 (t, J=7.8 Hz, 1H), 4.34-4.31 (m, 1H), 4.12 (dd, J=8.6, 4.5 Hz, 1H), 3.81-3.36 (m, 10H), 2.48 (dd, J=15.6, 7.6 Hz, 1H), 2.39 (dd, J=15.2, 4.8 Hz, 1H), 2.27-2.20 (m, 1H), 2.10-2.03 (m, 1H), 2.00-1.91 (m, 2H), 1.81-1.63 (m, 3H), 1.59-1.46 (m, 1H). tR=5.588 min (CHIRALPAK IG-3, 0.46*10 cm; 3 um, MtBE (0.1% DEA):EtOH=80:20, 1.0 mL/min), isomer C (67.1 mg 18.5%) as a white solid. LCMS (ESI, m/z): 541.10 [M+H]⁺, ¹HNMR (Methanol-d4, 400 MHz) δ 8.13 (s, 1H), 8.06 (d, J=2.4 Hz, 1H), 7.55 (dd, J=9.2, 2.8 Hz, 1H), 6.79 (d, J=9.2 Hz, 1H), 4.44-4.33 (m, 2H), 4.00-3.92 (m, 1H), 3.71-3.35 (m, 10H), 2.81 (dd, J=14.0, 8.0 Hz, 1H), 2.53 (dd, J=14.0, 4.4 Hz, 1H), 2.25-2.16 (m, 3H), 1.98-1.91 (m, 1H), 1.82-1.58 (m, 4H). tR=2.182 min (Repaired IA-3, 0.46*10 cm; 5 um, (Hex:DCM=3:1)(10 mmol NH3):MeOH=70:30, 1.0 mL/min) and isomer D (25.1 mg 6.90%) as a white solid. LCMS (ESI, m/z): 541.10 [M+H]⁺: 1HNMR (Methanol-d4, 400 MHz) δ 8.27 (s, 1H), 8.09 (d, J=2.4, 1H), 7.57 (dd, J=8.8, 2.4 Hz, 1H), 6.84 (d, J=8.8, 1H), 4.51-4.44 (m, 1H), 4.36-4.25 (m, 1H), 3.82-3.32 (m, 11H), 2.88 (dd, J=14.8, 7.2 Hz, 1H), 2.59 (dd, J=14.8, 5.2 Hz, 1H), 2.28-1.94 (m, 4H), 1.82-1.59 (m, 4H). tR=2.755 min (Repaired IA-3, 0.46*10 cm; 5 um, (Hex:DCM=3:1)(10 mmol NH3):MeOHOH=70:30, 1.0 mL/min).

Example 149: 5-[(2S)-2-[(2S,5S)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one, 5-[(2S)-2-[(2S,5R)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one, 5-[(2S)-2-[(2R,5S)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one and 5-[(2S)-2-[(2R,5R)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one

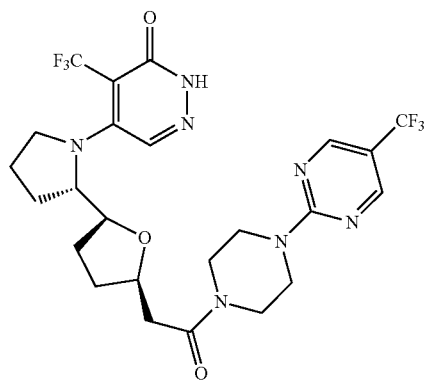

isomer A

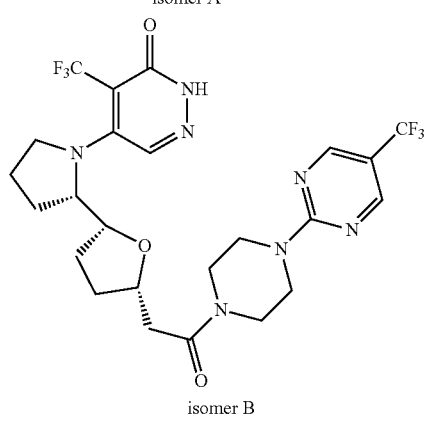

isomer B

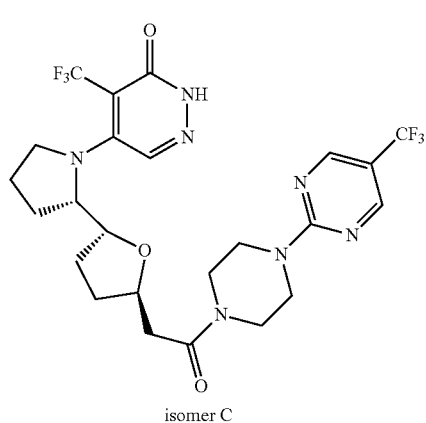

isomer C

-continued

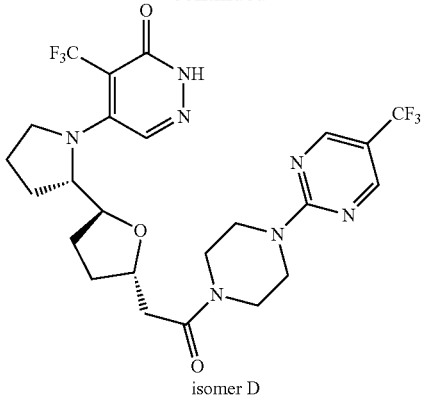

isomer D

Step 1: Synthesis of Tert-Butyl (2S)-2-[5-(2-oxo-2-[4-[5-(trifluoromethyl)pyrimidin-2-yl]piperazin-1-yl]ethyl)oxolan-2-yl]pyrrolidine-1-carboxylate A solution of 2-[5-[(2S)-1-[(tert-butoxy)carbonyl]pyrrolidin-2-yl]oxolan-2-yl]acetic acid (1.1 g, 3.67 mmol, 1.00 equiv), DEIA (1.42 g, 3.00 equiv), Int-A2 (1.12 g, 3.67 mmol, 1.10 equiv), HATU (1.54 g, 4.05 mmol, 1.10 equiv) in DMF (15 mL) was stirred for 1 h at 25° C. After concentration, the residue was purified by C18 reverse phase chromatography eluting with $H_2O/CH_3CN$ to afford 1.08 g (57%) of the title compound as yellow oil. LCMS (ESI, m/z): 514.26 $[M+H]^+$

Step 2: Synthesis of 2-[5-[(2S)-pyrrolidin-2-yl]oxolan-2-yl]-1-[4-[5-(trifluoromethyl)pyrimidin-2-yl]piperazin-1-yl]ethan-1-one Hydrochloride A solution of tert-butyl (2S)-2-[5-(2-oxo-2-[4-[5-(trifluoromethyl)pyrimidin-2-yl]piperazin-1-yl]ethyl)oxolan-2-yl]pyrrolidine-1-carboxylate (1.08 g, 2.10 mmol, 1.00 equiv) in dioxane/HCl (50 mL, 4 M) was stirred for 2 h at 25° C. The resulting solution was concentrated under vacuum to afford 900 mg (95%) of the title compound as yellow oil. LCMS (ESI, m/z): 414.20 $[M+H]^+$

Step 3: Synthesis of 5-[(2S)-2-[5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2-[[2-(trimethylsilyl)ethoxy]methyl]-2,3-dihydropyridazin-3-one A solution of 2-[5-[(2S)-pyrrolidin-2-yl]oxolan-2-yl]-1-[4-[5-(trifluoromethyl)pyrimidin-2-yl]piperazin-1-yl]ethan-1-one hydrochloride (870 mg, 1.93 mmol, 1.00 equiv), TEA (637 mg, 6.30 mmol, 3.00 equiv), Int-A6 (920 mg, 2.80 mmol, 1.00 equiv) in EtOH (20 mL) was stirred for 2 h at 60° C. After concentration, the residue was applied onto a silica gel column with EtOAc/petroleum ether (3/2) to afford 1.23 g (90%) the title compound as yellow oil. LCMS (ESI, m/z): 706.29 $[M+H]^+$ Step 4: Synthesis of 5-[(2S)-2-[(2S,5S)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one, 5-[(2S)-2-[(2S,5R)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one, 5-[(2S)-2-[(2R,5S)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one and 5-[(2S)-2-[(2R,5R)-5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2,3-dihydropyridazin-3-one A solution of 5-[(2S)-2-[5-(2-oxo-2-[4-[5-(trifluoromethyl)pyrimidin-2-yl]piperazin-1-yl]ethyl)oxolan-2-yl]pyrrolidin-1-yl]-4-(trifluoromethyl)-2-[[2-(trimethylsilyl)ethoxy]methyl]-2,3-dihydropyridazin-3-one (1 g, 1.42 mmol, 1.00 equiv), TFA (4 mL) in DCM (20 mL) was stirred for 2 h at 25° C. The pH value of the solution was adjusted to 8 with ethanolamine. The solvent was concentrated under vacuum and the residue was purified by C18 reverse phase chromatography eluting with $H_2O/CH_3CN$. Then the residue was further purified by Chiral-Prep-HPLC yielding (after arbitrary assignment of stereochemistry) the title compounds, respectively, isomer A (381.1 mg, 46.70%) as a white solid. LCMS (ESI, m/z): 576.21 [M+H]$^+$, $^1$H NMR (DMSO-d$_6$, 400 MHz) δ: 10.80 (s, 1H), 8.71 (s, 2H), 8.05 (s, 1H), 4.45 (q, J=8.0 Hz, 1H), 4.30 (p, J=6.4 Hz, 1H), 3.95-3.77 (m, 3H), 3.72-3.43 (m, 7H), 3.22-3.13 (m, 1H), 2.68 (dd, J=14.7, 6.8 Hz, 1H), 2.40 (dd, J=14.7, 6.0 Hz, 1H), 2.20-2.11 (m, 1H), 2.04 (t, J=10.2 Hz, 2H), 1.86 (d, J=11.3 Hz, 1H), 1.71-1.62 (m, 4H). tR=4.347 min (CHIRALPAK ID-3, 0.46*10 cm; 3 um, MtBE (0.1% DEA):EtOH=80:20, 1.0 mL/min, isomer B (9.5 mg, 1.16%) as a white solid. LCMS (ESI, m/z): 576.21 [M+H]$^+$, $^1$H NMR (DMSO-d$_6$, 400 MHz) δ: 12.34 (s, 1H), 8.73 (d, J=0.9 Hz, 2H), 8.10 (s, 1H), 4.65 (s, 1H), 4.17 (s, 1H), 4.09 (t, J=6.4 Hz, 1H), 3.90-3.71 (m, 4H), 3.52 (d, J=31.6 Hz, 5H), 3.23 (s, 1H), 2.66 (dd, J=15.0, 6.8 Hz, 1H), 2.43 (dd, J=14.9, 5.8 Hz, 1H), 2.04 (d, J=14.8 Hz, 3H), 1.89 (s, 1H), 1.63-1.54 (m, 4H). tR=3.343 min (CHIRALPAK ID-3, 0.46*10 cm; 3 um, MtBE (0.1% DEA):EtOH=80:20, 1.0 mL/min, isomer C (75.2 mg, 9.21%) as a white solid. LCMS (ESI, m/z): 576.21 [M+H]$^+$, $^1$H NMR (DMSO-d$_6$, 400 MHz) δ 12.30 (s, 1H), 8.74 (d, J=0.9 Hz, 2H), 8.16 (s, 1H), 4.48 (q, J=7.6 Hz, 1H), 4.20 (p, J=6.3 Hz, 1H), 3.86 (t, J=5.2 Hz, 2H), 3.80 (d, J=4.8 Hz, 2H), 3.72 (q, J=7.1 Hz, 1H), 3.54 (q, J=6.1, 5.7 Hz, 5H), 3.20 (dd, J=10.5, 6.6 Hz, 1H), 2.72 (dd, J=15.4, 6.2 Hz, 1H), 2.50-2.42 (m, 1H), 2.11-1.97 (m, 2H), 1.90 (ddt, J=17.2, 10.5, 4.7 Hz, 2H), 1.63-1.54 (m, 4H). 1.60 (ddt, J=34.2, 13.3, 6.5 Hz, 4H). tR=8.697 min (CHIRALPAK ID-3, 0.46*10 cm; 3 um, MtBE (0.1% DEA):EtOH=80:20, 1.0 mL/min and isomer D (11.2 mg, 1.37%) as a white solid. LCMS (ESI, m/z): 576.21 [M+H]$^+$, $^1$H NMR (DMSO-d$_6$, 400 MHz) δ: 12.25 (s, 1H), 8.71 (d, J=0.9 Hz, 2H), 8.05 (s, 1H), 4.46 (q, J=8.0 Hz, 1H), 4.30 (q, J=6.6 Hz, 1H), 3.91-3.77 (m, 3H), 3.70-3.39 (m, 7H), 3.18 (t, J=8.8 Hz, 1H), 2.68 (dd, J=14.7, 6.8 Hz, 1H), 2.40 (dd, J=14.6, 6.0 Hz, 1H), 2.15 (d, J=10.1 Hz, 1H), 2.04 (d, J=12.4, 7.7 Hz, 2H), 1.86 (d, J=10.7 Hz, 1H), 1.71-1.62 (m, 4H). tR=5.195 min (CHIRALPAK ID-3, 0.46*10 cm; 3 um, MtBE (0.1% DEA):EtOH=80:20, 1.0 mL/min.

Example 150: 5-[5-(Piperidin-4-yloxy)-2,3-dihydro-1H-isoindol-2-yl]-4-(trifluoromethyl)-2,3-dihydropyridazin-3-one

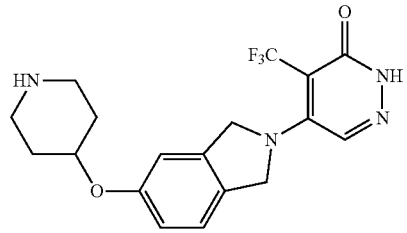 [SMILES: O=c1[nH]ncc(N2Cc3ccc(OC4CCNCC4)cc3C2)c1C(F)(F)F]

Step 1: 5-(5-Hydroxy-2,3-dihydro-1H-isoindol-2-yl)-4-(trifluoromethyl)-2-[[2-(trimethylsilyl)ethoxy]methyl]-2,3-dihydropyridazin-3-one A solution of Int-A6 (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of EtOAc and the organic layers combined and concentrated under reduced pressure to afford 4.5 g of the title compound as a yellow oil. LCMS: [M+H]$^+$ 428.23.

Step 2: Tert-Butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of EtOAc and the organic layers combined and concentrated under reduced pressure. The residue was applied onto a silica gel column eluting with EtOAc/petroleum ether to afford the title compound (2 g, 31%) as a yellow oil. LCMS: [M+H]$^+$ 611.15.

Step 3: 5-[5-(Piperidin-4-yloxy)-2,3-dihydro-1H-isoindol-2-yl]-4-(trifluoromethyl)-2,3-dihydropyridazin-3-one A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (150 mg, 0.25 mmol, 1.00 equiv) in HCl/dioxane (5 mL) was stirred overnight at 45° C. The resulting mixture was concentrated under reduced pressure and the crude product was purified by C18 reverse phase chromatography eluting with $H_2O/CH_3CN$ to afford the title compound as a white solid LCMS: [M+H]$^+$ 381.28. $^1$H NMR (400 MHz, Methanol-d$_4$) δ 8.05 (s, 1H), 7.27 (d, J=8.4 Hz, 1H), 7.02-6.91 (m, 2H), 5.00 (d, J=10.6 Hz, 4H), 4.61-4.48 (m, 1H), 3.21-3.10 (m, 2H), 2.89-2.78 (m, 2H), 2.11-2.08 (m, 2H), 1.82-1.69 (m, 2H).

Further example compounds of the invention prepared by the methods described herein are provided in Table E1

TABLE E1

| Example # | Structure | MS (M + H)+ |
|---|---|---|
| 151 | 4-Chloro-5-(isoindolin-2-yl)pyridazin-3(2H)-one | 247.90 |
| 152 | 4-Chloro-5-(1,3-dihydro-2H-pyrrolo[3,4-c]pyridin-2-yl)pyridazin-3(2H)-one | 249.05 |
| 153 | 4-Chloro-5-(4-methoxyisoindolin-2-yl)pyridazin-3(2H)-one | 277.65 |
| 154 | 4-Chloro-5-(5,7-dihydro-6H-pyrrolo[3,4-b]pyridin-6-yl)pyridazin-3(2H)-one | 249.10 |
| 155 | 4-Chloro-5-(5-methoxyisoindolin-2-yl)pyridazin-3(2H)-one | 278.05 |

TABLE E1-continued

| Example # | Structure | MS (M + H)+ |
|---|---|---|
| 156 | 4-Chloro-5-(5-(2-methoxyethoxy)isoindolin-2-yl)pyridazin-3(2H)-one | 322.35 |
| 157 | 4-Chloro-5-(5-(2-hydroxyethoxy)isoindolin-2-yl)pyridazin-3(2H)-one | 308.30 |
| 158 | 4-Chloro-5-(5-(piperidin-4-yloxy)isoindolin-2-yl)pyridazin-3(2H)-one | 347.35 |
| 159 | 5-(Isoindolin-2-yl)-4-methylpyridazin-3(2H)-one | 228.20 |
| 160 | 5-(Isoindolin-2-yl)-4-(trifluoromethyl)pyridazin-3(2H)-one | 282.05 |

TABLE E1-continued

| Example # | Structure | MS (M + H)+ |
|---|---|---|
| 161 | 4-Chloro-5-(4-(2-hydroxyethoxy)isoindolin-2-yl)pyridazin-3(2H)-one | 308.00 |
| 162 | 4-Chloro-5-(4-(2-methoxyethoxy)isoindolin-2-yl)pyridazin-3(2H)-one | 322.20 |
| 163 | 5-(4-(2-Aminoethoxy)isoindolin-2-yl-)-4-chloropyridazin-3(2H)-one | 307.20 |
| 164 | 5-(4-Methoxyisoindolin-2-yl)-4-(trifluoromethyl)pyridazin-3(2H)-one | 312.10 |
| 165 | 4-Chloro-5-(4-(piperidin-4-yloxy)isoindolin-2-yl)pyridazin-3(2H)-one | 347.40 |

TABLE E1-continued

| Example # | Structure | MS (M + H)+ |
|---|---|---|
| 166 | 4-Chloro-5-(4-(2-(dimethylamino)ethoxy)isoindolin-2-yl)pyridazin-3(2H)-one | 335.35 |
| 167 | 5-(4-Methoxyisoindolin-2-yl)-4-methylpyridazin-3(2H)-one | 258.20 |
| 168 | 4-Bromo-5-(4-(2-hydroxyethoxy)isoindolin-2-yl)pyridazin-3(2H)-one | 354.00 |
| 169 | 5-(5-Fluoroisoindolin-2-yl)-4-(trifluoromethyl)pyridazin-3(2H)-one | 300.1 |
| 170 | 5-(4-(Piperidin-4-yloxy)isoindolin-2-yl)-4-(trifluoromethyl)pyridazin-3(2H)-one | 381.15 |

TABLE E1-continued

| Example # | Structure | MS (M + H)+ |
|---|---|---|
| 171 | 5-(4-(2-Hydroxyethoxy)isoindolin-2-yl)-4-methylpyridazin-3(2H)-one | 288.20 |
| 172 | 4-Bromo-5-(4-(piperidin-4-yloxy)isoindolin-2-yl)pyridazin-3(2H)-one | 391.00 |
| 173 | 5-(5-Methoxyisoindolin-2-yl)-4-methylpyridazin-3(2H)-one | 258.20 |
| 174 | 5-(5-Methoxyisoindolin-2-yl)-4-(trifluoromethyl)pyridazin-3(2H)-one | 312.05 |
| 175 | 4-Methyl-5-(4-(piperidin-4-yloxy)isoindolin-2-yl)pyridazin-3(2H)-one | 327.25 |

TABLE E1-continued

| Example # | Structure | MS (M + H)+ |
|---|---|---|
| 176 | 5-(4-(2-Hydroxyethoxy)isoindolin-2-yl)-3-oxo-2,3-dihydropyridazine-4-carbonitrile | 299.20 |
| 177 | 5-(5-(2-Hydroxyethoxy)isoindolin-2-yl)-4-(trifluoromethyl)pyridazin-3(2H)-one | 342.20 |
| 178 | 5-(4-(Dimethylamino)isoindolin-2-yl)-4-(trifluoromethyl)pyridazin-3(2H)-one | 325.25 |
| 179 | N-(2-(6-Oxo-5-(trifluoromethyl)-1,6-dihydropyridazin-4-yl)isoindolin-4-yl)acetamide | 339.00 |
| 180 | 5-(4-Fluoroisoindolin-2-yl)-4-(trifluoromethyl)pyridazin-3(2H)-one | 300.0 |

TABLE E1-continued

| Example # | Structure | MS (M + H)+ |
|---|---|---|
| 181 | 5-(4-(2-Hydroxyethoxy)isoindolin-2-yl)-4-(trifluoromethyl)pyridazin-3(2H)-one | 342.00 |
| 182 | 3-Oxo-5-(4-(piperidin-4-yloxy)isoindolin-2-yl)-2,3-dihydropyridazine-4-carbonitrile formic acid | 338.40 |
| 183 | 4-Cyclopropyl-5-(4-(piperidin-4-yloxy)isoindolin-2-yl)pyridazin-3(2H)-one formic acid | 353.40 |
| 184 | 5-(4-(2-Hydroxyethoxy)isoindolin-2-yl)-4-methoxypyridazin-3(2H)-one | 304.20 |
| 185 | 4-Ethyl-5-(4-(2-hydroxyethoxy)isoindolin-2-yl)pyridazin-3(2H)-one | 302.05 |

TABLE E1-continued

| Example # | Structure | MS (M + H)+ |
|---|---|---|
| 186 | 4-Cyclopropyl-5-(4-(2-hydroxyethoxy)isoindolin-2-yl)pyridazin-3(2H)-one | 314.40 |
| 187 | 4-Methyl-5-(5-(piperidin-4-yloxy)isoindolin-2-yl)pyridazin-3(2H)-one | 327.40 |
| 188 | 5-(5-(2-Hydroxyethoxy)isoindolin-2-yl)-4-methylpyridazin-3(2H)-one | 288.20 |
| 189 | 5-(Isoindolin-2-yl)-4-(methylthio)pyridazin-3(2H)-one | 260.10 |
| 190 | 5-(5-(Piperidin-4-yloxy)isoindolin-2-yl)-4-(trifluoromethyl)pyridazin-3(2H)-one | 381.40 |

TABLE E1-continued

| Example # | Structure | MS (M + H)+ |
|---|---|---|
| 191 | 4-Chloro-5-(1-(hydroxymethyl)isoindolin-2-yl)pyridazin-3(2H)-one | 278.15 |
| 192 | 5-(4-Ethoxyisoindolin-2-yl)-4-(trifluoromethyl)pyridazin-3(2H)-one | 326.20 |
| 193 | 5-(4-Isopropoxyisoindolin-2-yl)-4-(trifluoromethyl)pyridazin-3(2H)-one | 340.20 |
| 194 | 5-(4-((Tetrahydro-2H-pyran-4-yl)oxy)isoindolin-2-yl)-4-(trifluoromethyl)pyridazin-3(2H)-one | 382.20 |
| 195 | 5-(4-(Pyrimidin-4-yloxy)isoindolin-2-yl)-4-(trifluoromethyl)pyridazin-3(2H)-one | 376.15 |

TABLE E1-continued

| Example # | Structure | MS (M + H)+ |
|---|---|---|
| 196 | 5-(4-(Pyridin-4-ylmethoxy)isoindolin-2-yl)-4-(trifluoromethyl)pyridazin-3(2H)-one | 389.15 |
| 197 | 5-(4-(Pyridin-3-ylmethoxy)isoindolin-2-yl)-4-(trifluoromethyl)pyridazin-3(2H)-one | 389.20 |
| 198 | 5-(4-(Pyridin-2-ylmethoxy)isoindolin-2-yl)-4-(trifluoromethyl)pyridazin-3(2H)-one | 389.15 |
| 199 | 5-(4-((Tetrahydro-2H-pyran-3-yl)methoxy)isoindolin-2-yl)-4-(trifluoromethyl)pyridazin-3(2H)-one | 396.20 |
| 200 | 5-(4-((Tetrahydrofuran-3-yl)methoxy)isoindolin-2-yl)-4-(trifluoromethyl)pyridazin-3(2H)-one | 382.10 |

TABLE E1-continued

| Example # | Structure | MS (M + H)+ |
|---|---|---|
| 201 | 5-(4-((Tetrahydrofuran-2-yl)methoxy)isoindolin-2-yl)-4-(trifluoromethyl)pyridazin-3(2H)-one | 382.05 |
| 202 | 5-(4-((2-Oxotetrahydrofuran-3-yl)oxy)isoindolin-2-yl)-4-(trifluoromethyl)pyridazin-3(2H)-one | 382.15 |
| 203 | 5-(4-((Tetrahydrofuran-3-yl)oxy)isoindolin-2-yl)-4-(trifluoromethyl)pyridazin-3(2H)-one | 367.95 |
| 204 | 2-((2-(6-Oxo-5-(trifluoromethyl)-1,6-dihydropyridazin-4-yl)isoindolin-4-yl)oxy)acetamide | 355.10 |
| 205 | 5-(4-Aminoisoindolin-2-yl)-4-(trifluoromethyl)pyridazin-3(2H)-one | 297.10 |

TABLE E1-continued

| Example # | Structure | MS (M + H)+ |
|---|---|---|
| 206 | 2-(6-Oxo-5-(trifluoromethyl)-1,6-dihydropyridazin-4-yl)isoindoline-4-carbonitrile | 307.10 |
| 207 | 4-Chloro-5-(1-(methoxymethyl)isoindolin-2-yl)pyridazin-3(2H)-one | 292.05 |
| 208 | 4-Chloro-5-(1-methylisoindolin-2-yl)pyridazin-3(2H)-one | 262.00 |
| 209 | 5-(4-(2-Aminoethoxy)isoindolin-2-yl)-4-(trifluoromethyl)pyridazin-3(2H)-one | 341.15 |
| 210 | 5-(4-((1-Methylpiperidin-4-yl)oxy)isoindolin-2-yl)-4-(trifluoromethyl)pyridazin-3(2H)-one | 395.15 |

TABLE E1-continued

| Example # | Structure | MS (M + H)+ |
|---|---|---|
| 211 | N-(2-((2-(6-Oxo-5-(trifluoromethyl)-1,6-dihydropyridazin-4-yl)isoindolin-4-yl)oxy)ethyl)acetamide | 383.15 |
| 212 | 5-(4-(2-(Dimethylamino)ethoxy)isoindolin-2-yl)-4-(trifluoromethyl)pyridazin-3(2H)-one | 369.20 |
| 213 | 5-(4-(2-(Piperidin-1-yl)ethoxy)isoindolin-2-yl)-4-(trifluoromethyl)pyridazin-3(2H)-one | 409.15 |
| 214 | 5-(4-(2-Morpholinoethoxy)isoindolin-2-yl)-4-(trifluoromethyl)pyridazin-3(2H)-one | 411.45 |
| 215 | 5-(4-(Methylamino)isoindolin-2-yl)-4-(trifluoromethyl)pyridazin-3(2H)-one | 311.15 |

TABLE E1-continued

| Example # | Structure | MS (M + H)+ |
|---|---|---|
| 216 | 5-(4-((Tetrahydro-2H-pyran-2-yl)methoxy)isoindolin-2-yl)-4-(trifluoromethyl)pyridazin-3(2H)-one | 396.20 |
| 217 | 5-(4-(2-(Methylamino)ethoxy)isoindolin-2-yl)-4-(trifluoromethyl)pyridazin-3(2H)-one | 355.15 |
| 218 | 5-(5-(Pyrrolidin-3-yloxy)isoindolin-2-yl)-4-(trifluoromethyl)pyridazin-3(2H)-one | 367.15 |
| 219 | 5-(5-Hydroxyisoindolin-2-yl)-4-(trifluoromethyl)pyridazin-3(2H)-one | 298.15 |
| 220 | 4-Chloro-5-(4-(2-(piperazin-1-yl)ethoxy)isoindolin-2-yl)pyridazin-3(2H)-one | 376.2 |

TABLE E1-continued

| Example # | Structure | MS (M + H)⁺ |
|---|---|---|
| 221 | 5-(4-(Aminomethyl)isoindolin-2-yl)-4-(trifluoromethyl)pyridazin-3(2H)-one | 311.15 |
| 222# | (S)-5-(4-((Tetrahydrofuran-2-yl)methoxy)isoindolin-2-yl)-4-(trifluoromethyl)pyridazin-3(2H)-one | 382.10 |
| 223# | (R)-5-(4-((Tetrahydrofuran-2-yl)methoxy)isoindolin-2-yl)-4-(trifluoromethyl)pyridazin-3(2H)-one | 382.10 |
| 224 | N-Methyl-N-(2-((2-(6-oxo-5-(trifluoromethyl)-1,6-dihydropyridazin-4-yl)isoindolin-4-yl)oxy)ethyl)acetamide | 397.15 |
| 225 | 5-(4-((1-Acetylpiperidin-4-yl)oxy)isoindolin-2-yl)-4-(trifluoromethyl)pyridazin-3(2H)-one | 422.95 |

TABLE E1-continued

| Example # | Structure | MS (M + H)+ |
|---|---|---|
| 226 | 5-(4-(2-(4-Methylpiperazin-1-yl)ethoxy)isoindolin-2-yl)-4-(trifluoromethyl)pyridazin-3(2H)-one | 424.15 |
| 227 | 5-(4-(2-(Piperazin-1-yl)ethoxy)isoindolin-2-yl)-4-(trifluoromethyl)pyridazin-3(2H)-one | 410.40 |
| 228 | 5-(4-(2-(4-Acetylpiperazin-1-yl)ethoxy)isoindolin-2-yl)-4-(trifluoromethyl)pyridazin-3(2H)-one | 452.15 |
| 229 | 5-(5-(2-Methoxyethoxy)isoindolin-2-yl)-4-(trifluoromethyl)pyridazin-3(2H)-one | 356.1 |
| 230 | 5-(4-(2-(4-Acetylpiperazin-1-yl)ethoxy)isoindolin-2-yl)-4-chloropyridazin-3(2H)-one | 418.2 |

TABLE E1-continued

| Example # | Structure | MS (M + H)+ |
|---|---|---|
| 231 | 5-(1-(Aminomethyl)isoindolin-2-yl)-4-chloropyridazin-3(2H)-one | 277.10 |
| 232 | 5-(4-(pyridin-4-yloxy)isoindolin-2-yl)-4-(trifluoromethyl)pyridazin-3(2H)-one trifluoroacetic acid | 375.20 |
| 233 | 5-(4-(Pyridin-3-yloxy)isoindolin-2-yl)-4-(trifluoromethyl)pyridazin-3(2H)-one | 375.20 |
| 234 | 5-(5-Fluoro-6-methoxyisoindolin-2-yl)-4-(trifluoromethyl)pyridazin-3(2H)-one | 330.05 |

TABLE E1-continued
| Example # | Structure | MS (M + H)+ |
|---|---|---|
| 235 | 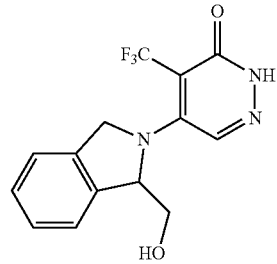 [SMILES: O=c1[nH]ncc(N2Cc3ccccc3C2CO)c1C(F)(F)F]<br>5-(1-(Hydroxymethyl)isoindolin-2-yl)-4-(trifluoromethyl)pyridazin-3(2H)-one | 311.95 |
| 236 | 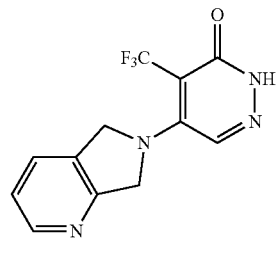 [SMILES: O=c1[nH]ncc(N2Cc3cccnc3C2)c1C(F)(F)F]<br>5-(5,7-Dihydro-6H-pyrrolo[3,4-b]pyridin-6-yl)-4-(trifluoromethyl)pyridazin-3(2H)-one | 282.9 |
| 237 | 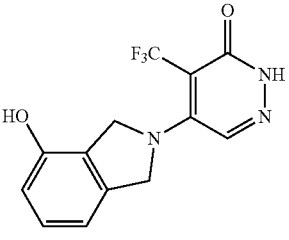<br>5-(4-Hydroxyisoindolin-2-yl)-4-(trifluoromethyl)pyridazin-3(2H)-one | 297.25 |
| 238 | 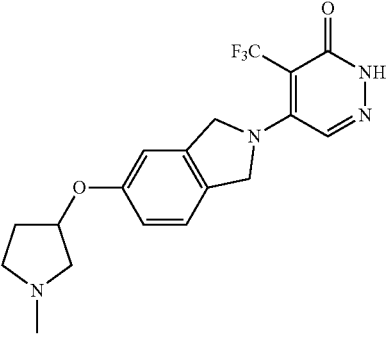 [SMILES: CN1CCC(Oc2ccc3c(c2)CN(c2cn[nH]c(=O)c2C(F)(F)F)C3)C1]<br>5-(5-((1-Methylpyrrolidin-3-yl)oxy)isoindolin-2-yl)-4-(trifluoromethyl)pyridazin-3(2H)-one | 381.40 |

TABLE E1-continued

| Example # | Structure | MS (M + H)+ |
|---|---|---|
| 239 | 5-(1-(Methoxymethyl)isoindolin-2-yl)-4-(trifluoromethyl)pyridazin-3(2H)-one | 326.10 |
| 240 | 4-Chloro-5-(4-(2-morpholinoethoxy)isoindolin-2-yl)pyridazin-3(2H)-one | 377.2 |
| 241 | N-(2-((2-(5-Chloro-6-oxo-1,6-dihydropyridazin-4-yl)isoindolin-4-yl)oxy)ethyl)acetamide | 349.1 |
| 242 | 4-Chloro-5-(4-(pyrrolidin-3-yloxy)isoindolin-2-yl)pyridazin-3(2H)-one | 333.1 |
| 243 | 5-(4-(2-Hydroxyethoxy)isoindolin-2-yl)-4-isopropylpyridazin-3(2H)-one | 316.15 |

TABLE E1-continued
| Example # | Structure | MS (M + H)+ |
|---|---|---|
| 244 | 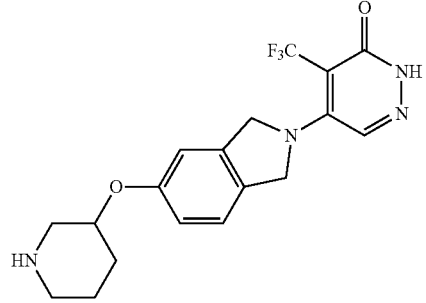  5-(5-(Piperidin-3-yloxy)isoindolin-2-yl)-4-(trifluoromethyl)pyridazin-3(2H)-one | 381.15 |
| 245 | 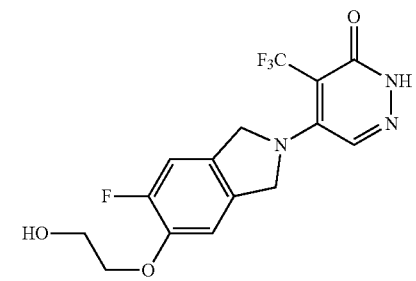 [SMILES: O=c1[nH]ncc(N2Cc3cc(F)c(OCCO)cc3C2)c1C(F)(F)F]  5-(5-Fluoro-6-(2-hydroxyethoxy)isoindolin-2-yl)-4-(trifluoromethyl)pyridazin-3(2H)-one | 360.05 |
| 246# | 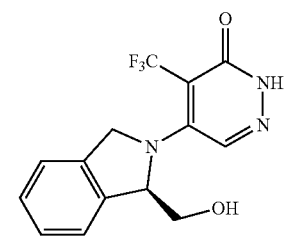 [SMILES: O=c1[nH]ncc(N2Cc3ccccc3[C@@H]2CO)c1C(F)(F)F]  (R)-5-(1-(Hydroxymethyl)isoindolin-2-yl)-4-(trifluoromethyl)pyridazin-3(2H)-one | 312.05 |
| 247# | 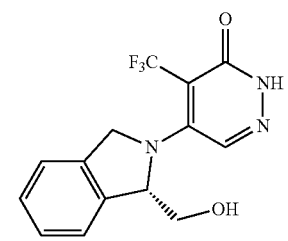 [SMILES: O=c1[nH]ncc(N2Cc3ccccc3[C@H]2CO)c1C(F)(F)F]  (S)-5-(1-(Hydroxymethyl)isoindolin-2-yl)-4-(trifluoromethyl)pyridazin-3(2H)-one | 312.05 |
| 248 | 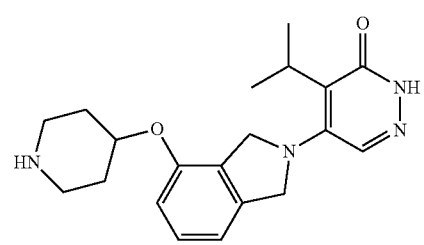 [SMILES: CC(C)c1c(N2Cc3cccc(OC4CCNCC4)c3C2)cn[nH]c1=O] | 355.20 |

TABLE E1-continued

| Example # | Structure | MS (M + H)+ |
|---|---|---|
| | 4-Isopropyl-5-(4-(piperidin-4-yloxy)isoindolin-2-yl)pyridazin-3(2H)-one | |
| 249 | 5-(1-Methylisoindolin-2-yl)-4-(trifluoromethyl)pyridazin-3(2H)-one | 296.05 |
| 250# | (S)-5-(1-Methylisoindolin-2-yl)-4-(trifluoromethyl)pyridazin-3(2H)-one | 296.05 |
| 251# | (R)-5-(1-Methylisoindolin-2-yl)-4-(trifluoromethyl)pyridazin-3(2H)-one | 296.05 |
| 252 | 5-(4-(1-(Pyridin-4-yl)ethoxy)isoindolin-2-yl)-4-(trifluoromethyl)pyridazin-3(2H)-one | 403.10 |
| 253 | 5-(4-Morpholinoisoindolin-2-yl)-4-(trifluoromethyl)pyridazin-3(2H)-one | 367.15 |

TABLE E1-continued

| Example # | Structure | MS (M + H)+ |
|---|---|---|
| 254 | 5-(4-(((Tetrahydrofuran-2-yl)methyl)amino)isoindolin-2-yl)-4-(trifluoromethyl)pyridazin-3(2H)-one | 381.13 |
| 255 | 4-Chloro-5-(4-(2-(4-methylpiperazin-1-yl)ethoxy)isoindolin-2-yl)pyridazin-3(2H)-one | 390.2 |
| 256 | 4-Chloro-5-(4-(2-(piperidin-1-yl)ethoxy)isoindolin-2-yl)pyridazin-3(2H)-one | 375.1 |
| 257 | 4-Chloro-5-(4-((1-methylpiperidin-4-yl)oxy)isoindolin-2-yl)pyridazin-3(2H)-one | 361.1 |
| 258 | 5-(4-((1-Acetylpiperidin-4-yl)oxy)isoindolin-2-yl)-4-chloropyridazin-3(2H)-one | 389.1 |

TABLE E1-continued

| Example # | Structure | MS (M + H)+ |
|---|---|---|
| 259 | 4-Chloro-5-(4-((1-methylpyrrolidin-3-yl)oxy)isoindolin-2-yl)pyridazin-3(2H)-one | 347.1 |
| 260 | 5-(4-(Methoxymethyl)isoindolin-2-yl)-4-(trifluoromethyl)pyridazin-3(2H)-one | 326.25 |
| 261 | 5-(4-(Hydroxymethyl)isoindolin-2-yl)-4-(trifluoromethyl)pyridazin-3(2H)-one | 312.05 |
| 262 | 5-(4-((Methylamino)methyl)isoindolin-2-yl)-4-(trifluoromethyl)pyridazin-3(2H)-one | 325.10 |
| 263 | 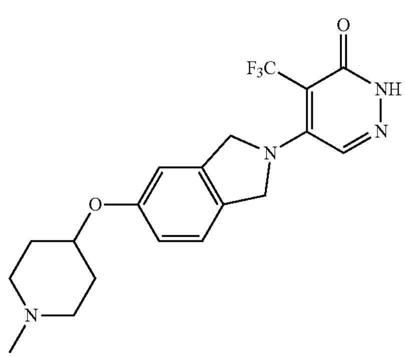 [SMILES: CN1CCC(Oc2ccc3c(c2)CN(c2cn[nH]c(=O)c2C(F)(F)F)C3)CC1] | 395.10 |

TABLE E1-continued

| Example # | Structure | MS (M + H)+ |
|---|---|---|
| | 5-(5-((1-Methylpiperidin-4-yl)oxy)isoindolin-2-yl)-4-(trifluoromethyl)pyridazin-3(2H)-one | |
| 264 | *[structure]* N-((2-(6-Oxo-5-(trifluoromethyl)-1,6-dihydropyridazin-4-yl)isoindolin-1-yl)methyl)acetamide | 353.15 |
| 265 | *[structure]* 5-(4-Chloroisoindolin-2-yl)-4-(trifluoromethyl)pyridazin-3(2H)-one | 315.85 |
| 266 | *[structure]* 5-(4-((Pyridin-4-ylmethyl)amino)isoindolin-2-yl)-4-(trifluoromethyl)pyridazin-3(2H)-one | 388.15 |
| 267 | *[structure]* 5-(4-Fluoro-7-methoxyisoindolin-2-yl)-4-(trifluoromethyl)pyridazin-3(2H)-one | 330.05 |

TABLE E1-continued

| Example # | Structure | MS (M + H)+ |
|---|---|---|
| 268 | 5-(4-((Tetrahydro-2H-pyran-3-yl)oxy)isoindolin-2-yl)-4-(trifluoromethyl)pyridazin-3(2H)-one | 382.20 |
| 269 | 2-(6-Oxo-5-(trifluoromethyl)-1,6-dihydropyridazin-4-yl)isoindoline-4-carboxamide | 325.15 |
| 270 | 5-(4-(Methyl((tetrahydrofuran-2-yl)methyl)amino)isoindolin-2-yl)-4-(trifluoromethyl)pyridazin-3(2H)-one | 395.15 |
| 271 | 5-(4-((1-(Pyridin-4-yl)ethyl)amino)isoindolin-2-yl)-4-(trifluoromethyl)pyridazin-3(2H)-one | 402.10 |
| 272 | 4-Ethyl-5-(4-(piperidin-4-yloxy)isoindolin-2-yl)pyridazin-3(2H)-one | 341.20 |

TABLE E1-continued

| Example # | Structure | MS (M + H)+ |
|---|---|---|
| 273 | 5-(4-Fluoro-6-methoxyisoindolin-2-yl)-4-(trifluoromethyl)pyridazin-3(2H)-one | 330.10 |
| 274 | 5-(6-Fluoro-4-methoxyisoindolin-2-yl)-4-(trifluoromethyl)pyridazin-3(2H)-one | 330.10 |
| 275 | 5-(1-(Aminomethyl)isoindolin-2-yl)-4-(trifluoromethyl)pyridazin-3(2H)-one | 311.10 |
| 276 | N-Methyl-N-((2-(6-oxo-5-(trifluoromethyl)-1,6-dihydropyridazin-4-yl)isoindolin-1-yl)methyl)acetamide | 367.10 |

TABLE E1-continued

| Example # | Structure | MS (M + H)+ |
|---|---|---|
| 277 | N,N-Dimethyl-2-(6-oxo-5-(trifluoromethyl)-1,6-dihydropyridazin-4-yl)isoindoline-4-carboxamide | 353.10 |
| 278 | 5-(4-(1-Hydroxyethyl)isoindolin-2-yl)-4-(trifluoromethyl)pyridazin-3(2H)-one | 326.15 |
| 279 | 5-(5-Fluoro-6-(piperidin-4-yloxy)isoindolin-2-yl)-4-(trifluoromethyl)pyridazin-3(2H)-one | 399.25 |
| 280 | 5-(1,3-Dihydro-2H-pyrrolo[3,4-c]pyridin-2-yl)-4-(trifluoromethyl)pyridazin-3(2H)-one | 283.00 |
| 281 | 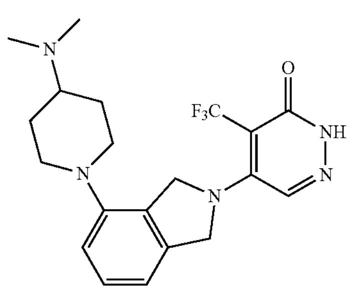 [SMILES: CN(C)C1CCN(c2cccc3c2CN(c2cn[nH]c(=O)c2C(F)(F)F)C3)CC1] | 408.30 |

TABLE E1-continued

| Example # | Structure | MS (M + H)+ |
|---|---|---|
| | 5-(4-(4-(Dimethylamino)piperidin-1-yl)isoindolin-2-yl)-4-(trifluoromethyl)pyridazin-3(2H)-one | |
| 282 | 5-(4-(Methyl(tetrahydro-2H-pyran-4-yl)amino)isoindolin-2-yl)-4-(trifluoromethyl)pyridazin-3(2H)-one | 395.15 |
| 283 | 5-(4-Fluoro-7-(2-hydroxyethoxy)isoindolin-2-yl)-4-(trifluoromethyl)pyridazin-3(2H)-one | 360.15 |
| 284 | 5-(4-(Pyrrolidin-1-yl)isoindolin-2-yl)-4-(trifluoromethyl)pyridazin-3(2H)-one | 351.15 |
| 285 | 5-(4-(3-(Dimethylamino)pyrrolidin-1-yl)isoindolin-2-yl)-4-(trifluoromethyl)pyridazin-3(2H)-one | 394.20 |

TABLE E1-continued

| Example # | Structure | MS (M + H)+ |
|---|---|---|
| 286 | 5-(4-Fluoro-7-(2-morpholinoethoxy)isoindolin-2-yl)-4-(trifluoromethyl)pyridazin-3(2H)-one | 429.15 |
| 287 | 4-Isopropyl-5-(5-(piperidin-3-yloxy)isoindolin-2-yl)pyridazin-3(2H)-one | 355.15 |
| 288# | (R)-5-(5-(Piperidin-3-yloxy)isoindolin-2-yl)-4-(trifluoromethyl)pyridazin-3(2H)-one | 381.20 |
| 289# | (S)-5-(5-(Piperidin-3-yloxy)isoindolin-2-yl)-4-(trifluoromethyl)pyridazin-3(2H)-one | 381.20 |

TABLE E1-continued
| Example # | Structure | MS (M + H)+ |
|---|---|---|
| 290 | 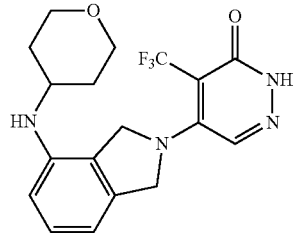<br>5-(4-((Tetrahydro-2H-pyran-4-yl)amino)isoindolin-2-yl)-4-(trifluoromethyl)pyridazin-3(2H)-one | 381.15 |
| 291 | 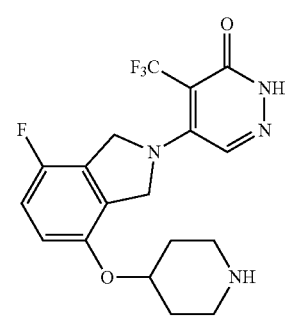 [SMILES: O=c1[nH]ncc(N2Cc3c(F)ccc(OC4CCNCC4)c3C2)c1C(F)(F)F]<br>5-(4-Fluoro-7-(piperidin-4-yloxy)isoindolin-2-yl)-4-(trifluoromethyl)pyridazin-3(2H)-one | 399.14 |
| 292# | 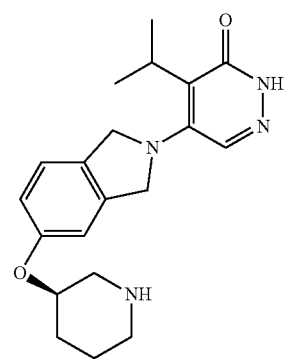 [SMILES: CC(C)c1c(N2Cc3ccc(O[C@@H]4CCCNC4)cc3C2)cn[nH]c1=O]<br>(R)-4-Isopropyl-5-(5-(piperidin-3-yloxy)isoindolin-2-yl)pyridazin-3(2H)-one | 355.20 |
| 293# | 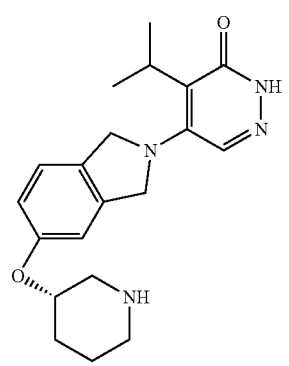<br>(S)-4-Isopropyl-5-(5-(piperidin-3-yloxy)isoindolin-2-yl)pyridazin-3(2H)-one | 355.20 |

TABLE E1-continued

| Example # | Structure | MS (M + H)+ |
|---|---|---|
| 294 | 5-(4-(4-Acetylpiperazin-1-yl)isoindolin-2-yl)-4-(trifluoromethyl)pyridazin-3(2H)-one | 407.90 |
| 295 | 5-(4-(Piperazin-1-yl)isoindolin-2-yl)-4-(trifluoromethyl)pyridazin-3(2H)-one | 365.95 |
| 296 | 5-(4-(4-Aminopiperidin-1-yl)isoindolin-2-yl)-4-(trifluoromethyl)pyridazin-3(2H)-one | 379.90 |
| 297 | 5-(4-(Piperidin-4-ylamino)isoindolin-2-yl)-4-(trifluoromethyl)pyridazin-3(2H)-one | 380.10 |
| 298# | (R)-5-(4-(Methyl((tetrahydrofuran-2-yl)methyl)amino)isoindolin-2-yl)-4-(trifluoromethyl)pyridazin-3(2H)-one | 394.10 |

TABLE E1-continued

| Example # | Structure | MS (M + H)+ |
|---|---|---|
| 299# | (S)-5-(4-(Methyl((tetrahydrofuran-2-yl)methyl)amino)isoindolin-2-yl)-4-(trifluoromethyl)pyridazin-3(2H)-one | 394.10 |
| 300 | 5-(4-((2,2,6,6-Tetramethylpiperidin-4-yl)amino)isoindolin-2-yl)-4-(trifluoromethyl)pyridazin-3(2H)-one | 436.25 |
| 301 | 5-(4-(3-Aminopiperidin-1-yl)isoindolin-2-yl)-4-(trifluoromethyl)pyridazin-3(2H)-one | 380.15 |
| 302 | 5-(4-(Methyl(piperidin-4-yl)amino)isoindolin-2-yl)-4-(trifluoromethyl)pyridazin-3(2H)-one | 394.20 |
| 303 | 5-(2-Methoxy-5,7-dihydro-6H-pyrrolo[3,4-b]pyridin-6-yl)-4-(trifluoromethyl)pyridazin-3(2H)-one | 313.10 |

TABLE E1-continued

| Example # | Structure | MS (M + H)+ |
|---|---|---|
| 304 | 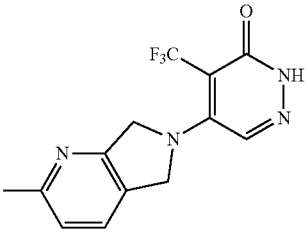<br>5-(2-Chloro-5,7-dihydro-6H-pyrrolo[3,4-b]pyridin-6-yl)-4-(trifluoromethyl)pyridazin-3(2H)-one | 317.05 |
| 305 | 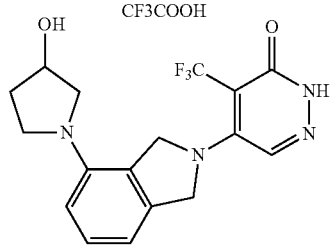 [SMILES: O=c1[nH]ncc(N2Cc3cccc(N4CCC(O)C4)c3C2)c1C(F)(F)F ; "CF3COOH"]<br>5-(4-(3-Hydroxypyrrolidin-1-yl)isoindolin-2-yl)-4-(trifluoromethyl)pyridazin-3(2H)-one 2,2,2-trifluoroacetic acid | 367.10 |
| 306 | 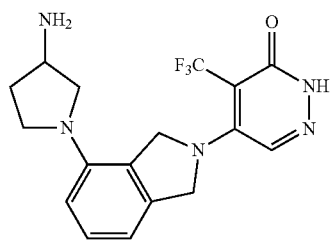 [SMILES: NC1CCN(c2cccc3c2CN(c2cn[nH]c(=O)c2C(F)(F)F)C3)C1]<br>5-(4-(3-Aminopyrrolidin-1-yl)isoindolin-2-yl)-4-(trifluoromethyl)pyridazin-3(2H)-one | 365.90 |
| 307 | 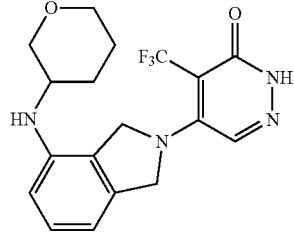 [SMILES: O=c1[nH]ncc(N2Cc3cccc(NC4CCCOC4)c3C2)c1C(F)(F)F]<br>5-(4-((Tetrahydro-2H-pyran-3-yl)amino)isoindolin-2-yl)-4-(trifluoromethyl)pyridazin-3(2H)-one | 380.85 |
| 308 | 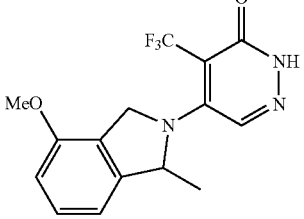<br>5-(4-Methoxy-1-methylisoindolin-2-yl)-4-(trifluoromethyl)pyridazin-3(2H)-one | 326.00 |

TABLE E1-continued
| Example # | Structure | MS (M + H)+ |
|---|---|---|
| 309 | 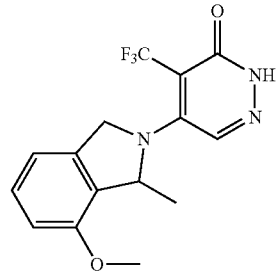 [SMILES: COc1cccc2c1C(C)N(c1cn[nH]c(=O)c1C(F)(F)F)C2]<br>5-(7-Methoxy-1-methylisoindolin-2-yl)-4-(trifluoromethyl)pyridazin-3(2H)-one | 326.00 |
| 310 | 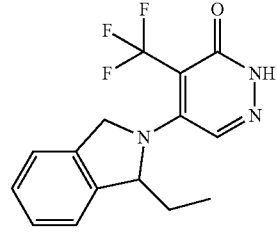 [SMILES: CCC1c2ccccc2CN1c1cn[nH]c(=O)c1C(F)(F)F]<br>5-(1-Ethylisoindolin-2-yl)-4-(trifluoromethyl)pyridazin-3(2H)-one | 310.10 |
| 311 | 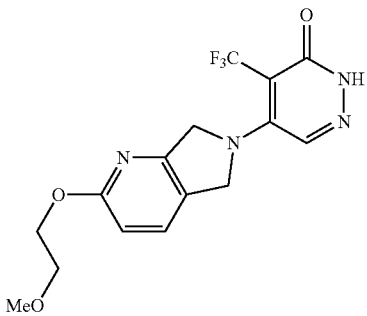 [SMILES: COCCOc1ccc2c(n1)CN(c1cn[nH]c(=O)c1C(F)(F)F)C2]<br>5-(2-(2-Methoxyethoxy)-5,7-dihydro-6H-pyrrolo[3,4-b]pyridin-6-yl)-4-(trifluoromethyl)pyridazin-3(2H)-one | 356.80 |
| 312 | 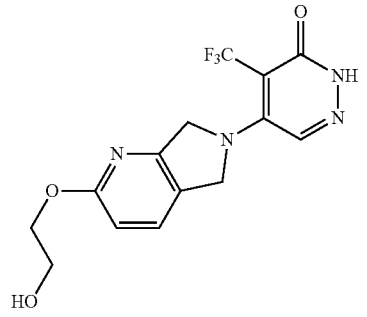 [SMILES: O=c1[nH]ncc(N2Cc3ccc(OCCO)nc3C2)c1C(F)(F)F]<br>5-(2-(2-Hydroxyethoxy)-5,7-dihydro-6H-pyrrolo[3,4-b]pyridin-6-yl)-4-(trifluoromethyl)pyridazin-3(2H)-one | 343.10 |

TABLE E1-continued

| Example # | Structure | MS (M + H)+ |
|---|---|---|
| 313 | 5-(2-(Pyridin-3-ylmethoxy)-5,7-dihydro-6H-pyrrolo[3,4-b]pyridin-6-yl)-4-(trifluoromethyl)pyridazin-3(2H)-one | 390.05 |
| 314 | 5-(4-(4-Methylpiperazin-1-yl)isoindolin-2-yl)-4-(trifluoromethyl)pyridazin-3(2H)-one | 379.85 |
| 315 | 5-(5-Fluoro-6-methoxy-1-methylisoindolin-2-yl)-4-(trifluoromethyl)pyridazin-3(2H)-one | 344.10 |
| 316 | 5-(2-(2-Morpholinoethoxy)-5,7-dihydro-6H-pyrrolo[3,4-b]pyridin-6-yl)-4-(trifluoromethyl)pyridazin-3(2H)-one | 412.10 |

TABLE E1-continued

| Example # | Structure | MS (M + H)+ |
|---|---|---|
| 317 | 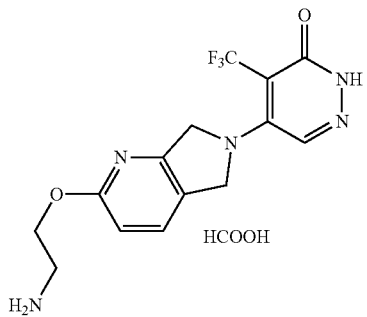 [SMILES: NCCOc1ccc2c(n1)CN(c1cn[nH]c(=O)c1C(F)(F)F)C2 ; "HCOOH"]<br>5-(2-(2-Aminoethoxy)-5,7-dihydro-6H-pyrrolo[3,4-b]pyridin-6-yl)-4-(trifluoromethyl)pyridazin-3(2H)-one formic acid | 341.85 |
| 318 | 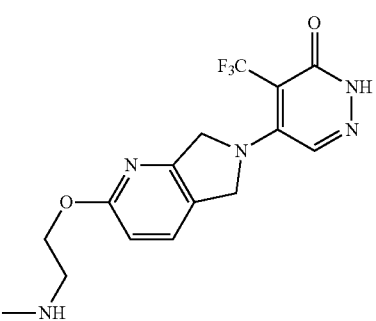 [SMILES: CNCCOc1ccc2c(n1)CN(c1cn[nH]c(=O)c1C(F)(F)F)C2]<br>5-(2-(2-(Methylamino)ethoxy)-5,7-dihydro-6H-pyrrolo[3,4-b]pyridin-6-yl)-4-(trifluoromethyl)pyridazin-3(2H)-one | 356.10 |
| 319 | 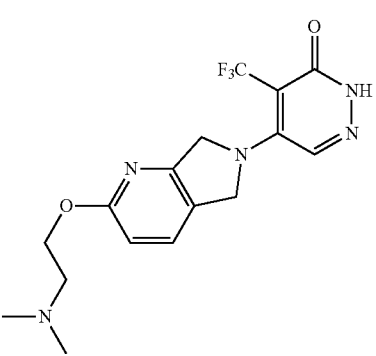 [SMILES: CN(C)CCOc1ccc2c(n1)CN(c1cn[nH]c(=O)c1C(F)(F)F)C2]<br>5-(2-(2-(Dimethylamino)ethoxy)-5,7-dihydro-6H-pyrrolo[3,4-b]pyridin-6-yl)-4-(trifluoromethyl)pyridazin-3(2H)-one | 369.80 |
| 320 | 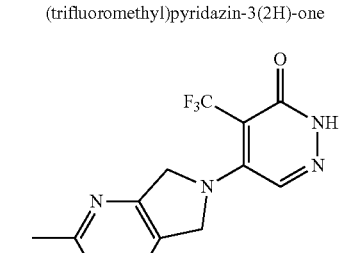<br>5-(2-Methyl-5,7-dihydro-6H-pyrrolo[3,4-b]pyridin-6-yl)-4-(trifluoromethyl)pyridazin-3(2H)-one | 297.05 |

TABLE E1-continued

| Example # | Structure | MS (M + H)+ |
|---|---|---|
| 321 | 5-(2-(Pyridin-4-ylmethoxy)-5,7-dihydro-6H-pyrrolo[3,4-b]pyridin-6-yl)-4-(trifluoromethyl)pyridazin-3(2H)-one | 390.05 |
| 322 | 5-(5-(Aminomethyl)isoindolin-2-yl)-4-(trifluoromethyl)pyridazin-3(2H)-one | 311.15 |
| 323 | 5-(4-Fluoro-6-(2-hydroxyethoxy)isoindolin-2-yl)-4-(trifluoromethyl)pyridazin-3(2H)-one | 359.85 |
| 324 | 5-(2-(Piperidin-4-yloxy)-5,7-dihydro-6H-pyrrolo[3,4-b]pyridin-6-yl)-4-(trifluoromethyl)pyridazin-3(2H)-one | 381.85 |

TABLE E1-continued

| Example # | Structure | MS (M + H)+ |
|---|---|---|
| 325 | 5-(3-(2-Morpholinoethoxy)-5,7-dihydro-6H-pyrrolo[3,4-b]pyridin-6-yl)-4-(trifluoromethyl)pyridazin-3(2H)-one | 412.10 |
| 326 | 5-(3-Methoxy-5,7-dihydro-6H-pyrrolo[3,4-b]pyridin-6-yl)-4-(trifluoromethyl)pyridazin-3(2H)-one | 313.05 |
| 327 | 5-(5-(Aminomethyl)-6-fluoroisoindolin-2-yl)-4-(trifluoromethyl)pyridazin-3(2H)-one | 329.20 |
| 328 | 5-(4-((Methyl(pyridin-4-ylmethyl)amino)methyl)isoindolin-2-yl)-4-(trifluoromethyl)pyridazin-3(2H)-one | 416.15 |

TABLE E1-continued
| Example # | Structure | MS (M + H)+ |
|---|---|---|
| 329 | 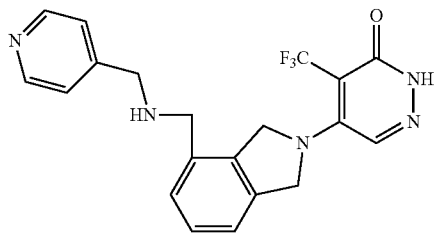 [SMILES: O=c1[nH]ncc(N2Cc3cccc(CNCc4ccncc4)c3C2)c1C(F)(F)F]<br>5-(4-(((Pyridin-4-ylmethyl)amino)methyl)isoindolin-2-yl)-4-(trifluoromethyl)pyridazin-3(2H)-one | 402.15 |
| 330 | 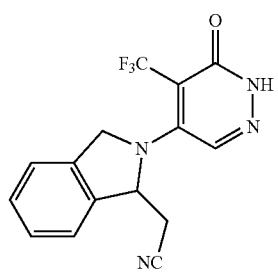 [SMILES: N#CCC1c2ccccc2CN1c1cn[nH]c(=O)c1C(F)(F)F]<br>2-(2-(6-Oxo-5-(trifluoromethyl)-1,6-dihydropyridazin-4-yl)isoindolin-1-yl)acetonitrile | 321.05 |
| 331 | 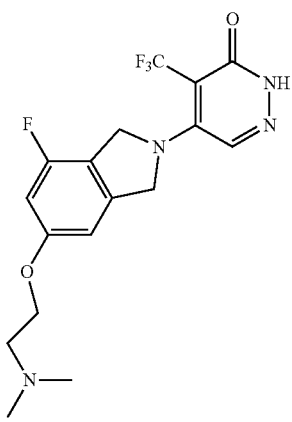 [SMILES: CN(C)CCOc1cc(F)c2c(c1)CN(c1cn[nH]c(=O)c1C(F)(F)F)C2]<br>5-(6-(2-(Dimethylamino)ethoxy)-4-fluoroisoindolin-2-yl)-4-(trifluoromethyl)pyridazin-3(2H)-one | 387.10 |
| 332 | 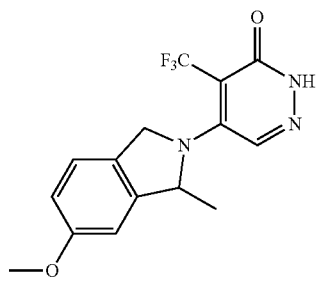 [SMILES: COc1ccc2c(c1)C(C)N(c1cn[nH]c(=O)c1C(F)(F)F)C2]<br>5-(6-Methoxy-1-methylisoindolin-2-yl)-4-(trifluoromethyl)pyridazin-3(2H)-one | 326.20 |

TABLE E1-continued

| Example # | Structure | MS (M + H)+ |
|---|---|---|
| 333 | 5-(2-((1-Acetylpiperidin-4-yl)oxy)-5,7-dihydro-6H-pyrrolo[3,4-b]pyridin-6-yl)-4-(trifluoromethyl)pyridazin-3(2H)-one | 424.10 |
| 334 | 5-(3-(2-Aminoethoxy)-5,7-dihydro-6H-pyrrolo[3,4-b]pyridin-6-yl)-4-(trifluoromethyl)pyridazin-3(2H)-one | 342.10 |
| 335 | 5-(3-(2-(Dimethylamino)ethoxy)-5,7-dihydro-6H-pyrrolo[3,4-b]pyridin-6-yl)-4-(trifluoromethyl)pyridazin-3(2H)-one | 370.10 |
| 336 | 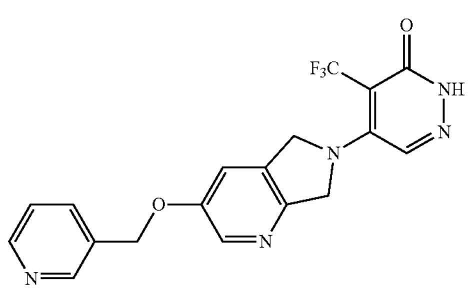 [SMILES: O=c1[nH]ncc(N2Cc3cc(OCc4cccnc4)cnc3C2)c1C(F)(F)F] | 390.05 |

TABLE E1-continued

| Example # | Structure | MS (M + H)+ |
|---|---|---|
| | 5-(3-(Pyridin-3-ylmethoxy)-5,7-dihydro-6H-pyrrolo[3,4-b]pyridin-6-yl)-4-(trifluoromethyl)pyridazin-3(2H)-one | |
| 337 | 5-(4-Methoxy-5,7-dihydro-6H-pyrrolo[3,4-b]pyridin-6-yl)-4-(trifluoromethyl)pyridazin-3(2H)-one | 313.05 |
| 338 | 5-(4-((1-Acetylpiperidin-4-yl)oxy)-5,7-dihydro-6H-pyrrolo[3,4-b]pyridin-6-yl)-4-(trifluoromethyl)pyridazin-3(2H)-one | 424.15 |
| 339 | 5-(4-((Pyridin-4-ylamino)methyl)isoindolin-2-yl)-4-(trifluoromethyl)pyridazin-3(2H)-one | 388.10 |

TABLE E1-continued

| Example # | Structure | MS (M + H)+ |
|---|---|---|
| 340 | 6-(4-(3-((2-(6-Oxo-5-(trifluoromethyl)-1,6-dihydropyridazin-4-yl)isoindolin-1-yl)methoxy)benzoyl)piperazin-1-yl)nicotinonitrile | 602.05 |
| 341 | 5-(1-((3-(4-(Pyridin-2-yl)piperazine-1-carbonyl)phenoxy)methyl)isoindolin-2-yl)-4-(trifluoromethyl)pyridazin-3(2H)-one | 577.15 |
| 342 | 3-((2-(6-Oxo-5-(trifluoromethyl)-1,6-dihydropyridazin-4-yl)isoindolin-1-yl)methoxy)benzoic acid | 432.00 |

TABLE E1-continued

| Example # | Structure | MS (M + H)⁺ |
|---|---|---|
| 343 | 6-(4-(3-(Methyl((2-(6-oxo-5-(trifluoromethyl)-1,6-dihydropyridazin-4-yl)isoindolin-1-yl)methyl)amino)benzoyl)piperazin-1-yl)nicotinonitrile | 614.85 |
| 344 | 5-(1-((Methyl(3-(4-(pyridin-2-yl)piperazine-1-carbonyl)phenyl)amino)methyl)isoindolin-2-yl)-4-(trifluoromethyl)pyridazin-3(2H)-one | 590.30 |
| 345 | 3-(Methyl((2-(6-oxo-5-(trifluoromethyl)-1,6-dihydropyridazin-4-yl)isoindolin-1-yl)methyl)amino)benzoic acid | 445.05 |

TABLE E1-continued
| Example # | Structure | MS (M + H)+ |
|---|---|---|
| 346 | 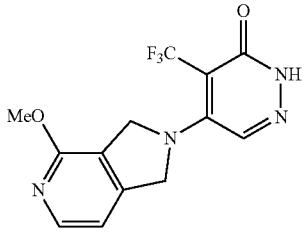 [SMILES: COc1nccc2c1CN(c1cn[nH]c(=O)c1C(F)(F)F)C2] 5-(4-Methoxy-1,3-dihydro-2H-pyrrolo[3,4-c]pyridin-2-yl)-4-(trifluoromethyl)pyridazin-3(2H)-one | 313.10 |
| 347 | 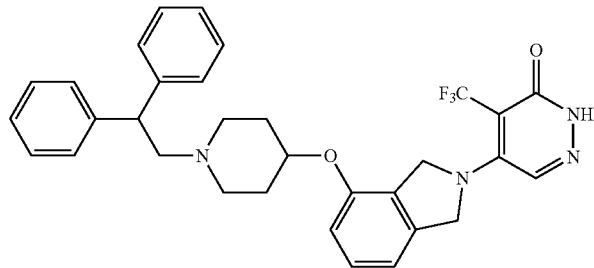 [SMILES: O=c1[nH]ncc(N2Cc3cccc(OC4CCN(CC(c5ccccc5)c5ccccc5)CC4)c3C2)c1C(F)(F)F] 5-(4-((1-(2,2-Diphenylethyl)piperidin-4-yl)oxy)isoindolin-2-yl)-4-(trifluoromethyl)pyridazin-3(2H)-one | 561.10 |
| 348 | 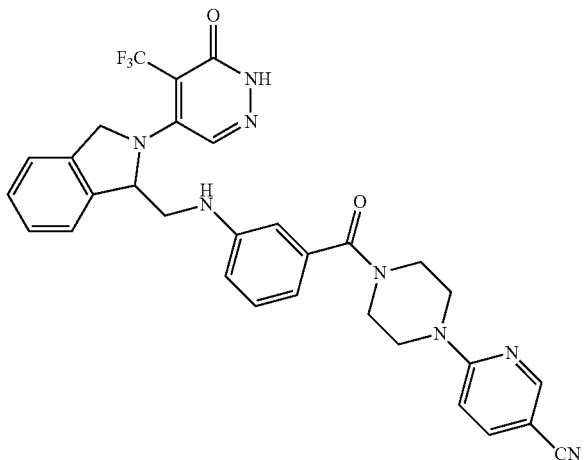 6-(4-(3-(((2-(6-Oxo-5-(trifluoromethyl)-1,6-dihydropyridazin-4-yl)isoindolin-1-yl)methyl)amino)benzoyl)piperazin-1-yl)nicotinonitrile | 601.10 |

TABLE E1-continued

| Example # | Structure | MS (M + H)+ |
|---|---|---|
| 349* | (S)-5-(1-(((3-(4-(Pyridin-2-yl)piperazine-1-carbonyl)phenoxy)methyl)isoindolin-2-yl)-4-(trifluoromethyl)pyridazin-3(2H)-one | 557.10 |
| 350* | (R)-5-(1-(((3-(4-(Pyridin-2-yl)piperazine-1-carbonyl)phenoxy)methyl)isoindolin-2-yl)-4-(trifluoromethyl)pyridazin-3(2H)-one | 557.10 |
| 351 | 5-(1-(((3-(4-(Pyridin-2-yl)piperazine-1-carbonyl)phenyl)amino)methyl)isoindolin-2-yl)-4-(trifluoromethyl)pyridazin-3(2H)-one | 576.25 |

TABLE E1-continued
| Example # | Structure | MS (M + H)+ |
|---|---|---|
| 352 | 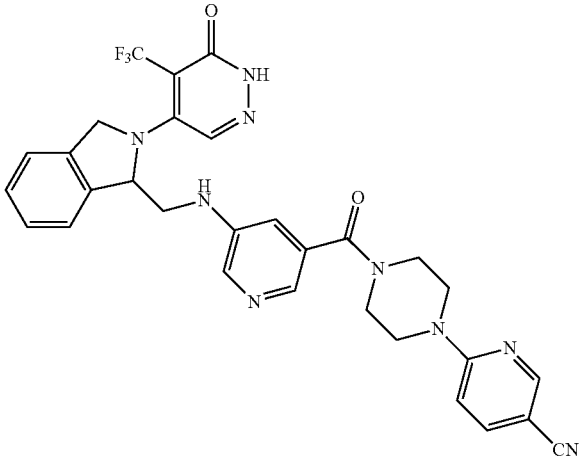 [SMILES: N#Cc1ccc(N2CCN(C(=O)c3cncc(NCC4c5ccccc5CN4c4cn[nH]c(=O)c4C(F)(F)F)c3)CC2)nc1]<br>6-(4-(5-((2-(6-Oxo-5-(trifluoromethyl)-1,6-dihydropyridazin-4-yl)isoindolin-1-yl)methoxy)nicotinoyl)piperazin-1-yl)nicotinonitrile | 603.10 |
| 353* | 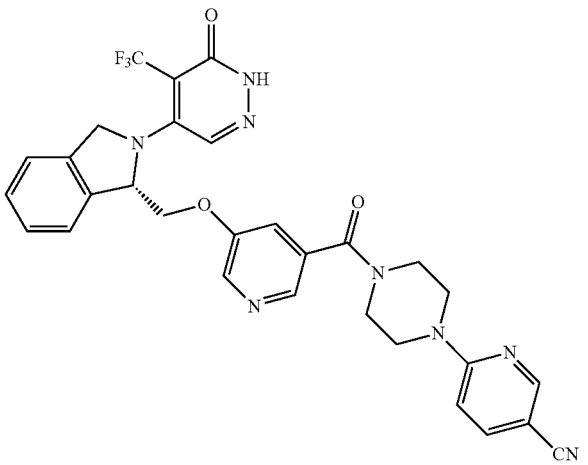<br>(S)-6-(4-(5-((2-(6-Oxo-5-(trifluoromethyl)-1,6-dihydropyridazin-4-yl)isoindolin-1-yl)methoxy)nicotinoyl)piperazin-1-yl)nicotinonitrile | 603.10 |
| 354* | 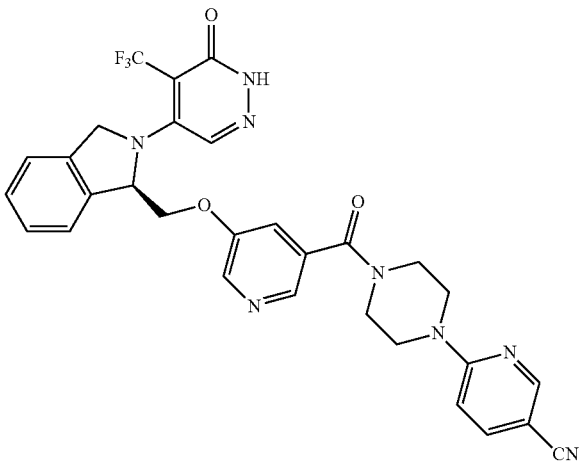 | 603.10 |

TABLE E1-continued

| Example # | Structure | MS (M + H)+ |
|---|---|---|
| | (R)-6-(4-(5-((2-(6-Oxo-5-(trifluoromethyl)-1,6-dihydropyridazin-4-yl)isoindolin-1-yl)methoxy)nicotinoyl)piperazin-1-yl)nicotinonitrile | |
| 355 | 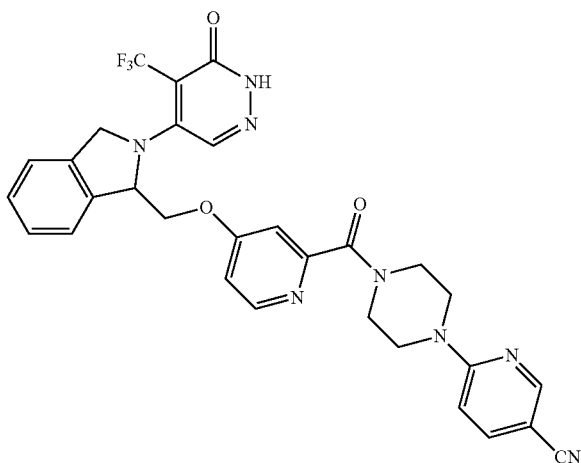 | 603.10 |
| | 6-(4-(4-((2-(6-Oxo-5-(trifluoromethyl)-1,6-dihydropyridazin-4-yl)isoindolin-1-yl)methoxy)picolinoyl)piperazin-1-yl)nicotinonitrile | |
| 356* | 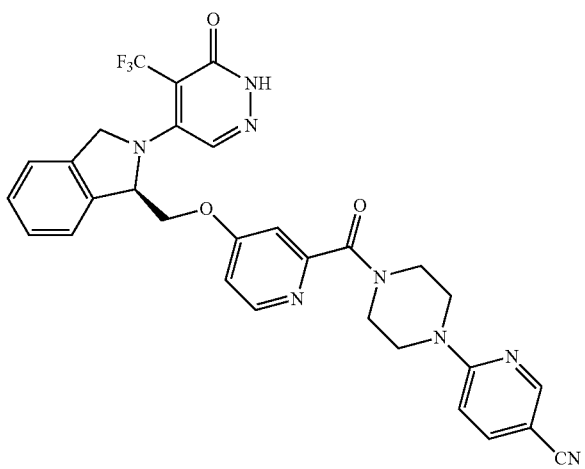 [SMILES: N#Cc1ccc(N2CCN(C(=O)c3cc(OC[C@H]4c5ccccc5CN4c4cn[nH]c(=O)c4C(F)(F)F)ccn3)CC2)nc1] | 603.10 |
| | (R)-6-(4-(4-((2-(6-Oxo-5-(trifluoromethyl)-1,6-dihydropyridazin-4-yl)isoindolin-1-yl)methoxy)picolinoyl)piperazin-1-yl)nicotinonitrile | |

TABLE E1-continued

| Example # | Structure | MS (M + H)+ |
|---|---|---|
| 357* | (S)-6-(4-(4-((2-(6-Oxo-5-(trifluoromethyl)-1,6-dihydropyridazin-4-yl)isoindolin-1-yl)methoxy)picolinoyl)piperazin-1-yl)nicotinonitrile | 603.10 |
| 358 | 2-(4-(3-((2-(6-Oxo-5-(trifluoromethyl)-1,6-dihydropyridazin-4-yl)isoindolin-1-yl)methoxy)benzoyl)piperazin-1-yl)nicotinonitrile | 602.10 |
| 359* | (S)-2-(4-(3-((2-(6-Oxo-5-(trifluoromethyl)-1,6-dihydropyridazin-4-yl)isoindolin-1-yl)methoxy)benzoyl)piperazin-1-yl)nicotinonitrile | 602.10 |

TABLE E1-continued
| Example # | Structure | MS (M + H)+ |
|---|---|---|
| 360* | 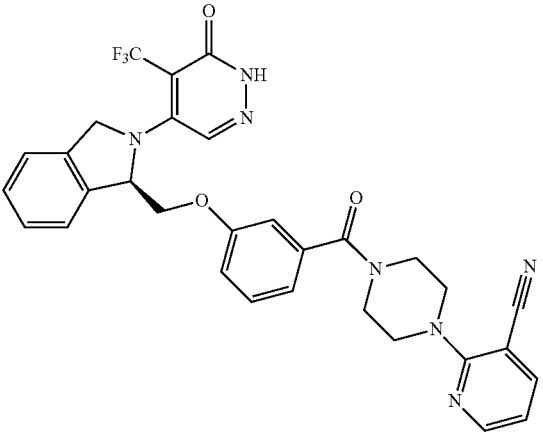 [SMILES: N#Cc1cccnc1N1CCN(C(=O)c2cccc(OC[C@H]3c4ccccc4CN3c3cn[nH]c(=O)c3C(F)(F)F)c2)CC1] (R)-2-(4-(3-((2-(6-Oxo-5-(trifluoromethyl)-1,6-dihydropyridazin-4-yl)isoindolin-1-yl)methoxy)benzoyl)piperazin-1-yl)nicotinonitrile | 602.10 |
| 361 | 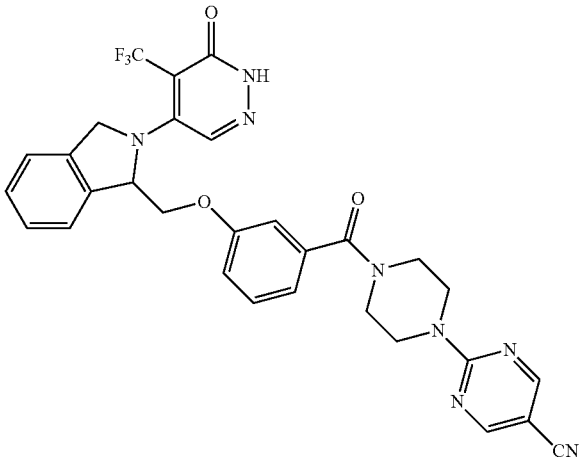 2-(4-(3-((2-(6-Oxo-5-(trifluoromethyl)-1,6-dihydropyridazin-4-yl)isoindolin-1-yl)methoxy)benzoyl)piperazin-1-yl)pyrimidine-5-carbonitrile | 603.00 |
| 362 | 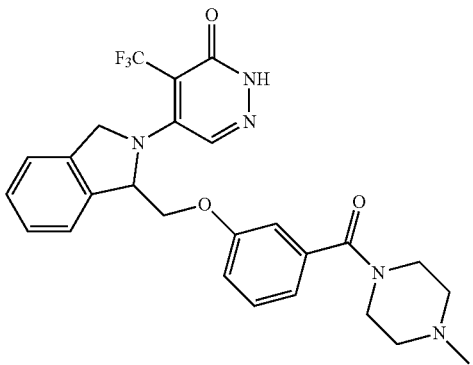 [SMILES: CN1CCN(C(=O)c2cccc(OCC3c4ccccc4CN3c3cn[nH]c(=O)c3C(F)(F)F)c2)CC1] 5-(1-((3-(4-Methylpiperazine-1-carbonyl)phenoxy)methyl)isoindolin-2-yl)-4-(trifluoromethyl)pyridazin-3(2H)-one | 514.10 |

TABLE E1-continued

| Example # | Structure | MS (M + H)+ |
|---|---|---|
| 363 | 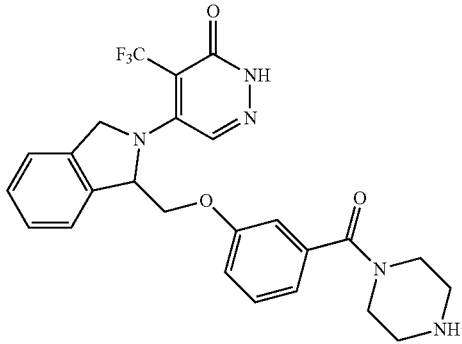 [SMILES: O=C(c1cccc(OCC2c3ccccc3CN2c2cn[nH]c(=O)c2C(F)(F)F)c1)N1CCNCC1] 5-(1-((3-(Piperazine-1-carbonyl)phenoxy)methyl)isoindolin-2-yl)-4-(trifluoromethyl)pyridazin-3(2H)-one | 500.10 |
| 364* | 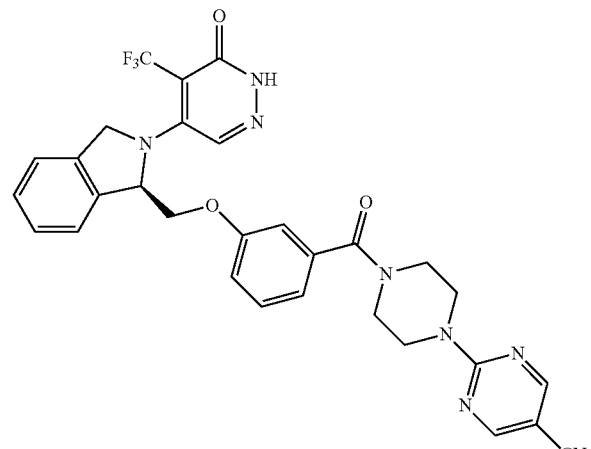 (R)-2-(4-(3-((2-(6-oxo-5-(trifluoromethyl)-1,6-dihydropyridazin-4-yl)isoindolin-1-yl)methoxy)benzoyl)piperazin-1-yl)pyrimidine-5-carbonitrile | 603.00 |
| 365* | 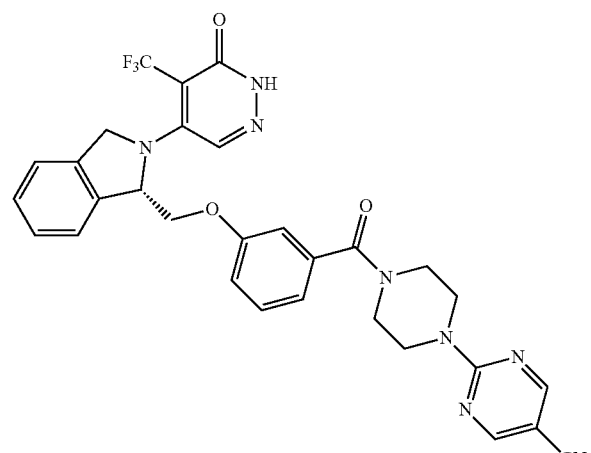 (S)-2-(4-(3-((2-(6-oxo-5-(trifluoromethyl)-1,6-dihydropyridazin-4-yl)isoindolin-1-yl)methoxy)benzoyl)piperazin-1-yl)pyrimidine-5-carbonitrile | 603.00 |

TABLE E1-continued

| Example # | Structure | MS (M + H)+ |
|---|---|---|
| 366 | 5-(4-(3-((2-(6-Oxo-5-(trifluoromethyl)-1,6-dihydropyridazin-4-yl)isoindolin-1-yl)methoxy)benzoyl)piperazin-1-yl)pyrazine-2-carbonitrile | 603.20 |
| 367 | 4-(Trifluoromethyl)-5-(1-((3-(3-(trifluoromethyl)-5,6,7,8-tetrahydro-[1,2,4]triazolo[4,3-a]pyrazine-7-carbonyl)phenoxy)methyl)isoindolin-2-yl)pyridazin-3(2H)-one | 606.00 |
| 368 | 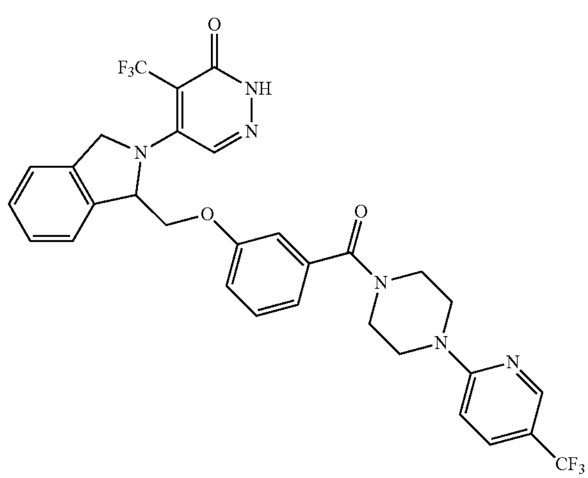 [SMILES: O=C(c1cccc(OCC2c3ccccc3CN2c2cn[nH]c(=O)c2C(F)(F)F)c1)N1CCN(c2ccc(C(F)(F)F)cn2)CC1] | 645.20 |

TABLE E1-continued

| Example # | Structure | MS (M + H)+ |
|---|---|---|
| | 4-(Trifluoromethyl)-5-(1-((3-(4-(5-(trifluoromethyl)pyridin-2-yl)piperazine-1-carbonyl)phenoxy)methyl)isoindolin-2-yl)pyridazin-3(2H)-one | |
| 369* | 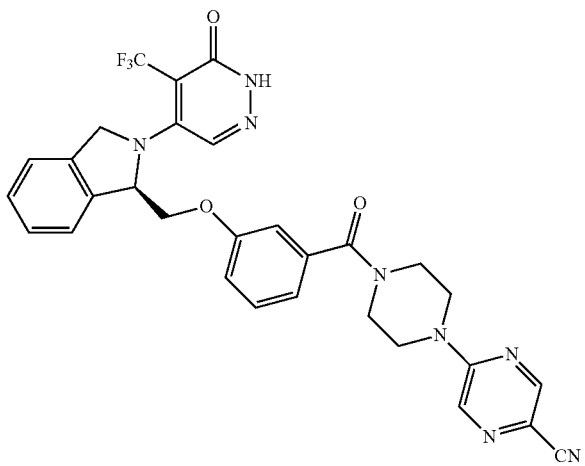 [SMILES: N#Cc1cnc(N2CCN(C(=O)c3cccc(OC[C@H]4c5ccccc5CN4c4cn[nH]c(=O)c4C(F)(F)F)c3)CC2)cn1]  (R)-5-(4-(3-((2-(6-Oxo-5-(trifluoromethyl)-1,6-dihydropyridazin-4-yl)isoindolin-1-yl)methoxy)benzoyl)piperazin-1-yl)pyrazine-2-carbonitrile | 603.20 |
| 370* | 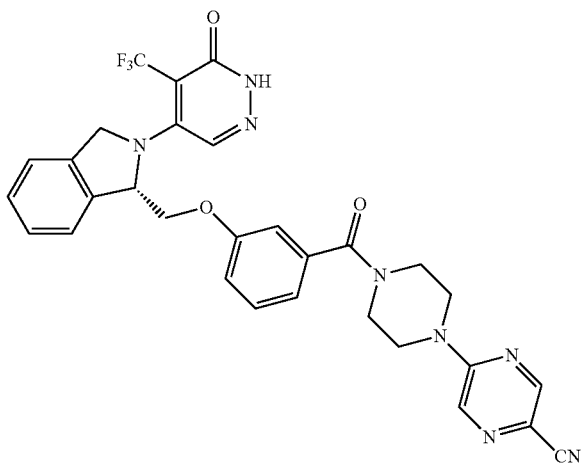  (S)-5-(4-(3-((2-(6-Oxo-5-(trifluoromethyl)-1,6-dihydropyridazin-4-yl)isoindolin-1-yl)methoxy)benzoyl)piperazin-1-yl)pyrazine-2-carbonitrile | 603.20 |

TABLE E1-continued

| Example # | Structure | MS (M + H)+ |
|---|---|---|
| 371 | 6-(4-(4-((2-(6-Oxo-5-(trifluoromethyl)-1,6-dihydropyridazin-4-yl)isoindolin-1-yl)methoxy)benzoyl)piperazin-1-yl)nicotinonitrile | 602.20 |
| 372* | (R)-4-(Trifluoromethyl)-5-(1-((3-(3-(trifluoromethyl)-5,6,7,8-tetrahydro-[1,2,4]triazolo[4,3-a]pyrazine-7-carbonyl)phenoxy)methyl)isoindolin-2-yl)pyridazin-3(2H)-one | 606.00 |
| 373* | (S)-4-(Trifluoromethyl)-5-(1-((3-(3-(trifluoromethyl)-5,6,7,8-tetrahydro-[1,2,4]triazolo[4,3-a]pyrazine-7-carbonyl)phenoxy)methyl)isoindolin-2-yl)pyridazin-3(2H)-one | 606.00 |

TABLE E1-continued

| Example # | Structure | MS (M + H)⁺ |
|---|---|---|
| 374 | 4-(Trifluoromethyl)-5-(1-(((5-(4-(5-(trifluoromethyl)pyridin-2-yl)piperazine-1-carbonyl)pyridin-3-yl)oxy)methyl)isoindolin-2-yl)pyridazin-3(2H)-one | 646.15 |
| 375 | 5-(1-(((5-(4-(5-Fluoropyridin-2-yl)piperazine-1-carbonyl)pyridin-3-yl)oxy)methyl)isoindolin-2-yl)-4-(trifluoromethyl)pyridazin-3(2H)-one | 596.10 |
| 376 | 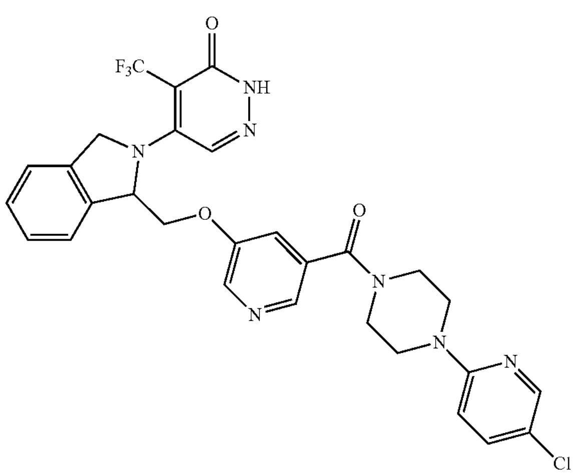 | 612.05 |

TABLE E1-continued

| Example # | Structure | MS (M + H)+ |
|---|---|---|
| | 5-(1-(((5-(4-(5-Chloropyridin-2-yl)piperazine-1-carbonyl)pyridin-3-yl)oxy)methyl)isoindolin-2-yl)-4-(trifluoromethyl)pyridazin-3(2H)-one | |
| 377 | 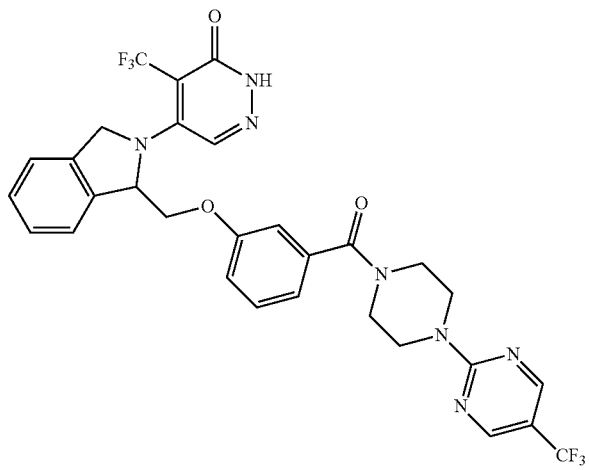 [SMILES: O=C(c1cccc(OCC2c3ccccc3CN2c2cn[nH]c(=O)c2C(F)(F)F)c1)N1CCN(c2ncc(C(F)(F)F)cn2)CC1]<br>4-(Trifluoromethyl)-5-(1-((3-(4-(5-(trifluoromethyl)pyrimidin-2-yl)piperazine-1-carbonyl)phenoxy)methyl)isoindolin-2-yl)pyridazin-3(2H)-one | 646.25 |
| 378 | 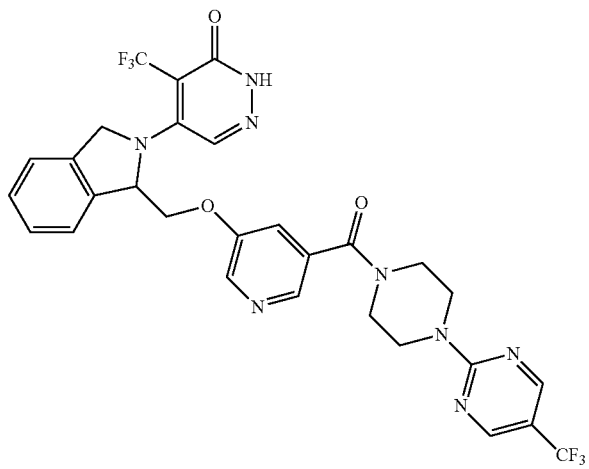<br>4-(Trifluoromethyl)-5-(1-(((5-(4-(5-(trifluoromethyl)pyrimidin-2-yl)piperazine-1-carbonyl)pyridin-3-yl)oxy)methyl)isoindolin-2-yl)pyridazin-3(2H)-one | 647.05 |

TABLE E1-continued

| Example # | Structure | MS (M + H)+ |
|---|---|---|
| 379 | 2-(4-(5-((2-(6-Oxo-5-(trifluoromethyl)-1,6-dihydropyridazin-4-yl)isoindolin-1-yl)methoxy)nicotinoyl)piperazin-1-yl)pyrimidine-5-carbonitrile | 604.20 |
| 380 | 2-(4-(4-((2-(6-Oxo-5-(trifluoromethyl)-1,6-dihydropyridazin-4-yl)isoindolin-1-yl)methoxy)picolinoyl)piperazin-1-yl)pyrimidine-5-carbonitrile | 604.05 |
| 381 | 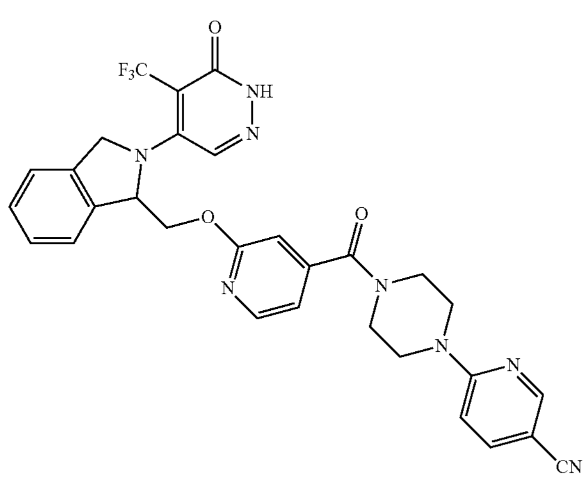 | 603.10 |

TABLE E1-continued

| Example # | Structure | MS (M + H)+ |
|---|---|---|
| | 6-(4-(2-((2-(6-Oxo-5-(trifluoromethyl)-1,6-dihydropyridazin-4-yl)isoindolin-1-yl)methoxy)isonicotinoyl)piperazin-1-yl)nicotinonitrile | |
| 382 | 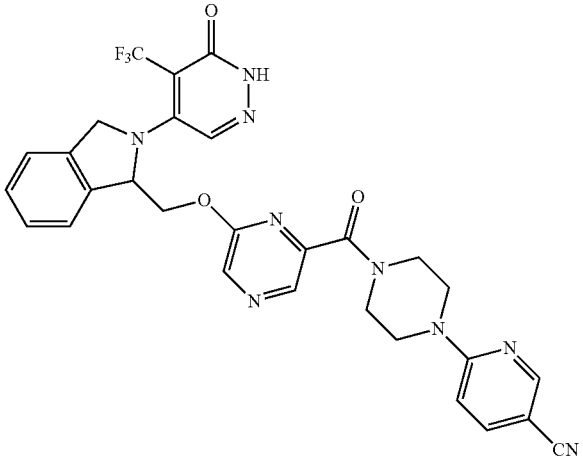 [SMILES: N#Cc1ccc(N2CCN(C(=O)c3cncc(OCC4c5ccccc5CN4c4cn[nH]c(=O)c4C(F)(F)F)n3)CC2)nc1] 6-(4-(6-((2-(6-Oxo-5-(trifluoromethyl)-1,6-dihydropyridazin-4-yl)isoindolin-1-yl)methoxy)pyrazine-2-carbonyl)piperazin-1-yl)nicotinonitrile | 604.55 |
| 383 | 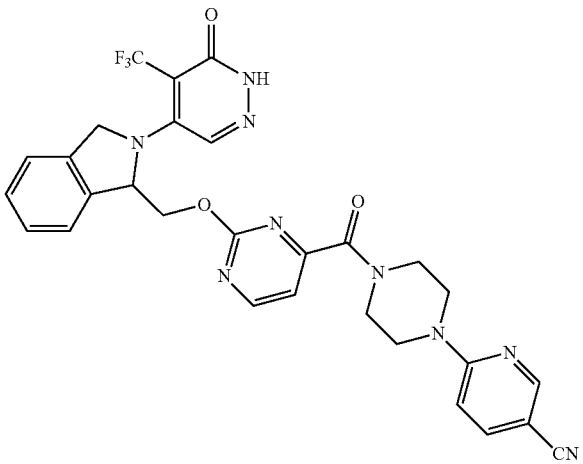 6-(4-(2-((2-(6-Oxo-5-(trifluoromethyl)-1,6-dihydropyridazin-4-yl)isoindolin-1-yl)methoxy)pyrimidine-4-carbonyl)piperazin-1-yl)nicotinonitrile | 604.20 |

TABLE E1-continued

| Example # | Structure | MS (M + H)+ |
|---|---|---|
| 384* | (S)-4-(Trifluoromethyl)-5-(1-(((5-(4-(5-(trifluoromethyl)pyridin-2-yl)piperazine-1-carbonyl)pyridin-3-yl)oxy)methyl)isoindolin-2-yl)pyridazin-3(2H)-one | 646.05 |
| 385* | (R)-4-(Trifluoromethyl)-5-(1-(((5-(4-(5-(trifluoromethyl)pyridin-2-yl)piperazine-1-carbonyl)pyridin-3-yl)oxy)methyl)isoindolin-2-yl)pyridazin-3(2H)-one | 646.05 |
| 386* | 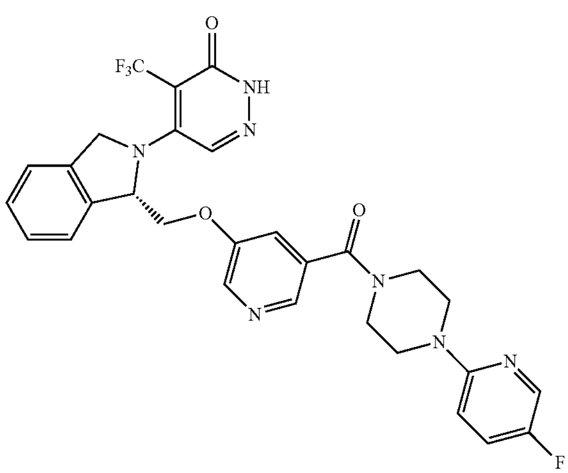 [SMILES: O=C(c1cncc(OC[C@@H]2c3ccccc3CN2c2cn[nH]c(=O)c2C(F)(F)F)c1)N1CCN(c2ccc(F)cn2)CC1] | 596.50 |

TABLE E1-continued

| Example # | Structure | MS (M + H)+ |
|---|---|---|
| 387* | (S)-5-(1-(((5-(4-(5-Fluoropyridin-2-yl)piperazine-1-carbonyl)pyridin-3-yl)oxy)methyl)isoindolin-2-yl)-4-(trifluoromethyl)pyridazin-3(2H)-one 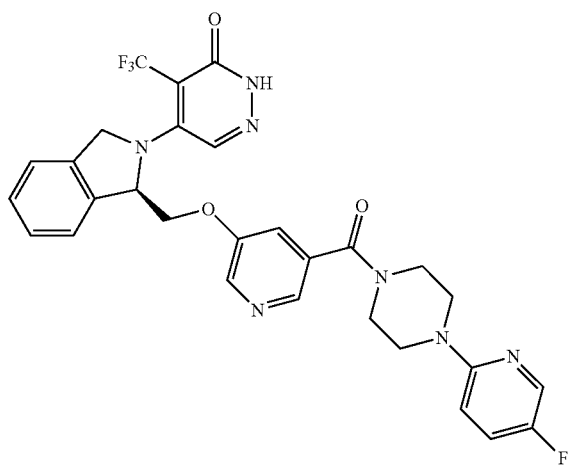 [SMILES: O=C(c1cncc(OC[C@H]2c3ccccc3CN2c2cn[nH]c(=O)c2C(F)(F)F)c1)N1CCN(c2ccc(F)cn2)CC1] (R)-5-(1-(((5-(4-(5-Fluoropyridin-2-yl)piperazine-1-carbonyl)pyridin-3-yl)oxy)methyl)isoindolin-2-yl)-4-(trifluoromethyl)pyridazin-3(2H)-one | 596.50 |
| 388* | 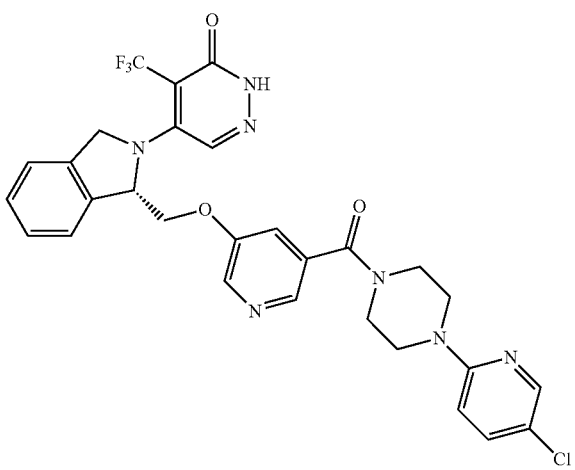 [SMILES: O=C(c1cncc(OC[C@@H]2c3ccccc3CN2c2cn[nH]c(=O)c2C(F)(F)F)c1)N1CCN(c2ccc(Cl)cn2)CC1] (S)-5-(1-(((5-(4-(5-Chloropyridin-2-yl)piperazine-1-carbonyl)pyridin-3-yl)oxy)methyl)isoindolin-2-yl)-4-(trifluoromethyl)pyridazin-3(2H)-one | 612.05 |

TABLE E1-continued

| Example # | Structure | MS (M + H)+ |
|---|---|---|
| 389* | (R)-5-(1-(((5-(4-(5-Chloropyridin-2-yl)piperazine-1-carbonyl)pyridin-3-yl)oxy)methyl)isoindolin-2-yl)-4-(trifluoromethyl)pyridazin-3(2H)-one | 612.05 |
| 390* | (S)-4-(Trifluoromethyl)-5-(1-((3-(4-(5-(trifluoromethyl)pyrimidin-2-yl)piperazine-1-carbonyl)phenoxy)methyl)isoindolin-2-yl)pyridazin-3(2H)-one | 646.25 |
| 391* | 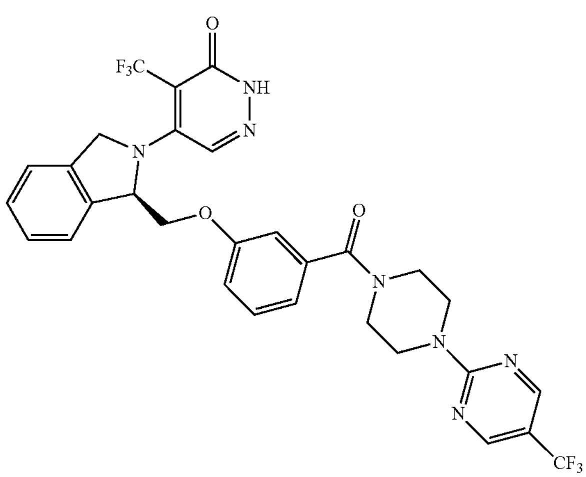 [SMILES: O=C(c1cccc(OC[C@H]2c3ccccc3CN2c2cn[nH]c(=O)c2C(F)(F)F)c1)N1CCN(c2ncc(C(F)(F)F)cn2)CC1] | 646.25 |

TABLE E1-continued

| Example # | Structure | MS (M + H)+ |
|---|---|---|
| | (R)-4-(Trifluoromethyl)-5-(1-(((3-(4-(5-(trifluoromethyl)pyrimidin-2-yl)piperazine-1-carbonyl)phenoxy)methyl)isoindolin-2-yl)pyridazin-3(2H)-one | |
| 392* | 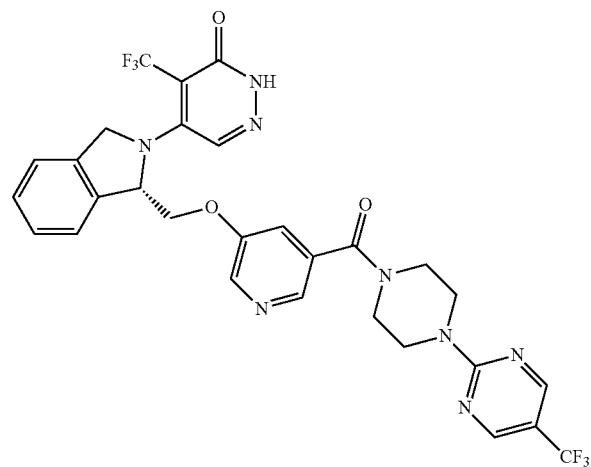 [SMILES: O=C(c1cncc(OC[C@@H]2c3ccccc3CN2c2cn[nH]c(=O)c2C(F)(F)F)c1)N1CCN(c2ncc(C(F)(F)F)cn2)CC1] (S)-4-(Trifluoromethyl)-5-(1-(((5-(4-(5-(trifluoromethyl)pyrimidin-2-yl)piperazine-1-carbonyl)pyridin-3-yl)oxy)methyl)isoindolin-2-yl)pyridazin-3(2H)-one | 647.05 |
| 393* | 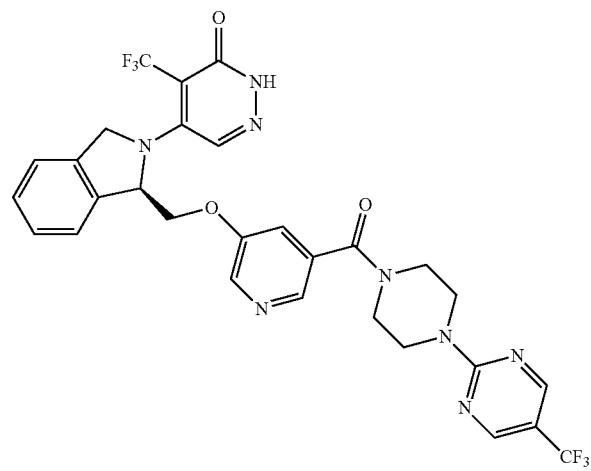 [SMILES: O=C(c1cncc(OC[C@H]2c3ccccc3CN2c2cn[nH]c(=O)c2C(F)(F)F)c1)N1CCN(c2ncc(C(F)(F)F)cn2)CC1] (R)-4-(Trifluoromethyl)-5-(1-(((5-(4-(5-(trifluoromethyl)pyrimidin-2-yl)piperazine-1-carbonyl)pyridin-3-yl)oxy)methyl)isoindolin-2-yl)pyridazin-3(2H)-one | 647.05 |

TABLE E1-continued

| Example # | Structure | MS (M + H)+ |
|---|---|---|
| 394 | 3-((5-Cyanopyridin-2-yl)amino)-N-(3-((2-(6-oxo-5-(trifluoromethyl)-1,6-dihydropyridazin-4-yl)isoindolin-1-yl)methoxy)phenyl)propanamide | 576.20 |
| 395* | (S)-2-(4-(5-((2-(6-Oxo-5-(trifluoromethyl)-1,6-dihydropyridazin-4-yl)isoindolin-1-yl)methoxy)nicotinoyl)piperazin-1-yl)pyrimidine-5-carbonitrile | 604.20 |
| 396* | 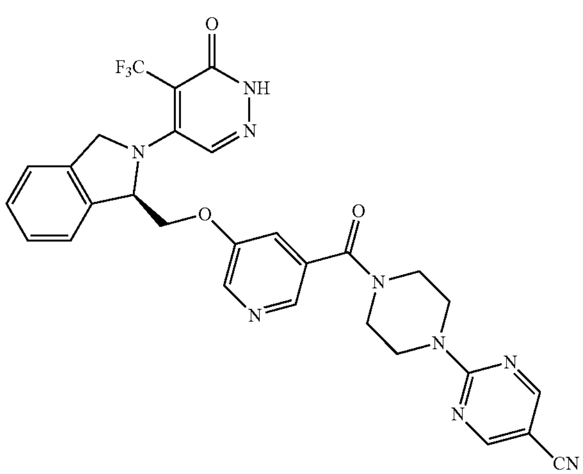 [SMILES: N#Cc1cnc(N2CCN(C(=O)c3cncc(OC[C@H]4c5ccccc5CN4c4cn[nH]c(=O)c4C(F)(F)F)c3)CC2)nc1] | 604.20 |

TABLE E1-continued

| Example # | Structure | MS (M + H)+ |
|---|---|---|
| | (R)-2-(4-(5-((2-(6-Oxo-5-(trifluoromethyl)-1,6-dihydropyridazin-4-yl)isoindolin-1-yl)methoxy)nicotinoyl)piperazin-1-yl)pyrimidine-5-carbonitrile | |
| 397 | 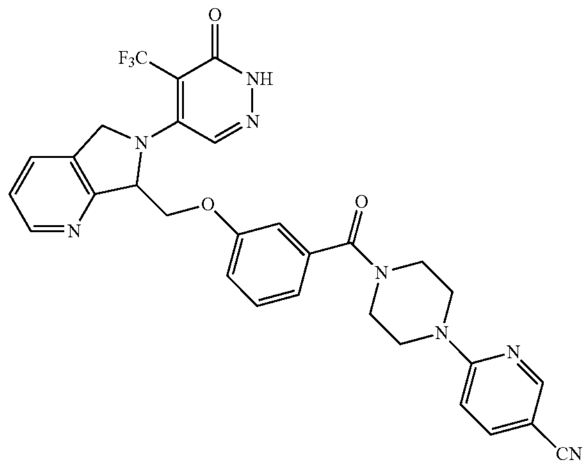 | 603.05 |
| | 6-(4-(3-((6-(6-Oxo-5-(trifluoromethyl)-1,6-dihydropyridazin-4-yl)-6,7-dihydro-5H-pyrrolo[3,4-b]pyridin-7-yl)methoxy)benzoyl)piperazin-1-yl)nicotinonitrile | |
| 398 | 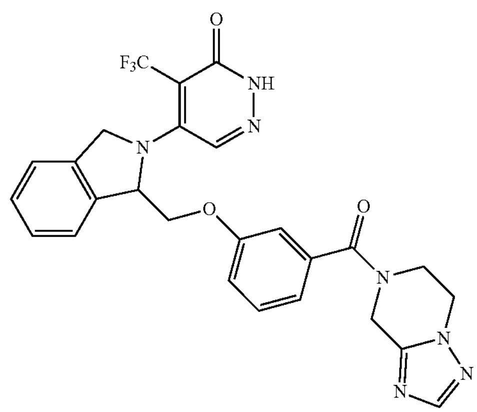 [SMILES: O=C(c1cccc(OCC2c3ccccc3CN2c2cn[nH]c(=O)c2C(F)(F)F)c1)N1CCn2ncnc2C1] | 538.10 |
| | 5-(1-((3-(5,6,7,8-Tetrahydro-[1,2,4]triazolo[1,5-a]pyrazine-7-carbonyl)phenoxy)methyl)isoindolin-2-yl)-4-(trifluoromethyl)pyridazin-3(2H)-one | |
| 399 | 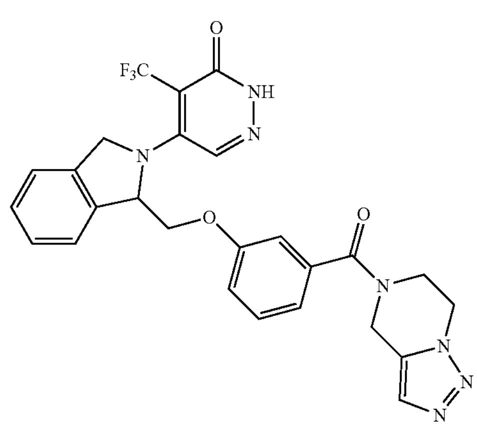 [SMILES: O=C(c1cccc(OCC2c3ccccc3CN2c2cn[nH]c(=O)c2C(F)(F)F)c1)N1CCn2nncc2C1] | 538.10 |

TABLE E1-continued
| Example # | Structure | MS (M + H)+ |
|---|---|---|
| | 5-(1-((3-(4,5,6,7-Tetrahydro-[1,2,3]triazolo[1,5-a]pyrazine-5-carbonyl)phenoxy)methyl)isoindolin-2-yl)-4-(trifluoromethyl)pyridazin-3(2H)-one | |
| 400 | 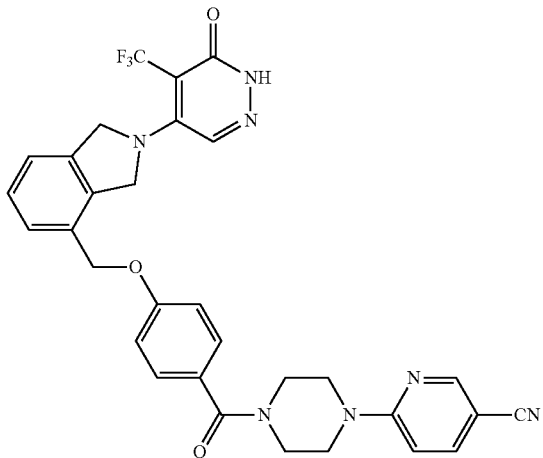 [SMILES: N#Cc1ccc(N2CCN(C(=O)c3ccc(OCc4cccc5c4CN(c4cn[nH]c(=O)c4C(F)(F)F)C5)cc3)CC2)nc1] 6-(4-(4-((2-(6-Oxo-5-(trifluoromethyl)-1,6-dihydropyridazin-4-yl)isoindolin-4-yl)methoxy)benzoylpiperazin-1-yl)nicotinonitrile | 602.60 |
| 401 | 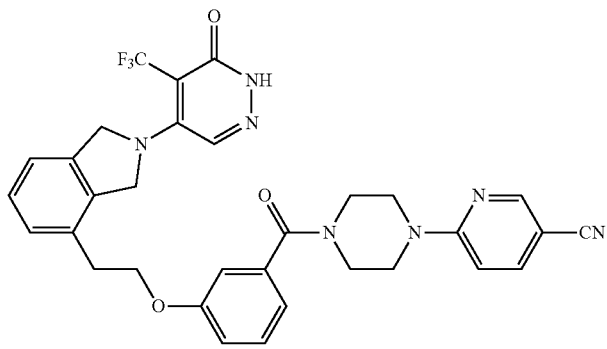 [SMILES: N#Cc1ccc(N2CCN(C(=O)c3cccc(OCCc4cccc5c4CN(c4cn[nH]c(=O)c4C(F)(F)F)C5)c3)CC2)nc1] 6-(4-(3-(2-(2-(6-Oxo-5-(trifluoromethyl)-1,6-dihydropyridazin-4-yl)isoindolin-4-yl)ethoxy)benzoyl)pierazin-1-yl)nicotinonitrile | 616.60 |

TABLE E1-continued
| Example # | Structure | MS (M + H)+ |
|---|---|---|
| 402 | 6-(4-(4-(2-(2-(6-Oxo-5-(trifluoromethyl)-1,6-dihydropyridazin-4-yl)isoindolin-4-yl)ethoxy)benzoyl)piperazin-1-yl)nicotinonitrile | 616.20 |
| 403 | 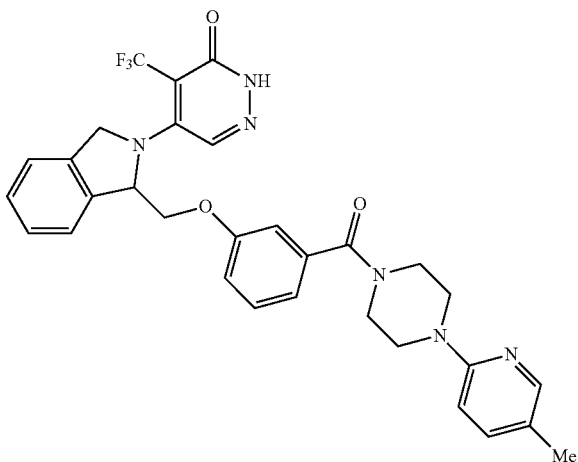 [SMILES: Cc1ccc(N2CCN(C(=O)c3cccc(OCC4c5ccccc5CN4c4cn[nH]c(=O)c4C(F)(F)F)c3)CC2)nc1] 5-(1-((3-(4-(5-Methylpyridin-2-yl)piperazine-1-carbonyl)phenoxy)methyl)isoindolin-2-yl)-4-(trifluoromethyl)pyridazin-3(2H)-one | 591.25 |

TABLE E1-continued

| Example # | Structure | MS (M + H)+ |
|---|---|---|
| 404 | 5-(1-((3-(4,5,6,7-Tetrahydropyrazolo[1,5-a]pyrazine-5-carbonyl)phenoxy)methyl)isoindolin-2-yl)-4-(trifluoromethyl)pyridazin-3(2H)-one | 537.10 |
| 405 | 5-(1-((3-(4-Acetylpiperazine-1-carbonyl)phenoxy)methyl)isoindolin-2-yl)-4-(trifluoromethyl)pyridazin-3(2H)-one | 542.10 |
| 406* | (R)-5-(1-((3-(4-Acetylpiperazine-1-carbonyl)phenoxy)methyl)isoindolin-2-yl)-4-(trifluoromethyl)pyridazin-3(2H)-one | 542.10 |

TABLE E1-continued

| Example # | Structure | MS (M + H)+ |
|---|---|---|
| 407* | (S)-5-(1-((3-(4-Acetylpiperazine-1-carbonyl)phenoxy)methyl)isoindolin-2-yl)-4-(trifluoromethyl)pyridazin-3(2H)-one | 542.10 |
| 408 | 6-(4-(4-((2-(6-Oxo-5-(trifluoromethyl)-1,6-dihydropyridazin-4-yl)isoindolin-1-yl)methoxy)butanoyl)piperazin-1-yl)nicotinonitrile | 568.20 |
| 409* | (R)-6-(4-(4-((2-(6-Oxo-5-(trifluoromethyl)-1,6-dihydropyridazin-4-yl)isoindolin-1-yl)methoxy)butanoyl)piperazin-1-yl)nicotinonitrile | 568.20 |

TABLE E1-continued

| Example # | Structure | MS (M + H)+ |
|---|---|---|
| 410* | 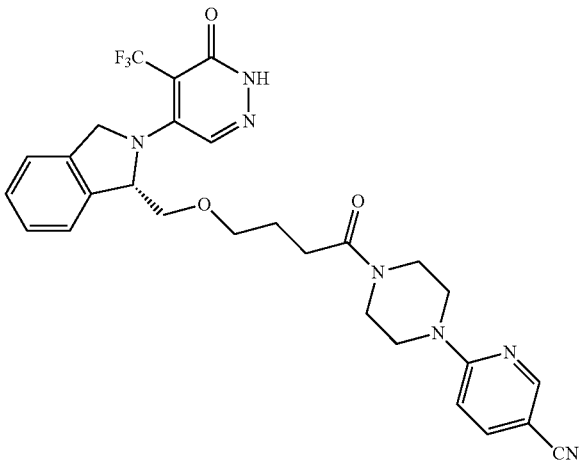 [SMILES: N#Cc1ccc(N2CCN(C(=O)CCCOC[C@@H]3c4ccccc4CN3c3cn[nH]c(=O)c3C(F)(F)F)CC2)nc1]<br>(S)-6-(4-(4-((2-(6-Oxo-5-(trifluoromethyl)-1,6-dihydropyridazin-4-yl)isoindolin-1-yl)methoxy)butanoyl)piperazin-1-yl)nicotinonitrile | 568.20 |
| 411 | 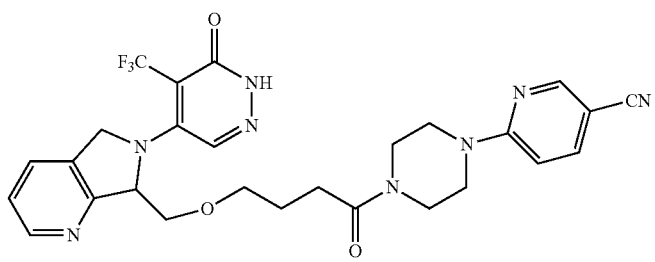 [SMILES: N#Cc1ccc(N2CCN(C(=O)CCCOCC3c4ncccc4CN3c3cn[nH]c(=O)c3C(F)(F)F)CC2)nc1]<br>6-(4-(4-((6-(6-Oxo-5-(trifluoromethyl)-1,6-dihydropyridazin-4-yl)-6,7-dihydro-5H-pyrrolo[3,4-b]pyridin-7-yl)methoxy)butanoyl)piperazin-1-yl)nicotinonitrile | 569.10 |
| 412 | 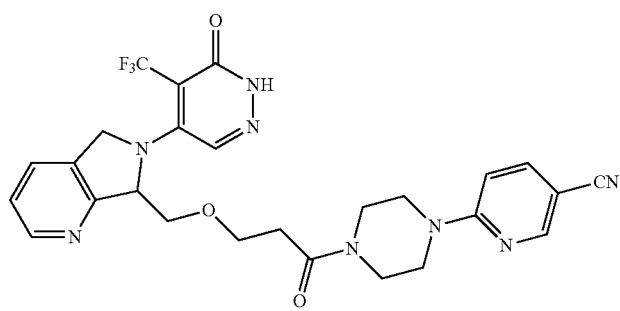 [SMILES: N#Cc1ccc(N2CCN(C(=O)CCOCC3c4ncccc4CN3c3cn[nH]c(=O)c3C(F)(F)F)CC2)nc1]<br>6-(4-(3-((6-(6-Oxo-5-(trifluoromethyl)-1,6-dihydropyridazin-4-yl)-6,7-dihydro-5H-pyrrolo[3,4-b]pyridin-7-yl)methoxy)propanoyl)piperazin-1-yl)nicotinonitrile | 555.10 |

TABLE E1-continued

| Example # | Structure | MS (M + H)+ |
|---|---|---|
| 413* | (S)-6-(4-(3-((2-(5-Chloro-6-oxo-1,6-dihydropyridazin-4-yl)isoindolin-1-yl)methoxy)propanoyl)piperazin-1-yl)nicotinonitrile | 520.10 |
| 414* | (R)-6-(4-(3-((2-(5-Chloro-6-oxo-1,6-dihydropyridazin-4-yl)isoindolin-1-yl)methoxy)propanoyl)piperazin-1-yl)nicotinonitrile | 520.10 |
| 415* | (S)-4-Chloro-5-(1-((3-oxo-3-(4-(5-(trifluoromethyl)pyrimidin-2-yl)piperazin-1-yl)propoxy)methyl)isoindolin-2-yl)pyridazin-3(2H)-one | 564.10 |
| 416* | 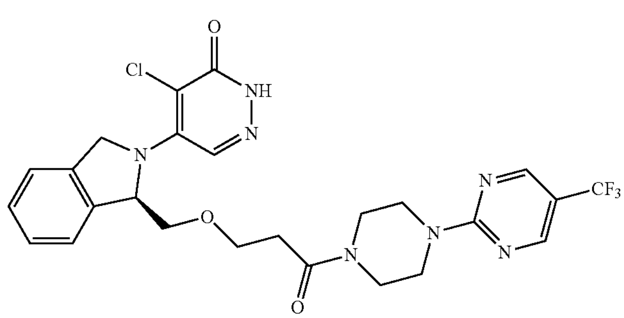 [SMILES: O=C(CCOC[C@H]1c2ccccc2CN1c1cn[nH]c(=O)c1Cl)N1CCN(c2ncc(C(F)(F)F)cn2)CC1] | 564.10 |

TABLE E1-continued

| Example # | Structure | MS (M + H)+ |
|---|---|---|
| 417* | (R)-4-Chloro-5-(1-((3-oxo-3-(4-(5-(trifluoromethyl)pyrimidin-2-yl)piperazin-1-yl)propoxy)methyl)isoindolin-2-yl)pyridazin-3(2H)-one | 452.05 |
| 418* | (S)-5-(1-((3-Oxo-3-(piperazin-1-yl)propoxy)methyl)isoindolin-2-yl)-4-(trifluoromethyl)pyridazin-3(2H)-one  0.4HCOOH  (R)-5-(1-((3-Oxo-3-(piperazin-1-yl)propoxy)methyl)isoindolin-2-yl)-4-(trifluoromethyl)pyridazin-3(2H)-one 0.4 formic acid | 452.05 |
| 419* | (S)-5-(1-((3-(4-Acetylpiperazin-1-yl)-3-oxopropoxy)methyl)isoindolin-2-yl)-4-(trifluoromethyl)pyridazin-3(2H)-one | 494.15 |

TABLE E1-continued

| Example # | Structure | MS (M + H)+ |
|---|---|---|
| 420* | (R)-5-(1-((3-(4-Acetylpiperazin-1-yl)-3-oxopropoxy)methyl)isoindolin-2-yl)-4-(trifluoromethyl)pyridazin-3(2H)-one | 494.15 |
| 421* | (S)-5-(1-((3-(4-Methylpiperazin-1-yl)-3-oxopropoxy)methyl)isoindolin-2-yl)-4-(trifluoromethyl)pyridazin-3(2H)-one | 466.15 |
| 422* | (R)-5-(1-((3-(4-Methylpiperazin-1-yl)-3-oxopropoxy)methyl)isoindolin-2-yl)-4-(trifluoromethyl)pyridazin-3(2H)-one | 466.15 |
| 423* | (S)-4-Oxo-4-(4-(3-((2-(6-oxo-5-(trifluoromethyl)-1,6-dihydropyridazin-4-yl)isoindolin-1-yl)methoxy)propanoyl)piperazin-1-yl)butanenitrile | 533.20 |

TABLE E1-continued

| Example # | Structure | MS (M + H)+ |
|---|---|---|
| 424* | (R)-4-Oxo-4-(4-(3-((2-(6-oxo-5-(trifluoromethyl)-1,6-dihydropyridazin-4-yl)isoindolin-1-yl)methoxy)propanoyl)piperazin-1-yl)butanenitrile | 533.20 |
| 425* | (R)-6-(4-(3-(((2-(5-Chloro-6-oxo-1,6-dihydropyridazin-4-yl)isoindolin-1-yl)methyl)amino)propanoyl)piperazin-1-yl)nicotinonitrile | 519.10 |
| 426* | (S)-6-(4-(3-(((2-(5-Chloro-6-oxo-1,6-dihydropyridazin-4-yl)isoindolin-1-yl)methyl)amino)propanoyl)piperazin-1-yl)nicotinonitrile | 519.10 |
| 427* | (S)-6-(4-(3-(Methyl((2-(6-oxo-5-(trifluoromethyl)-1,6-dihydropyridazin-4-yl)isoindolin-1- | 567.30 |

TABLE E1-continued

| Example # | Structure | MS (M + H)+ |
|---|---|---|
| | yl)methyl)amino)propanoyl)piperazin-1-yl)nicotinonitrile | |
| 428* | (R)-6-(4-(3-(Methyl((2-(6-oxo-5-(trifluoromethyl)-1,6-dihydropyridazin-4-yl)isoindolin-1-yl)methyl)amino)propanoyl)piperazin-1-yl)nicotinonitrile | 567.30 |
| 429* | (S)-6-(4-(3-(((2-(5-Chloro-6-oxo-1,6-dihydropyridazin-4-yl)isoindolin-1-yl)methyl)(methyl)amino)propanoyl)piperazin-1-yl)nicotinonitrile | 533.20 |
| 430* | (R)-6-(4-(3-(((2-(5-Chloro-6-oxo-1,6-dihydropyridazin-4-yl)isoindolin-1-yl)methyl)(methyl)amino)propanoyl)piperazin-1-yl)nicotinonitrile | 533.20 |
| 431* | 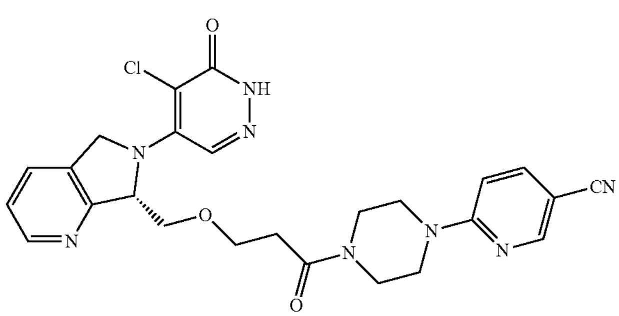 [SMILES: N#Cc1ccc(N2CCN(C(=O)CCOC[C@@H]3c4ncccc4CN3c3cn[nH]c(=O)c3Cl)CC2)nc1] | 521.15 |

TABLE E1-continued

| Example # | Structure | MS (M + H)+ |
|---|---|---|
| 432* | (S)-6-(4-(3-((6-(5-Chloro-6-oxo-1,6-dihydropyridazin-4-yl)-6,7-dihydro-5H-pyrrolo[3,4-b]pyridin-7-yl)methoxy)propanoyl)piperazin-1-yl)nicotinonitrile<br>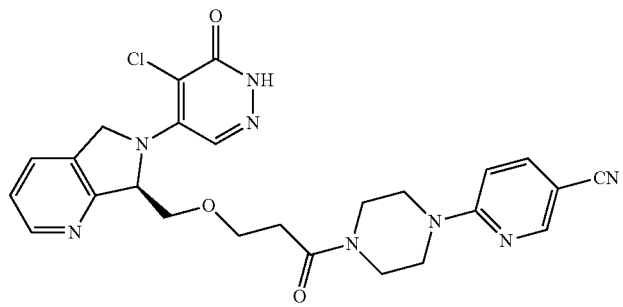 [SMILES: N#Cc1ccc(N2CCN(C(=O)CCOC[C@H]3c4ncccc4CN3c3cn[nH]c(=O)c3Cl)CC2)nc1] | 521.15 |
| 433* | (R)-6-(4-(3-((6-(5-Chloro-6-oxo-1,6-dihydropyridazin-4-yl)-6,7-dihydro-5H-pyrrolo[3,4-b]pyridin-7-yl)methoxy)propanoyl)piperazin-1-yl)nicotinonitrile<br>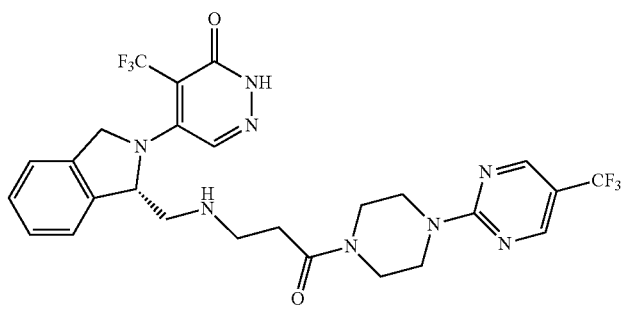 [SMILES: O=C(CCNC[C@@H]1c2ccccc2CN1c1cn[nH]c(=O)c1C(F)(F)F)N1CCN(c2ncc(C(F)(F)F)cn2)CC1]<br>(S)-5-(1-(((3-Oxo-3-(4-(5-(trifluoromethyl)pyrimidin-2-yl)piperazin-1-yl)propyl)amino)methyl)isoindolin-2-yl)-4-(trifluoromethyl)pyridazin-3(2H)-one | 597.25 |
| 434* | 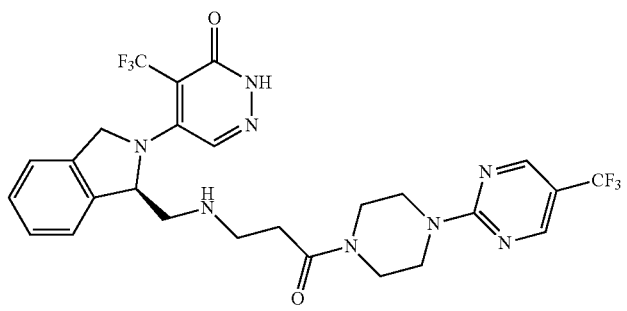 [SMILES: O=C(CCNC[C@H]1c2ccccc2CN1c1cn[nH]c(=O)c1C(F)(F)F)N1CCN(c2ncc(C(F)(F)F)cn2)CC1]<br>(R)-5-(1-(((3-Oxo-3-(4-(5-(trifluoromethyl)pyrimidin-2-yl)piperazin-1-yl)propyl)arnino)methyl)isoindolin-2-yl)-4-(trifluoromethyl)pyridazin-3(2H)-one | 597.25 |

TABLE E1-continued
| Example # | Structure | MS (M + H)+ |
|---|---|---|
| 435 | 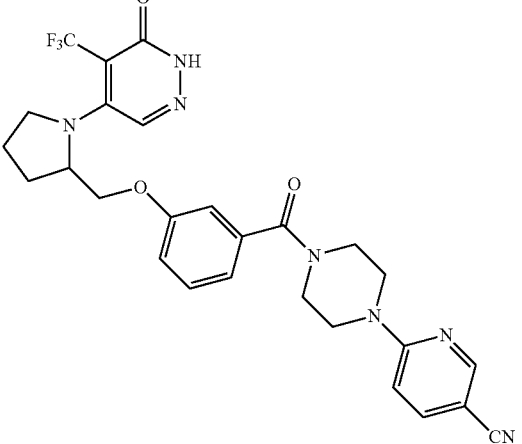 6-(4-(3-((1-(6-Oxo-5-(trifluoromethyl)-1,6-dihydropyridazin-4-yl)pyrrolidin-2-yl)methoxy)benzoyl)piperazin-1-yl)nicotinonitrile | 554.45 |
| 436 | 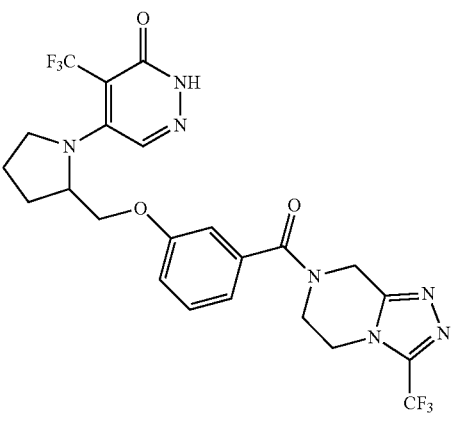 [SMILES: O=C(c1cccc(OCC2CCCN2c2cn[nH]c(=O)c2C(F)(F)F)c1)N1CCn2c(nnc2C(F)(F)F)C1] 4-(Trifluoromethyl)-5-(2-((3-(3-(trifluoromethyl)-5,6,7,8-tetrahydro-[1,2,4]triazolo[4,3-a]pyrazine-7-carbonyl)phenoxy)methyl)pyrrolidin-1-yl)pyridazin-3(2H)-one | 558.05 |
| 437 | 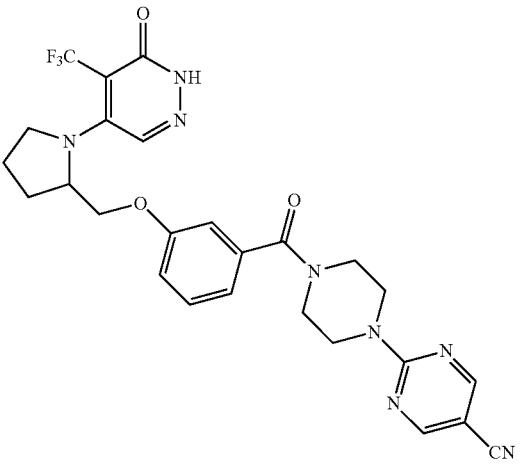 [SMILES: N#Cc1cnc(N2CCN(C(=O)c3cccc(OCC4CCCN4c4cn[nH]c(=O)c4C(F)(F)F)c3)CC2)nc1] 2-(4-(3-((1-(6-Oxo-5-(trifluoromethyl)-1,6-dihydropyridazin-4-yl)pyrrolidin-2- | 555.05 |

TABLE E1-continued
| Example # | Structure | MS (M + H)+ |
|---|---|---|
yl)methoxy)benzoyl)piperazin-1-yl)pyrimidine-5-carbonitrile
438*  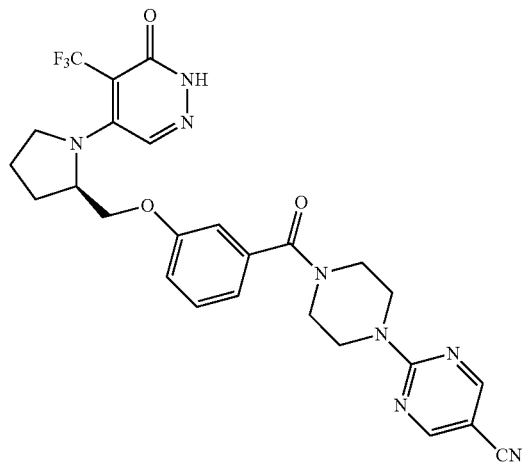 [SMILES: N#Cc1cnc(N2CCN(C(=O)c3cccc(OC[C@H]4CCCN4c4cn[nH]c(=O)c4C(F)(F)F)c3)CC2)nc1]  555.10
(R)-2-(4-(3-((1-(6-Oxo-5-(trifluoromethyl)-1,6-dihydropyridazin-4-yl)pyrrolidin-2-yl)methoxy)benzoyl)piperazin-1-yl)pyrimidine-5-carbonitrile
439*  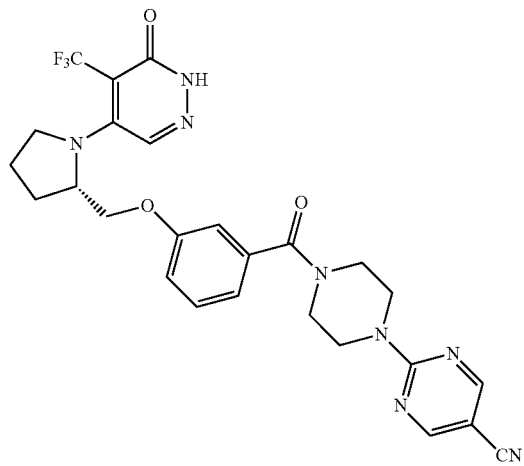 [SMILES: N#Cc1cnc(N2CCN(C(=O)c3cccc(OC[C@@H]4CCCN4c4cn[nH]c(=O)c4C(F)(F)F)c3)CC2)nc1]  555.10
(S)-2-(4-(3-((1-(6-Oxo-5-(trifluoromethyl)-1,6-dihydropyridazin-4-yl)pyrrolidin-2-yl)methoxy)benzoyl)piperazin-1-yl)pyrimidine-5-carbonitrile TABLE E1-continued
| Example # | Structure | MS (M + H)+ |
|---|---|---|
| 440 | 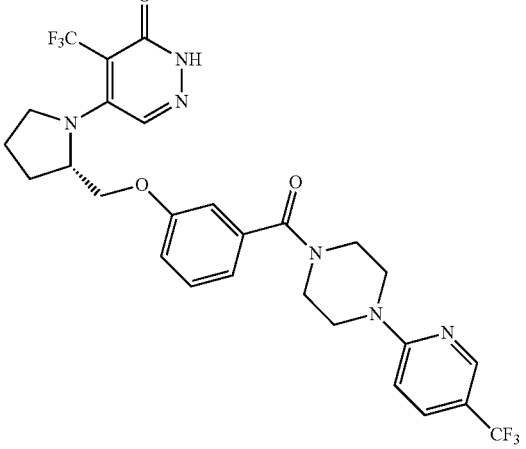<br>(S)-4-(Trifluoromethyl)-5-(2-((3-(4-(5-(trifluoromethyl)pyridin-2-yl)piperazine-1-carbonyl)phenoxy)methyl)pyrrolidin-1-yl)pyridazin-3(2H)-one | 597.05 |
| 441 | 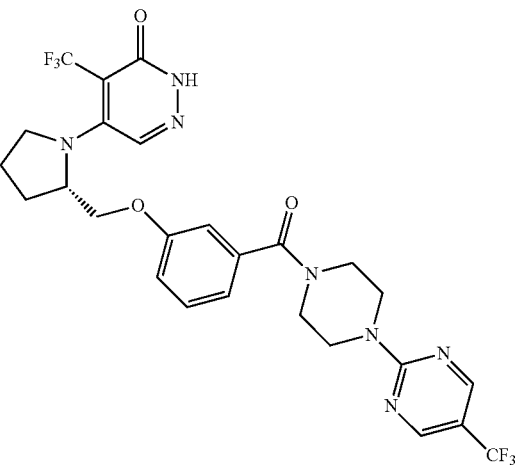 [SMILES: O=C(c1cccc(OC[C@@H]2CCCN2c2cn[nH]c(=O)c2C(F)(F)F)c1)N1CCN(c2ncc(C(F)(F)F)cn2)CC1]<br>(S)-4-(Trifluoromethyl)-5-(2-((3-(4-(5-(trifluoromethyl)pyrimidin-2-yl)piperazine-1-carbonyl)phenoxy)methyl)pyrrolidin-1-yl)pyridazin-3(2H)-one | 598.10 |
| 442 | 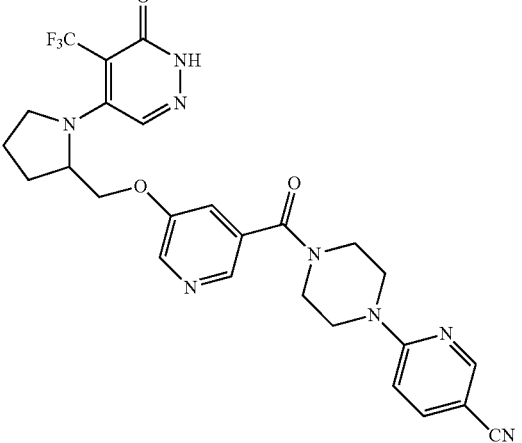 | 555.40 |

TABLE E1-continued

| Example # | Structure | MS (M + H)+ |
|---|---|---|
| | 6-(4-(5-((1-(6-Oxo-5-(trifluoromethyl)-1,6-dihydropyridazin-4-yl)pyrrolidin-2-yl)methoxy)nicotinoyl)piperazin-1-yl)nicotinonitrile | |
| 443 | 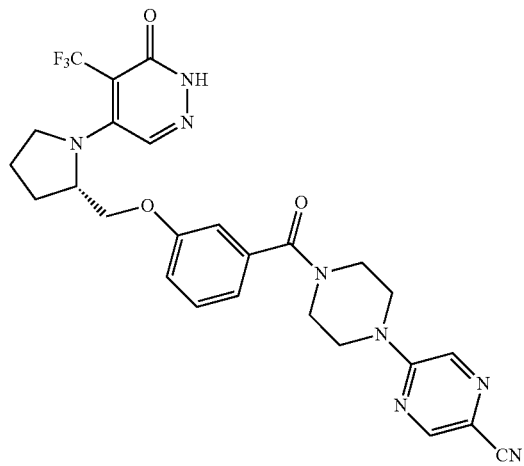 [SMILES: N#Cc1cnc(N2CCN(C(=O)c3cccc(OC[C@@H]4CCCN4c4cn[nH]c(=O)c4C(F)(F)F)c3)CC2)cn1] (S)-5-(4-(3-((1-(6-Oxo-5-(trifluoromethyl)-1,6-dihydropyridazin-4-yl)pyrrolidin-2-yl)methoxy)benzoyl)piperazin-1-yl)pyrazine-2-carbonitrile | 555.05 |
| 444 | 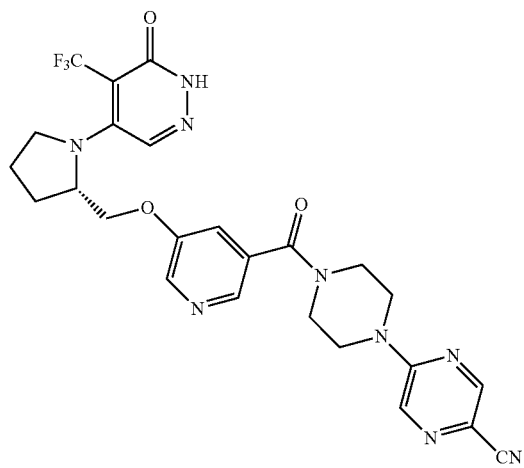 [SMILES: N#Cc1cnc(N2CCN(C(=O)c3cncc(OC[C@@H]4CCCN4c4cn[nH]c(=O)c4C(F)(F)F)c3)CC2)cn1] (S)-5-(4-(5-((1-(6-Oxo-5-(trifluoromethyl)-1,6-dihydropyridazin-4-yl)pyrrolidin-2-yl)methoxy)nicotinoyl)piperazin-1-yl)pyrazine-2-carbonitrile | 556.05 |

TABLE E1-continued

| Example # | Structure | MS (M + H)+ |
|---|---|---|
| 445 | (S)-5-(2-((3-(4-(Pyrimidin-2-yl)piperazine-1-carbonyl)phenoxy)methyl)pyrrolidin-1-yl)-4-(trifluoromethyl)pyridazin-3(2H)-one | 530.10 |
| 446 | (S)-5-(2-((3-(4-(5-Methylpyridin-2-yl)piperazine-1-carbonyl)phenoxy)methyl)pyrrolidin-1-yl)-4-(trifluoromethyl)pyridazin-3(2H)-one | 543.15 |
| 447 | (S)-5-(2-((3-(4-(5-Methylpyrimidin-2-yl)piperazine-1-carbonyl)phenoxy)methyl)pyrrolidin-1-yl)-4-(trifluoromethyl)pyridazin-3(2H)-one | 544.15 |

TABLE E1-continued

| Example # | Structure | MS (M + H)+ |
|---|---|---|
| 448 | (S)-5-(2-((2-Oxo-2-(4-(pyridin-2-yl)piperazin-1-yl)ethoxy)methyl)pyrrolidin-1-yl)-4-(trifluoromethoyl)pyridazin-3(2H)-one | 467.10 |
| 449 | (S)-5-(2-((3-(4-Acetylpiperazine-1-carbonyl)phenoxy)methyl)pyrrolidin-1-yl)-4-(trifluoromethyl)pyridazin-3(2H)-one | 494.20 |
| 450 | 6-(3-methyl-4-(3-(((S)-1-(6-Oxo-5-(trifluoromethyl)-1,6-dihydropyridazin-4-yl)pyrrolidin-2-yl)methoxy)benzoyl)piperazin-1-yl)nicotinonitrile | 568.15 |

TABLE E1-continued

| Example # | Structure | MS (M + H)+ |
|---|---|---|
| 451 | (S)-5-(2-((3-(5,6,7,8-Tetrahydro-[1,2,4]triazolo[4,3-a]pyrazine-7-carbonyl)phenoxy)methyl)pyrrolidin-1-yl)-4-(trifluoromethyl)pyridazin-3(2H)-one | 490.20 |
| 452 | 6-(4-(3-(((2S,4S)-4-Cyano-1-(6-oxo-5-(trifluoromethyl)-1,6-dihydropyridazin-4-yl)pyrrolidin-2-yl)methoxy)benzoyl)piperazin-1-yl)nicotinonitrile | 579.25 |
| 453 | (S)-2-(4-(4-(3-((1-(6-Oxo-5-(trifluoromethyl)-1,6-dihydropyridazin-4-yl)pyrrolidin-2-yl)methoxy)benzoyl)piperazin-1-yl)phenyl)acetonitrile | 567.20 |

TABLE E1-continued

| Example # | Structure | MS (M + H)+ |
|---|---|---|
| 454 | (S)-5-(2-((3-Oxo-3-(4-(pyridin-2-yl)piperazin-1-yl)propoxy)methyl)pyrrolidin-1-yl)-4-(trifluoromethyl)pyridazin-3(2H)-one | 481.10 |
| 455 | 6-(4-(3-(((1-(6-Oxo-5-(trifluoromethyl)-1,6-dihydropyridazin-4-yl)pyrrolidin-2-yl)methyl)amino)benzoyl)piperazin-1-yl)nicotinonitrile | 553.10 |
| 456 | (S)-5-(2-((3-Oxo-3-(4-(pyrimidin-2-yl)piperazin-1-yl)propoxy)methyl)pyrrolidin-1-yl)-4-(trifluoromethyl)pyridazin-3(2H)-one | 482.05 |

TABLE E1-continued

| Example # | Structure | MS (M + H)+ |
|---|---|---|
| 457 | (S)-5-(2-((3-Oxo-3-(4-(5-(trifluoromethyl)pyrimidin-2-yl)piperazin-1-yl)propoxy)methyl)pyrrolidin-1-yl)-4-(trifluoromethyl)pyridazin-3(2H)-one | 550.25 |
| 458 | (S)-5-(2-((3-Oxo-3-(4-(5-(trifluoromethyl)pyridin-2-yl)piperazin-1-yl)propoxy)methyl)pyrrolidin-1-yl)-4-(trifluoromethyl)pyridazin-3(2H)-one | 549.20 |
| 459* | 6-(4-(3-(((2R,3S)-3-methyl-1-(6-oxo-5-(trifluoromethyl)-1,6-dihydropyridazin-4-yl)pyrrolidin-2-yl)methoxy)benzoyl)piperazin-1-yl)nicotinonitrile | 568.25 |

TABLE E1-continued

| Example # | Structure | MS (M + H)+ |
|---|---|---|
| 460* | 6-(4-(3-(((2S,3R)-3-methyl-1-(6-oxo-5-(trifluoromethyl)-1,6-dihydropyridazin-4-yl)pyrrolidin-2-yl)methoxy)benzoyl)piperazin-1-yl)nicotinonitrile | 568.25 |
| 461 | (S)-2-(4-(3-((1-(6-Oxo-5-(trifluoromethyl)-1,6-dihydropyridazin-4-yl)pyrrolidin-2-yl)methoxy)propanoyl)piperazin-1-yl)pyrimidine-5-carbonitrile | 507.10 |
| 462 | (S)-4-(4-(3-((1-(6-Oxo-5-(trifluoromethyl)-1,6-dihydropyridazin-4-yl)pyrrolidin-2-yl)methoxy)propanoyl)piperazin-1-yl)benzonitrile | 505.15 |

TABLE E1-continued

| Example # | Structure | MS (M + H)+ |
|---|---|---|
| 463 | (S)-2-(4-(3-((1-(6-Oxo-5-(trifluoromethyl)-1,6-dihydropyridazin-4-yl)pyrrolidin-2-yl)methoxy)propanoyl)piperazin-1-yl)nicotinonitrile | 506.10 |
| 464 | 6-(4-(3-(((2S,4R)-4-Cyano-1-(6-oxo-5-(trifluoromethyl)-1,6-dihydropyridazin-4-yl)pyrrolidin-2-yl)methoxy)benzoyl)piperazin-1-yl)nicotinonitrile | 579.15 |
| 465 | 6-(4-(4-(2-((1-(6-Oxo-5-(trifluoromethyl)-1,6-dihydropyridazin-4-yl)pyrrolidin-3-yl)methoxy)ethoxy)benzoyl)piperazin-1-yl)nicotinonitrile | 598.30 |

TABLE E1-continued

| Example # | Structure | MS (M + H)+ |
|---|---|---|
| 466 | 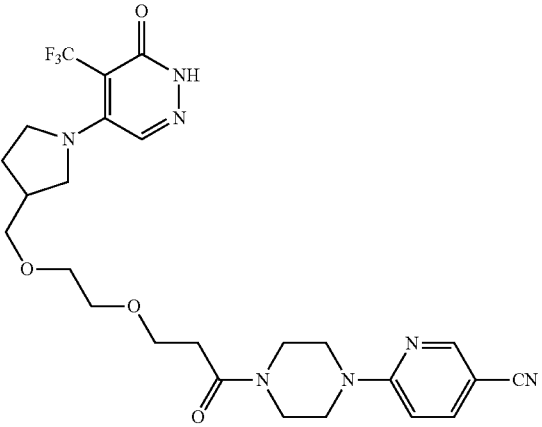 [SMILES: N#Cc1ccc(N2CCN(C(=O)CCOCCOCC3CCN(c4cn[nH]c(=O)c4C(F)(F)F)C3)CC2)nc1] 6-(4-(3-(2-((1-(6-Oxo-5-(trifluoromethyl)-1,6-dihydropyridazin-4-yl)pyrrolidin-3-yl)methoxy)ethoxy)propanoyl)piperazin-1-yl)nicotinonitrile | 550.10 |
| 467 | 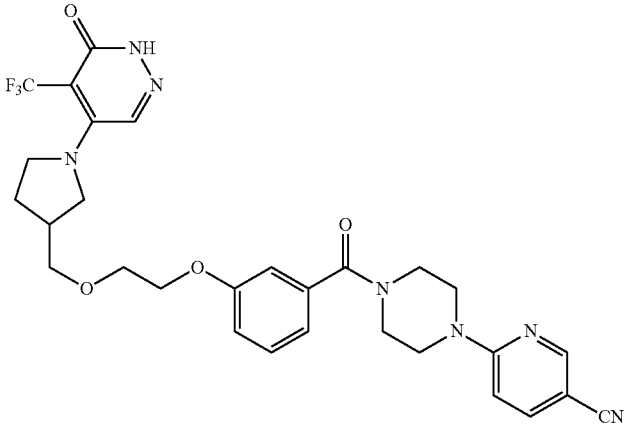 [SMILES: N#Cc1ccc(N2CCN(C(=O)c3cccc(OCCOCC4CCN(c5cn[nH]c(=O)c5C(F)(F)F)C4)c3)CC2)nc1] 6-(4-(3-(2-((1-(6-Oxo-5-(trifluoromethyl)-1,6-dihydropyridazin-4-yl)pyrrolidin-3-yl)methoxy)ethoxy)benzoyl)piperazin-1-yl)nicotinonitrile | 598.20 |
| 468 | 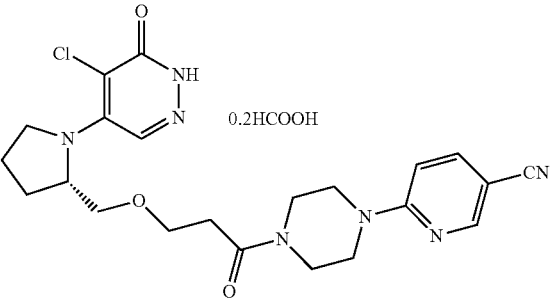 [SMILES: N#Cc1ccc(N2CCN(C(=O)CCOC[C@@H]3CCCN3c3cn[nH]c(=O)c3Cl)CC2)nc1] 0.2HCOOH (S)-6-(4-(3-((1-(5-Chloro-6-oxo-1,6-dihydropyridazin-4-yl)pyrrolidin-2-yl)methoxy)propanoyl)piperazin-1-yl)nicotinonitrile | 472.10 |

TABLE E1-continued

| Example # | Structure | MS (M + H)+ |
|---|---|---|
| 469 | 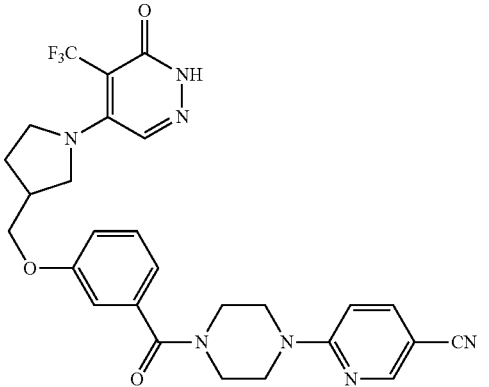 [SMILES: N#Cc1ccc(N2CCN(C(=O)c3cccc(OCC4CCN(c5cn[nH]c(=O)c5C(F)(F)F)C4)c3)CC2)nc1]<br>6-(4-(3-((1-(6-Oxo-5-(trifluoromethyl)-1,6-dihydropyridazin-4-yl)pyrrolidin-3-yl)methoxy)benzoyl)piperazin-1-yl)nicotinonitrile | 554.10 |
| 470* | 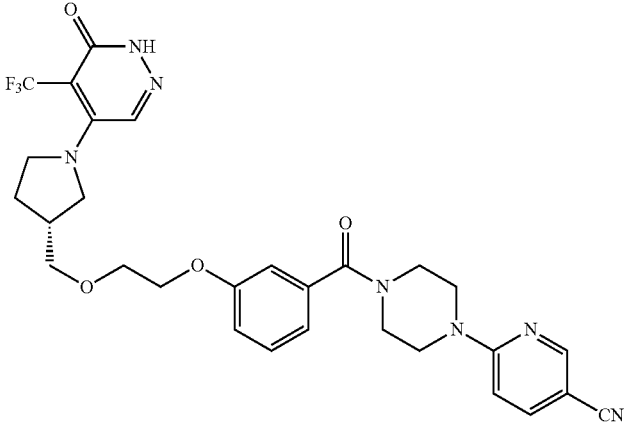 [SMILES: N#Cc1ccc(N2CCN(C(=O)c3cccc(OCCOC[C@@H]4CCN(c5cn[nH]c(=O)c5C(F)(F)F)C4)c3)CC2)nc1]<br>(R)-6-(4-(3-(2-((1-(6-Oxo-5-(trifluoromethyl)-1,6-dihydropyridazin-4-yl)pyrrolidin-3-yl)methoxy)ethoxy)benzoyl)piperazin-1-yl)nicotinonitrile | 598.20 |
| 471* | 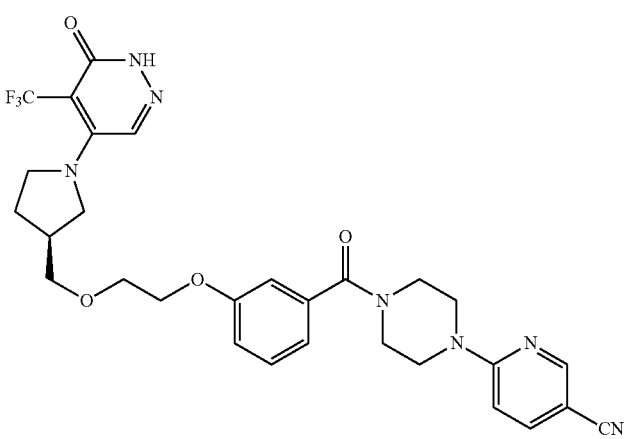 [SMILES: N#Cc1ccc(N2CCN(C(=O)c3cccc(OCCOC[C@H]4CCN(c5cn[nH]c(=O)c5C(F)(F)F)C4)c3)CC2)nc1]<br>(S)-6-(4-(3-(2-((1-(6-oxo-5-(trifluoromethyl)-1,6-dihydropyridazin-4-yl)pyrrolidin-3-yl)methoxy)ethoxy)benzoyl)piperazin-1-yl)nicotinonitrile | 598.20 |

TABLE E1-continued

| Example # | Structure | MS (M + H)+ |
|---|---|---|
| 472 | (S)-5-(2-((prop-2-yn-1-yloxy)methyl)pyrrolidin-1-yl)-4-(trifluoromethyl)pyridazin-3(2H)-one | 302.10 |
| 473 | 6-(3-Methyl-4-(3-(((S)-1-(6-oxo-5-(trifluoromethyl)-1,6-dihydropyridazin-4-yl)pyrrolidin-2-yl)methoxy)propanoyl)piperazin-1-yl)nicotinonitrile | 520.30 |
| 474 | (S)-5-(4-(3-((1-(6-Oxo-5-(trifluoromethyl)-1,6-dihydropyridazin-4-yl)pyrrolidin-2-yl)methoxy)propanoyl)piperazin-1-yl)pyrazine-2-carbonitrile | 507.30 |
| 475 | (S)-5-(4-(3-((1-(6-Oxo-5-(trifluoromethyl)-1,6-dihydropyridazin-4-yl)pyrrolidin-2-yl)methoxy)propanoyl)piperazin-1-yl)picolinonitrile | 506.15 |

TABLE E1-continued

| Example # | Structure | MS (M + H)⁺ |
|---|---|---|
| 476 | (S)-5-(4-(3-((1-(6-Oxo-5-(trifluoromethyl)-1,6-dihydropyridazin-4-yl)pyrrolidin-2-yl)methoxy)propanoyl)piperazin-1-yl)pyrimidine-2-carbonitrile | 507.20 |
| 477 | 6-(4-(4-((1-(6-Oxo-5-(trifluoromethyl)-1,6-dihydropyridazin-4-yl)pyrrolidin-3-yl)methoxy)benzoyl)piperazin-1-yl)nicotinonitrile | 554.15 |
| 478 | 6-(4-(2-(2-((1-(6-Oxo-5-(trifluoromethyl)-1,6-dihydropyridazin-4-yl)pyrrolidin-3-yl)methoxy)ethoxy)acetyl)piperazin-1-yl)nicotinonitrile | 536.10 |

TABLE E1-continued

| Example # | Structure | MS (M + H)+ |
|---|---|---|
| 479 | (S)-6-(4-(4-(((1-(6-Oxo-5-(trifluoromethyl)-1,6-dihydropyridazin-4-yl)pyrrolidin-2-yl)methoxy)methyl)cubane-1-carbonyl)piperazin-1-yl)nicotinonitrile | 594.10 |
| 480 | (S)-6-(4-(3-((1-(5-Methyl-6-oxo-1,6-dihydropyridazin-4-yl)pyrrolidin-2-yl)methoxy)propanoyl)piperazin-1-yl)nicotinonitrile | 452.15 |
| 481 | (S)-5-(2-((3-(4-(5-Chloropyridin-2-yl)piperazin-1-yl)-3-oxopropoxy)methyl)pyrrolidin-1-yl)-4-(trifluoromethyl)pyridazin-3(2H)-one | 515.25 |
| 482 | 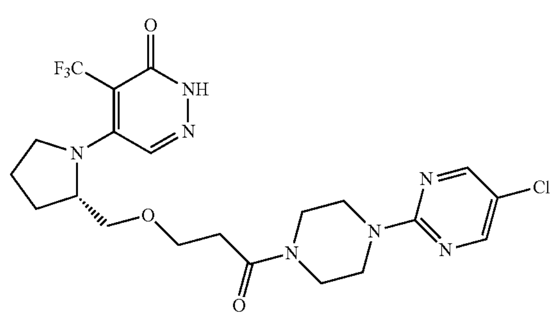 [SMILES: O=C(CCOC[C@@H]1CCCN1c1cn[nH]c(=O)c1C(F)(F)F)N1CCN(c2ncc(Cl)cn2)CC1] | 516.10 |

TABLE E1-continued

| Example # | Structure | MS (M + H)+ |
|---|---|---|
| | (S)-5-(2-((3-(4-(5-Chloropyrimidin-2-yl)piperazin-1-yl)-3-oxopropoxy)methyl)pyrrolidin-1-yl)-4-(trifluoromethyl)pyridazin-3(2H)-one | |
| 483 | 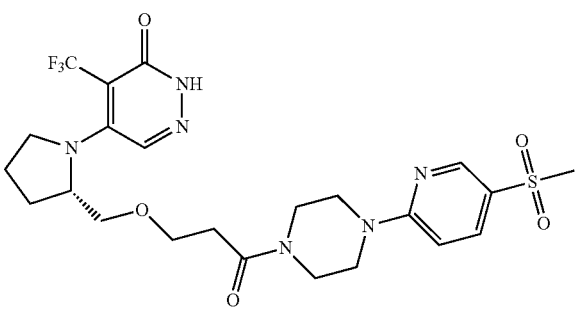 [SMILES: CS(=O)(=O)c1ccc(N2CCN(C(=O)CCOC[C@@H]3CCCN3c3cn[nH]c(=O)c3C(F)(F)F)CC2)nc1] (S)-5-(2-((3-(4-(5-(Methylsulfonyl)pyridin-2-yl)piperazin-1-yl)-3-oxopropoxy)methyl)pyrrolidin-1-yl)-4-(trifluoromethyl)pyridazin-3(2H)-one | 559.05 |
| 484 | 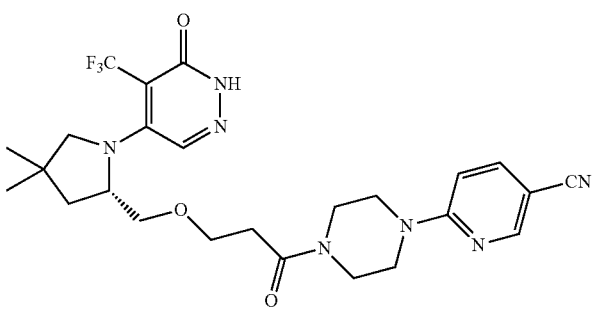 [SMILES: CC1(C)C[C@@H](COCCC(=O)N2CCN(c3ccc(C#N)cn3)CC2)N(c2cn[nH]c(=O)c2C(F)(F)F)C1] (S)-6-(4-(3-((4,4-Dimethyl-1-(6-oxo-5-(trifluoromethyl)-1,6-dihydropyridazin-4-yl)pyrrolidin-2-yl)methoxy)propanoyl)piperazin-1-yl)nicotinonitrile | 534.15 |
| 485 | 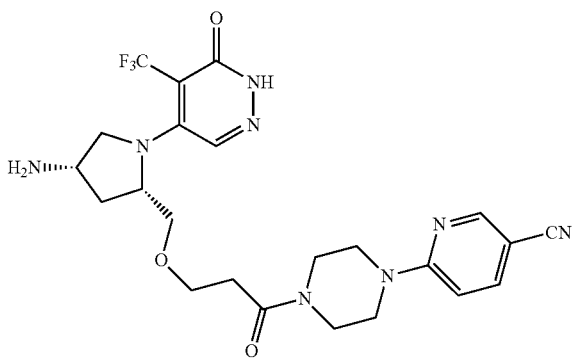 [SMILES: N#Cc1ccc(N2CCN(C(=O)CCOC[C@@H]3C[C@H](N)CN3c3cn[nH]c(=O)c3C(F)(F)F)CC2)nc1] 6-(4-(3-(((2S,4S)-4-Amino-1-(6-oxo-5-(trifluoromethyl)-1,6-dihydropyridazin-4-yl)pyrrolidin-2-yl)methoxy)propanoyl)piperazin-1-yl)nicotinonitrile | 521.25 |

TABLE E1-continued

| Example # | Structure | MS (M + H)+ |
|---|---|---|
| 486 | 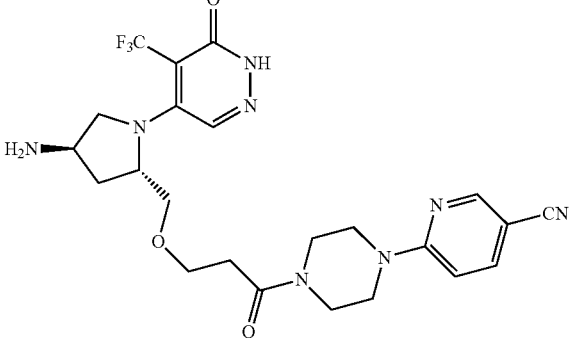 6-(4-(3-(((2S,4R)-4-Amino-1-(6-oxo-5-(trifluoromethyl)-1,6-dihydropyridazin-4-yl)pyrrolidin-2-yl)methoxy)propanoyl)piperazin-1-yl)nicotinonitrile | 521.25 |
| 487 | 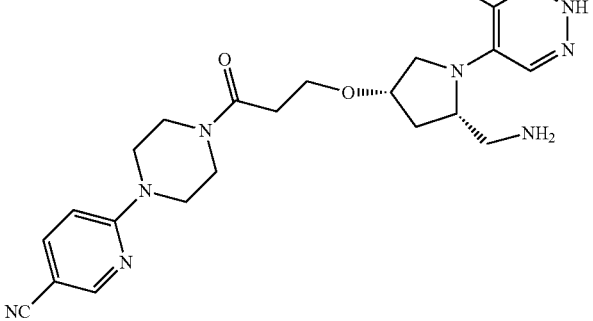 6-(4-(3-(((3S,5S)-5-(Aminomethyl)-1-(6-oxo-5-(trifluoromethyl)-1,6-dihydropyridazin-4-yl)pyrrolidin-3-yl)oxy)propanoyl)piperazin-1-yl)nicotinonitrile | 521.25 |
| 488 | 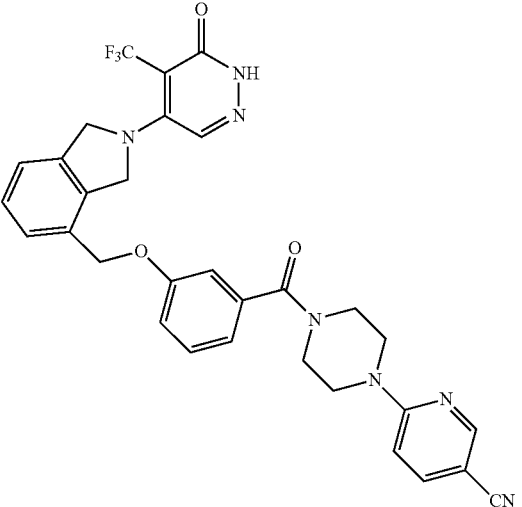 [SMILES: N#Cc1ccc(N2CCN(C(=O)c3cccc(OCc4cccc5c4CN(c4cn[nH]c(=O)c4C(F)(F)F)C5)c3)CC2)nc1] 6-(4-(3-((2-(6-Oxo-5-(trifluoromethyl)-1,6-dihydropyridazin-4-yl)isoindolin-4-yl)methoxy)benzoyl)piperazin-1-yl)nicotinonitrile | 602.10 |

TABLE E1-continued
| Example # | Structure | MS (M + H)+ |
|---|---|---|
| 489 | 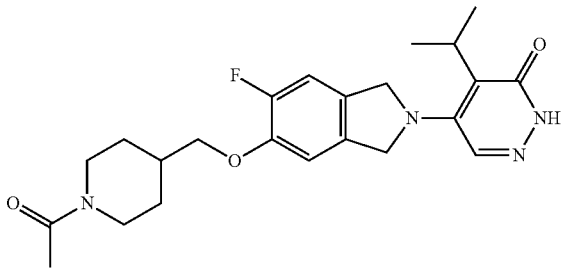 [SMILES: CC(=O)N1CCC(COc2cc3c(cc2F)CN(c2cn[nH]c(=O)c2C(C)C)C3)CC1] 5-(5-((1-Acetylpiperidin-4-yl)methoxy)-6-fluoroisoindolin-2-yl)-4-isopropylpyridazin-3(2H)-one | 429.2 |
| 490 | 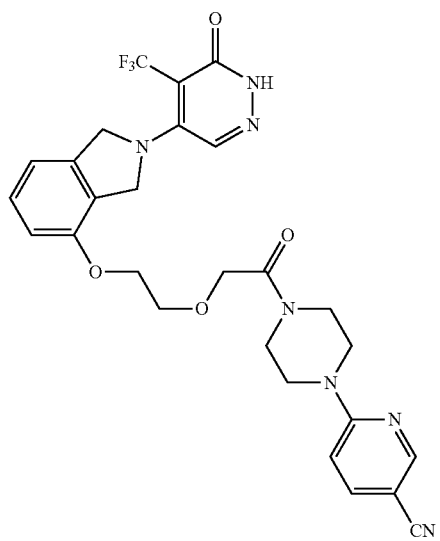 [SMILES: N#Cc1ccc(N2CCN(C(=O)COCCOc3cccc4c3CN(c3cn[nH]c(=O)c3C(F)(F)F)C4)CC2)nc1] 6-(4-(2-(2-((2-(6-Oxo-5-(trifluoromethyl)-1,6-dihydropyridazin-4-yl)isoindolin-4-yl)oxy)ethoxy)acetyl)piperazin-1-yl)nicotinonitrile | 570.15 |
| 491 | 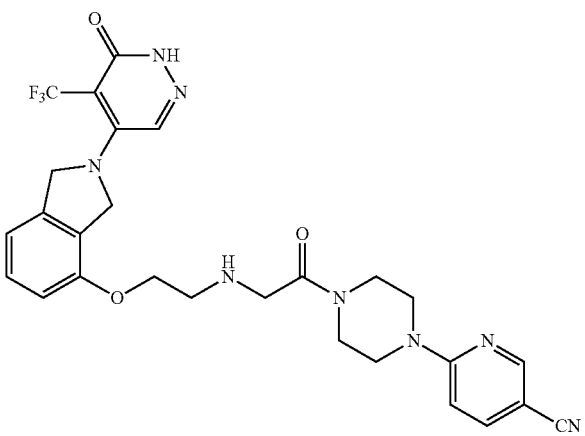 [SMILES: N#Cc1ccc(N2CCN(C(=O)CNCCOc3cccc4c3CN(c3cn[nH]c(=O)c3C(F)(F)F)C4)CC2)nc1] 6-(4-((2-((2-(6-Oxo-5-(trifluoromethyl)-1,6-dihydropyridazin-4-yl)isoindolin-4-yl)oxy)ethyl)glycyl)piperazin-1-yl)nicotinonitrile | 569.05 |

TABLE E1-continued
| Example # | Structure | MS (M + H)+ |
|---|---|---|
| 492 | 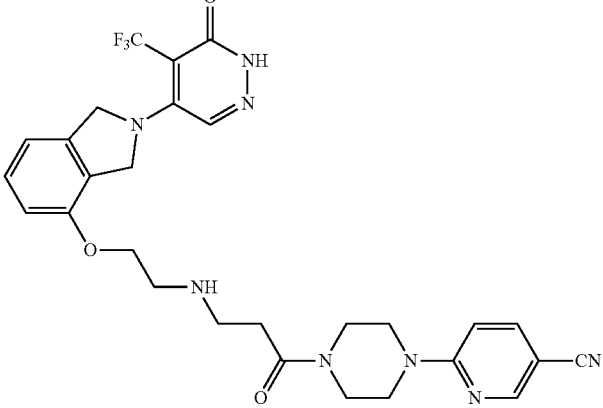<br>6-(4-(3-((2-(((2-(6-Oxo-5-(trifluoromethyl)-1,6-dihydropyridazin-4-yl)isoindolin-4-yl)oxy)ethyl)amino)propanoyl)piperazin-1-yl)nicotinonitrile | 583.25 |
| 493 | 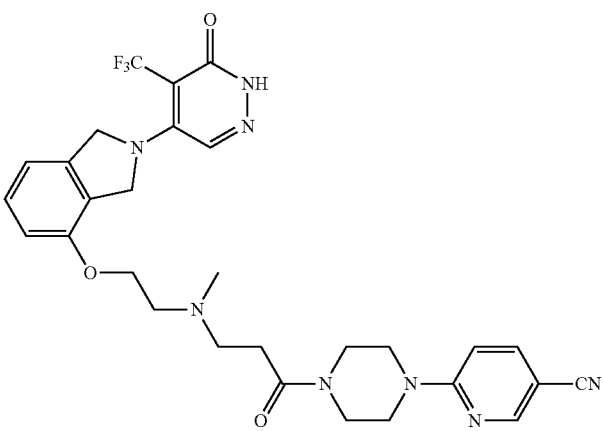 [SMILES: CN(CCOc1cccc2c1CN(c1cn[nH]c(=O)c1C(F)(F)F)C2)CCC(=O)N1CCN(c2ccc(C#N)cn2)CC1]<br>6-(4-(3-(Methyl(2-((2-(6-oxo-5-(trifluoromethyl)-1,6-dihydropyridazin-4-yl)isoindolin-4-yl)oxy)ethyl)amino)propanoyl)piperazin-1-yl)nicotinonitrile | 597.05 |
| 494 | 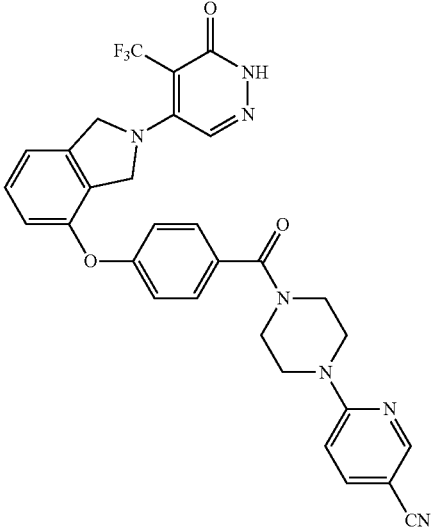 [SMILES: N#Cc1ccc(N2CCN(C(=O)c3ccc(Oc4cccc5c4CN(c4cn[nH]c(=O)c4C(F)(F)F)C5)cc3)CC2)nc1] | 588.15 |

TABLE E1-continued

| Example # | Structure | MS (M + H)+ |
|---|---|---|
| | 6-(4-(4-((2-(6-Oxo-5-(trifluoromethyl)-1,6-dihydropyridazin-4-yl)isoindolin-4-yl)oxy)benzoyl)piperazin-1-yl)nicotinonitrile | |
| 495 | *[structure]* | 554.30 |
| | 6-(4-(3-((2-(6-Oxo-5-(trifluoromethyl)-1,6-dihydropyridazin-4-yl)isoindolin-4-yl)methoxy)propanoyl)piperazin-1-yl)nicotinonitrile | |
| 496 | *[structure]* | 568.30 |
| | 6-(4-(4-((2-(6-Oxo-5-(trifluoromethyl)-1,6-dihydropyridazin-4-yl)isoindolin-4-yl)methoxy)butanoyl)piperazin-1-yl)nicotinonitrile | |
| 497 | *[structure]* | 289.20 |
| | 5-((4aR,7aR)-Octahydro-6H-pyrrolo[3,4-b]pyridin-6-yl)-4-(trifluoromethyl)pyridazin-3(2H)-one | |

TABLE E1-continued

| Example # | Structure | MS (M + H)+ |
|---|---|---|
| 498 | 5-((4aS,7aS)-Octahydro-6H-pyrrolo[3,4-b]pyridin-6-yl)-4-(trifluoromethyl)pyridazin-3(2H)-one | 289.20 |

Absolute stereochemistry arbitrarily assigned.
*The absolute stereochemistry was assigned based on a protein X-ray crystal structure obtained of Example 18, isomer B which confirmed (S)-absolute stereochemistry and was observed to be the more potent enantiomer.

Example 499: 6-[4-[2-(2-[[6-Oxo-5-(trifluoromethyl)-1,6-dihydropyridazin-4-yl]amino]ethoxy)acetyl]piperazin-1-yl]pyridine-3-carbonitrile

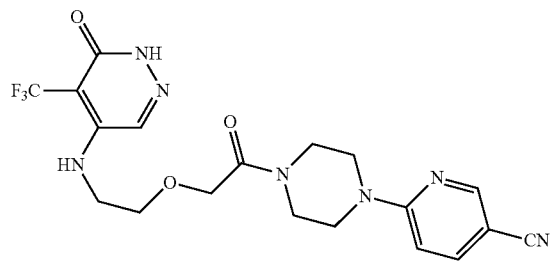 [SMILES: N#Cc1ccc(N2CCN(C(=O)COCCNc3cn[nH]c(=O)c3C(F)(F)F)CC2)nc1]

Step 1: 5-[(2-Hydroxyethyl)amino]-4-(trifluoromethyl)-2-[[2-(trimethylsilyl)ethoxy]methyl]-2,3-dihydropyridazin-3-one A solution of Int-A6 (10 g, 30.4 mmol, 1 equiv), TEA (9.2 g, 90.9 mmol, 2.989 equiv), 2-aminoethan-1-ol (2.1 g, 34.38 mmol, 1.130 equiv) in EtOH (100 mL) was stirred for 2 h at RT. The resulting mixture was concentrated under reduced pressure and crude residue purified by silica gel column eluting with EtOAc/petroleum ether (60/40) to afford 8.7 g (81%) of title compound as a yellow oil. LCMS: [M+H]+ 354.14.

Step 2: Ethyl 2-(2-[[6-oxo-5-(trifluoromethyl)-1-[[2-(trimethylsilyl)ethoxy]methyl]-1,6-dihydropyridazin-4-yl]amino]ethoxy)acetate A solution of 5-[(2-hydroxyethyl)amino]-4-(trifluoromethyl)-2-[[2-(trimethylsilyl)ethoxy]methyl]-2,3-dihydropyridazin-3-one (3 g, 8.49 mmol, 1 equiv), Cs2CO3 (8.3 g, 25.47 mmol, 3.00 equiv), ethyl 2-bromoacetate (4.2 g, 25.15 mmol, 2.96 equiv) in DMF (30 mL) was stirred for 12 h at room temperature. The reaction was then quenched by the addition of 20 mL of water. The resulting solution was extracted with 3×30 mL of EtOAc and the organic layers combined and dried over anhydrous sodium sulfate. The organic layer was concentrated under reduced pressure and purified by silica gel chromatography eluting with EtOAc/petroleum ether (20/80) to afford 1 g (27%) of title compound as a yellow oil. LCMS: [M+H]+ 440.18.

Step 3: 2-(2-[[6-Oxo-5-(trifluoromethyl)-1-[[2-(trimethylsilyl)ethoxy]methyl]-1,6-dihydropyridazin-4-yl]amino]ethoxy)acetic Acid A solution of ethyl 2-(2-[[6-oxo-5-(trifluoromethyl)-1-[[2-(trimethylsilyl)ethoxy]methyl]-1,6-dihydropyridazin-4-yl]amino]ethoxy)acetate (1 g, 2.28 mmol, 1 equiv), LiOH.H2O (286 mg, 6.82 mmol, 3.00 equiv) in MeOH (20 mL) was stirred for 2 h at RT. The resulting solution was extracted with 3×30 mL of ethyl acetate. The pH of the solution was adjusted to 6 with HCl (35%) and the solids were collected by filtration to afford 160 mg of the title compound (17%) as a yellow oil. LCMS: [M+H]+ 412.14.

Step 4: 2-[[6-Oxo-5-(trifluoromethyl)-1-[[2-(trimethylsilyl)ethoxy]methyl]-1,6-dihydropyridazin-4-yl]amino]ethyl 4-(5-cyanopyridin-2-yl)piperazine-1-carboxylate A solution of 2-(2-[[6-oxo-5-(trifluoromethyl)-1-[[2-(trimethylsilyl)ethoxy]methyl]-1,6-dihydropyridazin-4-yl]amino]ethoxy)acetic acid (160 mg, 0.40 mmol, 1 equiv), DIPEA (100.8 mg, 0.78 mmol, 1.94 equiv), EDCI (111.7 mg, 0.58 mmol, 1.45 equiv), HOBT (78.6 mg, 0.58 mmol, 1.44 equiv), Int-A4 (95.4 mg, 0.51 mmol, 1.26 equiv) in DMF (4 mL) was stirred for 2 h at RT. After concentration, the residue was purified by C18 reverse phase chromatography eluting with H2O/CH3CN to afford 70 mg (30.6%) of title compound as a white solid. LCMS: [M+H]+ 582.24.

Step 5: 6-[4-[2-(2-[[6-Oxo-5-(trifluoromethyl)-1,6-dihydropyridazin-4-yl]amino]ethoxy)acetyl]piperazin-1-yl]pyridine-3-carbonitrile A solution of 2-[[6-oxo-5-(trifluoromethyl)-1-[[2-(trimethylsilyl)ethoxy]methyl]-1,6-dihydropyridazin-4-yl]amino]ethyl 4-(5-cyanopyridin-2-yl)piperazine-1-carboxylate (70 mg, 0.12 mmol, 1 equiv), TFA (0.25 mL) in DCM (5 mL) was stirred for 2 h at RT. After concentration, the residue was purified by C18 reverse phase chromatography eluting with H2O/CH3CN and then the residue was further purified by Prep-HPLC to afford the title compound as a white solid. LCMS: [M+H]⁺ 452.40. ¹H NMR (300 MHz, DMSO-d₆) δ: 12.46 (s, 1H), 8.52 (d, J=2.3 Hz, 1H), 7.91 (d, J=10.3 Hz, 2H), 7.16 (s, 1H), 6.95 (d, J=9.2 Hz, 1H), 4.29 (m, 2H), 3.73-3.54 (m, 10H), 3.47 (m, 2H).

Example 500: 6-[4-[3-(2-[[6-Oxo-5-(trifluoromethyl)-1,6-dihydropyridazin-4-yl]amino]ethoxy)propanoyl]piperazin-1-yl]pyridine-3-carbonitrile

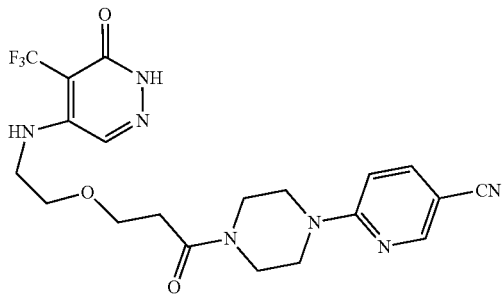 [SMILES: N#Cc1ccc(N2CCN(C(=O)CCOCCNc3cn[nH]c(=O)c3C(F)(F)F)CC2)nc1]

A solution of Int-A12 (1000 mg, 3.39 mmol, 1 equiv), DIPEA (1313.4 mg, 10.16 mmol, 3 equiv), EDCI (974.0 mg, 5.08 mmol, 1.5 equiv), HOBT (686.6 mg, 5.08 mmol, 1.5 equiv), Int-A4 (837.2 mg, 3.73 mmol, 1.1 equiv) in DMF (5 mL) was stirred for 1 h at RT. After concentration, the residue was purified by C18 reverse phase chromatography eluting with H₂O/CH₃CN and the residue was further purified by Prep-HPLC to afford the title compound as a white solid (64.7 mg, 4.1%). LCMS: [M+H]⁺ 466.17. ¹H NMR (300 MHz, DMSO-d6) δ: 12.41 (s, 1H), 8.49 (d, J=2.3 Hz, 1H), 7.90-7.86 (m, 2H), 6.96-6.83 (m, 2H), 3.65 (m, 6H), 3.53 (d, J=9.6 Hz, 8H), 2.57 (t, J=6.4 Hz, 2H).

Example 501: 6-[4-[3-(2-[[6-Oxo-5-(trifluoromethyl)-1,6-dihydropyridazin-4-yl]oxy]ethoxy)propanoyl]piperazin-1-yl]pyridine-3-carbonitrile

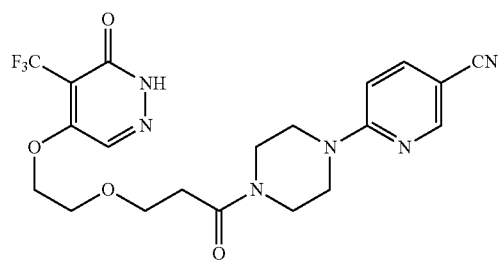 [SMILES: N#Cc1ccc(N2CCN(C(=O)CCOCCOc3cn[nH]c(=O)c3C(F)(F)F)CC2)nc1]

A solution of Int-A11 (67 mg, 0.23 mmol, 1 equiv), DIPEA (87.7 mg, 0.68 mmol, 3.00 equiv), EDCI (65.0 mg, 0.34 mmol, 1.5 equiv), HOBT (45.8 mg, 0.34 mmol, 1.5 equiv), Int-A4 (55.9 mg, 0.25 mmol, 1.1 equiv) in DMF (3 mL) was stirred for 3 h at RT. After concentration, the residue was purified by C18 reverse phase chromatography eluting with H₂O/CH₃CN and further purified by Prep-HPLC to afford the title compound as a white solid (16.5 mg, 15.6%). LCMS: [M+H]⁺ 467.16. ¹H NMR (400 MHz, DMSO-d6) δ: 13.30 (s, 1H), 8.50 (d, J=2.3 Hz, 1H), 8.24 (s, 1H), 7.88 (dd, J=9.1, 2.4 Hz, 1H), 6.92 (d, J=9.1 Hz, 1H), 4.57-4.48 (m, 2H), 3.77-3.51 (m, 12H), 2.61 (t, J=6.5 Hz, 2H).

Example 502: 6-(4-[3-[(2-[[6-Oxo-5-(trifluoromethyl)-1,6-dihydropyridazin-4-yl]oxy]ethyl)amino]propanoyl]piperazin-1-yl)pyridine-3-carbonitrile

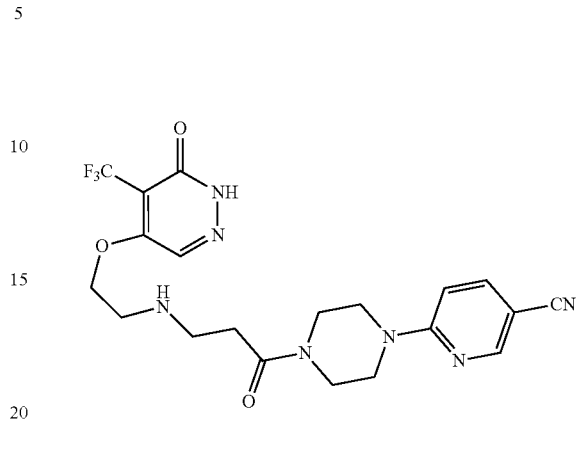

Step 1: 6-(4-[3-[(2-Hydroxyethyl)amino]propanoyl]piperazin-1-yl)pyridine-3-carbonitrile A solution of Int-A25 (400 mg, 1.65 mmol, 1 equiv) and 2-aminoethan-1-ol (5 mL) was stirred for 2 h at RT. The reaction was then quenched by the addition of 10 mL of water. The resulting solution was extracted with 3×20 mL of EtOAc and the organic layers combined and dried over anhydrous sodium sulfate. The organic layers were concentrated under vacuum. After concentration, the residue was purified by C18 reverse phase chromatography eluting with H₂O/ACN to afford 270 mg (53.9%) of title compound as a yellow oil. LCMS: [M+H]⁺ 304.17.

Step 2: 5-Tert-butyl N-[3-[4-(5-cyanopyridin-2-yl)piperazin-1-yl]-3-oxopropyl]-N-(2-hydroxyethyl)carbamate A solution of 6-(4-[3-[(2-hydroxyethyl)amino]propanoyl]piperazin-1-yl)pyridine-3-carbonitrile (270 mg, 0.89 mmol, 1 equiv), TEA (269.1 mg, 2.66 mmol, 2.99 equiv), and (Boc)₂O (233.1 mg, 1.07 mmol, 1.2 equiv) in DCM (15 mL) was stirred for 3 h at RT. The reaction was then quenched by the addition of 20 mL of water. The organic layers were combined and dried over anhydrous sodium sulfate and concentrated under reduced pressure to afford 350 mg (97%) of title compound as a yellow oil. LCMS: [M+H]⁺ 304.22.

Step 3: Tert-butyl N-[3-[4-(5-cyanopyridin-2-yl)piperazin-1-yl]-3-oxopropyl]-N-(2-[[6-oxo-5-(trifluoromethyl)-1-[[2-(trimethylsilyl)ethoxy]methyl]-1,6-dihydropyridazin-4-yl]oxy]ethyl)carbamate A solution of tert-butyl N-[3-[4-(5-cyanopyridin-2-yl)piperazin-1-yl]-3-oxopropyl]-N-(2-hydroxyethyl)carbamate (404 mg, 1.00 mmol, 1 equiv), Cs₂CO₃ (975 mg, 2.99 mmol, 2.99 equiv), Int-A6 (360.8 mg, 1.10 mmol, 1.10 equiv) in DMF (20 mL) was stirred for 3 days at RT. The reaction was then quenched by the addition of 20 mL of water. The resulting solution was extracted with EtOAc and the organic layers combined and dried over anhydrous sodium sulfate. The organic layers were concentrated under vacuum and the residue was purified by silica gel chromatography eluting with DCM/MeOH to afford 550 mg (79%) of title compound as a colorless oil. LCMS: [M+H]$^+$ 696.31.

Step 4: 6-(4-[3-[(2-[[6-oxo-5-(trifluoromethyl)-1,6-dihydropyridazin-4-yl]oxy]ethyl)amino]propanoyl]piperazin-1-yl)pyridine-3-carbonitrile A solution of tert-butyl N-[3-[4-(5-cyanopyridin-2-yl)piperazin-1-yl]-3-oxopropyl]-N-(2-[[6-oxo-5-(trifluoromethyl)-1-[[2-(trimethylsilyl)ethoxy]methyl]-1,6-dihydropyridazin-4-yl]oxy]ethyl)carbamate (500 mg, 0.72 mmol, 1 equiv) and TFA (0.5 mL, 6.73 mmol, 9.37 equiv) in DCM (10 mL) was stirred for 2 h at RT. After concentration, the residue was purified by C18 reverse phase chromatography eluting with H$_2$O/ACN followed by further purification by Prep-HPLC to afford the title compound (39.3 mg, 12%) as a white solid. LCMS: [M+H]$^+$ 466.43; $^1$H NMR (300 MHz, DMSO-d6) δ: 12.48 (s, 1H), 8.50 (d, J=2.3 Hz, 1H), 7.97 (s, 1H), 7.90 (dd, J=9.1, 2.4 Hz, 1H), 6.95 (d, J=9.1 Hz, 1H), 4.77 (t, J=5.2 Hz, 1H), 3.74-3.60 (m, 6H), 3.55 (m, 6H), 3.44 (m, 2H), 2.70 (t, J=6.7 Hz, 2H).

Example 503: 5-[(2-[3-[4-(5-Chloropyrimidin-2-yl)piperazin-1-yl]-3-oxopropoxy]ethyl)amino]-4-(trifluoromethyl)-2,3-dihydropyridazin-3-one

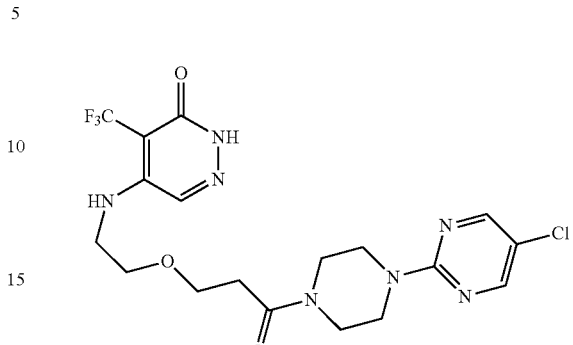

A solution of Int-A12 (200 mg, 0.68 mmol, 1 equiv), Int-A3 (201 mg, 0.74 mmol, 1.09 equiv), HATU (283.4 mg, 0.75 mmol, 1.1 equiv), DIPEA (262.7 mg, 2.03 mmol, 3 equiv) in DMF (10 mL) was stirred for 1 h at 25° C. After concentration, the residue was purified by C18 reverse phase chromatography eluting with H$_2$O/ACN followed by further purification by Prep-HPLC to afford the title compound (82.4 mg, 26%) as a white solid. LCMS: [M+H]$^+$ 476.13. $^1$H NMR (400 MHz, DMSO-d$_6$) δ 12.40 (s, 1H), 8.44 (s, 2H), 7.87 (s, 1H), 6.86 (s, 1H), 3.70 (dt, J=22.7, 5.8 Hz, 6H), 3.53 (dd, J=10.6, 4.4 Hz, 8H), 2.59 (t, J=6.4 Hz, 2H).

The following examples in Table E2 were similarly prepared from the appropriate intermediates according to the method described for Example 503.

TABLE E2

| Example | Name, structure, analytical data | Int. |
|---|---|---|
| Example 504 | 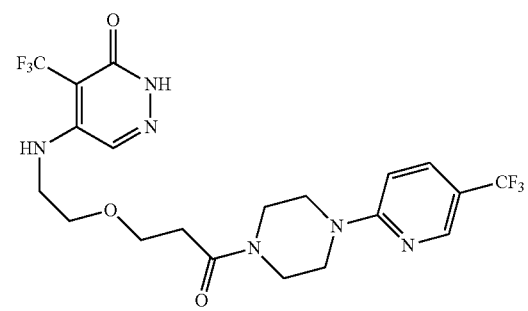 [SMILES: O=C(CCOCCNc1cn[nH]c(=O)c1C(F)(F)F)N1CCN(c2ccc(C(F)(F)F)cn2)CC1]<br>5-[[2-(3-Oxo-3-[4-[5-(Trifluoromethyl)pyridin-2-yl]piperazin-1-yl]propoxy)ethyl]amino]-4-(trifluoromethyl)-2,3-dihydropyridazin-3-one;<br>LCMS: [M + H]$^+$ 509.17;<br>$^1$H NMR (300 MHz, DMSO-d$_6$) δ 12.34 (s, 1H), 8.90-8.85 (s, 1H), 7.89 (m, 1H), 7.00-6.90 (m, 1H), 6.85 (s, 1H), 3.66 (m, 14H), 2.57 (t, J = 6.4 Hz, 2H). | Int-A12 and Int-A18 |

TABLE E2-continued

| Example | Name, structure, analytical data | Int. |
|---|---|---|
| Example 505 | 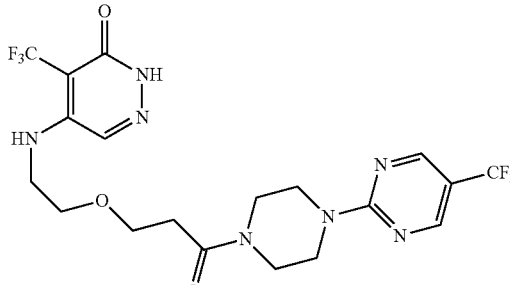<br>5-[[2-(3-Oxo-3-[4-[5-(Trifluoromethyl)pyrimidin-2-yl]piperazin-1-yl]propoxy)ethyl]amino]-4-(trifluoromethyl)-2,3-dihydropyridazin-3-one;<br>LCMS: [M + H]⁺ 510.16;<br>$^1$H NMR (300 MHz, DMSO-d$_6$) δ: 12.43 (s, 1H), 8.74 (s, 2H), 7.89 (s, 1H), 6.89 (s, 1H), 3.90 (m, 4H), 3.69 (t, J = 6.4 Hz, 2H), 3.57 (q, J = 3.6 Hz, 8H), 2.61 (t, J = 6.4 Hz, 2H). | Int-A12 and Int-A2 |
| Example 506 | 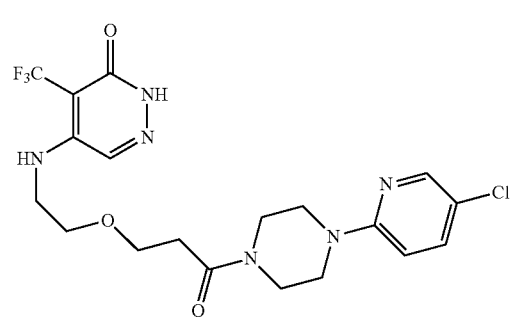 [SMILES: O=C(CCOCCNc1cn[nH]c(=O)c1C(F)(F)F)N1CCN(c2ccc(Cl)cn2)CC1]<br>5-[(2-[3-[4-(5-Chloropyridin-2-yl)piperazin-1-yl]-3-oxopropoxy]ethyl)amino]-4-(trifluoromethyl)-2,3-dihydropyridazin-3-one;<br>LCMS: [M + H]⁺ 475.14;<br>$^1$H NMR (300 MHz, DMSO-d$_6$) δ 12.41 (s, 1H), 8.10 (d, J = 2.7 Hz, 1H), 7.86 (s, 1H), 7.60 (dd, J = 9.1, 2.7 Hz, 1H), 6.86 (d, J = 9.2 Hz, 2H), 3.65 (t, J = 6.3 Hz, 2H), 3.57-3.47 (m, 10H), 3.44 (s, 2H), 2.56 (t, J = 6.4 Hz, 2H). | Int-A12 and Int-A5 |

Example 507: 6-[4-(3-[2-[(5-Chloro-6-oxo-1,6-dihydropyridazin-4-yl)amino]ethoxy]propanoyl)piperazin-1-yl]pyridine-3-carbonitrile

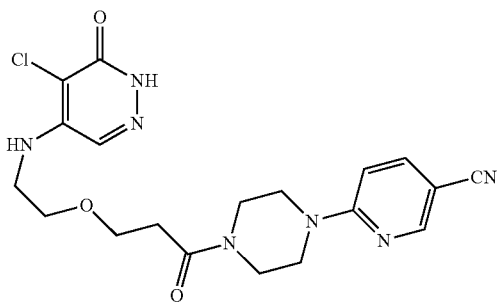 [SMILES: N#Cc1ccc(N2CCN(C(=O)CCOCCNc3cn[nH]c(=O)c3Cl)CC2)nc1]

A solution of Int-A10 (100 mg, 0.38 mmol, 1.00 equiv), DMF (1 mL), DIPEA (148 mg, 1.15 mmol, 3.00 equiv), HATU (147 mg, 0.39 mmol, 1.01 equiv), and Int-A4 (72 mg, 0.38 mmol, 1.00 equiv) was stirred for 1 h at 25° C. After concentration under reduced pressure, the residue was purified by silica gel column chromatography eluting with DCM/MeOH (92:8, v:v). The solution was concentrated under vacuum and the solids were collected by filtration to afford the title compound (84.5 mg, 51%) as a white solid. LCMS: [M+H]⁺ 432.15. $^1$H NMR (400 MHz, DMSO-d$_6$) δ: 12.54 (s, 1H), 8.51 (s, 1H), 7.89-7.85 (m, 2H), 6.94-6.92 (d, J=8.8 Hz, 1H), 6.49 (s, 1H), 3.69-3.66 (m, 6H), 3.55-3.50 (m, 8H), 2.61-2.58 (t, J=6.4 Hz, 2H).

The following examples in Table E3 were similarly prepared from Int-A10 and the appropriate intermediates, respectively, Int-A2 and Int-A18 according to the method described for Example 507.

TABLE E3

| Example | Name, structure, analytical data | Int. |
|---|---|---|
| Example 508 | 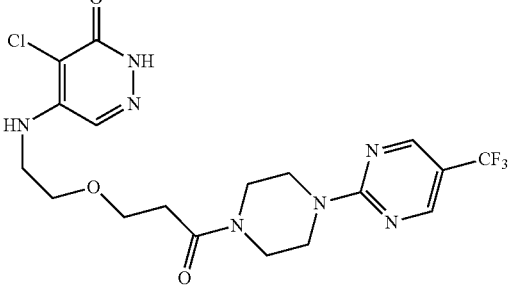<br>4-Chloro-5-[[2-(3-oxo-3-[4-[5-(trifluoromethyl)pyrimidin-2-yl]piperazin-1-yl]propoxy)ethyl]amino]-2,3-dihydropyridazin-3-one;<br>LCMS: [M + H]$^+$ 476.15;<br>$^1$H NMR (400 MHz, DMSO-$d_6$) δ 12.54 (s, 1H), 8.73 (s, 2H), 7.85 (s, 1H), 6 49 (t, J = 6.0 Hz, 1H), 3.83 (dt, J = 19.2, 4.9 Hz, 4H), 3.68 (t, J = 6.4 Hz, 2H), 3.60-3.46 (m, 8H), 2.60 (t, J = 6.4 Hz, 2H) | Int-A10 and Int-A2 |
| Example 509 | 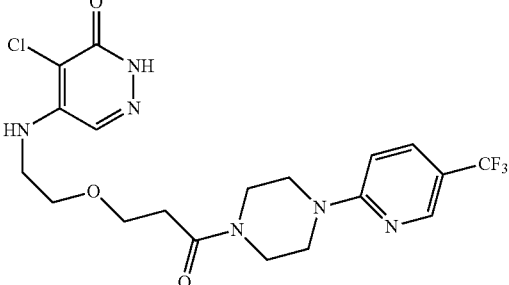 [SMILES: O=C(CCOCCNc1cn[nH]c(=O)c1Cl)N1CCN(c2ccc(C(F)(F)F)cn2)CC1]<br>4-Chloro-5-[[2-(3-oxo-3-[4-[5-(trifluoromethyl)pyridin-2-yl]piperazin-1-yl]propoxy)ethyl]amino]-2,3-dihydropyridazin-3-one;<br>LCMS: [M + H]$^+$ 475.15;<br>$^1$H NMR (400 MHz, DMSO-$d_6$) δ 12.54 (s, 1H), 8.43 (s, 1H), 7.84-7.81 (m, 2H), 6.96-6.94 (d, J = 8.8 Hz, 1H), 6.49 (s, 1H), 3.67-3.46 (m, 14H), 2.60 (t, J = 6.0Hz, 2H). | Int-A10 and Int-A18 |

Example 510: 6-[4-[3-(2-[Methyl[6-oxo-5-(trifluoromethyl)-1,6-dihydropyridazin-4-yl]amino]ethoxy)propanoyl]piperazin-1-yl]pyridine-3-carbonitrile

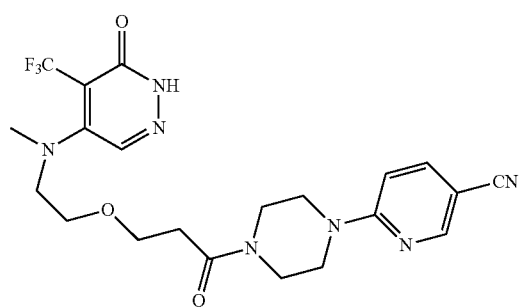 [SMILES: CN(CCOCCC(=O)N1CCN(c2ccc(C#N)cn2)CC1)c1cn[nH]c(=O)c1C(F)(F)F]

Step 1: 5-[(2-Hydroxyethyl)(methyl)amino]-4-(trifluoromethyl)-2-[[2-(trimethylsilyl)ethoxy]methyl]-2,3-dihydropyridazin-3-one A solution of Int-A6 (2.0 g, 6.08 mmol, 1 equiv), TEA (1.2 g, 12.2 mmol, 2 equiv), 2-(methylamino)ethan-1-ol (456.9 mg, 6.08 mmol, 1 equiv) in EtOH (10 mL) was stirred for 2 h at RT. The resulting mixture was concentrated under vacuum. The residue was applied onto a silica gel column eluting with EtOAc/petroleum ether (50/50, v/v) to afford 1600 mg (72%) of title compound as a yellow oil. LCMS: [M+H]$^+$ 368.15.

Step 2: Methyl 3-(2-[methyl[6-oxo-5-(trifluoromethyl)-1-[[2-(trimethylsilyl)ethoxy]methyl]-1,6-dihydropyridazin-4-yl]amino]ethoxy)propanoate A solution of 5-[(2-hydroxyethyl)(methyl)amino]-4-(trifluoromethyl)-2-[[2-(trimethylsilyl)ethoxy]methyl]-2,3-dihydropyridazin-3-one (1.6 g, 4.35 mmol, 1.00 equiv), methyl prop-2-enoate (750 mg, 8.71 mmol, 2.00 equiv), Cs$_2$CO$_3$ (2.8 g, 8.59 mmol, 2.00 equiv) in ACN (100 mL) was stirred for 14 h at RT. The resulting mixture was concentrated under reduced pressure and the residue was applied onto a silica gel column eluting with EtOAc/petroleum ether (1:4) to afford 600 mg (30%) of title compound as a yellow oil. LCMS: [M+H]$^+$ 454.19.

Step 3: Methyl 3-(2-[methyl[6-oxo-5-(trifluoromethyl)-1,6-dihydropyridazin-4-yl]amino]ethoxy)propanoate A solution of methyl 3-(2-[methyl[6-oxo-5-(trifluoromethyl)-1-[[2-(trimethylsilyl)ethoxy]methyl]-1,6-dihydropyridazin-4-yl]amino]ethoxy)propanoate (660 mg, 1.46 mmol, 1 equiv) in DCM (5 mL) and TFA (0.5 mL) was stirred for 2 h at RT. The reaction was then quenched by the addition of 5 mL of water. The resulting solution was extracted with 3×30 mL of DCM and the organic layers combined and dried over anhydrous sodium sulfate. The resulting mixture was concentrated under vacuum to afford 489 mg of the title compound as a yellow oil. LCMS: [M+H]⁺ 324.11.

Step 4: 3-(2-[Methyl[6-oxo-5-(trifluoromethyl)-1,6-dihydropyridazin-4-yl]amino]ethoxy)propanoic Acid A solution of methyl 3-(2-[methyl[6-oxo-5-(trifluoromethyl)-1,6-dihydropyridazin-4-yl]amino]ethoxy)propanoate (489 mg, 1.51 mmol, 1 equiv), LiOH.H$_2$O (317.4 mg, 7.56 mmol, 5.00 equiv) in MeOH (5 mL) and H$_2$O (1 mL) was stirred for 3 h at RT. The pH value of the solution was adjusted to 7 with HCl (2M). After concentration, the residue was purified by C18 reverse phase chromatography eluting with H$_2$O/ACN to afford 469 mg of title compound as a yellow oil. LCMS: [M+H]⁺ 310.09.

Step 5: 6-[4-[3-(2-[Methyl[6-oxo-5-(trifluoromethyl)-1,6-dihydropyridazin-4-yl]amino]ethoxy)propanoyl]piperazin-1-yl]pyridine-3-carbonitrile A solution of 3-(2-[methyl[6-oxo-5-(trifluoromethyl)-1,6-dihydropyridazin-4-yl]amino]ethoxy)propanoic acid (469 mg, 1.52 mmol, 1 equiv), Int-A4 (340.8 mg, 1.52 mmol, 1 equiv), HOBT (307.4 mg, 2.27 mmol, 1.5 equiv), EDCI (436.1 mg, 2.27 mmol, 1.5 equiv), and DIPEA (588.0 mg, 4.55 mmol, 3 equiv) in DMF (2 mL) was stirred for 2 h at 30° C. After concentration, the residue was purified by C18 reverse phase chromatography eluting with H$_2$O/ACN and further purified by Prep-HPLC to afford the title compound (80.6 mg, 11%) as a white solid. LCMS: [M+H]⁺ 480.19. ¹H NMR (400 MHz, DMSO-d$_6$) δ 12.43 (s, 1H), 8.50 (d, J=2.2 Hz, 1H), 7.94-7.87 (m, 2H), 6.92 (d, J=9.1 Hz, 1H), 3.61 (ddd, J=29.4, 20.2, 14.0 Hz, 14H), 3.02 (s, 3H), 2.56 (d, J=6.3 Hz, 2H).

Example 511: 6-[4-(6-[[6-Oxo-5-(trifluoromethyl)-1,6-dihydropyridazin-4-yl]amino]hexanoyl)piperazin-1-yl]pyridine-3-carbonitrile

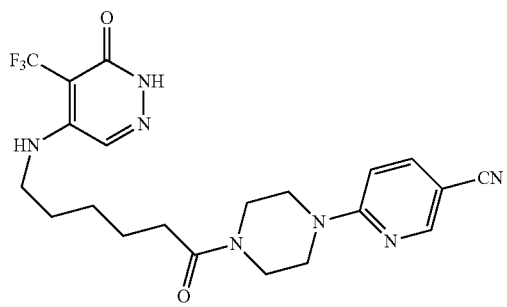 [SMILES: N#Cc1ccc(N2CCN(C(=O)CCCCCNc3cn[nH]c(=O)c3C(F)(F)F)CC2)nc1]

Step 1: Tert-butyl N-[6-[4-(5-cyanopyridin-2-yl)piperazin-1-yl]-6-oxohexyl]carbamate A solution of 6-[[(tert-butoxy)carbonyl]amino]hexanoic acid (1 g, 4.32 mmol, 1.00 equiv), HATU (1.6 g, 4.21 mmol, 1.00 equiv), DIPEA (2.2 g, 17.02 mmol, 4.00 equiv), Int-A4 (814 mg, 4.32 mmol, 1.00 equiv) in DMF (5 mL) was stirred for 1 h at RT. The resulting solution was extracted with 3×30 mL of diethyl ether and the organic layers combined and concentrated under reduced pressure to afford 1.5 g (86%) of title compound as a white solid. LCMS: [M+H]⁺ 402.24.

Step 2: 6-[4-(6-Aminohexanoyl)piperazin-1-yl]pyridine-3-carbonitrile

A solution of tert-butyl N-[6-[4-(5-cyanopyridin-2-yl)piperazin-1-yl]-6-oxohexyl]carbamate (1.5 g, 3.74 mmol, 1.00 equiv) in HCl/dioxane (20 mL) was stirred for 2 h at RT. The resulting mixture was concentrated under reduced pressure to afford 1 g (89%) of title compound as a yellow oil. LCMS: [M+H]⁺ 302.19.

Step 3: 6-[4-(6-[[6-Oxo-5-(trifluoromethyl)-1-[[2-(trimethylsilyl)ethoxy]methyl]-1,6-dihydropyridazin-4-yl]amino]hexanoyl)piperazin-1-yl]pyridine-3-carbonitrile A solution of 6-[4-(6-aminohexanoyl)piperazin-1-yl]pyridine-3-carbonitrile (500 mg, 1.66 mmol, 1.00 equiv), TEA (335 mg, 3.31 mmol, 2.00 equiv), and Int-A6 (544 mg, 1.65 mmol, 1.00 equiv) in EtOH (10 mL) was stirred for 2 h at 60° C. After concentration, the residue was purified by silica gel chromatography eluting with EtOAc/petroleum ether (1/1) to afford 252 mg (26%) of title compound as a yellow solid. LCMS: [M+H]⁺ 594.28.

Step 4: 6-[4-(6-[[6-Oxo-5-(trifluoromethyl)-1,6-dihydropyridazin-4-yl]amino]hexanoyl)piperazin-1-yl]pyridine-3-carbonitrile A solution of 6-[4-(6-[[6-oxo-5-(trifluoromethyl)-1-[[2-(trimethylsilyl)ethoxy]methyl]-1,6-dihydropyridazin-4-yl]amino]hexanoyl)piperazin-1-yl]pyridine-3-carbonitrile (252 mg, 0.42 mmol, 1.00 equiv) and TFA (3 mL) in DCM (12 mL) was stirred for 1 h at RT. After concentration, the residue was purified by C18 reverse phase chromatography eluting with H$_2$O/ACN to afford the title compound (94.4 mg, 48%) as a white solid. LCMS: [M+H]⁺ 464.19. ¹H NMR (300 MHz, CD$_3$OD) δ 8.42 (dd, J=2.4, 0.8 Hz, 1H), 7.89 (d, J=0.7 Hz, 1H), 7.76 (dd, J=9.1, 2.4 Hz, 1H), 6.86 (dd, J=9.1, 0.9 Hz, 1H), 3.79 (dd, J=6.5, 3.8 Hz, 2H), 3.74-3.62 (m, 6H), 3.42 (t, J=7.1 Hz, 2H), 2.47 (t, J=7.4 Hz, 2H), 1.76-1.59 (m, 4H), 1.44 (qd, J=9.9, 9.1, 5.7 Hz, 2H).

Example 512: 6-[4-(6-[[6-Oxo-5-(trifluoromethyl)-1,6-dihydropyridazin-4-yl]oxy]hexanoyl)piperazin-1-yl]pyridine-3-carbonitrile

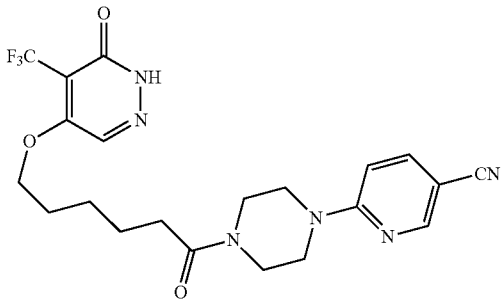 [SMILES: N#Cc1ccc(N2CCN(C(=O)CCCCCOc3cn[nH]c(=O)c3C(F)(F)F)CC2)nc1]

Step 1: 6-[4-(6-Hydroxyhexanoyl)piperazin-1-yl]pyridine-3-carbonitrile

A solution of 6-hydroxyhexanoic acid (500 mg, 3.78 mmol, 1.00 equiv), HATU (1.43 g, 3.76 mmol, 1.00 equiv), DIPEA (1.46 g, 11.30 mmol, 3.00 equiv) and Int-A4 (1.06 g, 5.63 mmol, 1.50 equiv) in DMF (10 mL) was stirred for 2 h at RT. The resulting solution was diluted with 30 mL of H$_2$O and extracted with 3×30 mL of EtOAc. The organic layer was combined, washed with 1×20 mL of brine, dried over anhydrous sodium sulfate and concentrated under reduced pressure. The residue was purified by a silica gel column eluting with EtOAc/petroleum ether (7/3, v/v) to afford 1.06 g (93%) of title compound as a yellow oil. LCMS: [M+H]$^+$ 303.17.

Step 2: 6-[4-(6-[[6-Oxo-5-(trifluoromethyl)-1-[[2-(trimethylsilyl)ethoxy]methyl]-1,6-dihydropyridazin-4-yl]oxy]hexanoyl)piperazin-1-yl]pyridine-3-carbonitrile A solution of 6-[4-(6-hydroxyhexanoyl)piperazin-1-yl]pyridine-3-carbonitrile (600 mg, 1.98 mmol, 1.00 equiv), Cs$_2$CO$_3$ (1.29 g, 3.96 mmol, 2.00 equiv) and Int-A6 (651 mg, 1.98 mmol, 1.00 equiv) in ACN (10 mL) was stirred for 15 h at 40° C. The resulting solution was diluted with 20 mL of H$_2$O, extracted with 3×20 mL of EtOAc and the organic layer was combined, washed with 1×20 mL of brine and concentrated under reduced pressure. The residue was purified by silica gel column chromatography eluting with EtOAc/petroleum ether (7/3, v/v) to afford 240 mg (20%) of title compound as a yellow oil. LCMS: [M+H]$^+$ 595.26.

Step 3: 6-[4-(6-[[6-Oxo-5-(trifluoromethyl)-1,6-dihydropyridazin-4-yl]oxy]hexanoyl)piperazin-1-yl]pyridine-3-carbonitrile A solution of 6-[4-(6-[[6-oxo-5-(trifluoromethyl)-1-[[2-(trimethylsilyl)ethoxy]methyl]-1,6-dihydropyridazin-4-yl]oxy]hexanoyl)piperazin-1-yl]pyridine-3-carbonitrile (370 mg, 0.62 mmol, 1.00 equiv) and TFA (2 mL) in DCM (10 mL) was stirred for 2 h at RT. After concentration, the residue was purified by C18 reverse phase chromatography eluting with H$_2$O/CH$_3$CN to afford the title compound (68.5 mg, 24%) as a white solid. LCMS: [M+H]$^+$ 465.00. $^1$H NMR (300 MHz, Methanol-d4) δ 8.44 (s, 1H), 8.21 (s, 1H), 7.79 (dd, J=9.0, 2.4 Hz, 1H), 6.90 (dd, J=9.0, 0.6 Hz, 1H), 4.44 (t, J=6.0 Hz, 2H), 3.83-3.68 (m, 8H), 2.53 (t, J=7.2 Hz, 2H), 1.93 (dt, J=13.7, 6.4 Hz, 2H), 1.77-1.67 (m, 2H), 1.62-1.51 (m, 2H).

Example 513 Isomer A: (S)-6-(4-(3-(2-(6-Oxo-5-(trifluoromethyl)-1,6-dihydropyridazin-4-ylamino)propoxy)propanoyl)piperazin-1-yl)nicotinonitrile and

Example 513 Isomer B: (R)-6-(4-(3-(2-(6-Oxo-5-(trifluoromethyl)-1,6-dihydropyridazin-4-ylamino)propoxy)propanoyl)piperazin-1-yl)nicotinonitrile Example 513

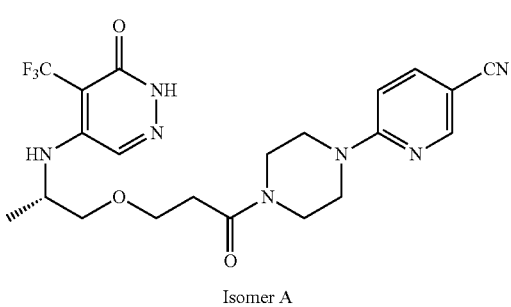

Isomer A

Example 513

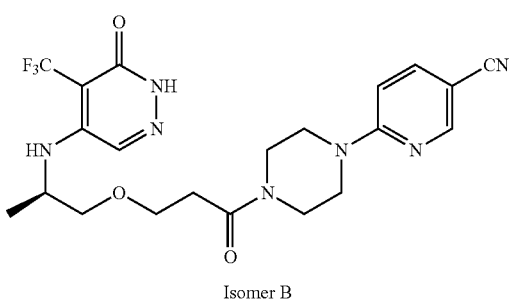

Isomer B

Step 1: Methyl 3-(2-[[(tert-butoxy)carbonyl]amino]propoxy)propanoate

A solution of tert-butyl N-(1-hydroxypropan-2-yl)carbamate (3.15 g, 18.0 mmol, 1.00 equiv), Na (100 mg), and methyl prop-2-enoate (1.7 g, 20.0 mmol, 1.10 equiv) in THF (40 mL) was stirred for 2 h at RT. The resulting mixture was concentrated under reduced pressure. The residue was purified by silica gel column chromatography eluting with DCM/petroleum ether (1:10) to afford 1.5 g (32%) of title compound as a white oil. LCMS: [M+H]$^+$ 262.16.

Step 2: Methyl 3-(2-aminopropoxy)propanoate Hydrochloride

A solution of methyl 3-(2-[[(tert-butoxy)carbonyl]amino]propoxy)propanoate (1.38 g, 5.28 mmol, 1.00 equiv) in HCl/dioxane (10 mL) was stirred for 2 h at RT. The solvent was concentrated under reduced pressure to afford 1 g (95%) of title compound as a white oil. LCMS: [M+H]$^+$ 162.15

Step 3: Methyl 3-(2-[[6-oxo-5-(trifluoromethyl)-1-[[2-(trimethylsilyl)ethoxy]methyl]-1,6-dihydropyridazin-4-yl]amino]propoxy)propanoate A solution of methyl 3-(2-aminopropoxy)propanoate hydrochloride (1 g, 5.06 mmol, 1.00 equiv), TEA (2 mL), and Int-A6 (1.64 g, 4.99 mmol, 1.00 equiv) in EtOH (10 mL) was stirred for 2 h at 60° C. The resulting mixture was concentrated under vacuum. The residue was purified by silica gel column chromatography eluting with EtOAc/petroleum ether (1:5) to afford 1 g (44%) of title compound as a white oil. LCMS: [M+H]$^+$ 454.19.

Step 4: 3-(2-[[6-Oxo-5-(trifluoromethyl)-1-[[2-(trimethylsilyl)ethoxy]methyl]-1,6-dihydro-pyridazin-4-yl]amino]propoxy)propanoic Acid A solution of ethyl 3-(2-[[6-oxo-5-(trifluoromethyl)-1-[[2-(trimethylsilyl)ethoxy]methyl]-1,6-dihydropyridazin-4-yl]amino]propoxy)propanoate (400 mg, 0.86 mmol, 1.00 equiv), water (5 mL), and LiOH (103 mg, 4.30 mmol, 5.00 equiv) in MeOH (15 mL) was stirred for 2 h at RT. The resulting mixture was concentrated under vacuum to afford 460 mg of title compound as a yellow solid. LCMS: [M+H]$^+$ 440.18.

Step 5: 6-[4-[3-(2-[[6-Oxo-5-(trifluoromethyl)-1-[[2-(trimethylsilyl)ethoxy]methyl]-1,6-dihydro-pyridazin-4-yl]amino]propoxy)propanoyl]piperazin-1-yl]pyridine-3-carbonitrile A solution of 3-(2-[[6-oxo-5-(trifluoromethyl)-1-[[2-(trimethylsilyl)ethoxy]methyl]-1,6-dihydropyridazin-4-yl]amino]propoxy)propanoic acid (460 mg, 1.05 mmol, 1.00 equiv), HATU (520 mg, 1.37 mmol, 1.30 equiv), DIPEA (271 mg, 2.10 mmol, 2.00 equiv), and Int-A4 (197 mg, 1.05 mmol, 1.00 equiv) in DMF (15 mL) was stirred for 2 h at RT. The resulting mixture was concentrated under vacuum. The residue was applied onto a silica gel column eluting with EtOAc/petroleum ether (1:1) to afford 350 mg (55%) of title compound as a yellow oil. LCMS: [M+H]$^+$ 610.28.

Step 6: (S)-6-(4-(3-(2-(6-oxo-5-(trifluoromethyl)-1,6-dihydropyridazin-4-ylamino)propoxy)propanoyl)piperazin-1-yl)nicotinonitrile and (R)-6-(4-(3-(2-(6-oxo-5-(trifluoromethyl)-1,6-dihydropyridazin-4-ylamino)propoxy)propanoyl)piperazin-1-yl)nicotinonitrile A solution of 6-[4-[3-(2-[[6-oxo-5-(trifluoromethyl)-1-[[2-(trimethylsilyl)ethoxy]methyl]-1,6-dihydropyridazin-4-yl]amino]propoxy)propanoyl]piperazin-1-yl]pyridine-3-carbonitrile (350 mg, 0.57 mmol, 1.00 equiv), TFA (1 mL) in DCM (5 mL) was stirred for 0.5 h at RT. After concentration, the residue was purified by C18 reverse phase chromatography eluting with H$_2$O/ACN. The residue was further purified by Prep-HPLC and Chiral-Prep-HPLC (CHIRALPAK IG-3, 3 rpm, 0.46×10 cm column, eluting with a gradient of MtBE (0.1% DEA):EtOH=70:30, at a flow rate of 1 mL/min) to afford the title compounds as white solids. The absolute stereochemistry was assigned based on a protein X-ray crystal structure obtained of Example 513A, which confirmed (S)-absolute stereochemistry of the more potent enantiomer.

Example 513 Isomer A 10.9 mg, 8%, LCMS: [M+H]$^+$ 480.15. $^1$H NMR (300 MHz, Methanol-d$_4$) δ 8.43 (dd, J=2.4, 0.8 Hz, 1H), 7.95 (s, 1H), 7.77 (dd, J=9.1, 2.4 Hz, 1H), 6.86 (dd, J=9.1, 0.8 Hz, 1H), 4.21-4.12 (m, 1H), 3.91-3.79 (m, 4H), 3.78-3.60 (m, 7H), 3.56-3.51 (m, 1H), 2.70 (t, J=6.0 Hz, 2H), 1.27 (d, J=6.6 Hz, 3H). tR=2.492 min.

Example 513 Isomer B 9.3 mg, 7%, LCMS: [M+H]$^+$ 480.15. tR=3.349 min.

Example 514 Isomer A: 6-(4-[3-[(2R)-2-[[6-Oxo-5-(trifluoromethyl)-1,6-dihydropyridazin-4-yl]amino]-2-phenylethoxy]propanoyl]piperazin-1-yl)pyridine-3-carbonitrile and Example 514 Isomer B: 6-(4-[3-[(2S)-2-[[6-Oxo-5-(trifluoromethyl)-1,6-dihydropyridazin-4-yl]amino]-2-phenylethoxy]propanoyl]piperazin-1-yl)pyridine-3-carbonitrile Example 514

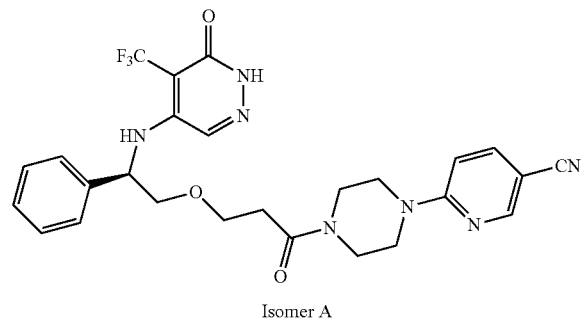

Isomer A

Example 514

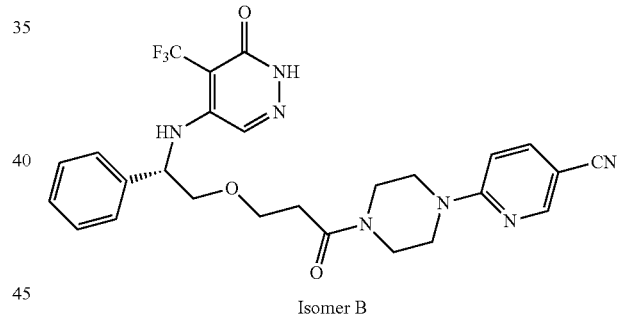

Isomer B

Step 1: Methyl 3-(2-[[(tert-butoxy)carbonyl]amino]-2-phenylethoxy)propanoate

A solution of tert-butyl N-(2-hydroxy-1-phenylethyl)carbamate (1 g, 4.21 mmol, 1.00 equiv), methyl prop-2-enoate (1.8 g, 20.91 mmol, 5.00 equiv) and Cs$_2$CO$_3$ (2.7 g, 8.29 mmol, 2.00 equiv) in ACN (20 mL) was stirred for 1 h at RT. The solid was filtered out and the resulting solution was diluted with 150 mL of H$_2$O, and extracted with 3×50 mL of EtOAc. The organic layers were combined, dried over anhydrous sodium sulfate and concentrated under vacuum to afford 1.3 g (95%) of title compound as a yellow oil. LCMS: [M+H]$^+$ 324.7.

Step 2: 3-(2-[[(Tert-butoxy)carbonyl]amino]-2-phenylethoxy)propanoic Acid

A solution of methyl 3-(2-[[(tert-butoxy)carbonyl]amino]-2-phenylethoxy)propanoate (324 mg, 1.00 mmol, 1.00 equiv) and LiOH (84 mg, 3.51 mmol, 2.00 equiv) in THF (5 mL) and water (0.5 mL) was stirred for 2 h at RT. The resulting solution was concentrated under vacuum, and then the residue was diluted with 20 mL of H$_2$O, and extracted with 3×20 mL of EtOAc. The organic layers were combined, dried over anhydrous sodium sulfate, and concentrated under vacuum to afford 300 mg (97%) of title compound as a yellow oil. LCMS: [M+H]$^+$ 310.16.

Step 3: Tert-butyl N-(2-[3-[4-(5-cyanopyridin-2-yl) piperazin-1-yl]-3-oxopropoxy]-1-phenylethyl)carbamate A solution of 3-(2-[[(tert-butoxy)carbonyl]amino]-2-phenylethoxy)propanoic acid (300 mg, 0.97 mmol, 1.00 equiv), HATU (366 mg, 0.96 mmol, 1.00 equiv), Int-A4 (180 mg, 0.96 mmol, 1.00 equiv) and DIPEA (249 mg, 1.93 mmol, 2.00 equiv) in DMF (3 mL) was stirred for 1 h at RT. The resulting solution was diluted with 60 mL of EtOAc and washed with 3×20 mL of H$_2$O. The organic layers were dried over anhydrous sodium sulfate and concentrated under vacuum to afford 560 mg of title compound as a yellow crude oil. LCMS: [M+H]$^+$ 480.25.

Step 4: 6-[4-[3-(2-Amino-2-phenylethoxy)propanoyl]piperazin-1-yl]pyridine-3-carbonitrile A solution of tert-butyl N-(2-[3-[4-(5-cyanopyridin-2-yl) piperazin-1-yl]-3-oxopropoxy]-1-phenylethyl)carbamate (560 mg, 1.17 mmol, 1.00 equiv) and TFA (1 mL) in DCM (5 mL) was stirred for 1 h at RT. The resulting solution was concentrated under vacuum to afford 380 mg (86%) of title compound as a yellow crude oil. LCMS: [M+H]$^+$ 380.20.

Step 5: 6-[4-[3-(2-[[6-Oxo-5-(trifluoromethyl)-1-[[2-(trimethylsilyl)ethoxy]methyl]-1,6-dihydropyridazin-4-yl]amino]-2-phenylethoxy)propanoyl]piperazin-1-yl]pyridine-3-carbonitrile A solution of 6-[4-[3-(2-amino-2-phenylethoxy)propanoyl]piperazin-1-yl]pyridine-3-carbonitrile (380 mg, 1.00 mmol, 1.00 equiv), Int-A6 (329 mg, 1.00 mmol, 1.00 equiv) and Cs$_2$CO$_3$ (652 mg, 2.00 mmol, 2.00 equiv) in ACN (20 mL) was stirred for 1 h at 80° C. The solids were filtered and the resulting solution was concentrated under vacuum. The residue was purified by silica gel column chromatography eluting with EtOAc/petroleum ether to afford 120 mg (18%) of title compound as a yellow oil. LCMS: [M+H]$^+$ 672.29.

Step 6: 6-(4-[3-[(2R)-2-[[6-oxo-5-(trifluoromethyl)-1,6-dihydropyridazin-4-yl]amino]-2-phenylethoxy] propanoyl]piperazin-1-yl)pyridine-3-carbonitrile and of 6-(4-[3-[(2S)-2-[[6-oxo-5-(trifluoromethyl)-1,6-dihydropyridazin-4-yl]amino]-2-phenylethoxy]propanoyl]piperazin-1-yl)pyridine-3-carbonitrile A solution of 6-[4-[3-(2-[[6-oxo-5-(trifluoromethyl)-1-[[2-(trimethyl silyl)ethoxy]methyl]-1,6-dihydropyridazin-4-yl]amino]-2-phenylethoxy)propanoyl]piperazin-1-yl]pyridine-3-carbonitrile (100 mg, 0.15 mmol, 1.00 equiv) and TFA (0.5 mL) in DCM (2.5 mL) was stirred for 1 h at RT. After concentration, the residue was purified by C18 reverse phase chromatography eluting with H$_2$O/CH$_3$CN. Then the residue was further purified by Prep-HPLC and Chiral-Prep-HPLC (CHIRAL Cellulose-SB, 3 µm, 0.46×15 cm column, eluting with a gradient of MtBE (0.1% DEA):EtOH=50:50, at a flow rate of 1 mL/min) to afford the title compounds, respectively, as white solids. The absolute stereochemistry was assigned in analogy to Example 513A, based on the PARP7 potency of the more potent enantiomer and in analogy to the Example 513A X-ray.

Example 514 Isomer A 10.7 mg, 35%, LCMS: [M+H]$^+$ 542.25. $^1$H NMR (300 MHz, Methanol-d$_4$) δ 8.44 (d, J=1.8 Hz, 1H), 7.79 (dd, J=9.0, 2.4 Hz, 1H), 7.58 (s, 1H), 7.45-7.32 (m, 5H), 6.87 (d, J=9.0 Hz, 1H), 5.08-5.06 (m, 1H), 3.91-3.72 (m, 12H), 2.75 (t, J=5.4 Hz, 2H). tR=2.982 min.

Example 514 Isomer B 10.0 mg, 36%, LCMS: [M+H]$^+$ 542.25. tR=3.850 min.

Example 515 Isomer A: 6-(4-[3-[(2R)-2-[[6-Oxo-5-(trifluoromethyl)-1,6-dihydropyridazin-4-yl]amino]-2-phenylethoxy]propanoyl]piperazin-1-yl)pyridine-3-carbonitrile and Example 515 Isomer B: 6-(4-[3-[(2S)-2-[[6-Oxo-5-(trifluoromethyl)-1,6-dihydropyridazin-4-yl]amino]-2-phenylethoxy]propanoyl]piperazin-1-yl)pyridine-3-carbonitrile

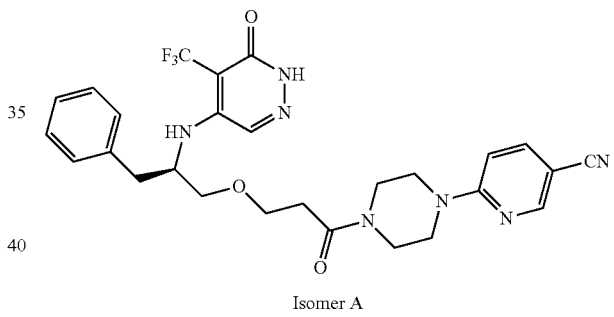

Example 515

Isomer A

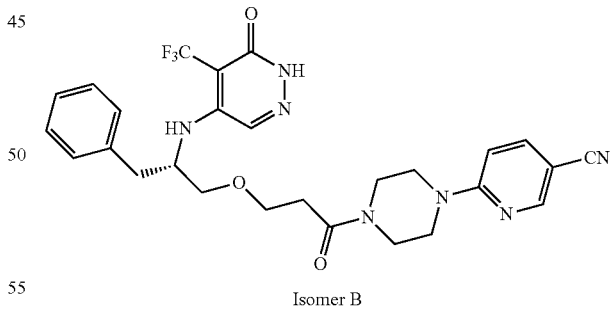

Example 515

Isomer B

Step 1: Methyl 3-(2-[[(tert-butoxy)carbonyl]amino]-3-phenylpropoxy)propanoate

A solution of tert-butyl N-(1-hydroxy-3-phenylpropan-2-yl)carbamate (2.51 g, 9.99 mmol, 1.00 equiv), NaH (600 mg, 25.0 mmol, 1.10 equiv), and methyl 3-bromopropanoate (1.8 g, 10.8 mmol, 1.10 equiv) in THF (30 mL) was stirred for 3 h at RT. The solvent was concentrated under vacuum and the residue was applied onto a silica gel column eluting with EtOAc/petroleum ether (1:5) to afford 1.2 g (36%) of title compound as a white solid. LCMS: [M+H]⁺ 338.20.

Step 2: 3-(2-[[(Tert-butoxy)carbonyl]amino]-3-phenylpropoxy)propanoic Acid

A solution of methyl 3-(2-[[(tert-butoxy)carbonyl]amino]-3-phenylpropoxy)propanoate (1.2 g, 3.56 mmol, 1.00 equiv), LiOH (420 mg, 17.54 mmol, 5.00 equiv), water (2 mL) in MeOH (20 mL) was stirred for 12 h at RT. The pH value of the solution was adjusted to 5 with HCl (36%). The resulting solution was extracted with EtOAc (3×30 mL) and the organic layers combined. The solution was dried over anhydrous sodium sulfate and concentrated under vacuum to afford 1 g of the title compound as a yellow oil. LCMS: [M+H]⁺ 324.20.

Step 3: 3-(2-Amino-3-phenylpropoxy)propanoic Acid Hydrochloride

A solution of 3-(2-[[(tert-butoxy)carbonyl]amino]-3-phenylpropoxy)propanoic acid (1 g, 3.09 mmol, 1.00 equiv) in HCl/dioxane (10 mL) was stirred for 1 h at RT. The resulting mixture was concentrated under vacuum to afford 800 mg of the title compound as a yellow oil. LCMS: [M+H]⁺ 324.20.

Step 4: 3-(2-[[6-Oxo-5-(trifluoromethyl)-1-[[2-(trimethylsilyl)ethoxy]methyl]-1,6-dihydropyridazin-4-yl]amino]-3-phenylpropoxy)propanoic Acid A solution of 3-(2-amino-3-phenylpropoxy)propanoic acid hydrochloride (800 mg, 3.08 mmol, 1.00 equiv), TEA (2 mL), and Int-A6 (1 g, 3.04 mmol, 1.00 equiv) in EtOH (10 mL) was stirred for 3 h at 60° C. The solvent was concentrated under vacuum and the residue was purified by silica gel column chromatography eluting with EtOAc/petroleum ether (1:1) to afford 1 g (63%) of title compound as a yellow oil. LCMS: [M+H]⁺ 516.20.

Step 5: 6-[4-[3-(2-[[6-Oxo-5-(trifluoromethyl)-1-[[2-(trimethylsilyl)ethoxy]methyl]-1,6-dihydropyridazin-4-yl]amino]-3-phenylpropoxy)propanoyl]piperazin-1-yl]pyridine-3-carbonitrile A solution of 3-(2-[[6-oxo-5-(trifluoromethyl)-1-[[2-(trimethylsilyl)ethoxy]methyl]-1,6-dihydropyridazin-4-yl]amino]-3-phenylpropoxy)propanoic acid (1.29 g, 2.50 mmol, 1.00 equiv), HATU (1.43 g, 3.76 mmol, 1.50 equiv), DIPEA (0.8 mL), and Int-A4 (470 mg, 2.50 mmol, 1.00 equiv) in DMF (3 mL) was stirred for 1 h at RT. After concentration, the residue was purified by C18 reverse phase chromatography eluting with H₂O/ACN to afford 430 mg (25%) of title compound as a white oil. LCMS: [M+H]⁺ 686.31.

Step 6: 6-(4-[3-[(2R)-2-[[6-oxo-5-(trifluoromethyl)-1,6-dihydropyridazin-4-yl]amino]-2-phenylethoxy]propanoyl]piperazin-1-yl)pyridine-3-carbonitrile and 6-(4-[3-[(2S)-2-[[6-oxo-5-(trifluoromethyl)-1,6-dihydropyridazin-4-yl]amino]-2-phenylethoxy]propanoyl]piperazin-1-yl)pyridine-3-carbonitrile A solution of 6-[4-[3-(2-[[6-oxo-5-(trifluoromethyl)-1-[[2-(trimethyl silyl)ethoxy]methyl]-1,6-dihydropyridazin-4-yl]amino]-2-phenylethoxy)propanoyl]piperazin-1-yl]pyridine-3-carbonitrile (180 mg, 0.27 mmol, 1.00 equiv) and TFA (2 mL) in DCM (12 mL) was stirred for 1 h at RT. After concentration, the residue was purified by C18 reverse phase chromatography eluting with H₂O/ACN. The residue was further purified by Prep-HPLC and Chiral-Prep-HPLC (CHIRALPAK IC-3, 3 µm, 0.46×10 cm column, eluting with a gradient of MtBE (0.1% DEA):EtOH=50:50, at a flow rate of 1 mL/min) to afford the title compounds as white solids. The absolute stereochemistry was assigned in analogy to Example 513A, based on the PARP7 potency of the more potent enantiomer and in analogy to the Example 513A X-ray.

Example 515 Isomer A 10.0 mg, 6%, LCMS: [M+H]⁺ 556.10. ¹H NMR (300 MHz, CD₃OD-d₄) δ 8.43 (s, 1H), 7.77 (dd, J=9.1, 2.3 Hz, 1H), 7.64 (s, 1H), 7.31-7.21 (m, 5H), 6.86 (dd, J=9.1, 0.8 Hz, 1H), 4.30 (s, 1H), 3.86-3.79 (m, 4H), 3.77-3.57 (m, 8H), 3.02-2.96 (m, 1H), 2.90-2.83 (m, 1H), 2.73 (t, J=5.9 Hz, 2H). tR=2.227 min.

Example 515 Isomer B 16.6 mg, 9%, LCMS: [M+H]⁺: 556.10. tR=4.973 min.

Example 516: 6-(4-[3-[Methyl(2-[[6-oxo-5-(trifluoromethyl)-1,6-dihydropyridazin-4-yl]oxy]ethyl)amino]propanoyl]piperazin-1-yl)pyridine-3-carbonitrile

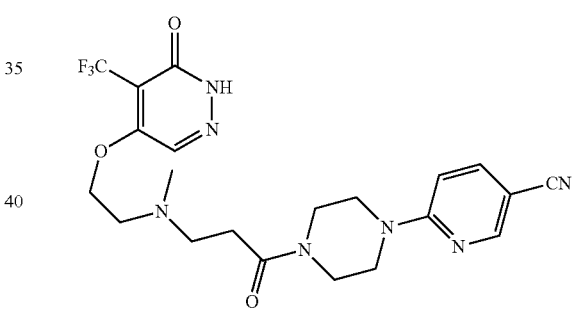

Step 1: 6-(4-[3-[(2-Hydroxyethyl)(methyl)amino]propanoyl]piperazin-1-yl)pyridine-3-carbonitrile A solution of Int-A25 (2.3 g, 9.5 mmol, 1 equiv) and 2-(methylamino)ethan-1-ol (1.4 g, 18.6 mmol, 1.96 equiv) in EtOH (20 mL) was stirred for 2 hr at 60° C. The solvent was concentrated under vacuum and the residue was purified by silica gel column chromatography eluting with DCM/MeOH (9/1) to afford 1.4 g of title compound as a yellow oil. LCMS: [M+H]⁺ 318.19.

Step 2: 6-(4-[3-[Methyl(2-[[6-oxo-5-(trifluoromethyl)-1-[[2-(trimethylsilyl)ethoxy]methyl]-1,6-dihydropyridazin-4-yl]oxy]ethyl)amino]propanoyl]piperazin-1-yl)pyridine-3-carbonitrile A solution of 6-(4-[3-[(2-hydroxyethyl)(methyl)amino]propanoyl]piperazin-1-yl)pyridine-3-carbonitrile (1.4 g, 4.4 mmol, 1 equiv), Cs₂CO₃ (2.86 g, 8.8 mmol, 1.99 equiv), and Int-A6 (1.7 g, 5.2 mmol, 1.2 equiv) in DMF (20 mL) was stirred for 2 days at RT. The reaction was then quenched by the addition of 20 mL of water. The resulting solution was extracted with 3×30 mL of EtOAc and the organic layers combined and dried over anhydrous sodium sulfate. The organic layers were concentrated under vacuum. The residue was purified by silica gel column chromatography diluting with DCM/MeOH (4/1) to afford 640 mg (24%) of title compound as a yellow oil. LCMS: [M+H]+ 610.27.

Step 3: 6-(4-[3-[Methyl(2-[[6-oxo-5-(trifluoromethyl)-1,6-dihydropyridazin-4-yl]oxy]ethyl)amino]propanoyl]piperazin-1-yl)pyridine-3-carbonitrile A solution of 6-(4-[3-[methyl(2-[[6-oxo-5-(trifluoromethyl)-1-[[2-(trimethyl silyl)ethoxy]methyl]-1,6-dihydro-pyridazin-4-yl]oxy]ethyl)amino]propanoyl]piperazin-1-yl) pyridine-3-carbonitrile (250 mg, 0.41 mmol, 1 equiv) and TFA (1 mL) in DCM (10 mL) was stirred for 1 hr at RT. The solvent was concentrated under vacuum and the residue was purified by C18 reverse phase chromatography eluting with H₂O/ACN followed by further purification by Prep-TLC to afford the title compound (11.0 mg, 5.6%) as a white solid. LCMS: [M+H]+ 480.1. ¹H NMR (300 MHz, DMSO-d₆) δ 13.28 (s, 1H), 8.51 (d, J=2.3 Hz, 1H), 8.27 (d, J=0.9 Hz, 1H), 7.89 (dd, J=9.1, 2.4 Hz, 1H), 6.94 (d, J=9.1 Hz, 1H), 4.46 (t, J=5.4 Hz, 2H), 3.75-3.52 (m, 8H), 2.78-2.61 (m, 4H), 2.51-2.43 (m, 2H), 2.25 (s, 3H).

Example 517: 6-(4-(2-(3-(6-Oxo-5-(trifluoromethyl)-1,6-dihydropyridazin-4-yloxy)propoxy)acetyl)piperazin-1-yl)nicotinonitrile

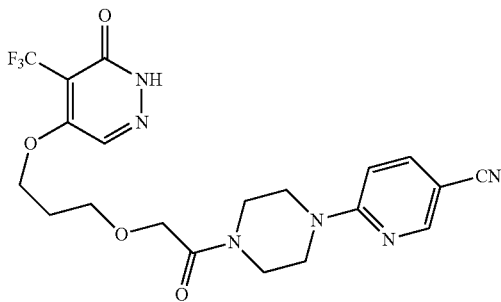 [SMILES: N#Cc1ccc(N2CCN(C(=O)COCCCOc3cn[nH]c(=O)c3C(F)(F)F)CC2)nc1]

Step 1: 6-[4-(2-Bromoacetyl)piperazin-1-yl]pyridine-3-carbonitrile

A solution of 2-bromoacetyl bromide (1 g, 4.95 mmol, 1.00 equiv), Int-A4 (945 mg, 5.02 mmol, 1.00 equiv), and TEA (1.275 g, 12.60 mmol, 2.50 equiv) in DCM (15 mL) was stirred for 0.5 h at RT. The solids were filtered and the resulting solution was concentrated under vacuum to afford 1.5 g of title compound as a yellow oil. LCMS: [M+H]+ 309.03.

Step 2: 6-[4-[2-(3-Hydroxypropoxy)acetyl]piperazin-1-yl]pyridine-3-carbonitrile

A solution of propane-1,3-diol (108.57 mg, 1.43 mmol, 2.00 equiv), 6-[4-(2-bromoacetyl)piperazin-1-yl]pyridine-3-carbonitrile (220 mg, 0.71 mmol, 1.00 equiv), and Cs₂CO₃ (692.3 mg, 2.12 mmol, 3.00 equiv) in DMF (10 mL) was stirred for 3 h at RT. After concentration, the residue was purified by C18 reverse phase chromatography eluting with H₂O/ACN to afford 81 mg (37%) of title compound as a yellow solid. LCMS: [M+H]+ 305.15.

Step 3: 6-[4-[2-(3-[[6-Oxo-5-(trifluoromethyl)-1-[[2-(trimethylsilyl)ethoxy]methyl]-1,6-dihydro-pyridazin-4-yl]oxy]propoxy)acetyl]piperazin-1-yl] pyridine-3-carbonitrile A solution of 6-[4-[2-(3-hydroxypropoxy)acetyl]piperazin-1-yl]pyridine-3-carbonitrile (76 mg, 0.25 mmol, 1.00 equiv), Int-A6 (98.4 mg, 0.30 mmol, 1.20 equiv), and Cs₂CO₃ (243.8 mg, 0.75 mmol, 3.00 equiv) in DMF (5 mL) was stirred for 2.5 h at 80° C. The solids were filtered and the resulting solution was extracted with EtOAc (3×30 mL) and the organic layers combined. The solution was dried over anhydrous sodium sulfate and concentrated under vacuum. The residue was applied by silica gel column chromatography eluting with EtOAc/hexane (1:2) to afford 40 mg (27%) of title compound as a yellow oil. LCMS: [M+H]+ 597.24.

Step 4: 6-(4-(2-(3-(6-Oxo-5-(trifluoromethyl)-1,6-dihydropyridazin-4-yloxy)propoxy)acetyl)piperazin-1-yl)nicotinonitrile A solution of 6-[4-[2-(3-[[6-oxo-5-(trifluoromethyl)-1-[[2-(trimethyl silyl)ethoxy]methyl]-1,6-dihydropyridazin-4-yl]oxy]propoxy)acetyl]piperazin-1-yl]pyridine-3-carbonitrile (55 mg, 0.09 mmol, 1.00 equiv) and TFA (1 mL) in DCM (5 mL) was stirred for 1 h at RT. After concentration, the residue was purified by Prep-HPLC eluting with H₂O/ACN to afford the title compound (8.4 mg, 20%) as a white solid. LCMS: [M+H]+ 467.05. ¹H NMR (300 MHz, Methanol-d₄) δ 8.44 (s, 1H), 8.24 (s, 1H), 7.77 (dd, J=9.2, 6.3 Hz, 1H), 6.87 (d, J=9.0 Hz, 1H), 4.55 (t, J=6.3 Hz, 2H), 4.30 (s, 2H), 3.72-3.78 (m, 8H), 3.70-3.61 (m, 2H), 2.10-2.18 (m, 2H).

Example 518 Isomer A: (R)-6-(4-(3-(3-Methoxy-2-((6-oxo-5-(trifluoromethyl)-1,6-dihydropyridazin-4-yl)amino)propoxy)propanoyl)piperazin-1-yl)nicotinonitrile and Example 518 Isomer B: (S)-6-(4-(3-(3-Methoxy-2-((6-oxo-5-(trifluoromethyl)-1,6-dihydropyridazin-4-yl)amino)propoxy)propanoyl)piperazin-1-yl)nicotinonitrile

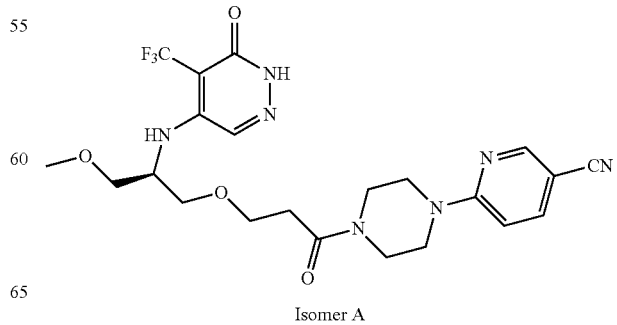

Example 518

Isomer A

Example 518

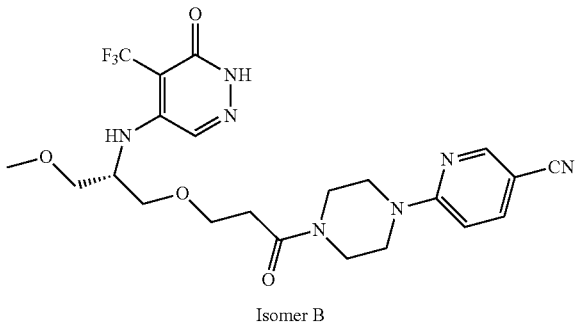

Isomer B

Step 1: 3-Methoxy-2-[[6-oxo-5-(trifluoromethyl)-1-[[2-(trimethylsilyl)ethoxy]methyl]-1,6-dihydropyridazin-4-yl]amino]propanoic Acid A solution of Int-A6 (3 g, 9.12 mmol, 1.00 equiv), 2-amino-3-methoxypropan-1-ol (1.2 g, 11.41 mmol, 1.00 equiv), and TEA (6 mL) in EtOH (20 mL) was stirred for 1 h at 50° C. The solvent was concentrated under reduced pressure and the residue was purified by silica gel column chromatography eluting with DCM/MeOH (3/1) to afford 2.8 g (75%) of title compound as a red solid. LCMS: [M+H]$^+$ 412.25.

Step 2: 5-[(1-Hydroxy-3-methoxypropan-2-yl)amino]-4-(trifluoromethyl)-2-[[2-(trimethylsilyl)ethoxy]methyl]-2,3-dihydropyridazin-3-one A solution of 3-methoxy-2-[[6-oxo-5-(trifluoromethyl)-1-[[2-(trimethylsilyl)ethoxy]methyl]-1,6-dihydropyridazin-4-yl]amino]propanoic acid (3 g, 7.29 mmol, 1.00 equiv) in B$_2$H$_6$·THF (35 mL, 5.00 equiv) was stirred for 2 h at 50° C. The reaction was then quenched by the addition of 20 mL of MeOH. The solvent was concentrated under reduced pressure and the residue was purified by silica gel column chromatography eluting with EtOAc/petroleum ether (3/2) to afford 800 mg (28%) of title compound as a yellow oil. LCMS: [M+H]$^+$ 398.35.

Step 3: Methyl 3-(3-methoxy-2-[[6-oxo-5-(trifluoromethyl)-1-[[2-(trimethylsilyl)ethoxy]methyl]-1,6-dihydropyridazin-4-yl]amino]propoxy)propanoate A solution of 5-[(1-hydroxy-3-methoxypropan-2-yl)amino]-4-(trifluoromethyl)-2-[[2-(trimethylsilyl)ethoxy]methyl]-2,3-dihydropyridazin-3-one (600 mg, 1.51 mmol, 1.00 equiv), methyl prop-2-enoate (600 mg, 7.0 mmol, 5.0 equiv), and Cs$_2$CO$_3$ (900 mg, 2.8 mmol, 2.00 equiv) in ACN (20 mL) was stirred overnight at 35° C. The resulting mixture was concentrated under reduced pressure and the residue purified by silica gel column chromatography eluting with EtOAc/petroleum ether to afford 150 mg (21%) of title compound as a yellow oil. LCMS: [M+H]$^+$ 484.15.

Step 4: Methyl 3-(3-methoxy-2-[[6-oxo-5-(trifluoromethyl)-1,6-dihydropyridazin-4-yl]amino]propoxy)propanoate A solution of methyl 3-(3-methoxy-2-[[6-oxo-5-(trifluoromethyl)-1-[[2-(trimethylsilyl)ethoxy]methyl]-1,6-dihydropyridazin-4-yl]amino]propoxy)propanoate (150 mg, 0.31 mmol, 1.00 equiv) in dioxane/HCl (4M, 4 mL) was stirred for 4 h at 25° C. The resulting mixture was concentrated under vacuum to afford 120 mg of title compound as a colorless oil. LCMS: [M+H]$^+$ 354.20.

Step 5: 3-(3-Methoxy-2-[[6-oxo-5-(trifluoromethyl)-1,6-dihydropyridazin-4-yl]amino]propoxy)propanoic Acid A solution of methyl 3-(3-methoxy-2-[[6-oxo-5-(trifluoromethyl)-1,6-dihydropyridazin-4-yl]amino]propoxy)propanoate (120 mg, 0.34 mmol, 1.00 equiv), and LiOH (100 mg, 4.18 mmol, 10.0 equiv) in MeOH (5 mL) and water (2 mL) was stirred overnight at 25° C. After concentration, the residue was purified by C18 reverse phase chromatography eluting with H$_2$O/ACN to afford 50 mg (43%) of title compound as a yellow oil. LCMS: [M+H]$^+$ 340.20.

Step 6: (R)-6-(4-(3-(3-Methoxy-2-((6-oxo-5-(trifluoromethyl)-1,6-dihydropyridazin-4-yl)amino)propoxy)propanoyl)piperazin-1-yl)nicotinonitrile and (S)-6-(4-(3-(3-methoxy-2-((6-oxo-5-(trifluoromethyl)-1,6-dihydropyridazin-4-yl)amino)propoxy)propanoyl)piperazin-1-yl)nicotinonitrile A solution of 3-(3-methoxy-2-[[6-oxo-5-(trifluoromethyl)-1,6-dihydropyridazin-4-yl]amino]propoxy)propanoic acid (50 mg, 0.15 mmol, 1.00 equiv), Int-A4 (35 mg, 0.16 mmol, 1.00 equiv), HATU (56 mg, 0.15 mmol, 1.00 equiv), and DIPEA (1 mL) in DMF (3 mL) was stirred for 1 h at 25° C. After concentration, the residue was purified by C18 reverse phase chromatography eluting with H$_2$O/ACN and further purified by Prep-HPLC. The enantiomers were separated by chiral Prep-HPLC (CHIRAL Cellulose-SB, 5 μm, 0.46×15 cm column, eluting with a gradient of Hexanes (0.1% DEA):EtOH=50:50, at a flow rate of 1 mL/min) to afford the title compounds as white solids. The absolute stereochemistry was assigned in analogy to Example 513A, based on the PARP7 potency of the more potent enantiomer and in analogy to the Example 513A X-ray.

Example 518 Isomer A 3.5 mg, 23%, LCMS: [M+H]$^+$ 510.15. $^1$H NMR (400 MHz, DMSO-d$_6$) δ 12.49 (s, 1H), 8.04 (d, J=2.4 Hz, 1H), 7.93 (s, 1H), 7.90-7.87 (dd, J=8.80, 2.20 Hz, 1H), 6.92 (d, J=9.2 Hz, 1H), 6.23-6.22 (dd, J=8.80, 4.80 Hz, 1H), 4.27 (s, 1H), 3.69-3.53 (m, 14H), 3.27 (s, 3H), 2.60-2.57 (m, 2H). tR=1.080 min.

Example 518 Isomer B 4.3 mg, 29%, LCMS: [M+H]⁺ 510.15, tR=1.073 min.

Example 519: 6-[4-[3-(2-Methyl-2-[[6-oxo-5-(trifluoromethyl)-1,6-dihydropyridazin-4-yl]amino]propoxy)propanoyl]piperazin-1-yl]pyridine-3-carbonitrile

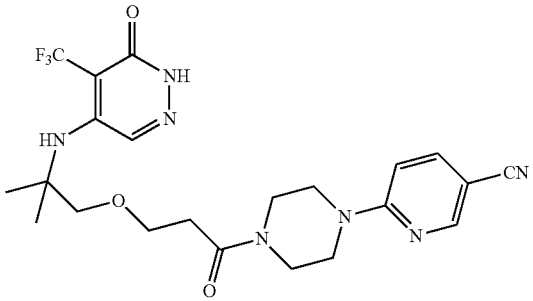 [SMILES: CC(C)(COCCC(=O)N1CCN(c2ccc(C#N)cn2)CC1)Nc1cn[nH]c(=O)c1C(F)(F)F]

Step 1: 3-Methoxy-2-[[6-oxo-5-(trifluoromethyl)-1-[[2-(trimethylsilyl)ethoxy]methyl]-1,6-dihydropyridazin-4-yl]amino]propanoic Acid A solution of tert-butyl N-(1-hydroxy-2-methylpropan-2-yl)carbamate (3.78 g, 20.0 mmol, 1.00 equiv) in HCl/dioxane (40 mL) was stirred for 1 h at 25° C. The solids were collected by filtration to afford the title compound (2.2 g, 68%) as a white solid. LCMS: [M−Cl]⁺ 90.08.

Step 2: 5-[(1-Hydroxy-2-methylpropan-2-yl)amino]-4-(trifluoromethyl)-2-[[2-(trimethylsilyl)ethoxy]methyl]-2,3-dihydropyridazin-3-one A solution of Int-A6 (1 g, 3.04 mmol, 1.00 equiv), 2-amino-2-methylpropan-1-ol dihydrochloride (1.4 g, 8.64 mmol, 3.00 equiv), and TEA (924 mg, 9.13 mmol, 3.00 equiv) in DMF (4 mL) was stirred for 30 min at 60° C. The solvent was concentrated under reduced pressure and the residue was purified by silica gel column chromatography eluting with EtOAc/petroleum ether (3:7) to afford 700 mg (60%) of title compound as a yellow oil. LCMS: [M+H]⁺ 382.17.

Step 3: Methyl 3-(2-methyl-2-[[6-oxo-5-(trifluoromethyl)-1-[[2-(trimethylsilyl)ethoxy]methyl]-1,6-dihydropyridazin-4-yl]amino]propoxy)propanoate A solution of 5-[(1-hydroxy-2-methylpropan-2-yl)amino]-4-(trifluoromethyl)-2-[[2-(trimethylsilyl)ethoxy]methyl]-2,3-dihydropyridazin-3-one (537 mg, 1.41 mmol, 1.00 equiv), methyl prop-2-enoate (1.2 g, 13.9 mmol, 10.0 equiv), and Cs₂CO₃ (917 mg, 2.81 mmol, 2.00 equiv) in ACN (10 mL) was stirred for 4 h at RT. The solvent was concentrated under reduced pressure and purified by silica gel column chromatography eluting with EtOAc/petroleum ether (24:76) to afford 320 mg (49%) of the title compound as a colorless oil. LCMS: [M+H]⁺ 468.21.

Step 4: Methyl 3-(2-methyl-2-[[6-oxo-5-(trifluoromethyl)-1,6-dihydropyridazin-4-yl]amino]propoxy)propanoate A solution of methyl 3-(2-methyl-2-[[6-oxo-5-(trifluoromethyl)-1-[[2-(trimethyl silyl)ethoxy]methyl]-1,6-dihydropyridazin-4-yl]amino]propoxy)propanoate (300 mg, 0.64 mmol, 1.00 equiv) and TFA/DCM (12 mL) in DCM (10 mL) was stirred for 1 h at RT. The resulting mixture was concentrated under reduced pressure to afford 200 mg (92%) of title compound as a yellow oil. LCMS: [M+H]⁺ 338.12.

Step 5: 3-(2-Methyl-2-[[6-oxo-5-(trifluoromethyl)-1,6-dihydropyridazin-4-yl]amino]propoxy)propanoic Acid A solution of methyl 3-(2-methyl-2-[[6-oxo-5-(trifluoromethyl)-1,6-dihydropyridazin-4-yl]amino]propoxy)propanoate (220 mg, 0.65 mmol, 1.00 equiv) and LiOH.H₂O (42 mg, 1.00 mmol, 1.50 equiv) in MeOH/H₂O (4 mL) was stirred overnight at RT. The pH of the solution was adjusted to 6 with HCl and the resulting mixture was concentrated under reduced pressure to afford 200 mg (95%) of title compound as a yellow oil which was used directly in the next step. LCMS: [M+H]⁺ 324.11.

Step 6: 6-[4-[3-(2-Methyl-2-[[6-oxo-5-(trifluoromethyl)-1,6-dihydropyridazin-4-yl]amino]propoxy)propanoyl]piperazin-1-yl]pyridine-3-carbonitrile A solution of 3-(2-methyl-2-[[6-oxo-5-(trifluoromethyl)-1,6-dihydropyridazin-4-yl]amino]propoxy)propanoic acid (200 mg, 0.62 mmol, 1.00 equiv), DIPEA (239 mg, 1.85 mmol, 3.00 equiv), HATU (237 mg, 0.62 mmol, 1.01 equiv), and Int-A4 (116 mg, 0.62 mmol, 1.00 equiv) in DMF (2 mL) was stirred for 15 min at RT followed by the addition of three drops of ethanolamine. The residue was purified by C18 reverse phase chromatography eluting with H₂O/ACN to afford 143.4 mg (47%) of title compound as a white solid. LCMS: [M+H]⁺ 494.25. ¹H NMR (400 MHz, DMSO-d₆) δ 8.43 (d, J=2.0 Hz, 1H), 8.10 (s, 1H), 7.78-7.75 (m, 1H), 6.88-6.85 (d, J=9.2 Hz, 1H), 3.89-3.86 (m, 2H), 3.83-3.82 (m, 2H), 3.74-3.72 (m, 6H), 3.51 (s, 2H), 2.78-2.75 (t, J=6.0 Hz, 2H), 1.48 (s, 6H).

Example 520: 4-Chloro-5-[2-(3-oxo-3-[4-[5-(trifluoromethyl)pyrimidin-2-yl]piperazin-1-yl]propoxy)ethoxy]-2,3-dihydropyridazin-3-one

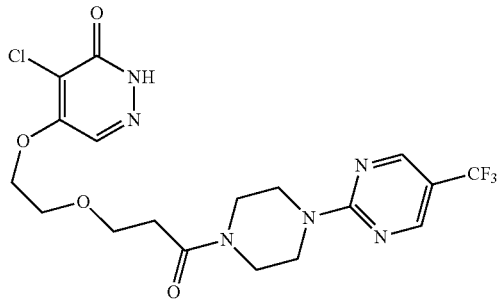 [SMILES: O=C(CCOCCOc1cn[nH]c(=O)c1Cl)N1CCN(c2ncc(C(F)(F)F)cn2)CC1]

Step 1: 4-Chloro-5-[2-(3-oxo-3-[4-[5-(trifluoromethyl)pyrimidin-2-yl]piperazin-1-yl]propoxy)ethoxy]-2,3-dihydropyridazin-3-one A solution of Int-A9 (132.05 mg, 0.50 mmol, 1.00 equiv), HATU (229.9 mg, 0.60 mmol, 1.20 equiv), DIPEA (195.05 mg, 1.51 mmol, 3.00 equiv), and Int-A2 (140.4 mg, 0.60 mmol, 1.20 equiv) in DMF (3 mL) was stirred for 2 h at RT. After concentration, the residue was purified by C18 reverse phase chromatography eluting with H₂O/ACN and the residue further purified by Prep-HPLC to afford the title compound as a white solid. LCMS: [M+H]⁺ 477.05. ¹H NMR (300 MHz, Chloroform-d₄) δ 8.53 (s, 2H), 7.92 (s, 1H), 4.45 (t, J=4.4 Hz, 2H), 3.95-3.76 (m, 8H), 3.82-3.45 (m, 4H), 2.69 (t, J=6.3 Hz, 2H).

The following examples in Table E4 were similarly prepared from Int-A9 and the appropriate intermediates according to the method described for Example 520.

TABLE E4

| Example | Name, structure, analytical data | Int. |
|---|---|---|
| Example 521 | 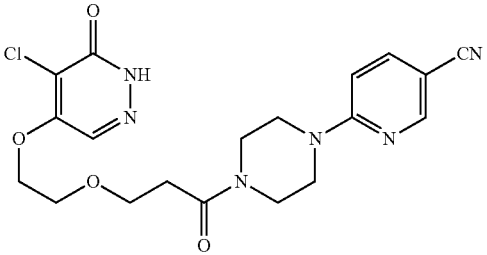 [SMILES: N#Cc1ccc(N2CCN(C(=O)CCOCCOc3cn[nH]c(=O)c3Cl)CC2)nc1]<br>6-[4-(3-[2-[(5-Chloro-6-oxo-1,6-dihydropyridazin-4-yl)oxy]ethoxy]propanoyl)piperazin-1-yl]pyridine-3-carbonitrile;<br>LCMS: [M + H]⁺ 433.05;<br>¹H NMR (300 MHz, Chloroform-d₄) δ 12.08 (s, 1H), 8.42 (d, J = 2.3 Hz, 1H), 7.93 (s, 1H), 7.66 (dd, J = 9.0, 2.4 Hz, 1H), 6.62 (d, J = 9.0 Hz, 1H), 4.45 (dd, J = 5.5, 3.2 Hz, 2H), 3.92-3.90 (m, 4H), 3.78 (dd, J = 6.5, 3.8 Hz, 4H), 3.72-3.60 (m, 4H), 2.67 (t, J = 6.2 Hz, 2H). | Int-A9 and Int-A4 |
| Example 522* | 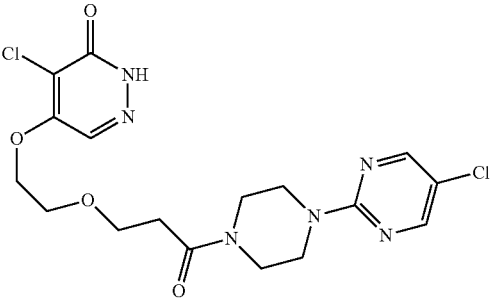 [SMILES: O=C(CCOCCOc1cn[nH]c(=O)c1Cl)N1CCN(c2ncc(Cl)cn2)CC1]<br>4-Chloro-5-(2-[3-[4-(5-chloropyrimidin-2-yl)piperazin-1-yl]-3-oxopropoxy]ethoxy)-2,3-dihydropyridazin-3-one;<br>LCMS: [M + H]⁺ 443.09;<br>¹H NMR (300 MHz, DMSO-d6) δ 13.27 (s, 1H), 8.45 (s, 2H), 8.19 (s, 1H), 4.48 (t, J = 4.5 Hz, 2H), 3.79-3.65 (m, 8H), 3.55 (s, 4H), 2.63 (t, J = 6.5 Hz, 2H). | Int-A9 and Int-A3 |
| Example 523* | 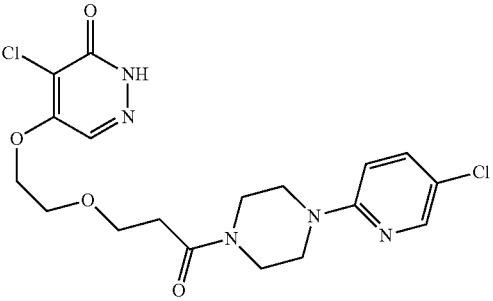 [SMILES: O=C(CCOCCOc1cn[nH]c(=O)c1Cl)N1CCN(c2ccc(Cl)cn2)CC1]<br>4-Chloro-5-(2-[3-[4-(5-chloropyridin-2-yl)piperazin-1-yl]-3-oxopropoxy]ethoxy)-2,3-dihydropyridazin-3-one;<br>LCMS: [M + H]⁺ 442.10;<br>¹H NMR (400 MHz, DMSO-d6) δ 13.28 (s, 1H), 8.18 (s, 1H), 8.11 (d, J = 2.7 Hz, 1H), 7.61 (dd, J = 9.1, 2.7 Hz, 1H), 6.87 (d, J = 9.1 Hz, 1H), 4.50-4.43 (m, 2H), 3.78-3.69 (m, 4H), 3.58-3.41 (m, 6H), 3.34 (s, 2H), 2.62 (t, J = 6.5 Hz, 2H). | Int-A9 and Int-A5 |

*Examples 522 and 523 were made according to a similar procedure as that of Example 520 but using HOBT (1.5 equiv) and EDCI (1.5 equiv) as coupling reagents.

Example 524: 6-(4-[2-[(3-[[6-Oxo-5-(trifluoromethyl)-1,6-dihydropyridazin-4-yl]oxy]propyl)amino]acetyl]piperazin-1-yl)pyridine-3-carbonitrile

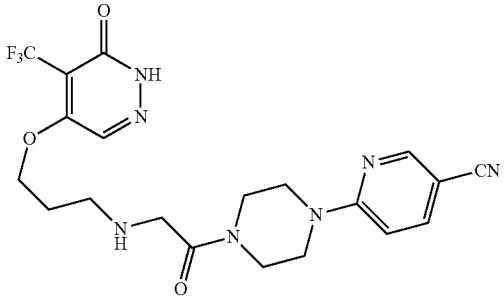 [SMILES: N#Cc1ccc(N2CCN(C(=O)CNCCCOc3cn[nH]c(=O)c3C(F)(F)F)CC2)nc1]

Step 1: 6-(4-[2-[(3-Hydroxypropyl)amino]acetyl]piperazin-1-yl)pyridine-3-carbonitrile A solution of 6-[4-(2-chloroacetyl)piperazin-1-yl]pyridine-3-carbonitrile (1.5 g, 5.67 mmol, 1 equiv), TEA (1.14 g, 11.27 mmol, 1.99 equiv), and 3-aminopropan-1-ol (0.424 g, 5.64 mmol, 1.00 equiv) in EtOH (20 mL) was stirred for 2 h at RT. The resulting mixture was concentrated under reduced pressure and purified by silica gel column chromatography eluting with DCM/MeOH (95/5) to afford 1.7 g (99%) of title compound as a yellow oil. LCMS: [M+H]$^+$ 304.17.

Step 2: Tert-butyl N-[2-[4-(5-cyanopyridin-2-yl)piperazin-1-yl]-2-oxoethyl]-N-(3-hydroxypropyl)carbamate A solution of 6-(4-[2-[(3-hydroxypropyl)amino]acetyl]piperazin-1-yl)pyridine-3-carbonitrile (1.7 g, 5.60 mmol, 1 equiv), TEA (1.1 g, 10.87 mmol, 1.94 equiv), and (Boc)$_2$O (1.5 g, 6.87 mmol, 1.23 equiv) in THF (20 mL) was stirred for 16 h at RT. The resulting mixture was concentrated under reduced pressure. The residue was purified by silica gel column chromatography with DCM/MeOH (98/2) to afford 800 mg (35%) of the title compound as a yellow oil. LCMS: [M+H]$^+$ 404.22.

Step 3: Tert-butyl N-[2-[4-(5-cyanopyridin-2-yl)piperazin-1-yl]-2-oxoethyl]-N-(3-[[6-oxo-5-(trifluoromethyl)-1-[[2-(trimethylsilyl)ethoxy]methyl]-1,6-dihydropyridazin-4-yl]oxy]propyl)carbamate A solution of tert-butyl N-[2-[4-(5-cyanopyridin-2-yl)piperazin-1-yl]-2-oxoethyl]-N-(3-hydroxypropyl)carbamate (800 mg, 1.98 mmol, 1 equiv), Cs$_2$CO$_3$ (1.3 g, 3.99 mmol, 2.01 equiv), and Int-A6 (977 mg, 2.97 mmol, 1.50 equiv) in ACN (20 mL) was stirred for 16 h at RT. The resulting mixture was concentrated under reduced pressure and purified by silica gel column chromatography eluting with EtOAc/petroleum ether (7/3) to afford 280 mg (20%) of title compound as a yellow oil. LCMS: [M+H]$^+$ 696.31.

Step 4: 6-(4-[2-[(3-[[6-Oxo-5-(trifluoromethyl)-1,6-dihydropyridazin-4-yl]oxy]propyl)amino]acetyl]piperazin-1-yl)pyridine-3-carbonitrile A solution of tert-butyl N-[2-[4-(5-cyanopyridin-2-yl)piperazin-1-yl]-2-oxoethyl]-N-(3-[[6-oxo-5-(trifluoromethyl)-1-[[2-(trimethylsilyl)ethoxy]methyl]-1,6-dihydropyridazin-4-yl]oxy]propyl)carbamate (280 mg, 0.40 mmol, 1 equiv), and TFA (1 mL) in DCM (10 mL) was stirred for 2 h at RT. After concentration, the residue was purified by C18 reverse phase chromatography eluting with H$_2$O/ACN followed by further purification by Prep-HPLC to afford the title compound as a white solid (31.7 mg, 17%). LCMS: [M+H]$^+$ 466.2. $^1$H NMR (300 MHz, DMSO-d6) δ 8.51 (d, J=2.3 Hz, 1H), 8.26 (s, 1H), 7.89 (dd, J=9.1, 2.4 Hz, 1H), 6.94 (d, J=9.0 Hz, 1H), 4.45 (t, J=6.1 Hz, 2H), 3.68 (d, J=5.8 Hz, 4H), 3.42 (s, 4H), 3.32 (s, 2H), 2.65 (t, J=6.7 Hz, 2H), 1.87 (q, J=6.4 Hz, 2H).

Example 525: 6-[4-[4-(2-[[6-Oxo-5-(trifluoromethyl)-1,6-dihydropyridazin-4-yl]oxy]ethoxy)butanoyl]piperazin-1-yl]pyridine-3-carbonitrile

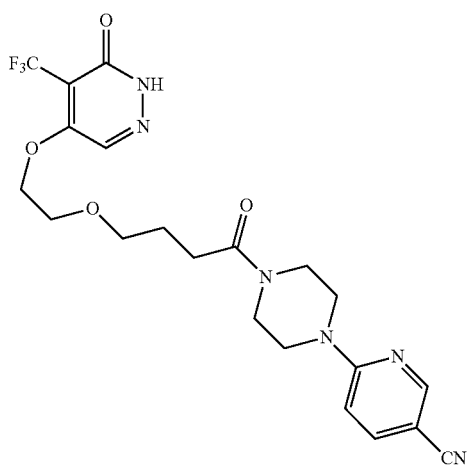 [SMILES: N#Cc1ccc(N2CCN(C(=O)CCCOCCOc3cn[nH]c(=O)c3C(F)(F)F)CC2)nc1]

Step 1: 5-(2-Hydroxyethoxy)-4-(trifluoromethyl)-2-[[2-(trimethylsilyl)ethoxy]methyl]-2,3-dihydropyridazin-3-one A solution of Int-A6 (5 g, 15.21 mmol, 1 equiv), TEA (3.07 g, 0.03 mmol) and ethane-1,2-diol (945 mg, 15.23 mmol, 1.00 equiv) in ACN (50 mL, 1.22 mmol, 0.08 equiv) was stirred for 5 h at 40° C. The solids were filtered and the resulting mixture was concentrated under reduced pressure and purified by C18 reverse phase chromatography eluting with H$_2$O/ACN to afford 600 mg (11%) of title compound as a yellow oil. LCMS: [M+H]$^+$ 355.15.

Step 2: Methyl (2E)-4-(2-[[6-oxo-5-(trifluoromethyl)-1-[[2-(trimethylsilyl)ethoxy]methyl]-1,6-dihydropyridazin-4-yl]oxy]ethoxy)but-2-enoate A solution of 5-(2-hydroxyethoxy)-4-(trifluoromethyl)-2-[[2-(trimethylsilyl)ethoxy]methyl]-2,3-dihydropyridazin-3-one (510 mg, 1.44 mmol, 1 equiv), methyl (2E)-4-bromobut-2-enoate (1288.0 mg, 7.20 mmol, 5.00 equiv), Rockphos (101.2 mg, 0.22 mmol, 0.15 equiv), Cs$_2$CO$_3$ (937.7 mg, 2.88 mmol, 2.0 equiv) and Pd$_2$(allyl)$_2$Cl$_2$ (26.3 mg, 0.07 mmol, 0.05 equiv) in toluene (12 mL) was stirred for 4 h at 80° C. The solids were filtered and the resulting mixture was concentrated under reduced pressure and the residue was purified by silica gel column chromatography eluting with EtOAc/petroleum ether (1:2) to afford 200 mg (31%) of title compound as a yellow oil. LCMS: [M+H]+ 453.00.

Step 3: Methyl 4-(2-[[6-oxo-5-(trifluoromethyl)-1-[[2-(trimethylsilyl)ethoxy]methyl]-1,6-dihydropyridazin-4-yl]oxy]ethoxy)butanoate A solution of methyl (2E)-4-(2-[[6-oxo-5-(trifluoromethyl)-1-[[2-(trimethylsilyl)ethoxy]methyl]-1,6-dihydropyridazin-4-yl]oxy]ethoxy)but-2-enoate (200 mg, 0.44 mmol, 1 equiv) and Pd/C (20 mg, 0.19 mmol, 0.43 equiv) in MeOH (10 mL) under an atmosphere of hydrogen gas was stirred for 1 h at RT. The solids were filtered and the resulting mixture was concentrated under reduced pressure to afford 160 mg (80%) of title compound as a light yellow solid. LCMS: [M+H]+ 455.15.

Step 4: Methyl 4-(2-[[6-oxo-5-(trifluoromethyl)-1,6-dihydropyridazin-4-yl]oxy]ethoxy)butanoate A solution of methyl 4-(2-[[6-oxo-5-(trifluoromethyl)-1-[[2-(trimethylsilyl)ethoxy]methyl]-1,6-dihydropyridazin-4-yl]oxy]ethoxy)butanoate (200 mg, 0.44 mmol, 1.00 equiv) and trifluoroacetic acid (1 mL) in DCM (5 mL) was stirred for 40 min at RT, and then the resulting mixture was concentrated under reduced pressure to afford 170 mg of title compound as a yellow oil. LCMS: [M+H]+ 325.05.

Step 5: 4-(2-[[6-Oxo-5-(trifluoromethyl)-1,6-dihydropyridazin-4-yl]oxy]ethoxy)butanoic Acid To a solution of methyl 4-(2-[[6-oxo-5-(trifluoromethyl)-1,6-dihydropyridazin-4-yl]oxy]ethoxy)butanoate (178 mg, 0.55 mmol, 1.00 equiv) in THF (5 mL) was added LiOH (69 mg, 2.88 mmol, 3.00 equiv) in water (1 mL). The resulting solution was stirred for 1 h at RT. HCl (1M) was added to adjust the pH to 4, and the resulting mixture was concentrated under reduced pressure to afford 114.0 mg (67%) of title compound as a yellow solid. LCMS: [M+H]+ 311.00.

Step 6: 6-[4-[4-(2-[[6-Oxo-5-(trifluoromethyl)-1,6-dihydropyridazin-4-yl]oxy]ethoxy)butanoyl]piperazin-1-yl]pyridine-3-carbonitrile A solution of 4-(2-[[6-oxo-5-(trifluoromethyl)-1,6-dihydropyridazin-4-yl]oxy]ethoxy)butanoic acid (70 mg, 0.23 mmol, 1 equiv), HOBT (45.7 mg, 0.34 mmol, 1.50 equiv), EDCI (64.9 mg, 0.34 mmol, 1.50 equiv), and DIPEA (58.3 mg, 0.45 mmol, 2.00 equiv) in DMF (5 mL), and Int-A4 (51.0 mg, 0.27 mmol, 1.20 equiv) was added and stirred for 20 min at RT. The resulting solution was stirred for another 3 h at 60° C. The reaction was then diluted by the addition of 10 mL of water, extracted with 2×10 mL of EtOAc, washed with 1×10 mL of brine and concentrated under reduced pressure. The crude product was purified by C18 reverse phase column chromatography eluting with H2O/ACN to afford 33.2 mg (31%) of the title compound as a white solid. LCMS: [M+H]+ 481.05. 1H NMR (300 MHz, CD3OD-d4) δ 8.46 (dd, J=2.4, 0.8 Hz, 1H), 8.26 (d, J=0.9 Hz, 1H), 7.79 (dd, J=9.1, 2.4 Hz, 1H), 6.89 (dd, J=9.1, 0.8 Hz, 1H), 4.59-4.56 (m, 2H), 3.82-3.79 (m, 4H), 3.77-3.60 (m, 6H), 3.58 (t, J=6.0 Hz, 2H), 2.50 (dd, J=8.1, 6.9 Hz, 2H), 1.97-1.82 (m, 2H).

Example 526: 6-[4-[3-(2-[Methyl[6-oxo-5-(trifluoromethyl)-1,6-dihydropyridazin-4-yl]amino]ethoxy) propyl]piperazin-1-yl]pyridine-3-carbonitrile

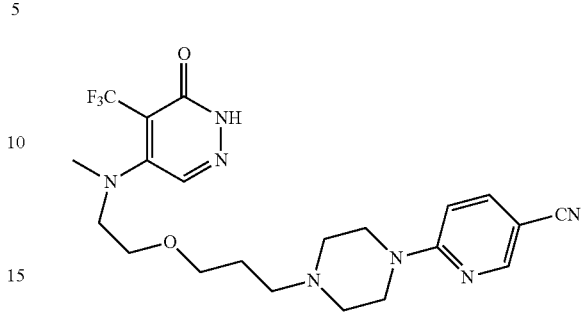

Step 1: 6-[4-(3-Hydroxypropyl)piperazin-1-yl]pyridine-3-carbonitrile

A solution of 3-(piperazin-1-yl)propan-1-ol (1 g, 6.93 mmol, 1.00 equiv), DIPEA (1.79 g, 13.85 mmol, 2.00 equiv), and 6-chloropyridine-3-carbonitrile (958 mg, 6.91 mmol, 1.00 equiv) in NMP (5 mL) was stirred for 1 h at 80° C. The resulting solution was extracted with 3×30 mL of DC and the organic layers combined and concentrated under vacuum. After concentration, the residue was purified by C18 reverse phase chromatography eluting with H2O/ACN to afford 1.43 g (84%) of title compound as a white solid. LCMS: [M+H]+ 247.20.

Step 2: 3-[4-(5-Cyanopyridin-2-yl)piperazin-1-yl] propyl methanesulfonate

A solution of 6-[4-(3-hydroxypropyl)piperazin-1-yl]pyridine-3-carbonitrile (1.1 g, 4.47 mmol, 1.00 equiv), TEA (904 mg, 8.93 mmol, 2.00 equiv), and methanesulfonyl methanesulfonate (1.17 g, 6.72 mmol, 1.50 equiv) in DCM (15 mL) was stirred for 3 h at RT. The resulting mixture was concentrated under vacuum. The residue was applied onto a silica gel column with DCM/methanol (93:7) to afford 1.02 g (70%) of title compound as a yellow solid. LCMS: [M+H]+ 324.25.

Step 3: Tert-butyl N-(2-[3-[4-(5-cyanopyridin-2-yl) piperazin-1-yl]propoxy]ethyl)-N-methylcarbamate To a solution of tert-butyl N-(2-hydroxyethyl)-N-methylcarbamate (2.18 g, 12.44 mmol, 2.00 equiv) in THF (10 mL) was added sodium hydride (250 mg, 6.25 mmol, 2.00 equiv) in several batches at 0° C. The mixture was stirred for 10 min and then 3-[4-(5-cyanopyridin-2-yl)piperazin-1-yl]propyl methanesulfonate (1.02 g, 3.14 mmol, 1.00 equiv) was added. The resulting solution was stirred for 2 h at RT. The reaction was then quenched by the addition of 15 mL of water. The resulting solution was extracted with 3×30 mL of EtOAc and the organic layers combined. After concentration, the residue was applied onto a silica gel column eluting with EtOAc/petroleum ether (7:3) to afford 1.6 g of title compound as a yellow oil. LCMS: [M+H]+ 404.25.

Step 4: 6-(4-[3-[2-(Methylamino)ethoxy]propyl] piperazin-1-yl)pyridine-3-carbonitrile hydrochloride A solution of tert-butyl N-(2-[3-[4-(5-cyanopyridin-2-yl) piperazin-1-yl]propoxy]ethyl)-N-methylcarbamate (500 mg, 1.24 mmol, 1.00 equiv) in HCl/dioxane (5 mL) was was stirred for 30 min at RT. The resulting mixture was concentrated under vacuum to afford 500 mg of title compound as a yellow solid. LCMS: [M+H]+ 304.25.

Step 5: 6-[4-[3-(2-[Methyl[6-oxo-5-(trifluoromethyl)-1-[[2-(trimethylsilyl)ethoxy]methyl]-1,6-dihydropyridazin-4-yl]amino]ethoxy)propyl]piperazin-1-yl]pyridine-3-carbonitrile A solution of 6-(4-[3-[2-(methylamino)ethoxy]propyl] piperazin-1-yl)pyridine-3-carbonitrile hydrochloride (400 mg, 1.18 mmol, 1 equiv), TEA (238.2 mg, 2.35 mmol, 2 equiv), and Int-A6 (387.0 mg, 1.18 mmol, 1 equiv) in EtOH (10 mL) was stirred for 5 h at RT. The resulting mixture was concentrated under reduced pressure and purified by silica gel column chromatography eluting with DCM/MeOH (93/7) to afford 500 mg (71%) of title compound as a yellow oil. LCMS: [M+H]+ 596.29.

Step 6: 6-[4-[3-(2-[Methyl[6-oxo-5-(trifluoromethyl)-1,6-dihydropyridazin-4-yl]amino]ethoxy)propyl]piperazin-1-yl]pyridine-3-carbonitrile A solution of 6-[4-[3-(2-[methyl[6-oxo-5-(trifluoromethyl)-1-[[2-(trimethyl silyl)ethoxy]methyl]-1,6-dihydropyridazin-4-yl]amino]ethoxy)propyl]piperazin-1-yl]pyridine-3-carbonitrile (490 mg, 0.82 mmol, 1 equiv) in DCM (10 mL) and TFA (1 mL) was stirred for 2 h at RT. The reaction was then quenched by the addition of 10 mL of water and the resulting solution was extracted with 3×30 mL of DCM and the organic layers combined and concentrated under reduced pressure. The residue was purified by C18 reverse phase chromatography eluting with H₂O/ACN and further purified by Prep-HPLC to afford the title compound as a white solid (71.7 mg, 19%). LCMS: [M+H]+ 466.21. ¹H NMR (300 MHz, DMSO-d6) δ 8.48 (d, J=2.4 Hz, 1H), 8.02 (s, 1H), 7.85 (dd, J=9.1, 2.4 Hz, 1H), 6.93 (d, J=9.2 Hz, 1H), 3.60 (m, 8H), 3.41 (t, J=6.3 Hz, 2H), 3.05 (d, J=2.5 Hz, 3H), 2.37 (t, J=5.1 Hz, 4H), 2.26 (t, J=7.4 Hz, 2H), 1.62 (s, 2H).

Example 527 Isomer A: 6-(4-[3-[(2S)-2-[[6-Oxo-5-(trifluoromethyl)-1,6-dihydropyridazin-4-yl]amino]-2-(pyridin-4-yl)ethoxy]propanoyl]piperazin-1-yl) pyridine-3-carbonitrile and Example 527 Isomer B: 6-(4-[3-[(2R)-2-[[6-Oxo-5-(trifluoromethyl)-1,6-dihydropyridazin-4-yl]amino]-2-(pyridin-4-yl)ethoxy]propanoyl]piperazin-1-yl) pyridine-3-carbonitrile Example 527

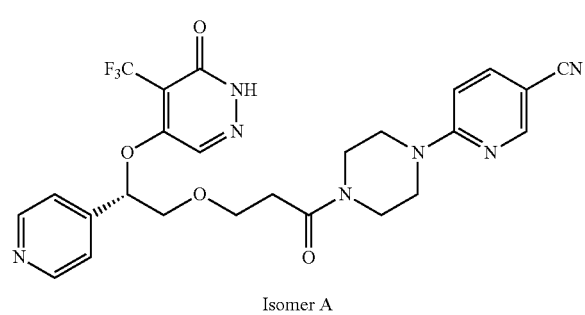

Isomer A

Example 527

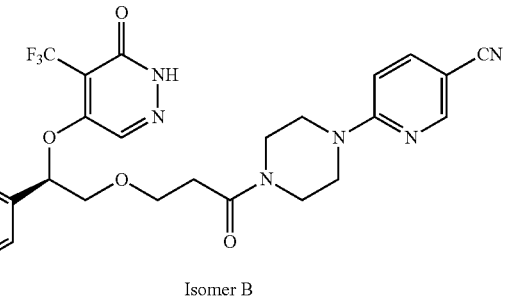

Isomer B

Step 1: 5-[[2-Hydroxy-1-(pyridin-4-yl)ethyl]amino]-4-(trifluoromethyl)-2-[[2-(trimethylsilyl)ethoxy] methyl]-2,3-dihydropyridazin-3-one A solution of 2-amino-2-(pyridin-4-yl)ethan-1-ol (1 g, 7.24 mmol, 1.00 equiv), TEA (2.93 g, 28.96 mmol, 4.00 equiv), Int-A6 (2.85 g, 8.67 mmol, 1.20 equiv) in EtOH (21 mL) was stirred for 1 h at 60° C. The resulting mixture was concentrated under reduced pressure. The residue was purified by silica gel column chromatography eluting with EtOAc/petroleum ether (2/1) to afford 1 g (32%) of title compound as a yellow oil. LCMS: [M+H]+ 431.17.

Step 2: Methyl 3-(2-[[6-oxo-5-(trifluoromethyl)-1-[[2-(trimethylsilyl)ethoxy]methyl]-1,6-dihydropyridazin-4-yl]amino]-2-(pyridin-4-yl)ethoxy)propanoate A solution of 5-[[2-hydroxy-1-(pyridin-4-yl)ethyl] amino]-4-(trifluoromethyl)-2-[[2-(trimethylsilyl)ethoxy] methyl]-2,3-dihydropyridazin-3-one (730 mg, 1.70 mmol, 1.00 equiv), methyl prop-2-enoate (1.46 g, 16.96 mmol, 10.00 equiv), and Cs₂CO₃ (1.1 g, 3.38 mmol, 2.00 equiv) in DMF (15 mL) was stirred for 6 h at RT. The resulting solution was quenched by 50 mL of water and was extracted with EtOAc (3×50 mL), and then the organic layers combined. The solution was dried over anhydrous sodium sulfate and concentrated under reduced pressure. The residue was purified by silica gel column chromatography with EtOAc/petroleum ether (1:2) to afford 400 mg (46%) of title compound as a yellow oil. LCMS: [M+H]+ 517.21.

Step 3: Methyl 3-(2-[[6-oxo-5-(trifluoromethyl)-1,6-dihydropyridazin-4-yl]amino]-2-(pyridin-4-yl) ethoxy)propanoate A solution of methyl 3-(2-[[6-oxo-5-(trifluoromethyl)-1-[[2-(trimethylsilyl)ethoxy]methyl]-1,6-dihydropyridazin-4-yl]amino]-2-(pyridin-4-yl)ethoxy)propanoate (370 mg, 0.72 mmol, 1.00 equiv) in DCM/TFA (18 mL) was stirred 0.5 h at RT. The resulting mixture was concentrated under reduced pressure to afford 278 mg title compound as a yellow oil. LCMS: [M+H]+ 387.13.

Step 4: Methyl 3-(2-[[6-oxo-5-(trifluoromethyl)-1,6-dihydropyridazin-4-yl]amino]-2-(pyridin-4-yl) ethoxy)propanoic Acid A solution of methyl 3-(2-[[6-oxo-5-(trifluoromethyl)-1, 6-dihydropyridazin-4-yl]amino]-2-(pyridin-4-yl)ethoxy)

propanoate (278 mg, 0.72 mmol, 1.00 equiv), LiOH (52 mg, 2.17 mmol, 3.00 equiv), and water (4.5 mL) in MeOH (4.5 mL) was stirred for 6 h at RT. The pH of the solution was adjusted to 5 with HCl. The resulting mixture was concentrated under reduced pressure to afford 260 mg title compound as a crude yellow oil. LCMS: [M+H]+ 373.11.

Step 5: 6-(4-[3-[(2S)-2-[[6-Oxo-5-(trifluoromethyl)-1,6-dihydropyridazin-4-yl]amino]-2-(pyridin-4-yl)ethoxy]propanoyl]piperazin-1-yl)pyridine-3-carbonitrile and 6-(4-[3-[(2R)-2-[[6-oxo-5-(trifluoromethyl)-1,6-dihydropyridazin-4-yl]amino]-2-(pyridin-4-yl)ethoxy]propanoyl]piperazin-1-yl)pyridine-3-carbonitrile A solution of 3-(2-[[6-oxo-5-(trifluoromethyl)-1,6-dihydropyridazin-4-yl]amino]-2-(pyridin-4-yl)ethoxy)propanoic acid (260 mg, 0.70 mmol, 1.00 equiv), HATU (319 mg, 0.84 mmol, 1.20 equiv), DIPEA (0.5 mL, 2.00 equiv), and Int-A4 (130 mg, 0.69 mmol, 1.00 equiv) in DMF (5 mL) was stirred for 1 h at RT. After concentration, the residue was purified by C18 reverse phase chromatography eluting with H₂O/ACN followed by further purification by Prep-HPLC. The enantiomers were separated by Chiral-Prep-HPLC (Repaired Chiral IA, 5 μm, 0.46×10 cm column, eluting with a gradient of MtBE (1% DEA):EtOH=70:30, at a flow rate of 1 mL/min) to afford the title compounds as white solids. The absolute stereochemistry was assigned in analogy to Example 513A, based on the PARP7 potency of the more potent enantiomer and in analogy to the Example 513A X-ray.

Example 527 Isomer A 31.2 mg, 8%, LCMS: [M+H]+ 543.21. ¹H NMR (300 MHz, Methanol-d4) δ 8.56 (d, J=3.3 Hz, 2H), 8.44 (dd, J=2.4, 0.7 Hz, 1H), 7.78 (dd, J=9.1, 2.4 Hz, 1H), 7.58 (s, 1H), 7.47 (dd, J=4.8, 1.5 Hz, 1H), 6.86 (dd, J=9.1, 0.8 Hz, 1H), 5.20 (m, 1H), 4.00-3.73 (m, 6H), 3.71-3.64 (m, 6H), 2.77-2.66 (m, 2H). tR=2.156 min.

Example 527 Isomer B 27.3 mg, 8%, LCMS: [M+H]+ 543.21. tR=6.396 min.

Example 528 Isomer A: (S)-6-(4-(3-(3-Methoxy-2-((6-oxo-5-(trifluoromethyl)-1,6-dihydropyridazin-4-yl)amino)propoxy)propanoyl)piperazin-1-yl)nicotinonitrile and Example 528 Isomer B: (R)-6-(4-(3-(3-Methoxy-2-((6-oxo-5-(trifluoromethyl)-1,6-dihydropyridazin-4-yl)amino)propoxy)propanoyl)piperazin-1-yl)nicotinonitrile Example 528

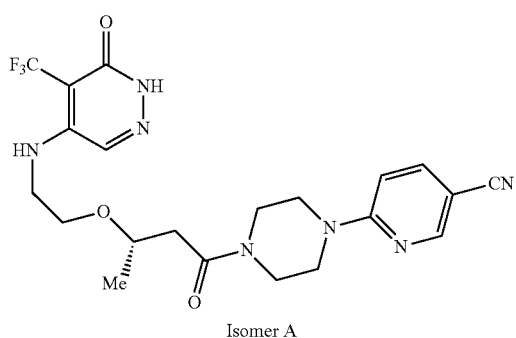

Isomer A

-continued

Example 528

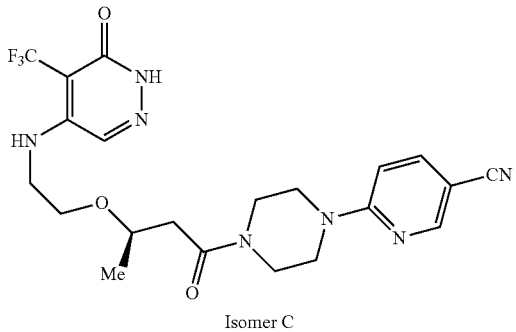

Isomer C

Step 1: Tert-butyl 3-(2-[[(tert-butoxy)carbonyl]amino]ethoxy)butanoate

A solution of tert-butyl N-(2-hydroxyethyl)carbamate (3.2 g, 19.85 mmol, 1.00 equiv), Cs₂CO₃ (1.5 g, 4.60 mmol, 2.00 equiv), (Z)-tert-butylbut-2-enoate (28 g, 196.9 mmol, 10.00 equiv) in ACN (20 mL) was stirred for 1 overnight at 25° C. The resulting mixture was concentrated under reduced pressure and purified by silica gel column chromatography eluting with EtOAc/petroleum ether (1:4) to afford 420 mg (7%) of title compound as a colorless oil. LCMS: [M+H]+ 304.39.

Step 2: 3-(2-Aminoethoxy)butanoic Acid

A solution of tert-butyl 3-(2-[[(tert-butoxy)carbonyl]amino]ethoxy)butanoate (420 mg, 1.38 mmol, 1.00 equiv), a solution of HCl/dioxane (15 mL) in dioxane (15 mL) was stirred overnight at 25° C. The resulting mixture was concentrated under reduced pressure to afford 200 mg (98%) of title compound as a yellow oil. LCMS: [M+H]+ 148.18.

Step 3: 3-(2-[[6-Oxo-5-(trifluoromethyl)-1-[[2-(trimethylsilyl)ethoxy]methyl]-1,6-dihydropyridazin-4-yl]amino]ethoxy)butanoic Acid A solution of Int-A6 (400 mg, 1.22 mmol, 1.00 equiv), TEA (369 mg, 3.65 mmol, 3.00 equiv), EtOH (12 mL), and 3-(2-aminoethoxy)butanoic acid (180 mg, 1.22 mmol, 1.00 equiv) in EtOH (12 mL) was stirred for 40 min at 60° C. The resulting mixture was concentrated under reduced pressure to afford 500 mg (94%) of title compound as a yellow oil. LCMS: [M+H]+ 440.18.

Step 4: 6-[4-[3-(2-[[6-Oxo-5-(trifluoromethyl)-1-[[2-(trimethylsilyl)ethoxy]methyl]-1,6-dihydropyridazin-4-yl]amino]ethoxy)butanoyl]piperazin-1-yl]pyridine-3-carbonitrile A solution of 3-(2-[[6-oxo-5-(trifluoromethyl)-1-[[2-(trimethylsilyl)ethoxy]methyl]-1,6-dihydropyridazin-4-yl]amino]ethoxy)butanoic acid (500 mg, 1.14 mmol, 1.00 equiv), HATU (430 mg, 1.13 mmol, 1.01 equiv), DIPEA (294 mg, 2.27 mmol, 2.00 equiv), Int-A4 (200 mg, 1.06 mmol, 1.00 equiv) in DMF (3 mL) was stirred for 30 min at 25° C. After concentration under reduced pressure, the residue was purified by C18 reverse phase chromatography eluting with H₂O/ACN to afford 300 mg (43%) of title compound as a yellow oil. LCMS: [M+H]+ 610.20.

Step 5: (S)-6-[4-[3-(2-[[6-Oxo-5-(trifluoromethyl)-1,6-dihydropyridazin-4-yl]amino]ethoxy)butanoyl]piperazin-1-yl]pyridine-3-carbonitrile and (R)-6-[4-[3-(2-[[6-oxo-5-(trifluoromethyl)-1,6-dihydropyridazin-4-yl]amino]ethoxy)butanoyl]piperazin-1-yl]pyridine-3-carbonitrile A solution of 6-[4-[3-(2-[[6-oxo-5-(trifluoromethyl)-1-[[2-(trimethylsilyl)ethoxy]methyl]-1,6-dihydropyridazin-4-yl]amino]ethoxy)butanoyl]piperazin-1-yl]pyridine-3-carbonitrile (300 mg, 0.49 mmol, 1.00 equiv), and a solution of TFA/DCM (12 mL) in DCM (10 mL) was stirred for 30 min at 25° C. After concentration, the residue was purified by C18 reverse phase chromatography eluting with $H_2O$/$CH_3CN$. The residue was further purified by Prep-HPLC and Chiral-Prep-HPLC (Chiralpak IA, 5 μm, 2×25 cm column, eluting with a gradient of Hexanes (0.1% DEA):EtOH=50:50, at a flow rate of 1 mL/min) to afford (after arbitrary assignment of stereoisomers) the title compounds as white solids.

Example 528 Isomer A 61.7 mg, 32%, LCMS: [M+H]$^+$ 480.15. $^1$H NMR (400 MHz, DMSO-d$_6$) δ 12.41 (s, 1H), 8.51 (d, J=2.3 Hz, 1H), 7.89-7.86 (dd, J=2.0, 8.8 Hz, 2H), 6.94-6.92 (d, J=9.1 Hz, 1H), 6.83-6.82 (s, 1H), 3.92-3.84 (m, 1H), 3.69-3.51 (m, 12H), 2.67-2.60 (dd, J=15.7, 7.2 Hz, 1H), 2.39-2.35 (dd, J=15.7, 5.1 Hz, 1H), 1.12 (d, J=6.1 Hz, 3H). tR=1.03.

Example 528 Isomer B 57.9 mg, 30%, LCMS: [M+H]$^+$ 480.15. tR=1.04 min.

Example 529: 6-[4-[3-(3-Hydroxy-2-[[6-oxo-5-(trifluoromethyl)-1,6-dihydropyridazin-4-yl]amino]propoxy)propanoyl]piperazin-1-yl]pyridine-3-carbonitrile

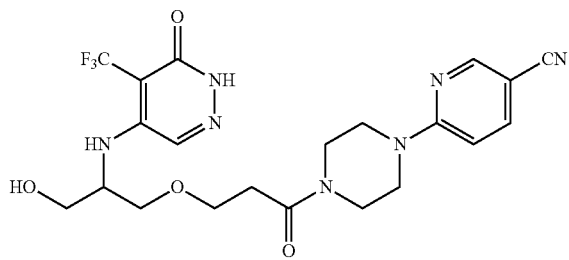 [SMILES: N#Cc1ccc(N2CCN(C(=O)CCOCC(CO)Nc3cn[nH]c(=O)c3C(F)(F)F)CC2)nc1]

Step 1: Tert-butyl 4-(hydroxymethyl)-2,2-dimethyl-1,3-oxazolidine-3-carboxylate

A solution of 3-tert-butyl 4-methyl 2,2-dimethyl-1,3-oxazolidine-3,4-dicarboxylate (5 g, 19.28 mmol, 1.00 equiv) and CaCl$_2$ (4.28 g, 2.00 equiv) in THF (100 mL) and MeOH (20 mL), followed by NaBH$_4$ (1.46 g, 38.59 mmol, 2.00 equiv) was added and stirred for 4 h at RT. The resulting solution was stirred for another 30 min at RT. The reaction was quenched by the addition of 20 mL of water, extracted with 3×100 mL of EtOAc, dried over anhydrous sodium sulfate and concentrated under reduced pressure to afford 4.3 g (96%) of title compound as a yellow oil. LCMS: [M+H]$^+$ 232.15.

Step 2: Tert-butyl 4-[(3-methoxy-3-oxopropoxy)methyl]-2,2-dimethyl-1,3-oxazolidine-3-carboxylate To a solution of tert-butyl 4-(hydroxymethyl)-2,2-dimethyl-1,3-oxazolidine-3-carboxylate (1 g, 4.32 mmol, 1.00 equiv) and Cs$_2$CO$_3$ (2.81 g, 8.62 mmol, 2.00 equiv) in ACN (25 mL) was added methyl prop-2-enoate (1.88 g, 21.84 mmol, 5.00 equiv) dropwise. The reaction mixture was stirred for 20 min at RT and the resulting solution was stirred for another 3 h at RT. The solids were filtered and the residue was concentrated under reduced pressure to afford 1.1 g (80%) of title compound as a yellow oil. LCMS: [M+H]$^+$ 318.18.

Step 3: Methyl 3-((2,2-dimethyloxazolidin-4-yl)methoxy)propanoate

A solution of tert-butyl 4-[(3-methoxy-3-oxopropoxy)methyl]-2,2-dimethyl-1,3-oxazolidine-3-carboxylate (1 g, 3.12 mmol, 1.00 equiv) in HCl/dioxane (10 mL, 4M) was stirred for 40 min at RT, and the residue was then concentrated under reduced pressure to afford 920 mg of title compound as a brown oil. LCMS: [M+H]$^+$ 218.18.

Step 4: Methyl 3-(3-hydroxy-2-[[6-oxo-5-(trifluoromethyl)-1-[[2-(trimethylsilyl)ethoxy]methyl]-1,6-dihydropyridazin-4-yl]amino]propoxy)propanoate A solution of methyl 3-[(2,2-dimethyl-1,3-oxazolidin-4-yl)methoxy]propanoate (1.29 g, 5.94 mmol, 1.00 equiv), DIPEA (1.01 g, 7.81 mmol, 2.00 equiv) and Int-A6 (860 mg, 2.62 mmol, 1.00 equiv) in IPA (10 mL) was stirred for 1 h at 60° C. The resulting mixture was concentrated under reduced pressure and the residue was purified by silica gel column chromatography eluting with EtOAc/petroleum ether (2:3) to afford 570 mg (20%) of title compound as a yellow oil. LCMS: [M+H]$^+$ 470.10.

Step 5: Methyl 3-(3-hydroxy-2-[[6-oxo-5-(trifluoromethyl)-1,6-dihydropyridazin-4-yl]amino]propoxy)propanoate A solution of methyl 3-(3-hydroxy-2-[[6-oxo-5-(trifluoromethyl)-1-[[2-(trimethyl silyl)ethoxy]methyl]-1,6-dihydropyridazin-4-yl]amino]propoxy)propanoate (550 mg, 1.17 mmol, 1.00 equiv) and TFA (2 mL) in DCM (10 mL) was stirred for 40 min at RT, and then concentrated under reduced pressure to afford 500 mg of title compound as a yellow oil. LCMS: [M+H]$^+$ 340.00.

Step 6: 3-(3-Hydroxy-2-[[6-oxo-5-(trifluoromethyl)-1,6-dihydropyridazin-4-yl]amino]propoxy)propanoic Acid A solution of methyl 3-(3-hydroxy-2-[[6-oxo-5-(trifluoromethyl)-1,6-dihydropyridazin-4-yl]amino]propoxy)propanoate (550 mg, 1.62 mmol, 1.00 equiv) and LiOH.H$_2$O (203 mg, 4.84 mmol, 3.00 equiv) in water (3 mL) and THF (15 mL) was stirred for 2 h at RT, and then diluted with 5 mL of water, extracted with 10 mL of EtOAc and the aqueous layers combined. The aqueous layers were adjusted to pH 4 and concentrated under reduced pressure to afford 300 mg (57%, containing some lithium chloride) of crude title compound as a yellow solid. LCMS: [M+H]$^+$ 326.09.

541

Step 7: 6-[4-[3-(3-Hydroxy-2-[[6-oxo-5-(trifluoromethyl)-1,6-dihydropyridazin-4-yl]amino]propoxy)propanoyl]piperazin-1-yl]pyridine-3-carbonitrile A solution of 3-(3-hydroxy-2-[[6-oxo-5-(trifluoromethyl)-1,6-dihydropyridazin-4-yl]amino]propoxy)propanoic acid (105 mg, 0.32 mmol, 1 equiv), HOBT (65.4 mg, 0.48 mmol, 1.5 equiv), EDCI (92.8 mg, 0.48 mmol, 1.5 equiv), DIPEA (83.4 mg, 0.65 mmol, 2.0 equiv) and Int-A4 (72.9 mg, 0.39 mmol, 1.20 equiv) in DMF (10 mL) was stirred for 3 h at RT followed by washing with 1×20 mL of H₂O, and extraction with 3×20 mL of EtOAc. The organic layer was combined, washed with 1×20 mL of brine and concentrated under reduced pressure. The residue was purified by C18 reverse phase chromatography eluting with H₂O/ACN to afford 11.3 mg (7%) of title compound as a white solid. LCMS: [M+H]$^+$ 496.10. $^1$H NMR (300 MHz, DMSO-$d_6$) δ 12.32-12.89 (br, 1H), 8.51 (s, 1H), 7.94-7.84 (m, 2H), 6.94 (d, J=9.0 Hz, 1H), 6.25 (dd, J=8.8, 4.5 Hz, 1H), 5.08 (t, J=5.4 Hz, 1H), 4.06 (s, 1H), 3.73-3.62 (m, 6H), 3.55-3.50 (m, 8H), 2.64-2.51 (t, J=6.4 Hz, 2H).

Example 530 Isomer A: 6-(4-[3-[(2S)-2-[[6-Oxo-5-(trifluoromethyl)-1,6-dihydropyridazin-4-yl]oxy]propoxy]propanoyl]piperazin-1-yl)pyridine-3-carbonitrile and Example 530 Isomer B: 6-(4-[3-[(2R)-2-[[6-Oxo-5-(trifluoromethyl)-1,6-dihydropyridazin-4-yl]oxy]propoxy]propanoyl]piperazin-1-yl)pyridine-3-carbonitrile and Example 530 Isomer C: 6-[4-(3-[[(2S)-1-[[6-Oxo-5-(trifluoromethyl)-1,6-dihydropyridazin-4-yl]oxy]propan-2-yl]oxy]propanoyl)piperazin-1-yl]pyridine-3-carbonitrile and Example 530 Isomer D: 6-[4-(3-[[(2R)-1-[[6-Oxo-5-(trifluoromethyl)-1,6-dihydropyridazin-4-yl]oxy]propan-2-yl]oxy]propanoyl)piperazin-1-yl]pyridine-3-carbonitrile Example 530

Isomer A

542

Example 530

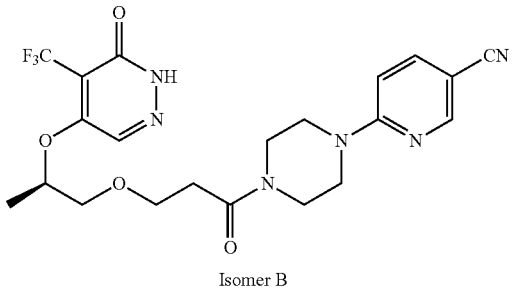

Isomer B

Example 530

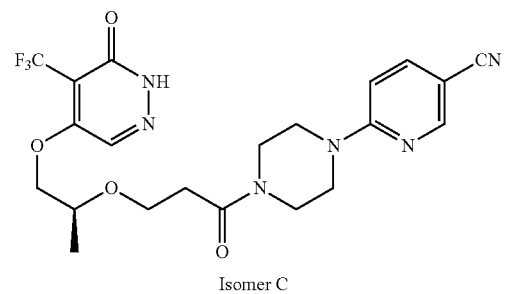

Isomer C

Example 530

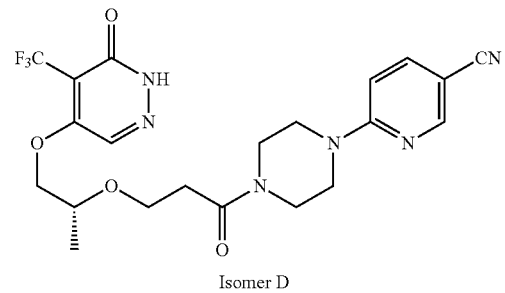

Isomer D

Step 1: Mixture of 6-[4-[3-(2-hydroxypropoxy)propanoyl]piperazin-1-yl]pyridine-3-carbonitrile and 6-(4-(3-(1-hydroxypropan-2-yloxy)propanoyl)piperazin-1-yl)nicotinonitrile A solution of propane-1,2-diol (1.9 g, 25.0 mmol, 5.00 equiv), Cs₂CO₃ (3.25 g, 10.0 mmol, 2.00 equiv), and Int-A25 (1.21 g, 4.99 mmol, 1.00 equiv) in ACN (25 mL) was stirred for 5 h at 60° C. After concentration under reduced pressure, the residue was purified by C18 reverse phase chromatography eluting with H₂O/ACN to afford 1.25 g (76%) of a mixture of the title compounds as white oils. LCMS: [M+H]$^+$ 319.18.

Step 2: Mixture of 6-[4-[3-(2-[[6-oxo-5-(trifluoromethyl)-1-[[2-(trimethylsilyl)ethoxy]methyl]-1,6-dihydropyridazin-4-yl]oxy]propoxy)propanoyl]piperazin-1-yl]pyridine-3-carbonitrile and 6-(4-(3-(1-(6-oxo-5-(trifluoromethyl)-((2-(triethylsilyl)ethoxy)ethyl)-((2-(trimethylsilyl)ethoxy)methyl)-1,6-dihydropyridazin-4-yloxy)propan-2-yloxy)propanoyl)piperazin-1-yl)nicotinonitrile A solution of the mixture of 6-[4-[3-(2-hydroxypropoxy)propanoyl]piperazin-1-yl]pyridine-3-carbonitrile and 6-(4-(3-(1-(6-oxo-5-(trifluoromethyl)-1-((2-(trimethyl silyl)

ethoxy)methyl)-1,6-dihydropyridazin-4-yloxy)propan-2-yloxy)propanoyl)piperazin-1-yl)nicotinonitrile (1.25 g, 3.93 mmol, 1.00 equiv), Cs$_2$CO$_3$ (1.9 g, 5.83 mmol, 1.50 equiv), and Int-A6 (1.55 g, 4.71 mmol, 1.20 equiv) in DMF (20 mL) was stirred for 6 h at 80° C. The solids were filtered and the resulting solution was quenched by water (30 mL) and extracted with EtOAc (3×30 mL) and the organic layers combined. The solution was dried over anhydrous sodium sulfate and concentrated under reduced pressure. The residue was purified by silica gel column chromatography with EtOAc/petroleum ether (1:1) to afford 1.2 g (50%) of the mixture of the title compounds as a yellow oil. LCMS: [M+H]$^+$ 611.26.

Step 3: Synthesis of 6-(4-[3-[(2S)-2-[[6-oxo-5-(trifluoromethyl)-1,6-dihydropyridazin-4-yl]oxy]propoxy]propanoyl]piperazin-1-yl)pyridine-3-carbonitrile, 6-(4-[3-[(2R)-2-[[6-oxo-5-(trifluoromethyl)-1,6-dihydropyridazin-4-yl]oxy]propoxy]propanoyl]piperazin-1-yl)pyridine-3-carbonitrile, 6-[4-(3-[[(2S)-1-[[6-oxo-5-(trifluoromethyl)-1,6-dihydropyridazin-4-yl]oxy]propan-2-yl]oxy]propanoyl)piperazin-1-yl]pyridine-3-carbonitrile and 6-[4-(3-[[(2R)-1-[[6-oxo-5-(trifluoromethyl)-1,6-dihydropyridazin-4-yl]oxy]propan-2-yl]oxy]propanoyl)piperazin-1-yl]pyridine-3-carbonitrile A solution of 6-[4-[3-(2-[[6-oxo-5-(trifluoromethyl)-1,6-dihydropyridazin-4-yl]oxy]propoxy)propanoyl]piperazin-1-yl]pyridine-3-carbonitrile and 6-(4-(3-(1-(6-oxo-5-(trifluoromethyl)-1-((2-(trimethylsilyl)ethoxy)methyl)-1,6-dihydropyridazin-4-yloxy)propan-2-yloxy)propanoyl)piperazin-1-yl)nicotinonitrile mixture (260 mg, 0.54 mmol, 1.00 equiv) in TFA/DCM (30 mL) was stirred for 1 h at RT. After concentration, the residue was purified by C18 reverse phase chromatography eluting with H$_2$O/ACN. The residue was further purified by Prep-HPLC and Chiral-Prep-HPLC to separate out isomers A and B (CHIRALPAK IF-3, 3 rpm, 0.46×5 cm column, eluting with a gradient of hexanes (0.1% DEA):DCM=50:50, at a flow rate of 1 mL/min) and isomers C and D (CHIRALPAK IC-3, 3 μm, 0.46×5 cm column, eluting with hexanes:DCM (3:1) (0.1% DEA):EtOH=50:50, at a flow rate of 1 mL/min) to afford the title compounds as white solids. The two enantiomers isomers A and B absolute stereochemistry was assigned in analogy to Example 513A, based on the PARP7 potency of the more potent enantiomer and in analogy to the Example 513A X-ray. The stereochemistry of isomers C and D was arbitrarily assigned. The position of the methyl group was confirmed by $^1$H-NMR.

Example 530 Isomer A 54.3 mg, 21%, LCMS: [M+H]$^+$ 481.15. $^1$H NMR (300 MHz, Methanol-d$_4$) δ 8.41 (s, 1H), 8.21 (s, 1H), 7.75 (dd, J=9.1, 2.3 Hz, 1H), 6.83 (dd, J=9.1, 0.8 Hz, 1H), 5.14-5.08 (m, 1H), 3.85-3.54 (m, 12H), 2.63 (t, J=5.9 Hz, 2H), 1.34 (d, J=6.3 Hz, 3H). tR=1.453 min.

Example 530 Isomer B 59.7 mg, 23%, LCMS: [M+H]$^+$ 481.10, tR=2.988 min.

Example 530 Isomer C 18.2 mg, 7%, LCMS: [M+H]$^+$ 481.10. $^1$H NMR (300 MHz, Methanol-d$_4$) δ 8.41 (d, J=1.8 Hz, 1H), 8.19 (s, 1H), 7.74 (dd, J=9.1, 2.4 Hz, 1H), 6.83 (dd, J=9.1, 0.8 Hz, 1H), 4.41-4.32 (m, 2H), 3.93-3.85 (m, 2H), 3.84-3.76 (m, 3H), 3.75-3.65 (m, 6H), 2.65 (t, J=6.0 Hz, 2H), 1.24 (d, J=6.4 Hz, 3H). tR=2.331 min.

Example 530 Isomer D 38.2 mg, 15%, LCMS: [M+H]$^+$ 481.15. tR=2.810 min.

Example 531: 6-[4-(3-[[(3R,4S)-4-[[6-Oxo-5-(trifluoromethyl)-1,6-dihydropyridazin-4-yl]oxy]oxolan-3-yl]oxy]propanoyl)piperazin-1-yl]pyridine-3-carbonitrile

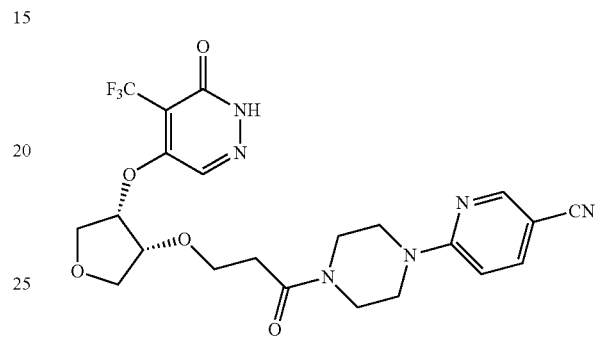

Step 1: 6-(4-(3-((3R,4S)-4-Hydroxy-tetrahydrofuran-3-yloxy)propanoyl)piperazin-1-yl)nicotinonitrile A solution of (3S,4R)-tetrahydrofuran-3,4-diol (1 g, 9.61 mmol, 1 equiv), Cs$_2$CO$_3$ (6.3 g, 19.2 mmol, 2 equiv), 6-[4-(prop-2-enoyl)piperazin-1-yl]pyridine-3-carbonitrile (2.3 g, 9.6 mmol, 1 equiv) in ACN (20 mL) was stirred for 5 h at 60° C. The solvent was concentrated under reduced pressure and the residue was purified by silica gel column chromatography eluting with DCM/MeOH (99/1) to afford 100 mg (3%) of title compound as a white oil. LCMS: [M+H]$^+$ 347.16.

Step 2: 6-(4-(3-((3R,4S)-4-(6-Oxo-5-(trifluoromethyl)-1-((2-(trimethylsilyl)ethoxy)methyl)-1,6-dihydropyridazin-4-yloxy)-tetrahydrofuran-3-yloxy)propanoyl)piperazin-1-yl)nicotinonitrile A solution of 6-(4-(3-((3R,4S)-4-hydroxy-tetrahydrofuran-3-yloxy)propanoyl)piperazin-1-yl)nicotinonitrile (100 mg, 0.28 mmol, 1 equiv), Cs$_2$CO$_3$ (188 mg, 0.56 mmol, 2 equiv), Int-A6 (475 mg, 0.14 mmol, 5 equiv) in ACN (20 mL) was stirred for 1 day at RT. The resulting mixture was concentrated under reduced pressure and the residue was purified by silica gel column chromatography eluting with DCM/MeOH (95/5) to afford 50 mg (28%) of title compound as a white oil. LCMS: [M+H]$^+$ 639.25.

Step 3: 6-[4-(3-[[(3R,4S)-4-[[6-Oxo-5-(trifluoromethyl)-1,6-dihydropyridazin-4-yl]oxy]oxolan-3-yl]oxy]propanoyl)piperazin-1-yl]pyridine-3-carbonitrile A solution of 6-(4-(3-((3R,4S)-4-(6-oxo-5-(trifluoromethyl)-1-((2-(trimethyl silyl)ethoxy)methyl)-1,6-dihydropyridazin-4-yloxy)-tetrahydrofuran-3-yloxy)propanoyl)piperazin-1-yl)nicotinonitrile (50 mg, 0.078 mmol, 1 equiv), TFA (1 mL, 13.5 mmol, 43.0 equiv) in DCM (10 mL) was stirred for 1 h at RT. The solvent was concentrated under reduced pressure and the residue was purified by C18 reverse phase chromatography eluting with H₂O/CH₃CN. Then the residue was further purified by Prep-HPLC to afford the title compound (16.6 mg, 43%) as a white solid. LCMS: [M+H]⁺ 509.2. ¹H NMR (300 MHz, DMSO-d6) δ 8.52 (d, J=2.3 Hz, 1H), 8.29 (s, 1H), 7.89 (dd, J=9.1, 2.3 Hz, 1H), 6.94 (d, J=9.1 Hz, 1H), 5.50 (s, 1H), 4.35 (q, J=6.1 Hz, 1H), 4.03 (dd, J=10.8, 4.7 Hz, 1H), 3.98-3.82 (m, 2H), 3.69-3.52 (m, 7H), 3.50-3.48 (m, 4H), 2.46 (m, 2H).

Example 532 Isomer A: 6-(4-[3-[(2S)-3-Methoxy-2-[[6-oxo-5-(trifluoromethyl)-1,6-dihydropyridazin-4-yl]oxy]propoxy]propanoyl]piperazin-1-yl)pyridine-3-carbonitrile and Example 532 Isomer B: 6-(4-[3-[(2R)-3-Methoxy-2-[[6-oxo-5-(trifluoromethyl)-1,6-dihydropyridazin-4-yl]oxy]propoxy]propanoyl]piperazin-1-yl)pyridine-3-carbonitrile Example 532

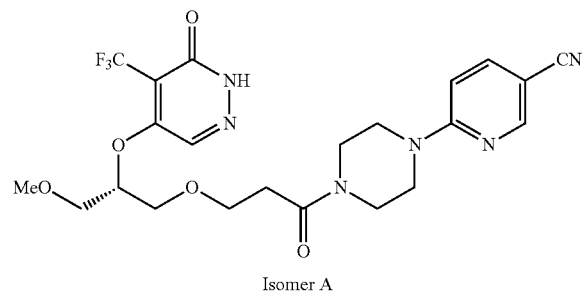

Isomer A

Example 532

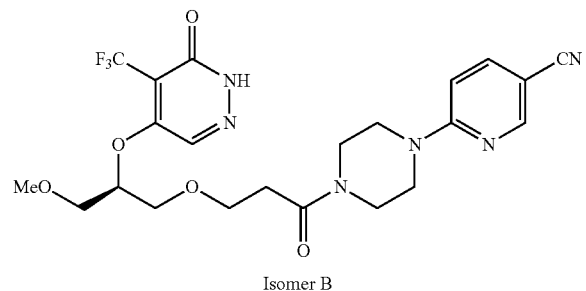

Isomer B

Step 1: 6-[4-[3-(2-Hydroxy-3-methoxypropoxy)propanoyl]piperazin-1-yl]pyridine-3-carbonitrile A solution of Int-A25 (1.3 g, 5.37 mmol, 1.00 equiv), Cs₂CO₃ (3.49 g, 10.71 mmol, 2.00 equiv), and 3-methoxypropane-1,2-diol (2.28 g, 21.48 mmol, 4.00 equiv) in ACN (30 mL) was stirred for 5 h at 70° C. The solvent was concentrated under reduced pressure and the residue was purified by silica gel column chromatography with chloroform/MeOH (1:10) to afford 1.41 g (75%) of title compound as a white oil. LCMS: [M+H]⁺ 349.00.

Step 2: 6-[4-[3-(3-Methoxy-2-[[6-oxo-5-(trifluoromethyl)-1-[[2-(trimethylsilyl)ethoxy]methyl]-1,6-dihydropyridazin-4-yl]oxy]propoxy)propanoyl]piperazin-1-yl]pyridine-3-carbonitrile A solution of 6-[4-[3-(2-hydroxy-3-methoxypropoxy)propanoyl]piperazin-1-yl]pyridine-3-carbonitrile (1.29 g, 3.70 mmol, 1.00 equiv), Cs₂CO₃ (1.8 g, 5.52 mmol, 1.50 equiv), and Int-A6 (1.46 g, 4.44 mmol, 1.20 equiv) in ACN (30 mL) was stirred for 8 h at 80° C. The resulting mixture was concentrated under reduced pressure and the residue was applied onto a silica gel column with EtOAc/petroleum ether (1:1) to afford 1.58 g (67%) of title compound as a brown oil. LCMS: [M+H]⁺ 641.00.

Step 6: 6-(4-[3-[(2S)-3-Methoxy-2-[[6-oxo-5-(trifluoromethyl)-1,6-dihydropyridazin-4-yl]oxy]propoxy]propanoyl]piperazin-1-yl)pyridine-3-carbonitrile and 6-(4-[3-[(2R)-3-methoxy-2-[[6-oxo-5-(trifluoromethyl)-1,6-dihydropyridazin-4-yl]oxy]propoxy]propanoyl]piperazin-1-yl)pyridine-3-carbonitrile A solution of 6-[4-[3-(3-methoxy-2-[[6-oxo-5-(trifluoromethyl)-1,6-dihydropyridazin-4-yl]oxy]propoxy)propanoyl]piperazin-1-yl]pyridine-3-carbonitrile (1.56 g, 3.06 mmol, 1 equiv), TFA (6 mL) in DCM (30 mL) was stirred for 40 min at RT. After concentration under reduced pressure, the residue was further purified by Prep-HPLC and Chiral-Prep-HPLC (CHIRALPAK ID-3, 3 μm, 0.46×10 cm column, eluting with MTBE (0.1% DEA):EtOH=70:30, at a flow rate of 1 mL/min) yielding the title compounds as white solids. The absolute stereochemistry was assigned in analogy to Example 513A, based on the PARP7 potency of the more potent enantiomer and in analogy to the Example 513A X-ray.

Example 532 Isomer A 21.7 mg, LCMS: [M+H]⁺ 511.05. ¹H NMR (300 MHz, Chloroform-d4) δ 11.22 (s, 1H), 8.44 (d, J=2.4 Hz, 1H), 8.06 (s, 1H), 7.68 (dd, J=9.0, 2.4 Hz, 1H), 6.64 (d, J=9.0 Hz, 1H), 4.89-4.82 (m, 1H), 3.94-3.90 (m, 1H), 3.89-3.71 (m, 7H), 3.71-3.64 (m, 2H), 3.64-3.55 (m, 4H), 3.39 (s, 3H), 2.69-2.51 (m, 2H). tR=1.935 min Example 532 Isomer B 40.5 mg, LCMS [M+H]⁺ 511.05. tR=2.359 min.

Example 533: 5-(2-[3-[4-(5-Chloropyrimidin-2-yl)piperazin-1-yl]-3-oxopropoxy]ethoxy)-4-(trifluoromethyl)-2,3-dihydropyridazin-3-one

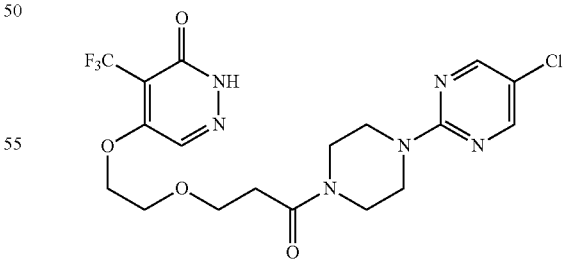

A solution of Int-A11 (50 mg, 0.17 mmol, 1 equiv), DIPEA (65.5 mg, 0.51 mmol, 3 equiv), HOBT (34.2 mg, 0.25 mmol, 1.5 equiv), EDCI (48.5 mg, 0.25 mmol, 1.5 equiv), and Int-A3 (43.7 mg, 0.19 mmol, 1.1 equiv) in DMF (1.5 mL) was stirred for 4 h at RT. After concentration, the residue was purified by C18 reverse phase chromatography eluting with H₂O/CH₃CN and the residue was further purified by Prep-HPLC to afford the title compound as a white solid (21 mg, 26%). LCMS [M+H]⁺ 477.12. ¹H NMR (300 MHz, DMSO-d6) δ 8.45 (s, 2H), 8.25 (s, 1H), 4.53 (s, 2H), 3.74-3.69 (m, 8H), 3.54 (d, J=5.6 Hz, 4H), 2.61 (t, J=6.5 Hz, 2H).

The following examples in Table E5 were similarly prepared according to the method described for Example 533.

TABLE E5

| Example | Name, structure, analytical data | Int. |
|---|---|---|
| Example 534 | 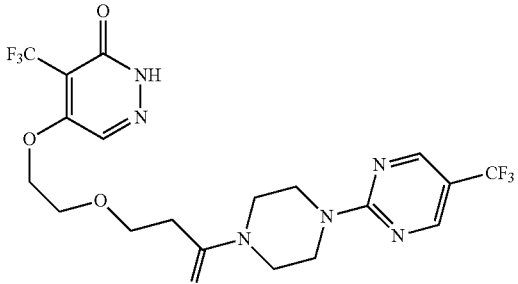<br>5-[2-(3-Oxo-3-[4-[5-(trifluoromethyl)pyrimidin-2-yl]piperazin-1-yl]propoxy)ethoxy]-4-(trifluoromethyl)-2,3-dihydropyridazin-3-one;<br>LCMS: [M + H]⁺ 511.15;<br>¹H NMR (300 MHz, DMSO-d6) δ 13.28 (s, 1H), 8.72 (d, J = 0.6 Hz, 2H), 8.26-8.19 (m, 1H), 4.50 (t, J = 4.4 Hz, 2H), 3.86-3.63 (m, 4H), 3.72 (m, 4H), 3.56 (m, 4H), 2.59 (t, J = 6.5 Hz, 2H). | Int-A2 and Int-A11 |
| Example 535 | 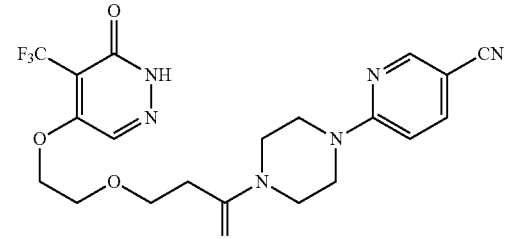<br>5-(2-[3-[4-(5-Chloropyridin-2-yl)piperazin-1-yl]-3-oxopropoxy]ethoxy)-4-(trifluoromethyl)-2,3-dihydropyridazin-3-one;<br>LCMS: [M + H]⁺ 476.12;<br>¹H NMR (300 MHz, DMSO-d6) δ 13.30 (s, 1H), 8.25 (s, 1H), 8.13 (d, J = 2.7 Hz, 1H), 7.62 (dd, J = 9.1, 2.7 Hz, 1H), 6.88 (d, J = 9.0 Hz, 1H), 4.52 (d, J = 4.8 Hz, 2H), 3.71 (t, J = 6.3 Hz, 4H), 3.48 (m, 8H), 2.61 (t, J = 6.5 Hz, 2H). | Int-A5 and Int-A11 |
| Example 536 | 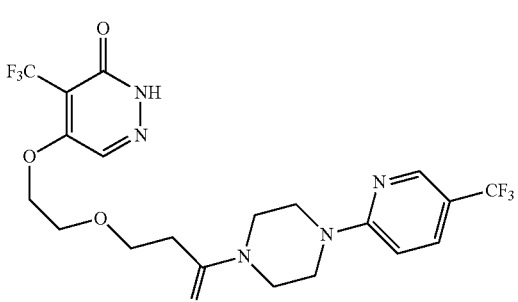<br>5-[2-(3-Oxo-3-[4-[5-(trifluoromethyl)pyridin-2-yl]piperazin-1-yl]propoxy)ethoxy]-4-(trifluoromethyl)-2,3-dihydropyridazin-3-one;<br>LCMS: [M + H]⁺ 510.15;<br>¹H NMR (300 MHz, DMSO-d6) δ 13.27 (s, 1H), 8.40 (s, 1H), 8.22 (s, 1H), 7.80 (dd, J = 9.1, 2.6 Hz, 1H), 6.93 (d, J = 9.2 Hz, 1H), 4.50 (t, J = 4.4 Hz, 2H), 3.67-3.30 (m, 12H), 2.58 (t, J = 6.5 Hz, 2H). | Int-A11 and Int-A18 |

549

Example 537 Isomer A: 6-[4-(3-[[(1S,2S)-1-[[6-Oxo-5-(trifluoromethyl)-1-[[2-(trimethylsilyl)ethoxy]methyl]-1,6-dihydropyridazin-4-yl]amino]-2,3-dihydro-1H-inden-2-yl]oxy]propanoyl)piperazin-1-yl]pyridine-3-carbonitrile and Example 537 Isomer B: 6-[4-(3-[[(1R,2R)-1-[[6-Oxo-5-(trifluoromethyl)-1-[[2-(trimethylsilyl)ethoxy]methyl]-1,6-dihydropyridazin-4-yl]amino]-2,3-dihydro-1H-inden-2-yl]oxy]propanoyl)piperazin-1-yl]pyridine-3-carbonitrile Example 537

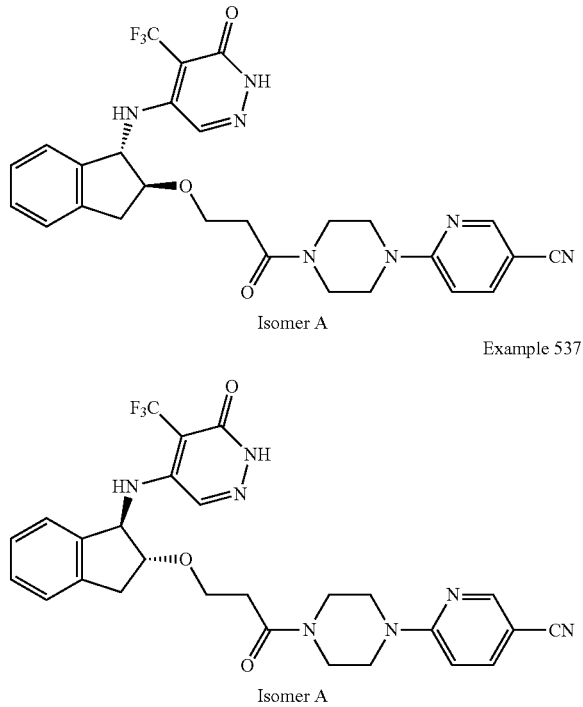

Isomer A

Example 537

Isomer A

Step 1: 5-[(2-Hydroxy-2,3-dihydro-1H-inden-1-yl)amino]-4-(trifluoromethyl)-2-[[2-(trimethylsilyl)ethoxy]methyl]-2,3-dihydropyridazin-3-one A solution of Int-A6 (2.00 equiv), 1-amino-2,3-dihydro-1H-inden-2-ol (226 mg, 1.51 mmol, 1.00 equiv), and TEA (308 mg, 3.04 mmol, 2.00 equiv) in ethanol (12 mL) was stirred for 1 h at 60° C. The resulting solution was concentrated under vacuum and then the residue was applied onto a silica gel column eluting with EtOAc/petroleum ether (35:65) to afford 356 mg (53%) of the title compound as a light yellow solid. LCMS [M+H]$^+$.

Step 2: Methyl 3-[(1-[[6-oxo-5-(trifluoromethyl)-1-[[2-(trimethylsilyl)ethoxy]methyl]-1,6-dihydropyridazin-4-yl]amino]-2,3-dihydro-1H-inden-2-yl)oxy]propanoate A solution of 5-[(2-hydroxy-2,3-dihydro-1H-inden-1-yl)amino]-4-(trifluoromethyl)-2-[[2-(trimethylsilyl)ethoxy]methyl]-2,3-dihydropyridazin-3-one (340 mg, 0.77 mmol, 1.00 equiv), $Cs_2CO_3$ (752 mg, 2.31 mmol, 3.00 equiv) and methyl prop-2-enoate (200 mg, 2.32 mmol, 3.00 equiv) in ACN (10 mL) was stirred for 3 days at RT, and then the resulting solution was diluted with 80 mL of EtOAc, washed with 3×50 mL of $H_2O$, and the organic layers were combined and dried over anhydrous sodium sulfate. After concentration under reduced pressure, the residue was purified by silica gel column chromatography eluting with EtOAc/petroleum ether (35:65) to afford 152 mg (37%) of title compound as a brown oil. LCMS [M+H]$^+$ 528.21.

Step 3: Methyl 3-[(1-[[6-oxo-5-(trifluoromethyl)-1,6-dihydropyridazin-4-yl]amino]-2,3-dihydro-1H-inden-2-yl)oxy]propanoate TFA salt A solution of methyl 3-[(1-[[6-oxo-5-(trifluoromethyl)-1-[[2-(trimethylsilyl)ethoxy]methyl]-1,6-dihydropyridazin-4-yl]amino]-2,3-dihydro-1H-inden-2-yl)oxy]propanoate (147 mg, 0.28 mmol, 1.00 equiv) and TFA (1 mL) in DCM (4 mL) was stirred for 1 h at RT, and then the resulting mixture was concentrated under vacuum to afford 115 mg (83%) of title compound as a light brown oil. LCMS [M+H]$^+$ 398.12.

Step 4: 3-[(1-[[6-Oxo-5-(trifluoromethyl)-1,6-dihydropyridazin-4-yl]amino]-2,3-dihydro-1H-inden-2-yl)oxy]propanoic Acid A solution of methyl 3-[(1-[[6-oxo-5-(trifluoromethyl)-1,6-dihydropyridazin-4-yl]amino]-2,3-dihydro-1H-inden-2-yl)oxy]propanoate TFA salt (115 mg, 0.29 mmol, 1.00 equiv) and $LiOH \cdot H_2O$ (122 mg, 10.00 equiv) in MeOH (2.5 mL) and water (0.5 mL) was stirred for 1 h at 30° C., and then the pH value of the solution was adjusted to 4 with HCl (36.5%), and then the resulting mixture was concentrated under vacuum to afford 110 mg (99%, crude product, mixed with LiCl) of title compound as a light yellow solid. LCMS [M+H]$^+$ 384.11.

Step 5: 6-[4-(3-[[(1S,2S)-1-[[6-Oxo-5-(trifluoromethyl)-1-[[2-(trimethylsilyl)ethoxy]methyl]-1,6-dihydropyridazin-4-yl]amino]-2,3-dihydro-1H-inden-2-yl]oxy]propanoyl)piperazin-1-yl]pyridine-3-carbonitrile and 6-[4-(3-[[(1R,2R)-1-[[6-oxo-5-(trifluoromethyl)-1-[[2-(trimethylsilyl)ethoxy]methyl]-1,6-dihydropyridazin-4-yl]amino]-2,3-dihydro-1H-inden-2-yl]oxy]propanoyl)piperazin-1-yl]pyridine-3-carbonitrile A solution of 3-[(1-[[6-oxo-5-(trifluoromethyl)-1,6-dihydropyridazin-4-yl]amino]-2,3-dihydro-1H-inden-2-yl)oxy]propanoic acid (110 mg, 0.29 mmol, 1.00 equiv), HATU (87 mg, 0.23 mmol, 0.80 equiv), DIPEA (74 mg, 0.57 mmol, 2.00 equiv) and Int-A4 (53.7 mg, 0.29 mmol, 1.00 equiv) in DMF (2.5 mL) was stirred for 2 h at RT, then the residue was purified by C18 reverse phase chromatography eluting with $H_2O/CH_3CN$, and then the residue was further purified by Prep-HPLC and Chiral-Prep-HPLC (CHIRAL Repaired IC, 5 μm, 0.46×10 cm column, eluting with MTBE (0.1% DEA):EtOH=70:30, at a flow rate of 1 mL/min) yielding the title compounds. The absolute stereochemistry was assigned in analogy to Example 513A, based on the PARP7 potency of the more potent enantiomer and in analogy to the Example 513A X-ray.

Example 537 Isomer A 5.9 mg, 19%, LCMS [M+H]$^+$ 554.15. $^1$H NMR (300 MHz, Methanol-d$_4$) δ 8.40 (s, 1H), 8.10 (s, 1H), 7.76 (dd, J=9.1, 2.4 Hz, 1H), 7.28 (d, J=7.2 Hz, 1H), 7.16-7.13 (m, 2H), 7.09 (d, J=7.2 Hz, 1H), 6.77 (d, J=8.7 Hz, 1H), 5.46 (d, J=4.5 Hz, 1H), 4.85 (d, J=6.9 Hz, 1H), 4.47-4.42 (m, 1H), 3.94-3.91 (m, 1H), 3.84-3.67 (m, 4H), 3.53-3.44 (m, 3H), 3.29-3.09 (m, 3H), 2.81-2.73 (m, 1H), 2.60-2.49 (m, 1H). tR=2.583 min.

Example 537 Isomer B 4.9 mg, 16%, LCMS [M+H]$^+$ 554.15. tR=3.468 min.

Example 538 Isomer A: 6-[4-[(3R)-3-(2-[[6-Oxo-5-(trifluoromethyl)-1,6-dihydropyridazin-4-yl]oxy]ethoxy)butanoyl]piperazin-1-yl]pyridine-3-carbonitrile and Example 538 Isomer B: 6-[4-[(3S)-3-(2-[[6-Oxo-5-(trifluoromethyl)-1,6-dihydropyridazin-4-yl]oxy]ethoxy)butanoyl]piperazin-1-yl]pyridine-3-carbonitrile

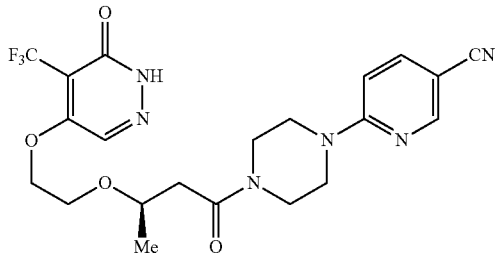

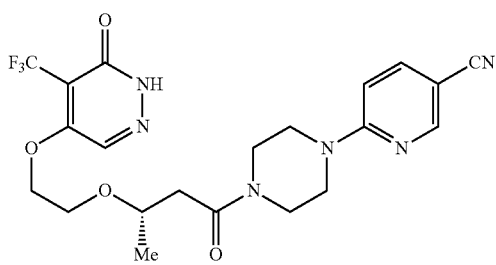 [SMILES: N#Cc1ccc(N2CCN(C(=O)CCOCCOc3cn[nH]c(=O)c3C(F)(F)F)CC2)nc1]

Step 1: 6-[4-[(2E)-But-2-enoyl]piperazin-1-yl]pyridine-3-carbonitrile

A solution of (2E)-but-2-enoyl (2E)-but-2-enoate (1.05 g, 6.81 mmol, 1.30 equiv), TEA (1.5 g, 15.0 mmol, 3.00 equiv), and Int-A4 (1 g, 5.31 mmol, 1.00 equiv) in DCM (20 mL) was stirred for 1 h at RT. The solvent was concentrated under vacuum and the residue was purified by silica gel column chromatography eluting with EtOAc/petroleum ether (1:1) to afford 1.28 g (94%) of title compound as a white solid. LCMS [M+H]$^+$ 257.00.

Step 2: 6-[4-[3-(2-Hydroxyethoxy)butanoyl]piperazin-1-yl]pyridine-3-carbonitrile A solution of 6-[4-[(2E)-but-2-enoyl]piperazin-1-yl]pyridine-3-carbonitrile (1.3 g, 4.93 mmol, 1.00 equiv), Cs$_2$CO$_3$ (3.2 g, 9.82 mmol, 2.00 equiv), and ethane-1,2-diol (1.5 g, 24.2 mmol, 5.00 equiv) in ACN (30 mL) was stirred for 2 days at 75° C. The solvent was concentrated under vacuum and the residue was purified by silica gel column chromatography eluting with chloroform/MeOH (1:10) to afford 1.01 g (64%) of title compound as a white solid. LCMS [M+H]$^+$ 319.

Step 3: 6-[4-[3-(2-[[6-Oxo-5-(trifluoromethyl)-1-[[2-(trimethylsilyl)ethoxy]methyl]-1,6-dihydropyridazin-4-yl]oxy]ethoxy)butanoyl]piperazin-1-yl]pyridine-3-carbonitrile A solution of 6-[4-[3-(2-hydroxyethoxy)butanoyl]piperazin-1-yl]pyridine-3-carbonitrile (818 mg, 2.57 mmol, 1.00 equiv), Cs$_2$CO$_3$ (1 g, 3.07 mmol, 1.20 equiv), and Int-A6 (2.5 g, 7.60 mmol, 3.00 equiv) in DMF (20 mL) was stirred for 5 h at 80° C. The resulting solution was quenched by 50 mL of water and extracted with EtOAc (3×50 mL) and the organic layers combined. The solution was dried over anhydrous sodium sulfate and concentrated under vacuum. The residue was purified by silica gel column chromatography eluting with EtOAc/petroleum ether (1:1) to afford 280 mg (18%) of title compound as a brown oil. LCMS [M+H]$^+$ 611.

Step 4: 6-[4-[(3R)-3-(2-[[6-Oxo-5-(trifluoromethyl)-1,6-dihydropyridazin-4-yl]oxy]ethoxy)butanoyl]piperazin-1-yl]pyridine-3-carbonitrile and 6-[4-[(3S)-3-(2-[[6-oxo-5-(trifluoromethyl)-1,6-dihydropyridazin-4-yl]oxy]ethoxy)butanoyl]piperazin-1-yl]pyridine-3-carbonitrile A solution of 6-[4-[3-(2-[[6-oxo-5-(trifluoromethyl)-1,6-dihydropyridazin-4-yl]oxy]ethoxy)butanoyl]piperazin-1-yl]pyridine-3-carbonitrile (250 mg, 0.52 mmol, 1.00 equiv), TFA (3 mL) in DCM (15 mL) was stirred for 0.5 h at RT. After concentration, the residue was purified by C18 reverse phase chromatography eluting with H$_2$O/ACN. The residue was further purified by Prep-HPLC and Chiral-Prep-HPLC (CHIRAL PAK IG-3, 3 μm, 0.46×5 cm column, eluting with Hexanes (0.1% DEA):DCM=3:1, at a flow rate of 1 mL/min) yielding (after arbitrary assignment of stereochemistry) the title compounds as white solids.

Example 538 Isomer A 14.0 mg, 6%, LCMS [M+H]$^+$ 481.30. $^1$H NMR (300 MHz, Methanol-d$_4$) δ 8.42 (s, 1H), 8.20 (s, 1H), 7.76 (dd, J=9.1, 2.4 Hz, 1H), 6.84 (d, J=9.1, 1H), 4.53 (t, J=4.2 Hz, 2H), 4.09-3.87 (m, 2H), 3.83-3.56 (m, 9H), 2.77 (dd, J=15.1, 8.1 Hz, 1H), 2.45 (dd, J=15.0, 4.4 Hz, 1H), 1.31-1.14 (m, 3H). tR=2.027 min.

Example 538 Isomer B 24.5 mg, 5%, LCMS [M+H]$^+$ 481.25, tR=2.848 min.

553

Example 539 Isomer A: (S)-5-(1-(3-(4-(5-Chloro-pyridin-2-yl)piperazin-1-yl)-3-oxopropoxy)propan-2-yloxy)-4-(trifluoromethyl)pyridazin-3(2H)-one and Example 539 Isomer B: (S)-5-(2-(3-(4-(5-Chloro-pyridin-2-yl)piperazin-1-yl)-3-oxopropoxy) propoxy)-4-(trifluoromethyl)pyridazin-3(2H)-one and Example 539 Isomer C: (R)-5-(2-(3-(4-(5-Chloro-pyridin-2-yl)piperazin-1-yl)-3-oxopropoxy) propoxy)-4-(trifluoromethyl)pyridazin-3(2H)-one and Example 539 Isomer D: (R)-5-(1-(3-(4-(5-Chloro-pyridin-2-yl)piperazin-1-yl)-3-oxopropoxy)propan-2-yloxy)-4-(trifluoromethyl)pyridazin-3(2H)-one

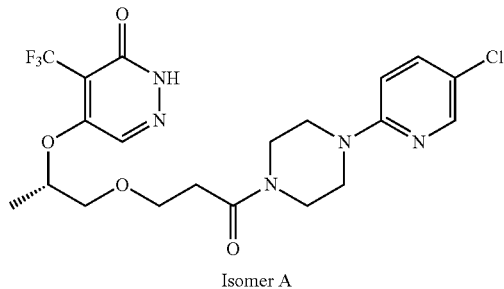

Example 539
Isomer A

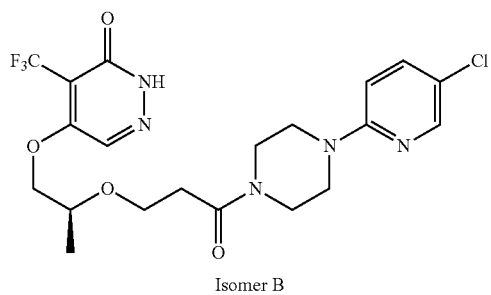

Example 539
Isomer B

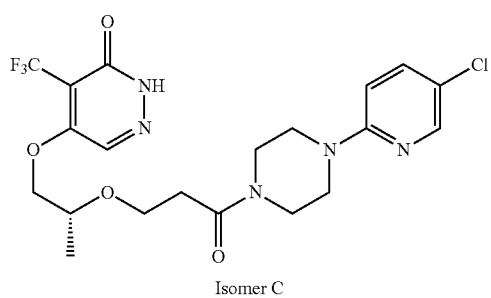

Example 539
Isomer C

554

-continued

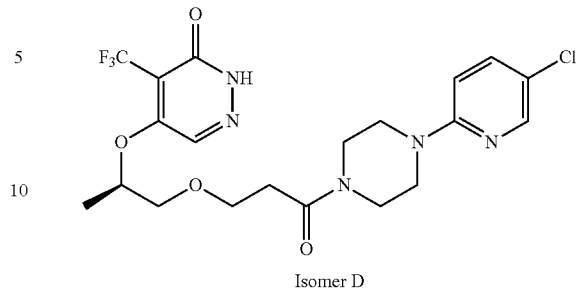

Example 539
Isomer D

Step 1: 1-[4-(5-Chloropyridin-2-yl)piperazin-1-yl]-3-(2-hydroxypropoxy)propan-1-one and 1-(4-(5-chloropyridin-2-yl)piperazin-1-yl)-3-(1-hydroxypropan-2-yloxy)propan-1-one A solution of propane-1,2-diol (1.9 g, 25.3 mmol, 5.00 equiv), $Cs_2CO_3$ (3.32 g, 10.2 mmol, 2.00 equiv), and Int-A22 (1.3 g, 5.1 mmol, 1.00 equiv) in ACN (40 mL) was stirred for 6 h at 75° C. After concentration, the residue was purified by C18 reverse phase chromatography eluting with $H_2O$/ACN to afford 800 mg (48%) of a mixture of title compounds as a yellow oil. LCMS $[M+H]^+$ 328.14.

Step 2: 5-[(1-[3-[4-(5-Chloropyridin-2-yl)piperazin-1-yl]-3-oxopropoxy]propan-2-yl)oxy]-4-(trifluoromethyl)-2-[[2-(trimethylsilyl)ethoxy]methyl]-2,3-dihydropyridazin-3-one and 5-(2-(3-(4-(5-chloropyridin-2-yl)piperazin-1-yl)-3-oxopropoxy)propoxy)-4-(trifluoromethyl)-2-((2-(trimethylsilyl)ethoxy)methyl)pyridazin-3(2H)-one A solution of 1-[4-(5-chloropyrimidin-2-yl)piperazin-1-yl]-3-(2-hydroxypropoxy)propan-1-one and 1-(4-(5-chloropyridin-2-yl)piperazin-1-yl)-3-(1-hydroxypropan-2-yloxy)propan-1-one mixture (800 mg, 2.43 mmol, 1 equiv), $Cs_2CO_3$ (2.38 g, 7.32 mmol, 3 equiv), and Int-A6 (2.38 g, 7.32 mmol, 3.00 equiv) in DMF (30 mL) was stirred 6 h at 80° C. The solids were filtered and the resulting solution was extracted with EtOAc (3×60 mL) and the organic layers combined. The solution was dried over anhydrous sodium sulfate and concentrated under vacuum. The residue was applied onto a silica gel column eluting with EtOAc/petroleum ether (1:1) to afford 1 g (66%) of the title compounds as yellow oil. LCMS $[M+H]^+$ 620.23.

Step 3: (S)-5-(1-(3-(4-(5-Chloropyridin-2-yl)piperazin-1-yl)-3-oxopropoxy)propan-2-yloxy)-4-(trifluoromethyl)pyridazin-3(2H)-one and (S)-5-(2-(3-(4-(5-chloropyridin-2-yl)piperazin-1-yl)-3-oxopropoxy) propoxy)-4-(trifluoromethyl)pyridazin-3(2H)-one and (R)-5-(2-(3-(4-(5-chloropyridin-2-yl)piperazin-1-yl)-3-oxopropoxy)propoxy)-4-(trifluoromethyl) pyridazin-3(2H)-one and (R)-5-(1-(3-(4-(5-chloropyridin-2-yl)piperazin-1-yl)-3-oxopropoxy)propan-2-yloxy)-4-(trifluoromethyl)pyridazin-3 (2H)-one A solution of the mixture of 5-[(1-[3-[4-(5-chloropyridin-2-yl)piperazin-1-yl]-3-oxopropoxy]propan-2-yl)oxy]-4-(trifluoromethyl)-2-[[2-(trimethylsilyl)ethoxy]methyl]-2,3-dihydropyridazin-3-one and 5-(2-[3-[4-(5-chloropyridin-2-yl)piperazin-1-yl]-3-oxopropoxy]propoxy)-4-

(trifluoromethyl)-2-[[2-(trimethylsilyl)ethoxy]methyl]-2,3-dihydropyridazin-3-one mixture (750.0 mg, 1.21 mmol, 1.00 equiv) and TFA (4 mL) in DCM (20 mL) was stirred for 1 h at RT. After concentration, the residue was purified by C18 reverse phase chromatography eluting with H₂O/ACN and the residue was further purified by Prep-HPLC and Chiral-Prep-HPLC (CHIRALPAK ID-3, 3 μm, 0.46×10 cm column, eluting with MtBE (3% iPrNH₂):MeOH=80:20, at a flow rate of 1 mL/min) to afford Isomer A and D and by Prep-HPLC and Chiral-Prep HPLC (CHIRALPAK IG-3, 3 μm, 0.46×10 cm column, eluting with MtBE (3% iPrNH₂):MeOH=80:20, at a flow rate of 1.0 mL/min) to afford Isomer B and C. The absolute stereochemistry of Example 539 Isomer A and D was assigned in analogy to Example 513A, based on the PARP7 potency of the more potent enantiomer and in analogy to the Example 513A X-ray. The absolute stereochemistry of the enantiomers of Isomers B and C was arbitrarily assigned.

Example 539 Isomer A 57.4 mg, 29%, LCMS [M+H]⁺ 490.20. ¹H NMR (300 MHz, Methanol-d₄) δ 8.21 (s, 1H), 8.06 (s, 1H), 7.53 (dd, J=9.1, 2.7 Hz, 1H), 6.79 (d, J=9.1 Hz, 1H), 5.13-5.06 (m, 1H), 3.85-3.78 (m, 1H), 3.75-3.54 (m, 7H), 3.51-3.48 (m, 4H), 2.62 (t, J=6.0 Hz, 2H), 1.34 (d, J=6.3 Hz, 3H). tR=2.064 min Example 539 Isomer B LCMS [M+H]⁺ 490.20, ¹H NMR (300 MHz, Methanol-d₄) δ 8.18 (s, 1H), 8.05 (s, 1H), 7.53 (dd, J=9.1, 2.7 Hz, 1H), 6.79 (d, J=9.1 Hz, 1H), 4.40-4.31 (m, 2H), 3.93-3.79 (m, 3H), 3.78-3.65 (m, 4H), 3.56-3.45 (m, 4H), 2.65 (t, J=6.0 Hz, 2H), 1.24 (d, J=6.4 Hz, 3H). tR=2. 485 min.

Example 539 Isomer C 28.2 mg, 14%, LCMS [M+H]⁺ 490.20, tR=3.126 min.

Example 539 Isomer D 26.7 mg, 14%, LCMS [M+H]⁺ 490.20, tR=3.919 min.

Example 540: 6-(4-[3-[(1-[[6-Oxo-5-(trifluoromethyl)-1,6-dihydropyridazin-4-yl]oxy]-2,3-dihydro-1H-inden-2-yl)oxy]propanoyl]piperazin-1-yl)pyridine-3-carbonitrile

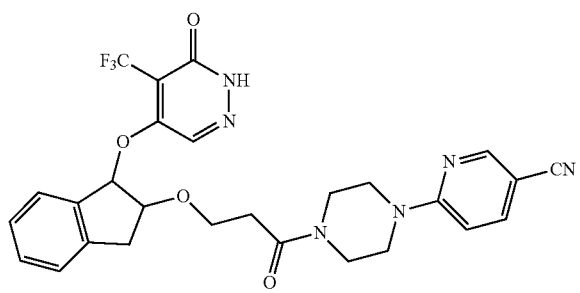 [SMILES: N#Cc1ccc(N2CCN(C(=O)CCOC3Cc4ccccc4C3Oc3cn[nH]c(=O)c3C(F)(F)F)CC2)nc1]

Step 1: 6-(4-[3-[(1-Hydroxy-2,3-dihydro-1H-inden-2-yl)oxy]propanoyl]piperazin-1-yl)pyridine-3-carbonitrile A solution of 2,3-dihydro-1H-indene-1,2-diol (900 mg, 5.99 mmol, 3.00 equiv), Int-A25 (500 mg, 2.06 mmol, 1.00 equiv) and Cs₂CO₃ (4000 mg, 12.28 mmol, 6.00 equiv) in ACN (20 mL) was stirred for 2 h at 35° C., and then the solids were filtered and the resulting solution was concentrated under vacuum, and then the residue was purified by C18 reverse phase chromatography eluting with H₂O/ACN to afford 620 mg (77%) of title compound as a white solid. LCMS [M+H]⁺ 393.19.

Step 2: 6-(4-[3-[(1-[[6-Oxo-5-(trifluoromethyl)-1-[[2-(trimethylsilyl)ethoxy]methyl]-1,6-dihydropyridazin-4-yl]oxy]-2,3-dihydro-1H-inden-2-yl)oxy]propanoyl]piperazin-1-yl)pyridine-3-carbonitrile A solution of 6-(4-[3-[(1-hydroxy-2,3-dihydro-1H-inden-2-yl)oxy]propanoyl]piperazin-1-yl)pyridine-3-carbonitrile (150 mg, 0.38 mmol, 1 equiv), Cs₂CO₃ (249.1 mg, 0.76 mmol, 2 equiv) and Int-A6 (188.5 mg, 0.57 mmol, 1.5 equiv) in ACN (2 mL) was stirred for 1 h at 60° C., and then the solids were filtered out and the resulting solution was concentrated under vacuum. The residue was purified by C18 reverse phase chromatography eluting with H₂O/CH₃CN to afford 180 mg (69%) of title compound as a yellow oil. LCMS [M+H]⁺ 685.27.

Step 3: 6-(4-[3-[(1-[[6-Oxo-5-(trifluoromethyl)-1,6-dihydropyridazin-4-yl]oxy]-2,3-dihydro-1H-inden-2-yl)oxy]propanoyl]piperazin-1-yl)pyridine-3-carbonitrile A solution of 6-(4-[3-[(1-[[6-oxo-5-(trifluoromethyl)-1-[[2-(trimethylsilyl)ethoxy]methyl]-1,6-dihydropyridazin-4-yl]oxy]-2,3-dihydro-1H-inden-2-yl)oxy]propanoyl]piperazin-1-yl)pyridine-3-carbonitrile (80 mg, 0.16 mmol, 1 equiv) and TFA (0.5 mL) in DCM (2 mL) was stirred for 30 min at RT, and then the resulting solution was concentrated under vacuum, and then the residue was purified by C18 reverse phase chromatography eluting with H₂O/ACN. Then the residue was further purified by Prep-HPLC to afford the title compound (3.7 mg, 6%) as a white solid. LCMS [M+H]⁺ 555.15. ¹H NMR (300 MHz, Methanol-d4) δ 8.43 (d, J=1.8 Hz, 1H), 8.39 (s, 1H), 7.78 (dd, J=9.0, 2.4 Hz, 1H), 7.46 (d, J=6.9 Hz, 1H), 7.32-7.26 (m, 3H), 6.83 (dd, J=9.1, 0.9 Hz, 1H), 5.63 (q, J=5.3 Hz, 1H), 5.16 (d, J=4.8 Hz, 1H), 4.08-3.88 (m, 2H), 3.78-3.59 (m, 8H), 3.36 (d, J=16.4 Hz, 1H), 3.28 (dd, J=16.3, 4.9 Hz, 1H), 2.73-2.50 (m, 2H).

Example 541: 6-(4-[3-[(1S,2R)-2-[[6-Oxo-5-(trifluoromethyl)-1,6-dihydropyridazin-4-yl]amino]cyclobutoxy]propanoyl]piperazin-1-yl)pyridine-3-carbonitrile

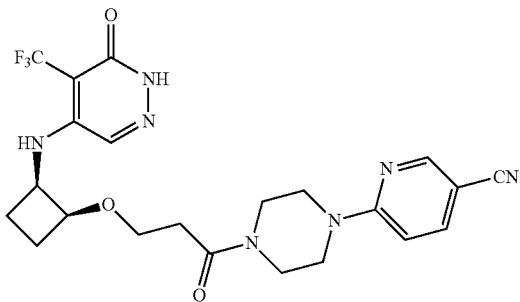 [SMILES: N#Cc1ccc(N2CCN(C(=O)CCO[C@H]3CC[C@H]3Nc3cn[nH]c(=O)c3C(F)(F)F)CC2)nc1]

Step 1: 5-[[(2S)-2-Hydroxycyclobutyl]amino]-4-(trifluoromethyl)-2-[[2-(trimethylsilyl)ethoxy]methyl]-2,3-dihydropyridazin-3-one A solution of Int-A6 (1.3 g, 3.95 mmol, 1 equiv), (1R, 2S)-2-aminocyclobutan-1-ol hydrochloride (0.5 g, 4.05 mmol, 1.02 equiv), TEA (0.8 g, 7.91 mmol, 2.00 equiv) in EtOH (20 mL) was stirred for 1 hr at 60° C. The resulting mixture was concentrated under vacuum. The residue was applied onto a silica gel column eluting with EtOAc/petroleum ether (1/4) to afford 900 mg (60%) of title compound as a yellow oil. LCMS [M+H]$^+$ 380.15.

Step 2: Methyl 3-[(1S,2R)-2-[[6-oxo-5-(trifluoromethyl)-1-[[2-(trimethylsilyl)ethoxy]methyl]-1,6-dihydropyridazin-4-yl]amino]cyclobutoxy]propanoate A solution of 5-[[(2S)-2-hydroxycyclobutyl]amino]-4-(trifluoromethyl)-2-[[2-(trimethylsilyl)ethoxy]methyl]-2,3-dihydropyridazin-3-one (900 mg, 2.37 mmol, 1 equiv), Cs$_2$CO$_3$ (1500 mg, 4.60 mmol, 1.94 equiv), methyl prop-2-enoate (412 mg, 4.79 mmol, 2.02 equiv) in ACN (20 mL) was stirred for 6 hr at RT. The resulting mixture was concentrated under vacuum. The residue was applied onto a silica gel column eluting with EtOAc/petroleum ether (1/4) to afford 750 mg (68%) of title compound as a yellow oil. LCMS [M+H]$^+$ 466.19.

Step 3: Methyl 3-[(1S,2R)-2-[[6-oxo-5-(trifluoromethyl)-1,6-dihydropyridazin-4-yl]amino]cyclobutoxy]propanoate A solution of methyl 3-[(1S,2R)-2-[[6-oxo-5-(trifluoromethyl)-1-[[2-(trimethylsilyl)ethoxy]methyl]-1,6-dihydropyridazin-4-yl]amino]cyclobutoxy]propanoate (750 mg, 1.61 mmol, 1 equiv), TFA (1 mL) in DCM (10 mL) was stirred for 16 h at RT. The resulting mixture was concentrated under vacuum to afford 770 mg crude of title compound as a yellow oil. LCMS [M+H]$^+$ 336.11.

Step 4: Synthesis of 3-[(1S,2R)-2-[[6-oxo-5-(trifluoromethyl)-1,6-dihydropyridazin-4-yl]amino]cyclobutoxy]propanoic Acid A solution of methyl 3-[(1S,2R)-2-[[6-oxo-5-(trifluoromethyl)-1,6-dihydropyridazin-4-yl]amino]cyclobutoxy]propanoate (770 mg, 2.30 mmol, 1 equiv), LiOH.H$_2$O (290 mg, 6.91 mmol, 3.01 equiv) in MeOH (10 mL) was stirred for 3 h at RT. The pH value of the solution was adjusted to 4 with HCl (1 mol/L). The resulting mixture was concentrated under vacuum. After concentration, the residue was purified by C18 reverse phase chromatography eluting with H$_2$O/CH$_3$CN to afford 340 mg (46%) of title compound as a white solid. LCMS [M+H]$^+$ 322.09.

Step 5: 6-(4-[3-[(1S,2R)-2-[[6-Oxo-5-(trifluoromethyl)-1,6-dihydropyridazin-4-yl]amino]cyclobutoxy]propanoyl]piperazin-1-yl)pyridine-3-carbonitrile A solution of 3-[(1S,2R)-2-[[6-oxo-5-(trifluoromethyl)-1,6-dihydropyridazin-4-yl]amino]cyclobutoxy]propanoic acid (300 mg, 0.93 mmol, 1 equiv), HATU (389.5 mg, 1.02 mmol, 1.10 equiv), Int-A4 (193.7 mg, 1.03 mmol, 1.10 equiv), DIPEA (242.3 mg, 1.87 mmol, 2.01 equiv) in DMF (5 mL) was stirred for 1 h at RT. After concentration, the residue was purified by C18 reverse phase chromatography eluting with H$_2$O/CH$_3$CN and then the residue was further purified by Prep-HPLC to afford the title compound (154.5 mg, 34%) as a white solid. LCMS [M+H]$^+$ 492.2. $^1$H NMR (300 MHz, DMSO-d6) δ 12.60 (s, 1H), 8.52 (d, J=2.3 Hz, 1H), 7.89 (dd, J=9.1, 2.4 Hz, 1H), 7.66 (s, 1H), 6.95 (d, J=9.1 Hz, 1H), 6.66-6.57 (m, 1H), 4.37-4.34 (m, 1H), 4.33-4.20 (m, 1H), 3.77-3.55 (m, 10H), 2.64 (t, J=6.3 Hz, 2H), 2.21-2.06 (m, 2H), 2.10-1.93 (m, 1H), 1.80 (m, 1H).

Example 542: 6-(4-[3-[3-(Dimethylamino)-2-[[6-oxo-5-(trifluoromethyl)-1,6-dihydropyridazin-4-yl]oxy]propoxy]propanoyl]piperazin-1-yl)pyridine-3-carbonitrile

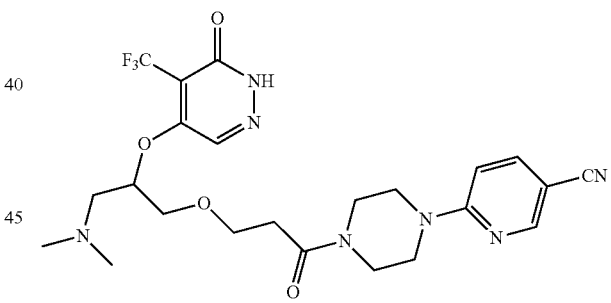

Step 1: Tert-butyl 3-[3-(dimethylamino)-2-hydroxypropoxy]propanoate

A solution of 3-(dimethylamino)propane-1,2-diol (2.38 g, 19.97 mmol, 1 equiv), tert-butyl prop-2-enoate (2.6 g, 0.02 mmol, 1 equiv), and Cs$_2$CO$_3$ (9.8 g, 30.08 mmol, 1.51 equiv) in ACN (30 mL) was stirred for 3 h at RT. The solids were filtered and the resulting mixture was concentrated to afford 400 mg (8%) of title compound as an oil. LCMS [M+H]$^+$ 248.18.

Step 2: 3-[3-(Dimethylamino)-2-[[6-oxo-5-(trifluoromethyl)-1-[[2-(trimethylsilyl)ethoxy]methyl]-1,6-dihydropyridazin-4-yl]oxy]propoxy]propanoate A solution of tert-butyl 3-[3-(dimethylamino)-2-hydroxypropoxy]propanoate (400 mg, 1.62 mmol, 1 equiv), Int-A6

(531.7 mg, 1.62 mmol, 1.00 equiv), Cs₂CO₃ (790.4 mg, 2.43 mmol, 1.5 equiv) in DMF (5 mL) was stirred for 3 h at 100° C. The reaction was then quenched by the addition of 20 mL of water. The resulting solution was extracted with 3×10 mL of EtOA and the residue was purified by silica gel column chromatography with EtOAc/petroleum ether (2/3) to afford 116 mg (13%) of title compound as a yellow oil. LCMS [M+H]⁺ 540.30.

Step 3: 3-[3-(Dimethylamino)-2-[[6-oxo-5-(trifluoromethyl)-1,6-dihydropyridazin-4-yl]oxy]propoxy]propanoic Acid A solution of tert-butyl 3-[3-(dimethylamino)-2-[[6-oxo-5-(trifluoromethyl)-1-[[2-(trimethylsilyl)ethoxy]methyl]-1,6-dihydropyridazin-4-yl]oxy]propoxy]propanoate (116 mg, 0.21 mmol, 1 equiv), 2,2,2-trifluoroacetaldehyde (1 mL) in DCM (4 mL) was stirred for 4 h at RT. The resulting mixture was concentrated to afford 72 mg (95%) of title compound as a solid. LCMS [M+H]⁺ 354.05.

Step 4: 6-(4-[3-[3-(Dimethylamino)-2-[[6-oxo-5-(trifluoromethyl)-1,6-dihydropyridazin-4-yl]oxy]propoxy]propanoyl]piperazin-1-yl)pyridine-3-carbonitrile A solution of 3-[3-(dimethylamino)-2-[[6-oxo-5-(trifluoromethyl)-1,6-dihydropyridazin-4-yl]oxy]propoxy]propanoic acid (72 mg, 0.20 mmol, 1 equiv), Int-A4 (38.4 mg, 0.20 mmol, 1.00 equiv), HATU (77.5 mg, 0.20 mmol, 1 equiv), DIPEA (79.0 mg, 0.61 mmol, 3 equiv) in DMF (3 mL) was stirred for 2 h at RT. The reaction was then quenched by the addition of 10 mL of water. The resulting solution was extracted with 3×5 mL of EtOA. The organic layers were combined and concentrated. The residue was applied onto a silica gel column with DCM/MeOH (6/1) and the crude product was further purified by Prep-HPLC to afford the title compound (7.1 mg, 7%) as a white solid. LCMS [M+H]⁺ 524.10. ¹H NMR (400 MHz, Methanol-d₄) δ 8.43 (s, 1H), 8.25 (s, 1H), 7.78 (dd, J=9.1, 2.4 Hz, 1H), 6.87 (d, J=9.2 Hz, 1H), 5.16 (d, J=7.4 Hz, 1H), 3.88-3.79 (m, 1H), 3.83-3.58 (m, 12H), 2.79-2.60 (m, 3H), 2.57 (dd, J=13.8, 3.5 Hz, 1H), 2.41 (s, 1H), 2.30 (s, 6H).

Example 543 Isomer A (S)-5-(1-(3-(4-(5-Chloropyrimidin-2-yl)piperazin-1-yl)-3-oxopropoxy)propan-2-yloxy)-4-(trifluoromethyl)pyridazin-3 (2H)-one and Example 543 Isomer B (S)-5-(2-(3-(4-(5-Chloropyrimidin-2-yl)piperazin-1-yl)-3-oxopropoxy)propoxy)-4-(trifluoromethyl)pyridazin-3 (2H)-one and Example 543 Isomer C (R)-5-(2-(3-(4-(5-chloropyrimidin-2-yl)piperazin-1-yl)-3-oxopropoxy)propoxy)-4-(trifluoromethyl)pyridazin-3 (2H)-one and Example 543 Isomer D (R)-5-(1-(3-(4-(5-chloropyrimidin-2-yl)piperazin-1-yl)-3-oxopropoxy)propan-2-yloxy)-4-(trifluoromethyl)pyridazin-3 (2H)-one

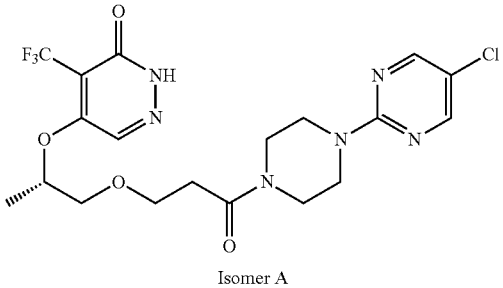

Example 543

Isomer A

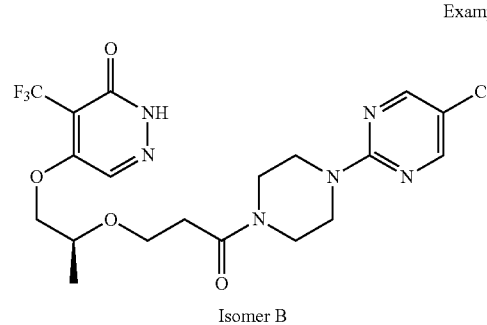

Example 543

Isomer B

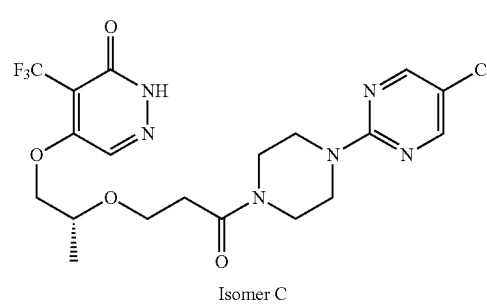

Example 543

Isomer C

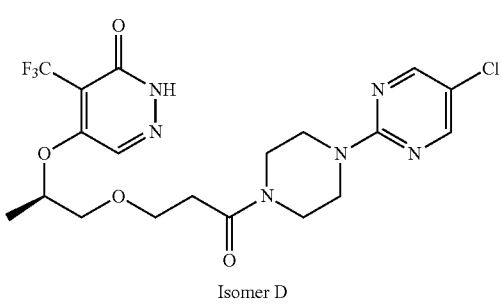

Example 543

Isomer D

Step 2: 1-[4-(5-Chloropyrimidin-2-yl)piperazin-1-yl]-3-(2-hydroxypropoxy)propan-1-one and 1-(4-(5-chloropyrimidin-2-yl)piperazin-1-yl)-3-(1-hydroxypropan-2-yloxy)propan-1-one A solution of Int-A23 (1.5 g, 5.94 mmol, 1 equiv), Cs₂CO₃ (3.9 g, 11.87 mmol, 2 equiv), and propane-1,2-diol (2.3 g, 30.21 mmol, 5.09 equiv) in ACN (40 mL) was stirred for 4 h at 75° C. After concentration, the residue was purified by C18 reverse phase chromatography eluting with H₂O/CH₃CN to afford 1.4 g (72%) of the mixture of the title compounds as white solids. LCMS [M+H]⁺ 329.12.

Step 3: 5-[(1-[3-[4-(5-Chloropyrimidin-2-yl)piperazin-1-yl]-3-oxopropoxy]propan-2-yl)oxy]-4-(trifluoromethyl)-2-[[2-(trimethylsilyl)ethoxy]methyl]-2,3-dihydropyridazin-3-one and 5-(2-(3-(4-(5-chloropyrimidin-2-yl)piperazin-1-yl)-3-oxopropoxy)propoxy)-4-(trifluoromethyl)-2-((2-(trimethylsilyl)ethoxy)methyl)pyridazin-3(2H)-one A solution of the mixture of 1-[4-(5-chloropyrimidin-2-yl)piperazin-1-yl]-3-(2-hydroxypropoxy)propan-1-one and 1-(4-(5-chloropyrimidin-2-yl)piperazin-1-yl)-3-(1-hydroxypropan-2-yloxy)propan-1-one (1.4 g, 4.26 mmol, 1 equiv), Cs$_2$CO$_3$ (4.2 g, 12.77 mmol, 3 equiv), and Int-A6 (4.2 g, 12.77 mmol, 3.00 equiv) in DMF (30 mL) was stirred for 4 h at 80° C. The solids were filtered out and the resulting solution was quenched by 50 mL of water and extracted with EtOAc (3×30 mL). The organic layers were combined and the solution was dried over anhydrous sodium sulfate and concentrated under vacuum. The residue was applied onto a silica gel column eluting with EtOAc/petroleum ether (1:1) to afford 1.07 g (40%) of the mixture of the title compounds as a yellow oil. LCMS [M+H]$^+$ 621.22.

Step 4: Mixture of (S)-5-(1-(3-(4-(5-chloropyrimidin-2-yl)piperazin-1-yl)-3-oxopropoxy)propan-2-yloxy)-4-(trifluoromethyl)pyridazin-3(2H)-one, (S)-5-(2-(3-(4-(5-chloropyrimidin-2-yl)piperazin-1-yl)-3-oxopropoxy)propoxy)-4-(trifluoromethyl)pyridazin-3(2H)-one, (R)-5-(2-(3-(4-(5-chloropyrimidin-2-yl)piperazin-1-yl)-3-oxopropoxy)propoxy)-4-(trifluoromethyl)pyridazin-3(2H)-one and (R)-5-(1-(3-(4-(5-chloropyrimidin-2-yl)piperazin-1-yl)-3-oxopropoxy)propan-2-yloxy)-4-(trifluoromethyl)pyridazin-3(2H)-one A solution of the mixture of 5-(2-[3-[4-(5-chloropyrimidin-2-yl)piperazin-1-yl]-3-oxopropoxy]propoxy)-4-(trifluoromethyl)-2-[[2-(trimethylsilyl)ethoxy]methyl]-2,3-dihydropyridazin-3-one and 5-[(1-[3-[4-(5-chloropyrimidin-2-yl)piperazin-1-yl]-3-oxopropoxy]propan-2-yl)oxy]-4-(trifluoromethyl)-2-[[2-(trimethylsilyl)ethoxy]methyl]-2,3-dihydropyridazin-3-one (1 g, 1.60 mmol, 1.00 equiv), TFA (4 mL) in DCM (20 mL) was stirred for 1 h at RT. After concentration, the residue was purified by C18 reverse phase chromatography eluting with H$_2$O/ACN. The residue was further purified by Prep-HPLC and Chiral-Prep-HPLC (CHIRALPAK ID-3, 3 μm, 0.46×10 cm column, eluting with MtBE (0.01M NH$_3$):MeOH=80:20, at a flow rate of 1 mL/min) to afford the title compounds as white solids. The stereochemistry of isomer A and isomer D was assigned in analogy to Example 513A, based on the PARP7 potency of the more potent enantiomer and in analogy to the Example 513A X-ray.

The absolute stereochemistry for isomer B and C was arbitrarily assigned. (The position of the methyl group was confirmed by $^1$H-NMR).

Example 543 Isomer A 102.8 mg, 26%, LCMS [M+H]$^+$ 491.1 $^1$H NMR (300 MHz, Methanol-d4) δ 8.31 (s, 2H), 8.21 (s, 1H), 5.11 (t, J=6.7 Hz, 1H), 3.88-3.53 (m, 12H), 2.63 (t, J=5.8 Hz, 2H), 1.34 (d, J=6.3 Hz, 3H), tR=2.283 min.

Example 543 Isomer B 95.9 mg, 24%, LCMS [M+H]$^+$ 491.1. $^1$H NMR (300 MHz, Methanol-d4) δ 8.30 (s, 2H), 8.19 (s, 1H), 4.43-4.29 (m, 2H), 3.93-3.86 (m, 2H), 3.86-3.74 (m, 5H), 3.93-3.86 (m, 4H), 2.65 (t, J=6.0 Hz, 2H), 1.24 (d, J=6.4 Hz, 3H). tR=2.890 min.

Example 543 Isomer C 87.6 mg, 21%, LCMS [M+H]$^+$ 491.1, tR=3.584 min.

Example 543 Isomer D 91.8 mg, 23%, LCMS [M+H]$^+$ 491.1, tR=6.313 min.

Example 544 Isomer A: (S)-5-(1-(3-Oxo-3-(4-(5-(trifluoromethyl)pyrimidin-2-yl)piperazin-1-yl)propoxy)propan-2-yloxy)-4-(trifluoromethyl)pyridazin-3(2H)-one and Example 544 Isomer B: (R)-5-(1-(3-Oxo-3-(4-(5-(trifluoromethyl)pyrimidin-2-yl)piperazin-1-yl)propoxy)propan-2-yloxy)-4-(trifluoromethyl)pyridazin-3(2H)-one and Example 544 Isomer C: (S)-5-(2-(3-Oxo-3-(4-(5-(trifluoromethyl)pyrimidin-2-yl)piperazin-1-yl)propoxy)propoxy)-4-(trifluoromethyl)pyridazin-3(2H)-one and Example 544 Isomer D: (R)-5-(2-(3-Oxo-3-(4-(5-(trifluoromethyl)pyrimidin-2-yl)piperazin-1-yl)propoxy)propoxy)-4-(trifluoromethyl)pyridazin-3(2H)-one

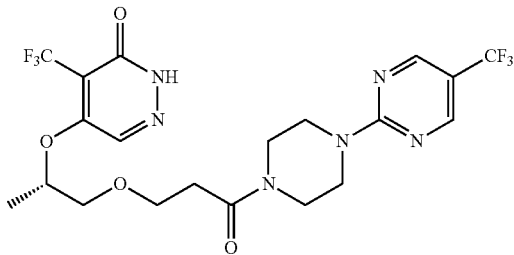

Example 544

Isomer A

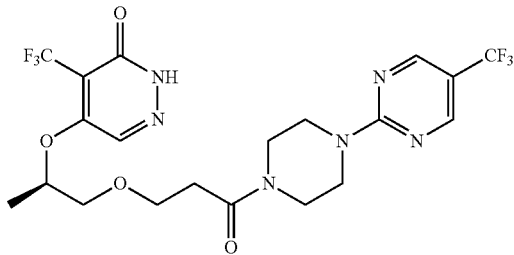

Example544

Isomer B

Example 544

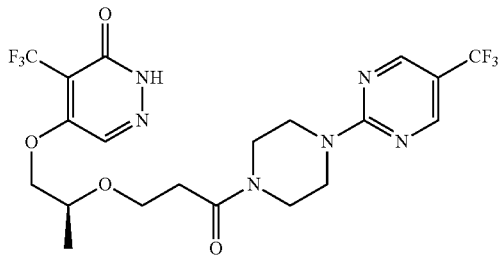

Isomer C

Example 544

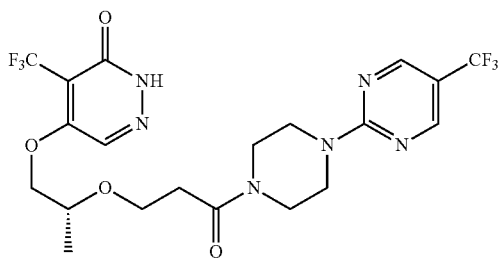

Isomer D

Step 1: Mixture of 3-(2-hydroxypropoxy)-1-(4-(5-(trifluoromethyl)pyrimidin-2-yl)piperazin-1-yl)propan-1-one and 3-(1-hydroxypropan-2-yloxy)-1-(4-(5-(trifluoromethyl)pyrimidin-2-yl)piperazin-1-yl)propan-1-one A solution of Int-A21 (1 g, 3.49 mmol, 1.00 equiv), propane-1,2-diol (1.33 g, 17.48 mmol, 5.00 equiv), and $Cs_2CO_3$ (2.3 g, 7.06 mmol, 2.00 equiv) in ACN (30 mL) was stirred for 8 h at 75° C. After concentration, the residue was purified by C18 reverse phase chromatography eluting with $H_2O$/ACN to afford 930 mg (73%) of the mixture of the title compounds mixture as a white solid. LCMS [M+H]+ 363.17.

Step 2: Mixture of 5-(1-(3-oxo-3-(4-(5-(trifluoromethyl)pyrimidin-2-yl)piperazin-1-yl)propoxy)propan-2-yloxy)-4-(trifluoromethyl)-2-((2-(trimethylsilyl)ethoxy)methyl)pyridazin-3(2H)-one and 5-(2-(3-oxo-3-(4-(5-(trifluoromethyl)pyrimidin-2-yl)piperazin-1-yl)propoxy)propoxy)-4-(trifluoromethyl)-2-((2-(trimethylsilyl)ethoxy)methyl)pyridazin-3(2H)-one A solution of the mixture of 3-(2-hydroxypropoxy)-1-(4-(5-(trifluoromethyl)pyrimidin-2-yl)piperazin-1-yl)propan-1-one and 3-(1-hydroxypropan-2-yloxy)-1-(4-(5-(trifluoromethyl)pyrimidin-2-yl)piperazin-1-yl)propan-1-one mixture (1.3 g, 3.59 mmol, 1.00 equiv), Int-A6 (1.4 g, 4.26 mmol, 1.20 equiv), and $Cs_2CO_3$ (3.5 g, 10.74 mmol, 3.00 equiv) in DMF (15 mL) was stirred for 6 h at 80° C. The solids were filtered and the resulting solution was quenched by water (50 mL) and extracted with EtOAc (3×60 mL) and the organic layers combined. The solution was dried over anhydrous sodium sulfate and concentrated under vacuum. The residue was applied onto a silica gel column eluting with EtOAc/hexane (1:1) to afford 1.6 g (68%) of the title compounds as yellow oil. LCMS [M+H]+ 655.25.

Step 3: (S)-5-(1-(3-oxo-3-(4-(5-(trifluoromethyl)pyrimidin-2-yl)piperazin-1-yl)propoxy)propan-2-yloxy)-4-(trifluoromethyl)pyridazin-3(2H)-one, (R)-5-(1-(3-oxo-3-(4-(5-(trifluoromethyl)pyrimidin-2-yl)piperazin-1-yl)propoxy)propan-2-yloxy)-4-(trifluoromethyl)pyridazin-3(2H)-one, (S)-5-(2-(3-oxo-3-(4-(5-(trifluoromethyl)pyrimidin-2-yl)piperazin-1 yl)propoxy)propoxy)-4-(trifluoromethyl)pyridazin-3(2H)-one and (R)-5-(2-(3-oxo-3-(4-(5-(trifluoromethyl)pyrimidin-2-yl)piperazin-1-yl)propoxy)propoxy)-4-(trifluoromethyl)pyridazin-3(2H)-one A solution of 5-(1-(3-oxo-3-(4-(5-(trifluoromethyl)pyrimidin-2-yl)piperazin-1-yl)propoxy)propan-2-yloxy)-4-(trifluoromethyl)-2-((2-(trimethylsilyl)ethoxy)methyl)pyridazin-3(2H)-one and 5-(2-(3-oxo-3-(4-(5-(trifluoromethyl)pyrimidin-2-yl)piperazin-1-yl)propoxy)propoxy)-4-(trifluoromethyl)-2-((2-(trimethylsilyl)ethoxy)methyl)pyridazin-3 (2H)-one mixture (1.54 g, 2.35 mmol, 1 equiv), and TFA (2 mL) in DCM (10 mL) was stirred for 0.5 h at RT. After concentration, the residue was purified by C18 reverse phase chromatography eluting with $H_2O$/ACN. The residue was further purified by Prep-HPLC and Chiral-Prep-HPLC (Lux Amylose-1, 3 μm, 4.6×100 mm column, eluting with EtOH (0.1% DEA), at a flow rate of 4 mL/min). The absolute stereochemistry of isomer A and B was assigned in analogy to Example 513A, based on the PARP7 potency of the more potent enantiomer and in analogy to the Example 513A X-ray. The absolute stereochemistry for isomer C and isomer D was arbitrarily assigned. (The position of methyl group was confirmed by $^1$H-NMR). Isomers A-D were isolated as white solids.

Example 544 Isomer A 102.5 mg, 8%, LCMS [M+H]+ 525.25. $^1$H NMR (300 MHz, Methanol-$d_4$) δ 8.61 (s, 2H), 8.23 (s, 1H), 5.16-5.09 (m, 1H), 3.99-3.78 (m, 4H), 3.81-3.68 (m, 1H), 3.67 (m, 1H), 3.65-3.56 (m, 6H), 2.71-2.61 (t, J=5.7 Hz, 2H), 1.37 (d, J=6.3 Hz, 3H). tR=1.369 min., Example 544 Isomer B 56.3 mg, 5%, LCMS [M+H]+ 525.20, tR=1.636 min.

Example 544 Isomer C 39 mg, 3%, LCMS [M+H]+ 525.25, $^1$H NMR (300 MHz, Methanol-$d_4$) δ 8.60 (s, 2H), 8.22 (s, 1H), 4.47-4.32 (m, 2H), 4.00-3.75 (m, 7H), 3.70-3.68 (m, 4H), 2.68 (t, J=6.0 Hz, 2H), 1.27 (d, J=6.4 Hz, 3H). tR=2.835 min.

Example 544 Isomer D 27.2 mg, 2%, LCMS [M+H]+ 525.25, tR=2.039 min.

Example 545 Isomer A: 5-[[(2S,5S)-5-(2-Oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one and Example 545 Isomer B: 5-[[(2S,5R)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one and Example 545 Isomer C: 5-[[(2R,5R)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one and Example 545 Isomer D: 5-[[(2R,5S)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one Example 545

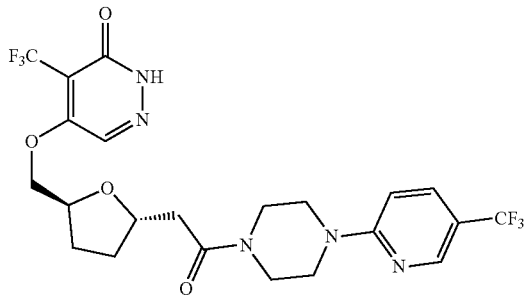

Isomer A

Example 545

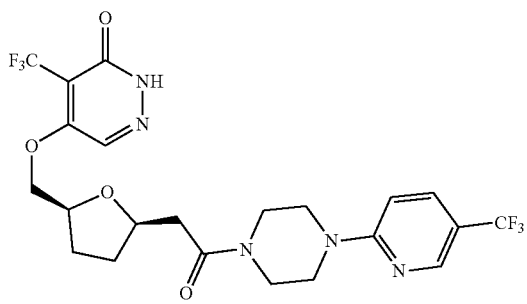

Isomer B

Example 545

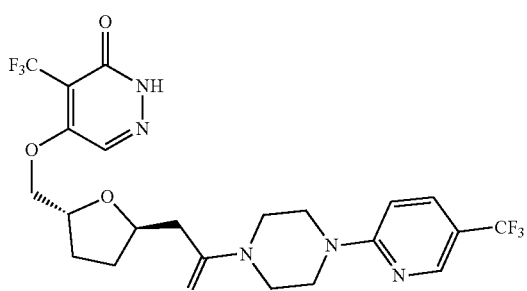

Isomer C

-continued

Example 545

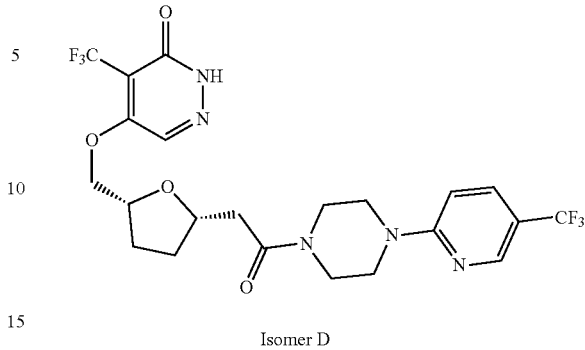

Isomer D

Step 1: 5-[[5-(2-Oxo-2-[4-[5-(trifluoromethyl)pyridin-2-yl]piperazin-1-yl]ethyl)oxolan-2-yl]methoxy]-4-(trifluoromethyl)-2-[[2-(trimethylsilyl)ethoxy]methyl]-2,3-dihydropyridazin-3-one A solution of Int-A17 (700 mg, 1.87 mmol, 1 equiv), Int-A6 (1849.2 mg, 5.62 mmol, 3.00 equiv), and $Cs_2CO_3$ (1.8 g, 5.62 mmol, 3 equiv) in ACN (10 mL) was stirred for 2 h at 80° C. The solids were filtered and the resulting mixture was concentrated under reduced pressure. The residue was purified by silica gel column chromatography eluting with EtOAc/petroleum ether (99/1) to afford 788 mg (63%) of title compound as a yellow oil. LCMS $[M+H]^+$ 666.10.

Step 2: 5-[[(2S,5S)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one, 5-[[(2S,5R)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one, 5-[[(2R,5R)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one and 5-[[(2R,5S)-5-(2-oxo-2-[4-[5-(trifluoromethyl)pyridin-2-yl]piperazin-1-yl]ethyl)oxolan-2-yl]methoxy]-4-(trifluoromethyl)-2,3-dihydropyridazin-3-one A solution 5-[[5-(2-oxo-2-[4-[5-(trifluoromethyl)pyridin-2-yl]piperazin-1-yl]ethyl)oxolan-2-yl]methoxy]-4-(trifluoromethyl)-2-[[2-(trimethylsilyl)ethoxy]methyl]-2,3-dihydropyridazin-3-one (888 mg, 1.33 mmol, 1 equiv) and TFA (2 mL) in DCM (10 mL) was stirred for 3 h at RT. After concentration, the residue was purified by C18 reverse phase chromatography eluting with $H_2O$/ACN. The residue was then further purified by Prep-HPLC and Chiral-Prep-HPLC (CHIRALPAK IA-3, 3 μm, 0.46×5 cm column, eluting with hexane:DCM (5:1)/(0.1% TEA):EtOH=85:15, at a flow rate of 1 mL/min) yielding (after arbitrary assignment of stereochemistry) the title compounds.

Example 545 Isomer A 18.4 mg, 3%, LCMS $[M+H]^+$ 536.30. $^1H$ NMR (300 MHz, Methanol-$d_4$) δ 8.37 (d, J=2.3 Hz, 1H), 8.25 (d, J=0.9 Hz, 1H), 7.75 (dd, J=9.1, 2.5 Hz, 1H), 6.88 (d, J=9.1 Hz, 1H), 4.56 (dd, J=10.7, 3.2 Hz, 1H), 4.47-4.23 (m, 3H), 3.72 (tdd, J=17.5, 13.2, 8.4 Hz, 8H), 2.78 (dd, J=15.0, 7.7 Hz, 1H), 2.58 (dd, J=14.9, 4.9 Hz, 1H), 2.27-1.90 (m, 2H), 1.98-1.88 (m, 1H), 1.83-1.66 (m, 1H). tR=2.571 min.

Example 545 Isomer B 17.2 mg, 2%, LCMS [M+H]+ 536.30. ¹H NMR (300 MHz, Methanol-d₄) δ 8.38 (dt, J=2.7, 0.9 Hz, 1H), 8.23 (d, J=0.8 Hz, 1H), 7.76 (dd, J=9.0, 2.5 Hz, 1H), 6.90 (d, J=9.1 Hz, 1H), 4.54-4.31 (m, 4H), 3.86-3.66 (m, 8H), 3.71-3.57 (m, 2H), 2.83 (dd, J=14.5, 7.8 Hz, 1H), 2.59 (dd, J=14.5, 4.8 Hz, 1H), 2.33-2.12 (m, 2H), 2.01-1.65 (m, 2H), tR=3.197 min.

Example 545 Isomer C 16.7 mg 2%, LCMS [M+H]+ 536.30, ¹H NMR (300 MHz, Methanol-d₄) δ 8.37 (dt, J=2.8, 0.9 Hz, 1H), 8.25 (d, J=0.8 Hz, 1H), 7.80-7.70 (m, 1H), 6.88 (d, J=9.1 Hz, 1H), 4.56 (dd, J=10.7, 3.2 Hz, 1H), 4.47-4.23 (m, 3H), 3.72 (tdd, J=17.5, 13.2, 8.4 Hz, 8H), 2.78 (dd, J=14.9, 7.7 Hz, 1H), 2.58 (dd, J=14.9, 4.9 Hz, 1H), 2.27-2.08 (m, 2H), 2.02-1.89 (m, 1H). 1.83-1.64 (m, 1H), tR=5.305 min.

Example 545 Isomer D 18.4 mg, 3%, LCMS [M+H]+ 536.30, ¹H NMR (300 MHz, Methanol-d₄) δ 8.38 (dt, J=2.7, 1.0 Hz, 1H), 8.22 (d, J=0.8 Hz, 1H), 7.76 (dd, J=9.1, 2.6 Hz, 1H), 6.90 (d, J=9.1 Hz, 1H), 4.54-4.31 (m, 4H), 3.86-3.63 (m, 8H), 2.83 (dd, J=14.6, 7.7 Hz, 1H), 2.59 (dd, J=14.5, 4.8 Hz, 1H), 2.33-2.17 (m, 2H), 2.01-1.65 (m, 2H), tR=6.548 min.

Example 546 Isomer A: 5-([[[(2S,5S)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one and Example 546 Isomer B: 5-([[[(2R,5R)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one and Example 546 Isomer C: 5-([[[(2S,5R)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one and Example 546 Isomer D: 5-([[[(2R,5S)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one Example 546

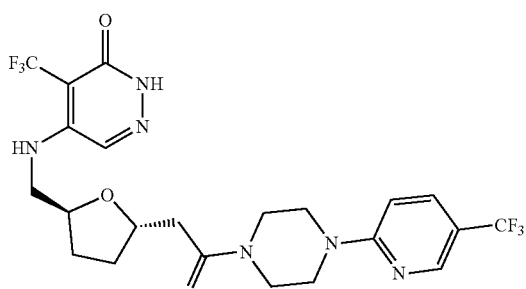

Isomer A

Example 546

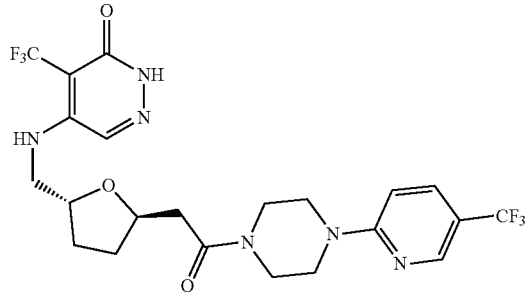

Isomer B

Example 546

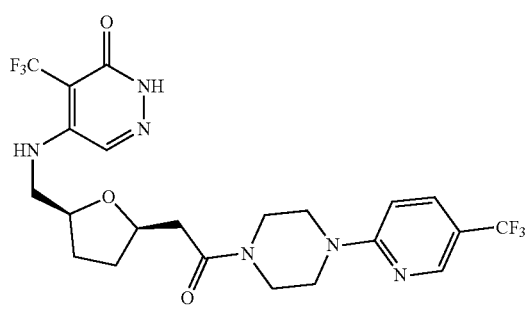

Isomer C

Example 546

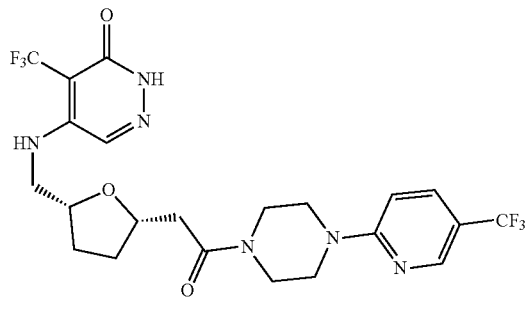

Isomer D

Step 1: 2-[5-(Azidomethyl)oxolan-2-yl]-1-[4-[5-(trifluoromethyl)pyridin-2-yl]piperazin-1-yl]ethan-1-one A solution of Int-A17 (1 g, 2.68 mmol, 1 equiv), DPPA (3.7 g, 13.44 mmol, 5.02 equiv), and DBU (1.2 g, 8.03 mmol, 3 equiv) was stirred for 2 days at 80° C. The resulting mixture was concentrated under reduced pressure and the residue purified by silica gel column chromatography with EtOAc/petroleum ether (2/3) to afford 500 mg (47%) of title compound as a yellow oil. LCMS [M+H]+ 399.17.

Step 2: 2-[5-(Aminomethyl)oxolan-2-yl]-1-[4-[5-(trifluoromethyl)pyridin-2-yl]piperazin-1-yl]ethan-1-one A solution of 2-[5-(azidomethyl)oxolan-2-yl]-1-[4-[5-(trifluoromethyl)pyridin-2-yl]piperazin-1-yl]ethan-1-one (550 mg, 1.38 mmol, 1 equiv), Pd/C (100 mg, 0.94 mmol, 0.68 equiv) in MeOH was stirred for 2 h at RT under H₂ (g) atmosphere. The solids were filtered and the resulting mixture was concentrated under reduced pressure to afford 360 mg (70%) of title compound as a yellow oil. LCMS [M+H]⁺ 373.19.

Step 3: 5-([[5-(2-Oxo-2-[4-[5-(trifluoromethyl)pyridin-2-yl]piperazin-1-yl]ethyl)oxolan-2-yl]methyl]amino)-4-(trifluoromethyl)-2-[[2-(trimethylsilyl)ethoxy]methyl]-2,3-dihydropyridazin-3-one A solution of Int-A6 (317.8 mg, 0.97 mmol, 1.00 equiv), 2-[5-(aminomethyl)oxolan-2-yl]-1-[4-[5-(trifluoromethyl)pyridin-2-yl]piperazin-1-yl]ethan-1-one (360 mg, 0.97 mmol, 1 equiv), TEA (195.6 mg, 1.93 mmol, 2 equiv) in EtOH (10 mL) was stirred for 2 h at 50° C. The resulting mixture was concentrated under reduced pressure and the residue was applied onto a silica gel column with DCM/MeOH (9/1) to afford 520 mg (81%) of title compound as a yellow oil. LCMS [M+H]⁺ 665.26.

Step 4: 5-([[(2S,5S)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one, 5-([[(2R,5R)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one, 5-([[(2S,5R)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one and 5-([[(2R,5S)-5-(2-oxo-2-[4-[5-(trifluoromethyl)pyridin-2-yl]piperazin-1-yl]ethyl)oxolan-2-yl]methyl]amino)-4-(trifluoromethyl)-2,3-dihydropyridazin-3-one A solution of 5-([[5-(2-oxo-2-[4-[5-(trifluoromethyl)pyridin-2-yl]piperazin-1-yl]ethyl)oxolan-2-yl]methyl]amino)-4-(trifluoromethyl)-2-[[2-(trimethylsilyl)ethoxy]methyl]-2,3-dihydropyridazin-3-one (520 mg, 0.78 mmol, 1 equiv), and 2,2,2-trifluoroacetaldehyde (2 mL, 0.02 mmol, 0.03 equiv) in DCM (8 mL) was stirred for 5 h at RT. After concentration under reduced pressure, the residue was purified by C18 reverse phase chromatography eluting with H₂O/ACN. Then the residue was further purified by Prep-HPLC and Chiral-Prep-HPLC (CHIRALPAK IE-3, 3 μm, 0.46×10 cm column, eluting with (Hex:DCM=5:1)(0.1% DEA):EtOH=50:50, at a flow rate of 1 mL/min) yielding (after arbitrary assignment of stereochemistry) the title compounds.

Example 546 Isomer A 16.4 mg, 4%, LCMS [M+H]⁺ 535.10, ¹H NMR (300 MHz, DMSO-d6) δ 12.41 (s, 1H), 8.44 (s, 1H), 7.94 (s, 1H), 7.83 (dd, J=9.0, 2.6 Hz, 1H), 6.95 (d, J=8.9 Hz, 2H), 4.17 (q, J=6.3 Hz, 1H), 4.08-3.90 (m, 1H), 3.76-3.35 (m, 10H), 2.62 (dd, J=15.3, 6.4 Hz, 1H), 2.45-2.35 (m, 1H), 2.05-1.89 (m, 2H), 1.70 (dq, J=12.1, 6.4 Hz, 1H), 1.62-1.47 (m, 1H). tR=2.294 min.

Example 546 Isomer B 27.2 mg, 7%, LCMS [M+H]⁺ 535.10, ¹H NMR (300 MHz, DMSO-d6) δ 12.38 (s, 1H), 8.42 (d, J=2.5 Hz, 1H), 7.91 (s, 1H), 7.82 (dd, J=9.1, 2.6 Hz, 1H), 6.94 (d, J=9.0 Hz, 2H), 4.27 (q, J=6.4 Hz, 1H), 4.18-4.10 (m, 1H), 3.85-3.45 (m, 10H), 2.69 (dd, J=15.1, 6.5 Hz, 1H), 2.50-2.39 (m, 1H), 2.09 (dd, J=11.2, 6.6 Hz, 1H), 2.18-1.90 (m, 2H), 1.78-1.60 (m, 2H). tR=2.793 min.

Example 546 Isomer C 40.6 mg, 10%, LCMS [M+H]⁺ 535.10, ¹H NMR (300 MHz, DMSO-d6) δ 12.39 (s, 1H), 8.42 (d, J=2.4 Hz, 1H), 7.91 (s, 1H), 7.82 (dd, J=9.2, 2.6 Hz, 1H), 6.94 (d, J=9.0 Hz, 2H), 4.25 (q, J=6.3 Hz, 1H), 4.18-4.10 (m, 1H), 3.80-3.40 (m, 10H), 2.69 (dd, J=15.2, 6.5 Hz, 1H), 2.49-2.39 (m, 1H), 2.08-1.90 (m, 2H), 1.80-1.60 (m, 2H). tR=3.208 min.

Example 546 Isomer D 11.1 mg, 3%, LCMS [M+H]⁺ 535.10, ¹H NMR (300 MHz, DMSO-d6) δ 12.41 (s, 1H), 8.43 (s, 1H), 7.94 (s, 1H), 7.83 (dd, J=9.1, 2.6 Hz, 1H), 6.95 (d, J=9.0 Hz, 2H), 4.18 (t, J=6.6 Hz, 1H), 4.08-3.90 (m, 1H), 3.69-3.36 (m, 10H), 2.62 (dd, J=15.4, 6.4 Hz, 1H), 2.41 (dd, J=15.4, 6.3 Hz, 1H), 2.11-1.85 (m, 2H), 1.69 (s, 1H), 1.59-1.47 (m, 1H). tR=4.088 min Example 547: 4-Bromo-5-(2-[3-[4-(5-chloropyrimidin-2-yl)piperazin-1-yl]-3-oxopropoxy]ethoxy)-2,3-dihydropyridazin-3-one

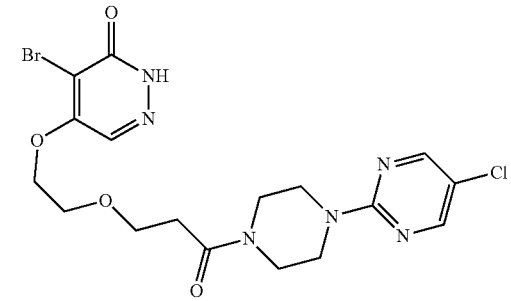 [SMILES: O=C(CCOCCOc1cn[nH]c(=O)c1Br)N1CCN(c2ncc(Cl)cn2)CC1]

Step 1: 4-Bromo-5-(2-[3-[4-(5-chloropyrimidin-2-yl)piperazin-1-yl]-3-oxopropoxy]ethoxy)-2,3-dihydropyridazin-3-one A solution of Int-A14 (150 mg, 0.49 mmol, 1 equiv), HOBT (99.0 mg, 0.73 mmol, 1.5 equiv), EDCI (140.5 mg, 0.73 mmol, 1.5 equiv), DIPEA (189.4 mg, 1.47 mmol, 3 equiv) and Int-A3 (97.0 mg, 0.49 mmol, 1.00 equiv) in DMF (7 mL, 0.10 mmol, 0.20 equiv) was stirred for 1 h at RT, and then the resulting solution was purified by C18 reverse phase chromatography eluting with H₂O/CH₃CN and further purified by Prep-HPLC to afford the title compound as a white solid (13.3 mg, 6%). LCMS [M+H]⁺ 489.10 [M+H], ¹H NMR (300 MHz, DMSO-d₆) δ 13.16 (s, 1H), 8.43 (s, 2H), 8.07 (s, 1H), 4.47-4.50 (m, 2H), 3.75-3.66 (m, 8H), 3.60-3.52 (m, 4H), 2.64 (t, J=6.5 Hz, 2H).

The following example in Table E6 was similarly prepared from Int-A14 and the appropriate intermediate Int-A2 according to the method described for Example 547.

TABLE E6

| Example | Name, structure, analytical data | Int. |
|---|---|---|
| Example 548 | 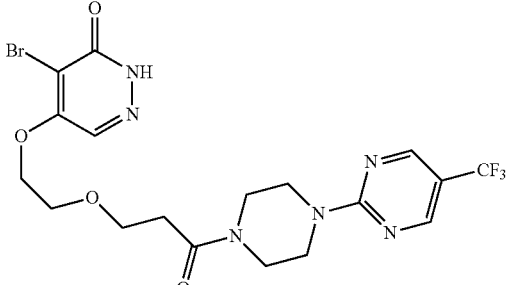<br>4-Bromo-5-[2-(3-oxo-3-[4-[5-(trifluoromethyl)pyrimidin-2-yl]piperazin-1-yl]propoxy)ethoxy]-2,3-dihydropyridazin-3-one;<br>LCMS: [M + H]$^+$ 522.95;<br>$^1$H NMR (300 MHz, DMSO-d$_6$) δ 8.72 (s, 2H), 8.08 (s, 1H), 4.48-4.45 (m, 2H), 3.84-3.72 (m, 8H), 3.62-3.55 (m, 4H), 2.65 (t, J = 6.5 Hz, 2H). | Int-A2 and Int-A14 |

Example 549: 5-(2-[3-[4-(5-Chloropyrimidin-2-yl)piperazin-1-yl]-3-oxopropoxy]ethoxy)-4-methyl-2,3-dihydropyridazin-3-one

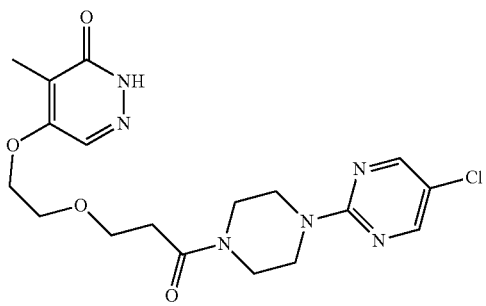 [SMILES: Cc1c(OCCOCCC(=O)N2CCN(c3ncc(Cl)cn3)CC2)cn[nH]c1=O]

Step 1: 5-(2-[3-[4-(5-Chloropyrimidin-2-yl)piperazin-1-yl]-3-oxopropoxy]ethoxy)-4-methyl-2,3-dihydropyridazin-3-one A solution of Int-A15 (300 mg, 1.24 mmol, 1 equiv), Int-A3 (370.0 mg, 1.36 mmol, 1.1 equiv), DIPEA (480.2 mg, 3.72 mmol, 3 equiv), and HATU (518.0 mg, 1.36 mmol, 1.1 equiv) in DMF (8 mL) was stirred 2 h at 25° C. After concentration, the residue was purified by C18 reverse phase chromatography eluting with H$_2$O/ACN and the residue was further purified by Prep-HPLC to afford the title compound (76.3 mg, 15%) as a white solid. LCMS [M+H]$^+$ 423.15, $^1$H NMR (300 MHz, DMSO-d$_6$) δ 12.78 (s, 1H), 8.44 (s, 2H), 8.01 (s, 1H), 4.36-4.27 (m, 2H), 3.80-3.63 (m, 8H), 3.54 (d, J=5.8 Hz, 4H), 2.63 (t, J=6.5 Hz, 2H), 1.85 (s, 3H).

The following examples in Table E7 were similarly prepared from Int-A15 and the appropriate intermediates according to the method described for Example 549.

TABLE E7

| Example | Name, structure, analytical data | Int. |
|---|---|---|
| Example 550 | 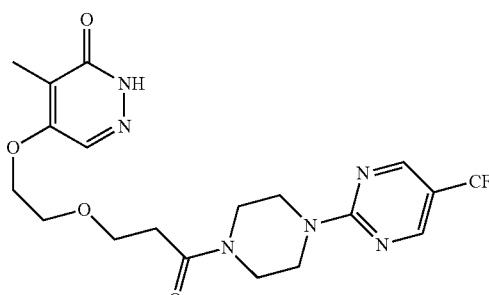<br>4-Methyl-5-[2-(3-oxo-3-[4-[5-(trifluoromethyl)pyrimidin-2-yl]piperazin-1-yl]propoxy)ethoxy]-2,3-dihydropyridazin-3-one;<br>LCMS: [M + H]$^+$ 457.17;<br>$^1$H NMR (300 MHz, DMSO-d$_6$) δ: 12.76 (s, 1H), 8.70 (d, J = 0.9 Hz, 2H), 7.99 (s, 1H), 4.30 (dd, J = 5.5, 3.4 Hz, 2H), 3.79 (dd, J = 15.3, 5.5 Hz, 4H), 3.74-3.65 (m, 4H), 3.55 (s, 4H), 2.61 (t, J = 6.5 Hz, 2H), 1.83 (s, 3H). | Int-A2 and Int-A15 |

TABLE E7-continued

| Example | Name, structure, analytical data | Int. |
|---|---|---|
| Example 551 | ![structure]<br><br>6-[4-(3-[2-[(5-Methyl-6-oxo-1,6-dihydropyridazin-4-yl)oxy]ethoxy]propanoyl)piperazin-1-yl]pyridine-3-carbonitrile;<br>LCMS: [M + H]$^+$ 413.19;<br>$^1$H NMR (300 MHz, DMSO-d6) δ 8.51 (d, J = 2.3 Hz, 1H), 8.02 (s, 1H), 7.88 (dd, J = 9.1, 2.4 Hz, 1H), 6.92 (d, J = 9.1 Hz, 1H), 4.37-4.28 (m, 2H), 3.78-3.53 (m, 12H), 2.64 (t, J = 6.5 Hz, 2H), 1.86 (s, 3H). | Int-A4 and Int-A15 |

Example 552: 5-(2-[3-[4-(5-Chloropyrimidin-2-yl)piperazin-1-yl]-3-oxopropoxy]ethoxy)-3-oxo-2,3-dihydropyridazine-4-carbonitrile

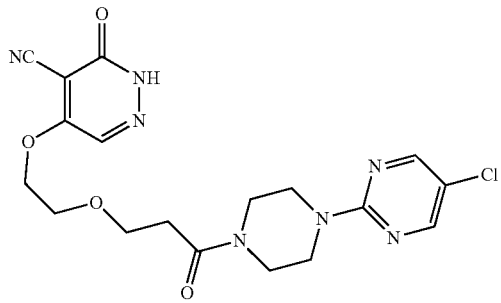 [SMILES: N#Cc1c(OCCOCCC(=O)N2CCN(c3ncc(Cl)cn3)CC2)cn[nH]c1=O]

Step 1: 5-(2-[3-[4-(5-Chloropyrimidin-2-yl)piperazin-1-yl]-3-oxopropoxy]ethoxy)-3-oxo-2,3-dihydropyridazine-4-carbonitrile A solution of Int-A16 (150 mg, 0.59 mmol, 1 equiv), EDCI (124.8 mg, 0.65 mmol, 1.10 equiv), HOBT (88 mg, 0.65 mmol, 1.10 equiv), and Int-A3 (130 mg, 0.65 mmol, 1.10 equiv) in DMF (15 mL) was stirred for 1.5 h at RT. After concentration under reduced pressure, the residue was purified by C18 reverse phase chromatography eluting with H$_2$O/ACN and the residue was further purified by Prep-HPLC to afford (34.8 mg, 14%) as a white solid. LCMS [M+H]$^+$ 433.85, $^1$H NMR (300 MHz, DMSO-d6) δ 13.52 (s, 1H), 8.45 (s, 2H), 8.30 (s, 1H), 4.65-4.57 (m, 2H), 3.81-3.64 (m, 8H), 3.34 (s, 4H), 2.63 (t, J=6.4 Hz, 2H).

The following example in Table E8 was similarly prepared from Int-A16 and the appropriate intermediate, Int-A2, according to the method described for Example 552.

TABLE E8

| Example | Name, structure, analytical data | Int. |
|---|---|---|
| Example 553 | ![structure]<br><br>3-Oxo-5-[2-(3-oxo-3-[4-[5-(trifluoromethyl)pyrimidin-2-yl]piperazin-1-yl]propoxy)ethoxy]-2,3-dihydropyridazine-4-carbonitrile;<br>LCMS: [M + H]$^+$ 468.2;<br>$^1$H NMR (300 MHz, DMSO-d6) δ 13.49 (s, 1H), 8.70 (d, J = 0.9 Hz, 2H), 8.27 (s, 1H), 4.58 (dd, J = 5.1, 3.2 Hz, 2H), 3.98-3.76 (m, 8H), 3.55 (t, J = 5.3 Hz, 4H), 2.61 (t, J = 6.4 Hz, 2H). | Int-A2 and Int-A16 |

Example 554: 5-(2-[3-[4-(5-Cyanopyridin-2-yl)piperazin-1-yl]-3-oxopropoxy]ethoxy)-3-oxo-2,3-dihydropyridazine-4-carbonitrile

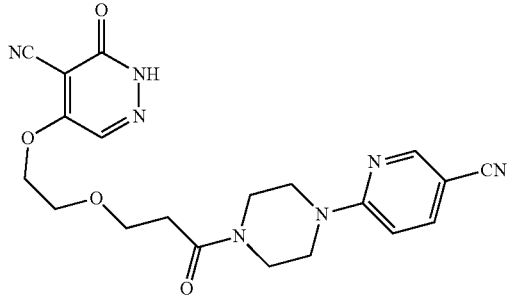 [SMILES: N#Cc1ccc(N2CCN(C(=O)CCOCCOc3cn[nH]c(=O)c3C#N)CC2)nc1]

Step 1: 5-(2-[3-[4-(5-Cyanopyridin-2-yl)piperazin-1-yl]-3-oxopropoxy]ethoxy)-3-oxo-2-[[2-(trimethylsilyl)ethoxy]methyl]-2,3-dihydropyridazine-4-carbonitrile A solution of Int-A19 (130 mg, 0.21 mmol, 1 equiv) and CuCN (40 mg, 0.45 mmol, 2.09 equiv) in NMP (10 mL) was stirred 1 day at 120° C. The reaction was then quenched by the addition of 20 mL of water. The resulting solution was extracted with EtOAc and the organic layers were combined and dried over anhydrous sodium sulfate. After concentration, the residue was purified by C18 reverse phase chromatography eluting with $H_2O/ACN$ to afford 50 mg (42%) of title compound as a yellow oil. LCMS $[M+H]^+$ 554.25.

Step 2: 5-(2-[3-[4-(5-Cyanopyridin-2-yl)piperazin-1-yl]-3-oxopropoxy]ethoxy)-3-oxo-2,3-dihydropyridazine-4-carbonitrile A solution of 5-(2-[3-[4-(5-cyanopyridin-2-yl)piperazin-1-yl]-3-oxopropoxy]ethoxy)-3-oxo-2-[[2-(trimethylsilyl)ethoxy]methyl]-2,3-dihydropyridazine-4-carbonitrile (50 mg, 0.09 mmol, 1 equiv) in HCl/dioxane (2 mL) was stirred for 24 h at RT. The solvent was concentrated under vacuum and the residue was purified by C18 reverse phase chromatography eluting with $H_2O/CH_3CN$ followed by further purification by Prep-HPLC to afford the title compound (3.4 mg, 9%) as a white solid. LCMS $[M+H]^+$ 424.3, $^1H$ NMR (300 MHz, DMSO-d6) δ 8.50 (d, J=2.4 Hz, 1H), 8.29 (s, 1H), 7.87 (dd, J=9.1, 2.4 Hz, 1H), 6.89 (d, J=9.2 Hz, 1H), 4.59 (d, J=4.9 Hz, 2H), 3.80-3.68 (m, 8H), 3.56 (s, 4H), 2.62 (t, J=6.4 Hz, 2H).

Example 555: 6-[4-(3-[2-[(5-Bromo-6-oxo-1,6-dihydropyridazin-4-yl)oxy]ethoxy]propanoyl)piperazin-1-yl]pyridine-3-carbonitrile

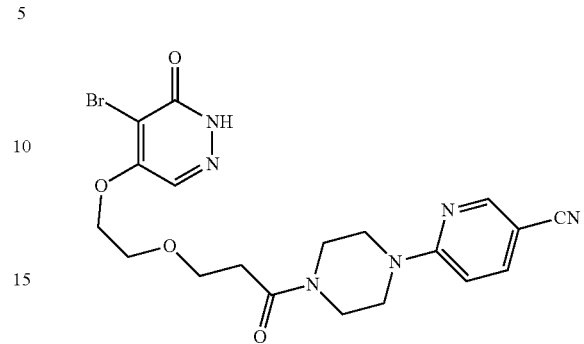

A solution of Int-A19 (170 mg, 0.28 mmol, 1 equiv) and TFA (0.7 mL) in DCM (7 mL) was stirred for 3 h at RT. The solvent was concentrated under vacuum and the residue was purified by C18 reverse phase chromatography eluting with $H_2O/ACN$ and then the residue was further purified by Prep-HPLC to afford the title compound (38.5 mg, 29%) as a white solid. LCMS $[M+H]^+$ 477.31, $^1H$ NMR (300 MHz, DMSO-d6) δ 9.65 (s, 1H), 8.47 (d, J=2.3 Hz, 1H), 8.05 (s, 1H), 7.85 (dd, J=9.1, 2.4 Hz, 1H), 6.89 (d, J=9.2 Hz, 1H), 4.44 (dd, J=5.2, 3.4 Hz, 2H), 3.77-3.57 (m, 8H), 3.35-3.30 (m, 4H), 2.60 (t, J=6.5 Hz, 2H).

Example 556: 5-[[(2R)-1-[3-[4-(5-Chloropyrimidin-2-yl)piperazin-1-yl]-3-oxopropoxy]propan-2-yl]amino]-4-(trifluoromethyl)-2,3-dihydropyridazin-3-one

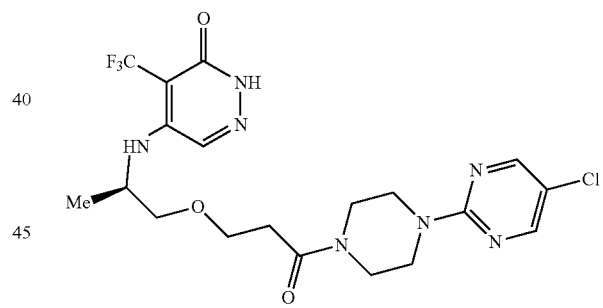

Step 1: 5-[[(2R)-1-Hydroxypropan-2-yl]amino]-4-(trifluoromethyl)-2-[[2-(trimethylsilyl)ethoxy]methyl]-2,3-dihydropyridazin-3-one A solution of Int-A6 (1 g, 3.04 mmol, 1.00 equiv), (2R)-2-aminopropan-1-ol (229 mg, 3.05 mmol, 1.00 equiv) and TEA (616 mg, 6.09 mmol, 2.00 equiv) in EtOH (20 mL) was stirred for 1 h at 60° C. The resulting solution was concentrated under vacuum, and the residue was purified by silica gel column chromatography eluting with EtOAc/petroleum ether (1:1) to afford 1.03 g (92%) of title compound as a light brown oil. LCMS $[M+H]^+$ 368.15.

Step 2: Methyl 3-[(2R)-2-[[6-oxo-5-(trifluoromethyl)-1-[[2-(trimethylsilyl)ethoxy]methyl]-1,6-dihydropyridazin-4-yl]amino]propoxy]propanoate A solution of 5-[[(2R)-1-hydroxypropan-2-yl]amino]-4-(trifluoromethyl)-2-[[2-(trimethylsilyl)ethoxy]methyl]-2,3- dihydropyridazin-3-one (1 g, 2.72 mmol, 1.00 equiv), methyl prop-2-enoate (1.17 g, 0.01 mmol, 5.00 equiv) and Cs$_2$CO$_3$ (2.65 g, 8.13 mmol, 3.00 equiv) in ACN (25 mL) was stirred for 3 h at RT. The solids were filtered and the resulting solution was concentrated under vacuum, and the residue was purified by silica gel column chromatography eluting with EtOAc/petroleum ether (3:7) to give 604 mg (49%) of title compound as a light brown oil. LCMS [M+H]$^+$ 454.53.

Step 3: Methyl 3-[(2R)-2-[[6-oxo-5-(trifluoromethyl)-1,6-dihydropyridazin-4-yl]amino]propoxy]propanoate A solution of methyl 3-[(2R)-2-[[6-oxo-5-(trifluoromethyl)-1-[[2-(trimethyl silyl)ethoxy]methyl]-1,6-dihydropyridazin-4-yl]amino]propoxy]propanoate (600 mg, 1.32 mmol, 1.00 equiv) and TFA (1.5 mL) in DCM (6 mL) was stirred for 1 h at RT. The resulting solution was concentrated under vacuum, and the residue was dissolved in NH$_3$ (g) in MeOH (2 mL, 7M) and stirred for 15 min at RT. The resulting solution was concentrated under vacuum to afford 400 mg (94%) of title compound as a light brown oil. LCMS [M+H]$^+$ 324.11.

Step 4: 3-[(2R)-2-[[6-oxo-5-(trifluoromethyl)-1,6-dihydropyridazin-4-yl amino Propoxy Propanoic Acid A solution of methyl 3-[(2R)-2-[[6-oxo-5-(trifluoromethyl)-1,6-dihydropyridazin-4-yl]amino]propoxy]propanoate (400 mg, 1.24 mmol, 1 equiv) and LiOH (148.2 mg, 6.19 mmol, 5.00 equiv) in MeOH (5 mL) and H$_2$O (1 mL) was stirred for 4 h at RT, and then the pH value of the solution was adjusted to 4 with HCl (1 M). The solid was collected by filtration to afford 115 mg (30%) of title compound as a yellow solid. LCMS [M+H]$^+$ 310.10.

Step 5: 5-[[(2R)-1-[3-[4-(5-Chloropyrimidin-2-yl)piperazin-1-yl]-3-oxopropoxy]propan-2-yl]amino]-4-(trifluoromethyl)-2,3-dihydropyridazin-3-one A solution of 3-[(2R)-2-[[6-oxo-5-(trifluoromethyl)-1,6-dihydropyridazin-4-yl]amino]propoxy]propanoic acid (115 mg, 0.37 mmol, 1 equiv), Int-A3 (73.9 mg, 0.37 mmol, 1.00 equiv), HATU (141.4 mg, 0.37 mmol, 1.00 equiv) and DIPEA (96.1 mg, 0.74 mmol, 2.00 equiv) in DMF (4 mL) was stirred for 40 min at RT, and then the resulting solution was diluted with 20 mL of H$_2$O, extracted with 3×20 mL of EtOAc and the organic layer was combined, washed with 1×20 mL of brine and concentrated under vacuum. The residue was purified by C18 reverse phase chromatography eluting with H$_2$O/CH$_3$CN to afford the title compound as a white solid. LCMS [M+H]$^+$ 490.05, $^1$H NMR (300 MHz, DMSO-d6) δ 12.32 (s, 1H), 8.46 (d, J=5.7 Hz, 2H), 7.91 (s, 1H), 6.29 (dd, J=8.4, 4.2 Hz, 1H), 4.19-4.10 (m, 1H), 3.74-3.62 (m, 6H), 3.53-3.48 (m, 6H), 2.59 (t, J=6.5 Hz, 2H), 1.15 (d, J=6.5 Hz, 3H).

Example 557: 5-[[(2R)-1-[3-[4-(5-Chloropyrimidin-2-yl)piperazin-1-yl]-3-oxopropoxy]-3-methoxypropan-2-yl]amino]-4-(trifluoromethyl)-2,3-dihydropyridazin-3-one

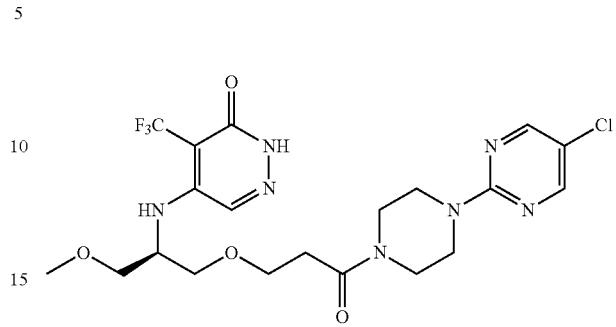

Step 1: (2R)-3-Methoxy-2-[[6-oxo-5-(trifluoromethyl)-1-[[2-(trimethylsilyl)ethoxy]methyl]-1,6-dihydropyridazin-4-yl]amino]propanoic Acid A solution of (2R)-2-amino-3-methoxypropanoic acid hydrochloride (310 mg, 1.99 mmol, 1.00 equiv), TEA (500 mg, 4.94 mmol, 2.00 equiv) and Int-A6 (800 mg, 2.43 mmol, 1.20 equiv) in EtOH (5 mL) was stirred for 1 h at 60° C., and then the resulting solution was concentrated under vacuum to afford 1.2 g of crude title compound as a yellow oil. LCMS [M+H]$^+$ 412.15.

Step 2: 5-[[(2S)-1-Hydroxy-3-methoxypropan-2-yl]amino]-4-(trifluoromethyl)-2-[[2-(trimethylsilyl)ethoxy]methyl]-2,3-dihydropyridazin-3-one A solution of (2R)-3-methoxy-2-[[6-oxo-5-(trifluoromethyl)-1-[[2-(trimethylsilyl)ethoxy]methyl]-1,6-dihydropyridazin-4-yl]amino]propanoic acid (1.2 g, 2.92 mmol, 1.00 equiv) in BH$_3$-THF (1M, 20 mL) was stirred for 1 h at RT, and then the resulting solution was quenched by the addition of 100 mL of water, extracted with 3×100 mL of EtOAc and the organic layers combined and concentrated under vacuum. The residue was then purified by C18 reverse phase chromatography eluting with H$_2$O/ACN to afford 840 mg (72%) of title compound as a yellow oil. LCMS [M+H]$^+$ 398.17.

Step 3: Methyl 3-[(2R)-3-methoxy-2-[[6-oxo-5-(trifluoromethyl)-1-[[2-(trimethylsilyl)ethoxy]methyl]-1,6-dihydropyridazin-4-yl)amino)propoxy)propanoate A solution of 5-[[(2S)-1-hydroxy-3-methoxypropan-2-yl]amino]-4-(trifluoromethyl)-2-[[2-(trimethylsilyl)ethoxy]methyl]-2,3-dihydropyridazin-3-one (800 mg, 2.01 mmol, 1.00 equiv), Cs$_2$CO$_3$ (1967.4 mg, 6.04 mmol, 3 equiv) and methyl prop-2-enoate (1732.8 mg, 20.13 mmol, 10 equiv) in ACN (10 mL) was stirred for 2 h at RT, and then the solids were filtered. The resulting solution was concentrated under vacuum, and the residue was purified by silica gel column chromatography eluting with EtOAc/petroleum ether to afford 420 mg (43%) of title compound as a yellow oil. LCMS [M+H]$^+$ 484.20.

Step 4: Methyl 3-[(2R)-3-methoxy-2-[[6-oxo-5-(trifluoromethyl)-1,6-dihydropyridazin-4-yl]amino]propoxy]propanoate A solution of methyl 3-[(2R)-3-methoxy-2-[[6-oxo-5-(trifluoromethyl)-1-[[2-(trimethyl silyl)ethoxy]methyl]-1,6-dihydropyridazin-4-yl]amino]propoxy]propanoate (400 mg, 0.83 mmol, 1 equiv) and TFA (1 mL) in DCM (5 mL) was stirred for 1 h at RT, and then the resulting solution was concentrated under vacuum to afford 500 mg of title compound as a yellow crude oil. LCMS [M+H]⁺ 354.12.

Step 5: Methyl 3-[(2R)-3-methoxy-2-[[6-oxo-5-(trifluoromethyl)-1,6-dihydropyridazin-4-yl]amino]propoxy]propanoate A solution of methyl 3-[(2R)-3-methoxy-2-[[6-oxo-5-(trifluoromethyl)-1,6-dihydropyridazin-4-yl]amino]propoxy]propanoate (500 mg, 1.42 mmol, 1 equiv) and LiOH (67.8 mg, 2.83 mmol, 2.00 equiv) in MeOH (10 mL) and H₂O (2 mL) was stirred for 2 h at RT, and then the pH of the resulting solution was adjusted to 5 with TFA and concentrated under vacuum. The residue was purified by C18 reverse phase chromatography eluting with H₂O/ACN to afford 230 mg (48%) of title compound as a yellow oil. LCMS [M+H]⁺ 340.11.

Step 6: 5-[[(2R)-1-[3-[4-(5-Chloropyrimidin-2-yl)piperazin-1-yl]-3-oxopropoxy]-3-methoxypropan-2-yl]amino]-4-(trifluoromethyl)-2,3-dihydropyridazin-3-one A solution of 3-[(2R)-3-methoxy-2-[[6-oxo-5-(trifluoromethyl)-1,6-dihydropyridazin-4-yl]amino]propoxy]propanoic acid (200 mg, 0.59 mmol, 1 equiv), DIPEA (152.4 mg, 1.18 mmol, 2 equiv), HATU (224.1 mg, 0.59 mmol, 1 equiv) and Int-A3 (117.1 mg, 0.59 mmol, 1 equiv) in DMF (2 mL) was stirred for 1 h at RT, and then the resulting solution was purified by C18 reverse phase chromatography eluting with H₂O/ACN. The residue was further purified by Prep-HPLC to afford the title compound (84.2 mg, 27%) as a white solid. LCMS [M+H]⁺ 520.10, ¹H NMR (300 MHz, Methanol-d₄) δ 8.33 (s, 2H), 7.97 (s, 1H), 4.21 (t, J=5.3 Hz, 1H), 3.86-3.51 (m, 14H), 3.38 (s, 3H), 2.70 (t, J=6.0 Hz, 2H).

Example 558: 5-[[(2S)-1-[3-[4-(5-Chloropyrimidin-2-yl)piperazin-1-yl]-3-oxopropoxy]-3-methoxypropan-2-yl]amino]-4-(trifluoromethyl)-2,3-dihydropyridazin-3-one

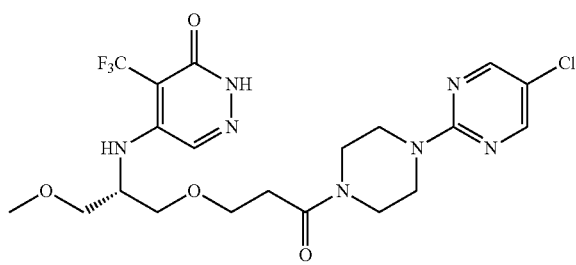

Step 1: (2R)-2-Amino-3-methoxypropan-1-ol

A solution of (2S)-2-amino-3-methoxypropanoic acid (2 g, 16.79 mmol, 1 equiv) in BH₃-THF (20 mL, 1M) was stirred for 1 h at RT upon which the reaction was quenched with MeOH (20 mL). The resulting solution was concentrated under vacuum to afford 2.2 g of title compound as a colorless crude oil. LCMS [M+H]⁺ 106.08.

Step 2: 5-[[(2R)-1-Hydroxy-3-methoxypropan-2-yl]amino]-4-(trifluoromethyl)-2-[[2-(trimethylsilyl)ethoxy]methyl]-2,3-dihydropyridazin-3-one A solution of (2R)-2-amino-3-methoxypropan-1-ol (500 mg, 4.76 mmol, 1 equiv), TEA (962.5 mg, 9.51 mmol, 2.0 equiv) and Int-A6 (1560 mg, 4.74 mmol, 1.00 equiv) in EtOH (10 mL) was stirred for 1 h at 60° C. The resulting solution was concentrated under vacuum, and then the residue was purified by silica gel column chromatography eluting with EtOAc/petroleum ether (1/1) to afford 850 mg (45%) of title compound as a yellow oil. LCMS [M+H]⁺ 398.17.

Step 3: Methyl 3-[(2S)-3-methoxy-2-[[6-oxo-5-(trifluoromethyl)-1-[[2-(trimethylsilyl)ethoxy]methyl]-1,6-dihydropyridazin-4-yl]amino]propoxy]propanoate A solution of 5-[[(2R)-1-hydroxy-3-methoxypropan-2-yl]amino]-4-(trifluoromethyl)-2-[[2-(trimethylsilyl)ethoxy]methyl]-2,3-dihydropyridazin-3-one (800 mg, 2.01 mmol, 1 equiv), Cs₂CO₃ (1967.4 mg, 6.04 mmol, 3 equiv) and methyl prop-2-enoate (1732.8 mg, 20.13 mmol, 10 equiv) in ACN (10 mL) was stirred for 2h at RT. The solids were filtered and the resulting solution was concentrated under reduced pressure. The residue was applied onto a silica gel column eluting with EtOAc/petroleum ether to afford 620 mg (64%) of title compound as a yellow oil. LCMS [M+H]⁺ 484.20.

Step 4: Methyl 3-[(2S)-3-methoxy-2-[[6-oxo-5-(trifluoromethyl)-1,6-dihydropyridazin-4-yl]amino]propoxy]propanoate A solution of methyl 3-[(2S)-3-methoxy-2-[[6-oxo-5-(trifluoromethyl)-1-[[2-(trimethyl silyl)ethoxy]methyl]-1,6-dihydropyridazin-4-yl]amino]propoxy]propanoate (600 mg, 1.24 mmol, 1 equiv) and TFA (1 mL) in DCM (5 mL) was stirred for 1 h at RT and then the resulting solution was concentrated under vacuum to afford 650 mg of title compound as a yellow oil. LCMS [M+H]⁺ 354.12.

Step 5: 3-[(2S)-3-Methoxy-2-[[6-oxo-5-(trifluoromethyl)-1,6-dihydropyridazin-4-yl]amino]propoxy]propanoic Acid A solution of methyl 3-[(2S)-3-methoxy-2-[[6-oxo-5-(trifluoromethyl)-1,6-dihydropyridazin-4-yl]amino]propoxy]propanoate (600 mg, 1.70 mmol, 1 equiv) and LiOH (406.7 mg, 16.98 mmol, 10 equiv) in MeOH (10 mL) and H₂O (2 mL) was stirred for 2h at RT, and then the resulting solution was concentrated under vacuum and the residue was purified by C18 reverse phase chromatography eluting with H₂O/CH₃CN to afford 260 mg (45%) of title compound as a yellow oil. LCMS [M+H]⁺ 340.11.

Step 6: 5-[[(2S)-1-[3-[4-(5-Chloropyrimidin-2-yl)piperazin-1-yl]-3-oxopropoxy]-3-methoxypropan-2-yl]amino]-4-(trifluoromethyl)-2,3-dihydropyridazin-3-one A solution of 3-[(2S)-3-methoxy-2-[[6-oxo-5-(trifluoromethyl)-1,6-dihydropyridazin-4-yl]amino]propoxy]propanoic acid (250 mg, 0.74 mmol, 1 equiv), HATU (280.2 mg, 0.74 mmol, 1.0 equiv), DIPEA (190.5 mg, 1.47 mmol, 2.0 equiv) and Int-A3 (146.4 mg, 0.74 mmol, 1 equiv) in DMF (2 mL) was stirred for 1 h at RT, and then the resulting solution was purified by C18 reverse phase chromatography eluting with H₂O/ACN. The residue was further purified by Prep-HPLC to afford the title compound (121 mg, 32%) as a white solid. LCMS [M+H]⁺ 520.05. ¹H NMR (300 MHz, Methanol-d₄) δ 8.33 (s, 2H), 7.96 (s, 1H), 4.21 (t, J=5.3 Hz, 1H), 3.84-3.55 (m, 14H), 3.38 (s, 3H), 2.72 (t, J=6.0 Hz, 2H).

Example 559: 5-[[(2S)-1-Methoxy-3-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one

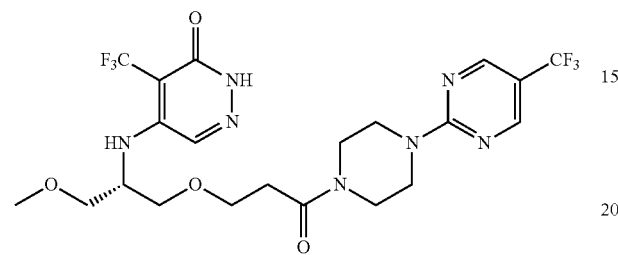

A solution of 3-[(2S)-3-methoxy-2-[[6-oxo-5-(trifluoromethyl)-1,6-dihydropyridazin-4-yl]amino]propoxy]propanoic acid (Example 558, Step 5; 100 mg, 0.29 mmol, 1 equiv), HATU (112.1 mg, 0.29 mmol, 1.0 equiv), Int-A2 (68.4 mg, 0.29 mmol, 1 equiv) and DIPEA (76.2 mg, 0.59 mmol, 2.0 equiv) in DMF (2 mL) was stirred for 1 h at RT. The resulting solution was purified by C18 reverse phase chromatography eluting with H₂O/ACN which after concentrated under reduced pressure. The residue was further purified by Prep-HPLC to afford the title compound (56.7 mg, 35%) as a white solid. LCMS [M+H]⁺ 554.30. ¹H NMR (300 MHz, Methanol-d4) δ 8.61 (d, J=0.9 Hz, 2H), 7.98 (s, 1H), 4.23 (t, J=5.1 Hz, 1H), 3.98-3.60 (m, 12H), 3.59-3.52 (m, 2H) 3.39 (s, 3H), 2.71 (t, J=5.9 Hz, 2H).

Example 560 Isomer A: 5-[(2S)-2-[3-[4-(5-chloropyrimidin-2-yl)piperazin-1-yl]-3-oxopropoxy]-3-methoxypropoxy]-4-(trifluoromethyl)-2,3-dihydropyridazin-3-one and Example 560 Isomer B: 5-[(2R)-2-[3-[4-(5-chloropyrimidin-2-yl)piperazin-1-yl]-3-oxopropoxy]-3-methoxypropoxy]-4-(trifluoromethyl)-2,3-dihydropyridazin-3-one and Example 560 Isomer C: 5-[[(2S)-1-[3-[4-(5-chloropyrimidin-2-yl)piperazin-1-yl]-3-oxopropoxy]-3-methoxypropan-2-yl]oxy]-4-(trifluoromethyl)-2,3-dihydropyridazin-3-one Example 560

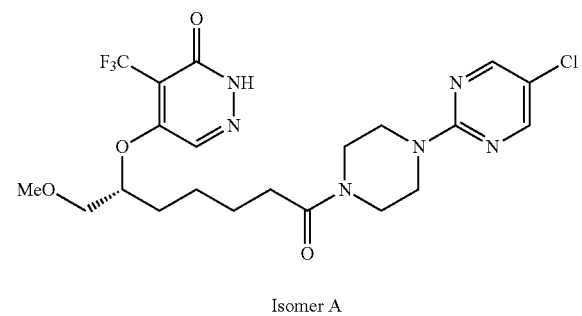

Isomer A

Example 560

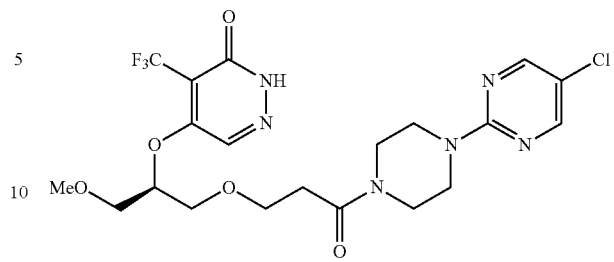

Isomer B

Example 560

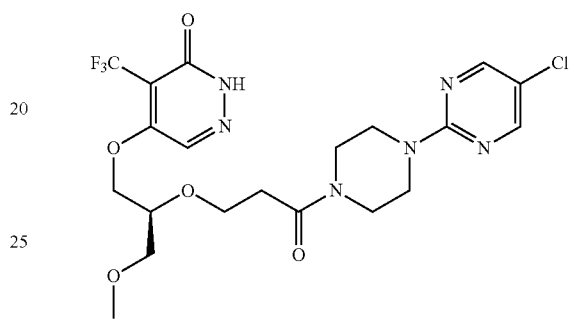

Isomer C

Example 560

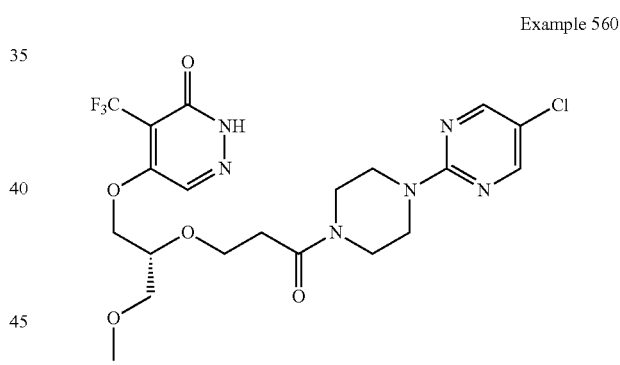

Isomer D

Step 1: Mixture of 1-[4-(5-chloropyrimidin-2-yl)piperazin-1-yl]-3-(2-hydroxy-3-methoxypropoxy)propan-1-one and 1-(4-(5-chloropyrimidin-2-yl)piperazin-1-yl)-3-((1-hydroxy-3-methoxypropan-2-yl)oxy)propan-1-one A solution of Int-A23 (1 g, 3.96 mmol, 1 equiv), 3-methoxypropane-1,2-diol (5.0 g, 0.05 mmol, 12 equiv) and Cs₂CO₃ (2.6 g, 0.01 mmol, 2.0 equiv) in ACN (30 mL) was stirred for 15 h at 70° C., and then the solids were filtered and the resulting solution was concentrated under reduced pressure. The residue was purified by C18 reverse phase chromatography eluting with H₂O/ACN to afford 800 mg (56%) of the mixture of the title compounds as a white oil. LCMS: [M+H]⁺ 359.14.

Step 2: Mixture of 5-((1-(3-(4-(5-chloropyrimidin-2-yl)piperazin-1-yl)-3-oxopropoxy)-3-methoxypropan-2-yl)oxy)-4-(trifluoromethyl)-2-((2-(trimethylsilyl)ethoxy)methyl)pyridazin-3(2H)-one and 5-(2-(3-(4-(5-chloropyrimidin-2-yl)piperazin-1-yl)-3-oxopropoxy)-3-methoxypropoxy)-4-(trifluoromethyl)-2-((2-(trimethylsilyl)ethoxy)methyl)pyridazin-3(6H)-one A mixture of 1-[4-(5-chloropyrimidin-2-yl)piperazin-1-yl]-3-(2-hydroxy-3-methoxypropoxy)propan-1-one and 1-(4-(5-chloropyrimidin-2-yl)piperazin-1-yl)-3-((1-hydroxy-3-methoxypropan-2-yl)oxy)propan-1-one (0.72 g, 2.01 mmol, 1 equiv), Cs$_2$CO$_3$ (0.98 g, 3.01 mmol, 1.50 equiv) and Int-A6 (2.4 g, 7.30 mmol, 3.64 equiv) in ACN (15 mL) was stirred for 4 h at 80° C., and then the solids were filtered out and the resulting solution was concentrated under reduced pressure. The residue was applied onto a silica gel column eluting with EtOAc/petroleum ether to afford 420 mg (32%) of the mixture of title compounds as a yellow oil. LCMS: [M+H]$^+$ 651.15.

Step 3: Isomer A: 5-[(2S)-2-[3-[4-(5-chloropyrimidin-2-yl)piperazin-1-yl]-3-oxopropoxy]-3-methoxypropoxy]-4-(trifluoromethyl)-2,3-dihydropyridazin-3-one and Isomer B: 5-[(2R)-2-[3-[4-(5-chloropyrimidin-2-yl)piperazin-1-yl]-3-oxopropoxy]-3-methoxypropoxy]-4-(trifluoromethyl)-2,3-dihydropyridazin-3-one and Isomer C: 5-[[(2S)-1-[3-[4-(5-chloropyrimidin-2-yl)piperazin-1-yl]-3-oxopropoxy]-3-methoxypropan-2-yl]oxy]-4-(trifluoromethyl)-2,3-dihydropyridazin-3-one and Isomer D: 5-[[(2R)-1-[3-[4-(5-chloropyrimidin-2-yl)piperazin-1-yl]-3-oxopropoxy]-3-methoxypropan-2-yl]oxy]-4-(trifluoromethyl)-2,3-dihydropyridazin-3-one A mixture of 5-((1-(3-(4-(5-chloropyrimidin-2-yl)piperazin-1-yl)-3-oxopropoxy)-3-methoxypropan-2-yl)oxy)-4-(trifluoromethyl)-2-((2-(trimethylsilyl)ethoxy)methyl)pyridazin-3(2H)-one and 5-(2-(3-(4-(5-chloropyrimidin-2-yl)piperazin-1-yl)-3-oxopropoxy)-3-methoxypropoxy)-4-(trifluoromethyl)-2-((2-(trimethylsilyl)ethoxy)methyl)pyridazin-3 (6H)-one (400 mg, 0.61 mmol, 1 equiv) and TFA (2 mL) in DCM (10 mL) was stirred for 1 h at RT, and then the resulting mixture was concentrated under reduced pressure. The residue was purified by C18 reverse phase chromatography eluting with H$_2$O/ACN, and then the residue was further purified by Prep-HPLC and Chiral-Prep-HPLC. The absolute stereochemistry of Example 560 Isomer A and Example 560 Isomer B was assigned based on a protein X-ray crystal structure obtained of Example 513A, which confirmed (S)-absolute stereochemistry of the more potent enantiomer. The stereochemistry of Examples 560 Isomers C and D was arbitrarily assigned. (The position of the methyl group was confirmed by $^1$H-NMR).

Example 560 Isomers A and B: Chiral-Prep-HPLC (CHIRALPAK IE-3, 3 µm, 0.46×10 cm column, eluting with a gradient of MtBE (0.1% DEA):EtOH=90:10, at a flow rate of 1 mL/min) to afford the title compounds as white solids.

Example 560 Isomer A

LCMS: [M+H]$^+$ 521.05, $^1$H NMR (300 MHz, DMSO-d$_6$) δ 13.23 (s, 1H), 8.45 (d, J=5.7 Hz, 2H), 8.27 (s, 1H), 5.18 (dd, J=6.3, 3.0 Hz, 1H), 3.74-3.50 (m, 14H), 3.31 (s, 3H), 2.57 (t, J=6.4 Hz, 2H). tR=3.682 min.

Example 560 Isomer B

LCMS: [M+H]$^+$ 521.05, $^1$H NMR (300 MHz, DMSO-d$_6$) δ 13.23 (s, 1H), 8.46 (d, J=5.7 Hz, 2H), 8.28 (s, 1H), 5.18 (dd, J=6.6, 3.5 Hz, 1H), 3.74-3.49 (m, 14H), 3.31 (s, 3H), 2.56 (t, J=6.5 Hz, 2H). tR=8.735 min.

Example 560 Isomers C and D: Chiral-Prep-HPLC (CHIRALPAK IG-3, 3 µm, 0.46×10 cm column, eluting with a gradient of MtBE (0.1% DEA):EtOH=70:30, at a flow rate of 1 mL/min) to afford the title compounds as white solids.

Example 560 Isomer C

LCMS: [M+H]$^+$ 521.05, $^1$H NMR (300 MHz, DMSO-d$_6$) δ 13.31 (s, 1H), 8.46 (d, J=5.7 Hz, 2H), 8.24 (s, 1H), 4.52 (dd, J=10.7, 3.7 Hz, 1H), 4.42 (dd, J=10.7, 5.6 Hz, 1H), 3.81-3.65 (m, 11H), 3.45 (d, J=5.2 Hz, 2H), 3.31 (s, 3H), 2.58 (t, J=6.6 Hz, 2H). tR=2.653 min.

Example 560 Isomer D

LCMS: [M+H]$^+$ 521.05, $^1$H NMR (300 MHz, DMSO-d$_6$) δ 13.31 (s, 1H), 8.47 (d, J=5.7 Hz, 2H), 8.25 (s, 1H), 4.53 (dd, J=10.7, 3.7 Hz, 1H), 4.46-4.32 (m, 1H), 3.83-3.63 (m, 7H), 3.53-3.46 (m, 4H), 3.45 (d, J=5.1 Hz, 2H), 3.30 (s, 3H), 2.59 (t, J=6.7 Hz, 2H). tR=3.471 min.

Example 561: 5-[[(2S)-1-(3-Oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one

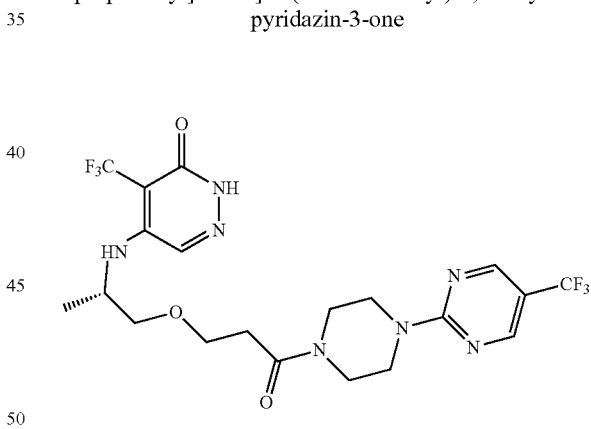

A solution of Int-A13 (150 mg, 0.485 mmol, 1 equiv), HATU (184 mg, 0.484 mmol, 1 equiv), DIPEA (0.32 mL, 2 mmol, 4 equiv), and Int-A2 (148 mg, 0.487 mmol, 1 equiv) in DMF (2 mL) was stirred for 0.5 h at 25° C. To the resulting mixture was added ethanolamine (0.5 mL) and the reaction mixture was stirred for 0.5 h at 25° C. After concentration under reduced pressure, the residue was purified by C18 reverse phase chromatography eluting with H$_2$O/CH$_3$CN to afford the title compound (50.7 mg, 20%) as a white solid. LCMS: [M+H]$^+$ 524.20, $^1$H NMR (300 MHz, DMSO-d$_6$) δ: 12.45 (s, 1H), 8.73 (s, 2H), 7.92 (s, 1H), 6.28 (dd, J=8.5, 4.2 Hz, 1H), 4.13-4.18 (m, 1H), 3.90-3.75 (m, 4H), 3.63-3.73 (m, 2H), 3.60-3.45 (m, 6H), 2.60 (t, J=6.6 Hz, 2H), 1.16 (d, J=6.1 Hz, 3H).

Example 561 was also prepared according to the procedure outlined below.

Step 1: 1-(4-(5-Trifluoromethyl)pyrimidin-2-yl) piperazin-1-yl)prop-2-en-1-one

A solution of Int-A2 (300 g, 1.1 mol, 1 equiv), prop-2-enoyl prop-2-enoate (156 g, 1.24 mol, 1.1 equiv) and TEA (375 g, 3.71 mol, 3.3 equiv) in DCM (2.5 L) was stirred for 30 min at −40° C. 2 L of DCM was added to the resulting solution after the reaction completed and the resulting solution was extracted with 2×1 L of water. The organic layer was concentrated and the residue was applied onto a silica gel column eluting with EtOAc/petroleum ether (1/4). The collected fractions were combined and concentrated to afford 200 g (62.6%) of title compound as a white solid. LCMS: [M+H]$^+$ 287.23.

Step 2: (S)-Tert-butyl 1-(3-oxo-3-(4-(5-(trifluoromethyl)pyrimidin-2-yl)piperazin-1-yl)propoxy)propan-2-ylcarbamate A solution of tert-butyl N-[(2S)-1-hydroxypropan-2-yl] carbamate (244 g, 1.39 mol, 2 equiv), 1-(4-(5-(trifluoromethyl)pyrimidin-2-yl)piperazin-1-yl)prop-2-en-1-one (200 g, 699 mmol, 1 equiv), and Cs$_2$CO$_3$ (273 g, 838 mmol, 1.2 equiv) in CH$_3$CN (1.4 L) was stirred for 24 h at 25° C. The solids were filtered and the filtrate was concentrated under reduced pressure. The residue was applied onto a silica gel column eluting with EtOAc/petroleum ether (1/3) to afford 257 g (80%) of title compound as a white solid. LCMS: [M+H]$^+$ 462.27.

Step 3: (S)-3-(2-Aminopropoxy)-1-(4-(5-(trifluoromethyl)pyrimidin-2-yl)piperazin-1-yl)propan-1-one A solution of 1-(4-(5-(trifluoromethyl)pyrimidin-2-yl) piperazin-1-yl)prop-2-en-1-one (257 g, 557 mmol, 1 equiv) and dioxane/HCl (4 mol/L, 1 L) was stirred for 2 h at 25° C. The pH value of the reaction mixture was adjusted to 7 by the addition of NaOH (aqueous). After concentration under reduced pressure, the residue was purified by C18 reverse phase chromatography eluting with H$_2$O/CH$_3$CN to afford 167 g (83.0%) of title compound as a white solid. LCMS: [M+H]$^+$ 362.34.

Step 4: (S)-2-(4-Methoxybenzyl)-5-(1-(3-oxo-3-(4-(5-(trifluoromethyl)pyrimidin-2-yl)piperazin-1-yl) propoxy)propan-2-ylamino)-4-(trifluoromethyl) pyridazin-3(2H)-one A solution of (S)-3-(2-aminopropoxy)-1-(4-(5-(trifluoromethyl)pyrimidin-2-yl)piperazin-1-yl)propan-1-one (167 g, 462 mmol, 1 equiv), Int-A20 (161 g, 505 mmol, 1.1 equiv), and TEA (210 g, 2.08 mol, 4.5 equiv) in CH$_3$CN (1.2 L) was stirred for 6 h at 25° C. The solids were filtered and the filtrate was combined and concentrated under reduced pressure. The residue was applied onto a silica gel column with EtOAc/petroleum ether (1/1) to afford 230 g (77.3%) of title compound as a white solid. LCMS: [M+H]$^+$ 644.41.

Step 5: 5-[[(2S)-1-(3-oxo-3-[4-[5-(trifluoromethyl) pyrimidin-2-yl]piperazin-1-yl]propoxy)propan-2-yl] amino]-4-(trifluoromethyl)-2,3-dihydropyridazin-3-one A solution of (S)-2-(4-methoxybenzyl)-5-(1-(3-oxo-3-(4-(5-(trifluoromethyl)pyrimidin-2-yl)piperazin-1-yl)propoxy) propan-2-ylamino)-4-(trifluoromethyl)pyridazin-3(2H)-one (230 g, 358 mmol, 1 equiv) and TfOH (115 mL) in TFA (1.0 L) was stirred for 2 h at 25° C. The reaction was then quenched by the addition of 4.0 L of water. The resulting solution was extracted with 2×1 L of EtOAc. The pH value of the organic layers was adjusted to 8 by aqueous K$_2$CO$_3$ solution. The organic layer was combined and concentrated. The residue was applied onto a silica gel column with EtOAc/petroleum ether (4/1). The fractions were combined and concentrated followed by further washing with EtOAc to afford 114 g (61.2%) of title compound as a white crystalline solid. LCMS: [M+H]$^+$ 524.25[M+H]$^+$, $^1$H NMR (400 MHz, DMSO-d$_6$) δ: 12.45 (s, 1H), 8.73 (s, 2H), 7.91 (s, 1H), 6.29-6.26 (m, 1H), 4.12-4.19 (m, 1H), 3.81-3.85 (m, 4H), 3.73-3.79 (m, 2H), 3.54-3.69 (m, 6H), 2.60 (t, J=9.2 Hz, 2H), 1.16 (d, J=12.4 Hz, 3H).

Characterization of Crystalline 5-[[(2S)-1-(3-oxo-3-[4-[5-(trifluoromethyl)pyrimidin-2-yl]piperazin-1-yl] propoxy)propan-2-yl]amino]-4-(trifluoromethyl)-2, 3-dihydropyridazin-3-one (Form A)

The solid product from Step 5 was confirmed as a crystalline solid according to XRPD analysis. The XRPD pattern of crystalline 5-[[(2S)-1-(3-oxo-3-[4-[5-(trifluoromethyl)pyrimidin-2-yl]piperazin-1-yl]propoxy)propan-2-yl] amino]-4-(trifluoromethyl)-2,3-dihydropyridazin-3-one ("Compound 561 Form A" or "Form A") is shown in FIG. 8 and the peak data is given below in Table X1.

TABLE X1

| XRPD Peak Data for Form A. | | | | |
|---|---|---|---|---|
| Pos. [°2Th.] | Height [cts] | FWHM Left [°2Th.] | d-spacing [Å] | Rel. Int. [%] |
| 5.8 | 929.0 | 0.1 | 15.4 | 33.0 |
| 10.8 | 932.8 | 0.1 | 8.2 | 33.1 |
| 11.2 | 202.2 | 0.1 | 7.9 | 7.2 |
| 11.9 | 791.4 | 0.2 | 7.5 | 28.1 |
| 12.3 | 213.6 | 0.1 | 7.2 | 7.6 |
| 13.3 | 515.1 | 0.1 | 6.7 | 18.3 |
| 13.5 | 437.1 | 0.1 | 6.6 | 15.5 |
| 13.8 | 172.1 | 0.1 | 6.4 | 6.1 |
| 15.5 | 541.5 | 0.1 | 5.7 | 19.2 |
| 15.8 | 270.0 | 0.1 | 5.6 | 9.6 |
| 16.6 | 127.7 | 0.1 | 5.4 | 4.5 |
| 17.2 | 2814.9 | 0.1 | 5.1 | 100.0 |
| 17.7 | 645.6 | 0.1 | 5.0 | 22.9 |
| 18.0 | 611.5 | 0.1 | 4.9 | 21.7 |
| 18.4 | 417.5 | 0.1 | 4.8 | 14.8 |
| 18.7 | 163.9 | 0.1 | 4.7 | 5.8 |
| 19.5 | 604.9 | 0.1 | 4.5 | 21.5 |
| 20.1 | 278.7 | 0.1 | 4.4 | 9.9 |
| 20.5 | 506.0 | 0.1 | 4.3 | 18.0 |
| 21.0 | 1121.6 | 0.1 | 4.2 | 39.9 |
| 21.6 | 2094.1 | 0.1 | 4.1 | 74.4 |
| 21.8 | 1357.3 | 0.1 | 4.1 | 48.2 |
| 22.1 | 851.6 | 0.1 | 4.0 | 30.3 |
| 22.4 | 613.7 | 0.1 | 4.0 | 21.8 |
| 22.7 | 1295.5 | 0.1 | 3.9 | 46.0 |
| 23.0 | 2760.9 | 0.1 | 3.9 | 98.1 |
| 23.4 | 1332.8 | 0.1 | 3.8 | 47.4 |
| 24.2 | 379.7 | 0.1 | 3.7 | 13.5 |
| 24.7 | 349.2 | 0.2 | 3.6 | 12.4 |
| 24.9 | 1343.4 | 0.1 | 3.6 | 47.7 |
| 25.5 | 125.9 | 0.1 | 3.5 | 4.5 |
| 26.2 | 113.9 | 0.1 | 3.4 | 4.1 |
| 26.7 | 449.2 | 0.1 | 3.3 | 16.0 |
| 27.5 | 93.8 | 0.2 | 3.2 | 3.3 |
| 28.0 | 176.1 | 0.1 | 3.2 | 6.3 |
| 28.7 | 136.0 | 0.2 | 3.1 | 4.8 |
| 30.8 | 272.1 | 0.1 | 2.9 | 9.7 |
| 31.4 | 138.3 | 0.3 | 2.8 | 4.9 |
| 32.7 | 79.4 | 0.2 | 2.7 | 2.8 |
| 36.5 | 40.6 | 0.3 | 2.5 | 1.4 |

Form A exhibits a DSC thermogram having an endotherm peak at a temperature of about 174° C. Form A shows a weight loss of about 0.5% when heated to 150° C. FIG. 9 shows a DSC thermogram and a TGA thermogram of Compound 561 Form A. FIG. 10 shows a DVS isotherm of Compound 561 Form A. The data suggest that Form A may be an anhydrous crystalline form.

The following examples in Table E9 were similarly prepared according to the method described for Example 561.

TABLE E9

| Example | Name, structure, analytical data | Int. |
|---|---|---|
| Example 562 | 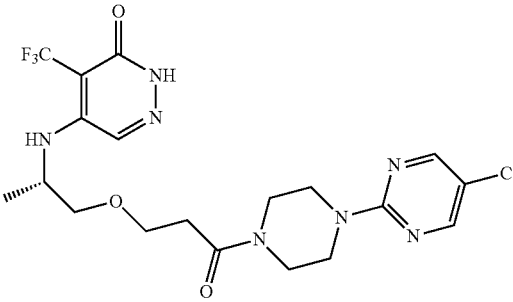<br>5-[[(2S)-1-[3-[4-(5-Chloropyrimidin-2-yl)piperazin-1-yl]-3-oxopropoxy]propan-2-yl]amino]-4-(trifluoromethyl)-2,3-dihydropyridazin-3-one;<br>LCMS: [M + H]$^+$ 490.0;<br>$^1$H NMR (400 MHz, Methanol-$d_4$) δ 8.33 (s, 2H), 7.95 (s, 1H), 4.17 (q, J = 6.1 Hz, 1H), 3.89-3.75 (m, 6H), 3.78-3.57 (m, 5H), 3.52 (dd, J = 9.7, 6.8 Hz, 1H), 2.71 (t, J = 6.0 Hz, 2H), 1.27 (d, J = 6.6 Hz, 3H). | Int-A13 and Int-A3 |
| Example 563 | 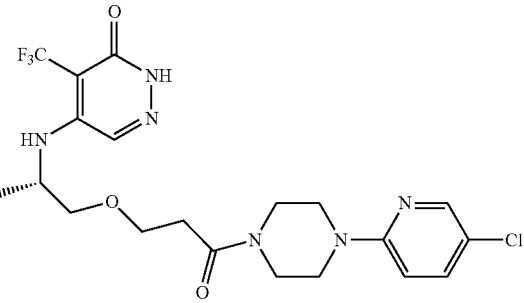 [SMILES: C[C@@H](COCCC(=O)N1CCN(c2ccc(Cl)cn2)CC1)Nc1cn[nH]c(=O)c1C(F)(F)F]<br>5-[[(2S)-1-[3-[4-(5-Chloropyridin-2-yl)piperazin-1-yl]-3-oxopropoxy]propan-2-yl]amino]-4-(trifluoromethyl)-2,3-dihydropyridazin-3-one;<br>LCMS: [M + H]$^+$ 489.35;<br>$^1$HNMR (400 MHz, Methanol-$d_4$) δ: 8.08 (d, J = 2.4 Hz, 1H), 7.95 (s, 1H), 7.55 (dd, J = 9.1, 2.7 Hz, 1H), 6.81 (d, J = 9.1 Hz, 1H), 4.20-4.10 (m, 1H), 3.90-3.69 (m, 2H), 3.74-3.51 (m, 4H), 3.49-3.37 (m, 6H), 2.70 (t, J = 6.0 Hz, 2H), 1.27 (d, J = 6.6 Hz, 3H). | Int-A13 and Int-A5 |
| Example 564 | 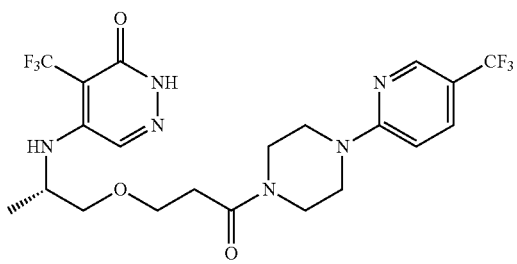 [SMILES: C[C@@H](COCCC(=O)N1CCN(c2ccc(C(F)(F)F)cn2)CC1)Nc1cn[nH]c(=O)c1C(F)(F)F]<br>5-[[(2S)-1-(3-Oxo-3-[4-[5-(trifluoromethyl)pyridin-2-yl]piperazin-1-yl]propoxy)propan-2-yl]amino]-4-(trifluoromethyl)-2,3-dihydropyridazin-3-one;<br>LCMS: [M + H]$^+$ 523.30;<br>$^1$H NMR (300 MHz, Methanol-$d_4$) δ 8.36 (s, 1H), 7.93 (s, 1H), 7.74 (dd, J = 9.1, 2.5 Hz, 1H), 6.87 (d, J = 9.1 Hz, 1H), 4.20-4.14 (m, 1H), 3.85-3.80 (m, 2H), 3.78-3.68 (m, 8H), 3.61 (dd, J = 9.7, 4.0 Hz, 1H), 3.49 (dd, J = 9.7, 6.8 Hz, 1H), 2.68 (t, J = 6.0 Hz, 2H), 1.25 (d, J = 6.6 Hz, 3H). | Int-A13 and Int-A18 |

Example 565 Isomer A: 5-[[(2S,5S)-5-[2-[4-(5-Chloropyrimidin-2-yl)piperazin-1-yl]-2-oxoethyl]oxolan-2-yl]methoxy]-4-(trifluoromethyl)-2,3-dihydropyridazin-3-one and Example 565 Isomer B: 5-[[(2R,5R)-5-[2-[4-(5-Chloropyrimidin-2-yl)piperazin-1-yl]-2-oxoethyl]oxolan-2-yl]methoxy]-4-(trifluoromethyl)-2,3-dihydropyridazin-3-one and Example 565 Isomer C: 5-[[(2S,5R)-5-[2-[4-(5-Chloropyrimidin-2-yl)piperazin-1-yl]-2-oxoethyl]oxolan-2-yl]methoxy]-4-(trifluoromethyl)-2,3-dihydropyridazin-3-one and Example 565 Isomer D: 5-[[(2R,5S)-5-[2-[4-(5-Chloropyrimidin-2-yl)piperazin-1-yl]-2-oxoethyl]oxolan-2-yl]methoxy]-4-(trifluoromethyl)-2,3-dihydropyridazin-3-one Example 565

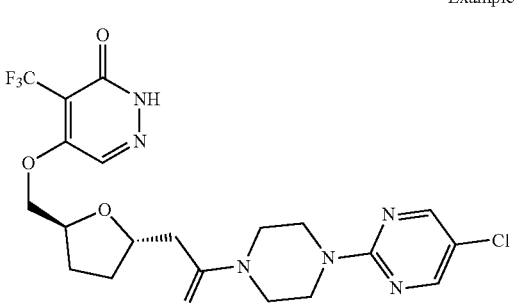

Isomer A

Example 565

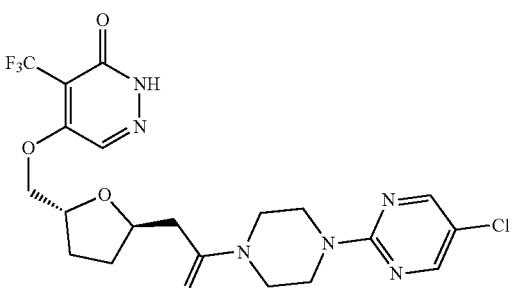

Isomer B

Example 565

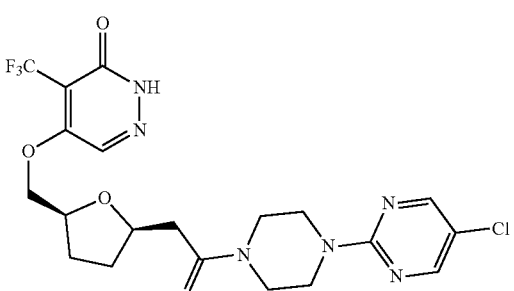

Isomer C

Example 565

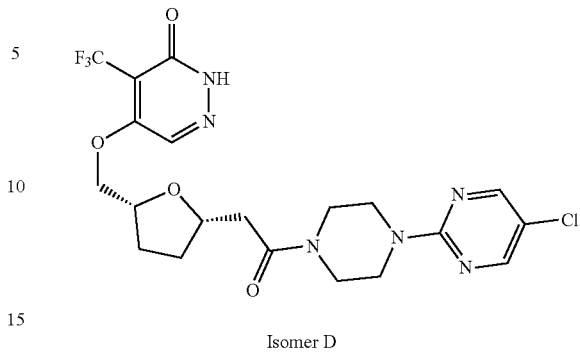

Isomer D

Step 1: 2-[5-[(Benzyloxy)methyl]oxolan-2-yl]-1-[4-(5-chloropyrimidin-2-yl)piperazin-1-yl]ethan-1-one A solution of 2-[5-[(benzyloxy)methyl]oxolan-2-yl]acetic acid (2 g, 7.99 mmol, 1 equiv), HATU (3949.7 mg, 10.39 mmol, 1.3 equiv), DIPEA (4130.9 mg, 31.96 mmol, 4 equiv), and Int-A3 (1587.3 mg, 7.99 mmol, 1 equiv) in DMF (25 mL) was stirred for 1.5 h at RT. After concentration under reduced pressure, the residue was purified by C18 reverse phase chromatography eluting with $H_2O$/ACN to afford 2.6 g (76%) of the title compound as a yellow oil. LCMS: $[M+H]^+$ 431.18.

Step 2: 1-[4-(5-Chloropyrimidin-2-yl)piperazin-1-yl]-2-[5-(hydroxymethyl)oxolan-2-yl]ethan-1-one A solution of 2-[5-[(benzyloxy)methyl]oxolan-2-yl]-1-[4-(5-chloropyrimidin-2-yl)piperazin-1-yl]ethan-1-one (2.17 g, 5 mmol, 1 equiv), TMSI (5 g, 25 mmol, 5.00 equiv) in DCM (20 mL) was stirred overnight at 40° C. After concentration, the residue was purified by C18 reverse phase chromatography eluting with $H_2O$/ACN to afford 1.6 g (94%) of the title compound as a yellow solid. LCMS: $[M+H]^+$ 341.14.

Step 3: Methyl 5-[(5-[2-[4-(5-chloropyrimidin-2-yl)piperazin-1-yl]-2-oxoethyl]oxolan-2-yl)methoxy]-4-(trifluoromethyl)-2-[[2-(trimethylsilyl)ethoxy]methyl]-2,3-dihydropyridazin-3-one A solution of 1-[4-(5-chloropyrimidin-2-yl)piperazin-1-yl]-2-[5-(hydroxymethyl)oxolan-2-yl]ethan-1-one (800 mg, 2.35 mmol, 1 equiv), $Cs_2CO_3$ (2294.4 mg, 7.04 mmol, 3 equiv), Int-A6 (1543.6 mg, 4.69 mmol, 2.00 equiv) in DMF (20 mL) was stirred for 3 h at 80° C. The solids were filtered and the resulting solution was quenched with water (50 mL) and extracted with EtOAc (3×60 mL) and the organic layers combined. The solution was dried over anhydrous sodium sulfate and concentrated under vacuum. The residue was applied onto a silica gel column with EtOAc/petroleum ether (1:1) to afford 600 mg (40%) of the title compound as a yellow solid. LCMS: $[M+H]^+$ 633.22.

Step 4: 5-[[(2S,5S)-5-[2-[4-(5-Chloropyrimidin-2-yl)piperazin-1-yl]-2-oxoethyl]oxolan-2-yl]methoxy]-4-(trifluoromethyl)-2,3-dihydropyridazin-3-one, 5-[[(2R,5R)-5-[2-[4-(5-chloropyrimidin-2-yl)piperazin-1-yl]-2-oxoethyl]oxolan-2-yl]methoxy]-4-(trifluoromethyl)-2,3-dihydropyridazin-3-one, 5-[[(2S,5R)-5-[2-[4-(5-chloropyrimidin-2-yl)piperazin-1-yl]-2-oxoethyl]oxolan-2-yl]methoxy]-4-(trifluoromethyl)-2,3-dihydropyridazin-3-one and 5-[[(2R,5S)-5-[2-[4-(5-chloropyrimidin-2-yl)piperazin-1-yl]-2-oxoethyl]oxolan-2-yl]methoxy]-4-(trifluoromethyl)-2,3-dihydropyridazin-3-one A solution of 5-[(5-[2-[4-(5-chloropyrimidin-2-yl)piperazin-1-yl]-2-oxoethyl]oxolan-2-yl)methoxy]-4-(trifluoromethyl)-2-[[2-(trimethylsilyl)ethoxy]methyl]-2,3-dihydropyridazin-3-one (600 mg, 0.95 mmol, 1 equiv) and TFA (4 mL) in DCM (20 mL) was stirred for 1 h at RT. After concentration, the residue was purified by C18 reverse phase chromatography eluting with H$_2$O/ACN. The residue was further purified by Prep-HPLC and Chiral-Prep-HPLC (CHIRALPAK IA-3, 3 µm, 0.46×5 cm column, eluting with a gradient of MtBE (10 mM NH$_3$):IPA=85:15, at a flow rate of 1 mL/min) yielding (after arbitrary assignment of absolute stereochemistry) the title compounds as white solids.

Example 565 Isomer A 46.5 mg, 10%, LCMS: [M+H]$^+$ 503.20, $^1$H NMR (300 MHz, Methanol-d$_4$) δ 8.29 (s, 2H), 8.22 (s, 1H), 4.54 (dd, J=10.7, 3.1 Hz, 1H), 4.41-4.24 (m, 3H), 3.90-3.74 (m, 2H), 3.73-3.58 (m, 4H), 3.56-3.53 (m, 2H), 2.76 (dd, J=14.8, 7.8 Hz, 1H), 2.55 (dd, J=14.8, 4.8 Hz, 1H), 2.15-2.06 (m, 2H), 1.96-1.92 (m, 1H), 1.80-1.68 (m, 1H). tR=1.725 min.

Example 565 Isomer B 46.3 mg, 10%, LCMS: [M+H]$^+$ 503.20, $^1$H NMR (300 MHz, Methanol-d$_4$) δ 8.29 (s, 2H), 8.20 (s, 1H), 4.46-4.33 (m, 4H), 3.90-3.56 (m, 8H), 2.80 (dd, J=14.8, 7.8 Hz, 1H), 2.55 (dd, J=14.8, 4.8 Hz, 1H), 2.24-2.18 (m, 2H), 1.89-1.76 (m, 1H), 1.73-1.72 (m, 1H). tR=2.396 min.

Example 565 Isomer C 34.5 mg 7%, LCMS: [M+H]$^+$ 503.20, $^1$H NMR (300 MHz, Methanol-d$_4$) δ 8.29 (s, 2H), 8.20 (s, 1H), 4.46-4.33 (m, 4H), 3.90-3.54 (m, 8H), 2.80 (dd, J=14.8, 7.8 Hz, 1H), 2.55 (dd, J=14.8, 4.8 Hz, 1H), 2.24-2.17 (m, 2H), 1.89-1.76 (m, 1H), 1.73-1.72 (m, 1H). tR=3.189 min.

Example 565 Isomer D 35.2 mg 7%, LCMS: [M+H]$^+$ 503.20, $^1$H NMR (300 MHz, Methanol-d$_4$) δ 8.29 (s, 2H), 8.22 (s, 1H), 4.54 (dd, J=10.7, 3.1 Hz, 1H), 4.41-4.24 (m, 3H), 3.90-3.74 (m, 2H), 3.73-3.58 (m, 4H), 3.56-3.55 (m, 2H), 2.76 (dd, J=14.8, 7.8 Hz, 1H), 2.55 (dd, J=14.8, 4.8 Hz, 1H), 2.17-2.06 (m, 2H), 1.96-1.92 (m, 1H), 1.80-1.68 (m, 1H). tR=3.805 min.

Example 566 Isomer A: 4-Chloro-5-[[(2S,5S)-5-[2-[4-(5-chloropyrimidin-2-yl)piperazin-1-yl]-2-oxoethyl]oxolan-2-yl]methoxy]-2,3-dihydropyridazin-3-one and Example 566 Isomer B: 4-Chloro-5-[[(2R,5R)-5-[2-[4-(5-chloropyrimidin-2-yl)piperazin-1-yl]-2-oxoethyl]oxolan-2-yl]methoxy]-2,3-dihydropyridazin-3-one Example 566 Isomer C: 4-Chloro-5-[[(2S,5R)-5-[2-[4-(5-chloropyrimidin-2-yl)piperazin-1-yl]-2-oxoethyl]oxolan-2-yl]methoxy]-2,3-dihydropyridazin-3-one and Example 566 Isomer D: 4-Chloro-5-[[(2R,5S)-5-[2-[4-(5-chloropyrimidin-2-yl)piperazin-1-yl]-2-oxoethyl]oxolan-2-yl]methoxy]-2,3-dihydropyridazin-3-one

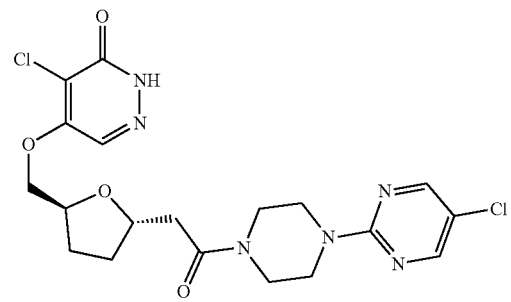

Example 566
Isomer A

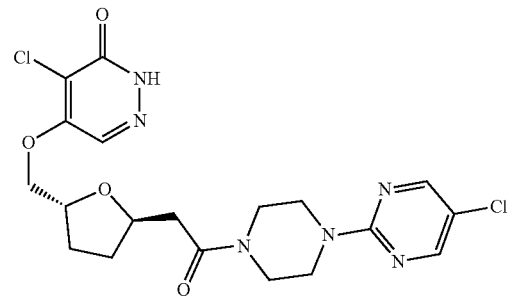

Example 566
Isomer B

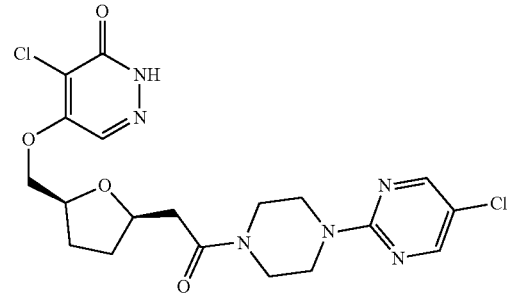

Example 566
Isomer C

Example 566

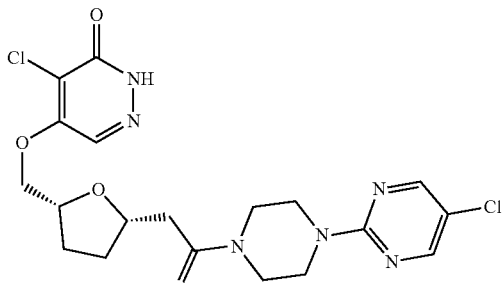

Isomer D

Step 1: 4-Chloro-5-[(5-[2-[4-(5-chloropyrimidin-2-yl)piperazin-1-yl]-2-oxoethyl]oxolan-2-yl)methoxy]-2-[[2-(trimethylsilyl)ethoxy]methyl]-2,3-dihydro-pyridazin-3-one A solution of 1-[4-(5-chloropyrimidin-2-yl)piperazin-1-yl]-2-[5-(hydroxymethyl)oxolan-2-yl]ethan-1-one (840 mg, 2.46 mmol, 1 equiv), NaH (118.3 mg, 4.93 mmol, 2 equiv), and Int-A7 (2183.0 mg, 7.39 mmol, 3.00 equiv) in ACN (20 mL) was stirred for 1.5 h at RT. The solvent was concentrated under reduced pressure and the residue was applied onto a silica gel column eluting with EtOAc/petroleum ether (1:1) to afford 850 mg (58%) of the title compound as a yellow oil. LCMS: [M+H]$^+$ 599.20.

Step 2: 4-Chloro-5-[[(2S,5S)-5-[2-[4-(5-chloropyrimidin-2-yl)piperazin-1-yl]-2-oxoethyl]oxolan-2-yl]methoxy]-2,3-dihydropyridazin-3-one, 4-chloro-5-[[(2S,5R)-5-[2-[4-(5-chloropyrimidin-2-yl)piperazin-1-yl]-2-oxoethyl]oxolan-2-yl]methoxy]-2,3-dihydropyridazin-3-one, 4-chloro-5-[[(2R,5R)-5-[2-[4-(5-chloropyrimidin-2-yl)piperazin-1-yl]-2-oxoethyl]oxolan-2-yl]methoxy]-2,3-dihydropyridazin-3-one and 4-chloro-5-[[(2R,5S)-5-[2-[4-(5-chloropyrimidin-2-yl)piperazin-1-yl]-2-oxoethyl]oxolan-2-yl]methoxy]-2,3-dihydropyridazin-3-one A solution of 4-chloro-5-[(5-[2-[4-(5-chloropyrimidin-2-yl)piperazin-1-yl]-2-oxoethyl]oxolan-2-yl)methoxy]-2-[[2-(trimethylsilyl)ethoxy]methyl]-2,3-dihydropyridazin-3-one (800 mg, 1.33 mmol, 1 equiv) and TFA (4 mL) in DCM (20 mL) was stirred for 1 h at RT. After concentration, the residue was purified by C18 reverse phase chromatography eluting with H$_2$O/ACN. The residue was further purified by Prep-HPLC and Chiral-Prep-HPLC (CHIRALPAK IA-3, 3 μm, 0.46×15 cm column, eluting with a gradient of MtBE (0.3% isopropylamine):IPA=75:25, at a flow rate of 1 mL/min) yielding (after arbitrary assignment of absolute stereochemistry) the title compounds as white solids.

Example 566 Isomer A 49.1 mg, 8%, LCMS: [M+H]$^+$ 469.10, $^1$H NMR (300 MHz, Methanol-d$_4$) δ 8.28 (s, 2H), 8.15 (s, 1H), 4.51-4.47 (m, 1H), 4.35-4.28 (m, 3H), 3.86-3.62 (m, 6H), 3.58-3.51 (m, 2H), 2.79 (dd, J=14.7, 7.9 Hz, 1H), 2.56 (dd, J=14.7, 4.7 Hz, 1H), 2.18-2.11 (m, 2H), 2.00-1.98 (m, 1H), 1.96-1.95 (m, 1H); tR=2.184 min.

Example 566 Isomer B 66.9 mg, 11%, LCMS: [M+H]$^+$ 469.15, $^1$H NMR (300 MHz, Methanol-d$_4$) δ 8.28 (s, 2H), 8.14 (s, 1H), 4.43-4.31 (m, 4H), 3.94-3.60 (m, 5H), 3.58-3.51 (m, 3H), 2.79 (dd, J=14.7, 7.9 Hz, 1H), 2.56 (dd, J=14.7, 4.7 Hz, 1H), 2.24-2.17 (m, 2H), 1.89-1.85 (m, 1H), 1.77-1.74 (m, 1H). tR=3.458 min Example 566 Isomer C 47.7 mg, 8%, LCMS: [M+H]$^+$ 469.10, $^1$H NMR (300 MHz, Methanol-d$_4$) δ 8.28 (s, 2H), 8.15 (s, 1H), 4.51-4.47 (m, 1H), 4.35-4.28 (m, 3H), 3.86-3.62 (m, 6H), 3.58-3.51 (m, 2H), 2.79 (dd, J=14.7, 7.9 Hz, 1H), 2.56 (dd, J=14.7, 4.7 Hz, 1H), 2.18-2.11 (m, 2H), 2.00-1.98 (m, 1H), 1.96-1.95 (m, 1H). tR=4.325 min Example 566 Isomer D 37.0 mg, 6%, LCMS: [M+H]$^+$ 469.10, $^1$H NMR (300 MHz, Methanol-d$_4$) δ 8.31 (s, 2H), 8.14 (s, 1H), 4.44-4.31 (m, 4H), 3.94-3.85 (m, 2H), 3.79-3.52 (m, 6H), 2.79 (dd, J=14.7, 7.9 Hz, 1H), 2.56 (dd, J=14.7, 4.7 Hz, 1H), 2.26-2.20 (m, 2H), 1.89-1.85 (m, 1H), 1.77-1.74 (m, 1H). tR=5.695 min.

Example 567 Isomer A: 5-((((2S,5R)-5-(2-(4-(5-Chloropyrimidin-2-yl)piperazin-1-yl)-2-oxoethyl)tetrahydrofuran-2-yl)methyl)amino)-4-(trifluoromethyl)pyridazin-3(2H)-one and Example 567 Isomer B: 5-((((2R,5S)-5-(2-(4-(5-Chloropyrimidin-2-yl)piperazin-1-yl)-2-oxoethyl)tetrahydrofuran-2-yl)methyl)amino)-4-(trifluoromethyl)pyridazin-3(2H)-one Example 567 Isomer C: 5-((((2S,5S)-5-(2-(4-(5-Chloropyrimidin-2-yl)piperazin-1-yl)-2-oxoethyl)tetrahydrofuran-2-yl)methyl)amino)-4-(trifluoromethyl)pyridazin-3(2H)-one and Example 567 Isomer D: 5-((((2R,5R)-5-(2-(4-(5-Chloropyrimidin-2-yl)piperazin-1-yl)-2-oxoethyl)tetrahydrofuran-2-yl)methyl)amino)-4-(trifluoromethyl)pyridazin-3(2H)-one Example 567

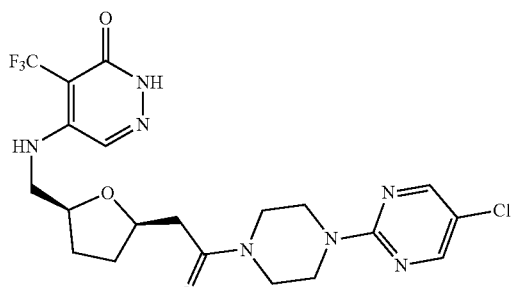

Isomer A

Example 567

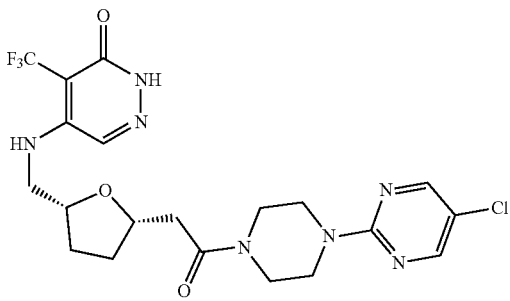

Isomer B

Example 567

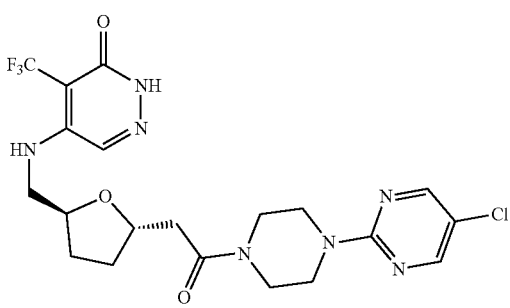

Isomer C

Example 567

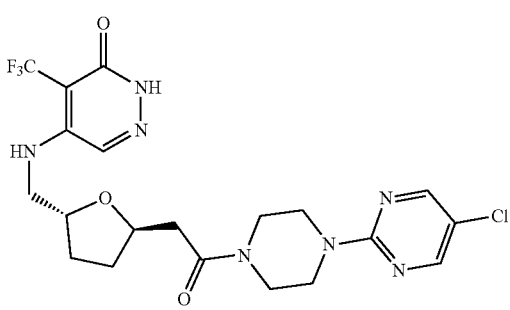

Isomer D

Step 1: (5-[2-[4-(5-Chloropyrimidin-2-yl)piperazin-1-yl]-2-oxoethyl]oxolan-2-yl)methyl methanesulfonate A solution of 1-[4-(5-chloropyrimidin-2-yl)piperazin-1-yl]-2-[5-(hydroxymethyl)oxolan-2-yl]ethan-1-one (1 g, 2.93 mmol, 1 equiv), TEA (890.7 mg, 8.80 mmol, 3 equiv), and methanesulfonyl methanesulfonate (766.7 mg, 4.40 mmol, 1.5 equiv) in DCM (20 mL) was stirred for 1 h at 25° C. To the resulting solution was added 20 mL of aqueous NaHCO$_3$, and the resulting solution was extracted with 3×20 mL of DCM and the organic layers combined. The resulting solution was washed with 20 mL of NH$_4$Cl(aq) and the organic layers were combined and dried over anhydrous sodium sulfate and concentrated under vacuum to afford 1.1 g (90%) of the title compound as a yellow oil. LCMS: [M+H]$^+$ 419.11.

Step 2: 2-[5-(Azidomethyl)oxolan-2-yl]-1-[4-(5-chloropyrimidin-2-yl)piperazin-1-yl]ethan-1-one A solution of (5-[2-[4-(5-chloropyrimidin-2-yl)piperazin-1-yl]-2-oxoethyl]oxolan-2-yl)methyl methanesulfonate (1.1 g, 2.63 mmol, 1 equiv), and NaN$_3$ (0.2 g, 3.15 mmol, 1.2 equiv) in DMF (20 mL) was stirred for 4 h at 90° C. The resulting solution was diluted with 30 mL of water and extracted with 3×20 mL of EtOAc. The organic layers were combined and the resulting solution was washed with 3×20 mL of saturated sodium chloride, dried over anhydrous sodium sulfate and concentrated to afford 600 mg (62%) of the title compound as a yellow oil. LCMS: [M+H]$^+$ 366.14.

Step 3: 2-[5-(Aminomethyl)oxolan-2-yl]-1-[4-(5-chloropyrimidin-2-yl)piperazin-1-yl]ethan-1-one A solution of 2-[5-(azidomethyl)oxolan-2-yl]-1-[4-(5-chloropyrimidin-2-yl)piperazin-1-yl]ethan-1-one (500 mg, 1.37 mmol, 1 equiv) and triphenylphosphine (537.7 mg, 2.05 mmol, 1.5 equiv) in THF (20 mL) and H$_2$O (5 mL) was stirred 5 h at 60° C. After concentration, the residue was purified by C18 reverse phase chromatography eluting with H$_2$O/ACN to afford 450 mg (97%) of the title compound as a yellow oil. LCMS: [M+H]$^+$ 340.15.

Step 4: 5-[[(5-[2-[4-(5-Chloropyrimidin-2-yl)piperazin-1-yl]-2-oxoethyl]oxolan-2-yl)methyl]amino]-4-(trifluoromethyl)-2-[[2-(trimethylsilyl)ethoxy]methyl]-2,3-dihydropyridazin-3-one A solution of 2-[5-(aminomethyl)oxolan-2-yl]-1-[4-(5-chloropyrimidin-2-yl)piperazin-1-yl]ethan-1-one (300 mg, 0.88 mmol, 1 equiv), Int-A6 (348.3 mg, 1.06 mmol, 1.2 equiv), and TEA (268.0 mg, 2.65 mmol, 3 equiv) in EtOH (20 mL) was stirred for 2 h at 60° C. The solvent was concentrated under vacuum and the residue was applied onto a silica gel column eluting with EtOAc/petroleum ether (1/1) to afford 480 mg (86%) of the title compound as a yellow oil. LCMS: [M+H]$^+$ 632.23.

Step 5: 5-((((2S,5R)-5-(2-(4-(5-chloropyrimidin-2-yl)piperazin-1-yl)-2-oxoethyl)tetrahydrofuran-2-yl)methyl)amino)-4-(trifluoromethyl)pyridazin-3(2H)-one, 5-((((2R,5S)-5-(2-(4-(5-chloropyrimidin-2-yl)piperazin-1-yl)-2-oxoethyl)tetrahydrofuran-2-yl)methyl)amino)-4-(trifluoromethyl)pyridazin-3(2H)-one, 5-((((2S,5S)-5-(2-(4-(5-chloropyrimidin-2-yl)piperazin-1-yl)-2-oxoethyl)tetrahydrofuran-2-yl)methyl)amino)-4-(trifluoromethyl)pyridazin-3(2H)-one and 5-((((2R,5R)-5-(2-(4-(5-chloropyrimidin-2-yl)piperazin-1-yl)-2-oxoethyl)tetrahydrofuran-2-yl)methyl)amino)-4-(trifluoromethyl)pyridazin-3(2H)-one A solution of 5-[[(5-[2-[4-(5-chloropyrimidin-2-yl)piperazin-1-yl]-2-oxoethyl]oxolan-2-yl)methyl]amino]-4-(trifluoromethyl)-2-[[2-(trimethylsilyl)ethoxy]methyl]-2,3-dihydropyridazin-3-one (470 mg, 0.74 mmol, 1 equiv) and TFA (2 mL) in DCM (10 mL) was stirred for 2 h at 25° C. After concentration, the residue was purified by C18 reverse phase chromatography eluting with H$_2$O/ACN. The residue was further purified by Prep-HPLC and Chiral-Prep-HPLC yielding (after arbitrary assignment of the stereochemistry), the title compounds as white solids.

Chiral-Prep-HPLC purification of Isomer A and D by Repaired IA, 5 μm, 0.46×10 cm column, eluting with a gradient of (Hexanes/DCM=3:1)(0.1% DEA):EtOH=95:5, at a flow rate of 1 mL/min. Chiral Prep-HPLC purification of Isomer B and C by CHIRALPAK IG-3, 3 μm, 0.46×10 cm column, eluting with a gradient of (Hexanes/DCM=1:1) (0.1% DEA):MeOH=50:50, at a flow rate of 1 mL/min.

Example 567 Isomer A 41.6 mg, 11%, LCMS: [M+H]$^+$ 502.15, $^1$H NMR (300 MHz, DMSO-d$_6$) δ 12.39 (s, 1H), 8.43 (s, 2H), 7.91 (s, 1H), 6.92 (s, 1H), 4.21-4.10 (m, 1H), 3.97 (s, 1H), 3.77-3.61 (m, 4H), 3.61-3.33 (m, 6H), 2.58 (dd, J=15.4, 6.4 Hz, 1H), 2.37 (dd, J=15.4, 6.4 Hz, 1H), 2.09-1.83 (m, 2H), 1.68 (s, 1H), 1.52 (d, J=10.5 Hz, 1H). tR=4.364 min

Example 567 Isomer B (42.3 mg, 11.34%), LCMS: [M+H]$^+$: 502.15, $^1$H NMR (300 MHz, DMSO-d$_6$) 12.35 (s, 1H), 8.41 (s, 2H), 7.88 (s, 1H), 6.91 (s, 1H), 4.23 (s, 1H), 4.08 (s, 1H), 3.71 (m, 10H), 2.64 (d, J=7.1 Hz, 1H), 2.45 (d, 1H), 2.03 (d, J=29.9 Hz, 2H), 1.56 (s, 2H). tR=1.333 min.

Example 567 Isomer C 42.2 mg, 11%, LCMS: [M+H]$^+$ 502.15, $^1$H NMR (300 MHz, DMSO-d$_6$) δ 12.35 (s, 1H), 8.41 (s, 2H), 7.88 (s, 1H), 6.99-6.81 (m, 1H), 4.25 (q, J=6.4 Hz, 1H), 4.08 (t, J=5.9 Hz, 1H), 3.78-3.38 (m, 10H), 2.66 (dd, J=15.0, 6.6 Hz, 1H), 2.42 (dd, J=14.9, 6.2 Hz, 1H), 2.12-1.91 (m, 2H), 1.68-1.47 (m, 2H). tR=1.719 min.

Example 567 Isomer D 31.8 mg, 9%, LCMS: [M+H]$^+$ 502.15, $^1$H NMR (300 MHz, DMSO-d$_6$) δ 12.39 (s, 1H), 8.43 (s, 2H), 7.91 (s, 1H), 6.93 (s, 1H), 4.15 (q, J=6.5 Hz, 1H), 3.97 (s, 1H), 3.77-3.61 (m, 4H), 3.61-3.33 (m, 6H), 2.58 (dd, J=15.4, 6.5 Hz, 1H), 2.37 (dd, J=15.3, 6.3 Hz, 1H), 2.07-1.80 (m, 2H), 1.65 (dd, J=12.7, 6.2 Hz, 1H), 1.58-1.42 (m, 1H). tR=6.678 min.

Example 568 Isomers A-D

Using the same sequence of reactions as described for Example 567, but starting with 2-(5-(hydroxymethyl)tetrahydrofuran-2-yl)-1-(4-(5-(trifluoromethyl)pyrimidin-2-yl)piperazin-1-yl)ethan-1-one, the title compounds were prepared.

| Example | Name and structure | LCMS: [M + H]$^+$ |
|---|---|---|
| Example 568 Isomer A$^\#$ | 5-((((2S,5S)-5-(2-Oxo-2-(4-(5-(trifluoromethyl)pyrimidin-2-yl)piperazin-1-yl)ethyl)tetrahydrofuran-2-yl)methyl)amino)-4-(trifluoromethyl)pyridazin-3(2H)-one | 536.30 |
| Example 568 Isomer B$^\#$ | 5-((((2R,5R)-5-(2-Oxo-2-(4-(5-(trifluoromethyl)pyrimidin-2-yl)piperazin-1-yl)ethyl)tetrahydrofuran-2-yl)methyl)amino)-4-(trifluoromethyl)pyridazin-3(2H)-one | 536.30 |

| Example | Name and structure | LCMS: [M + H]⁺ |
|---|---|---|
| Example 568 Isomer C# | 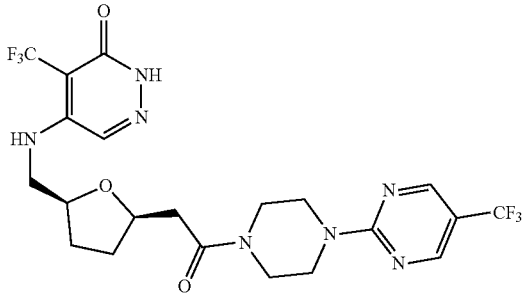 [SMILES: O=C(C[C@H]1CC[C@@H](CNc2cn[nH]c(=O)c2C(F)(F)F)O1)N1CCN(c2ncc(C(F)(F)F)cn2)CC1]<br>5-((((2S,5R)-5-(2-Oxo-2-(4-(5-(trifluoromethyl)pyrimidin-2-yl)piperazin-1-yl)ethyl)tetrahydrofuran-2-yl)methyl)amino)-4-(trifluoromethyl)pyridazin-3(2H)-one | 536.30 |
| Example 568 Isomer D# | 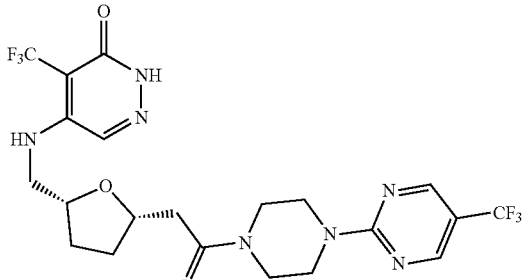<br>5-((((2R,5S)-5-(2-Oxo-2-(4-(5-(trifluoromethyl)pyrimidin-2-yl)piperazin-1-yl)ethyl)tetrahydrofuran-2-yl)methyl)amino)-4-(trifluoromethyl)pyridazin-3(2H)-one | 536.30 |

The absolute stereochemistry of the isomers of Example 568 were arbitrarily assigned after isolation of each diastereoisomer by chiral HPLC.

Example 569: 6-(4-[3-[(2R)-2-[[6-Oxo-5-(trifluoromethyl)-1,6-dihydropyridazin-4-yl]oxy]propoxy]butanoyl]piperazin-1-yl)pyridine-3-carbonitrile

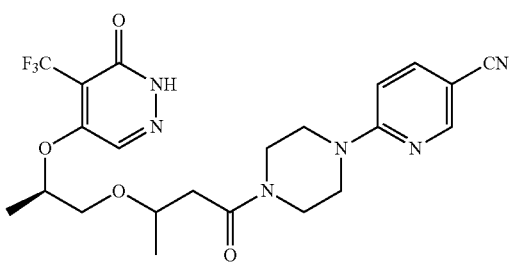 [SMILES: CC(CC(=O)N1CCN(c2ccc(C#N)cn2)CC1)OC[C@@H](C)Oc1cn[nH]c(=O)c1C(F)(F)F]

Step 1: 6-(4-[3-[(2R)-2-Hydroxypropoxy]butanoyl]piperazin-1-yl)pyridine-3-carbonitrile A solution of 6-[4-[(2E)-but-2-enoyl]piperazin-1-yl]pyridine-3-carbonitrile (2.5 g, 9.75 mmol, 1.00 equiv), Cs₂CO₃ (6.49 g, 19.92 mmol, 2.00 equiv), (2R)-propane-1,2-diol (3.7 g, 48.62 mmol, 5.00 equiv) in ACN (30 mL) was stirred for 24 h at 75° C. After concentration, the residue was purified by C18 reverse phase chromatography eluting with H₂O/ACN to afford 1.3 g (40%) of the title compound as a brown oil. LCMS: [M+H]⁺ 333.00.

Step 2: 6-(4-[3-[(2R)-2-[[6-Oxo-5-(trifluoromethyl)-1-[[2-(trimethylsilyl)ethoxy]methyl]-1,6-dihydropyridazin-4-yl]oxy]propoxy]butanoyl]piperazin-1-yl)pyridine-3-carbonitrile A solution of 6-(4-[3-[(2R)-2-hydroxypropoxy]butanoyl]piperazin-1-yl)pyridine-3-carbonitrile (350 mg, 1.05 mmol, 1 equiv), Int-A6 (1.0 g, 3.16 mmol, 3 equiv), and Cs₂CO₃ (686.1 mg, 2.11 mmol, 2 equiv) in CAN (15 mL) was stirred for 6 h at 70° C. The resulting mixture was concentrated and the residue was applied onto a silica gel column with EtOAc/petroleum ether (1:1) to afford 70 mg (11%) of the title compound as a brown oil. LCMS: [M+H]⁺ 625.00.

Step 6: 6-(4-[3-[(2R)-2-[[6-Oxo-5-(trifluoromethyl)-1,6-dihydropyridazin-4-yl]oxy]propoxy]butanoyl]piperazin-1-yl)pyridine-3-carbonitrile A solution of 6-(4-[3-[(2R)-2-[[6-oxo-5-(trifluoromethyl)-1-[[2-(trimethylsilyl)ethoxy]methyl]-1,6-dihydropyridazin-4-yl]oxy]propoxy]butanoyl]piperazin-1-yl)pyridine-3-carbonitrile (200 mg, 0.32 mmol, 1 equiv) and TFA (2 ml) in DCM (10 mL) was stirred for 0.5 h at RT. After concentration, the residue was purified by C18 reverse phase chromatography eluting with H₂O/ACN. The residue was further purified by Prep-HPLC yielding the title compound (18.6 mg, 12%) as a white solid. LCMS: [M+H]⁺ 495.10, ¹H NMR (300 MHz, Methanol-d₄) δ 8.43 (s, 1H), 8.23 (d, J=6.8 Hz, 1H), 7.77 (dd, J=9.1, 2.2 Hz, 1H), 6.85 (dd, J=9.1, 2.6

Hz, 1H), 5.11-5.01 (m, 1H), 4.08-3.89 (m, 1H), 3.89-3.47 (m, 10H), 2.83-2.53 (m, 1H), 2.52-2.30 (m, 1H), 1.36 (dd, J=6.3, 1.4 Hz, 3H), 1.33-1.07 (m, 3H).

Example 570 Isomer A (S)-5-(1-Methoxy-3-(3-oxo-3-(4-(5-(trifluoromethyl)pyrimidin-2-yl)piperazin-1-yl)propoxy)propan-2-yloxy)-4-(trifluoromethyl)pyridazin-3(2H)-one Example 570 Isomer B (R)-5-(1-Methoxy-3-(3-oxo-3-(4-(5-(trifluoromethyl)pyrimidin-2-yl)piperazin-1-yl)propoxy)propan-2-yloxy)-4-(trifluoromethyl)pyridazin-3(2H)-one Example 570

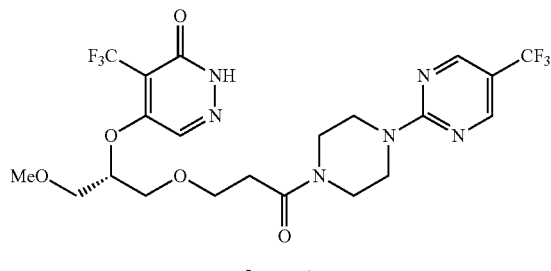

Isomer A

Example 570

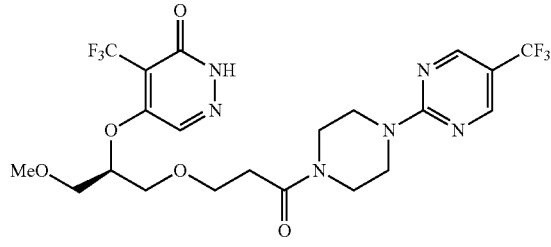

Isomer B

Step 1: 3-(2-Hydroxy-3-methoxypropoxy)-1-(4-(5-(trifluoromethyl)pyrimidin-2-yl)piperazin-1-yl)propan-1-one A solution of Int-A21 (1.4 g, 4.89 mmol, 1.00 equiv), 3-methoxypropane-1,2-diol (2.6 g, 24.50 mmol, 5.00 equiv), and $Cs_2CO_3$ (3.18 g, 9.76 mmol, 2.00 equiv) in ACN (30 mL) was stirred for 5 h at 80° C. After concentration, the residue was purified by C18 reverse phase chromatography eluting with $H_2O$/ACN to afford 1.45 g (76%) of the title compound as a white solid. LCMS: [M+H]$^+$ 393.17.

Step 2: 5-(1-Methoxy-3-(3-oxo-3-(4-(5-(trifluoromethyl)pyrimidin-2-yl)piperazin-1-yl)propoxy)propan-2-yloxy)-4-(trifluoromethyl)-2-((2-(trimethylsilyl)ethoxy)methyl)pyridazin-3(2H)-one A solution of 3-(2-hydroxy-3-methoxypropoxy)-1-[4-[5-(trifluoromethyl)pyrimidin-2-yl]piperazin-1-yl]propan-1-one (1.3 g, 3.31 mmol, 1 equiv), $Cs_2CO_3$ (2.2 g, 6.75 mmol, 2.04 equiv), and Int-A6 (6.5 g, 19.78 mmol, 5.97 equiv) in ACN (20 mL) was stirred for 1.3 h at 80° C. The solids were filtered and the resulting solution was extracted with EtOAc (3×30 mL) and the organic layers combined. The solution was dried over anhydrous sodium sulfate and concentrated under vacuum. The residue was applied onto a silica gel column eluting with EtOAc/hexane (1:1) to afford 1.3 g (57%) of the title compound as a yellow oil. LCMS: [M+H]$^+$ 685.25.

Step 3: (S)-5-(1-Methoxy-3-(3-oxo-3-(4-(5-(trifluoromethyl)pyrimidin-2-yl)piperazin-1-yl)propoxy)propan-2-yloxy)-4-(trifluoromethyl)pyridazin-3 (2H)-one and (R)-5-(1-methoxy-3-(3-oxo-3-(4-(5-(trifluoromethyl)pyrimidin-2-yl)piperazin-1-yl)propoxy)propan-2-yloxy)-4-(trifluoromethyl)pyridazin-3 (2H)-one A solution of 5-[[1-methoxy-3-(3-oxo-3-[4-[5-(trifluoromethyl)pyrimidin-2-yl]piperazin-1-yl]propoxy)propan-2-yl]oxy]-4-(trifluoromethyl)-2-[[2-(trimethylsilyl)ethoxy]methyl]-2,3-dihydropyridazin-3-one (1.3 g, 1.90 mmol, 1 equiv) and TFA (4 mL, 49.37 mmol, 26.00 equiv) in DMF (20 mL) was stirred for 1 h at RT. After concentration, the residue was purified by C18 reverse phase chromatography eluting with $H_2O$/ACN. The residue was further purified by Prep-HPLC and Chiral-Prep-HPLC (CHIRALPAK ID-3, 3 μm, 0.46×5 cm column, eluting with a gradient of MtBE (10 mM $NH_3$):EtOH=90:10, at a flow rate of 1 mL/min) yielding the title compounds as white solids. The absolute stereochemistry was assigned based on a protein X-ray crystal structure obtained of Example 513A, which confirmed (S)-absolute stereochemistry of the more potent enantiomer.

Example 570 Isomer A

LCMS: [M+H]$^+$ 555.30, $^1$H NMR (300 MHz, Methanol-d$_4$) δ 8.61 (s, 2H), 8.25 (s, 1H), 5.13-5.11 (m, 1H), 3.96-3.91 (m, 4H), 3.90-3.61 (m, 10H), 3.37 (s, 3H), 2.69 (t, J=6.0 Hz, 2H). tR=1.439 min.

Example 570 Isomer B

LCMS: [M+H]$^+$ 555.30.

603

Example 571 Isomer A: 6-[4-[(3R)-3-[(2R)-3-Methoxy-2-[[6-oxo-5-(trifluoromethyl)-1,6-dihydropyridazin-4-yl]oxy]propoxy]butanoyl]piperazin-1-yl]pyridine-3-carbonitrile and Example 571 Isomer B: 6-[4-[(3S)-3-[(2S)-3-Methoxy-2-[[6-oxo-5-(trifluoromethyl)-1,6-dihydropyridazin-4-yl]oxy]propoxy]butanoyl]piperazin-1-yl]pyridine-3-carbonitrile and Example 571 Isomer C: 6-[4-[(3R)-3-[(2R)-3-Methoxy-2-[[6-oxo-5-(trifluoromethyl)-1,6-dihydropyridazin-4-yl]oxy]propoxy]butanoyl]piperazin-1-yl]pyridine-3-carbonitrile and Example 571 Isomer D: 6-[4-[(3R)-3-[(2S)-3-Methoxy-2-[[6-oxo-5-(trifluoromethyl)-1,6-dihydropyridazin-4-yl]oxy]propoxy]butanoyl]piperazin-1-yl]pyridine-3-carbonitrile Example 571

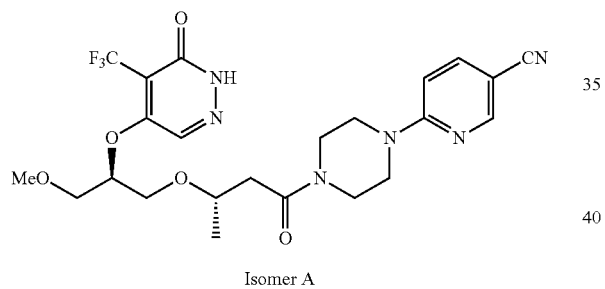

Isomer A

Example 571

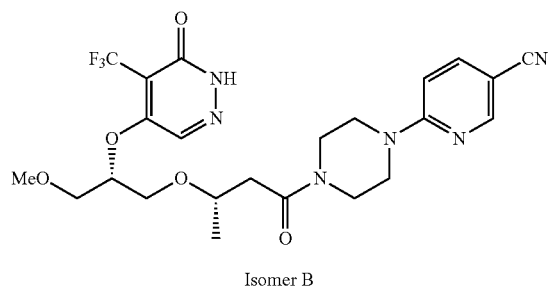

Isomer B

604

-continued

Example 571

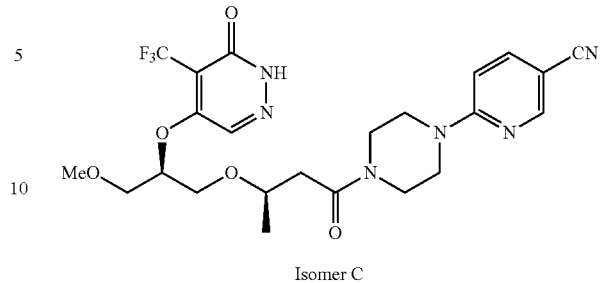

Isomer C

Example 571

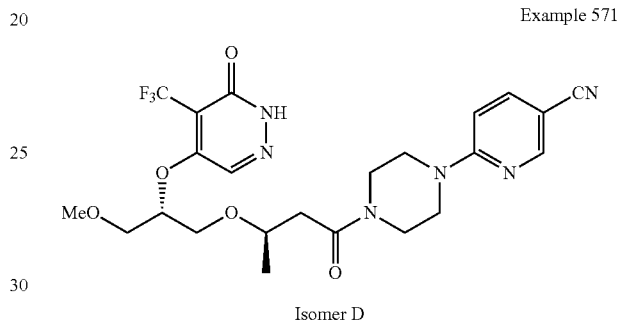

Isomer D

Step 1: 6-[4-[3-(2-Hydroxy-3-methoxypropoxy)butanoyl]piperazin-1-yl]pyridine-3-carbonitrile A solution of 6-[4-[(2E)-but-2-enoyl]piperazin-1-yl]pyridine-3-carbonitrile (1.5 g, 5.85 mmol, 1.00 equiv), 3-methoxypropane-1,2-diol (3.1 g, 29.21 mmol, 5.00 equiv) and $Cs_2CO_3$ (3.8 g, 11.66 mmol, 2.00 equiv) in ACN (20 mL) was stirred for 2 days at 70° C. The solids were filtered and the resulting solution was concentrated under vacuum. The residue was purified by C18 reverse phase chromatography eluting with $H_2O$/ACN to afford 668 mg (31%) of the title compound as a light brown oil. LCMS: $[M+H]^+$ 363.20.

Step 2: 6-[4-[3-(3-Methoxy-2-[[6-oxo-5-(trifluoromethyl)-1-[[2-(trimethylsilyl)ethoxy]methyl]-1,6-dihydropyridazin-4-yl]oxy]propoxy)butanoyl]piperazin-1-yl]pyridine-3-carbonitrile A solution of 6-[4-[3-(2-hydroxy-3-methoxypropoxy)butanoyl]piperazin-1-yl]pyridine-3-carbonitrile (630 mg, 1.74 mmol, 1.00 equiv), Int-A6 (3.4 g, 10.34 mmol, 6.00 equiv) and $Cs_2CO_3$ (1.69 g, 5.19 mmol, 3.00 equiv) in ACN (25 mL) was stirred for 2 h at 80° C. The solids were filtered and the resulting solution was concentrated under vacuum. The residue was applied onto a silica gel column eluting with EtOAc/petroleum ether (85:15) to afford 170 mg (15%) of the title compound as a light brown oil. LCMS: $[M+H]^+$ 655.28.

Step 3: 6-[4-[(3R)-3-[(2R)-3-Methoxy-2-[[6-oxo-5-(trifluoromethyl)-1,6-dihydropyridazin-4-yl]oxy]propoxy]butanoyl]piperazin-1-yl]pyridine-3-carbonitrile and 6-[4-[(3R)-3-[(2S)-3-methoxy-2-[[6-oxo-5-(trifluoromethyl)-1,6-dihydropyridazin-4-yl]oxy]propoxy]butanoyl]piperazin-1-yl]pyridine-3-carbonitrile and 6-[4-[(3S)-3-[(2R)-3-methoxy-2-[[6-oxo-5-(trifluoromethyl)-1,6-dihydropyridazin-4-yl]oxy]propoxy]butanoyl]piperazin-1-yl]pyridine-3-carbonitrile and 6-[4-[(3S)-3-[(2S)-3-methoxy-2-[[6-oxo-5-(trifluoromethyl)-1,6-dihydropyridazin-4-yl]oxy]propoxy]butanoyl]piperazin-1-yl]pyridine-3-carbonitrile A solution of 6-[4-[3-(3-methoxy-2-[[6-oxo-5-(trifluoromethyl)-1-[[2-(trimethylsilyl)ethoxy]methyl]-1,6-dihydropyridazin-4-yl]oxy]propoxy)butanoyl]piperazin-1-yl]pyridine-3-carbonitrile (110 mg, 0.17 mmol, 1.00 equiv) and TFA (1.25 mL) in DCM (5 mL) was stirred for 1 h at RT, and then the resulting solution was concentrated under vacuum. The residue was dissolved in $NH_3$ (gas)/MeOH (2 mL, 7 M) and stirred for 30 min at RT, and then the resulting solution was concentrated under vacuum. The residue was purified by C18 reverse phase chromatography eluting with $H_2O$/ACN. The residue was further purified by Prep-HPLC and Chiral-Prep-HPLC (Repaired IA, 5 μm, 0.46×10 cm column, eluting with a gradient of MtBE (10 mmol $NH_3$):MeOH=90:10, at a flow rate of 1 mL/min) yielding the title compounds as white solids. The absolute stereochemistry was arbitrarily assigned for the title compounds.

Example 571 Isomer A 2.1 mg, 4%, LCMS: [M+H]$^+$ 525.30, $^1$H NMR (300 MHz, Methanol-$d_4$) δ 8.43 (s, 1H), 8.24 (s, 1H), 7.79 (dd, J=9.0, 2.4 Hz, 1H), 6.87 (d, J=9.0 Hz, 1H), 5.12-5.03 (m, 1H), 4.03-3.93 (m, 1H), 3.87-3.55 (m, 12H), 3.36 (s, 3H), 2.76 (dd, J=15.3, 7.8 Hz, 1H), 2.45 (dd, J=15.3, 4.2 Hz, 1H), 1.26 (d, J=6.3 Hz, 3H). tR=4.653 min Example 571 Isomer B 1.6 mg, 3%, LCMS: [M+H]$^+$ 525.30, $^1$H NMR (300 MHz, Methanol-$d_4$) δ 8.43 (s, 1H), 8.24 (s, 1H), 7.79 (dd, J=9.0, 2.4 Hz, 1H), 6.87 (d, J=9.0 Hz, 1H), 5.09-5.07 (m, 1H), 4.00-3.96 (m, 1H), 3.87-3.55 (m, 12H), 3.36 (s, 3H), 2.76 (dd, J=15.3, 5.1 Hz, 1H), 2.45 (dd, J=15.3, 4.5 Hz, 1H), 1.26 (d, J=6.3 Hz, 3H). tR=5.481 min Example 571 Isomer C 6.0 mg, 12%, LCMS: [M+H]$^+$ 525.30, $^1$H NMR (300 MHz, Methanol-$d_4$) δ 8.44 (s, 1H), 8.23 (s, 1H), 7.79 (dd, J=9.0, 2.4 Hz, 1H), 6.88 (d, J=8.7 Hz, 1H), 5.14-5.07 (m, 1H), 4.04-3.97 (m, 1H), 3.78-3.60 (m, 12H), 3.37 (s, 3H), 2.77 (dd, J=15.3, 8.4 Hz, 1H), 2.46 (dd, J=15.3, 4.2 Hz, 1H), 1.21 (d, J=6.3 Hz, 3H). tR=7.604 min Example 571 Isomer D 5.3 mg, 11%), LCMS: [M+H]$^+$ 525.30, $^1$H NMR (300 MHz, Methanol-$d_4$) δ 8.44 (s, 1H), 8.23 (s, 1H), 7.79 (dd, J=9.0, 2.4 Hz, 1H), 6.87 (d, J=8.4 Hz, 1H), 5.11-5.09 (m, 1H), 4.04-3.97 (m, 1H), 3.81-3.56 (m, 12H), 3.37 (s, 3H), 2.77 (dd, J=15.3, 9.1 Hz, 1H), 2.46 (dd, J=15.3, 4.2 Hz, 1H), 1.21 (d, J=6.3 Hz, 3H). tR=9.953 min Example 572 Isomer A: 6-[4-(3-[[(1S,2S)-2-[[6-Oxo-5-(trifluoromethyl)-1,6-dihydropyridazin-4-yl]oxy]cyclopentyl]oxy]propanoyl)piperazin-1-yl]pyridine-3-carbonitrile and Example 572 Isomer B: 6-[4-(3-[[(1R,2R)-2-[[6-Oxo-5-(trifluoromethyl)-1,6-dihydropyridazin-4-yl]oxy]cyclopentyl]oxy]propanoyl)piperazin-1-yl]pyridine-3-carbonitrile Example 572

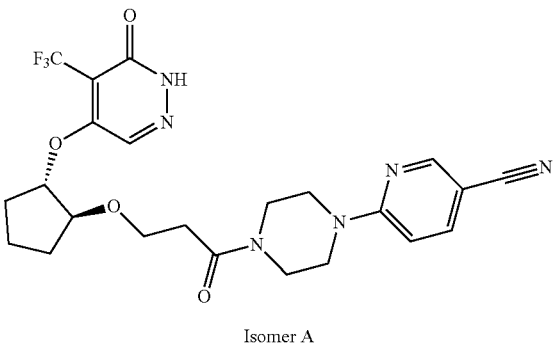

Isomer A

Example 572

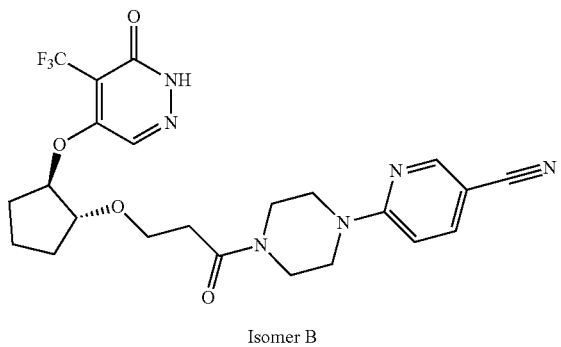

Isomer B

Step 1: 5-[(2-Hydroxycyclopentyl)oxy]-4-(trifluoromethyl)-2-[[2-(trimethylsilyl)ethoxy]methyl]-2,3-dihydropyridazin-3-one A solution of Int-A6 (2.4 g), cyclopentane-1,2-diol (1.5 g, 1 equiv), and $Cs_2CO_3$ (2.4 g) in ACN (20 mL) was stirred for 6 h at 25° C. The solids were filtered and the solution was combined and concentrated under reduced pressure. The residue was applied onto a silica gel column with EtOAc/petroleum ether (1/3) to afford 500 mg (9%) of the title compound as a solid. LCMS: [M+H]$^+$ 395.18.

Step 2: Methyl 3-[(2-[[6-oxo-5-(trifluoromethyl)-1-[[2-(trimethylsilyl)ethoxy]methyl]-1,6-dihydropyridazin-4-yl]oxy]cyclopentyl)oxy]propanoate A solution of 5-[(2-hydroxycyclopentyl)oxy]-4-(trifluoromethyl)-2-[[2-(trimethylsilyl)ethoxy]methyl]-2,3-dihydropyridazin-3-one (500 mg, 1.27 mmol, 1 equiv), methyl prop-2-enoate (2.5 mL), and $Cs_2CO_3$ (300 mg, 0.92 mmol, 0.73 equiv) in ACN (20 mL) was stirred for 6 h at 25° C. The solution was combined and concentrated under vacuum. The residue was applied onto a silica gel column with EtOAc/ petroleum ether (1/2) to afford 200 mg (33%) of the title compound as a yellow solid. LCMS: [M+H]+ 481.27.

Step 3: Methyl 3-[(2-[[6-oxo-5-(trifluoromethyl)-1,6-dihydropyridazin-4-yl]oxy]cyclopentyl)oxy]propanoate A solution of methyl 3-[(2-[[6-oxo-5-(trifluoromethyl)-1-[[2-(trimethylsilyl)ethoxy]methyl]-1,6-dihydropyridazin-4-yl]oxy]cyclopentyl)oxy]propanoate (200 mg, 0.42 mmol, 1 equiv) in DCM (5 mL) and TFA (1 mL) was stirred for 1 h at 25° C. The resulting mixture was concentrated to afford 150 mg of the title compound as a colorless oil. LCMS: [M+H]+ 351.37.

Step 4: 3-[(2-[[6-Oxo-5-(trifluoromethyl)-1,6-dihydropyridazin-4-yl]oxy]cyclopentyl)oxy]propanoic Acid A solution of methyl 3-[(2-[[6-oxo-5-(trifluoromethyl)-1,6-dihydropyridazin-4-yl]oxy]cyclopentyl)oxy]propanoate (150 mg, 0.43 mmol, 1 equiv) and LiOH.H$_2$O (60 mg, 1.43 mmol, 3.34 equiv) in MeOH (5 mL) and H$_2$O (5 mL) was stirred for 4 h at 25° C. After concentration under reduced pressure, the residue was purified by C18 reverse phase chromatography eluting with H$_2$O/ACN to afford 100 mg (69%) of the title compound as a white solid. LCMS: [M+H]+ 337.35.

Step 5: 6-[4-(3-[[(1S,2S)-2-[[6-Oxo-5-(trifluoromethyl)-1,6-dihydropyridazin-4-yl]oxy]cyclopentyl]oxy]propanoyl)piperazin-1-yl]pyridine-3-carbonitrile and 6-[4-(3-[[(1R,2R)-2-[[6-oxo-5-(trifluoromethyl)-1,6-dihydropyridazin-4-yl]oxy]cyclopentyl]oxy]propanoyl)piperazin-1-yl]pyridine-3-carbonitrile A solution of 3-[(2-[[6-oxo-5-(trifluoromethyl)-1,6-dihydropyridazin-4-yl]oxy]cyclopentyl)oxy]propanoic acid (100 mg, 0.30 mmol, 1 equiv), Int-A4 (60 mg, 0.32 mmol, 1.07 equiv), HATU (115 mg, 0.30 mmol, 1.02 equiv), and DIPEA (0.3 mL) in DMF (4 mL) was stirred for 1 h at 25° C. After concentration by reduced pressure, the residue was purified by C18 reverse phase chromatography eluting with H$_2$O/ACN. The residue was further purified by Prep-HPLC and Chiral-Prep-HPLC (CHIRALPAK IF, 5 µm, 2×25 cm column, eluting with a gradient of Hexanes (0.1% DEA): EtOH=50:50, at a flow rate of 1 mL/min) yielding (after arbitrary assignment of stereochemistry) the title compounds as white solids.

Example 572 Isomer A 46.7 mg, 29%, LCMS: [M+H]+ 507.35, $^1$H NMR (400 MHz, DMSO-d$_6$): δ 13.33 (s, 1H), 8.50 (d, J=4.0 Hz, 1H), 8.26 (s, 1H), 7.90-7.86 (dd, J=4.0, 12.0 Hz 1H), 6.93 (d, J=5.6 Hz, 1H), 5.14-5.12 (m, 1H), 3.98-3.96 (m, 1H), 3.90-3.48 (m, 10H), 2.66-2.60 (m, 2H), 2.16-2.08 (m, 1H), 1.98-1.92 (m, 1H), 1.72-1.55 (m, 4H). tR=2.982 min.

Example 572 Isomer B 41.9 mg, 26%, LCMS: [M+H]+ 507.35, tR=3.054 min.

Example 573 Isomer A: 6-[4-(3-[[(2S)-1-Hydroxy-3-[[6-oxo-5-(trifluoromethyl)-1,6-dihydropyridazin-4-yl]oxy]propan-2-yl]oxy]propanoyl)piperazin-1-yl]pyridine-3-carbonitrile and Example 573 Isomer B: 6-(4-[3-[(2R)-3-Hydroxy-2-[[6-oxo-5-(trifluoromethyl)-1,6-dihydropyridazin-4-yl]oxy]propoxy]propanoyl]piperazin-1-yl)pyridine-3-carbonitrile and Example 573 Isomer C: 6-(4-[3-[(2S)-3-Hydroxy-2-[[6-oxo-5-(trifluoromethyl)-1,6-dihydropyridazin-4-yl]oxy]propoxy]propanoyl]piperazin-1-yl)pyridine-3-carbonitrile and Example 573 Isomer D: 6-[4-(3-[[(2R)-1-Hydroxy-3-[[6-oxo-5-(trifluoromethyl)-1,6-dihydropyridazin-4-yl]oxy]propan-2-yl]oxy]propanoyl)piperazin-1-yl]pyridine-3-carbonitrile

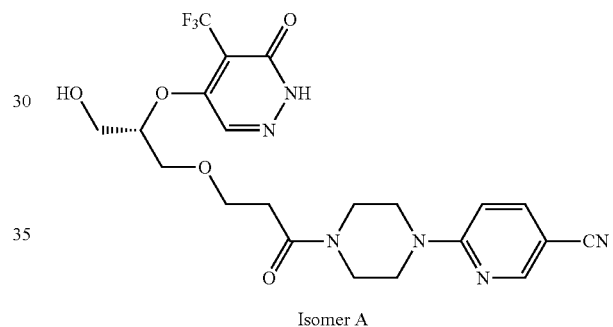

Example 573

Isomer A

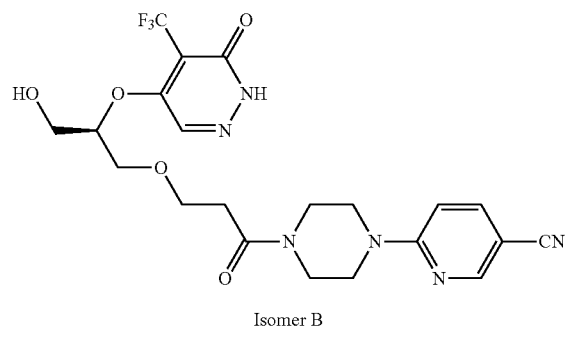

Example 573

Isomer B

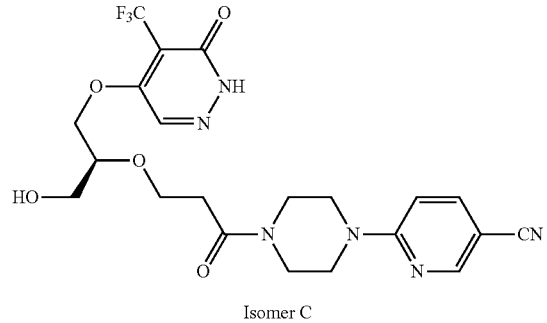

Example 573

Isomer C

Example 573

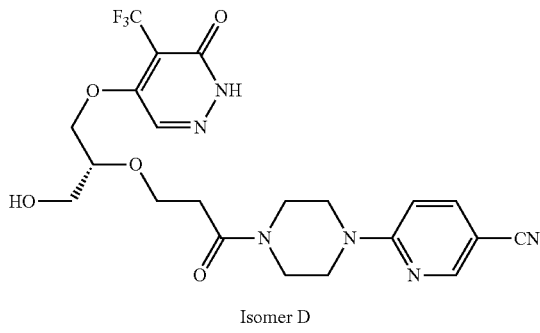

Isomer D

Step 2: Mixture of 6-(4-[3-[3-(benzyloxy)-2-hydroxypropoxy]propanoyl]piperazin-1-yl)pyridine-3-carbonitrile and 6-(4-(3-((1-(benzyloxy)-3-hydroxypropan-2-yl)oxy)propanoyl)piperazin-1-yl)nicotinonitrile A solution of 6-[4-(prop-2-enoyl)piperazin-1-yl]pyridine-3-carbonitrile (1 g, 4.13 mmol, 1 equiv), 3-(benzyloxy)propane-1,2-diol (1.5 g, 8.23 mmol, 1.99 equiv) and $Cs_2CO_3$ (4.0 g, 12.28 mmol, 2.97 equiv) in ACN (10 mL) was stirred for 2 h at 80° C. The solids were filtered and the resulting solution was concentrated under reduced pressure. The residue was applied onto a silica gel column eluting with EtOAc/petroleum ether (1:4) to afford 687 mg (390) of the mixture of the title compounds as a light yellow oil. LCMS: [M+H]$^+$ 425.21.

Step 2. Mixture of 6-(4-[3-[3-(benzyloxy)-2-[[6-oxo-5-(trifluoromethyl)-1-[[2-(trimethylsilyl)ethoxy]methyl]-1,6-dihydropyridazin-4-yl]oxy]propoxy]propanoyl]piperazin-1-yl)pyridine-3-carbonitrile and 6-(4-(3-((1-(benzyloxy)-3-((6-oxo-5-(trifluoromethyl)-1-[[2-(trimethylsilyl)ethoxy]methyl]-3,6-dihydropyridazin-4-yl)oxy)propan-2-yl)oxy)propanoyl)piperazin-1-yl)nicotinonitrile A solution of Int-A6 (482 mg, 1.47 mmol, 1 equiv), 684.5 mg (1.61 mmol, 1.1 equiv) and the mixture of 6-(4-[3-[3-(benzyloxy)-2-hydroxypropoxy]propanoyl]piperazin-1-yl)pyridine-3-carbonitrile and 6-(4-(3-((1-(benzyloxy)-3-hydroxypropan-2-yl)oxy)propanoyl)piperazin-1-yl)nicotinonitrile, and $Cs_2CO_3$ (955.3 mg, 2.93 mmol, 2.00 equiv) in ACN (30 mL) was stirred for 1 h at 60° C. The solids were filtered and the resulting solution was concentrated under vacuum, and the residue was applied onto a silica gel column eluting with EtOAc/petroleum ether (1:7) to afford 434 mg (41%) of the title compounds as a yellow oil. LCMS: [M+H]$^+$ 717.30 [M+H]$^+$

Step 3: Mixture of 6-[4-(3-[[(2S)-1-hydroxy-3-[[6-oxo-5-(trifluoromethyl)-1,6-dihydropyridazin-4-yl]oxy]propan-2-yl]oxy]propanoyl)piperazin-1-yl]pyridine-3-carbonitrile, 6-(4-[3-[(2R)-3-hydroxy-2-[[6-oxo-5-(trifluoromethyl)-1,6-dihydropyridazin-4-yl]oxy]propoxy]propanoyl]piperazin-1-yl)pyridine-3-carbonitrile, 6-(4-[3-[(2S)-3-hydroxy-2-[[6-oxo-5-(trifluoromethyl)-1,6-dihydropyridazin-4-yl]oxy]propoxy]propanoyl]piperazin-1-yl)pyridine-3-carbonitrile and 6-[4-(3-[[(2R)-1-hydroxy-3-[[6-oxo-5-(trifluoromethyl)-1,6-dihydropyridazin-4-yl]oxy]propan-2-yl]oxy]propanoyl)piperazin-1-yl]pyridine-3-carbonitrile To a solution of the mixture of 6-(4-[3-[3-(benzyloxy)-2-[[6-oxo-5-(trifluoromethyl)-1-[[2-(trimethylsilyl)ethoxy]methyl]-1,6-dihydropyridazin-4-yl]oxy]propoxy]propanoyl]piperazin-1-yl)pyridine-3-carbonitrile and 6-(4-(3-((1-(benzyloxy)-3-((6-oxo-5-(trifluoromethyl)-1-[[2-(trimethylsilyl)ethoxy]methyl]-3,6-dihydropyridazin-4-yl)oxy)propan-2-yl)oxy)propanoyl)piperazin-1-yl)nicotinonitrile (434 mg, 0.61 mmol, 1 equiv) in DCM (4 mL) was added $BCl_3$ (70.8 mg, 0.61 mmol, 1.00 equiv) dropwise at 0° C. and the resulting solution was stirred for 1 h at 0° C. The resulting mixture was concentrated under vacuum and the residue was purified by C18 reverse phase chromatography eluting with $H_2O$/ACN. The residue was further purified by Prep-HPLC and Chiral-Prep-HPLC (CHIRALCEL OJ-3, 3 μm, 0.46×50 cm column, eluting with a gradient of EtOH (0.1% DEA), at a flow rate of 1 mL/min) yielding the title compounds as white solids. The absolute stereochemistry for Isomers A and B was assigned in analogy to Example 513A, based on the PARP7 potency of the more potent enantiomer and in analogy to the Example 513A X-ray. The stereochemistry of Examples 573 Isomers C and D was arbitrarily assigned. (The position of the methyl group was confirmed by $^1$H-NMR).

Example 573 Isomer A 5.1 mg, 2%, LCMS: [M+H]$^+$ 497.10, 1 H NMR (300 MHz, DMSO-$d_6$) δ13.28 (s, 1H), 8.50 (d, J=1.8 Hz, 1H), 8.27 (d, J=3.9 Hz, 1H), 7.90 (dd, J=9.3, 2.4 Hz, 1H), 6.94 (d, J=9.0 Hz, 1H), 5.27 (d, J=4.8 Hz, 1H), 4.39-4.35 (m, 1H), 3.91 (d, J=4.5 Hz, 1H), 3.69-3.65 (m, 6H), 3.57-3.55 (m, 5H), 3.44 (d, J=5.7 Hz, 2H), 2.62 (t, J=6.3 Hz, 2H). tR=2.06 min.

Example 573 Isomer B 20.2 mg, 7%, LCMS: [M+H]$^+$ 497.10, $^1$H NMR (300 MHz, DMSO-$d_6$) δ 13.30 (s, 1H), 8.51 (d, J=1.8 Hz, 1H), 8.24 (s, 1H), 7.90 (dd, J=9.0, 2.4 Hz, 1H), 6.94 (d, J=9.3 Hz, 1H), 4.82 (t, J=5.7 Hz, 1H), 4.50 (dd, J=10.6, 3.6 Hz, 2H), 3.81-3.74 (m, 2H), 3.70-3.62 (m, 5H), 3.59-3.47 (m, 6H), 2.58 (t, J=6.4 Hz, 2H), tR=1.19 min.

Example 573 Isomer C 28.0 mg, 9%, LCMS: [M+H]$^+$ 497.25, $^1$H NMR (300 MHz, DMSO-$d_6$) δ 12.24 (br, 1H), 8.50 (d, J=2.3 Hz, 1H), 8.30-8.24 (m, 1H), 7.88 (dd, J=9.0, 2.4 Hz, 1H), 6.94 (d, J=9.0 Hz, 1H), 5.26-4.81 (br, 1H), 4.81-4.35 (m, 2H), 3.91-3.71 (m, 7H), 3.69-3.55 (m, 5H), 3.49-3.42 (m, 1H), 2.61 (dt, J=11.9, 6.2 Hz, 2H). tR=2.11 min.

Example 573 Isomer D 38.8 mg, 13%, LCMS: [M+H]$^+$ 497.25, $^1$H NMR (300 MHz, DMSO-$d_6$) δ 12.26 (s, 1H), 8.51 (d, J=2.1, 1H), 8.27

(d, J=4.5 Hz, 1H), 7.90 (dd, J=9.0, 2.4 Hz, 1H), 6.94 (d, J=9.0 Hz, 1H), 5.27 (d, J=5.1 Hz, 1H), 4.39-4.31 (m, 2H), 3.93 (dt, J=9.9, 4.8 Hz, 1H), 3.71-3.63 (m, 6H), 3.57-3.55 (m, 4H), 3.44 (d, J=5.7 Hz, 2H), 2.64 (t, J=6.3 Hz, 2H). tR=2.14 min.

Example 574 Isomer A: 5-(((2S,5S)-5-(2-Oxo-2-(4-(5-(trifluoromethyl)pyrimidin-2-yl)piperazin-1-yl)ethyl)-tetrahydrofuran-2-yl)methoxy)-4-(trifluoromethyl)pyridazin-3(2H)-one and Example 574 Isomer B: 5-(((2R,5R)-5-(2-Oxo-2-(4-(5-(trifluoromethyl)pyrimidin-2-yl)piperazin-1-yl)ethyl)-tetrahydrofuran-2-yl)methoxy)-4-(trifluoromethyl)pyridazin-3(2H)-one and Example 574 Isomer C: 5-(((2S,5R)-5-(2-Oxo-2-(4-(5-(trifluoromethyl)pyrimidin-2-yl)piperazin-1-yl)ethyl)-tetrahydrofuran-2-yl)methoxy)-4-(trifluoromethyl)pyridazin-3(2H)-one and Example 574 Isomer D: 5-(((2R,5S)-5-(2-Oxo-2-(4-(5-(trifluoromethyl)pyrimidin-2-yl)piperazin-1-yl)ethyl)-tetrahydrofuran-2-yl)methoxy)-4-(trifluoromethyl)pyridazin-3(2H)-one Example 574

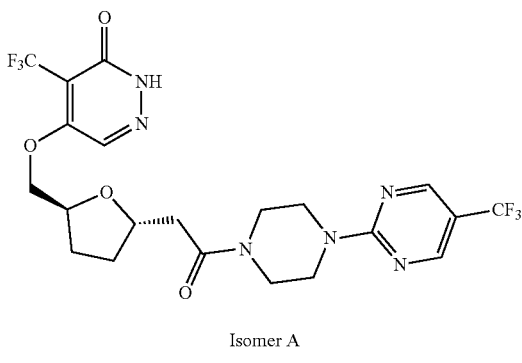

Isomer A

Example 574

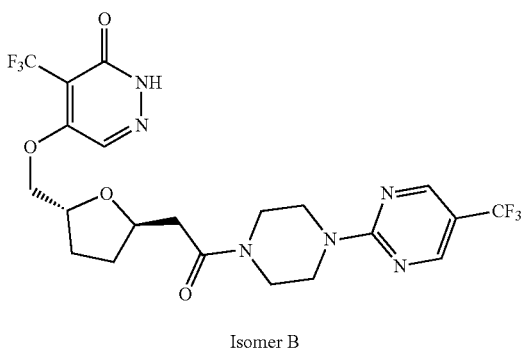

Isomer B

Example 574

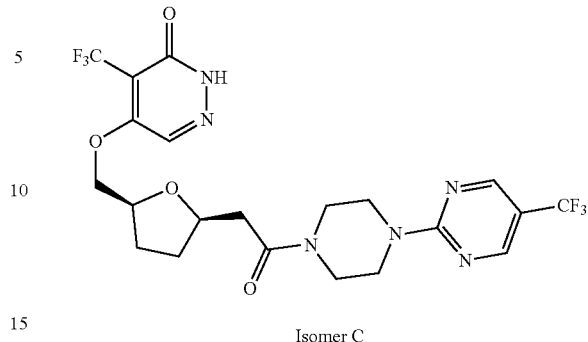

Isomer C

Example 574

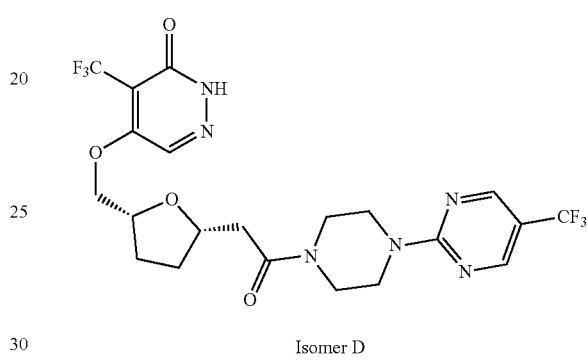

Isomer D

Step 1: 2-[5-[(Benzyloxy)methyl]oxolan-2-yl]-1-[4-[5-(trifluoromethyl)pyrimidin-2-yl]piperazin-1-yl]ethan-1-one A solution of 2-[5-[(benzyloxy)methyl]oxolan-2-yl]acetic acid (2 g, 7.19 mmol, 1 equiv), HATU (3.344 g, 8.8 mmol, 1.22 equiv), DIPEA (5.3 mL, 32 mmol, 4.46 equiv), and Int-A2 (2.39 g, 8 mmol) in DMF (20 mL) was stirred for 1 h at 25° C. The reaction was quenched by the addition of 150 mL of water. The resulting mixture was washed with 2×150 mL of DCM and 2×15 mL of saturated sodium chloride aqueous solution. The mixture was dried over anhydrous sodium sulfate and concentrated under vacuum. The residue was applied onto a silica gel column (80 g) with EtOAc/petroleum ether (9/11) to afford 2.45 g (62.34%) of the title compound as a yellow solid. LCMS (ESI, m/z): 465.20 [M+H]$^+$ Step 2: 2-[5-(Hydroxymethyl)oxolan-2-yl]-1-[4-[5-(trifluoromethyl)pyrimidin-2-yl]piperazin-1-yl]ethan-1-one A solution of 2-[5-[(benzyloxy)methyl]oxolan-2-yl]-1-[4-[5-(trifluoromethyl)pyrimidin-2-yl]piperazin-1-yl]ethan-1-one (2.43 g, 5 mmol, 1 equiv, 85%), Pd/C (0.6 g) in CH$_3$OH (40 mL) was stirred for 2 days at 50° C. under H$_2$(g) atmosphere. The solids were filtered out. The resulting mixture was concentrated to afford 1.73 g (64%) of the title compound as a yellow solid. LCMS (ESI, m/z): 375.36 [M+H]$^+$ Step 3: 5-[[5-(2-Oxo-2-[4-[5-(trifluoromethyl)py-rimidin-2-yl]piperazin-1-yl]ethyl)oxolan-2-yl] methoxy]-4-(trifluoromethyl)-2-[[2-(trimethylsilyl) ethoxy]methyl]-2,3-dihydropyridazin-3-one A solution of 2-[5-(hydroxymethyl)oxolan-2-yl]-1-[4-[5-(trifluoromethyl)pyrimidin-2-yl]piperazin-1-yl]ethan-1-one (800 mg, 2.1 mmol, 1 equiv), Int-A6 (3.444 g, 10.5 mmol, 5 equiv), and $Cs_2CO_3$ (2.086 g, 6.3 mmol, 3 equiv) in ACN (10 mL) was stirred for 5 h at 60° C. The solids were filtered and washed with 15 mL x 2 of EtOAc, the organic layers were combined and concentrated. After concentration, the residue was purified by C18 reverse phase chromatography eluting with $H_2O$/ACN (1/1) to afford 0.88 g (69.49%) of 5-[[5-(2-oxo-2-[4-[5-(trifluoromethyl)pyrimidin-2-yl]piper-azin-1-yl]ethyl)oxolan-2-yl]methoxy]-4-(trifluoromethyl)-2-[[2-(trimethylsilyl)ethoxy]methyl]-2,3-dihydropyridazin-3-one as a white solid. LCMS (ESI, m/z): 667.25 [M+H]$^+$ Step 4: 5-(((2S,5S)-5-(2-oxo-2-(4-(5-(trifluorom-ethyl)pyrimidin-2-yl)piperazin-1-yl)ethyl)-tetrahy-drofuran-2-yl)methoxy)-4-(trifluoromethyl) pyridazin-3(2H)-one, 5-(((2R,5R)-5-(2-oxo-2-(4-(5-(trifluoromethyl)pyrimidin-2-yl)piperazin-1-yl) ethyl)-tetrahydrofuran-2-yl)methoxy)-4-(trifluoromethyl)pyridazin-3(2H)-one, 5-(((2S,5R)-5-(2-oxo-2-(4-(5-(trifluoromethyl)pyrimidin-2-yl) piperazin-1-yl)ethyl)-tetrahydrofuran-2-yl)methoxy)-4-(trifluoromethyl)pyridazin-3(2H)-one, and 5-(((2R,5S)-5-(2-oxo-2-(4-(5-(trifluoromethyl)py-rimidin-2-yl)piperazin-1-yl)ethyl)-tetrahydrofuran-2-yl)methoxy)-4-(trifluoromethyl)pyridazin-3(2H)-one A solution of 5-[[5-(2-oxo-2-[4-[5-(trifluoromethyl)py-rimidin-2-yl]piperazin-1-yl]ethyl)oxolan-2-yl]methoxy]-4-(trifluoromethyl)-2-[[2-(trimethylsilyl)ethoxy]methyl]-2,3-dihydropyridazin-3-one (0.86 g, 1.291 mmol), and TFA (2 mL) in DCM (8 mL) was stirred for 1 h at 25° C. After concentration, the residue was purified by C18 reverse phase chromatography eluting with $H_2O$/ACN. Then the diaste-reomeric mixture was purified by Chiral-Prep-HPLC (CHI-RALPAK IA-3, 0.46*5 cm; 3 um, MtBE (10mMNH$_3$): EtOH=80:20, 1.0 mL/min) yielding (after arbitrary assignment of stereochemistry) the title compounds as white solids.

Example 574 Isomer A 17.3 mg, 10%, LCMS: 537.05 [M+H]$^+$, $^1$H NMR (400 MHz, DMSO-d$_6$) δ 13.33 (s, 1H), 8.72 (s, 2H), 8.27 (s, 1H), 4.48-4.56 (m, 1H), 4.36-4.40 (m, 1H), 4.19-4.25 (m, 1H), 4.18-4.11 (m, 1H), 3.83-3.89 (m, 4H), 3.65-3.44 (m, 4H), 2.68 (t, J=6.4 Hz, 1H), 2.44 (t, J=6 Hz, 1H), 2.04-2.10 (m, 2H), 1.84-1.71 (m, 1H), 1.55-1.63 (m, 1H). tR=1.56 min.

Example 574 Isomer B 19.1 mg, 11%, LCMS (ESI) m/z): 537.05 [M+H]$^+$, $^1$H NMR (400 MHz, DMSO-d$_6$) δ 13.29 (s, 1H), 8.73 (s, 2H), 8.25 (s, 1H), 4.47-4.34 (m, 2H), 4.25-4.31 (m, 2H), 3.95-3.68 (m, 3H), 3.65-3.45 (m, 4H), 2.73 (dd, J=15.1, 6.6 Hz, 1H), 2.52-2.43 (m, 1H), 2.18-2.00 (m, 1H), 1.68-1.77 (m, 1H), 1.54-1.64 (m, 1H). tR=2.06 min.

Example 574 Isomer C 15.6 mg, 9%, LCMS (ESI, m/z): 537.05 [M+H]$^+$, $^1$H NMR (400 MHz, DMSO-d$_6$) δ 13.30 (s, 1H), 8.73 (s, 2H), 8.25 (s, 1H), 4.47-4.34 (m, 2H), 4.25-4.31 (m, 2H), 3.94-3.78 (m, 4H), 3.81-3.68 (m, 4H), 2.73 (dd, J=15.1, 6.6 Hz, 1H), 2.52-2.43 (m, 1H), 2.16-2.00 (m, 2H), 1.68-1.77 (m, 1H), 1.66-1.54 (m, 1H). tR=3.79 min.

Example 574 Isomer D 19.1 mg, 11%, LCMS (ESI, m/z): 537.05 [M+H]$^+$, $^1$H NMR (400 MHz, DMSO-d$_6$) δ 13.33 (s, 1H), 8.72 (s, 2H), 8.27 (s, 1H), 4.38 (dd, J=10.6, 5.2 Hz, 1H), 4.17-4.25 (m, 1H), 4.12-4.17 (m, 1H), 3.91-3.67 (m, 4H), 3.66-3.45 (m, 4H), 2.66-2.74 (m, 1H), 2.44 (dd, J=15.2, 6.1 Hz, 1H), 2.13-1.92 (m, 2H), 1.82-1.73 (m, 1H), 1.55-1.63 (m, 1H). tR=4.41 min.

Example 575 Isomer A: 4-Chloro-5-(((2S,5S)-5-(2-oxo-2-(4-(5-(trifluoromethyl)pyrimidin-2-yl)piper-azin-1-yl)ethyl)-tetrahydrofuran-2-yl)methoxy) pyridazin-3(2H)-one and Example 575 Isomer B: 4-Chloro-5-(((2R,5R)-5-(2-oxo-2-(4-(5-(trifluoromethyl)pyrimidin-2-yl)piper-azin-1-yl)ethyl)-tetrahydrofuran-2-yl)methoxy) pyridazin-3(2H)-one and Example 575 Isomer C: 4-Chloro-5-(((2S,5R)-5-(2-oxo-2-(4-(5-(trifluoromethyl)pyrimidin-2-yl)piper-azin-1-yl)ethyl)-tetrahydrofuran-2-yl)methoxy) pyridazin-3(2H)-one and Example 575 Isomer D: 4-Chloro-5-(((2R,5S)-5-(2-oxo-2-(4-(5-(trifluoromethyl)pyrimidin-2-yl)piper-azin-1-yl)ethyl)-tetrahydrofuran-2-yl)methoxy) pyridazin-3(2H)-one

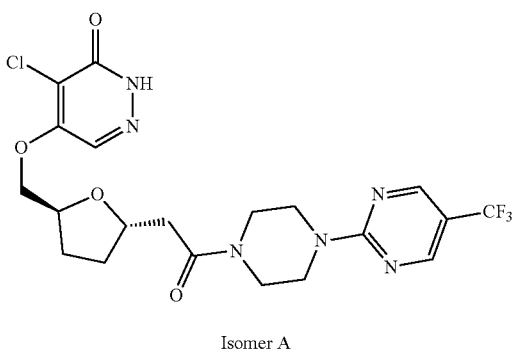

Isomer A

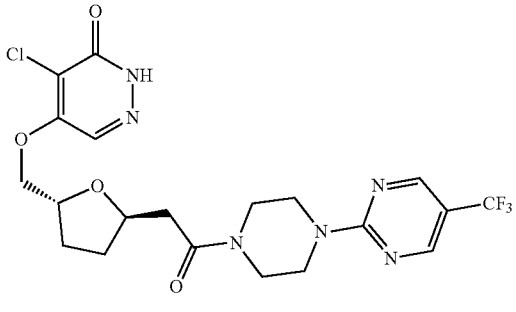

Isomer B

-continued

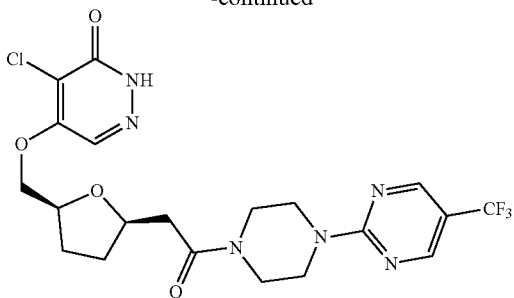

Isomer C

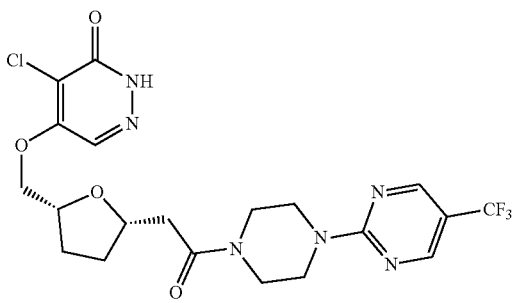

Isomer D

Step 1: 4-Chloro-5-((5-(2-oxo-2-(4-(5-(trifluoromethyl)pyrimidin-2-yl)piperazin-1-yl)ethyl)-tetrahydrofuran-2-yl)methoxy)-2-((2-(trimethylsilyl)ethoxy)methyl)pyridazin-3(2H)-one A solution of 2-[5-(hydroxymethyl)oxolan-2-yl]-1-[4-[5-(trifluoromethyl)pyrimidin-2-yl]piperazin-1-yl]ethan-1-one (900 mg, 2.40 mmol, 1 equiv), NaH (115.4 mg, 4.81 mmol, 2 equiv), Int-A7 (2.1 g, 7.11 mmol, 2.96 equiv) in ACN (15 mL) was stirred for 1 h at 60° C. The solvent was concentrated under vacuum and the residue was applied onto a silica gel column eluting with EtOAc/hexane ether (2:1) to afford 920 mg (60.44%) of the title compound as yellow oil. LCMS (ESI, m/z): 633 [M+H]$^+$ Step 2: 4-chloro-5-(((2S,5S)-5-(2-oxo-2-(4-(5-(trifluoromethyl)pyrimidin-2-yl)piperazin-1-yl)ethyl)-tetrahydrofuran-2-yl)methoxy)pyridazin-3(2H)-one, 4-chloro-5-(((2R,5R)-5-(2-oxo-2-(4-(5-(trifluoromethyl)pyrimidin-2-yl)piperazin-1-yl)ethyl)-tetrahydrofuran-2-yl)methoxy)pyridazin-3(2H)-one, 4-chloro-5-(((2S,5R)-5-(2-oxo-2-(4-(5-(trifluoromethyl)pyrimidin-2-yl)piperazin-1-yl)ethyl)-tetrahydrofuran-2-yl)methoxy)pyridazin-3(2H)-one and 4-chloro-5-(((2R,5S)-5-(2-oxo-2-(4-(5-(trifluoromethyl)pyrimidin-2-yl)piperazin-1-yl)ethyl)-tetrahydrofuran-2-yl)methoxy)pyridazin-3(2H)-one A solution of 4-chloro-5-[[5-(2-oxo-2-[4-[5-(trifluoromethyl)pyrimidin-2-yl]piperazin-1-yl]ethyl)oxolan-2-yl]methoxy]-2-[[2-(trimethylsilyl)ethoxy]methyl]-2,3-dihydropyridazin-3-one (570 mg, 0.90 mmol, 1 equiv), TFA (4 mL) in DCM (20 mL) was stirred for 1 h at RT. After concentration, the residue was purified by C18 reverse phase chromatography eluting with H$_2$O/CH$_3$CN. Then the residue was further purified by Prep-HPLC and Chiral-Prep-HPLC (CHIRALPAK IA-3, 0.46*5 cm; 3 um, (Hex:DCM=3:1) (0.1% DEA):EtOH=50:50, 1.0 mL/min) yielding (after arbitrary assignment of stereochemistry) the title compounds as white solids.

Example 575 Isomer A 14.8 mg, 3.27%, LCMS (ESI, m/z): 503.30 [M+H]$^+$, $^1$HNMR (Methanol-d$_4$, 300 MHz) δ: 8.58 (d, J=0.8 Hz, 2H), 8.18 (s, 1H), 4.55-4.51 (m, 1H), 4.39-4.33 (m, 3H), 4.09-3.91 (m, 2H), 3.86-3.74 (m, 4H), 3.61-3.56 (m, 2H), 2.82 (dd, J=14.7, 8.0 Hz, 1H), 2.59 (dd, J=14.7, 4.6 Hz, 1H), 2.28-2.08 (m, 2H), 2.11-1.92 (m, 1H), 1.90-1.75 (m, 1H). tR=2.199 min.

Example 575 Isomer B 11.4 mg, 2.52%, LCMS (ESI, m/z): 503.10 [M+H]$^+$, $^1$HNMR (Methanol-d$_4$, 300 MHz) δ: 8.60 (d, J=0.9 Hz, 2H), 8.16 (s, 1H), 4.52-4.28 (m, 4H), 4.19-3.91 (m, 2H), 3.96-3.73 (m, 4H), 3.71-3.51 (m, 2H), 2.84 (dd, J=14.4, 7.9 Hz, 1H), 2.59 (dd, J=14.4, 4.5 Hz, 1H), 2.36-2.13 (m, 2H), 2.01-1.80 (m, 1H), 1.83-1.68 (m, 1H). tR=4.243 min.

Example 575 Isomer C 31.9 mg, 7.05%, LCMS (ESI, m/z): 503.10 [M+H]$^+$, $^1$HNMR (Methanol-d$_4$, 300 MHz) δ: 8.58 (d, J=0.8 Hz, 2H), 8.18 (s, 1H), 4.58-4.47 (m, 1H), 4.39-4.33 (m, 3H), 4.09-3.91 (m, 2H), 3.86-3.74 (m, 4H), 3.61-3.56 (m, 2H), 2.82 (dd, J=14.7, 8.0 Hz, 1H), 2.59 (dd, J=14.7, 4.6 Hz, 1H), 2.28-2.05 (m, 2H), 2.10-1.92 (m, 1H), 1.90-1.75 (m, 1H). tR=5.652 min.

Example 575 Isomer D 13.5 mg, 2.98%, LCMS (ESI, m/z): 503.10 [M+H]$^+$, $^1$HNMR (Methanol-d$_4$, 300 MHz) δ: 8.60 (d, J=0.9 Hz, 2H), 8.16 (s, 1H), 4.52-4.28 (m, 4H), 4.19-3.91 (m, 2H), 3.96-3.73 (m, 4H), 3.71-3.51 (m, 2H), 2.84 (dd, J=14.4, 7.9 Hz, 1H), 2.59 (dd, J=14.4, 4.5 Hz, 1H), 2.36-2.13 (m, 2H), 2.01-1.80 (m, 1H), 1.83-1.68 (m, 1H). tR=8.327 min.

Example 576 Isomer A: 6-[4-[(3R)-3-[(2S)-2-[[6-Oxo-5-(trifluoromethyl)-1,6-dihydropyridazin-4-yl]oxy]propoxy]butanoyl]piperazin-1-yl]pyridine-3-carbonitrile and Example 576 Isomer B: 6-[4-[(3S)-3-[(2S)-2-[[6-oxo-5-(trifluoromethyl)-1,6-dihydropyridazin-4-yl]oxy]propoxy]butanoyl]piperazin-1-yl]pyridine-3-carbonitrile

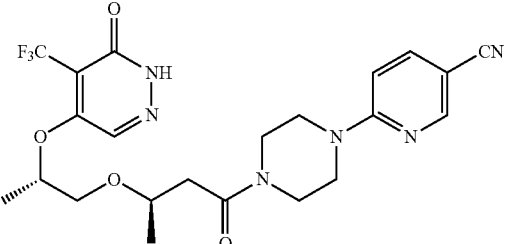

Isomer A

617

-continued

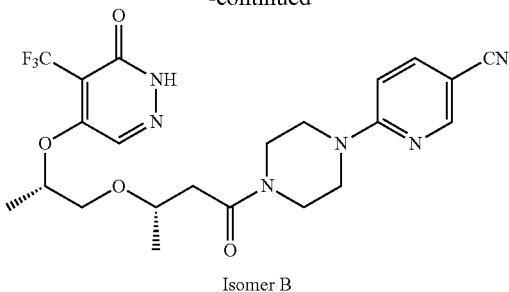

Isomer B

Step 1: (E)-6-[4-[But-2-enoyl]piperazin-1-yl]pyridine-3-carbonitrile

A solution of (2E)-but-2-enoyl (E)-but-2-enoate (1.05 g, 6.81 mmol, 1.30 equiv), TEA (1.515 g), Int-A4 (1 g, 5.31 mmol, 1.00 equiv) in DCM (20 mL) was stirred for 1 h at room temperature. The resulting mixture was concentrated under vacuum. The residue was applied onto a silica gel column with EtOAc/petroleum ether (1/1) to afford 1.28 g (94%) of the title compound as a white solid. LCMS (ESI, m/z): 257.33 [M+H]+

Step 2: (S)-6-(4-[3-[2-[[6-Oxo-5-(trifluoromethyl)-1-[[2-(trimethylsilyl)ethoxy]methyl]-1,6-dihydropyridazin-4-yl]oxy]propoxy]propanoyl]piperazin-1-yl)pyridine-3-carbonitrile A solution of (E)-6-[4-[but-2-enoyl]piperazin-1-yl]pyridine-3-carbonitrile (3 g, 11.70 mmol, 1 equiv), Cs$_2$CO$_3$ (7.6 g) in (S)-propane-1,2-diol (10 mL) was stirred for 3 days at 80° C. The solids were filtered out. After concentration, the residue was purified by C18 reverse phase chromatography eluting with H$_2$O/CH$_3$CN to afford 800 mg (20.56%) of the title compound as a yellow solid. LCMS (ESI, m/z): 333.27 [M+H]+

Step 3: (S)-6-(4-[3-[2-[[6-Oxo-5-(trifluoromethyl)-1-[[2-(trimethylsilyl)ethoxy]methyl]-1,6-dihydropyridazin-4-yl]oxy]propoxy]butanoyl]piperazin-1-yl)pyridine-3-carbonitrile A solution of (S)-6-(4-[3-[2-hydroxypropoxy]butanoyl]piperazin-1-yl)pyridine-3-carbonitrile (800 mg, 2.41 mmol, 1 equiv), Int-A6 (8 g, 24.33 mmol, 10.11 equiv), Cs$_2$CO$_3$ (1.6 g, 4.91 mmol, 2.04 equiv) in ACN (40 mL) was stirred for 5 h at 70° C. The solids were filtered out. The solution was concentrated under vacuum. The residue was applied onto a silica gel column eluting with EtOAc/petroleum ether to afford 300 mg (19.95%) of the title compound as yellow oil. LCMS (ESI, m/z): 625.34[M+H]+

Step 4: 6-[4-[(3R)-3-[(2S)-2-[[6-oxo-5-(trifluoromethyl)-1,6-dihydropyridazin-4-yl]oxy]propoxy]butanoyl]piperazin-1-yl]pyridine-3-carbonitrile and 6-[4-[(3S)-3-[(2S)-2-[[6-oxo-5-(trifluoromethyl)-1,6-dihydropyridazin-4-yl]oxy]propoxy]butanoyl]piperazin-1-yl]pyridine-3-carbonitrile A solution of (S)-6-(4-[3-[2-[[6-oxo-5-(trifluoromethyl)-1-[[2-(trimethyl silyl)ethoxy]methyl]-1,6-dihydropyridazin-4-yl]oxy]propoxy]butanoyl]piperazin-1-yl)pyridine-3-carbonitrile (300 mg, 0.48 mmol, 1 equiv) in TFA (1 mL) and DCM (5 mL) was stirred for 1 h at 25° C. After concentration, the residue was purified by C18 reverse phase chromatography eluting with H$_2$O/CH$_3$CN. Then the residue was further purified by Prep-HPLC and Chiral-Prep-HPLC (CHIRALPAK IE, 2*25 cm, 5 um; Hex(0.1% DEA): EtOH=50:50, 1.0 mL/min) yielding the title compounds as white solids.

Example 576 Isomer A 13.8 mg, 5.81%, LCMS (ESI, m/z): 495.15 [M+H]+, $^1$H NMR (DMSO-d$_6$, 400 MHz) δ 13.19 (s, 1H), 8.50 (d, J=4.0 Hz, 1H), 8.26 (s, 1H), 7.90-7.86 (dd, J=2.0, 12.4 Hz, 1H), 6.92 (d, J=12.0 Hz, 1H), 5.11-5.10 (m, 1H), 3.89-3.83 (m, 1H), 3.69-3.48 (m, 10H), 2.66-2.64 (m, 1H), 2.35-2.28 (m, 1H), 1.25 (d, J=12.4 Hz, 3H), 1.12 (d, J=12.4 Hz, 3H). tR=1.486 min.

Example 576 Isomer B 12.3 mg, 5.18%, LCMS (ESI, m/z): 495.15 [M+H]+, tR=2.479 min.

Example 577 Isomer A: 4-Chloro-5-[[(2S)-1-[3-[4-(5-chloropyrimidin-2-yl)piperazin-1-yl]-3-oxopropoxy]propan-2-yl]oxy]-2,3-dihydropyridazin-3-one and Example 577 Isomer B: 4-Chloro-5-[(2S)-2-[3-[4-(5-chloropyrimidin-2-yl)piperazin-1-yl]-3-oxopropoxy]propoxy]-2,3-dihydropyridazin-3-one

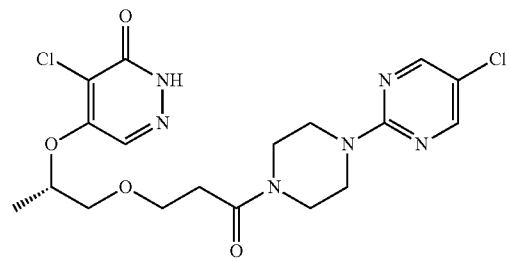

Isomer A

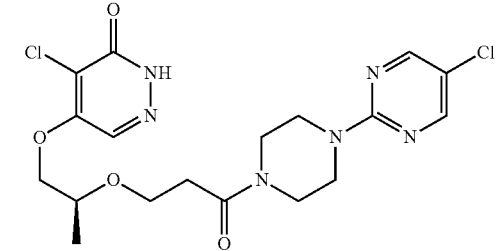

Isomer B

Step 1: (S)-1-(4-(5-chloropyrimidin-2-yl)piperazin-1-yl)-3-(2-hydroxypropoxy)propan-1-one and (S)-1-(4-(5-chloropyrimidin-2-yl)piperazin-1-yl)-3-(1-hydroxypropan-2-yloxy)propan-1-one A solution of 1-[4-(5-chloropyrimidin-2-yl)piperazin-1-yl]prop-2-en-1-one (1.2 g, 4.75 mmol, 1 equiv), (2S)-propane-1,2-diol (1806.8 mg, 23.74 mmol, 5 equiv), Cs$_2$CO$_3$ (3094.5 mg, 9.50 mmol, 2 equiv) in CH₃CN (20 mL) was stirred for 2 days at 75° C. After concentration, the residue was purified by C18 reverse phase chromatography eluting with H₂O/CH₃CN to afford 650 mg (41.63%) of the mixture of the title compounds as brown oil. LCMS (ESI, m/z): 329.00 [M+H]⁺

Step 2: Mixture of (S)-4-chloro-5-(1-(3-(4-(5-chloropyrimidin-2-yl)piperazin-1-yl)-3-oxopropoxy)propan-2-yloxy)-2-((2-(trimethylsilyl)ethoxy)methyl)pyridazin-3(2H)-one and (S)-4-chloro-5-(2-(3-(4-(5-chloropyrimidin-2-yl)piperazin-1-yl)-3-oxopropoxy)propoxy)-2-((2-(trimethylsilyl)ethoxy)methyl)pyridazin-3(2H)-one A solution of (S)-1-(4-(5-chloropyrimidin-2-yl)piperazin-1-yl)-3-(2-hydroxypropoxy)propan-1-one and (S)-1-(4-(5-chloropyrimidin-2-yl)piperazin-1-yl)-3-(1-hydroxypropan-2-yloxy)propan-1-one mixture (630 mg, 1.92 mmol, 1 equiv), Int-A7 (1.7 g, 5.76 mmol, 3.01 equiv), Cs₂CO₃ (1.2 g, 3.83 mmol, 2 equiv) in ACN (15 mL) was stirred for 2 days at 80° C. The residue was applied onto a silica gel column eluting with EtOAc/petroleum ether (1:1) to afford 480 mg (42.64%) of the title compounds as brown oil. LCMS (ESI, m/z): 588.00 [M+H]⁺

Step 3: Mixture of 4-chloro-5-[[(2S)-1-[3-[4-(5-chloropyrimidin-2-yl)piperazin-1-yl]-3-oxopropoxy]propan-2-yl]oxy]-2,3-dihydropyridazin-3-one and 4-chloro-5-[(2S)-2-[3-[4-(5-chloropyrimidin-2-yl)piperazin-1-yl]-3-oxopropoxy]propoxy]-2,3-dihydropyridazin-3-one A mixture of (S)-4-chloro-5-(1-(3-(4-(5-chloropyrimidin-2-yl)piperazin-1-yl)-3-oxopropoxy)propan-2-yloxy)-2-((2-(trimethylsilyl)ethoxy)methyl)pyridazin-3(2H)-one and (S)-4-chloro-5-(2-(3-(4-(5-chloropyrimidin-2-yl)piperazin-1-yl)-3-oxopropoxy)propoxy)-2-((2-(trimethylsilyl)ethoxy)methyl)pyridazin-3(2H)-one mixture (470 mg, 0.80 mmol, 1 equiv), TFA (2 mL) in DCM (10 ml) was stirred for 0.5 h at room temperature. After concentration, the residue was purified by C18 reverse phase chromatography eluting with H₂O/CH₃CN. The residue was further purified by Prep-HPLC yielding the title compounds as white solids.

Example 577 Isomer A 54.2 mg, 14.82%, LCMS (ESI, m/z): 457.15 [M+H]⁺, 1HNMR (300 MHz, Methanol-d₄) δ 8.32 (d, J=2.7 Hz, 2H), 8.16 (s, 1H), 5.02 (qd, J=6.5, 3.3 Hz, 1H), 3.93-3.69 (m, 6H), 3.74-3.53 (m, 6H), 2.66 (t, J=6.0 Hz, 2H), 1.37 (s, 3H).

Example 577 Isomer B 30.1 mg, 8.23%, LCMS (ESI, m/z): 457.15 [M+H]+, ¹HNMR (300 MHz, Methanol-d₄) δ 8.32 (d, J=1.5 Hz, 2H), 8.15 (s, 1H), 4.46-4.22 (m, 2H), 4.02-3.86 (m, 2H), 3.91-3.74 (m, 5H), 3.66 (dt, J=7.3, 3.3 Hz, 4H), 2.68 (t, J=6.0 Hz, 2H), 1.28 (dd, J=76.8, 6.0 Hz, 3H).

Example 578 Isomer A (S)-4-Chloro-5-(1-(3-oxo-3-(4-(5-(trifluoromethyl)pyrimidin-2-yl)piperazin-1-yl)propoxy)propan-2-yloxy)pyridazin-3 (2H)-one and Example 578 Isomer B (S)-4-Chloro-5-(2-(3-oxo-3-(4-(5-(trifluoromethyl)pyrimidin-2-yl)piperazin-1-yl)propoxy)propoxy)pyridazin-3 (2H)-one

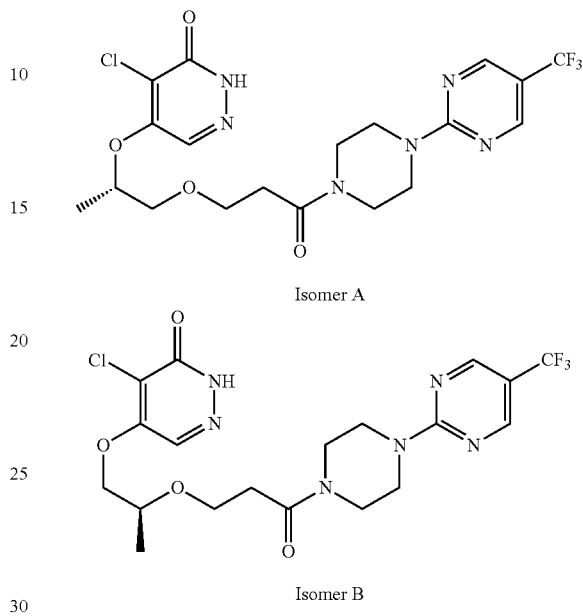

Isomer A

Isomer B

Step 1: (S)-3-(2-hydroxypropoxy)-1-(4-(5-(trifluoromethyl)pyrimidin-2-yl)piperazin-1-yl)propan-1-one and (S)-3-(1-hydroxypropan-2-yloxy)-1-(4-(5-(trifluoromethyl)pyrimidin-2-yl)piperazin-1-yl)propan-1-one A solution of 1-[4-[5-(trifluoromethyl)pyrimidin-2-yl]piperazin-1-yl]prop-2-en-1-one (1.2 g, 4.19 mmol, 1 equiv), Cs₂CO₃ (2.7 g, 8.29 mmol, 1.98 equiv), (2S)-propane-1,2-diol (1.6 g, 21.03 mmol, 5.02 equiv) in ACN (20 mL) was stirred for 9 h at 75° C. After concentration, the residue was purified by C18 reverse phase chromatography eluting with H₂O/CH₃CN to afford 1.1 g (71.42%) of the mixture of title compounds as a white solid. LCMS (ESI, m/z): 363.16 [M+H]⁺

Step 2: Mixture of (S)-4-chloro-5-(1-(3-oxo-3-(4-(5-(trifluoromethyl)pyrimidin-2-yl)piperazin-1-yl)propoxy)propan-2-yloxy)-2-((2-(trimethylsilyl)ethoxy)methyl)pyridazin-3(2H)-one and (S)-4-chloro-5-(2-(3-oxo-3-(4-(5-(trifluoromethyl)pyrimidin-2-yl)piperazin-1-yl)propoxy)propoxy)-2-((2-(trimethylsilyl)ethoxy)methyl)pyridazin-3(2H)-one A solution of the mixture of (S)-3-(2-hydroxypropoxy)-1-(4-(5-(trifluoromethyl)pyrimidin-2-yl)piperazin-1-yl)propan-1-one and (S)-3-(1-hydroxypropan-2-yloxy)-1-(4-(5-(trifluoromethyl)pyrimidin-2-yl)piperazin-1-yl)propan-1-one (700 mg, 1.93 mmol, 1 equiv), Cs₂CO₃ (1255.7 mg, 3.86 mmol, 2 equiv), Int-A7 (1711.0 mg, 5.80 mmol, 3 equiv) in ACN (15 mL) was stirred for 28 h at 80° C. The solids were filtered out, the resulting solution was extracted with EtOAc (3×60 mL) and the organic layers combined. The solution was dried over anhydrous sodium sulfate and concentrated under vacuum. The residue was applied onto a silica gel column eluting with EtOAc/hexane (2:1) to afford 670 mg (55.84%) of the mixture of title compounds as yellow oil. LCMS (ESI, m/z): 621.22 [M+H]$^+$ Step 3: Mixture of (S)-4-chloro-5-(1-(3-oxo-3-(4-(5-(trifluoromethyl)pyrimidin-2-yl)piperazin-1-yl)propoxy)propan-2-yloxy)pyridazin-3(2H)-one and (S)-4-chloro-5-(2-(3-oxo-3-(4-(5-(trifluoromethyl)pyrimidin-2-yl)piperazin-1-yl)propoxy)propoxy)pyridazin-3(2H)-one A solution of the mixture of (S)-1-(3-oxo-3-[4-[5-(trifluoromethyl)pyrimidin-2-yl]piperazin-1-yl]propoxy)propan-2-yl]oxy]-2-[[2-(trimethylsilyl)ethoxy]methyl]-2,3-dihydropyridazin-3-one and (S)-4-chloro-5-(2-(3-oxo-3-(4-(5-(trifluoromethyl)pyrimidin-2-yl)piperazin-1-yl)propoxy)propoxy)-2-((2-(trimethylsilyl)ethoxy)methyl)pyridazin-3(2H)-one mixture (480 mg, 0.77 mmol, 1 equiv), TFA (2 mL) in DCM (10 mL) was stirred for 1 h at RT. After concentration, the residue was purified by C18 reverse phase chromatography eluting with H$_2$O/CH$_3$CN. Then the residue was further purified by Prep-HPLC and Chiral-Prep-HPLC (CHIRALPAK IA-3, 0.46*10 cm; 5 um, MtBE (10mMNH3):EtOH=80:20, 1.0 mL/min) yielding the title compounds as white solids.

Example 578 Isomer A 84.6 mg, 22.30%, LCMS (ESI, m/z): 491.20[M+H]$^+$, $^1$HNMR (Methanol-d$_4$, 300 MHz) δ: 8.60 (d, J=0.9 Hz, 2H), 8.16 (s, 1H), 5.08-5.00 (m, 1H), 3.94-3.91 (m, 4H), 3.89-3.82 (m, 2H), 3.80-3.62 (m, 6), 2.67 (t, J=5.9 Hz, 2H), 1.38 (d, J=6.3 Hz, 3H). tR=2.125 min.

Example 578 Isomer B 51.5 mg, 13.58%, LCMS (ESI, m/z): 491.05 [M+H]$^+$, $^1$H NMR (Methanol-d$_4$, 300 MHz) δ: 8.60 (d, J=0.8 Hz, 2H), 8.15 (s, 1H), 4.41-4.29 (m, 2H), 3.98-3.80 (m, 7H), 3.70-3.67 (m, 4H), 2.69 (t, J=6.0 Hz, 2H), 1.28 (d, J=6.4 Hz, 3H). tR=3.775 min.

Example 579: 2-(4-[3-[(2S)-2-[[6-Oxo-5-(trifluoromethyl)-1,6-dihydropyridazin-4-yl]oxy]propoxy]propanoyl]piperazin-1-yl)pyrimidine-5-carbonitrile

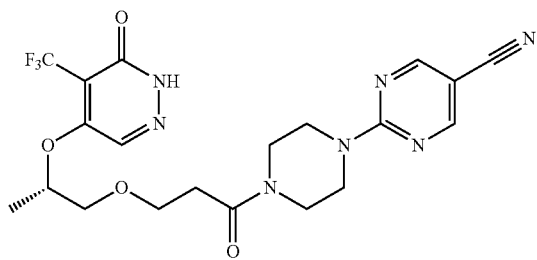 [SMILES: C[C@@H](COCCC(=O)N1CCN(c2ncc(C#N)cn2)CC1)Oc1cn[nH]c(=O)c1C(F)(F)F]

Step 1: 2-[4-(Prop-2-enoyl)piperazin-1-yl]pyrimidine-5-carbonitrile

A solution of Int-A1 (6.4 g, 33.82 mmol, 1 equiv), prop-2-enoyl prop-2-enoate (5.1 g, 40.44 mmol, 1.20 equiv) and TEA (6.8 g, 67.20 mmol, 1.99 equiv) in DCM (40 mL) was stirred for 1 h at room temperature. The resulting solution was concentrated under vacuum, and the residue was applied onto a silica gel column eluting with EtOAc/petroleum ether (7:3) to afford 3.6 g (43.75%) of the title compound as a white solid. LCMS (ESI, m/z): 244.12 [M+H]$^+$.

Step 2: 2-(4-[3-[(2S)-2-hydroxypropoxy]propanoyl]piperazin-1-yl)pyrimidine-5-carbonitrile A solution of 2-[4-(prop-2-enoyl)piperazin-1-yl]pyrimidine-5-carbonitrile (1 g, 4.11 mmol, 1 equiv), (2S)-propane-1,2-diol (0.3 g, 3.94 mmol, 0.96 equiv) and Cs$_2$CO$_3$ (2.7 g, 8.29 mmol, 2.02 equiv) in ACN (10 mL) was stirred for 1 h at 80° C. in an oil bath. The solids were filtered and the resulting solution was concentrated under vacuum, and the residue was applied onto a silica gel column eluting with EtOAc/petroleum ether (3:2) to afford 594 mg (45.25%) of the title compound as yellow oil. LCMS (ESI, m/z): 320.16 [M+H]$^+$.

Step 3: (S)-2-(4-(3-(2-((6-oxo-5-(trifluoromethyl)-1-((2-(trimethylsilyl)ethoxy)methyl)-1,6-dihydropyridazin-4-yl)oxy)propoxy)propanoyl)piperazin-1-yl)pyrimidine-5-carbonitrile A solution of methyl 2-(4-[3-[(2S)-2-hydroxypropoxy]propanoyl]piperazin-1-yl)pyrimidine-5-carbonitrile (674 mg, 2.11 mmol, 1 equiv), Int-A6 (1.4 g, 4.22 mmol, 2.00 equiv) and Cs$_2$CO$_3$ (2.1 g, 6.33 mmol, 3.00 equiv) in ACN (10 mL). The resulting solution was stirred for 1 h at 60° C. in an oil bath, then the solids were filtered out and the resulting solution was concentrated under vacuum, then the residue was applied onto a silica gel column eluting with EtOAc/petroleum ether (3:1) to afford 144 mg (11.15%) of the title compound as yellow oil. LCMS (ESI, m/z): 612.25 [M+H]$^+$.

Step 4: 2-(4-[3-[(2S)-2-[[6-oxo-5-(trifluoromethyl)-1,6-dihydropyridazin-4-yl]oxy]propoxy]propanoyl]piperazin-1-yl)pyrimidine-5-carbonitrile A solution of 2-(4-[3-[(2S)-2-[[6-oxo-5-(trifluoromethyl)-1-[[2-(trimethylsilyl)ethoxy]methyl]-1,6-dihydropyridazin-4-yl]oxy]propoxy]propanoyl]piperazin-1-yl)pyrimidine-5-carbonitrile (144 mg, 0.24 mmol, 1 equiv) and TFA (2 mL) in DCM (10 mL) was stirred for 1 h at room temperature. The mixture was concentrated and the residue was purified by Prep-HPLC yielding the title compound (27.9 mg, 24.62%) as a white solid. LCMS (ESI, m/z): 482.05 [M+H]+, $^1$H NMR (CD$_3$OD-d4, 300 MHz) δ8.63 (s, 2H), 8.23 (s, 1H), 5.18-5.08 (m, 1H), 3.95-3.90 (m, 4H), 3.87-3.80 (m, 1H), 3.78-3.70 (m, 1H), 3.69-3.56 (m, 6H), 2.66 (t, J=5.9 Hz, 2H), 1.36 (d, J=6.3 Hz, 3H).

Example 580 Isomer A: 6-(4-[2-[(2S,5S)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and Example 580 Isomer B: 6-(4-[2-[(2R,5R)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and Example 580 Isomer C: 6-(4-[2-[(2R,5S)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and Example 580 Isomer D: 6-(4-[2-[(2S,5R)-5-([[6-oxo-5-(trifluoromethyl)-1,6-dihydropyridazin-4-yl]oxy]methyl)oxolan-2-yl]acetyl]piperazin-1-yl)pyridine-3-carbonitrile

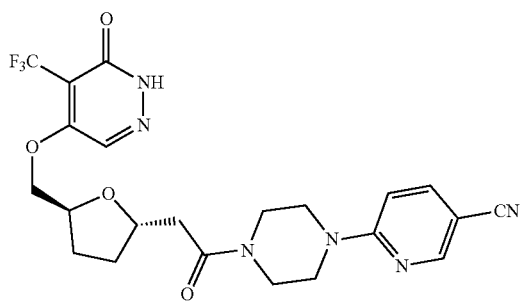

Isomer A

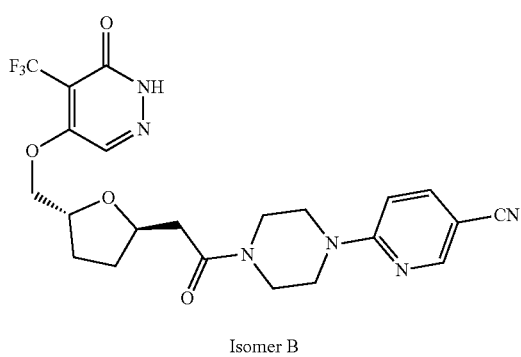

Isomer B

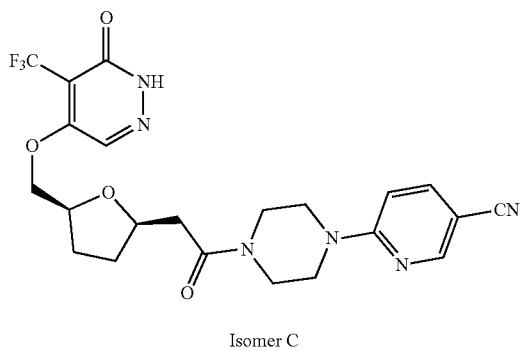

Isomer C

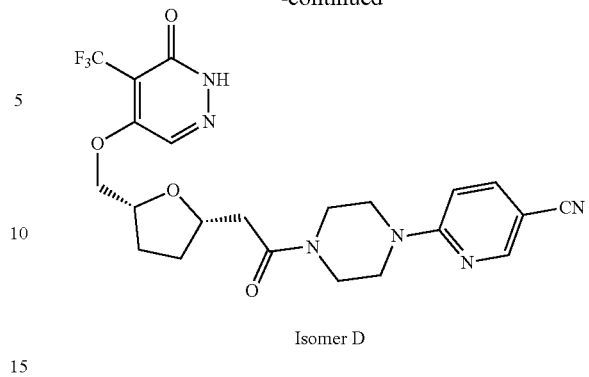

Isomer D

Step 1: 1-(Benzyloxy)hex-5-en-2-ol

To a solution of bromo(prop-2-en-1-yl)magnesium (27.4 mL, 1.50 equiv) in THF (20 mL) was added 2-[(benzyloxy)methyl]oxirane (3 g, 18.27 mmol, 1.00 equiv) dropwise under nitrogen at −40° C., and then the resulting solution was stirred for 1 h at −40° C. The resulting solution was quenched by 100 mL of aqueous NH$_4$Cl and extracted with 3×100 mL of EtOAc. The organic layers were combined, washed with 1×100 mL of brine, dried over anhydrous sodium sulfate and concentrated under vacuum, and then the residue was applied onto a silica gel column eluting with EtOAc/petroleum ether (1:5) to afford 2.16 g (57%) of the title compound as a yellow oil. LCMS (ESI, m/z): 207.13 [M+H]$^+$.

Step 2: Methyl (2Z)-7-(benzyloxy)-6-hydroxyhept-2-enoate

Under nitrogen, a solution of 1-(benzyloxy)hex-5-en-2-ol (2 g, 9.70 mmol, 1.00 equiv), methyl prop-2-enoate (4.17 g, 48.44 mmol, 5.00 equiv) and Grubbs 2nd generation catalyst (82 mg, 0.01 equiv) in DCM (25 mL) was stirred for 4 h at 40° C. The resulting solution was concentrated under vacuum and the residue was purified by C18 reverse phase chromatography eluting with H$_2$O/ACN to afford 1.4 g (55%) of the title compound as a yellow oil. LCMS (ESI, m/z): 265.14 [M+H]$^+$.

Step 3: Methyl 2-[5-[(benzyloxy)methyl]oxolan-2-yl]acetate

A solution of methyl (2Z)-7-(benzyloxy)-6-hydroxyhept-2-enoate (46 g, 1 equiv) and NaH (0.7 g, 0.1 equiv) in THF (200 mL) was stirred for 12 h at 25° C. The resulting solution was quenched with 200 mL of water, extracted with 3×200 mL of DCM, and the organic layers were combined and washed with 1×100 mL of brine, dried over anhydrous sodium sulfate and concentrated under vacuum to afford 46 g of the title compound as a brown oil. LCMS (ESI, m/z): 265.14 [M+H]+

Step 4: 2-[5-[(Benzyloxy)methyl]oxolan-2-yl]acetic Acid

A solution of methyl 2-[5-[(benzyloxy)methyl]oxolan-2-yl]acetate (46 g, 174.03 mmol, 1 equiv) and LiOH.H$_2$O (14.6 mg, 0.35 mmol, 2 equiv) in THF (200 mL) and H$_2$O (200 mL) was stirred for 2 h at 25° C. The resulting solution was washed with 1×200 ml of DCM, the aqueous layers was combined and the pH value of the aqueous layer was adjusted to 4 with HCl (1 M). The resulting solution was extracted with 1×200 mL EtOH, and the organic layers was combined and concentrated under vacuum to afford 40 g (91.83%) of the title compound as light yellow oil. LCMS (ESI, m/z): 251.12 [M+H]+.

Step 5: Synthesis of 6-[4-(2-[5-[(benzyloxy)methyl]oxolan-2-yl]acetyl)piperazin-1-yl]pyridine-3-carbonitrile A solution of 2-[5-[(benzyloxy)methyl]oxolan-2-yl]acetic acid (1 g, 4.00 mmol, 1.00 equiv), Int-A4 (752 mg, 4.00 mmol, 1.00 equiv), HATU (1.52 g, 4.00 mmol, 1.00 equiv) and DIPEA (1.55 g, 11.99 mmol, 3.00 equiv) in DMF (10 mL) was stirred for 1 h at RT. The resulting solution was diluted with 50 mL of EtOAc and washed with 3×40 mL of H$_2$O. The organic layers was combined, dried over anhydrous sodium sulfate and concentrated under vacuum, and the residue was applied onto a silica gel column eluting with EtOAc/petroleum ether (6:4) to afford 1.28 g (76%) of the title compound as a brown oil. LCMS (ESI, m/z): 421.22 [M+H]$^+$.

Step 6: 6-(4-[2-[5-(Hydroxymethyl)oxolan-2-yl]acetyl]piperazin-1-yl)pyridine-3-carbonitrile To a solution of 6-[4-(2-[5-[(benzyloxy)methyl]oxolan-2-yl]acetyl)piperazin-1-yl]pyridine-3-carbonitrile (1.28 g, 3.04 mmol, 1.00 equiv) in DCM (120 mL) was added BCl$_3$/DCM (9.1 mL, 1M) dropwise, and then the resulting solution was stirred for 20 min at 0° C. The solution was quenched by 10 mL of MeOH and concentrated under vacuum and the residue was purified was purified by C18 reverse phase chromatography eluting with H$_2$O/ACN to afford 600 mg (60%) of the title compound as a light yellow solid. LCMS (ESI, m/z): 331.17 [M+H]$^+$.

Step 7: 6-(4-[2-[5-([[6-oxo-5-(trifluoromethyl)-1-[[2-(trimethylsilyl)ethoxy]methyl]-1,6-dihydropyridazin-4-yl]oxy]methyl)oxolan-2-yl]acetyl]piperazin-1-yl)pyridine-3-carbonitrile A solution of 6-(4-[2-[5-(hydroxymethyl)oxolan-2-yl]acetyl]piperazin-1-yl)pyridine-3-carbonitrile (160 mg, 1.00 equiv), Int-A6 (480 mg, 3.00 equiv) and Cs$_2$CO$_3$ (480 mg, 3.00 equiv) in ACN (8 mL) was stirred for 1 h at 80° C. The resulting solution was diluted with 30 mL of EtOAc, washed with 2×20 ml of H$_2$O and 20 ml of brine. The organic layers were combined, dried over anhydrous sodium sulfate and concentrated under vacuum, and then the residue was applied onto a silica gel column eluting with EtOAc to afford 120 mg of the title compound as a brown solid. LCMS (ESI, m/z): 623.25 [M+H]$^+$ Step 8: 6-(4-[2-[(2S,5S)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and 6-(4-[2-[(2R,5R)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and 6-(4-[2-[(2R,5S)-5-([[6-oxo-5-(trifluoromethyl)-1,6-dihydropyridazin-4-yl]oxy]methyl)oxolan-2-yl]acetyl]piperazin-1-yl)pyridine-3-carbonitrile and 6-(4-[2-[(2S,5R)-5-([[6-oxo-5-(trifluoromethyl)-1,6-dihydropyridazin-4-yl]oxy]methyl)oxolan-2-yl]acetyl]piperazin-1-yl)pyridine-3-carbonitrile A solution of 6-(4-[2-[5-([[6-oxo-5-(trifluoromethyl)-1-[[2-(trimethyl silyl)ethoxy]methyl]-1,6-dihydropyridazin-4-yl]oxy]methyl)oxolan-2-yl]acetyl]piperazin-1-yl)pyridine-3-carbonitrile (730 mg, 1.17 mmol, 1 equiv) and TFA (1.25 mL) in DCM (5 mL) was stirred for 1 h at room temperature. The resulting solution was concentrated under vacuum, and the residue was dissolved in NH$_3$(gas)/MeOH (2 mL, 7 M) and stirred for 20 min at room temperature. After concentration, the residue was purified by C18 reverse phase chromatography eluting with H$_2$O/ACN. The residue was further purified by Prep-HPLC and Chiral-Prep-HPLC (CHIRALAPK ID-3, 0.46*10 cm; 3 um, MtBE (0.2% IPAmine):EtOH=70:30, 1.0 mL/min) yielding (after arbitrary assignment of stereochemistry) the title compounds as white solids.

Example 580 Isomer A 69 mg, 16.43%, LCMS (ESI, m/z): 493.10 [M+H]$^+$, $^1$H NMR (Methanol-d$_4$, 300 MHz) δ 8.41 (s, 1H), 8.24 (s, 1H), 7.77 (dd, J=9.0, 2.1 Hz, 1H), 6.85 (dd, J=9.0, 0.6 Hz, 1H), 4.57 (dd, J=10.5, 3.0 Hz, 1H), 4.39-4.25 (m, 3H), 3.80-3.62 (m, 8H), 2.81 (dd, J=15.0, 7.8 Hz, 1H), 2.61 (dd, J=15.0, 4.8 Hz, 1H), 2.17-2.10 (m, 2H), 1.94-1.89 (m, 1H), 1.81-1.66 (m, 1H). tR=2.526 min.

Example 580 Isomer B 45.4 mg, 10.81%, LCMS (ESI, m/z): 493.10 [M+H]$^+$, $^1$H NMR 8.43 (s, 1H), 8.22 (s, 1H), 7.78 (dd, J=9.0, 2.4 Hz, 1H), 6.88 (dd, J=9.0, 0.6 Hz, 1H), 4.48-4.37 (m, 4H), 3.81-3.62 (m, 8H), 2.86 (dd, J=14.4, 7.8 Hz, 1H), 2.61 (dd, J=14.7, 4.8 Hz, 1H), 2.30-2.19 (m, 2H), 1.94-1.82 (m, 1H), 1.81-1.69 (m, 1H). tR=4.043 min.

Example 580 Isomer C 49 mg, 11.67%, LCMS (ESI, m/z): 493.10 [M+H]$^+$, $^1$H NMR (Methanol-d$_4$, 300 MHz) δ 8.41 (s, 1H), 8.24 (s, 1H), 7.77 (dd, J=9.0, 2.1 Hz, 1H), 6.85 (dd, J=9.3, 0.8 Hz, 1H), 4.58 (dd, J=10.8, 3.0 Hz, 1H), 4.43-4.26 (m, 3H), 3.80-3.62 (m, 8H), 2.81 (dd, J=15.0, 7.8 Hz, 1H), 2.61 (dd, J=15.0, 4.8 Hz, 1H), 2.17-2.08 (m, 2H), 1.98-1.94 (m, 1H), 1.77-1.73 (m, 1H). tR=3.168 min.

Example 580 Isomer D 55.5 mg, 13.21%, (ESI, m/z): 493.10 [M+H]$^+$, $^1$H NMR (Methanol-d$_4$, 300 MHz) δ 8.43 (s, 1H), 8.22 (s, 1H), 7.79 (dd, J=9.0, 2.4 Hz, 1H), 6.88 (d, J=9.3, 0.8 Hz, 1H), 4.48-4.38 (m, 4H), 3.85-3.62 (m, 8H), 2.86 (dd, J=14.7, 7.8 Hz, 1H), 2.61 (dd, J=14.7, 4.8 Hz, 1H), 2.24-2.19 (m, 2H), 1.95-1.85 (m, 1H), 1.78-1.69 (m, 1H). tR=4.930 min.

Example 581 Isomer A: 6-(4-[2-[(2R,5S)-5-([[6-oxo-5-(trifluoromethyl)-1,6-dihydropyridazin-4-yl]amino]methyl)oxolan-2-yl]acetyl]piperazin-1-yl)pyridine-3-carbonitrile and Example 581 Isomer B: 6-(4-[2-[(2S,5S)-5-([[6-oxo-5-(trifluoromethyl)-1,6-dihydropyridazin-4-yl]amino]methyl)oxolan-2-yl]acetyl]piperazin-1-yl)pyridine-3-carbonitrile and Example 581 Isomer C: 6-(4-[2-[(2R,5R)-5-([[6-oxo-5-(trifluoromethyl)-1,6-dihydropyridazin-4-yl]amino]methyl)oxolan-2-yl]acetyl]piperazin-1-yl)pyridine-3-carbonitrile and Example 581 Isomer D: 6-(4-[2-[(2S,5R)-5-([[6-oxo-5-(trifluoromethyl)-1,6-dihydropyridazin-4-yl]amino]methyl)oxolan-2-yl]acetyl]piperazin-1-yl)pyridine-3-carbonitrile

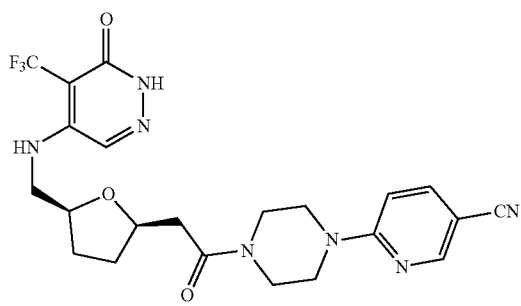

Isomer A

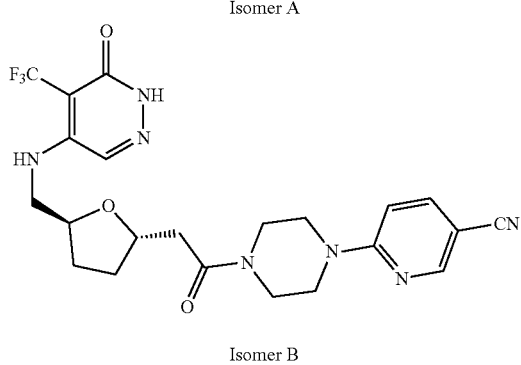

Isomer B

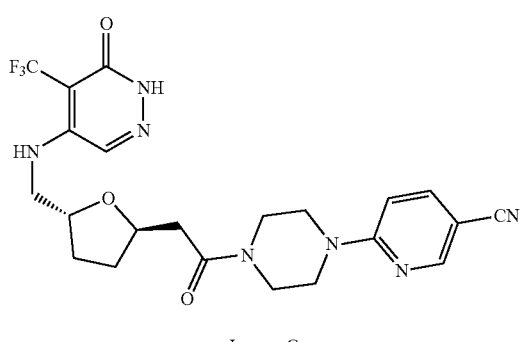

Isomer C

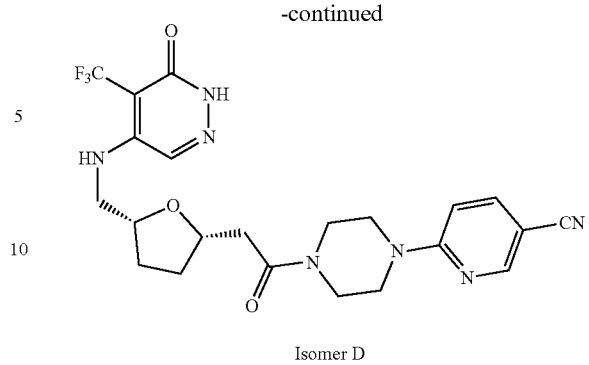

Isomer D

Step 1: (5-[2-[4-(5-cyanopyridin-2-yl)piperazin-1-yl]-2-oxoethyl]oxolan-2-yl)methyl methanesulfonate A solution of 6-(4-[2-[5-(hydroxymethyl)oxolan-2-yl]acetyl]piperazin-1-yl)pyridine-3-carbonitrile (1.5 g, 4.54 mmol, 1 equiv), TEA (0.9 g, 8.89 mmol, 1.96 equiv), Ms$_2$O (0.95 g) in DCM (20 mL) was stirred for 5 h at room temperature. The resulting solution was diluted with 20 mL of water and extracted with 3×20 mL DCM. The organic layers were combined and dried over anhydrous sodium sulfate and concentrated under vacuum to afford 2.3 g (crude) of the title compound as a yellow oil. LCMS (ESI, m/z): 409.15[M+H]$^+$ Step 2: 6-(4-[2-[5-(Azidomethyl)oxolan-2-yl]acetyl]piperazin-1-yl)pyridine-3-carbonitrile A solution of (5-[2-[4-(5-cyanopyridin-2-yl)piperazin-1-yl]-2-oxoethyl]oxolan-2-yl)methyl methanesulfonate (1.85 g, 4.53 mmol, 1 equiv), NaN$_3$ (442 mg, 6.80 mmol, 1.50 equiv) in DMF (20 mL) was stirred for 2 h at 90° C. The reaction was then quenched by the addition of 20 mL of water. The resulting solution was extracted with 3×30 mL of EtOAc, and the organic layers were combined, dried over anhydrous sodium sulfate, and concentrated under vacuum to afford 1.8 g (crude) of the title compound as a yellow oil. LCMS (ESI, m/z): 356.18 [M+H]$^+$ Step 3: 6-(4-[2-[5-(Aminomethyl)oxolan-2-yl]acetyl]piperazin-1-yl)pyridine-3-carbonitrile A solution of 6-(4-[2-[5-(azidomethyl)oxolan-2-yl]acetyl]piperazin-1-yl)pyridine-3-carbonitrile (1.6 g, 4.50 mmol, 1 equiv), triphenylphosphine (1.4 g, 5.34 mmol, 1.19 equiv) in THF (20 mL) and H$_2$O (5 mL) was stirred 3 h at 80° C. After concentration, the residue was purified by C18 reverse phase chromatography eluting with H$_2$O/ACN to afford 1.1 g (74.18%) of the title compound as a yellow oil. LCMS (ESI, m/z): 330.19[M+H]$^+$ Step 4: 6-(4-[2-[5-([[6-Oxo-5-(trifluoromethyl)-1-[[2-(trimethylsilyl)ethoxy]methyl]-1,6-dihydropyridazin-4-yl]amino]methyl)oxolan-2-yl]acetyl]piperazin-1-yl)pyridine-3-carbonitrile A solution of 6-(4-[2-[5-(aminomethyl)oxolan-2-yl]acetyl]piperazin-1-yl)pyridine-3-carbonitrile (400 mg, 1.21 mmol, 1 equiv), TEA (242.4 mg, 2.40 mmol, 1.97 equiv), and Int-A6 (434 mg, 1.32 mmol, 1.09 equiv) in EtOH (20 mL) was stirred for 2 h at 80° C. The solvent was concentrated under vacuum and the residue was applied onto a silica gel column eluting with EtOAc/petroleum ether (1/1) to afford 800 mg of the title compound as a yellow solid. LCMS (ESI, m/z): 622.27[M+H]+

Step 5: 6-(4-[2-[(2R,5S)-5-([[6-oxo-5-(trifluoromethyl)-1,6-dihydropyridazin-4-yl]amino]methyl)oxolan-2-yl]acetyl]piperazin-1-yl)pyridine-3-carbonitrile, 6-(4-[2-[(2S,5S)-5-([[6-oxo-5-(trifluoromethyl)-1,6-dihydropyridazin-4-yl]amino]methyl)oxolan-2-yl]acetyl]piperazin-1-yl)pyridine-3-carbonitrile, 6-(4-[2-[(2R,5R)-5-([[6-oxo-5-(trifluoromethyl)-1,6-dihydropyridazin-4-yl]amino]methyl)oxolan-2-yl]acetyl]piperazin-1-yl)pyridine-3-carbonitrile and 6-(4-[2-[(2S,5R)-5-([[6-oxo-5-(trifluoromethyl)-1,6-dihydropyridazin-4-yl]amino]methyl)oxolan-2-yl]acetyl]piperazin-1-yl)pyridine-3-carbonitrile A solution of 6-(4-[2-[5-([[6-oxo-5-(trifluoromethyl)-1-[[2-(trimethylsilyl)ethoxy]methyl]-1,6-dihydropyridazin-4-yl]amino]methyl)oxolan-2-yl]acetyl]piperazin-1-yl)pyridine-3-carbonitrile (800 mg, 1.29 mmol, 1 equiv), TFA (1 mL) in DCM (10 mL) was stirred for 2 h at room temperature. After concentration, the residue was purified by C18 reverse phase chromatography eluting with H$_2$O/CH$_3$CN. Then the residue was further purified by Prep-HPLC and Chiral-Prep-HPLC (Repaired IC, 0.46*10 cm; 3 um, (Hex:DCM=1:1)(0.1% DEA):EtOH=50:50, 1.0 mL/min) yielding (after arbitrary assignment of stereochemistry) the title compounds as white solids.

Example 581 Isomer A 27.4 mg, 4.33%, LCMS (ESI, m/z): 491.47 [M+H]+, $^1$H NMR (300 MHz, DMSO-d6) δ: 12.35 (s, 1H), 8.48 (d, J=2.3 Hz, 1H), 7.91-7.80 (m, 2H), 6.92-6.89 (m, 2H), 4.24 (q, J=6.4 Hz, 1H), 4.08 (t, J=5.9 Hz, 1H), 3.69-3.32 (m, 10H), 2.87-2.65 (m, 1H), 2.51-2.42 (m, 1H), 2.02 (m, 2H), 1.69-1.45 (m, 2H). tR=3.364 min.

Example 581 Isomer B 24.7 mg, 3.91%, LCMS (ESI, m/z): 491.47 [M+H]+, $^1$H NMR (300 MHz, DMSO-d6) δ: 12.35 (s, 1H), 8.49 (d, J=2.3 Hz, 1H), 7.94-7.81 (m, 2H), 6.90 (d, J=9.1 Hz, 2H), 4.17 (q, J=6.4 Hz, 1H), 4.02-3.92 (m, 1H), 3.69-3.36 (m, 10H), 2.59 (dd, J=15.4, 6.6 Hz, 1H), 2.38 (dd, J=15.4, 6.2 Hz, 1H), 2.00-1.80 (m, 2H), 1.66 (dt, J=12.3, 5.5 Hz, 1H), 1.50 (s, 1H). tR=4.177 min.

Example 581 Isomer C 33.6 mg, 5.31%, LCMS (ESI, m/z): 491.47 [M+H]+, $^1$H NMR (300 MHz, DMSO-d6) δ: 12.42 (s, 1H), 8.52 (d, J=2.4 Hz, 1H), 7.97-7.85 (m, 2H), 6.93 (d, J=9.1 Hz, 2H), 4.19 (t, J=6.4 Hz, 1H), 4.00 (s, 1H), 3.67-3.34 (m, 10H), 2.62 (dd, J=15.5, 6.5 Hz, 1H), 2.41 (dd, J=15.3, 6.1 Hz, 1H), 2.01-1.90 (m, 2H), 1.71 (s, 1H), 1.53 (s, 1H). tR=7.477 min.

Example 581 Isomer D 39.6 mg, 6.26%, LCMS (ESI, m/z): 491.47 [M+H]+, $^1$H NMR (300 MHz, DMSO-d6) δ: 12.39 (s, 1H), 8.51 (d, J=2.2 Hz, 1H), 7.95-7.83 (m, 2H), 6.93 (t, J=8.0 Hz, 2H), 4.26 (t, J=6.3 Hz, 1H), 4.16-4.07 (m, 1H), 3.67-3.34 (m, 10H), 2.69 (dd, J=15.1, 6.5 Hz, 1H), 2.45 (dd, J=15.0, 6.3 Hz, 1H), 2.11-2.00 (m, 2H), 1.65-1.54 (m, 2H). tR=10.970 min.

Example 582 Isomer A: 6-(4-[2-[(2S,5S)-5-[[(5-Chloro-6-oxo-1,6-dihydropyridazin-4-yl)oxy]methyl]oxolan-2-yl]acetyl]piperazin-1-yl)pyridine-3-carbonitrile and Example 582 Isomer B: 6-(4-[2-[(2R,5R)-5-[[(5-Chloro-6-oxo-1,6-dihydropyridazin-4-yl)oxy]methyl]oxolan-2-yl]acetyl]piperazin-1-yl)pyridine-3-carbonitrile and Example 582 Isomer C: 6-(4-[2-[(2R,5S)-5-[[(5-Chloro-6-oxo-1,6-dihydropyridazin-4-yl)oxy]methyl]oxolan-2-yl]acetyl]piperazin-1-yl)pyridine-3-carbonitrile and Example 582 Isomer D: 6-(4-[2-[(2S,5R)-5-[[(5-Chloro-6-oxo-1,6-dihydropyridazin-4-yl)oxy]methyl]oxolan-2-yl]acetyl]piperazin-1-yl)pyridine-3-carbonitrile

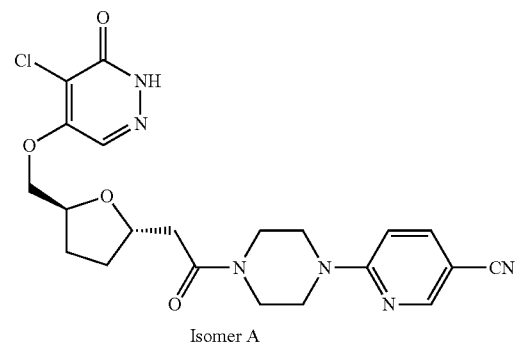

Isomer A

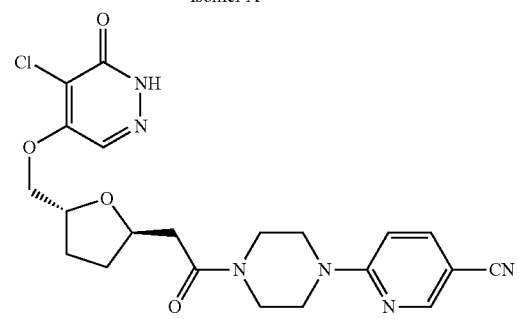

Isomer B

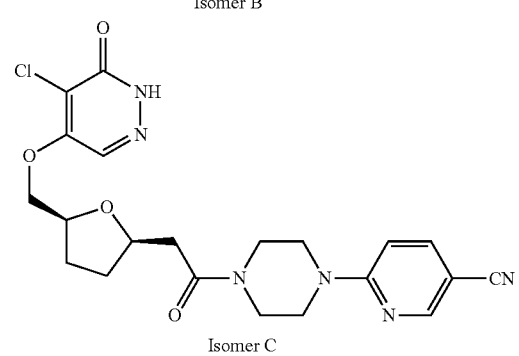

Isomer C

-continued

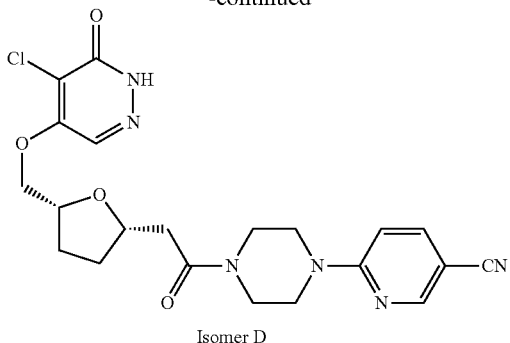

Isomer D

Step 1: 6-[4-[2-(5-[[(5-chloro-6-oxo-1-[[2-(trimethylsilyl)ethoxy]methyl]-1,6-dihydropyridazin-4-yl)oxy]methyl]oxolan-2-yl)acetyl]piperazin-1-yl]pyridine-3-carbonitrile A solution of Int-A7 (1.3 g, 4.5 mmol, 3 equiv), 6-(4-[2-[5-(hydroxymethyl)oxolan-2-yl]acetyl]piperazin-1-yl)pyridine-3-carbonitrile (500 mg, 1.5 mmol, 1 equiv), NaH (121 mg, 3.0 mmol, 2 equiv, 60%) in ACN (10 mL) was stirred for 1 h at 40° C. The resulting mixture was concentrated and the residue was applied onto a silica gel column eluting with EtOAc/petroleum ether (1:1) to afford 420 mg (47.10%) of the title compound as yellow oil. LCMS (ESI, m/z): 589.24 [M+H]+

Step 2: 6-(4-[2-[(2S,5S)-5-[[(5-chloro-6-oxo-1,6-dihydropyridazin-4-yl)oxy]methyl]oxolan-2-yl]acetyl]piperazin-1-yl)pyridine-3-carbonitrile, 6-(4-[2-[(2R,5R)-5-[[(5-chloro-6-oxo-1,6-dihydropyridazin-4-yl)oxy]methyl]oxolan-2-yl]acetyl]piperazin-1-yl)pyridine-3-carbonitrile, 6-(4-[2-[(2R,5S)-5-[[(5-chloro-6-oxo-1,6-dihydropyridazin-4-yl)oxy]methyl]oxolan-2-yl]acetyl]piperazin-1-yl)pyridine-3-carbonitrile and 6-(4-[2-[(2S,5R)-5-[[(5-chloro-6-oxo-1,6-dihydropyridazin-4-yl)oxy]methyl]oxolan-2-yl]acetyl]piperazin-1-yl)pyridine-3-carbonitrile A solution of 6-[4-[2-(5-[[(5-chloro-6-oxo-1-[[2-(trimethylsilyl)ethoxy]methyl]-1,6-dihydropyridazin-4-yl)oxy]methyl]oxolan-2-yl)acetyl]piperazin-1-yl]pyridine-3-carbonitrile (410 mg, 0.70 mmol, 1 equiv), and TFA (2 mL) in DCM (10 mL) was stirred for 0.5 h at RT. After concentration, the residue was purified by C18 reverse phase chromatography eluting with H₂O/ACN. Then the residue was further purified by Prep-HPLC and Chiral-HPLC yielding (after arbitrary assignment of stereochemistry) the title compounds as white solids.

Example 582 Isomer A 12.6 mg, 3.95%, LCMS (ESI, m/z): 459.30 [M+H]+, $^1$H NMR (300 MHz, Methanol-d4) δ 8.40 (d, J=0.8 Hz, 1H), 8.17 (s, 1H), 7.75 (dd, J=9.1, 2.4 Hz, 1H), 6.82 (dd, J=9.1, 0.9 Hz, 1H), 4.57-4.47 (m, 1H), 4.44-4.27 (m, 3H), 3.86-3.59 (m, 8H), 2.80 (dd, J=14.8, 7.8 Hz, 1H), 2.59 (dd, J=14.7, 4.7 Hz, 1H), 2.17-2.07 (m, 2H), 2.02-1.92 (m, 1H), 1.90-1.75 (m, 1H). tR=3.894 min.

Example 582 Isomer B 3.0 mg, 4.07%, LCMS (ESI, m/z): 459.30 [M+H]+, $^1$H NMR (300 MHz, Methanol-d₄) δ 8.40 (s, 1H), 8.17 (s, 1H), 7.75 (dd, J=9.1, 2.4 Hz, 1H), 6.82 (d, J=9.1 Hz, 1H), 4.57-4.47 (m, 1H), 4.44-4.27 (m, 3H), 3.86-3.59 (m, 8H), 2.80 (dd, J=14.8, 7.8 Hz, 1H), 2.59 (dd, J=14.8, 4.7 Hz, 1H), 2.20-2.09 (m, 2H), 2.08-2.03 (m, 1H), 1.90-1.75 (m, 1H). tR=4.613 min.

Example 582 Isomer C 24.4 mg, 7.64%, LCMS (ESI, m/z): 459.30 [M+H]+, $^1$H NMR (300 MHz, Methanol-d₄) δ 8.43 (s, 1H), 8.15 (s, 1H), 7.77 (dd, J=9.1, 2.4 Hz, 1H), 6.86 (d, J=9.1 Hz, 1H), 4.50-4.28 (m, 4H), 3.94-3.55 (m, 8H), 2.83 (dd, J=14.4, 7.9 Hz, 1H), 2.58 (dd, J=14.4, 4.6 Hz, 1H), 2.35-2.13 (m, 2H), 2.01-1.92 (m, 1H), 1.90-1.75 (m, 1H). tR=8.158 min.

Example 582 Isomer D 18.5 mg, 5.79%, LCMS (ESI, m/z): 459.30 [M+H]+, $^1$H NMR (300 MHz, Methanol-d4) δ 8.43 (s, 1H), 8.16 (s, 1H), 7.77 (dd, J=9.1, 2.4 Hz, 1H), 6.82 (dd, J=9.1, 0.9 Hz, 1H), 4.45-4.28 (m, 4H), 3.94-3.55 (m, 8H), 2.83 (dd, J=14.4, 7.9 Hz, 1H), 2.58 (dd, J=14.4, 4.6 Hz, 1H), 2.27-2.13 (m, 2H), 2.01-1.76 (m, 2H). tR=5.253 min.

Example 583 Isomer A: 6-(4-[2-[(2S,6S)-6-([[6-oxo-5-(trifluoromethyl)-1,6-dihydropyridazin-4-yl]oxy]methyl)oxan-2-yl]acetyl]piperazin-1-yl)pyridine-3-carbonitrile and Example 583 Isomer B: 6-(4-[2-[(2R,6R)-6-([[6-oxo-5-(trifluoromethyl)-1,6-dihydropyridazin-4-yl]oxy]methyl)oxan-2-yl]acetyl]piperazin-1-yl)pyridine-3-carbonitrile

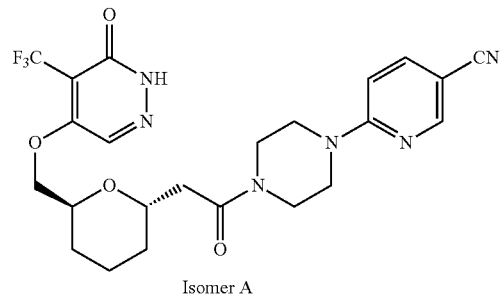

Isomer A

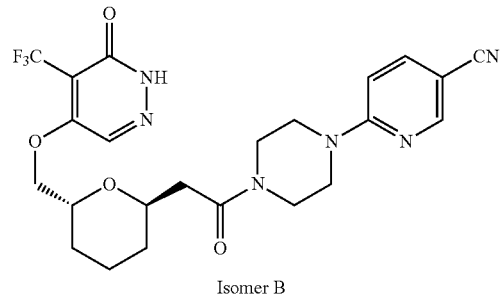

Isomer B

Step 1: 1-(Benzyloxy)hept-6-en-2-ol

To a solution of CuI (234 mg, 1.23 mmol, 0.10 equiv) in THF (40 mL) was added bromo(but-3-en-1-yl)magnesium (18.3 mL, 114.68 mmol, 1.5 equiv) at −40° C., and the resulting solution was stirred for 10 min at −40° C. 2-[(benzyloxy)methyl]oxirane (2 g, 12.18 mmol, 1 equiv) was dropped in and then the resulting solution was stirred for another 1.5 h at this temperature. The reaction was quenched by the addition of 50 mL of NH$_4$Cl, extracted with 3×50 ml of EtOAc, washed with 1×50 ml of brine, dried over anhydrous sodium sulfate and concentrated under vacuum. The residue was applied onto a silica gel column eluting with EtOAc/petroleum ether (1:5) to afford 1.17 g (43.60%) of the title compound as a yellow oil. LCMS (ESI, m/z): 221.10 [M+H]$^+$ Step 2: Methyl (2Z)-8-(benzyloxy)-7-hydroxyoct-2-enoate A solution of 1-(benzyloxy)hept-6-en-2-ol (1.6 g, 7.26 mmol, 1 equiv), methyl prop-2-enoate (3.12 g, 0.04 mmol) and Grubbs 2nd generation catalyst (61.7 mg, 0.07 mmol, 0.01 equiv) in DCM (32 mL) was stirred for 12 h at 50° C. in an oil bath. The resulting mixture was concentrated under vacuum and the residue was applied onto a silica gel column eluting with EtOAc/petroleum ether (1:3) to afford 1.57 g (77.67%) of the title compound as light brown oil. LCMS (ESI, m/z): 279.05 [M+H]$^+$ Step 3: Methyl 2-[6-[(benzyloxy)methyl]oxan-2-yl]acetate To a solution of methyl (2Z)-8-(benzyloxy)-7-hydroxyoct-2-enoate (1.4 g, 5.03 mmol, 1 equiv) in THF (10 mL) was added NaH (241 mg, 10.04 mmol, 2.00 equiv) in several batches. The resulting solution was stirred for 6 h at room temperature. The reaction was then quenched by the addition of 20 mL of water, extracted with 3×30 ml of EtOAc, washed with 20 ml of brine, dried over anhydrous sodium sulfate and concentrated under vacuum. The residue was applied onto a silica gel column eluting with EtOAc/petroleum ether (1:3) to afford 560 mg (40.0%) of the title compound as yellow oil. LCMS (ESI, m/z): 279.05 [M+H]$^+$ Step 4: 2-[6-[(benzyloxy)methyl]oxan-2-yl]acetic Acid A solution of methyl 2-[6-[(benzyloxy)methyl]oxan-2-yl]acetate (510 mg, 1.83 mmol, 1 equiv) and NaOH (220 mg, 5.50 mmol, 3.00 equiv) in H$_2$O (2 mL) in THF (10 mL) was stirred for 4 h at room temperature. 1 M HCl was added to adjust the pH to 4, and the solution was extracted with 3×5 ml of ethyl acetate. The organic portion was dried over anhydrous sodium sulfate and concentrated under vacuum. This resulted in 410 mg (84.66%) of the title compound as a yellow solid. LCMS (ESI, m/z): 265.10 [M+H]$^+$ Step 5: 6-[4-(2-[6-[(benzyloxy)methyl]oxan-2-yl]acetyl)piperazin-1-yl]pyridine-3-carbonitrile A solution of 2-[6-[(benzyloxy)methyl]oxan-2-yl]acetic acid (400 mg, 1.51 mmol, 1 equiv), HATU (575 mg, 1.51 mmol, 1.00 equiv), DIPEA (587 mg, 4.54 mmol, 3.00 equiv) and Int-A4 in DMF (5 mL) was stirred for 40 min at room temperature. Then resulting solution was diluted with 15 mL of water, extracted with 3×15 mL of EtOAc, washed with 1×15 mL of brine, dried over anhydrous sodium sulfate and concentrated under vacuum. The residue was applied onto a silica gel column eluting with DCM/MeOH (10:1) to afford 490 mg (71.53%) of the title compound as a light brown solid. LCMS (ESI, m/z): 435.15 [M+H]$^+$ Step 6: 6-(4-[2-[6-(Hydroxymethyl)oxan-2-yl] acetyl]piperazin-1-yl)pyridine-3-carbonitrile To a solution of 6-[4-(2-[6-[(benzyloxy)methyl]oxan-2-yl]acetyl)piperazin-1-yl]pyridine-3-carbonitrile (2.1 g, 4.83 mmol, 1 equiv) in DCM (200 mL) at 0° C. was added BCl$_3$ (7.2 mL, 1.5 equiv) dropwise. The resulting solution was stirred for 2 h at 0° C. in a water/ice bath. The reaction was quenched by the addition of 100 mL of MeOH, and the pH value of the solution was adjusted to 4 with HCl (1 M) and concentrated under vacuum. The residue was purified by C18 reverse phase chromatography eluting with H$_2$O/ACN to afford 680 mg (40.85%) of the title compound as a yellow solid. LCMS (ESI, m/z): 345.10 [M+H]$^+$ Step 7: 6-(4-[2-[6-([[6-Oxo-5-(trifluoromethyl)-1-[[2-(trimethylsilyl)ethoxy]methyl]-1,6-dihydropyridazin-4-yl]oxy]methyl)oxan-2-yl]acetyl]piperazin-1-yl)pyridine-3-carbonitrile A solution of 6-(4-[2-[6-(hydroxymethyl)oxan-2-yl]acetyl]piperazin-1-yl)pyridine-3-carbonitrile (680 mg, 1.97 mmol, 1 equiv), Cs$_2$CO$_3$ (1.93 g, 0.01 mmol) and Int-A6 (1.94 g, 0.01 mmol) in ACN (20 mL) was stirred for 3 h at 70° C. in an oil bath. The solids were filtered out and the residue was applied onto a silica gel column eluting with EtOAc/petroleum ether (1:4) to afford 860 mg crude product. The crude product was purified by C18 reverse phase chromatography eluting with H$_2$O/ACN to afford 720 mg (57.27%) of the title compound as a white solid. LCMS (ESI, m/z): 637.25 [M+H]$^+$ Step 8: 6-(4-[2-[(2S,6S)-6-([[6-oxo-5-(trifluoromethyl)-1,6-dihydropyridazin-4-yl]oxy]methyl)oxan-2-yl]acetyl]piperazin-1-yl)pyridine-3-carbonitrile and 6-(4-[2-[(2R,6R)-6-([[6-oxo-5-(trifluoromethyl)-1,6-dihydropyridazin-4-yl]oxy]methyl)oxan-2-yl] acetyl]piperazin-1-yl)pyridine-3-carbonitrile A solution of 6-(4-[2-[6-([[6-oxo-5-(trifluoromethyl)-1-[[2-(trimethylsilyl)ethoxy]methyl]-1,6-dihydropyridazin-4-yl]oxy]methyl)oxan-2-yl]acetyl]piperazin-1-yl)pyridine-3-carbonitrile (720 mg, 1.13 mmol, 1 equiv) and TFA (6 mL, 0.05 mmol, 0.05 equiv) in DCM (30 mL) was stirred for 1 h at RT. The resulting mixture was concentrated and the crude product was purified by C18 reverse phase chromatography eluting with H$_2$O/ACN. The crude product was further purified by Prep-HPLC and Chiral-Prep-HPLC (CHIRALCEL OJ-3, 4.6*50 mm, 3 um; MeOH (0.1% DEA), 2.0 ml/min) yielding (after arbitrary assignment of stereochemistry) the title compounds as white solids.

Example 583 Isomer A 80.3 mg, 43.8%, LCMS (ESI, m/z): 507.30 [M+H]$^+$, $^1$H NMR (CD$_3$OD-d$_4$, 300 MHz) δ: 8.38 (dd, J=2.4, 0.8 Hz, 1H), 8.17 (d, J=0.9 Hz, 1H), 7.73 (dd, J=9.1, 2.4 Hz, 1H), 6.78 (dd, J=9.1, 0.8 Hz, 1H), 4.46-4.31 (m, 2H), 3.90-3.75 (m, 6H), 3.65-3.57 (m, 4H), 2.76 (dd, J=14.5, 8.7 Hz, 1H), 2.45 (dd, J=14.4, 3.8 Hz, 1H), 1.96 (d, J=10.8 Hz, 1H), 1.78-1.60 (m, 3H), 1.56-1.28 (m, 2H). tR=2.027 min.

Example 583 Isomer B 78.1 mg, 42.6%, LCMS (ESI, m/z): 507.30 [M+H]+, $^1$H NMR (CD$_3$OD-d4, 300 MHz) δ 8.38 (dd, J=2.4, 0.8 Hz, 1H), 8.17 (d, J=0.9 Hz, 1H), 7.73 (dd, J=9.1, 2.4 Hz, 1H), 6.78 (dd, J=9.1, 0.8 Hz, 1H), 4.46-4.32 (m, 2H), 3.90-3.74 (m, 6H), 3.65-3.56 (m, 4H), 2.76 (dd, J=14.5, 8.7 Hz, 1H), 2.45 (dd, J=14.4, 3.8 Hz, 1H), 1.97 (d, J=13.3 Hz, 1H), 1.78-1.60 (m, 3H), 1.56-1.28 (m, 2H). tR=2.408 min.

Example 584: 5-[[(2S)-1-(3-oxo-3-[4-[5-(trifluoromethyl)pyridin-2-yl]piperazin-1-yl]propoxy)propan-2-yl]oxy]-4-(trifluoromethyl)-2,3-dihydropyridazin-3-one

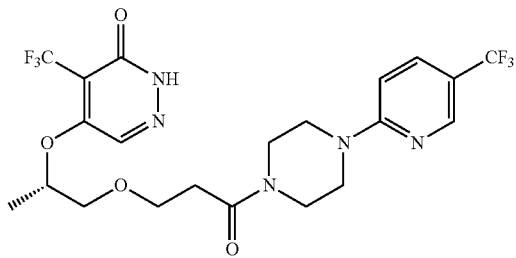

Step 1: 1-[4-[5-(Trifluoromethyl)pyridin-2-yl]piperazin-1-yl]prop-2-en-1-one

A solution of Int-A18 (1 g, 4.32 mmol, 1 equiv), prop-2-enoyl prop-2-enoate (600 mg, 4.76 mmol, 1.10 equiv) and TEA (1.3 g, 12.85 mmol, 2.97 equiv) in DCM (50 mL) was stirred for 1 h at room temperature. The resulting solution was concentrated under vacuum and the residue was applied onto a silica gel column eluting with EtOAc/petroleum ether (1:1) to afford 750 mg (60.79%) of the title compound as a white solid. LCMS (ESI, m/z): 286.11 [M+H]+

Step 2: 3-[(2S)-2-Hydroxypropoxy]-1-[4-[5-(trifluoromethyl)pyridin-2-yl]piperazin-1-yl]propan-1-one A solution of 1-[4-[5-(trifluoromethyl)pyridin-2-yl]piperazin-1-yl]prop-2-en-1-one (750 mg, 1.0 equiv), (2S)-propane-1,2-diol (600 mg, 3.0 equiv) and Cs₂CO₃ (2.5 g, 3.0 equiv) in ACN (50 mL) was stirred for 18 h at 80° C. The solid was filtered out and the resulting solution was concentrated under vacuum. The residue was applied onto a silica gel column eluting with EtOAc/petroleum ether (2:98), and the residue was further purified by C18 reverse phase chromatography eluting with H₂O/ACN to afford 276 mg of the title compound as a white solid. LCMS (ESI, m/z): 362.16[M+H]+

Step 3: 5-[[(2S)-1-(3-Oxo-3-[4-[5-(trifluoromethyl)pyridin-2-yl]piperazin-1-yl]propoxy)propan-2-yl]oxy]-4-(trifluoromethyl)-2-[[2-(trimethylsilyl)ethoxy]methyl]-2,3-dihydropyridazin-3-one A solution of 3-[(2S)-2-hydroxypropoxy]-1-[4-[5-(trifluoromethyl)pyridin-2-yl]piperazin-1-yl]propan-1-one (225 mg, 0.62 mmol, 1 equiv), Int-A6 (1.2 g, 3.65 mmol, 5.86 equiv) and Cs₂CO₃ (506 mg, 1.55 mmol, 2.49 equiv) in ACN (8 mL) was stirred for 2 h at 80° C. The solid was filtered out and the resulting solution was concentrated under vacuum, and the residue was applied onto a silica gel column eluting with EtOAc/petroleum ether (88:12) to afford 70 mg (17.20%) of the title compound as a brown solid. LCMS (ESI, m/z): 654.25 [M+H]+

Step 4: 5-[[(2S)-1-(3-oxo-3-[4-[5-(trifluoromethyl)pyridin-2-yl]piperazin-1-yl]propoxy)propan-2-yl]oxy]-4-(trifluoromethyl)-2,3-dihydropyridazin-3-one A solution of 5-[[(2S)-1-(3-oxo-3-[4-[5-(trifluoromethyl)pyridin-2-yl]piperazin-1-yl]propoxy)propan-2-yl]oxy]-4-(trifluoromethyl)-2-[[2-(trimethylsilyl)ethoxy]methyl]-2,3-dihydropyridazin-3-one (125 mg, 0.19 mmol, 1 equiv) and TFA (2 mL) in DCM (5 mL) was stirred for 2 h at room temperature, then the resulting solution was concentrated under vacuum and the residue was purified by Pre-HPLC yielding the title compound (11.8 mg, 11.79%) as a white solid. LCMS (ESI, m/z): 524.10 [M+H]+. ¹H NMR (Methanol-d4, 300 MHz) δ 8.38 (dt, J=2.1, 1.0 Hz, 1H), 8.23 (s, 1H), 7.78 (dd, J=9.0, 2.4 Hz, 1H), 6.90 (d, J=9.0 Hz, 1H), 5.18-5.08 (m, 1H), 3.87-3.58 (m, 12H), 2.67 (t, J=6.0 Hz, 2H), 1.37 (d, J=6.3 Hz, 3H).

Example 585: 5-[[(2S)-1-(3-Oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one

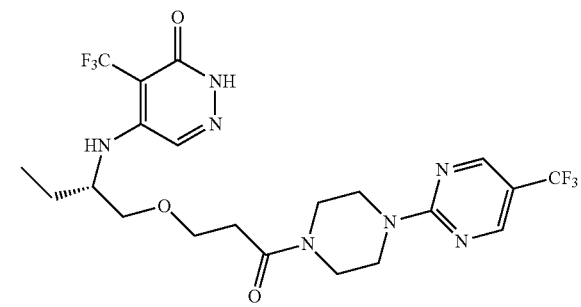 [SMILES: CC[C@@H](COCCC(=O)N1CCN(c2ncc(C(F)(F)F)cn2)CC1)Nc1cn[nH]c(=O)c1C(F)(F)F]

Step 1: 5-[[(2S)-1-Hydroxybutan-2-yl]amino]-4-(trifluoromethyl)-2-[[2-(trimethylsilyl)ethoxy]methyl]-2,3-dihydropyridazin-3-one A solution of (2S)-2-aminobutan-1-ol (534 mg, 5.99 mmol, 1 equiv), TEA (1212.4 mg, 11.98 mmol, 2 equiv) and Int-A6 (1969.7 mg, 5.99 mmol, 1.0 equiv) in EtOH (20 mL) was stirred for 1 h at 60° C. The solvent was concentrated under vacuum and the residue was applied onto a silica gel column eluting with EtOAc/petroleum ether (4/6) to afford 1.1 g (48.13%) of the title compound as yellow oil. LCMS (ESI, m/z): 382.17 [M+H]

Step 2: Methyl 3-[(2S)-2-[[6-oxo-5-(trifluoromethyl)-1-[[2-(trimethylsilyl)ethoxy]methyl]-1,6-dihydropyridazin-4-yl]amino]butoxy]propanoate A solution of 5-[[(2S)-1-hydroxybutan-2-yl]amino]-4-(trifluoromethyl)-2-[[2-(trimethylsilyl)ethoxy]methyl]-2,3-dihydropyridazin-3-one (1.0 g, 2.62 mmol, 1 equiv), Cs₂CO₃ (2562.3 mg, 7.86 mmol, 3 equiv) and methyl prop-2-enoate (2256.8 mg, 26.21 mmol, 10 equiv) in ACN (20 mL) was stirred for 6 h at RT. The solid was filtered out and the resulting solution was concentrated under vacuum. The residue was purified by C18 reverse phase chromatography eluting with H₂O/ACN to afford 450 mg (36.71%) of the title compound as a yellow oil. LCMS (ESI, m/z): 468.21 [M+H]+.

Step 3: Methyl 3-[(2S)-2-[[6-oxo-5-(trifluoromethyl)-1,6-dihydropyridazin-4-yl]amino]butoxy]propanoate A solution of methyl 3-[(2S)-2-[[6-oxo-5-(trifluoromethyl)-1-[[2-(trimethylsilyl)ethoxy]methyl]-1,6-dihydropyridazin-4-yl]amino]butoxy]propanoate (450 mg, 0.96 mmol, 1 equiv) and TFA (0.6 mL) in DCM (3 mL) was stirred for 1 h at room temperature. The resulting mixture was concentrated under vacuum to afford 340 mg of the title compound as a yellow oil. LCMS (ESI, m/z): 338.13 [M+H]$^+$.

Step 4: 3-[(2S)-2-[[6-Oxo-5-(trifluoromethyl)-1,6-dihydropyridazin-4-yl]amino]butoxy]propanoic Acid A solution of methyl 3-[(2S)-2-[[6-oxo-5-(trifluoromethyl)-1,6-dihydropyridazin-4-yl]amino]butoxy]propanoate (340 mg, 1.01 mmol, 1 equiv) and LiOH (241.4 mg, 10.08 mmol, 10 equiv) in MeOH (10 mL) and H$_2$O (2 mL) was stirred for 2 h at RT. The resulting solution was concentrated under vacuum and the residue was purified by C18 reverse phase chromatography eluting with H$_2$O/ACN to afford 220 mg (67.51%) of the title compound as a yellow oil. LCMS (ESI, m/z): 324.11 [M+H]$^+$.

Step 5: 5-[[(2S)-1-(3-oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one A solution of 3-[(2S)-2-[[6-oxo-5-(trifluoromethyl)-1,6-dihydropyridazin-4-yl]amino]butoxy]propanoic acid (200 mg, 0.62 mmol, 1 equiv), HATU (235.2 mg, 0.62 mmol, 1 equiv), DIPEA (159.9 mg, 1.24 mmol, 2 equiv) and Int-A2 (143.7 mg, 0.62 mmol, 1 equiv) in DMF (5 mL) was stirred for 1 h at room temperature and the resulting solution was purified by C18 reverse phase chromatography eluting with H$_2$O/ACN. The residue was further purified by Prep-HPLC yielding the title compound (43.2 mg, 13%) as a white solid. LCMS (ESI, m/z): 538.30 [M+H]$^+$, $^1$H NMR (Methanol-d$_4$, 300 MHz) δ: 8.61 (d, J=0.9 Hz, 2H), 7.96 (s, 1H), 4.01-3.91 (m, 5H), 3.86-3.52 (m, 8H), 2.72 (t, J=6.0 Hz, 2H), 1.75-1.55 (m, 2H), 1.01 (t, J=7.5 Hz, 3H).

The following examples in Table E10 were similarly prepared from 3-[(2S)-2-[[6-oxo-5-(trifluoromethyl)-1,6-dihydropyridazin-4-yl]amino]butoxy]propanoic acid and the appropriate intermediates as described for Example 585.

TABLE E10

| Example | Name, structure, analytical data | Int. |
|---|---|---|
| 586 | 5-[[(2S)-1-[3-[4-(5-Chloropyridin-2-yl)piperazin-1-yl]-3-oxopropoxy]butan-2-yl]amino]-4-(trifluoromethyl)-2,3-dihydropyridazin-3-one; LCMS [M + H]$^+$ 503.25; $^1$H NMR (400 MHz, Methanol-d$_4$) δ 8.07 (d, J = 2.4 Hz, 1H), 7.95 (s, 1H), 7.54 (dd, J = 9.2, 2.4 Hz, 1H), 6.81 (d, J = 9.2 Hz, 1H), 3.96 (d, J = 8.0 Hz, 1H), 3.84-3.50 (m, 12H), 2.68 (t, J = 6.0 Hz, 2H), 1.78-1.52 (m, 2H), 0.98 (t, J = 7.4 Hz, 3H). | 3-[(2S)-2-[[6-oxo-5-(trifluoromethyl)-1,6-dihydropyridazin-4-yl]amino]butoxy]propanoic acid and Int-A5 |
| 587 | 5-[[(2,S)-1-(3-Oxo-3-[4-[5-(trifluoromethyl)pyridin-2-yl]piperazin-1-yl]propoxy)butan-2-yl]amino]-4-(trifluoromethyl)-2,3-dihydropyridazin-3-one; LCMS [M + H]$^+$ 537.35; $^1$H NMR (300 MHz, Methanol-d$_4$) δ 8.38 (s, 1H), 7.97 (s, 1H), 7.77 (dd, J = 9.1, 2.6 Hz, 1H), 6.90 (d, J = 9.1 Hz, 1H), 3.97-3.85 (m, 1H), 3.83-3.62 (m, 11H), 3.58-3.52 (m, 1H), 2.70 (t, J = 6.0 Hz, 2H), 1.76-1.55 (m, 2H), 0.99 (t, J = 7.4 Hz, 3H). | 3-[(2S)-2-[[6-oxo-5-(trifluoromethyl)-1,6-dihydropyridazin-4-yl)amino]butoxy]propanoic acid and Int-A18 |

TABLE E10-continued

| Example | Name, structure, analytical data | Int. |
|---|---|---|
| 588 | 5-[[(2S)-1-[3-[4-(5-Chloropyrimidin-2-yl)piperazin-1-yl]-3-oxopropoxy]butan-2-yl]amino]-4-(trifluoromethyl)-2,3-dihydropyridazin-3-one; LCMS [M + H]⁺ 504.35; ¹H NMR (300 MHz, DMSO-d6) δ 12.41 (s, 1H), 8.45 (s, 2H), 7.93 (s, 1H), 6.25-6.20 (m, 1H), 3.98 (d, J = 7.7 Hz, 1H), 3.76-3.61 (m, 6H), 3.58-3.49 (m, 6H), 2.60 (t, J = 6.6 Hz, 2H), 1.54 (td, J = 7.2, 3.6 Hz, 2H), 0.87 (t, J = 7.4 Hz, 3H). | 3-[(2S)-2-[[6-oxo-5-(trifluoromethyl)-1,6-dihydropyridazin-4-yl]amino]butoxy]propanoic acid and Int-A3 |

Example 589: 6-(4-[3-[(2S)-2-[[6-Oxo-5-(trifluoromethyl)-1,6-dihydropyridazin-4-yl]oxy]butoxy]propanoyl]piperazin-1-yl)pyridine-3-carbonitrile

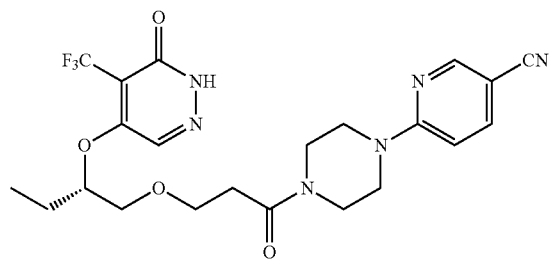 [SMILES: CC[C@@H](COCCC(=O)N1CCN(c2ccc(C#N)cn2)CC1)Oc1cn[nH]c(=O)c1C(F)(F)F]

Step 1: 6-(4-[3-[(2S)-2-hydroxybutoxy]propanoyl]piperazin-1-yl)pyridine-3-carbonitrile A solution of (2S)-butane-1,2-diol (1080 mg, 3 equiv), Cs₂CO₃ (2600 mg, 2 equiv) and 6-[4-(prop-2-enoyl)piperazin-1-yl]pyridine-3-carbonitrile (968 mg, 1 equiv) in ACN (10 mL) was stirred for 6 h at 60° C. The solids were filtered out and the resulting solution was concentrated under vacuum, and the residue was purified by C18 reverse phase chromatography eluting with H₂O/ACN to afford 400 mg (30.12%) of the title compound as colorless oil. LCMS (ESI, m/z): 333.19 [M+H]⁺

Step 2: 6-(4-[3-[(2S)-2-([1-[(4-Methoxyphenyl)methyl]-6-oxo-5-(trifluoromethyl)-1,6-dihydropyridazin-4-yl]oxy)butoxy]propanoyl]piperazin-1-yl)pyridine-3-carbonitrile A solution of 6-(4-[3-[(2S)-2-hydroxybutoxy]propanoyl]piperazin-1-yl)pyridine-3-carbonitrile (400 mg, 1.20 mmol, 1 equiv), Cs₂CO₃ (784.2 mg, 2.41 mmol, 2 equiv) and Int-A20 (575.2 mg, 1.81 mmol, 1.5 equiv) in ACN (10 mL, 0.24 mmol, 0.20 equiv) was stirred for 6 h at 80° C. The solids were filtered out and the resulting solution was concentrated under vacuum. The residue was applied onto a silica gel column eluting with EtOAc/petroleum ether to afford 320 mg (43.27%) of the title compound as a red oil. LCMS (ESI, m/z): 625.27 [M+H]⁺.

Step 3: 6-(4-[3-[(2S)-2-[[6-Oxo-5-(trifluoromethyl)-1,6-dihydropyridazin-4-yl]oxy]butoxy]propanoyl]piperazin-1-yl)pyridine-3-carbonitrile A solution of 6-(4-[3-[(2S)-2-([1-[(4-methoxyphenyl)methyl]-6-oxo-5-(trifluoromethyl)-1,6-dihydropyridazin-4-yl]oxy)butoxy]propanoyl]piperazin-1-yl)pyridine-3-carbonitrile (300 mg, 0.49 mmol, 1 equiv) and H₂SO₄ (95.7 mg, 0.98 mmol, 2 equiv) in TFA (5 mL, 0.04 mmol, 0.09 equiv) was stirred for 6 h at RT. The resulting solution was quenched by ice/water (5 mL), and extracted by EtOAc (5 mL), and the organic layer was concentrated under vacuum. The residue was purified by C18 reverse phase chromatography eluting with H₂O/CH₃CN, and then the residue was further purified by Prep-HPLC yielding the title compound (58.1 mg, 24.07%) as a white solid. LCMS (ESI, m/z): 495.15 [M+H]⁺, ¹H NMR (Methanol-d₄, 300 MHz) δ 8.43 (d, J=1.8 Hz, 1H), 8.24 (s, 1H), 7.79 (dd, J=9.0, 2.4 Hz, 1H), 6.87 (d, J=9.0 Hz, 1H), 5.03-4.96 (m, 1H), 3.89-3.59 (m, 12H), 2.63 (t, J=6.0 Hz, 2H), 1.79 (td, J=8.3, 7.8, 5.9 Hz, 2H), 1.04 (t, J=7.4 Hz, 3H).

Example 590: 2-(4-(3-(2-(6-Oxo-5-(trifluoromethyl)-1,6-dihydropyridazin-4-yloxy)ethoxy)propanoyl)piperazin-1-yl)pyrimidine-5-carbonitrile

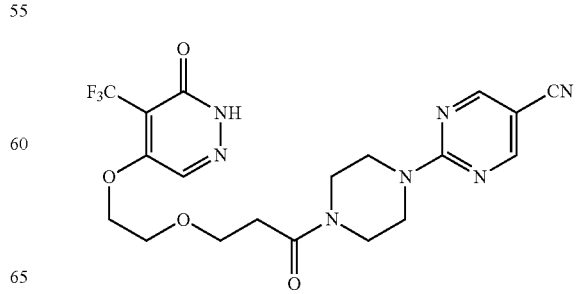

Step 1: 2-(4-(3-(2-(6-Oxo-5-(trifluoromethyl)-1,6-dihydropyridazin-4-yloxy)ethoxy)propanoyl)piperazin-1-yl)pyrimidine-5-carbonitrile A solution of Int-A11 (310 mg, 1.05 mmol, 1.00 equiv), HOBt (212.0 mg, 1.57 mmol, 1.5 equiv), EDCI (300.7 mg, 1.57 mmol, 1.5 equiv), Int-A1 (197.9 mg, 1.05 mmol, 1 equiv) in DMF (5 mL) was stirred for 4.5 h at RT. After concentration, the residue was purified by C18 reverse phase chromatography eluting with H$_2$O/ACN to afford 22.4 mg (4.58%) of the title compound (22.4 mg, 4.58%) as a white solid. LCMS (ESI, m/z): 468.15 [M+H]$^+$, $^1$H NMR (Methanol-d$_4$, 300 MHz) δ: 8.63 (s, 2H), 8.22 (s, 1H), 4.56 (t, J=1.8 Hz, 2H), 3.97-3.91 (m, 4H), 3.86-3.82 (m, 4H), 3.70-3.69 (m, 4H), 2.72 (t, J=6.0 Hz, 2H).

Example 591 Isomer A: 5-[[(2S)-1-[3-[4-(5-Chloropyrimidin-2-yl)piperazin-1-yl]-3-oxopropoxy]butan-2-yl]oxy]-4-(trifluoromethyl)-2,3-dihydropyridazin-3-one and Example 591 Isomer B: 5-[(2S)-2-[3-[4-(5-Chloropyrimidin-2-yl)piperazin-1-yl]-3-oxopropoxy]butoxy]-4-(trifluoromethyl)-2,3-dihydropyridazin-3-one

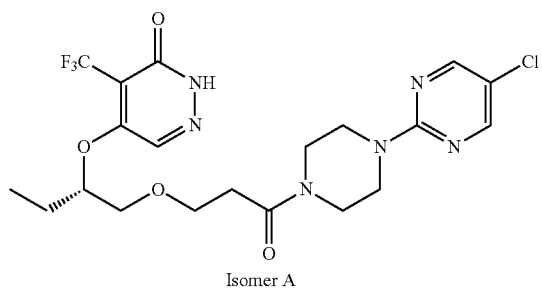

Isomer A

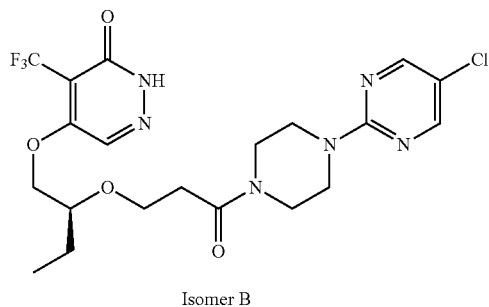

Isomer B

Step 1: 1-[4-(5-chloropyrimidin-2-yl)piperazin-1-yl]-3-[(2S)-2-hydroxybutoxy]propan-1-one and (S)-1-(4-(5-chloropyrimidin-2-yl)piperazin-1-yl)-3-(1-hydroxybutan-2-yloxy)propan-1-one A solution of (2S)-butane-1,2-diol (1426.5 mg, 15.83 mmol, 4 equiv), Cs$_2$CO$_3$ (2578.7 mg, 7.91 mmol, 2.00 equiv), 1-[4-(5-chloropyrimidin-2-yl)piperazin-1-yl]prop-2-en-1-one (1 g, 3.96 mmol, 1 equiv) in ACN (20 mL) was stirred for 5 h at 75° C. After concentration, the residue was purified by C18 reverse phase chromatography eluting with H$_2$O/CH$_3$CN to afford 820 mg (60.44%) of the mixture of the mixture of title compounds as a white solid. LCMS (ESI, m/z): 343.15 [M+H]$^+$ Step 2: 5-[[(2S)-1-[3-[4-(5-chloropyrimidin-2-yl)piperazin-1-yl]-3-oxopropoxy]butan-2-yl]oxy]-2-[(4-methoxyphenyl)methyl]-4-(trifluoromethyl)-2,3-dihydropyridazin-3-one and (S)-5-(2-(3-(4-(5-chloropyrimidin-2-yl)piperazin-1-yl)-3-oxopropoxy)butoxy)-2-(4-methoxybenzyl)-4-(trifluoromethyl)pyridazin-3 (2H)-one A solution of the mixture 1-[4-(5-chloropyrimidin-2-yl)piperazin-1-yl]-3-[(2S)-2-hydroxybutoxy]propan-1-one and (S)-1-(4-(5-chloropyrimidin-2-yl)piperazin-1-yl)-3-(1-hydroxybutan-2-yloxy)propan-1-one (290 mg, 0.85 mmol, 1 equiv), Cs$_2$CO$_3$ (551.2 mg, 1.69 mmol, 2 equiv), and Int-A20 (808.7 mg, 2.54 mmol, 3.00 equiv) in DMF (20 mL) was stirred for 6 h at 80° C. After concentration, the residue was purified by C18 reverse phase chromatography eluting with H$_2$O/ACN to afford 400 mg (75.65%) of the mixture of title compounds as a yellow solid. LCMS (ESI, m/z): 625.21 [M+H]$^+$ Step 3: 5-[[(2S)-1-[3-[4-(5-chloropyrimidin-2-yl)piperazin-1-yl]-3-oxopropoxy]butan-2-yl]oxy]-2-[(4-methoxyphenyl)methyl]-4-(trifluoromethyl)-2,3-dihydropyridazin-3-one and 5-[(2S)-2-[3-[4-(5-chloropyrimidin-2-yl)piperazin-1-yl]-3-oxopropoxy]butoxy]-4-(trifluoromethyl)-2,3-dihydropyridazin-3-one A solution of 5-[[(2S)-1-[3-[4-(5-chloropyrimidin-2-yl)piperazin-1-yl]-3-oxopropoxy]butan-2-yl]oxy]-2-[(4-methoxyphenyl)methyl]-4-(trifluoromethyl)-2,3-dihydropyridazin-3-one and (S)-5-(2-(3-(4-(5-chloropyrimidin-2-yl)piperazin-1-yl)-3-oxopropoxy)butoxy)-2-(4-methoxybenzyl)-4-(trifluoromethyl)pyridazin-3 (2H)-one mixture (336 mg, 0.53 mmol, 1 equiv), and H$_2$SO$_4$ (525.0 mg, 5.35 mmol, 10 equiv) in TFA (10 mL) was stirred overnight at RT. After concentration, the residue was purified by C18 reverse phase chromatography eluting with H$_2$O/CH$_3$CN. The residue was further purified by Prep-HPLC and Chiral-Prep-HPLC yielding the title compounds as white solids.

Example 591 Isomer A 34.7 mg, 32.10%, LCMS (ESI, m/z): 505.25 [M+H]$^+$, 1H NMR (300 MHz, Methanol-d$_4$) δ 8.31 (s, 2H), 8.22 (s, 1H), 4.96-4.92 (m, 1H), 3.84-3.66 (m, 7H), 3.64-3.53 (m, 5H), 2.61 (t, J=5.9 Hz, 2H), 1.72 (p, J=6.9 Hz, 2H), 1.00 (t, J=7.4 Hz, 3H) and Example 591 Isomer B 24.4 mg, 22.57%, LCMS (ESI, m/z): 505.25 [M+H]$^+$, $^1$H NMR (300 MHz, Methanol-d$_4$) δ 8.31 (s, 2H), 8.21 (s, 1H), 4.47-4.36 (m, 2H), 3.89-3.76 (m, 6H), 3.68-3.54 (m, 5H), 2.66 (t, J=6.0 Hz, 2H), 1.64 (p, J=7.3 Hz, 2H), 0.98 (t, J=7.5 Hz, 3H).

Example 592: 2-(4-[3-[(2S)-2-[[6-oxo-5-(trifluoromethyl)-1,6-dihydropyridazin-4-yl]oxy]butoxy]propanoyl]piperazin-1-yl)pyrimidine-5-carbonitrile

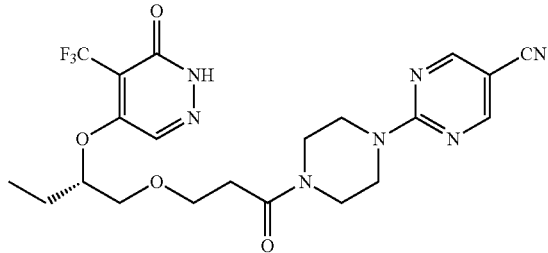 [SMILES: CC[C@@H](COCCC(=O)N1CCN(c2ncc(C#N)cn2)CC1)Oc1cn[nH]c(=O)c1C(F)(F)F]

Step 1: 2-(4-[3-[(2S)-2-Hydroxybutoxy]propanoyl]piperazin-1-yl)pyrimidine-5-carbonitrile A solution of 2-[4-(prop-2-enoyl)piperazin-1-yl]pyrimidine-5-carbonitrile (1.5 g, 6.17 mmol, 1 equiv), (2S)-butane-1,2-diol (2.8 g, 31.07 mmol, 5.04 equiv) and $Cs_2CO_3$ (4.0 g, 12.28 mmol, 1.99 equiv) in ACN (16 mL) was stirred for 1 h at 80° C. in an oil bath. The solids were filtered out and the resulting mixture was concentrated under vacuum, and the residue was applied onto a silica gel column eluting with EtOAc/petroleum ether (3:2) to afford 1.25 g (60.81%) of the title compound as yellow oil. LCMS (ESI, m/z): 334.18 $[M+H]^+$.

Step 2: 2-(4-[3-[(2S)-2-([1-[(4-Methoxyphenyl)methyl]-6-oxo-5-(trifluoromethyl)-1,6-dihydropyridazin-4-yl]oxy)butoxy]propanoyl]piperazin-1-yl)pyrimidine-5-carbonitrile A solution of 2-(4-[3-[(2S)-2-hydroxybutoxy]propanoyl]piperazin-1-yl)pyrimidine-5-carbonitrile (684 mg, 2.05 mmol, 1 equiv), Int-A20 (980.7 mg, 3.08 mmol, 1.50 equiv) and $Cs_2CO_3$ (1336.9 mg, 4.10 mmol, 2.00 equiv) in ACN (17.5 mL) was stirred for 6 h at 80° C. in an oil bath. The solids were filtered out, the resulting solution was concentrated under vacuum, and the residue was purified by C18 reverse phase chromatography eluting with $H_2O$/ACN to afford 1.04 g (82.34%) of the title compound as a white solid LCMS (ESI, m/z): 616.25 $[M+H]^+$.

Step 3: 2-(4-[3-[(2S)-2-[[6-Oxo-5-(trifluoromethyl)-1,6-dihydropyridazin-4-yl]oxy]butoxy]propanoyl]piperazin-1-yl)pyrimidine-5-carbonitrile A solution of 2-(4-[3-[(2S)-2-([1-[(4-methoxyphenyl)methyl]-6-oxo-5-(trifluoromethyl)-1,6-dihydropyridazin-4-yl]oxy)butoxy]propanoyl]piperazin-1-yl)pyrimidine-5-carbonitrile (1.04 g, 1.69 mmol, 1 equiv) and $H_2SO_4$ (1.7 g, 16.89 mmol, 10 equiv) in TFA (16 mL) was stirred for 1 h at RT. The resulting solution was concentrated under vacuum and the residue was purified by Prep-HPLC yielding the title compound (25.2 mg, 3.01%) as a white solid. LCMS (ESI, m/z): 496.10 $[M+H]^+$, $^1H$ NMR ($CD_3OD$-$d_4$, 300 MHz,) δ 8.64 (s, 2H), 8.24 (d, J=0.9 Hz, 1H), 4.98 (d, J=6.5 Hz, 1H), 3.94-3.88 (m, 4H), 3.84-3.68 (m, 8H), 2.63 (t, J=5.9 Hz, 2H), 1.77-1.67 (m, 2H), 1.02 (t, J=7.4 Hz, 3H).

Example 593: 5-[[(2S)-1-[3-[4-(5-Chloropyridin-2-yl)piperazin-1-yl]-3-oxopropoxy]-3-methoxypropan-2-yl]amino]-4-(trifluoromethyl)-2,3-dihydropyridazin-3-one

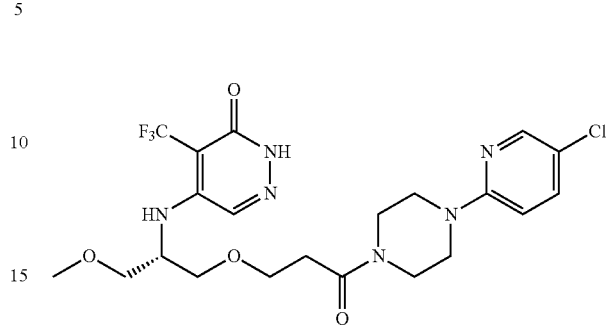

A solution of 3-[(2S)-3-methoxy-2-[[6-oxo-5-(trifluoromethyl)-1,6-dihydropyridazin-4-yl]amino]propoxy]propanoic acid (180 mg, 0.53 mmol, 1 equiv), HATU (242.1 mg, 0.64 mmol, 1.2 equiv), DIPEA (205.7 mg, 1.59 mmol, 3 equiv), and Int-A5 (125.8 mg, 0.64 mmol, 1.2 equiv) in DMF (3 mL) was stirred for 1 h at RT. After concentration, the residue was purified by C18 reverse phase chromatography eluting with $H_2O$/ACN yielding the title compound (28.2 mg, 10.24%) as a white solid. LCMS (ESI, m/z): 519.25 $[M+H]^+$, 1HNMR (300 MHz, Methanol-$d_4$) δ 8.09 (d, J=2.7 Hz, 1H), 7.97 (s, 1H), 7.56 (dd, J=9.1, 2.7 Hz, 1H), 6.85 (d, J=9 Hz, 1H), 4.35-4.13 (m, 1H), 3.94-3.74 (m, 2H), 3.76-3.61 (m, 6H), 3.61-3.51 (m, 6H), 3.39 (s, 3H), 2.70 (t, J=6.0 Hz, 2H).

Example 594: 5-[[(2S)-1-Methoxy-3-(3-oxo-3-[4-[5-(trifluoromethyl)pyridin-2-yl]piperazin-1-yl]propoxy)propan-2-yl]amino]-4-(trifluoromethyl)-2,3-dihydropyridazin-3-one

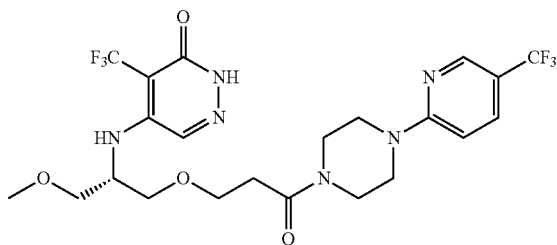 [SMILES: COC[C@@H](COCCC(=O)N1CCN(c2ccc(C(F)(F)F)cn2)CC1)Nc1cn[nH]c(=O)c1C(F)(F)F]

5-[[(2S)-1-methoxy-3-(3-oxo-3-[4-[5-(trifluoromethyl)pyridin-2-yl]piperazin-1-yl]propoxy)propan-2-yl]amino]-4-(trifluoromethyl)-2,3-dihydropyridazin-3-one A solution of 3-[(2S)-3-methoxy-2-[[6-oxo-5-(trifluoromethyl)-1,6-dihydropyridazin-4-yl]amino]propoxy]propanoic acid (180 mg, 0.53 mmol, 1 equiv), HATU (242.1 mg, 0.64 mmol, 1.2 equiv), DIPEA (205.7 mg, 1.59 mmol, 3 equiv), Int-A4 (147.2 mg, 0.64 mmol, 1.20 equiv) in DMF (3 mL) was stirred for 1 h at room temperature. After concentration, the residue was purified by C18 reverse phase chromatography eluting with $H_2O$/ACN yielding the title compound as a white solid (45.5 mg, 15.52%). LCMS (ESI, m/z): 553.30 $[M+H]^+$ 1H NMR (Methanol-$d_4$, 300 MHz) δ 7.95 (s, 1H), 7.76 (s, 1H), 7.75 (dd, J=9.1, 2.5 Hz, 1H), 6.91 (d, J=9.0 Hz, 1H), 4.22-4.18 (m, 1H), 3.92-3.58 (m, 12H), 3.56-3.47 (m, 2H), 3.32 (s, 3H), 2.71 (dd, J=6.0, 6.3 Hz, 2H).

Example 595: 6-(4-[3-[(2S)-3-Methyl-2-[[6-oxo-5-(trifluoromethyl)-1,6-dihydropyridazin-4-yl]amino]butoxy]propanoyl]piperazin-1-yl)pyridine-3-carbonitrile

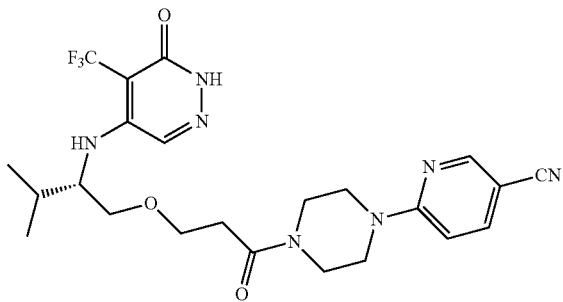 [SMILES: CC(C)[C@@H](COCCC(=O)N1CCN(c2ccc(C#N)cn2)CC1)Nc1cn[nH]c(=O)c1C(F)(F)F]

Step 1: 5-[[(2S)-1-Hydroxy-3-methylbutan-2-yl]amino]-4-(trifluoromethyl)-2-[[2-(trimethylsilyl)ethoxy]methyl]-2,3-dihydropyridazin-3-one A solution of Int-A6 (1 g, 3.04 mmol, 1 equiv), TEA (613.8 mg, 6.07 mmol, 1.99 equiv), and (2S)-2-amino-3-methylbutan-1-ol (347.7 mg, 3.37 mmol, 1.11 equiv) in EtOH (30 mL) was stirred for 15.5 h at RT. The resulting mixture was concentrated under vacuum. The residue was applied onto a silica gel column eluting with EtOAc/petroleum ether (1/4) to afford 600 mg (49.88%) of the title compound as yellow oil. LCMS (ESI, m/z): 396.19 [M+H]$^+$ Step 2: Methyl 3-[(2S)-3-methyl-2-[[6-oxo-5-(trifluoromethyl)-1-[[2-(trimethylsilyl)ethoxy]methyl]-1,6-dihydropyridazin-4-yl]amino]butoxy]propanoate A solution of 5-[[(2S)-1-hydroxy-3-methylbutan-2-yl]amino]-4-(trifluoromethyl)-2-[[2-(trimethylsilyl)ethoxy]methyl]-2,3-dihydropyridazin-3-one (1.2 g, 3.03 mmol, 1 equiv), Cs$_2$CO$_3$ (1.97 g, 2 mmol), and methyl prop-2-enoate (395.4 mg, 4.59 mmol, 1.51 equiv) in ACN (20 mL) was stirred for 2 h at RT. The resulting mixture was concentrated under vacuum. The residue was applied onto a silica gel column with EtOAc/petroleum ether (3/17) to afford 470 mg (32.17%) of the title compound as a yellow oil. LCMS (ESI, m/z): 482.22 [M+H]$^+$ Step 3: Methyl 3-[(2S)-3-methyl-2-[[6-oxo-5-(trifluoromethyl)-1,6-dihydropyridazin-4-yl]amino]butoxy]propanoate A solution of methyl 3-[(2S)-3-methyl-2-[[6-oxo-5-(trifluoromethyl)-1-[[2-(trimethylsilyl)ethoxy]methyl]-1,6-dihydropyridazin-4-yl]amino]butoxy]propanoate (470 mg, 0.98 mmol, 1 equiv), TFA (1 mL) in DCM (10 mL) was stirred 2 h at RT. The resulting mixture was concentrated under vacuum to afford 400 mg of the title compound as a yellow crude oil. LCMS (ESI, m/z): 352.14 [M+H]$^+$ Step 4: 3-[(2S)-3-Methyl-2-[[6-oxo-5-(trifluoromethyl)-1,6-dihydropyridazin-4-yl]amino]butoxy]propanoic Acid A solution of methyl 3-[(2S)-3-methyl-2-[[6-oxo-5-(trifluoromethyl)-1,6-dihydropyridazin-4-yl]amino]butoxy]propanoate (400 mg, 1.14 mmol, 1 equiv), and LiOH.H$_2$O (143 mg, 3.41 mmol, 2.99 equiv) in MeOH (10 mL) was stirred for 6 h at RT. The pH value of the solution was adjusted to 4 with HCl (1 M). The resulting mixture was concentrated under vacuum. After concentration, the residue was purified by C18 reverse phase chromatography eluting with H$_2$O/ACN to afford 130 mg (33.85%) of the title compound as a yellow oil. LCMS (ESI, m/z): 338.12 [M+H]$^+$ Step 5: 6-(4-[3-[(2S)-3-Methyl-2-[[6-oxo-5-(trifluoromethyl)-1,6-dihydropyridazin-4-yl]amino]butoxy]propanoyl]piperazin-1-yl)pyridine-3-carbonitrile A solution of 3-[(2S)-3-methyl-2-[[6-oxo-5-(trifluoromethyl)-1,6-dihydropyridazin-4-yl]amino]butoxy]propanoic acid (100 mg, 0.30 mmol, 1 equiv), HATU (123.9 mg, 0.33 mmol, 1.10 equiv), DIPEA (77 mg, 0.60 mmol, 2.01 equiv), Int-A4 (62 mg, 0.33 mmol, 1.11 equiv) in DMF (4 mL) was stirred for 1 h at room temperature. After concentration, the residue was purified by C18 reverse phase chromatography eluting with H$_2$O/ACN. Then the residue was further purified by Prep-HPLC yielding the title compound (106.5 mg, 70.78%) as a white solid. LCMS (ESI, m/z): 508.2 [M+H]$^+$, $^1$H NMR (300 MHz, DMSO-d6) δ: 12.39 (s, 1H), 8.48 (d, J=2.3 Hz, 1H), 7.93 (s, 1H), 7.85 (dd, J=9.1, 2.4 Hz, 1H), 6.89 (d, J=9.1 Hz, 1H), 6.08 (m, 1H), 3.84 (s, 1H), 3.65-3.52 (m, 12H), 2.55 (t, J=6.4 Hz, 2H), 1.85 (q, J=6.8 Hz, 1H), 0.87 (dd, J=8.8, 6.7 Hz, 6H).

Example 596: 6-(4-[3-[(2R,3R)-3-Methoxy-2-[[6-oxo-5-(trifluoromethyl)-1,6-dihydropyridazin-4-yl]amino]butoxy]propanoyl]piperazin-1-yl)pyridine-3-carbonitrile

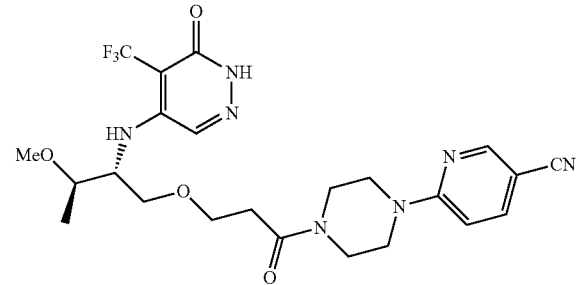 [SMILES: CO[C@H](C)[C@@H](COCCC(=O)N1CCN(c2ccc(C#N)cn2)CC1)Nc1cn[nH]c(=O)c1C(F)(F)F]

Step 1: (2R,3R)-2-amino-3-methoxybutan-1-ol

A solution of (2S,3R)-2-amino-3-methoxybutanoic acid (1 g, 7.51 mmol, 1 equiv), diborane hydrogen (15.0 mL, 1 mol/L, 2 equiv) in THF (15 mL) was stirred for 12 h at RT. The reaction was quenched by the addition of 15 mL of methanol. The resulting mixture was diluted with 15 mL of water and washed with 2×30 ml of DCM. The organic layers were combined and dried over Na$_2$SO$_4$. The resulting mixture was concentrated to afford 2.2 g (crude) of the title compound as colorless oil. LCMS (ESI, m/z): 120.09 [M+H]$^+$ Step 2: 5-[[(2R,3R)-1-Hydroxy-3-methoxybutan-2-yl]amino]-4-(trifluoromethyl)-2-[[2-(trimethylsilyl)ethoxy]methyl]-2,3-dihydropyridazin-3-one A solution of (2R,3R)-2-amino-3-methoxybutan-1-ol (2.18 g, 18.29 mmol, 1 equiv), Int-A6 (2.46 g, 7.48 mmol, 0.41 equiv), and TEA (3.7 g, 36.56 mmol, 2.00 equiv) in EtOH (10 mL, 1.00 equiv) was stirred for 1 h at 80° C. The resulting mixture was concentrated under vacuum. The residue was applied onto a silica gel column eluting with EtOAc/petroleum ether (3/7) to afford 1.63 g (21.6%) of the title compound as a yellow oil. LCMS (ESI, m/z): 412.18 [M+H]$^+$ Step 3: Methyl 3-[(2R,3R)-3-methoxy-2-[[6-oxo-5-(trifluoromethyl)-1-[[2-(trimethylsilyl)ethoxy] methyl]-1,6-dihydropyridazin-4-yl]amino]butoxy] propanoate A solution of 5-[[(2R,3R)-1-hydroxy-3-methoxybutan-2-yl]amino]-4-(trifluoromethyl)-2-[[2-(trimethylsilyl)ethoxy] methyl]-2,3-dihydropyridazin-3-one (1.62 g, 3.94 mmol, 1 equiv), Cs$_2$CO$_3$ (2.6 g, 7.87 mmol, 2.00 equiv), and methyl prop-2-enoate (1.7 g, 19.68 mmol, 5.00 equiv) in ACN (10 mL) was stirred for 1 h at RT. The resulting mixture was concentrated under vacuum. The residue was applied onto a silica gel column eluting with EtOAc/petroleum ether (3/7) to afford 870 mg (44.4%) of the title compound as yellow oil. LCMS (ESI, m/z): 498.22[M+H]$^+$ Step 4: Methyl 3-[(2R,3R)-3-methoxy-2-[[6-oxo-5-(trifluoromethyl)-1,6-dihydropyridazin-4-yl]amino] butoxy]propanoate A solution of methyl 3-[(2R,3R)-3-methoxy-2-[[6-oxo-5-(trifluoromethyl)-1-[[2-(trimethylsilyl)ethoxy]methyl]-1,6-dihydropyridazin-4-yl]amino]butoxy]propanoate (850 mg, 1.71 mmol, 1 equiv) in DCM (10 mL) and TFA (1 mL) was stirred for 1 h at RT. The pH value of the solution was adjusted to 8 with ethanolamine. The resulting solution was diluted with 20 mL of water and extracted with 4×20 mL of DCM. The organic layers were combined and dried over Na$_2$SO$_4$. The resulting solution was concentrated under vacuum to afford 640 mg of the title compound as yellow oil. LCMS (ESI, m/z): 368.14 [M+H]$^+$ Step 5: 3-[(2R,3R)-3-Methoxy-2-[[6-oxo-5-(trifluoromethyl)-1,6-dihydropyridazin-4-yl]amino]butoxy] propanoic Acid A solution of methyl 3-[(2R,3R)-3-methoxy-2-[[6-oxo-5-(trifluoromethyl)-1,6-dihydropyridazin-4-yl]amino]butoxy] propanoate (620 mg, 1.69 mmol, 1 equiv), and LiOH.H$_2$O (354.2 mg, 8.44 mmol, 5.00 equiv) in MeOH (15 mL) and water (5 mL, 277.54 mmol, 164.43 equiv) was stirred for 1 h at RT. After concentration, the pH value of the solution was adjusted to 5 with HCl (1 M). The resulting solution was extracted with 5×25 mL of DCM. The organic layers were combined and dried over Na$_2$SO$_4$. The resulting solution was concentrated under vacuum to afford 500 mg (84%) of the title compound as a yellow solid. LCMS (ESI, m/z): 354.12 [M+H]$^+$ Step 6: 6-(4-[3-[(2R,3R)-3-Methoxy-2-[[6-oxo-5-(trifluoromethyl)-1,6-dihydropyridazin-4-yl]amino] butoxy]propanoyl]piperazin-1-yl)pyridine-3-carbonitrile A solution of 3-[(2R,3R)-3-methoxy-2-[[6-oxo-5-(trifluoromethyl)-1,6-dihydropyridazin-4-yl]amino]butoxy]propanoic acid (200 mg, 0.57 mmol, 1 equiv), DIPEA (219.5 mg, 1.70 mmol, 3.0 equiv), Int-A4 (127.2 mg, 0.57 mmol, 1.00 equiv), and HATU (322.9 mg, 0.85 mmol, 1.5 equiv) in DMF (4 mL) was stirred for 1 h at room temperature. The resulting solution was purified by C18 reverse phase chromatography eluting with H$_2$O/CH$_3$CN. The residue was further purified by Prep-HPLC yielding the title compound (58.4 mg, 19.7%) as a white solid. LCMS (ESI, m/z): 524.51 [M+H]$^+$, $^1$H NMR (400 MHz, Methanol-d$_4$) δ: 8.44 (dd, J=2.4, 0.8 Hz, 1H), 7.95 (s, 1H), 7.77 (dd, J=9.1, 2.3 Hz, 1H), 6.87 (dd, J=9.1, 0.8 Hz, 1H), 3.99 (s, 1H), 3.87-3.54 (m, 13H), 3.37 (s, 3H), 2.68 (t, J=5.9 Hz, 2H), 1.20 (d, J=6.2 Hz, 3H).

Example 597: 6-(4-[3-[(2S)-2-[(5-Chloro-6-oxo-1,6-dihydropyridazin-4-yl)amino]propoxy]propanoyl] piperazin-1-yl)pyridine-3-carbonitrile

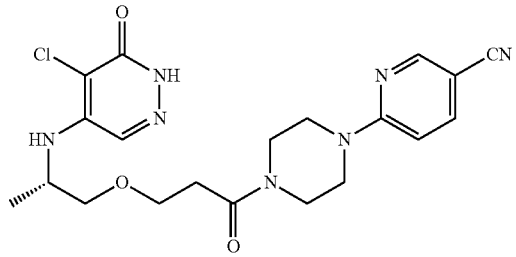 [SMILES: C[C@@H](COCCC(=O)N1CCN(c2ccc(C#N)cn2)CC1)Nc1cn[nH]c(=O)c1Cl]

Step 1: 4-Chloro-5-[[(2S)-1-hydroxypropan-2-yl] amino]-2-[[2-(trimethylsilyl)ethoxy]methyl]-2,3-dihydropyridazin-3-one A solution of Int-A7 (3 g, 10.16 mmol, 1 equiv), TEA (3.1 g, 30.48 mmol, 3 equiv), and (2S)-2-aminopropan-1-ol (2.3 g, 30.48 mmol, 3 equiv) in EtOH (30 mL) was stirred for 16 h at 80° C. After concentration, the residue was applied onto a silica gel column eluting with EtOAc/petroleum ether (1:1) to afford 2 g (58.95%) of the title compound as a yellow oil. LCMS (ESI, m/z): 334.13 [M+H]$^+$ Step 2: (S)-Ethyl 3-(2-(5-chloro-6-oxo-1-((2-(trimethylsilyl)ethoxy)methyl)-1,6-dihydropyridazin-4-ylamino)propoxy)propanoate A solution of 4-chloro-5-[[(2S)-1-hydroxypropan-2-yl]amino]-2-[[2-(trimethylsilyl)ethoxy]methyl]-2,3-dihydropyridazin-3-one (2 g, 5.99 mmol, 1 equiv), Cs$_2$CO$_3$ (3.9 g, 11.98 mmol, 2 equiv), and ethyl prop-2-enoate (6.0 g, 59.90 mmol, 10 equiv) in ACN (30 mL) was stirred for 1 h at RT. The solids were filtered out. The resulting mixture was concentrated under vacuum to afford 2.3 g (88.47%) of the title compound as a yellow oil. LCMS (ESI, m/z): 434.18 [M+H]$^+$ Step 3: (S)-Ethyl 3-(2-(5-chloro-6-oxo-1,6-dihydropyridazin-4-ylamino)propoxy)propanoate A solution of (S)-ethyl 3-(2-(5-chloro-6-oxo-1-((2-(trimethylsilyl)ethoxy)methyl)-1,6-dihydropyridazin-4-ylamino) propoxy)propanoate (5.3 g, 12.21 mmol, 1 equiv), and TFA (6 mL, 80.78 mmol, 6.61 equiv) in DCM (30 mL) was stirred for 1 h at RT. The resulting mixture was concentrated under vacuum to afford 3.34 g crude of the title compound as yellow oil. LCMS (ESI, m/z): 304.10 [M+H]$^+$

Step 4: 3-[(2S)-2-[(5-Chloro-6-oxo-1,6-dihydropyridazin-4-yl)amino]propoxy]propanoic Acid A solution of (S)-ethyl 3-(2-(5-chloro-6-oxo-1,6-dihydropyridazin-4-ylamino)propoxy)propanoate (5.2 g, 17.12 mmol, 1 equiv), LiOH (3.6 g, 85.60 mmol, 5 equiv), H$_2$O (10 mL) in MeOH (30 mL) was stirred for 4 h at room temperature. The pH value of the solution was adjusted to 5 with HCl (1 M). After concentration, the residue was purified by C18 reverse phase chromatography eluting with H$_2$O/CH$_3$CN to afford 2.14 g (45.34%) of the title compound as yellow oil. LCMS (ESI, m/z): 276.07 [M+H]$^+$

Step 5: 6-(4-[3-[(2S)-2-[(5-Chloro-6-oxo-1,6-dihydropyridazin-4-yl)amino]propoxy]propanoyl]piperazin-1-yl)pyridine-3-carbonitrile A solution of 3-[(2S)-2-[(5-chloro-6-oxo-1,6-dihydropyridazin-4-yl)amino]propoxy]propanoic acid (209 mg, 0.76 mmol, 1 equiv), DIEA (285 mg, 2.27 mmol, 3 equiv), HATU (275 mg, 0.76 mmol, 1 equiv), Int-A4 (135 mg, 0.76 mmol, 1 equiv) in DMF (1 mL) was stirred for 2 h at room temperature. 2-aminoethan-1-ol (0.2 mL) was added and stirred for 2 h at room temperature. The residue was purified by C18 reverse phase chromatography eluting with H$_2$O/ACN yielding the title compound (121.1 mg 35.45%) as a white solid. LCMS (ESI, m/z): 446.15 [M+H]$^+$, $^1$H NMR (DMSO-d$_6$, 300 MHz) δ: 8.51 (d, J=2.3 Hz, 1H), 7.90-7.86 (m, 2H), 6.92 (dd, J=9.2, 0.8 Hz, 1H), 6.01 (d, J=9.0 Hz, 1H), 4.10-4.01 (m, 1H), 3.72-3.62 (m, 6H), 3.56-3.54 (ddd, J=12.9, 7.1, 4.1 Hz, 4H), 3.47-3.39 (m, 2H), 2.63-2.49 (t, J=6.5 Hz, 2H), 1.15 (d, J=6.5 Hz, 3H).

Example 598: 4-Chloro-5-[[(2S)-1-[3-[4-(5-chloropyrimidin-2-yl)piperazin-1-yl]-3-oxopropoxy]propan-2-yl]amino]-2,3-dihydropyridazin-3-one

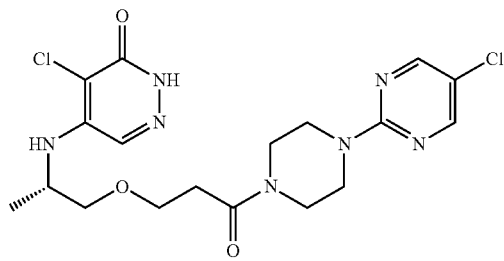 [SMILES: C[C@@H](COCCC(=O)N1CCN(c2ncc(Cl)cn2)CC1)Nc1cn[nH]c(=O)c1Cl]

A solution of 3-[(2S)-2-[(5-chloro-6-oxo-1,6-dihydropyridazin-4-yl)amino]propoxy]propanoic acid (198 mg, 0.72 mmol, 1 equiv), DIEA (491 mg, 3.80 mmol, 5 equiv), HATU (275 mg, 0.72 mmol, 1 equiv) in DMF (0.5 mL) and Int-A3 (199 mg, 1.00 mmol, 1 equiv) in DMF (0.5 mL) was stirred for 0.5 h at RT. The residue was purified by C18 reverse phase chromatography eluting with H$_2$O/CH$_3$CN yielding the title compound (171.8 mg 52.32%) as a white solid. LCMS (ESI, m/z): 456.05 [M+H]$^+$, $^1$H NMR (DMSO-d$_6$, 300 MHz) δ: 12.48 (s, 1H), 8.44 (s, 2H), 7.87 (s, 1H), 6.02 (d, J=9.1 Hz, 1H), 4.09-4.00 (dt, J=15.3, 6.5 Hz, 1H), 3.70-3.61 (m, 6H), 3.53-3.45 (m, 6H), 2.59-2.51 (t, J=6.5 Hz, 2H), 1.16 (d, J=6.5 Hz, 3H).

Example 599: (S)-4-Chloro-5-(1-(3-oxo-3-(4-(5-(trifluoromethyl)pyrimidin-2-yl)piperazin-1-yl)propoxy)propan-2-ylamino)pyridazin-3(2H)-one

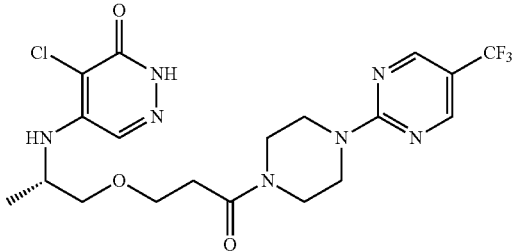 [SMILES: C[C@@H](COCCC(=O)N1CCN(c2ncc(C(F)(F)F)cn2)CC1)Nc1cn[nH]c(=O)c1Cl]

A solution of 3-[(2S)-2-[(5-chloro-6-oxo-1,6-dihydropyridazin-4-yl)amino]propoxy]propanoic acid (200 mg, 0.73 mmol, 1 equiv), HATU (413.8 mg, 1.09 mmol, 1.5 equiv), DIEA (281.3 mg, 2.18 mmol, 3 equiv), Int-A2 (202.1 mg, 0.87 mmol, 1.2 equiv) in DMF (3 mL) was stirred for 1 h at RT. After concentration, the residue was purified by Prep-HPLC yielding the title compound (174.6 mg, 49.13%) as a white solid. LCMS (ESI, m/z): 490.25 [M+H]$^+$, $^1$HNMR (Methanol-d$_4$, 300 MHz) δ: 8.60 (d, J=0.9 Hz, 2H), 7.92 (s, 1H), 4.09 (q, J=7.0, 4.2 Hz, 1H), 3.98-3.87 (m, 4H), 3.85-3.73 (m, 2H), 3.70-3.61 (m, 5H), 3.52 (dd, J=9.7, 7.5 Hz, 1H), 2.69 (t, J=5.9 Hz, 2H), 1.27 (d, J=6.6 Hz, 3H).

Example 600: 6-(4-[3-[(2S)-2-[(5-Bromo-6-oxo-1,6-dihydropyridazin-4-yl)amino]propoxy]propanoyl]piperazin-1-yl)pyridine-3-carbonitrile

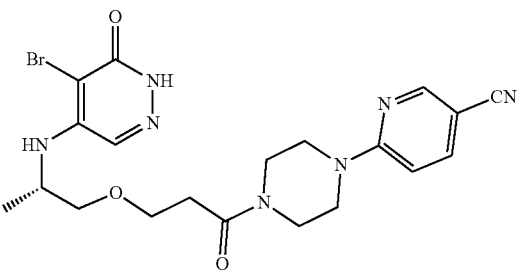 [SMILES: C[C@@H](COCCC(=O)N1CCN(c2ccc(C#N)cn2)CC1)Nc1cn[nH]c(=O)c1Br]

Step 1: 4-Bromo-5-[[(2S)-1-hydroxypropan-2-yl]amino]-2-[[2-(trimethylsilyl)ethoxy]methyl]-2,3-dihydropyridazin-3-one A solution of Int-A8 (6 g, 15.62 mmol, 1 equiv), (2S)-2-aminopropan-1-ol (3519.5 mg, 46.86 mmol, 3.00 equiv) and TEA (4741.5 mg, 46.86 mmol, 3 equiv) in EtOH (50 mL) was stirred for 4 h at 80° C. The resulting solution was concentrated under vacuum, and the residue was applied onto a silica gel column eluting with EtOAc/petroleum ether (1:1) to afford 4.2 g (71.07%) of the title compound as a white solid. LCMS (ESI, m/z): 378.08 [M+H]$^+$

Step 2: Tert-butyl 3-[(2S)-2-[(5-bromo-6-oxo-1-[[2-(trimethylsilyl)ethoxy]methyl]-1,6-dihydropyridazin-4-yl)amino]propoxy]propanoate A solution of 4-bromo-5-[[(2S)-1-hydroxypropan-2-yl]amino]-2-[[2-(trimethylsilyl)ethoxy]methyl]-2,3-dihydropyridazin-3-one (4.1 g, 10.84 mmol, 1 equiv), Cs₂CO₃ (7061.7 mg, 21.67 mmol, 2 equiv) and tert-butyl prop-2-enoate (13889.6 mg, 108.37 mmol, 10 equiv) in ACN (80 mL) was stirred for 1.5 h at 40° C. The solids was filtered out and the resulting solution was concentrated under vacuum. The residue was purified by C18 reverse phase chromatography eluting with H₂O/ACN to afford 4.2 g (76.4%) of the title compound as a yellow oil. LCMS (ESI, m/z): 506.17 [M+H]⁺

Step 3: 3-[(2S)-2-[(5-Bromo-6-oxo-1,6-dihydropyridazin-4-yl)amino]propoxy]propanoic Acid A solution of tert-butyl 3-[(2S)-2-[(5-bromo-6-oxo-1-[[2-(trimethylsilyl)ethoxy]methyl]-1,6-dihydropyridazin-4-yl)amino]propoxy]propanoate (2.7 g, 5.33 mmol, 1 equiv) and TFA (6 mL) in DCM (30 mL) was stirred for 4 h at room temperature. The resulting solution was concentrated under vacuum, and the residue was purified by C18 reverse phase chromatography eluting with H₂O/CH₃CN to afford 2 g of the title compound as a crude yellow solid. LCMS (ESI, m/z): 320.02 [M+H]⁺

Step 4: 6-(4-[3-[(2S)-2-[(5-bromo-6-oxo-1,6-dihydropyridazin-4-yl)amino]propoxy]propanoyl]piperazin-1-yl)pyridine-3-carbonitrile A solution of 3-[(2S)-2-[(5-bromo-6-oxo-1,6-dihydropyridazin-4-yl)amino]propoxy]propanoic acid (200 mg, 0.62 mmol, 1 equiv), HOBT (126.6 mg, 0.94 mmol, 1.5 equiv), EDCI (179.6 mg, 0.94 mmol, 1.5 equiv), DIPEA (242.2 mg, 1.87 mmol, 3.0 equiv) and Int-A4 (117.6 mg, 0.62 mmol, 1.00 equiv) in DMF (4 mL) was stirred for 2 h at room temperature. The resulting solution was purified by C18 reverse phase chromatography eluting with H₂O/CH₃CN. After concentration, the residue was further purified by Prep-HPLC yielding the title compound (36.1 mg, 11.78%) as a white solid. LCMS (ESI, m/z): 492.10 [M+H]+, ¹HNMR (DMSO-d₆, 300 MHz) δ 12.50 (s, 1H), 8.51 (d, J=1.8 Hz, 1H), 7.90 (dd, J=9.0, 2.4 Hz, 1H), 7.79 (s, 1H), 6.93 (d, J=9.0 Hz, 1H), 5.77 (d, J=9.3 Hz, 1H), 4.10-4.01 (m, 1H), 3.73-3.44 (m, 12H), 2.60 (t, J=6.4 Hz, 2H), 1.16 (d, J=6.5 Hz, 3H).

Example 601: 4-Bromo-5-[[(2S)-1-(3-oxo-3-[4-[5-(trifluoromethyl)pyrimidin-2-yl]piperazin-1-yl]propoxy)propan-2-yl]amino]-2,3-dihydropyridazin-3-one

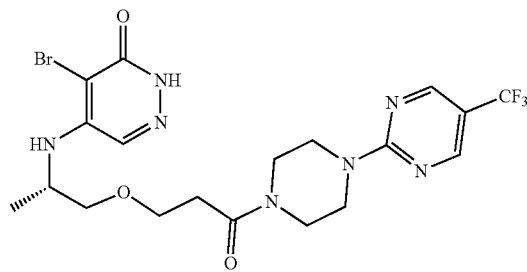 [SMILES: C[C@@H](COCCC(=O)N1CCN(c2ncc(C(F)(F)F)cn2)CC1)Nc1cn[nH]c(=O)c1Br]

A solution of 3-[(2S)-2-[(5-bromo-6-oxo-1,6-dihydropyridazin-4-yl)amino]propoxy]propanoic acid (200 mg, 0.62 mmol, 1 equiv), HOBT (126.6 mg, 0.94 mmol, 1.5 equiv), EDCI (179.6 mg, 0.94 mmol, 1.5 equiv), DIPEA (242.2 mg, 1.87 mmol, 3.0 equiv) and Int-A2 (144.4 mg, 0.62 mmol, 1.00 equiv) in DMF (4 mL) was stirred for 2 h at room temperature. The resulting solution was purified by C18 reverse phase chromatography eluting with H₂O/ACN. After concentration, the residue was further purified by Prep-HPLC yielding the title compound (14.9 mg, 4.46%) as a white solid. LCMS (ESI, m/z): 536.10 [M+H]+, ¹H NMR (DMSO-d₆, 300 MHz) δ 12.50 (s, 1H), 8.73 (d, J=0.6 Hz, 2H), 7.79 (s, 1H), 5.76 (d, J=9.3 Hz, 1H), 4.12-4.01 (m, 1H), 3.87-3.47 (m, 12H), 2.60 (t, J=6.5 Hz, 2H), 1.16 (d, J=6.5 Hz, 3H).

Example 602: 4-Bromo-5-[[(2S)-1-(3-oxo-3-[4-[5-(trifluoromethyl)pyrimidin-2-yl]piperazin-1-yl]propoxy)propan-2-yl]amino]-2,3-dihydropyridazin-3-one

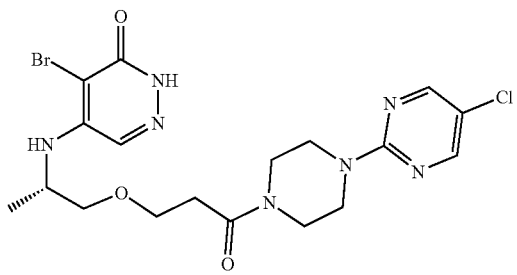 [SMILES: C[C@@H](COCCC(=O)N1CCN(c2ncc(Cl)cn2)CC1)Nc1cn[nH]c(=O)c1Br]

A solution of 3-[(2S)-2-[(5-bromo-6-oxo-1,6-dihydropyridazin-4-yl)amino]propoxy]propanoic acid (200 mg, 0.62 mmol, 1 equiv), HOB\T (126.6 mg, 0.94 mmol, 1.5 equiv), EDCI (179.6 mg, 0.94 mmol, 1.5 equiv), DIPEA (242.2 mg, 1.87 mmol, 3.0 equiv) and Int-A3 (124.1 mg, 0.62 mmol, 1.00 equiv) in DMF (4 mL) was stirred for 2h at room temperature. The resulting solution was purified by C18 reverse phase chromatography eluting with H₂O/ACN. After concentration, the residue was further purified by Prep-HPLC yielding the title compound (15.3 mg, 4.89%) as a white solid. LCMS (ESI, m/z): 500.05 [M+H]+, ¹HNMR (DMSO-d₆, 300 MHz) δ 12.48 (s, 1H), 8.45 (s, 2H), 7.78 (s, 1H), 5.75 (d, J=9.0 Hz, 1H), 4.10-4.01 (m, 1H), 3.71-3.47 (m, 12H), 2.60 (t, J=6.5 Hz, 2H), 1.17 (d, J=6.5 Hz, 3H).

Example 603: 5-[[(2S)-1-Hydroxy-3-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one

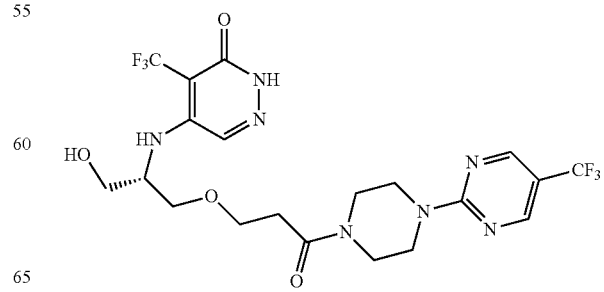

Step 1: Tert-butyl (4R)-4-(hydroxymethyl)-2,2-dimethyl-, 3-oxazolidine-3-carboxylate A solution of 3-tert-butyl 4-methyl (4S)-2,2-dimethyl-1,3-oxazolidine-3,4-dicarboxylate (10 g, 38.565 mmol, 1.00 equiv), NaBH$_4$ (2.92 g, 77.130 mmol, 2.00 equiv), MeOH (30 mL), and CaCl$_2$ (12.84 g, 115.695 mmol, 3.00 equiv) in THF (150 mL) was stirred for 1 h at RT. The reaction was quenched by the addition of 30 mL of water, extracted with 3×100 mL of EtOAc, dried over anhydrous sodium sulfate and concentrated under vacuum to afford 9.38 g of the title compound as a yellow oil LCMS (ESI, m/z): 232.15 [M+H]+.

Step 2: Tert-butyl (4R)-4-[(3-methoxy-3-oxopropoxy)methyl]-2,2-dimethyl-1,3-oxazolidine-3-carboxylate A solution of tert-butyl (4R)-4-(hydroxymethyl)-2-methyl-1,3-oxazolidine-3-carboxylate (9.38 g, 43.17 mmol, 1.00 equiv), Cs$_2$CO$_3$ (28.1 g, 86.24 mmol, 2.00 equiv), and methyl prop-2-enoate (18.6 g, 216.05 mmol, 5.00 equiv) in ACN (80 mL) was stirred for 3 h at room temperature. The solids were filtered out and the residue was concentrated under vacuum to afford 9.92 g of the title compound as a crude yellow oil LCMS (ESI, m/z): 318.18 [M+H]$^+$

Step 3: Methyl 3-[[(4R)-2,2-dimethyl-1,3-oxazolidin-4-yl]methoxy]propanoate

A solution of tert-butyl (4R)-4-[(3-methoxy-3-oxopropoxy)methyl]-2,2-dimethyl-1,3-oxazolidine-3-carboxylate (9.92 g, 31.26 mmol, 1.00 equiv) in HCl/dioxane (100 mL) was stirred for 1 h at room temperature. The resulting mixture was concentrated to afford 9.6 g of the title compound as a crude yellow oil. LCMS (ESI, m/z): 218.14 [M+H]$^+$.

Step 4: Methyl 3-[(2S)-3-hydroxy-2-[[6-oxo-5-(trifluoromethyl)-1-[[2-(trimethylsilyl)ethoxy]methyl]-1,6-dihydropyridazin-4-yl]amino]propoxy]propanoate A solution of methyl 3-[[(4R)-2,2-dimethyl-1,3-oxazolidin-4-yl]methoxy]propanoate (9.6 g, 44.19 mmol, 1.00 equiv), DIPEA (11421.4 mg, 88.37 mmol, 2.00 equiv), Int-A6 (14527.8 mg, 44.19 mmol, 1.00 equiv) in IPA (80 mL) was stirred for 1 h at 60° C. The resulting mixture was concentrated under vacuum and the residue was applied onto a silica gel column eluting with EtOAc/petroleum ether (2:3) to afford 5.5 g (26.51%) of the title compound as a yellow oil. LCMS (ESI, m/z): LCMS (ESI, m/z): 470.10 [M+H]$^+$.

Step 5: Methyl 3-[(2S)-3-hydroxy-2-[[6-oxo-5-(trifluoromethyl)-1,6-dihydropyridazin-4-yl]amino]propoxy]propanoate A solution of methyl 3-[(2S)-3-hydroxy-2-[[6-oxo-5-(trifluoromethyl)-1-[[2-(trimethyl silyl)ethoxy]methyl]-1,6-dihydropyridazin-4-yl]amino]propoxy]propanoate (5.5 g, 11.71 mmol, 1.00 equiv), and TFA (5 mL) in DCM (25 mL) was stirred for 40 min at RT. The resulting mixture was concentrated to afford 570 mg (14.34%) of the title compound as a yellow oil. LCMS (ESI, m/z): 340.00 [M+H]$^+$.

Step 6: Methyl 3-[(2S)-3-hydroxy-2-[[6-oxo-5-(trifluoromethyl)-1,6-dihydropyridazin-4-yl]amino]propoxy]propanoic Acid A solution of methyl 3-[(2S)-3-hydroxy-2-[[6-oxo-5-(trifluoromethyl)-1,6-dihydropyridazin-4-yl]amino]propoxy]propanoate (570 mg, 1.68 mmol, 1.00 equiv), LiOH (120.70 mg, 5.04 mmol, 3.00 equiv), and H$_2$O (3 mL) in THF (15 mL) was stirred for 3 h at RT. The mixture was diluted with 5 mL of water, and extracted with 10 mL of EtOAc. The aqueous layers were combined, the pH was adjusted to 4 with HCl (1M), and concentrated under vacuum to afford 380 mg (69.54%) of the title compound as yellow oil. LCMS (ESI, m/z): 326.09 [M+H]+.

Step 7: 5-[[(2S)-1-hydroxy-3-(3-oxo-3-[4-[5-(trifluoromethyl)pyrimidin-2-yl]piperazin-1-yl]propoxy)propan-2-yl]amino]-4-(trifluoromethyl)-2,3-dihydropyridazin-3-one A solution of 3-(3-hydroxy-2-[[6-oxo-5-(trifluoromethyl)-1,6-dihydropyridazin-4-yl]amino]propoxy)propanoic acid (100 mg, 0.31 mmol, 1 equiv), DIPEA (80 mg, 0.62 mmol, 2.00 equiv), EDCl (89.8 mg, 0.47 mmol, 1.50 equiv), HOBt (62.8 mg, 0.47 mmol, 1.50 equiv), and Int-A2 (69.4 mg, 0.37 mmol, 1.20 equiv) in DMF (3 mL) was stirred for 1 h at room temperature. After concentration, the residue was purified by C18 reverse phase chromatography eluting with H$_2$O/ACN. The residue was further purified by Prep-HPLC yielding the title compound (28.1 mg, 16.94%) as a white solid. LCMS (ESI, m/z): 540.30 [M+H]+, $^1$H NMR (300 MHz, Methanol-d$_4$) δ 8.61 (d, J=0.8 Hz, 2H), 7.98 (s, 1H), 4.09 (d, J=5.7 Hz, 1H), 3.99-3.92 (m, 4H), 3.84 (dd, J=5.2, 3 Hz, 2H), 3.79-3.62 (m, 8H), 2.72 (d, J=5.9 Hz, 2H).

Example 604: 5-[[(2S)-1-Hydroxy-3-(3-oxo-3-[4-[5-(trifluoromethyl)pyridin-2-yl]piperazin-1-yl]propoxy)propan-2-yl]amino]-4-(trifluoromethyl)-2,3-dihydropyridazin-3-one

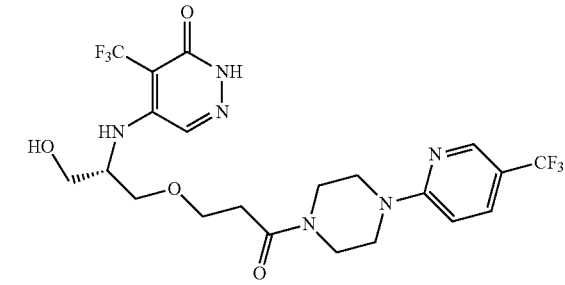 [SMILES: O=C(CCOC[C@H](CO)Nc1cn[nH]c(=O)c1C(F)(F)F)N1CCN(c2ccc(C(F)(F)F)cn2)CC1]

A solution of 3-(3-hydroxy-2-[[6-oxo-5-(trifluoromethyl)-1,6-dihydropyridazin-4-yl]amino]propoxy)propanoic acid (100 mg, 0.31 mmol, 1 equiv), DIEA (80 mg, 0.62 mmol, 2.00 equiv), EDCl (89.8 mg, 0.47 mmol, 1.50 equiv), HOBt (62.8 mg, 0.47 mmol, 1.50 equiv), and Int-A18 (69.4 mg, 0.37 mmol, 1.20 equiv) in DMF (3 mL) was stirred for 1 h at room temperature. After concentration, the residue was purified by C18 reverse phase chromatography eluting with H$_2$O/ACN. The residue was further purified by Prep-HPLC yielding the title compound (27.9 mg, 16.85%) as a white solid. LCMS (ESI, m/z): 539.30 [M+H]+, $^1$H NMR (300 MHz, Methanol-d$_4$) δ 8.38 (s, 1H), 7.98 (s, 1H), 7.77 (dd, J=9.0, 2.6 Hz, 1H), 6.91 (d, J=9.0 Hz, 1H), 4.14-4.04 (m, 1H), 3.89-3.78 (m, 2H), 3.78-3.63 (m, 12H), 2.71 (d, J=6.0 Hz, 2H).

Example 605: (S)-6-[4-[3-[2-Cyclopropyl-2-[[6-oxo-5-(trifluoromethyl)-1,6-dihydropyridazin-4-yl]amino]ethoxy]propanoyl]piperazin-1-yl]nicotinonitrile

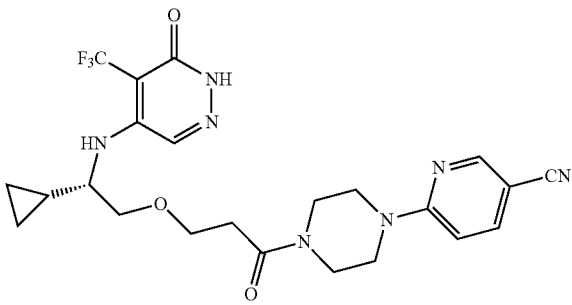 [SMILES: N#Cc1ccc(N2CCN(C(=O)CCOC[C@@H](Nc3cn[nH]c(=O)c3C(F)(F)F)C3CC3)CC2)nc1]

Step 1: 5-[[(1S)-1-cyclopropyl-2-hydroxyethyl]amino]-4-(trifluoromethyl)-2-[[2-(trimethylsilyl)ethoxy]methyl]-2,3-dihydropyridazin-3-one A solution of (2S)-2-amino-2-cyclopropylethan-1-ol hydrochloride (1 g, 7.27 mmol, 1 equiv), Int-A6 (2.45 g, 7.45 mmol, 1.03 equiv) and TEA (1.7 mL) in EtOH (15 mL) was stirred overnight at 60° C. The resulting solution was diluted with 200 mL of EtOAc and washed with 50 mL of NH$_4$Cl and 50 mL of brine. The organic layer was dried over anhydrous sodium sulfate and concentrated. The residue was applied onto a silica gel column with EtOAc/petroleum ether (1:2) to give 2.2 g (76.94%) of the title compound as a solid. LCMS (ESI, m/z): 394.18 [M+H]$^+$.

Step 2: Ethyl 3-[(2S)-2-cyclopropyl-2-[[6-oxo-5-(trifluoromethyl)-1-[[2-(trimethylsilyl)-ethoxy]methyl]-1,6-dihydropyridazin-4-yl]amino]ethoxy]propanoate A solution of 5-[[(1S)-1-cyclopropyl-2-hydroxyethyl]amino]-4-(trifluoromethyl)-2-[[2-(trimethylsilyl)ethoxy]methyl]-2,3-dihydropyridazin-3-one (2.1 g, 5.34 mmol, 1 equiv), ethyl prop-2-enoate (0.8 mL) and Cs$_2$CO$_3$ (2 g, 6.14 mmol, 1.15 equiv) in ACN (15 mL) was stirred overnight at 35° C. The solids were filtered out. The resulting mixture was concentrated. The residue was applied onto a silica gel column with EtOAc/petroleum ether (1:1). This resulted in 580 mg (crude) of the title compound as a solid. LCMS (ESI, m/z): 494.23 [M+H]$^+$ Step 3: Ethyl 3-[(2S)-2-cyclopropyl-2-[[6-oxo-5-(trifluoromethyl)-1,6-dihydropyridazin-4-yl]amino]ethoxy]propanoate A solution of ethyl 3-[(2S)-2-cyclopropyl-2-[[6-oxo-5-(trifluoromethyl)-1-[[2-(trimethyl silyl)ethoxy]methyl]-1,6-dihydropyridazin-4-yl]amino]ethoxy]propanoate (550 mg, 1.11 mmol, 1 equiv) in HCl/dioxane (20 mL) was stirred overnight at RT. The resulting mixture was concentrated. The crude product was purified by Prep-HPLC to give 300 mg (74.10%) of the title compound as a solid. LCMS (ESI, m/z): 364.15 [M+H]$^+$.

Step 4: 3-[(2S)-2-Cyclopropyl-2-[[6-oxo-5-(trifluoromethyl)-1,6-dihydropyridazin-4-yl]amino]ethoxy]propanoic Acid To a stirred solution of ethyl 3-[(2S)-2-cyclopropyl-2-[[6-oxo-5-(trifluoromethyl)-1,6-dihydropyridazin-4-yl]amino]ethoxy]propanoate (300 mg, 0.83 mmol, 1 equiv) in THF (9 mL) and H$_2$O (3 mL), LiOH.H$_2$O (140 mg, 3.5 mmol, 4.21 equiv) was added. The resulting solution was stirred for 5 h at room temperature. The pH value of the solution was adjusted to 1 with HCl (1 M). The resulting mixture was concentrated to give 260 mg (crude) of the title compound as a solid. LCMS (ESI, m/z): 336.12 [M+H]$^+$.

Step 5: (S)-6-[4-[3-[2Cyclopropyl-2-[[6-oxo-5-(trifluoromethyl)-1,6-dihydropyridazin-4-yl]amino]ethoxy]propanoyl]piperazin-1-yl]nicotinonitrile To a stirred solution of 3-[(2S)-2-cyclopropyl-2-[[6-oxo-5-(trifluoromethyl)-1,6-dihydropyridazin-4-yl]amino]ethoxy]propanoic acid (130 mg, 0.39 mmol, 1.00 equiv) in DMF (10 mL), and Int-A4 (80 mg, 0.43 mmol, 1.09 equiv), DIPEA (0.5 mL) and HATU (180 mg, 0.47 mmol, 1.2 equiv) were added. The resulting solution was stirred for 2 h at room temperature. After concentration, the residue was purified by C18 reverse phase chromatography eluting with H$_2$O/CH$_3$CN. The residue was further purified by Prep-HPLC yielding the title compound (75.9 mg, 39%) as a white solid. LCMS (ESI, m/z): 506.25 [M+H]$^+$. $^1$H NMR (400 MHz, DMSO-d$_6$) δ 12.40 (s, 1H), 8.51 (d, J=2.3 Hz, 1H), 7.97-7.81 (m, 2H), 6.92 (d, J=9.1 Hz, 1H), 6.50-6.37 (m, 1H), 3.74-3.49 (m, 13H), 2.57 (t, J=6.4 Hz, 2H), 1.12-1.00 (m, 1H), 0.53-0.39 (m, 2H), 0.37-0.27 (m, 2H).

Example 606: (S)-5-[(1-Cyclopropyl-2-[3-oxo-3-[4-[5-(trifluoromethyl)pyrimidin-2-yl)piperazin-1-yl]propoxy]-ethyl]amino]-4-(trifluoromethyl)pyridazin-3(2H)-one

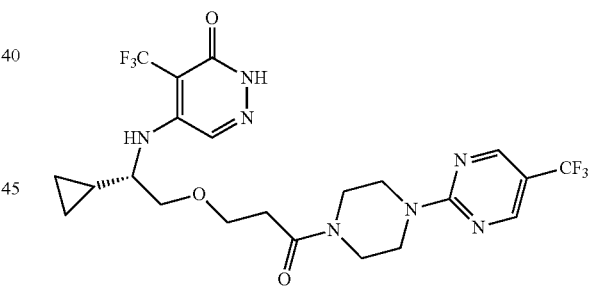

To a stirred solution of 3-[(2S)-2-cyclopropyl-2-[[6-oxo-5-(trifluoromethyl)-1,6-dihydropyridazin-4-yl]amino]ethoxy]propanoic acid (130 mg, 0.39 mmol, 1.00 equiv) in DMF (10 mL), and Int-A2 (80 mg, 0.43 mmol, 1.09 equiv), DIPEA (0.5 mL) and HATU (180 mg, 0.47 mmol, 1.2 equiv) were added. The resulting solution was stirred for 2 h at room temperature. After concentration, the residue was purified by C18 reverse phase chromatography eluting with H$_2$O/CH$_3$CN. The residue was further purified by Prep-HPLC yielding the title compound (79.3 mg, 37%) as a white solid. LCMS (ESI, m/z): 550.25 [M+H]$^+$. $^1$H NMR (400 MHz, DMSO-d$_6$) δ 12.40 (s, 1H), 8.73 (s, 2H), 7.88 (s, 1H), 6.51-6.38 (m, 1H), 3.94-3.44 (m, 13H), 2.58 (t, J=6.5 Hz, 2H), 1.15-1.01 (m, 1H), 0.55-0.40 (m, 2H), 0.38-0.25 (m, 2H).

Example 607: 5-[[(2R,3R)-3-Methoxy-1-(3-oxo-3-[4-[5-(trifluoromethyl)pyrimidin-2-yl]piperazin-1-yl] propoxy)butan-2-yl]amino]-4-(trifluoromethyl)-2,3-dihydropyridazin-3-one

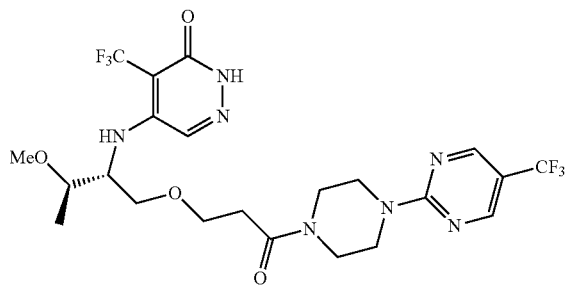 [SMILES: CO[C@H](C)[C@@H](COCCC(=O)N1CCN(c2ncc(C(F)(F)F)cn2)CC1)Nc1cn[nH]c(=O)c1C(F)(F)F]

Step 1: (2R,3R)-2-amino-3-methoxybutan-1-ol

A solution of (2S,3R)-2-amino-3-methoxybutanoic acid (1 g, 7.51 mmol, 1 equiv), diborane (15.0 mL, 1 M, 2 equiv) in THF (15 mL) was stirred for 12 h at room temperature. The reaction was quenched by the addition of 15 mL of methanol. The resulting mixture was concentrated, diluted with 15 mL of water and washed with 2×30 ml of DCM. The organic layers were combined and dried over Na$_2$SO$_4$. The resulting mixture was concentrated to afford 2.2 g (crude) of the title compound as colorless oil. LCMS (ESI, m/z): 120.09 [M+H]$^+$ Step 2: 5-[[(2R,3R)-1-hydroxy-3-methoxybutan-2-yl]amino]-4-(trifluoromethyl)-2-[[2-(trimethylsilyl)ethoxy]methyl]-2,3-dihydropyridazin-3-one A solution of (2R,3R)-2-amino-3-methoxybutan-1-ol (2.18 g, 18.29 mmol, 1 equiv), Int-A6 (2.46 g, 7.48 mmol, 0.41 equiv), and TEA (3.7 g, 36.56 mmol, 2.00 equiv) in ethanol (10 mL, 1.00 equiv) was stirred for 1 h at 80° C. The resulting mixture was concentrated under vacuum. The residue was applied onto a silica gel column eluting with EtOAc/petroleum ether (3/7) to afford 1.63 g (21.6%) of the title compound as yellow oil. LCMS (ESI, m/z): 412.18[M+H]$^+$ Step 3: Methyl 3-[(2R,3R)-3-methoxy-2-[[6-oxo-5-(trifluoromethyl)-1-[[2-(trimethylsilyl)ethoxy]methyl]-1,6-dihydropyridazin-4-yl]amino]butoxy]propanoate A solution of 5-[[(2R,3R)-1-hydroxy-3-methoxybutan-2-yl]amino]-4-(trifluoromethyl)-2-[[2-(trimethylsilyl)ethoxy]methyl]-2,3-dihydropyridazin-3-one (1.62 g, 3.94 mmol, 1 equiv), Cs$_2$CO$_3$ (2.6 g, 7.87 mmol, 2.00 equiv), methyl prop-2-enoate (1.7 g, 19.68 mmol, 5.00 equiv) in ACN (10 mL) was stirred for 1 h at room temperature. The resulting mixture was concentrated under vacuum. The residue was applied onto a silica gel column eluting with EtOAc/petroleum ether (3/7) to afford 870 mg (44.4%) of the title compound as yellow oil. LCMS (ESI, m/z): 498.22[M+H]$^+$ Step 4: Methyl 3-[(2R,3R)-3-methoxy-2-[[6-oxo-5-(trifluoromethyl)-1,6-dihydropyridazin-4-yl]amino]butoxy]propanoate A solution of methyl 3-[(2R,3R)-3-methoxy-2-[[6-oxo-5-(trifluoromethyl)-1-[[2-(trimethylsilyl)ethoxy]methyl]-1,6-dihydropyridazin-4-yl]amino]butoxy]propanoate (850 mg, 1.71 mmol, 1 equiv) in DCM (10 mL) and TFA (1 mL) was stirred for 1 h at RT. The pH value of the solution was adjusted to 8 with ethanolamine. The resulting solution was diluted with 20 mL of water and extracted with 4×20 mL of DCM. The organic layers combined and dried over Na$_2$SO$_4$. The resulting solution was concentrated under vacuum to afford 640 mg of the title compound as yellow oil. LCMS (ESI, m/z): 368.14 [M+H]$^+$ Step 5: 3-[(2R,3R)-3-Methoxy-2-[[6-oxo-5-(trifluoromethyl)-1,6-dihydropyridazin-4-yl]amino]butoxy] propanoic Acid A solution of methyl 3-[(2R,3R)-3-methoxy-2-[[6-oxo-5-(trifluoromethyl)-1,6-dihydropyridazin-4-yl]amino]butoxy]propanoate (620 mg, 1.69 mmol, 1 equiv), LiOH.H$_2$O (354.2 mg, 8.44 mmol, 5.00 equiv) in methanol (15 mL) and water (5 mL, 277.54 mmol, 164.43 equiv) was stirred for 1 h at room temperature. After concentration, the pH value of the solution was adjusted to 5 with HCl (1 M). The resulting solution was extracted with 5×25 mL of DCM. The organic layers combined and dried over Na$_2$SO$_4$. The resulting solution was concentrated under vacuum to afford 500 mg (84%) of the title compound as a yellow solid. LCMS (ESI, m/z): 354.12 [M+H]$^+$ Step 6: 5-[[(2R,3R)-3-methoxy-1-(3-oxo-3-[4-[5-(trifluoromethyl)pyrimidin-2-yl]piperazin-1-yl] propoxy)butan-2-yl]amino]-4-(trifluoromethyl)-2,3-dihydropyridazin-3-one A solution of 3-[(2R,3R)-3-methoxy-2-[[6-oxo-5-(trifluoromethyl)-1,6-dihydropyridazin-4-yl]amino]butoxy]propanoic acid (100 mg, 0.28 mmol, 1 equiv), DIPEA (109.7 mg, 0.85 mmol, 3 equiv), Int-A2 (76.0 mg, 0.28 mmol, 1 equiv), HATU (161.4 mg, 0.42 mmol, 1.5 equiv) in DMF (3 mL) was stirred for 1 h at RT. The resulting solution was purified by C18 reverse phase chromatography eluting with H$_2$O/ACN. The residue was further purified by Prep-HPLC yielding the title compound (44.5 mg, 27.70%) as a white solid. LCMS (ESI, m/z): 568.47 [M+H]$^+$, $^1$H NMR (400 MHz, DMSO-d$_6$) δ: 12.49 (s, 1H), 8.74 (d, J=0.9 Hz, 2H), 7.91 (s, 1H), 6.01 (dd, J=9.3, 4.8 Hz, 1H), 4.07 (d, J=7.3 Hz, 1H), 3.83 (dt, J=19.5, 5.5 Hz, 4H), 3.70 (tt, J=9.3, 4.8 Hz, 2H), 3.54 (ddt, J=12.8, 6.3, 3.6 Hz, 7H), 3.27 (s, 3H), 2.60 (t, J=6.4 Hz, 2H), 1.11 (d, J=6.3 Hz, 3H).

Example 608: 4-Bromo-5-[[(2S)-1-(3-oxo-3-[4-[5-(trifluoromethyl)pyrimidin-2-yl]piperazin-1-yl] propoxy)propan-2-yl]oxy]-2,3-dihydropyridazin-3-one

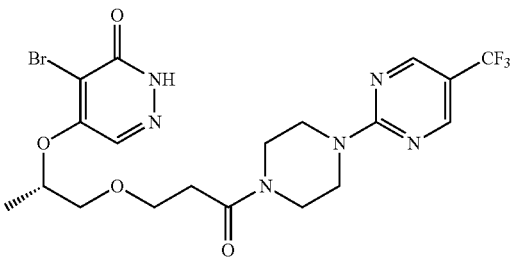 [SMILES: C[C@@H](COCCC(=O)N1CCN(c2ncc(C(F)(F)F)cn2)CC1)Oc1cn[nH]c(=O)c1Br]

Step 1: 1-[4-[5-(Trifluoromethyl)pyrimidin-2-yl]piperazin-1-yl]prop-2-en-1-one A solution of Int-A2 (5 g), prop-2-enoyl prop-2-enoate (3 g), and TEA (6.7 g) in DCM (80 mL) was stirred for 1 h at RT. The resulting solution was concentrated under reduced pressure and then the residue was applied onto a silica gel column eluting with EtOAc/petroleum ether (38:62) to afford 4.2 g of the title compound as a white solid. LCMS: [M+H]$^+$ 287.10.

Step 2: 3-[(2S)-2-(Benzyloxy)propoxy]-1-[4-[5-(trifluoromethyl)pyrimidin-2-yl]piperazin-1-yl]propan-1-one A solution of 1-[4-[5-(trifluoromethyl)pyrimidin-2-yl]piperazin-1-yl]prop-2-en-1-one (Int-A21: 1 g. 3.49 mmol, 1 equiv), Cs$_2$CO$_3$ (3.4 g, 10.44 mmol. 2.99 equiv), and (2S)-2-(benzyloxy)propan-1-ol (1.74 g, 0.01 mmol) in ACN (50 mL) was stirred for 36 h at 80° C. The solids were filtered and then the resulting solution was concentrated under vacuum. The residue was applied onto a silica gel column eluting with EtOAc/petroleum ether (1:1) to afford 480 mg (30%) of the title compound as a brown oil. LCMS: [M+H]$^+$ 453.20.

Step 3: 3-[(2S)-2-Hydroxypropoxy]-1-[4-[5-(trifluoromethyl)pyrimidin-2-yl]piperazin-1-yl]propan-1-one A solution of 3-[(2S)-2-(benzyloxy)propoxy]-1-[4-[5-(trifluoromethyl)pyrimidin-2-yl]piperazin-1-yl]propan-1-one (460 mg, 1.02 mmol, 1 equiv) in DCM (10 mL) was stirred for 10 min at 0° C. BCl$_3$ in DCM (3 mL, 3.0 equiv) was then added and the resulting solution was stirred for another 3 h at 0° C. The resulting solution was concentrated under vacuum and was purified by Flash-Prep-HPLC with the following conditions (IntelFlash-1): Column, C18 silica gel; mobile phase, ACN:H$_2$O=5.95 increasing to ACN:H$_2$O=47.53 within 25 min; Detector, UV 254 nm. The title compound was obtained by concentration under reduced pressure to afford 190 mg (52%) of the title compound as a white solid. LCMS: [M+H]$^+$ 363.16.

Step 4: 4-Bromo-5-[[(2S)-1-(3-oxo-3-[4-[5-(trifluoromethyl)pyrimidin-2-yl]piperazin-1-yl]propoxy)propan-2-yl]oxy]-2-[[2-(trimethylsilyl)ethoxy]methyl]-2,3-dihydropyridazin-3-one A solution of 3-[(2S)-2-hydroxypropoxy]-1-[4-[5-(trifluoromethyl)pyrimidin-2-yl]piperazin-1-yl]propan-1-one (170 mg, 0.47 mmol, 1 equiv), ACN (8 mL, 152.20 mmol, 324.41 equiv), Cs$_2$CO$_3$ (458 mg, 1.41 mmol, 3.00 equiv), and Int-A8 (538 mg, 1.40 mmol, 2.99 equiv) was stirred for 10 h at 80° C. The solids were filtered and then the residue was applied onto a silica gel column eluting with EtOAc/petroleum ether (2:3) to afford 150 mg (48%) of the title compound as a brown oil LCMS: [M+H]$^+$ 665.17[M+H]$^+$, 667.17[M+H]$^+$.

Step 5: 4-Bromo-5-[[(2S)-1-(3-oxo-3-[4-[5-(trifluoromethyl)pyrimidin-2-yl]piperazin-1-yl]propoxy)propan-2-yl]oxy]-2,3-dihydropyrimidin-3-one A solution of 4-bromo-5-[[(2S)-1-(3-oxo-3-[4-[5-(trifluoromethyl)pyrimidin-2-yl]piperazin-1-yl]propoxy)propan-2-yl]oxy]-2-[[2-(trimethylsilyl)ethoxy]methyl]-2,3-dihydropyridazin-3-one (120 mg, 0.18 mmol, 1 equiv), DCM (3 mL), and TFA (0.6 mL, 8.08 mmol, 44.80 equiv) was stirred for 1.5 h at RT The resulting mixture was concentrated under vacuum and was purified by Flash-Prep-HPLC. The crude product was further purified by Chiral-Prep-HPLC yielding the title compound (10.8 mg, 11%) as a white solid. LCMS: [M+H]$^+$ 535.10, 537.10. $^1$H NMR (300 MHz, Methanol-d$_4$) δ 8.58 (s, 2H), 8.05 (s, 1H), 5.02 (td, J=6.6, 3.2 Hz, 1H), 3.89 (q, J=5.6, 5.2 Hz, 4H), 3.83-3.70 (m, 1H), 3.74-3.57 (m, 7H), 2.65 (t, J=5.9 Hz, 2H), 1.36 (d, J=6.3 Hz, 3H).

Example 609: 4-Bromo-5-[[(2S)-1-[3-[4-(5-chloropyrimidin-2-yl)piperazin-1-yl]-3-oxopropoxy]propan-2-yl]oxy]-2,3-dihydropyridazin-3-one

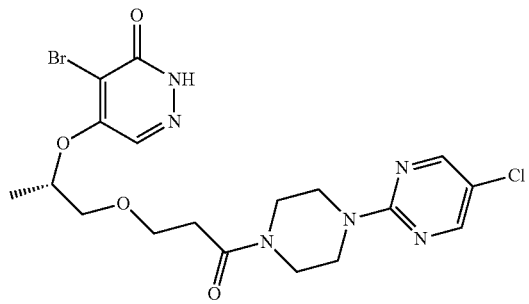 [SMILES: C[C@@H](COCCC(=O)N1CCN(c2ncc(Cl)cn2)CC1)Oc1cn[nH]c(=O)c1Br]

Step 1: 3-[(2S)-2-(Benzyloxy)propoxy]-1-[4-(5-chloropyrimidin-2-yl)piperazin-1-yl]propan-1-one A solution of 1-[4-(5-chloropyrimidin-2-yl)piperazin-1-yl]but-3-en-1-one (1 g, 3.75 mmol, 1 equiv), (2S)-2-(benzyloxy)propan-1-ol (1.2 g, 7.50 mmol, 2.0 equiv), and Cs$_2$CO$_3$ (2.4 g, 7.50 mmol, 2.0 equiv) in ACN (10 mL) was stirred for 16 h at 80° C. The solids were filtered and the resulting mixture was concentrated. The residue was applied onto a silica gel column with EtOAc/petroleum ether (2:3) to afford 894 mg (57%) of the title compound as a yellow oil. LCMS: [M+H]$^+$ 419.20.

Step 2: 1-[4-(5-Chloropyrimidin-2-yl)piperazin-1-yl]-3-[(2S)-2-hydroxypropoxy]propan-1-one To a solution of 3-[(2S)-2-(benzyloxy)propoxy]-1-[4-(5-chloropyrimidin-2-yl)piperazin-1-yl]propan-1-one (874 mg, 2.09 mmol, 1 equiv) in DCM (3 mL) was added BCl$_3$ (10 mL) at 0° C. The resulting solution was stirred for 1 h at 0° C. and the resulting solution was concentrated under vacuum. The residue was purified by C18 reverse phase chromatography eluting with H$_2$O/CH$_3$CN to afford 1.04 g (53%) of the title compound as a yellow oil. LCMS: [M+H]$^+$ 329.15.

Step 3: 4-Bromo-5-[[(2S)-1-[3-[4-(5-chloropyrimidin-2-yl)piperazin-1-yl]-3-oxopropoxy]propan-2-yl]oxy]-2-[[2-(trimethylsilyl)ethoxy]methyl]-2,3-dihydropyridazin-3-one A solution of 1-[4-(5-chloropyrimidin-2-yl)piperazin-1-yl]-3-[(2S)-2-hydroxypropoxy]propan-1-one (406 mg, 1.23 mmol, 1 equiv), Int-A8 (948.7 mg, 2.47 mmol, 2.0 equiv), and Cs$_2$CO$_3$ (804.6 mg, 2.47 mmol, 2.0 equiv) in ACN (10 mL) was stirred for 8 h at 60° C. The resulting solids were filtered and the resulting mixture was concentrated. The residue was applied onto a silica gel column with EtOAc/ petroleum ether (1:1) to afford 260 mg (33%) of the title compound as a yellow oil. LCMS: [M+H]$^+$ 631.14, 633.14.

Step 4: 4-Bromo-5-[[(2S)-1-[3-[4-(5-chloropyrimidin-2-yl)piperazin-1-yl]-3-oxopropoxy]propan-2-yl]oxy]-2,3-dihydropyridazin-3-one A solution of 4-bromo-5-[[(2S)-1-[3-[4-(5-chloropyrimidin-2-yl)piperazin-1-yl]-3-oxopropoxy]propan-2-yl]oxy]-2-[[2-(trimethylsilyl)ethoxy]methyl]-2,3-dihydropyridazin-3-one (260 mg, 0.41 mmol, 1 equiv), DCM (10 L), and TFA (2 mL) was stirred for 1 h at RT. The resulting solution was concentrated under vacuum and the residue was purified by Prep-HPLC yielding the title compound (39.9 mg, 19%) as a white solid. LCMS: [M+H]$^+$ 500.95, 502.95. $^1$H NMR (300 MHz, CD$_3$OD-d$_4$) δ 8.32 (s, 2H), 8.06 (s, 1H), 5.03 (td, J=6.6, 3.3 Hz, 1H), 3.93-3.57 (m, 12H), 2.66 (t, J=5.9 Hz, 2H), 1.38 (d, J=6.3 Hz, 3H).

Example 610: 5-[[(2R,3R)-3-Hydroxy-1-(3-oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one

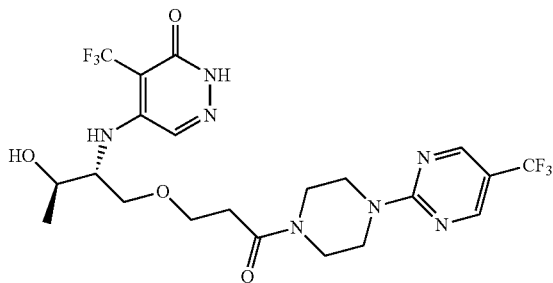 [SMILES: C[C@@H](O)[C@@H](COCCC(=O)N1CCN(c2ncc(C(F)(F)F)cn2)CC1)Nc1cn[nH]c(=O)c1C(F)(F)F]

Step 1: (2S,3R)-3-Hydroxy-2-[[6-oxo-5-(trifluoromethyl)-1-[[2-(trimethylsilyl)ethoxy]methyl]-1,6-dihydropyridazin-4-yl]amino]butanoic Acid A solution of (2S,3R)-2-amino-3-hydroxybutanoic acid (1190 mg, 9.99 mmol, 1 equiv), TEA (2021.8 mg, 19.98 mmol, 2 equiv), and Int-A6 (3284.6 mg, 9.99 mmol, 1 equiv) in EtOH (20 mL) was stirred for 1 h at RT. After concentration under reduced pressure, the crude material was purified by C18 reverse phase chromatography eluting with H$_2$O/CH$_3$CN to afford 900 mg (22%) of the title compound as a yellow oil. LCMS: [M+H]$^+$ 411.45.

Step 2: 5-[[(2R,3R)-1,3-Dihydroxybutan-2-yl]amino]-4-(trifluoromethyl)-2-[[2-(trimethylsilyl)ethoxy]methyl]-2,3-dihydropyridazin-3-one A solution of (2S,3R)-3-hydroxy-2-[[6-oxo-5-(trifluoromethyl)-1-[[2-(trimethylsilyl)ethoxy]methyl]-1,6-dihydropyridazin-4-yl]amino]butanoic acid (900 mg, 2.19 mmol, 1 equiv) in BH$_3$-THF (10 mL) was stirred for 2 h at 0° C. The reaction was then quenched by the addition of 100 mL of water/ice and the resulting solution was extracted with 3×100 mL of EtOAc. The organic layers were concentrated, and then the resulting solution was purified by C18 reverse phase chromatography eluting with H$_2$O/CH$_3$CN to afford 776 mg (89%) of the title compound as a yellow oil. LCMS: [M+H]$^+$ 397.47.

Step 3: Methyl 3-[(2R,3R)-3-hydroxy-2-[[6-oxo-5-(trifluoromethyl)-1-[[2-(trimethylsilyl)ethoxy]methyl]-1,6-dihydropyridazin-4-yl]amino]butoxy]propanoate A solution of 5-[[(2R,3R)-1,3-dihydroxybutan-2-yl]amino]-4-(trifluoromethyl)-2-[[2-(trimethylsilyl)ethoxy]methyl]-2,3-dihydropyridazin-3-one (776 mg, 1.95 mmol, 1 equiv), Cs$_2$CO$_3$ (1272.2 mg, 3.90 mmol, 2.0 equiv), methyl prop-2-enoate (336.2 mg, 3.90 mmol, 2.0 equiv) and ACN (10 mL) was stirred for 1 h at RT. The solids were filtered and the resulting solution was concentrated under vacuum. The solution was purified by C18 reverse phase chromatography eluting with H$_2$O/CH$_3$CN to afford 450 mg (48%) of the title compound as a yellow oil. LCMS: [M+H]$^+$ 483.55.

Step 4: Methyl 3-[(2R,3R)-3-hydroxy-2-[[6-oxo-5-(trifluoromethyl)-1,6-dihydropyridazin-4-yl]amino]butoxy]propanoate A solution of methyl 3-[(2R,3R)-3-hydroxy-2-[[6-oxo-5-(trifluoromethyl)-1-[[2-(trimethylsilyl)ethoxy]methyl]-1,6-dihydropyridazin-4-yl]amino]butoxy]propanoate (450 mg, 0.93 mmol, 1 equiv) and TFA (1 mL) in DCM (5 mL) was stirred for 1 h at RT. The resulting solution was concentrated under vacuum to afford 650 mg of the title compound as a yellow oil. LCMS: [M+H]$^+$ 353.29.

Step 5: 3-[(2R,3R)-3-Hydroxy-2-[[6-oxo-5-(trifluoromethyl)-1,6-dihydropyridazin-4-yl]amino]butoxy]propanoic Acid A solution of methyl 3-[(2R,3R)-3-hydroxy-2-[[6-oxo-5-(trifluoromethyl)-1,6-dihydropyridazin-4-yl]amino]butoxy]propanoate (650 mg, 1.84 mmol, 1 equiv), LiOH (220.3 mg, 9.20 mmol, 5.0 equiv) in H$_2$O (1 mL):MeOH (5 mL) was stirred for 1 h at RT. The pH value of the solution was adjusted to 2 with HCl (1 M) and then the resulting solution was purified by C18 reverse phase chromatography eluting with H$_2$O/CH$_3$CN to afford 120 mg (19%) of the title compound as a yellow oil. LCMS: [M+H]$^+$ 339.27.

Step 6: 5-[[(2R,3R)-3-Hydroxy-1-(3-oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one A solution of 3-[(2R,3R)-3-hydroxy-2-[[6-oxo-5-(trifluoromethyl)-1,6-dihydropyridazin-4-yl]amino]butoxy]propanoic acid (120 mg, 0.35 mmol, 1 equiv), HATU (134.5 mg, 0.35 mmol, 1.0 equiv), Int-A2 (82.1 mg, 0.35 mmol, 1 equiv), and DIPEA (91.4 mg, 0.71 mmol, 2.0 equiv) in DMF (2 mL) was stirred for 1 h at RT and then the resulting solution was purified by C18 reverse phase chromatography eluting with H$_2$O/CH$_3$CN. The residue was further purified by Prep-HPLC yielding the title compound (56.7 mg, 29%) as a white solid. LCMS: [M+H]$^+$ 554.25. $^1$H NMR (300 MHz, Methanol-d4) δ 8.62 (s, 2H), 7.96 (s, 1H), 4.08-3.80 (m, 6H), 3.85-3.80 (m, 2H), 3.79-3.55 (m, 6H), 2.70 (t, J=5.9 Hz, 2H), 1.21 (d, J=6.3 Hz, 3H).

Example 611: 5-[[(2R,3S)-3-Hydroxy-1-(3-oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one

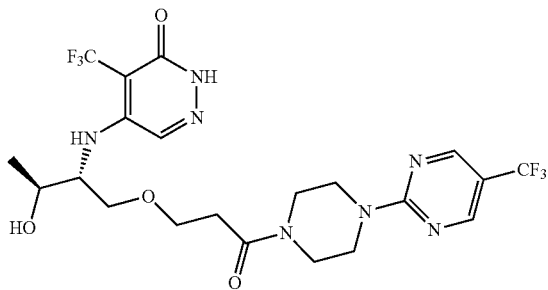 [SMILES: C[C@H](O)[C@@H](COCCC(=O)N1CCN(c2ncc(C(F)(F)F)cn2)CC1)Nc1cn[nH]c(=O)c1C(F)(F)F]

Step 1: (2S,3S)-3-Hydroxy-2-[[6-oxo-5-(trifluoromethyl)-1-[[2-(trimethylsilyl)ethoxy]methyl]-1,6-dihydropyridazin-4-yl]amino]butanoic Acid A solution of (2S,3S)-2-amino-3-hydroxybutanoic acid (2.38 g, 0.02 mmol, 1 equiv), TEA (4.0 g, 0.04 mmol, 2 equiv), Int-A6 (6.6 g, 0.02 mmol, 1 equiv) in EtOH (50 mL) was stirred for 1 h at RT. After concentration under reduced pressure, the crude residue was purified by C18 reverse phase chromatography eluting with $H_2O/CH_3CN$ to afford 2.1 g (26%) of the title compound as a yellow oil. LCMS: $[M+H]^+$ 411.45.

Step 2: 5-[[(2R,3S)-1,3-Dihydroxybutan-2-yl]amino]-4-(trifluoromethyl)-2-[[2-(trimethylsilyl)ethoxy]methyl]-2,3-dihydropyridazin-3-one A solution of (2S,3S)-3-hydroxy-2-[[6-oxo-5-(trifluoromethyl)-1-[[2-(trimethylsilyl)ethoxy]methyl]-1,6-dihydropyridazin-4-yl]amino]butanoic acid (2 g, 4.86 mmol, 1 equiv) in $BH_3$-THF (50 mL) was stirred for 2 h at 0° C. The reaction was then quenched by the addition of 100 mL of water/ice and the resulting solution was extracted with 3×100 mL of EtOAc. The organic layers were concentrated under reduced pressure and then the resulting solution was purified by C18 reverse phase chromatography eluting with $H_2O/CH_3CN$ to afford 1.5 g (78%) of the title compound as a yellow oil. LCMS: $[M+H]^+$ 397.47.

Step 3: Methyl 3-[(2R,3S)-3-hydroxy-2-[[6-oxo-5-(trifluoromethyl)-1-[[2-(trimethylsilyl)ethoxy]methyl]-1,6-dihydropyridazin-4-yl]amino]butoxy]propanoate A solution of 5-[[(2R,3S)-1,3-dihydroxybutan-2-yl]amino]-4-(trifluoromethyl)-2-[[2-(trimethylsilyl)ethoxy]methyl]-2,3-dihydropyridazin-3-one (1500 mg, 3.774 mmol, 1 equiv), $Cs_2CO_3$ (2459.20 mg, 7.548 mmol, 2.0 equiv), and methyl prop-2-enoate (487.34 mg, 5.661 mmol, 1.5 equiv) in MeCN (50 mL) was stirred for 1 h at RT. The solids were filtered and the resulting solution was concentrated under vacuum to afford the crude product which was purified by C18 reverse phase chromatography eluting with $H_2O/CH_3CN$ to afford 720 mg (39%) of the title compound as a yellow oil. LCMS: $[M+H]^+$ 483.55.

Step 4: Methyl 3-[(2R,3S)-3-hydroxy-2-[[6-oxo-5-(trifluoromethyl)-1,6-dihydropyridazin-4-yl]amino]butoxy]propanoate A solution of methyl 3-[(2R,3S)-3-hydroxy-2-[[6-oxo-5-(trifluoromethyl)-1-[[2-(trimethylsilyl)ethoxy]methyl]-1,6-dihydropyridazin-4-yl]amino]butoxy]propanoate (720 mg, 1.489 mmol, 1 equiv) and TFA (1 mL) in DCM (5 mL) was stirred for 1 h at RT. The resulting solution was concentrated under vacuum to afford 1 g of the title compound as a yellow oil. LCMS: $[M+H]^+$ 353.29.

Step 5: 3-[(2R,3S)-3-Hydroxy-2-[[6-oxo-5-(trifluoromethyl)-1,6-dihydropyridazin-4-yl]amino]butoxy]propanoic Acid A solution of methyl 3-[(2R,3S)-3-hydroxy-2-[[6-oxo-5-(trifluoromethyl)-1,6-dihydropyridazin-4-yl]amino]butoxy]propanoate (1000 mg, 2.830 mmol, 1 equiv), and LiOH (338.92 mg, 14.152 mmol, 5 equiv) in $H_2O$ (1 mL)/MeOH (5 mL) was stirred for 1 h at RT. The pH value of the solution was adjusted to 2 with HCl (1M) and then the crude product was purified by C18 reverse phase chromatography eluting with $H_2O/CH_3CN$ to afford 190 mg (20%) of the title compound as a yellow oil. LCMS: $[M+H]^+$ 339.27.

Step 6: 5-[[(2R,3S)-3-Hydroxy-1-(3-oxo-3-[4-[5-(trifluoromethyl)pyrimidin-2-yl]piperazin-1-yl]propoxy)butan-2-yl]amino]-4-(trifluoromethyl)-2,3-dihydropyridazin-3-one A solution of 3-[(2R,3S)-3-hydroxy-2-[[6-oxo-5-(trifluoromethyl)-1,6-dihydropyridazin-4-yl]amino]butoxy]propanoic acid (120 mg, 0.35 mmol, 1 equiv), HATU (134.5 mg, 0.35 mmol, 1.0 equiv), Int-A2 (82.1 mg, 0.35 mmol, 1 equiv), and DIPEA (91.4 mg, 0.71 mmol, 2.0 equiv) in DMF (2 mL) was stirred for 1 h at RT and then the crude product was purified by C18 reverse phase chromatography eluting with $H_2O/CH_3CN$. The residue was further purified by Prep-HPLC yielding the title compound (32 mg, 16%) as a white solid. LCMS: $[M+H]^+$ 554.25. $^1$H NMR (300 MHz, Methanol-d4) δ 8.61 (s, 2H), 7.99 (s, 1H), 4.08-3.91 (m, 6H), 3.97-3.79 (m, 3H), 3.79-3.59 (m, 5H), 2.69 (t, J=5.9 Hz, 2H), 1.24 (d, J=6.4 Hz, 3H).

665

Example 612 Isomer A: 6-(4-[2-[(2R,5S)-5-[(1R)-2-[6-Oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile and Example 612 Isomer B: 6-(4-[2-[(2R,5S)-5-[(1S)-2-[6-Oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile and Example 612 Isomer C: 6-(4-[2-[(2R,5R)-5-[(1S)-2-[6-Oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile and Example 612 Isomer D: 6-(4-[2-[(2S,5S)-5-[(1R)-2-[6-Oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile Example 612

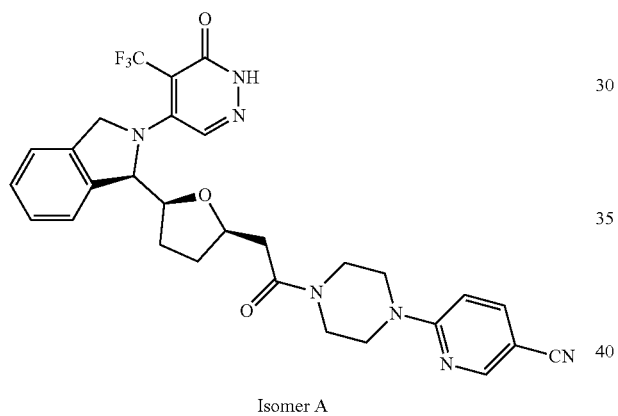

Isomer A

Example 612

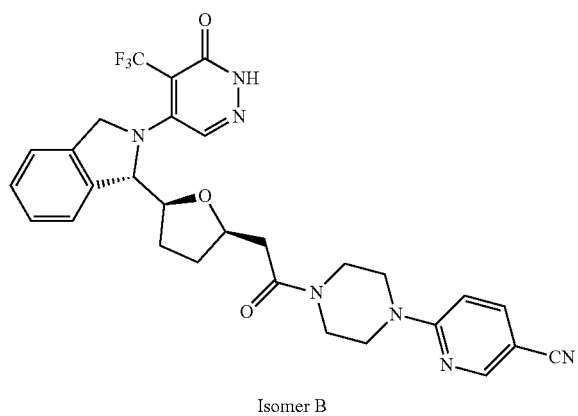

Isomer B

666

Example 612

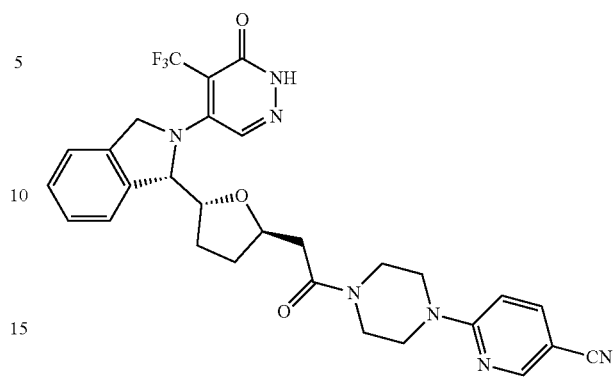

Isomer C

Example 612

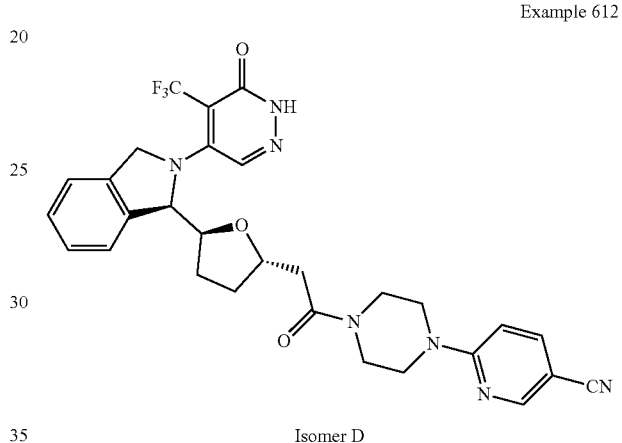

Isomer D

Step 1: Tert-butyl 1-(hydroxymethyl)-2,3-dihydro-1H-isoindole-2-carboxylate

A solution of 2-[(tert-butoxy)carbonyl]-2,3-dihydro-1H-isoindole-1-carboxylic acid (3.6 g, 13.67 mmol, 1 equiv) and $B_2H_6$/THF (27 mL) in THF (40 mL) was stirred for 12 h at RT. The resulting solution was quenched by the addition of 30 mL of $NH_4Cl$ solution and extracted with 3×50 mL of EtOAc. The organic layers were combined and dried over $Na_2SO_4$. The reaction mixture was concentrated under vacuum to afford 3.9 g of the title compound as a brown solid. LCMS: [M+H]$^+$ 250.14.

Step 2: Tert-butyl 1-formyl-2,3-dihydro-1H-isoindole-2-carboxylate

A solution of tert-butyl 1-(hydroxymethyl)-2,3-dihydro-1H-isoindole-2-carboxylate (3.9 g, 15.64 mmol, 1 equiv) and Dess-Martin (10.1 g, 23.81 mmol, 1.52 equiv) in DCM (40 mL) was stirred for 12h at RT. The reaction was quenched by the addition of 40 mL of $Na_2SO_3$/$H_2O$. The resulting solution was extracted with 3×50 mL of DCM and the organic layers combined, and washed with 2×50 mL of $NaHCO_3$. The organic layers were combined and dried over $Na_2SO_4$ and concentrated under reduced pressure. The residue was applied onto a silica gel column eluting with EtOAc/petroleum ether (1/9) to afford 830 mg (21%) of the title compound as a yellow oil. LCMS: [M+H]$^+$ 248.12.

Step 3: Tert-butyl 1-(1-hydroxypent-4-en-1-yl)-2,3-dihydro-1H-isoindole-2-carboxylate A solution of tert-butyl 1-formyl-2,3-dihydro-1H-isoindole-2-carboxylate (830 mg, 3.36 mmol, 1 equiv), bromo(but-3-en-1-yl)magnesium (5.0 mL, 5.00 mmol, 1.49 equiv) in THF (20 mL) was stirred for 1 h under the atmosphere of nitrogen at RT. The resulting solution was quenched by the addition of 20 mL of water and extracted with 3×30 mL of EtOAc. The resulting mixture was concentrated under vacuum to afford 945 mg (93%) of the title compound as a yellow oil. LCMS: [M+H]$^+$ 304.18.

Step 4: Tert-butyl 1-[(4Z)-1-hydroxy-6-methoxy-6-oxohex-4-en-1-yl]-2,3-dihydro-1H-isoindole-2-carboxylate A solution of tert-butyl 1-(1-hydroxypent-4-en-1-yl)-2,3-dihydro-1H-isoindole-2-carboxylate (945 mg, 3.11 mmol, 1 equiv), methyl prop-2-enoate (1340.7 mg, 15.57 mmol, 5.00 equiv), and Grubbs 2nd generation catalyst (26.4 mg, 0.03 mmol, 0.01 equiv) in DCM (25 mL) was stirred for 1.5h under a nitrogen atmosphere at 45° C. The reaction mixture was concentrated under vacuum and the residue was applied onto a silica gel column eluting with EtOAc/petroleum ether (1/9) to afford 930 mg (83%) of the title compound as a yellow oil. LCMS: [M+H]$^+$ 362.19.

Step 5: Tert-butyl 1-[5-(2-methoxy-2-oxoethyl)oxolan-2-yl]-2,3-dihydro-1H-isoindole-2-carboxylate A solution of tert-butyl 1-[(4Z)-1-hydroxy-6-methoxy-6-oxohex-4-en-1-yl]-2,3-dihydro-1H-isoindole-2-carboxylate (930 mg, 2.57 mmol, 1 equiv) and sodium hydride (185.2 mg, 7.72 mmol, 3.00 equiv) in THF (20 mL) was stirred for 12h at RT. The reaction was then quenched by the addition of water and the resulting solution was extracted with 4×50 mL of EtOAc and the organic layers combined and concentrated under vacuum. The residue was applied onto a silica gel column eluting with EtOAc/petroleum ether (15/85) to afford 630 mg (68%) of the title compound as a yellow oil. LCMS: [M+H]$^+$ 362.19.

Step 6: 2-(5-[2-[(Tert-butoxy)carbonyl]-2,3-dihydro-1H-isoindol-1-yl]oxolan-2-yl)acetic Acid A solution of tert-butyl 1-[5-(2-methoxy-2-oxoethyl)oxolan-2-yl]-2,3-dihydro-1H-isoindole-2-carboxylate (610 mg, 1.69 mmol, 1 equiv) and LiOH.H$_2$O (354.1 mg, 8.44 mmol, 5.00 equiv) in MeOH (15 mL) and water (5 mL) was stirred for 2 h at RT. The resulting mixture was concentrated and the pH of the solution was adjusted to 6 with HCl (1M) and extracted with 5×30 mL of DCM. The organic layers were combined and dried over Na$_2$SO$_4$. The resulting mixture was concentrated under vacuum to afford 520 mg (89%) of the title compound as a yellow solid. LCMS: [M+H]$^+$ 348.17.

Step 7: Tert-butyl 1-(5-[2-[4-(5-cyanopyridin-2-yl)piperazin-1-yl]-2-oxoethyl]oxolan-2-yl)-2,3-dihydro-1H-isoindole-2-carboxylate A solution of 2-(5-[2-[(tert-butoxy)carbonyl]-2,3-dihydro-1H-isoindol-1-yl]oxolan-2-yl)acetic acid (500 mg, 1.44 mmol, 1 equiv), DIPEA (558.0 mg, 4.32 mmol, 3.00 equiv), Int-A4 (323.4 mg, 1.44 mmol, 1 equiv), HATU (820.9 mg, 2.16 mmol, 1.5 equiv) in DMF (5 mL) was stirred for 1 h at RT. The residue was purified by C18 reverse phase chromatography eluting with H$_2$O/CH$_3$CN to afford 670 mg (90%) of the title compound as an off-white solid. LCMS: [M+H]$^+$ 518.27.

Step 8: 6-(4-[2-[5-(2,3-Dihydro-1H-isoindol-1-yl)oxolan-2-yl]acetyl]piperazin-1-yl)pyridine-3-carbonitrile Hydrochloride A solution of tert-butyl 1-(5-[2-[4-(5-cyanopyridin-2-yl)piperazin-1-yl]-2-oxoethyl]oxolan-2-yl)-2,3-dihydro-1H-isoindole-2-carboxylate (620 mg, 1.20 mmol, 1 equiv) in HCl/dioxane (10 mL) was stirred for 30 min at RT. The resulting mixture was concentrated under vacuum to afford 520 mg (96%) of the title compound as a yellow solid. LCMS: [M+H]$^+$ 418.22.

Step 9: 6-[4-[2-[5-[2-[6-Oxo-5-(trifluoromethyl)-1-[[2-(trimethylsilyl)ethoxy]methyl]-1,6-dihydropyridazin-4-yl]-2,3-dihydro-1H-isoindol-1-yl]oxolan-2-yl]acetyl]piperazin-1-yl]pyridine-3-carbonitrile A solution of 6-(4-[2-[5-(2,3-dihydro-1H-isoindol-1-yl)oxolan-2-yl]acetyl]piperazin-1-yl)pyridine-3-carbonitrile hydrochloride (520 mg, 1.15 mmol, 1 equiv), Int-A6 (376.6 mg, 1.15 mmol, 1 equiv) and TEA (231.8 mg, 2.29 mmol, 2 equiv) in EtOH (20 mL) was stirred for 1 h at 80° C. The reaction mixture was concentrated under vacuum and the residue was applied onto a silica gel column eluting with EtOAc/petroleum ether (6/4) to afford 730 mg (90%) of the title compound as a yellow solid. LCMS: [M+H]$^+$ 710.30.

Step 10: 6-(4-[2-[(2R,5S)-5-[(1R)-2-[6-Oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile, 6-(4-[2-[(2R,5S)-5-[(1S)-2-[6-oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile, 6-(4-[2-[(2R,5R)-5-[(1S)-2-[6-oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile and 6-(4-[2-[(2S,5S)-5-[(1R)-2-[6-oxo-5-(trifluoromethyl)-1,6-dihydropyridazin-4-yl]-2,3-dihydro-1H-isoindol-1-yl]oxolan-2-yl]acetyl]piperazin-1-yl)pyridine-3-carbonitrile A solution of 6-[4-[2-[5-[2-[6-oxo-5-(trifluoromethyl)-1-[[2-(trimethylsilyl)ethoxy]methyl]-1,6-dihydropyridazin-4-yl]-2,3-dihydro-1H-isoindol-1-yl]oxolan-2-yl)acetyl]piperazin-1-yl]pyridine-3-carbonitrile (710 mg, 1.00 mmol, 1 equiv) in TFA (2 mL) and DCM (10 mL) was stirred for 1.5 h at RT After concentration, the residue was purified by C18 reverse phase chromatography eluting with H$_2$O/CH$_3$CN. The residue was further purified by Prep-HPLC and Chiral-Prep-HPLC (Chiralpak Cellulose-SB, 3 µm, 0.46×15 cm column, eluting with a gradient of MtBE (0.1% DEA):EtOH=80:20, at a flow rate of 1 mL/min) yielding the title compounds as white solids and with the stereochemistry arbitrarily assigned.

Example 612 Isomer A

LCMS: [M+H]⁺ 580.57, ¹H NMR (400 MHz, DMSO-d₆) δ 12.48 (s, 1H), 8.52 (d, J=2.3 Hz, 1H), 8.29 (s, 1H), 7.89 (dd, J=9.1, 2.4 Hz, 1H), 7.44-7.36 (m, 2H), 7.36-7.30 (m, 2H), 6.93 (d, J=9.3 Hz, 1H), 5.91-5.89 (d, J=5.8 Hz, 1H), 5.05-5.02 (m, 1H), 4.45 (d, J=14.7 Hz, 1H), 4.17 (p, J=6.4 Hz, 1H), 3.99 (q, J=6.8 Hz, 1H), 3.69-3.68 (m, 4H), 3.63-3.53 (m, 4H), 2.69 (dd, J=15.3, 6.0 Hz, 1H), 2.43 (dd, J=15.4, 6.8 Hz, 1H), 2.10-1.94 (m, 1H), 1.88 (dq, J=13.8, 7.0, 6.6 Hz, 1H), 1.71 (dq, J=15.5, 7.8 Hz, 1H), 1.56-1.43 (m, 1H). tR=4.821 min

Example 612 Isomer B

LCMS: [M+H]⁺ 580.57 [M+H]⁺, ¹H NMR (400 MHz, DMSO-d₆) δ 12.45 (s, 1H), 8.50 (d, J=2.3 Hz, 1H), 8.24 (s, 1H), 7.87 (dd, J=9.1, 2.4 Hz, 1H), 7.43-7.33 (m, 2H), 7.32-7.22 (m, 2H), 6.89 (d, J=9.1 Hz, 1H), 5.90 (d, J=6.0 Hz, 1H), 5.01 (d, J=14.8 Hz, 1H), 4.43 (d, J=14.8 Hz, 1H), 4.25 (t, J=7.2 Hz, 1H), 4.13 (q, J=6.7 Hz, 1H), 3.65-3.62 (m, 2H), 3.34-3.28 (m, 6H), 2.72-2.62 (m, 1H), 2.41 (dd, J=14.9, 5.7 Hz, 1H), 2.07-2.05 (m, 1H), 1.98 (s, 1H), 1.76 (p, J=8.8 Hz, 1H), 1.56-1.43 (m, 1H). tR=6.334 min.

Chiral-Prep-HPLC purification by ((R,R)-Whelk, 3.5 μm, 0.46×15 cm column, eluting with a gradient of MtBE (0.1% DEA):EtOH=90:10, at a flow rate of 1 mL/min) afforded isomer C and isomer D as an arbitrary assignment of stereochemistry.

Example 612 Isomer C

LCMS: [M+H]⁺ 580.57, ¹H NMR (400 MHz, DMSO-d₆) δ 12.48 (s, 1H), 8.51 (d, J=2.3 Hz, 1H), 8.29 (s, 1H), 7.89 (dd, J=9.1, 2.4 Hz, 1H), 7.44-7.36 (m, 2H), 7.36-7.28 (m, 2H), 6.93 (d, J=9.3 Hz, 1H), 5.91 (d, J=5.8 Hz, 1H), 5.04 (d, J=14.7 Hz, 1H), 4.45 (d, J=14.8 Hz, 1H), 4.17 (p, J=6.5 Hz, 1H), 3.99 (q, J=6.8 Hz, 1H), 3.69 (d, J=5.3 Hz, 2H), 3.63 (d, J=5.4 Hz, 2H), 3.53 (t, J=5.3 Hz, 4H), 2.69 (dd, J=15.4, 6.0 Hz, 1H), 2.43 (dd, J=15.5, 6.9 Hz, 1H), 2.10-1.94 (m, 1H), 1.88 (dq, J=13.6, 6.6 Hz, 1H), 1.71 (dq, J=15.7, 7.7 Hz, 1H), 1.56-1.43 (m, 1H). tR=2.826 min.

Example 612 Isomer D

LCMS: [M+H]⁺ 580.57, ¹H NMR (400 MHz, DMSO-d₆) δ 12.48 (s, 1H), 8.51 (d, J=2.3 Hz, 1H), 8.29 (s, 1H), 7.89 (dd, J=9.1, 2.4 Hz, 1H), 7.44-7.36 (m, 2H), 7.36-7.28 (m, 2H), 6.93 (d, J=9.3 Hz, 1H), 5.91 (d, J=5.8 Hz, 1H), 5.04 (d, J=14.7 Hz, 1H), 4.45 (d, J=14.8 Hz, 1H), 4.17 (p, J=6.5 Hz, 1H), 3.99 (q, J=6.8 Hz, 1H), 3.69 (d, J=5.3 Hz, 2H), 3.63 (d, J=5.4 Hz, 2H), 3.53 (t, J=5.3 Hz, 4H), 2.69 (dd, J=15.4, 6.0 Hz, 1H), 2.43 (dd, J=15.5, 6.9 Hz, 1H), 2.10-1.94 (m, 1H), 1.88 (dq, J=13.6, 6.6 Hz, 1H), 1.71 (dq, J=15.7, 7.7 Hz, 1H), 1.56-1.43 (m, 1H). tR=3.640 min.

Example 613: (S)-5-((1-(3-Oxo-3-(4-(5-(trifluoromethyl)pyrazin-2-yl)piperazin-1-yl)propoxy)propan-2-yl)amino)-4-(trifluoromethyl)pyridazin-3(2H)-one

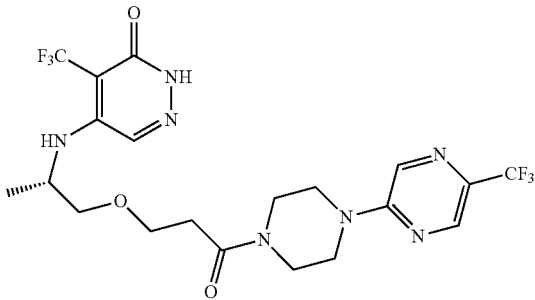 [SMILES: C[C@@H](COCCC(=O)N1CCN(c2cnc(C(F)(F)F)cn2)CC1)Nc1cn[nH]c(=O)c1C(F)(F)F]

Step 1: Tert-butyl 4-(5-(trifluoromethyl)pyrazin-2-yl)piperazine-1-carboxylate A solution of 2-chloro-5-(trifluoromethyl)pyrazine (1.5 g, 8.22 mmol, 1 equiv), K₂CO₃ (2.27 g, 16.4 mmol, 2 equiv), and tert-butyl piperazine-1-carboxylate (1.53 g, 8.22 mmol, 1 equiv) in NMP (15 mL) was stirred for 1 h at 80° C. followed by the addition of 50 mL of water. The resulting solids were collected by filtration to afford 2.5 g (91.5%) of the title compound. LCMS: [M+H]⁺ 332.

Step 2: 2-(Piperazin-1-yl)-5-(trifluoromethyl)pyrazine

A solution of tert-butyl 4-[5-(trifluoromethyl)pyrazin-2-yl]piperazine-1-carboxylate (2.5 g, 7.52 mmol, 1 equiv) in HCl (gas) in 1,4-dioxane (20 mL) was stirred for 1 h at RT. The solids were collected by filtration to afford 1 g (57.3%) of title compound as a white solid. LCMS: [M+H]⁺ 232.

Step 3: (S)-5-((1-(3-Oxo-3-(4-(5-(trifluoromethyl)pyrazin-2-yl)piperazin-1-yl)propoxy)propan-2-yl)amino)-4-(trifluoromethyl)pyridazin-3(2H)-one A solution of Int-A13 (151.4 mg, 0.490 mmol, 1.4 equiv), DIPEA (180.8 mg, 1.40 mmol, 4 equiv), HATU (172.9 mg, 0.455 mmol, 1.3 equiv), and 2-(piperazin-1-yl)-5-(trifluoromethyl)pyrazine (81.2 mg, 0.350 mmol, 1 equiv) in DMF (2 mL) was stirred for 1 h at RT. The crude product was purified by Prep-HPLC (YMC-Actus Triart C18, 5 μm, 30×250 cm column, eluting with a gradient of water 10 mmol/L NH₄HCO₃ in ACN) to afford 73.9 mg (40.4%) of title compound as a white solid. LCMS: [M+H]⁺ 524.24. ¹H NMR (300 MHz, Methanol-d₄) δ 8.43 (s, 1H), 8.30 (s, 1H), 7.96 (s, 1H), 4.18 (q, J=6.2 Hz, 1H), 3.82-3.76 (m, 10H), 3.64 (dd, J=9.7, 3.9 Hz, 1H), 3.52 (dd, J=9.7, 6.8 Hz, 1H), 2.71 (t, J=5.9 Hz, 2H), 1.27 (d, J=6.6 Hz, 3H).

Example 614 Isomer A: 5-(((S)-2-(3-Oxo-3-(4-(5-(trifluoromethyl)pyrimidin-2-yl)piperazin-1-yl)propoxy)-1-((S)-tetrahydrofuran-3-yl)ethyl)amino)-4-(trifluoromethyl)pyridazin-3(2H)-one and Example 614 Isomer B: 5-(((R)-2-(3-Oxo-3-(4-(5-(trifluoromethyl)pyrimidin-2-yl)piperazin-1-yl)propoxy)-1-((R)-tetrahydrofuran-3-yl)ethyl)amino)-4-(trifluoromethyl)pyridazin-3(2H)-one and Example 614 Isomer C: 5-(((S)-2-(3-oxo-3-(4-(5-(trifluoromethyl)pyrimidin-2-yl)piperazin-1-yl)propoxy)-1-((R)-tetrahydrofuran-3-yl)ethyl)amino)-4-(trifluoromethyl)pyridazin-3(2H)-one and Example 614 Isomer D: 5-(((R)-2-(3-Oxo-3-(4-(5-(trifluoromethyl)pyrimidin-2-yl)piperazin-1-yl)propoxy)-1-((S)-tetrahydrofuran-3-yl)ethyl)amino)-4-(trifluoromethyl)pyridazin-3(2H)-one Example 614

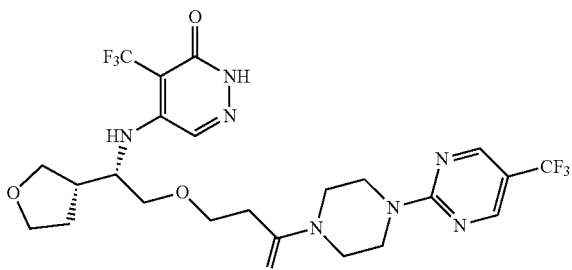

Isomer A

Example 614

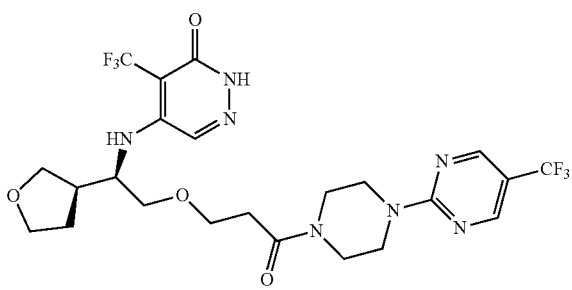

Isomer B

Example 614

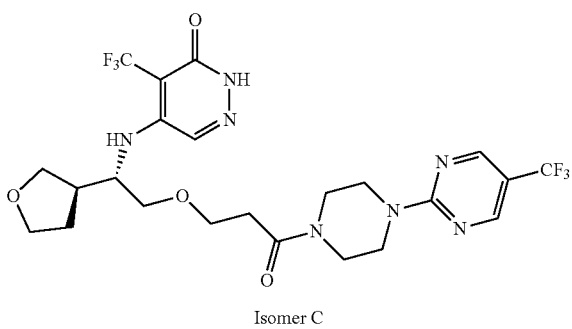

Isomer C

Example 614

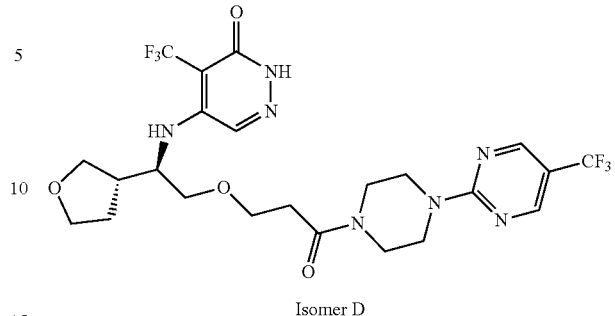

Isomer D

Step 1: 5-((2-Hydroxy-1-(tetrahydrofuran-3-yl)ethyl)amino)-4-(trifluoromethyl)-2-((2-(trimethylsilyl)ethoxy)methyl)pyridazin-3(2H)-one A solution of 2-amino-2-(tetrahydrofuran-3-yl)ethan-1-ol (2 g, 15.25 mmol, 1 equiv), Int-A6 (5.0 g, 15.25 mmol, 1.0 equiv), and TEA (3.1 g, 30.5 mmol, 2.0 equiv) in EtOH (20 mL) was stirred for 1 h at 60° C. After concentration under reduced pressure, the residue was purified by silica gel chromatography eluting with EtOAc/petroleum ether to afford 2.5 g of title compound as a yellow oil. LCMS: [M+H]+ 424.18.

Step 2: Methyl 3-(2-((6-oxo-5-(trifluoromethyl)-1-((2-(trimethylsilyl)ethoxy)methyl)-1,6-dihydropyridazin-4-yl)amino)-2-(tetrahydrofuran-3-yl)ethoxy)propanoate A solution of 5-((2-hydroxy-1-(tetrahydrofuran-3-yl)ethyl)amino)-4-(trifluoromethyl)-2-((2-(trimethylsilyl)ethoxy)methyl)pyridazin-3(2H)-one (1.3 g, 3.07 mmol, 1 equiv), Cs$_2$CO$_3$ (2.0 g, 6.14 mmol, 2.0 equiv), and methyl acrylate (0.5 g, 6.14 mmol, 2.0 equiv) in CH$_3$CN (10 mL) was stirred for 3 h at RT. The solid was filtered and the resulting filtrate was concentrated under reduced pressure. The resulting crude residue was purified by reverse phase column chromatography eluting with water/CH$_3$CN to afford 128 mg of title compound as a yellow oil. LCMS: [M+H]+ 510.22.

Step 3: 3-(2-((6-Oxo-5-(trifluoromethyl)-1,6-dihydropyridazin-4-yl)amino)-2-(tetrahydrofuran-3-yl)ethoxy)propanoic Acid A solution of methyl 3-(2-((6-oxo-5-(trifluoromethyl)-1-((2-(trimethyl silyl)ethoxy)methyl)-1,6-dihydropyridazin-4-yl)amino)-2-(tetrahydrofuran-3-yl)ethoxy)propanoate (128 mg, 0.25 mmol, 1 equiv) and TFA (1 mL) in DCM (5 mL) was stirred for 1 h at RT followed by concentration under reduced pressure to afford methyl 3-(2-((6-oxo-5-(trifluoromethyl)-1,6-dihydropyridazin-4-yl)amino)-2-(tetrahydrofuran-3-yl)ethoxy)propanoate (68 mg, 0.18 mmol, 1 equiv), to which was added LiOH (21.5 mg, 0.90 mmol, 5.0 equiv), and water (0.4 mL) in MeOH (2 mL). The resulting mixture was stirred for 4 h at RT, concentrated under reduced pressure, and the pH value of the solution was adjusted to 5 with HCl (1 mol/mL). The crude product was purified by C18 reverse phase column chromatography eluting with water/CH$_3$CN to afford 40 mg of title compound as an oil. LCMS: [M+H]+ 366.12.

Step 4: 5-(((S)-2-(3-Oxo-3-(4-(5-(trifluoromethyl) pyrimidin-2-yl)piperazin-1-yl)propoxy)-1-((S)-tetrahydrofuran-3-yl)ethyl)amino)-4-(trifluoromethyl) pyridazin-3(2H)-one and 5-(((R)-2-(3-Oxo-3-(4-(5-(trifluoromethyl)pyrimidin-2-yl)piperazin-1-yl)propoxy)-1-((R)-tetrahydrofuran-3-yl)ethyl)amino)-4-(trifluoromethyl) pyridazin-3(2H)-one and 5-(((S)-2-(3-oxo-3-(4-(5-(trifluoromethyl)pyrimidin-2-yl)piperazin-1-yl)propoxy)-1-((R)-tetrahydrofuran-3-yl)ethyl)amino)-4-(trifluoromethyl)pyridazin-3(2H)-one and 5-(((R)-2-(3-Oxo-3-(4-(5-(trifluoromethyl)pyrimidin-2-yl)piperazin-1-yl)propoxy)-1-((S)-tetrahydrofuran-3-yl)ethyl)amino)-4-(trifluoromethyl) pyridazin-3(2H)-one A solution of 3-(2-((6-oxo-5-(trifluoromethyl)-1,6-dihydropyridazin-4-yl)amino)-2-(tetrahydrofuran-3-yl)ethoxy) propanoic acid (40 mg, 0.109 mmol, 1 equiv), DIPEA (28.3 mg, 0.219 mmol, 2.0 equiv), HATU (41.63 mg, 0.109 mmol, 1.0 equiv), and Int-A2 (30.51 mg, 0.131 mmol, 1.2 equiv) in DMF (2 mL) was stirred for 40 minutes at RT. The resulting solution was diluted with 5 mL of water, extracted with 3×10 mL of EtOAc, and the organic layers were combined. After concentration under reduced pressure, the crude product was purified by C18 reverse phase column chromatography eluting with water/CH$_3$CN. The racemic compound was then separated by Chiral-Prep-HPLC (CHIRALPAK IC, 5 μm, 2×25 cm column, eluting with a gradient of Hexanes: DCM (3:1) in 10 mM NH$_3$/EtOH mobile phase at a flow rate of 20 mL/min). The stereochemistry of the four enantiomers was arbitrarily assigned.

Example 614 Isomer A-C

LCMS: [M+H]$^+$ 580.10

Example 614 Isomer D: 5-(((R)-2-(3-Oxo-3-(4-(5-(trifluoromethyl)pyrimidin-2-yl)piperazin-1-yl) propoxy)-1-((S)-tetrahydrofuran-3-yl)ethyl)amino)-4-(trifluoromethyl)pyridazin-3(2H)-one LCMS: [M+H]$^+$ 580.10, $^1$H NMR (300 MHz, Methanol-d$_4$) δ 8.65-8.58 (d, J=0.9 Hz, 2H), 7.99 (s, 1H), 3.99-3.86 (m, 6H), 3.88-3.54 (m, 11H), 2.70 (d, J=5.9 Hz, 2H), 2.58 (m, 1H), 2.09 (m, 1H), 1.79-1.68 (m, 1H).

Example 615: (S)-5-((1-((3-Oxo-3-(4-(5-(trifluoromethyl)pyrimidin-2-yl)piperazin-1-yl)propyl) amino)propan-2-yl)oxy)-4-(trifluoromethyl) pyridazin-3(2H)-one

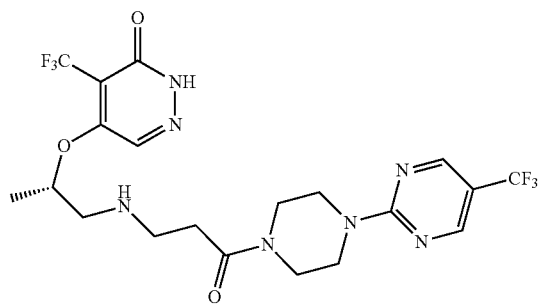 [SMILES: C[C@@H](CNCCC(=O)N1CCN(c2ncc(C(F)(F)F)cn2)CC1)Oc1cn[nH]c(=O)c1C(F)(F)F]

Step 1: (S)-3-((2-Hydroxypropyl)amino)-1-(4-(5-(trifluoromethyl)pyrimidin-2-yl)piperazin-1-yl)propan-1-one A solution of (S)-1-aminopropan-2-ol (1 g, 13.3 mmol, 1 equiv) and Int-A21 (3.81 g, 13.3 mmol, 1 equiv) in MeOH (50 mL) was stirred for 4 h at 60° C. The resulting solution was concentrated under reduced pressure and the residue was purified by Prep-HPLC eluting with H$_2$O/CH$_3$CN to afford 3.2 g (69.2%) of title compound as a white solid. LCMS: [M+H]$^+$ 362.17.

Step 2: Tert-butyl (S)-(2-hydroxypropyl)(3-oxo-3-(4-(5-(trifluoromethyl)pyrimidin-2-yl)piperazin-1-yl) propyl)carbamate A solution of (S)-3-((2-hydroxypropyl)amino)-1-(4-(5-(trifluoromethyl)pyrimidin-2-yl)piperazin-1-yl)propan-1-one (3.2 g, 8.855 mmol, 1 equiv), di-tert-butyl dicarbonate (1.93 g, 8.86 mmol, 1 equiv) and TEA (1.79 g, 17.7 mmol, 2.0 equiv) in DCM (50 mL) was stirred for 1 h at RT. The resulting solution was concentrated under reduced pressure, and the residue was purified by Prep-HPLC eluting with H$_2$O/CH$_3$CN to afford 4.1 g title compound as a white solid. LCMS: [M+H]$^+$ 462.22.

Step 3: Tert-butyl (S)-(2-((1-(4-methoxybenzyl)-6-oxo-5-(trifluoromethyl)-1,6-dihydropyridazin-4-yl) oxy)propyl)(3-oxo-3-(4-(5-(trifluoromethyl)pyrimidin-2-yl)piperazin-1-yl)propyl)carbamate A solution of tert-butyl (S)-(2-hydroxypropyl)(3-oxo-3-(4-(5-(trifluoromethyl)pyrimidin-2-yl)piperazin-1-yl)propyl)carbamate (4 g, 8.7 mmol, 1 equiv), Int-A20 (2.76 g, 8.7 mmol, 1.0 equiv) and tert-BuONa (1.25 g, 13.0 mmol, 1.5 equiv) in DCM (100 mL) was stirred for 1 h at 0° C. The resulting solution was diluted with 200 mL of water, extracted with 3×100 mL of EtOAc, and the organic layer was combined and concentrated under reduced pressure. The residue was purified by Prep-HPLC eluting with H$_2$O/CH$_3$CN to afford 4 g (62.1%) of title compound as a yellow solid. LCMS: [M+H]$^+$ 744.29.

Step 4: (3)-5-((1-((3-Oxo-3-(4-(5-(trifluoromethyl) pyrimidin-2-yl)piperazin-1-yl)propyl)amino)propan-2-yl)oxy)-4-(trifluoromethyl)pyridazin-3(2H)-one A solution of tert-butyl (S)-(2-((1-(4-methoxybenzyl)-6-oxo-5-(trifluoromethyl)-1,6-dihydropyridazin-4-yl)oxy) propyl)(3-oxo-3-(4-(5-(trifluoromethyl)pyrimidin-2-yl)piperazin-1-yl)propyl)carbamate (500 mg, 0.672 mmol, 1 equiv) and H$_2$SO$_4$ (1 mL) in TFA (5 mL) was stirred for 2 h at 0° C., and the resulting solution was quenched with 20 mL of ice water, extracted with 3×20 mL of EtOAc, and the organic layers combined and concentrated under reduced pressure. The residue was purified by Prep-HPLC eluting with H$_2$O/CH$_3$CN to afford 33.7 mg (9.58%) of the title compound as a white solid. LCMS. [M+H]$^+$ 524.20. $^1$H NMR (300 MHz, Methanol-d$_4$) δ 8.61 (d, J=0.9 Hz, 2H), 8.06 (s, 1H), 4.11-3.74 (m, 6H), 3.64 (dq, J=5.8, 3.2, 2.7 Hz, 5H), 3.49 (dd, J=14.5, 3.9 Hz, 1H), 3.41-3.27 (m, 1H), 2.80 (t, J=6.4 Hz, 2H), 1.16 (d, J=6.2 Hz, 3H).

Example 616: (S)-5-((1-(Methyl(3-oxo-3-(4-(5-(trifluoromethyl)pyrimidin-2-yl)piperazin-1-yl)propyl)amino)propan-2-yl)oxy)-4-(trifluoromethyl)pyridazin-3(2H)-one

Example 617 Isomer A: 5-(((S)-1-((R)-2-Amino-4-oxo-4-(4-(5-(trifluoromethyl)pyrimidin-2-yl)piperazin-1-yl)butoxy)propan-2-yl)amino)-4-(trifluoromethyl)pyridazin-3(2H)-one and

Example 617 Isomer B: 5-(((S)-1-((S)-2-Amino-4-oxo-4-(4-(5-(trifluoromethyl)pyrimidin-2-yl)piperazin-1-yl)butoxy)propan-2-yl)amino)-4-(trifluoromethyl)pyridazin-3(2H)-one

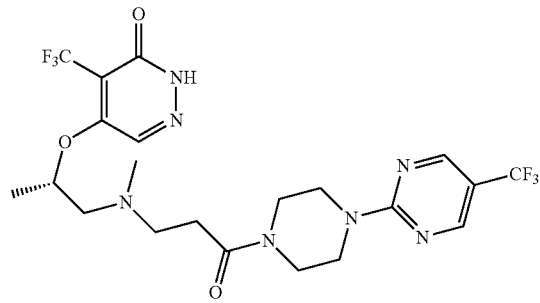 [SMILES: C[C@@H](CN(C)CCC(=O)N1CCN(c2ncc(C(F)(F)F)cn2)CC1)Oc1cn[nH]c(=O)c1C(F)(F)F]

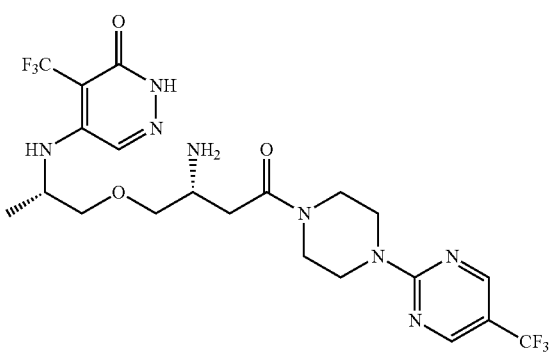

Example 617

Isomer A

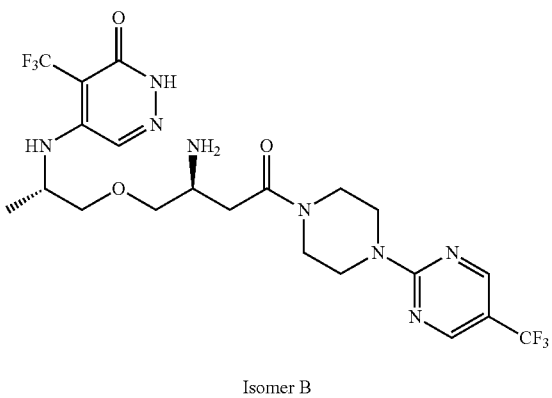

Example 617

Isomer B

Step 1: (S)-2-(4-Methoxybenzyl)-5-((1-(methyl(3-oxo-3-(4-(5-(trifluoromethyl)pyrimidin-2-yl)piperazin-1-yl)propyl)amino)propan-2-yl)oxy)-4-(trifluoromethyl)pyridazin-3(2H)-one A solution of (S)-2-(4-methoxybenzyl)-5-((1-((3-oxo-3-(4-(5-(trifluoromethyl)pyrimidin-2-yl)piperazin-1-yl)propyl)amino)propan-2-yl)oxy)-4-(trifluoromethyl)pyridazin-3(2H)-one (500 mg, 0.777 mmol, 1 equiv), polyoxymethylene (93.23 mg, 3.108 mmol, 4 equiv) and sodium cyanoborohydride (96.33 mg, 1.554 mmol, 2 equiv) in MeOH (5 mL) was stirred for 2 h at 60° C., and then the resulting solution was concentrated under reduced pressure and the residue was purified by Prep-HPLC eluting with H$_2$O/MeOH to afford 350 mg (68.5%) of title compound as a yellow oil. LCMS: [M+H]$^+$ 658.25.

Step 2: (S)-5-((1-(Methyl(3-oxo-3-(4-(5-(trifluoromethyl)pyrimidin-2-yl)piperazin-1-yl)propyl)amino)propan-2-yl)oxy)-4-(trifluoromethyl)pyridazin-3(2H)-one A solution of (S)-2-(4-methoxybenzyl)-5-((1-(methyl(3-oxo-3-(4-(5-(trifluoromethyl)pyrimidin-2-yl)piperazin-1-yl)propyl)amino)propan-2-yl)oxy)-4-(trifluoromethyl)pyridazin-3(2H)-one (300 mg, 0.456 mmol, 1 equiv) and H$_2$SO$_4$ (1 mL) in TFA (5 mL) was stirred for 2 h at 0° C., and then the resulting solution was concentrated under reduced pressure. The residue was purified by Prep-HPLC eluting with H$_2$O/CH$_3$CN to afford (68.9 mg, 28.1%) of the title compound as a white solid. LCMS: [M+H]$^+$ 538.25. $^1$H NMR (300 MHz, DMSO-d$_6$) δ 13.14 (s, 1H), 8.72 (d, J=0.9 Hz, 2H), 8.28 (s, 1H), 5.11 (s, 1H), 3.81 (d, J=19.2 Hz, 4H), 3.51 (t, J=5.4 Hz, 4H), 2.67-2.49 (m, 4H), 2.39 (d, J=7.6 Hz, 2H), 2.19 (m, 3H), 1.25 (d, J=6.1 Hz, 3H).

Step 1: (S)-5-((1-Hydroxypropan-2-yl)amino)-4-(trifluoromethyl)-2-((2-(trimethylsilyl)ethoxy)methyl)pyridazin-3(2H)-one A solution of Int-A6 (8 g, 24 mmol, 1 equiv), TEA (2.463 g, 24 mmol, 1 equiv), and (S)-2-aminopropan-1-ol (1.829 g, 24 mmol, 1 equiv) in EtOH (60 mL) was stirred for 1 h at 60° C. The solvent was concentrated under vacuum and the residue was applied onto a silica gel column eluting with EtOAc/petroleum ether (1/1) to afford 5.39 g (58.5%) of title compound as a yellow oil. LCMS: [M+H]$^+$ 367.44.

Step 2: Ethyl (S,E)-4-(2-(6-oxo-5-(trifluoromethyl)-1-((2-(trimethylsilyl)ethoxy)methyl)-1,6-dihydropyridazin-4-ylamino)propoxy)but-2-enoate A solution of (S)-5-(1-hydroxypropan-2-ylamino)-4-(trifluoromethyl)-2-((2-(trimethylsilyl)ethoxy)methyl)pyridazin-3(2H)-one (1.7 g, 4.63 mmol, 1 equiv), Pd$_2$(allyl)$_2$Cl$_2$ (85 mg, 0.23 mmol, 0.05 equiv), diisopropyl(2',4',6'- triisopropyl-3-methoxy-6-methylbiphenyl-2-yl)phosphine (217 mg, 0.46 mmol, 0.10 equiv), Cs$_2$CO$_3$ (4.5 g, 13.81 mmol, 2.99 equiv), and ethyl (E)-4-bromobut-2-enoate (2.7 g, 13.99 mmol, 3.02 equiv) in toluene (30 mL) was stirred for 15 h at 80° C. and maintained with an inert atmosphere of nitrogen. The solids were filtered and the solvent was concentrated under reduced pressure and the residue was applied onto a silica gel column eluting with EtOAc/petroleum ether (30:70) to afford 1.13 g (50.9%) of the title compound as a brown oil. LCMS: [M+H]$^+$ 368.17.

Step 3: Ethyl 3-(benzylamino)-4-((S)-2-(6-oxo-5-(trifluoromethyl)-1-((2-(trimethylsilyl)ethoxy)methyl)-1,6-dihydropyridazin-4-ylamino)propoxy)butanoate A solution of ethyl (S,E)-4-(2-((6-oxo-5-(trifluoromethyl)-1-((2-(trimethylsilyl)ethoxy)methyl)-1,6-dihydropyridazin-4-yl)amino)propoxy)but-2-enoate (1.11 g, 2.315 mmol, 1 equiv), and phenylmethanamine (1.24 g, 0.012 mmol, 5 equiv) in butan-1-ol (30 mL) was stirred for 4 h at 100° C. The solvent was concentrated under reduced pressure and the residue was applied onto a silica gel column eluting with EtOAc/petroleum ether (61:39) to afford 725 mg (53.4%) of the title compound as a yellow solid. LCMS: [M+H]$^+$ 587.30.

Step 4: Ethyl 3-((tert-butoxycarbonyl)amino)-4-((S)-2-((6-oxo-5-(trifluoromethyl)-1-((2-(trimethylsilyl)ethoxy)methyl)-1,6-dihydropyridazin-4-yl)amino)propoxy)butanoate A solution of ethyl 3-(benzylamino)-4-((S)-2-(6-oxo-5-(trifluoromethyl)-1-((2-(trimethylsilyl)ethoxy)methyl)-1,6-dihydropyridazin-4-ylamino)propoxy)butanoate (594 mg, 1.012 mmol, 1 equiv), Pd/C (76.13 mg, 0.202 mmol, 0.20 equiv), H$_2$ (gas), and (Boc)$_2$O (662.86 mg, 3.037 mmol, 3 equiv) in MeOH (30 mL) was stirred for 20 h at RT. The solids were filtered and the solvent was concentrated under reduced pressure. The residue was applied onto a silica gel column eluting with EtOAc/petroleum ether (30:70) to afford 594 mg (98.3%) of title compound as a yellow solid. LCMS: [M+H]$^+$ 597.31.

Step 5: 3-((Tert-butoxycarbonyl)amino-4-((S)-2-((6-oxo-5-(trifluoromethyl)-1-((2-(trimethylsilyl)ethoxy)methyl)-1,6-dihydropyridazin-4-yl)amino)propoxy)butanoic Acid A solution of ethyl 3-((tert-butoxycarbonyl)amino)-4-((S)-2-((6-oxo-5-(trifluoromethyl)-1-((2-(trimethylsilyl)ethoxy)methyl)-1,6-dihydropyridazin-4-yl)amino)propoxy)butanoate (550 mg, 0.922 mmol, 1 equiv), LiOH (44.15 mg, 1.843 mmol, 2 equiv), and H$_2$O (3 mL) in THF (15 mL) was stirred for 6 h at RT. The pH value of the solution was adjusted to 7 with HCl (10 mmol/L). The resulting mixture was concentrated under reduced pressure. After concentration, the residue was purified by C18 reverse phase chromatography eluting with H$_2$O/CH$_3$CN to afford 170 mg (32.4%) of title compound as a yellow oil. LCMS: [M+H]$^+$ 569.27.

Step 6: Tert-butyl (4-oxo-1-((S)-2-((6-oxo-5-(trifluoromethyl)-1-((2-(trimethylsilyl)ethoxy)methyl)-1,6-dihydropyridazin-4-yl)amino)propoxy)-4-(4-(5-(trifluoromethyl)pyrimidin-2-yl)piperazin-1-yl)butan-2-yl)carbamate A solution of 3-[[(tert-butoxy)carbonyl]amino]-4-[(2S)-2-[[6-oxo-5-(trifluoromethyl)-1-[[2-(trimethylsilyl)ethoxy]methyl]-1,6-dihydropyridazin-4-yl]amino]propoxy]butanoic acid (150 mg, 0.264 mmol, 1 equiv), Int-A18 (73.5 mg, 0.317 mmol, 1.20 equiv), HATU (120.4 mg, 0.317 mmol, 1.2 equiv), and DIPEA (102.3 mg, 0.791 mmol, 3 equiv) in DMF (3 mL) was stirred for 1 h at RT. After concentration under reduced pressure, the residue was purified by C18 reverse phase chromatography eluting with H$_2$O/CH$_3$CN to afford 158 mg (76.5%) of title compound as a yellow oil. LCMS: [M+H]$^+$ 783.36.

Step 7: 5-(((S)-1-((R)-2-Amino-4-oxo-4-(4-(5-(trifluoromethyl)pyrimidin-2-yl)piperazin-1-yl)butoxy)propan-2-yl)amino)-4-(trifluoromethyl)pyridazin-3(2H)-one and 5-(((S)-1-((S)-2-Amino-4-oxo-4-(4-(5-(trifluoromethyl)pyrimidin-2-yl)piperazin-1-yl)butoxy)propan-2-yl)amino)-4-(trifluoromethyl)pyridazin-3(2H)-one A solution of tert-butyl (4-oxo-1-((S)-2-((6-oxo-5-(trifluoromethyl)-1-((2-(trimethyl silyl)ethoxy)methyl)-1,6-dihydropyridazin-4-yl)amino)propoxy)-4-(4-(5-(trifluoromethyl)pyrimidin-2-yl)piperazin-1-yl)butan-2-yl)carbamate (148 mg, 0.189 mmol, 1 equiv), and TFA (2 mL) in DCM (10 mL) was stirred for 1 h at RT. After concentration by reduced pressure, the residue was purified by C18 reverse phase chromatography eluting with H$_2$O/CH$_3$CN. The residue was further purified by Prep-HPLC and Chiral Prep-HPLC (CHIRALPAK ID-3, 3 μm, 0.46×5 cm column, eluting with a gradient of MtBE (0.1% DEA):EtOH=70:30, at a flow rate of 1 mL/min) yielding the title compounds as white solids and with the stereochemistry arbitrarily assigned.

Example 617 Isomer A (6.4 mg, 6.1%) as a white solid. LCMS: [M+H]$^+$ 553.22, $^1$H NMR (300 MHz, Methanol-d$_4$) δ 8.62 (s, 2H), 8.04 (s, 1H), 4.24 (s, 1H), 4.03-3.89 (m, 4H), 3.75-3.57 (m, 5H), 3.57-3.37 (m, 4H), 2.62 (dd, J=16.1, 4.2 Hz, 1H), 2.44 (dd, J=16.4, 8.1 Hz, 1H), 1.31 (d, J=6.6 Hz, 3H). tR=1.245 min.

Example 617 Isomer B (7.0 mg, 6.7%) as a white solid. LCMS: [M+H]$^+$ 553.22, tR=1.639 min.

Example 618: (S)-5-((1-(3-Oxo-3-(4-(5-(trifluoromethyl)pyrimidin-2-yl)piperazin-1-yl)propoxy)propan-2-yl)thio)-4-(trifluoromethyl)pyridazin-3(2H)-one

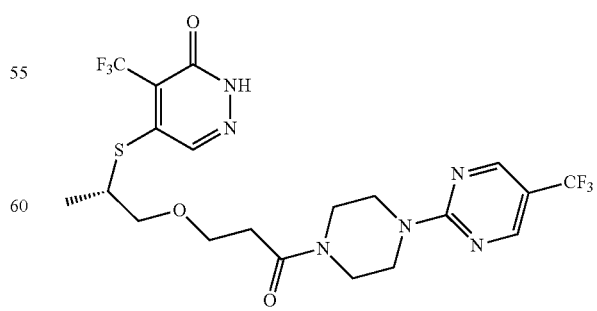

Step 1: (R)-3-(2-(Benzyloxy)propoxy)-1-(4-(5-(trifluoromethyl)pyrimidin-2-yl)piperazin-1-yl)propan-1-one A solution of (R)-2-(benzyloxy)propan-1-ol (1.66 g, 10 mmol, 2 equiv), Int-A21 (1.43 g, 5 mmol, 1 equiv), and NaH (20 mg, 0.1 mmol, 0.1 equiv) in 1-methoxy-2-(2-methoxyethoxy)ethane (2.5 mL) was stirred for 24 h at RT. The reaction was quenched with $H_2O$ (30 mL) and the resulting solution was extracted with EtOAc (3×50 mL) and the organic layers combined. The solvent was concentrated under reduced pressure and the residue was applied onto a silica gel column eluting with EtOAc/petroleum ether (45:65) to afford 2.1 g of title compound as a yellow oil. LCMS: $[M+H]^+$ 453.22.

Step 2: (R)-3-(2-Hydroxypropoxy)-1-(4-(5-(trifluoromethyl)pyrimidin-2-yl)piperazin-1-yl)propan-1-one A solution of $BCl_3$ in DCM (1M, 8.2 mL) and (R)-3-(2-(benzyloxy)propoxy)-1-(4-(5-(trifluoromethyl)pyrimidin-2-yl)piperazin-1-yl)propan-1-one (1.23 g, 2.718 mmol, 1 equiv) in DCM (10 mL, 157.300 mmol, 57.87 equiv) was stirred for 3 h at −10° C. The reaction was quenched with MeOH (20 mL). After concentration under reduced pressure, the residue was purified by C18 reverse phase chromatography eluting with $H_2O/CH_3CN$ to afford 370 mg (37.6%) of title compound as a white solid. LCMS: $[M+H]^+$ 363.18.

Step 3: (S)-2-(4-Methoxybenzyl)-5-((1-(3-oxo-3-(4-(5-(trifluoromethyl)pyrimidin-2-yl)piperazin-1-yl)propoxy)propan-2-yl)thio)-4-(trifluoromethyl)pyridazin-3(2H)-one A solution of (R)-3-(2-hydroxypropoxy)-1-(4-(5-(trifluoromethyl)pyrimidin-2-yl)piperazin-1-yl)propan-1-one (225 mg, 0.621 mmol, 1 equiv), Int-A29 (294 mg, 0.929 mmol, 1.50 equiv), dibenzyl (E)-diazene-1,2-dicarboxylate (1.07 g, 4.647 mmol, 20%), and triphenylphosphine (244 mg, 0.930 mmol, 1.50 equiv) in THF (1 mL) and toluene (5 mL) was stirred for 12 h at RT. After concentration under reduced pressure, the residue was purified by C18 reverse phase chromatography eluting with $H_2O/CH_3CN$ to afford 300 mg (73.1%) of title compound as a white solid. LCMS: $[M+H]^+$ 661.22.

Step 4: (S)-5-((1-(3-Oxo-3-(4-(5-(trifluoromethyl)pyrimidin-2-yl)piperazin-1-yl)propoxy)propan-2-yl)thio)-4-(trifluoromethyl)pyridazin-3(2H)-one A solution of (S)-2-(4-methoxybenzyl)-5-((1-(3-oxo-3-(4-(5-(trifluoromethyl)pyrimidin-2-yl)piperazin-1-yl)propoxy)propan-2-yl)thio)-4-(trifluoromethyl)pyridazin-3(2H)-one (530 mg, 0.802 mmol, 1 equiv), and TfOH (1 mL) in TFA (10 mL) was stirred for 1 h at 0° C. The resulting solution was extracted with EtOAc (3×30 mL) and the organic layers combined and concentrated under reduced pressure. The residue was purified by C18 reverse phase chromatography eluting with $H_2O/CH_3CN$ followed by further purified by Prep-HPLC (YMC-Actus Triart C18 column) using a water/MeCN to afford the title compound (24.7 mg, 5.7%) as a white solid. LCMS: $[M+H]^+$ 541.16, $^1H$ NMR (300 MHz, Methanol-$d_4$) δ 8.60 (s, 2H), 8.16 (s, 1H), 4.12-4.06 (m, 1H), 4.03-3.91 (m, 4H), 3.88-3.62 (m, 7H), 3.57-3.51 (m, 1H), 2.70-2.66 (m, 2H), 1.41 (d, J=6.9 Hz, 3H).

Example 619 Isomer A: 5-(((S)-1-(3-((S)-2-Methyl-4-(5-(trifluoromethyl)pyrimidin-2-yl)piperazin-1-yl)-3-oxopropoxy)propan-2-yl)amino)-4-(trifluoromethyl)pyridazin-3(2H)-one and Example 619 Isomer B: 5-(((S)-1-(3-((R)-2-Methyl-4-(5-(trifluoromethyl)pyrimidin-2-yl)piperazin-1-yl)-3-oxopropoxy)propan-2-yl)amino)-4-(trifluoromethyl)pyridazin-3(2H)-one and Example 619

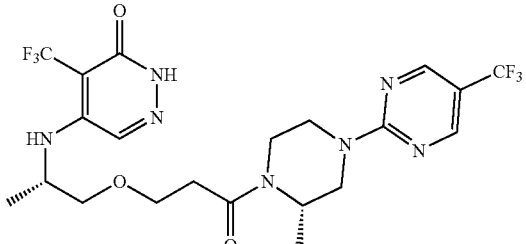

Isomer A

Example 619

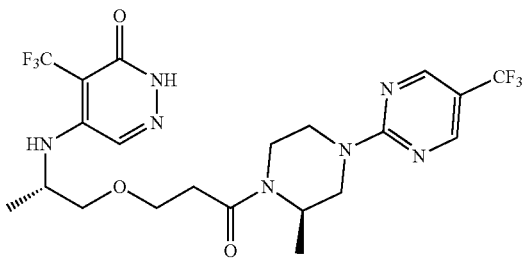

Isomer B

Step 1: Tert-butyl 2-methyl-4-(5-(trifluoromethyl)pyrimidin-2-yl)piperazine-1-carboxylate A solution of tert-butyl 2-methylpiperazine-1-carboxylate (1.5 g, 7.49 mmol, 1 equiv), 2-chloro-5-(trifluoromethyl)pyrimidine (1.37 g, 7.50 mmol, 1.00 equiv), and $K_2CO_3$ (2.07 g, 15.0 mmol, 2.00 equiv) in NMP (20 mL) was stirred for 16 h at 85° C. The reaction mixture was cooled to RT, followed by addition of water. The resulting solids were precipitated and collected by filtration, and then washed with water and drying under vacuum to afford 2.5 g of title compound as a light yellow solid. LCMS: $[M+H]^+$ 347.

Step 2: 2-(3-Methylpiperazin-1-yl)-5-(trifluoromethyl)pyrimidine

A solution of tert-butyl 2-methyl-4-(5-(trifluoromethyl)pyrimidin-2-yl)piperazine-1-carboxylate (3.34 g, 1 equiv) and HCl in 1,4-dioxane (30 mL) was stirred for 1 h at RT. After concentration under reduced pressure, the residue was purified by C18 reverse phase chromatography eluting with $H_2O/CH_3CN$ to afford 687 mg (31.8%) of title compound as an orange solid. LCMS: $[M+H]^+$ 247.

Step 3: 5-(((S)-1-(3-((S)-2-Methyl-4-(5-(trifluoromethyl)pyrimidin-2-yl)piperazin-1-yl)-3-oxopropoxy)propan-2-yl)amino)-4-(trifluoromethyl)pyridazin-3(2H)-one and 5-(((S)-1-(3-((R)-2-methyl-4-(5-(trifluoromethyl)pyrimidin-2-yl)piperazin-1-yl)-3-oxopropoxy)propan-2-yl)amino)-4-(trifluoromethyl)pyridazin-3(2H)-one A solution of Int-A13 (200.4 mg, 0.648 mmol, 1 equiv), 2-(3-methylpiperazin-1-yl)-5-(trifluoromethyl)pyrimidine (280 mg, 1.14 mmol, 1.20 equiv), DIPEA (250 mg, 1.944 mmol, 3.00 equiv), and HATU (295 mg, 1.001 mmol, 1.20 equiv) in DMF was stirred for 1 h at RT. After concentration under reduced pressure, the residue was purified by C18 reverse phase chromatography eluting with $H_2O/CH_3CN$, followed by chiral chromatography purification (CHIRAL-PAK IA-3, 5 μm, 2×25 cm column, eluting with a gradient of Hexanes (0.1% DEA):EtOH gradient, at a flow rate of 20 mL/min) yielding the title compounds as white solids and with the stereochemistry arbitrarily assigned.

Example 619 Isomer A 29.4 mg, 8.4%; LCMS: $[M+H]^+$ 538.29, $^1$H NMR (300 MHz, DMSO-$d_6$) δ 12.45 (s, 1H), 8.70 (d, J=0.9 Hz, 2H), 7.90 (s, 1H), 6.27 (s, 1H), 4.8-4.5 (m, 3H), 4.4-4.1 (m, 2H), 3.9-3.8 (m, 1H), 3.80-3.6 (m, 2H), 3.35 (s, 2H), 3.36-3.00 (d, J=5.7 Hz, 2H), 2.9-2.7 (m, 1H), 2.8-2.6 (m, 2H), 1.2 (s, 3H), 1.1-0.97 (d, J=6.8 Hz, 3H).

Example 619 Isomer B 26.7 mg, 7.7%; LCMS: $[M+H]^+$ 538.29, $^1$H NMR (300 MHz, DMSO-$d_6$) δ 12.45 (s, 1H), 8.70 (d, J=0.9 Hz, 2H), 7.90 (s, 1H), 6.27 (s, 1H), 4.80-4.50 (m, 3H), 4.50-4.00 (m, 2H), 3.9-3.8 (m, 1H), 3.80-3.60 (m, 2H), 3.55 (s, 2H), 3.30-3.10 (m, 2H), 3.10-2.90 (m, 1H), 2.80-2.60 (m, J=6.4 Hz, 2H), 1.20 (s, 3H), 1.1-0.97 (d, J=6.8 Hz, 3H).

Example 620: (S)-4-(Trifluoromethyl)-5-((1-(2-((4-(5-(trifluoromethyl)pyrimidin-2-yl)piperazin-1-yl)sulfonyl)ethoxy)propan-2-yl)amino)pyridazin-3(2H)-one

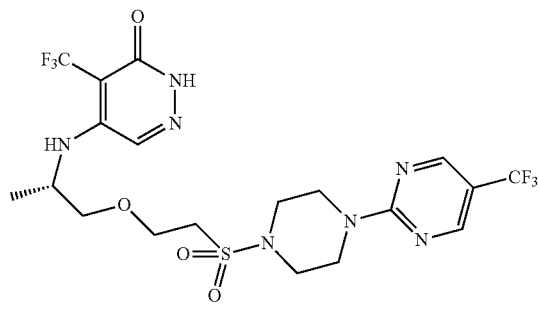 [SMILES: C[C@@H](COCCS(=O)(=O)N1CCN(c2ncc(C(F)(F)F)cn2)CC1)Nc1cn[nH]c(=O)c1C(F)(F)F]

Step 1: (S)-5-((1-Hydroxypropan-2-yl)amino)-2-(4-methoxybenzyl)-4-(trifluoromethyl)pyridazin-3(2H)-one A solution of Int-A20 (300 mg, 0.94 mmol, 1 equiv), (S)-2-aminopropan-1-ol (77.8 mg, 1.04 mmol, 1.10 equiv) and TEA (286 mg, 2.82 mmol, 3.00 equiv) in EtOH (5 mL) was stirred for 2 h at 60° C. The resulting solution was diluted with water and extracted with EtOAc. The organic layers were combined, dried over anhydrous magnesium sulfate, and filtered. The filtrate was concentrated under reduced pressure to afford 350 mg of title compound as a crude colorless oil. LCMS: $[M+H]^+$ 358.13.

Step 2: (S)-2-(4-Methoxybenzyl)-4-(trifluoromethyl)-5-((1-(2-((4-(5-(trifluoromethyl)pyrimidin-2-yl)piperazin-1-yl)sulfonyl)ethoxy)propan-2-yl)amino)pyridazin-3(2H)-one A solution of (S)-5-((1-hydroxypropan-2-yl)amino)-2-(4-methoxybenzyl)-4-(trifluoromethyl)pyridazin-3(2H)-one (200 mg, 0.56 mmol, 1 equiv), Int-A26 (180.4 mg, 0.56 mmol, 1.00 equiv), and $Cs_2CO_3$ (359.3 mg, 1.10 mmol, 1.97 equiv) in MeCN (4 mL) was stirred for 16 h at RT. The solids were filtered and the resulting mixture was concentrated under reduced pressure to afford a residue which was eluted onto a silica gel column with EtOAc/petroleum ether (1:1) to afford 120 mg (31.6%) of the title compound as a light yellow oil. LCMS: $[M+H]^+$ 680.20.

Step 3: (S)-4-(Trifluoromethyl)-5-((1-(2-((4-(5-(trifluoromethyl)pyrimidin-2-yl)piperazin-1-yl)sulfonyl)ethoxy)propan-2-yl)amino)pyridazin-3(2H)-one A solution of (S)-2-(4-methoxybenzyl)-4-(trifluoromethyl)-5-((1-(2-((4-(5-(trifluoromethyl)pyrimidin-2-yl)piperazin-1-yl)sulfonyl)ethoxy)propan-2-yl)amino)pyridazin-3(2H)-one (110 mg, 0.162 mmol, 1 equiv) and TfOH (0.4 mL) in TFA (4 mL) was stirred for 1 h at RT. After concentration under reduced pressure, the residue was purified by C18 reverse phase chromatography eluting with $H_2O/CH_3CN$ to afford 19.1 mg (21.1%) of the title compound as a white solid. LCMS: $[M+H]^+$ 560.14. $^1$H NMR (400 MHz, DMSO-$d_6$) δ 12.46 (s, 1H), 8.74 (s, 2H), 7.90 (s, 1H), 6.27 (dd, J=8.6, 4.2 Hz, 1H), 4.14 (s, 1H), 3.92 (t, J=5.1 Hz, 4H), 3.78 (t, J=6.0 Hz, 2H), 3.53 (m, 2H), 3.35 (d, J=5.9 Hz, 2H), 3.25 (t, J=5.1 Hz, 4H), 1.13 (d, J=6.5 Hz, 3H).

Example 621 Isomer A: (S)-5-((1-((3-Oxo-3-(4-(5-(trifluoromethyl)pyrimidin-2-yl)piperazin-1-yl)propyl)thio)propan-2-yl)oxy)-4-(trifluoromethyl)pyridazin-3(2H)-one and Example 621 Isomer B: (R)-5-((1-((3-Oxo-3-(4-(5-(trifluoromethyl)pyrimidin-2-yl)piperazin-1-yl)propyl)thio)propan-2-yl)oxy)-4-(trifluoromethyl)pyridazin-3(2H)-one Example 621

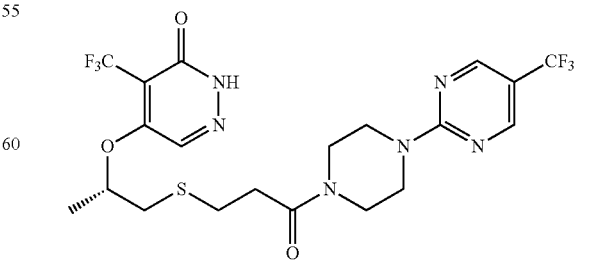

Isomer A

Example 621

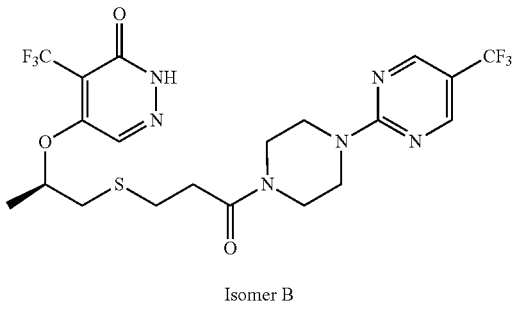

Isomer B

Step 1: Methyl 3-((2-oxopropyl)thio)propanoate

A solution of 3-mercaptopropanoate (2 g, 16.6 mmol, 1 equiv), 1-bromopropan-2-one (2.28 g, 16.6 mmol, 1.00 equiv), and TEA (2.53 g, 25.0 mmol, 1.5 equiv) in DCM (20 mL) was stirred for 30 min at RT. The reaction was then quenched by the addition of 50 mL of water and the resulting solution was extracted with 3×50 mL of DCM, the organic layers dried over anhydrous sodium sulfate, and concentrated under reduced pressure to afford the title compound 2.9 g (98.9%) as a colorless oil.

Step 2: Methyl 3-((2-hydroxypropyl)thio)propanoate

A solution of methyl 3-((2-oxopropyl)thio)propanoate (2.9 g, 16.5 mmol, 1 equiv) and $NaBH_4$ (934 mg, 24.7 mmol, 1.5 equiv) in MeOH (50 mL) was stirred for 30 min at RT. The reaction was then quenched by the addition of 50 mL of water. The resulting solution was extracted with 3×50 mL of EtOAc, dried over anhydrous sodium sulfate, and concentrated under reduced pressure to afford the title compound (2.67 g, 91.0%) as a colorless oil.

Step 3: Methyl 3-((2-((1-(4-methoxybenzyl)-6-oxo-5-(trifluoromethyl)-1,6-dihydropyridazin-4-yl)oxy)propyl)thio)propanoate A solution of Int-A20 (804.5 mg, 2.53 mmol, 0.9 equiv), methyl 3-((2-hydroxypropyl)thio)propanoate (500 mg, 2.805 mmol, 1.0 equiv), and sodium metal (168.3 mg, 4.21 mmol, 1.5 equiv) in THF (5 mL) was stirred for 6 h at RT. The reaction mixture was poured into 20 mL HCl (1 M) and the resulting solution was extracted with 3×50 mL of EtOAc, the combined organic layers were dried over anhydrous sodium sulfate, and concentrated under reduced pressure. The residue was applied onto a silica gel column with EtOAc/petroleum ether (1:1) to afford 850 mg of title compound as a white solid. LCMS: $[M+H]^+$ 461.31.

Step 4: 3-((2-((1-(4-Methoxybenzyl)-6-oxo-5-(trifluoromethyl)-1,6-dihydropyridazin-4-yl)oxy)propyl)thio)propanoic Acid A solution of methyl 3-((2-((1-(4-methoxybenzyl)-6-oxo-5-(trifluoromethyl)-1,6-dihydropyridazin-4-yl)oxy)propyl)thio)propanoate (850 mg, 1.85 mmol, 1 equiv), lithium hydroxide (309 mg, 7.36 mmol, 3.99 equiv), and $H_2O$ (4 mL) in THF (12 mL) was stirred for 2 h at RT. The reaction mixture was diluted with $H_2O$ and extracted with DCM. The pH value of the water layer was adjusted to 5 with HCl, followed by extraction with 3×30 mL of EtOAc. The organic layers were combined, dried over anhydrous sodium sulfate, and concentrated under reduced pressure to afford 150 mg (18.2%) of the title compound as a yellow oil. LCMS: $[M+H]^+$ 447.11.

Step 5: 2-(4-Methoxybenzyl)-5-((1-((3-oxo-3-(4-(5-(trifluoromethyl)pyrimidin-2-yl)piperazin-1-yl)propyl)thio)propan-2-yl)oxy)-4-(trifluoromethyl)pyridazin-3(2H)-one A solution of 3-[[2-([1-[(4-methoxyphenyl)methyl]-6-oxo-5-(trifluoromethyl)-1,6-dihydropyridazin-4-yl]oxy)propyl]sulfanyl]propanoic acid (200 mg, 0.448 mmol, 1.0 equiv), Int-A2 (114.4 mg, 0.492 mmol, 1.1 equiv), DIPEA (202.5 mg, 1.57 mmol, 3.5 equiv), and HATU (204.5 mg, 0.538 mmol, 1.2 equiv) in DMF (3 mL) was stirred for 2 h at RT. The reaction was then quenched by the addition of 30 mL of water and the resulting solution was extracted with 3×30 mL of EtOAc, organic layers dried over anhydrous sodium sulfate, and concentrated under reduced pressure. The residue was eluted onto a silica gel column with EtOAc/petroleum ether (2:1) to afford 230 mg of title compound as a yellow oil. LCMS: $[M+H]^+$ 661.20.

Step 6: (S)-5-((1-((3-Oxo-3-(4-(5-(trifluoromethyl)pyrimidin-2-yl)piperazin-1-yl)propyl)thio)propan-2-yl)oxy)-4-(trifluoromethyl)pyridazin-3(2H)-one and (R)-5-((1-((3-oxo-3-(4-(5-(trifluoromethyl)pyrimidin-2-yl)piperazin-1-yl)propyl)thio)propan-2-yl)oxy)-4-(trifluoromethyl)pyridazin-3(2H)-one A solution of 2-(4-methoxybenzyl)-5-((1-((3-oxo-3-(4-(5-(trifluoromethyl)pyrimidin-2-yl)piperazin-1-yl)propyl)thio)propan-2-yl)oxy)-4-(trifluoromethyl)pyridazin-3 (2H)-one (210 mg, 0.318 mmol, 1.0 equiv), and TfOH (381.6 mg, 2.54 mmol, 8.00 equiv) in TFA (3 mL) was stirred for 30 min at RT. The resulting mixture was concentrated under reduced pressure. The reaction mixture was then quenched by the addition of 20 mL of $NH_3$ (7 M in MeOH). After concentration under reduced pressure, the residue was purified by C18 reverse phase chromatography eluting with $H_2O$/$CH_3CN$ and then separated by chiral HPLC (CHIRALPAK IC, 5 μm, 2×25 cm column, eluting with a gradient of Hexanes (0.1% formic acid):EtOH gradient, at a flow rate of 20 mL/min) yielding the title compounds as white solids. The absolute stereochemistry was assigned based on a protein X-ray crystal structure obtained of Example 513A, which confirmed (S)-absolute stereochemistry of the more potent enantiomer.

Example 621 Isomer A 8.6 mg, 10.0%, LCMS: $[M+H]^+$ 541.14, $^1H$ NMR (300 MHz, DMSO-$d_6$) δ 13.29 (s, 1H), 8.74 (d, J=0.9 Hz, 2H), 8.34 (s, 1H), 5.14 (q, J=6.0 Hz, 1H), 3.83 (dd, J=17.2, 5.7 Hz, 4H), 3.57 (dd, J=6.6, 4.0 Hz, 4H), 2.95-2.62 (m, 6H), 1.38 (d, J=6.0 Hz, 3H).

Example 621 Isomer B 8.9 mg, 10.4%, LCMS: $[M+H]^+$ 541.14, $^1H$ NMR (300 MHz, DMSO-$d_6$) δ 13.29 (s, 1H), 8.74 (d, J=0.9 Hz, 2H), 8.34 (s, 1H), 5.14 (q, J=6.0 Hz, 1H), 3.83 (dd, J=17.5, 5.7 Hz, 4H), 3.57 (dd, J=6.6, 3.9 Hz, 4H), 3.04-2.60 (m, 6H), 1.38 (d, J=6.0 Hz, 3H).

Example 622: (S)-5-((1-(3-Oxo-3-(4-(5-(trifluoromethyl)thiazol-2-yl)piperazin-1-yl)propoxy)propan-2-yl)amino)-4-(trifluoromethyl)pyridazin-3(2H)-one Example 623: (S)-5-((1-(3-(4-(5-(Tert-butyl)pyrimidin-2-yl)piperazin-1-yl)-3-oxopropoxy)propan-2-yl)amino)-4-(trifluoromethyl)pyridazin-3(2H)-one

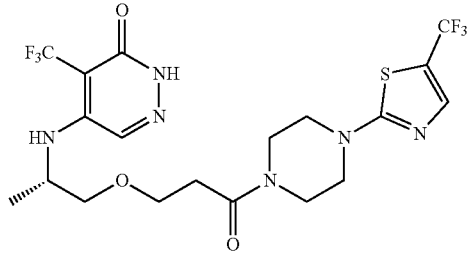 [SMILES: C[C@@H](COCCC(=O)N1CCN(c2ncc(C(F)(F)F)s2)CC1)Nc1cn[nH]c(=O)c1C(F)(F)F]

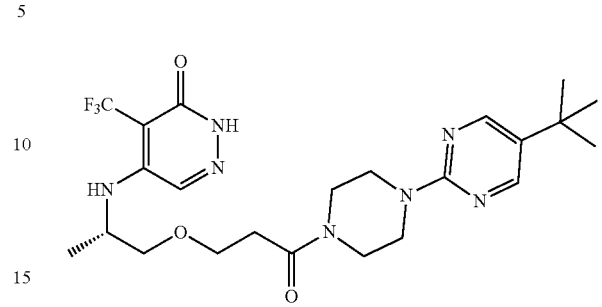

Step 1: (S)-2-(4-Methoxybenzyl)-5-((1-(3-oxo-3-(4-(5-(trifluoromethyl)thiazol-2-yl)piperazin-1-yl)propoxy)propan-2-yl)amino)-4-(trifluoromethyl)pyridazin-3(2H)-one A solution of (S)-3-(2-((1-(4-methoxybenzyl)-6-oxo-5-(trifluoromethyl)-1,6-dihydropyridazin-4-yl)amino)propoxy)propanoic acid (200 mg, 0.466 mmol, 1 equiv), Int-A27 (140 mg, 0.590 mmol, 1.27 equiv), DIPEA (181 mg, 1.400 mmol, 3.01 equiv), and HATU (266 mg, 0.700 mmol, 1.50 equiv) in DMF (2 mL) was stirred for 1 h at RT. The crude product was purified by reverse phase column chromatography to afford 256 mg (84.7%) of title compound as a yellow oil. LCMS: [M+H]$^+$ 648.20.

Step 2: (S)-5-((1-(3-oxo-3-(4-(5-(trifluoromethyl)thiazol-2-yl)piperazin-1-yl)propoxy)propan-2-yl)amino)-4-(trifluoromethyl)pyridazin-3(2H)-one A solution of (S)-2-(4-methoxybenzyl)-5-((1-(3-oxo-3-(4-(5-(trifluoromethyl)thiazol-2-yl)piperazin-1-yl)propoxy)propan-2-yl)amino)-4-(trifluoromethyl)pyridazin-3(2H)-one (240 mg, 0.370 mmol, 1 equiv), and TfOH (0.3 mL) in TFA (3 mL) was stirred for 1 h at RT. The reaction was then quenched by the addition of water and the pH value of the solution was adjusted to 8 with NaHCO$_3$(aq). The resulting solution was extracted with 3×30 mL of DCM dried over anhydrous sodium sulfate and concentrated under reduced pressure. The crude product was purified by reverse phase column chromatography and further purification by Prep-HPLC to afford the title compound (48.5 mg, 24.8%) as a white solid. LCMS: [M+H]$^+$ 529.14. $^1$HNMR (300 MHz, DMSO-d$_6$) δ 12.44 (s, 1H), 7.89 (s, 1H), 7.72 (d, J=1.5 Hz, 1H), 6.25 (dd, J=4.2, 3.9 Hz, 1H), 4.16-4.08 (m, 1H), 3.69-3.66 (m, 2H), 3.66-3.57 (m, 4H), 3.56-3.45 (m, 6H), 2.57 (d, J=6.4 Hz, 2H), 1.12 (d, J=6.0 Hz, 3H).

Step 1: 2-(Tert-butyl)malonaldehyde

A solution of 2-(tert-butyl)malononitrile (3.66 g, 30.0 mmol, 1 equiv) and diisobutylaluminum hydride (60 mL, 90 mmol, 1.5 M) in toluene (70 mL) was stirred for 1 h at −60° C. The resulting solution was stirred for additional 3 h at RT. The reaction was then quenched by the addition of 1M HCl and the pH value of the solution was adjusted to 5 with HCl. The resulting solution was extracted with EtOAc and the organic layers combined and concentrated under reduced pressure to afford 2 g (52.1%) of the title compound as a white oil. LCMS: [M+H]$^+$ 129.10.

Step 2: 5-(Tert-butyl)pyrimidin-2(1H)-one

A solution of urea (1,124.5 mg, 18.7 mmol, 1.2 equiv) and HCl (4 mL, 47 mmol, 3 equiv) in EtOH (40 mL) was stirred for 10 min at RT followed by addition of 2-(tert-butyl)malonaldehyde (2 g, 15.6 mmol, 1 equiv). The reaction mixture was stirred for 16 h at 75° C. The resulting mixture was concentrated under reduced pressure to afford 3.5 g of the title compound as a crude white solid. LCMS: [M+H]$^+$ 153.11.

Step 3: 5-(Tert-butyl)-2-chloropyrimidine

A solution of 5-(tert-butyl)pyrimidin-2(1H)-one (3.5 g, 23.0 mmol, 1 equiv) and phosphoryl trichloride (40 mL) was stirred for 5 h at 160° C. The resulting mixture was concentrated under reduced pressure, quenched by the addition of water, and the pH value of the solution was adjusted to 8 with aqueous NaOH (1M). The resulting solution was extracted with DCM and the organic layers combined and concentrated under reduced pressure to afford 2 g (51.0%) of the title compound as a dark brown solid. LCMS: [M+H]$^+$ 171.08.

Step 4: Tert-butyl 4-(5-(tert-butyl)pyrimidin-2-yl)piperazine-1-carboxylate

A solution of 5-(tert-butyl)-2-chloropyrimidine (2 g, 11.7 mmol, 1 equiv), tert-butyl piperazine-1-carboxylate (4366.0 mg, 23.4 mmol, 2 equiv), and K$_2$CO$_3$ (4049.6 mg, 29.3 mmol, 2.5 equiv) in NMP (30 mL) was stirred for 3 h at 80° C. The resulting solution was extracted with EtOAc and the organic layers combined and concentrated under reduced pressure. The residue was applied onto a silica gel column with EtOAc/petroleum ether (1:10) to afford 1.1 g (29.3%) of title compound as a solid. LCMS: [M+H]$^+$ 321.24.

Step 5: 5-(Tert-butyl)-2-(piperazin-1-yl)pyrimidine

A solution of tert-butyl 4-(5-(tert-butyl)pyrimidin-2-yl)piperazine-1-carboxylate (1.1 g, 3.43 mmol, 1 equiv) in HCl (gas) in 1,4-dioxane (20 mL) was stirred for 1 h at RT. The resulting mixture was concentrated under reduced pressure and the residue was dissolved in 10 mL of water. The pH value of the solution was adjusted to 7 with aqueous NaOH (1 mol/L). After concentration under reduced pressure, the residue was purified by C18 reverse phase chromatography eluting with H$_2$O/CH$_3$CN to afford 170 mg (22.5%) of title compound as a yellow solid. LCMS: [M+H]$^+$ 221.19.

Step 6: (S)-5-((1-(3-(4-(5-(Tert-butyl)pyrimidin-2-yl)piperazin-1-yl)-3-oxopropoxy)propan-2-yl)amino)-2-(4-methoxybenzyl)-4-(trifluoromethyl)pyridazin-3(2H)-one A solution of 5-(tert-butyl)-2-(piperazin-1-yl)pyrimidine (80 mg, 0.363 mmol, 1 equiv), (S)-3-(2-((1-(4-methoxybenzyl)-6-oxo-5-(trifluoromethyl)-1,6-dihydropyridazin-4-yl)amino)propoxy)propanoic acid (187.10 mg, 0.436 mmol, 1.2 equiv), HATU (165.68 mg, 0.436 mmol, 1.2 equiv), and DIPEA (140.79 mg, 1.089 mmol, 3 equiv) in DMF (4 mL) was stirred for 1 h at RT. The resulting solution was extracted with EtOAc and the organic layers combined. After concentration, the residue was purified by C18 reverse phase chromatography eluting with H$_2$O/CH$_3$CN to afford 210 mg (91.6%) of the title compound as a yellow oil. LCMS: [M+H]$^+$ 632.33.

Step 7: (S)-5-((1-(3-(4-(5-(Tert-butyl)pyrimidin-2-yl)piperazin-1-yl)-3-oxopropoxy)propan-2-yl)amino)-4-(trifluoromethyl)pyridazin-3(2H)-one A solution of (S)-5-((1-(3-(4-(5-(tert-butyl)pyrimidin-2-yl)piperazin-1-yl)-3-oxopropoxy)propan-2-yl)amino)-2-(4-methoxybenzyl)-4-(trifluoromethyl)pyridazin-3 (2H)-one (200 mg, 0.317 mmol, 1 equiv) and TfOH (1 mL) in TFA (10 mL) was stirred for 1 h at RT. The resulting solution was extracted with EtOAc (3×30 mL) and the organic layers combined. After concentration, the residue was purified by C18 reverse phase chromatography eluting with H$_2$O/CH$_3$CN and then the crude product was further purified by Prep-HPLC (YMC-Actus Triart C18, 5 μm, 20×250 mm column, eluting with a gradient of water (10 mmol/L NH$_4$HCO$_3$)/ACN, at a flow rate of 60 mL/min) to afford the title compound as a white solid (73.5 mg, 45.4%). LCMS: [M+H]$^+$ 512.27, $^1$H NMR (300 MHz, DMSO-d$_6$) δ 12.46 (s, 1H), 8.43 (s, 2H), 7.91 (s, 1H), 6.28 (dd, J=8.6, 4.3 Hz, 1H), 4.14 (s, 1H), 3.68-3.64 (m, 6H), 3.49-3.47 (m, 6H), 2.60-2.56 (m, 2H), 1.26 (s, 9H), 1.14 (d, J=6.5 Hz, 3H).

Example 624: (S)-5-((1-Methoxy-3-(2-((4-(5-(trifluoromethyl)pyrimidin-2-yl)piperazin-1-yl)sulfonyl)ethoxy)propan-2-yl)amino)-4-(trifluoromethyl)pyridazin-3(2H)-one

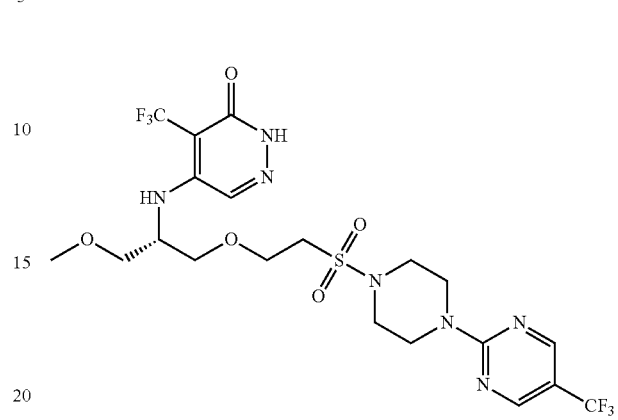

Step 1: (R)-5-((1-Hydroxy-3-methoxypropan-2-yl)amino)-4-(trifluoromethyl)-2-((2-(trimethylsilyl)ethoxy)methyl)pyridazin-3(2H)-one A solution of (R)-2-amino-3-methoxypropan-1-ol hydrochloride (300.0 mg, 2.12 mmol, 1.00 equiv), Int-A6 (696.6 mg, 2.12 mmol, 1.00 equiv), and TEA (643.2 mg, 6.36 mmol, 3.00 equiv) in EtOH (10.0 mL) was stirred for 1 h at 60° C. After concentration under reduced pressure, the residue was purified by C18 reverse phase chromatography eluting with H$_2$O/CH$_3$CN to afford 460 mg (54.6%) of title compound as a yellow oil. LCMS [M+H]+ 398.18.

Step 2: (S)-5-((1-Methoxy-3-(2-((4-(5-(trifluoromethyl)pyrimidin-2-yl)piperazin-1-yl)sulfonyl)ethoxy)propan-2-yl)amino)-4-(trifluoromethyl)-2-((2-(trimethylsilyl)ethoxy)methyl)pyridazin-3(2H)-one A solution of Cs$_2$CO$_3$ (288.6 mg, 0.886 mmol, 0.80 equiv), (R)-5-((1-hydroxy-3-methoxypropan-2-yl)amino)-4-(trifluoromethyl)-2-((2-(trimethylsilyl)ethoxy)methyl)pyridazin-3(2H)-one (440.0 mg, 1.107 mmol, 1.00 equiv) and Int-A26 (356.8 mg, 1.107 mmol, 1.00 equiv) in CH$_3$CN (10.00 mL) was stirred for 5 h at RT. The solid were filtered and filtrate concentrated under reduced pressure to afford a residue which was purified by C18 reverse phase chromatography eluting with H$_2$O/CH$_3$CN to yield 450 mg (56.5%) of title compound as a yellow oil. LCMS [M+H]+ 720.26.

Step 3: (S)-5-((1-Methoxy-3-(2-((4-(5-(trifluoromethyl)pyrimidin-2-yl)piperazin-1-yl)sulfonyl)ethoxy)propan-2-yl)amino)-4-(trifluoromethyl)pyridazin-3 (2H)-one A solution of (S)-5-((1-methoxy-3-(2-((4-(5-(trifluoromethyl)pyrimidin-2-yl)piperazin-1-yl)sulfonyl)ethoxy)propan-2-yl)amino)-4-(trifluoromethyl)-2-((2-(trimethylsilyl)ethoxy)methyl)pyridazin-3(2H)-one (430.0 mg, 0.597 mmol, 1.00 equiv) and TFA (2.0 mL) in DCM (10.0 mL) was stirred for 1 h at RT. The resulting mixture was concentrated under reduced pressure and the pH value of the solution was adjusted to 7 with aqueous NaOH (1 mol/L). After concentration under reduced pressure, the residue was purified by C18 reverse phase chromatography eluting with H$_2$O/

CH₃CN and further purified by Prep-HPLC (Xselect CSH F-Phenyl OBD, 5 μm, 19×150 mm column, eluting with a gradient of water (10 mmol/L NH₄HCO₃)/ACN, at a flow rate of 25 mL/min) to afford the title compound (193.8 mg, 55.0%) as a white solid. LCMS [M+H]+ 590.17, ¹H NMR (300 MHz, DMSO-d₆) δ 12.50 (s, 1H), 8.74 (s, 2H), 7.92 (s, 1H), 6.24 (dd, J=8.9, 4.4 Hz, 1H), 4.28 (dd, J=3.6, 3.0 Hz, 1H), 3.93-3.90 (m, 4H), 3.80-3.76 (m, 2H), 3.59 (d, J=5.7, 2H), 3.44 (dd, J=6.3, 5.4 Hz, 2H), 3.40-3.34 (m, 5H). 3.27-3.26 (m, 4H).

Example 625: (S)-4-(Trifluoromethyl)-5-((1-(2-((4-(5-(trifluoromethyl)thiazol-2-yl)piperazin-1-yl)sulfonyl)ethoxy)propan-2-yl)oxy)pyridazin-3(2H)-one

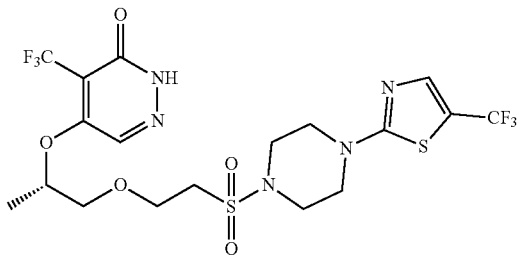 [SMILES: C[C@@H](COCCS(=O)(=O)N1CCN(c2ncc(C(F)(F)F)s2)CC1)Oc1cn[nH]c(=O)c1C(F)(F)F]

Step 1: (S)-2-(4-((2-(2-(Benzyloxy)propoxy)ethyl)sulfonyl)piperazin-1-yl)-5-(trifluoromethyl)thiazole A solution of Int A-28 (1.10 g, 3.36 mmol, 1.00 equiv), (S)-2-(benzyloxy)propan-1-ol (0.56 g, 3.36 mmol, 1.00 equiv), and Cs₂CO₃ (2.19 g, 6.72 mmol, 2.00 equiv) in CH₃CN (10.0 mL) was stirred for 2 h at RT. The solids were filtered and the resulting solution was concentrated under reduced pressure and the resulting residue was purified by silica gel column chromatography with EtOAc/petroleum ether (27/73) to afford 1.5 g (85.0%) of the title compound as a yellow oil. LCMS [M+H]+ 494.13.

Step 2. (S)-1-(2-((4-(5-(Trifluoromethyl)thiazol-2-yl)piperazin-1-yl)sulfonyl)ethoxy)propan-2-ol A solution of (S)-2-(4-((2-(2-(benzyloxy)propoxy)ethyl)sulfonyl)piperazin-1-yl)-5-(trifluoromethyl)thiazole (300.0 mg, 0.405 mmol, 1.00 equiv), and BCl₃ (0.50 mL, 1 M, 1.00 equiv) in DCM (5.00 mL) was stirred for 1 h at 0° C. in a water/ice bath. The pH value of the solution was adjusted to 7 with NaOH/H₂O and then the resulting solution was extracted with 3×20 mL of DCM. The organic layer was combined and concentrated under reduced pressure to afford 200 mg (97.9%) of title compound as a yellow solid. LCMS [M+H]+ 404.08.

Step 3: (S)-2-(4-Methoxybenzyl)-4-(trifluoromethyl)-5-((1-(2-((4-(5-(trifluoromethyl)thiazol-2-yl)piperazin-1-yl)sulfonyl)ethoxy)propan-2-yl)oxy)pyridazin-3(2H)-one A solution of (S)-1-(2-((4-(5-(trifluoromethyl)thiazol-2-yl)piperazin-1-yl)sulfonyl)ethoxy)propan-2-ol (140.0 mg, 0.347 mmol, 1.00 equiv), Int-A20 (110.6 mg, 0.347 mmol, 1.00 equiv), and t-BuONa (6.67 mg, 0.069 mmol, 0.20 equiv) in DCM (5.0 mL) was stirred for 4 h at 0° C. in a water/ice bath. The reaction was then quenched by the addition of water and the resulting solution was extracted with 3×30 mL of EtOAC. After concentration under reduced pressure, the residue was purified by C18 reverse phase chromatography eluting with H₂O/CH₃CN to afford 80 mg (31.3%) of title compound. LCMS [M+H]+ 686.15.

Step 4: (S)-4-(Trifluoromethyl)-5-((1-(2-((4-(5-(trifluoromethyl) thiazol-2-yl)piperazin-1-yl)sulfonyl)ethoxy)propan-2-yl)oxy)pyridazin-3(2H)-one A solution of (S)-2-(4-methoxybenzyl)-4-(trifluoromethyl)-5-((1-(2-((4-(5-(trifluoromethyl)thiazol-2-yl)piperazin-1-yl)sulfonyl)ethoxy)propan-2-yl)oxy)pyridazin-3(2H)-one (75.0 mg, 0.109 mmol, 1.00 equiv), and H₂SO₄ (0.75 mL) in TfOH (5.0 mL) was stirred for 30 min at 0° C. in a water/ice bath. The reaction mixture was then quenched by the addition of water and the pH value of the solution was adjusted to 8 with NaOH/H₂O. The resulting solution was extracted with 3×30 mL of EtOAc. After concentration, the residue was purified by C18 reverse phase chromatography eluting with H₂O/CH₃CN to afford 27.2 mg (41.8%) of title compound as a white solid. LCMS [M+H]+ 566.00. ¹H NMR (300 MHz, Methanol-d₄) δ 8.21 (s, 1H), 7.58 (q, J=1.4 Hz, 1H), 5.11 (td, J=6.8, 2.9 Hz, 1H), 3.96-3.77 (m, 2H), 3.76-3.57 (m, 6H), 3.39 (dd, J=6.3, 4.0 Hz, 4H), 3.32-3.21 (m, 2H), 1.34 (d, J=6.3 Hz, 3H).

Example 626: 5-(((2S)-1-(2-Hydroxy-3-(4-(5-(trifluoromethyl)pyrimidin-2-yl)piperazin-1-yl)propoxy)propan-2-yl)amino)-4-(trifluoromethyl)pyridazin-3(2H)-one

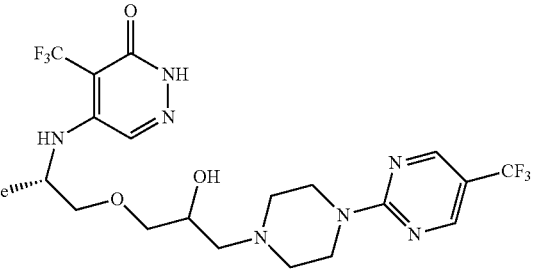

Step 1: Tert-butyl ((2S)-1-(oxiran-2-ylmethoxy)propan-2-yl)carbamate

A solution of 2-(chloromethyl)oxirane (0.52 g, 10.8 mmol, 1.00 equiv), tert-butyl (S)-(1-hydroxypropan-2-yl)carbamate (1 g, 0.011 mmol, 1.00 equiv), and NaH (274 mg, 13.0 mmol, 1.2 equiv) in DMF (5.00 mL) was stirred for 1 h at 0° C. in a water/ice bath. The reaction was quenched by the addition of water and the resulting solution was extracted with 3×30 mL of EtOAc and the organic layers combined and dried over anhydrous sodium sulfate and concentrated under reduced pressure to afford 900 mg (70%) of title compound as a yellow oil. LCMS [M+H]+ 232.25.

Step 2: Tert-butyl ((2S)-1-(2-hydroxy-3-(4-(5-(trifluoromethyl)pyrimidin-2-yl)piperazin-1-yl)propoxy)propan-2-yl)carbamate A solution of tert-butyl ((2S)-1-(oxiran-2-ylmethoxy)propan-2-yl)carbamate (860 mg, 3.70 mmol, 1.00 equiv), Int- A3 (860 mg, 3.70 mmol, 1.00 equiv), and DIPEA (1.99 g, 0.432 mmol, 5 equiv) in EtOH (10.0 mL) was stirred for 1 h at 60° C. in an oil bath. The resulting solution was applied onto a silica gel column eluting with EtOAc/petroleum ether (50:50) to afford 300 mg of title compound as a yellow oil. LCMS [M+H]+ 364.24.

Step 3: 1-((S)-2-Aminopropoxy)-3-(4-(5-(trifluoromethyl)pyrimidin-2-yl)piperazin-1-yl)propan-2-ol A solution of tert-butyl ((2S)-1-(2-hydroxy-3-(4-(5-(trifluoromethyl)pyrimidin-2-yl)piperazin-1-yl)propoxy)propan-2-yl)carbamate (300.0 mg, 0.647 mmol, 1.00 equiv) and HCl (gas) in 1,4-dioxane (2.00 mL) was stirred for 30 min at RT. The resulting mixture was concentrated under reduced pressure to afford 200 mg (90%) of title compound as a white solid. LCMS [M+H]+ 364.19.

Step 4: 5-(((2S)-1-(2-Hydroxy-3-(4-(5-(trifluoromethyl)pyrimidin-2-yl)piperazin-1-yl)propoxy)propan-2-yl)amino)-2-(4-methoxybenzyl)-4-(trifluoromethyl)pyridazin-3(2H)-one A solution of 1-((S)-2-aminopropoxy)-3-(4-(5-(trifluoromethyl)pyrimidin-2-yl)piperazin-1-yl)propan-2-ol (256 mg, 0.70 mmol, 1.5 equiv), Int-A20 (150 mg, 0.47 mmol, 1.00 equiv), TEA (95 mg, 0.94 mmol, 2 equiv), and EtOH (5 mL) was stirred for 1 h at 40° C. After concentration under reduced pressure of the reaction mixture, the residue was applied onto a silica gel column eluting with EtOAc/petroleum ether (95/5) to afford 200 mg (65.8%) of title compound as a white solid. LCMS [M+H]+ 646.25.

Step 5: 5-(((2S)-1-(2-Hydroxy-3-(4-(5-(trifluoromethyl)pyrimidin-2-yl)piperazin-1-yl)propoxy)propan-2-yl)amino)-4-(trifluoromethyl)pyridazin-3(2H)-one A solution of 5-(((2S)-1-(2-hydroxy-3-(4-(5-(trifluoromethyl)pyrimidin-2-yl)piperazin-1-yl)propoxy)propan-2-yl)amino)-2-(4-methoxybenzyl)-4-(trifluoromethyl)pyridazin-3 (2H)-one (190.0 mg, 0.294 mmol, 1.00 equiv) and $H_2SO_4$ (0.50 mL) in TfOH (5.00 mL) was stirred for 1 h at −10° C. The reaction mixture was quenched by the addition of water and was extracted with 3×20 mL of EtOAc. After concentration under reduced pressure, the residue was purified by C18 reverse phase chromatography eluting with $H_2O$/$CH_3CN$ to afford the title compound (29.3 mg, 19%) as a white solid. LCMS [M+H]+ 526.25. $^1$H NMR (300 MHz, DMSO-$d_6$) δ 12.44 (s, 1H), 8.68 (s, 2H), 7.93 (s, 1H), 6.30 (s, 1H), 4.60 (s, 1H), 4.17 (s, 1H), 3.77 (m, 6H), 3.5-3.26 (m, 4H), 2.42 (m, 3H), 2.29 (m, 2H), 1.15 (d, J=6.5 Hz, 3H).

Further example compounds of the invention prepared by the methods described herein are provided in Table E11.

TABLE E11

| Example No. | Structure | MS (M + H)+ |
|---|---|---|
| 627* | (S)-5-(1-(((3-(4-(5-Chloropyrimidin-2-yl)piperazin-1-yl)-3-oxopropyl)amino)methyl)isoindolin-2-yl)-4-(trifluoromethyl)pyridazin-3(2H)-one | 563.18 |
| 628* | (R)-5-(1-(((3-(4-(5-Chloropyrimidin-2-yl)piperazin-1-yl)-3-oxopropyl)amino)methyl)isoindolin-2-yl)-4-(trifluoromethyl)pyridazin-3(2H)-one | 563.18 |

TABLE E11-continued

| Example No. | Structure | MS (M + H)+ |
|---|---|---|
| 629* | (S)-5-(1-(((3-Oxo-3-(4-(5-(trifluoromethyl)pyridin-2-yl)piperazin-1-yl)propyl)amino)methyl)isoindolin-2-yl)-4-(trifluoromethyl)pyridazin-3(2H)-one | 596.21 |
| 630* | (R)-5-(1-(((3-Oxo-3-(4-(5-(trifluoromethyl)pyridin-2-yl)piperazin-1-yl)propyl)amino)methyl)isoindolin-2-yl)-4-(trifluoromethyl)pyridazin-3(2H)-one | 596.21 |
| 631 | (S)-4-Bromo-5-((1-(3-(4-(5-chloropyrimidin-2-yl)piperazin-1-yl)-3-oxopropoxy)propan-2-yl)oxy)pyridazin-3(2H)-one | 501.06 |
| 632 | 5-(((2R,3R)-3-Hydroxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 554.19 |

TABLE E11-continued

| Example No. | Structure | MS (M + H)+ |
|---|---|---|
| 633 | (S)-5-((1-(3-(4-(5-Chloropyridin-2-yl)piperazin-1-yl)-3-oxopropoxy)-3-hydroxypropan-2-yl)amino)-4-(trifluoromethyl)pyridazin-3(2H)-one | 505.15 |
| 634 | (S)-5-((1-(4-Oxo-4-(4-(5-(trifluoromethyl)pyrimidin-2-yl)piperazin-1-yl)butoxy)propan-2-yl)amino)-4-(trifluoromethyl)pyridazin-3(2H)-one | 538.19 |
| 635 | 5-(((2R,3S)-3-Hydroxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 554.19 |
| 636 | (S)-4-Chloro-5-(methyl(1-(3-oxo-3-(4-(5-(trifluoromethyl)pyrimidin-2-yl)piperazin-1-yl)propoxy)propan-2-yl)amino)pyridazin-3(2H)-one | 504.17 |

TABLE E11-continued

| Example No. | Structure | MS (M + H)+ |
|---|---|---|
| 637 | (S)-5-((1-(3-Oxo-3-(4-(5-(trifluoromethyl)pyrimidin-2-yl)piperazin-1-yl)propoxy)-3-(pyridin-3-yl)propan-2-yl)amino)-4-(trifluoromethyl)pyridazin-3(2H)-one | 601.20 |
| 638# | 6-(4-(2-((2R,5R)-5-(((6-Oxo-5-(trifluoromethyl)-1,6-dihydropyridazin-4-yl)oxy)methyl)pyrrolidin-2-yl)acetyl)piperazin-1-yl)nicotinonitrile | 492.19 |
| 639# | 6-(4-(2-((2S,5S)-5-(((6-Oxo-5-(trifluoromethyl)-1,6-dihydropyridazin-4-yl)oxy)methyl)pyrrolidin-2-yl)acetyl)piperazin-1-yl)nicotinonitrile | 492.19 |
| 640 | (S)-5-((4-(3-Oxo-3-(4-(5-(trifluoromethyl)pyrimidin-2-yl)piperazin-1-yl)propoxy)butan-2-yl)amino)-4-(trifluoromethyl)pyridazin-3(2H)-one | 538.19 |

TABLE E11-continued

| Example No. | Structure | MS (M + H)+ |
|---|---|---|
| 641 | (S)-5-(Methyl(1-(3-oxo-3-(4-(5-(trifluoromethyl)pyrimidin-2-yl)piperazin-1-yl)propoxy)propan-2-yl)amino)-4-(trifluoromethyl)pyridazin-3(2H)-one | 538.19 |
| 642 | 5-((5-(2-Oxo-2-(4-(5-(trifluoromethyl)pyrimidin-2-yl)piperazin-1-yl)ethyl)pyrrolidin-2-yl)methoxy)-4-(trifluoromethyl)pyridazin-3(2H)-one | 536.18 |
| 643 | (S)-5-((4-Hydroxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 554.19 |
| 644 | (S)-5-((1-(3-(4-(5-Chloropyrazin-2-yl)piperazin-1-yl)-3-oxopropoxy)propan-2-yl)amino)-4-(trifluoromethyl)pyridazin-3(2H)-one | 490.15 |

TABLE E11-continued

| Example No. | Structure | MS (M + H)+ |
|---|---|---|
| 645 | (S)-6-(4-(3-(Methyl(2-((6-oxo-5-(trifluoromethyl)-1,6-dihydropyridazin-4-yl)oxy)propyl)amino)propanoyl)piperazin-1-yl)nicotinonitrile | 494.20 |
| 646 | (S)-1'-(3-(2-((6-Oxo-5-(trifluoromethyl)-1,6-dihydropyridazin-4-yl)oxy)propoxy)propanoyl)-1',2',3',6'-tetrahydro-[2,4'-bipyridine]-5-carbonitrile | 478.16 |
| 647 | (S)-5-((1-(3-Oxo-3-(4-(5-(trifluoromethyl)pyrimidin-2-yl)piperazin-1-yl)propoxy)-3-(pyridin-4-yl)propan-2-yl)amino)-4-(trifluoromethyl)pyridazin-3(2H)-one | 601.20 |
| 648# | (S)-5-((1-(3-Oxo-3-(4-(5-(trifluoromethyl)pyrimidin-2-yl)piperazin-1-yl)propoxy)-3-(piperidin-4-yl)propan-2-yl)amino)-4-(trifluoromethyl)pyridazin-3(2H)-one | 607.25 |

TABLE E11-continued

| Example No. | Structure | MS (M + H)+ |
|---|---|---|
| 649# | (R)-5-((1-(3-Oxo-3-(4-(5-(trifluoromethyl)pyrimidin-2-yl)piperazin-1-yl)propoxy)-3-(piperidin-4-yl)propan-2-yl)amino)-4-(trifluoromethyl)pyridazin-3(2H)-one | 607.25 |
| 650 | (S)-6-(4-(3-(2-((5-Bromo-6-oxo-1,6-dihydropyridazin-4-yl)oxy)propoxy)propanoyl)piperazin-1-yl)nicotinonitrile | 491.10 |
| 651 | (S)-4-Chloro-5-((1-methoxy-3-(3-oxo-3-(4-(5-(trifluoromethyl)pyrimidin-2-yl)piperazin-1-yl)propoxy)propan-2-yl)amino)pyridazin-3(2H)-one | 520.16 |
| 652 | (S)-5-((1-(3-Oxo-3-(4-(5-(trifluoromethyl)pyrimidin-2-yl)-3,6-dihydropyridin-1(2H)-yl)propoxy)propan-2-yl)amino)-4-(trifluoromethyl)pyridazin-3(2H)-one | 521.17 |

TABLE E11-continued

| Example No. | Structure | MS (M + H)+ |
|---|---|---|
| 653# | (S)-5-((2-(3-Oxo-3-(4-(5-(trifluoromethyl)pyrimidin-2-yl)piperazin-1-yl)propoxy)-1-(piperidin-4-yl)ethyl)amino)-4-(trifluoromethyl)pyridazin-3(2H)-one | 593.23 |
| 654# | (R)-5-((2-(3-Oxo-3-(4-(5-(trifluoromethyl)pyrimidin-2-yl)piperazin-1-yl)propoxy)-1-(piperidin-4-yl)ethyl)amino)-4-(trifluoromethyl)pyridazin-3(2H)-one | 340.20 |
| 655 | (S)-6-(4-(3-(2-((6-Oxo-5-(trifluoromethyl)-1,6-dihydropyridazin-4-yl)thio)propoxy)propanoyl)piperazin-1-yl)nicotinonitrile | 497.15 |
| 656 | (S)-2-(6-(4-(3-(2-((6-Oxo-5-(trifluoromethyl)-1,6-dihydropyridazin-4-yl)oxy)propoxy)propanoyl)piperazin-1-yl)pyridin-3-yl)acetonitrile | 495.19 |

TABLE E11-continued

| Example No. | Structure | MS (M + H)+ |
|---|---|---|
| 657 | (S)-4-Bromo-5-((1-(3-oxo-3-(4-(5-(trifluoromethyl)pyrimidin-2-yl)piperazin-1-yl)propoxy)butan-2-yl)oxy)pyridazin-3(2H)-one | 549.10 |
| 658 | (S)-6-(1-(3-(2-((6-Oxo-5-(trifluoromethyl)-1,6-dihydropyridazin-4-yl)oxy)propoxy)propanoyl)piperidin-4-yl)nicotinonitrile | 480.18 |
| 659 | (S)-4-Bromo-5-((1-hydroxy-3-(3-oxo-3-(4-(5-(trifluoromethyl)pyrimidin-2-yl)piperazin-1-yl)propoxy)propan-2-yl)amino)pyridazin-3(2H)-one | 537.10 |
| 660 | (S)-4-Bromo-5-((1-(3-oxo-3-(4-(5-(trifluoromethyl)pyrimidin-2-yl)piperazin-1-yl)propoxy)propan-2-yl)oxy)pyridazin-3(2H)-one | 550.09 |

TABLE E11-continued

| Example No. | Structure | MS (M + H)+ |
|---|---|---|
| 661 | (S)-5-((1-(3-Oxo-3-(4-(5-(trifluoromethyl)pyrimidin-2-yl)piperazin-1-yl-2,2,3,3,5,5,6,6-d8)propoxy)propan-2-yl)amino)-4-(trifluoromethyl)pyridazin-3(2H)-one | 532.23 |
| 662 | (S)-5-((1-(3-Oxo-3-(4-(5-(trifluoromethyl)pyrazin-2-yl)piperazin-1-yl)propoxy)propan-2-yl)oxy)-4-(trifluoromethyl)pyridazin-3(2H)-one | 525.16 |
| 663 | (S)-6-(4-(3-(3-Morpholino-2-((6-oxo-5-(trifluoromethyl)-1,6-dihydropyridazin-4-yl)oxy)propoxy)propanoyl)piperazin-1-yl)nicotinonitrile | 566.23 |
| 664 | (S)-5-((1-(3-Oxo-3-(4-(5-(trifluoromethyl)pyrimidin-2-yl)piperidin-1-yl)propoxy)propan-2-yl)amino)-4-(trifluoromethyl)pyridazin-3(2H)-one | 523.18 |

TABLE E11-continued

| Example No. | Structure | MS (M + H)+ |
|---|---|---|
| 665 | (S)-5-((1-(3-(4-(5-Chloropyrimidin-2-yl)piperazin-1-yl)-3-oxopropoxy)-3-hydroxypropan-2-yl)amino)-4-(trifluoromethyl)pyridazin-3(2H)-one | 506.15 |
| 666* | (S)-4-Bromo-5-((1-methoxy-3-(3-oxo-3-(4-(5-(trifluoromethyl)pyrimidin-2-yl)piperazin-1-yl)propoxy)propan-2-yl)oxy)pyridazin-3(2H)-one | 565.09 |
| 667* | (R)-4-Bromo-5-((1-methoxy-3-(3-oxo-3-(4-(5-(trifluoromethyl)pyrimidin-2-yl)piperazin-1-yl)propoxy)propan-2-yl)oxy)pyridazin-3(2H)-one | 565.09 |
| 668 | (S)-4-Bromo-5-((1-methoxy-3-(3-oxo-3-(4-(5-(trifluoromethyl)pyrimidin-2-yl)piperazin-1-yl)propoxy)propan-2-yl)amino)pyridazin-3(2H)-one | 564.11 |

TABLE E11-continued

| Example No. | Structure | MS (M + H)+ |
|---|---|---|
| 669 | (S)-5-((1-(3-Oxo-3-(4-(5-(trifluoromethyl)pyrimidin-2-yl)-1,4-diazepan-1-yl)propoxy)propan-2-yl)amino)-4-(trifluoromethyl)pyridazin-3(2H)-one | 538.19 |
| 670 | (S)-5-((1-(3-(4-(5-Methylpyrimidin-2-yl)piperazin-1-yl)-3-oxopropoxy)propan-2-yl)amino)-4-(trifluoromethyl)pyridazin-3(2H)-one | 470.20 |
| 671 | (S)-5-((1-(3-(4-(5-Methylpyridin-2-yl)piperazin-1-yl)-3-oxopropoxy)propan-2-yl)amino)-4-(trifluoromethyl)pyridazin-3(2H)-one | 469.21 |
| 672 | (R)-5-((1-(3-Oxo-3-(4-(5-(trifluoromethyl)pyrimidin-2-yl)piperazin-1-yl)propoxy)propan-2-yl)amino)-4-(trifluoromethyl)pyridazin-3(2H)-one | 524.18 |

TABLE E11-continued

| Example No. | Structure | MS (M + H)+ |
|---|---|---|
| 673 | (S)-5-((1-(3-(4-(5-(Aminomethyl)pyridin-2-yl)piperazin-1-yl)-3-oxopropoxy)propan-2-yl)oxy)-4-(trifluoromethyl)pyridazin-3(2H)-one | 485.20 |
| 674 | (S)-5-((1-(3-Oxo-3-(4-(4-(trifluoromethyl)pyridin-2-yl)piperazin-1-yl)propoxy)propan-2-yl)amino)-4-(trifluoromethyl)pyridazin-3(2H)-one | 523.18 |
| 675 | (S)-5-((1-(3-Oxo-3-(4-(pyridin-2-yl)piperazin-1-yl)propoxy)propan-2-yl)amino)-4-(trifluoromethyl)pyridazin-3(2H)-one | 455.19 |
| 676 | (S)-2-(4-(3-(2-((6-Oxo-5-(trifluoromethyl)-1,6-dihydropyridazin-4-yl)amino)propoxy)propanoyl)piperazin-1-yl)nicotinonitrile | 480.19 |

TABLE E11-continued

| Example No. | Structure | MS (M + H)+ |
|---|---|---|
| 677 | (S)-5-((1-(3-Oxo-3-(4-(3-(trifluoromethyl)pyridin-2-yl)piperazin-1-yl)propoxy)propan-2-yl)amino)-4-(trifluoromethyl)pyridazin-3(2H)-one | 523.18 |
| 678 | (S)-5-((1-(3-(4-(5-Chloropyrazin-2-yl)piperazin-1-yl)-3-oxopropoxy)-3-methoxypropan-2-yl)amino)-4-(trifluoromethyl)pyridazin-3(2H)-one | 520.16 |
| 679 | (S)-5-((1-(3-(4-(5-Fluoropyrimidin-2-yl)piperazin-1-yl)-3-oxopropoxy)propan-2-yl)amino)-4-(trifluoromethyl)pyridazin-3(2H)-one | 474.18 |
| 680 | (S)-2-(4-(3-(2-((6-Oxo-5-(trifluoromethyl)-1,6-dihydropyridazin-4-yl)amino)propoxy)propanoyl)piperazin-1-yl)thiazole-5-carbonitrile | 486.15 |

TABLE E11-continued

| Example No. | Structure | MS (M + H)+ |
|---|---|---|
| 681 | (S)-5-((1-Methoxy-3-(3-oxo-3-(4-(5-(trifluoromethyl)pyrazin-2-yl)piperazin-1-yl)propoxy)propan-2-yl)amino)-4-(trifluoromethyl)pyridazin-3(2H)-one | 554.19 |
| 682 | (S)-5-((1-(3-(4-(5-Methylpyridin-2-yl)piperazin-1-yl)-3-oxopropoxy)propan-2-yl)oxy)-4-(trifluoromethyl)pyridazin-3(2H)-one | 470.19 |
| 683 | (S)-5-(4-(3-(2-((6-Oxo-5-(trifluoromethyl)-1,6-dihydropyridazin-4-yl)amino)propoxy)propanoyl)piperazin-1-yl)pyrazine-2-carbonitrile | 481.18 |
| 684 | (S)-5-((1-(3-(4-(5-Fluoropyridin-2-yl)piperazin-1-yl)-3-oxopropoxy)propan-2-yl)amino)-4-(trifluoromethyl)pyridazin-3(2H)-one | 473.18 |

TABLE E11-continued

| Example No. | Structure | MS (M + H)+ |
|---|---|---|
| 685 | (S)-5-((1-(3-Oxo-3-(4-(6-(trifluoromethyl)pyridin-3-yl)piperazin-1-yl)propoxy)propan-2-yl)amino)-4-(trifluoromethyl)pyridazin-3(2H)-one | 523.18 |
| 686 | (S)-5-((4-Methoxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 568.20 |
| 687 | (S)-5-((1-(3-(4-(5-Methylpyrimidin-2-yl)piperazin-1-yl)-3-oxopropoxy)propan-2-yl)oxy)-4-(trifluoromethyl)pyridazin-3(2H)-one | 471.19 |
| 688# | 5-(((S)-1-(3-Oxo-3-((3aR,6aR)-4-(5-(trifluoromethyl)pyrimidin-2-yl)hexahydropyrrolo[3,2-b]pyrrol-1(2H)-yl)propoxy)propan-2-yl)amino)-4-(trifluoromethyl)pyridazin-3(2H)-one | 550.19 |

TABLE E11-continued

| Example No. | Structure | MS (M + H)+ |
|---|---|---|
| 689# | 5-(((S)-1-(3-Oxo-3-((3aS,6aS)-4-(5-(trifluoromethyl)pyrimidin-2-yl)hexahydropyrrolo[3,2-b]pyrrol-1(2H)-yl)propoxy)propan-2-yl)amino)-4-(trifluoromethyl)pyridazin-3(2H)-one | 550.19 |
| 690 | (S)-5-((1-Methoxy-3-(3-(4-(5-methylpyrimidin-2-yl)piperazin-1-yl)-3-oxopropoxy)propan-2-yl)amino)-4-(trifluoromethyl)pyridazin-3(2H)-one | 500.22 |
| 691# | (S)-5-((1-Methoxy-3-(3-oxo-3-(4-(5-(trifluoromethyl)pyrimidin-2-yl)piperazin-1-yl)propoxy)propan-2-yl)thio)-4-(trifluoromethyl)pyridazin-3(2H)-one | 571.15 |
| 692# | (R)-5-((1-Methoxy-3-(3-oxo-3-(4-(5-(trifluoromethyl)pyrimidin-2-yl)piperazin-1-yl)propoxy)propan-2-yl)thio)-4-(trifluoromethyl)pyridazin-3(2H)-one | 571.15 |

TABLE E11-continued

| Example No. | Structure | MS (M + H)+ |
|---|---|---|
| 693 | (S)-4-Bromo-5-((1-(3-(4-(5-chloropyrazin-2-yl)piperazin-1-yl)-3-oxopropoxy)-3-methoxypropan-2-yl)amino)pyridazin-3(2H)-one | 530.08 |
| 694 | (S)-5-((1-(3-(4-(5-Chloropyrazin-2-yl)piperazin-1-yl)-3-oxopropoxy)propan-2-yl)oxy)-4-(trifluoromethyl)pyridazin-3(2H)-one | 491.14 |
| 695 | (S)-5-((1-Methoxy-3-(3-(4-(5-methylpyrazin-2-yl)piperazin-1-yl)-3-oxopropoxy)propan-2-yl)amino)-4-(trifluoromethyl)pyridazin-3(2H)-one | 500.22 |
| 696* | (S)-5-((1-(3-(4-(5-Chloropyrazin-2-yl)piperazin-1-yl)-3-oxopropoxy)-3-methoxypropan-2-yl)oxy)-4-(trifluoromethyl)pyridazin-3(2H)-one | 521.14 |

TABLE E11-continued

| Example No. | Structure | MS (M + H)+ |
|---|---|---|
| 697* | (R)-5-((1-(3-(4-(5-Chloropyrazin-2-yl)piperazin-1-yl)-3-oxopropoxy)-3-methoxypropan-2-yl)oxy)-4-(trifluoromethyl)pyridazin-3(2H)-one | 521.14 |
| 698# | 5-(((2R,3S)-3-Methoxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 568.20 |
| 699# | 5-(((2R,3R)-3-Methoxy-1-(3-oxo-3-(4-(5-(trifluoromethyl)pyrimidin-2-yl)piperazin-1-yl)propoxy)butan-2-yl)amino)-4-(trifluoromethyl)pyridazin-3(2H)-one | 568.20 |
| 700 | (S)-4-Bromo-5-((1-(3-oxo-3-(4-(5-(trifluoromethyl)pyrimidin-2-yl)piperazin-1-yl)propoxy)propan-2-yl)thio)pyridazin-3(2H)-one | 551.06 |

TABLE E11-continued

| Example No. | Structure | MS (M + H)+ |
|---|---|---|
| 701 | (S)-4-Chloro-5-((1-(3-oxo-3-(4-(5-(trifluoromethyl)pyrimidin-2-yl)piperazin-1-yl)propoxy)propan-2-yl)thio)pyridazin-3(2H)-one | 507.11 |
| 702* | (S)-5-((1-((3-Oxo-3-(4-(5-(trifluoromethyl)pyrimidin-2-yl)piperazin-1-yl)propyl)thio)propan-2-yl)amino)-4-(trifluoromethyl)pyridazin-3(2H)-one | 540.15 |
| 703* | (R)-5-((1-((3-Oxo-3-(4-(5-(trifluoromethyl)pyrimidin-2-yl)piperazin-1-yl)propyl)thio)propan-2-yl)amino)-4-(trifluoromethyl)pyridazin-3(2H)-one | 540.15 |
| 704* | (R)-5-((1-(3-(4-(5-Chloropyrimidin-2-yl)piperazin-1-yl)-3-oxopropoxy)-4-hydroxybutan-2-yl)oxy)-4-(trifluoromethyl)pyridazin-3(2H)-one | 521.14 |

TABLE E11-continued

| Example No. | Structure | MS (M + H)+ |
|---|---|---|
| 705* | (S)-5-((1-(3-(4-(5-Chloropyrimidin-2-yl)piperazin-1-yl)-3-oxopropoxy)-4-hydroxybutan-2-yl)oxy)-4-(trifluoromethyl)pyridazin-3(2H)-one | 521.14 |
| 706 | (S)-5-((1-(3-(4-(5-(Difluoromethyl)pyrimidin-2-yl)piperazin-1-yl)-3-oxopropoxy)propan-2-yl)amino)-4-(trifluoromethyl)pyridazin-3(2H)-one | 506.19 |
| 707 | (S)-5-((1-(3-(4-(5-(1,1-Difluoroethyl)pyrimidin-2-yl)piperazin-1-yl)-3-oxopropoxy)propan-2-yl)amino)-4-(trifluoromethyl)pyridazin-3(2H)-one | 520.20 |
| 708 | (S)-5-((1-(3-Oxo-3-(4-(5-(trifluoromethyl)thiazol-2-yl)piperazin-1-yl)propoxy)propan-2-yl)oxy)-4-(trifluoromethyl)pyridazin-3(2H)-one | 530.12 |

TABLE E11-continued

| Example No. | Structure | MS (M + H)+ |
|---|---|---|
| 709 | (S)-5-((1-(3-Oxo-3-(4-(2-(trifluoromethyl)thiazol-5-yl)piperazin-1-yl)propoxy)propan-2-yl)amino)-4-(trifluoromethyl)pyridazin-3(2H)-one | 529.14 |
| 710 | 5-(((2S)-1-(3-Oxo-3-(3-((5-(trifluoromethyl)pyrimidin-2-yl)amino)pyrrolidin-1-yl)propoxy)propan-2-yl)amino)-4-(trifluoromethyl)pyridazin-3(2H)-one | 524.18 |
| 711 | (S)-2-(4-(3-(2-((6-Oxo-5-(trifluoromethyl)-1,6-dihydropyridazin-4-yl)oxy)propoxy)propanoyl)piperazin-1-yl)thiazole-5-carbonitrile | 487.13 |
| 712 | (S)-5-((1-Methoxy-3-(3-oxo-3-(4-(5-(trifluoromethyl)thiazol-2-yl)piperazin-1-yl)propoxy)propan-2-yl)amino)-4-(trifluoromethyl)pyridazin-3(2H)-one | 559.15 |

TABLE E11-continued

| Example No. | Structure | MS (M + H)+ |
|---|---|---|
| 713 | (S)-2-(4-(3-(3-Methoxy-2-((6-oxo-5-(trifluoromethyl)-1,6-dihydropyridazin-4-yl)amino)propoxy)propanoyl)piperazin-1-yl)thiazole-5-carbonitrile | 516.16 |
| 714 | (S)-6-(4-(3-(2-((6-Oxo-5-(trifluoromethyl)-1,6-dihydropyridazin-4-yl)oxy)propoxy)propanoyl)piperazin-1-yl-2,2,3,3,5,5,6,6-d8) nicotinonitrile | 489.22 |
| 715 | (S)-5-((1-(3-(4-(5-Chloropyrimidin-2-yl)piperazin-1-yl-2,2,3,3,5,5,6,6-d8)-3-oxopropoxy)propan-2-yl)oxy)-4-(trifluoromethyl)pyridazin-3(2H)-one | 499.18 |
| 716 | 5-(((2S)-1-(3-Oxo-3-(3-((5-(trifluoromethyl)pyrimidin-2-yl)oxy)pyrrolidin-1-yl)propoxy)propan-2-yl)amino)-4-(trifluoromethyl)pyridazin-3(2H)-one | 525.16 |

TABLE E11-continued

| Example No. | Structure | MS (M + H)+ |
|---|---|---|
| 717 | 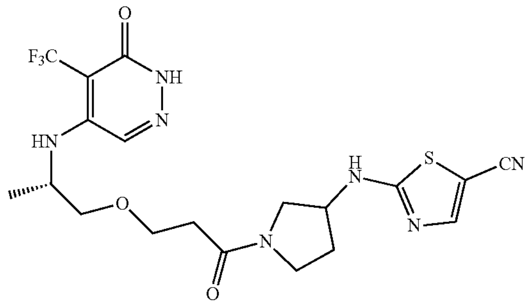 [SMILES: C[C@@H](COCCC(=O)N1CCC(Nc2ncc(C#N)s2)C1)Nc1cn[nH]c(=O)c1C(F)(F)F] | 486.15 |

2-((1-(3-((S)-2-((6-Oxo-5-(trifluoromethyl)-1,6-dihydropyridazin-4-yl)amino)propoxy)propanoyl)pyrrolidin-3-yl)amino)thiazole-5-carbonitrile

| 718 | | 487.13 |

2-((1-(3-((S)-2-((6-Oxo-5-(trifluoromethyl)-1,6-dihydropyridazin-4-yl)amino)propoxy)propanoyl)pyrrolidin-3-yl)oxy)thiazole-5-carbonitrile

| 719 | | 395.15 |

5-(((2S)-1-(3-Oxo-3-(3-((5-(trifluoromethyl)thiazol-2-yl)amino)pyrrolidin-1-yl)propoxy)propan-2-yl)amino)-4-(trifluoromethyl)pyridazin-3(2H)-one

| 720 | | 530.12 |

5-(((2S)-1-(3-Oxo-3-(3-((5-(trifluoromethyl)thiazol-2-yl)oxy)pyrrolidin-1-yl)propoxy)propan-2-yl)amino)-4-(trifluoromethyl)pyridazin-3(2H)-one TABLE E11-continued

| Example No. | Structure | MS (M + H)+ |
|---|---|---|
| 721 | (S)-5-((1-(3-(4-(5-Chlorothiazol-2-yl)piperazin-1-yl)-3-oxopropoxy)propan-2-yl)amino)-4-(trifluoromethyl)pyridazin-3(2H)-one | 495.11 |
| 722 | (S)-5-((1-(3-Oxo-3-(4-(5-(trifluoromethyl)-1,3,4-thiadiazol-2-yl)piperazin-1-yl)propoxy)propan-2-yl)amino)-4-(trifluoromethyl)pyridazin-3(2H)-one | 530.13 |
| 723 | (S)-5-((1-(3-(4-(5-Chlorothiazol-2-yl)piperazin-1-yl)-3-oxopropoxy)propan-2-yl)oxy)-4-(trifluoromethyl)pyridazin-3(2H)-one | 496.10 |
| 724 | 4-(Trifluoromethyl)-5-(2-(2-((4-(5-(trifluoromethyl)pyrimidin-2-yl)piperazin-1-yl)sulfonyl)ethoxy)ethoxy)pyridazin-3(2H)-one | 547.11 |

TABLE E11-continued

| Example No. | Structure | MS (M + H)+ |
|---|---|---|
| 725 | (S)-5-((1-(2-((4-(5-(Tert-butyl)pyrimidin-2-yl)piperazin-1-yl)sulfonyl)ethoxy)propan-2-yl)amino)-4-(trifluoromethyl)pyridazin-3(2H)-one | 548.22 |
| 726 | (S)-4-(Trifluoromethyl)-5-((1-(2-((4-(5-(trifluoromethyl)thiazol-2-yl)piperazin-1-yl)sulfonyl)ethoxy)propan-2-yl)amino)pyridazin-3(2H)-one | 565.20 |
| 727 | (S)-4-Bromo-5-((1-(3-(4-(5-chloropyrimidin-2-yl)piperazin-1-yl)-3-oxopropoxy)butan-2-yl)oxy)pyridazin-3(2H)-one | 515.07 |
| 728 | (S)-4-(Trifluoromethyl)-5-((1-(2-((4-(5-(trifluoromethyl)pyrimidin-2-yl)piperazin-1-yl)sulfonyl)ethoxy)propan-2-yl)oxy)pyridazin-3(2H)-one | 561.13 |

TABLE E11-continued

| Example No. | Structure | MS (M + H)+ |
|---|---|---|
| 729 | (S)-4-Chloro-5-((1-(3-oxo-3-(4-(5-(trifluoromethyl)thiazol-2-yl)piperazin-1-yl)propoxy)propan-2-yl)oxy)pyridazin-3(2H)-one | 496.10 |
| 730 | (S)-4-Bromo-5-((1-(3-oxo-3-(4-(5-(trifluoromethyl)thiazol-2-yl)piperazin-1-yl)propoxy)propan-2-yl)oxy)pyridazin-3(2H)-one | 540.10 |
| 731 | (S)-4-Chloro-5-((1-(2-((4-(5-(trifluoromethyl)thiazol-2-yl)piperazin-1-yl)sulfonyl)ethoxy)propan-2-yl)amino)pyridazin-3(2H)-one | 531.00 |
| 732 | (S)-4-Bromo-5-((1-(2-((4-(5-(trifluoromethyl)thiazol-2-yl)piperazin-1-yl)sulfonyl)ethoxy)propan-2-yl)amino)pyridazin-3(2H)-one | 575.00 |

TABLE E11-continued

| Example No. | Structure | MS (M + H)⁺ |
|---|---|---|
| 733 | (S)-5-((1-(3-(4-(5-Methylthiazol-2-yl)piperazin-1-yl)-3-oxopropoxy)propan-2-yl)amino)-4-(trifluoromethyl)pyridazin-3(2H)-one | 475.20 |

Absolute stereochemistry arbitrarily assigned.
*The absolute stereochemistry was assigned based on a protein X-ray crystal structure obtained of Example 18, isomer B which confirmed (S)-absolute stereochemistry and was observed to be the more potent enantiomer.

Example A. Enzymatic Assay for Inhibition of PARP7

Displacement of Probe A, a biotinylated probe binding to the TIPARP active site, was measured using a time-resolved fluorescence energy transfer (TR-FRET) assay. 20 nL of a dose response curve of each test compound was spotted in black 384-well polystyrene proxiplates (Perkin Elmer) using a Mosquito (TTP Labtech). Reactions were performed in a 8 μL volume by adding 6 JAL of TIPARP and Probe A in assay buffer (20 mM HEPES pH=8, 100 mM NaCl, 0.1% bovine serum albumin, 2 mM DTT and 0.002% Tween20), incubating with test compound at 25° C. for 30 min, then adding 2 μL of ULight-anti 6×His and LANCE Eu-W1024 labeled streptavidin (Perkin Elmer). The final concentrations of TIPARP and Probe A were 6 nM and 2 nM, respectively. The final concentration of ULight-anti 6×His and LANCE Eu-W1024 labeled streptavidin were 4 nM and 0.25 nM, respectively. Reactions were incubated at 25° C. for an additional 30 min, then read on an Envision plate reader equipped with a LANCE/DELFIA top mirror (Perkin Elmer) using excitation of 320 nm and emission of 615 nm and 665 nM with a 90 μs delay. The ratio of the 665/615 nm emission were calculated for each well to determine the amount of complex of TIPARP and Probe A in each well. Control wells containing a negative control of 0.25% DMSO vehicle or a positive control of 100 μM Example 190 were used to calculate the % inhibition as described below:

$$\% \text{ inhibition} = 100 \times \frac{TRF_{cmpd} - TRF_{min}}{TRF_{max} - TRF_{min}}$$

where $TRF_{cmpd}$ is the TR-FRET ratio from the compound treated well, $TRF_{min}$ is the TR-FRET ratio from the Example 190-treated positive control well and $TRF_{max}$ is the TR-FRET ratio from the DMSO-treated negative control well.

The % inhibition values were plotted as a function of compound concentration and the following 4-parameter fit was applied to derive the $IC_{50}$ values:

$$Y = \text{Bottom} + \frac{(\text{Top} - \text{Bottom})}{\left(1 + \left(\frac{X}{IC_{50}}\right)^{Hill\ Coefficient}\right)}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

Synthesis of Probe A

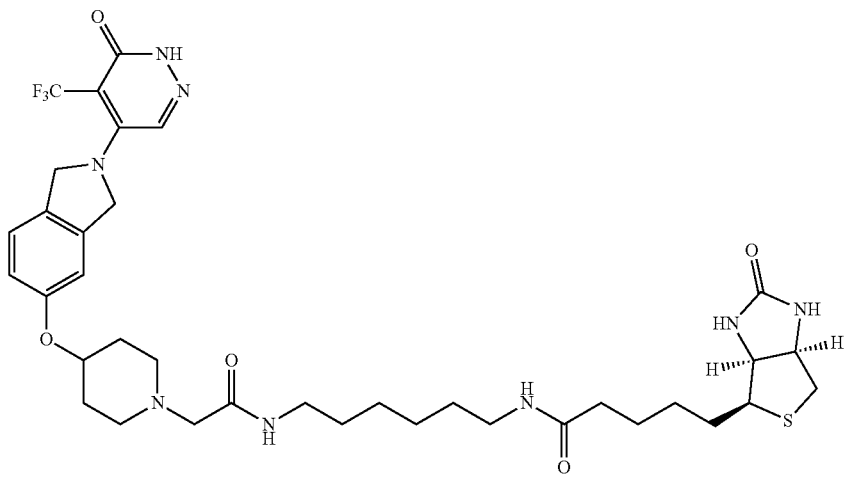 [SMILES: O=C(CCCC[C@@H]1SC[C@@H]2NC(=O)N[C@@H]21)NCCCCCCNC(=O)CN1CCC(Oc2ccc3c(c2)CN(c2cn[nH]c(=O)c2C(F)(F)F)C3)CC1]

Step 1: 5-(5-Hydroxy-2,3-dihydro-1H-isoindol-2-yl)-4-(trifluoromethyl)-2-[[2-(trimethylsilyl)ethoxy]methyl]-2,3-dihydropyridazin-3-one A solution of 5-chloro-4-(trifluoromethyl)-2-[[2-(trimethylsilyl)ethoxy]methyl]-2,3-dihydropyridazin-3-one (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of ethyl acetate and the organic layers combined and concentrated under reduced pressure to afford 4.5 g of the title compound as a yellow oil. LCMS: [M+H]$^+$ 428.23.

Step 2: Tert-Butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of ethyl acetate and the organic layers combined and concentrated under reduced pressure. The residue was applied onto a silica gel column eluting with ethyl acetate/petroleum ether to afford the title compound (2 g, 31%) as a yellow oil. LCMS: [M+H]$^+$ 611.15.

Step 3: 5-[5-(Piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (2 g, 3.27 mmol, 1.00 equiv), dioxane/HCl (5 mL), and dioxane (45 mL) was stirred for 6 h at 25° C. The resulting mixture was concentrated under reduced pressure. The residue was applied onto a silica gel column and eluted with ethyl acetate/petroleum ether to afford 1 g of title compound as a yellow oil. LCMS: [M+H]$^+$ 511.28.

Step 4: Tert-Butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate A solution of 5-[5-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one (1 g, 1.96 mmol, 1.00 equiv), tert-butyl 2-chloroacetate (450 mg, 2.99 mmol, 3.00 equiv), DIPEA (5 mL), and dichloromethane (10 mL) was stirred overnight at 25° C. The residue was purified by C18 reverse phase chromatography eluting with H$_2$O/CH$_3$CN to afford the title compound (540 mg, 44%) as a yellow oil. LCMS: [M+H]$^+$ 625.20.

Step 5: 2-[4-([2-[6-Oxo-5-(trifluoromethyl)-1,6-dihydropyridazin-4-yl]-2,3-dihydro-1H-isoindol-5-yl]oxy)piperidin-1-yl]hydrochloride A solution of tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate (540 mg, 0.86 mmol, 1.00 equiv) and dioxane/HCl (8 mL) was stirred overnight at 25° C. The resulting mixture was concentrated under reduced pressure. The residue was purified by C18 reverse phase chromatography eluting with H$_2$O/CH$_3$CN to afford 200 mg (53%) of title compound as a white solid. LCMS: [M+H]$^+$ 439.31.

Step 6: Tert-butyl N-(6-[5-[(3aS,4S,6aR)-2-oxo-hexahydro-1H-thieno[3,4-d]imidazolidin-4-yl]pentanamido]hexyl)carbamate A solution of 5-[(3aS,4S,6aR)-2-oxo-hexahydro-1H-thieno[3,4-d]imidazolidin-4-yl]pentanoic acid (reagent was purchased from Beijing Dragon Rui Trading Company, 976 mg, 3.99 mmol, 1.00 equiv), DIPEA (1.55 g, 11.99 mmol, 3.00 equiv), HATU (1.82 g, 4.79 mmol, 1.20 equiv), tert-butyl N-(6-aminohexyl)carbamate (864 mg, 3.99 mmol, 1.00 equiv) in DMF (15 mL) was stirred overnight at 25° C. The reaction was then quenched by the addition of 50 mL of water. The solids were collected by filtration to afford 1.5 g (85%) of the title compound as a white solid. LCMS: [M+H]$^+$ 443.26.

Step 7: 5-[(3aS,4S,6aR)-2-Oxo-hexahydro-1H-thieno[3,4-d]imidazolidin-4-yl]-N-(6-aminohexyl)pentanamide Hydrochloride A solution of tert-butyl N-(6-[5-[(3aS,4S,6aR)-2-oxo-hexahydro-1H-thieno[3,4-d]imidazolidin-4-yl]pentanamido]hexyl)carbamate (800 mg, 1.81 mmol, 1.00 equiv) in hydrogen chloride/dioxane (20 mL) was stirred overnight at 25° C. The resulting mixture was concentrated under reduced pressure to afford 600 mg (88%) of the title compound as a gray crude oil. LCMS: [M+H]$^+$ 343.21.

Step 8: 5-[(3aS,4S,6aR)-2-Oxo-hexahydro-1H-thieno[3,4-d]imidazolidin-4-yl]-N-(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)pentanamide A solution of 2-[4-([2-[6-oxo-5-(trifluoromethyl)-1,6-dihydropyridazin-4-yl]-2,3-dihydro-1H-isoindol-5-yl]oxy)piperidin-1-yl]hydrochloride (175 mg, 0.40 mmol, 1.00 equiv), DIPEA (258 mg, 2.00 mmol, 5.00 equiv), HATU (228 mg, 0.60 mmol, 1.50 equiv), 5-[(3 aS,4S,6aR)-2-oxo-hexahydro-1H-thieno[3,4-d]imidazolidin-4-yl]-N-(6-aminohexyl)pentanamide hydrochloride (228 mg, 0.60 mmol, 1.50 equiv) in DMF (3 mL) was stirred for 4 h at 25° C. The crude product was purified by C18 reverse phase chromatography eluting with H$_2$O/CH$_3$CN to afford the title compound as a white solid (118.3 mg, 39%). LCMS: [M+H]$^+$ 763.35.

$^1$H NMR (DMSO-d$_6$, 400 MHz) δ: 12.52 (s, 1H), 7.98 (s, 1H), 7.81-7.68 (m, 2H), 7.26 (d, J=8.4 Hz, 1H), 7.00 (d, J=2.2 Hz, 1H), 6.91 (dd, J=8.4, 2.3 Hz, 1H), 6.45-6.39 (m, 1H), 6.36 (s, 1H), 4.91 (d, J=6.1 Hz, 4H), 4.45 (m, 1H), 4.26 (m, 1H), 4.17-4.08 (m, 1H), 3.14-2.96 (m, 5H), 2.91 (s, 2H), 2.82 (dd, J=12.4, 5.1 Hz, 1H), 2.73-2.63 (m, 2H), 2.58 (d, J=12.4 Hz, 1H), 2.33 (ddd, J=11.8, 9.4, 3.1 Hz, 2H), 2.11-1.90 (m, 4H), 1.76-1.54 (m, 3H), 1.57-1.20 (m, 13H).

IC$_{50}$ data for the Example compounds is provided below in Table A-1 ("+" is <0.1 µM; "++" is ≥0.1 µM<1 µM; and "+++" is ≥1 µM).

TABLE A-1

IC$_{50}$ Data for Example Compounds

| Example No. | IC$_{50}$ |
|---|---|
| 1 | + |
| 2 | + |
| 3 | + |
| 4 | + |
| 5 | ++ |
| 6 | ++ |
| 7 | ++ |
| 8 | ++ |
| 9 | ++ |
| 10 | ++ |
| 11 | + |
| 12 | ++ |
| 13 | + |
| 14 | + |
| 15 | + |
| 16 | ++ |
| 17 | + |
| 18A | ++ |
| 18B | + |
| 19 | + |
| 20 | + |
| 21 | + |
| 22 | + |
| 23 | + |
| 24 | + |
| 25 | + |
| 26 | + |
| 27 | ++ |
| 28 | + |
| 29 | + |
| 30A | +++ |
| 30B | + |
| 31 | +++ |
| 32 | + |
| 33 | + |
| 34 | + |
| 35A | +++ |
| 35B | ++ |
| 36A | +++ |
| 36B | + |
| 37 | + |
| 38A | + |
| 38B | + |
| 39 | + |
| 40 | ++ |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56A | + |
| 56B | ++ |
| 57A | ++ |
| 57B | + |
| 57C | ++ |
| 57D | ++ |
| 58 | + |
| 59 | + |
| 60 | ++ |
| 61 | + |
| 62 | + |
| 63 | + |
| 64A | +++ |
| 64B | + |
| 65 | + |
| 66 | + |
| 67 | + |
| 68 | + |
| 69 | + |
| 70 | + |
| 71 | ++ |
| 72A | + |
| 72B | + |
| 73 | + |
| 74 | + |
| 75 | + |
| 76 | + |
| 77 | + |
| 78 | + |
| 79A | + |
| 79B | + |
| 79C | + |
| 79D | + |
| 80A | ++ |
| 80B | ++ |
| 81A | ++ |
| 81B | +++ |
| 82A | + |
| 82B | ++ |
| 83 | ++ |
| 84 | ++ |
| 85 | + |
| 86 | ++ |
| 87 | + |
| 88 | + |
| 89 | + |
| 90 | + |
| 91 | ++ |
| 92 | + |
| 93A | + |
| 93B | ++ |
| 94A | + |
| 94B | + |
| 95A | + |
| 95B | + |
| 96A | + |
| 96B | + |
| 97 | + |
| 98 | + |
| 99 | ++ |
| 100A | + |
| 100B | + |
| 101 | + |
| 102 | + |
| 103 | ++ |
| 104 | +++ |
| 105 | ++ |
| 106 | + |
| 107 | + |
| 108 | ++ |
| 109 | ++ |
| 110 | + |
| 111 | ++ |
| 112A | ++ |
| 112B | +++ |
| 113 | + |
| 114 | +++ |
| 115 | + |
| 116 | + |
| 117 | ++ |
| 118 | + |
| 119 | + |
| 120 | +++ |
| 121A | + |
| 121B | + |
| 122 | + |
| 123A | + |
| 123B | + |
| 124 | + |
| 125 | + |

TABLE A-1-continued

IC$_{50}$ Data for Example Compounds

| Example No. | IC$_{50}$ |
|---|---|
| 126 | + |
| 127 | + |
| 128A | + |
| 128B | + |
| 129A | ++ |
| 129B | + |
| 130 | ++ |
| 131 | ++ |
| 132 | ++ |
| 133 | + |
| 134 | +++ |
| 135 | + |
| 136 | + |
| 137A | + |
| 137B | + |
| 138 | +++ |
| 139 | + |
| 140A | + |
| 140B | ++ |
| 141A | + |
| 141B | + |
| 141C | ++ |
| 141D | ++ |
| 142 | +++ |
| 143 | +++ |
| 144A | + |
| 144B | ++ |
| 145A | + |
| 145B | + |
| 146A | + |
| 146B | + |
| 147A | + |
| 147B | + |
| 147C | ++ |
| 147D | + |
| 148A | + |
| 148B | ++ |
| 148C | + |
| 148D | + |
| 149A | + |
| 149B | + |
| 149C | + |
| 149D | + |
| 150 | + |
| 151 | ++ |
| 152 | ++ |
| 153 | ++ |
| 154 | ++ |
| 155 | ++ |
| 156 | ++ |
| 157 | ++ |
| 158 | ++ |
| 159 | +++ |
| 160 | + |
| 161 | ++ |
| 162 | ++ |
| 163 | +++ |
| 164 | + |
| 165 | +++ |
| 166 | +++ |
| 167 | ++ |
| 168 | ++ |
| 169 | + |
| 170 | + |
| 171 | +++ |
| 172 | ++ |
| 173 | ++ |
| 174 | + |
| 175 | +++ |
| 176 | +++ |
| 177 | + |
| 178 | + |
| 179 | ++ |
| 180 | + |
| 181 | + |
| 182 | +++ |
| 183 | +++ |
| 184 | +++ |
| 185 | +++ |
| 186 | +++ |
| 187 | +++ |
| 188 | ++ |
| 189 | ++ |
| 190 | + |
| 191 | +++ |
| 192 | + |
| 193 | + |
| 194 | + |
| 195 | + |
| 196 | + |
| 197 | + |
| 198 | + |
| 199 | + |
| 200 | + |
| 201 | + |
| 202 | + |
| 203 | + |
| 204 | ++ |
| 205 | + |
| 206 | + |
| 207 | +++ |
| 208 | +++ |
| 209 | + |
| 210 | ++ |
| 211 | + |
| 212 | ++ |
| 213 | ++ |
| 214 | + |
| 215 | + |
| 216 | + |
| 217 | ++ |
| 218 | + |
| 219 | + |
| 220 | ++ |
| 221 | +++ |
| 222 | + |
| 223 | + |
| 224 | + |
| 225 | + |
| 226 | + |
| 227 | + |
| 228 | + |
| 229 | + |
| 230 | ++ |
| 231 | +++ |
| 232 | + |
| 233 | + |
| 234 | + |
| 235 | +++ |
| 236 | + |
| 237 | + |
| 238 | + |
| 239 | +++ |
| 240 | ++ |
| 241 | ++ |
| 242 | ++ |
| 243 | +++ |
| 244 | ++ |
| 245 | + |
| 246 | +++ |
| 247 | +++ |
| 248 | +++ |
| 249 | ++ |
| 250 | ++ |
| 251 | +++ |
| 252 | + |
| 253 | ++ |
| 254 | ++ |
| 255 | +++ |
| 256 | +++ |

TABLE A-1-continued

IC$_{50}$ Data for Example Compounds

| Example No. | IC$_{50}$ |
|---|---|
| 257 | +++ |
| 258 | +++ |
| 259 | +++ |
| 260 | + |
| 261 | ++ |
| 262 | +++ |
| 263 | + |
| 264 | +++ |
| 265 | + |
| 266 | + |
| 267 | + |
| 268 | + |
| 269 | + |
| 270 | + |
| 271 | + |
| 272 | +++ |
| 273 | + |
| 274 | + |
| 275 | +++ |
| 276 | +++ |
| 277 | ++ |
| 278 | ++ |
| 279 | + |
| 280 | ++ |
| 281 | ++ |
| 282 | ++ |
| 283 | ++ |
| 284 | + |
| 285 | + |
| 286 | + |
| 287 | +++ |
| 288 | + |
| 289 | + |
| 290 | ++ |
| 291 | ++ |
| 292 | +++ |
| 293 | +++ |
| 294 | + |
| 295 | ++ |
| 296 | ++ |
| 297 | ++ |
| 298 | + |
| 299 | + |
| 300 | ++ |
| 301 | ++ |
| 302 | ++ |
| 303 | + |
| 304 | + |
| 305 | + |
| 306 | + |
| 307 | ++ |
| 308 | ++ |
| 309 | ++ |
| 310 | +++ |
| 311 | ++ |
| 312 | ++ |
| 313 | + |
| 314 | ++ |
| 315 | ++ |
| 316 | ++ |
| 317 | ++ |
| 318 | ++ |
| 319 | ++ |
| 320 | + |
| 321 | + |
| 322 | ++ |
| 323 | + |
| 324 | ++ |
| 325 | ++ |
| 326 | + |
| 327 | ++ |
| 328 | + |
| 329 | + |
| 330 | +++ |
| 331 | + |
| 332 | ++ |
| 333 | + |
| 334 | ++ |
| 335 | ++ |
| 336 | + |
| 337 | + |
| 338 | + |
| 339 | + |
| 340 | + |
| 341 | + |
| 342 | +++ |
| 343 | +++ |
| 344 | ++ |
| 345 | +++ |
| 346 | + |
| 347 | + |
| 348 | + |
| 349 | + |
| 350 | ++ |
| 351 | ++ |
| 352 | + |
| 353 | + |
| 354 | ++ |
| 355 | + |
| 356 | ++ |
| 357 | + |
| 358 | + |
| 359 | + |
| 360 | +++ |
| 361 | + |
| 362 | ++ |
| 363 | +++ |
| 364 | +++ |
| 365 | + |
| 366 | + |
| 367 | + |
| 368 | + |
| 369 | ++ |
| 370 | + |
| 371 | ++ |
| 372 | +++ |
| 373 | + |
| 374 | + |
| 375 | + |
| 376 | + |
| 377 | + |
| 378 | + |
| 379 | + |
| 380 | + |
| 381 | + |
| 382 | + |
| 383 | + |
| 384 | + |
| 385 | ++ |
| 386 | + |
| 387 | +++ |
| 388 | + |
| 389 | ++ |
| 390 | + |
| 391 | +++ |
| 392 | + |
| 393 | ++ |
| 394 | + |
| 395 | + |
| 396 | +++ |
| 397 | + |
| 398 | + |
| 399 | ++ |
| 400 | + |
| 401 | + |
| 402 | + |
| 403 | + |
| 404 | ++ |
| 405 | + |
| 406 | +++ |

TABLE A-1-continued

IC$_{50}$ Data for Example Compounds

| Example No. | IC$_{50}$ |
|---|---|
| 407 | + |
| 408 | + |
| 409 | ++ |
| 410 | + |
| 411 | + |
| 412 | + |
| 413 | + |
| 414 | ++ |
| 415 | + |
| 416 | ++ |
| 417 | ++ |
| 418 | +++ |
| 419 | + |
| 420 | +++ |
| 421 | ++ |
| 422 | +++ |
| 423 | + |
| 424 | +++ |
| 425 | +++ |
| 426 | + |
| 427 | + |
| 428 | ++ |
| 429 | + |
| 430 | ++ |
| 431 | + |
| 432 | ++ |
| 433 | + |
| 434 | +++ |
| 435 | + |
| 436 | ++ |
| 437 | + |
| 438 | +++ |
| 439 | + |
| 440 | + |
| 441 | + |
| 442 | + |
| 443 | + |
| 444 | + |
| 445 | + |
| 446 | + |
| 447 | + |
| 448 | ++ |
| 449 | ++ |
| 450 | + |
| 451 | ++ |
| 452 | + |
| 453 | + |
| 454 | + |
| 455 | + |
| 456 | + |
| 457 | + |
| 458 | + |
| 459 | ++ |
| 460 | + |
| 461 | + |
| 462 | + |
| 463 | + |
| 464 | +++ |
| 465 | + |
| 466 | + |
| 467 | + |
| 468 | + |
| 469 | + |
| 470 | + |
| 471 | + |
| 472 | +++ |
| 473 | + |
| 474 | + |
| 475 | + |
| 476 | ++ |
| 477 | + |
| 478 | ++ |
| 479 | ++ |
| 480 | + |
| 481 | + |
| 482 | + |
| 483 | + |
| 484 | + |
| 485 | + |
| 486 | + |
| 487 | ++ |
| 488 | + |
| 489 | +++ |
| 490 | + |
| 491 | + |
| 492 | + |
| 493 | + |
| 494 | + |
| 495 | + |
| 496 | + |
| 497 | +++ |
| 498 | +++ |
| 499 | + |
| 500 | + |
| 501 | + |
| 502 | +++ |
| 503 | + |
| 504 | + |
| 505 | + |
| 506 | + |
| 507 | + |
| 508 | + |
| 509 | + |
| 510 | + |
| 511 | + |
| 512 | + |
| 513A | + |
| 513B | ++ |
| 514A | +++ |
| 514B | + |
| 515A | +++ |
| 515B | + |
| 516 | + |
| 517 | + |
| 518A | +++ |
| 518B | + |
| 519 | + |
| 520 | + |
| 521 | + |
| 522 | + |
| 523 | + |
| 524 | ++ |
| 525 | + |
| 526 | ++ |
| 527A | + |
| 527B | +++ |
| 528A | + |
| 528B | + |
| 529 | + |
| 530A | + |
| 530B | ++ |
| 530C | ++ |
| 530D | + |
| 531 | + |
| 532A | + |
| 532B | ++ |
| 533 | + |
| 534 | + |
| 535 | + |
| 536 | + |
| 537A | +++ |
| 537B | + |
| 538A | ++ |
| 538B | + |
| 539A | + |
| 539B | ++ |
| 539C | + |
| 539D | ++ |
| 540 | ++ |
| 541 | + |

TABLE A-1-continued

IC$_{50}$ Data for Example Compounds

| Example No. | IC$_{50}$ |
|---|---|
| 542 | + |
| 543A | + |
| 543B | + |
| 543C | + |
| 543D | ++ |
| 544A | + |
| 544B | ++ |
| 544C | + |
| 544D | ++ |
| 545A | ++ |
| 545B | ++ |
| 545C | + |
| 545D | + |
| 546A | + |
| 546B | + |
| 546C | + |
| 546D | + |
| 547 | + |
| 548 | + |
| 549 | + |
| 550 | + |
| 551 | + |
| 552 | + |
| 553 | + |
| 554 | + |
| 555 | + |
| 556 | ++ |
| 557 | + |
| 558 | + |
| 559 | + |
| 560A | + |
| 560B | ++ |
| 560C | + |
| 560D | ++ |
| 561 | + |
| 562 | + |
| 563 | + |
| 564 | + |
| 565A | ++ |
| 565B | ++ |
| 565C | + |
| 565D | + |
| 566A | +++ |
| 566B | +++ |
| 566C | ++ |
| 566D | +++ |
| 567A | + |
| 567B | + |
| 567C | + |
| 567D | + |
| 568A | + |
| 568B | + |
| 568C | + |
| 568D | + |
| 569 | ++ |
| 570A | + |
| 570B | ++ |
| 571A | + |
| 571B | ++ |
| 571C | +++ |
| 571D | ++ |
| 572A | + |
| 572B | ++ |
| 573A | + |
| 573B | + |
| 573C | + |
| 573D | + |
| 574A | ++ |
| 574B | ++ |
| 574C | + |
| 574D | + |
| 575A | +++ |
| 575B | +++ |
| 575C | ++ |
| 575D | +++ |
| 576A | + |
| 576B | + |
| 577A | + |
| 577B | + |
| 578A | + |
| 578B | + |
| 579 | + |
| 580A | ++ |
| 580B | ++ |
| 580C | + |
| 580D | + |
| 581A | + |
| 581B | + |
| 581C | + |
| 581D | + |
| 582A | +++ |
| 582B | ++ |
| 582C | +++ |
| 582D | +++ |
| 583A | + |
| 583B | +++ |
| 584 | + |
| 585 | + |
| 586 | + |
| 587 | + |
| 588 | + |
| 589 | + |
| 590 | + |
| 591A | + |
| 591B | + |
| 592 | + |
| 593 | + |
| 594 | + |
| 595 | + |
| 596 | + |
| 597 | + |
| 598 | + |
| 599 | + |
| 600 | + |
| 601 | + |
| 602 | + |
| 603 | + |
| 604 | + |
| 605 | + |
| 606 | + |
| 607 | + |
| 608 | + |
| 609 | + |
| 610 | + |
| 611 | + |
| 612A | + |
| 612B | + |
| 612C | +++ |
| 612D | +++ |
| 613 | + |
| 614A | +++ |
| 614B | + |
| 614C | + |
| 614D | + |
| 615 | ++ |
| 616 | + |
| 617A | + |
| 617B | + |
| 618 | + |
| 619A | + |
| 619B | + |
| 620 | + |
| 621A | ++ |
| 621B | + |
| 622 | + |
| 623 | + |
| 624 | + |
| 625 | + |
| 626 | + |
| 627 | + |

TABLE A-1-continued

IC$_{50}$ Data for Example Compounds

| Example No. | IC$_{50}$ |
|---|---|
| 628 | +++ |
| 629 | + |
| 630 | +++ |
| 631 | + |
| 632 | + |
| 633 | + |
| 634 | + |
| 635 | + |
| 636 | ++ |
| 637 | + |
| 638 | ++ |
| 639 | +++ |
| 640 | + |
| 641 | ++ |
| 642 | ++ |
| 643 | + |
| 644 | + |
| 645 | + |
| 646 | + |
| 647 | + |
| 648 | +++ |
| 649 | + |
| 650 | + |
| 651 | + |
| 652 | + |
| 653 | +++ |
| 654 | + |
| 655 | + |
| 656 | + |
| 657 | + |
| 658 | + |
| 659 | + |
| 660 | + |
| 661 | + |
| 662 | + |
| 663 | + |
| 664 | + |
| 665 | + |
| 666 | + |
| 667 | +++ |
| 668 | + |
| 669 | + |
| 670 | + |
| 671 | + |
| 672 | ++ |
| 673 | + |
| 674 | + |
| 675 | + |
| 676 | + |
| 677 | + |
| 678 | + |
| 679 | + |
| 680 | + |
| 681 | + |
| 682 | + |
| 683 | + |
| 684 | + |
| 685 | + |
| 686 | + |
| 687 | + |
| 688 | + |
| 689 | ++ |
| 690 | + |
| 691 | + |
| 692 | ++ |
| 693 | + |
| 694 | |
| 695 | + |
| 696 | + |
| 697 | ++ |
| 698 | + |
| 699 | + |
| 700 | + |
| 701 | + |
| 702 | + |

TABLE A-1-continued

IC$_{50}$ Data for Example Compounds

| Example No. | IC$_{50}$ |
|---|---|
| 703 | ++ |
| 704 | + |
| 705 | ++ |
| 706 | + |
| 707 | + |
| 708 | + |
| 709 | + |
| 710 | ++ |
| 711 | + |
| 712 | + |
| 713 | + |
| 714 | + |
| 715 | + |
| 716 | + |
| 717 | + |
| 718 | + |
| 719 | + |
| 720 | + |
| 721 | + |
| 722 | + |
| 723 | + |
| 724 | + |
| 725 | + |
| 726 | + |
| 727 | + |
| 728 | + |
| 729 | ++ |
| 730 | ++ |
| 731 | + |
| 732 | + |
| 733 | + |

Example B: PARP7 amplification in various cancer types

FIG. 1 illustrates that PARP7 amplification occurs in cancer with the highest frequency in lung, esophagus, ovarian, cervical and head and neck (upper aerodigestive). FIG. 1A shows PARP7 amplification across TCGA primary tumor samples. The results here are in whole or part based upon publicly available data generated by the TCGA Research Network: https://www.cancer.gov/tcga. The Cancer Genome Atlas program collected, characterized, and analyzed cancer samples from over 11,000 primary cancer and matched normal samples spanning 33 cancer types. The PARP7 gene is located on chromosome 3 (3q25) in a region that is frequently amplified in cancers of squamous histology (Gao et al. 2013, Cerami et al. 2012). See also: Gao et al., Integrative analysis of complex cancer genomics and clinical profiles using the cBioPortal. *Sci. Signal.* 6, pl1 (2013); and Cerami et al., The cBio Cancer Genomics Portal: An Open Platform for Exploring Multidimensional Cancer Genomics Data. *Cancer Discov* 2, 401-4 (2012).

Figure 1B:
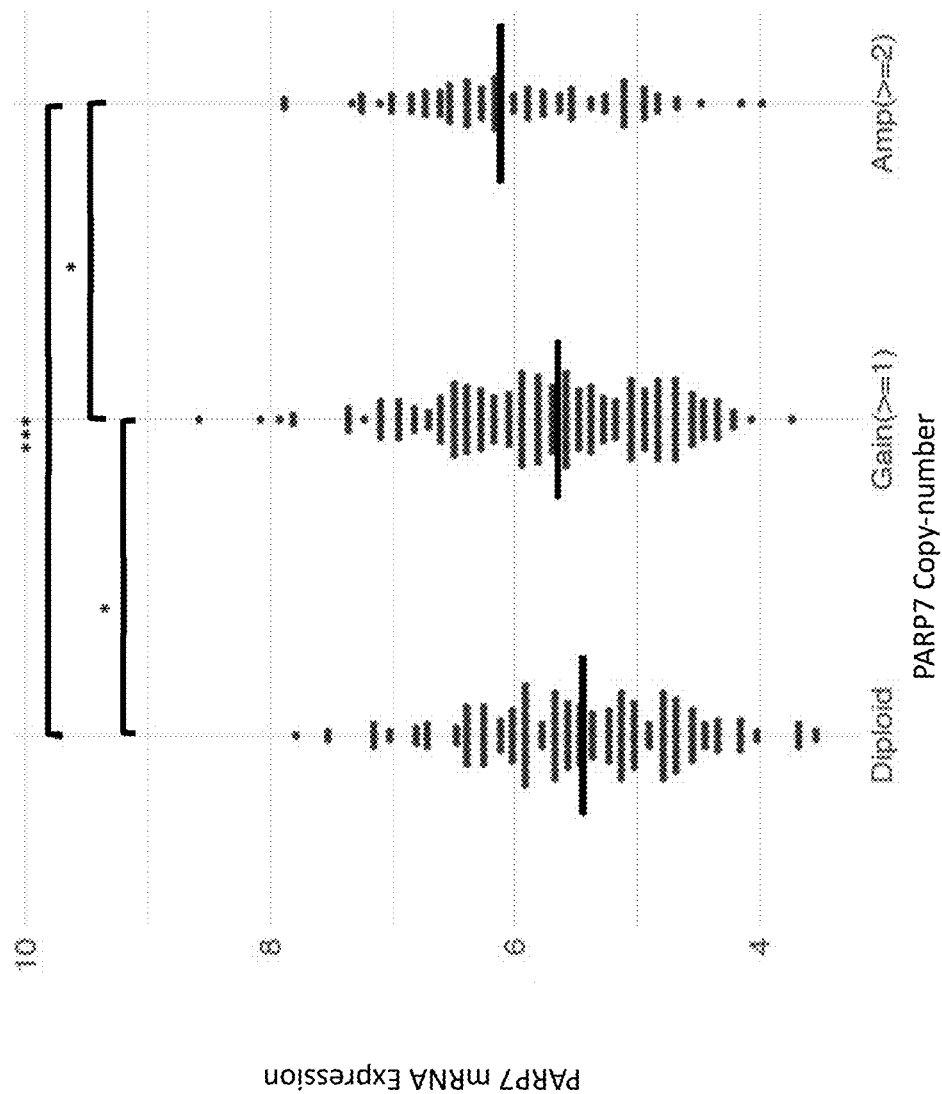
FIG. 1B illustrates that PARP7 copy-number amplifications correspond to increased levels of PARP7 mRNA expression levels in TCGA (The Cancer Genome Atlas) lung squamous tumor samples.

FIG. 1B shows PARP7 copy-number amplifications correspond to increased levels of PARP7 mRNA expression levels in TCGA lung squamous tumor samples. Patient samples included 198 samples with diploid, 234 amplification gain >1 and 92 with amplification gain >2.

Example C: Inhibition of Cancer Cell Growth by Treatment with PARP7 Inhibitors

FIG. 2 illustrates a dose-dependent decrease in growth of NCI-H1373 lung cancer cells. Table A-2 and Table A-3 (below) represents the concentration that causes 50% growth inhibition (GI$_{50}$) in a panel of cancer cell lines with Compound 18B and Compound 561. Cells were plated into 384-well plates at a pre-specified density in fetal bovine serum-containing media. Cells were treated with compound or vehicle (DMSO) 24 hrs later, and a day zero plate was collected for analysis. Test compound plates were incubated continuously for 72 hrs (Table A-2) or 144 hours (Table A-3) cell growth was assessed using a luminescent cell viability assay (CellTiter-Glo, Promega). The $GI_{50}$ was determined by correcting for the cell count at time zero (time of treatment) and plotting data as percent growth relative to vehicle-treated cells.

$GI_{50}$ data for the Example compound is provided below in Table A-2 ("+" is <0.1 µM; "++" is ≥0.1 µM and <1 µM; and "+++" is ≥1 µM).

TABLE A-2

Growth Inhibition in Different Cancer Cell Lines

| Cell Line | Primary Site | Histological Subtype | Compound 18B $GI_{50}$ |
|---|---|---|---|
| JHOS-2 | ovary | adenocarcinoma | + |
| NCI-H1373 | lung | adenocarcinoma | + |
| SCC-25 | upper aerodigestive tract | squamous cell carcinoma | + |
| TE-8 | oesophagus | squamous cell carcinoma | + |
| NCI-H2347 | lung | adenocarcinoma | + |
| TYK-nu | ovary | undifferentiated carcinoma | + |
| COLO-680N | oesophagus | squamous cell carcinoma | + |
| NCI-H1437 | lung | adenocarcinoma | + |
| T3M-10 | lung | large cell carcinoma | + |
| HCC1937 | breast | ductal carcinoma | + |
| EFE-184 | endometrium | not specified | + |
| Panc 03.27 | pancreas | ductal carcinoma | + |
| CAL 27 | upper aerodigestive tract | squamous cell carcinoma | + |
| EBC-1 | squamous cell lung | carcinoma | + |
| YD-10B | upper aerodigestive tract | squamous cell carcinoma | + |
| YH-13 | central nervous system | astrocytoma Grade IV | + |
| NCI-H596 | lung | mixed adenosquamous carcinoma | + |
| NCI-H1963 | lung | small cell carcinoma | + |
| TUHR1OTKB | kidney | not specified | + |
| NCI-H647 | lung | mixed adenosquamous carcinoma | + |
| GSU | stomach | adenocarcinoma | + |
| IA-LM | lung | large cell carcinoma | + |
| MDA-MB-468 | breast | not specified | + |
| SW 900 | lung | squamous cell carcinoma | + |
| NCI-H1930 | lung | small cell carcinoma | + |
| Caki-1 | kidney | clear cell renal cell carcinoma | + |
| HCC1599 | breast | ductal carcinoma | ++ |
| HCC-2279 | lung | adenocarcinoma | ++ |
| DCF-289 | lung | adenocarcinoma | ++ |
| OVISE | ovary | clear cell carcinoma | ++ |
| Hs 578T | breast | ductal carcinoma | ++ |
| HCC1187 | breast | ductal carcinoma | ++ |
| COR-L105 | lung | adenocarcinoma | ++ |
| NCI-H2066 | lung | small cell carcinoma | ++ |
| HCC827 | lung | adenocarcinoma | ++ |
| SK-BR-3 | breast | not specified | ++ |
| HCC-1195 | lung | mixed adenosquamous carcinoma | ++ |
| CFPAC-1 | pancreas | ductal carcinoma | ++ |
| NCI-H1975 | lung | non small cell carcinoma | ++ |
| HDQ-P1 | breast | ductal carcinoma | ++ |
| NCI-H2081 | lung | not specified | ++ |
| KMBC-2 | urinary tract | not specified | ++ |
| NCI-H2228 | lung | adenocarcinoma | ++ |
| L5123 | large intestine | adenocarcinoma | ++ |
| KMRC-3 | kidney | clear cell renal cell carcinoma | ++ |
| LUDLU-1 | lung | squamous cell carcinoma | ++ |
| SNU-719 | stomach | not specified | ++ |
| SW620 | large intestine | adenocarcinoma | ++ |
| EN | endometrium | not specified | ++ |
| GSS | stomach | adenocarcinoma | ++ |
| FaDu | upper aerodigestive tract | squamous cell carcinoma | ++ |
| NCI-H441 | lung | adenocarcinoma | ++ |

NT: Not Tested.

TABLE A-3

Growth Inhibition in Different Cancer Cell Lines with Compound 561.

| Cell Line | Cancer Type | Compound 561 $GI_{50}$ |
|---|---|---|
| TYK-nu | high grade ovarian serous adenocarcinoma | + |
| Caki-1 | clear cell renal cell carcinoma | + |
| SCC-25 | tongue squamous cell carcinoma | + |
| GCT | undifferentiated pleiomorphic sarcoma | + |
| NCI-H647 | lung adenosquamous carcinoma | + |
| NCI-H1373 | lung adenocarcinoma | + |
| EBC-1 | squamous cell lung carcinoma | + |
| NCI-H2347 | lung adenocarcinoma | + |
| Panc 03.27 | pancreatic adenocarcinoma | + |
| HCC827 | lung adenocarcinoma | + |
| TUHR1OTKB | renal cell carcinoma | + |
| IA-LM | large cell lung carcinoma | + |
| CFPAC-1 | pancreatic ductal adenocarcinoma | ++ |
| COR-L105 | lung adenocarcinoma | ++ |
| SW900 | squamous cell lung carcinoma | ++ |
| NCI-H2066 | squamous cell lung carcinoma | +++ |
| TE-11 | esophageal squamous cell carcinoma | +++ |
| MSTO-211H | biphasic mesothelioma | +++ |
| NCI-H2009 | lung adenocarcinoma | +++ |
| SK-LU-1 | lung adenocarcinoma | +++ |
| NCI-H2087 | lung adenocarcinoma | +++ |
| NCI-H1930 | small cell lung carcinoma | +++ |
| H4 | neuroglioma | +++ |
| LN-18 | glioblastoma | +++ |
| CAL-27 | tongue squamous cell carcinoma | +++ |
| A101D | melanoma | +++ |
| ACC-MESO-1 | mesothelioma | +++ |
| AGS | gastric adenocarcinoma | +++ |
| COLO 680N | esophageal squamous cell carcinoma | +++ |
| HCC1954 | ductal breast carcinoma | +++ |
| HPAF-II | pancreatic adenocarcinoma | +++ |
| HT-1080 | fibrosarcoma | +++ |
| KAL S-1 | glioblastoma | +++ |
| KMBC-2 | bladder carcinoma | +++ |
| KMRC-3 | clear cell renal carcinoma | +++ |
| MCAS | ovarian mucinous cy stadenocarcinoma | +++ |
| MDA-MIB-468 | breast adenocarcinoma | +++ |
| NCI-H1437 | lung adenocarcinoma | +++ |
| NCI-H1648 | lung adenocarcinoma | +++ |
| NCI-H1944 | lung adenocarcinoma | +++ |

TABLE A-3-continued

Growth Inhibition in Different Cancer Cell Lines with Compound 561.

| Cell Line | Cancer Type | Compound 561 GI$_{50}$ |
|---|---|---|
| NCI-H1963 | small cell lung carcinoma | +++ |
| NCI-H2291 | lung adenocarcinoma | +++ |
| NCI-H2444 | non-small cell lung carcinoma | +++ |
| NCI-H441 | papillary adenocarcinoma of the lung | +++ |
| NUGC-3 | gastric adenocarcinoma | +++ |
| SCaBER | bladder squamous cell carcinoma | +++ |
| SF126 | glioblastoma multiforme | +++ |
| SK-MEL-2 | malignant melanoma | +++ |
| SK-MES-1 | squamous cell lung carcinoma | +++ |
| SNU-840 | malignant ovarian Brenner tumor | +++ |
| T84 | colon adenocarcinoma | +++ |
| YD-10B | tongue squamous cell carcinoma | +++ |

Figure 3:
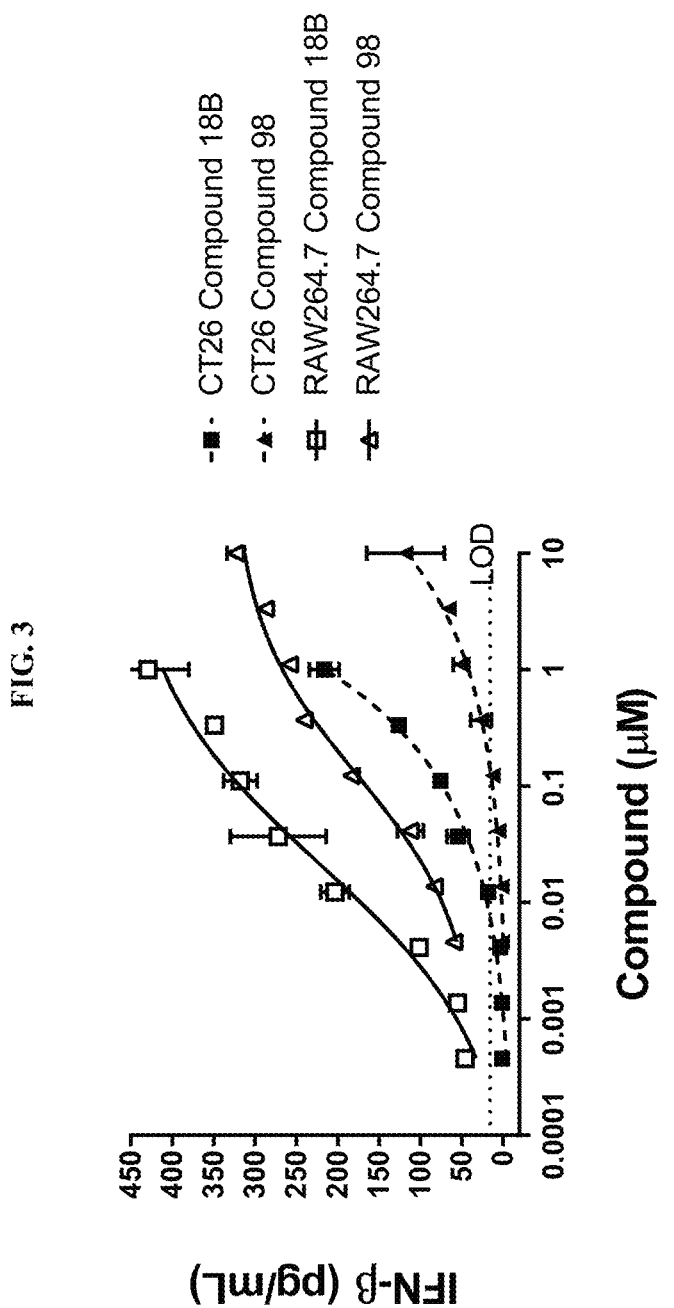
FIG. 3 illustrates the induction of interferon-beta (IFN-β) levels by PARP7 inhibitors (compounds of Examples 18B and 98) in CT26 mouse colon cancer cells and RAW264.7 mouse macrophages in the presence of a STING agonist, DMXAA (also known as Vadimezan or ASA404).

Example D: Induction of Interferon Beta-Levels by Treatment with PARP7 Inhibitors FIG. 3 illustrates the induction of interferon-beta (IFN-β) levels by PARP7 inhibitors in CT26 mouse colon cancer cells and RAW264.7 mouse macrophages in the presence of a STING agonist, DMXAA. CT26 cells were plated in a 96-well plate and allowed to adhere overnight. Cells were co-treated with a dose-titration of PARP7 inhibitor and 50 µg/mL DMXAA for 24 hours and supernatants were harvested and immediately processed by ELISA (Invivogen, luex-mifnb) according to kit instructions. Assay limit of detection defined by 2× the lowest concentration of the standard curve (LOD=16 pg/mL). IFN-β concentrations interpolated from the standard curve and non-linear regression analysis was performed using a 4-parameter (variable slope) fit in GraphPad Prism.

Figure 4:
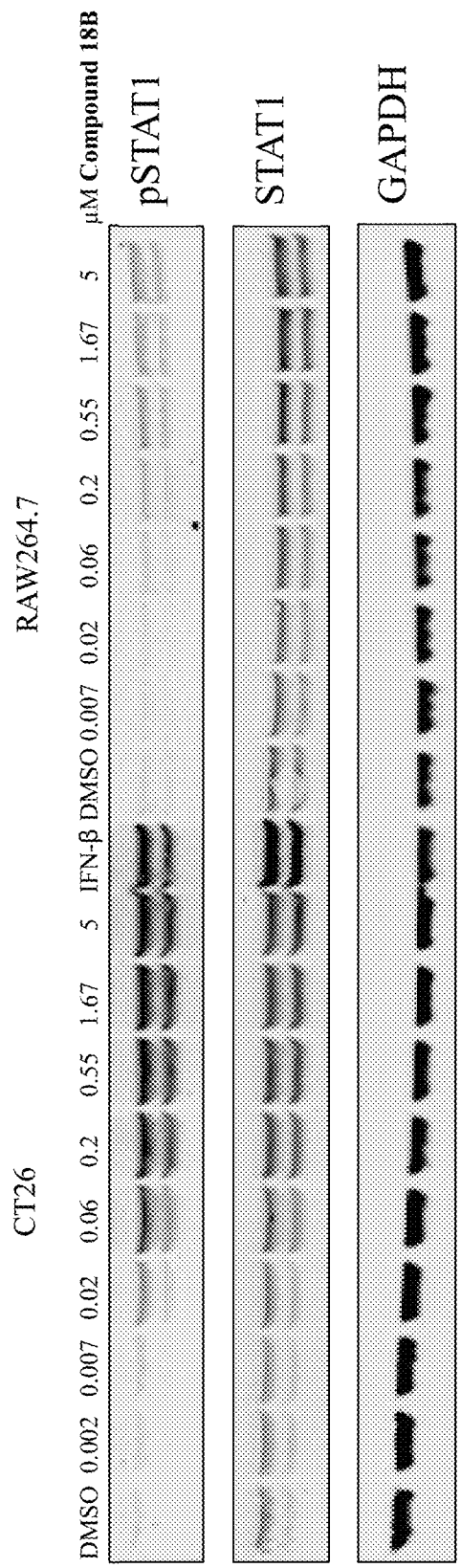
FIG. 4 illustrates the induction of STAT1 phosphorylation by a PARP7 inhibitor in CT26 mouse colon cancer cells and RAW264.7 mouse macrophages.

Example E: Induction of STAT1 Phosphorylation by Treatment with PARP7 Inhibitors FIG. 4 illustrates the induction of STAT1 phosphorylation by a PARP7 inhibitor in CT26 mouse colon cancer cells and RAW264.7 mouse macrophages. CT26 cells were plated in 6-well dishes and allowed to adhere overnight. Cells were treated with PARP7 inhibitor (5 µM top dose, 1:3 serial dilution) or interferon-beta (10 ng/mL) for 24 hours prior to harvest by scraping on ice in RIPA lysis buffer (Millipore, 20-188) with HALT protease and phosphatase inhibitor (Thermo, 78444). Lysates (30 µg) were subjected to western immunoblotting using primary antibodies diluted 1:1000 (Cell Signaling Technologies, 9167, 9172, and 5174). After washing with TBST, blots were incubated with secondary antibody (Licor, 926-32211) diluted at 1:15,000 in blocking buffer and subsequently scanned using a Licor Odyssey CLx Imager.

Example F: Proliferation of CT26 Cells in the Presence of PARP7 Inhibitors

Figure 5:
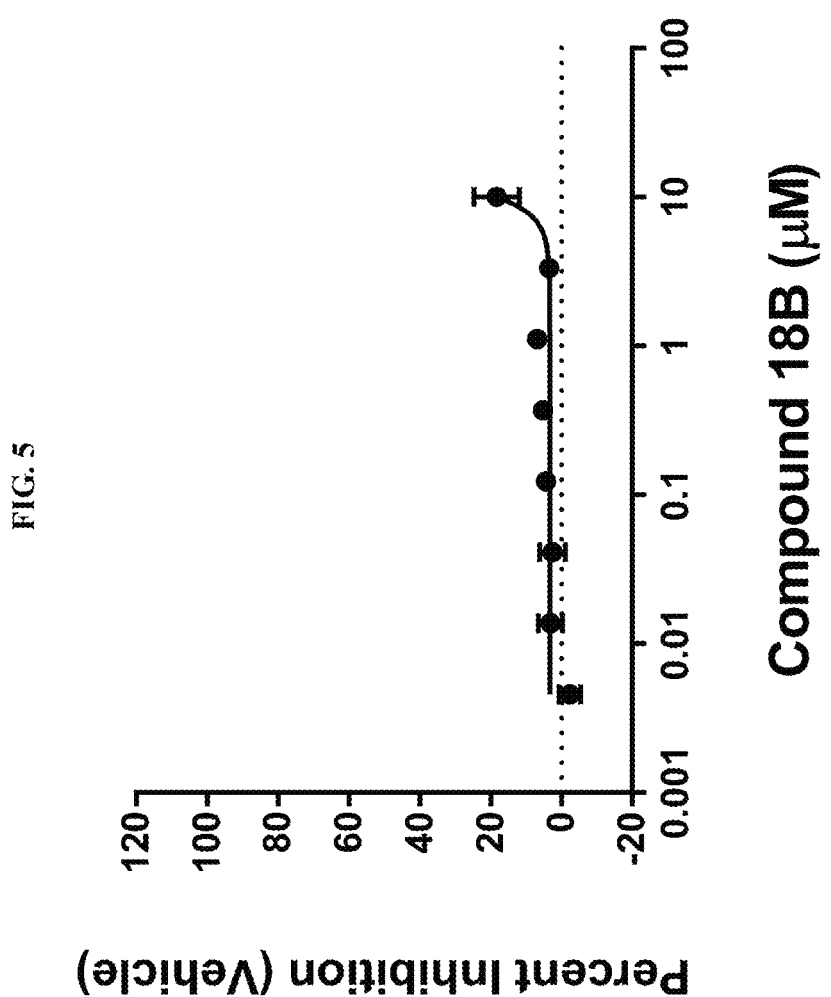
FIG. 5 illustrates proliferation in CT26 cells in vitro in the presence of PARP7 inhibitor (compound of Example 18B).

FIG. 5 illustrates that PARP7 inhibitors do not inhibit proliferation in CT26 cells in vitro. CT26 cells were plated in a 384-well plate and allowed to adhere for several hours before being treated with Compound 18B. Cells were incubated with compound for 4 days prior to processing with CellTiter-Glo reagent (Promega). Luminescence was measured with a Perkin Elmer Envision and percent inhibition was calculated using the vehicle (DMSO) average as 0% inhibition. Non-linear regression analysis was performed using a 4 parameter (variable slope) fit in GraphPad Prism.

Example G: Inhibition of Tumor Growth by Treatment with PARP7 Inhibitors

FIG. 6 illustrates that PARP7 inhibitors significantly reduce tumor growth in murine syngeneic models (FIGS. 6A, 6B, and 6C) CT26 and (FIGS. 6D, 6E, and 6F) 4T1. For the CT26 study BALB/c mice were inoculated subcutaneously at the right flank with CT26 cells for tumor development. Four days after tumor inoculation, 36 mice with tumor size ranging from 40-55 mm$^3$ (average tumor size 47 mm$^3$) were selected and assigned into 3 groups using stratified randomization with 12 mice in each group based upon their tumor volumes. The treatments were started from the next day post randomization (defined randomization day as day 0) and were treated with vehicle (0.5% methylcellulose+0.2% Tween 80), Compound 98 (500 mg/kg S.C. QD*21 days), Compound 93A (100 mg/kg S.C. BID*21 days) respectively. The tumor sizes were measured three times per week during the treatment. The entire study was terminated on day 21.

For the 4T1 study female BALB/c mice were inoculated orthotopically in the mammary fat pad with 4T1-luc2-1A4 cells for tumor development. Eight days after tumor inoculation, 45 mice with tumor size ranging from 63-88 mm$^3$ (average tumor size 67 mm$^3$) were selected and assigned into 3 groups using stratified randomization with 15 mice in each group based upon their tumor volumes. The treatments were started from the next day post randomization (defined randomization day as D0) and were treated with vehicle (0.5% methylcellulose+0.2% Tween 80), Compound 98 (500 mg/kg S.C. QD*21 days), Compound 93A (100 mg/kg S.C. BID*21 days) respectively. The tumor sizes were measured three times per week during the treatment. The entire study was terminated on D20.

Mean tumor volume and SEM for both studies are plotted. Statistical significance, calculated using two-tailed unpaired t-tests in which each treatment group was compared to vehicle control, is indicated by an asterisk. Statistics were performed on groups with less than 20% animal loss (D21 for CT26, D17 for 4T1).

Example H: Inhibition of Tumor Growth by Oral Dosing with a PARP7 Inhibitor

The effect of Compound 561 on tumor growth was studied in a human NCI-H1373 lung cancer xenograft and a murine CT26 colon cancer syngeneic model.

For the NCI-H1373 study, SCID mice were inoculated subcutaneously in the right flank with NCI-H1373 cells for tumor development. After 5 days of tumor growth, mice with 89-148 mm$^3$ tumors were randomized into treatment groups with mean tumor volumes of 121 mm$^3$. The treatments were started from the next day post randomization (defined randomization day as day 0) and were treated with vehicle (50% Labrasol) or Compound 561 (62.5, 125, 250, and 500 mg/kg) once a day for 28 days by oral gavage. Tumor volumes were determined by manual calipers every 2-3 days. Mean tumor volume and SEM are plotted. QD: once a day; PO: per oral administration. Statistical significance is calculated using two-way ANOVA followed by Bonferroni post-tests in which the treatment groups were compared to vehicle control (****P<0.0001). FIG. 7A illustrates that once daily administration of PARP7 inhibitor Compound 561 significantly reduces tumor growth in a human NCI-H1373 lung cancer xenograft. In the mouse NCI-H1373 human lung cancer cell model, Compound 561 at doses of 62.5 to 500 mg/kg administered once a day for 28 days caused complete tumor regression at all dose levels.

For the CT26 study, BALB/c mice were inoculated subcutaneously in the right flank with CT26 cells for tumor development. After 5 days of cell inoculation, mice with 36-79 mm$^3$ tumors were randomized into treatment groups with mean tumor volumes of 54 mm$^3$. The treatments were started from the next day post randomization (defined randomization day as day 0) and were treated with vehicle (25 or 50% Labrasol) or Compound 561 BID (2 times a day every 12 hours) at doses ranging from 125-500 mg/kg or QD (once a day) at 500 mg/kg for 21 days by oral gavage or needle subcutaneously. Tumor volumes were determined by manual calipers every 2-3 days. Mean tumor volume and SEM are plotted. BID: twice a day; PO: per oral administration; QD: once a day; SC: per subcutaneous administration. The first two doses for vehicle and Compound 561 500 mg/kg in the QD groups were delivered by subcutaneous injection. Statistical analysis for tumor growth inhibition (TGI) was performed when at least 8 of the 10 mice were remaining in the vehicle group (Day 16). Statistical significance is calculated using two-way ANOVA followed by Bonferroni post-tests in which the treatment groups were compared to vehicle control (****P<0.0001). FIG. 7B illustrates that once or twice daily administration of PARP7 inhibitor Compound 561 significantly reduces tumor growth in a murine CT26 colon cancer syngeneic model.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient in need of treatment comprising administering to said patient a therapeutically effective amount of a compound having the structure:

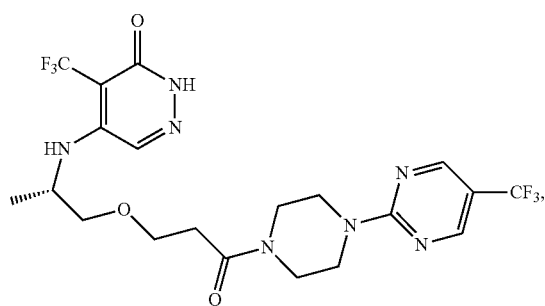 [SMILES: C[C@@H](COCCC(=O)N1CCN(c2ncc(C(F)(F)F)cn2)CC1)Nc1cn[nH]c(=O)c1C(F)(F)F]

or a pharmaceutically acceptable salt thereof, wherein said cancer is breast cancer, cancer of the central nervous system, endometrium cancer, kidney cancer, large intestine cancer, lung cancer, oesophagus cancer, ovarian cancer, pancreatic cancer, prostate cancer, stomach cancer, head and neck cancer (upper aerodigestive cancer), urinary tract cancer, or colon cancer.

2. The method of claim 1 wherein said cancer is lung cancer.

3. The method of claim 1 wherein said cancer is breast cancer.

4. The method of claim 1 wherein said cancer is cancer of the central nervous system.

5. The method of claim 1 wherein said cancer is endometrium cancer.

6. The method of claim 1 wherein said cancer is kidney cancer.

7. The method of claim 1 wherein said cancer is large intestine cancer.

8. The method of claim 1 wherein said cancer is oesophagus cancer.

9. The method of claim 1 wherein said cancer is ovarian cancer.

10. The method of claim 1 wherein said cancer is pancreatic cancer.

11. The method of claim 1 wherein said cancer is prostate cancer.

12. The method of claim 1 wherein said cancer is stomach cancer.

13. The method of claim 1 wherein said cancer is head and neck cancer (upper aerodigestive cancer).

14. The method of claim 1 wherein said cancer is urinary tract cancer.

15. The method of claim 1 wherein said cancer is colon cancer.

16. A method of treating cancer in a patient in need of treatment comprising administering to said patient a therapeutically effective amount of a compound having the structure:

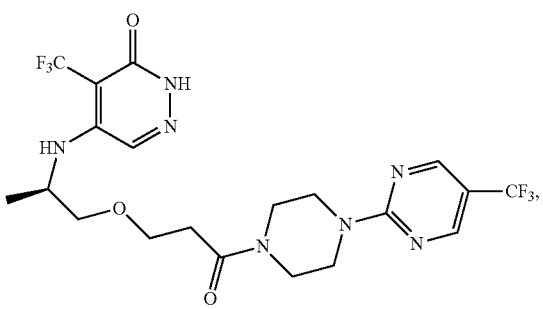 [SMILES: C[C@H](COCCC(=O)N1CCN(c2ncc(C(F)(F)F)cn2)CC1)Nc1cn[nH]c(=O)c1C(F)(F)F]

or a pharmaceutically acceptable salt thereof, wherein said cancer is breast cancer, cancer of the central nervous system, endometrium cancer, kidney cancer, large intestine cancer, lung cancer, oesophagus cancer, ovarian cancer, pancreatic cancer, prostate cancer, stomach cancer, head and neck cancer (upper aerodigestive cancer), urinary tract cancer, or colon cancer.

17. The method of claim 16 wherein said cancer is lung cancer.

18. The method of claim 16 wherein said cancer is breast cancer.

19. The method of claim 16 wherein said cancer is cancer of the central nervous system.

20. The method of claim 16 wherein said cancer is endometrium cancer.

21. The method of claim 16 wherein said cancer is kidney cancer.

22. The method of claim 16 wherein said cancer is large intestine cancer.

23. The method of claim 16 wherein said cancer is oesophagus cancer.

24. The method of claim 16 wherein said cancer is ovarian cancer.

25. The method of claim 16 wherein said cancer is pancreatic cancer.

26. The method of claim 16 wherein said cancer is prostate cancer.

27. The method of claim 16 wherein said cancer is stomach cancer.

28. The method of claim 16 wherein said cancer is head and neck cancer (upper aerodigestive cancer).

29. The method of claim 16 wherein said cancer is urinary tract cancer.

30. The method of claim 16 wherein said cancer is colon cancer.

* * * * *